US011629348B2

(12) United States Patent
Anderson et al.

(10) Patent No.: US 11,629,348 B2
(45) Date of Patent: Apr. 18, 2023

(54) LINKAGE MODIFIED OLIGOMERIC COMPOUNDS AND USES THEREOF

(71) Applicant: Ionis Pharmaceuticals, Inc., Carlsbad, CA (US)

(72) Inventors: Brooke A. Anderson, San Diego, CA (US); Xue-hai Liang, Del Mar, CA (US); William John Drury, III, Oceanside, CA (US); Michael Oestergaard, Carlsbad, CA (US); Michael T. Migawa, Carlsbad, CA (US); Punit P. Seth, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/671,924

(22) Filed: Feb. 15, 2022

(65) Prior Publication Data

US 2022/0186222 A1 Jun. 16, 2022

Related U.S. Application Data

(63) Continuation of application No. PCT/US2020/046561, filed on Aug. 14, 2020.

(60) Provisional application No. 63/050,042, filed on Jul. 9, 2020, provisional application No. 62/989,442, filed on Mar. 13, 2020, provisional application No. 62/953,121, filed on Dec. 23, 2019, provisional application No. 62/887,525, filed on Aug. 15, 2019.

(51) Int. Cl.
*C12N 15/113* (2010.01)

(52) U.S. Cl.
CPC ........ *C12N 15/113* (2013.01); *C12N 2310/11* (2013.01); *C12N 2310/314* (2013.01); *C12N 2310/315* (2013.01); *C12N 2310/321* (2013.01); *C12N 2310/341* (2013.01); *C12N 2310/351* (2013.01)

(58) Field of Classification Search
CPC .............. C12N 15/113; C12N 2310/11; C12N 2310/14; C12N 2310/314; C12N 2310/315; C12N 2310/321; C12N 2310/341; C12N 2310/351; C12N 2320/32; C12N 2320/51
USPC .... 435/6.1, 91.1, 91.31, 455, 458; 536/23.1, 536/24.5
See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,458,066 | A | 7/1984 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,668,777 | A | 5/1987 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lableu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,194,599 | A | 3/1993 | Froehler |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,276,019 | A | 1/1994 | Cohen et al. |
| 5,278,302 | A | 1/1994 | Caruthers et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |

(Continued)

FOREIGN PATENT DOCUMENTS

| | | |
|---|---|---|
| EP | 0679657 | 11/1995 |
| WO | WO 1989/009221 | 10/1989 |

(Continued)

OTHER PUBLICATIONS

English machine translation of WO2018/156056, Jun. 2022, 109 pages.*

(Continued)

*Primary Examiner* — Jane J Zara
(74) *Attorney, Agent, or Firm* — McNeill Baur PLLC

(57) ABSTRACT

The present disclosure provides oligomeric compounds (including oligomeric compounds that are antisense agents or portions thereof) comprising a modified oligonucleotide having at least one modified internucleoside linking group.

28 Claims, 2 Drawing Sheets

Specification includes a Sequence Listing.

(56) References Cited

U.S. PATENT DOCUMENTS

| | | | |
|---|---|---|---|
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |
| 5,399,676 | A | 3/1995 | Froehler |
| 5,403,711 | A | 4/1995 | Walder et al. |
| 5,405,938 | A | 4/1995 | Sumerton et al. |
| 5,405,939 | A | 4/1995 | Suhadolnik et al. |
| 5,432,272 | A | 7/1995 | Benner |
| 5,434,257 | A | 7/1995 | Matteucci |
| 5,446,137 | A | 8/1995 | Maag et al. |
| 5,453,496 | A | 9/1995 | Caruthers et al. |
| 5,455,233 | A | 10/1995 | Spielvogel et al. |
| 5,457,187 | A | 10/1995 | Gmelner et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,491,133 | A | 2/1996 | Walder et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,711 | A | 6/1996 | Hawkins et al. |
| 5,527,899 | A | 6/1996 | Froehler |
| 5,536,821 | A | 7/1996 | Agrawal et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,555 | A | 10/1996 | Froehler et al. |
| 5,567,811 | A | 10/1996 | Mistura et al. |
| 5,571,799 | A | 11/1996 | Tkachuk et al. |
| 5,576,427 | A | 11/1996 | Cook et al. |
| 5,587,361 | A | 12/1996 | Cook et al. |
| 5,587,469 | A | 12/1996 | Cook et al. |
| 5,591,722 | A | 1/1997 | Montgomery et al. |
| 5,594,121 | A | 1/1997 | Froehler et al. |
| 5,596,086 | A | 1/1997 | Matteucci |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bishofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci |
| 5,652,355 | A | 7/1997 | Metelev et al. |
| 5,652,356 | A | 7/1997 | Agrawal |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,700,920 | A | 12/1997 | Altmann et al. |
| 5,700,922 | A | 12/1997 | Cook |
| 5,721,218 | A | 2/1998 | Froehler |
| 5,750,692 | A | 5/1998 | Cook et al. |
| 5,763,588 | A | 6/1998 | Matteucci et al. |
| 5,792,608 | A | 8/1998 | Swaminathan et al. |
| 5,792,847 | A | 8/1998 | Buhr et al. |
| 5,830,653 | A | 11/1998 | Froehler et al. |
| 6,005,096 | A | 12/1999 | Matteucci et al. |
| 6,268,490 | B1 | 7/2001 | Imanishi et al. |
| 6,365,577 | B1 | 4/2002 | Iversen |
| 6,426,220 | B1 | 7/2002 | Bennett et al. |
| 6,600,032 | B1 | 7/2003 | Manoharan et al. |
| 6,770,748 | B2 | 8/2004 | Imanishi et al. |
| 6,794,499 | B2 | 9/2004 | Wengel et al. |
| 7,053,207 | B2 | 5/2006 | Wengel |
| 7,067,641 | B2 | 6/2006 | Dellinger |
| 7,399,845 | B2 | 7/2008 | Seth et al. |
| 7,427,672 | B2 | 9/2008 | Imanishi et al. |
| 2003/0082807 | A1 | 5/2003 | Wengel |
| 2003/0207841 | A1 | 11/2003 | Kaneko et al. |
| 2003/0224377 | A1 | 12/2003 | Wengel et al. |
| 2004/0143114 | A1 | 7/2004 | Imanishi et al. |
| 2004/0171570 | A1 | 9/2004 | Allerson et al. |
| 2004/0192918 | A1 | 9/2004 | Imanishi et al. |
| 2005/0130923 | A1 | 6/2005 | Bhat et al. |
| 2017/0130224 | A1 | 5/2017 | Oestergaard et al. |

FOREIGN PATENT DOCUMENTS

| | | | |
|---|---|---|---|
| WO | WO 1994/002499 | 2/1994 | |
| WO | WO 1994/017093 | 8/1994 | |
| WO | WO 1999/014226 | 3/1999 | |
| WO | WO 2002/036743 | 5/2002 | |
| WO | WO 2003/002587 | 1/2003 | |
| WO | WO 2005/121371 | 12/2005 | |
| WO | WO 2005/121372 | 12/2005 | |
| WO | WO 2007/059816 | 5/2007 | |
| WO | WO 2007/134181 | 11/2007 | |
| WO | WO 2007/146511 | 12/2007 | |
| WO | WO 2008/101157 | 8/2008 | |
| WO | WO 2008/109080 | 9/2008 | |
| WO | WO 2008/150729 | 12/2008 | |
| WO | WO 2008/154401 | 12/2008 | |
| WO | WO 2009/006478 | 1/2009 | |
| WO | WO 2009/067647 | 5/2009 | |
| WO | WO 2011/139699 | 11/2011 | |
| WO | WO 2011/139702 | 11/2011 | |
| WO | WO 2013/075035 | 5/2013 | |
| WO | WO 2016/028187 | 2/2016 | |
| WO | WO 2016/028649 | 2/2016 | |
| WO | WO 2018/098328 | 5/2018 | |
| WO | WO 2018/156056 | 8/2018 | |
| WO | WO-2019073018 A1 * | 4/2019 | ......... A61K 31/7125 |
| WO | WO 2019/157531 | 8/2019 | |
| WO | WO 2019/200185 | 10/2019 | |
| WO | WO 2019/217459 | 11/2019 | |
| WO | WO 2020/072991 | 4/2020 | |
| WO | WO 2020/160163 | 8/2020 | |
| WO | WO 2021/030763 | 2/2021 | |
| WO | WO 2021/030778 | 2/2021 | |

OTHER PUBLICATIONS

Albaek et al., "Bi- and Tricyclic Nucleoside Derivatives Restricted in S-Type Conformations and Obtained by RCM-Reactions" Nucleosides, Nucleotides & Nucleic Acids (2003) 22(5-8):723-725.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Altmann et al. "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides & Nucleotides (1997) 16: 917-926.

Altmann et al. "Second Generation of Antisense Oligonucleotides: Structure-activity relationships and the design of improved signal-transduction inhibitors" RNA Interactions (1996) 24: 630-637.

(56) References Cited

OTHER PUBLICATIONS

Altmann et al. "Second Generation of Antisense Oligonucleotides: From Nuclease Resistance to Biological Efficacy in Animals" Chimia (1996) 168-176.
Altschul et al., "Basic Local Alignment Search Tool" J. Mol. Biol. (1990) 215:403-410.
Anderson et al., "Towards next generation antisense oligonucleotides: mesylphosphoramidate modification improves therapeutic index and duration of effect of gapmer antisense oligonucleotides" Nucl Acids Res (2021) 1-16.
Anderson et al., "Towards Next Generation Antisense Oligonucleotides-Mesylphosphoramidate Modification Improves Therapeutic Index and Duration of Effect of Gapmer Antisense Oligonucleotides" Abstract for 17th Annual OTS—Oligonucleotide Therapeutics Society Meeting (Sep. 26-29, 2021).
Anderson et al., "Towards Next Generation Antisense Oligonucleotides-Mesylphosphoramidate Modification Improves Therapeutic Index and Duration of Effect of Gapmer Antisense Oligonucleotides" Poster for 17th Annual OTS—Oligonucleotide Therapeutics Society Meeting (Sep. 26-29, 2021).
Baker et al. "2'-O-(2-Methoxy )ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J Biol Chem (1997) 272(18): 11994-12000.
Bala et al., "Synthesis of α-1-Threofuranosyl Nucleoside 3'-Monophosphates, 3'-Phosphoro(2-Methyl)imidazolides, and 3'-Triphosphates" J Org Chem (2017) 82: 5910-5916.
Barany et al., "A New Amino Protecting Group Removable by Reduction. Chemistry of the Dithiasuccinoyl (Dts) Function" J. Am. Chem. Soc. (1977) 99:7363-7365.
Barany et al., "Kinetics and Mechanisms of the Thiolytic Removal of the Dithiasuccinoyl (Dts) Amino Protecting Group" J. Am. Chem. Soc. (1980) 102:3084-3095.
Bass, "Double-stranded RNA as a template for gene silencing" Cell (2000) 101:235-238.
Beaucage et al., "Advances in the Synthesis of Oligonucleotides by the Phosphoramidite Approach" Tetrahedron (1992) 48(12):2223-2311.
Beaucage et al., "The Functionalization of Oligonucleotides Via Phosphoramidite Derivatives" Tetrahedron (1993) 49(10):1925-1963.
Beaucage et al., "The Synthesis of Specific Ribonucleotides and Unrelated Phosphorylated Biomolecules by the Phosphoramidite Method" Tetrahedron (1993) 49(46):10441-10488.
Belikova et al., "Synthesis of Ribonucleosides and Diribonucleoside Phosphates Containing 2-Chloro-Ethylamine and Nitrogen Mustard Residues" Tet. Lett. (1967) 37:3557-3562.
Biscans et al., "The chemical structure and phosphorothioate content of hydrophobically modified siRNAs impact extra hepatic distribution and efficacy" Nucl Ac Res (2020) 1-16.
Boissonnet et al., "α,β-D-CAN featuring canonical and noncanonical α/β torsional angles behaviours within oligonucleotides" New J. Chem. (2011) 35: 1528-1533.
Borsting et al. "Dinucleotides containing two allyl groups by combinations of allyl phosphotriesters, 5-allyl-, 2'-O-allyl- and 2'-arabino-O-allyl uridine derivatives as substiates for ring-closing metathesis" Tetrahedron (2004) 60: 10955-10966.
Braasch et al., "Locked nucleic acid (LNA): fine-tuning the recognition of DNA and RNA" Chem. Biol. (2001) 8:1-7.
Brazma et al., "Gene expression data analysis" FEBS Letters (2000) 480:17-24.
Burakova et al., "New Oligodeoxynucleotide Derivatives Containing N-(Sulfonyl)-Phosphoramide Groups" Russian J of Bioorg Chem (2019) 45: 662-668.
Carulli et al., "High Throughput Analysis of Differential Gene Expression" J. Cell. Biochem. Suppl. (1998) 30:286-296.
Celis et al., "Gene expression profiling: monitoring transcription and translation products using DNA microarrays and proteomics" FEBS Lett (2000) 480:2-16.
Chappell et al., "Mechanisms of palmitic acid-conjugated antisense oligonucleotide distribution in mice" Nucleic Acids Res (2020) 48(8): 4382-4395.
Chelobanov et al, "New Oligodeoxynucleotide Derivatives Containing N-(Methanesulfonyl)-Phosphoramidate (Mesyl Phosphoramidate) Intemucleotide Group" Russain J Bioorg Chem (2017) 43: 664-668.
Chiang et al., "Antisense Oligonucleotides Inhibit Intercellular Adhesion Molecule 1 Expression by Two Distinct Mechanisms" J. Biol. Chem. (1991) 266:18162-18171.
Conte et al. "Conformational properties and thermodynamics of the RNA duplex r(CGCAAAUUUGCG)2: comparison with the DNA analogue d(CGCAAATTTGCG)2" Nucleic Acids Research (1997) 25: 2627-2634.
Crooke et al., "Pharmacokinetic Properties of Several Novel Oligonucleotide Analogs in mice" J. Pharmacol. Exp. Ther. (1996) 277(2):923-937.
Dupouy et al., "Watson-Crick Base-Pairing Properties of Nucleic Acid Analogues with Stereocontrolled α and β Torsion Angles (α,β-D-CNAs)" Angew. Chem. Int. Ed. Engl. (2014) 45: 3623-3627.
Dupouy et al., "Synthesis and Structure of Dinucleotides with S-Type Sugar Puckering and Noncanonical ε and ζ Torsion Angle Combination" Eur. J. Org. Chem . . . , 2008, 1285-1294.
Dupouy et al., "Synthesis and Structure of Dinucleotides Featuring Canonical and Non-canonical A-Type Duplex α, β and δ Torsion Angle Combinations (LNA/α,β-D-CAN)" Eur. J. Org. Chem. (2007) 5256-5264.
Egli et al., "Probing the Influence of Stereoelectronic Effects on the Biophysical Properties of Oligonucleotides: Comprehensive Analysis of the RNA Affinity, Nuclease Resistance, and Crystal Structure of Ten 2'-O-Ribonucleic Acid Modifications" Biochemistry (2005) 44(25):9045-9057.
Elayadi et al., "Application of PNA and LNA oligomers to chemotherapy" Curr. Opinion Invens. Drugs (2001)2:558-561.
Elbashir, "Duplexes of 21-nucleotide RNAs mediate RNA interference in cultured mammalian cells" Nature (2001) 411:494-498.
Elbashir, "RNA interference is mediated by 21- and 22-nucleotide RNAs" Genes & Devel. (2001) 15:188-200.
Englisch et al., "Chemically Modified Oligonucleotides as Probes and Inhibitors" Agnew Chem. Int. Ed. Engl. (1991) 30:613-629.
Fire et al., "Potent and Specific Genetic Interference by Double-Stranded RNA in Caenorhabditis Elegans" Nature (1998) 391:806-811.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fuchs et al., "Identification of Differentially Expressed Genes by Mutually Subtracted RNA Fingerprinting" Anal. Biochem. (2000) 286:91-98.
Gait et al., "Application of chemically synthesized RNA" RNA: Protein Interactions (1998) 1-36.
Gait, "Oligoribonucleotides" Antisense Research and Applications (1993), CRC Press, Boca Raton, pp. 289-301.
Gallo et al., "2'-C-Methyluridine Phosphoramidite: A New Building Block for the Preparation of RNA Analogues Carrying the 2'-Dydroxyl Group" Tetrahedron (2001) 57: 5707-5713..
Going et al., "Molecular Pathology and Future Developments" Eur. J. Cancer (1999) 35:1895-1904.
International Search Report for PCT/US20/046561 dated Dec. 31, 2020.
Jungblut et al., "Proteomics in human disease: Cancer, heart and infections diseases" Electrophoresis (1999) 20:2100-2110.
Jurecic et al., "Long-distance DD-PCR and cDNA microarrays" Curr. Opin. Microbiol. (2000) 3:316-321.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.

(56) References Cited

OTHER PUBLICATIONS

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotech. (2000) 80:143-157.
Letsinger et al., "Cholesteryl-conjugated oligonucleotides: Synthesis, properties, and activity as inhibitors of replication of human immunodeficiency virus in cell culture" PNAS (1989) 86:6553-6556.
Lesnik et al. "Relative Thermodynamic Stability of DNA, RNA, and DNA:RNA Hybrid Duplexes: Relationship with Base Composition and Structure" Biochemistry (1995) 34: 10807-10815.
Leumann et al., "DNA Analogues: From Supramolecular Principles to Biological Properties" Bioorganic & Medicinal Chemistry (2002) 10:841-854.
Madden et al., "Serial analysis of gene expression: from gene discovery to target identification" DDT (2000) 5:415-425.
Manoharan et al., "Chemical Modifications to Improve Uptake and Bioavailability of Antisense Oligonucleotides" Ann. N.Y. Acad. Sci. (1992) 660: 306-309.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Cholic Acid-Oligonucleotide Conjugates for Antisense Applications" Bioorg. Med. Chem. Lett. (1994) 4:1053-1060.
Manoharan et al., "Oligonucleotide Conjugates: Alteration of the Pharmacokinetic Properties of Antisense Agents" Nucleosides & Nucleotides (1995) 14(3-5):969-973.
Manoharan et al., "Lipidic Nucleic Acids" Tetrahedron Lett. (1995) 36(21):3651-3654.
Manoharan et al. "Oligonucleotide Conjugates as Potential Antisense Drugs with Improved Uptake, Biodistribution, Targeted Delivery, and Mechanism of Action" Antisense & Nucleic Acid Drug Development (2002) 12:103-128.
Martin et al. "A New Access to 2'O-Alkylated Ribonucleosides and Properties of 2'-O-Alkylated Oligoribonucleotides" Helvetica Chimica Acta (1995) 78: 486-504.
Martinez et al., "α,β-D-constrained nucleic acids are strong terminators of thermostable DNA polymerases in polymerase chain reaction" PLoS One (2011) 6: e25510.
Miroshnichenko et al., "Mesyl phosphoramidate antisense oligonucleotides as an alternative to phosphorothioates with improved biochemical and biological properties" PNAS (2019) 116: 1229-1234.
Mishra et al., "Improved leishmanicidal effect of phosphorotioate antisense oligonucleotides by LDL-mediated delivery" Biochim. Biophys. Acta (1995) 1264:229-237.
Miura et al., "Fluorometric determination of total mRNA with oligo(dT) immobilized on microtiter plates" Clin. Chem. (1996) 42:1758-1764.
Montgomery et al., "RNA as a target of double-stranded RNA-mediated genetic interference in Caenorhabditis elegans" Proc Natl. Acad. Sci. (1998) 95:15502-7.
Nishikura et al., "A Short Primer on RNAi: RNA-Directed RNA Polymerase Acts as a Key Catalyst" Cell (2001) 107:415-418.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Ostergaard et al., "Differential effects on allele selective silencing of mutant huntingtinby two stereoisomers of α,β-constrained nucleic acid" ACS Chem. Biol. (2014) 9: 1975-1979.
Patutina et al., "Mesyl phosphoramidate backbone modified antisense oligonucleotides targeting niR-21 with enhanced in vivo therapeutic potency" PNAS (2020) 117: 32370-32379.
Prashar et al., "READS: A Method for Display of 3'-End Fragment of Restriction Enzyme-Digested cDNAs for Analysis of Differential Gene Expression" Methods Enzymol. (1999) 303:258-272.
Pubchem, Substance Record for SID 136357381, Modify Date: Oct. 9, 2015 [retrieved on Oct. 19, 2020] from https://pubchem.ncbi.nlm.nih.gov/substance/136357381 : entire document.
Pubchem, Substance Record for SID 57553290, Available Date: Apr. 13, 2009 [retrieved on Oct. 19, 2020] from https://pubchem.ncbi.nlm.nih.gov/substance/57553290 : entire document.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi, Chapter 15, Antisense Research and Applications, Crooke and Lebleu ed., CRC Press (1993).
Scaringe, "RNA Oligonucleotide Synthesis via 5'-Silyl-2'-Orthoester Chemistry" Methods (2001) 23:206-217.
Searle et al. "On the stability of nucleic acid structures in solution: enthalpy—entropy compensations, internal rotations and reversability" Nucleic Acids Research (1993) 21: 2051-2056.
Shea et al., "Synthesis, hybridization properties and antiviral activity of lipid-oligodeoxy nucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Singh et al. "Synthesis of Novel Bicyclo[2.2.1] Ribonucleosides: 2'-Amino- and 2'-Thio-LNA Monomeric Nucleosides" J Org Chem (1998) 63: 6078-6079.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Sutcliffe et al., "TOGA: An automated parsing technology for analyzing expression of nearly all genes" PNAS (2000) 97:1976-1981.
Svinarchuk et al., "Inhibition of HIV proliferation in MT-4 cells by antisense oligonucleotide conjugated to lipophilic groups" Biochimie (1993) 75:49-54.
Tabara et al., "RNAi in C. elegans: Soakinginthe Genome Sequence" Science (1998)282:430-431.
Tijsterman et al., "RNA hellcase MUT-14-dependent gene silencing triggered in C. elegans by short antisense RNAs" Science (2002) 295:694-7.
Timmons et al., "Ingestion of bacterially expressed dsRNAs can produce specific and potent genetic interference in Caenorhabditis Elegans" Gene (2001) 263:103-112.
Timmons et al., "Specific Interference by Ingested dsRNA" Nature (1998) 395:854.
To, "Identification of Differential Gene Expression by High Throughput Analysis" Comb. Chem. High Throughput Screen (2000) 3:235-241.
Tuschl et al., "Targeted mRNA degradation by double-stranded RNA in vitro" Genes Dev. (1999) 13:3191-7.
Wahlestedt et al., "Potent and nontoxic antisense oligonucleotide containing locked nucleic acids" Proc. Natl. Acad. Sci. USA (2000) 97: 5633-5638.

(56) References Cited

OTHER PUBLICATIONS

Wouters et al., "5-Substituted Pyrimidine 1,5-Anhydrohexitols: Conformational Analysis and Interaction with Viral Thymidine Kinase" Bioorg. Med. Chem. Lett. (1999) 9:1563-1566.
Zamecnik et al., "Inhibition of Rous sarcoma virus replication and cell transformation by a specific oligodeoxynucleotide" PNAS (1978) 75:280-284.
Zhang et al., "PowerBLAST: A New Network BLAST Application for Interactive or Automated Sequence Analysis and Annotation" Genome Res. (1997) 7:649-656,.
Zhou et al., "Double sugar and phosphate backbone-constrained nucleotides: synthesis, structure, stability and their incorporation into oligodeoxynucleotides" J. Org. Chem. (2009) 74(1):3248-3265.
Zhou et al., "Fine Tuning of Electrostatics around the Intemucleotidic Phosphate through Incorporation of Modified 2',4'-Carbocyclic-LNAs and -ENAs Leads to Significant Modulation of Antisense Properties" J. Org. Chem. (2009) 74:118-134.
English translation of WO 2018/156056, dated Aug. 30, 2018, Stetsenko et al., 96 pages.

* cited by examiner

2'-β-D-deoxyribosyl
"DNA"
d

2'-α-D-deoxyribosyl
[aDd]

2'-β-D-deoxyxylosyl
[dx]

2'-α-D-deoxyxylosyl
[aDdx]

2'-β-L-deoxyribosyl
[bLd]

2'-α-L-deoxyribosyl
[aLd]

2'-β-L-deoxyxylosyl
[bLdx]

2'-α-L-deoxyxylosyl
[aLdx]

2'-O-methyl-
β-D-xylosyl
[m2bDx]

2'-O-methyl-
β-D-arabinosyl
[m2bDa]

2'-O-methyl-
α-D-arabinosyl
[m2aDa]

2'-O-methyl-
α-L-arabinosyl
[m2aLa]

2′-fluoro-
β-D-arabinosyl
[f2bDa]

2′-fluoro-
β-D-xylosyl
[f2bDx]

2′-fluoro-
α-D-ribosyl
[f2aDr]

2′-fluoro-
α-D-arabinosyl
[f2aDa]

2′-fluoro-
α-D-xylosyl
[f2aDx]

2′-fluoro-
α-L-ribosyl
[f2aLr]

2′-fluoro-
β-L-xylosyl
[f2bLx]

2′-fluoro-
α-L-arabinosyl
[f2aLa]

2′-fluoro-
α-L-xylosyl
[f2aLx]

2′-fluoro-
β-L-ribosyl
[f2bLr]

2′-fluoro-
β-L-arabinosyl
[f2bLa]

SEQUENCE LISTING

<160> NUMBER OF SEQ ID NOS: 93

<210> SEQ ID NO 1
<211> LENGTH: 14836
<212> TYPE: DNA
<213> ORGANISM: Mus musculus

<400> SEQUENCE: 1

```
cctccccgt gtctccccac acccgggttg gggttgtttt ggttgaccag agtggaacac      60

aacgatctat tggcagggct gaacaccaat gggtctattt gtaaagcgcc aatgaccact    120

ttctgaagca gggttttagg gagcggggcc ttagggaact ctttggtcct ttttagaaca    180

ctggactttc ttctggaaag gcaggaaaca ctgaagttta agaagttgtt tccagcttcc    240

attaactgaa cacacattaa aaccaagcac agagaatcag gacgtttcgc gggagtgaga    300

cccagtcatt tctcctccgt ttccattctg cagggtgaga gttgtaatca cccacccact    360

attcgtacca tccacccacc cccagtcgag agaatagggg tacagagggg aggtggcaaa    420

gaaaattcac gatactgagt atctctggga gacctgtttg gtctctttgc tcggtagcgc    480
```

-continued

```
agccctacgt tagaatgcat cttcccggga atgactgtag tgagactttg gctgggaatc    540
caagttattc taactgtaga ttggtccacg ttgccctaag cctagcagtc cactgcggca    600
cagacaccct ggacatgagg tgggtcagct taagttcctg gcacgaaaga aagggtactc    660
tggcaacttt tggatgcggc gaaacagact gtttcgtctc tcaggttctt atttcacggc    720
ttgtgccttt gacagcccct tagtttctct atctgcagga tgggagcatt aagctctacg    780
acccagcctc tttacaattc aggtccaaag agcccgccca agttggggac tgggaagatc    840
aaaggtctca gcacccagcg gagccgcgga cactgagggc gccaagaagg gggtgggtag    900
gtagggaact ggaagggcgg ctgctccgca ggggatgcgc gtcagagacc ccagccacac    960
tccaggcccg ccccttgatg agccccgccc cgccccgcct ggttttcgcc tctaaagcgc   1020
ccagcgctcg cctcccgctg ccgcactttc actctcggtc cacctcggtg tcctcttgct   1080
gtccagctct gcagcctccg gcgcgccctc ccgcccacgc catggacgcc aaggtcgtcg   1140
ccgtgctggc cctggtgctg gccgcgctct gcatcagtga cggtgagtgc aatccgcggc   1200
cgggcccggg aaaggctcgc agctctgcgc cggagctcct tcgggtccgc ggttcctctg   1260
cccgcgccga agtcgcggag aaagaactcg gtcggcgccg ttcactacaa gcgaacttgg   1320
ggcagtccac tttgcagggc gcactcccac cgggtgccct ttcccgtgtc ccacgggtcg   1380
caccgaggtt ttgtgctctg cgaagtgcgg ccataggacc tagagagggc tgcaggggag   1440
gacccgcagg attgttgggc aagagtgggt tcggcgcgga atggaagcgt gggcgattgt   1500
gtccggggct tgggccccgg agcgcgccag ctgcactcag ctagtgtcta ccggcgccca   1560
gatgtttcca gaggcgaagg gcagcgcggt cccggagttg accgtgcaag aggttcactc   1620
gggtggtgcg tgtgtcagca aactctcaaa gaccggtcaa gtagctcgaa gtgcatggct   1680
tggctatagg ttcagtggtg aggctgagtt tcgtcccctg cgggtgtagc gtgttctctt   1740
acagcaccct cgaggggctc agggccacca gcagcgcagc gcagctcttg aactcgcgct   1800
gccagccagg gccgcgcttc tgcacagttc gttggtccgt agcgacgcgg acctgagcac   1860
gcgtctcttc actgcccctt tttcttctta cccgggtcac tagacaaagg ctcagcagtt   1920
acccaagcta tatgcacacc tctccccaac ccccaaacac acctgcaaac gggcgctttt   1980
gtagccagcc ccggagtcct cagctctgga atgagagctg cagcggagtt cagtctccca   2040
gacccagggt ggtgtcttct ttcactggga aagggctttc attttgtttt cttttttga    2100
cactgaagag aaaactctca gcgctgttac aagacaccgt tgctgcaaaa caaaacaaac   2160
cattgcctct gaacacaaaa caaaatccta ctagtcgatc ccctgccttc ctccgcagtg   2220
gtgtttcctg gagagaactg agggacagtc ggggctcttg gtgagactga gctctaaatg   2280
ctgcccaagt acaccaactc gttcgtttgg gttctttccc tgtgacaacg gggtacggga   2340
atggttggag ttgcctagtc cgagggaaat gttctgtaaa agaatagtca gttgctgatc   2400
ggagtagtaa aaaaaaagaa atgaaaggca gtttcgattt tttttttttt tttttttttt   2460
ttttttgtta ccgagaacac ccgggaggct gagccttccc actggtcccc cagtgccccg   2520
tcatggagca cattgatttg ggcattaata attgaatgag ctggtgatgt tgcaagggtc   2580
acagcctctg gcaagttagg tatggggcaa gaatgtagga ctcaggtcct caaggttgga   2640
gtgcaattat ccagagtaaa agttgtctca ccctcaacat attctgaccc taggaagagt   2700
cggattgttg acagtgtctg gatcagacct gttctctagg caggacccca ttgtgctgcc   2760
cgaatgaact tttttacctc ctagtgcctg tgtgccctct gatcttacac agccctcaag   2820
ttgcagcacg gctaaccttg ctgtggttcc tgtcttttcc catcagctac tccaactcag   2880
```

aagctagata gtagacaccg gaggcttctt tggttaaacc cagagcagca ggcttgccag 2940
gcttgttaga ttgaatggac ccctggttcc ctaagccaag ctctctagat tcccaagtcc 3000
agggtggcag cagagctgga ttagactttg gtctgtacct gaagtctggt tttcctatgc 3060
tttagagtct aaagacacta cccttcctgg ggcatgcatc ccttagctaa ataatgcttg 3120
cagaagaaga taatcccatc atatatttaa ttcggtccac ttctccagct gcttcccaaa 3180
ggcagtgaac ttcagaatac ccagaagtct cctggaactc taaataagca aacttaaaat 3240
cctggggcta actattctca gtcatacttt taaactttgg tgaaaagacc cataaattga 3300
aacatttggg gatgctcagt agagctagga taaaaccctg ttgttggggg agcagctaca 3360
aatccagcag tcctcagggt ttgcaattct agacttaaag ggtggttctt aaggggggt 3420
tctaaaggag ccccttgcta atttacacta atgagtgtca attatagcat tttgcaaatt 3480
ggtgaattgg caaacaaagc tggtaatagg atccaggagg cctaggcatc caggtagtga 3540
ccataaaagc cacggttgac cccagctttt gggaaaagct ggatagaagg taaatccggg 3600
tcctcccctc tggattcttt tgtgatttcc agggcttagg atagggtgag tgggaggagg 3660
gaaaactgca ggtggtagaa gtgaagcccc ccacctccag gcctgcacca gagggccaca 3720
agggagccca gaactctgcc accccacttc tcctgggtcc ttttgtcctt tagaggctga 3780
gcccagtcag atctcactgt gatccctggc cgaggggatg gtctttgcaa gaaactttct 3840
gtaaccattc ctgctgatgt tcctgagtct tccccacaag agccaccaaa ccccctgcac 3900
caggcagata atgactggcc ccacttttct ctctacacct cctctaggta aaccagtcag 3960
cctgagctac cgatgcccct gccggttctt cgagagccac atcgccagag ccaacgtcaa 4020
gcatctgaaa atcctcaaca ctccaaactg tgcccttcag attgtgtaag tcctagccgc 4080
catcccccaa agaggagcat ggtatagaag cctcggactt ggcataacta ggggcagctg 4140
ttaccaccac caccacgggg acactgatat gccatcagac atgggtttca aaggatactt 4200
ttgttcccca gagccctgat gtcctcagtg tttctcactc ttgctttcca agctgtttct 4260
tgcagcacag tgggccgcct ctctacagaa aaagccatgg acttgatgga ggtcagccct 4320
cagctgacag ttgggtctgt cttgtcagtt tcaaggttct ggtgtccaaa gttaatcctt 4380
tctcacatag aaaaaaaaat tacaagaccc ggatggcacg gggggggggg gggttcagtt 4440
ttactcactt gcactcactt gctcagaggt catttttgtt ttagagtttt agagtttgct 4500
ggagtgtgat ggtagctgcc agtatttgat ttaaatttac ctgggaaata agaaaagccc 4560
aaaaaaggta taaatgatgt gaatatctca ctcagagtct ggtagacttg gcagagatgt 4620
gtcctgtgct agtctgtcct gctcactgcc ccccagcagg ggttcccatc ctcgggagac 4680
tcaacactaa caacagtata aggatgcagc agctggagca atgctagcct gacggctttg 4740
tcacccaacg gtgactgctt cagactttct gtgctcatca gccttcctct ccagcctccg 4800
ctgctgtgtt atgtacagta ggctttagag acctagatga tgaatattat ttttgctgtt 4860
ttgattaaaa tacaatactc tcccgagaaa gggattttaa agatgatgag tttacgtttg 4920
aataggctgt gctggtgcac tgtcccggga agggcccttg aacttagagg gtcaaataca 4980
actattgatt ctgggtgatc actaagttaa taaatggcag gatccagact gacacccctg 5040
atccctgttg aagttacatc cctctgaacg actggtcaac tgcagggcag cctgcttgaa 5100
gagggttacc tgtccctagg acactgaaca ggcatttgtt tttcctagaa gacagttcac 5160
cagctggaga ggagtcgtct cccgtagttt ctgtttggtt gcttttggtt tttgtttggt 5220

```
tttggttttt taattatctg gcatccagga cttgatggaa aataaccaga gctaagctca   5280
ccggttcatc tgcccattag gaagttctag ggatgggaga aagaacacgg cgtcaattaa   5340
caaatccaca aagctaagac cttgaagcat tctgtgaact tgtaaacgcg ctcaggcaac   5400
cattggacaa tttgtctaga ctgctccttg cccacctgaa ctgccctgtt cctccccttc   5460
tggactcctg ccgtcttcct ccagagctac ctttaaggtt gtcccatgta ctatcaaggt   5520
gctctgtcaa aagttcttag gctgcttctg gcactctcca gaatttttcca agacctcccc   5580
cccaccatga tatcagtcat ccgcgccttc tgggtggttc ttcctccaca ccctttgggc   5640
actttgactc ctgtgggata ttcgtccttc cttttccttt agctttcctc acttgccaag   5700
ctccaacttg gccagaagct caaatgcctc cactgtggtc tcttctctgt gtcccctggg   5760
agacatcctt agcacgtccc taactctgcg gtggtggtcc caacacgatt caagtgctat   5820
gtcttccaaa actgaagctt ccgggagcag cagctgggcc ctgcagtgag gacctttagc   5880
tgggtgtgtt gggtgagccc acaggatcgc tttctcccgc ttggctgtac agcgtctctc   5940
cccttgtgtt ttggcagtgc acggctgaag aacaacaaca gacaagtgtg cattgacccg   6000
aaattaaagt ggatccaaga gtacctggag aaagctttaa acaagtaagc acaacagccc   6060
aaaggacttt ccagtagacc cccgaggaag gctgacatcc gtgggagatg caagggcagt   6120
ggtggggagg agggcctgaa ccctggccag gatggccggc gggacagcac tgactggggt   6180
catgctaagg tttgccagca taaagacact ccgccatagc atatggtacg atattgcagc   6240
ttatattcat ccctgccctc gcccgtgcac aatggagctt ttataactgg ggtttttcta   6300
aggaattgta ttaccctaac cagttagctt catccccatt ctcctcatcc tcatcttcat   6360
tttaaaaagc agtgattact tcaagggctg tattcagttt gctttggagc ttctctttgc   6420
cctggggcct ctgggcacag ttatagacgg tggctttgca gggagcccta gagagaaacc   6480
ttccaccaga gcagagtccg aggaacgctg cagggcttgt cctgcagggg gcgctcctcg   6540
acagatgcct tgtcctgagt caacacaaga tccggcagag ggaggctcct ttatccagtt   6600
cagtgccagg gtcgggaagc ttcctttaga agtgatccct gaagctgtgc tcagagaccc   6660
tttcctagcc gttcctgctc tctgcttgcc tccaaacgca tgcttcatct gacttccgct   6720
tctcacctct gtagcctgac ggaccaatgc tgcaatggaa gggaggagag tgatgtgggg   6780
tgccccctcc ctctcttccc tttgctttcc tctcacttgg gccctttgtg agatttttct   6840
ttggcctcct gtagaatgga gccagaccat cctggataat gtgagaacat gcctagattt   6900
acccacaaaa cacaagtctg agaattaatc ataaacggaa gtttaaatga ggatttggac   6960
tttggtaatt gtccctgagt cctatatatt tcaacagtgg ctctatgggc tctgatcgaa   7020
tatcagtgat gaaaataata ataataataa taataacgaa taagccagaa tcttgccatg   7080
aagccacagt ggggattctg ggttccaatc agaaatggag acaagataaa acttgcatac   7140
attcttatga tcacagacgg ccctggtggt ttttggtaac tatttacaag gcattttttt   7200
acatatattt ttgtgcactt tttatgtttc tttggaagac aaatgtattt cagaatatat   7260
ttgtagtcaa ttcatatatt tgaagtggag ccatagtaat gccagtagat atctctatga   7320
tcttgagcta ctggcaactt gtaaagaaat atatatgaca tataaatgta ttgtagcttt   7380
ccggtgtcag ccacggtgta tttttccact tggaatgaaa ttgtatcaac tgtgacatta   7440
tatgcactag caataaaatg ctaattgttt catgctgtaa acctcctacc gtatgtggga   7500
atttatttac ctgaaataaa atctactagt tgttagatgg agtgcacata catttctgaa   7560
gatggagaaa aacaggtgtg cctgctgatc aggtgctgtg ggctgccctg cagtcctggt   7620
```

```
gagcgacaga cactgaggca ggcttgtctc atgaacaggc tgcctctgca gtgaaagttt   7680
ttgtgtattt tttttaaccc aagctagttt tctaatgaat aatacttgac tcactaattt   7740
cccctcctcc tccttctcct cagttctcct aacatcctca tgtgatcccc agactcaact   7800
ccagtaatat caagctttcc tattttccca tgtaaaaaaa tcccatgact ctgggccatg   7860
ttaatatcag gcttttgtgg gaacaggtgg cctcacccca taaatcatta aataccattc   7920
agcttgaatc attttaatgt gacagtcaca aaccagttgc tctaataaaa actctgctaa   7980
ccatccttct ccttagctct ctagaacaat ctcagttatc cctagggatg ctccccagca   8040
tccagaaaag agaagtggga tcaatcatcc tgcctttctc cccctcctct cttggagggc   8100
tgcctgagcc cgtggcctcc acctcccctg ctttgtataa tttgaaatgc agatttgtag   8160
tgaaggcaga gttcacctct gcattgaaag ggaaggcagg cccagagctt ccttccctgc   8220
cctctgagat gtgcatttat gtctcaggat ggatgagctt tggtaggaat gctcaaaacc   8280
aggaccagcc agacaaactg gcagtccctg taagcggttc ccgggtcata gggttagggc   8340
acccctgttt aactttgggg tggggaaagt atctggtttt ctttgataaa ttgcttgtga   8400
accacatttg ccaagtggcc tccaggcctc aaactcaaag accgagctaa atcgactcgg   8460
aaggcaatgc tgaatgaaga ttgtgggaac tgagatagat acactcctct atgttgcaat   8520
gtgattaatg gttctactaa ttttatctaa gggggcgcag agaagaaaaa gtggggaaaa   8580
aagaaaagat aggaaaaaag aagcgacaga agaagagaaa ggctgcccag aaaaggaaaa   8640
actagttccc cgcttcctgc cgatggaccg cagtgcgctc tgctctggcg ctttgtaact   8700
cgctcctccc tcttcggggg cagaccccac actccgggca ggtgctcaaa cctgacggta   8760
aactcttccc tcttcggggg cagaccccat accccggggc gggtgcttag gctttcctgc   8820
cctggtggcc acaccagctg ctgtatttat gtgcttcata aggccctgct ctgtctgcta   8880
aagctatgaa gaaagatgtg cagagactgg ggtggagact aagccaaaga ggagctgcct   8940
agcctggcag cattgccccg agctgagccc ccttggccag gacttcacaa ggctcacacc   9000
tacaatccca tgaaggccag ggtggtctgc ttagccagga aagggcaagt gccttcccct   9060
cggccacact gccccttgtg gccttctcgg gacatgtggt aactgacttg ctctcaggcc   9120
cacccgcagc ttttccaaat acctgcagcc ttcagccctg ctgccctgcc tgtgggagca   9180
gctttgactc cagtccagaa gggtttctgc agactgtgtt gggtgagacg cagaaaggat   9240
gaaatctcag aacacatgtc agctgcttct caggaaatct tttctttgga caattcactt   9300
tagagtcttt aaacgggtct ctcgtgggga ggatagatgt gctctggaac tttctgaagg   9360
accagcagct tcagggactc ttagtctgtc cttccccact tttggtccca acatccctgg   9420
gatggtgtgc tgtctgggca ccacggtctc catcctcact cctgagagat ttctgccttc   9480
tgtgagttgg gttaaagctc tggaattatc tactatccca atccactacc ctcacctggc   9540
aatatttgtc tgtttttgtt tgtttgtttg tttgtttttg tcttttgcca gtttgaatta   9600
gaaggcaagg ctctgatttt agtagtgttt tggaaaagga cttttttctt caccttcctc   9660
tttgcctcat gtgtacacac acacacacat cttgtacccc agacctctgg gtataatttt   9720
cataattggt gcagaaagaa gaaatgatct gaagatgtgt taaatggatt gcaggggaag   9780
gaaggcccag ggccctgtgt gtcatgccct cttgggttcc taagttctat gttccttaga   9840
ggttctagca ttaaacagat aaagcccttc atggtcctgg ctgaggaaga gtcttgctag   9900
ggggattcag ggaagacccg tgttaccagc tcttaccctt tatctggaca gctctcctac   9960
```

-continued

```
cctgtatctt ctcctcagat ctgaggatag caggctggac tattggtggg cacctttcaa  10020
gcccagggct actgtttgtc ctgtggcagc cggctacagt ctcgtctgag tggcctcatc  10080
tggacccttc ctgttattaa taaaacgctt ctggaggcca gatctgtgct caagccatag  10140
ttctgcttag aaagggatgc cccaccctta ccggacactg ggaagaactg ttggccccta  10200
gaaaccaaag gccaaactga ggctgccctg agttggaaga ccactttctg aaatgcccat  10260
ggactctgcc tcccaaccat tcgtctctca ctcctagcag agctgtctgt gcagactgtt  10320
tcttaggagg cacagcaagc tccagggaac cctctgtgct tatgaagctc gtctggtggg  10380
caaccccagc ccactggaca gagtcctcat ggaaatgcct gggaagctga tttcatctaa  10440
ggatgggttg aagtaggatg tgctcctgcg acttctcagg caggtgagag gggtagtcct  10500
tacactgtct agcataaacg ccttccggaa ggacctgcag ctccagagac cacctcctga  10560
gcaccaagac ctcttctggt ggtgtggaac cagccaagag atttcaagga agagtgatta  10620
tttgatgaat gctatgggaa tggcctcttc tcttggagtt ctgaggcctg gggatgccca  10680
ggaacactgg gcacctgctg ctgttagggc caatgcatag tctcagcacc ggtgtcctaa  10740
ggttaaggcg gtgcgccttg tcatgtgctc cttgtaccat gccatctgtg ccagtgtgtg  10800
tctgcctcac cctgtgcttg acatgttcac ccatcttctc tgcttcccgc caccatccag  10860
atcctcagcg gccgccccgg ctgtgccctt ccctgctctc ccgctctctc aggcctcgga  10920
aggaagatcg gtggctgcga gctgaactaa ggagtagggc ctgtggctca gcgctaggcc  10980
acgcacgcag catcccaggc atgtggtgag aaactgcctt aatgtgtctc ctctgttctt  11040
gtcaacagga ggctcaagat gtgagaggtg tgagtcagac gcccgaggaa cttacaggag  11100
gagcctaggt ctgaagtcag tgttagggaa gggcccatag ccacttcctc tgctcctgag  11160
cagggctgaa gccgtttgca agggacttgc tttgcacagt tttgctgtac tttcacattt  11220
tattatgtag caagatacat ggtgattttt tttttttca tttagcctga ttttccaacg  11280
tcattggtga caggccaagg ccactatgtt atttcctttg ttctggtatc cttcccttgg  11340
aggaccttct ctgagtagtg gctccccagg tttgtccttt gagctgaggc aggaggctca  11400
cccattcttc tgaataggaa ctgggtgttc ccaccccca aggactgcag ggctttccca  11460
agctgaggca ggaacgtgag gccagggaag agtgagcttc accctcatcc cacgctgtcc  11520
tcctcaaccc accatgctca tcattctgtc tcatccatcc atccatccat ccattcatcg  11580
ccatgtgtcc gcaagactgt ctccatgacc ctgaaaaagg actctcgaga tgaaatcctt  11640
tattcaaatg ggacagcaag aaggaaaagc caatgtctgg tgtctctccc cccgccccta  11700
ccctgcgcgc atctatgtct tgtttggaat attgtctctt caaccccctg ttcatgtcct  11760
tctcactcat gatcgatgtc ttgtctgtgc actgtctcta acccaaatgc aaaggctgag  11820
tgtgaggtga tggccccgag gtccaggttg tagtcatgga aagagccctg ctgtctccct  11880
tctcaggggg cccattttag acacacaaag cccaaagaaa ggtggtttgc aacagtgctt  11940
agctcgagcc tccatatttc cataactgtt agcttaaaac tgtggggttt taccttcctg  12000
gaaccaaatg cattcttctg ttgaggagta acaggtctca attcttttca attaatttta  12060
aaagtcaatc actaagagca tcggctttgg gccctgatgg gcaggcattt ccctggaaag  12120
ggggtgaact acctacctct cctcaagaca gccgaagggt gggattggtg ccgctctggg  12180
aagcgtggcc ccaggagttt tgtcctctgc agtttttaat gcaagttcac tgccactttg  12240
acaaaagccc aattagaagc cagtctctag ttccttaaac aaaacagaca gagtaaggaa  12300
aggaaggagg gtggcagcca gctggctgga cactcgagaa agacggggaa gtaagctaca  12360
```

gaaagatagt cttcaaaaac aggtgtttga gagtgaatac tctgtagaat tgttagtggg 12420
gtgtgtgtgg tggtggtggg gggatttcta caaaatagtc ctttaagttg agtttacagc 12480
agatgaaaaa tccaaccagc aaaattttga tcaaatttga acaaaaaccc aaaaacctaa 12540
aactgttgag caggttgcga tgaggagcac agggctagct gcagagctgg atcctcagga 12600
ggatagcgaa ttattttcaa ccctggaata gaaaccacac actggcttgc tgtgcaccag 12660
ccactttgca tctaatccaa gctttgaagg gtgttgcttg ggaggaaaca aatacagcct 12720
tccatcttca ctccagttag ggatcctttc aaagtctcct tcacagtgag gaaaaagaga 12780
agggtagaaa ctttagggag ccggatttgt gtatcaattc ctccgctgac agtcagtttc 12840
tagatggaga cagcctgctt aaagcaaatc cgaatttaaa taggacattt acatcggaaa 12900
agtctctccc taccttaatc ccccattctc ttgctttcaa aatacaagca cagcagtcct 12960
tgaatggctg ttgacccagg gcacctagct gtccctgctg gtcctggggc tgccagaatt 13020
cccttgggcg ccaagcaacc tgccaggtag ccagtccctc tgttacaagc ctttgcatct 13080
ggatagggaa aggggtggag acatacagtc tgctttgtgt tgaaacccag atttgtaccc 13140
tgtgtttata cactgctgct ggctcccgag gacagtggga ctttagcaag gaagtgcagc 13200
cgaggggtaa agagccctct ggttcattgc ctgatcggct ttgagagagg gtttggaggg 13260
caaggggctg cattcctctg agggacttgg cctgaggcct ttcgggcctc tccagtgggt 13320
tctgtttatc ctctcatggg tgattatctc agtggtgtca ccaggggctt cctcccagaa 13380
gtcagtcatc cccaggccgt gcaccctttt cagctggatg agagccaggg atgcattctc 13440
tccaaacagc taccctggcc cattttaagg taatctcatt cttcaaaatg ttccatagaa 13500
tcctccaaat tcccccagca gacttctacc ctcgccaagt tcccaaaacc cactcagcaa 13560
agttgccaac ctcgacgggc tagcagtgtc taagcagcga tgggttcagt gttgtgtgtg 13620
gtgaatactg tattttgttt cagttctgtc tcccagataa tgtgaaaacg gtccaggaga 13680
aggcagcttc ctatatgcag cgtgtgcttt cttattctta tttttaatat atgacagtta 13740
tttgagaagc catttctact ttgaagtcat tatcgatgaa agtgatgtat cttcacctac 13800
cattttccta ataaagttct gtattcaaat atagctgcca agcatcctca gtgaatgtta 13860
ccatgtggaa ttttccacac ttggttttac cccctcaaac ctgactctga ccgtgcagtc 13920
ttagcagaag agcttagcag gtcctagtgt tcactcttgg tctaactgct ggtgtcagaa 13980
gatctctaca gggagaggtg ttccattttc tccacatgac ctggattgct ccttagaggt 14040
cagacagcct tgcactgtac aaggcaatgg cttagggtaa agtcccagga gttttcccta 14100
cagtcccaag aatttggaag aggaaggccc acactacaca tgcaggtcat ggtggaaggt 14160
gacagaggaa ggactctgtc cctgtaagac agctggaaac cacaatattc tgcatgttcc 14220
tatcctgggt gaggacgcta atggaagtca aaggggaatt tgctaactgc tgttggccag 14280
cttcctccaa gaatcctgct tccccaacag acagagcctt tgtctcttat agtttggtct 14340
tcagattctc tttatcccac attcagccat ttttgtaaaa gagaggctag caccagctcc 14400
aaatatccaa atctgcagtg tttgagatct cactgcgcct cctccatacc aacacatttg 14460
ccattactta tagggtagtt ttcatgtgag ttctaagttg attaacacac aagaattaga 14520
agggtgggag gctctaggaa aggcactgtg ggactatttg actgcatggg tgtgaaaatg 14580
taaggaacag gcaagagctt ggatcccatt ctctctgccc acattgtgac ttgagatata 14640
ctaattgctc ttgggggtct cagtcatata ccatccataa cagagttaaa ctgagagaga 14700

-continued

```
tacaggatca gctagaatga aaagcccacc ccatgcttcc agaaagtccc ctctttatac  14760

ctcctgtgat atgaactaga ggaaaagcaa ttgactttgc ttctcaaaca gcctacggca  14820

aagccctgtg agtttg                                                  14836


<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2

ccagagccaa cgtcaagcat                                                 20


<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3

cagccgtgca acaatctgaa                                                 20


<210> SEQ ID NO 4
<211> LENGTH: 29
<212> TYPE: DNA
<213> ORGANISM: Artificial sequence
<220> FEATURE:
<223> OTHER INFORMATION: Probe

<400> SEQUENCE: 4

tgaaaatcct caacactcca aactgtgcc                                       29


<210> SEQ ID NO 5
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 5

gcatgttctc acatta                                                     16


<210> SEQ ID NO 6
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 6

gauaauguga gaacaugccu                                                 20


<210> SEQ ID NO 7
<211> LENGTH: 9001
<212> TYPE: DNA
<213> ORGANISM: Mus musculus

<400> SEQUENCE: 7

ggcagatttc taagtttgag gccagcctgg tctacagagt gagttccagg acagtcaggg     60

ctacacagag aaaccctgtc tcgaaaaaaa aaaaaaaatc cctttctctg gctataagga    120

tggctcagtg gttaagagca ctgactgctc tgccagaggt cctgagttca agtcccagca    180
```

```
accatctgta atgggaaata atgcactctt ctagtgtgtg tctgaagaca gctgtagtgt    240
actcatataa ataaaaaata aatcctaaaa aaaaaaagaa ttcccttcct cttattgata    300
ccctttcttg tctctaggga ccccccatat atctttctag acatttctga gaactcatgt    360
aaatacatgc tgagcccccct ctttgtagtt tgtaaccttt gctcattcca taccatttta    420
acaaatattt tccttgaaac actatttctc acccattgca tggaggtatc acataggact    480
ttatcaggca tcctgttctc cagtgtgtgg cttagagcca gtggaatgca cggcgtgtcc    540
gagaaccact tcacacaggg aagagaatac agatttttac tcagcaagta acaccagctg    600
ggaatggtgg ggcagacaag caatcctagt tactagggat gctgaggcag gaggatctta    660
aattcaagtt tagtccctat ctcaaaaatt aaaaaagaac ccctctaacc ccagcaactg    720
agaggcagag gccagggaga tctctgtgag ttcaaggtca gcctgtctgt tctacacaat    780
gagttccatg agagccaaag gtacacagtg tgatattttt aaaaaggtat gtgtgtcttt    840
ttttttttca aatttttatt attttcttca tttacatttc aaatgctatc tggggagtcc    900
cctataccac gcccccctgc tcccctcccc acccactccc acttcttggc cctggcattc    960
cactgtactg aggcatataa atttgcaaga ccaagggcct ctcctcccag tgattgtcga   1020
gttggccatc ttctgctaca tatgcagcta gaaacacgag ctccggaggt actgggtagt   1080
tcatattgtt gttccaccta tagggttgta gaccccttca gctccttggg tactttctct   1140
agctcctcca ttaggggccc tgtgttccat ccaatagatg actgtgaaca tccacttctg   1200
tatttgccag gcactggcaa agccttacac gagacagcta tatcagggtc ctttcagcaa   1260
aatcttgctg gcatacgcaa tagtgtctgc atttggtggc tgattatggc acggatctcc   1320
aggtggggca gtctctggat ggtccatcct tttgtctcag ctccaaactg tgtctctgta   1380
actccgtcca tgggtatttt gttcgttatt ttaaggagga atgaagtatc cacacgttgg   1440
tcttccttcc tcttgatttt cttgtgtttt gcgtgtgtgt gtgtgtgtgt gtgtgtgtgt   1500
gtgtgtctta actggcagag cacttgtctg tcatgcaggg ggcggggtgg ggggtgggga   1560
ctgtctaatc tccagctcta gtaacaaaaa taaaagaagt aaaaaataag taagaaacgg   1620
gggtgtgtct agagatagaa catgggcttt acacatttta gacatcatga gaaaataaag   1680
ctggaaatga cactgggcat ccatcttggc gcatctcaac tttcacactg caaccgaggc   1740
gcgctgtgca aagtcagtga caatccgcat ttccagacac agtgggttca gaccttccag   1800
gcgcgcacgc gggcctcgtg ttctcggttt ccgcggcgac tcggccgacg tcacagttag   1860
aagacaatag cgactttccc cgctcaggct cctcgggaac tttctcagtc cgcacgctcc   1920
aggagccgga gctaccctcc gccccgcccc cagcgtgccc cgcggccagg gagctccacg   1980
aagggcgggc ggaggccgcg ggtagcgatt ggttccgtgc caaggtgggc gtggtcagac   2040
tcaggcctat aaaagctccg tggcgccagg gcctcgtttt tttgcgcggt cctttcctgc   2100
ggcgccttcc gtccgtcggc ttctcgtctt gctctctctg gtccctccgg aggaggccgc   2160
cgcgcgtctc ccggggaagc atggcgatga aagcggtgtg cgtgctgaag ggcgacggtc   2220
cggtgcaggg aaccatccac ttcgagcaga aggcaaggcc cggggcgcgg ggcgcaggcc   2280
gcggtgacgc ggcgcacctg tgcgggagca cgccacgccc ccgccacggc ctgagcccgc   2340
taagtgctga gtcaccgtgg cctggggcag gggctgggcg ccgggaagcg aggcccgggg   2400
cgccgcgggg ccttccgggc gggcgggggc ctccccgcgc cccggagcgg ctgggcctgc   2460
ccgggagagc cggcttggca tccgttatcc ttctggggct gctgcttttc cggtgtccgt   2520
```

-continued

```
gtcccacagg ctcagagccc cgtggccacc ggctgcgatt gttgtaagaa tatttgaacc   2580
cggtggtgcc agaccggact aaggccgcag gacgcgtttg cggcacttta aagcaaagtc   2640
ctgggctgtt ctgtactagg tcagggtcgt gtcgcaaggc ggaaagaaag agatggcctt   2700
ggacagccgt cccttgcttt gcactccaga gagagacccg gctgtgggtt ttttctacca   2760
cagcgagttt ctgagcacat tttggaaaag tacatagaga tattttcgaa aatactgtga   2820
ccctgcaaaa acacatgcgt cacagggaag atgtgtgtgg taaggttgtg tccagagcct   2880
tagggaggtt accgttgttg tattcacctt aatcccgaga gaatatttga taaatgagcg   2940
ttatgtgctc tctgaagtgg tggacatacg tgtgagaagg cagacaccat agtgaatccc   3000
aagtgtttgg tttacgacga gaactgataa cggcaattta gagtttttcg taactagcct   3060
cgtttccagc agtttcttgg cattgaaatg cgttttgttg ttttcctgtg gaagtttttt   3120
gtttttgtct ttttctcctc cccacgtaat tcactgtgag aaagacgaag ttcggctggg   3180
tcttacccct gtgtgtgggt ttctgtcatc ttccaccatg ccatgccaga gcagctcgca   3240
ctatttttgt gacgctgcaa actacacatc gctggtgccc tttgtaccca atgaaacgat   3300
agttaagcat tccagattgg cagttgtaat caaagctggt tgatttaacc tgttgccaac   3360
ttttcagaat cagatttttc tacccaaagt tcatattccc ttattctgtt gcaaaagttg   3420
gacatttaaa aaaaaaaaaa cctaaaaaat gattgtcctt gcttgttggt cggttgctct   3480
tacattttct ccctattgct acactttctg gagcagtact aatttgaatt ttgggtgttc   3540
ttttcttttt tgttaagtgg caaattttct agatttggat agctaatgag attttttttt   3600
taaggtagct ctggttagac ccaaatggat ctccacaggc agtaggacaa aggcattttc   3660
tgaccactaa ataaaaatag gggaactgat aaaatcactg aatgtggaga acagggttct   3720
cggcagccag tgttctgtaa gagtcaagtc tgacagtgca gtagccatct cttccccagg   3780
cctggcattc agtagcccct gtttgttcca cctggtgctt tctaaatgct gttcagtcca   3840
ggtgcctgca cacatggcat ctggcagcaa gtgttaggag aagtgtgaca gggagagaga   3900
ggcctagagc tgagcgtctc cagagccacc ctgtaggaag tgggtctact tggatctgaa   3960
cataggtttg attttcactg ttgtgtgttt tgacttgagc tttttactgt gcttggttag   4020
ggtgtaaccc agcaacagcc ctggtgcagg agtatttaca ctcaaacttg atgtcttcat   4080
ttttgtattt ttttaaatca aggcaagcgg tgaaccagtt gtgttgtcag gacaaattac   4140
aggattaact gaaggccagc atgggttcca cgtccatcag tatggggaca atacacaagg   4200
taggtcctag gctggctagt gaccagtgat ggaaaggaac tgagtcagga cccaattact   4260
aaccatttaa aactatctcg tttgttttct ttttctttta gataaagtta aaatgaccac   4320
ttaggtcaac cttggaaagt agccacaaaa gtattttatt tagtatcaag tattgcttgc   4380
ttccttaagt gtgggaaggt aaagaaggtg atttttcttc attgtaatta taattaagca   4440
gcaccttgct tattctgggt gtttattggg tgcttatttg ggtgtttgga gctgggcgtt   4500
gaggatggat gcattaggca gagtgtctaa ggacaaccat gccttagcat gagaggcata   4560
gcgggacaga agtgacaaaa actgaagatt caatataaat gcttaagtaa gatttatttt   4620
ctctatttgg gattagaatc aagtcagtaa aaagtagtgg cttaaattgc agttagtgaa   4680
cttttaccat attggagtaa tgatctgaat ttgcttaccg tcatttaaga gcctcatcca   4740
tgttgcgaga gccttttcct ttcctctcct tctcccctgc cttcttccct tctccacata   4800
gcccacggtg gcctggaatt tagtcttgtg tgtgctgtgt taaaggcatg taccatcaac   4860
ctgtgtgcta tgtgccataa tttgttctac agttacttag gattgggttt gacccatttg   4920
```

```
ataattacta aagttacccc gagttgcctc tggcctggta gctttgattt gttaagctcc   4980
ttccagaatc ctgcccagtt cctattttct tggtctgagt aaacactgga agtcctgcat   5040
ataaaaggac ttgctgcatt gttgagctgt gccttgtgac tggcatccct tagcccacat   5100
gagtagtgtg gtacacctcc tggagttgag gacaccagcc ctggcccttg ggaacaagcc   5160
atctaacagt ctgcctgccc caagtaaaag ctagacaggt gagctgtttg gtggcacatg   5220
gtctagaaag ataagtattt ttatcatgaa gtatgctccc ttcttaaaag ccaaggtctt   5280
taaatgtggg actttaactt tagaagtgcc attaaagatc acatctgttc cagttacaag   5340
gaaggaacaa gagccaggca tgctgtcctg acactgccat ggccctaagg ctaaggtggg   5400
agggtcatag gtcgcagata tcctgagctg tagtagtgag acactgtctc aaaactcaaa   5460
agcaaacaaa aagaaaaatg tgacagtcta ggaaaaaaag gtagcctgag aatgtaaggc   5520
tatacagtgc agctacttac accagggcgc tgctgcctgt ttttatcgcc ccagcacata   5580
ccaggtcagt gtttgctatg ttggaggttg taagaatgcc tgtgttgtta catatagggg   5640
tttacttcat aatctgactg ctggtttctg gtaaataggc tgtaccagtg caggacctca   5700
ttttaatcct cactctaaga aacatggtgg cccggcggat gaagagaggt gagcagcacg   5760
ctctgtatgc atggtggagg agaggggtct gtggaggacc ccagtaagac agaactgcat   5820
ggcctcctgc ctctgctttt gtgtttgttt ccattcaccc aactcactcc cacaacccca   5880
cgtgctagaa tagcttctgt tgggtgaagg agctgacaaa tgtggactct taaagtgatt   5940
tggttttgta gcatttattg aagatgaact aatacaagtg ccaaaaggaa ccaatacaga   6000
aaatatcatg gataacagta ctgtcagtca ctggcaaagt aaatcattgt ataataggac   6060
gctaatgcag ataatgaaaa ctagttgaga ttccatttgt atgtgaaacc ttaggaaagt   6120
cctaaataaa gaagggctag cctgttttta gaatgggggc ctgggagcaa acctttgcta   6180
actcaggagc tggcatactt tactaaagcc ccagattatg actcttctca gagcactacc   6240
tttaaacttg aagaactgtc tgtcaaggta tcctgtagct acctgttttg aactttgtgt   6300
ttccagacct ttgccggtct ggaaaagcca tcatagttga taatgtatgt gtactttttc   6360
atccactcat acgtatttga cttagtcaga ttttaactta gttattgaac tctagtgatg   6420
tgaaatagac atcattgttc atccacctga tgctgtttta atgttaggca tgttggagac   6480
ctgggcaatg tgactgctgg aaaggacggt gtggccaatg tgtccattga agatcgtgtg   6540
atctcactct caggagagca ttccatcatt ggccgtacaa tggtggtaag tttttcatat   6600
aaggatatat acataggatt tcttctaaca tagttatgta ccttcccatg actttatggt   6660
ggttaaacta gtttctaaag agtcacataa attgttaaga gttcagggta ggaaaaaagt   6720
tcttttattg gctgtgatag taaagaatta atttgcctag gtcagttaag aacactgttg   6780
tgctgaaatg cagtagaaag cagttacatt tgatgagact ggatctgagt tgaggataca   6840
atagtcttta gtctaaaaca gccggatttt cttgccatga ttgccccccc ccttgcaaca   6900
tttcgttgag tctaaaatct gcgatggatg gcagtattca agtctgtagg ttatcgcttg   6960
gttaccatat gggagccgtc ttcccaagtt accctcggga gatgcatctg ggtcatgcag   7020
aacaccaagt agtaaaggct cttgcccacc tcgggcagct aacttttcag taggcacttc   7080
cttccttgca gttgaccctt tatccttaga atgctcttca gccctattgg tgaagcagaa   7140
cagtcattca taagtgttgt aaaataaagc tttagagtct tgttgctaag tagagatact   7200
tagaattgcc tcttatgtgt aggcctatag ttctttcaac atgagatttt gatagagaaa   7260
```

-continued

```
tttgtaagaa tgactactgt gtagttgggg aggagctaag atcagcatgt acctggtagt   7320

tacttgggtc ttagtatttc atctagaaat agccactagc aaggaaaaac ttagtggtct   7380

gctcttaact gctagtattt aagtctgtag tattgctggg aagaagtact agttacttga   7440

tcattcaaac ctaaatgttc ttcttttcaa aggtccatga gaaacaagat gacttgggca   7500

aaggtggaaa tgaagaaagt acaaagactg gaaatgctgg gagccgcttg gcctgtggag   7560

tgattgggat tgcgcagtaa acattccctg tgtggtctga gtctcagact catctgctac   7620

cctcaaacca ttaaactgta atctgaagag ttgtaactgt gtgactcctt tgactgggct   7680

aaggacagca atgacagctg atggagactg tgtacaactc actgaattca aatctgtttc   7740

tgtgcctttc catattttgc cagactacac aggtgataag ctgaaattct catttgagcc   7800

tgttagtaaa tatgtgtggc acttattttg agcctattaa tgtgtacaaa aaaaaatttt   7860

aagttagctc tatacattga gcatcaataa cagactcaat gatgctaact catagtattt   7920

cattttgaaa gtgttttatg tgataccatc aaaatggtgg gtggtagccc aaacaaaatt   7980

tgagcagaaa atttctgcc ccttatcaga gaaattattg aaagctctca agattcagag   8040

tacttaacct tatattttaa aattgtatta ggattagatg tcatgattta agaaaaagcc   8100

ctttagtaaa cttgtatcaa actcatagaa ggcaaacatg gagcctcagc tagctctact   8160

agccaagtga agttggtacc acccatcttt aaggttggca ctcagggaaa acacaatagc   8220

tcggggaatg acaccaagtt tgactggagg ttctggctaa atcgactttt atagccccag   8280

gtaatgaaat tgagtgcctt aatacccaag aaagagtgcc tttgaaagga aatattaaca   8340

ggcttgtgac tatctgaaat agttcaattg aagtattttc aacaaattgg gtgtaaacca   8400

tagttctcac tgatatactg aagtcactga agaagagaca actaaattgg aaaagcacat   8460

aatttggtgt ttccaacctt aaaattttta agtttagatt tccaatctaa gattgctcat   8520

aatgcttttt caagtagtta tgttgaagtt ccaggtaaat cctatgtaac tgatttcctt   8580

aatgtagttt tgatgtgggg gatgactcaa tgcggattaa cttggtaatc acaaaccatt   8640

tagtggctca cgtctcagta tttttagttg gaaagacaag ctgcaagtct gtccttggaa   8700

tctgacattg gatcatcgtc ggatgcatgt tttatgatac tctaataagg acttaaaagc   8760

ctaagtaggg tcaccagaaa gctgaagcct ggcaaagcta cagacacatt tcttccatca   8820

ttaggaagag ctcagatcta aatgtcaaat gggaacatac aaaaaggaac ttctaggtac   8880

gataaagcta agtttgacaa gtttttgtt taacctagca ccttgtagtt ttaaaaatca   8940

tttttagggt gtgtgcacta agaggaaaac aagttcatat tcttccacct tttattgtcc   9000

c                                                                   9001
```

<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8

```
ttttttgcgc ggtcctttc                                                  19
```

<210> SEQ ID NO 9
<211> LENGTH: 22
<212> TYPE: DNA
<213> ORGANISM: Artificial sequence
<220> FEATURE:
<223> OTHER INFORMATION: Primer

<400> SEQUENCE: 9
gagggaccag agagagcaag ac 22

<210> SEQ ID NO 10
<211> LENGTH: 19
<212> TYPE: DNA
<213> ORGANISM: Artificial sequence
<220> FEATURE:
<223> OTHER INFORMATION: Probe

<400> SEQUENCE: 10
cgccttccgt ccgtcggct 19

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
tgaggtcctg cactgg 16

<210> SEQ ID NO 12
<211> LENGTH: 33000
<212> TYPE: DNA
<213> ORGANISM: Mus musculus

<400> SEQUENCE: 12
caattggata ctgtcttagt tagggtttta ctgctgtgag caggcaccat gaccaaggca 60
actcttatga gaacaacatt taattgggac tggcttacag gttcagaggt tcagtccatt 120
atcatcaagg caggatcatg gcagcgtcca ggcaggtgtg atctaggaag agctgagagt 180
tctacatgtt catctgaagg ctgctaggcg aagactgact tccaggcagc taggatgagg 240
gtattaaacc catgcccaca gtgacacacc tactccagcc tcttccctga catttgaagt 300
taggttctac tgatgcaagg aataatagcg gctataatca ctcttatcaa aatggatatt 360
acatctcaaa tagcatctgc tcatatggtt taaatattat tccatgtgga ttatcttttt 420
tttttattgc tgagaactgt ggttttatta attggttttt tttttgtttg cgttttttgt 480
ttttgttttt gtttttttta atgtcaaatg gtaaattttc attttatttt atacttttta 540
aaaattaggt attttcttca tttacatttc aaatgctatc ccaaaagtcc cccataccct 600
ctccccccca gtcccctacc cacccactcc cacttcttgg ccctggcatt cccctgtact 660
gaggcatata aaatttgcaa gaccaagggg tctctcttcc caatgatggc caactaggcc 720
atcttctgct acatatgcag ctagagacac gagctccggg ggtactggtt agttcatatt 780
gttgtttcac ctatagggtt gcagacccct ttagttcttt gggtattttc tctagctccc 840
catgtggatt atcttaagag ggtttcaata gtcacataag aaagtctctc attttagggg 900
tgaagaccac tttaaaaaaa ttcaaatggc ttgctgaaag ccacagacac tagagaaata 960
attatgttta gggtaaagtc ggcttgtcct cttgtgaaac tgtgtccaac ggagacaagc 1020
tgaggaatta tgggcaatga taacatgtta aatgttgagc taaatgtatt aaaaagcgca 1080
aaaaaacagg tgtggtgggg gaacagaggc tagaagtctc cctgaaaaaa atcaagtctt 1140
atttcctact tcccccgtgt ttggtctggg gaagaacaat agtgtttgct taagcatctc 1200
attctgtttt caaaaccttg catggttgac ttgggaactg atagagaaaa tgaagcaaac 1260

```
aatactctgt aatcaacatt aacatcaaag ctagctctct ccactgtggt ccctgaccca   1320
accacgttaa tctcccaggg tcttgttaaa actgtaggct tgggagagaa gtggttgtgg   1380
tgaggggtac cttggagtaa ttctaagtct cttggggtta agcctggaag attggtgctt   1440
tatgtattaa gagtcctggg gatccgaaag tagaaaaata atgatttttg ttagtgactc   1500
agtatggttc ttacttcaac acctcctctt aagggaggaa gtagtgtgtg catgtagctg   1560
gaattttaaa taataacagt tcaggtgtgt gagtatttca ttagacagtc agcttccatc   1620
ctttatgcat cctttaagca ggttggttta gacaggtgca caataaacgc caggctatta   1680
aacacaggga ctccaatatt taaaccaatt cttttgaatt gtctggctag aagcacatcc   1740
agtctgataa agtagacaaa gcacgtggag tcttgaaaag ttcgacaccc cttcggtcct   1800
cagatgacta ttatttagca attgagagca ctatactcct tcttttgccc acacctataa   1860
ggagatggac atggcacgta catcccagca cttttgacag ctttaaatgg tgtttattac   1920
gagcaggtat ggatgctggg aacagtgctt ataccgagtc ctggaaatgc ttattaaacc   1980
caggagatac aaggagtctg ccattaacct ctctgtaact caagagtagt tatcaggagc   2040
caatgaggga gaacaagaga attgaaacac gtgggaatat cggaccacca ggtagcgggt   2100
gtgtgtgtgg ggggaggcag ccctagggag ctctcaagcc gaggcccctc ggggtccccg   2160
cggcacgtgg cgggctcggg ccggagcgtc gcggcggtgg gggaggggag cggcatgagc   2220
cctggaggag gggtctagac tgcccgggat tcgtttgagc aggcgcggag tgcgcaggct   2280
cggcccaggc gcaaccagtg cgcgtaagac cgaggggtga acctcactgc tgcgcgtccg   2340
ggtctctgag caaggggcta aagtccgctt gtgcgcacct ccggactgtg tgtgactacc   2400
cgtagaaaca ctactgtcgc cctggccggt ggcgtccact ccgtcccggt cgctccctcc   2460
cgaccgtagt tgtggtgccc ccctccgcgc agccgcagtg gtcgctcccg cctcgcagcc   2520
ccgccgcccg gaggcctacc cctgccgagt gtcgcgcgtc ggcgccgctg cctatcccgc   2580
tctgtgccct acggccctcc cggcacccgc cgccgtcccg ctccgggctg cccttgctcc   2640
gagggctgca gcaccggccg tccccgtcag ccctcttgtc tggccgccgg gccgcggcgg   2700
gcgggagcag ccggaggagg agccgcagcc gggaggcggc ggcctgagcc catggcgtac   2760
agtcaaggag gcggcaagaa gaaagtgtgc tactactatg atggtgagtg gccgaggagc   2820
ctgcagccgg gatgcgggga gggcgcggcg gggtgtcggg ggtggcagcc cgcggggaca   2880
ccaacacggc ctacccagcg gtggcgtctc ggggacgccc gccttcgctc ctctcgggtc   2940
ctctcgggca cacgcaggtt tagggtgcac tgcctctgac cggtctcccg aggaacccca   3000
gttggcaccc tgggcctgac tgcacaaagc tggcgtcctg gagctccgcc ccacgtccct   3060
gtcccctccc ccgctctccc ggtcccccct tctcgccccc gatctgtccg cgctgcgctt   3120
ccagcctcac ccgggacccc ggcacccggg tggggctgcg gaggagttac tgctggccgg   3180
tggccaagtt cgcagagcgg cgctgtctcg ctggtgtttt gcgtggacta catccctcgc   3240
ctttgttcgc gttcttcgag ctccactttc tcagggttca aatggaaggg ctgcacttcc   3300
tcggtgacaa ttaaggggtt ttgagttgga agtaggtagg tcgttgggaa gtggtaggag   3360
agaggaagcg tgcagttgtt cttgtttgat gggtcctggc atgtctctat gggaggttat   3420
tacctccccc ttctttgttg ctctttgttc gatctgctat aataccctgc tctggggggt   3480
taggaaagaa caccggcatc ttgcttagga actcttctac tgtggtgaag accttgctgc   3540
aggaaacttt gagaagtgga ctaaatattc acaatgcagt gaacggtaca aggtgactgt   3600
aaggattttc taatttggag tataagtagt aatagtctct gggttcagtt acaccaaatg   3660
```

gaatggtgcc ctgcctatac agatttcacc caagacatca atagataaac cattgagaga 3720
agtaataagg aaatttgaca gaactttcga agctcattga ttgaacgctt gatctccaca 3780
aagcaatatg aaattgggag cgttttctgt agttgtattg aagtcacagt gtttggagag 3840
gtagattaga gaactaggct gaatgaaaca cttaaacttg ttaaaatagt cgtgcatttt 3900
cttggtttga cagaatcttt taatacaagc tttaaataaa atagccacct gtcattggct 3960
ggaaaaccaa aaaccttaca gaaagctagg ccaaaatgga aaaggctgtt ttgttttttg 4020
agacaggctc taagttgacc tggctgtcct gaaactcact gtgtaaatga ggctctaact 4080
catagagatc cacctgcctc tgcctcccag atcctgggat taaagatatg tgccaccatg 4140
gcctggctta attggaagtt tgagaggact caaactgtat tgcatgttta tttgaagtta 4200
caccatcatg gagagcagag atgggagagc atgtcggttt aaacatgagt tacattatga 4260
cgttggggtc atagcaaagc cctgacctgc attctctgat ccattggaaa ttacagcctt 4320
tctaaagtaa agtcctgctc ttgttagagt caggggaaag gttgagctgt tggggaacag 4380
ctcagtctct tcagctgtca gcttctgtca tcagtgatga actctaagtc ccattaactt 4440
tcaccaggcc tgatggagaa ccagagagga ctctctgtct tgaacagctc cttcctggct 4500
tcatgcgtag ggatgagcct ttgctgagga gtgggataga cattggtcat ggagataagg 4560
tgtggaggga ggcatttttc agtcatgtga ttttcgactt atgcccatgc agctgcttta 4620
cctagttgtg agtgaccaac tgtataattg atggtggaaa tctgctgagt tatctatctg 4680
tggttcttac ttgacttgtt tttagaatgt acttaactta tttttattct gactatttgc 4740
atttggggga cgctaacaaa aattgaagat atataaattg gtgtcatagt taagctaatt 4800
aacatgtcat agcatgctag actacagaga attctctgca gagaattccc ttcacgtctg 4860
acttgattac agaaaccctc ttcttgttag tttataaagg tagcagcaat ctttaattgt 4920
ctttattaaa ttctaaacaa gaggagcaag taaagtgact tttgtaccaa gaaagtgcat 4980
gactttcaga cgcatgcagg gttgggttgg tggagaaccc ggccagtagg attggggctc 5040
gaatagtata ctagtcttat gttagtgctt ttaacttggt tggtagggga ggagatcagg 5100
aaaggaggag gttaacgggg cactaggcac ccagagagcc tcttgacaac tcatgtgagt 5160
gttttcctgc taagactgtg tgcttagtga agaatacttc tgaagattga atatggtttt 5220
ctccgtgtgt gctgcagtct tcagaattgt acttgtaggg tctctgtgcc actgatctgt 5280
gaactttcag ataggagcgt atgaactatc cctaaacctc acaagagaaa tcagagttgt 5340
tcttagtgga ctgtgactac tgactggtca tcataactcc cagaaacaca tttcagaatg 5400
ttggctaatc tcttactaaa ctaaaagaca aagatcggta aatgatataa agctaattat 5460
gtgtctacac tgagatcctt tctgacctct ttcccgtttt tctcaaagtg taattgagca 5520
gatggggcta catttagttc taattgcaag gctcaggctt ttaatacttt atctagaaat 5580
ataaactttg cctggtttag agtgaagctt gggaccaatc atgtagtgcc ttctaatgta 5640
tagtgtataa cagaattgaa tgtatgcata atttatgtaa ttagacacca attgctttat 5700
gctttgttta ttttctctga tagagataat cagaatcaaa atgtttggag acatagtcca 5760
gaggaaagca cgtggcaaca aaaatataga atataacaat tactataatt atatttccca 5820
gtgtactcct aagtttctta acagatacaa gagtactaca gagtggccat cggttgtcag 5880
atttatttta cttttattta aaatgtgtgt gcttcttgtg tatgcctggt gcccttgatg 5940
tttaggagtg gttgtgagct accacgtaga tgctggaaac caaatttggg tcttctggaa 6000
gagcaataaa tgctcttaag ctactctcca gcctgtccgt tcccactata acagtaggca 6060
ggaggatggt taggcttctg ccacttatag atgaaaacag gtggacactt catattctcc 6120
acatgggttt tctttcccca cataggtttc tgttttaatg tctaagaaag attcgtacct 6180
agaatacaaa gattttattt ttcttttgca gagttttgtt cttctgtccc taaaaaaatg 6240
tattaataat tggttttttt cttagcaaaa ttaaatgtta gtaaattctt aaaacacatg 6300
gagttggtga acaaaaggaa aatttcttac attagcaaaa tgaaatgtga agtcattaag 6360
taacggtttg ggctttttta aggccgccat tgctatggat aatgacaccg agatttattt 6420
ctgtttagta ataaatgcct aggccttaag ctaggcctac tcccaactag ctcatcactc 6480
aattatctca tttatacttc tcagtttcct acaaccaact tcctccgagt ccgaataggg 6540
aataccccac gcctaattct gagttcctct ctcttccaga tgtcccacct tactatcctg 6600
ccttttgctg taagccatag gctttttatt ttaatctgtc aggaggtgcc ttaggcagtt 6660
ggggaaggat agagacacat cttcacacag tgtaccgaaa catcacccta acaccattac 6720
attgaagttc tactctcacc atgttggtta gtcggtctca ctctggtttc atggtttatg 6780
cttgtacatg aagtcagttt ggggttcaga aacataagat tgttttaagt ccctgctttg 6840
tcccatatag acaaagatta cttaagaagg aaatgggtgt ttgtaacaga gtaaaagagg 6900
aatggagtaa taaaacaagc atctctagga agcatatgcg ccagtcttaa aacagtcctc 6960
cctgtgaaac aacaaaggcc aagtccttgg aatgtgttgt acccaaaaga agggcaaccc 7020
agagataggg atgctgggct gagccccaag ggccaggca cagcaagctt ggttgaaaga 7080
gagtttgact cttagaggga gtgtcttgga gcttttaaag tggaggctag tcaataagag 7140
aattggtgag aagtagaatg taggctagag gaaagtgtta aagtgaaagg aaatggttgt 7200
ctttagatag aatcgggtac atttgagagt ggtttataaa ccaagaaaaa aatacatcaa 7260
aactacttgt tggtggcttg gacgagggat tagggctggg agttgtgatt tctggactgg 7320
tcatgagatg gacaacatac tgtccattga gattatatgg aatcaagggc tctatattgg 7380
ctattatgta tttgagatct tgatttagat caaatgaaaa tacttccaaa aattacctgg 7440
aacccaggga gaagtagtat ttcttagctg gtaagtgata aatactgacg tgtttgttga 7500
aggtaatggt atggagagac acagactccg gaaattgttc ctgagaagtc ataggatgaa 7560
gtcactcttg gtgtactgct tggccagtga caagctcttg acttatgagg aaagtgaaga 7620
aaagctgaga tttaaaaggt ttggaggaag tgagcttaga gaaggaacac aatggaggac 7680
agaattgtgg agatccagac tccacagtgt ttcaaggagg agggagggtc taacagtgtt 7740
aaaaccttca cagaactaat gttgtgtggc agacagaaat tgcacagtag tctttttatt 7800
cttgattttt tcccctccct cgagcccccc cacacacact acttttggca gcttctctat 7860
gtacagtgtg aaagtacatt tcacagtcct gaaatttaca atgatctgaa attttgttca 7920
ctcagaatca aaagcttatc ctgaaattaa cgaaattaca atttattgtc tttattccac 7980
taactgtgat aattacacat ttttgcttta gaaatacctt tgattataga atgttgtccc 8040
agttttagta cattatatat ttttatcttg agtcaaactt ttctggatat tcttaattgg 8100
taaaactata tttaagtatt tgaacaaaaa atgggatcac attttaaatg cccaaattat 8160
gtaactgaca gagactatag gtacatgaaa ttaagaaatt atgtaactga cagagactat 8220
aggtacatga aattaagaaa ttatgtaact gacagagact ataggtacat gaaattaaga 8280
aattatgtaa ctggcagaga ctataggtac atgaaattaa gaaattatgt aactgacaga 8340
gactataggt acatgaaatt aagaaaagaa gagcagtgtg aggtttgatc ttgctgtgca 8400
ttgcaatact aagtgcaggc cccaagatct ggagtctgca cacagacctg agtaacagta 8460
tgtggccttg ccttcaagtt atttctgact ggtaaataaa gatgcctaca gccaatagct 8520
gagcagaaga gttgtatgtg gggcttagga ttcctattgt aaatataaag gttgtgtgta 8580
tcttttatct ggaaactaaa tggtcaaagc cagggtagaa acgccaggtt gggattaagc 8640
gttttaacaa cagggctgga tggcttagca gtttaaaacc ctggctgctc tttcagagga 8700
cctgggttgg attcccagca ctcacagggt tgttcacagg ggtcattcac tacagccaca 8760
ggggatctga tgctgtctcc tgccctccat ggccaccaga cacagtcata tgtatggcaa 8820
aatcaccatg cacattaaat aaaatttaaa aagaatcagt tcagaaaaca ttttcttaaa 8880
aaagaaaaag gcagaaggtt ttttagtaag aaatagatga cttcaaagtc gccatgtata 8940
aaactaatag tgaacaggaa acattagaaa tgaagattct tccctctcct cctcccagaa 9000
tcacctaccc tctgctgcta gagtgctggt ttaaaggtgc cttgcccaca aaaatggttc 9060
ttgtttgttt ttgaaattat aatatgatca caccattttc ttccttcctt tactccctcc 9120
aacccctcct gtgtagcctt ccacctgctc tctttcaaat ccataccctt ggatttcttt 9180
aactgttgat acatataaat actcctaaat acataaatac agtgttacta tatgtttta 9240
gagctggcta tttgttattg gataaccaat gggttggtca ttacctggag gagattcttt 9300
gtcctatcct tagtccttag ttgtctgtag ttctttgtct aggcttgagg cctcctgacc 9360
ttcactaacg tgtctgttaa tgaccttgtt caggtcatgt ttagccagtc atgttggtga 9420
gactttgtgg atgttgcttc tgacatgtct cactgacagg cttacagtaa actccttgtt 9480
cttcaagctc tttaaaccct ctctctcttc cccaatgccc tctgacccta aggtgtaggg 9540
gttgtattgt agatgtgtca cttggtactg ggctccaaaa ctctgcattt caattgtgct 9600
tttctgtaat ggtctctgct acaaggagaa cttttccttt ataggggtga ggactacagg 9660
ctcctgtgtt tacaaggaca attatgtaga atgtagatcg ggatgctgct gcttttgtaa 9720
agtagcaatt gcatatttta ttcaaagatg gatgacttca gtagtcttga gttggctagg 9780
tctccaatac taggcatgat ttccctcttg ctgaatggat ctgaaatcca attagaaagc 9840
tgttggttac tgtaaaggtc tgcgtgccac cactccacat ttatgctgcc atggtggttg 9900
ttactgtggt tcagaggtgt cataactgcg taggactatt ggttgcttcc ctcctctgga 9960
gccttgcatg actccttttt ataatatgaa gggtagtcct caagaaggat taggctctca 10020
gttctgtcca gctcaggggc ttcttgggcc ctgcatctca agtgcatgat gtcttcagca 10080
atatgcagtt acctctaggg ggcaaccaag ggcaatagcg tataagattt tgggagtctc 10140
ttggatagtc ctgaccagca actccaaaga cggctgcgta gtttttttgtt tgtttgtttg 10200
tttgttttgt tttgttttgt ttttgtggat aatggctcct ggagggagcc tgtgtctatt 10260
tatacacagt cttatgtgta ttataggtac agtagggcaa tggcatgatt gtgcttgatc 10320
cttgagacat cctcactgtt cctctaccgt cctcattcct tgtcctgtat ttgtcttcct 10380
ccctagttag aagccccact ccattcccct tacatttcct ttccttcccc ttccttctcc 10440
ccctttgcgt tcccgtcgct cccctttgt gcagaggaat taaaccaaaa gcttgtacat 10500
gctagagaaa tgttccacca ctgtatatct caagcctttg gagggattcg gaaaaattca 10560
tattatggct cagctgccct cgtgaatatg tgtcttttag gctaaatgaa tattcttact 10620
gagaataagg cctcaaaatt atgacagaag tttgtcgaaa gctgtatata ttaatataac 10680
gttaggagtc tcatagttag aaggtaactc ccttcataaa ttaggtaagc catccatttt 10740

-continued

```
gttcatattc gtcaaatgaa caaattcgat gctgagcaca agcatgtata ctgtattctt  10800
tcctcattcg ccattgtcct gctattacat tgctgtgcca gtgacaatac aaaagaatat  10860
tcactgcctg tgctctcttc ttcctaaatc tgaatgtagc tcctatctgc tagttgtata  10920
attttggcta cattatttaa catgcttctc ggcagttata aagttgtggt acatcctaga  10980
gttgagaaat aaaagctgat gctgagtact aggaaaatgt tcttgctgtt acttctcaaa  11040
cactacaact taaagttggc tgcataggga gaacatctgg aaggattagg ggaggggaaa  11100
ataggacaaa aatatattta aatttaaagt taaataataa tataataaag aaagtttcta  11160
cttaggtcaa caagatgtat tgttttctgg ttctgaagtt ttcatttacc tttgaaaaac  11220
tagttagcat tctgagtgct cctaaatttg taaatcattt tgtgaaaaaa ttgaactaaa  11280
taaatcagag gtactatacc aacagattca tactgtttga aggcaggttt tgtaaacctg  11340
aatgttcagc tgggtctggt ggcaaaagcc agtggtctct cagtggaatc atgaattcaa  11400
tgcctgcctg ggacacatag ctagaatttt gtctcaaggg ggaacaaaag caaatgtttt  11460
ctggattatt gtcaagtaga tagatagtat gaaaatttct ggatttttga ttgcccctat  11520
ataagtgaaa aggtactatg agaggagagt ttgaaatggg gatgtttgtg tttgagagct  11580
ggtcttgctg tgttgtctgg ccagcctgga gtcctgtttg caggtagata aggcttgcct  11640
tgatcttaca gagactcctg cttctgtttc cctcagtgtt agattaaagg tgtgcactac  11700
cataccctgc ttaagctttg tccttataag ggcagatata tgaagtgtgg gggctgtctt  11760
ttgttgtata aacctgtgct gaaacagtaa gatctgcagg ctgttaaagt caggtcaact  11820
gtcctaacaa attatgaata tttgatttta aactataaca ttaatagtaa tttctcattt  11880
cttgcttgat aaggccattg taaaattatt ccttataggg caggagaaat tactcagcag  11940
ttaaaagcat tggcagctcc tactaaggac ccagggttgt gttcctagca tatagccatc  12000
tgtaactcca tttccagggg atctgacaca tcgtgaccac cacaggcacc aggtgtcaat  12060
gcaggctgcc tatgtatata taggcaagct cgcaggcaca taaaagtaga tagtgtccct  12120
caccttagaa aaagtaatac ataagttttc taagcttgtt gacaagcttt cttattgtct  12180
aaaagtattt tgtggttgaa aatcagattt tggcattatt ctgtgtgttg ttttaagaca  12240
ttggcatctg tcttacttag tttgggtttt actgctgtga acagacacca tgacctaggc  12300
aactcttaca aatgcaaaca tttatttggg gctagcttag tttcagaggt ttagctcatt  12360
atcatggtgg gaagcatggc agcatgcagg tagacatagt gctggaagag ggttctacat  12420
ccttattcaa aggcagcagc aggagactcc ttcacaggca gccaggagga gggccttttc  12480
cataccaggt agagcctgag cataggaggc ctcaaaaccc acctccatag tgacacactt  12540
tctctaacaa ggccccacct cctaataatg ccacttccca tgggccaagc atattcaaac  12600
caccacagca tctaagatgt tttaatgcac aggctactac tgtgtagtcc tgagaaatga  12660
agacaagagt gtctttatta ccctgaaaaa tgctgtgact ctcccacttg tggacactga  12720
acatttaagc ccttccataa ttccagctcg actgtaaggt atttctacag gattccaata  12780
agttatccaa gaagcactac tagctgacaa attagatcct actccgtact tcaagaatac  12840
ttcttatgta tctaaattta caaaatgaac aacaacaaca acaaaaatcc actaaaaatg  12900
gatttcacct taaggaacca aaccagggaa attggaaaac taaaagtcag aaaaactttc  12960
tctctccaca aagaatgtga atcctaggca tgtataaaat ctgcataata tattagattt  13020
ctaatgtaat ttgaatgtta caaaaacaac tcttgtttaa atataaattt tttgatgttg  13080
ggtacatgtc agtggtggta tttaataagc atcttttctc ttttaggtga tattggcaat  13140
```

tattattatg gccagggtca tcccatgaag cctcatagaa tccggatgac tcataacttg 13200
ctgctaaatt atggtttata ccgaaaaatg gaaatatatg taagtactag ttggcactgt 13260
gtttttaaac tggtatttga aagctcttct taggctgctg tgggagatgc atgtggtaga 13320
tgaaaagatc tgaacgaaca cagacaggtc ttgtggttgt gtccctcaga gaacgcttaa 13380
ggaattggag tagtcctctc ttccctctga tcatttcaaa caccaaatat ttttgtgaca 13440
atactgttaa gttgcctgtg ctgctagaaa caattgtcct ggggttggtg agatgactta 13500
ataggtagag gtgcttgcca ccaactggat ggcctgttta ccttccccag aactctcaca 13560
gtagaaggag agacctaatt cccccaaatt gttttctaat tccacgtggg catgaggaca 13620
cacctccaat aataagtaac cacagtgtaa ttttaaaaag aaataaaaga gaattgacct 13680
gaattattgc aagagtttgg tagaaaatta atcataaata tttatttggt taacatacat 13740
atgaaatgtt gccaatgata acaaggtaag taaaaaatgg tgtaagatac acagccacct 13800
aaaaagtctt cgaaacatgg gcaggagcat acataaaaag tgcaaggtag gataaggctt 13860
aactaactac tccaggagaa gagggctaga cagtgttata ggaagcattt ctttaagata 13920
caggtatttt agagaaatgg gaagacttgt ggaagaagtc tgtggtaagt gaagctgagc 13980
tcttcagagc agaagttaga ataaacgaag gctaagggag atctcaagct ggtgttctta 14040
gaaacctttg atgaaagtca gtgggtagac agcagcgagg ctatgctggg aaagagcctg 14100
aacaaacagg agtagcctcg cttggagagg ggctgccggc tgcctgctgc ctgccacaaa 14160
tgtgtgcatt tgaattagca ttgtaacttg ctactcaggt ggatctggtt catttagaga 14220
gactgatcgt ggaaacttac acatatcatt tgataattct catttaacaa ctgatacttc 14280
caacatcctg gtgtttttct tttcagaggc ctcataaagc cactgctgaa gaaatgacta 14340
aataccacag cgatgagtat atcaagtttc tacgatcaat aagaccagat aatatgtctg 14400
agtacagtaa gcagatgcag agatgtacgt tataaataat tattttacta gtgctgaatg 14460
taaatgaatc tttttaaagt ttctgatcag agttgcctca ataggtattt ttcctcataa 14520
tttaaaatat taatataatt attaattcag aaggtcattg aaccaatatt aatgttactt 14580
tagaaaacaa acctatttaa atttgttctt ttacttttta ttttgcaccc atgaaaagtt 14640
tgggattggt agggagatca cagagttaca agagaaaaat atatttcttt cttttttttt 14700
ttttttaata attttttga gacagggtct gactttgtaa ccagctgtcc tggagattgc 14760
taatgcagat caggctggcc tcaaactccc agagttccac ctgcttctct cttgcattaa 14820
caatcctcca tttcaccttc tgtgtactcc agtcacattg ttctgtaatg taaagatgtt 14880
gccttttgtt ggcttctttg tgtttctttt tattcttcta catgtttttg attataggtg 14940
aaagtgtatt gttattggta gtcaattgta ttaactggta gtcaagtgta ttaaagaaat 15000
attgccaagt atcctgaaac tgtgggctgc tgtcttttga agcttaatac cggagcccat 15060
ttcctcagtg agaggtggat ttagttcagt gatgacgaat gataaggatt tctcaagttc 15120
actgaacacc atatttccct accgtatgtt atcgcatttg gttgactcaa gactggaata 15180
ggacggacgg atgctattac atctattgtt ttttgggttt tttatttggg atttacacag 15240
taatgggtag ccagcccttg ggtaaatgac aggatttgtt taaaccatta tagtgcttgt 15300
ttatattaaa ttctatttga gcataaaaaa ctaaaacttt ttttatagta tctgtaggtc 15360
tgtaaaaccc ctgccctctt gctaacgtgt gatctgagaa gtgaagaatg actagggatg 15420
ggccacacac acttctgttg tgttttttcc tctcagcaca gggagccaac catgtcatga 15480
ccaagtgaca tgtcatctgt cttatgttcc atgaaactga ttcattcatg gctgcttctg 15540
aagtcagtgt tagccacaga aaaaaaacaa agtaacttaa tattttgata ctcactaaaa 15600
catgtttcgg agtcagggac actgtgtgtg agggtcagta agatgagtta gaaaggggtt 15660
gcagccactt aatctttaac tcactatcat atttaaagag aaaactagat ttgtgcctat 15720
tttcatatag gcttttgatt tatgttgttg gtgatggtgg tggttgggta gagtgacttc 15780
acaaatttcc taataagatt tggtaatgga attacataga taacaattta attatcttgt 15840
aaaataagca ttatattata aaattataac ttttataata ctacctacat tgaagtacta 15900
ctccctgtga attttaaaat tcataggtaa tattttaaaa ttacaaattt cacattgcta 15960
ccatgaaata ttatattatt acctatgatt gcctgaaaca aatattttta atagtttata 16020
agaaaaagcc ttcaatgact tgataataga ttgactttaa tgaagttcac cttccacagt 16080
taacgtcgga gaagattgtc cggtgtttga tggactcttt gagttttgtc agctctccac 16140
gggtggttca gttggtgagt atcctaaatc agtcagcctc aagaggatct gaaggggtta 16200
gagtgtctgt aggttttgtc taaagcggaa gttgtaatgg tagtaaggtt gtgttggctt 16260
gattttgctg tatcacccag gtgggcctcc gtctcagcca cctctgtggc tacctcccaa 16320
atgcttgctt acagacatgt gctatcattc caacttaatg agtacccaag ctgtcttgta 16380
gttcactgtg gggcccgggc tgaccttgat attgtggaaa tcctcccctg gagcctctca 16440
atcattggga ttagaggctt ggaatattat gatattgcta ttcactcttc tgttaatgta 16500
acaaaacctg cggtaacttt taaaagaatg gtttatcttg gttcacagtt tgggagctta 16560
actggccctg tccttgggga ctgtgatagc acattatggt atgtgcattt gggagaaggc 16620
cagtttacct catggccgct gaatggagaa aagaggattc cagtatccct ttcaagcaag 16680
atcagatctc cagtaaacta aaatcagatc ttggctctta gagagtccac cccttccag 16740
tggtaccata ctggtgacta aatgttccct ggggttctta gaaggcattt caggttcaaa 16800
gtagcaagta taattgtctt taaaatgcca gtgtttaaca gtttttactt gaacacagtc 16860
tttaagcttg tgtcttttta ctcagagacc tttttctcct cttctttctt ccgccatttt 16920
tactaagact ttgcatgtgc actgtgattt agttgggtaa actgtaggaa aatggttatc 16980
tgaggaaagc ttaggctccg aagttataat cctttgcttt tgaatgccaa accttttgtg 17040
cttacacatg gcatatttaa tagggcttcg cttatatgta ttttgtgtaa cctgattttt 17100
taaaattctg agtattttat aaataacata gcatgtatct ccttcttagc tggggctgtg 17160
aaattaaacc ggcaacaaac tgatatggct gtcaattggg ctggaggact acatcatgcc 17220
aagaagtcag aagcatcagg gttctgctat gttaatgata ttgtgcttgc catcctcgaa 17280
ttacttaagt aagttaattc aaactgaatt ttccctgtga tcagatctct taattgaaag 17340
aaaaaaatga ttttaaagac tatcaaataa atggtaatag attaatgctg agtcttccag 17400
ggtttgttgt gagcccctgc agaagtgtga gaaatagacc actacagtgg gagagcgaga 17460
gggcagacag tgccgtgcct gagactgccg gtaaatggtc tctgctcatt taggtttgca 17520
gtcgtctaag ctgattaaaa atggctgcta gagatccgga aatgtgaatg ctaaagtaac 17580
ttgaagtcaa gcctttgcaa cttgtgttat aagaagtttg tctggccact tagtagcgtg 17640
gctgacccca gttctctcat ccatcctcta cacagacaca cagaacacat agataataga 17700
cacacagtga tgcccaactg ctgaaggggt tttggaagtt atccttcact gctttttcag 17760
aagtgtgaag gtccttagga gtgtggacac ttgtgaaact agcttatttt ccactgttag 17820
ctataatgct gcagtgagtt gtatttcagc tttgactgca gctgtgttct gtgggctttg 17880
agagtgatgc tcttgccccg catgtacatc ccaagagtta acttcctgac cttaaataaa 17940
cagcagctaa gtgctgtcag tgtaacatat ctgactcccc caaccgacag aaaccggaaa 18000
tctccttcat tgacttgaag cttcttccac tggcttcagt tctagagatc tgctgctttt 18060
tccttcatag cttagtcttg agtaagccca gttctgtaca gttcttcacc tggtaaatct 18120
gaacatgatt tgattggttt ggtaagcagc tctctttgct catctaaaca cattgggcat 18180
ttgatcatgt ttgattttga actttatgaa gaagttctgc tatgatgaag cccgctcgct 18240
gtttgcacta ttttagattt tcttagtgtt gcttttctgt gccttgagaa cataaatgcc 18300
tgggtttgat catgccagct tacgttgtat gagcacagtt acagcatctt taaataataa 18360
acaaaatgtt ttaagtcagc cacagtgaca agataatcat ttactacctt aaatggtgaa 18420
tttaaatttc attttgtatg tattggtgtt ttgcctgcgt gtgtgtctat gcaccacatg 18480
tgtgcagtgc ccatggagga cagaagaggc cggtagatcc ccaggaactg ctgtaagaga 18540
tggttgtgag tcaccatgtg ggtgctgggg atttaacctg gattctctag aaggcagcca 18600
gtgctcctaa ctactagtcc aactttccaa caccagtagc ttttttaaa tacagttttt 18660 ttctatttgc actttgacat agggatggaa ctgatgtcat tctatggtgg agtgactaca 18720
gaagctcatt tgagtagttg ctgtgactgg tggtgtacag agcatcaggg aatgatgaag 18780
gcacttgtga tctgtcacag tcatgaggtc ttagtatgct gtagatgatg tgtaaaatgt 18840
gctcatctcg ctgtaaaagg tgtttatgga tatggacatt ggactgtctc agaactgtca 18900
tgttataaaa tactctgagt tttgttttat tcttggacca ttggaaaccg gggagtgggg 18960
tggcacaccg gcatgccaga ggcaggtagg tttgagatga gcctggatga gcagctatca 19020
aaataaccac agggaaaagg aaacaaccta tagttctgct cactccaaag ctgttgaaag 19080
aataaaaata ataacagcac tatgttggtt acagttgccc atagattatt ttataatgct 19140
gaaatttttt taattgattt attttcactt tatgtcattt gtgttttgtt tacacatgtg 19200
tctgtgtatg tgttggatta cctggaactg gagttacagg taactgtgag cctgctgtgt 19260
gggtgctggg gactgaacct gcggcctctg gaagagcagc cagtactgcc aactgttgag 19320
ccatctccag ccctccctcc ctccctccat gttgagttgt gttgtttgtt tgtttgagat 19380
agggttcctc tgtgtagcca tgggtctcct agaattttct ctgtagacca ggctgacctc 19440
agactcaaga gacccacctg cctgtacctc ctgatggctg tgatgaaagg tgtatgtcac 19500
taagcccaac aattctgaaa ttgtgtaatg tagcccttgg catacccttt aggtgtgagt 19560
acatagataa tgtctgcccg tttttaaagt gtaaagacaa gggtagacct cagagtacag 19620
tactcgattg tcttggtagc ccgaggagac gtgacgtgct ggggtctgga tgctgagact 19680
gcgggggaag aagggtgagc attcgctgta agatgaagga cctgcttcca cattccggct 19740
tgcgctttcc tttcaggtat catcagagag tcttatatat tgacatagac atccaccatg 19800
gtgatggtgt tgaggaagct ttttatacaa cagatcgcgt gatgaccgtc tcattccata 19860
aatatgggga atactttcct ggaacaggag acttgagggt aagactgagt tctgtcagaa 19920
taaatataag aagagcatag gaggttgcta atttctggaa gagccatgtt gtcttagtca 19980
ttttgtttgt gtatttgtga tgggacctcg gcatctggtg tgtatggttt tttttgtttg 20040
tttccggaga tgtggcctca ccttagttga gcagttgttg ggatcattgc ttactgttag 20100
gatttgtcac atgtggaccc actgaatgct gcttgttgtt cagctgtgat tactttgaat 20160
atgtagaaac gagggatcag aagtggtctc aactcagtta ggtgtaagtg ctgatcctaa 20220

```
aaagtttgct gtcctctcca ggttgcatag gttgtcttgg gtagcagggg tggggtcaca  20280
atgggaatgg acagtgttct ataggtgtgg ggtacagatt atcacactgt cttgtggtag  20340
gttgggagag gtcaggcagt gtctttatct gagatcacag gcatagagtc ccagggtgtc  20400
ttattaggtg gtgttgaaga ctgattttgg gctccctacc tggggttgtg ttctcaggac  20460
tccatgttgc cccagagtgg cgcagtggat gtagaagctc tgaggatccc tccctaccta  20520
tgggtctggg tcacagggct cctcactttg agaatggtgg ataagtgggc tctactttta  20580
catcttgtaa aattgtttca tgcctcaaac tgaggtttgt aagaactttt tagtttattt  20640
tgtgtggtgg ggaggagcac atgtgtgccc tgttacatgt gcaggagtcc tcctgccatg  20700
ggtggatcct ggggatcaaa ccgtggggat ctcacttgtt gggctttatc tacccaggta  20760
tttcgccagc ccaaactaca gtgcttgtgt gttatctaaa aactgcctta gagcttaaaa  20820
cgtacttcta caacctagaa tacccaagac acaatttaca aaactcatga aactcaagaa  20880
gaaggaagac caaagtgtgg acactttgtt ccttcttaga agggggaata aaatacccac  20940
ggaaagagtt tcagagacaa aattcagagc aaagactgaa ggcatggcca tccagagact  21000
gccccacctg gggatccatt ccataaacaa ccaccatacc cagacattat tacatatacc  21060
aacaagattt tgctgacagg accctgatat agctgtctcc tgtgaggcta tgccagtccc  21120
tggcaaatac agaagtggat gctcacagtc atctatagga tggaacacag ggcccccaat  21180
ggaggagcta gagaaagcac ccaaggagct gaaggggtct gcaactctat aggaggaaca  21240
acaatatgaa ctaaccagta cccccagagc tcgtgtctct agctgcatat gtagcagaag  21300
aaggcctagt cggccatcac tgggaggaga ggcccttggt cttgggaaga ttatatgccc  21360
cagtacaggg gaatgccagt gacaggaagc aggaaatggg agtgggtggg tagggaagca  21420
gagggagggg ggaggatata aggaattttt ggagaggaaa ctaggaaagg ggatagcatt  21480
tgaaatgtaa atgaagaaaa catttaattt tttcagaatt gtgtgttact tggtctttta  21540
atcattttaa aatatgtcag actttttgtt atgaaatagt cttctaagat ctacttttgt  21600
gttttaggat attggtgctg gaaagggaaa atactatgct gtcaatttc ccatgagaga  21660
tggtatagat gatgaatcat atggacaaat ttttaagcct gtaagtactg ctttcagaaa  21720
taaaatggga gttgtaaata tccttagata ctaatgtgtc ttattctgtg gctagatcat  21780
ctcaaaagtg atggagatgt accagcctag cgcggtggtg ctgcagtgtg gcgcagactc  21840
cctgtctggg gacaggcttg gttgtttcaa tctaactgtc aaaggtaagc agttcacgtt  21900
ccccctggtg tggtgtttct cctccccaag aacttcccat aaaagttttc attgctgagg  21960
gctggagaga tggttaagaa cacatgttcc ttttgtagaa gacttgggtt ggatcccagc  22020
tcctacatgt tggctcaaaa tctagcactc tcttctgatt tgcatgcatg tggtacgcac  22080
catacatgtt taaaaacata tttttaattt ctcattgtta ccttttgctt gccaactcga  22140
tgccaaactc tatatttgaa tttttagtgg atttttattt gttgttgttg tttgtttttg  22200
ttatgtggct gactagttaa tttagttccc caagtcttac atgttatcat atttatgttt  22260
atgtatttat ccatgagtag tttgttgcca tgtcagcgcc agcagttttt aatcagtttt  22320
ttcagaagac ctgtaccttg ttgtctgatt cagttgctgt tacagagtat gaggatttag  22380
cttggcgcac tttattctat catggttact ctcttcctta cccaacccta agaacttcgg  22440
tcgctgtggc tagtgctcag cagcagtggt ttttagctta gcagtcttct ctactggcaa  22500
gactcacttt tttttcttct ggattttttt gtttgcttag tttccatatt ccttattact  22560
aaactatgaa tttctaatgt attctgctca gctatctcag gtgctctgtc actgagctcc  22620
```

-continued

```
tcctgttcgg acttagtgtc ctcatgggtt taatgggaca gagagctctc tgcttctgct  22680
ttattatgtc tcctgatcag tgggcactgt atctaacttg ctggtggaac acataagtgt  22740
cttcatgagg aaagaagccc aagtgtaaat gtgtaaggtg gtgttgaaat tctcaagtcc  22800
ttacgaagag ccgaagtcca catgctgaat acaagtctca tattgctgtt atgggatgaa  22860
cttcgagggt ttcagaatga agcaaagttg catgtggcag cgcatgcttt tagactcagc  22920
attagaacag cagagatggg tccaggccag ctaaggcttt atatatagta aaaccttgtc  22980
tcataaagaa aaagataaat aaaataaatc tttttaataa agttaatgtt tggattagaa  23040
atgacttagc atgcacattg catgttttac tttagacttt ctgtgtgaac tttgaggtag  23100
taagtaacat cttgctttga gttctcttac agaactttta agataattaa atatagatgt  23160
taagaacttc tcatgattgt actctgcaga ccagcctcag cactgtggca tgctctggta  23220
ctctccttcg tatctagttg ggtcatacaa aattagttgg ccactctcct ggaggtcagc  23280
attcagttaa cagcactttc atgtgggcca tagaatgttc atagatatct cgtgtttccg  23340
agcagataag acttaaccgg aagtcatcag ccaccaggta gttcctttct ttttaggagc  23400
tatatactgt tagtgttctc ttttgtaact gaaagtttat aatgcttgta tttaaaagta  23460
gtagctttca ttataaactg catttgactc tttatagtac atctgcattg tgtttcaaca  23520
ggtagaagtt catttgtgaa tttgcaattc cattttcaga cttagaatac actgctgcga  23580
ctggcttcaa ctacattgtc tcaggcctag tgaagccaag cagccagctg ctgtccacct  23640
tgcctcctta attatttctt cttgtggtgt tcttttccgt gcttcctctt acgggttata  23700
gccttcattg tataaaaccc ctttgtagta atttttcctg ctgttgggtg gtagaatgct  23760
ggtcttgtct gggctctttc attgtactct gaagttaact tctgtcctta aaaatgtcca  23820
agagacactg ttgtagtaga agatgcctgg ttgataatgt acatgaagaa aacagagaag  23880
gcactataaa ctctcactag gtaatgagga tttttttttc ttttgtggca ttttcttttt  23940
ttccaaatat tttaagcttt gttatagaaa agttacaaaa acaaacaaca aaaataaaat  24000
cacacactga aattaaccag acccaaagat tcaatgactt ttgtgcttag agcagccagc  24060
gtctcaatac caggtgaaag cccactgcaa aaggaaatga ctttgttttt taaaaaaaaa  24120
aaaaatcttt tttttaataa ggctaaaatc catgaatctc tgctgtcatc attgagggac  24180
tttctttctt taatggttga attatgtgcc tgaatggcac cagaagttac tggaaacttg  24240
taacttgttc ctgtgtgagg cttgtaatct gttttgtttt ttttttgttt tttttttttt  24300
tttttttggt ttttcgagaa agggtttttc tgtgtagccc cggctgtcct ggaactcact  24360
ctgtagacca ggctggcctc gcactcagag atccgcctgc ctctgctggg tgctgggatt  24420
aaaggcggag gtttgtaatc ttaaataaat taagaaaatt atccacaata ccagcaataa  24480
ggatactctg tggtcaaact ttttggtatt gcttttcgaa attaagccac acatgtctgt  24540
gcgggagaaa caaaatttag catttgttta ttgtgttctc tcccttatgt gatctctcat  24600
gaacgtcttc tatggtagta aaatacatgt gtgcgtattt taacacttag tacaagttat  24660
tagttggata tacacccccc caggcccccc accctcgtca tcatcccctg tcattgttcc  24720
tccctgcccc ccccacccct accccccccc ccccaccttg tgttgaggtg cctgccttgt  24780
agtcatgctg tatagactgg cctcccaatt ctgatccacg taccttagcc tcccaagagc  24840
tgggattgct ggtatgtgcc actctgcctg gctgtctaca gacatttttt ggttgagtaa  24900
aattgtttgt atttatcctt tttaaggtcc tattttaaat tgctaaagaa tacatatttc  24960
```

attgttaccc aaatcttctt tgtctaaggt catgctaaat gtgtagaagt agtgaaaact 25020
tttaacttgc cattgctgat gctcggtgga ggaggctaca caatccggaa tgttgcccga 25080
tgttggacat atgagactgc agttgccctt gattgtgaaa ttcccaatgg taggtgttca 25140
ggttgcagta tctagaagaa catctgctat gtacaaatgg atgcatggga gagtctactg 25200
ccacacccct gaaatgtgtg atctcttctg atggatgagt ggttagattg caaatctgtg 25260
tgagagcatt ccatgtgcac tttcaagctt tcctttggga atagttcttt tatctggatt 25320
cggattatgt ttctgagatt atacggaagc taagctttta atgtgtaact tgtttttttca 25380 ttgtttttaa tagagttgcc atataatgat tactttgagt attttggacc agacttcaaa 25440
ctgcatatta gtccttcaaa catgacaaac cagaacactc cagaatatat ggaaaagata 25500
aagtaagaaa tcacttcggc ttaatgaaac ttcaggaggc tatagaaggt caaataaagg 25560
aagttggttt agcatataca tcagatactt cctaacctta ggctattcct gttttttaat 25620
ctcttatatt aatacaaata tgtaaccttt gtaaatagaa acattcttat tagatcaaat 25680
gctttatgtc tacagaatgt agaaacattg atcagaacgg gctgtgtcct ctctcccata 25740
gaccagttgt atgacattta taagtacacc tcattgtcaa atagaggtga aaaggtacat 25800
gtttgtgtgc tgtgggttca gtcagctaat atatgcagtg atctgatgct tagatagtgt 25860
cccattcagt ggttagtaaa tgaaagctcg ttcttgttta gttcctcctg tgtataacag 25920
aaactttaca tacagtggat tttgtctaat aaattgtgtc atttagacag cgtttatttg 25980
aaaatctacg tatgttacca catgcacctg gtgttcaaat gcaagctatt ccagaggatg 26040
ctgttcatga agacagtgga gatgaggatg gagaagaccc ggacaaaaga atttccagta 26100
agaaaaccct tgctatgtct tcttgcattt ttcttatgtg tcaaaataag acttaaaatt 26160
gaaggtacac agggaatggt tcacagcaca tgttgtgatt ttccttctct ccattttaat 26220
tacatataga tttagctccc tgatgtctca aagcctgaat taatatcacc agtttcattt 26280
tgtgtgacta cacagacatg gctgtgtcca gaaagtaggc acttgatata tctatctatc 26340
tatctgtctt acctatgcaa tgattgtaga acctgtggct attatcaaat ttataaaatc 26400
ttttgtgtat cagttcgagc atcagacaaa cggatagctt gcgatgaaga gttttcagat 26460
tctgaggatg aaggtgaagg aggtcgtagg aatgttgctg atcataagaa aggagcaaag 26520
aaggctagga ttgaagaaga caagaaggag acagaggaca agaagacagg tcggtttatg 26580
ttttggtgac catttcactt tccctactta agggttgcac tgtgtctctt agcgatcctg 26640
cagtcacacg tctcacttta ggcaggtaac ttttcctggt gtaagagata gttagttacc 26700
gctcatgctt actgtttagt gcttcagagc tgacttaaag gttttacagt tgtgctcaaa 26760
ttttctttgt ggtatagaaa ccttcctttt aataacatag tagtaaacgt tacatgtcat 26820
gggatggggt taaggggatg acagtagtta cagatgttgg gcctcagaac atttactgta 26880
gcttaggtgg acttagactc agtgctcttc tgccttgtcc tcttatatac tgggattgaa 26940
ggcatgccag tacacctggc taaaattcta aataatttat actggttaaa gctgacttca 27000
tgtagcaaaa gttaagctac atagtccttt gaaaagttac tttaagagtg aagactcttt 27060
aggaactgaa gaaactaaaa ctgaggaaag ataggaaggg gcagtttctg gtgtcttccg 27120
gtatttcatt cagagtgttt atttagcatg ccattacagc acctcgttag cactctcagg 27180
tttctcattg ctatgctgaa ctgtgcaggg gtaaggagtg ggcagtagcc tctttaaaca 27240
tgataatgct gcaagtttta gttgacctac tagtcaagtg aggctgcctg gctttactag 27300
gcctcactat atagacatgg ctgctccggc tacttactgg gtggccttgg attcacacca 27360

-continued

```
ttgtcctttc tcagatgcct gggtgctggg attacagaaa tgtgccacca cctccaactc  27420
agtttctttc tattttaaaa tatcttctgc attttctttt ttttttccaa ataggaaagt  27480
gataaagtaa attgactctt ggtattttag acaaaatacc acaataatct atgggtcata  27540
acctcaaata agacccacca ccaccccctc ttggcactga gtaaaaattt agccagaatt  27600
atccaagaca ctaaaatgtg aaatctccat tgtcggcatg tagatttgta tgggaggtga  27660
cagcagtgcc ctgcagtgtc tgcattgccc aagcgtgctg ctgtccctgc acctctccat  27720
gaggccattg cttcataact aatttacaca gagaaaatac tctggctaat ctgggacatt  27780
tactttaatt actgtattta agttatgaag ttcagtttag tagtaattaa aaatttaagg  27840
ttagaacaat gggatattgt gggccagcaa ggtaaaggtg cttgctgcca agcctgatta  27900
catatgatct gcatgttgga ggaagactcc tgacttctac aagctgtctt ttgacctccc  27960
tatggaagtc atggtgtgga tgcccaaaca tacacacaca ctctgaataa ataaatgtta  28020
aaaacaaaaa acataatcta gcctcttgcc tttaggatca cgtccttctt acagtgcaga  28080
cacagttctc ttgagctcct tctgtcttac cactgcttcc gtgcctcagt ccttttacag  28140
ttttccctgg aagataccct ttcctcttac ctgagagttt gttcattctt tgggacccac  28200
attctagaga actgtgtctg cactgtaaga aggaagtgat cctaaaggca agaagctaaa  28260
ttattttttt gtttttaaca tttattatat atacactata tacatacata tatatattgt  28320
gtgtcttata tttcaaaata gacatcaata tttttcttct gtctttagat gttaaggaag  28380
aagacaaatc caaggacaat agtggtgaga aaacagaccc caaagggtga gcgatgcttg  28440
tgtctgtaga cgtcatgcat gtcttggggg ttgggcgggg gcatgcatac ttgagaaata  28500
ctggcacagc ctgagaacat acaatgagtg caggtctgcg tgtgggtaac gtgcttaggc  28560
tatttgaccg gtaacttttta tgtatgcaat cgtgtttttc atgatgctca tattactgtg  28620
cttagaatac tttgatgtta ggagacaggc tagtttaagg aaaaaacatt gggctaagtg  28680
aaagcctatt ggagaatttt gttatcagaa tgcatgtatg gctaggtagg tgaagtgttg  28740
cggtaaatct ccaacccaaa tatgccctgg caatgaaaca caactcaatt aatatgaata  28800
catgctgtgt gcctagaatg ggcagatcta ccgctacact accatcgtca acaactgtga  28860
gagcccttag aacttgcagt ttctccaggc cacgtgcttc tgctccactt ttcttcttcc  28920
ccctcctctg catcctcacc ctcccctatt ttctcctctc tctccccacc ttcttctcca  28980
ccttcccttt atctgcccaa tcatcagctc tcctttattt tacaaattag gtgggaagca  29040
ggtttatggg aagtaaacct gagtgctgac tcattgcttg tttgtaggcc ctcactggag  29100
aaggaagtag catcaaatat aataagtaag ccccagggct atccacacct gtgaagaggc  29160
ttgagtctat aatctcagtc cactggagag gctgagccca gaggattgcc atgaatttaa  29220
atccacacta agctacatag tgatttttaa atcgtcactc tgggctgaag aatgagagtc  29280
tgtgttagaa gcaagcacgt gtgcttggtc acccagttgt ttgctaattt tgaaggataa  29340
cttagaatgc tcagttgtaa aacaactgga aagattaagg cttttattgc tcagaaaaaa  29400
aagaaaaaac aacaacaaca acaacagtga atagcttggt gtgaatctat aagactgtgc  29460
aagtagccag gtcagtgctc ctaaaccaag actattactt ttaatatttc atgatcctct  29520
ttcaacagag ccaagtcaga acaactcagc aacccttgaa tttgactctc caactttagg  29580
aacctcgaaa agtgagacga ttctgggata agaaaccttc cctgtttgag gacattggct  29640
tcattttata ctgttttggc atggactgta tttattttca aaatggcttg tttttgtttt  29700
```

-continued

```
tcttggcaag ttttattgtg agtttttcta attatgaagc aaattttttt ttccaccatg  29760
ctttatgtga ttgtatttaa attgatgtgt tattatgtca aaagccggat ctattaaaga  29820
aacaattggc ctttctgagc tgatttttcc atcttttgta attatcttta ttaaaaaatt  29880
gtacttggat cgttttctgt ctgtttatta tgaaagcttg tttccaagtc aatgacttga  29940
tggtcttaag actggaacat accaaaagga atgtcagtgt cagagaccat cactagatct  30000
acacagtgct tactggctct aacagctatt tcttacttca ggaaaaataa cagtgtcact  30060
ttgtgtcagg aagactggta tttcataaat tatttccaaa ttcataatct gtgcacttgg  30120
gatgaagcaa ttatttttga actgaatcaa atactcagaa attggaaatt gtgaattgaa  30180
aaaagaaacc tgtccaacca ataactggcc caacttaaga cccatcccat gagccagcac  30240
cagtccctga cacttaatga tactctgtta tacttgcaga ccggagccta gtgtggctgt  30300
cctctgagag gctccaccca gcagctgact aggacagatg cagataccca cagccaaaca  30360
gtggatggag cttggggact tttatggaat aggaggaagg atttcaggcc tccaaggaga  30420
taggaactct acaggaagac caactgagtc aactagcctg gacctttgtg gctctcagag  30480
actgaaccac taaccaaaga gcatacacgg gctggaccta ggtctaccca catagatgta  30540
gcagatgtgc agcttggtat ttgtgtgagt cccagacaac tggagaggag gctatgccaa  30600
aagcagttgc ctgtctggat cttccagctt ggctaccttg tctggcctca atgggaaagg  30660
atgtgcctag cctcagactt gatgtgtcag ggcatgtata caaaagattg taggcggtag  30720
aaacataccc ttttgtgatg tcagtgtaaa atgaaccagc tagcaaaacc tggttcttgc  30780
cctgtagttt gatcacaacc agggtttcta ctcaagaagt aaaacttaat atgctttggc  30840
attccgcatt cattgagtgt ctactcacct tttggtaata actgcagctg aatagaattt  30900
taagtgcttt cacctaaact tagattgtta ttgtagaaag cccacaaatg gagtttcctc  30960
tcccagtgtg tacaacagaa aaatgtttta ggaatttgcc aaagttggtg aaaccatcct  31020
acttgctaga atcaggttgc tgattttgag attaggagaa cagagtggta gaaaggaggc  31080
agtcgtggag aatgttctta cattgtcctg aggttcgaag gtttcatgtt catgggtttt  31140
ccccttttgc tatgtatttg ccaggagtcc atatccttta tgactaagga agcaggatcc  31200
cttcgctgca gagacttatt tagtgtgtaa ttttcatgaa acaaagtgta tcctttggat  31260
acttcatctg gtattgtgat ctgccttctg gcacatgtcg cataataatt acagtgtgtt  31320
aagttctggt ctatgaatct actagaatga tgtcccagat gccacagtga ttctccttgg  31380
ttggatctgg gaggttctgg tttcatagtt taaggctgtg aaactaagca gtttcagaac  31440
aggtgatttg ggacggtaaa aatacacaga taccagtaat ttgtaaagtc aaactacagc  31500
ccacattgtt tggaagaaca aaggctcctt ttgcatagca gtaatcacaa tttctacaaa  31560
tgtgtaaaac tgattctatg cataatgaat aagatgagtg ttaataatag cctgtcggga  31620
caagggttga aaatcaaaac aatgaggaaa taacaagaac caggtggagg gaggcgaagt  31680
tcatttttct gtcacaagag tgagatttat aaatagaaaa gacaacaaaa cagaacctgg  31740
taaaagccat gggaattttt caaaagtgaa ggccaaagct tgacaccgaa ccccacataa  31800
gttacatact taacagaagt tctctagacc agcaaaaaca agtaaaataa gatagggaac  31860
cccggcagtg gtggcgcact cctttaatcc cagcacttgg gaggcagagg caggtggatt  31920
cctgagtcta cagagtgagt tccaggacag cctggactgc acagagaaac cctgtctcgg  31980
aaaacccaaa aaaaaaaaaa aaaaaaaaag atatgggaac cataatggac ttgttccacc  32040
tcaaagaact ttatttcttt attttaaaaa taaagggtct ttgtttttgg ccaggggtag  32100
```

agagaaaatt cagtggttag gagtatttgc tgctcttaca cagggtccag gtttgattcc 32160
aaccacatgc tcacagccat ctgaggatct gacacccctt tctttgagta ccaggtatac 32220
atgtataaaa cacccataca tgttaactaa aaatagctta aaaatttgac aagagttcaa 32280
tgaaacccat gaatgtagta tcttgttagg aagacacaat gtccaaggta attcttataa 32340
aggaaaacat ttaattgagg ctggctttcc atcgcatagg ttcagtccat tatcgtgatg 32400
ggaagcatgg cttgcagata gacatggtct tgatcagcag ggaacaggag gagactgttc 32460
cacactcggc cgaacttgag cataggagac ctcaaagcct gcccccacag tgacacactt 32520
cctctaacaa agccatacct acaacaagac cactaatagt gccactacct atgggccaaa 32580
catttaaaca catgtctagg ggtgggggtt agtacctatt caaaccacta cattccacct 32640
tctgggcccc atagtcttgt acctttacca taatgcaaaa tgaatttaat ttcaaaagtc 32700
cacatagttt agcacagttt cagcagtgtt taagtccaaa gtctcttctg agattcatgc 32760
actctttttt attagatatt ttcttcattt acatttcaaa tgctattctg aaagtaccca 32820
ataccctccc cccccaactc cccccccccc ccgccctgct ccccaaccca ctcacttctg 32880
cttcctggcc ctggcattac cctgtactgg ggcatataat ctttgtaaga ccaagggcct 32940
ctcctcccaa ttatggccga ctaggccatc ctctgctaca cattcatgta ctctcttaac 33000

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
tagtctctgt cagtta 16

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
tcatgtacct atagtc 16

<210> SEQ ID NO 15
<211> LENGTH: 23
<212> TYPE: DNA
<213> ORGANISM: Artificial sequence
<220> FEATURE:
<223> OTHER INFORMATION: Primer

<400> SEQUENCE: 15
tgatggtgtt gaggaagctt ttt 23

<210> SEQ ID NO 16
<211> LENGTH: 21
<212> TYPE: DNA
<213> ORGANISM: Artificial sequence
<220> FEATURE:
<223> OTHER INFORMATION: Primer

<400> SEQUENCE: 16
tccctcaagt ctcctgttcc a 21

<210> SEQ ID NO 17
<211> LENGTH: 26
<212> TYPE: DNA
<213> ORGANISM: Artificial sequence
<220> FEATURE:
<223> OTHER INFORMATION: Probe

<400> SEQUENCE: 17
acaacagatc gcgtgatgac cgtctc 26

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
tgcagtgggg tgattt 16

<210> SEQ ID NO 19
<211> LENGTH: 5292
<212> TYPE: DNA
<213> ORGANISM: Homo sapiens

<400> SEQUENCE: 19
ctcttgcagt gaggtgaaga catttgaaaa tcaccccact gcaaactcct ccccctgcta 60
gaaacctcac attgaaatgc tgtaaatgac gtgggccccg agtgcaatcg cgggaagcca 120
gggtttccag ctaggacaca gcaggtcgtg atccgggtcg ggacactgcc tggcagaggc 180
tgcgagcatg gggccctggg gctggaaatt gcgctggacc gtcgccttgc tcctcgccgc 240
ggcggggact gcagtgggcg acagatgcga aagaaacgag ttccagtgcc aagacgggaa 300
atgcatctcc tacaagtggg tctgcgatgg cagcgctgag tgccaggatg gctctgatga 360
gtcccaggag acgtgcttgt ctgtcacctg caaatccggg gacttcagct gtgggggccg 420
tgtcaaccgc tgcattcctc agttctggag gtgcgatggc caagtggact gcgacaacgg 480
ctcagacgag caaggctgtc cccccaagac gtgctcccag gacgagtttc gctgccacga 540
tgggaagtgc atctctcggc agttcgtctg tgactcagac cgggactgct tggacggctc 600
agacgaggcc tcctgcccgg tgctcacctg tggtcccgcc agcttccagt gcaacagctc 660
cacctgcatc ccccagctgt gggcctgcga caacgacccc gactgcgaag atggctcgga 720
tgagtggccg cagcgctgta ggggtcttta cgtgttccaa ggggacagta gcccctgctc 780
ggccttcgag ttccactgcc taagtggcga gtgcatccac tccagctggc gctgtgatgg 840
tggccccgac tgcaaggaca aatctgacga ggaaaactgc gctgtggcca cctgtcgccc 900
tgacgaattc cagtgctctg atggaaactg catccatggc agccggcagt gtgaccggga 960
atatgactgc aaggacatga gcgatgaagt tggctgcgtt aatgtgacac tctgcgaggg 1020
acccaacaag ttcaagtgtc acagcggcga atgcatcacc ctggacaaag tctgcaacat 1080
ggctagagac tgccgggact ggtcagatga acccatcaaa gagtgcggga ccaacgaatg 1140
cttggacaac aacggcggct gttcccacgt ctgcaatgac cttaagatcg gctacgagtg 1200
cctgtgcccc gacggcttcc agctggtggc ccagcgaaga tgcgaagata tcgatgagtg 1260
tcaggatccc gacacctgca gccagctctg cgtgaacctg gagggtggct acaagtgcca 1320
gtgtgaggaa ggcttccagc tggacccccca cacgaaggcc tgcaaggctg tgggctccat 1380
cgcctacctc ttcttcacca accggcacga ggtcaggaag atgacgctgg accggagcga 1440
gtacaccagc ctcatcccca acctgaggaa cgtggtcgct ctggacacgg aggtggccag 1500
caatagaatc tactggtctg acctgtccca gagaatgatc tgcagcaccc agcttgacag 1560
agcccacggc gtctcttcct atgacaccgt catcagcaga gacatccagg cccccgacgg 1620
gctggctgtg gactggatcc acagcaacat ctactggacc gactctgtcc tgggcactgt 1680
ctctgttgcg gataccaagg gcgtgaagag gaaaacgtta ttcagggaga acggctccaa 1740
gccaagggcc atcgtggtgg atcctgttca tggcttcatg tactggactg actggggaac 1800
tcccgccaag atcaagaaag gggcctgaa tggtgtggac atctactcgc tggtgactga 1860
aaacattcag tggcccaatg gcatcaccct agatctcctc agtggccgcc tctactgggt 1920
tgactccaaa cttcactcca tctcaagcat cgatgtcaac gggggcaacc ggaagaccat 1980
cttggaggat gaaaagaggc tggcccaccc cttctccttg gccgtctttg aggacaaagt 2040
attttggaca gatatcatca acgaagccat tttcagtgcc aaccgcctca caggttccga 2100
tgtcaacttg ttggctgaaa acctactgtc cccagaggat atggttctct tccacaacct 2160
cacccagcca agaggagtga actggtgtga gaggaccacc ctgagcaatg gcggctgcca 2220
gtatctgtgc ctccctgccc cgcagatcaa cccccactcg cccaagttta cctgcgcctg 2280
cccggacggc atgctgctgg ccagggacat gaggagctgc ctcacagagg ctgaggctgc 2340
agtggccacc caggagacat ccaccgtcag gctaaaggtc agctccacag ccgtaaggac 2400
acagcacaca accacccgac ctgttcccga cacctcccgg ctgcctgggg ccacccctgg 2460
gctcaccacg gtggagatag tgacaatgtc tcaccaagct ctgggcgacg ttgctggcag 2520
aggaaatgag aagaagccca gtagcgtgag ggctctgtcc attgtcctcc ccatcgtgct 2580
cctcgtcttc ctttgcctgg gggtcttcct tctatggaag aactggcggc ttaagaacat 2640
caacagcatc aactttgaca accccgtcta tcagaagacc acagaggatg aggtccacat 2700
ttgccacaac caggacggct acagctaccc ctcgagacag atggtcagtc tggaggatga 2760
cgtggcgtga acatctgcct ggagtcccgt ccctgcccag aacccttcct gagacctcgc 2820
cggccttgtt ttattcaaag acagagaaga ccaaagcatt gcctgccaga gctttgtttt 2880
atatatttat tcatctggga ggcagaacag gcttcggaca gtgcccatgc aatggcttgg 2940
gttgggattt tggtttcttc ctttcctcgt gaaggataag agaaacaggc ccggggggac 3000
caggatgaca cctccatttc tctccaggaa gttttgagtt tctctccacc gtgacacaat 3060
cctcaaacat ggaagatgaa aggggagggg atgtcaggcc cagagaagca agtggctttc 3120
aacacacaac agcagatggc accaacggga ccccctggcc ctgcctcatc caccaatctc 3180
taagccaaac ccctaaactc aggagtcaac gtgtttacct cttctatgca agccttgcta 3240
gacagccagg ttagcctttg ccctgtcacc cccgaatcat gacccaccca gtgtctttcg 3300
aggtgggttt gtaccttcct taagccagga aagggattca tggcgtcgga aatgatctgg 3360
ctgaatccgt ggtggcaccg agaccaaact cattcaccaa atgatgccac ttcccagagg 3420
cagagcctga gtcactggtc acccttaata tttattaagt gcctgagaca cccggttacc 3480
ttggccgtga ggacacgtgg cctgcaccca ggtgtggctg tcaggacacc agcctggtgc 3540
ccatcctccc gacccctacc cacttccatt cccgtggtct ccttgcactt tctcagttca 3600
gagttgtaca ctgtgtacat ttggcatttg tgttattatt ttgcactgtt ttctgtcgtg 3660
tgtgttggga tgggatccca ggccagggaa agcccgtgtc aatgaatgcc ggggacagag 3720
aggggcaggt tgaccgggac ttcaaagccg tgatcgtgaa tatcgagaac tgccattgtc 3780

-continued

```
gtctttatgt ccgcccacct agtgcttcca cttctatgca aatgcctcca agccattcac   3840

ttccccaatc ttgtcgttga tgggtatgtg tttaaaacat gcacggtgag gccgggcgca   3900

gtggctcacg cctgtaatcc cagcactttg ggaggccgag gcgggtggat catgaggtca   3960

ggagatcgag accatcctgg ctaacacgtg aaaccccgtc tctactaaaa atacaaaaaa   4020

ttagccgggc gtggtggcgg gcacctgtag tcccagctac tcgggaggct gaggcaggag   4080

aatggtgtga acccgggaag cggagcttgc agtgagccga gattgcgcca ctgcagtccg   4140

cagtctggcc tgggcgacag agcgagactc cgtctcaaaa aaaaaaaaca aaaaaaaacc   4200

atgcatggtg catcagcagc ccatggcctc tggccaggca tggcgaggct gaggtgggag   4260

gatggtttga gctcaggcat ttgaggctgt cgtgagctat gattatgcca ctgctttcca   4320

gcctgggcaa catagtaaga ccccatctct taaaaaatga atttggccag acacaggtgc   4380

ctcacgcctg taatcccagc actttgggag gctgagctgg atcacttgag ttcaggagtt   4440

ggagaccagg cctgagcaac aaagcgagat cccatctcta caaaaaccaa aaagttaaaa   4500

atcagctggg tacggtggca cgtgcctgtg atcccagcta cttgggaggc tgaggcagga   4560

ggatcgcctg agcccaggag gtggaggttg cagtgagcca tgatcgagcc actgcactcc   4620

agcctgggca acagatgaag accctatttc agaaatacaa ctataaaaaa ataaataaat   4680

cctccagtct ggatcgtttg acgggacttc aggttctttc tgaaatcgcc gtgttactgt   4740

tgcactgatg tccggagaga cagtgacagc ctccgtcaga ctcccgcgtg aagatgtcac   4800

aagggattgg caattgtccc cagggacaaa acactgtgtc ccccccagtg cagggaaccg   4860

tgataagcct ttctggtttc ggagcacgta aatgcgtccc tgtacagata gtggggattt   4920

tttgttatgt ttgcactttg tatattggtt gaaactgtta tcacttatat atatatatat   4980

acacacatat atataaaatc tatttatttt tgcaaaccct ggttgctgta tttgttcagt   5040

gactattctc ggggccctgt gtagggggtt attgcctctg aaatgcctct tctttatgta   5100

caaagattat ttgcacgaac tggactgtgt gcaacgcttt ttgggagaat gatgtccccg   5160

ttgtatgtat gagtggcttc tgggagatgg gtgtcacttt ttaaaccact gtatagaagg   5220

tttttgtagc ctgaatgtct tactgtgatc aattaaattt cttaaatgaa ccaatttgtc   5280

taaaaaaaaa aa                                                       5292
```

<210> SEQ ID NO 20
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 20

```
ugcagugggg ugauuu                                                     16
```

<210> SEQ ID NO 21
<211> LENGTH: 23
<212> TYPE: RNA
<213> ORGANISM: Artificial sequence
<220> FEATURE:
<223> OTHER INFORMATION: Synthetic oligonucleotide

<400> SEQUENCE: 21

```
auaaaaucua cagucauagg aau                                             23
```

<210> SEQ ID NO 22
<211> LENGTH: 1435

<212> TYPE: DNA
<213> ORGANISM: Homo sapiens

<400> SEQUENCE: 22
ggcggggcct gcttctcctc agcttcaggc ggctgcgacg agccctcagg cgaacctctc 60
ggctttcccg cgcggcgccg cctcttgctg cgcctccgcc tcctcctctg ctccgccacc 120
ggcttcctcc tcctgagcag tcagcccgcg cgccggccgg ctccgttatg gcgacccgca 180
gccctggcgt cgtgattagt gatgatgaac caggttatga ccttgattta ttttgcatac 240
ctaatcatta tgctgaggat ttggaaaggg tgtttattcc tcatggacta attatggaca 300
ggactgaacg tcttgctcga gatgtgatga aggagatggg aggccatcac attgtagccc 360
tctgtgtgct caaggggggc tataaattct ttgctgacct gctggattac atcaaagcac 420
tgaatagaaa tagtgataga tccattccta tgactgtaga ttttatcaga ctgaagagct 480
attgtaatga ccagtcaaca ggggacataa aagtaattgg tggagatgat ctctcaactt 540
taactggaaa gaatgtcttg attgtggaag atataattga cactggcaaa acaatgcaga 600
ctttgctttc cttggtcagg cagtataatc caaagatggt caaggtcgca agcttgctgg 660
tgaaaaggac cccacgaagt gttggatata agccagactt tgttggattt gaaattccag 720
acaagtttgt tgtaggatat gcccttgact ataatgaata cttcagggat ttgaatcatg 780
tttgtgtcat tagtgaaact ggaaaagcaa aatacaaagc ctaagatgag agttcaagtt 840
gagtttggaa acatctggag tcctattgac atcgccagta aaattatcaa tgttctagtt 900
ctgtggccat ctgcttagta gagctttttg catgtatctt ctaagaattt tatctgtttt 960
gtactttaga aatgtcagtt gctgcattcc taaactgttt atttgcacta tgagcctata 1020
gactatcagt tccctttggg cggattgttg tttaacttgt aaatgaaaaa attctcttaa 1080
accacagcac tattgagtga aacattgaac tcatatctgt aagaaataaa gagaagatat 1140
attagttttt taattggtat tttaattttt atatatgcag gaaagaatag aagtgattga 1200
atattgttaa ttataccacc gtgtgttaga aaagtaagaa gcagtcaatt ttcacatcaa 1260
agacagcatc taagaagttt tgttctgtcc tggaattatt ttagtagtgt ttcagtaatg 1320
ttgactgtat tttccaactt gttcaaatta ttaccagtga atctttgtca gcagttccct 1380
tttaaatgca aatcaataaa ttcccaaaaa tttaaaaaaa aaaaaaaaaa aaaaa 1435

<210> SEQ ID NO 23
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 23
uccuaugacu guagauuuua u 21

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 24

-continued

```
tuaucuauaa ugaucaggua a                                              21


<210> SEQ ID NO 25
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 25

accugaucau uauagauaa                                                 19


<210> SEQ ID NO 26
<211> LENGTH: 8515
<212> TYPE: DNA
<213> ORGANISM: Homo sapiens

<400> SEQUENCE: 26

gttctctcct ctcggaagct gcagccatga tggaagtttg agagttgagc cgctgtgagg     60

cgaggccggg ctcaggcgag ggagatgaga gacggcggcg gccgcggccc ggagcccctc    120

tcagcgcctg tgagcagccg cgggggcagc gccctcgggg agccggccgg cctgcggcgg    180

cggcagcggc ggcgtttctc gcctcctctt cgtcttttct aaccgtgcag cctcttcctc    240

ggcttctcct gaaagggaag gtggaagccg tgggctcggg cgggagccgg ctgaggcgcg    300

gcggcggcgg cggcacctcc cgctcctgga gcggggggga gaagcggcgg cggcggcggc    360

cgcggcggct gcagctccag ggagggggtc tgagtcgcct gtcaccattt ccagggctgg    420

gaacgccgga gagttggtct ctccccttct actgcctcca acacggcggc ggcggcggct    480

ggcacatcca gggacccggg ccggttttaa acctcccgtg cgccgccgcc gcaccccccg    540

tggcccgggc tccggaggcc gccggcggag gcagccgttc ggaggattat tcgtcttctc    600

cccattccgc tgccgccgct gccaggcctc tggctgctga ggagaagcag gcccagtcgc    660

tgcaaccatc cagcagccgc cgcagcagcc attacccggc tgcggtccag agccaagcgg    720

cggcagagcg aggggcatca gctaccgcca agtccagagc catttccatc ctgcagaaga    780

agccccgcca ccagcagctt ctgccatctc tctcctcctt tttcttcagc cacaggctcc    840

cagacatgac agccatcatc aaagagatcg ttagcagaaa caaaaggaga tatcaagagg    900

atggattcga cttagacttg acctatattt atccaaacat tattgctatg ggatttcctg    960

cagaaagact tgaaggcgta tacaggaaca atattgatga tgtagtaagg tttttggatt   1020

caaagcataa aaaccattac aagatataca atctttgtgc tgaaagacat tatgacaccg   1080

ccaaatttaa ttgcagagtt gcacaatatc cttttgaaga ccataaccca ccacagctag   1140

aacttatcaa acccttttgt gaagatcttg accaatggct aagtgaagat gacaatcatg   1200

ttgcagcaat tcactgtaaa gctggaaagg gacgaactgg tgtaatgata tgtgcatatt   1260

tattacatcg gggcaaattt ttaaaggcac aagaggccct agatttctat ggggaagtaa   1320

ggaccagaga caaaaaggga gtaactattc ccagtcagag gcgctatgtg tattattata   1380

gctacctgtt aaagaatcat ctggattata gaccagtggc actgttgttt cacaagatga   1440

tgtttgaaac tattccaatg ttcagtggcg gaacttgcaa tcctcagttt gtggtctgcc   1500

agctaaaggt gaagatatat tcctccaatt caggacccac acgacgggaa gacaagttca   1560

tgtactttga gttccctcag ccgttacctg tgtgtggtga tatcaaagta gagttcttcc   1620

acaaacagaa caagatgcta aaaaaggaca aaatgtttca cttttgggta aatacattct   1680

tcataccagg accagaggaa acctcagaaa aagtagaaaa tggaagtcta tgtgatcaag   1740
```

aaatcgatag catttgcagt atagagcgtg cagataatga caaggaatat ctagtactta 1800
ctttaacaaa aaatgatctt gacaaagcaa ataaagacaa agccaaccga tacttttctc 1860
caaattttaa ggtgaagctg tacttcacaa aaacagtaga ggagccgtca aatccagagg 1920
ctagcagttc aacttctgta acaccagatg ttagtgacaa tgaacctgat cattatagat 1980
attctgacac cactgactct gatccagaga atgaaccttt tgatgaagat cagcatacac 2040
aaattacaaa agtctgaatt tttttttatc aagagggata aaacaccatg aaaataaact 2100
tgaataaact gaaaatggac cttttttttt ttaatggcaa taggacattg tgtcagatta 2160
ccagttatag gaacaattct cttttcctga ccaatcttgt tttaccctat acatccacag 2220
ggttttgaca cttgttgtcc agttgaaaaa aggttgtgta gctgtgtcat gtatatacct 2280
ttttgtgtca aaaggacatt taaaattcaa ttaggattaa taaagatggc actttcccgt 2340
tttattccag ttttataaaa agtggagaca gactgatgtg tatacgtagg aatttttttcc 2400
ttttgtgttc tgtcaccaac tgaagtggct aaagagcttt gtgatatact ggttcacatc 2460
ctaccccttt gcacttgtgg caacagataa gtttgcagtt ggctaagaga ggtttccgaa 2520
gggttttgct acattctaat gcatgtattc gggttagggg aatggaggga atgctcagaa 2580
aggaaataat tttatgctgg actctggacc atataccatc tccagctatt tacacacacc 2640
tttctttagc atgctacagt tattaatctg gacattcgag gaattggccg ctgtcactgc 2700
ttgttgtttg cgcatttttt tttaaagcat attggtgcta gaaaaggcag ctaaaggaag 2760
tgaatctgta ttggggtaca ggaatgaacc ttctgcaaca tcttaagatc cacaaatgaa 2820
gggatataaa aataatgtca taggtaagaa acacagcaac aatgacttaa ccatataaat 2880
gtggaggcta tcaacaaaga atgggcttga aacattataa aaattgacaa tgatttatta 2940
aatatgtttt ctcaattgta acgacttctc catctcctgt gtaatcaagg ccagtgctaa 3000
aattcagatg ctgttagtac ctacatcagt caacaactta cacttatttt actagttttc 3060
aatcataata cctgctgtgg atgcttcatg tgctgcctgc aagcttcttt tttctcatta 3120
aatataaaat attttgtaat gctgcacaga aattttcaat ttgagattct acagtaagcg 3180
tttttttct ttgaagattt atgatgcact tattcaatag ctgtcagccg ttccaccctt 3240
ttgaccttac acattctatt acaatgaatt ttgcagtttt gcacattttt taaatgtcat 3300
taactgttag ggaattttac ttgaatactg aatacatata atgtttatat taaaaaggac 3360
atttgtgtta aaaaggaaat tagagttgca gtaaactttc aatgctgcac acaaaaaaaa 3420
gacatttgat ttttcagtag aaattgtcct acatgtgctt tattgatttg ctattgaaag 3480
aatagggttt tttttttttt tttttttttt ttttttaaat gtgcagtgtt gaatcatttc 3540
ttcatagtgc tcccccgagt tgggactagg gcttcaattt cacttcttaa aaaaaatcat 3600
catatatttg atatgcccag actgcatacg attttaagcg gagtacaact actattgtaa 3660
agctaatgtg aagatattat taaaaaggtt ttttttttcca gaaatttggt gtcttcaaat 3720
tataccttca ccttgacatt tgaatatcca gccattttgt ttcttaatgg tataaaattc 3780
cattttcaat aacttattgg tgctgaaatt gttcactagc tgtggtctga cctagttaat 3840
ttacaaatac agattgaata ggacctacta gagcagcatt tatagagttt gatggcaaat 3900
agattaggca gaacttcatc taaaatattc ttagtaaata atgttgacac gttttccata 3960
ccttgtcagt ttcattcaac aatttttaaa tttttaacaa agctcttagg atttacacat 4020
ttatatttaa acattgatat atagagtatt gattgattgc tcataagtta aattggtaaa 4080

-continued

```
gttagagaca actattctaa cacctcacca ttgaaattta tatgccacct tgtctttcat   4140
aaaagctgaa aattgttacc taaaatgaaa atcaacttca tgttttgaag atagttataa   4200
atattgttct ttgttacaat ttcgggcacc gcatattaaa acgtaacttt attgttccaa   4260
tatgtaacat ggagggccag gtcataaata atgacattat aatgggcttt tgcactgtta   4320
ttatttttcc tttggaatgt gaaggtctga atgagggttt tgattttgaa tgtttcaatg   4380
tttttgagaa gccttgctta cattttatgg tgtagtcatt ggaaatggaa aaatggcatt   4440
atatatatta tatatataaa tatatattat acatactctc cttactttat ttcagttacc   4500
atccccatag aatttgacaa gaattgctat gactgaaagg ttttcgagtc ctaattaaaa   4560
ctttatttat ggcagtattc ataattagcc tgaaatgcat tctgtaggta atctctgagt   4620
ttctggaata ttttcttaga ctttttggat gtgcagcagc ttacatgtct gaagttactt   4680
gaaggcatca cttttaagaa agcttacagt tgggccctgt accatcccaa gtcctttgta   4740
gctcctcttg aacatgtttg ccatactttt aaaagggtag ttgaataaat agcatcacca   4800
ttctttgctg tggcacaggt tataaactta agtggagttt accggcagca tcaaatgttt   4860
cagctttaaa aaataaaagt agggtacaag tttaatgttt agttctagaa attttgtgca   4920
atatgttcat aacgatggct gtggttgcca caaagtgcct cgtttacctt taaatactgt   4980
taatgtgtca tgcatgcaga tggaaggggt ggaactgtgc actaaagtgg gggctttaac   5040
tgtagtattt ggcagagttg ccttctacct gccagttcaa aagttcaacc tgttttcata   5100
tagaatatat atactaaaaa atttcagtct gttaaacagc cttactctga ttcagcctct   5160
tcagatactc ttgtgctgtg cagcagtggc tctgtgtgta aatgctatgc actgaggata   5220
cacaaaaata ccaatatgat gtgtacagga taatgcctca tcccaatcag atgtccattt   5280
gttattgtgt ttgttaacaa ccctttatct cttagtgtta taaactccac ttaaaactga   5340
ttaaagtctc attcttgtca ttgtgtgggt gttttattaa atgagagttt ataattcaaa   5400
ttgcttaagt ccattgaagt tttaattaat gggcagccaa atgtgaatac aaagttttca   5460
gttttttttt ttcctgctgt ccttcaaagc ctactgttta aaaaaaaaaa aaaaaaaaaa   5520
catggcctga gagtagagta tctgtctact catgtttaat taaggaaaaa cacttatttt   5580
tagggcttta gtcatcactt cataaattgt ataagcacat taaatagcgt tctagtcctg   5640
aaaaagtcca agattcttag aaaattgtgc atatttttat tatgacagat gtttgaagat   5700
aattccccag aatggatttg atactttaga tttcaatttt gtggcttttg tctattattc   5760
tgtactctgc catcagcata tggaaagctt catttactca tcatgacttg tgccatataa   5820
aaattgatat ttcggaatag tctaaaggac tttttgtact tgaatttaat catgttgttt   5880
ctaatattct taaaagcttg aagactaaag catatccttt caacaaagca tagtaaggta   5940
ataagaaagt gtagtttgta caagtgttaa aaaaataaag tagacaatgt tacagtggga   6000
cttattattt caagtttaca ttttctccat gtaatttttt aaaaagtaaa tgaaaaaatg   6060
tgcaataatg taaaatatga agtgtatgtg tacacacatt ttatttttcg gtatcttggg   6120
tatacgtatg gttgaaaact atactggagt ctaaaagtat tctaatttat aagaagacat   6180
tttggtgatg tttgaaaaat agaaatgtgc tagttttgtt tttatatcat gtcctttgta   6240
cgttgtaata tgagctggct tggttcagta aatgccatca ccatttccat tgagaattta   6300
aaactcacca gtgtttaata tgcaggcttc caaaggctta tgaaaaaaat caagacccctt  6360
aaatctagtt aatttgctgc taacatgaaa ctctttggtt cttttatttt tgccagataa   6420
ttagacacac atctaaagct tagtcttaaa tggcttaagt gtagctattg attagtgctg   6480
```

-continued

```
ttgctagttc agaaagaaat gtttgtgaat ggaaacaaga atattcagtc caaactgttg   6540
taaggacagt acctgaaaac caggaaacag gataatggaa aaagtctttt aaagatgaaa   6600
tgttggagcc aactttctta tagaattaat tgtatgtggc tatagaaagc ctaatgattg   6660
ttgcttattt ttgagagcat attattcttt tatgaccata atcttgctgt ttttccatct   6720
tccaaaagat cttccttcta atatgtatat cagaatgtgg gtagccagtc agacaaattc   6780
atattggttg gtagctttaa aaagtttgta atgtgaagac aggaaaggac aaaatagttt   6840
gctttggtgg tagtactctg gttgttaagc taggtatttt gagactactt ccccatcaca   6900
acaacaataa aataatcact cataatccta tcacctggag acatagccat cgttaatatg   6960
ttagtgacta tacaatcatg ttttcttctg tatatccatg tatattcttt aaaaatgaaa   7020
tttatactgt acctgatctc aaagcttttt agcttagtat atctgtcatg aatttgtagg   7080
atgttccatt gcatcagaaa acggacagtg atttgattac tttctaatgc cacagatgca   7140
gattacatgt agttattgag aatcctttcg aattcagtgg cttaatcatg aatgtctaaa   7200
tattgttgac attaggatga tacatgtaaa ttaaagttac atttgtttag catagacaag   7260
cttaacattg tagatgtttc tcttcaaaaa tcatcttaaa catttgcatt tggaattgtg   7320
ttaaatagaa tgtgtgaaac actgtattag taaacttcat cacctttcta cttccttata   7380
gtttgaactt ttcagttttt gtagttccca aacagttgct caatttagag caaattaatt   7440
taacacctgc caaaaaaagg ctgctgttgg cttatcagtt gtctttaaat tcaaatgctc   7500
atgtgacttt tatcacatca aaaaatattt cattaatgat tcacctttag ctctgaaaat   7560
taccgcgttt agtaattata gtgggcttat aaaaacatgc aactcttttt gatagttatt   7620
tgagaatttt ggtgaaaaat atttagctga gggcagtata gaacttataa accaatatat   7680
tgatattttt aaaacatttt tacatataag taaactgcca tctttgagca taactacatt   7740
taaaaataaa gctgcatatt tttaaatcaa gtgtttaaca agaatttata tttttttattt   7800
tttaaaatta aaaataattt atatttcctc tgttgcatga ggattctcat ctgtgcttat   7860
aatggttaga gattttattt gtgtggaatg aagtgaggct tgtagtcatg gttctagtgt   7920
ttcagtttgc caagtctgtt tactgcagtg aaattcatca aatgtttcag tgtggttttc   7980
tgtagcctat catttactgg ctattttttt atgtacacct ttaggatttt ctgcctactc   8040
tatccagttg tccaaatgat atcctacatt ttacaaatgc cctttcagtt tctattttct   8100
ttttccatta aattgccctc atgtcctaat gtgcagtttg taagtgtgtg tgtgtgtgtc   8160
tgtgtgtgtg tgaatttgat tttcaagagt gctagacttc caatttgaga gattaaataa   8220
tttaattcag gcaaacattt ttcattggaa tttcacagtt cattgtaatg aaaatgttaa   8280
tcctggatga cctttgacat acagtaatga atcttggata ttaatgaatt tgttagtagc   8340
atcttgatgt gtgttttaat gagttatttt caaagttgtg cattaaacca aagttggcat   8400
actggaagtg tttatatcaa gttccatttg gctactgatg gacaaaaaat agaaatgcct   8460
tcctatggag agtatttttc ctttaaaaaa ttaaaaaggt taattatttt gacta        8515
```

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
tgcatggtgt agcccccctg 20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
gttttcaaac acaccttcat 20

<210> SEQ ID NO 29
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: n is a, c, g, or t

<400> SEQUENCE: 29
nnnnnnnnnn nnnnnn 16

<210> SEQ ID NO 30
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 30
cauuuuaauc cucacucuaa a 21

<210> SEQ ID NO 31
<211> LENGTH: 23
<212> TYPE: RNA
<213> ORGANISM: Artificial sequence
<220> FEATURE:
<223> OTHER INFORMATION: Synthetic oligonucleotide

<400> SEQUENCE: 31
uuuagaguga ggauuaaaau gaa 23

<210> SEQ ID NO 32
<211> LENGTH: 141001
<212> TYPE: DNA
<213> ORGANISM: Homo sapiens

<400> SEQUENCE: 32
aatttataaa ggaaaaaggt ttaattgact cacagttcag catgtctggg gaagtgttag 60
gaaacttaca atcatggcag aagagaaagc aaaccatcct ttctcacatg gtgacaggaa 120
gagcaaagcg gggtaagccc cttacaaaac caccagatct catgagaact cactatcacg 180
agaacaccat ggaggtaact gcccccatga ttcaattacc tcccaccagg tccctcccac 240
gacatgtggg gattatgcga actccaactc aagatgagat ttgggtgggg acacagccaa 300
accatatcag aagcttaacc ttctttggag catgattatt cagttgaacc taagttcagt 360
agtcacccag ttatgctgtc ttcagctact attttccata tgtttctcaa acatctgata 420
tatcacactg gctagtgcac tttcttccac cagcatacca tctcaattta ccactttaac 480
aattggactg ccactttgtg tcagggacta tctgtgctcc aactactaca agtgataagg 540

```
tcctcactga cagccaggga gcaagtgatc cagctctaaa actcacctta tcatctgctt    600
tcctagacca ctcctaacaa ccaactattc tgggttgagt tctccaagag gcagagagtt    660
caggatacag aatgttgttt tgtttttgtt gttgttgctg ttgttgtttg tgtgtgtgtt    720
tgggcttttt tgagacggag tctcactctg ttgcccaggt agaagtgcag tggcatgatc    780
tcagctccct gcaacctcca cctcctgggt ttaagtgatt cccctgcctc cacctcctga    840
gtagctggga ctacaagtgt gcgccaccac acccagctaa tttttgtgtt tttagtagaa    900
atggggtttt accatgttgg ctaggctgct cccaaactcc tgacctccag tgatccacct    960
acctctgcct cccaaagtgc tgggattaca ggcgtgagcc accacaccca gcccagaatg   1020
tttattagaa tgcacaatta ataccagagg cagtggggaa ggaaggactg agcagaggag   1080
gaagttgagt tgtgattcaa cccaacaact gcctggctgg catggggagc tctggagtta   1140
aatagggcca tcagactttc ccagtgtggg gccaacatga ctgggtcttt ataccccccac   1200
ctctgtcagt cactcaacgt ggtctccctg caacaaggtg actcttgcag ccgagacaat   1260
ccctgaaggg acagagggct gaagcctgtc tgccaacagc actcccagtg gctggaacaa   1320
gtccttccct ataggggaat ctgggcggca cacctccatc tccatgtcca tcacatacga   1380
tatcacagac atttaaatat tttgataact gtacataaga gtttccttta taatcttata   1440
gatcttattt tatgcatttg aaaatattct tctgagacag ggcttttatc atattgccat   1500
agggtgccac gatataaaaa aggttaaata ctctctgatt cagaagtatc caatgatgac   1560
ttctctctca tgcatttaat tgaaaatctg gtttttctcc ttctctgcta gttctctacc   1620
tctctcccca cctcccacat catagcctat tcacatatgt ctgaatctca tgatagacaa   1680
gttcaggttc ttttcccagg ttctttttac cacatccccc cacccccaca taaaaagtat   1740
atatggcaca gcctaggttc cacccaaatc ctttctcctc ttcttcctgg gcccacaact   1800
ctcctacata cattggtata ccttgcgctt agggatggcc atgtgactaa gttctaacag   1860
tggaacatga tcagatgcca cttccagcct ctaagacagc cagtgtgttt cctccataag   1920
ctccttctct tcctcccaac tggagactct aaatgatgac cctgcctcaa gcaagcaaac   1980
aacaagtccc tcaggggtgg tgtaggctgc aaatggaagg agcttgagtc ccaaaccttc   2040
cacggagaag gctggctacc aacctggatc actcacccaa gactgctcga agagttggtt   2100
tgaaccattg tgttttgggg tctatttatt acaacagttt agcttgcttt gtgaatagat   2160
ttagtggcag agcctccaaa ttctatagat acattgatct cagtcctaac cgcatctgga   2220
acaccattaa ataaaggaat tgcaaaccca gagaaggtaa tgaatttgtc taaggtcata   2280
caagatggct aggatcagga cccaactctc cagttttctt tcttctctgc tattctgcct   2340
tctgtgatcc tacataagtg ggcatgattg tataacatat gcggccatga gatttctctt   2400
tcagcaagag aaagggacag gaagaaagag agggaatgca ttttcttggc ctgaattagt   2460
gtgagccatt agttacctac attgactaaa ttatctggaa tgaacattca actctacatc   2520
acatatagtt aaaatgacag atctgcttaa gattgtttct agcatacgtt atttcaattt   2580
aggcaaatgt gaccattcag tgtgagggga ccatactgtc attaggtccc tgtcagttct   2640
caattatact gttatcttag agggggaaaa atgtgaaatt tgaatgtaga cgagtgttga   2700
tttgactgct acagtttatt ttacgtatag aaataaaata atgtgtagca aaagcattat   2760
tacaaagatg ataatgaaat aactagtatt tataatagta taatagtata gtatttataa   2820
tagtatgata gtttaatgac tatttgtcag atgttgtgta agaaacttta tacacacaca   2880
```

```
cacacacacc tcatttaatt cctgtatcaa tcaggataca ggacgctgtg gtaacaactc   2940
ctcaaatctc ggtggcttgc acaacaaatg cttatttctt ttttttttt gacaccaagt    3000
cttgctctgt aacaggctgg agtgcaatgg tgcaatctcg gctcactgca gcctctgcct   3060
cctgggttca agcgattctc ctgcctcagt ctctcgagta gctgggaaca caggcacgcg   3120
ccaccacatc tggctaattt ttgtgatttt agtagagatg ggatttcacc atgttgctca   3180
ggctggcctt gaactcctga cctcaagcga tccacccacc tcagcctccc aaagtgctgg   3240
gattacaggc atgagccact gcgcccagcc ccaaatgttt atttcttgct catgtgacat   3300
gtacttcctc gagtttttcc ttcctgagat ctaagctgaa ggaacagctc tctggagcca   3360
cgccattctg gtggcggaaa ggaagagtaa aagtggtaga accttgcaat gctcttgaag   3420
cgcctatttg gaatgtctac atcatgtaaa tggtaatgga caagtatgta taatccccac   3480
accaaaaaaa ggggacacta ttggggacaa taaccacatt tcaatgctgc aagacggata   3540
ttgactgcac ccccttccca ctttcagaaa gaagaagagt aattttgctg aactccttct   3600
agagactgga aatgtccctt ccagttgggg tgattaggga aggctttggt aaaatttgag   3660
ctagagtttg aaggttaggt agactactgg tgggtgaaga aagaacaagg acctttgtag   3720
gcaaaggaaa acctcagaat tacagaggtg gaaaaagagt tctagtcaag ccacttcagc   3780
tggctacaga gtaggtggga aagaaaatgg gaggacaagg gctcagatga tgggggggttg  3840
gggcattggg gggacacttg aaagctaaac taaggggttg aacttaattt aggaggcagt   3900
tagaagcttt tacatatttt tgagcaagag agtgacataa ttaaaatgat ctgggccagg   3960
tgtggtggct cacacctgta atcccagcac tttgggaggc tgaggagctt gggtcacctg   4020
aggtcaggag atcgagacca gcctggccaa catggtgaaa tcccgtccta ctaaaaatac   4080
aaaaattagc cgggagtggt ggcatatgcc tgtaatccca gtagctggga ggctgagaca   4140
ggaaaatcgc ttgaacccgg gaaacaggtt gcagtgagcc gagatcgtgc cactgcactc   4200
cagcctgggc aacagagcga gactccatct caaaaaaaca aaacaaacac acacaaaaaa   4260
ccaaaaataa ataaataaaa tgatcacttc tgaatactga tctaactagg ggttgcaggg   4320
tgggctgata tagggagaaa ctggagagca aggagatcac taaggtccct acatgtccag   4380
aaccaagata gaggtcttga actaggatgg tggcagttag aacaacaaca acaaaaagtc   4440
aattccaggc tgagtgcagt ggctcatgcc tgtaatccca acgctttggg aggctgaggt   4500
gggagttaga aagcagcctg ggcaacactg caagacctcc tctctaaaaa aaaaaaaaaa   4560
aaaaagttag ccaggtgtgg tggtgcccac ctgtagtccc agcaactcag aaggctgagg   4620
tgggaagatt gcttgagccc caggagttca agcttgccgt gagctacgat tgtgccactg   4680
cactccagcc tgagcaagac cttgtctcca aaaaaaggtc aattccactg actttcttaa   4740
ggtgtacacc atcaaggggc agctccatct ccaggccatt ggctcatgag acattctgta   4800
gtcagaaggc tagggcagat tgctttgagc aagcccccat ggtggttctc actcctactt   4860
ctttgggtat atgcccctct gtttaaaaat aaagttaata tgcatttaaa aaaaaaaagg   4920
agaaaaaggt cagttccaga aactgtgtga ataaagcatt ttacttgctt tttctattaa   4980
tctataacat atgttgattt tttaaaaaga atataagagc tatgcaaatt ggagcttcaa   5040
gacaacttcc catctcccta ggaggagatg gctgccctaa acccccctac atagaaatca   5100
tcccactgct tgggcttaaa cttgatgttg gggaaatgaa aaatccaagc taaggccgaa   5160
gcctggggcc tgggcgacca gcagaatgag gaccactggt cagtttcagg ctgaggtgcg   5220
tcttccaggg gacaatctct agctggccct taaacattca gacttcaagc tctatttaca   5280
```

```
gcataaaggt gtttcaaaag acgtgataca aataactgca aatgctctgc gatgtgttaa   5340
gcactgtttg aaattcgtct aatttaagat tttttttct gacgtaacgg ttagattcac    5400
gtttcttttt ttttaagtac agttctactg tattgtaact gagttagctt gctttaagcc   5460
gatttgttaa ggaaaggatt caccttggtc agtaacaaaa aaggtgggaa aaaagcaagg   5520
agaaaggaag cagcctgggg gaaagagacc ttagccaggg gggcggtttc gggactacga   5580
agggtcgggg cggacggact cgagggccgg ccacgtggaa ggccgctcag gacttctgta   5640
ggagaggaca ccgccccagg ctgactgaaa gtaaagggca gcggacccag cggcggagcc   5700
actggccttg ccccgacccc gcatggcccg aaggaggaca cccacccccg caacgacaca   5760
aagactccaa ctacaggagg tggagaaagc gcgtgcgcca cggaacgcgc gtgcgcgctg   5820
cggtcagcgc cgcggcctga ggcgtagcgg gagggggacc gcgaaagggc agcgccgaga   5880
ggaacgagcc gggagacgcc ggacggccga gcggcagggc gctcgcgcgc gcccactagt   5940
ggccggagga gaaggctccc gcggaggccg cgctgcccgc cccctcccct ggggaggctc   6000
gcgttcccgc tgctcgcgcc tgcgccgccc gccggcctca ggaacgcgcc ctcttcgccg   6060
gcgcgcgccc tcgcagtcac cgccacccac cagctccggc accaacagca gcgccgctgc   6120
caccgcccac cttctgccgc cgccaccaca gccaccttct cctcctccgc tgtcctctcc   6180
cgtcctcgcc tctgtcgact atcaggtaag cgccgcggct ccgaaatctg cctcgccgtc   6240
cgcctctgtg cacccctgcg ccgccgcccc tcgccctccc tctccgcaga ctggggcttc   6300
gtgcgccggg catcggtcgg ggccaccgca gggcccctcc ctgcctcccc tgctcggggg   6360
ctggggccag ggcggcctgg aaagggacct gagcaaggga tgcacgcacg cgtgagtgcg   6420
cgcgtgtgtg tgtgctggag ggtcttcacc accagattcg cgcagacccc aggtggaggc   6480
tgtgccggca gggtggggcg cggcggcggt gacttggggg agggggctgc ccttcactct   6540
cgactgcagc cttttgccgc aatgggcgtg tgtgtgtgtg tgtgtgtgtg tgtgtgtgtg   6600
tgtgtgtgtg gaggggtccg ataacgaccc ccgaaaccga atctgaaatc cgctgtccct   6660
gccgctgttc gccatcagct ctaagaaaga cgtggatcgg gttctagaaa agatgactcc   6720
ctgcacgccc ctccctgcac ctcccgagca gtgattccga cagggccttc actgcccctg   6780
attttaggcg ggggccggcc ccctcccctt ttcctccttc agaaacccgt aggggacatt   6840
tgggggctgg gagaaatcga ggagatgggg aggggtccac gcgctgtcac tttagttgcc   6900
cttccccctg cgcacgcctg gcacagagac gcgagcagcg ccgtgcctga gaacagtgcg   6960
cggatcccac tgtgcacgct cgcaaaggca gggttcacct ggcctggcga tgtggacgga   7020
ctcggcggcc gctggtcccc gttcgcgggc acgcacagcc gcagccacgc acggatgggc   7080
gcggggctgc aggtgcatct cggggcggat ttctttctca gcgctcggag cgcagggcgc   7140
ccggcgtgtg cgctccctgc cggaggcgcg gggctggcgc gcagggctcg cccctcactg   7200
cggcagtggg tgtggaccct ggtgggcgag gaagggggag gataggctgt gcctcctccc   7260
actcccgccc ccagccccccc tttttttccc cctcggaacg cgaggtgcca tcttttttcg  7320
gcgtgtcacg tctttacggt gccatgccaa accgggtggc cgggcttcat aggacagggc   7380
ggggcctggc attaaaggga gggggacaat cagcgctgaa atcttggcgt tttgctgctg   7440
cgggcgtgag cactgggggc gttcgcccag caccttcttc gggggctctt tgctttgtct   7500
gtagaggtta cgtgatctgc gctcccagcc ctggtttctg gcttttattc tgagggtgtt   7560
cagtcaacct ccccccctacg cccatgcgcc tctctttcct ttttcgctcc tcatttccga  7620
```

```
gcccattgtt ggatctcgag gcttgctggg ttcgatgaac tcgagtcaac cccccgaccc   7680
ccggcacgca tggaacgggc gtgaccgcgc gcagcctcgt ctcggagtct gccggcgccg   7740
ggaagcttct gaagggatgg gattcgagtc tccgtgcgcg ctgcgggcgg cggcagaggg   7800
atctcgcccc tccctacacc ccaagtgtcc tgagggccac gccacaccag gttgcccagc   7860
gagggacgct ggctacccat ccggggatgg gtggggagcc ctggcggggc ctctccggct   7920
ttacgccctg ttgcttcgcc tggccggaga atgtgaggaa ggggcataag gttactggtg   7980
cttcggccac acccatcttt ctgagcccac tggactgggc gcagaggggg gattgccatg   8040
gaaaccacag gtgtccggag aggggatctt ggggctggcc tcaccccttc cctgcggaga   8100
ttggggaccc tggggtaggg ggagccgcgc ccagtcggcc tcctggagga cacgggagga   8160
agccccgaac cccgcgcct gaggctgttt ctgattggcc cctggaggcc gcagacacgc   8220
agataggcgg ccctgggtgt atttttatta atattatgtc cgtactgatt aatattattt   8280
atcttaaata aatttcaccc gtgtccaagt tcaccgcgcc cccaaaaccg agtctggggc   8340
ggcaggggga actcctggcc aacgaatcca tgcctcgccc tcctgtgatg aacctggtac   8400
gcacggtttt ctggttaatt ctatcgctga aaactggtgc ggggggcgca cttctgagac   8460
ggaagagcat ctaggagctg aatcctccac gcgggtcgcc caggttgatc tgaatttctg   8520
gggaatggct tggctgcccg cccgggacca ggccgaccct ccttgacggt ggcgtagagg   8580
gctggagcct gggtactgcg aggctcctcg catggctggg cccgccgcga ggggttgcag   8640
agcggctcag ggatcgattc aagcatcgtc tctcctccct cgcccccaga cagagctggg   8700
cgcggggttc cccttccaga tggagcgagg gtctcggggt ggccccggaa aaggggagcc   8760
cgcggccacg gctacgtatt gccatctcgc gagcagagat gtcacctcct gcctttggag   8820
gaaagggagc ccggtgggga tgagcgcatt tagcccaatg ctgggaacaa agcgcactcc   8880
gcgcttctgc gatttcgctc cattttgaaa tgtgttggcg ctttggtggg gccgctgcgg   8940
tgggcaaggc cgggggcgct gttaatggag gaacctcagg gggacggtcc ttcgtaggaa   9000
actctatcct ggctctgcgc gcgctttaag gaaatggctt ccctccagga cctcgaggga   9060
tgcagctttt gcgcggatga cggtggggtg ctgaaccagc cggtgcgcct ctggaaatgt   9120
ctgggcacgg atcctggggc catcgacgac tcctccccat tcccagcagg cgggagctct   9180
tacattccga gcgagtgacc cctctcaccc tctggcgctc acacacctgt aactccaaac   9240
ctccgtctca gaatggtcca ggctggaagg gatgatgggg gctccgacag cgactgccta   9300
gctcacccct ctgcgtgctc aggctccagg ctcagcagga ccaatttgag ttctatctga   9360
tccccctcgg ccccttaact gacccatcct acaggagaca gggaaatgtc tttcctaccg   9420
cggttgattc tggggtgtca ttttgtgttt tgtgatggct gcttatattt actgtataag   9480
cattgtattt actgtataag cattgtatta taattactgt ataagctgct tatatttact   9540
gtataagcat ctccaaatcc tccctctacg taaacaaatt aatggataaa cagataagtg   9600
tatcccctgc ccccacccct gctacgcagg tccggagtga ctcttgaagc tcatacattc   9660
cttggccaag tttgcttctc taacagatgt ttatatagca ataacctggc ttggctcttg   9720
ggttcacctt tggacgattt ggggaagggg cttgttggct ttgctgggtt ttggatgagt   9780
gacagtccat gactgttcct gctggaaggg cgtgactttt aagtggtttc taatatcagg   9840
cattgctcct ccgacaggaa caaaagaaat ggatactgcc cataaattgt tagaaaactt   9900
agaatcgctt tgattgagga aaggttagat ttattccggt tggaaaaagt ggcctttcta   9960
ttaaacgtgc cctttgaccc tcatgccctt ggaggtcggt gccagcctgg agatgggata  10020
```

-continued

```
agattgtggt tttccttctg cctttttaac atctgttgtt acagtccatt tgttgaaaat  10080
ttaaagaaac tgttttattc cactttccct cagcatttat gtgtgtggtt tcagtagctc  10140
tgtggctata tgtacgaaca cgtgttattt ttccaattgg acatgtgata attttccaac  10200
tggaccttgc cttctattga tgtatttatt tagcatcttc cttactccct ccttgaaaaa  10260
gaatcactca aaaacaaata aaaacagccg taggggccta atacagtgct agacatacaa  10320
gaggtattcg gtccatacca aatggatttt atccatgaag gataaatggg gaaatacagt  10380
gggaagcagg tgggaaactg cgtttgactc tgctctttcc tccaccacca ctttcctcat  10440
caccgtgttc agagaccccc aaagccccct cacactccca gaaacacccc cctggccact  10500
cctaacttgc catgcccagg agttaggtgc ttccactagt gacatggagc tggcgtttgg  10560
ggggcacctc agcaggtgac gggaagagaa gaccccagcc tcaccagctg ggctgcagca  10620
gggagaggag tcctcatgtt ccagcaggga ctctcagctg ttttcctgta aaaccatggt  10680
tctcaactgg gggccactga gatgtctaga gagatgtttt tgttttcaca actcggggag  10740
ggtgctactg acatcttgtg ggtagaggcc aggaatgctg ttaaacatcc tacaaggaag  10800
gcacaggaca gtctcctaca tcaaaatatg acccagtccc aatgtcacca ctgctggggt  10860
tgacactggc actgctatct taattacatt cattgagtgt cttttaggag gccctattct  10920
aagtgcttgc taagattatc tcatttaatc ctcacaacac ttccgctatg tagcaggtgc  10980
tgttattatc tccgtgatgg ggaaactgaa gcacagagag ggttagtaac ttgctaaagg  11040
tcacagagcc agtgggtggt ggagctggtt gcctgacact agttccctcc cctctcagcc  11100
acatgtgggt ttacttggcc attgtggact agtctgggaa cccagatatg atctataaca  11160
ttgacccagt agaatattga ttccaaaacc actgtctcac aaatgaattt ttacaagagt  11220
ctgtaatcgg agcatgaccc agaataaggt tagggagatg tggagttaaa gctctcaatt  11280
tcttatctgg ccccgacaca gagagcaagg catttcactc tacattggtg ctctgtttat  11340
aaaacaaaga gcaaatatct cttcctaagg tccttaaacc tcttccccca atccagggtt  11400
tctggactgc tctgccatat gacggggcag ctggtttgat tgacccaggg aaggctggaa  11460
atcaagactg gggggatcaag acgtagattc agtgtggcca aggtcaagtc tctgaggttt  11520
agggacatca gatccccagc ttaggttctg tacctcggca aggtgaaagc gttggcgccc  11580
actgatgagg cctgctctga gattgtgggt gtgggttgag ttgggtgggc ataggcaagt  11640
cctcttgtaa gaatcttttg gcaaagatgg gcctgggagg cttttctcac ttcctggggc  11700
ccaggctttg caataagtat tccattatac tgtggtacct tggggctacc tgagaatcct  11760
ctgtctcgcc cctgttgcct tgccaaagag tttgctgtcc aagaattcct ttcctgtctc  11820
caggtgccat gctcctgcca cctctgccag gttccctgcc tgcccagatg gctcccaact  11880
gagtgtgagg aggaatttga gacaggtttt gagctttctg ggttctccag ttaggaaact  11940
ttctgtaagc atgcagatag aatgggcttc agcaaaatac aaactcgaac aacttccatg  12000
tatagtccct taattttctt tgcttttttc atatttcatc aggctccatg ctgagcccaa  12060
tcagggaccc gatagaaatc caaacaccat gtcagcgagt ccccaagaaa tgcattttgt  12120
gccaaggcta ttcaaggaag gtttgggagc agctcaaggg cagacactgt taccctcccc  12180
caggtcccca gtgcagggca gtgttctgca tgtggaggca gtttggccta atggttaagg  12240
aggtaggctc tgatcgggcc tcctgggcac aaatcccagc tccctgctca ctgtgagacc  12300
taagccatat tgtttagctg cttggagagt tttttgtcat ccacaacttg gagtatgatg  12360
```

gtacctgtct cacgggttgc catggggttc acacaagcta acccggtact cactagggcc 12420
aagcacatag taactgctca gtaaatggca tcatcggcgg tgtcctgtgg atgagtgctt 12480
gtgattggct gaatgaccag aggggtctaa agatcctggt gatggaatca gttgtacaga 12540
taaattgtta cactgagtag ggatcaagat aggaaaagtc ggcaactacc cagctcccct 12600
gcaccaaact gggcagaagt ggatcctctg aaaattgcac acacccatgt ttaaatgtac 12660
acacagaact cttgccacag gcaagcggag atttgtcatc tgctgtccct gcctcatctt 12720
cttcctgaaa tccactccat gccaggaata aactgcatgc tctccaccag cccaaactga 12780
cctgccttcc cgccagccat cccgggcagg gtgacctggc ttagtacatc gggttcagag 12840
atctttccag tttactcgtt gaataaaaag tgagggctga tcgagaaagt aatggcagtc 12900
agggaaggcg aaggaggtaa agaagagatt ttacaaatga agtaattcaa cagagtgctg 12960
acattggtaa actggcaaac agatttcagg gtggttggtt gagagtagag tagaaaagga 13020
ttaaataaag caaacttgtg gtgtactgaa tcttaggaat tccatgtatc caataagtat 13080
agtcatttat gaattaataa attcggccta agaagccttc ttatcgctta aatcaagact 13140
aagtaacaat atatcagttt taaaaagtca ttatatcaga aaatcattta aatgatacac 13200
atagatttcc aagattttac tttaaccgaa actatataaa tgtgaatttg ttcacccatc 13260
ttttgacaca gggctcaggt cttctcttgg tgtctggatc agccagttga aatttcttgt 13320
ctgttttgcc tatgccacat taataatgca ctgtctgggt cctccgattt cagtttggat 13380
tttgggttta cattgtggag tcatctgaat gcagaatcct tcagggattt tacttttttt 13440
tttttttttc atggtcttta ccatcccatt tgatagtaaa tattactcac ctttatgaag 13500
tctttccaaa acattcaact aaattttctt aaaatcattg aatgatttga agagcttatt 13560
cctcagcact tttactccat cagcttgcac cttatttttt aatctttttt tgagacggag 13620
tctcgctcta tcgcccaggc ttaagtgcaa tggcgcgatc ttggctcact gcgacctcca 13680
cctcctgggt tcaagcaatt ccgcctcagc ctccgccgta gccgggacta caggtacaca 13740
ccataatgct cggctgattt ttgtattttt gtagggatgg ggtatcgcca tgttggccag 13800
gctggtcccg aacttctgac ccaagtgatc cacccacctc ggcctcccaa agtgctggga 13860
ttacaggtgt gagccaccgc gcccggccag cttgcacctt atttaggata tgtgattatt 13920
atagcaagtc tggtgtacat acaagatttt gaatgggcac agatgacctt tagtaagtgc 13980
ttggctgtga taagaggcag tcctgactgc agatcaggct gtgtggaccc cagccttgca 14040
tgtttacaga ccttcatgtc ttattcttac agggtatcag aagaacacct actggggaaa 14100
cttataaatt agtaaaaggt gggcattctc cccgcccatc ttctgtctgt ctgccaggac 14160
tagcacagca ctttgaagtc attcacatag aatcccaact taagagggta aaatcctcct 14220
caacagactg aaaataagtt taaattccct ttgctatatt aactcccctg aggaaagagt 14280
cttagatcaa tgtccaacac taaaaacagt tttaaatcag caagtgagaa ttaaatctga 14340
agcaattgat aataatgttt cattcattcc tctcctttgg ccccgtccac cctactgcta 14400
aatccaggca tcaaagagaa gagggacata attatctcta gtcccagctg ctggttttcc 14460
ttccagccta tggcccagtt ttctgtttta ctgagaaggc tggtgatgtt atcttgggat 14520
ctaagtctgc agtttcacca caaaaagtcc agggatgcac tttcatgctt gtgtcctcct 14580
ccctgggata gcaaggatat tagaagaccc ctggctctgt aattgcttgt catgtgctct 14640
acagacgcca cagaatgcca agaacgaagt gctgggaagg acaaattcat ggaaccgtgg 14700
gacggtgctc ctcccccagc gtaaaggaca gctcctcctc ctgaattgga gccagcgttc 14760

```
taaatcatgt gtcaacagag ttgtcctgga tcggatccag ttctgccatt gatttgcagg  14820
tcatttcagt ggtacctgtt tccagttgtt cttaattgaa cagtggcacc aaactattgt  14880
cttgcctcat cccccctccca tggcctgtcc cccaaaaaga gacttcttgg gtaattaatc  14940
agggcaacat caggcagtct gggcgcggtg gctcacgcct gtaatcccag cactttggga  15000
ggccgaggcg ggcagatcat gaggttagga gattgagacc atcctggctt tgtgaaaccc  15060
cgtctctact aaaaatacaa aaaattagcc gggcgtggtg gcgggcgcct gtagtcccag  15120
ctactcgaga ggctgaggca ggggaatggc gtgaacccgg gaggtggagg ttgcagtgag  15180
ccgagatcgc accactgcac tctagcctgg gcgacagagc tagacttctt ctcaaaaaaa  15240
aaaaaaaaaa ggaatctctt tggttttata tatatttttt ttatatatat aatatatatt  15300
aaaatataat atatatattt atataatata atatataaat atattatata ttatatattt  15360
tatatattat atattatata tattatatat tatatattta tatatttata tattatatat  15420
atttatatat tatatattta tatatattat atatttatat ataatatata ttatatatta  15480
tatattatat attatatatt atatatttat atatattata tattatatat attatatatt  15540
atatatttat atattatata tttatatata ttatatatta tatattatat atttatatat  15600
tatatattta tatattatat atatttatat atattatata ttatatatta tatatgtata  15660
tattatatat gttatatatt atatatattt atatatataa tatattgtat atattatata  15720
tctaatatat tatatatatt atatatatta tatattataa tatatattat atattatata  15780
ttatatatat ttttatatat ataatatgta taatatataa tatatataaa aacatatata  15840
atatatatta tatattatat atatattata tatattatat atattaaata tattttatat  15900
atattatata tatatacaca tatatatata taaatgaggc caggctcggt ggctcacact  15960
tgtaatccca gcactgtggg aggatcactt gaagccagga gtctgagact agcctgggca  16020
acaaaacaag atcctgtctc tacaaaagga aactgtaaaa attagctggg catgatggca  16080
tgtgtctgta gccctagcta cttgggaggc cgaagcagga ggatcgcttg agcccaggag  16140
ttcaaggcta cagtgagcta tgattgtccc atagcactcc agcctgggta acacagcaag  16200
gccctgtctc taaacttttt ttttttaatt ctatttatat ttacatgtat ttaaatgtga  16260
atattcacta cctatttgtt gcatgcctgc atttttttata ctgggcttgc caaaaacccg  16320
aacagctttc tactttgaca atgtatcaga atttaaatca gcaatatgtt aataagccaa  16380
gcaaaggtta tatatgcaaa taaaactgtt gtctataacc tcctgttaca ctggggcaca  16440
gcaaaagtca tggtgtagtc gcatgtgaac ctgtcccttt catagctgct cattgccagg  16500
aaacatcagg aatagccatt tggaagagtc atcagccctc ccaccatccg ttttctgtct  16560
tgtcttttcc ctatgagcag gggaaattcc acgctggccc caatccccag tgcagcggct  16620
cagcctctgc ctctgctgct ggtccccatg aggccagctt agaaacggag gattttgcag  16680
aacatcccta aatccgcttg aataatgaag tgatcattca taaactcacc tgaaccttat  16740
taaaacctat ttaatatttt tcctggataa tcctataggg ataacttgcc tcctgggctt  16800
ctctccaccg ggttcagttc ttcctttagt ggtgaagttc ctcccttctt agcatctcaa  16860
ctgtgcctga gaaaaggcca gtggcggctg cactctgttc cctgtggagt gttaataaag  16920
actgaataaa ttgaaataaa tccctttcaa tgtcattaag tgctataaat aatcatgaac  16980
caatgttcga tggctgatga gaaatgcaag aaaaaatttt taatcagtag gattcataag  17040
ttgacaatct gggccaagtt aaaaaaaata aaaataaaaa gacttttaaa aagatcttat  17100
```

```
cgtttgttac cagtaagact gaattccaga agcaagctac tccctcattt gtgggcccct  17160
gttatcactg gctgcttagg gttgccaagc cctgaattca tttgtcaact aagagatttt  17220
tggccaagat taagatttcc catgcctcca tatttccatc tgagaaatgg agattatact  17280
gtcttccccc tcagaatgga tgataatgtg gtctctcttc tgttcgcata gtcatagaac  17340
tgaaataaaa caacttaaga gaattccttt gagcttctca gaagtgctgc agggctgggg  17400
gatgcctccc aggagccgca gtcaggtgct gatctgaagt ctttggtggg ctgactttag  17460
cctgacctga aatagtatag ctgctgccac ctggctccct tagcgtcagt cagacggtgc  17520
agctggttcc taggggtgag ggctgagcca gcagggtccg tgcccaggag ggatgcatgg  17580
gtggccacag cccagcctgc actgatcttg tctgtcccct tctttggaag gaaggagccc  17640
caaaccaggg tgcaagacag tgggtggggg tgccttgagc atgacctcaa gtgatttcca  17700
gcccctgcca gtgctgactt ctctggggaa gggctgggac ttccttctgg gctcaagtca  17760
cgacccttgg atggaatttc ctgggagctt ttctgttttt tctggagttt tcagtttttt  17820
cctaaccaga cagggacttg gtacagaatc tcatattcta attatgccta ggagcagcct  17880
ctccccacca ctcacagtgt ttagcatgtg acaggaatcg attaaggcat gagtgattaa  17940
attaaagcca ggcattgact tggatggtgt aatattctga catctgtttg gtgtcaaagg  18000
cacggggcag gcgcgttaat tgaactgctt gcacctggca tttgaattga gccagagcgg  18060
ggctaaagtc agtttgcctt caccctgtaa atggagggtt tctccggagc gtggatggtg  18120
ggaggtattt cagggtgtat gcataacccc caccctgaca atggcccatc tcttctccag  18180
cgtggccagg tttgagtgcc agtcctgggt gtccagtggc cccatagcct tgcgttttag  18240
taaaatgctg cccccattac cacctggtct gtgcacttcg gtcactggaa tttgccatct  18300
tccagtcccg aatgtggcaa gccatggagc cttaagctct tctccctcca catcctggaa  18360
cagacccgcc agtttcttcc aggcattgcc tcagtttgcc cctctgtttc cagtcacact  18420
ctcaccagcg ataaaatgat tttagacctt atcatctcac cctcggatcc ttatggaaac  18480
aataatgagt tgttccctgt ttcaattcca aaattcatat ccaatccgtt ttgcatgcca  18540
ttgccaaatt cctcccagag caaccccgtc acctgccctg gccctctcca agtgtggtcc  18600
tgccatgggc atcgcctgct aagccaagct ggcctcgagc tgcctgcccg ggtccccaca  18660
ccttggctca cctccctgcc cagtcccgcc tcctgccagc ctgccctgtg gctccttcat  18720
agatgccgtg ctctttctgc cccttgctca cccatggcag ccttgcccct ctctccctgc  18780
cccacccccct atttaaattg acctgacctt cctcagtgtc catcttcccc gaagctttcc  18840
ccagccttgg cactcaaggt ccagaggcta cgcgtttcct ctcacctgtg gcagcgccgt  18900
gctccccagt gcctcacagt ttccttcttg cccccgcttc ctgtgtagga ctcatctgcc  18960
cacaggttgc acgtcctgtg agggcaagga ctgtgtctta tgtgactttc cttctccagt  19020
cacagagctg ggcacataga tagctcaaaa ccctctttat taacacagtt ggatgttgag  19080
aaatcaaaca ggccaatgtc aaatgagctc tccttattta aatcaagtca gttctccacc  19140
tcctagcact cagttccagt actctatata catggaaata ataaaaaaca catttccttt  19200
gaaacattct ataatcgttc ctttgcccta cttcagacca acttaacgca ctccccattg  19260
gtccaaatga gttttgctat acgaagatgc tgataataat agcagcagtg gattattctg  19320
ctaaaaccat tgcctcgtta atcctcagtc ccgaggtggg gattattatc ctcattttgc  19380
agagaagcaa actgagactc agagatttca cagctgggga gggagccagc tcatccctct  19440
gtccaggccc aagctctctc ccgcttgcct tcctgcctct gcaacctcag agcatccccc  19500
```

atctggttct actgcctgtg ctagtcgtgc aggagccaaa agacacgtct ttagtgctaa 19560
ggactggaga agccatgccc tccagcctct gtgaatgggt catatgtaac atgagcctgg 19620
agaaattatt tgaaaccaaa ggcaagcctc taaaccaggc tgctgcttca tggcgccggt 19680
gacggcagaa ccaaatttag tgctgtgggc aggtccacac ttatcaaata gagaagctca 19740
tttttcttcc ggctcacatc aagcatgaaa aatgttcaca catacccccc acacacacat 19800
gctttccgga ggggtccatg tggctagagg ctggaagatg tggatgagag gagcctggca 19860
ggtaagccca gggaagatga cattcagctt cccagacagc atctacaggg agaaatttaa 19920
ttaaaagtgg ggcggtttcc ctgagcaagg cagacaaagt cagccctcta ctgttaagaa 19980
aaagggtcac agtgagaggg gaggtgagga gactgagtct gtattttcta gtctgttggg 20040
ctacactacc tgatccccct tcctcaaaaa tccactttac tttccccatg tctacaccaa 20100
tgtggttcac actctgggac caggaaaagg gggagtgatg gggaacagag aagggaggag 20160
ctcacacagc tgaggctggg gttatgcata tcgaattact tagaatttgc aacctcacag 20220
ggtactttca tggcgttgaa atacacttcc cacagccacc ctccctctaa ctaaaagcaa 20280
gagtcatttc tcagttctgg tcttgcctcc cacgttctcc tccacattta agaaaatcca 20340
ccagctacaa agtgaagata ccatatgtga tatcccaccc tagtttctgt tttatcaggg 20400
tttggagcag gtggagcagg cagagggatc atttcagcct ataaattgta ttaagggtga 20460
gtactgagtc attcttcaag aaaagtttta gaagcatcca aaactgaagg gtggagccac 20520
ctggagacag tatcatcagt cctggccccg agcatggcct gcataggccc ccatggatcc 20580
cagcgggagc tgcagagtgc gggcaccttg gcacacagcc ctgagtgcaa aattaggagc 20640
tgggcagagg gcatctctct gtcgccattg ggcagcccag ggcacactgg tcatagcctt 20700
agaccacgaa caccctgtgc ccgggggaca gatgcaacca gtgtgccctg ggctgcccaa 20760
tggcaacaga gagatcgaca cctggacccc atgtcacggg gactccacta ctaaggctcc 20820
taagactgcc accttccagt gggataagcc ctgcctccta ctgggcccac aatgtgcaga 20880
gaacacttgg gactacctgg ctttctggat acacaaatat tgatccaatc tggactaatt 20940
agaaggtcag tcccaataac aaatcgaagt cagctgggcg tgatggctca ctcctataat 21000
cccagcactt tgggaggctg aggtgggcag atcatttgaa gccagaagtt caagaccagc 21060
ctgggcaaca tagcaaaacc ctgtctctac taaaaataca aataattagg ctgggtgtgg 21120
tggctcatgc ctgtaatccc aacagtttgg gaggctgagg caggtggtca cctgaggtca 21180
ggagtttgag accagcctgg ccaacagggt gaaaccccgt gtctactaaa aacataaaaa 21240
ttagccaagc atgatggcat gtgcctataa tcctggctac tagggaggct gagacaggag 21300
agaatcgctt gaatccagga ggtggttgca gtgagctgag atggtgccac tgcactccag 21360
cctggttgac agagcaagac tctgtctcaa aaaaaaaaaa aaaaaaaaaa aagccatgcc 21420
tggtggagca ctacgtgtaa tctcagctat ttgggaggct gaggcacgag aatcacttga 21480
acctgggagg cagtggttgc agtgagctga gatcgcgcca ctgcactcca gcctgggcga 21540
cagagtgagt gagactccat ttcaaaaaaa taataaatct gagtcacttt aatattgtta 21600
tttggatgtc aacctctagg tgtttgagac aggagagtga tatgggggca ctggaaacac 21660
acaggcacgg ggtgtcctca cacttgggta gcccacacga tgtgatttca gggtgctggg 21720
aggtcccccc actccccaaa ttactaacaa gtggatagta ctttacagtt tatatgatct 21780
catttgattc ttaacatgag cctgtgagtg aaaaattcct tcccctcttc tacagattag 21840

```
gacgttgaga ttcagggagg ttcagaggga ttcagggaag tcaagtggca cctggagtcc  21900
cgtggctaat ttgaggccgg taggggattc gaacccagga tttgtgcttc ttatgcctgg  21960
gcttctgctc cctggggcat ggtcttcccc ctagctttcc cattcactgc tttagcctag  22020
gggtcctacc ctttattaaa ctgccagtgc ctcactgctt ttctccccca aagacaaaaa  22080
aaaagtgttt ttgcttttgt tttgtttttc atgggcagag acctggaatt tcagcttgag  22140
aatttgtgcc atatgataaa taaatcaaca gatggctttt tccttaaaaa aaaaaaaaaa  22200
aaaaactaag atgtatttgc agtgaggcat aatttgtacc aaaaagtgct caccacactg  22260
tagtcatggg ggcaggaggc agccgcgggt gaagggagaa atcttggagt ccaggcagcc  22320
cccttctggg ctgaactggg gagctggggg tgctgccagc cctgccaggt tctcctagga  22380
ggcggcagct catatggctg tgggaggagg cagagggagc ctcatatgca cccacatttc  22440
cagggatcta gaagacagaa ggaggaaaac caccatcatg ttaaagcaga cagttaggta  22500
acacatcctg taatacaagt tattttttcc acatctaaag gctaaaaata gttgttagaa  22560
tttaaagata attggtaaat gagtttctat ccttctagtt tcacatcaaa tggaatcatg  22620
ctgccttcac atcactagtg cccgttattt gtgtttaatt tccacaatgt tgtctaattc  22680
cactctttgg gcttccccag ggatccagcc tccctcactc gcccatcgca gggagatgct  22740
ttattcatct ttgtgtcttc tgtgccgggc atagcgcatg gcacagaata agcactcagt  22800
aattgattca cgagtgaata aatggatgag tgggtgagtt caatattgac tacaaaaacc  22860
ctaaggccac actggtgagt ggctgcgcct gtagtcccag ctgctgggga atctgaggca  22920
ggaggatctc ttgagcccag gagtttgaaa ctagcctggg cgatatagcg agaacctgtc  22980
tcaaatgaca aaaacagggc caggtgcagt ggctcacgcc tggaatccca gcactttagg  23040
aggccaagat gggaggatca cttgaggcca ggagtccgag accagcctgg gcaacatagg  23100
gagaccctgt ctctacaaaa aattttttaa aaattagctg ggcatggcgg tgtgcgcttg  23160
tagtcccagc tactcaggag gctgaggcag gaggatcact tgagcccagg aaattgaggc  23220
tgcagcgagc catgatggca ccactgcact gcagcctggg cgtcagaacg agacctgctc  23280
tcaaaaaaac aaacaaacaa caaaaaaaaa ggctttctta aagagacttg agaacagaaa  23340
ggggaacaga tacataactt atatatttat ttgttcatct ttccaccttc ctggagggtg  23400
gaggggaaca ggtctgtatt tggagttttg aatgctaaaa gtgggaatac atgtactgtt  23460
tgccatgatc tgttcaaaag ttaagccaaa tgccttagat tctcctgaaa actggaatgc  23520
cactgtaaac tataagcccc acttcaaaga taaaagatct tgatgaacag ggctgggtct  23580
gtggactggg cctctcccca ccacacaagg aagggtggtg ccagttgaag gaaaatcact  23640
taaatccttg ctgtctccta ataaggtgtg gtcccaggta gggctgtcag aattagcaaa  23700
ttaaaacaca gggcatctgt gaaaattaga atttcagata acaacaaata attggcatag  23760
gctgcataat gtccctcaaa gatatcaggt cctaatctcc agaacctgta aatgtgatct  23820
tatttggaaa aggggtcttt gtagatgtgg ttaaattaag gattttgaga tggggggatt  23880
atcctgtatt atctaggtag gtcctaaatg cagtcacact catccttgta agaggaagga  23940
agagagagat ggaaaacaca gaagagaaga caatgtggtg atggaggcag agattggagt  24000
gaggtggcca caagccaagg actgctggca gctaccagca gccagaaaag tccaggaacc  24060
aattctctct tggagctcca gagggagtgt ggccctgctg acaccttagc ttcaacctag  24120
tgatcctgat tttggacttt ggccttcaga agtgtgaggg aatgaatatc tgttgtttta  24180
agccaccaag tttatggtca tttcctacag cagccacagg aatcaaaaac agtaagtatg  24240
```

tcccatgcaa tgtttgtgac acacaccaaa aatattactt gttgttcacc tgaaattcaa 24300
atttaactgg gtctcctgta ttttatttgg ccaacctagt tcccaggccc aaagaaagag 24360
gcttttgaaa tttgcaagaa agctggttgg agctgtcaga aagtggactt tgtaaacaca 24420
gtaccaccga accaatttga actgtactac ctctagacaa aagagagggc agtcagacag 24480
ttgttcgtga tttcttcttt caacagtcat ttgagcactt actacaaaac agaagctatg 24540
tgtaagggtg gaggcgttag ctgttaatca ggacctccag gctaagtttc tgtattagtc 24600
cgttttcacg ctgctgataa agacataccc gagactgggg aatttacaaa agaaagaggt 24660
ttaattggac ttacagttcc aagtggctgg ggaagcctca caatcatggc agaaggcaag 24720
gaggagcaag ccacatctta catggatggc agcagacaga cagggagaga gagcttgtgc 24780
aggggaactc ctctttttaa aaccatcaga tctcgttaga cttattcact atcaagagaa 24840
cagcacagaa aagacctgcc cccatgattc agttacttcc caccagatcc ctcccacaac 24900
atgtgggaat tcaagatgag atttgttacc atatcagtta ccaacccttc cagataaatc 24960
acgtgaaata tcgccattaa cagagtgagc tcaggtggtt cttcagtgca tttctgatac 25020
ctgaaccttc cctgggaatt tcacagacca tcaggctctc cacccttga tagcaggata 25080
gcagggccca ggttctgcag gaggagatgt taccacaggc ctgaaaggga gggaggggca 25140
gatgctacag gaagatgctg gctctggatt cgctggagga gctttcaagg gaagtagata 25200
cacactgtct ccatcatttc atgtccatca cactctaaaa tgctttggac aagaagcaaa 25260
tgttaaagac aaatgtggcc cattttcctg tacaaagagg gctgctccca tgccaggcta 25320
ttggcactgg tgggcatgag gcttctctgc tgccctggcc ggggggttct ctcactcacc 25380
attggctctc tgacacctgg agagaccacc acccttgggc tttcatgatg ctcacagaat 25440
ccacactgtt ggagctttaa ggagcctgga tcaactggaa caggcaggga gtactaggac 25500
agcccagcat tgccccaaaa tatccaggcc tgataaaaga gaaaaacagg tagctcacag 25560
gaaaaggata aaaaaaggag gagggattta acatgaaaag gtgcttgatc tccctcataa 25620
taaaaagact gctgattcca tccaggcaag tgacagaaaa aaaaaaatta atttaaaaag 25680
actgctgata aaaccacagc gagacactgc tgctcaggga tctgagggtg tgggcagcca 25740
ggctgccacg catcatgggt cggagaggaa gaccacaccc ctggagcaga gggcggctga 25800
tctgtcagat gccctttgac agcacctcag cttccaagaa ttaacccttt ctatgtgagc 25860
agaggcatcc atggggggac acactggtga atcatctgtt atgtagaagt ctggaaaaca 25920
tcaggatgga actggtgaaa taagtgtggc ctctgacgga atggagcggt ccgtctgcac 25980
tgctgcgggt gcccctcaga tcctgtgggt cagtgagaaa agcagtgagg aacaaggcag 26040
gtactgtgta ctgtcctctg cgtgcaagga aggccagcgc atgcaacaga gtccacacag 26100
acatagccta actctggaag gaagaatgag aatgcagttt cagtggtggc ctctggtggg 26160
gagaaactgg gtgaagggag atgtcatttc catttctcta ctattaattt tgtattacca 26220
tgcttaaatg ttacttttta cctttttttt tttttttgag acagggtctc tctctgttgc 26280
ccaggcagga gtgcagtggt acaatcatgg ttcactgcag cctgaacctc ccaggctcaa 26340
gcaatcctcc cacctcagcc tcctgagtag ctgggactat aggcacgcat accaccgtgc 26400
ccagctattt tttttaatca agatggagtt tttctatgtt gcccaggctg gtctcaagct 26460
cctggactca agcaatcctc ctgcctcagc ctcccaaagg gctgagatta aaacgtgagt 26520
caccctgccc agccaattgc tttttaaaaa agattaaatg catgtatacg ctcaggcatc 26580
agcacacttg gaaaggatga aaatatccgg aagaagggtt cttttaaaag gctcctcaag 26640
tgatgctggc aggcatgacg aatgtccctg gtcacaaaag ctctgatctg gcctaaccct 26700
gtcatgttag agactggagt gcgtgtgtgt gcgcgcaaag tgtgggggga tgggggtgag 26760
tgtgtgtggt gtgtaagcat gagtgtgtat gtgtgtggtg tgggggtgtg tgctgtgtga 26820
gcgtgtgtga gtctgtgtgt gtagtgtgtg tgtgaagtat gtggtgtgta tgtgtgacgt 26880
gaggtgtgtg tggtgtgtga gttgtgtatg gtgtgtgcat gagcatgtgt gtgggcatgt 26940
gatgtgtgtg tggtgtgtaa gcatgtgtga gtgtgtatgt ttgagcatgt gtggtgtgtt 27000
gtgatatgtg tgtggtgtgt gagcatgtgt gtgtgatgtg tctgtgtgtg gtgtgtgtga 27060
gcatgtgtgt tgtgtgtgtg gtgcatgtgt gtggcgtgtg agcgtgtgtg tgcattgtgt 27120
ctgtgagcat gtgtgagtgt gtgtgtgttc agcatatata aggcatgtaa ctgaacacag 27180
cactttagag ggctctcctg gagtcagagg gggtgggtag gaggagaagg gaggtgggct 27240
agtgtgctga agtatctact ccttgtcata gtctgtgaca acccagacta gcccatgagc 27300
caccctgttc cctgcatttc caatgagacc tcggtggaca tgttccctga ggtgaggctg 27360
actgatgtca tttgacgatc ttgatgccaa atccttttat atcaaaaaca accagaacac 27420
tctcttttct cttagtgctt tcacccagat gaccacattt catcctccca gccactctgg 27480
gccaggtggc actgctggtt tgaaagggag gtctcccctg gagtaacttc cgtgggcgga 27540
ttcacaccct gcccacagtc ctgtcccagt cagcccacca tggtggtctc cggttcctcc 27600
agaattcccg cttttcagct catccccaca ttcccggagg gactgagagc gcagccccag 27660
ggccctgctc tttgggggcc gtctctacac ccagagaagc agcaaggcat tcctaggttt 27720
ctctttcaga tgcagaactt cagtgttcag agatgttccc actggtcctg agagggctca 27780
gttcagcttt aatgactgcg ctgttgcgtg tgctctgcag agggcgggtg gcccagcgtg 27840
gctgactgca gttttcctga cgtggagccc gagcctgccc cgctgtttat taattaagga 27900
tcactctgct tgcagaaccc tgaactcccc agaactgtga ggtgggagaa ccccgagagg 27960
ccacctggcc ccacttccca cctgctgccc aaaccccctc tctgccttcc tgacagtcac 28020
cccaactccc agtgatcccc atcaaccatc tgacaagggg actgagaggg aagagaaagg 28080
aggggcccaa agaggaaggt aaaactgtcg ggaacagccc ccaaatgtgt gacagccttc 28140
agtggagttg cccactttcc cttttctcct ccctgcagga cctcccttct ccccagtcct 28200
ccccaacttc tgaggttaca ttgagaaaag tctgcagaga ggtgccagca tcacaaggtg 28260
ttaaggacca cgagtttggc attttaacag atgccagagc cacttgagaa atgtggtaac 28320
taagcccaga gaggtacagt taacctcccc agagtcacac agcaggttca tggcaaagct 28380
ggactagcac aggtgtcctt cccctgcaga tccccttctg tgccccacat cacctccctc 28440
cagtgtctgg gccacctgga gatgggccct cagactcacc cggccagagg tgccatctca 28500
tgggagaggt ctggccagga agcatcgata tttgagatcc caagaaatga agacttggcc 28560
tgtcagatga cagacttcgg tcatgggaac acgtgatctg ttttacacat gcgtcccctc 28620
agcagcagct ttccagaaca ttcccacttt cttctgtagt gagaagaact ctttccctgc 28680
agcctcctgc ccaactcctc cttcagtgtc tttgcttcag tgtctttgat aaaccattct 28740
gctttgcaga gtgcgagctc tgccttgcag ggttcgcatc tgcctgtgct gagtaaccaa 28800
cgctaaggtc gagtggtcgg tcacctctca taagagctag ggttgtctca tgctgatgac 28860
taggacttgc cctcaaggag aaaaataaat caaaacaaaa gcaaaaacag caaacatgca 28920
tctcttaaag aaggctctga gtccaggtaa atttccttcc actgaagcag ccaggctgaa 28980
ttcgaattat ctttgcccct gcttaaaaac taatgcaaat tttcctagag aatatccact 29040
aattcctgga gggggcatgg gcattcctga tgcccatgag aggaccattt gctcttccct 29100
cagtatgcta aataacagaa gcgacatttg ttgctggaaa gtatcagtga agttaataag 29160
gtttttcttg cccagggtga gggaacagtt cccaatgaca aatgctgtat gggaaggggc 29220
tgtagaactg ccagcccctt tggtccatcc gtaaagtgaa ctctgtggat cctggaggat 29280
tccagcgtct tttttttttt ttctttttttt ttaagacaga gccttgctgt cacccaggct 29340
ggagtgcagt ggcacgatct cagttcactg caacctccgc ctcccgggtt caagcgattc 29400
tcatgtctcg gcctcccgag cagcaagact acaggtgcgc accaccatgc ccgactaatt 29460
tttgtattat tagtagagac gggggtttca ctctgttggc caggctggtc tcaaactcct 29520
gacctcaggt gatccacccg cctcagcctc ccaaagtgct gggattacag gcatgagcca 29580
ccatgcccag ccagcatctt tcatttttct gtctgctttg gccctttcct ctctcactgt 29640
cttccttttc catttccaaa gtcagtccat ctcactatta gcacaaaaac tgctagagcg 29700
cttgtcattg gtcatctctc cctgcacctg gctggtctgt tcttggccac tgaagcgttt 29760
cccccagctg ttgctttaat cattttattg ttattatgcc ttacttaaga aatggatatg 29820
agatgcattt acctgtctct tcctgccact ctgcagagcc agtaagatgt ggtggaaagg 29880
gcccaggctt tggaggaggg ctggctgggg ttggatcttg gctgcccccct actagctgtg 29940
tgaccttggg taagtagctg gacctctctg agcctggttc ggaatcatag cacctctctt 30000
tcagggctgc tgtaaggaat agcagtggtg tgtataaagc agagcgcaca gccagcaact 30060
ggcccctagc cacactgctg agcacctact gtgataagct gccattgtgg tgtgtgaagc 30120
aaaggggaaa catgcctgct gtagtgagct tcctgtaggg caggttgtag aaccagaggt 30180
gggttccaag gttacaaagg gactcttagt gtattagtct gttctcacat tactataaag 30240
acctacctga gactggatca tttataaaga aaagaggttt aattggctca cattggctgg 30300
gtgcggtggc tcacgcctgt aatcccagca ttttgggagg ccaaggccgg cggatcactt 30360
gaggtcagga atttgagacc agcctggcca acatggtgaa accctgtctc ttctaaaata 30420
aaatacaaaa attagctggc catggtggtg tgcgcctgga atcccagcta ctcaggaggc 30480
tgaggtggaa gaattgcttg agcccgggag gtggaggttg cagtgagcca agatcgcccc 30540
actgcactct agcctgggca gcagactgag actctgtctc aataaaaaaa aaaaaaaaga 30600
aaagaaaaag aattgcaaga aataaattat tgtttatgag ctatatggtc tgtggtacct 30660
tgttgtggga ctgggagtct tggcgtctcc ctgaccctgc ctgttgctgc agcaccgctc 30720
agccctgcct gctccctacc tgcctcccct cggcctctcc tgcctccacc gggcccctgg 30780
tgcctcctct agagacagtc ctcctgggac cgattgtgtt ctcacttaca cgaggcatcc 30840
aggactacag ataaccagag gaaggggcgc ccccccgcc tgccctcctc cctggcatcc 30900
tcacgctgca gaggtcagag cctcatccca gccccttacc tgcccctact ctgtggagaa 30960
ccgtggtcag ttcgccaggc cggatccacg aacggccttg tggaagatgg tgagctcaca 31020
cccagagctg gctccgatga ccctgtctcc tttacatgtt tctaccttcc cctccctacc 31080
ttcccccact gctgggcgca gagtggaggc agatgaggtt taaagctcag aagggcttaa 31140
acgggttggg gcgcagtggc tcatgcctgt aatcccggca ctttgggagg ccaaggcaga 31200
ggatcacttg agcccaggag ttcgagacca acctgagcaa catagtgaga ccgcgtctct 31260
acaaaaaata aaataaataa aattagcttt gcagggtggc atgcacctgc agtccctgct 31320
actcagaagg ctgaggtggg aggatcgctt gtgcccagga gtttgaggct gcagtgagct 31380
atgctggcac cacagcactc cagcctgagt aacagaatga gatcctgtct caaaacaaac 31440
aaacaaacaa acaaaagaag gcttaaaggg ggctccaggt gggcttggca gcacaaagct 31500
atgaagttct atcttagaca caagttctgt tactgggcct ttgcaggctg gcctgggtac 31560
ctggctgcca tagacaggga accttccaga tgagctgcag gcgtggagca caggagccag 31620
ggtgctcttc ctgggctctg tccacaggca gaacgtacac agtctttgta cacgtccggc 31680
ggctctggtg cctatttttg tttgtgtttt tcttttgttt ggggggatgg atttggtttc 31740
ccccgagccc tctgtcctcc tgtcacctgg ctggtgctcg gcaatgttga ccagctgcct 31800
ggctggagtt ggcagtggct aaggctgtga cagctaacat gttcctgagt cctctcattt 31860
cttcaccata atgccctgtt gagtttgcag atactgtctc tgtttttatc tcccggggaa 31920
actgaggctc agagtggcta ggccaccttc ccatggtccc tcagctcatg agggccacac 31980
agggcattgc ggtggccttc tcctcagcct tgaccctccg gccccagcat tgctgcctca 32040
aggggtctcc tctgctgagc cgtgcacctt ctgcctggca gctccaactc tgtggctgtg 32100
ttcagtggct cagcactgcc ccttgaccct ccctggcctt ctgcggatgc cagactggag 32160
cactctgaca aggtctgggg tggttgtatg ggtcctgtga cctctataca cctcccagtg 32220
cctgggaatc ctgcagatac accctcctta gccgtcccta accatagagg acatttctga 32280
ggtccccgag agagtggggc acccctgcag gatccaactg ctgggcccag gaaggatagc 32340
agcagcatga ggggttccat tagccacaaa ctcacggcat ggaaccttca cccacctcgc 32400
ccctcatctg ctgtttagca cctggcacgc cgtgtatact tactgattat tacattttaa 32460
tggcaaatta tagtggcaaa cgtatgcatc tttgcacaat tgttgtacag catgatgaac 32520
aagtcattaa tagtaaagaa taaatgtgaa agtgagaaaa atctgactgc caaagttttt 32580
actccttcct tccctcccca gacttttaaa tgaaagttta gggataatcc cttagttgtc 32640
ctgctagtag gacttgcaat taaaagaatt gggccaagaa cacttctacg cttctccttt 32700
taggtttggg tgtaaattcg gggtatttct cactgatgaa agcctggtgc agggcagacc 32760
gtgggaagct ttcatttccg gaatggacca tcaacatccc ttggagaaga attctcttct 32820
ccagacccag acctggtgtc ctggcaccca ttgggcaagt gggtcctaga agacaaacct 32880
ggtcagagcc tggaggctgc ttagcattcc ccacgcacat tagcagctcg gagagctcag 32940
gaagccgcag cccctccttg cctcaccagc ctggatcagg acagcatccc ctggaagaca 33000
cacagggcct ggcctctgat tacccagcct ggagggaaag ctcaatcgag catcatgtca 33060
cccggtgccc ccatgcaggg tggcactggt gagaccccca agccaatgat accacctcac 33120
aggagtgcag gcccattgtg gccagatcat cttgactttt caagataaat cagaaatcgt 33180
atttccatga gatatcccta tttgcaagtg atggtgacta aattagaagt ttttgaatat 33240
tgtaacatgt tcgtaggctg tttgtctggt ttaaactcta tctggaggaa ttcaagctag 33300
acttcaggaa taacttcttg aggcaaggat tttgagacct tagggaaaga aggacgtctt 33360
gggggtattc tgactgttgt cctcctggaa gggaagaaca gagaactaga agactgccct 33420
tagcgaagtt caaagcacct aagcccggga ccctcagcaa gtgttcttga gtcacagatt 33480
ctccctgagg cgcctctttc tggctccata gaatggctga ttctgtaact cggtgagttt 33540
gctttttttt tttcctccat cacccaggct ggagtgcagt gaagctggag tgccgtggag 33600
cgatcactgc aacctctgtc tcccaggttc aagcaattct ccttcctcag cctcccaagt 33660
agctgggatt acaagcatgc agcaccacac ctggctaatt tttgtgtttt taatagagac 33720
ggcccgaagt gctaggatta caggcatgag ccaccgcggc cagccataac tctgtgactc 33780
ttgttacaaa ggccttatat tttgctcttt gagggtggtt ttggtttgat gcctgttggt 33840
tgccatcttt taactaggga tgttttatca aaatgcccag ccaaagtgtc caaacaaatt 33900
ataccttaaa gtttgaaaat gtctggcact tctaattcaa tgcctgttgt gccaggcact 33960
gggctgctga ggaactgagt cccgtccctg caggctagct agagaacaca cacacacaca 34020
cacacacaca cacacacaga gtggtcttac aagtcagttt tatattctac ctatatgcaa 34080
taaaggtatt attatgttga ggtgccttga tataaaaatt tttcttaaag gagaggatgc 34140
ctaaaacagg cattacctga aacctcctct ctccagcatt ggttgtcttc tgtcatgact 34200
cagggttttc actgagaatg ggatggaaat gtggtctaaa gatagggcca atgttgggac 34260
tggatcccct ctgggaagtc agaccaggct agggcaggtc cttgaagcca tcaggaaaag 34320
cctctggagc cagaaacaaa acaaaaaaaa aatggtgtta actaaactca gtctcaaatc 34380
ctgaatagga ctcaagtcaa gcaaaataat taaaggagtt agcaaagggc aagtcagaga 34440
gaccgagcaa caccaatgtc ttccgggagc cctgtggcga gtgacagagc ctggactctg 34500
gagtagaact catcttgtgt cttcttctgc cactcgttag ctgggtgacc ttgagccaag 34560
ccccttaacc tcttggaccc tatgttctta tctctaagta ggggctggta atatcttccc 34620
ctttgaggaa tgccctctaa ggggtgttgt gaagattcgg taaggtggca ggggtaggac 34680
tcctggccag aaacaggcac ataataaatg ctaagtctct ccttctctcc acctgctgga 34740
tgctgtagat actaaggatt tcgatgtgaa tgagacaaaa cccctgcctt ccaggagcct 34800
ttgagaatca gagaactaga cccatttcca gaacaagggg atgcagggtc tggataaagt 34860
tttggggatc aatagagcag agggctccca gaggatccca tagggttgac tcctaactca 34920
agggcatgag acaaccccca ggaagggcac cctggaaggg gtccggctgt ccctgattta 34980
cttgtgggca ctgggggaat gcccggagcc atccagccct cagggctctg tgtgattctg 35040
ggttcctccc ataaaagata atcagattct ttcacgttaa tgtctttctc cacctcattg 35100
cacatcatgc agctattcat tgactcagca agtatcagct ttgcatgcga ccttggccta 35160
cccactttag cttttagtaa tagctccctt cttgaataat acaaccagtg gggaaacaga 35220
acctaactct tacctctggg aggcttattt gctttgagaa catatgtcct gcagttttgt 35280
tcatatggca gtgaagtttc gtgcacacac tctagagcca ggcagcctgg gttcaaagcg 35340
cagctctgcc aggtcctaac tgcatgaatt tgggcaagtc gctcaacctc tccatgcctg 35400
agtttcctca tctgtaagat tggagcaatg gtaatacctg ctttttaggg ttgagaagag 35460
aattaaatga attaagatgg gtaaagtgct tagagtggag ctttgcaagt agtaagtgct 35520
atgtaagtgt tcgatttaaa atgaaagacc cttaaataca ttctttgttc atttcacaag 35580
cccttcattt cacaacctta catttcacaa ccaagctctg tctcccctgg aatccagcca 35640
taactctgct cacaagtgtg agacaggccc cagcagagct gcacgaagag gagagaaggc 35700
agccccccag actcccaacc ccctgtccaa gatggcaaaa ccagaacaca gcctctgtac 35760
caccccagca ggtattcaga atctgcaatc tccaaagccc acttcaattg taaatgtaga 35820
gccacgtgcg ctttaagtca cctgtcactc tggaggctct tttgctcagt tcctcaccat 35880
tagcagggat gacagggagt gcaggagtgc ggtcgactcc cagatattgg agagcgctgg 35940
gctagctgcc cattctcccg gcctccactc ctctttgctg tccagccatc acttgctctt 36000
tgaaggcaaa caaaacagaa aacagtgcca aaagtatggg aagaaagcca gcttctcccc 36060

-continued

```
tggggtgcct gtgatgccat gcccaccctc cctgaccacg cagcccctgt ggaccctcag  36120
ggccccaagc ccccatttcc atcacatgcg tacacccatg tgtgtccata gccgcccatc  36180
tcagtcaata aggctgctcc tgcccacttg gaatagtggt gacaaccagg agtggcttat  36240
gggaactatc ccaatggcct gacagcatgt ccgctgcaaa ccgctgaggt aggacactgc  36300
cctcatgtct agctgatcag caagaggcgc agttgctttc ttaggtaaca ttgctgctgt  36360
gtcctggcca ttgctggggg gtggcactta atctacacca gaattttccc tcctgtatct  36420
tccaagctgc ttggatcttg gtgctgaatt aggttggact ttgtcttgtg gggaagggag  36480
gactatagac cctcaacgta agcaatggtc agactattct aagaaaactc gccgaattaa  36540
agcatgaggt aaatttagtt ctgacttctg tccaccccac tgccactgtc cccttttatc  36600
ccatgatccc ttgcttttct tttcctcctc tctccctatc tcttgtgttt gacgcatgat  36660
aggaattcag aaatatatgt ttgtggattt gtttattcac gtagcaaacc atttcttgag  36720
tgcctaccat gggccaggta gaatgggcgg ccccgggctg cagtggtttc ttcagcccct  36780
ctccagggtt tacactgtgc aagacggttt gtgatgggtc ctcccatcga ggaccacact  36840
cttctttctc tgtgcccctt ggtcctcagt ctctgacccc acttcaaagg cagcattcac  36900
tcagggaagc tcccatacaa tgctagtcag agtaaaagtt tggacaaatt gccaggaagc  36960
agcttgtcag tatgcataaa cagcctttaa aatattacta ctctttgacc cagaatttca  37020
cttctaggaa tctgtcctaa ggaagtagtc acatgcaaaa gatttatgta ccaagatgtt  37080
catcaaagtg ttgttttata acaggaagtc tcagaagctg gataaatatc caacctctgg  37140
aaatggttag atagaatagt atgtagccat tagaaaatta tgtctatggg gtttaaaatg  37200
tcatgggaaa acacttctga cataaaagag catgagaact gtatatttag cataatctta  37260
actatgtttt agaatgcaca ggaaaaaaat gtacaaacat attcatagtg atgtctctgg  37320
tggtaggatt atgatcagta agtacttctg tctcttcata ttttcctgta tttgataata  37380
catgcatatg ttgtttttaa aataagaaaa attttaagtt taaaattgga gctgaaaagt  37440
gtttttaggt caggcgaggt ggctcacacc tgtaatagca ccactttggg aggctgaggc  37500
agtcagatca cttgagccca ggagttcgag accagcctgg ccaacatggt gaaaccccat  37560
ctctactaaa aataaaaaaa ttagccatgt gtggtggcac acatctgtaa tcccagctac  37620
ttgggaggct gaggcatgag aattgcttga acccaggagg tggaggttgc agtgagccaa  37680
gatcgtgcca ctgcactcta gtctgggcaa cagagtaaga ctctatgtca aagaaaaaaa  37740
aaaaagaaaa gcctttttaa acagtagcag acataactat ataatcctta ctaagctgtc  37800
ggtcaaattt ttatttatat atttatttta ttcatttatt atttttagac agggtctcac  37860
tctgttgccc aggctggagt acagtggcgt gatcatggct ctcttcaaac ttgacctccc  37920
gggctcaagt gatcctccca tcttagcctc ccaagtagat gggaccacag gtgcatacca  37980
ccacacctgg ctaatttttt ttattttttta tttttagaga tggtgtttac tatgttgccc  38040
aggctagtct caaactcctg ggctcaagct atcctcccac ctcggcctcc cgaagtgctg  38100
gggttaccag catgagccac tgtacccagc cctcaaattt ttaaaaatct ataagagaca  38160
ttattggaca attagagaaa ttcacatatg gacttataat agtatcagag tgtgtggtgt  38220
gatggttctg gagggaatgg actttttctt tggagacagg cttttctatg cccacccttt  38280
tatcttgcta acttatcatc atccaggttc cagcagaaac attacttccc ccaggaaatt  38340
tcttaagggt gcagtatcat gatgtctgca gcaaattctc aaatagctca ggaaaaaagt  38400
acgtgtgtgg tatgagtgtg tgtatgtatg tgtgtatata tatacacata tatacacata  38460
```

tatatacata tatgtgtata tatatacata tatgtgtata tatatacaca cacatacaca 38520
tatatataca cacacacata catacatgta tttttatata attatatatg cagagagtgc 38580
aaatgttgcc aagttaaaga ttggtgagtc taggtgaagg gaatatggta tttattgtat 38640
tatttgtgca acttttctta agtttgaaaa ttttcaaaac aaaaaattgg aggaagaagg 38700
catgccagtc taccccaagc cctccattgg aatgctgaaa atctaaacaa tgtgatttgg 38760
caatttcatt tcttttctgt tgtgggccag tagtccttag atgttgggga agggggtagt 38820
cgctgaggtg tggttgactt aggatggaag aagcagaagt caagactccc agggtcaaag 38880
tggtttgctc tgctgaccca agtgtgggag gcccagagtc agcgtttcag gtgtgctaat 38940
tcagcatggt tctattcacg gccaaagtcc accctgggca cctctctggc agcaatcttg 39000
ggtgactcta ctaaggccag gcctccatga ccctatgtct ggatcccata tctccacctc 39060
tcccactgtc tcaggaacgg tgcttagctt tttcttttcc ctctcctgtc ttctttgcca 39120
gcatgtagaa agtttaaata attcccctct ttacaacaaa acaaaacata ccccccttcag 39180
tcaaccaccc tagctctctt ctccttttcc cagccagatt tttttaaaag catcctaggc 39240
caggcgcggt gactcacgcc tgtaattcca gcactttggg aggccaaggt gggtggatca 39300
caaggtcagg agatcgagac catcctggct aacatggtga aaccccatct ctactaaaaa 39360
tacaaaaaag tagccgggag tggtggcagg tgcctgtagt cccagctact cgggaggctg 39420
aggcaggaga atggcgtgaa cctggtaggc ggaggttgca gtgagccgag atggcgccac 39480
tgcactccag cctgggtgac agagtgagac tccgtctcag gaaaaaaaaa aaaaaaaaaa 39540
aaaaaagcat cctcagcact ttggcaactc catctcctcc caacatgtcc ctgttactgg 39600
aatccagcca ggactcagcc ccgatctttc tactctaacc agttgtctca gttaacaagg 39660
acaggtttat gctgcagtga caaacaagat cccaaattct tgtggcttca cacatctggc 39720
accacctcat cttccagcct taggagtcat cttttagttc cttgaaaact ctttacagtt 39780
ttctgttggg gccttgtcat atactattcc cctggaatgt tctttcctat cccctccctt 39840
tcaccttgct aacttgtgcc catccttcag gtctcagcag aaacatcact tccttgggga 39900
agttttctcc aacacccaca ctacacaggt gtcccatcta cactcctatg actttgtggt 39960
acttgtctca cttcattttc cactgccttc cccacaaggc acctgcacaa gggcaaggac 40020
cgtaccactg tacctatgtc actcattgct gtggtcacct gcactctggc tgcctacctt 40080
aactacacat tagaatcacc tgaggagctt ttaaagccac aatgcaagac tccaccctag 40140
gccaattgga tccaaatccc tggggtaggg ccagacatca gtggagttat atatacatat 40200
atatatttg tttgtttgtt tgtttgtttt ttgagacaga gttttgctct gtcacccagg 40260
ctggagtgca gtggcgcgat cttggctcac tgcaagctcc gcctctcggg ttcacaccat 40320
tctcctgcct cagcctcctg agtggctgga actacaagtg ctcgccacca cgcccagcta 40380
atttttttgt gtttttagta gagatggggt ttcaccgtgt tagccaggat ggtctcgatc 40440
tcctgacctc atgatctgcc tgcctcatca gcctcccaga gtgctgggat tacaggcatg 40500
agccactgca cccggccatc agtggatata tttttaaagc actgcagaga attctgttgc 40560
atcagcttga gaaccactga tctgccttgt gcttcacatt taaaactttt ttttaatgaa 40620
taaataaacc ccaaaaaatt aatctcccta agcctcccta gaagatagga tggtaaggat 40680
attttcctag gtaaaaatat gttaatttca tatttcatga aatttcatgt ttcatttcaa 40740
tcaagctctg tcatacacct tacatggggc aagcccagtg cctgggcagg gtgtaattat 40800

```
actcattaca caggcaagga aaagtcacat taggtgatgg agcacaaata ggcagttaat  40860
ggtttcaggg ctagttagga tatgtttgtc tttcaattgc aagtaataga agcccaaaga  40920
aattggttat ttatataata taattgattg gttcccaaat ttgaaaaatt caggaataga  40980
cccagcttag gtacagctgg atccagtcac tcaaacaatg tcacaaagaa ccctttgaca  41040
ggaatgtatc ctgtgttgac tctactttgc tctgagtagt ctttccccag gtgatgataa  41100
aaatggtcat catcgccagg cttgtgtcct gtttagtagg aatatacaag aagagctcag  41160
taaatgctgg ccccaccact aagcaaaaac aaaacttttg ttgttgttat tgttgtttta  41220
aataacagct tagacctttc ttctttcctt gttattctct ttcatctgta atccagtttt  41280
ctacttctga agtatagaat gttctgatga tttattcttc attacccaca acttgcacat  41340
gtttatttaa aaatgccagg attgcctggc cgttgtgtgc tgttaacctt tgtttgctgt  41400
tagtggatcc ctgaagttca ggctcccagg ggagcagata atgggtatcc agttcctgca  41460
atatccaccc tctggcaagc caagttcctt cctgggtaag gttttgccta cctgcattcc  41520
tagggaagtt tctgggcctg accaccaagc cagctctgag aaggggtgca taagccccac  41580
catgctttgg ctctgtccct atagaatatt ttatgttgtt actgaaaact aaaggaagat  41640
gggtgcggtg gctcatgcct gtaatcccag cactttggga ggccaagaca gattgatcac  41700
tcgatgccag gagttcaaga ccagcctggc caacatggtg aaaccttgtc tctacaaaaa  41760
caaaacaaaa caaaaattag ccgggtatgg tggcatgcac ctgtggtacc agctactcaa  41820
gaggctgagg cacaagaatc tcttgaacct gggaggtaga ggttgcagtg agccgagatc  41880
gcactactgc attccagcct gggtgacaga gcaagattct gtctccaaaa aaaaaaaaaa  41940
aaagaaaagg aaagctaaag gagagagact aaaatgatat caggttcctg gagaacaaac  42000
agacatgatt ttgcttcatg gcaggacagc cggaagaagt gggattatat cctcacatta  42060
caaataagaa aactgagact cagaatggtt aagtcacttg tcccaggcca cacagccagt  42120
aaattacaga aacagaattt gaacccaaat cttccagctc caaagcttgt gttcttttca  42180
ctacctcctg cttaattttt taatttctaa gattagaccc ttcatctatc catgacacct  42240
gcctgtcatc ccctgaaaaa aggtgaacgc cgttcagaaa tttttctagc ctgagctcac  42300
tcccagttca cttatttttg ctttgtcatg gctgcccagt ccccacttgt agaccaggaa  42360
taggtcatgg ctgcggggac tacacgctgt cgctgctgca agggccggcc tctgtttccg  42420
gggctgagtg ggggccagac ctgccaggag caccatcttc tgtgggtcct gcctggatgt  42480
cacatcccgg ccccaagaag tcactgcaaa ccttcgtatt attgagcttc acatcctaga  42540
atttgctgtc actgtggctg ctgcatgaag ttgtcctgag agaaacgggc attgtcatta  42600
acagggaaat tgatggtctg ggggaaaagt catcctcatt ctcttgcaga tctatgggtg  42660
attgagactg gctgatgttg aaggggtttc tcagccatcg tgtgccatgt tatggaacag  42720
tggtgtagcc agccatttga cacccagcgc tgacctttgt ttaacaacct cacctatata  42780
tgacaaaatg attgtcagaa ataatcgtgt aatgaaatga ctgtaataat ggccagaaaa  42840
gaaacgcaga tagtaaaatg tttctcttgt tgaactctgt acatataatt gcaccaggat  42900
tttttcaaa taaaaagtaa atattatact acaaaaaagg gaaaaagcac aagcatttat  42960
taaatagctt tctatatctt tctgagtttt gatcctttga ttgcagactg atgtaatatt  43020
ttatgtaaat cattgcttgg ttactaagtg aactttaaga aaagtgagac gtctgcagaa  43080
gttgcccata atttagcagc tactgtattg taccattgat gtacggcttt attttcttga  43140
ttaattattt aaacaatata attcacaatt ttaaaataat aaatttccac ttaaaatggt  43200
```

atttaaactc agcaaaatat atcatctatg agtaaaattt gtatttacca agcaaaaata 43260
ttacagtttg tggttcacat gctgtctcac tgttttaaat tttaaataca aaaactccaa 43320
gtaggctggg tgtggtggct cacacctgta atcccagtac tttgggaggc tgaggcaggc 43380
atatcgcttg agttcaggag ttcaagattt gcctgggcaa catagtgaga tcctgtctct 43440
actgaaaaca attagctggg tgtggtggca catgcctgcg gtcccagcta ctcaggaggc 43500
tgagatagga ggatcacttg aaccctgggg gacagaggtt gcagtgaggc aagattgcac 43560
cactgcactc cagcctgggt gacagattga gaccctgtct caaaaaaaga aaaaaaaaaa 43620
agaaacacaa aaactccagg tggtcgcaca gaatgacagg actgaagtaa cttagctcca 43680
atttctgtct tcataatcac tgtcctacca ttgtctgtgc ttagaatcta cttgcttaat 43740
gcaggaacat gtgttctcac agagatggaa aatgcaaatg gcgccagaag caagctggaa 43800
attctgaacc attaagaatt tactctctgc caggcacggt ggctcacgcc tgtaatccca 43860
ggactttggg aggctgaggc aggcagatca tctgaggtca ggagttcaag accagcctgg 43920
ccaacatggt gaaacttcat ctctacaaaa atacaaaaat tagccaggca tgatggtggg 43980
tgcctgtaat cccagctact cgggaggctg aggcaggaga atcgcttgca cctgagaggt 44040
ggaggttgca gtgagccgag atctatctgc accattgcac ttcagcctgg gagacagagt 44100
aagactccat ctcaaaaaaa aaaaaaaaaa aaaagaactt actctcaaaa taaatacgtg 44160
tggctgactc cacatatggt agggccaact gtataactag aagttctcca aataacttct 44220
gtggagaaaa aaaagtttat taaaggttaa ctttttaaa gtgctaacta gaaccttact 44280
aacactgaga tcgcaccaat tgtttataac ttagacaggg ccgggtgcag tggctcatgc 44340
ctataatccc aacactttgg gaggccgagg caggtggatc acttgatgtc aggagttcga 44400
gaccagccta accaacatga tgaaacccca tctctactaa aaatacaaaa attagccagg 44460
cacggtggta cacgcctgta atcccagcta ctggggaggg tgaggcagga gaatctcttg 44520
aacccaggag gcggagattg cagtgggcca agatcgcacc attgcactct agccccagca 44580
acaagagtga aactctgttt caaacaaaca aacaaaaaaa aaaacctctt ggaccaggaa 44640
aatatttttt aagggaggag tattttatca ctggcattgt ttaggattgc aggcacatga 44700
tgctaatgaa aagcagacta actattagtt ggttttatta ctgtttttga actctctctc 44760
tccctttttt ttttttttga gacagagtct ctctctctgt cacccaggct ggaatgcagt 44820
gactgcagtc tcagctcact acatcctctg cctcctcagt tcaagtgatt ctcgtgcctc 44880
agcctcccga gtagctggga ttacagggca ccacaccagg ctaagttttt gtatttttag 44940
tagaggcagg gtttcaccat gttgcccagg ctggtctcaa actcctggcc tcaagcgatc 45000
tgcccatctt gacctcccaa agtgttggga ttacaggcgt gagccaccgt gcctagccct 45060
gtttttgaac tctctagaga cagtccagcc ccttattact tgtcctgagg cagctgctcc 45120
cttcacctgg ccccccgcat tgtgttccgg acccttgtcc tggtggtgct aaagaatatc 45180
tctgtcgatc ctttggggac tggggaaact gaggcccagt gccacgcgat gccatttgtt 45240
cagggaagat taggtcatct gctaggtccc cagtcacttg accttcttcc cagacaggaa 45300
gaagctgctc tgggtctctc agtgctccac gtgtctttgc acattgaaat gttttctgat 45360
ttttttttt tttttttgct gttacattta cttttaaaaa ataacaagca ataaaatgtt 45420
acatttgaga aggttgaaat gagaattgat ttgagttaaa ttctagcaga tttttcttag 45480
aagaatgata tcatcatctc cagctacctg caattgatct actctgaatt aagaaagaga 45540

-continued

```
cttccatttg ttgtttatat tttgcactct tgatgtgttt ctttaaatta tggtcatggg  45600
ccaggtgtag gagctcacac ctgtaatccc agcaccttgg gactctgagg agggaggatc  45660
actggaggcc aggagttcaa gacctcgtct gtacagtaaa ttttaaaaat tagccaggca  45720
tggtagcatt cacctgtagt cttagctact tgggaggctg agatgggagg attgcttgag  45780
ccagaacttt gaggctacag tgagttattt tcacgccact gccctctagc ctggctgaca  45840
gagcaagacc tgcctcaaaa aaataagtaa aaaataaatt aaatttcaat cattagcagt  45900
cattaggata tttaaataca gtatgttgaa tcaaagttac gcatgtgtgt attttttttt  45960
ccagagagtt gtttatcatg tgggttttaa tttaacttta aaaaaatgtt ggctggacag  46020
ttgcccaaat ggtatcatca gccatttggt tgagaacgta tgtcctgcgg gctcctctgt  46080
cactggagtt ttgctagctg acagccactg gctagttaga gactgcagtc agcacagatg  46140
caggcgtgga cttgcgcacg taaccatgtc aatgcaaagc catcacttct taaaaattct  46200
gaaccctgct gtctgagatg gtggtgcagc ggatagaact ctgctctaag aggcagtagc  46260
taattccatg tcttctttgc ccttgactag ctgagtgact ttgcacatgg ggcttgcctc  46320
tctgttgcct tgtctgcaaa gtggaatcat cttttccttg ctagacagaa ggtggaccct  46380
ggacctatgg cctttttgag tttccccccc gcttcttaga aggacctctg atcctactga  46440
gtttaatacc cacgggttaa taattgggaa aagcaaagga agcgcttctg tttaggtaat  46500
tatatgcatg tttttgtctt tttctggctg gaaagatatc caagccactg ggaaggtccg  46560
tggctaccca gggtagccct ctctggggag ggctgctata tccaagagcc cctcatgaga  46620
atttgaaaat cgaccatggt agggcctgct gacttttgac agctaatggt gtgctgagaa  46680
ttgtccctcc aaagatgcct ttccattccc tcgggagagt ctgggcagcc cctactgggg  46740
gctgggatgc tggctcttcc ctcagcctcc accccaactg ctctcttccc tcctcccctc  46800
cccagccccc taatttctct cacaaggctt tgttctgcag caacctttcc taatgcagtc  46860
ctggcctctt cgcagcttca ttacataacc ttccgtggac tcctggtcca aggatcaccc  46920
cagaaagcca gtcagaggta ggcacgcagc tggggtccat ttacttacct tccccacccc  46980
ctcggaactc agaggtggtg caggaatttg gactccaaga attaacagct ccaccaccat  47040
caccagagcc aaaactcagg atgcatgtgc ttcatctgct gcttatttcc agctgagagc  47100
cagtggtgcc atggttcctt agggagccgg tcccctgatg ccggctcctg gccccaaatc  47160
tctctgatcc gggctcttcc agaatgtctt gtctccacca tcgcctttga ccaatggtgt  47220
ccctttgcct ggtaatgtcc cctttgcctg atgatggccc tgtcactcct ctctttagca  47280
cagaggaggc tgtttcatcc cttcaagcct gccctccctt caagtcttag ctcaagttca  47340
ccttctccgc agagccttct ccaatcttct tgactacgtc tcctctcagc tccagcaacc  47400
tctgtctctg gcactgattc cttacttagc taagagaatc acagacactt ggggctcagg  47460
acaatctgct ttctctcttc ttacccatgg ccttggactg tgtgtacctc tttgtctcca  47520
ctcccaaacc caaccccag agggcagaga gcatgttgtc tgtccctttg ctcagcatga  47580
agccatgcgt gtggtagatc ggcagagttc cataacttgt gttgaccgag gggtcacttt  47640
gctctgaaat tacccctgtg tccttcagta tttgcacaga tagcttcctg gccagaccga  47700
atatatccaa gggcatggcc cacctctgct cctgtttcca ggtccctggt gggggttagt  47760
tcatgccttc ctcataatct gcccactggc ctggtcctca aggtcttccc aactgctcag  47820
ccagagttga gaaaatgggt cgctccatcc tgtttgtgtc gttctctcct tcctggccca  47880
ctctcctgcc cacaggtatc caggggctgc ctgtagcatt agaggacata catgcacatg  47940
```

cgtgggcatg ggacactcac gtagcctcca agcacagcat caataatgca ttctgtgctt 48000
tatagcatgg aaagctgctc taaactttat tacacagtgg acatgtctga agcagctccc 48060
aaatccaccc ctgagtgtgt tggaattggc aagcctatca cttgggagtc tagttttttt 48120
gttcgttaat aatagatgct tcctgtggcc ccagcttggc aattttgatt taaagtgatc 48180
ttaactgaag agactaatgg acgggtctga atttgtgcct tttaagcaca aagtattgct 48240
cttaattaac tggattctat cctttgagca ggcagaggcc ttcccccaag ggcgtcatta 48300
acgatccaca tctggacatc ttccaaagcc ttcttctgtt tcaggccaac cgcaggtgtg 48360
ttcctgaaca cccaggaggc tatgagagcc acatatgcct cccaaataca cacagtgtgc 48420
atgcccaggg acatagagca gtgtgcaaag tcccattcca tctctctcca cctgggagag 48480
gatggctctt ctgtctgatt catggctcaa agtggtaaag gagctcccca ctccccgtcc 48540
cacgcctact cagagtctgc aaatatgtat gcgatatgag agctcgtcag ttagctgtct 48600
tcagtgtggc gcacatttga ggagtctgac tcccctccag cacaggccaa tgtgcactgc 48660
tctcctatct ttgtaccccc actgttgcac tgtgcagagg ttggagccat agaagtacca 48720
gagctgtgaa aggagaggcc ccctctcacc tctgccctgg tctccatccc cactttctct 48780
aggaagctag taggtgctga caggggagag aagggagggg aggggtccag aaacagtggc 48840
tcatgcctgc aatcctagca ctttgggagg ctgaggcagg aggatcattt gaggtcagga 48900
gtttgagacc agcctgggca atgtagcaag accctatctc tacaaaaaga aaaaatgtaa 48960
ttagctgggt gtggtggtgg gcacctgtag tcctagctac ttgggaggat gaggtgggag 49020
gattgcttga gcccaagagt ttgaggttac agtaagctgt gattgcacca ctgcactcca 49080
gcctgggcaa cagagctgag accctatctc aaaaaaagaa aaaaaaaaag aaaggagaga 49140
gagagaaaga aaagaaaaga aaaaaaaaaa agaagggaag ggaaagccca gaagagtgtg 49200
gggagaggag gcggccgtca ttctggggcc ctcagtgtgc acaaccagat aacacatgct 49260
ctgtgggctt ttgtaccatt ttgcttgagc ataaagaaag gaaggctgcc cctaaataga 49320
aagcactctg gaggcaaaca aatctgactc caatcctggc cctgccactt tcccagctga 49380
ggacttagac aagcacccta gcctcttgga cattctcaga gccatctgct gcaagtgggt 49440
gctgccatac ccaccttact gggcaggctt gggggaccaa gggtggtaaa tggctcagtc 49500
tttcatgatg cggccacaca gcaggtgcgc catccaggtc catttctttc cttcctttcc 49560
cccaaatcaa gttgtcatta aagtactagt ccacattaat gaaatcaact gtattaattt 49620
tctatttgct gctataataa atcatcagaa atttagtggc ttaaaccaac acaaatgtat 49680
taccttacag ttctggaggc cagaagccct ccataggtgt cactgggctg aaatcaaggt 49740
tttggcaagg ttgcggtcct ttctggaggg tccaggggag aatccatttt cttccttttt 49800
ccagcttcta aaggtttcat gcattccttg gctcatgatc ttctatagct atagtcagaa 49860
aaattttcca tcaatcatct tcaaagccag caatggcagg atgagtcctc acatcacctt 49920
gctctgacac cagttctctg cctccctctt ccacatgtca ggaccctcat gattactttg 49980
ggctcactct gataatctgg gatgatctct ctattttaga gtcagctgac tgggaacctt 50040
aattccatct acaaccccaa ttcctctttg ccatgtacag tgacatattc acaggttctg 50100
gggattagga cgagcctgtc tctgaaaggc tactttacat gaaaattcat ttttttaatt 50160
aagattttt tttcctcttg agacaaggtc tcactctatg gttcaggctg gagtgcagtg 50220
gtatgatcac agctcactgc agcctcgacg tctctgggct caggtgatcc tcccacctca 50280

```
gcttccctag tagctggaac tacaggggtg agcccccatg cccagctaat ttttttttt  50340
ttttttttt gagacagagt ctcactcagt cacccaggct ggtgtgcagt ggtgcaatct  50400
cagctcacag caacctccgc ctcctgggtt caagtgattc ttgtgcctca gcctcccaag  50460
gagctgggac tacaggtgtg caccaccacg cccgactaat ttttgtattt ttagtaaaga  50520
tggggtttca ccatgttggc caggctggtc tcaaactcct gatctcaagt gatccaccaa  50580
cctcagcctc tcaaagtgct gggattacag gtgtaagcca acatgcccgg ccccagctaa  50640
tttttaaata tttttttgt agagatgggg ttttaccatt ttgtctaggc tggtcttgaa  50700
ctcctgggct caagcaaacc tcccaccttg gtctcccaaa gtgctgggat tacagcatga  50760
gccactgcac tcggccttaa gagaagattt aataattaat actttacaac aagatctgga  50820
agaggtggga tgagtaacta aatgaggata caagtaaccc gggtcatatt tgctaatacc  50880
cttggtcaca ttgaacttga tatcttatca gattttccta atcagctcct ttagcagcag  50940
tgttgcagca tcttatctca ttttgttttt tgttttttg cctagcacat gcctgtaaat  51000
cactggattg aggtgtttag atgtttgttg tcctttggat gcttcttata aatccatatt  51060
tcatggctcc ctggaaagtg ctatgcaaat gataagctgc aaggatggaa aggaaattgc  51120
agtgctcctg aattgtaaat gggcttttac gaggaggttt ctaattactc gctctttctc  51180
ttgaactgag gagttgaagt gtaggtggca gatccataac agataatcat gtgtgtgatg  51240
tgacttcagc ctgagcgtcg aggaccaagt cacagagcag gaacagccac tctccagtgt  51300
ccttggggct acgtctgagg agaacctggg atttcatata tgacctgcac tggctggggg  51360
gctctcttga cgtaacgtgt tccctctgag catgttacag attctgacat tcttatgttc  51420
cttctgtgga gagacatgta cttagtgacc taactcactt tagcatattt ttgctcatcg  51480
tttgtgtagc ttaaaggaat cagataatta ccccctcccc actactttcg gaagcacaaa  51540
tgcaatgccc tagaattgta ctggggactc aaaaagaaaa gagagtagta aaatctatta  51600
aaggggacaa agacagccta tatactacaa gctttctatt tttatggcag agaatgccat  51660
tttctaagta aacagagaac tgcatttgac ctgcaatatc aaatgcatgg atttgatgct  51720
ttggaaagca actgttttct gcgttaatct gggtgtcttc cgtgaaatgt cctcctgcct  51780
ttggcttaaa cactagcttt gtctacagcc attccatcct gaacctgccc aatcttgtct  51840
gaatcctggt ttcaccactg acaagctgtg tgtccttggg caagttactt cacctgtctg  51900
tgcttcagag tcctcatctg tgagttgggg aatctggaca gaatctaccc catagggcgt  51960
agtgaggatg tgttgaatta tcccaagtgg ctacacagag taagcactca aatgatgtca  52020
tcgttgtcat gattgctgtt accagagcct agagttcatt ctgatactcg agtctgtggc  52080
ccatccagcc caggtaagga atagttggag gagttgggca tgttcagctt gaagaggaga  52140
cgacagggga tatgggatag ttgaatctgt gaagggcccc ctgggatgaa gaactggcat  52200
gttctgtgtg gctccagggc actgagcagg acccatttgc caaagtctca gggacacagt  52260
ttctagctat agacagaaaa attttctgtc actcagagga tgaaaataga atgagccccc  52320
ttaagaggta atgagctccc tgtcattgga aggattccag aagagctagg taaccacttt  52380
aggtgctatc aaggggcttt tttctttaaa gtcctttcca aaagcttctg agattgcata  52440
aacaatagga agccatcttg gtgctttaac acaaactctc cccagtgatg agggttgagc  52500
caaagccaga ttggcaagca gagaggagac ttgtgtacaa ggagttcctc gagtcaattg  52560
ctttttcctt gttctagcca gccagagggc tcctgttgga aaacaggaga ccggagaggc  52620
tgaggcctga ccaaaccagc ttctgcaggc cagctgggag gccacaactc ctacctacgg  52680
```

gaaaactgaa gggcatctct atttttagat tagcaaaaga aaataaattt aagtttgagt 52740
ctcctttgca acttttaaaa gacatcttta ttgagatgat cattcacatt ctataaaatt 52800
cccccacttt gagttacaat tcagtggttt tagtcttcct tgatgatttt gatggtcttt 52860
tcttaaggct cttggaagac ccagaagcct ctcagacaca ggtgggtgtg gagggcgtag 52920
cacagaggca gacttctcat ttcctgggtc tccccttaa tgactctcag agacccctcc 52980
ttccccctgc ccctggcttc taccccaggg gtgtagagtt ttgccatttt ccaagcagaa 53040
cttcatttcc tcttctgtgt ctacactctt tgtgcttctt tcttgccagc tttttctcct 53100
ttgcccgccc ttccttcctt ccttccctcc ctccccccctt ccctccttcc ctctttccct 53160
ccttcccccc ttccaccctt ccccccttcc ccccttccct ccttccttcc ttccttcctg 53220
cctgccttcc ttccttcctt ccttccttcc ttccttcctt ccttccttcc ttcctggtat 53280
gtgactaatt tctgtttcag gacataaatg ttgtccaggc tgttctttgg tctttctgtt 53340
ggataatgga catttggcat tgagagaggc tgctttttct gaaatcatgt tcttggggcc 53400
cagaacctag gtgtgtgctt ctgactttgt tttcttcctg atccaaattc tgatatgtcc 53460
atttaaattg atctagaccc acagggcact gtgggacaga tcctcagtgg aacatgactc 53520
tgtaacgaga gcattttgtt ttgtcaaaat gagaacatat tattgccttt catctgattg 53580
taaacataat acatgtttat aaaacagtat aatgagacaa aaatgtagac actaataagg 53640
gaaaatctcc ctaattgtat ttctcttcac agagaaagcc cctgttgggc atatatactc 53700
tagtttgttt atttgtttga ctacacatat atgtattctt ttcttatgta taaaaattct 53760
gaacatgcac atttctgcaa ctactgtttt cacttgatga tgcatggacc tctctagagt 53820
gtacgtttct tcttccttac aaagcagttg gcttcgccca gggtgcacca ggacacggtt 53880
ttggctctgt ccccagggtg tcacgggacc aggggatgat ctcacagggt ctgccatctg 53940
ccctgcctgg ccggaggctg catcgagagg gccaaggggc accacgtgtc gtgggtactg 54000
tcaaacaaga gccttcagag ccttccacag tctttctttt gcttcccagc attgcttccc 54060
cgctggtgga ctctgaatct agaactagct ccaggcgcct ctccaaattc agacgggagc 54120
tggggcacta ttataatgca aatctaggca aagccctccc aataccagga tccagaatgg 54180
ggtggggccc tttgccctga aaagctgttt agtttgaaaa tacaaacagg agacagaaaa 54240
gtttggctaa attaatggat aaagttttaa cgatggtaac catagtaggg ttcatcgaca 54300
gccagcgatg gttctgaaca cttgacatgt attaactcac ctaatcccca cattttacag 54360
acaatgcaaa ggaggctctg ggaggttgag tgacttgccc caaagtcgca cagctcctaa 54420
gtgaaggatt cggagtggac tccaggcagc ctggtctgac tccctgcact gcgctgtgct 54480
tatctctggc cccaatgccg ccatgcagaa gtgtctgggg gcactttgtc tctgtcagac 54540
agaattcgga gatgtgtatg cttgccctgg tatggcactt ctctttttttt gagacagaat 54600
ctcactctgt caccctggct ggagtgcagt ggcatgatct cagctcactg caacctccgc 54660
ctcccaggtt caagcaattc ttgtgcctca gcctcccaag tagctgggat tatagatgtg 54720
caccatcgtg cctagctaaa tttttgtact tttagtaaag atgttgtttt gctgtgttgg 54780
ccaagctgat ctcgaacttt tggcctcaag tgatctgcct acctcagcct cccaaagtgc 54840
tgggattaca ggcatgagcc accatgcctg gcagtgtggc acttcttacg tgtgttcagc 54900
ggacactgtt tatcttctgt ccctccaaga cggtgctgag ctcaggtcgt tcattactgg 54960
cagacaactg ctgatttcca acagaattgc catcctcttc tcccctgcga ctttcagagt 55020
gtgacctcag actcaaaaat tagaagtgaa aacatcttaa aaactatcac cttttcttcc 55080
taatcctcct ctcccctccc tgtcttcctt gttgtcccca tctaatgaac tatcatggca 55140
aaaagagccc atttctggtc attttctgtg gcctttcaaa ctcccaccta ccccactgct 55200
cctgggtgca ttacccgaaa gctgagactt cagtgcagaa agtgccaggc cctctgtccc 55260
cccagatcgc cttccttgtc ttccctgtgc ttgcctgtca cattgtgtgg gttccagcgc 55320
tggaaggaat gaggaacaga ttctctggtt ctccttttga agtttacctt cgctccacca 55380
cttctgagac cttcccggaa gttgcccctt gtttctctcc tctccagggc tgccccagag 55440
ctgcctctca cctcttcctg ctgtcacccc accaccatca gggcagaagt tgggacaaag 55500
cctctcctac tggctcctgc ttttctccct taggtccagc ctcctcttct ccatcttcag 55560
gagtctcctt ctccactcac acgtcatgac ttcagcacct cgcatcagtc cagaatatga 55620
ctgcttgttc aagtgccacc tttctcatgc atttttttct agtgacaatc acagccaccc 55680
tgtggggcag gagtgtcatc atccccatgt ttcaaatgaa gaattgcagt tcagagaggg 55740
caagtgactg gcccagcctc aacagctagc cagtggaccc caccagggct tctgactcca 55800
gtccgggttc cctttccacc caaatccatg gagggagctg agccgagaac aggtgtcctt 55860
caggaagacg tgaagccaaa gcctccacct ccaaactcag gggcccaggg agtccaggca 55920
cccatccact cacaaggctg gatatggtgc attccaggag aggggttggg ggcgagtggc 55980
ctctctgtgt acccgtgggg atagatgcgc aagtggcatc gccacatcgt gagtcctggc 56040
ttcatgggtg agctccaggt ccaacgagaa gccaagcagg gggcccttca agctcagctt 56100
tgggcccggg tcggggtaca gggtagagcg ggcctcccca gcccctgcca tgaggccaag 56160
gcagtgcatc gttcgcagcg tacattcaga aaccaaagcc taggagctgg ttatcattcc 56220
ggtttacagc tgatggaaga gcaggtgctt ccgagaaccc acagtgctct ttggccagtg 56280
acccaagggt gcctctgaga ggcctcgcag cacccggagg tgctgctgag gcaacgccct 56340
gactgtaaga aggaccattc atcctcagag agtggccgtg atgctgctgc gacagtccca 56400
ccatccctcc cgactctcac tcccaacaga cttcccactg taaagctgaa ctctccagca 56460
aatcacctct cgccagactc tctcctcact ctctctgggt ccactagagg ttcctcagcc 56520
tctctttgcc ttggttttcc cagctgtaaa atggagcaaa gagggcctat gtacccacaa 56580
aggtgtggtt ggagcgactc ctcctacatt agggcctcga gtggggcttc atgattggtt 56640
ggtggaggtc tccaaaccca cccagtgcca ccgaaggctg agactgcaga tgcaatgcca 56700
caggtgtcct tcctcagcct gggcagctga acatcatgtg taaaacgggg ataataagat 56760
aataacagcc ccttgcacct atgtggctgt gaggattaaa caagataaat gtgtaacagt 56820
gcctggctat agaaatattt actcttgtta ttaagggaag aatatgtgtg gctaaaaagg 56880
gatcgaagat gtaaaagcca atccctcccc ctctagcata tttaagggta atgttgagtt 56940
ggtttgtgga ccatttgctg cctgttagag ctggaaggta gggaccccct ctcaacagcg 57000
atgctacaaa ttatacccat tggaggtcaa ccaaaagaca aagcttattg gctggacatg 57060
gtggctcaca cctgtaatcc tagcactttg ggaggccaag gcaggcggat cacttgagat 57120
caggagttcg agaccagcct ggccaacatg gtgaaacccc atccctacta aaaatacaaa 57180
aattagctgg gcgtggtggt gcacacctgt aatcccagct actcaggagg ctgaggcagg 57240
agaatcacta gaacccagga ggtgaaggtt gcagtgagcc gagatcgcac cactgtactc 57300
aaaccgaggc aacagaggga gacgcaatct caaaaaaaaa gaaaaaaaga caaagcttgt 57360
taataccagc atattgttaa gggaataaag taggctgcag aacaactggt gtaatatggt 57420
gccatgtagg gaaaattaca tgtgtgcata ggagaggggt ctgcaaggtt gtgccctaag 57480
atgttagagt ggttcctttg cttttctctt ttataatttt gtatttgact tttaaataag 57540
gaccataaat cacttttata aaatacattc tctccagccc ctactactcc tttaaagaat 57600
aagagtggtt tgcccaagaa agacagtttt ttttgctctg gttttcttga ttctgacatc 57660
agaggaaact gcttctcatc cacttggggc tctgggttca ggggattcat ttcaggcaga 57720
ttaaagtggt gaccaggggc attcgtggac acagggaggg acaggagcac catcagtttg 57780
tctcacacaa ccactgtcat cctcactgaa ggctgttgcc tgatcaaaaa cagtattggg 57840
ccaggcacgg tggctcacac ctgtaatacc accactttgg gaggctgagg tgagtggatc 57900
acttgaggtc aggagttcga gatcaacctg gccaacatgg tgaaaccttg tctctactaa 57960
aagttcaaaa attagccagg cgtggtgggt gcctgtagtc ccagctactt gggaggctga 58020
ggcaggagaa ttgcttgaac ccgagaggta gaggttgcag tgagccgaga tggcaccacc 58080
acactccagc ctgggcgacc gagggggact ctgtcttaaa aaaaaaaaaa aaaaatatat 58140
atatatatat atatatatgt caaaaatggg gtagttttta gatctatagt agttctaaaa 58200
acaaaggcca tccaagcatg acagatttac aagcactatt ggctattcca gtagttacaa 58260
tggaggagag aagcttttag ttaaaacaaa caaacaacac aacaaaccca gaaaccttag 58320
gtcaaaacca aaattgtcct ctcagacaca atctgggaat tttctcatga cagtgggcat 58380
tagccaactg acatcagcag caaccatccg tgtgcacaca gtggcaccac ctcctcccaa 58440
aaagcagcct tcatctatgc cctcatacaa tcgttgatta ttctctttgg attgaggccc 58500
ggaattattt aagtttcttc ttgccagcat gagtctttcc tttctgtatg ctccttatct 58560
tctctcttta atttggcagt tctgcttgaa atctgggtct ttcattagta gtagttcaat 58620
ttggttccag aacattctgt ggtgtgatgc aatgtgacca gagctcacac ttcagagctc 58680
ttcaagggcc agtcttactg agcacctccc agtggctgcc tgtgtgctgg gcgccacttg 58740
tggtgggcag gagagaggag gggacacaaa aggagacaca gctccttctt agaagctcaa 58800
agttggggac cagctgccac agaagagtat gtttagcatc tgagacacca agatccagcg 58860
tcacaagggt gtttattaag cctcctcatc tctttctttt tctttttttt tttttttttc 58920
ctcaggcagt cttactctgt cacccaggct ggagtgcagt ggcatgatct cggctcactg 58980
catgcaacca ccacctcccg ggtttaagca attctcctgc ctcagcctcc ccagtagctg 59040
ggattacagg tgcccaccac cacacccagc taatttttgt gtttttagta gagacagggt 59100
ttcaccatgt tggtcaggct ggtctcgaac tcctgacctc agatgattca cccacctcgg 59160
cctcccagtg tgctgggatt acaggtgtga gccaccgcgc ctggccttgc tgttgattca 59220
tctatagtat gtttgacttg atgacctcca gttaccttag acagaggttc tcatctaagc 59280
tccaactttc catttccttt gtcctcgtct ttccccttaa cccctccaca tttctctcaa 59340
aatcacccca cttctaaaaa atactgttta tttttctttt aaatttcaaa ttatctatac 59400
tcattgaaat aaatcaaaat agcatggaat aagcgaaaaa aatggatccc acccttcccc 59460
actcccattc cctagggcta accatagtta accatttaat gactaggttt ttttgttgtt 59520
gttatttttt atttatttat tttgagacag agtcttactc tgtcacccag gctggagtgc 59580
agtggtgtga tctcggctca ctgcaacctc tgcctcccag gttcaagcat tctcctgcct 59640
ctgcctcctg agtagctggg attacaggtg cctgccacca cacctggcta atttttgtac 59700
ttttggtaga gacagggttt ctcaatgtta gccaggctgg tctcgaactc ctggcctcaa 59760
gtgatctgcc caccttggcc ttccaaaata ctgggattaa ggtatgagcc accgcaccca 59820
gccctcctgg gctcttttcc tttagttgca ctcgctcccc gctcctggag tagagggatt 59880
tccgagagac tgtgggctcc agccttcacc taggcccagg actaggatgc ctgccctaac 59940
atttatcttt ataccttaaa gcaaaacagc tggaccataa gcattcaaga acaaactgtg 60000
aataaggaga aagttctccc aggaaacaag agctttagtt ctgttgggcc agcccttata 60060
ttccttagct gttaccagtc actgcttgat ttaatctcgg ctatcacttg gcctgacagg 60120
tctgctgctg gtgccaggat gtctgggttt tgaagcctgg ctccattaca tacttcctgt 60180
gtgaccttgg gcaacttact caacctgtct gttcctcagt ttccccagct gtattatgtc 60240
agcataatag tttgttgtgt gaattaaatg aggtaataac tggaaatgct tcaaacatgg 60300
ttcctatcat gagaaatcct gctttccgcc taaatgtgct ggaaaattcc tggtggtgca 60360
gaacaggaga ccagagcaaa ggaaagacag ggtgcagaag ccaaaaatta ccttggagaa 60420
caaagcgcat gttaaggtta tttttggatt ctaggtttat ctctgcttgg tcttcagtta 60480
cctgcaagag atccatttag gggatttttg tttgttttta acgatagctt tattgagata 60540
taattcatat gccataaaag tcactctttt aaaatgtttc cggtatattc acaaggctgt 60600
gcagccttcc ctgtccttga ttccagtctg agtttttaac tgaagggata aggaggacca 60660
cgctttcccc agaccagaac cgcgggccag ggggcgattc tgctgagtca ccgcgggcgc 60720
ctggtgcgcg gcggcggagc ccgggacctt ccttggctgc cccctagcga gggccgcagc 60780
gcagcctgag acacccgccg gggccgctcc acggccgtcg gatttagact ggaagctcgg 60840
tccaggtccc cagcttgatg cgcccgcggt gtaggagacc agcccgactc gggcttcccc 60900
tgagcccctg gactcttgac tccagcaggg cctgggtaat gaacgtcagc tccccttccc 60960
caaaggggtt gctctgttgg gaaggcaccc gtttgataca gtagcataga gatgggtttt 61020
agcatcaaaa tatcagaatt caagccttgc tctctgctta ctagctgtgt gaccctaaaa 61080
aggtttctga acgtctctga gcttcagttt cctcatcatt ccttctcacg gggtggttgt 61140
gagcattaca gagatcctct ctgtgaagcc cctgtgagtg gctcatcctg agggctgaaa 61200
taaacatgtt attaataatc caaaactggc aagggatgtt gactggtccc cctcccttgc 61260
ccaaggagct ttctagaacc tgagttatca ttaccaaact gtactgcctt gagtaagaaa 61320
gttagaagga atgggaagga tggtggcagg tggaggaagg cggattggtc atcacctcct 61380
tgcagcaaga aacagcccca gatcgtggga aacctacaga cctgctagac agactaggag 61440
caaaagctgg ggctttaaga atccccaggg aggttctcct gagagagtag ccagttggat 61500
tttgtaagca gagatttgtt tggggaggag gtgacaacgt agggagcaga ggggcaaagc 61560
tgtcgggaat cctgccttga gggcagggat gtgtgttggg gggagttggg tcactggggc 61620
tcggtggcct tgggcaagtt tctacctctc aggtccttta cccacctagg gtcgccatcc 61680
tgcccacctc acaggttaca gtgagcctgg atgcactgtc atgggcaggt gcccaggaaa 61740
atggcagaca tgttccaaac agcacgcagc attccccagt gatgcccagg gtcaccttgg 61800
aggtgggcga gatgcctggg gtttctcgtc caccccacaa cacctcaggg gacagccaaa 61860
gctgtccctt caggtaagct gcacagaaga tgtgaactct gctgcaaaga ctctattctt 61920
tgggagcaaa agggacccag ggtctcacct gcacatccct gtccctgagg gcctaggggt 61980
tcttggaggc cccagccttg gcaaaatgag gaagaaggtg aaggttgtct gggcccctgc 62040
caggctcctt cctcggccac gcactcccct tcctgcacac acacccttct ccctccaccc 62100
catctccatt gttgtcagaa aagtcacaat aaaaaggtcc atattgtcta gttcccatac 62160

```
ttttaatttt taaaatttta tttatttatt tatttatgta ttttttgaga cagagtctta  62220
acccaggctg gagttcagtg gcatgatcta ggctcactgc aacctctccc tcctgggttc  62280
aagtgattct catgcctcag cctcccgagt agctgagatt acagatatgt gccactatgc  62340
ccagctaatt tttgtatttt tagtagagac ggggtttcac catgttggcc aggctggtct  62400
cgaactcctg gcctcaagtg atctgcctgc ctgagcctcc ggaagtgctg ggatttcagg  62460
tgtgagccac cgcactcggc tccacacttt tcacttatta aaagactgtg gtgtccatca  62520
atggatgaat gaataaacca atgtggacta tccctcccat tacccaagga atgaagcacg  62580
gagccgtgcc aagatctgga ttcacagtga aagaagccag tcaccaaaag ccacgtgctg  62640
tgtgacttcc cttatacgaa atatccagaa gagatacatc catggtgaca gaaagtagat  62700
gagcagctgg ggactggcga aggggagaag ggggagcagc tgtctatgag gtccagcctt  62760
tcttctgggt ttggtgagaa tgttttggaa ctagatagag gtgatagttg tacaacattg  62820
tgaatgtact aaatgccact gaatcattca ttttaaatcg ttctttacgt tgcatgaatt  62880
ttaagtcaat caaaaacagt tgtttgaaaa gagaaaagcc tatgggtagc ggcagcagtg  62940
attggattta tgattcgatt ccatggctca tccctcccct gcctcacccc ctcgccctcc  63000
gacgtcttct tcttttactc tgaactgtta tctttgttct catctctctc tctctctctc  63060
aaccctgcag acacttttcc ctttctttgt ctgccccccac cctccagatt tccgtgtctc  63120
cagtgtctcc ctacgaggca tgaattgaga ctgggagggt gtgattctga agaaggcacc  63180
aacagtgact cagctagccc cttcccccac cccgcccccc gggcctcaat ttagctaaaa  63240
aaccacaggg acggactcag gaggcaatac ctttccaagg gtccctaaaa aatgtcccat  63300
tttagtgtcc aggtttcact caactttagt gcctccccta aaatgtgttc cttacctccc  63360
accccactgc atctaagtca ctgcctgaga aaacaggatt gaggaaagga gaaaggaaga  63420
gagagagaga ggaggagaga gagagagagg gaggaaggct gatggattta gaaaagaaga  63480
aaacaagtgg tctgaggaaa acagccttgg tgtgtttatt ttcctgtctg tgtatcgctt  63540
ctcggccttt tggctaagat caagtgtatt ttcctgtctg tgtgtctcgc ttagattaca  63600
gggatctgtg ggtgatgaca cgtctggtcc aggctgcgta gtcacctcaa gggcatgctt  63660
attgatgtgt ttttcaattc actatctttg catgggagtc ccaggccaag aggcacagct  63720
gcgccatttg tctgttggtt tagatatcct ttatccagtt cttccagaga aatcatcctg  63780
cccttctgga ggaggtgggc agcaggggtc agagatggga gggaaaggaa ggagccaggt  63840
ccttggctag gatgccaggg tcccctgcct ctcacctggc ctgggctgga ggcctcctgc  63900
tgtcctgtca ctgatcacta ccccgcccca gcctcctgag ttagaagaca caggctaaag  63960
tagagtattt cttcattgaa aaacccatac aaaataaagg ttcataaaaa ataaaaattt  64020
agactgggtg ctgtggctca cacctgtgat cccagcactt tgggaggcca aggcaggtgg  64080
atcgcttgag ccctggggtt catgaccagc ctgggcaaca tagtgaaacc ccatctctac  64140
aaaaaataca aaaaattagc caggcatggt ggtgcatacc tgtggtccca gcttctcagc  64200
ctatggaccc acatagaata caatgtcagc ataagaaggg agccctgggg tcaccaaatg  64260
gtttgggcgg caaagaacct gaaggttgag agaagtggct tggttaccca gctgttggat  64320
gtgagacctg gccactgctt cttccatacc ctagacctgc accctgacat ctcaagtaaa  64380
aagttggggg atgttttatg gtccaggatg aaggaagggc agtgaggggc agcggagcat  64440
cactttgcat ttctgtctgc ctcttactgg ctgtgtgacc tggggcaggt aacttcccag  64500
```

actcctggga atcataacac ctatgatgat gatgatgatg atgatgatga tgacacctac 64560
ctcaaggatt gccctgaagg gtcacagaga tgcctgcaag gcacctgcat ggagcaagcg 64620
ccccttctct ggcaggtgct gggtgagcac tacctgctgc caggccctgg ggctatggca 64680
ctgcgtgacc ctgcaagtcc tacctggcga agctgtcgtt cttgtgctca gtcagtgttg 64740
gttgtaagac tgagaagagt cacttcattt tgctctccag ggacatcttt ctgggtccta 64800
ttttctgcct atgtcaagta gcgcctcaag gatgctcctg aaaatgggct tgtctttctt 64860
aacatggcag gtaggtccca aagcattagc atggggcagc tgacctagcc cagccaatgc 64920
agtgcagtga ctcttgcaac cgagtctaat cagaaggtcc atgaacctac gagcatttcc 64980
tgtcccagga tcagggtgga ggctgagcct ccctgcttag agattcttcc catgcattcc 65040 actttttttcc ccaaaagaaa atattgaccc ttgagaggca cacagtttat ttattttgca 65100
tagtaaatag tagcctgtat tttaaggatg agttgatttc tgcatcagcc cctgtaggtc 65160
atcagccttc tattggtgca tctgactctc tctagccctg cagggatggt ggaggggggag 65220 gggaaggagg gatctttatt ggaaaccagg acagtgagac tcattgccct gtcatctgct 65280
ctgtggtgct gaatgaggca gcccaacaga gaaataccct gagcgagcat ccccagcctc 65340
caaaacagtg gcgcattgcc ctgagtcctg ggaatgacct ttgattctcc tgctcctgac 65400
ttggaaccca tggaaacctc tagaagcagc tgaggaaaac ccaacatgaa aagcagaact 65460
ccacactgag aatataggag gtgatcggaa catacaatga ttcttgctaa gaccgattca 65520
cagtttttct tttttttcga tcgaagaaat actggagaag cctaaagaag gagtctaaaa 65580
actctggcac gtgggccaaa actgtccttg agctaagaat gattttcaca tttttaagtg 65640
gttgaaaaat gaaataaaat aagatgatgt tttgtgacac atgaaagcta tgggaaattc 65700
aaattctaat atctataaat agtgttttat cagaacacag tcatgctcat ttatttatgc 65760
tcgatggctg ctttcccgct acaattacgt tgagcagtta caacagagac cacgtggccc 65820
acaaagcctt acaatattta ctatctggcc ctttccagaa aaaaatgtgc cgactcttga 65880
ccttaacctc agcaatttgg gaggccgagg caggcggatc gcttgagctc tggagttcat 65940
gaccagcctg ggcaacatag taagactcca tctctacaaa aaatacaaaa cattagccag 66000
gcatggtggt gcacacctgt ggtcctagcc actcgggaga ctgaggtggg aggatcgcct 66060
gagcccagga agtcgaggct gcagtgagct gtgatggcac cactgcacct cagcctgggc 66120
gacagagcaa gaccttgtct ccaaataaat aaataatgca aagtaaaata aataaaacca 66180
tataaaaagg aatcaattta aaattataat gaaagctggc cgggcatggt ggctcacgcc 66240
tgtaatccca gcactttggg aggctgaggt gggtggatca cgaggccagg agatcgagac 66300
catcttggct aacacggtga aaccccgtct ctactaaaaa tacaaaaaaa aaattagccg 66360
ggcacagtgg cgggcgcctg tagtcccagc tactcgggag gctgaggcag gagaatgtct 66420
tgaacccggg aggtggagct tgcagtgagc cgagatcgtg ccacttgcag tccagcctgg 66480
gcgaaagagc gagactccgt ctcaaaaaca aaaacaaaaa caaaaacaaa aaaaaattat 66540
aatgaaagcc aaggggcata gtagaacaaa ttttctagag ctcattaagt caaatgagtc 66600
accagttagt aaaacgcagt cacggggaag agagggcagg attctttgaa gcagcggctc 66660
tcctaaaaac aacccaccct tgtccagctg ccttccctcc tgagggtgtt ccctttgact 66720
gtgtgacccc catcccctat ttcccaaccg tccaagccca cctctagcat aatacgagct 66780
tttaatccct ctccctgacc ccaacccgat tttgaagccc agtctagtat tttctcaaat 66840
acacttcttg gctccattcc ttcctttcca tcacctctgc cttttcactg catgcttgga 66900

-continued

```
ccactgcagt cagctcccta tgaacagttg ctctctaccc atccaatcgg ccccgcctgc  66960
tgctgccaaa ttcaccgagg gcacctctgt ggtgctgcct gtggacaaag tccaagccag  67020
ccacctcacc cacctacagg tgagtgggga gcagccagcg tgtccagtgg tttaccccat  67080
cgccacagac ttggtgatgt gtcgatgtgc agagaagggg tgttggcagc cacaacacaa  67140
gcaaccccgc cccatgtgag atctaagatg ggcgtgctgg gagccacctc tgagaatcca  67200
acagaaggca gaggggagaa cggctcacac ggcacaaaca ctccttcctt ttttttttt  67260
ctttttcctt tttgaaagga gtctcactct attgcccagg caggagtgca gtggtgcaat  67320
ctcagctcac tgcaacctcc gcctcctagg ttcaagcgat tctccagcct cagcttccca  67380
agtagctggg attacaggta cactccacca tgcccggcta atttttgtgt ttttagtaga  67440
gacggggttt ccctatgttg gccaggctgg tcttgagctc ctgacctcag gtgatctgcc  67500
tgccttggcc tcccaaagtg ctgggattac aggtgtgagc catggggcct agcctccttc  67560
catttaaatg tatgcctaat ttgcccattg agaacggctg agacgcattt taagtggcca  67620
gggtctactt agagttagtg ctcatgacca ggcccaggtc aagcctggct ggccagatgg  67680
tgcctttgac ctgctctgtc tctgtgcaaa ggaatgagct gaaggatggg ggtgcagtgt  67740
gtgggcagtg ggctggggct ggcaggactc agtgactaag ggaagagaac tttcctcact  67800
accagcctgt cttttcaggg caccgcgggg ggctttggga cttggtgatg aacacagcac  67860
agagagctgt ccagcatgcg ggtccctggc ttctcacact tcccaggctc cttcagaggc  67920
tctctccaaa gggagctgct ctctctagaa cccatgaatt tggaatatag gcaaccactg  67980
cattggggac cactgacctc aaacatagag accagagcaa atggggctca tcacgtgaaa  68040
ctcatctgga actctagcag gttcttttat atatatatat atatatatat atatatatat  68100
atatatatat atatatatat tttttattat tatactttaa gttctagggt acatgtgcac  68160
aacatgcagg tttgttacat atgtatacat gtgccatgtt ggtgtgctgc acccattaat  68220
tcatcattta cattaggtat atctcctaat gctatccctc cccactcccc ccaccccaca  68280
acaggcccca gtgtgtgatg ttccccttcc tgtgtccaag tgttctcatt gttcaattcc  68340
cacctacgag tgagaacatg ctgtgtttgg tttttttgtc cttgcgatag tttgctgaga  68400
atgatggttt ccagcttcat ccatgtccct acaaaggaca tgaactcatc atttttttatg  68460
gctgcatagt attccatggt gtatatgtgc cacattttct taatccagtc tatcattgtt  68520
ggacatttgg gttggttcca agtctttgct attgtgaata gtgccgcaat aaacatacgt  68580
gtgcatgtgt ctttataaca gcatgattta tattcctttg gttatatacc cagtaatgag  68640
atggctgggt caaatggtat ttctagttct agatccctga ggaatcgcca cactgtcttc  68700
cacaatggtt gaactagttt acagtcctac caacagtgta aaagtgttcc tatttctcca  68760
catcctctcc agcagctgtt gtttcctgac tttttaatga tcgccattct aactggtgtg  68820
agatgttatc tcatggtggt tttgatttgc atttctctga tggccagtga tgatgagcat  68880
tttttcacgt gtctgttggc gaactctagc agcttctttt cacaagttca tggagagagg  68940
tttcccactg agggaatcac atctgtctga tcaaaagagg cttgggaaat ggctctcctg  69000
ttcattccct gaaaacctct gatggaacca ctgccactgt ggcagcccca gcactggcac  69060
cccagccatg attggtgccc cagccacatc tctgctgtga gccccagagc cctggttaat  69120
taatcatcca cgtgttgatg gggagaggcc cattcacaaa agcgacataa agcccaggga  69180
gacgtggccg tggcaagaag ggtgtgggac tacattccgc cccaactga gagattcaga  69240
```

```
aaccagaaaa aaatggaaaa acatactgtg ctcttgggtg ggaaaactaa atatcatgaa  69300
gggagcaatt tttatagttt tggcctataa tacaattcca gccgaaatcc cagtggaact  69360
ttgagaattt gcaggaaaaa aaaaaatgtc taaagtacat ctggaagaca aacttacaag  69420
aaggtcaaat aattttgaaa aagaaaatga tatctaagcc cacctagaga ataagacttg  69480
agatccaaag ctaaatcagg aggctctagc aaaattgaca gataagcagg acagagtgca  69540
tggtgcattc acctggggaa gagggcagat tggtctacaa ataggcctgg gtccactgac  69600
tttagctgtt atatttgggg agaaactttt caacctcact ccatcttaaa cctaaaaata  69660
ttccagatga attaataaat ataaaaaatt agaccactaa aaatgtagaa gaaaatggat  69720
gatctttcta taccatagag caatggaata aatcacaaag gaaaacagat ttgactatat  69780
aaaacttaaa ccctgcccat caaaaaccat cagaaaccaa aataaaaggc aaccaactgg  69840
agaagatagt tgccacaaat atgatcaagg gttaatgtta ttcataaatt aagagcccac  69900
acaagtcatt agaataagca ctgagacctg aacagacaag caaaaagaat gagagtgggt  69960
cggcgcggcg gctcatgcct gtaatcccag cactttggaa ggctgaagca ggcggatcac  70020
ttgatcccag gagttccaac accagcctga gcaacatggt gaaaccctgc ctctacaaaa  70080
gtcataaata ttagccgggt gtgatggcac acgcctgtag tcccagctac tcaggaggct  70140
gaggtgggtg gatcacttga gcccgggagg tagagtctgc agtgagccaa gatcacaccg  70200
ctgcactcca gctggagcaa cagagtgaga ccctgactta aaagaaaaaa aaaaaaaaag  70260
aggagaaaaa tgctgatctc actagtaatt aaaacatcag gccaggcgca gtggctcaca  70320
cctttaatcc cagcactctg ggaggctgag gcaggcagat cacttgagat caggagttct  70380
agaccagctt ggccaacatg gtgaaatccc gtctctacaa aaaatacaaa aattcgccaa  70440
gcgtggtggc acatgcctgt gatcccagct actcgggagg ctgagacagg agaattgctt  70500
gaacacggga ggcagaggtt gcagtaagct gagatcgtac cattccagtc cagcctgggc  70560
tacagagcga gactctgtcc cagaaaaaat taaaacatca catatttaaa caactctagg  70620
atatcattta aaaaaacatt aatagactgt tttttagagc acttttaggt tcacagtgaa  70680
actgagtgga aggtacagag acttcccgta tgttccctgc cctccacgta cagcctcccc  70740
cactgccaac gtcctgcacc agagtggtac acttgttaca accaatgaat cctcattaac  70800
atatcattat cacccaagtt catagtttac attagtaaaa catcatcttt catctataag  70860
cacaaaaatt ttttggcatt tatttaggtg tatgattaac tcagtgttga caagactcac  70920
acttcatacc cacttgcact gcatctgaga agcaattggt gtctacagcc gctacaccct  70980
caacaagccc gatcttgttt gaaaagcaat tggtgatgct tctcaaaatt ctatggacaa  71040
agtcagccgg gcatggtggc tcatgcctgt aatccctaaa ctttgggagg ccgaggcagg  71100
cagatcacct gaggtctggt gaaaccctgt ctctactaaa aatgcaaaaa ttacccaggc  71160
atggtggctg gggcctgtaa tcccagctac tcgggaggct gaggcaggag aatcgcttga  71220
agcaaggagg cggaggtttc agtgagccaa gattgcacca ctgcactcca gcctgggtga  71280
caagagtgaa actccatcta aaaaaaaaaa attatggaca aagtttttca aaaagatatt  71340
taatgcaact ttatttgtaa tattggaaca tctgaggcca tttcagtgct aactattagg  71400
ggatggttag gaaaatatgg tacatatgtg gaaaggaaca tttggtagtt agtgcccctg  71460
atgtttacaa aggcttttag tgaccaacaa atgctcatgc tataatctta tgtgaaaaaa  71520
gcaagtagca taattgcaac tatattttta atgcatagaa taaaaggcta gaaggaaata  71580
tcacagatcc ttgacataca ttcccaaacc tttgtaaatc cgcggattca tgaaaacaga  71640
```

cacatttgca caagtgcctg atcttttctg ttatacattc attagaagtc aagccctggt 71700
gccacaaagt atctgccttt tcaaatgtga tcagaatgtt ctcttttgct tcaaggccat 71760
ttttcacgaa gcagtggcat ttttgcctct tcatcagagt caccgtgtgc cctggaggac 71820
tgagaacagc agagccgttt taggatggga cagggcagcc aggaggattg ggctcactcc 71880
ctactgagtg cctcactccc gtacagcccc catagaggaa gaggggttca aatttattcc 71940
tcagccagat ggcatgtgcc gcctgtcctg gaatttcaca tcacttatga tggaccaaaa 72000
ttccaaaagc tgaatccatg attgtcaaag tctggtatgg caggatgtca acagtaatcg 72060
tttctgggca gagggatgat ttctcttcc catcttgctt tgtataaata catttctat 72120
aataaggttg tattactttt ctcatcaaga aatagcaaag tactgtttta ctcaaaatat 72180
gaatagagcc aggcatggtg gcagcttatg cctgtaatcc caacactttg agaggcggat 72240
atgggaggat cactttagcc caggagtttg agaccagcct gggcaacata gtgagacccc 72300
cgtccccact cccccaaaga aaacccacaa agcatttatc ctggattatt cacaggggcc 72360
aaaaaaaaaa aaaaaaattc aggcctccta tagccatgag ctacgaatat gaaaatatgc 72420
aaatgtgtaa gaaaagccag cacatccgat ttttactttt actttcacac ctctgtccac 72480
catgttccaa gagaagaaac ttggtcattg aaaggaatag atcaaatcca aagaacaaaa 72540
ccactgtgct cattaaactt cttagtgttc acaaagcttt agctgcaggt tgaatggggc 72600
aacccgaatt ggctggctca cctgggctgc agggagcaga gatcgcgaca ctgcactcca 72660
gcctgggcaa caaagcgaga ctctatctca aaaaaaaaaa agttcataaa ttcaaagtta 72720
tgaattattt ttaaaataat aataatttac aataaagatg aggacaaagt gtgagtaaat 72780
ggtggtttct atccagctct gttgagctga agtggcatct ccctgctggg gcttttgggg 72840
aagaagggtg tgtgttgctc ttcagatccc aagcctcatg cccctactgg gccctgtggg 72900
gtgcttctca gcccaccagg agagccaccg ttggaacaca cacgtggggg acctggtggg 72960
tgccggtgtg gtgaatgggg gccacagcct gactccagga agccagcaaa ctcggagctg 73020
gaggagtcag gacacccccg atgagtcaag agttggtttt gctgccagtt gacatctgat 73080
tgaaccatct cttcacttct ccgtgcctca ctttccttac cagacaggct ctgctgatgc 73140
tgtccctctc ctgttcagtc gtgccctcac cgttaaagag aaagagcaaa ctgctgggca 73200
gcagcattga ttttttaat gaagtggaaa gagagctggg aataacaagt cgggcccacc 73260
tcacctgcct cacctggtgg gtttatttgt tttgtttttt ttttttgtt ttgagacaga 73320
gtttcaccct gtcacccagg ctggagtgca gtggtgtaat ctcagctcac tgcaacctcc 73380
acctgccagg ttcaattgat tctcctgcct cagcctcccc agtagctggg attacaggca 73440
cctgccacat gcctggctaa ttattgtatt tttagtagag atggggtttt accatgttgg 73500
ccaggctggt ctcgatcccc tgacctcagg tgatccaccc acctcggcct cccaaagtgc 73560
tgagatcaca ggcgtgagcc accatgcctg gccgtcacct ggtggtgttg aatatgaact 73620
gctgcggtgt tggtaaatta agcaagcaga tagatgtaaa taacgcttgg gcaggaatat 73680
ggagcacggg atgaggatgg gcggccaact gttagagagg gtagcaggga ggctgagatc 73740
tgcctgccat gaactgggag gagaggctcc tctctctctt cacccccact ctgcccccca 73800
acactcctca gaacttatcc tctcctcttc tttccccagg tgaactttga accaggatgg 73860
ctgagccccg ccaggagttc gaagtgatgg aagatcacgc tgggacgtac gggttggggg 73920
acaggaaaga tcagggggc tacaccatgc accaagacca agagggtgac acggacgctg 73980

```
gcctgaaagg ttagtggaca gccatgcaca gcaggcccag atcactgcaa gccaaggggt  74040
ggcgggaaca gtttgcatcc agaattgcaa agaaatttta aatacattat tgtcttagac  74100
tgtcagtaaa gtaaagcctc attaatttga gtgggccaag ataactcaag cagtgagata  74160
atggccagac acggtggctc acgcctgtaa tcccagcact ttggaaggcc caggcaggag  74220
gatcccttga ggccaggaat ttgagaccgg cctgggcaac atagcaagac cccgtctcta  74280
aaataattta aaaattagcc aggtgttgtg gtgcatgtct atagtcctag ctactcagga  74340
tgctgaggca gaaggatcac ttgagcccag gagttcaagg ttgcagtaag ctgtgattat  74400
aaaactgcac tccagcctga gcaacagagc aagaccctgt caaaaaaaaa agaaaagaaa  74460
aaagaaagaa agaaatttac cttgagttac ccacatgagt gaatgtaggg acagagattt  74520
tagggcctta acaatctctc aaatacaggg tactttttga ggcattagcc acacctgtta  74580
gcttataaat cagtggtatt gattagcatg taaaatatgt gactttaaac attgcttttt  74640
atctcttact tagatcaggc ctgagtggcc tctctttagc aagagttggt tagccctggg  74700
attcttactg tagccacatt aataaacaac atcgacttct aaacattcta taataccatc  74760
ttttggccaa attgacttcg cctcttcctc tctctttcca aatgaaatgt gtttcatttc  74820
actgtcagac cacatggttg gggaccccac agagcacaca gccctccctc tgccttccca  74880
tgctggccct tcacccactg ctggagtgcc aggttggtcc aagggttgga ccaagttgtc  74940
tgaggttgtc tcaaggttgg tcgaggctgt ctccgcgctg ggttgtgcta caaggagccc  75000
ttctttccat gggtgtggct ggcagtgagt gctcacagca acagcccaca gtgcagcccg  75060
agggcaggat ggactcagtc cctgcctcca tacccatttc taaggaggca aaatggcaaa  75120
cactctactt ttctctttta atgctaaaaa taagaaaaca ccttgcagcc caggtatgg  75180
gtagtgcatg gaagccgtgg agttgtgagg tgggaagtga cctctgctgg atatgtctat  75240
tcaggaagat tgctggagtg ggtggggtct ctgggaggtc ccctgagtgt gggaagctgg  75300
gaccaccagc tttctcgcac agggagtggc catcccagct tggagaggtt ccaggactgg  75360
ttgggaggca cgtttcagat ttctatctgt tgaatcagcg aagatattgg attatgagga  75420
atttgggaat taggaaagtg ggtgcaggtg ggttgggggt aggtgaagga agacatgggc  75480
gtattggggg agcaggggct gctcagaggt gttccagaag ctctgggtga ggaggtgaga  75540
gggaccgggg aatgcagctc ggcccagcct ccctgcctga ggtcagccat cacgtggtga  75600
tggcaagatg gaaatgtgct ttctgactgc tccagccagt gctgccagat tcagctcccc  75660
agggagggca cctgagaggc tccaagccag gagatctgtt ttctcctttg ttttgttttt  75720
ttttgttttg ttttgtttta ttatacttta agttctaggg tacatgtgca caacgtgcag  75780
gtttgttaca tatgtataca tgtgccatgt tggtgtgctg cacccatcaa cttgtcattt  75840
acattaggta tatctcctaa tgctatccct cccccctccc cccacccccct gttttctcct  75900
ttgaatcctt cttagaggcc gggcgcggtg gctcacgcct gtaatcccag cactttggga  75960
ggctgcggca ggaggattgc ttgagcccag gagttccaga ccagcctggg caacatagtg  76020
agacctcgtc tctacagata ataattttaa aaattatccg ggcatagtgg catgcaccta  76080
tagtcccagc tactcaagag gcagaggcag gaggatcact tgagcccagg aggcggaggt  76140
tgccgtgagc caagatccca ccactgcact ccagcctggg cgacagagac ccccatgtca  76200
aataataata ataataaata aatccttctc agtcccttcc tcactgtgtc cccctccact  76260
gaatttttcc acctcctctc ccacttcccc cactcccgct ttccctctcc ttctctcccc  76320
actccatctt tttctttctc tgctgtttct cgtccctccc tcctctccat cccacaacac  76380
```

tgcctaccct gtccctgccc caccctggtg ctcaggatgt gtgaagtgag gggtggtagc 76440
ccccaagacc tcaaccccga aggttagcct gttgaaacca ctttctccca gctgcccccc 76500
tggcagttgg tgctgctggg ggaaactggg attgggggcc agattttgcc tcttttcctg 76560
acaaagagag atgaagagtt ctctcaccag gtgcctggga ctggggtgtg ggtgtcccag 76620
cctatcccag cgcatctgtt ctgcatcatg attaatagtg ctgctttcag ccgggcgcgg 76680
tggctcacac ctgtaatccc agcactttgg gaggctaagg tgggcagatc acaaggtcag 76740
gagttcgaga ccagcctggc caacatggtg aaacctcgtc tctactaaaa atacaaaaat 76800
taaccaggtg tggtggtggg tgcctgtagt cccagctact tgggaggctg aggcaggaga 76860
atcacttgaa tctgggaagc agaggttgca gtgagccaag atcgtgccac tgcactccag 76920
cctgggtgac agagtgagac tccgtcctaa aaaaaaagga gttttgctct gtcgcccagg 76980
ctggagtgta gtggcgccat ctcggctcac cgcaacctgc gcctcccggg tgcaagcgat 77040
tctcctgcct cagcctccca agtagctagg attacaggcg cctaccacca cgcctggcca 77100
gttcttgtat ttttagaaga gacggggttt caccctgttg gccaggctcg tctgggactc 77160
ctgacctcag gtaatccgcc cacctcagcc tcccaaagtg ctgggattgc aggcatgagc 77220
caccgtgccc agtcaactcc ttctcaaaaa aaaaaaaata gtgctgcttt ctctttcaag 77280
tgtcctgatt tgggtgatag taaatgccac tctacttata agggatctac ctcagaatgc 77340
taattgggac atttttgtag cactctactg ttggcagcag gtgatgctca caacagcccg 77400
tgagggtgga tgacgtccgc ttcacagatg acaaaggagc ctcatgctca gaccgtgggc 77460
tgccagagca ggtccatggc tgcagcccca catggaccat atttccccct tgtcactctt 77520
tccaccaagc tcccttggaa cttcagttat taagctctct tgggtggaat ccaagttaga 77580
atcacaacat gtgcctcata tggattgtgc cagtgaaaaa tgacattcta tttagaggca 77640
gggcagcctg gcttagagtc agtttaaaat atgtattatg ctgcaacaaa tgtaccatga 77700
tcctgtaaga tgttcacaac aagggaactg gatgtggggt atactgtctg tactaacttc 77760
acaagttttc tgtaaatcta aaactgttcc aaaataacaa gttcgtttaa aattaactcc 77820
aggagaccag gtacggtagc taatgcctat aatcccagca cttcggaagg ctgaggcagg 77880
tggattgctt gagcccagga gtttgagaca agcctgggca acatggtgaa atcctgtctc 77940
taaaaaaaat cacaaaaatt agccaggtgt ggtggcgcat tcctgtagtc ccagctactt 78000
gcggggctga ggtgggagaa tcatctgagc ccaggagttt gaggctgcag tgagctgtga 78060
ttgtaccact gcactccaac ctgggcaaca gagcaagacc ctgtctcaaa aaacaaaaat 78120
gaaataaagt ccaggaaaga agtaggtttt accactctta ttttctgaag agaaaactaa 78180
atttaatgtg taaagtgagg acaagttcac caagttagtg tttgagttgc ctaaaatatg 78240
tttgctaaaa ctattcaaag ctttcacata aaacatgatc agaagttcta tgccaaaaca 78300
tatgtgtgtg tatatatata tgcactatat atactgtata taaaaatgca aaatctaaat 78360
tgccaacctt ttagaaattg ctctgaaagg aaagcatttc aagataattt gcttacccaa 78420
agaatatact ttccaagaaa gcaagtaata cttaaggtgt tcataatcct catcaaatta 78480
attcttgcta ctgaaagctt acaaggagct gttttgatgt cgggtgtgac aggtttgact 78540
tggcagaagg tgtcacttta ctaacaacat tttaaataag tgacagaaga caagaaacta 78600
cacgttaaat gccagaacaa agagtgtcta agtggatgct aagagttgaa atatggctgg 78660
atacctgccc aagagagctg aaaagtagat gaaagttggt tacctataaa ctagtgcacc 78720

```
ctaatgaatt aaaaggtgtt gatgagttaa cttgttatgc cttccagata agacatgcaa  78780
atggggcttc ttcctccttc actacttcca agggatttaa caaggagacc aatgcaaatg  78840
ataaggactg tagggctcaa gctggggaca gattggggaa agggggacca tcatgcccat  78900
atagatgtcc ctgtgccctg gcagtcaagg ctgctgaaaa ataacaaaac ccagaagtct  78960
gcgtgatgct gcctctccat ttgtccaaag ccttcttgcg gcagtttgca ggcttttgca  79020
aaagctccag gaccaaggag ctatgttcat gctggaagct tgttcaggat tagctgttct  79080
ttgtgggatg ggtgcagcca gggccaggtg tccagggaca gtgttttaac aaagggcatg  79140
aggtgtctga tctcacagtg gaactccact tgcctttttt tcatcttctc attctgcttc  79200
atgcacagaa ccagccccat cctgaaactg actctaaatt actcccgccc caggtggagt  79260
gcctttctcg gagttcaaca gagccttcct gtcgcccaag ggacaactcc actgaatgcc  79320
caagccacac ccaaaaccta acaagtaaaa accaaattct gtgctccccc atcctgggcc  79380
attcctggtt tctctactgc tgttggtgat accaccatca gcttgtccat catgaccctg  79440
gccagttcct cccacaaccc tccacagcac ccagggacct cacctccatt ccatccgaca  79500
cagatctcct caccacaaac cttggttttg caacagcagc catgagacct ttacaccctc  79560
cgcccttcat cctgtccccc actgaggccc cagagccatt ccttaaagca gcgcgccaca  79620
aactataacc cacaagccaa ttctggtacc cagcctgttt tgcacagcca gtgaactgac  79680
aatgatcttt tcatacagcc agaaaaacaa aacaaaacaa aaaacaacaa aaaaaaaccc  79740
caccattctg agcatgtgac ttccatgttc aagatgtctc atgttcagaa aggcccctgg  79800
aaaaggagga aggggagctg ggcacaaagg gagaccctct cagctgagct cctcccatcc  79860
agacattttc ctggacttcc tatccaatga cttcccttag cttcttatca gccacccctg  79920
tctgcccagg aggctggaag atgtggcctt ttaactgggc acagctctgt cctctatcat  79980
atcagggctc tgttcccaag gagggtagag agaatggaca ccaggtggac cctcagcagt  80040
ctgtgccaca gagggagtgt ttgcaatttc cagactaaaa gtccccatgt gcttgacggg  80100
gtatgtgact acaacgtgat gcttgacttt tcctcatatg accagagcca ctttgtccat  80160
ctggtacaat gtcagctatc tgctaggggc cctccaggat tcccagtcaa ttccatatct  80220
gcatcaccac cattggcact aaataaaata aaatactcaa gttcctgctg gtgagcatga  80280
gcagtgctac actgggccct tcaaccaagg tgacatgata atgactgaaa ataatcactg  80340
ccacttattg gggacgtctc atctgccagg catggtacaa agtgctttaa ataagcattc  80400
aacaatttca tgctgacaga agccctgtga gccagtggag ctactactat gcccattata  80460
caggggagaa aactgaggca gagagaggtt aggtaattcg ctcagcctca cacaaccaat  80520
aggtggtgga gccaggattt gggccccatc tgcctgactc tctagaggct ctatcttcca  80580
gtcttccaga gttgagtcta agccatgaat aggacaatta gacagcagag gaaacccatt  80640
cagccaccat gtgcatgaag agtaaggaat ttctgtcata cagaggggag tgaattcact  80700
gagctgagag ctgaggaacc attgatctga tggctgagac accactggga agactggaga  80760
ggcttttctg ggcatgcagt gccaggcaca ggaggagctg agggaagatg actaagaggt  80820
actggcaaag aattcagaaa ttctgatgga agctttacat gttaccatca catccatcca  80880
tctatccacc catccatcca cccatatctt cctccctcca cccaatcatg catacatcca  80940
gtcatctata caccacccac ccacccatcc atccatccat ccatcccttc atccatccca  81000
tcatccatcc aattatacat acatccaatc atatatctgt acataatcca ttcttccctc  81060
ggttcatcca tccatccatt catccatcca tccacccatc ccttccttca tccttcctat  81120
```

catccatcca atcatatatc tgtacataat ccattcttcc ctcggttcat ccatccatcc 81180
attcatccat ccatccaccc atcccttcct tcatccttcc tatcatccat ccaatcatac 81240
atatatccaa tcatacatct gcacatcacc agctcatcca tctatccatt tatccatcca 81300
tccttccttc catccatcat tcatccatca tacatacatc taaccataca tctctacatc 81360
attcattctt ccatcgattc atccaattat ccatcattcc ttcctccatc catcccatta 81420
tccatttgat catacatata tcatctatac atcatccatt catccatcca tccatccatc 81480
cacccatatc ttcatccaat caatcataca tacatcgaat catctacaca tcacccatcc 81540
atccatccat ccattcatct atccacccat ccatccatcc atccatccat tcatctatcc 81600
acccatccat ccatccatcc atccatccat ccatgtaacc atccagtcat atatccaatt 81660
acacatccat ccagttatac attcatacat gcatctaatc attcaattat acatacacac 81720
atccatataa ttctacatcc aattatacct ccatccaatt acacattcat acacccacct 81780
aataaattat taattcatat atccatccat ataattatac atcaattata catccatcta 81840
atcattcagt aattcaccca ccatccagtc atctatccaa taatacattc atccaatcat 81900
ccatccatcc atccacccat tcatccatcc atccgtccgt ccacccatca tggtatgagc 81960
catgatttac cacgatggtc ccctgtggac agcccaggtg gggcagaact gaagggaagc 82020
ccagggctgc ccccataaac atttgcctcc tttacatgga tgagaactag atccacatgt 82080
ataaatcctc atgatttgaa ggtgctttta ccaacattca ctcatgggat tctcccagga 82140
gctctaggag gaggcaggta gagttgaggt catctcacgc attttacaga tgaggaaacg 82200
gaggccctga gaggcaggtc caaggccacc tgaccagaaa gaagtggaac tgggacttga 82260
acccagccat cttgcccctt ggtcccatgc tctctagcct gtaactcctg cttcctggtg 82320
gggcatctcc aggaggaccc tatcggctgg ccatgggcct gccctggagt cttttgctct 82380
gtgtggccat ccttcctccc tcaggagagt gtgtgctccc agagcacagg ctgtatcttc 82440
tgagcatttt gtcccttccc agtacctagc actcagctct gtatacattg ggctctcaag 82500
aattctcaac cttccagagt gtaaggcctt gacctgctca gccctggata ctgcatgatg 82560
cattgataag cccataaaat aaccagggca gattgactcc cagtggccaa agtgccacag 82620
ggaagggaca attcagccct tctaggagga ggaggaggta gttttctcat ttctattaag 82680
gcaacaaaag ctgccttact aaggacattc ttggtggagg gcgtgactgt caaccactgt 82740
gatcatttgg gcctctcttg cccaggcttc ccattctgaa aggacagttt tattgtaggt 82800
acacatggct gccatttcaa atgtaactca cagcttgtcc atcagtcctt ggaggtcttt 82860
ctatgaaagg agcttggtgg cgtccaaaca ccacccaatg tccacttaga agtaagcacc 82920
gtgtctgccc tgagctgact ccttttccaa ggaaggggtt ggatcgctga gtgtttttcc 82980
aggtgtctac ttgttgttaa ttaatagcaa tgacaaagca gaaggttcat gcgtagctcg 83040
gctttctggt atttgctgcc cgttgaccaa tggaagataa acctttgcct caggtggcac 83100
cactagctgg ttaagaggca ctttgtcctt tcacccagga gcaaacgcac atcacctgtg 83160
tcctcatctg atggccctgg tgtggggcac agtcgtgttg gcagggaggg aggtggggtt 83220
ggtccccttt gtgggtttgt tgcgaggccg tgttccagct gtttccacag ggagcgattt 83280
tcagctccac aggacactgc tccccagttc ctcctgagaa caaaaggggg cgctggggag 83340
aggccaccgt tctgagggct cactgtatgt gttccagaat ctcccctgca gacccccact 83400
gaggacggat ctgaggaacc gggctctgaa acctctgatg ctaagagcac tccaacagcg 83460
gaaggtgggc ccccccttcag acgccccctc catgcctcca gcctgtgctt agccgtgctt 83520
tgagcctccc tcctggctgc atctgctgct ccccctggct gagagatgtg ctcactcctt 83580
cggtgctttg caggacagcg tggtgggagc tgagccttgc gtcgatgcct tgcttgctgg 83640
tgctgagtgt gggcaccttc atcccgtgtg tgctctggag gcagccaccc ttggacagtc 83700
ccgcgcacag ctccacaaag ccccgctcca tacgattgtc ctcccacacc cccttcaaaa 83760
gccccctcct ctctctttct tcaggggcca gtaggtccca gagcagccat ttggctgagg 83820
gaaggggcag gtcagtggac atctgatctt ggtttagtat ccttcatttt gggggctctg 83880
ggtgtggcct gggcctctgg actttggcca cggtgtttgt tccagccctt ctcctaacct 83940
gtcctttcca gacactcggc atctaggtta ttagcacctc gcatactttc tgacatgctc 84000
ctcagtcctg attttgacca tcttctcttg cttcccatct gtgtcagtca agactgcatt 84060
tggctgtaag aaacagaaac cccaactaac tgtggcattt acatgaagag gtttactttt 84120
ctcacataat cagatgtcta gacttggcca gcacctcaag ggtcattgat gctctcctgt 84180
ctttattttc tgtcatcttt agtggttgga ttgttgcctc atggttacaa agtggctgct 84240
gcacttccag gcatcacatc tgcctttgaa gcaggaacaa gttgcaaagt aaagtggcca 84300
aaagggccct gaaactaaat gtgtcccctt aggaaagcag gagttttctt gcaagtggca 84360
atcttctgct tatgtctcat tggccagagc tgggtcttac ggccacccct tgctgcgagc 84420
aaggctggga cattgagcat tttgccgtcc aacctcttta gcagaataaa ccaaggggga 84480
agaacgttaa tagtggcttt tgagtcacta gttggcagta tctgcccctc tatctttcca 84540
tcctccccat ggagtttcaa ggttcctttc tcagtacttc ttcaggctct gcacgttcat 84600
ttggatcttg tgtcttgggg tgaaaaactg gcccaagtgt ctccccaagc atccaccttt 84660
ggattaattt ggaaaatggc tgtcaagtgc ccgcctcttg cttggtataa tgctacagct 84720
ttagaggacg cagcaggcat gggccttgcc gctgaggttc ttagcctcat gagaatatcc 84780
agatcagatt ctcttggctc cttcttagag ccagtgatgc aagacacttc ctgctcatct 84840
tgtcgggacg gttttacaag ttgcctgcca tcctgagaaa gtctacaaaa cgatgccaga 84900
cctcatgcca gcttcccaag ccttgactct cagtgctccc tcaacaggat tctggaagaa 84960
tctcccaaac aagtcgcaat gccctctgga ccctgtgcag gcatgagact caagagcatt 85020
ggctcccacc cctggtggag ggaacactgc tggggctggg atcttgcctg gttgctccgc 85080
ctgcacccaa gacaaccata attaaaatgt ccttcattga acttggaaag ccttcaaagc 85140
tgacaactcc ttatgtgtac ccggaaaggc ctgggagtgt gccagggcat tgctcgggag 85200
ggacgctgat ttggaagcat ttacctgatg agagactgac agcagctcct ggtagccgag 85260
ctttccctcc tgcctctgct gtgaaggtgg acccatccaa cagtcaaatg cctgactctg 85320
gacaggagcg gacctattta ttgccatgca agggactctg cacttttgaa ttgtgggtca 85380
tgggcttgga tttaggggtt agagctggga gaagtcttgg aagtcaccta gagatgacac 85440
tgccattttg cagatgagga aaccgtccaa tcaaaatgga ccaaggactt gcccaaagcc 85500
tcacagcaaa accataggcc cccgcactaa ccccagagtc cctgtgctgt cttaaggatc 85560
atatagttgt aagcaatcat ctggttttca gtatttcttc ttttaaaatg cctggggcca 85620
tgcccagcag tctgtttcac tgcagcgttt acacagggct gccgggcttt cctggtggat 85680
gagctgggcg gttcatgagc cagaaccact cagcagcatg tcagtgtgct tcctggggag 85740
ctggtagcag gggctccggg ccctacttca gggctgcttt ctggcatatg gctgatcccc 85800
tcctcactcc tcctccctgc attgctcctg cgcaagaagc aaaggtgagg ggctgggtat 85860
ggctcgtcct ggcccctcta aggtggatct cggtggtttc tagatgtgac agcaccctta 85920
gtggatgagg gagctcccgg caagcaggct gccgcgcagc cccacacgga gatcccagaa 85980
ggaaccacag gtgagggtaa gccccagaga cccccaggca gtcaaggccc tgctgggtgc 86040
cccagctgac ctgtgacaga agtgagggag ctttgcgtgt ttatcctcct gtggggcagg 86100
aacatgggtg gattctggct cctgggaatc ttgggttgtg agtagctcga tgccttggtg 86160
ctcagttacc tccctggctg cctgccagcc tctcagagca tttagggcct tctggacttc 86220
tagatgctcc tcatcttgcc tcagtcagcg cgtcagttcc agagacttct ctgcagggtt 86280
ttctggggca ggtggtggca gacccgtgcc ttcttgacac ctgaggtcag tccaccctcc 86340
tgctcagact gcccagcaca gggtcacctc ccaaggggtg gaccccaaga tcacctgagc 86400
gcacagaggg tgcagatgac tggaccacac cttttggtga tcttaatgag gtggtcccag 86460
aggagctcag acatgcaatc tagcatccag ttctgggact ctgtctcctt ttcaaacgta 86520
ttcatgtaga acaggcatga cgagaatgcc ttgtcaacat gggtgatggg gaatcaatca 86580
gacagggcgc cgggctcaag gctgcagtca cccaagagtg gctcagccca ccaggcccta 86640
ggaaacgcct gcacagcctg gagctcctgg agtcatttcc ttcatgtctt cttcactgca 86700
cttacgtaaa gatgccagcc attggtttgg tgatttggag ggtgcccagt tgcccaacaa 86760
gaaatgcaga agaggcctag ccaggatttc accagcagtg gagagtagag aagatgtggc 86820
cagaaaagag tttcctttcc ctcctaaaga tggtactccc tgcagctact ggggaagcct 86880
gcagcattct ctagggctct gtgtgttgag agcagcccca ccctggcccc ttctgagtgc 86940
atttctgctt tgtgacttga tccgtgaagt cccctgagat gggcagaggg gatgtcctcg 87000
aagctggggc agagcctcat ccttgaacgt gaaggacgtt tgaagactgt ggcatgatca 87060
caggatgaga tcacagggaa cttgagtttc tctcctcctc tcccttcaca gttatttcac 87120
tgagggaaat ccctcccctg cccagaatga aaactctagc caactcttga cttttccatc 87180
actccaaagt agttgaaagt acattagtct ccacagtggc aaaacagtgt gcaaaagcta 87240
aataattaga acagccagtc ccatgtgaca gtcaaagctt ctaactccat tcaaagttgc 87300
agccattccc ctcgagggct ggcagggagg ggaggggtaa gagaaacagg aaggttctta 87360
ctgagttggt cctggtgtga gctgcgtcac actccctgca gaggtttcaa ggagactctc 87420
tctctctctg tctccatggg gaccttattt gaattcttct actcttaccc cagcctgcca 87480
tctccagcta tcctcccctg aagagccctt ctgctgcgct ggattctggt ggccatgtca 87540
tctcctcggc cccgtgggag tctgaagatc tggctgcagc ctcacctctg aggtcctgct 87600
agttgccacc tcttaaacat gatctgaggc tcccatgcac tctgacctgt gcccacatgg 87660
ggcccacggg aaacacgctg gcaagcaaac tgtgggtgtg cagacggttc tcagggctgc 87720
agcacctgtc ctttgctctg cccccaaagc aaggccagcc catcttccat cctctagtgt 87780
tccttggtgg ggccctgacc acagtccacc aggtccctaa ccagagggga cacacaccag 87840
gtgtcctcaa tgtattgcct tgaaacagtt gtgctgggac tgtgatgggg ggtggccatg 87900
tagccacccc caccaccccc aagccactct ctccaaggaa atcctcctaa agatcccttt 87960
acatcctcca tgtggtgggg aggttctaga gttgggtgca tgtgtcttca gctactgaca 88020
atgcagacct tagttggcac ctcgctctgg cctatcctgt ttgctgttct tggcgctcca 88080
gtgaaactcc ccatgggcca tccagttggg gtgcagtgtg gccacccccct tgcaggttcc 88140
tgccttgctg gagagcacag ggccctcctg gctcttgtaa aacactcccc atggtacaga 88200
gaggccagca gtgatgtgag gcccaacctc cctccatggt gttcccaagc agctcccttt 88260
ctggggtcaa ggggtggcaa agacagtgca gcgtccaatt tctgactcaa gccgggcctg 88320
gctatcgcag ctctgcactg tgtgtgacag caaggcaact cacccagtgc cgtggcagtg 88380
accgtgtccg aggaagcctc ctcacaccct ctgtctcaag gactctggca tttagctgga 88440
cttgctgtag ctctgagcct ttctgccatt gccatcacct tgtcagaaac tcaggccgaa 88500
tctgcactca gagttgtgcc caggcagttg agccaacact tgctcagcga tattgtcaca 88560
tgacaaggca ctgtcaccac tgggcatcgt gggtagcgca gtgtcggctg gatggacccg 88620
gagggtgtct gtgtcatgct agtgctagtg atgggagccc cgtgagccca ttgcccgccc 88680
tcccatgccc tcagcagctg cctggggaca gccaatggcc tgggtgtttc tgaggctacc 88740
acatggcttc caggaaactc gagaaccttt ctctcccttg cctacactct tcacacaggc 88800
ctgtgctggc cagcggtggg gatccggcat tcctatctta ggtgcagaga gtgactgact 88860
cattgcaggc ctgggagata agactgatgg cccagccagc aagatgtatg gatttctcag 88920
aggcagtggc ctctgtcatt gtcctcagga aatgctggtg attctggtgg cctgaggtca 88980
atgcatgtca acgtggccaa cttgccttat aaactttttt tctggacaat tgcgtgcact 89040
gtcctgtaac agtgtcctgt tgtttatgat gcagaaatag gtgtttttaa agcctattga 89100
ttttggtact attaatgtgg tcaggaactt tctcagtctt tcttgtttgg ggtgagctgt 89160
ggcttcctaa acaggaaccc aagacacccc caaaagctgc tcaccagcac tgccagcctc 89220
cctcttacca agtagcaccc gttcaggaca ttctgcgaaa ggcatttgcc cagaagttgg 89280
gaggaaggaa atgtaacatt ttggggcacc taccatatgc caggcaccag gctaaacgtg 89340
ttcacacaaa ttctcttact aaccctcacc atccttctac aagacaaact agtatcttca 89400
tcttggggtt caagatgagg aaatggaggc tcagagaggt tgaatgaatg ccggtgcctg 89460
gatatgaacc ccatctgcct gactccgcaa cccaggcaaa gtctttcctt gaacttccca 89520
gcagccactg cttagacaca gcctccacaa ccatggctca gcagcaaatt gcttctctga 89580
cctcactcag cctgtgtgtc cttgttgagt gaggcattca ggaccctggt cccaaagtgg 89640
agaaagtctt tcctactagg tcatagctac acctgcatgt gggtgctgtg ccttttgttt 89700
agtgaacttt tatcaccagc atcctcagca atgacatttg cagagaagcc agagctgagg 89760
caccttggta ttcttgggat gtgactttcc tgaatgttta agggaaaatg cccgaaggta 89820
cagagagctt ggtttctagt aaacaataac tgtcttgctt ttaccccccct tcatttgctg 89880 acacatacac cagctgaaga agcaggcatt ggagacaccc ccagcctgga agacgaagct 89940
gctggtcacg tgacccaagg tcagtgaact ggaattgcct gccatgactt gggggttggg 90000
gggagggaca tggggtgggc tctgccctga aaagatcatt tggacctgag ctctaattca 90060
caagtccagg agattttagg gagttggttc ttatcaaagg ttggctactc agatatagaa 90120
agagccctag tggttttttt ctaataccat ttctgggtaa ttcctaaggc atttagtgtt 90180
ctgaaagatg ctagccttgt ccagcctggg agttgagaat gaatgtctaa cagaaactct 90240
aggccgggcc tggtggctca cgcctctaat cccagcacta tgggagaccc aggtgggcag 90300
atcacctgag gtcaggagtt tgagaccagc ctggccaaca tgtgaaatcc tgtctcacta 90360
caaataaaaa aattagccgg gtgtggtggt aggtgcctat aatcccagct actcaggagg 90420
ctgaggcagg acaatcgctc gaacccagga ggtggacgtt gcagtgagcc gagatcgcat 90480
cattgcactc cagcctgggc aacaaaagca aaactccgtc tcaaaaaaaa aaaagaaact 90540
caaatatgtg tgacaggcga ttctcactgc aggctgccct gtggctgatc caggagcaag 90600

```
gccttaacca tgtcatcccc aagcgattgc ttgtaaactt tcttctgtgc agccttcaac  90660
ccttattatg attttcttct caggaaccaa actgctgtat tcaagaaagg cagctttgtg  90720
taatcattta tcataaatat cttaagaaaa atcctagaga ttcctaattt taggaaatgg  90780
gagacctatg gtactgatat aatgtgggct gggcttgttt tctgtcattt gctagataaa  90840
tgaacttgag agcctactgt aaaatgtgga agcttctaga ttgcagaagg gctggaaaga  90900
cactgttctt ttctcccgag tgatgggatc tgtccagtat ttagagctgc ctctgaggcc  90960
atctgattct aggagactct gcctcgttga ggatattttg aggcctaact acacattcct  91020
gcccccagag aggtcacagc ctatagcagg ctgatgtttc tcatgtcaca tggcacagaa  91080
aggcacattt tcgttctcag gctaacaaag agcttcaaaa actattagaa gggacagtgg  91140
ctataagaga agaacctcag tcaatgtgtg aaattaacta ggaacctggc tcctgtttct  91200
tttaggtcat gtttttcagc ttaggtaaaa ctagaggctt tgataaagca tgacctctag  91260
aaatcattgc ttttcataaa tggaagtggg tttgagtttt ttctactgat tgttagtgca  91320
ggtgatgtct acatgccccc agaacatatt ccatgcaaca aaaaaagccc aggtcaccgt  91380
ctttgctggg aacttgactt ttgtgctcac tgaattttaa gctttctgac agcagcctgg  91440
aatcatggag ggataaagta cctattagta agatggaaaa aggtgtttca ggttggagct  91500
gcagtctgtt gagagtaagc tatgggaagg cctgtatacg aggggtggac ttttcttctg  91560
taagtgtcca gagaccaggc ctcctgaaga gggcatgggg gcttaactta cctggactac  91620
tgtgtttaca atactcattt atcttgaact cctcctaacc cctgagaatt gctacattta  91680
gtatttgctg agtacttcct agcatcctag ggaatcaata gaacattctc ccaaccaggc  91740
tgggtgcggt ggctcatgtc tgtaatccca gcactttggg aggccaaggt aggcagatcc  91800
cttgaggcca ggagtgcaag actagcctgg ctgacatggt gaaaccccgt ctttactaaa  91860
aatacaaaag ttagccaggc atggtggtac acacctgtaa tcccagctac atgggaggag  91920
taggaggcag gagaattgct tgaacctggg aggtggaggt tgctgtgagc cgagatcatg  91980
ccactgcact ccagcctggg cgacagagtg agtgagactc tgtttaaaaa aaaaaaaaaa  92040
aagaacattc tcctaacctg gcttcttcct ccaggggtgt aattaatcat gtcagtttcc  92100
tcattgatac acacacacac acactacaat cctgtatcca ttacttttca aggtacattt  92160
actatttacg tttggggtcc ttgtctcttt tttaatagtg tttcttaaag tcttgtatta  92220
tatcagagta cagtaacatc ccagtcaaga gcactctagt aagctctagg aggaaagcga  92280
cttccggaag gcagtggaga cctgtcctgt tggggcagca taggggcagc ccctgcctct  92340
ggtcagttct ggcgctcagg ctcagggttg cctctgggct gttcttccca gagactgaca  92400
aagggctccc ataaggcacc tgcagagcct gtgagaagct gaagtcaatg ttttcctgac  92460
accagttgat ctgtgcagga tccattgatt taaccacctg ctgtgtggca tgcactgtgg  92520
tcgatgccag gaacaggaat tggaggggcc catgagcatg gccagtatca caggctggag  92580
gtgctgctgc gctctgaccg ggcctcttgg ggatgagccc atgtcaacca ccttgcctcc  92640
gatggggtcg ggcccacagg ttacctttgt gtgtccatga ccacaccttc ctccccgacc  92700
tcatccaaat ctctttcttt tccaagcccc tgaatccttc agggctgcag gttttgttta  92760
aagcagagct ggtgagttgc ataggttgtt gcattgggac tagatggggt gttcaaagag  92820
ttgggagtta aaaaacataa agggtattta ttaggagaac caaggagtgt aattctcctg  92880
ttcttaatat gcggccaggt taatgaatgt cacgtgaatg aaccagaaaa aaatgaagtg  92940
```

```
tgcccttgat cagctgggtt ggtgtgcagc aagctgtgtg accaggggac agcagtggtc  93000
ctgagggccg tcactgtctg ccgtgcagag cccttcctcc cacgggggcc tacctcacct  93060
gtgccaaggg cttgtctgtg gtcagtgacc tggatagatc tgaatggggc ttctttttcg  93120
aggagtctta tggcaggtct ctcagtaaag actccattct tgatgatcac acattttgga  93180
ttttccaaat ctgtcagaga atgggcttga ggcggggttt gtgggcacta gtttcactgg  93240
tttcatttac caaaaagggg agcagaagtc aagtatggtg gctcatccct gtaatcccag  93300
aggcaagaga attgcttgag cccaggagtt cgagaccagc ctgagcaaca taaggagacc  93360
ccgtctccac aaaaatgaaa aataacattt tagtcagacg tggtggcatg catctgtggt  93420
cccagctgct tgggagggtg agatgggagg gttgtttgag ccctggagtt aaagttgcaa  93480
tgagctgtga ttgcaccact gcactctagc ctgggtgaca gaacgagacc ctgtctcaaa  93540
aaaaaaaaaa aagaaagaaa gaaaggaaaa aaaaaactca tgcctgtaat cccagcactt  93600
tggggaccgg ggtgggcaga tcacgaggtc aggagatcaa gactatcctg gccaacatgg  93660
tgaaaccccg tttctactaa aaatacaaaa attagccagg tgtggtggca cgtgcctgta  93720
atcccagtta ctcgggaggc tgaggcagga gaatcgcttg aaccagggag tcagaggttg  93780
cagtgagctg agatcgtgcc actgtactcc agcctgggcg acagagtgag actctgtctc  93840
aaaccaaaaa aaaggggtgg ggggcggggg caggagaaca gtgagaggta gggagaggaa  93900
aggggattct cgctacaccc aaaccagata ccatctagag gctagaatct ttgggaggct  93960
caaattccct agaaagcagg agaagcttct gtagccctcc cgctttccca gtagattaag  94020
cccagggcgg ctccagatgt gtgacatgct ctgtgcccaa ccagagccca tcataggcag  94080
aggaataaca cccacaccag aagggccctc ggaggtcacc acgtccaaga accctcttta  94140
cagatgagga aactgaggcc cagagagggg agagccacct agcgagctgg tggcggctag  94200
accaggagag ctgtcattcc aagcaagcaa aggcaacgag acgagcccag agctgtgctc  94260
ccatctcttt gttagggggc ctgggatgcc ctctcagtgt cattttgtcc aggatgatgc  94320
tccctctctt aagcgattaa tgcgcccttg ctaacctttt gctatcgctg cctcttcaaa  94380
ccagaggagt tgagagttcc gggccggcag aggaaggcgc ctgaaaggcc cctggccaat  94440
gagattagcg cccacgtcca gcctggaccc tgcggagagg cctctggggt ctctgggccg  94500
tgcctcgggg agaaagagcc agaagctccc gtcccgctga ccgcgagcct tcctcagcac  94560
cgtcccgttt gcccagcgcc tcctccaaca ggaggccctc aggagccctc cctggagtgg  94620
ggacaaaaag gcggggactg ggccgagaag ggtccggcct ttccgaagcc cgccaccact  94680
gcgtatctcc acacagagcc tgaaagtggt aaggtggtcc aggaaggctt cctccgagag  94740
ccaggccccc caggtctgag ccaccagctc atgtccggca tgcctggggc tcccctcctg  94800
cctgagggcc ccagagaggc cacacgccaa ccttcgggga caggacctga ggacacagag  94860
ggcggccgcc acgcccctga gctgctcaag caccagcttc taggagacct gcaccaggag  94920
gggccgccgc tgaagggggc agggggcaaa gagaggccgg ggagcaagga ggaggtggat  94980
gaagaccgcg acgtcgatga gtcctccccc caagactccc ctccctccaa ggcctcccca  95040
gcccaagatg ggcggcctcc ccagacagcc gccagagaag ccaccagcat cccaggcttc  95100
ccagcggagg gtgccatccc cctccctgtg gatttcctct ccaaagtttc cacagagatc  95160
ccagcctcag agcccgacgg gcccagtgta gggcgggcca aagggcagga tgccccccctg  95220
gagttcacgt ttcacgtgga aatcacaccc aacgtgcaga aggagcaggc gcactcggag  95280
gagcatttgg gaagggctgc atttccaggg gcccctggag aggggccaga ggcccggggc  95340
```

-continued

```
ccctctttgg gagaggacac aaaagaggct gaccttccag agccctctga aaagcagcct  95400
gctgctgctc cgcgggggaa gcccgtcagc cgggtccctc aactcaaagg tctgtgtctt  95460
gagcttcttc gctccttccc tggggacctc ccaggcctcc caggctgcgg gcactgccac  95520
tgagcttcca ggcctcccga ctcctgctgc ttctgacgtt cctaggacgc cactaaatcg  95580
acacctgggt gcagctgctc cactccctcg gcctcctccc gtgctcaggc tgtggccgca  95640
cgcgcccctc acgcttgccc gccactctgc atgtcaccag cacccccgct ccgtgctacc  95700
caccttgttt gactctctgg ccacttgatt tgtccacaac ggcccatcag cccacaggag  95760
gtttggtggg tgccttccac cgacaggatg acgggtgccc tcatggtgtc tagaactctc  95820
caaccctccc atgtaggcat aagcagcccc actttgcaga tgaggaaacg gaggctcaga  95880
gaagtacagt aacttgccga aggccaatga gtagtaagtg acagagccag gtttgggatc  95940
caggtaggtt gtctctgaaa gacacgcctg tcctgcatcc cacaacgcct cccaggaggt  96000
gctggagtgt ggacgcctaa cacagagatg tgcagggcac acacagcagg tgacacacac  96060
agcatccaga ggtggcccag agctcatgct gtgcctttgg cccagtgccc tgcccccacc  96120
cactctgcct tgtggcagga agacaaggag cagacacaag atctccctgg tccacatgcc  96180
accacctccc tctgcagagg acaaggggat cctcatgctg gcattggagg gggttgagca  96240
gggcccacct tgagccctca ggagcacgac cacagcagcc ctgcagggag ggattggtgg  96300
gaggagagtc ccaagtatca gggagaggag agttggtgtc ccacaggaga cctcagagcc  96360
acaaggcgag cttgttcata aatttgggac ccttagcatt tcacagttat ttgcagagcc  96420
cagaaatgga tgttactgaa gctcacagtt gcaagcatct gttaaatttt tattagattt  96480
tacttttagg gaaaactttg aaatgctata aagaagcctg tgtttaaaag ttaagacaga  96540
ggctgggggc gatggctcac gcctgtaatc tcagcacttt gggaggccaa ggcaggtgga  96600
tcatttgagg ttaggagttc gagaccagcc tggccaacat ggtgagaccc tgtctctact  96660
aaaattacaa aaaattagct gggcgtggtg gcgggcacct gtagtcccag ctactgggga  96720
ggctgaagca ggataagtgc ttgaacccag gaggcagagg ttacagtgag ccaagatcac  96780
accactgtac cctaagcctg ggcgacagag tgagactctg tctcaaaaaa taaaataaaa  96840
taaagttaag agagaaaaaa atatatccta tatcctttgt taaattccaa aacagtaggg  96900
gacaaataac tgacttgaca ggttactaca atatttcctg aaatgatgtt ttcttgaata  96960
ctggcctact agaggttcat aggtgtgttt ggattaaaaa agagttccat ggcccagtga  97020
ctgggggaaa aaaataaaag actaaagtaa gttaaacagg cttttctgct gcaggacttg  97080
tcagagcctt taatgtacta atggccattg tgaccctctg agaaggtcac agagtgggtt  97140
tcccaaactt acttgattct acctgctaac atttcctgga ggaagtttgg gaaatgccga  97200
tttagcagat tcttttgttg tgccgtggat ggtgctggtt gatgtgggca aaacaaagaa  97260
cacgtgagtc agatccgcct ggggctctta ctaaagtgca ggttcccagg tgccacttta  97320
ggcttacaga cccagttgtg gggtaagcct gggagtcttt tagcaggtga ttctgccaca  97380
tagtatagtt ggaaaacctc tgggcatact cattgctggt ccctctagaa atccaggtga  97440
caatagccaa tgagaagctc caagagaccc agttgtccat ggggtagagg gaatgtgata  97500
ttgaaaccaa agaagaaaat ctatgatcag ttttcagcag tgactgtcaa gagaaggaga  97560
agggtgagtt agcgctgatg ctggctgaca ggtcagcggg ttggtttcac caaggagtgt  97620
gatgaaggct gatgttgtct gtgggaatgt atgatggtaa ctggtttgta gctaatttgg  97680
```

-continued

```
ggaagcagtg agaattcgtg ccctttgaag accagtaagt ggcaagaaac ccaccaggcc  97740
tggctcaggg ctgggctggg cttggctcgt ctcagagcag ctggggctgg tggccaaagc  97800
caccattagt gaggggcagg ccctgggggt acaaccagca actaggggac aaagacaacc  97860
ctgccagcct ctcctattct ggaggcgtgt gaccagaaat ggagatgggt tggtcagcat  97920
aagatggcca ggaaggtgga aatcaggact gctggcaatc tagccacatg ggcaggggag  97980
ccgggtggtt ccaggcagtt tccaaggcca agagggtgag caggcacctc acagggaatc  98040
agggccaagc ctggctgcag tgtggagaca atgcacccac ccccatcctt ggatcttgca  98100
ggaggctggg tcctcactga gctaccaaca tccatggccc tgaggctttt aaaacaccca  98160
tccatggagt ggggctggtc ccagtggggt gaggctgacc ctggcagaaa cagggcagga  98220
gcctgtgggt tagggagact gcaccttcct tagatagcct ccatgccatc atgtccccgt  98280
gacagtttct gctgcgtccc ctctgcatgg tcccaccctc ggccagcctg ctgccccctc  98340
ttgccaggtt gcgctaatca gtgaccccag tgtgctgtgt tgatactaac aatgcgaggc  98400
ctagcagatt caagggaaaa gagaaccaac tgggtttcca ccagacccaa ctaaacaaac  98460
atggacctat cccagagaaa tccagcttca ccacagctgg ctttctgtga acagtgaaaa  98520
tggagtgtga caagcattct tattttatat tttatcagct cgcatggtca gtaaaagcaa  98580
agacgggact ggaagcgatg acaaaaaagc caaggtaagc tgacgatgcc acggagctct  98640
gcagctggtc aagtttacag agaagctgtg ctttatgtct gattcattct catatataat  98700
gtggggagta tttgtcacta aagtacagct gtcatttaaa gtgctttgta ttttggggca  98760
ggcttttaaa aagtccagca tttattagtt ttgatactta ccccagggaa gagcagttgg  98820
caggttcatg aagtcatgct cctaattcca gctttcttag tgtactttca gtgagaccct  98880
gacagtaaat gaaggtgtgt ttgaaaacca aacccaggac agtaaatgaa ggtgtgtttg  98940
aaaaccagcc ctaggacagt aaatgaagcc atcttctcac tgcataaact gcacccagat  99000
cttcgcccat ccttctcagt atttcacttc acccattgtt tactgtctca atgactgggg  99060
aaatgtctgg ggaaatgctc ccgtaattgc acagtggcgt ttttcctgga aaatcccacc  99120
atggctctag ataagaccta tttttcttaa aggtatctaa aatttccagc ataaattctg  99180
tctgaaacac ctgaatttta atcagtactg gagcccggag ggcatctcca gttgccacat  99240
agctctgagc attcagtggt gtgttgaggg ctgctcccgg aagtgcctgc agagtcaggg  99300
ctccccagcc tcatctagtg aggcagtgga agggcctgtg gggatttgga gagctggcct  99360
gggtctctga agtgatagtg acagctgctt gtcaatcacg gtgcacattt agtgctgggg  99420
gcagggggca gggaatacca gcctcatgca tgcatgcatt catttgttcc ttccttcatt  99480
cattcattca gtacacatgg gtacaacatc cctgccctgg agttgcccag agtctaggga  99540
ggggaaagat ctattaccct gggcctcggc cagctgggga gtgctgctgg tggagagggg  99600
ccgtgtgcag cgagggaagg aggagtcgtc aataccccca ccccagcttt gctttcttgt  99660
catcagcccc agggccccag cctgtgtccc tcctctccca ttgctacttc atctcctggg  99720
tcctccttac caagcctgac cacacagagg gccttggccg cttccatggg gaattggaaa  99780
gcaataagat agcatcccct agaagcccag tgaagtctgg gacaggaccc ttctctgagc  99840
tctgacttgc tcttggaaac acttcgaggc ttagcctccc cactttgttt cccgagagtg  99900
tgacctgttc ccctccaaac accccccttct cctccagggc catgcccacc cgtcaaaatc  99960
ccccacgggc aggacgaact gtgggtgtca gtcaccatct atcctgcatc ctggttccag 100020
ggcccccccc agccccgcct ccatagggac aggcgtgcag acacccgtcc ctggctgctt 100080
```

cctcttgtgg aatgggttca aaagtaagca gtgttgttta cactgacaaa ctgaaaaaaa 100140
aagaaaaaga gataacattg gaggcttggc acagtggctc atgcctgtaa tcccagcact 100200
ttgggaggct aaggtgggag gatgtcccca gcccaagagt tctagaccag cctgggcaac 100260
atagcaagac cccatctcaa aaaaaaaatt taattggcca ggcagaggtg ggaggatcac 100320
ttgaacccaa agggtggagg ctgcagtgag ccgtgatggc accactgcac tccagccagg 100380
gcaacagagg gagaccctgt ctctaaaaca aacaaacaaa caaacaaaca aaagagttaa 100440
cattggccag attaggattc accagatagt gttaatatta gtttgatttg agactttaat 100500
cagaaagcac atgtgtggtg ggggtgggtg taacctaagt caggtagaat ctttccaact 100560
tgggggggc acactcctga ttgtagccat atgagtctgt cagtgtggtg gaagaggcca 100620
tgggttaatg ggcaggtaaa aaagcacctt gcctggaatt gagtagaaag taaggccctt 100680
cagaccccgt gacacacttg gggacatttt cttgagtaac atcctaagat tcatgtacct 100740
tgatgatctc catcaactta ctcatgtgaa gcacctttaa accagtcgtc tccaaattca 100800
ggggcacagt aacatccaac aggctggaga aagaacgtac tagaacttcc attccttttt 100860
catgtcctct tctaaaagct ttgtcagggc caggcgcggt ggctcacgcc tgtaatccca 100920
gcactttggg aggccgagac gggtggatca cgaggtcagg agatcgagac catcctggct 100980
aacacagtga aaccccatct ctactaaaaa tacaaaaaaa cgagccgggc gtggtggtgg 101040
gcgcctgtag tcccagctac tcgggaggct gaggcaggag aatggcgtga acccaggagg 101100
cagagcttgc agtgagccga gattgcacca ctgcagtcca gcctgggcga cagagcgaga 101160
ctccgtctca aaaaagaaaa agaaaaagaa aaagaactgt gattggggag gacggtcact 101220
ttcctgttct tactgatcag aagggatatt aagggtacct gattcaaaca gcctggagat 101280
cactgctttc aaccattacc tgccttattt atttttagtt actgtccttt tttcagtttg 101340
tttccctcct ccatgtgctg acttttattt tgattttatt tatgtttatg tttaagacat 101400
ccacacgttc ctctgctaaa accttgaaaa ataggccttg ccttagcccc aaacacccca 101460
ctcctggtag ctcagaccct ctgatccaac cctccagccc tgctgtgtgc ccagagccac 101520
cttcctctcc taaatacgtc tcttctgtca cttcccgaac tggcagttct ggagcaaagg 101580
agatgaaact caaggtaagg aaaccacctt tgaaaagaac caggctgctc tgctgtggtt 101640
tgcaaatgtg gggtttgttt atttgttttt tagcctcaaa gacctttctt caaatgagtt 101700
ctggcataga agcaccgtgt aaaatagtta gaattctggg caaaggggaa aagagagctg 101760
ggggccatcc ctctcagcac ccccacaggct ctcatagcag cagctcctaa gacacctggt 101820
gggaccttgg tttcgaaatc gctactctaa ggctgggcac ggtggctcac acctgtaatc 101880
ccagctcttt aggaggccga ggagggtgga tcacctgaga tcaggagttc gagaccagcc 101940
tggctaacat ggcaaaaccc tgtctctact aaaaatacaa aaattagccg ggcgtggtgg 102000
tatgcgtggt ggtaatcgca gctactcggg aggctgaggc acaaggattg cttgaacccc 102060
agaggcagag gttgtagtta gctccagctt gggcgacaga gcaagaccct gtcgcaaaaa 102120
ttgtttaaaa aacaaaccca aaattgctac tctcattggg ttcctttgcc cattcctgat 102180
tttggcaaga gaaatgcttc cagattgccc tgatctgggt aggacagcat cacgccatag 102240
caacactgcc ccgtgagctc actgccccct caactagctt gtggtccttg gttaatgtca 102300
gtttcttttt tgagtttgtg ttatgtctaa gggtcatctg ctgggtaacg gaacccaggg 102360
actgccctag tccctagact gtgccatgcc cgactctgcc agctttgtca gtgatgctgg 102420
tgctcgcctc ctcgggtgct cgcctggtct gagcacaccc aaggagttct tgaggcctta 102480
gggttgtttg cgagagaatg aaagaacacg acctagctct ctttagcatc cttggtcagg 102540
ttcaacactg cccccagggg cctctggtgg agccaaccac catcagccaa ataaatccat 102600
aattagagtc agaaaatgga tgtctgcata tgtgtagtgc actaatgtcc tgccgatgat 102660
tgacatggag tggagagtga cctgatcatt gctgtgagct ctgctggcct tggcacaact 102720
catgctgata actaatgcac acagttcctc tgggaggaaa tgtcctcagg gaacttggag 102780
tttgggtggg gatgtgggtt tgtgtgccca gcaagccctt gtggttgtag cagacactag 102840
tggcatctag gaggcaaagg gtcaccccag tcttagccac gttttgagtc aaggtggcgg 102900
agtggggctg gtgttgactc ttggtggcag taacttttcc caatggtgaa aaacccctct 102960
atcatgtttc atttacaggg ggctgatggt aaaacgaaga tcgccacacc gcggggagca 103020
gcccctccag gccagaaggg ccaggccaac gccaccagga ttccagcaaa aaccccgccc 103080
gctccaaaga caccacccag ctctggtaag aagaacgttc tcttgaatct tagaggaagc 103140
tgaagctctc agaggtacag ccttcatttt aggaggcctt aggccactga gaatgaataa 103200
cccctggcag ctggtcagca gcttgcagtt tactaagcac tggagtcttc attgccttct 103260
cagtcctttt gatttctgag gcaaatgttg aatccctacc tttttttttt tttttctttt 103320
gagacagagt ttcgcttttg ttatccaggc cggagtgcag tggtgtgatc tcagctcact 103380
gcatcctcca cctcccaggt tcaagcgatt ctcctacctc agcctcccta gtagctggga 103440
ttacaggcac ctgccactat gcccggctaa tttttgtat ttttagtaga gacagggttt 103500
caccatgttg gccaggctgg tctcgaacgc ctgacctcag gtgatccacc tgcctcggcc 103560
tcccaaagtg ctgggattac aggcatgagc caccactccc agcctgaatc ctcacttttt 103620
atcaatgaag aaattgaggc tgattctgca gcatgataaa aaaaaataca gaaaaaggaa 103680
aaaaaagaaa gaaatcgagc ctctgagagt ttgcttgact gagtctaacc agctcatttt 103740
aaacccgagg aaaatgcagt cacatgacta ctaagtggca gctctcggag cctctctggc 103800
cccaagtcca gggttccata gaggcagccc cagcatggca tgttttcagt ccccaaatga 103860
gactctggag acaaatgtct ctggagacag agcagcagcc tggataagtc acaatgggtg 103920
acgtcactca gggctcaacc cctgggcagc ttaacttgct agggacgtta ggagtctgct 103980
gcaaaacctg agggtcttag ctgagcagtc acaggctggg cccgttgccc tgggctcctg 104040
tgagtaaaac ccagtcaatt ttgagtaccc agtaaggcat ccattgagtt attttgcagc 104100
caggagtgct attaagaaca gtcgcggctg ggcgtggtgg ctcatgcctg taatcccagc 104160
actttgggag gccaaggtgg gcggatcacc tgaggtcagg agttcgagac cagcttggcc 104220
aacatggcaa aaccccgtct ctaataaaaa tacaaaataa ttagctgggc gtggtggcgg 104280
gcgcctgtaa tcccagcttc tcaggagggt gaggaaggag aatcacttga acccaggagg 104340
cagaggttgc agtgagctga gatcgcacca ttgcactcca gcctggatga caaaagtgag 104400
attccttctc aaaaaaaaaa aaaaaaaaac agtcgtcctc tttggggatt agggacagcc 104460
tgcctgcctg cccgagcact tctctcttcc attgccccag tgaagtattc caggcccctg 104520
ggtttagact ctgcaccatg taggggtgtc tgacctgcac ttgctccttg gtggcacggg 104580
cagcctatgg cacttgctgc gggctgtgac caaagcctgg cctggatctt ggatcttggt 104640
gactctgctt ctccctggcc tgagggagct gcccagagcc tgcccaccac ctgctgcgtg 104700
tctttgcggt ggcatttctc gcacacatgc cgtgcagtgg cacccccaag gatggccatt 104760
cactaaggcc cattgttttt gtcttttcgc ttcgtgtttt ctggcctggt gtttttctca 104820
tatacatgtg atccagggat aattcccaga attttgacag gattttaagt agcgtttgga 104880
tcctgctgtt ttttttcac ttaacatcgg gccagttgac tcacactctg tttttgttg 104940
ttgtttttt gagacggagt ctcactgtgt cacccaggct gaagtgcagt ggcacaatct 105000
tggcatactg caacctctgc ttcccaaatt caagcagttt tcctgcctca gcctcctgag 105060
tagctgggac tacaggcaca ggccaccacg ccctgctaat ttttgtattt ttagtaaaga 105120
cagggtttca ccattttggc cagcctagtc tcgaactcct gacctcaagt gatccgccca 105180
cctcggcctc ccaaagtgct gggattacag gggactcaca ctttgtaaca acctgaaaca 105240
acgtgatgca tttccctttg ggtcttacct gctcttcggt ggctgcctgc aggtggagag 105300
accctccccc ttgggcccct cgaccttgtt tcagaatggg gcccctgctg ggccagctgt 105360
gggtgcctgc cacgtgaagg actcattaag gccctgttta agcctgatga taataaggct 105420
ttcgtggatt tttctcttta agcgactaag caagtccaga gaagaccacc ccctgcaggg 105480
cccagatctg agagaggtac tcgggagcct acttcgctgg gagcagcctc cctttgcgtg 105540
tgtggccatt cactggcttg tgtttctaga gccgggagga ccctttctg caatgcaggg 105600
ttcacacagg gttcgcagcc tgaagatgga gcagtccgaa ttctcttccc tgtgcagttt 105660
gcgcagctgt gtttgtctga tgggctttct aatcctgtgt gctctccttg acttcaggga 105720
caatggcatt acaggcatga gccaccatgc ctggctgtct ccctatgttt cagatgaaga 105780
cataggctta aggaggtcag gtgacttgcc cacgaccact ctgtaaataa gaggcatgaa 105840
aagtatttgg agccaccacc accaagccca ctggtcaccc tgggtctctg aagtcaggga 105900
ggcaggagga tgggaggtct gaggaggcag agaggctgag cctggaggcc ctggaggccg 105960
aggccccatc tgttgtttcc ttatgtggaa aataagaggc ttcgtttgtc ctattgccac 106020
agagcgtact acttcaggaa catccaagac atggaaatcc gcagggcacg gtggctcacg 106080
tctataatcc cggcactttg ggaggttgag gtgggagaat cgcttgaggc cagaagttca 106140
agaccagcct gagcaacata gtcagacccc gtctctataa aaaacattat ttttaaaaaa 106200
gacatggaag tcaaattcta aaaactggtg ctggctgggt gcggtggctc atgcctataa 106260
tcccagcact ttgggaggcc gaggcgggtg gatcacctga ggtcaggagt tcaagaccag 106320
cctggccaac atggtaaaac ctctactaaa gaaatcttta ctgaaaatac aaaaatccag 106380
tctctactaa aataagtctc tactaaaaat acaaaaatta gccaggcgtg gtgctgcaca 106440
cctgtaatat cagctactcg ggaggctgag gcaggagact cgcttgatcc catgcagcgg 106500
aggttgcagt gagccgagat cacgccattg cactccagcc tgggcatcag aataagactc 106560
cgtctcaaaa aaaaaaccac aaaaaaaacaa aacaacaaca aaagaaaact agtgcttatt 106620
cgtcactggc caagctgccc attggctaca tgggtgcttc aaagagctgc ccttctccag 106680
gtctggccag caggtatgtg ttacagcaaa tgcctggggc agcggcaggg gcattgctgc 106740
gggaagcttc tggacttgca ggaaagctaa gttctcagac tgcaggggag ctaagcacac 106800
ctcggcacag ggtgaggcct gcggttctca gacttcagtc tttgtggagc ttgagaaaaa 106860
tgaggctttg caggtcccac ccctagagat tctgctctat ccactcttga aggggatcga 106920
gaaatttgca ttttgcaact cccactttcc tccttgaaag ctccggagat tctgacgcag 106980
ggttccgtgg gccacacttt ggaaaataca gacccatgag atagaatacc agactgttga 107040
agtgtaacgg gggcctggga agtgcagtaa cagaagcaag tttgagggta aaggacaccc 107100
agaggaggga gggacagcat ctgcatggag aggagaagag accccccagc agcttccagg 107160
gtgttggaag ggtgcgctag taactgctat gcatggcagg tggggaactg tacgtcaggg 107220
cacagcagca tgaagcggta tggctcgtgt ggacagctag ggacaggcag gcgtggagca 107280
ggcatcctgt tctgaaggcc aaatcccaca gaggagccag ggtgctggca ggagccctga 107340
actagccgaa cagctgaaca gctgaacatt caccctgtgg ggaaagggtc agaagcgtcc 107400
aggcttgagg gcacagctgg gtctcgtcac tgcatcaccc ttatttagga taaaggccct 107460
gaagaattgt attagaggtt ggcaaagcat atctaccacc tcctggagcc acgctggccg 107520
cagggattat aattatttcc attttcaaat taaggcctct gagctcagag aggggaagtt 107580
acttgtctga ggccacacag cttgttggag cccatctctt gacccaaaga ctgtggagcc 107640
gagttggcca cctctctggg agcgggtatt ggatggtggt tgatggtttt ccattgcttt 107700
cctgggaaag gggtgtctct gtccctaagc aaaaaggcag ggaggaagag atgcttcccc 107760
agggcagccg tctgctgtag ctgcgcttcc aacctggctt ccacctgcct aacccagtgg 107820
tgagcctggg aatggaccca cgggacaggc agcccccagg gccttttctg accccaccca 107880
ctcgagtcct ggcttcactc ccttccttcc ttcccaggtg aacctccaaa atcaggggat 107940
cgcagcggct acagcagccc cggctcccca ggcactcccg gcagccgctc ccgcaccccg 108000
tcccttccaa ccccacccac ccgggagccc aagaaggtgg cagtggtccg tactccaccc 108060
aagtcgccgt cttccgccaa gagccgcctg cagacagccc ccgtgcccat gccagacctg 108120
aagaatgtca agtccaagat cggctccact gagaacctga agcaccagcc gggaggcggg 108180
aaggtgagag tggctggctg cgcgtggagg tgtggggggc tgcgcctgga ggggtagggc 108240
tgtgcctgga agggtagggc tgcgcctgga ggtgcgcggt tgagcgtgga gtcgtgggac 108300
tgtgcatgga ggtgtggggc tccccgcacc tgagcacccc cgcataacac cccagtcccc 108360
tctggaccct cttcaaggaa gttcagttct ttattgggct ctccactaca ctgtgagtgc 108420
cctcctcagg cgagagaacg ttctggctct tctcttgccc cttcagcccc tgttaatcgg 108480
acagagatgg cagggctgtg tctccacggc cggaggctct catagtcagg gcacccacag 108540
cggttcccca cctgccttct gggcagaata cactgccacc cataggtcag catctccact 108600
cgtgggccat ctgcttaggt tgggttcctc tggattctgg ggagattggg ggttctgttt 108660
tgatcagctg attcttctgg gagcaagtgg gtgctcgcga gctctccagc ttcctaaagg 108720
tggagaagca cagacttcgg gggcctggcc tggatccctt tccccattcc tgtccctgtg 108780
cccctcgtct gggtgcgtta gggctgacat acaaagcacc acagtgaaag aacagcagta 108840
tgcctcctca ctagccaggt gtgggcgggt gggtttcttc caaggcctct ctgtggccgt 108900
gggtagccac ctctgtcctg caccgctgca gtcttccctc tgtgtgtgct cctggtagct 108960
ctgcgcatgc tcatcttctt ataagaacac catggcagct gggcgtagtg gctcacgcct 109020
ataatcccag cactttggga ggctgaggca ggcagatcac gaggtcagga gttcgagacc 109080
aacctgacca acagggtgaa acctcgtctc tactaaaaat acaaaaatac ctgggcgtgg 109140
tggtggtgcg cgcctataat cccagctact caggaggctg aggcaggaga atcgcttgaa 109200
cccaggaggc agaggttgca gtgagccgag atagtgccac tgcactccag tttgagcaac 109260
agagcgagac tctgtctcaa aacaaaataa aacaaaccaa aaaaacccac catggcttag 109320
ggcccagcct gatgacctca tttttcactt agtcacctct ctaaaggccc tgtctccaaa 109380
tagagtcaca ttctaaggta cgggggtgtt ggggaggggg gttagggctt caacatgtga 109440
atttgcgggg accacaattc agcccaggac cccgctcccg ccacccagca ctggggagct 109500
ggggaagggt gaagaggagg ctgggggtga gaaggaccac agctcactct gaggctgcag 109560

-continued atgtgctggg ccttctgggc actgggcctc ggggagctag ggggctttct ggaaccctgg 109620
gcctgcgtgt cagcttgcct cccccacgca ggcgctctcc acaccattga agttcttatc 109680
acttgggtct gagcctgggg catttggacg gagggtggcc accagtgcac atgggcacct 109740
tgcctcaaac cctgccacct ccccccaccc aggatccccc ctgcccccga acaagcttgt 109800
gagtgcagtg tcacatccca tcgggatgga aatggacggt cgggttaaaa gggacgcatg 109860
tgtagaccct gcctctgtgc atcaggcctc ttttgagagt ccctgcgtgc caggcggtgc 109920
acagaggtgg agaagactcg gctgtgcccc agagcacctc ctctcatcga ggaaaggaca 109980
gacagtggct cccctgtggc tgtggggaca agggcagagc tccctggaac acaggaggga 110040
gggaaggaag agaacatctc agaatctccc tcctgatggc aaacgatccg ggttaaatta 110100
aggtccggcc ttttcctgct caggcatgtg gagcttgtag tggaagaggc tctctggacc 110160
ctcatccacc acagtggcct ggttagagac cttggggaaa taactcacag gtgacccagg 110220
gcctctgtcc tgtaccgcag ctgagggaaa ctgtcctgcg cttccactgg ggacaatgcg 110280
ctccctcgtc tccagacttt ccagtcctca ttcggttctc gaaagtcgcc tccagaagcc 110340
ccatcttggg accaccgtga ctttcattct ccagggtgcc tggccttggt gctgcccaag 110400
accccagagg ggccctcact ggcctttcct gccttttctc ccattgccca cccatgcacc 110460
cccatcctgc tccagcaccc agactgccat ccaggatctc ctcaagtcac ataacaagca 110520
gcacccacaa ggtgctccct tccccctagc ctgaatctgc tgctccccgt ctggggttcc 110580
ccgcccatgc acctctgggg gcccctgggt tctgccatac cctgccctgt gtcccatggt 110640
ggggaatgtc cttctctcct tatctcttcc cttcccttaa atccaagttc agttgccatc 110700
tcctccagga agtcttcctg gattcccctc tctcttctta aagcccctgt aaactctgac 110760
cacactgagc atgtgtctgc tgctccctag tctgggccat gagtgagggt ggaggccaag 110820
tctcatgcat ttttgcagcc cccacaagac tgtgcaggtg gccggccctc attgaatgcg 110880
gggttaattt aactcagcct ctgtgtgagt ggatgattca ggttgccaga gacagaaccc 110940
tcagcttagc atgggaagta gcttccctgt tgaccctgag ttcatctgag gttggcttgg 111000
aaggtgtggg caccatttgg cccagttctt acagctctga agagagcagc aggaatgggg 111060
ctgagcaggg aagacaactt tccattgaag gccccttca gggccagaac tgtccctccc 111120
accctgcagc tgccctgcct ctgcccatga ggggtgagag tcaggcgacc tcatgccaag 111180
tgtagaaagg ggcagatggg agccccaggt tatgacgtca ccatgctggg tggaggcagc 111240
acgtccaaat ctactaaagg gttaaaggag aaagggtgac ttgacttttc ttgagatatt 111300
ttgggggacg aagtgtggaa aagtggcaga ggacacagtc acagcctccc ttaaatgcca 111360
ggaaagccta gaaaaattgt ctgaaactaa acctcagcca taacaaagac caacacatga 111420
atctccagga aaaaagaaaa agaaaaatgt catacagggt ccatgcacaa gagcctttaa 111480
aatgacccgc tgaagggtgt caggcctcct cctcctggac tggcctgaag gctccacgag 111540
cttttgctga gacctttggg tccctgtggc ctcatgtagt acccagtatg cagtaagtgc 111600
tcaataaatg tttggctaca aaagaggcaa agctggcgga gtctgaagaa tccctcaacc 111660
gtgccggaac agatgctaac accaaaggga aaagagcagg agccaagtca cgtttgggaa 111720
cctgcagagg ctgaaaactg ccgcagattg ctgcaaatca ttgggggaaa aacggaaaac 111780
gtctgttttc ccctttgtgc ttttctctgt tttcttcttt gtgcttttct ctgttttcag 111840
gatttgctac agtgaacata gattgctttg gggccccaaa tggaattatt ttgaaaggaa 111900
aatgcagata atcaggtggc cgcactggag caccagctgg gtaggggtag agattgcagg 111960
caaggaggag gagctgggtg gggtgccagg caggaagagc ccgtaggccc cgccgatctt 112020
gtgggagtcg tgggtggcag tgttccctcc agactgtaaa agggagcacc tggcgggaag 112080
agggaattct tttaaacatc attccagtgc ccgagcctcc tggacctgtt gtcatcttga 112140
ggtgggcctc ccctgggtga ctctagtgtg cagcctggct gagactcagt ggccctgggt 112200
tcttactgct gacacctacc ctcaacctca accactgcgg cctcctgtgc accctgatcc 112260
agtggctcat tttccacttt cagtcccagc tctatcccta tttgcagttt ccaagtgcct 112320
ggtcctcagt cagctcagac ccagccaggc cagcccctgg ttcccacatc ccctttgcca 112380
agctcatccc cgccctgttt ggcctgcggg agtgggagtg tgtccagaca cagagacaaa 112440
ggaccagctt ttaaaacatt ttgttggggc caggtgtggt ggctcacacc taatcccaac 112500
acctggggag gccaaggcag aaggatcact tgagtccagg agttcaagac cagcctgggc 112560
aacataggga gaccctgtct ctacaatttt ttttttaatt agctgggcct gttggcactc 112620
tcctgtagtt ccagctactc tagaggctga ggtgggagga ctgcttgagc ctgggaggtc 112680
agggctgcaa tgagccatgt tcacaccact gaacgccagc ctgggcgaga ccctgtatca 112740
aaaaagtaaa gtaaaatgaa tcctgtacgt tatattaagg tgccccaaat tgtacttaga 112800
aggatttcat agttttaaat acttttgtta tttaaaaaat taaatgactg cagcatataa 112860
attaggttct taatggaggg gaaaaagagt acaagaaaag aaataagaat ctagaaacaa 112920
agataagagc agaaataaac cagaaaacac aaccttgcac tcctaactta aaaaaaaaaa 112980
tgaagaaaac acaaccagta aaacaacata taacagcatt aagagctggc tcctggctgg 113040
gcgcggtggc gcatgcctgt aatcccaaca ctttgggagg ccgatgctgg aggatcactt 113100
gagaccagga gttcaaggtt gcagtgagct atgatcatac cactacaccc tagcctgggc 113160
aacacagtga gactgagact ctattaaaaa aaaaatgctg gttccttcct tatttcattc 113220
ctttattcat tcattcagac aacatttatg gggcacttct gagcaccagg ctctgtgcta 113280
agagcttttg cccccagggt ccaggccagg ggacaggggc aggtgagcag agaaacaggg 113340
ccagtcacag cagcaggagg aatgtaggat ggagagcttg gccaggcaag gacatgcagg 113400
gggagcagcc tgcacaagtc agcaagccag agaagacagg cagacccttg tttgggacct 113460
gttcagtggc ctttgaaagg acagccccca cccggagtgc tgggtgcagg agctgaagga 113520
ggatagtgga acactgcaac gtggagctct tcagagcaaa agcaaaataa acaactggag 113580
gcagctgggg cagcagaggg tgtgtgttca gcactaaggg gtgtgaagct tgagcgctag 113640
gagagttcac actggcagaa gagaggttgg ggcagctgca agcctctgga catcgcccga 113700
caggacagag ggtggtggac ggtggccctg aagagaggct cagttcagct ggcagtggcc 113760
gtgggagtgc tgaagcaggc aggctgtcgg catctgctgg ggacggttaa gcaggggtga 113820
gggcccagcc tcagcagccc ttcttggggg gtcgctggga aacatagagg agaactgaag 113880
aagcagggag tcccagggtc catgcagggc gagagagaag ttgctcatgt ggggcccagg 113940
ctgcaggatc aggagaactg gggaccctgt gactgccagc ggggagaagg gggtgtgcag 114000
gatcatgccc agggaagggc ccaggggccc aagcatgggg gggcctggtt ggctctgaga 114060
agatggagct aaagtcactt tctcggagga tgtccaggcc aatagttggg atgtgaagac 114120
gtgaagcagc acagagcctg gaagcccagg atggacagaa acctacctga gcagtggggc 114180
tttgaaagcc ttggggcggg gggtgcaata ttcaagatgg ccacaagatg gcaatagaat 114240
gctgtaactt tcttggttct gggccgcagc ctgggtggct gcttccttcc ctgtgtgtat 114300
tgatttgttt ctcttttttg agacagagtc ttgctgggtt gcccaggctg gagtgcagtg 114360
gtgcgatcat agctcactgc agccttgaag tcctgagctc aagagatcct tccacctcag 114420
cctcctgagt agttgggacc acaggcttgc accacagtgc ccaactaatt tcttatattt 114480
tttgtagaga tggggtttca ctgtgtcgcc caggatggtc ttgaactcct gggctcaagt 114540
gatcctcctg cctcagcctc gcaaattgct gggattacag gtgtgagcca ccatgcccga 114600
ccttctcttt ttaagggcgt gtgtgtgtgt gtgtgtgtgt gggcgcactc tcgtcttcac 114660
cttcccccag ccttgctctg tctctaccca gtcacctctg cccatctctc cgatctgttt 114720
ctctctcctt ttacccctct ttcctccctc ctcatacacc actgaccatt atagagaact 114780
gagtattcta aaaatacatt ttatttattt attttgagac agagtctcac tctgtcaccc 114840
aggctggagt gcagtggtgc aatctcggct cactgcaacc tccgcctccc aggttgaagc 114900
aactctcctg cctcagcctc cctagtagct gggattacaa gcacacacca ccatgcctag 114960
caaattttta tatttttagt agaggagggg tgtcaccatg tttgccaagc tggtctcaaa 115020
ctcctggcct caggtgatct gcctaccttg gtctcccaaa gtgctgggat tacaggtgtg 115080
agccaccacg cctgccctta aaaatacatt atatttaata gcaaagcccc agttgtcact 115140
ttaaaaagca tctatgtaga acatttatgt ggaataaata cagtgaattt gtacgtggaa 115200
tcgtttgcct ctcctcaatc agggccaggg atgcaggtga gcttgggctg agatgtcaga 115260
ccccacagta agtggggggc agagccaggc tgggaccctc ctctaggaca gctctgtaac 115320
tctgagaccc tccaggcatc ttttcctgta cctcagtgct tctgaaaaat ctgtgtgaat 115380
caaatcattt taaaggagct tggttcatc actgtttaaa ggacagtgta aataattctg 115440
aaggtgactc taccctgtta tttgatctct tctttggcca gctgacttaa caggacatag 115500
acaggttttc ctgtgtcagt tcctaagctg atcaccttgg acttgaagag gaggcttgtg 115560
tgggcatcca gtgcccaccc cgggttaaac tcccagcaga gtattgcact gggcttgctg 115620
agcctggtga ggcaaagcac agcacagcga gcaccaggca gtgctggaga caggccaagt 115680
ctgggccagc ctgggagcca actgtgaggc acggacgggg ctgtggggct gtggggctgc 115740
aggcttgggg ccagggaggg agggctgggc tctttggaac agccttgaga gaactgaacc 115800
caaacaaaac cagatcaagg tctagtgaga gcttagggct gctttgggtg ctccaggaaa 115860
ttgattaaac caagtggaca cacaccccca gccccacctc accacagcct ctccttcagg 115920
gtcaaactct gaccacagac atttctcccc tgactaggag ttccctggat caaaattggg 115980
agcttgcaac acatcgttct ctcccttgat ggtttttgtc agtgtctatc cagagctgaa 116040
gtgtaatata tatgttactg tagctgagaa attaaatttc aggattctga tttcataatg 116100
acaaccattc ctcttttctc tcccttctgt aaatctaaga ttctataaac ggtgttgact 116160
taatgtgaca attggcagta gttcaggtct gctttgtaaa tacccttgtg tctattgtaa 116220
aatctcacaa aggcttgttg ccttttttgt ggggttagaa caagaaaaag ccacatggaa 116280
aaaaaatttc tttttgttt ttttgtttgc ttgttttttt gagacagagt ttcactctgt 116340
cgcccaggct ggagtgcagt ggtgcgatct ccgcccactg caagctccac ctcccgggtt 116400
catgctattc tcctgtctca gcctcccaag tagctgggac tgcaggtgcc cgccaccaca 116460
cctggctaat ttttttgtat ttttagtaga gacggggttt caccgtgtta gccaggatgg 116520
tctcaatctc ctgacctcgt catctgcctg cctcggcctc ccaaagtgct gagattacag 116580
gcgtgagcca ccgtgcccgg ccagaaaaaa acatttctaa gtatgtggca gatactgaat 116640
tattgcttaa tgtcctttga ttcatttgtt taatttcttt aatggattag tacagaaaac 116700
aaagttctct tccttgaaaa actggtaagt tttctttgtc agataaggag agttaaataa 116760
cccatgacat ttcccttttt gcctcggctt ccaggaagct caaagttaaa tgtaatgatc 116820
actcttgtaa ttatcagtgt tgatgccctt cccttcttct aatgttactc tttacatttt 116880
cctgctttat tattgtgtgt gttttctaat tctaagctgt tcccactcct ttctgaaagc 116940
aggcaaatct tctaagcctt atccactgaa aagttatgaa taaaaaatga tcgtcaagcc 117000
tacaggtgct gaggctactc cagaggctga ggccagagga ccacttgagc ccaggaattt 117060
gagacctggg ctgggcagca tagcaagact ctatctccat taaaactatt tttttttatt 117120
taaaaaataa tccgcaaaga aggagtttat gtgggattcc ttaaaatcgg agggtggcat 117180
gaattgattc aaagacttgt gcagagggcg acagtgactc cttgagaagc agtgtgagaa 117240
agcctgtccc acctccttcc gcagctccag cctgggctga ggcactgtca cagtgtctcc 117300
ttgctggcag gagagaattt caacattcac caaaaagtag tattgttttt attaggttta 117360
tgaggctgta gccttgagga cagcccagga caactttgtt gtcacataga tagcctgtgg 117420
ctacaaactc tgagatctag attcttctgt ggctgcttct gacctgagaa agttgcggaa 117480
cctcagcgag cctcacatgg cctccttgtc cttaacgtgg ggacggtggg caagaaaggt 117540
gatgtggcac tagagattta tccatctcta aaggaggagt ggattgtaca ttgaaacacc 117600
agagaaggaa ttacaaagga agaatttgag tatctaaaaa tgtaggtcag gcgctcctgt 117660
gttgattgca gggctattca caatagccaa gatttggaag caacccaagt gtccatcaac 117720
agacaaatgg ataaagaaaa tgtggtgcat atacacaatg gaatactatt cagccatgaa 117780
aaagaatgag aatctgtcat ttgaaacaac atggatggaa ctggaggaca ttatgttaag 117840
tgaaataagc cagacagaag gacagacttc acatgttctc acacatttgt gggagctaaa 117900
aattaaactc atggagatag agagtagaag gatggttacc agaggctgag gagggtggag 117960
gggagcaggg agaaagtagg gatggttaat gggtacaaaa acgtagttag catgcataga 118020
tctagtattg gatagcacag cagggtgacg acagccaaca gtaatttata gtacatttaa 118080
aaacaactaa aagagtgtaa ttggactggc taacatggtg aaaccccgtc tctactaaaa 118140
atacaaaaat tagctgggca tggtggctca cgcctgtaat cccagcactt tgggaggccg 118200
aggcgggccg atcacgaggt caggagatcg agaccatcct agctaacatg gtgaaacccc 118260
gtctctacta caaatacaaa aaaaagaaaa aattagccgg gcatggtggt gggcgcctgt 118320
agtcccagct actcgggagg ctgaggcagg agaatggcgt gaacccggga ggcggagctt 118380
gcagtgagcc gagatcgcgc cactgcactc cagcctgggc gacaaggcaa gattctatct 118440
caaaaaaata aaaataaaat aaaataaaat aataaaataa aataaaataa aataaaataa 118500
ataaaataaa ataaaatgta taattggaat gtttataaca caagaaatga taaatgcttg 118560
aggtgataga taccccattc accgtgatgt gattattgca caatgtatgt ctgtatctaa 118620
atatctcatg taccccacaa gtatatacac ctactatgta cccatataaa tttaaaatta 118680
aaaaattata aaacaaaaat aaataagtaa attaaaatgt aggctggaca ccgtggttca 118740
cgcctgtaat cccagtgctt tgtgaggctg aggtgagaga atcacttgag cccaggagtt 118800
tgagaccggc ctgggtgaca tagcgagacc ccatcatcac aaagaatttt taaaaattag 118860
ctgggcgtgg tagcacatac cggtagttcc agctacttgg gagaccgagg caggaggatt 118920
gcttgagccc aggagtttaa ggctgcagtg agctacgatg gcgccactgc attccagcct 118980
gggtgacaga gtgagagctt gtctctattt taaaaataat aaaaagaata aataaaaata 119040
aattaaaatg taaatatgtg catgttagaa aaaatacacc catcagcaaa aagggggtaa 119100
aggagcgatt tcagtcataa ttggagagat gcagaataag ccagcaatgc agtttctttt 119160
attttggtca aaaaaaataa gcaaaacaat gttgtaaaca cccagtgctg gcagcaatgt 119220
ggtgaggctg gctctctcac cagggctcac agggaaaact catgcaaccc ttttagaaag 119280
ccatgtggag agttgtaccg agaggtttta gaatatttat aactttgacc cagaaattct 119340
attctaggac tctgtgttat gaaaataacc catcatatgg aaaaagctcc tttcagaaag 119400
aggttcatgg gaggctgttt gtattttttt tttctttgca tcaaatccag ctcctgcagg 119460
actgtttgta ttattgaagt acaaagtgga atcaatacaa atgttggata gcaggggaac 119520
aatattcaca aaatggaatg ggacatagta ttaaacatag tgcttctgat gaccgtagac 119580
catagacaat gcttaggata tgatatcact tcttttgttg ttttttgtat tttgagacga 119640
agtctcattc tgtcacccag gctggagttc agtggcgcca tctcagctca ctgcaacctc 119700
catctcccgg gttcaagcta ttctccttcc tcaacctccc gagtagctgg gttgcgcacc 119760
accatgcctg gctaactttt gtatttttag tacagacggg gtttcaccac gttggccagg 119820
ctgctcttga actcctgacg tcaggtgatc caccagcctt gacctcccaa agtgctagga 119880
ttacaggagc cactgtaccc agcctaggat atgatatcac ttcttagagc aagatacaaa 119940
attgcatgtg cacaataatt ctaccaagta taggtataca ggggtagtta tatataaatg 120000
agacttcaag gaaatacaac aaaatgcaat cgtgattgtg ttagggtggt aagaaaacgg 120060
tttttgcttt gatgagctct gtttttaaa atcgttatat tttctaataa aaatacatag 120120
tcttttgaag gaacataaaa gattatgaag aaatgagtta gatattgatt cctattgaag 120180
attcagacaa gtaaaattaa ggggaaaaaa aacgggatga accagaagtc aggctggagt 120240
tccaacccca gatccgacag cccaggctga tggggcctcc agggcagtgg tttccaccca 120300
gcattctcaa aagagccact gaggtctcag tgccattttc aagatttcgg aagcggcctg 120360
ggcacggctg gtccttcact gggatcacca cttggcaatt atttacacct gagacgaata 120420
aaaaccagag tgctgagatt acaggcatgg tggcttacgc ttgtaatcgg ctttgggaag 120480
ccgaggtggg ctgattgctt gagcccagga gtttcaaact atcctggaca acatagcatg 120540
acctcgtctc tacaaaaaat acaaaaaatt tgccaggtgt ggtggcatgt gcctgtggtc 120600
ccagctactt gggaggctga agtaggagaa tcccctgagc cctgggaagt cgaggctgca 120660
ctgagccgtg atggtgtcac tgcactccag cctgggtgac aaagtgagac cctatctcac 120720
aaagaaaaaa aacaaaacaa aaaacccaaa gcacactgtt tccactgttt ccagagttcc 120780
tgagaggaaa ggtcaccggg tgaggaagac gttctcactg atctggcaga gaaaatgtcc 120840
agtttttcca actccctaaa ccatggtttt ctatttcata gttcttaggc aaattggtaa 120900
aaatcatttc tcatcaaaac gctgatattt tcacacctcc ctggtgtctg cagaaagaac 120960
cttccagaaa tgcagtcgtg ggagacccat ccaggccacc cctgcttatg gaagagctga 121020
gaaaaagccc cacgggagca tttgctcagc ttccgttacg cacctagtgg cattgtgggt 121080
gggagagggc tggtgggtgg atggaaggag aaggcacagc ccccccttgc agggacagag 121140
ccctcgtaca gaagggacac cccacatttg tcttccccac aaagcggcct gtgtcctgcc 121200
tacggggtca gggcttctca aacctggctg tgtgtcagaa tcaccagggg aacttttcaa 121260
aactagagag actgaagcca gactcctaga ttctaattct aggtcagggc taggggctga 121320
gattgtaaaa atccacaggt gattctgatg cccggcaggc ttgagaacag ccgcagggag 121380
ttctctggga atgtgccggt gggtctagcc aggtgtgagt ggagatgccg gggaacttcc 121440
tattactcac tcgtcagtgt ggccgaacac atttttcact tgacctcagg ctggtgaacg 121500
ctcccctctg gggttcaggc ctcacgatgc catccttttg tgaagtgagg acctgcaatc 121560
ccagcttcgt aaagcccgct ggaaatcact cacacttctg ggatgccttc agagcagccc 121620
tctatccctt cagctcccct gggatgtgac tcaacctccc gtcactcccc agactgcctc 121680
tgccaagtcc gaaagtggag gcatccttgc gagcaagtag gcgggtccag ggtggcgcat 121740
gtcactcatc gaaagtggag gcgtccttgc gagcaagcag gcgggtccag ggtggcgtgt 121800
cactcatcct tttttctggc taccaaaggt gcagataatt aataagaagc tggatcttag 121860
caacgtccag tccaagtgtg gctcaaagga taatatcaaa cacgtcccgg gaggcggcag 121920
tgtgagtacc ttcacacgtc ccatgcgccg tgctgtggct tgaattatta ggaagtggtg 121980
tgagtgcgta cacttgcgag acactgcata gaataaatcc ttcttgggct ctcaggatct 122040
ggctgcgacc tctgggtgaa tgtagcccgg ctccccacat tcccccacac ggtccactgt 122100
tcccagaagc cccttcctca tattctagga gggggtgtcc cagcatttct gggtccccca 122160
gcctgcgcag gctgtgtgga cagaataggg cagatgacgg accctctctc cggaccctgc 122220
ctgggaagct gagaataccc atcaaagtct ccttccactc atgcccagcc ctgtccccag 122280
gagccccata gcccattgga agttgggctg aaggtggtgg cacctgagac tgggctgccg 122340
cctcctcccc cgacacctgg gcaggttgac gttgagtggc tccactgtgg acaggtgacc 122400
cgtttgttct gatgagcgga caccaaggtc ttactgtcct gctcagctgc tgctcctaca 122460
cgttcaaggc aggagccgat tcctaagcct ccagcttatg cttagcctgc gccaccctct 122520
ggcagagact ccagatgcaa agagccaaac caaagtgcga caggtccctc tgcccagcgt 122580
tgaggtgtgg cagagaaatg ctgcttttgg cccttttaga tttggctgcc tcttgccagg 122640
agtggtggct cgtgcctgta attccagcac tttgggagac taaggcggga ggttcgcttg 122700
agcccaggag ttcaagacca gcctgggcaa caatgagacc cctgtgtcta caaaaagaat 122760
taaaattagc caggtgtggt ggcacgcacc tgtagtccca gctacttggg aggctgaggt 122820
gggaggattg cctgagtccg ggaggcggaa gttgcaagga gccatgatcg cgccactgca 122880
cttcaaccta ggcaacagag tgagactttg tctcaaaaaa caatcatata ataattttaa 122940
aataaataga tttggcttcc tctaaatgtc cccggggact ccgtgcatct tctgtggagt 123000
gtctccgtga gattcgggac tcagatcctc aagtgcaact gacccacccg ataagctgag 123060
gcttcatcat cccctggccg gtctatgtcg actgggcacc cgaggctcct ctcccaccag 123120
ctctcttggt cagctgaaag caaactgtta acaccctggg gagctggacg tatgagaccc 123180
ttggggtggg aggcgttgat ttttgagagc aatcacctgg ccctggctgg cagtaccggg 123240
acactgctgt ggctccgggg tgggctgtct ccagaaaatg cctggcctga ggcagccacc 123300
cgcatccagc ccagagggtt tattcttgca atgtgctgct gcttcctgcc ctgagcacct 123360
ggatcccggc ttctgccctg aggccccttg agtcccacag gtagcaagcg cttgccctgc 123420
ggctgctgca tggggctaac taacgcttcc tcaccagtgt ctgctaagtg tctcctctgt 123480
ctcccacgcc ctgctctcct gtccccccag tttgtctgct gtgaggggac agaagaggtg 123540
tgtgccgccc ccacccctgc ccgggccctt gttcctggga ttgctgtttt cagctgtttg 123600
agctttgatc ctggttctct ggcttcctca aagtgagctc ggccagagga ggaaggccat 123660
gtgctttctg gttgaagtca agtctggtgc cctggtggag gctgtgctgc tgaggcggag 123720
ctggggagag agtgcacacg ggctgcgtgg ccaacccctc tgggtagctg atgcccaaag 123780
acgctgcagt gcccaggaca tctgggacct ccctggggcc cgcccgtgtg tcccgcgctg 123840
tgttcatctg cgggctagcc tgtgacccgc gctgtgctcg tctgcgggct agcctgtgtc 123900
ccgcgctctg cttgtctgcg gtctagcctg tgacctggca gagagccacc agatgtcccg 123960
ggctgagcac tgccctctga gcaccttcac aggaagccct tctcctggtg agaagagatg 124020
ccagcccctg gcatctgggg gcactggatc cctggcctga gccctagcct ctccccagcc 124080
tgggggcccc ttcccagcag gctggccctg ctccttctct acctgggacc cttctgcctc 124140
ctggctggac cctggaagct ctgcagggcc tgctgtcccc ctccctgccc tccaggtatc 124200
ctgaccaccg gccctggctc ccactgccat ccactcctct cctttctggc cgttccctgg 124260
tccctgtccc agccccctc cccctctcac gagttacctc acccaggcca gagggaagag 124320
ggaaggaggc cctggtcata ccagcacgtc ctcccacctc cctcggccct ggtccacccc 124380
ctcagtgctg gcctcagagc acagctctct ccaagccagg ccgcgcgcca tccatcctcc 124440
ctgtccccca acgtccttgc cacagatcat gtccgccctg acacacatgg gtctcagcca 124500
tctctgcccc agttaactcc ccatccataa agagcacatg ccagctgaca ccaaaataat 124560
tcgggatggt tccagtttag acctaagtgg aaggagaaac caccacctgc cctgcacctt 124620
gtttttggt gaccttgata aaccatcttc agccatgaag ccagctgtct cccaggaagc 124680
tccagggcgg tgcttcctcg ggagctgact gataggtggg aggtggctgc cccccttgcac 124740
cctcaggtga ccccacacaa ggccactgct ggaggccctg gggactccag gaatgtcaat 124800
cagtgacctg ccccccaggc cccacacagc catggctgca tagaggcctg cctccaaggg 124860
acctgtctgt ctgccactgt ggagtcccta cagcgtgccc cccacagggg agctggttct 124920
ttgactgaga tcagctggca gctcagggtc atcattccca gagggagcgg tgccctggag 124980
gccacaggcc tcctcatgtg tgtctgcgtc cgctcgagct tactgagaca ctaaatctgt 125040
tggtttctgc tgtgccacct acccaccctg ttggtgttgc tttgttccta ttgctaaaga 125100
caggaatgtc caggacactg agtgtgcagg tgcctgctgg ttctcacgtc cgagctgctg 125160
aactccgctg ggtcctgctt actgatggtc tttgctctag tgctttccag ggtccgtgga 125220
agcttttcct ggaataaagc ccacgcatcg accctcacag cgcctcccct ctttgaggcc 125280
cagcagatac cccactcctg cctttccagc aagatttttc agatgctgtg catactcatc 125340
atattgatca cttttttctt catgcctgat tgtgatctgt caatttcatg tcaggaaagg 125400
gagtgacatt tttacactta agcgtttgct gagcaaatgt ctgggtcttg cacaatgaca 125460
atgggtccct gtttttccca gaggctcttt tgttctgcag ggattgaaga cactccagtc 125520
ccacagtccc cagctcccct ggggcagggt tggcagaatt tcgacaacac atttttccac 125580
cctgactagg atgtgctcct catggcagct gggaaccact gtccaataag ggcctgggct 125640
tacacagctg cttctcattg agttacaccc ttaataaaat aatcccattt tatccttttt 125700
gtctctctgt cttcctctct ctctgccttt cctcttctct ctcctcctct ctcatctcca 125760
ggtgcaaata gtctacaaac cagttgacct gagcaaggtg acctccaagt gtggctcatt 125820
aggcaacatc catcataaac caggtagccc tgtggaaggt gagggttggg acgggagggt 125880
gcagggggtg gaggagtcct ggtgaggctg gaactgctcc agacttcaga aggggctgga 125940
aaggatattt taggtagacc tacatcaagg aaagtgttga gtgtgaaact tgcgggagcc 126000
caggaggcgt ggtggctcca gctcgctcct gcccaggcca tgctgcccaa gacaaggtga 126060
ggcgggagtg aagtgaaata aggcaggcac agaaagaaag cacatattct cggccgggcg 126120
ctgtggctca cgcctgtaat tccagcactt tgggaggcca aggtgggtgg atcatgaggt 126180
caggagattg agaccatcct ggctaacaca gtgaaacccc gtctctacta aaaatacaaa 126240
aaattagccg ggcgtggtgg tgggcgcctg tagtcccagc tactccggag gctgaggcag 126300
gaaaatggcg tgaacccgga aggcggagct tgcagtgagc ggagtgagca gagatcgcgc 126360
cactgcactc cagcctgggc gacagagcga gactccgtct caaaaaaaaa aagcacatgt 126420
tctcgcttct ttgtgggatc caggagatag agaatagaag gatggttacc agaggctggg 126480
aagggtagtg aggggatggt gggggatgg tcaatgggta caaaaaaaat agaataagac 126540
ctagtatttg atagtgcaac agggtgacta tagtcaataa taatttaatt gtacatttaa 126600
aaataactaa aagatagccg ggtgcagtgg cttacgtctg taatcccagt actttgggag 126660
gctgaggtgg gcgtttgaga ccagcctggc caacatggtg aaaccccatc tctactaaaa 126720
atacaaaaat tagccaggca tggtggcggg cgcctgtaat cccagctact cgggaggctg 126780
aggcaggaga atcacttgaa cctgggaggc agaggttgca gtgagccgag atcttgccac 126840
tgcactccag cctgggtgac agtgaaactc cgtctcaaaa ataaaaataa aaatacagct 126900
gggcacggtg gctcacgcct gtaatcccag cactttggga ggccgaggcg agcggatcac 126960
aaggtcagga gatatagacc atcctggcta acacggtgaa acccggtctc tactaaaaat 127020
acaaaaaatt agccaggcgt ggtggcaggt gcctatagtc ccagctactc acaaggctga 127080
ggcaggagaa tggcatgaac ctgggaggcg gagcttgcag tgagccgaga ttgtgccact 127140
gcactccagc ctgggcgaga gagtgagact ccgtctcaaa acaaaaacaa aaacaaaaac 127200
aaaaacaaac acacaacaaa aacctaaaag aatataaatg gattgtttgt aacacaaagg 127260
acaaatgttt gaggggatgg ataccccatt ttccatgatg tgattattat acattgtgtg 127320
tctgtatcaa aacatctcat gagccccata aatatataca cctaactatg tacccacaaa 127380
aattaaaaaa atatattttt taaggtgaag agggaggcga gatgctggcc ttaaccccta 127440
acccgttgtt ctccctgcaa gctgtccaca gggcctctca gactcgaggt tcagctatat 127500
ggatgcatga gcttggtccc cagccaacat gggagacact tcaccatcgg cagcagctac 127560
agcacaggaa ccctgggtca ctgccatgtc ccctctgtga ctttgtttaa acagaaaatg 127620
atgctctggg ccggctgtgg tggcccacac ctataatccc agcaccttgg gaggcggggg 127680
tgggcagatt gcctgaggtc aggagttgga gatcagcctg gccgacatgg cgaaacccca 127740
tgtctactaa aaatacaaaa actagccagg catggtggca catgcctgta atcccagcta 127800
cttgggaggc tgaagcagga gaatcacttg aacccaggag gcagaggctg agtgagccaa 127860
gatcgtgcca atgcactcca gcttgggtga gggagtgaga ctccgtctca aaaaaaaaaa 127920
aaaagaaaga aaaagaaaag aaagtgatcc tactggaacc atgcttactc ccctccccac 127980
ctcacactgt gtagaaatta gtgctgtcgg ccaggcgcgg tggctcatgc ctgtaatcgc 128040
agcactttgg gaggccaagg caggcggatc acgaggtcag gagatcaaga ccatcctggc 128100
taacacagtg aaaccctgtc tctactaaaa atacaaaaaa ttagccgggc atggtggcag 128160
gcacctgtag tcccaactac ttgggaggct gaggcaggag aatggcatga acctgggagg 128220
cggagcttgc agtgagccaa gatcgcgcca ctgcatacca gcctaggtga cagagtgaga 128280
ctcagcaaaa aaagaaagaa agaaagaaag aaatcagtgc tgtctatact tctttctgca 128340
gtgatggaaa tattctgtat ctgtgctgtc cagtatagta gccactagct acatgtggca 128400
cttgaaacat ggctggtaca gttgaggaag agtggctgcc atatcggacg acacagctat 128460
agattctgtc accccacccc gagagtccag agcggggact tctgccttag gccctattca 128520

```
gggctgattt ttacttgaac ccttactgtg ggaagagaag gccatgagaa gttcagtcta 128580
gaatgtgact ccttattttc tggctccctt ggacactttg tgggatttag tctccctgtg 128640
gaaagtattc cacaagtggt gccaccaccc cagctgtgag agcagctggg agctgctttt 128700
gtcatctttc cctggaaagt cctgtgggct gtctcttcct catgccttgt cccatgcttg 128760
ggcatggtgt caagcgtcag gagggagaaa gggtccttat ttatttattt agagagggac 128820
ccttcttctg ttcccaggct ggagtgcagt ggtgcgatct cggctcactg caacctccgc 128880
ctcctgggtt caagtgattc tcctgcctca gcctcctgag tagctgagat tacaggcaca 128940
tgccaacatg cctggctaat tttttttttt tttttttttt tttttttttg agatggagtt 129000
gtactctcat tgcccaggct ggaatgtaat ggcacaatct cggctcactg caacctccac 129060
ctcctggatt caagcaattc tcctgtctca gcttcccaag tagctgggat tacaggtgcc 129120
cgccaccatg ctcaactaat tttgtatttt tttttttagt agagacgagg tttcaccatg 129180
ttggtcagac tggtctcaaa ctcctgacct caggtgatcc acctgcctcg gcctcccaaa 129240
gtgctaggat tacaggcatg agccaccacg cccggcctga aagggttctt atttagtgtg 129300
cattttgaca ttcaatttaa ttccaaggtc ttgtggggtc atggtttaca ggatgttgat 129360
atagaaaaga cttcacttaa tgggccgggc gcagtggctc atgcctgtaa tcccagcact 129420
ttgggaggcc gaggcaggca gatcaggagg tcaggagatt gagaccatcc tggctaacac 129480
agtgaaaccc catctctact gaaaatacaa aaaattagct gggcgtggtg gcaggcacct 129540
gtagtcccag ccactcggtt ggctgaggca ggagaatggc atgaacccgg gaggcggagc 129600
ttgcagtgag cagagaccat gccactgcac tccagcctgg gcgacagagc aagactctgt 129660
ctcaagaaaa aaaaaaaaaa aacagacttt acttactgga agccaaccaa tgtatattta 129720
gagtaatttt tcctgggctg agctgtcatt tacttttgca gtatctcaag aagaagagtt 129780
tacagtgtaa atatttgatg cacactttga ttatatagat gaagcaaact attttcaaga 129840
gctttgcaag gacttacttg tatccaaaca ccattctaaa ggagtcttac ctacttctaa 129900
aggctggtct ctacttggaa ccacttgctt ggccctggtt caagtcctgc tgcaaacctg 129960
gaagtcctgt cattgtcttc ttccctccag agcagtggca cccaatctaa tttttgctgt 130020
gccccagcag cccctggcac tttgccctgt agactgcaga cctcatgtaa tgtatgttaa 130080
gtccacagaa ccacagaaga tgatggcaag atgctcttgt gtgtgttgtg ttctaggagg 130140
tggccaggtg gaagtaaaat ctgagaagct tgacttcaag gacagagtcc agtcgaagat 130200
tgggtccctg gacaatatca cccacgtccc tggcggagga aataaaaagg taaagggggt 130260
agggtgggtt ggatgctgcc cttgggtata tgggcattaa tcaagttgag tggacaaagg 130320
ctggtccagt tcccagagga ggaaaacaga ggcttctgtg ttgactggct ggatgtgggc 130380
cctcagcagc atccagtggg tctccactgc ctgtctcaat cacctggagc tttagcacgt 130440
ttcacacctg ggccccaacc tggagaggct gaccaatggg tctcaggggc agctcggttg 130500
ctggagtttt tgtttttatt tatttttatg tatttaaggc agggtctctg tattagtcca 130560
ttctcacact gctaataaag acatacccaa gactgggtaa tttataaagg aaagaggttt 130620
aatggactca cagttccaca tggctgggga ggcctcaaaa tcatggcgga aggcaaagga 130680
gaagcaaagg catttcttac atggcgacag gcaagagagc gtgtgcaggg gaactcccat 130740
ttataaaacc atcagacctc atgagattta ttcactatca tgagaacagc atgggaaaga 130800
cccgccccca tgattcagtt acctcccact gggtccctcc catgacacat ggaattatgg 130860
```

-continued

```
gagctacaat tcaagatgag atttgggtgg ggacacagcc aaaccatatc agtctccctc 130920
tgtcatccag gctggagtgc actggcatga tctcggctca ctgcagcctc tacctccctg 130980
ggtcaggtga tcttcccacc tcagcctccc aggtagctgg aactacaggt acctgccact 131040
atgcctggct aaatattttg tatttcctgt ggagacgagg ttttgccacg ttgcccaggc 131100
tggtcttgaa ctcctgaggt caagcaatat gcccacctcg gcctcccaag gtgctgggat 131160
tacaggtgtg agccacagtg ctcggcctaa gtcactgcag tttttaaagc tcccaggtga 131220
ttcttcagtg cagtcaaaag tgagaactgg ctgggtgcgg tggctcatgc ctgtaatccc 131280
agcaccttgg gaggcgaagg tgggcagatg gcttgaggtc aggagttcaa gaccagcctg 131340
gccaacatgg taaaacccca tctctactaa aaatacaaaa gttagctggg tgtggtggtg 131400
cgtgcctgta atcccagcta cttgggaggc tgaggcatga gaattgcttg aacccagggg 131460
acagaggttg tagtgagccg agatcgtgcc actgcactcc agcctgggca acagagtgag 131520
attccatctc acaaaaaaaa aaaaaaaagc gagaaccact gtcctaggcc ctgatgtttg 131580
caggcaacta aaaaaggaag tggacatccc cagtcagctg tggcgcacca agaacaagtc 131640
atgggaacat aacctaattt tctaaatggg ttactaggca cttagagcaa aacaatgatg 131700
ccgaaatcct gatttcagca aagcctctgc ctgcctgtct tggaagtatc cacatgaggc 131760
tgctggggcc ttggtgtccc cagcagtttc tagtctctag gtcttgctgt gggtgtctgt 131820
gcagtgaggg tgtgtgtggc gctgggtgag ctctgtctag gcctggcaca ggatgcggtc 131880
tggtagctgc tgcttctctt ctgcagaagc gcagccaagc accctctggg gtttcaggcc 131940
cacacccagc ctgaagttct gggagtggct cactttccaa ccttcagggt ctcccagcag 132000
ctgactgggg agtggtggag ggaaaaggga ttgtattagt ccgttttcac gccgctgatg 132060
aagacatacc cgatactggg cagtctaaaa gatagaggtc tgatggactc acagttccac 132120
gtgactgggg aggcctgaca atcatggtgg aaggtgaaag gcttgtctca cacggtggca 132180
gacaagagaa aagagcttgt gcaggggaac tccccttat aaaaccatca gatctcggga 132240
gacttattca ctatcatgag aacagcacgg gaaagaccct cctctatgat tcaattacct 132300
cccaccaggt ccctcccaca acatgtagga attgtgggaa ctacaattca agatgacatt 132360
tgggtgggga cacagccaaa ccatatcagg gcgtcccaga aagggtatag ggtctgagac 132420
ccaagtcagc atgagaaagt atgcttctca tggtggccca gttgggtgga agtggcagcc 132480
gggccgtctt tccaccaggc cactcaagta gcagctgaga gacccctgcc ctggccagtc 132540
cccgccctcc cctcttgcca ctgcctctgg ttctgaacag atgggcaccc tcatcttgta 132600
tttgtgatta atgtctaaca atgtagtttt gtgagaaggg tttgctgata cagccttgct 132660
gcagatgctg cgaactgtgg cctggggcag accttacctc cagacacgcc ctgaggcagg 132720
ggagggcact ggcccgtagc tggccgagag ctctcgggtt gcgcgacagg gatacttttc 132780
agcggctggg tcgctatcca aagtgagaaa acgaggaggg accaggaggc tgtccgcctc 132840
aagagatgtg gggccaggt ccagttatct ggggaagcag taagcttctc tgctgtttct 132900
aaccccaggc ctcccctggt ctaaggcagg gcctcccagc ctcggggcac tttaaagata 132960
tctgggcctg gccccatccc cacagtctga ctgagtgggt ctggataggg cctgagcatt 133020
ggtgatttcc tgggtgaaag gaggcccctc acagtctctg gaagcttctc tgtgttagga 133080
aaagctctgg gcttgactct gctttgaaag tcaagatccg caaatcctct cagcctcagt 133140
ttctccttca gcaagatgaa atggaaatgc tgtacctacg tcccggggtg gttgtgagac 133200
ccaaaaaaga caatgttctg gaaggttcct ggtgcgttgc agtcctctaa gaacctgagt 133260
```

tagagccacg ctgagtctca gcttcttggc tccttctgtt tcaaactcgt ccatgtgata 133320
gctcaggaag ggtaggcagg gccctgcccc ctactcagaa aacaccatcc tggtcctggg 133380
gatccccgca gcattagtcc cctgttttcc cagtgtattg agaaaaattg ctaacaagca 133440
gtggggcaca ccaccagcct cctgggttcc tttcagtttg gggatttttg gacattccca 133500
ggaatgtctt aaaaaacact tcaaaaaaca ttaacataaa tatttttatc aaagcctgta 133560
ttaaatggtc tttcaagaaa atacagtaac aggtcaggca tggtggctca tgcctgtaac 133620
cccagcactt tgggaggcca aggcaggcag atcacctgaa atcaggagtt caagaccaac 133680
ctggccaaca cagccaaatc ccatctctac aaaaaataca aaaattagct gggtgtggtg 133740
gcacacacct gtagtcccag ctacttggga ggccgaggca ggagaattgc ttgatcccgg 133800
aggcggaggt tgcagtgagc tgagatcgtg ccactgcact ccagcgtggg tgacaaggtg 133860
aatctttgtc tcaaaaaaaa aaaaaaaaaa aagataaaat acagtataca gtaatagaga 133920
acaatccttt tttcaaagta gtgaccccaa atgaacaaaa tatgcatcta gcttaaatgc 133980
gaacctggtt ttctctacgc ccattcaagc ccctgcaata ggggcccttc accccgcatc 134040
catggactcc taaaattata tggaaaatgg ctgtgtgtga gtgtggatgg acatgtgcac 134100
acatattttt ggctttacca gatgctcaaa gagcctagga cccaaaaagg gctgagaatg 134160
accgtgtcgg ccacttcagg gtcatcagga attgctgtgc actgctcact tctccagtga 134220
acactttctg cttctgtgtt tcctggtatc ctttgggact cctggctagg tcatgtgttt 134280
ctctactttc aaaagggctt cagccaggca cgatggcatg agcctgtagt cccagttgct 134340
ctggaggtta aggtgggaag attgcttgag cccaggaatt tgaggccagc ctgggcaagt 134400
agataggtag atgattgata gatagataga tagataaata gatggataga taagtcgcta 134460
gacagtcatc catccaccca tccacacata aaaaggcctt tgtcatgtca tgttttgtgg 134520
cccacctgcc agtgttgccc acagttgctg cccctccaaa ctcatcagtc actggcaaac 134580
aggaggaatg tgtggctcat gtctgggcat cagtggctgt gggagacatc cttgatcttc 134640
tccagcttct ccttccacat tttcctttgc aatctggcaa tatctattaa aataaaatgt 134700
gcatgccttt tgacctaaga gcttcacttc taggacccac ttacacgtgt gtgacatgat 134760
gttcatacgg gtttatttat ctgaggttgt tcatacacac cattgcctgt aatcactaaa 134820
ggcgggagca gcctacacat ccatccacag aggagtagat gccttttggt acatccgtgg 134880
cgacggaata ctaagcagcc tgtgtatcta tacactcaca cgtgtttgtt tatgtgtgga 134940
atatctctgg agggtacaca agaaacttaa aatgatcact gtctctgggg agggtacctg 135000
ggtgcctggg aggcaggtca gggaaggagt gggcacaggt attaccaatt ggaagacaat 135060
aaaaacaaca gctcctggcc aggcgcagtg gctcacgcct gtaatggcag cactctgaga 135120
ggctgaggcg ggcagattgc ttgcgtccag gagttcaaga ccagcctggg caacatagca 135180
aaaccccgtt tctattaaaa atacaaaaaa ttagccaggt gtggtggcat gcacctgtaa 135240
tcccagctac tcgggaggct gaggtgggag aatcacctga gcctgggagg tcaaggctgc 135300
agtgaggtga gattgtgcca ccgcactcta gcctgggcga tagagcaaga ccctgtctca 135360
aaaacaaaca aaaaacagtc cctggcactc tgggccaggc ctggcagggc agttggcagg 135420
gctggtcttt ctctggcact tcatctcacc ctccctccct tcctcttctt gcagattgaa 135480
acccacaagc tgaccttccg cgagaacgcc aaagccaaga cagaccacgg ggcggagatc 135540
gtgtacaagt cgccagtggt gtctggggac acgtctccac ggcatctcag caatgtctcc 135600
tccaccggca gcatcgacat ggtagactcg ccccagctcg ccacgctagc tgacgaggtg 135660
tctgcctccc tggccaagca gggtttgtga tcaggcccct ggggcggtca ataattgtgg 135720
agaggagaga atgagagagt gtggaaaaaa aaagaataat gacccggccc ccgccctctg 135780
cccccagctg ctcctcgcag ttcggttaat tggttaatca cttaacctgc ttttgtcact 135840
cggctttggc tcgggacttc aaaatcagtg atgggagtaa gagcaaattt catctttcca 135900
aattgatggg tgggctagta ataaaatatt taaaaaaaaa cattcaaaaa catggccaca 135960
tccaacattt cctcaggcaa ttccttttga ttcttttttc ttccccctcc atgtagaaga 136020
gggagaagga gaggctctga aagctgcttc tgggggattt caagggactg gggtgccaa 136080
ccacctctgg ccctgttgtg gggtgtcac agaggcagtg gcagcaacaa aggatttgaa 136140
acttggtgtg ttcgtggagc cacaggcaga cgatgtcaac cttgtgtgag tgtgacgggg 136200
gttggggtgg ggcgggaggc cacgggggag gccgaggcag gggctgggca gaggggagag 136260
gaagcacaag aagtgggagt gggagaggaa gccacgtgct ggagagtaga catccccctc 136320
cttgccgctg ggagagccaa ggcctatgcc acctgcagcg tctgagcggc cgcctgtcct 136380
tggtggccgg gggtgggggc ctgctgtggg tcagtgtgcc accctctgca gggcagcctg 136440
tgggagaagg gacagcgggt aaaaagagaa ggcaagctgg caggagggtg gcacttcgtg 136500
gatgacctcc ttagaaaaga ctgaccttga tgtcttgaga gcgctggcct cttcctccct 136560
ccctgcaggg tagggggcct gagttgaggg gcttccctct gctccacaga aaccctgttt 136620
tattgagttc tgaaggttgg aactgctgcc atgattttgg ccactttgca gacctgggac 136680
tttagggcta accagttctc tttgtaagga cttgtgcctc ttgggagacg tccacccgtt 136740
tccaagcctg ggccactggc atctctggag tgtgtggggg tctgggaggc aggtcccgag 136800
ccccctgtcc ttcccacggc cactgcagtc accccgtctg cgccgctgtg ctgttgtctg 136860
ccgtgagagc ccaatcactg cctatacccc tcatcacacg tcacaatgtc ccgaattccc 136920
agcctcacca ccccttctca gtaatgaccc tggttggttg caggaggtac ctactccata 136980
ctgagggtga aattaaggga aggcaaagtc caggcacaag agtgggaccc cagcctctca 137040
ctctcagttc cactcatcca actgggaccc tcaccacgaa tctcatgatc tgattcggtt 137100
ccctgtctcc tcctcccgtc acagatgtga gccagggcac tgctcagctg tgaccctagg 137160
tgtttctgcc ttgttgacat ggagagagcc ctttcccctg agaaggcctg gccccttcct 137220
gtgctgagcc cacagcagca ggctgggtgt cttggttgtc agtggtggca ccaggatgga 137280
agggcaaggc acccagggca ggcccacagt cccgctgtcc ccccacttgca ccctagcttg 137340
tagctgccaa cctcccagac agcccagccc gctgctcagc tccacatgca tagtatcagc 137400
cctccacacc cgacaaaggg gaacacaccc ccttggaaat ggttcttttc ccccagtccc 137460
agctggaagc catgctgtct gttctgctgg agcagctgaa catatacata gatgttgccc 137520
tgccctcccc atctgcaccc tgttgagttg tagttggatt tgtctgttta tgcttggatt 137580
caccagagtg actatgatag tgaaaagaaa aaaaaaaaaa aaaaaggacg catgtatctt 137640
gaaatgcttg taaagaggtt tctaacccac cctcacgagg tgtctctcac ccccacactg 137700
ggactcgtgt ggcctgtgtg gtgccaccct gctggggcct cccaagtttt gaaaggcttt 137760
cctcagcacc tgggacccaa cagagaccag cttctagcag ctaaggaggc cgttcagctg 137820
tgacgaaggc ctgaagcaca ggattaggac tgaagcgatg atgtcccctt ccctacttcc 137880
ccttggggct ccctgtgtca gggcacagac taggtcttgt ggctggtctg gcttgcggcg 137940
cgaggatggt tctctctggt catagcccga agtctcatgg cagtcccaaa ggaggcttac 138000
aactcctgca tcacaagaaa aaggaagcca ctgccagctg gggggatctg cagctcccag 138060
aagctccgtg agcctcagcc acccctcaga ctgggttcct ctccaagctc gccctctgga 138120
ggggcagcgc agcctcccac caagggccct gcgaccacag cagggattgg gatgaattgc 138180
ctgtcctgga tctgctctag aggcccaagc tgcctgcctg aggaaggatg acttgacaag 138240
tcaggagaca ctgttcccaa agccttgacc agagcacctc agcccgctga ccttgcacaa 138300
actccatctg ctgccatgag aaaagggaag ccgcctttgc aaaacattgc tgcctaaaga 138360
aactcagcag cctcaggccc aattctgcca cttctggttt gggtacagtt aaaggcaacc 138420
ctgagggact tggcagtaga aatccagggc ctcccctggg gctggcagct tcgtgtgcag 138480
ctagagcttt acctgaaagg aagtctctgg gcccagaact ctccaccaag agcctccctg 138540
ccgttcgctg agtcccagca attctcctaa gttgaaggga tctgagaagg agaaggaaat 138600
gtggggtaga tttggtggtg gttagagata tgccccccctc attactgcca acagtttcgg 138660
ctgcatttct tcacgcacct cggttcctct tcctgaagtt cttgtgccct gctcttcagc 138720
accatgggcc ttcttatacg gaaggctctg ggatctcccc cttgtggggc aggctcttgg 138780
ggccagccta agatcatggt ttagggtgat cagtgctggc agataaattg aaaaggcacg 138840
ctggcttgtg atcttaaatg aggacaatcc ccccagggct gggcactcct cccctcccct 138900
cacttctccc acctgcagag ccagtgtcct tgggtgggct agataggata tactgtatgc 138960
cggctccttc aagctgctga ctcactttat caatagttcc atttaaattg acttcagtgg 139020
tgagactgta tcctgtttgc tattgcttgt tgtgctatgg ggggaggggg gaggaatgtg 139080
taagatagtt aacatgggca aagggagatc ttggggtgca gcacttaaac tgcctcgtaa 139140
cccttttcat gatttcaacc acatttgcta gagggaggga gcagccacgg agttagaggc 139200
ccttggggtt tctcttttcc actgacaggc tttcccaggc agctggctag ttcattccct 139260
ccccagccag gtgcaggcgt aggaatatgg acatctggtt gctttggcct gctgccctct 139320
ttcaggggtc ctaagcccac aatcatgcct ccctaagacc ttggcatcct tccctctaag 139380
ccgttggcac ctctgtgcca cctctcacac tggctccaga cacacagcct gtgcttttgg 139440
agctgagatc actcgcttca ccctcctcat ctttgttctc caagtaaagc cacgaggtcg 139500
gggcgagggc agaggtgatc acctgcgtgt cccatctaca gacctgcagc ttcataaaac 139560
ttctgatttc tcttcagctt tgaaaagggt taccctgggc actggcctag agcctcacct 139620
cctaatagac ttagccccat gagtttgcca tgttgagcag gactatttct ggcacttgca 139680
agtcccatga tttcttcggt aattctgagg gtgggggggag ggacatgaaa tcatcttagc 139740
ttagctttct gtctgtgaat gtctatatag tgtattgtgt gttttaacaa atgatttaca 139800
ctgactgttg ctgtaaaagt gaatttggaa ataaagttat tactctgatt aaataaggtc 139860
tccattcatg gattccaagg acaagaaagt catatagaat gtctattttt taagttcttt 139920
cccacgcacc cttagataat ttagctcaga acaggaaatg atagtattaa taaaagctgg 139980
acatcaggat taacagctct ctctggggcc ctgaaggtga gagttctcag acttgctcat 140040
ttgcagttgc ttctttgtga tgctggcaaa ccatcctagt cccattcaaa gggcaataca 140100
aagccttgtg gctgacctca cgatgcagca ctcagtttgc aagaccggca ccagtgtatg 140160
caaacctgag aaggttgggg atgaggatat gggatctttc atccctggaa atttagtcca 140220
gaggcctggg gctggagcag aacaccaagc caatcagctt aatgaatggc ttagattcct 140280
gctaggtttg cagagctgcc ttctttcctt tggtacctta ttatagattg aggagtattt 140340
ctgctaaacc aagataggga taaccagata gcatcttcat agcaatgcca caaaggaaaa 140400
caaaaacaaa acagtaatcc atcatattat tccttagtaa ctatgccaag gtcatgatac 140460
tgaatcctta gattgtttca aaatactact tttctttgct cttcctgatg tgtttgccac 140520
cgcaggcaga tgtttaagta aaacagattt taactgcagc tacaaaagca gcaacaggcc 140580
agcaaaagag aagtgctatc tcagagagca tggctttcag agccacaaga gacagcctca 140640
ctggctgttt cagcttgact gccatgcaaa gaagagagca gagggagaac cagccccacc 140700
cacttattca tcttgtacaa aaaaaaagca cctaccagcc taggctacat agtgagacac 140760
tatctccaca aaaaacccac gaaaactagc tgggtatggt ggcacatgcc tacagtccca 140820
gctactggta aggctgtggt gggaggatct cttgaggcca ggaaggagat ccaggctgca 140880
gtgagccaag attgcaccac tgcactccag tctggacaat cgagcaagat cccatctcaa 140940
acaataaaaa aaaaaagcgt gtaacctcct cagaagaaag atgttataat ctcaggcagc 141000
a 141001

<210> SEQ ID NO 33
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 33
uuagagugag gauuaaaaug ag 22

<210> SEQ ID NO 34
<211> LENGTH: 12001
<212> TYPE: DNA
<213> ORGANISM: Rattus norvegicus

<400> SEQUENCE: 34
aggacaggtg aggtcctagg tggaggtacg tttttgggct tcatggggca gatgctgccc 60
taggaagggt acaagacttc tatagccctg ctggggaccc cattgtcctg gaaggcggcc 120
caactctcta ctcctgtgga atgggaagcc cttgcttggc tttccagcct ccaaacaaga 180
taccactgca gctcagtttg agcgcttcaa gagtagtaat cattgtctga gggaggccct 240
ttgtacccat ggcctgcttt ctcggcaggt ttacaatgga ctgaaatcca actctctaac 300
ttcctggaac ccaaagaaag tctggctttg gacaaaggcc ctttggctgg gatttgtgct 360
tatgtaattc ttccgtatgc atgcaagtca tctggagaat actagtgaga ataaggacaa 420
ccacagatat gtaagccttt taccttacat agacgtattt aacaatggtc taatacggcc 480
ttaagtgtga tcagtaagga agcggcaggg tacgtatctg aaagatgaca aaacgtgact 540
ggagtgcctc aagaaaaaat gtgaactgtg tatctctcac agaagacaca cctgggccgg 600
ctatgtgcct gtttccttca gttggatatg tgaccatcac tgcctagcga gttgtaagag 660
tgacttctac tcccaggccc tcacaatatc cgaccaacta acatttaccc aggaggccct 720
accctctctg aaggcatgca agtggttagc aattgctgag agatgaggct cttctgtggt 780
gtagtgtctg tgtccaccta tgctccccta agtaacccaa ataaacttgt ttatctgcca 840
tactgaattt gggcagaatt gtcatttctt cagtttgttc agtacctttt ctgtctgtgg 900
taaatagaag taagactccc agggctggag agatggctca gcggttaaga acactgactg 960
gtcttccaga ggtcctggag ttcaattccc agcaaccaca tggtggctca caatcatctg 1020
tgatgggatc cgatgccctc ttctggtgtg tctgaagaca tatttaaaag aaaagaaaga 1080

```
aataagactc tccaggatag tcatagagca gagcccaggg gtctacataa gtaactgtat   1140
cccagtgtag ccaatcagtt cctcctgttt ctctggccta gagttaggtt tcggtatttt   1200
gccatcctca gaattaaatc ctgcctcctg agtgtagcag aacatgcagt tttatgcatg   1260
agctcttggg agaccacaga gatttcaatt ttaaaaagag acagttttct tttttagttg   1320
agaaacaact ttaacggtcc ccagctccgg aaaaaaaaaa aaaaagaaag aaacaacttt   1380
aaaaagagac aattctgttt ttagttaaga attctctctc ttactgatac cctttcttgg   1440
ctccagggac tccccatata tctttctaga catttctgag aactcaagta aatatatggt   1500
gatgtctccc cacctttttt tgtagtttgt accttttgct cattccatac cgtcttagaa   1560
aatatcttcc ttgaagcact atgtctcacc cagtgcatgg aggtttcaca aatgacttca   1620
tcaggcatct tgttctccag cgcatggctg tctgagaacc acttcaaaca ggcaagagga   1680
tacagaatgt tactatgcaa gtaacaccag ctggggatgg tggggcagac gagcaattct   1740
agttattggg gatgctgaga caggaggatc tcaaatggaa gtttagtccc tatctctaaa   1800
gttaaaagaa agccaggtac acgcctctaa ccccagcaac tgggaggcag aggcagaggc   1860
agggagagcc ctgtgagttt gaggtcagcc tggtctgcat aatgagttct gtgatagcca   1920
aaggtataca cggtgtgata tttttaaaag gaggtgtgtc taactggcag agcacatgtc   1980
tgtcacgagg ggtgtgtgta tgtcaaatcc ccagtaccag taacaaaaac attagtgaag   2040
aataagtaac gtggtatgtg cccaggaatt agaaacctgc agagaggggt tggggattta   2100
gctcagtggt agagcgcttg cctaggaagc gcaaggccct gggttcgatt ccccagctcc   2160
gaaaaaaaga acccccccc aaaaaaaaag aaacctgcag agaaaaaaaa aaaacctgca   2220
gagacacaga ggtgtgtctg gagatagaac atgggcctta cacatattac accgagcatc   2280
catcttggct caccccaact ttcacacagc aactgcggcg cgctgcaaag tcagtcgcaa   2340
tccgcatttc tagacagagc ggcttcagac cttccaggcg cgcacgcagg cctcgccgag   2400
gttctcggtt tccgccgcga ctcggccgac gtcacagtta gaagacaata gcgactttcc   2460
cagctctgtc tcgattctgg aactttctca gtccgcaagc tcctgaagct ggcgctcccc   2520
tcagccccgc ccccaacgtg ccccgcggcc agggaacttc aggaagggta ggcagagacc   2580
gcggctagcg attggttccc tgccaaggtg ggagtggcca ggcgcaggca tataaaagct   2640
ccgcggcgct gggccctcgt tttgcacctt cgtttcctgc ggcggcttct gtcgtctcct   2700
tgctttttgc tctcccaggt tccgaggccg ccgcgcgtct cccggggaag catggcgatg   2760
aaggccgtgt gcgtgctgaa gggcgacggt ccggtgcagg gcgtcattca cttcgagcag   2820
aaggcaaggc ccggggcgct gggcgcaggc cgcggtgacg cggggcacct gtgcgggagc   2880
acgccacgcc cccgccgcgg cctgagcccg ttaaatgctg agtcaccgcg gccttgaggc   2940
aggggccggg cgcgggagag ggaggccggg gcgccgcggg gccttccggg cgggtccctc   3000
ttcgcgcccc cgagtggccg ggccggcccg agagagcggg cttggcatcc gctatccctc   3060
tggggctgct gcttttccgg tgtccctgtc ccacaggggc tcagaccctt gtggccaccg   3120
gctgcatttg ttgtaagaat atttgaacct ggtggtgcca aaccggacta acgcagcaag   3180
cagaacgcat ttgtggcatt ttaaagccaa gccctggcta tattaggtca gggtcgtgcc   3240
gcaaggggga aagaaaagag atggccttgg gcagttgttt tgccaccaag agctccaaga   3300
aagagacctg actctggttg ttgtctacga cagcgagtct ctgagcacaa tttgaaaagt   3360
atacagaaat attttcgaaa ctactgcagt tctgcaaaaa cacatgcgtc acaaggaaga   3420
```

-continued

```
tatttgtgtg gttaagagcg tgttcagagc cttagggggt taacattgta ctccttttaa   3480
tcccgagaga aatatttgat aaatgagcgt tatgtactct ctaaagtggt ttacataaat   3540
gtgaggagac cgacaccata gtgaatccaa gtgtttcctt tatgaggaga actgataacg   3600
ggaatttaga gtttttcata actagtctca gtttcttggc atttaaatgt attttgttgt   3660
tttcctgtgt aaatttttg tttttgtctt tctcttcttc ccacataatt cactgtgaga   3720
cagggctttt cccccaccct gagaaagctg aagactagct aggtctaccc cagtgtccac   3780
cttcccagag cagcttgcag cattctttgg tgacgctgcc ctttgtaccc gatcaaacga   3840
tagttaagca ttccaggttg gcagctgtaa caacttgact atcaaaactg tttgatttaa   3900
actgttgcca acttttcaaa atcagttttt ttctactcaa agttcctagt cccttatttt   3960
gttgaaaacg ttggagagtt aaagtagaaa ggtccggtat gagtgtcctt gtttgttgca   4020
gttggttgcg tcttgccttt tctccctgtt gctacaattt ctgaagtaat actaaatttg   4080
aattttggat gttcttttct tttttgttaa gtagcaaatt ctctagattt ggatgcctaa   4140
tgagactttt ttaaaaagta gctctggtta gacccaaatg gatcccccaca ggcagtagga   4200
cacaattatt ttctggctac tggataaaat tatgggaact gataaacatc actgaatgtg   4260
gagtagaggt ttctgggcag ccaatgttct gaaagaatca agcctgacac agtgcagtag   4320
ccatccattc cctagttctg acattgagct gccccctttt gttcctctgg gtgcttttca   4380
agtgctgttg agtccaggtg tctgcacacg tgcatctgga aacaagtgtt agggaagatg   4440
ggtagggagg gagaggccta gagctaagca gctctagagt caccctggag gaaatgggtc   4500
tacttggatt tggacatagg tttgattttg ttttgttttt tgacttgtgc cttttactgt   4560
gattcagaag tattaacaca aacttgatgt cttaattttt gtattttttt aaataaaggc   4620
aagcggtgaa ccagttgtgg tgtcaggaca gattacagga ttaactgaag gcgagcatgg   4680
gttccatgtc catcaatatg gggacaatac acaaggtaag tcttaatcta tctctacctg   4740
gctgactagt gagatgaatg ggactgagtc aggaccaatt actaaccatt taaaaccatc   4800
aattttttc tttttctttt agattaagtt aaaataacca cttaggtcaa cctcggaaaa   4860
tagccacaaa agtattttag ttagtatcga gtatttcttg actccttaag tgggaaggtg   4920
agggtaaatt ttcttaaatg tgattattat agcttgactt taatatacag aaacaaatac   4980
gcaccttcct tattttggat aatcctttga ggtgtttgga gctgggggtt gagggtgggt   5040
gctttaggca cagtgtctaa ggacagctat gcacgagagg catagtggga cagaagtgac   5100
aaaaactgaa gattcaatat aaatgcttag agtaaaattt tttatatttg ggattggaat   5160
caagtcagaa aatatagtgg cttacattgc atttagtgaa cttttaccat attggagtaa   5220
tgatctgtgt ttgtttataa tcttttaaga gcctcattca tgttgctaga gccttttctt   5280
cctttccctc ttctcccctg ctttcccctc cccacatagt gcatgctagc ctggaatctg   5340
tgctggagct taaaccattt agtcttagat gtgcagggtt aaaggccatc aacctgtgtg   5400
caatgtacag taatttggcc tacagttact tatgtttgtg tttgacccat tcggataatt   5460
actaaagttc aatcaagttg ctttgcctct ggcctggtag ctttggtttg ttaagttcct   5520
tccagaatcc tgccctgtac ctatttcttg gtctgggtag aaattgtaaa ctatgtaagt   5580
cctatttcct gagttgttgt tgctgttgag atgtcccttg tgaatgatgt cccttagccc   5640
acatgtacac ctctaatgct gtttacacct ggagttgaga agcacagcag ccttgacacg   5700
tggggataat ctaaaaatct gtctgcccca agtaaaagcc agatggctga gctgtttggt   5760
ggtgtaaggt cttgaaagat aagtgttttt atcatgatct taaaagcaaa gatctttaaa   5820
```

-continued

```
tgtgggactt taactttaga agtgccacta aaggtcgctt ctgttccagt agaggaagga   5880
accagagcta gacatgctgt gacactacca tgctcctggc acttggaagg ctaaggtagg   5940
agggtcatta actgcagata tcatgggctg tggtagtgag accctgtctc aaatctcaaa   6000
acaaacaaac atgacagtct agtgaaaaag cgggtagctt gaaaatgcaa ggccatatag   6060
tccagctatt tgtaccaggg tgctgcttcc tgtttgtatc actccagcac ataccagctc   6120
catgtttgct gtgttggaag ttgtaagaat tccgatgtca ttgcatacag aggtttactt   6180
cataatctga ctgctggttt ctggtaaata ggctgtacca ctgcaggacc tcattttaat   6240
cctcactcta agaaacatgg cggtccagcg gatgaagaga ggtgagcagc attctctcta   6300
tgcatggtgg tggagagggg tctgtggaaa acacctgaag acagaactga gtggtctcac   6360
tgccttttct tttgtatgtt tccattcacc caactcccac atccccaagt actggaatag   6420
tttatattgg gtgaaggagc tgacaaatgt ggactcttaa gtgatttagt tttgtagcat   6480
ttattgaaga tgaactaata caagtgccaa aaggaaccaa tacagaaaat atcatggata   6540
acagtactat cagtcactag caaagtaaat cattgtataa tatactaatg cagataataa   6600
aaactagttg agattccgtt tgtatgtgaa accttaggaa agtcctacat ttaaagaggg   6660
gctagcttgc ttttggaatg gaggcctggg agcaaacctt tgctaatcag gagctgacat   6720
ccttttcgaa agtcctagac tgtggctctc tcctttaaac tggaagagct atgtgtcaag   6780
gtatcctggc tacctgtttt gaaatttgtg tttccagacc tttgtctgga aaagccatca   6840
tatttgatag tgtatgtgca ctctttaatc cactcatagc atttgacttc gatgtgaatt   6900
tagctattga actctattga tgtgaaatag atatcattgc ttatccacct ggtgctgttt   6960
taatgttagg catgttggag acctgggcaa tgtggctgct ggaaaggacg gtgtggccaa   7020
tgtgtccatt gaagatcgtg tgatctcact ctcaggagag cattccatca ttggccgtac   7080
tatggtggta agtttccata tagtagtaga tgtaggattt cttctaacat agttatgtac   7140
ctttccatga cttcgtggtg gtggttaaac tagttcctaa aagatcacat aaattggtaa   7200
gagttcagaa taggaaaaaa tattatttta ttggatgtaa tagtaaagaa ttaatttgcc   7260
taggtcagtt aagaacgctg ttctgctgaa gtgcggtaga aagctggtta catttgatca   7320
gactggatct gagttgagga tacaatagtc tttagtttaa aacagctgga ttttcttgcc   7380
atgattgccc ccttacagtt aatcatttcg ttgagcttaa aatctgcgat ggatgtcagt   7440
attcaagtct gcaggttatc gcttggttac catatgggag ccgtcttccc aagttaccct   7500
cgggagatga atctggttca tgcagaacac caagtagtaa aagctcttgc ccacttcggg   7560
cagctaactt ttcagtaggc acttcctttc agttgaccct ttatccttag aattttcttc   7620
agccctattg gtgaagcaga acaatcattc ataaatgttc taaaaataaa atttaaaatc   7680
ttgttgctaa gtaaagatat ttagaattgc ctcttatgtg taggcctata gttcactcac   7740
caagagattt tgatagagaa atttgtaaga atgactactg tacagtgggg tgagggtgag   7800
ggctaagatc agcatgtgcc tggtagttat ttgggtcctt agtattcatc tagaaatagc   7860
cacgagcaag gaaacactta gtagtctgct tttagctgat agcataaaaa ttagcttatt   7920
gatttactaa tagatttgaa cattttctaa tatacatggt cctttgaagt attgctggga   7980
agaagtgcta attacttgat caccgaaacc taaatgttct taattctttt caaaggtcca   8040
cgagaaacaa gatgacttgg gcaaaggtgg aaatgaagaa agtacaaaga ctggaaatgc   8100
tggaagccgc ttggcttgtg gtgtgattgg gattgcccaa taaacattcc ctatgtggtc   8160
```

```
tgagtctcag actcatctgc tgtcctgcta aactgtagaa aaaaaccaaa ccattaaact   8220
gtaatcttaa cagttgttaa ctgtgtgact cctttgactt gctctaagga cttgcagtga   8280
gaggtgactg acgatgtttg gaggatgtgt agaacttcct gaatgtgtac aactcattga   8340
actaaaatct gttgtttctg tgccagacct cactggtgtt aagctgaaat tctcattcaa   8400
gcctctctct ctctctgtgt gtgtctgtgt gtgtgtgtgt gtgtgtgtgt gtgtgtgtgt   8460
gtgtgtgtgt gtgtgtgtgt gtgtgtgaga gagactgaga cttatttaga gcctcgagag   8520
atagagactt atttcaagcc tattaatgta taccaaaaag acctaagctc tatacactga   8580
gcatcaacaa cagactcaat gaggctctca tagtatttaa ttttgaaagt gtttcatgtg   8640
ataccatcaa aatgacgtgt ggtagcccaa accggatttg atcttagaaa attttctgcc   8700
ctttgttatc atcagaaatt actgaaagct ctctttaaga ttcagagtac ctaaccttat   8760
tttaaaatcg tattagagtt agaagccatg atttaagata aagcccttta gtaaacttgt   8820
ataaaactca taaaaggcaa ataggtagcc tcagctagcc aagtttaata cctcctctac   8880
ctgccaagtg aagttggtac cacctgcttt tttaaggttg gcactcagga aatacatagc   8940
actgggagat gagaccaagt ggttctggcg gttgtggcta aatcgacttt tacagcctca   9000
gttaatgaaa ctgagtacct taataaatac atcccaagaa agagagcttt gtaagggaaa   9060
tattaaccta aaaggctcgt gactatttgg aacagttcaa ctgaaatatt tctgacaaat   9120
ttggtgtaaa ccatagtcct cttaattttt caaatacaaa acactgaaaa ttggaaaaaa   9180
ataagtgttt ccaggtttaa aaattttaag tttaaatttc caatttaaga ttgcttataa   9240
ggaatgcatc cgtatgtagt tctgttgaag tttcaggtaa atcatacata acttatttcc   9300
ttaatgaagt tttgatgggg tgtgtgtgtg tgcgtgcgtg tgtgtgcgcc tgactcaatg   9360
cagactaact tgggaagcat ctggtggaat cacaaaccag tgtttatcag ctcatttctc   9420
ggtattttta gttggaaata caagctgcaa gtctgtcctt ggaatctggc tttgaatagt   9480
caggtgcatg ttttagcatc ttcccagaaa tattctagta gggacttaaa aagcccaagt   9540
agggtcacca taaaaccaga acctggcata gctacagaca catttcttac catcattagg   9600
aagatcttaa agagttaaat gtcaagtggg agcatcaaaa aggagcttct cagtactcta   9660
aggtctgatg aattattttt gtttagccta gcactttgta gttttaaaat cacattttca   9720
ggatgtgtgc aagagaggaa aacaagttca tgttcttcca cctgttttgt ccctgggatc   9780
acacaggcca tcaggattgg cagaaagtgt ctttactggc caagtcatct tgtctttcaa   9840
atgtaatttg atgaaaggaa cttccagact gtaaataaga ggtgctcaac ctgtgggtta   9900
caaccccttt ggaacttata tcattctgct tatcagatat ttacaatcca taatagccaa   9960
aattagttgt aaaataacaa aaataatttt atggttagcg gttggcacag catgaactat  10020
attagagagt cacagcattg ggaaggctga gaaccactgc tgtaaataaa tacctagcat  10080
taagtccctg actctagaca acactacccc accttcttgg gttttttttgt tttttttgttt  10140
tttgtttttt tttgtttttt ttttttgaca ggatttctct gtgtatagct tttactgtcc  10200
tggaattcac tgtgtagacc aggctggcct tgtctcacaa aagatccacc ctgcctttgc  10260
ctcctggggg ctgggattaa aggtgtgtac caccacctgg caaaatttgt ttgggtaaac  10320
ttttttttggt ttcttgagac agggtctgtg tagccctggc tgtcctgaac ttgctctgta  10380
gaccaagctg gtcttgaatt cagagatgca cctgcctgtg ccttcgctgg gattaaaggt  10440
gtgcactacg acgacccact gggctcggac aacactttta tgtcagtgct tccaataaat  10500
actattagag tcttggtttg gcttcacaag tagcagcaaa ggttcagtgt acttcttggg  10560
```

-continued

```
ctattgaaga tggtaaagac aacaggcaaa gcttacaaga aatgtcatac tgtacttaag  10620
tctataaaaa gctttctggt tgcatatgtt aacacgggcc tcattttaca ccttggaaat  10680
ttcaatggga tgattataaa cacgtcaacc ttctaaataa gtaatgccca agcaatcagg  10740
taatttatag tataatgtat aatgttggga atccaattat ttcccctaac aaatctttac  10800
aaattaatta gggcaacatt accacaaagc caagagggaa aaaagaactg acctgcagac  10860
acaaatttct tagttgaact ttaagatcac taacctttac cttatggtca aaatactaaa  10920
agtcaaaaga ataaaactcc aagcactggc aaatactacg taagtgtctt tctttcccca  10980
tcaaagaagt ctaatttaga ctccaacaat tattaacagc tcaatctttg atggttaaca  11040
tctgtccaat cttaatgcag tgtatgaaga atagcacaca ttaaagtttg ttacgaaaat  11100
agagtttatt aaaaacatcc ctattgtttg aggagctttt caccgttacc ttttcttaaa  11160
ttaaaaaaaa aaaatagaga gcacttctaa ttaggatttg taaactttta aaagtcaaaa  11220
cttttaaaaa gttacagcaa aaaaaggggt aatatatctt cagtattttt tgttattttg  11280
tggctatttt taaatagaag gaaagcaatc aaattgctca caatccccac caactactgt  11340
ggagtgatgt agcaggagcg aatattatac agcatctgta cacctcacgt tctacaccca  11400
agtgtcactg tcacattctg tcaaatccag tctctagcga ggagcctctg ctgctgagcc  11460
agaatccttc tcaggttcaa cggatgaggt agcctcagca ggtgactctt caggttttac  11520
cactgtggcc atggcctccc ccttattaag ttctgaaaca gtgtctgtgt ttcccacttg  11580
gctaagggga gcttcgacag ctttgttacc acctgccctg tctgccacct cgtgcttctc  11640
ctttcctcta ctttcttcct tctctctacg ggactctcta tctctagaat ccctgtctct  11700
gtcccgatgc ccactagagc gtctacttct ctcttccaag tctctgtgtc tgtcccgctc  11760
agggctcctc cttccccact ctctcctttc acggttgcta ttatctctct catcactacg  11820
gctcccatac cgctcccggt cattttccac cctacttcca aaagatcttc ttccaaacct  11880
ttcttggtct ctacctgagt tgaactgctg cctgttatca tttctaaact gctgtggctg  11940
ctgctgagct ggcgctggct gctgggatgg cgctggctgc tgctgtgtct gtgactgctg  12000
t                                                                  12001
```

<210> SEQ ID NO 35
<211> LENGTH: 21
<212> TYPE: DNA
<213> ORGANISM: Artificial sequence
<220> FEATURE:
<223> OTHER INFORMATION: Primer

<400> SEQUENCE: 35
cggatgaaga gaggcatgtt g 21

<210> SEQ ID NO 36
<211> LENGTH: 18
<212> TYPE: DNA
<213> ORGANISM: Artificial sequence
<220> FEATURE:
<223> OTHER INFORMATION: Primer

<400> SEQUENCE: 36
ttggccacac cgtccttt 18

<210> SEQ ID NO 37
<211> LENGTH: 23
<212> TYPE: DNA

<213> ORGANISM: Artificial sequence
<220> FEATURE:
<223> OTHER INFORMATION: Probe

<400> SEQUENCE: 37
agacctgggc aatgtggctg ctg 23

<210> SEQ ID NO 38
<211> LENGTH: 25001
<212> TYPE: DNA
<213> ORGANISM: Mus musculus

<400> SEQUENCE: 38
aagggtttct ttggcttaca cttttcttat tgttgttcat tattgaagga agtcaggaca 60
ggaattcaaa caagtcagga tcaaggaggc aggagctgat gcagaggcca tggagggatg 120
ttacttacta gcttacaccc cccccccccc cccggcttgc tcagctttct tttttttttt 180
tttttttttt tttttttag atattttcta atttacattt caaatgctac cctgaaagtc 240
ccctatacca tccccccaca ctgctcccca acccacccac tcctgcttcc tggccctggc 300
attcctctgt attgttgctc agctttctta tagaacccag gaccaccagc ccaggaatga 360
caccacccat agtaggctgt gccttcctcc actgatcacc aacggagaaa tatgggcaac 420
agcttgccca taggatgggt cactagttgg gttggttact gttgggccat tccctcagtc 480
tctgctccat cccccatctc tacatttctt gtagacagaa tcaattttgg gtcaaaagtt 540
ttgcaggcag gttgttgtcc ctcttacatt tctcatggag gcatttcctc aacttatttc 600
ctctctctga tgtctccagc tcatgtcaag ttgacacagt tgttcgggac ccacatgaag 660
accaagctgt tcatctgcta catgtgtggg gaggcctagg tccaacccgt gtatgctgtg 720
gtagttcagt ctctgagagc caaaacagtc caggttagtt gactctattg atcttccttt 780
ggagttccat cccctttggg gccctcaatc cttcccacaa ctctaccatc agagtcccca 840
agcttcatcc actgtttggc tgtgggtctc tgcatccgtc tgagtcagct gctgggtgga 900
gcctctcaga ggacaggctt tctagactcc tgtctgcaag catagcatta atagcatcag 960
ggattggtgc ttgcccatag gatggatcac tagttgggtt ggttactgtt ggccattccc 1020
tcagtctctg ctccatcccc catctctaca tttcttatag acagaatcaa ttttgggtca 1080
aaagttttgc aggcaggttg ttgtccctct tgctccactg aggttcctgc ctagctacat 1140
gaggtagcct ctttaggttt gatatcctca atgctgtgaa tcccaactaa gatcaccccc 1200
cattcattcc tggtgtctcc cctatctcag gtctcagata tgccttcaag atgccccccc 1260
cccacctctc cacctctgcc agctgcagat ttccattcat tctcatggcc atctggctat 1320
ctctcctgtt cctccccata cctggtcctg aacccccttc accccactcc ccatcccctc 1380
tcccacccag ttcctttcct ccatcttcct cctatgactc ttttattccc tcttctaaat 1440
aagattcaag catcctcgct tggacattcc ttcttattta gcttctttgg gtctgtggag 1500
tggagcgtga gtattccaac ttctaaggca cacagacaac ctcagattct ccagcccttt 1560
gtgtgtgttg cttatttgaa caaacgggtg aaagaaaaca cacaaagttg gcgtgttgaa 1620
agagttagtc gatcttctgg ggtaggtttc agtacagaga ccaaagggac attctcagac 1680
actagacaca ctatgcaaag acaggatgtc acatgacaaa ggataacggc acaagtaaac 1740
atttaagcaa cagtgttcca taccggctca cgtagaaaaa ggacaagact ataggaaaga 1800
aagcaaacac tccgccgagg actacagcaa agacagaaag tatctgcagg tacggcttca 1860
aaaggagcat ttctctcagc aacttatatc tgttaatgcc ctgtcttctg gaataagggc 1920
ttagttttta tcagtagaga gagattgatt tttaagatgt atctgatttt acattgtaga 1980
tctccttagt cacccccctgt agtaaactaa ggaaaacttc cgtggaggga gaggggaaga 2040
ttagtaactc gtagtgagta agaattctct ttcaagaaaa agattcaaga gcaatacaag 2100
gcctagatat gaaggtgtgt gtgtgtgtgt gtgtgtgtgt gtgtgtgtgt cttaacagcc 2160
tgttcagaat ttagtaggtc acatacactt acaagtaatg aagacaatat attaatgaat 2220
ttgcagtaat tttttgtttt agaaatagaa actgttgtaa ggaggataat cattcagagc 2280
tctttgatat gtatcactca cattcacata catgcataca cacagagaga gagaaagaga 2340
gatacagaga tagacagaga gagaacccaa aaatgtaaag agaggaaatg agttgaaaga 2400
aaaaatggga aactgggtta gggaggggtt cagatgacag tgactggggg ctttcagagt 2460
tgggagtgag gcagcgatgg agagagggca gggaggaggg agtgtccatt gtgacctctg 2520
cagaactctg actagactga gcagctcaca ccgtgttgga gctgtcctaa cactaccaag 2580
gggacggggg agaccccatg aacaccacct agggagttgc tcctttcatt ctgtgtaaag 2640
tctgatgtct tcaaacttgt tgtaaattta tactctgttc taaaaacagt gacattcttc 2700
tctttgtagg atgacctcat tacatcaggt gttatatttt atcttttttg cctcagtttc 2760
tagtggtaag ttgctgtatt tattttcccc taacataata ttttttatta cttgagagtt 2820
tcatacaatg caccctgatc acactcactt tccattcctt ctaagttcac cctcccactc 2880
ttgagccctg ccagctcact cccccccttct tgaaaaaaaa tcatcaagtc aatcaatttg 2940
tgttgagaat atatactcgt tgggaatgtg atcaaactcc caatggtcag ccccttaaag 3000
aaaagtgagt ctttttcctc ccccacttct ctccccactc ccttacccag ttggaagcca 3060
tcaactgtga agagttatac ttcagcatct ttactacaat tttaaaggac tctcttcagt 3120
atttaagtat ggcttagaaa tagctcattc cttgacctgt aatgtaggaa acagcctaag 3180
tccacaaaaa gaaattacac ttcagacccc atatattgtg gaataattcc atgctgtgaa 3240
ctccagggaa ggaaatagag tcgtttattt tccagtgaaa gctccccttt aatacatcaa 3300
agaaagaaag agatttaaat atagaattac aaagagtctt cacctatatc atctgaatgc 3360
tagtaatatc tgtctataga gttgcatctc tatctaccta cacaacacat tgccatgatt 3420
cctaggagca agattagaaa gagaagactc gactcacctc attgattatt attccataag 3480
ggattcagtc tagtatctct ctctgtctct gtctctctgt ctctgtctct gtctctctct 3540
gtctccgtct ctctctctct ctctttctct ctctctctct ctctctcacg cacacacaca 3600
cacacacaca cacacacaca cacactcacc aattcctgac tgaaaatgtt atagaaaaat 3660
taatgtgtgg cttacacatt tggttaattt accccttgca attatgcttc cattctacat 3720
tacatccagt aaatacattg cttaccattc agtagaatga aatgggaagt tacctcacca 3780
atactgatct taacaactta gtgtaagcac ttcttaaaat aatttattta tgttatattg 3840
aatgcctgag actgccattg acatattaag catagttagt tctttttggt gtgacacatg 3900
tgaacagtag cagatctaaa ataaaataaa catatgtaac atattaaatt atacagatta 3960
tagcttaatt tttctttgtg attagattga ttttcaggtt attccttcat tatcaatgtt 4020
ttgaaatccc attgttattt gtactgtctt gttcagtact gttttgacat gttgttgttg 4080
ttgttgttgt tgttgttgtt tgacacagag tttctatgtg tagccctggc tgtcctggag 4140
cttgatttgt agaccaagct gacctcaaac tcagagatct gcctgcctct acctccaagg 4200
gctgggattg aaggtgtgca ccatcatcgc tcggcagcct gtcttaacat cttaaacact 4260

-continued

```
gagttcaata actgtgtcga ttcacaagga cattctgaga attataagac tttttgctt   4320
atgaatatat atatgcaaat gtaactgaca aaatattatc cattgtggtt gtatcacact   4380
taaaaatctc agagccgaga aagttggggc aagatgatta aaagttcgag gacaggatgg   4440
gctacataac aaggttctgt ctcaaattgg ctataccaaa ccgtccaaca catattttaa   4500
agaaaaataa atgggaggct agagagatgg ctcagtagtt aagagcactt agtgctcttg   4560
catgggatca gttcaattct cagcgcccat gttagatagt tcacaacttc ctatgactct   4620
aacttccagg aatacagcac cctcttctgg cttctgtagg tacacacaca cacacacaca   4680
cacagacggc atacgtacat acatacatac atacatacat acatacatac atgcctacat   4740
acacatgtac atgcatacac aataaaaaag tttttaaaat cttttttttt aaagaaagaa   4800
aattaaaaga ccaattacat tggcatattt tggccaagtt tgcttaattc taggaacaag   4860
gagttacttt aatctaagaa aaacaatcaa tggatgcaat gtagatccaa aggaagtgaa   4920
agaagagagt cctacagaga tttgtcattt gtcttcctgc tatcgggcag agaaccagca   4980
agagagaaac gtgggcattt gaagcccact cagccgtgtc atagcacaag ttgggtcttc   5040
accaatggac agaaggttaa acaaaatata atatcacagt atgcacatgc aacacaaaac   5100
aggatattac tcagcgtgtg aggaagaaaa ttctccctca tactggggca tagctgagcc   5160
ttcgtggttt tatactcaac gaaatgagtc atttacaaat gaacacatga ctgaacccct   5220
aacgtttggt tcccagagat gccgatttca ggaaaacaaa agaccgaaga gaactgacca   5280
ggggctaatg ctaatgacta tttaatgggt acaagttttc agttggaaaa gctgaaggaa   5340
ttctagaata gtggtggaaa ttgtacctaa ggtacatact tcattccaca actctagaga   5400
cctgaaaagg gccggagtga caaactttat gtcatatata ttttgccata gaagaacaaa   5460
attaaaataa tctaacacat cgaagatttt aaagattttc ataataaaat agtttagcaa   5520
actcagaact ttcccaatga ctaagtagta ctgtaaaaca acaacaacta gaaaaacatt   5580
caaaccaaaa gttttcaaga aatctcatat gtaatggtga ctgaaatagt gtttccctga   5640
ggtactgggg taaggcagga gtatccacaa cttggctcct gtgaatagga aacaaggaac   5700
agagagatgc aagcatcttc aaaaagttgt cataggatcc atcatggaca ttccaggagg   5760
ggttcagttc tacttttagt tttctgtgac atctcattac aggttttgat tttttccccc   5820
catagcttcg ccagcatgga aatttattca caagtaccaa gtcagggagt ctgcctatgt   5880
gtccatcaat agatgaatgc aaagagcaaa cactggatgt aggcacagtg caggggggcag   5940
ggaggggtgg catgttctgc atttagctaa aatggttgtt ttagttttta ctaattcttc   6000
aagaatgcca tataccatat tttgctaatt tttacctcga ctccccaaac tccatccaga   6060
acccccccatt ctgtacccac ctaactctgt gttctccctg tttcatttgg ccacagtgag   6120
gaatgaaatc gtgccatttg tgtaacaatg gctgtgactg ggcatcatca ttattcagtg   6180
agataagtca gattgaagaa gataaatatc ccattttctc aaatttgtgg attctagacc   6240
ttatatggat acataaaatc cagtgtgtgt gtgtgtgtgt gtgtgtgtgt gtgtgtgtgt   6300
gtgtgtgtgc ttgagtgaca cactctaggc tccagagtct aggggaatga cagagactag   6360
aaggaaagag ggaaacgaaa agatatgaag aataaatata gtcgaagcac atgatacatg   6420
cctatgatat tatgatgtat acacacctat gcaggtgtcc catgaagccc cctgctatgc   6480
aacgaatacg tgtcaataaa tgtgttgaga gactatctac tgtcacttcc cttaaacatt   6540
atattagaga tcctgtgtag cacagtaggg aaggtcgaag gacctaagag tcaggagaaa   6600
gatggaaatt aactgactct tcccataaat gtggttatgt acatagaaaa attcaaagta   6660
```

atgaatgcac tgattatttc aggcagatca gcaaggagtt tacaaactcg atggaccccc 6720
gggagtggag gcacacactt gtaatctcat gactcaggag gcagagggca catcagagac 6780
cctaactcca gctcttccgt tcaaaatctt caatatacaa acagtagcca actctcgcca 6840
gtactaggaa ctgtactgag attatgaaag tcaatattat aggttaaatg attcaagtag 6900
tggctacatc ctaatcaaaa ctgcacattt attaatcctt taaaaatcaa ttcaacttat 6960
caaatcctgg tgttgtgctt gataagaaca ttttaatgtg ttatgatggc ttaatagtaa 7020
aatgttgcat ttcttagagt taacaggtaa actgtgaggt gggaatagac tgccaattag 7080
ctggaaacag acgcagtatg gtttggtggg agacaacact gaacttggaa aaagaagtcg 7140
gatctctatg tagctcctgg gatacttgcc tgtagtggag aaaaccatgt tccctaccaa 7200
gtctctgctg aattttggaa atggatctgt agtgaggttg ctcttcctcc ccacaaatcc 7260
cttccgaggc cccatggacg cagcggagcc tatccttgga ataacttttc taaaggcatg 7320
gactaaaaat atatagggtt gctggggaaa ttaattatat tgaaatatga gtagctaaag 7380
tggaaaatac tcagtacaga attagttgtg gctcggagtt aacaccttac atgacattag 7440
tggcatgccc aaaactgaat agaaataacc aacaaattat cgacaaatca taatgatgtt 7500
atatctcatc atcacataca tgacaaatac taatcatgtt aattgattac attaataata 7560
caggtatgta tgtaccacat tttggttagg gaatcaatga aaaaccacat gaggtttttt 7620
tgagctcgtt ggttatctag gtcctacaag cctcatagga gggttttgag actgctatgc 7680
acctacaatc ctctcaagac atgactgatg gctgttacag tagtctatat ttgagttaaa 7740
ttttattctt ctggaagtac ttccacgtga gtctggtaat gttttcaagt tataaagaga 7800
aatgggctag caacacctct ccatgggcat gtatggctgc atgaagtaat cttttattca 7860
gtcactaggc aacctactgt gtgaattatt agctatctct tctagcaaca gagcactttt 7920
gaatttttat gcattttggc tttttaaaaa ctaaagctga tgtaaggttt tcgctaaata 7980
gaactcagta agttttccct ggtaaatgtt ggtcatgaga ccatttttaa tgttcgcatg 8040
acatcataca agggcccctc agtcttggct tttagtttgt ggtagtgtca aaacaataaa 8100
tgaacgtaaa cacagcacac ccttgctgac cccctagagg ggtttcatgg ggaccgtgtt 8160
cttcttgccg gtcaacagct gagaaatcac tgagttgctc ctgcagcctt cccaagacaa 8220
tcactcataa atgtgacaac acggagggcc cccatgttgt ttgtgattta tagttccatc 8280
tggggctgtt cactgaagag cgttgcccga tctgatgtcc gaggtcaggc atatttagca 8340
ctgacttttt aacaaaccat gtaacgaggt aagtgcccac caacatctgc agtaatgtgc 8400
gcccgcgtgt ttttttcttc acagaatgcg ttactaaggt cttcaaagac atcagctttc 8460
aaggaggtga cctgagtact gttttcacac cgagcgccac atactgccgc ttggtctgca 8520
ctcaccaccc acggtgcttg ctcttcacgt tcatggctga gtcatcttcg gatgatccta 8580
ccaaatggta acagtttctg tttctctgaa gaggaactga tttccagtgc cagttactca 8640
ccaatgcaga ttaccttaca accccacttt tgtcatttta caaaagggga tgttagtggc 8700
tggaaagtga gtttccttcc acggaaatac taaatattac aggaaggata gcgcttaggc 8760
atattggtgg aaaaccgtaa taactcctgg gacctcaatc ttaaagtcac gtttttgctc 8820
ttcatccatg gtttgtctta cattcttttt ctgtcgtggc tattggctaa caatggtggg 8880
gttatctaga gcttccttct aacctttcaa ttagggggaa aatgtttaaa aagctacttt 8940
aaaaattatt acaacaattt tctacccccct ccaatatcct gtcatattat gtggctttct 9000

-continued

```
cggctcccat cagtggttca ataaggcatg cagactttta tataaaactt aaggcccttc   9060
attggggcag gcagactctc agctctcttc tctaatctta gatcgtctgc caagtagcta   9120
atgatttatc tcgtttccat tcctttccct atctgcctct gaatctccca cctctgcttt   9180
agttctctct ctctctctct ctctctctct ctctctctct ctctctctcc ctctctctct   9240
ctctctctct ctctctctct ctctctctcc ccctctctct gtcccacccc cagaagtccc   9300
acccttgtac ttcccgtccc actttaggca atatgagtgg gtgaggaagg acaagcactt   9360
acaaatcaga agctggtgat gggccataga catgacgata ccaaacatct gccagaactt   9420
agctctttgc cagtacagta atcaacaatt gcacaattga aagtacagag acacgcctta   9480
atacaatata aggaaggtca tcgcaacact gtcatatttg ctttacctac ctgtatatgg   9540
tcacagataa atactgaaag tgagtttaaa atatcatcga cctgcatatc taaatacttc   9600
aacatgaatt tcccaataag gaaactgtaa gaagcccaac aaagttaaac atacttgaaa   9660
tgttaatttt agctgttaat taaattctca tcaaatttca caggttccta tggctgtttt   9720
tccctctcta tcttattttt aaaatattgc atccatttct gtctctatgc taagcttgaa   9780
attttaatat ataaccttta atgcaaaatt aagctgccaa tatctttgtt attgctgttt   9840
tctcagatgg ttacatattg ctgtcaacat taaatattct tctgaaatct agaacagaga   9900
tcggcaagac aggaataaaa ctttaggctt tgttgaacca aatgcaaaaa gaacattctg   9960
tgtttctaac actgttttag aatgtaacca tgtgtgggct ggagggattg ctcagtggtt  10020
aagtttgctg gctgctcttc taaagggccc taggtttgtt accccaactt acagagattt  10080
gcaatcattg gtaactccag ctctagatgc catcttctgc ctttctcatg catgtgatca  10140
cacacacaca cacacacaca cacacacaca cagagagaga gagagagaga gagagagaga  10200
gagagagaga gagacagaga gagacagaga cagagacaga gacagagaca gagacagagg  10260
cagaggcaga gagagagaca gagagaggca gaggcacaga ctgagagaga gtgtgtgttt  10320
aaaatttaaa atgtagccat gtaaaaaata gaaaaccatt tctatctcaa ggataacaca  10380
aaaatggcag attttaagca acattttagc aataggttaa agtccttcca ttcttattca  10440
tgtcctgttg gaaaggaggg ccgtgtgtgt tcttttagat gtagggatgt tgtaataaaa  10500
aacaaagtca aatcttgcta attaaacatt tgttttggca ggaaacccag tcgtttgtct  10560
ccttctcttt gaccttagga tcccctcttt gaaagcatga attcctgctg aataatgtta  10620
ttttcatttt attttactat tttatttttt aaaaaagaac aggtttgcct gcatcctgaa  10680
ggacagcgtc acagaaatat tgccaatggt aaacatgaca ggcgcgatct ctggatattc  10740
cttcaagcaa tgccctcagc aattaagtag taagattttt tttatcaaat acaattaaaa  10800
ctagccatta gagtatatac gtgtaatcgt ttcagataca ggtttgtggc tataaaataa  10860
aatactacca cctaggacta aacttcccac caaggaacca tcttcctatg tagagtagag  10920
gacacagttt tctcccttcc tctccccata agcacactgt ctcgctttac catttcttag  10980
cctcataaag gcatgtcagc acctcagttc ttattattgc acacgaaagc cctcgttata  11040
aaagctaatt caaatcaaga ggagaaatgc agactgaagt ggcacatgtt ttaatagtgg  11100
aacgggcact tttcagtaag ttaaggggtg aaccagttgg tcagtgcggt ttgaggtcag  11160
aaagtcaaaa ttcaaattca caagctttct atttgttaaa aaaatttttt atttatttta  11220
tatgcattgg tgttttgcct ccatgtgtgt ttgcgtgagc gtgtcagatc ccctgaaact  11280
agagttacac acagttgtga gctgccatgt gggtgttggg aattggaccc aggacctctg  11340
gtagagcagc cagtggtttg aatcgctgag tcccctctcc agtctcaaat gtacaagctt  11400
```

aaagcggttc cagtctaaga ggcacattgg cttcctcgga atacctccta gtggaagtgg 11460
gaatcacagc tgagtgaaac aaaacataga acttccacgg gagagtgggc gagaagcgag 11520
cagtttccac gcgagagggc cagcagcgaa agcagcgtac tgtagttgcc cctcgcttct 11580
ggtgacgcct agattctccg cctttatttc cagcttgcag caaagatgtg tacgtgaacc 11640
tagacatgaa gggcatgaac tataacagct ctgtcgtgaa gaatgctcga gaatgccagg 11700
agagatgcac agacgatgcc cactgccagt ttttcacata cgcaacaggg tatttttccca 11760
gtgtggacca tcggtgagtg agcgggagtc cgagccgctg gatataagcc tgcccaggga 11820
aagaaaaccg ctggttccgt aggtattttc atcaatttga agcctaaact tcttttttta 11880
aaccccaaga tatttgcata acaacaatca ctgttttgtc atgaaaaggt catagcgtgt 11940
ctaacacaca tttacgacat attcaaattt cagaactgga ggatggctcg gtgggtgcgt 12000
aaacacactg cttatgcagg gaccctgagt ttggatccca gcatgcacat aaaagccaga 12060
tatgggtgtg tatgccttta accccagtgc ttgggacatg ggcacgggac agagggagga 12120
tggttggagc tcactggtta gctccaggcc tttattatta ttattattat taaatattgt 12180
ctttatttac atttcaaatg ttatctcctt tccctgcccc ccccccaacc ccctctccca 12240
tccccctccc atttctacta ggttgtttac ccacacacca acccactcct gcctccctgc 12300
cctggcattc ccctacactg gggcatagag ccttcacagg accaagggac tctcctccca 12360
ttgatgcctg acaagaacat tctctttagc tccaggctta gggagagatc ctgtctggag 12420
gggaaaagac agagaggtca tagggcagga actctaacac ccccccccca cttggacttc 12480
ctattctcac ttgcataccc acacccccac accccacaca caccatatac aatacataca 12540
gcgtggcctc acagattctg tgtatgttgt aaagcataca caagcttacc ctatctaact 12600
tcaaaaggca ttacattttc acgcttgtgg ttctgagagc tcggtttgct tggccatgct 12660
cttcccagtc taacaaatgt cctaacctaa aaatcatcaa aacttaaagt ttgtttctct 12720
atctacctac atgtacagtt ctgtccctta cccaagacga agtcattgga acccatgtgc 12780
aaagttttct cctgtttgat gtgggattcc aaactcctcc aaggaagaaa tctgttatat 12840
aaactaacga gagggaatga ctaaatctgc atcttcagtt taaattgttg ttagaaaagt 12900
atatgacttg ttcttttaca aacattttaa ttttgtgtgt gtgtgtgtat gtttatgtat 12960
gtgtgtgcct gtgcgtttag acacacacgt gtgcagataa ctatatagcc agaagagaca 13020
tctctcaatc tctcaaggtt catttttaga cttaggaatc tttgacatta tctagatttg 13080
cacagtaaac aacaggtatg tggtagttgg attttaacat tggctattcc tacttcactt 13140
tccataattc tggggggaa aagatgaatg ggaagtgaaa cattaaagat gtcttttaga 13200
atgaataata aaaaaatgga aagtagcctt ctatggctct ctttagctct cctcagagga 13260
catgttttat gtcttagact tcacagaatg ccaactgcag gctaggaaaa tgttcctagg 13320
gcttacacaa aagcgtattt ggagggctaa cgtgaacccg ttcacacaac cacctcacac 13380
cacatcaggt cttctgtgtt gtcctctcac tgatgagata acattattcc tgagtccaca 13440
gagcctccct gtggttagaa gagctgccag gactcatgca gccacctggc tctgcaggtg 13500
aacactcctg ggcagttcct ctgttattac agtcatttcc cccctgcgga ccgtaacttc 13560
ttatcctctc gtgtttttat acacttggaa agaacaatat tttgccattt ttgtttgtat 13620
tcagtaaaat gtgtcttttg aagtacaccc gaacggggac gccaaccaca ataacgaagc 13680
tcaatggcgt ggtatctgga ttttcactga agtcctgtgg actttcaaac ttgggtaact 13740 atcattttc tcaatgagat attggtacca ttaagcctga gtgaagcaga gactatgtgc 13800
aatgggtcta actttaaaaa cagctgatgg ttatacatga agcgaaccca gtaacctttt 13860
actgtcttca aagtgaaatg gttcactatg tcctggaaag catttccttc ttaaatttca 13920
aatttgttct ttttataaac aacaacaaca acaacaacaa cagcataaat aaataaataa 13980
ataaataaat aaataaataa ataaataaat aaataaggtc ttcggatgaa ctttccattt 14040
ataatacaat ttacaaaccc tgtctgggat gtctatgatt ttgctggtgc ccctgccttc 14100
ctaacacagt ttcttccctt ggacagcttg tatcagggac attttcccta acacggtgct 14160
ggcagacctt aacattgaca gcgtggtggc cccagatgct tttgtctgtc gtcgcatctg 14220
cacgcatcac cccacttgtt tgttcttcac attcttttcc caagcatggc cgaaagaatc 14280
tcagaggtaa ggcgttgtca ttaagggtca tctggtcttt ttaaaaaaac ggccaataaa 14340
aatgtgctgc acaatcaaga taggaaacgt ctaggcagca ggacacttct ggactccttg 14400
agatagattt gaattgcgga aaggaatggt accagcagga ggaaagactg ggaccacgga 14460
caatagggca aggttcaaaa gtgttttgaa aagttcttag tgacattaca atttacagaa 14520
cgcgacttgg tgattcaaga agcaatgtta ggatgaggtt gctattaaat gcttctctga 14580
gctaccttta tttgctatac ttgtaccaag tggtctttct ctttgctata ttttatctga 14640
tttattcata cactcccttt ggtcctttag acatctttgt ctccttaaaa cctctgaaag 14700
tggattacca agcacacgca ttacaaagag ccacgccctt tcgggcttca gtctccagca 14760
ctgcaggcac agtgtcccag gtaaacaatg caggctgtcc ctctctctga gctccacagc 14820
cccaaggaac tggatggctg tgaaggctac acacttcaaa cctggcgtgt gctttgttgt 14880
ctagtattct gccatccgtc cttttacaac gacactgatt tcttgggaga agagctggac 14940
atcgtcgatg tgaaaggcca agaaacctgt cagaaaacgt gtaccaataa cgcccgctgc 15000
cagttcttta cctactatcc atcgcacaga ctgtgcaatg agaggaagta aggcacaagt 15060
taggtggatg ctcttggagc atctccttgt aggatgagtt ttgcttacag agttttgttt 15120
tcagccgcag gggcagatgt tacctaaagc tttcctccaa tggatctcca acgagaatac 15180
ttcatgggag gggaggcatc tctggatact cactgaggct gtgcaaaatg gataatggtg 15240
aatacttgaa aaaatacaac tgaaggggaa tagtcaacct aacgttgcta gtctactaca 15300
cgaggctagt ctacaacaac catagagaga tggagacagc agcacaagga ggttgaggca 15360
ggagaatcag aaatttaata ccagattgga ttaaaaggca aaatcctgta taaaaaatga 15420
caacaaaata gacatggaag agagaacaaa gttaacaaat ttggaggttt tcccttacat 15480
atatgtatgt catatatata tatatactta tatatatatg tatatgtgta tgaatatgta 15540
tatgtatata tgtcatttca agtggcattt cctgtagaga cagacccaga gggccaattt 15600
ttgttttcaa gaagtgtttt ttttaattat cagagattaa actattaaac agtccattaa 15660
ataaattatt cattttcttc ccacttaata tttcagtgag ccatgattag atgctatgat 15720
atatgatatg atatatacac acacacatat atataatatc tctcatatat atatatatat 15780
atatatatat atatatatat atatatatat acatacacat acatacacac atgcatatat 15840
ataattccag atgttaagct atcctgtaaa ttgtgatgag atttcatcaa taaagtgtga 15900
ccctaattac tcctcgtgaa agtttcaaaa gtataaaacc tttttcatca gatcatttgc 15960
tattctagaa ggtgactcta tccttagttt cagaggacct gatttacagc acattgagat 16020
gttttatccc aacaactgca gtgccctaaa cagaaaacat gccttcctag aattcactgg 16080
tttgatagca atctctgggt ggcctgagcc tcttaagaca gttaattaag ttatagttca 16140
tacacactgt gttttgctca tgataaactt acctaataag aaggaacatt caagacaagt 16200
attgtcttaa ttctacttct tcatggtaga aggggcaact agaaagacgg ctaagtcatg 16260
tgagcatgct ttaaaaactg ggatccagaa cagatagctt gatacactga agattacatt 16320
tctcacccac ttctgccttc attatgtttg tctctgttga atttatagcc tggtctgtac 16380
aggtgacaga atggatcagt tgtagattga cagaagagaa aatgtggagg gtaataaacc 16440
tgtctgcctt ctcatgcata gagaagtggt tacactgtac aatattgggc tacaatactt 16500
acctttatgc aagagagaag atcgaactca gttgtttttc gtatttactc tgttgttggt 16560
ctctaatgta acttgacttc ctaaagacac ctagcaatgg acaccactaa aagaagtatt 16620
tcttcatccc caatgcaaag ttgagcacta taagttttca gcattctgtt caagttgatg 16680
gagcagacat cgagatagaa ctttttctga aggcttgcat tgggcttact gataatgtgt 16740
cctacttact gcttgcctgt taactttcta aaggttacct ttctgctgat ggactgaaag 16800
gtttctgagg gatttctcag aagcctttca ggacgaggga cattgaagcc taggtaactg 16860
ctaaccacac tctctctgtt gtagtgtgca caactaaaat caaccccaga gtggtaggag 16920
gagctgcgtc tgttcacggt gagtggccat ggcaggtgac tctgcacatc agccagggac 16980
acctgtgtgg aggctccatc attggaaacc aatggatact gacagcagct cattgtttct 17040
ctgggtgagt attattgcta ttctcctggg attgccatca tgaaggtgaa atctgggact 17100
atcataagag tcaataaaca ctttgaaaat gtaaatgatc ctgtttccta aattaattct 17160
ctctgtgtgg gcagggacga tggtgtagaa gagaccagtc ctcatcattt ggccacaata 17220
gaacaggggc aggagcagag cagattgccc acctctgcct tttcattcaa acgcaaatta 17280
tttccattgt cttcctgatg gtgcctggtg gcgaagcaca gggccagagt gaagcttaca 17340
atcctcagct ctctgaatcc tggttaccct agtctctctt tctctgcctc cgaatgctta 17400
gagttcagca cacaccatca gaccagatcc ccgcacttag cattgctttt cgatattggc 17460
caaatgtgaa catcttagcc ggggaagtgt gtatctcgag gaaattcggt tgagtgaaac 17520
ctttctgtgc tacttttagt gcctctgttg cttccagaca caggtttaga ggctaatcgt 17580
tttgttaatt tttttccatg catggatgca ttatgcacat aattcaatgc tacacttgag 17640
atcaatagtc ccctttgcaa gcacatatga aaaaacacag aaagtcccag tgacttttct 17700
ttaaattctg cccaagacaa ggttgagact aatacccaac tctcctgagc ttggagatgt 17760
gctggggagt agaaagacca tttatttaaa gtgtccaata ttagtgcaag aactaatcca 17820
gtgatttcac tgtagaggaa atatgtgact aaaagttttg agaataaaat cacttttttt 17880
accacctaaa ggtagaaaca gacacagagt ataaataact gtgaaacaca aatatttgga 17940
aattgcctag tgatagattt ttttttccat tctgtttgtt ccttaggata gagacaccta 18000
aaaagctgcg tgtctacggt ggcattgtaa atcaatcaga aataaatgaa gggactgctt 18060
tcttcagggt tcaagaaatg ataattcatg atcagtatac gacagcagaa agtgggtatg 18120
atattgccct gttaaaactg gaatcagcca tgaattacac aggtatatat atagagagag 18180
agagttttag gtgacctaga taaaacattc acgttaggag actcacagtc tcatctatgg 18240
ggtctaatca acagacagac aaggaaggtc tgaaaagatg gcctcactct gttgagacag 18300
agagtttgcc ttagaatact agattagcga tccatactta tctccttgta ctaaggtcaa 18360
atctaagtgg atcaaggaac ttcacataaa accagagaca ctgaaactta tagaggagaa 18420
agtggggaaa agccttgaag atatgggcac aggggaaaaa ttcctgaaca gaacagcaat 18480

```
ggcttgtgct gtaagattga gaattgacaa atgggaccta atgaaactcc aaagtttctg  18540
caaggcaaaa gataccgtca ataagacaaa aagaccacca acagattggg aaaggatctt  18600
tacctatccc aaatcagata ggggactaat atccaacata tataaagaac tcaagaaggt  18660
ggacttcaga aaatcaaata accccattaa aaaatggggc tcagaactga acaaagaatt  18720
ctcacctgag gaataccgaa tggcagagaa gcacctgaaa aaatgttcaa catccttaat  18780
catcagggaa atgcaaatca aaacaaccct gagattccac ctcacaccag tcagaatggc  18840
taagatcaaa aattcaggtg acagcagatg ctgtcgtgga tgtggagaaa gaggaacact  18900
cctccattgt tggtgggatt gcaggcttgt acaaccactc tggaaatcag tctggcggtt  18960
cctcagaaaa ttggacatag tactaccgga ggatccagca atacctctcc tgggcatata  19020
tccagaagat gccccaactg gtaagaagga cacgtgctcc actatgttca tagcagcctt  19080
atttataata gccagaagct ggaaagaacc cagatgcccc tcaacagagg aatggataca  19140
gaaaatgtgg tacatctaca caatggagta ctactcagct attaaaaaga atgaatttat  19200
gaaattccta ggcaaatgga tggacctgga gggcatcatc ctgagtgagg taacacattc  19260
acaaaggaac tcacacaata tgtactcact gataagtgga tattagccca aaacctagga  19320
tacccaagat ataagataca acttgctaaa cacatgaaac tcaagaaaaa tgaagactga  19380
agtgtggaca ctatgcccct ccttagaagt gggaacaaaa cacccatgga aggagctaca  19440
gagacaaagt ttggagctga gacgaaagga tagaccatgt agagactgcc atatccaggg  19500
atccacccca taatcagcat ccaaacgctg acacctttgc atacactagc aagattttat  19560
cgaaaggacc cagatgtagc tgtctcttgt gagactatgt cggggcctag caaacacaga  19620
agtggatgct cacagtcagc taatggatgg atcacagggc tctcaatgga ggagctagag  19680
aaagtaccca aggagctaaa gggatctgca acccaatagg tggaacaaca ttatgaacta  19740
accagtaccc tggagctctt gactctagct gcatatgtat caaaagatag cctagtcggc  19800
catcactgga aagagaggcc cattggacat gcaaacttta tatgccccag ttcaggggaa  19860
cgccagggcc aaaaaggagg agagggtggg taggggagtg gggggtgggtg ggtatggggg  19920
acttttggta tagcattgga aatgtaaatg agctaaatac ctaataaaaa tggaaaaaaa  19980
attaaaaaaa aagaatacta gattagactt tgagagtgca gacggagaga cttgccttca  20040
ggcttcttca ggtacataga atgacatcgt tttataaaat accgaagcaa taagaataat  20100
gattgatatt ttgctttagt aacaaagggc ttgacagcac agttgagcaa atgctacaga  20160
atattaaacc acattaaaaa tgaaaggtgg tgtaaagagg gcctgtctta ccctttccct  20220
tgtcccttct gcttgggaca tttcatatgt gccactgaac acatgacatg aaacacatga  20280
gaaaaagata acgaatatca taaagaaaga gagcatgatt aatgtcaggt gagataacac  20340
ccctttctgg gacaaatgat tggctttctt tctgcttcgg tcagcttttc gctactgtga  20400
caaaatgcct gatgtaacca ccctgtaaga aagaaaggtg atatgggctc tcttgatgtc  20460
agaggcttca gcctgcagtt gtgtgtgtgt gtgtgggggg ggggggtcca ctgctttgta  20520
gcccttggta agaaatgtgc agaggagcaa attttcacct cctggatgct gggaagcatt  20580
aatgaaggga cggggctcct gatagcccct tcaaaggccc accctcaatg acgtcacttc  20640
cttcctacac cttccccccc aacacacaca cacacacaca cacacacaca cacacacaca  20700
cacattctcc attatctcta agtagtgtca caggctggga tggagtcttt gaacatgggc  20760
ctttggggag acacctcaga tccaaaccgt agtggcctct gatgactaaa ctgtgatttt  20820
caaaattaga ttttcagcgg ccaatatgcc tgccttccaa aggagataga aacgcagtgc  20880
```

acacagaatg ctgggtgact ggatgggggt acacagcact aagaggtaac aaaccatgcc 20940
ttctatctct gctttattct gaagtcaaag aacagagctt aaccattgcc tctgttttct 21000
atctagtcat atggcccaaa cgtgagtcaa gtcacctact caataacagg aagactgata 21060
acaaagatca atacatctga tcagaaacgt taaatatgat taaacccctc taaagaccat 21120
tttaactgga gacttttagt ttgggaccta acactctatg taaaagttct agcctggttt 21180
ctaattattt tgtctgaaaa gaaattctac ttagtgtcag ttaattttga acttaataac 21240
attaatgaaa ttatgtacac aatagtagaa acaatgtctt ctttatactc catacttaca 21300
aaaattactt atgaatcaag cttagtaata ccacccccccc ccaggatttg tatgtacaat 21360
tttggctttt aaatataatt gtatataaac ctatagtaat tattcctcta aaacactaat 21420
atgacccttt tcaggtgaag tacaaagtac tcttcagaaa gccaaggttc cattggtgtc 21480
aaatgaagaa tgtcagacaa gatacagaag acacaaaata accaataaga tgatctgtgc 21540
aggctacaaa gaaggaggga aggatacgtg caaggtaagg cagtctcaag caatcagtca 21600
tgccagattg aagtgagagc ttaatgcatt tgtacaaacc actgtaccat tgagcagtgt 21660
ccgagtgtgc ttcctgttgc tgtgataaaa cactgaccaa acacaactca gggaaggaaa 21720
gggtttatca agcttacagg ttacacagtc caccatagcg gaaagtcaag gtaggcagga 21780
actgcagtag agacggtgga ggagtgctac ttcctggctt ctgtttagtc ttgtgttccc 21840
tacttttctt ttgtgacaat gtggttaaca attagcagtg gagaaagttc cccacagtcc 21900
aggctgatgg cagaggtgcc tcagctgtgt tccctcttcc caggtgtgtg aggttgacaa 21960
ctcagattag ccatcgcaag cagatcactt ggtgggttta ttttaggtaa actaaactct 22020
acaggaggaa ggaaagctgg ataaaggaga acaattggat gtttggatgc ttgtgagagg 22080
gccagaatat tatgtaaaat tgctgtgagc aatacttact taactcagga aatgcctacc 22140
atgatcccgg catgtgtctt ctttttctcc ccctttgaca gggagattct ggagggcccc 22200
tgtcctgcaa atacaatggg gtctggcact tggtgggcat cacaagctgg ggtgaaggct 22260
gtggtcagaa ggagagaccg ggggtctaca cgaacgtggc caagtacgtg gactggattc 22320
tggagaaaac tcaaacagtc tgaaagagtt caactggtat cactttgtgg ccctggaaga 22380
ttattccata gaaatgagct tgacgtctct gatgaagaca ctgggatact gactcttcca 22440
ctgtaaccaa ttgaatggcc ttgatgtacg taagaacacc cagaaagaaa actattattt 22500
tcagaattcc tgatctggga gaaccactgg ttgttttctg catccagcta ctactcaagg 22560
aaacaaatac agcaaggaga ttttaaaaat aaaaacacat cagatatata aggaaaatat 22620
caagtaaggg tgctgtctgc ctttttagtc tctgtgacaa atacctaaag tagttcacaa 22680
aaggaaaaat ttcttttgca cacctttcct caggtttcag cctacgatct ggttggctgg 22740
ccccattgct ttagcctgag gtgaggcaga accatatatc cataggaggc tgtggagaag 22800
gagtctgctc agttcatggt aggcaggaag caaatggaaa caggaatgta ttggggacac 22860
gaatggtcct tcaagaatat actgtcaatc atttacttct tccagagaca tcctgctccc 22920
taacctccct ttccttccca gataacacct ctgtcctagc tggccccaag agatcaggta 22980
gaaaggcaga ggaaaccata taaagagttg ttaagtgcaa aatcaaaacc agaaggaatg 23040
cagacaggag ctcaaaatgt ccatttataa gaatcttttt ttttctctgc ctatatgaat 23100
ccccctcctg tataaaggac tgactcaatt cagtgatggg ttttgagaag tctgtttgtg 23160
tgtgtgtgtg tgtgtgtgcg cgcgcgcgtg tgtgtgtgtc tgtctgtctg tgcacattca 23220

```
tgtttaggta tgtgcaggta cctggtgggg gcgatcaacc ttgcattatt tctcatgtgc  23280

catctaccct agcttttcaa agacagagtg tcttactggg attggagact tgggctaagc  23340

tagctatcta gcaagtccag ggaccattct gtctctacct ccccaaactg aaattaagaa  23400

gacatgccat ggtgcttaat ttaaacctct ctctgtcttt gtctctgtct ctgtctctgt  23460

ctctgtctct gtctctgtct cgctctctct ccttcctcct tctctccctc ccactctctc  23520

tttgggtgtg cacgtgcgca tgtgcaagtc atagtgtgtg tgcagggcag tggaccatct  23580

tcaggagtca atgctctcct tccatcatgt aaggtccagg gatggacatt aggtgttcag  23640

atttggtgac aaatgtctgt accttcttag ccacgtcaca agccagctgt tccgatttcc  23700

tacagatgct gggaatcaaa tctgagtcct cggggttgcc tggcaagcat cattactgac  23760

tgagctctcc agtggccttg tcagtcttct ctctgcattt tcccaaactg gcttggacaa  23820

gcaccattgc aggtgttaag tgcacacttc ctaatttcca catgggccga gtataggagg  23880

agcaattttc caggaagtgg tcccttgaag acacaccgta ctgatttgct tgcctcggaa  23940

agtatctcag cgtagcctgc actctttttg cagtgttagg ggaaagtaca ggtggatgga  24000

gataaggaag acaagccaaa acctaccaag atctgccagt gagtgggagt ttacaaagct  24060

gagtaatgaa tgtgctggac ggaaatgtgt gttgaaatcg tacatactac gggggggggg  24120

gggggggtgg ataatttggg agcaaatgtg gtttcaatag aggctgcagc ctcctcaaac  24180

agttctctgt attctgagta cctgactttt gtcctcacat ggggcaataa tgtagtattt  24240

ggactttgtc cccgtacttt tcagtcagcg ttgataacta tacaagttgt ccaaatgaaa  24300

agtatttatt gtgcccaatt atgtcagagt gtcttgttga gcttggggaa ctgaagcgcc  24360

agccaataaa ttatgaaggt ttcataaggt tttctgttga tttagtacga accgaagaga  24420

ggagctgcac aaaatctata ctttcaaaca aagatgacca tgacacaaag ggttctaaga  24480

aatgacaacg aagaagagtt agcagaagct aagagagtgg catggaaagg aagtggcccc  24540

aagcaagaca aagcaaagac agcaaacaag caaaagccag agatcgatgt cactgaaatg  24600

gcacgagcag gctggattca aaatgcttct agagtaagac agaattgaca tcaaatgggg  24660

tcacaacttc acaacccatg aacaagcagc gccttttata acctatttat tacatttcac  24720

ataggaaatc ttttataacc tatttattac atttcacata ggaaattgag gaggcattgc  24780

tgtcttctct gagaagtatt taaggaatgt tttcgtctta attttttttc agaacaagtg  24840

caacatctta attctgaata tctagtacct agaaaatgct atgagctata aggaataaga  24900

aattacgctg agcagattca catctccaca ccaacaagct gcgaatctgt atactttctg  24960

gcacttttct cacttaatct tctctctcct ggagctagct c                      25001
```

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39

```
ctgtttgagt tttctc                                                     16
```

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: bases at these positions are RNA

<400> SEQUENCE: 40
ctgtutgagt tttctc 16

<210> SEQ ID NO 41
<211> LENGTH: 20
<212> TYPE: DNA
<213> ORGANISM: Artificial sequence
<220> FEATURE:
<223> OTHER INFORMATION: Primer

<400> SEQUENCE: 41
acatgacagg cgcgatctct 20

<210> SEQ ID NO 42
<211> LENGTH: 25
<212> TYPE: DNA
<213> ORGANISM: Artificial sequence
<220> FEATURE:
<223> OTHER INFORMATION: Primer

<400> SEQUENCE: 42
tctaggttca cgtacacatc tttgc 25

<210> SEQ ID NO 43
<211> LENGTH: 26
<212> TYPE: DNA
<213> ORGANISM: Artificial sequence
<220> FEATURE:
<223> OTHER INFORMATION: Probe

<400> SEQUENCE: 43
ttccttcaag caatgccctc agcaat 26

<210> SEQ ID NO 44
<211> LENGTH: 34001
<212> TYPE: DNA
<213> ORGANISM: Mus musculus

<400> SEQUENCE: 44
tgcagctaga gacacgagct ccgggggtac tggttagttc atattgttgt ttcacctata 60
gggttgcaga cccctttagt tctttgggta ttttctctag ctccccatgt ggattatctt 120
aagagggttt caatagtcac ataagaaagt ctctcatttt aggggtgaag accactttaa 180
aaaaattcaa atggcttgct gaaagccaca gacactagag aaataattat gtttagggta 240
aagtcggctt gtcctcttgt gaaactgtgt ccaacggaga caagctgagg aattatgggc 300
aatgataaca tgttaaatgt tgagctaaat gtattaaaaa gcgcaaaaaa acaggtgtgg 360
tgggggaaca gaggctagaa gtctccctga aaaaaatcaa gtcttatttc ctacttcccc 420
cgtgtttggt ctggggaaga acaatagtgt ttgcttaagc atctcattct gttttcaaaa 480
ccttgcatgg ttgacttggg aactgataga gaaaatgaag caaacaatac tctgtaatca 540
acattaacat caaagctagc tctctccact gtggtccctg acccaaccac gttaatctcc 600
cagggtcttg ttaaaactgt aggcttggga gagaagtggt tgtggtgagg ggtaccttgg 660
agtaattcta agtctcttgg ggttaagcct ggaagattgg tgctttatgt attaagagtc 720
ctggggatcc gaaagtagaa aaataatgat ttttgttagt gactcagtat ggttcttact 780

-continued

```
tcaacacctc ctcttaaggg aggaagtagt gtgtgcatgt agctggaatt ttaaataata    840
acagttcagg tgtgtgagta tttcattaga cagtcagctt ccatccttta tgcatccttt    900
aagcaggttg gtttagacag gtgcacaata aacgccaggc tattaaacac agggactcca    960
atatttaaac caattctttt gaattgtctg gctagaagca catccagtct gataaagtag   1020
acaaagcacg tggagtcttg aaaagttcga cacccccttcg gtcctcagat gactattatt   1080
tagcaattga gagcactata ctccttcttt tgcccacacc tataaggaga tggacatggc   1140
acgtacatcc cagcactttt gacagcttta aatggtgttt attacgagca ggtatggatg   1200
ctgggaacag tgcttatacc gagtcctgga aatgcttatt aaacccagga gatacaagga   1260
gtctgccatt aacctctctg taactcaaga gtagttatca ggagccaatg agggagaaca   1320
agagaattga aacacgtggg aatatcggac caccaggtag cgggtgtgtg tgtgggggga   1380
ggcagcccta gggagctctc aagccgaggc ccctcggggt ccccgcggca cgtggcgggc   1440
tcgggccgga gcgtcgcggc ggtgggggag gggagcggca tgagccctgg aggaggggtc   1500
tagactgccc gggattcgtt tgagcaggcg cggagtgcgc aggctcggcc caggcgcaac   1560
cagtgcgcgt aagaccgagg ggtgaacctc actgctgcgc gtccgggtct ctgagcaagg   1620
ggctaaagtc cgcttgtgcg cacctccgga ctgtgtgtga ctacccgtag aaacactact   1680
gtcgccctgg ccggtggcgt ccactccgtc ccggtcgctc cctcccgacc gtagttgtgg   1740
tgccccccctc cgcgcagccg cagtggtcgc tcccgcctcg cagccccgcc gcccggaggc   1800
ctacccctgc cgagtgtcgc gcgtcggcgc cgctgcctat cccgctctgt gccctacggc   1860
cctcccggca cccgccgccg tcccgctccg ggctgccctt gctccgaggg ctgcagcacc   1920
ggccgtcccc gtcagccctc ttgtctggcc gccgggccgc ggcgggcggg agcagccgga   1980
ggaggagccg cagccgggag gcggcggcct gagcccatgg cgtacagtca aggaggcggc   2040
aagaagaaag tgtgctacta ctatgatggt gagtggccga ggagcctgca gccgggatgc   2100
ggggagggcg cggcggggtg tcgggggtgg cagcccgcgg ggacaccaac acggcctacc   2160
cagcggtggc gtctcgggga cgcccgcctt cgctcctctc gggtcctctc gggcacacgc   2220
aggtttaggg tgcactgcct ctgaccggtc tcccgaggaa ccccagttgg caccctgggc   2280
ctgactgcac aaagctggcg tcctggagct ccgccccacg tccctgtccc ctccccccgct   2340
ctcccggtcc cccccttctcg cccccgatct gtccgcgctg cgcttccagc ctcacccggg   2400
accccggcac ccgggtgggg ctgcggagga gttactgctg gccggtggcc aagttcgcag   2460
agcggcgctg tctcgctggt gttttgcgtg gactacatcc ctcgcctttg ttcgcgttct   2520
tcgagctcca ctttctcagg gttcaaatgg aagggctgca cttcctcggt gacaattaag   2580
gggttttgag ttggaagtag gtaggtcgtt gggaagtggt aggagagagg aagcgtgcag   2640
ttgttcttgt ttgatgggtc ctggcatgtc tctatgggag gttattacct cccccttctt   2700
tgttgctctt tgttcgatct gctataatac cctgctctgg ggggttagga aagaacaccg   2760
gcatcttgct taggaactct tctactgtgg tgaagacctt gctgcaggaa actttgagaa   2820
gtggactaaa tattcacaat gcagtgaacg gtacaaggtg actgtaagga ttttctaatt   2880
tggagtataa gtagtaatag tctctgggtt cagttacacc aaatggaatg gtgccctgcc   2940
tatacagatt tcacccaaga catcaataga taaaccattg agagaagtaa taaggaaatt   3000
tgacagaact ttcgaagctc attgattgaa cgcttgatct ccacaaagca atatgaaatt   3060
gggagcgttt tctgtagttg tattgaagtc acagtgtttg gagaggtaga ttagagaact   3120
aggctgaatg aaacacttaa acttgttaaa atagtcgtgc attttcttgg tttgacagaa   3180
```

```
tcttttaata caagctttaa ataaaatagc cacctgtcat tggctggaaa accaaaaacc   3240
ttacagaaag ctaggccaaa atggaaaagg ctgttttgtt ttttgagaca ggctctaagt   3300
tgacctggct gtcctgaaac tcactgtgta aatgaggctc taactcatag agatccacct   3360
gcctctgcct cccagatcct gggattaaag atatgtgcca ccatggcctg gcttaattgg   3420
aagtttgaga ggactcaaac tgtattgcat gtttatttga agttacacca tcatggagag   3480
cagagatggg agagcatgtc ggtttaaaca tgagttacat tatgacgttg gggtcatagc   3540
aaagccctga cctgcattct ctgatccatt ggaaattaca gcctttctaa agtaaagtcc   3600
tgctcttgtt agagtcaggg gaaaggttga gctgttgggg aacagctcag tctcttcagc   3660
tgtcagcttc tgtcatcagt gatgaactct aagtcccatt aactttcacc aggcctgatg   3720
gagaaccaga gaggactctc tgtcttgaac agctccttcc tggcttcatg cgtagggatg   3780
agcctttgct gaggagtggg atagacattg gtcatggaga taaggtgtgg agggaggcat   3840
ttttcagtca tgtgattttc gacttatgcc catgcagctg ctttacctag ttgtgagtga   3900
ccaactgtat aattgatggt ggaaatctgc tgagttatct atctgtggtt cttacttgac   3960
ttgtttttag aatgtactta acttattttt attctgacta tttgcatttg ggggacgcta   4020
acaaaaattg aagatatata aattggtgtc atagttaagc taattaacat gtcatagcat   4080
gctagactac agagaattct ctgcagagaa ttcccttcac gtctgacttg attacagaaa   4140
ccctcttctt gttagtttat aaaggtagca gcaatcttta attgtcttta ttaaattcta   4200
aacaagagga gcaagtaaag tgacttttgt accaagaaag tgcatgactt tcagacgcat   4260
gcagggttgg gttggtggag aacccggcca gtaggattgg ggctcgaata gtatactagt   4320
cttatgttag tgcttttaac ttggttggta ggggaggaga tcaggaaagg aggaggttaa   4380
cggggcacta ggcacccaga gagcctcttg acaactcatg tgagtgtttt cctgctaaga   4440
ctgtgtgctt agtgaagaat acttctgaag attgaatatg gttttctccg tgtgtgctgc   4500
agtcttcaga attgtacttg tagggtctct gtgccactga tctgtgaact ttcagatagg   4560
agcgtatgaa ctatccctaa acctcacaag agaaatcaga gttgttctta gtggactgtg   4620
actactgact ggtcatcata actcccagaa acacatttca gaatgttggc taatctctta   4680
ctaaactaaa agacaaagat cggtaaatga tataaagcta attatgtgtc tacactgaga   4740
tcctttctga cctctttccc gtttttctca aagtgtaatt gagcagatgg ggctacattt   4800
agttctaatt gcaaggctca ggcttttaat actttatcta gaaatataaa ctttgcctgg   4860
tttagagtga agcttgggac caatcatgta gtgccttcta atgtatagtg tataacagaa   4920
ttgaatgtat gcataattta tgtaattaga caccaattgc tttatgcttt gtttattttc   4980
tctgatagag ataatcagaa tcaaaatgtt tggagacata gtccagagga aagcacgtgg   5040
caacaaaaat atagaatata acaattacta taattatatt tcccagtgta ctcctaagtt   5100
tcttaacaga tacaagagta ctacagagtg gccatcggtt gtcagattta ttttactttt   5160
atttaaaatg tgtgtgcttc ttgtgtatgc ctggtgccct tgatgtttag gagtggttgt   5220
gagctaccac gtagatgctg gaaaccaaat ttgggtcttc tggaagagca ataaatgctc   5280
ttaagctact ctccagcctg tccgttccca ctataacagt aggcaggagg atggttaggc   5340
ttctgccact tatagatgaa aacaggtgga cacttcatat tctccacatg ggtttctttt   5400
ccccacatag gtttctgttt taatgtctaa gaaagattcg tacctagaat acaaagattt   5460
tatttttctt ttgcagagtt ttgttcttct gtccctaaaa aaatgtatta ataattggtt   5520
```

```
tttttcttag caaaattaaa tgttagtaaa ttcttaaaac acatggagtt ggtgaacaaa   5580
aggaaaattt cttacattag caaaatgaaa tgtgaagtca ttaagtaacg gtttgggctt   5640
ttttaaggcc gccattgcta tggataatga caccgagatt tatttctgtt tagtaataaa   5700
tgcctaggcc ttaagctagg cctactccca actagctcat cactcaatta tctcatttat   5760
acttctcagt ttcctacaac caacttcctc cgagtccgaa tagggaatac cccacgccta   5820
attctgagtt cctctctctt ccagatgtcc caccttacta tcctgccttt tgctgtaagc   5880
cataggcttt ttattttaat ctgtcaggag gtgccttagg cagttgggga aggatagaga   5940
cacatcttca cacagtgtac cgaaacatca ccctaacacc attacattga agttctactc   6000
tcaccatgtt ggttagtcgg tctcactctg gtttcatggt ttatgcttgt acatgaagtc   6060
agtttggggt tcagaaacat aagattgttt taagtccctg ctttgtccca tatagacaaa   6120
gattacttaa gaaggaaatg ggtgtttgta acagagtaaa agaggaatgg agtaataaaa   6180
caagcatctc taggaagcat atgcgccagt cttaaaacag tcctccctgt gaaacaacaa   6240
aggccaagtc cttggaatgt gttgtaccca aaagaagggc aacccagaga tagggatgct   6300
gggctgagcc ccaaggggcc aggcacagca agcttggttg aaagagagtt tgactcttag   6360
agggagtgtc ttggagcttt taaagtggag gctagtcaat aagagaattg gtgagaagta   6420
gaatgtaggc tagaggaaag tgttaaagtg aaaggaaatg gttgtcttta gatagaatcg   6480
ggtacatttg agagtggttt ataaaccaag aaaaaaatac atcaaaacta cttgttggtg   6540
gcttggacga gggattaggg ctgggagttg tgatttctgg actggtcatg agatggacaa   6600
catactgtcc attgagatta tatggaatca agggctctat attggctatt atgtatttga   6660
gatcttgatt tagatcaaat gaaaatactt ccaaaaatta cctggaaccc agggagaagt   6720
agtatttctt agctggtaag tgataaatac tgacgtgttt gttgaaggta atggtatgga   6780
gagacacaga ctccggaaat tgttcctgag aagtcatagg atgaagtcac tcttggtgta   6840
ctgcttggcc agtgacaagc tcttgactta tgaggaaagt gaagaaaagc tgagatttaa   6900
aaggtttgga ggaagtgagc ttagagaagg aacacaatgg aggacagaat tgtggagatc   6960
cagactccac agtgtttcaa ggaggaggga gggtctaaca gtgttaaaac cttcacagaa   7020
ctaatgttgt gtggcagaca gaaattgcac agtagtcttt ttattcttga ttttttcccc   7080
tccctcgagc ccccccacac acactacttt tggcagcttc tctatgtaca gtgtgaaagt   7140
acatttcaca gtcctgaaat ttacaatgat ctgaaatttt gttcactcag aatcaaaagc   7200
ttatcctgaa attaacgaaa ttacaattta ttgtctttat tccactaact gtgataatta   7260
cacatttttg ctttagaaat acctttgatt atagaatgtt gtcccagttt tagtacatta   7320
tatattttta tcttgagtca aacttttctg gatattctta attggtaaaa ctatatttaa   7380
gtatttgaac aaaaaatggg atcacatttt aaatgcccaa attatgtaac tgacagagac   7440
tataggtaca tgaaattaag aaattatgta actgacagag actataggta catgaaatta   7500
agaaattatg taactgacag agactatagg tacatgaaat taagaaatta tgtaactggc   7560
agagactata ggtacatgaa attaagaaat tatgtaactg acagagacta taggtacatg   7620
aaattaagaa aagaagagca gtgtgaggtt tgatcttgct gtgcattgca atactaagtg   7680
caggccccaa gatctggagt ctgcacacag acctgagtaa cagtatgtgg ccttgccttc   7740
aagttatttc tgactggtaa ataaagatgc ctacagccaa tagctgagca gaagagttgt   7800
atgtggggct taggattcct attgtaaata taaaggttgt gtgtatcttt tatctggaaa   7860
ctaaatggtc aaagccaggg tagaaacgcc aggttgggat taagcgtttt aacaacaggg   7920
```

-continued

```
ctggatggct tagcagttta aaaccctggc tgctctttca gaggacctgg gttggattcc   7980
cagcactcac agggttgttc acaggggtca ttcactacag ccacagggga tctgatgctg   8040
tctcctgccc tccatggcca ccagacacag tcatatgtat ggcaaaatca ccatgcacat   8100
taaataaaat ttaaaaagaa tcagttcaga aaacattttc ttaaaaaaga aaaaggcaga   8160
aggtttttta gtaagaaata gatgacttca aagtcgccat gtataaaact aatagtgaac   8220
aggaaacatt agaaatgaag attcttccct ctcctcctcc cagaatcacc taccctctgc   8280
tgctagagtg ctggtttaaa ggtgccttgc ccacaaaaat ggttcttgtt tgtttttgaa   8340
attataatat gatcacacca ttttcttcct tcctttactc cctccaaccc ctcctgtgta   8400
gccttccacc tgctctcttt caaatccata cccttggatt tctttaactg ttgatacata   8460
taaatactcc taaatacata aatacagtgt tactatatgt ttttagagct ggctatttgt   8520
tattggataa ccaatgggtt ggtcattacc tggaggagat tctttgtcct atccttagtc   8580
cttagttgtc tgtagttctt tgtctaggct tgaggcctcc tgaccttcac taacgtgtct   8640
gttaatgacc ttgttcaggt catgtttagc cagtcatgtt ggtgagactt tgtggatgtt   8700
gcttctgaca tgtctcactg acaggcttac agtaaactcc ttgttcttca agctctttaa   8760
accctctctc tcttccccaa tgccctctga ccctaaggtg taggggttgt attgtagatg   8820
tgtcacttgg tactgggctc caaaactctg catttcaatt gtgcttttct gtaatggtct   8880
ctgctacaag gagaactttt cctttatagg ggtgaggact acaggctcct gtgtttacaa   8940
ggacaattat gtagaatgta gatcgggatg ctgctgcttt tgtaaagtag caattgcata   9000
ttttattcaa agatggatga cttcagtagt cttgagttgg ctaggtctcc aatactaggc   9060
atgatttccc tcttgctgaa tggatctgaa atccaattag aaagctgttg gttactgtaa   9120
aggtctgcgt gccaccactc cacatttatg ctgccatggt ggttgttact gtggttcaga   9180
ggtgtcataa ctgcgtagga ctattggttg cttccctcct ctggagcctt gcatgactcc   9240
tttttataat atgaagggta gtcctcaaga aggattaggc tctcagttct gtccagctca   9300
ggggcttctt gggccctgca tctcaagtgc atgatgtctt cagcaatatg cagttacctc   9360
tagggggcaa ccaagggcaa tagcgtataa gattttggga gtctcttgga tagtcctgac   9420
cagcaactcc aaagacggct gcgtagtttt ttgtttgttt gtttgtttgt tttgttttgt   9480
tttgtttttg tggataatgg ctcctggagg gagcctgtgt ctatttatac acagtcttat   9540
gtgtattata ggtacagtag ggcaatggca tgattgtgct tgatccttga gacatcctca   9600
ctgttcctct accgtcctca ttccttgtcc tgtatttgtc ttcctcccta gttagaagcc   9660
ccactccatt cccccttacat ttcctttcct tccccttcct tctcccccctt tgcgttcccg   9720
tcgctcccct tttgtgcaga ggaattaaac caaaagcttg tacatgctag agaaatgttc   9780
caccactgta tatctcaagc ctttggaggg attcggaaaa attcatatta tggctcagct   9840
gccctcgtga atatgtgtct tttaggctaa atgaatattc ttactgagaa taaggcctca   9900
aaattatgac agaagtttgt cgaaagctgt atatattaat ataacgttag gagtctcata   9960
gttagaaggt aactcccttc ataaattagg taagccatcc attttgttca tattcgtcaa  10020
atgaacaaat tcgatgctga gcacaagcat gtatactgta ttctttcctc attcgccatt  10080
gtcctgctat tacattgctg tgccagtgac aatacaaaag aatattcact gcctgtgctc  10140
tcttcttcct aaatctgaat gtagctccta tctgctagtt gtataatttt ggctacatta  10200
tttaacatgc ttctcggcag ttataaagtt gtggtacatc ctagagttga gaaataaaag  10260
```

-continued

```
ctgatgctga gtactaggaa aatgttcttg ctgttacttc tcaaacacta caacttaaag  10320
ttggctgcat agggagaaca tctggaagga ttaggggagg ggaaaatagg acaaaaatat  10380
atttaaattt aaagttaaat aataatataa taaagaaagt ttctacttag gtcaacaaga  10440
tgtattgttt tctggttctg aagttttcat ttacctttga aaaactagtt agcattctga  10500
gtgctcctaa atttgtaaat cattttgtga aaaaattgaa ctaaataaat cagaggtact  10560
ataccaacag attcatactg tttgaaggca ggttttgtaa acctgaatgt tcagctgggt  10620
ctggtggcaa aagccagtgg tctctcagtg gaatcatgaa ttcaatgcct gcctgggaca  10680
catagctaga attttgtctc aagggggaac aaaagcaaat gttttctgga ttattgtcaa  10740
gtagatagat agtatgaaaa tttctggatt tttgattgcc cctatataag tgaaaaggta  10800
ctatgagagg agagtttgaa atggggatgt ttgtgtttga gagctggtct tgctgtgttg  10860
tctggccagc ctggagtcct gtttgcaggt agataaggct tgccttgatc ttacagagac  10920
tcctgcttct gtttccctca gtgttagatt aaaggtgtgc actaccatac cctgcttaag  10980
ctttgtcctt ataagggcag atatatgaag tgtgggggct gtcttttgtt gtataaacct  11040
gtgctgaaac agtaagatct gcaggctgtt aaagtcaggt caactgtcct aacaaattat  11100
gaatatttga ttttaaacta taacattaat agtaatttct catttcttgc ttgataaggc  11160
cattgtaaaa ttattcctta tagggcagga gaaattactc agcagttaaa agcattggca  11220
gctcctacta aggacccagg gttgtgttcc tagcatatag ccatctgtaa ctccatttcc  11280
aggggatctg acacatcgtg accaccacag gcaccaggtg tcaatgcagg ctgcctatgt  11340
atatataggc aagctcgcag gcacataaaa gtagatagtg tccctcacct tagaaaaagt  11400
aatacataag ttttctaagc ttgttgacaa gctttcttat tgtctaaaag tattttgtgg  11460
ttgaaaatca gattttggca ttattctgtg tgttgtttta agacattggc atctgtctta  11520
cttagtttgg gttttactgc tgtgaacaga caccatgacc taggcaactc ttacaaatgc  11580
aaacatttat ttggggctag cttagtttca gaggtttagc tcattatcat ggtgggaagc  11640
atggcagcat gcaggtagac atagtgctgg aagagggttc tacatcctta ttcaaaggca  11700
gcagcaggag actccttcac aggcagccag gaggagggcc ttttccatac caggtagagc  11760
ctgagcatag gaggcctcaa aacccacctc catagtgaca cactttctct aacaaggccc  11820
cacctcctaa taatgccact tcccatgggc caagcatatt caaaccacca cagcatctaa  11880
gatgttttaa tgcacaggct actactgtgt agtcctgaga aatgaagaca agagtgtctt  11940
tattaccctg aaaaatgctg tgactctccc acttgtggac actgaacatt taagcccttc  12000
cataattcca gctcgactgt aaggtatttc tacaggattc caataagtta tccaagaagc  12060
actactagct gacaaattag atcctactcc gtacttcaag aatacttctt atgtatctaa  12120
atttacaaaa tgaacaacaa caacaacaaa aatccactaa aaatggattt caccttaagg  12180
aaccaaacca gggaaattgg aaaactaaaa gtcagaaaaa ctttctctct ccacaaagaa  12240
tgtgaatcct aggcatgtat aaaatctgca taatatatta gatttctaat gtaatttgaa  12300
tgttacaaaa acaactcttg tttaaatata aatttttttga tgttgggtac atgtcagtgg  12360
tggtatttaa taagcatctt ttctctttta ggtgatattg gcaattatta ttatggccag  12420
ggtcatccca tgaagcctca tagaatccgg atgactcata acttgctgct aaattatggt  12480
ttataccgaa aaatggaaat atatgtaagt actagttggc actgtgtttt taaactggta  12540
tttgaaagct cttcttaggc tgctgtggga gatgcatgtg gtagatgaaa agatctgaac  12600
gaacacagac aggtcttgtg gttgtgtccc tcagagaacg cttaaggaat tggagtagtc  12660
```

```
ctctcttccc tctgatcatt tcaaacacca aatatttttg tgacaatact gttaagttgc  12720
ctgtgctgct agaaacaatt gtcctggggt tggtgagatg acttaatagg tagaggtgct  12780
tgccaccaac tggatggcct gtttaccttc cccagaactc tcacagtaga aggagagacc  12840
taattccccc aaattgtttt ctaattccac gtgggcatga ggacacacct ccaataataa  12900
gtaaccacag tgtaatttta aaaagaaata aaagagaatt gacctgaatt attgcaagag  12960
tttggtagaa aattaatcat aaatatttat ttggttaaca tacatatgaa atgttgccaa  13020
tgataacaag gtaagtaaaa aatggtgtaa gatacacagc cacctaaaaa gtcttcgaaa  13080
catgggcagg agcatacata aaaagtgcaa ggtaggataa ggcttaacta actactccag  13140
gagaagaggg ctagacagtg ttataggaag catttcttta agatacaggt attttagaga  13200
aatgggaaga cttgtggaag aagtctgtgg taagtgaagc tgagctcttc agagcagaag  13260
ttagaataaa cgaaggctaa gggagatctc aagctggtgt tcttagaaac ctttgatgaa  13320
agtcagtggg tagacagcag cgaggctatg ctgggaaaga gcctgaacaa acaggagtag  13380
cctcgcttgg agaggggctg ccggctgcct gctgcctgcc acaaatgtgt gcatttgaat  13440
tagcattgta acttgctact caggtggatc tggttcattt agagagactg atcgtggaaa  13500
cttacacata tcatttgata attctcattt aacaactgat acttccaaca tcctggtgtt  13560
tttcttttca gaggcctcat aaagccactg ctgaagaaat gactaaatac cacagcgatg  13620
agtatatcaa gtttctacga tcaataagac cagataatat gtctgagtac agtaagcaga  13680
tgcagagatg tacgttataa ataattattt tactagtgct gaatgtaaat gaatcttttt  13740
aaagtttctg atcagagttg cctcaatagg tatttttcct cataatttaa aatattaata  13800
taattattaa ttcagaaggt cattgaacca atattaatgt tactttagaa aacaaaccta  13860
tttaaatttg ttcttttact ttttattttg cacccatgaa aagtttggga ttggtaggga  13920
gatcacagag ttacaagaga aaaatatatt tctttctttt tttttttttt taataatttt  13980
tttgagacag ggtctgactt tgtaaccagc tgtcctggag attgctaatg cagatcaggc  14040
tggcctcaaa ctcccagagt tccacctgct tctctcttgc attaacaatc ctccatttca  14100
ccttctgtgt actccagtca cattgttctg taatgtaaag atgttgcctt ttgttggctt  14160
ctttgtgttt ctttttattc ttctacatgt ttttgattat aggtgaaagt gtattgttat  14220
tggtagtcaa ttgtattaac tggtagtcaa gtgtattaaa gaaatattgc caagtatcct  14280
gaaactgtgg gctgctgtct tttgaagctt aataccggag cccatttcct cagtgagagg  14340
tggatttagt tcagtgatga cgaatgataa ggatttctca agttcactga acaccatatt  14400
tccctaccgt atgttatcgc atttggttga ctcaagactg gaataggacg gacggatgct  14460
attacatcta ttgtttttg ggtttttat ttgggattta cacagtaatg ggtagccagc  14520
ccttgggtaa atgacaggat ttgtttaaac cattatagtg cttgtttata ttaaattcta  14580
tttgagcata aaaaactaaa actttttta tagtatctgt aggtctgtaa aacccctgcc  14640
ctcttgctaa cgtgtgatct gagaagtgaa gaatgactag ggatgggcca cacacacttc  14700
tgttgtgttt tttcctctca gcacagggag ccaaccatgt catgaccaag tgacatgtca  14760
tctgtcttat gttccatgaa actgattcat tcatggctgc ttctgaagtc agtgttagcc  14820
acagaaaaaa aacaaagtaa cttaatattt tgatactcac taaaacatgt ttcggagtca  14880
gggacactgt gtgtgagggt cagtaagatg agttagaaag gggttgcagc cacttaatct  14940
ttaactcact atcatattta aagagaaaac tagatttgtg cctattttca tataggcttt  15000
```

-continued

```
tgatttatgt tgttggtgat ggtggtggtt gggtagagtg acttcacaaa tttcctaata  15060
agatttggta atggaattac atagataaca atttaattat cttgtaaaat aagcattata  15120
ttataaaatt ataactttta taatactacc tacattgaag tactactccc tgtgaatttt  15180
aaaattcata ggtaatattt taaaattaca aatttcacat tgctaccatg aaatattata  15240
ttattaccta tgattgcctg aaacaaatat ttttaatagt ttataagaaa aagccttcaa  15300
tgacttgata atagattgac tttaatgaag ttcaccttcc acagttaacg tcggagaaga  15360
ttgtccggtg tttgatggac tctttgagtt ttgtcagctc tccacgggtg gttcagttgg  15420
tgagtatcct aaatcagtca gcctcaagag gatctgaagg ggttagagtg tctgtaggtt  15480
ttgtctaaag cggaagttgt aatggtagta aggttgtgtt ggcttgattt tgctgtatca  15540
cccaggtggg cctccgtctc agccacctct gtggctacct cccaaatgct tgcttacaga  15600
catgtgctat cattccaact taatgagtac ccaagctgtc ttgtagttca ctgtggggcc  15660
cgggctgacc ttgatattgt ggaaatcctc ccctggagcc tctcaatcat tgggattaga  15720
ggcttggaat attatgatat tgctattcac tcttctgtta atgtaacaaa acctgcggta  15780
acttttaaaa gaatggttta tcttggttca cagtttggga gcttaactgg ccctgtcctt  15840
ggggactgtg atagcacatt atggtatgtg catttgggag aaggccagtt tacctcatgg  15900
ccgctgaatg gagaaaagag gattccagta tccctttcaa gcaagatcag atctccagta  15960
aactaaaatc agatcttggc tcttagagag tccaccccct tccagtggta ccatactggt  16020
gactaaatgt tccctggggt tcttagaagg catttcaggt tcaaagtagc aagtataatt  16080
gtctttaaaa tgccagtgtt taacagtttt tacttgaaca cagtctttaa gcttgtgtct  16140
ttttactcag agaccttttt ctcctcttct ttcttccgcc atttttacta agactttgca  16200
tgtgcactgt gatttagttg ggtaaactgt aggaaaatgg ttatctgagg aaagcttagg  16260
ctccgaagtt ataatccttt gcttttgaat gccaaacctt ttgtgcttac acatggcata  16320
tttaataggg cttcgcttat atgtattttg tgtaacctga ttttttaaaa ttctgagtat  16380
tttataaata acatagcatg tatctccttc ttagctgggg ctgtgaaatt aaaccggcaa  16440
caaactgata tggctgtcaa ttgggctgga ggactacatc atgccaagaa gtcagaagca  16500
tcagggttct gctatgttaa tgatattgtg cttgccatcc tcgaattact taagtaagtt  16560
aattcaaact gaattttccc tgtgatcaga tctcttaatt gaaagaaaaa aatgatttta  16620
aagactatca aataaatggt aatagattaa tgctgagtct tccagggttt gttgtgagcc  16680
cctgcagaag tgtgagaaat agaccactac agtgggagag cgagagggca gacagtgccg  16740
tgcctgagac tgccggtaaa tggtctctgc tcatttaggt ttgcagtcgt ctaagctgat  16800
taaaaatggc tgctagagat ccggaaatgt gaatgctaaa gtaacttgaa gtcaagcctt  16860
tgcaacttgt gttataagaa gtttgtctgg ccacttagta gcgtggctga ccccagttct  16920
ctcatccatc ctctacacag acacacagaa cacatagata atagacacac agtgatgccc  16980
aactgctgaa ggggttttgg aagttatcct tcactgcttt ttcagaagtg tgaaggtcct  17040
taggagtgtg gacacttgtg aaactagctt attttccact gttagctata atgctgcagt  17100
gagttgtatt tcagctttga ctgcagctgt gttctgtggg ctttgagagt gatgctcttg  17160
ccccgcatgt acatcccaag agttaacttc ctgaccttaa ataaacagca gctaagtgct  17220
gtcagtgtaa catatctgac tcccccaacc gacagaaacc ggaaatctcc ttcattgact  17280
tgaagcttct tccactggct tcagttctag agatctgctg ctttttcctt catagcttag  17340
tcttgagtaa gcccagttct gtacagttct tcacctggta aatctgaaca tgatttgatt  17400
```

```
ggtttggtaa gcagctctct ttgctcatct aaacacattg ggcatttgat catgtttgat  17460
tttgaacttt atgaagaagt tctgctatga tgaagcccgc tcgctgtttg cactatttta  17520
gattttctta gtgttgcttt tctgtgcctt gagaacataa atgcctgggt ttgatcatgc  17580
cagcttacgt tgtatgagca cagttacagc atctttaaat aataaacaaa atgttttaag  17640
tcagccacag tgacaagata atcatttact accttaaatg gtgaatttaa atttcatttt  17700
gtatgtattg gtgttttgcc tgcgtgtgtg tctatgcacc acatgtgtgc agtgcccatg  17760
gaggacagaa gaggccggta gatccccagg aactgctgta agagatggtt gtgagtcacc  17820
atgtgggtgc tggggattta acctggattc tctagaaggc agccagtgct cctaactact  17880
agtccaactt tccaacacca gtagcttttt ttaaatacag tttttttcta tttgcacttt  17940
gacataggga tggaactgat gtcattctat ggtggagtga ctacagaagc tcatttgagt  18000
agttgctgtg actggtggtg tacagagcat cagggaatga tgaaggcact tgtgatctgt  18060
cacagtcatg aggtcttagt atgctgtaga tgatgtgtaa aatgtgctca tctcgctgta  18120
aaaggtgttt atggatatgg acattggact gtctcagaac tgtcatgtta taaaatactc  18180
tgagttttgt tttattcttg gaccattgga aaccggggag tggggtggca caccggcatg  18240
ccagaggcag gtaggtttga gatgagcctg gatgagcagc tatcaaaata accacaggga  18300
aaaggaaaca acctatagtt ctgctcactc caaagctgtt gaaagaataa aaataataac  18360
agcactatgt tggttacagt tgcccataga ttattttata atgctgaaat ttttttaatt  18420
gatttatttt cactttatgt catttgtgtt ttgtttacac atgtgtctgt gtatgtgttg  18480
gattacctgg aactggagtt acaggtaact gtgagcctgc tgtgtgggtg ctggggactg  18540
aacctgcggc ctctggaaga gcagccagta ctgccaactg ttgagccatc tccagccctc  18600
cctccctccc tccatgttga gttgtgttgt ttgtttgttt gagatagggt tcctctgtgt  18660
agccatgggt ctcctagaat ttctctgtta gaccaggctg acctcagact caagagaccc  18720
acctgcctgt acctcctgat ggctgtgatg aaaggtgtat gtcactaagc ccaacaattc  18780
tgaaattgtg taatgtagcc cttggcatac cctttaggtg tgagtacata gataatgtct  18840
gcccgttttt aaagtgtaaa gacaagggta gacctcagag tacagtactc gattgtcttg  18900
gtagcccgag gagacgtgac gtgctggggt ctggatgctg agactgcggg ggaagaaggg  18960
tgagcattcg ctgtaagatg aaggacctgc ttccacattc cggcttgcgc tttcctttca  19020
ggtatcatca gagagtctta tatattgaca tagacatcca ccatggtgat ggtgttgagg  19080
aagcttttta tacaacagat cgcgtgatga ccgtctcatt ccataaatat ggggaatact  19140
ttcctggaac aggagacttg agggtaagac tgagttctgt cagaataaat ataagaagag  19200
cataggaggt tgctaatttc tggaagagcc atgttgtctt agtcattttg tttgtgtatt  19260
tgtgatggga cctcggcatc tggtgtgtat ggtttttttt gtttgtttcc ggagatgtgg  19320
cctcacctta gttgagcagt tgttgggatc attgcttact gttaggattt gtcacatgtg  19380
gacccactga atgctgcttg ttgttcagct gtgattactt tgaatatgta gaaacgaggg  19440
atcagaagtg gtctcaactc agttaggtgt aagtgctgat cctaaaaagt ttgctgtcct  19500
ctccaggttg cataggttgt cttgggtagc aggggtgggg tcacaatggg aatggacagt  19560
gttctatagg tgtggggtac agattatcac actgtcttgt ggtaggttgg gagaggtcag  19620
gcagtgtctt tatctgagat cacaggcata gagtcccagg gtgtcttatt aggtggtgtt  19680
gaagactgat tttgggctcc ctacctgggg ttgtgttctc aggactccat gttgccccag  19740
```

-continued

```
agtggcgcag tggatgtaga agctctgagg atccctccct acctatgggt ctgggtcaca  19800
gggctcctca ctttgagaat ggtggataag tgggctctac ttttacatct tgtaaaattg  19860
tttcatgcct caaactgagg tttgtaagaa ctttttagtt tattttgtgt ggtggggagg  19920
agcacatgtg tgccctgtta catgtgcagg agtcctcctg ccatgggtgg atcctgggga  19980
tcaaaccgtg gggatctcac ttgttgggct ttatctaccc aggtatttcg ccagcccaaa  20040
ctacagtgct tgtgtgttat ctaaaaactg ccttagagct taaaacgtac ttctacaacc  20100
tagaataccc aagacacaat ttacaaaact catgaaactc aagaagaagg aagaccaaag  20160
tgtggacact ttgttccttc ttagaagggg gaataaaata cccacggaaa gagtttcaga  20220
gacaaaattc agagcaaaga ctgaaggcat ggccatccag agactgcccc acctggggat  20280
ccattccata aacaaccacc atacccagac attattacat ataccaacaa gattttgctg  20340
acaggaccct gatatagctg tctcctgtga ggctatgcca gtccctggca aatacagaag  20400
tggatgctca cagtcatcta taggatggaa cacagggccc ccaatggagg agctagagaa  20460
agcacccaag gagctgaagg ggtctgcaac tctataggag gaacaacaat atgaactaac  20520
cagtaccccc agagctcgtg tctctagctg catatgtagc agaagaaggc ctagtcggcc  20580
atcactggga ggagaggccc ttggtcttgg gaagattata tgccccagta caggggaatg  20640
ccagtgacag gaagcaggaa atgggagtgg gtgggtaggg aagcagaggg aggggggagg  20700
atataaggaa tttttggaga ggaaactagg aaaggggata gcatttgaaa tgtaaatgaa  20760
gaaaacattt aatttttttca gaattgtgtg ttacttggtc ttttaatcat tttaaaatat  20820
gtcagacttt ttgttatgaa atagtcttct aagatctact tttgtgtttt aggatattgg  20880
tgctggaaag ggaaaatact atgctgtcaa ttttcccatg agagatggta tagatgatga  20940
atcatatgga caaattttta agcctgtaag tactgctttc agaaataaaa tgggagttgt  21000
aaatatcctt agatactaat gtgtcttatt ctgtggctag atcatctcaa aagtgatgga  21060
gatgtaccag cctagcgcgg tggtgctgca gtgtggcgca gactccctgt ctggggacag  21120
gcttggttgt ttcaatctaa ctgtcaaagg taagcagttc acgttccccc tggtgtggtg  21180
tttctcctcc ccaagaactt cccataaaag ttttcattgc tgagggctgg agagatggtt  21240
aagaacacat gttccttttg tagaagactt gggttggatc ccagctccta catgttggct  21300
caaaatctag cactctcttc tgatttgcat gcatgtggta cgcaccatac atgtttaaaa  21360
acatattttt aatttctcat tgttaccttt tgcttgccaa ctcgatgcca aactctatat  21420
ttgaattttt agtggatttt tatttgttgt tgttgtttgt ttttgttatg tggctgacta  21480
gttaatttag ttccccaagt cttacatgtt atcatattta tgtttatgta tttatccatg  21540
agtagtttgt tgccatgtca gcgccagcag tttttaatca gttttttcag aagacctgta  21600
ccttgttgtc tgattcagtt gctgttacag agtatgagga tttagcttgg cgcactttat  21660
tctatcatgg ttactctctt ccttacccaa ccctaagaac ttcggtcgct gtggctagtg  21720
ctcagcagca gtggttttta gcttagcagt cttctctact ggcaagactc actttttttt  21780
cttctggatt tttttgtttg cttagtttcc atattcctta ttactaaact atgaatttct  21840
aatgtattct gctcagctat ctcaggtgct ctgtcactga gctcctcctg ttcggactta  21900
gtgtcctcat gggtttaatg ggacagagag ctctctgctt ctgctttatt atgtctcctg  21960
atcagtgggc actgtatcta acttgctggt ggaacacata agtgtcttca tgaggaaaga  22020
agcccaagtg taaatgtgta aggtggtgtt gaaattctca agtccttacg aagagccgaa  22080
gtccacatgc tgaatacaag tctcatattg ctgttatggg atgaacttcg agggtttcag  22140
```

aatgaagcaa agttgcatgt ggcagcgcat gcttttagac tcagcattag aacagcagag 22200
atgggtccag gccagctaag gctttatata tagtaaaacc ttgtctcata aagaaaaaga 22260
taaataaaat aaatcttttt aataaagtta atgtttggat tagaaatgac ttagcatgca 22320
cattgcatgt tttactttag actttctgtg tgaactttga ggtagtaagt aacatcttgc 22380
tttgagttct cttacagaac ttttaagata attaaatata gatgttaaga acttctcatg 22440
attgtactct gcagaccagc ctcagcactg tggcatgctc tggtactctc cttcgtatct 22500
agttgggtca tacaaaatta gttggccact ctcctggagg tcagcattca gttaacagca 22560
ctttcatgtg ggccatagaa tgttcataga tatctcgtgt ttccgagcag ataagactta 22620
accggaagtc atcagccacc aggtagttcc tttcttttta ggagctatat actgttagtg 22680
ttctcttttg taactgaaag tttataatgc ttgtatttaa aagtagtagc tttcattata 22740
aactgcattt gactctttat agtacatctg cattgtgttt caacaggtag aagttcattt 22800
gtgaatttgc aattccattt tcagacttag aatacactgc tgcgactggc ttcaactaca 22860
ttgtctcagg cctagtgaag ccaagcagcc agctgctgtc caccttgcct ccttaattat 22920
ttcttcttgt ggtgttcttt tccgtgcttc ctcttacggg ttatagcctt cattgtataa 22980
aacccctttg tagtaatttt tcctgctgtt gggtggtaga atgctggtct tgtctgggct 23040
ctttcattgt actctgaagt taacttctgt ccttaaaaat gtccaagaga cactgttgta 23100
gtagaagatg cctggttgat aatgtacatg aagaaaacag agaaggcact ataaactctc 23160
actaggtaat gaggattttt ttttcttttg tggcatttc tttttttcca aatattttaa 23220
gctttgttat agaaaagtta caaaaacaaa caacaaaaat aaaatcacac actgaaatta 23280
accagaccca aagattcaat gacttttgtg cttagagcag ccagcgtctc aataccaggt 23340
gaaagcccac tgcaaaagga aatgactttg tttttaaaa aaaaaaaaaa tcttttttt 23400
aataaggcta aaatccatga atctctgctg tcatcattga gggactttct ttctttaatg 23460
gttgaattat gtgcctgaat ggcaccagaa gttactggaa acttgtaact tgttcctgtg 23520
tgaggcttgt aatctgtttt gtttttttt tgtttttttt tttttttttt ttggtttttc 23580
gagaaagggt ttttctgtgt agccccggct gtcctggaac tcactctgta gaccaggctg 23640
gcctcgcact cagagatccg cctgcctctg ctgggtgctg ggattaaagg cggaggtttg 23700
taatcttaaa taaattaaga aaattatcca caataccagc aataaggata ctctgtggtc 23760
aaactttttg gtattgcttt tcgaaattaa gccacacatg tctgtgcggg agaaacaaaa 23820
tttagcattt gtttattgtg ttctctccct tatgtgatct ctcatgaacg tcttctatgg 23880
tagtaaaata catgtgtgcg tattttaaca cttagtacaa gttattagtt ggatatacac 23940
ccccccaggc cccccaccct cgtcatcatc ccctgtcatt gttcctccct gcccccccca 24000
cccctacccc ccccccccca ccttgtgttg aggtgcctgc cttgtagtca tgctgtatag 24060
actggcctcc caattctgat ccacgtacct tagcctccca agagctggga ttgctggtat 24120
gtgccactct gcctggctgt ctacagacat tttttggttg agtaaaattg tttgtattta 24180
tcctttttaa ggtcctattt taaattgcta aagaatacat atttcattgt tacccaaatc 24240
ttctttgtct aaggtcatgc taaatgtgta gaagtagtga aaacttttaa cttgccattg 24300
ctgatgctcg gtggaggagg ctacacaatc cggaatgttg cccgatgttg gacatatgag 24360
actgcagttg ccccttgattg tgaaattccc aatggtaggt gttcaggttg cagtatctag 24420
aagaacatct gctatgtaca aatggatgca tgggagagtc tactgccaca cccctgaaat 24480

-continued

```
gtgtgatctc ttctgatgga tgagtggtta gattgcaaat ctgtgtgaga gcattccatg  24540
tgcactttca agctttcctt tgggaatagt tcttttatct ggattcggat tatgtttctg  24600
agattatacg gaagctaagc ttttaatgtg taacttgttt tttcattgtt tttaatagag  24660
ttgccatata atgattactt tgagtatttt ggaccagact tcaaactgca tattagtcct  24720
tcaaacatga caaaccagaa cactccagaa tatatggaaa agataaagta agaaatcact  24780
tcggcttaat gaaacttcag gaggctatag aaggtcaaat aaaggaagtt ggtttagcat  24840
atacatcaga tacttcctaa ccttaggcta ttcctgtttt ttaatctctt atattaatac  24900
aaatatgtaa cctttgtaaa tagaaacatt cttattagat caaatgcttt atgtctacag  24960
aatgtagaaa cattgatcag aacgggctgt gtcctctctc ccatagacca gttgtatgac  25020
atttataagt acacctcatt gtcaaataga ggtgaaaagg tacatgtttg tgtgctgtgg  25080
gttcagtcag ctaatatatg cagtgatctg atgcttagat agtgtcccat tcagtggtta  25140
gtaaatgaaa gctcgttctt gtttagttcc tcctgtgtat aacagaaact ttacatacag  25200
tggattttgt ctaataaatt gtgtcattta gacagcgttt atttgaaaat ctacgtatgt  25260
taccacatgc acctggtgtt caaatgcaag ctattccaga ggatgctgtt catgaagaca  25320
gtggagatga ggatggagaa gacccggaca aaagaatttc cagtaagaaa acccttgcta  25380
tgtcttcttg catttttctt atgtgtcaaa ataagactta aaattgaagg tacacaggga  25440
atggttcaca gcacatgttg tgattttcct tctctccatt ttaattacat atagatttag  25500
ctccctgatg tctcaaagcc tgaattaata tcaccagttt cattttgtgt gactacacag  25560
acatggctgt gtccagaaag taggcacttg atatatctat ctatctatct gtcttaccta  25620
tgcaatgatt gtagaacctg tggctattat caaatttata aaatcttttg tgtatcagtt  25680
cgagcatcag acaaacggat agcttgcgat gaagagtttt cagattctga ggatgaaggt  25740
gaaggaggtc gtaggaatgt tgctgatcat aagaaaggag caaagaaggc taggattgaa  25800
gaagacaaga aggagacaga ggacaagaag acaggtcggt ttatgttttg gtgaccattt  25860
cactttccct acttaagggt tgcactgtgt ctcttagcga tcctgcagtc acacgtctca  25920
ctttaggcag gtaacttttc ctggtgtaag agatagttag ttaccgctca tgcttactgt  25980
ttagtgcttc agagctgact taaaggtttt acagttgtgc tcaaattttc tttgtggtat  26040
agaaaccttc cttttaataa catagtagta aacgttacat gtcatgggat ggggttaagg  26100
ggatgacagt agttacagat gttgggcctc agaacattta ctgtagctta ggtggactta  26160
gactcagtgc tcttctgcct tgtcctctta tatactggga ttgaaggcat gccagtacac  26220
ctggctaaaa ttctaaataa tttatactgg ttaaagctga cttcatgtag caaaagttaa  26280
gctacatagt cctttgaaaa gttactttaa gagtgaagac tctttaggaa ctgaagaaac  26340
taaaactgag gaaagatagg aaggggcagt ttctggtgtc ttccggtatt tcattcagag  26400
tgtttattta gcatgccatt acagcacctc gttagcactc tcaggtttct cattgctatg  26460
ctgaactgtg caggggtaag gagtgggcag tagcctcttt aaacatgata atgctgcaag  26520
ttttagttga cctactagtc aagtgaggct gcctggcttt actaggcctc actatataga  26580
catggctgct ccggctactt actgggtggc cttggattca caccattgtc ctttctcaga  26640
tgcctgggtg ctgggattac agaaatgtgc caccacctcc aactcagttt ctttctattt  26700
taaaatatct tctgcatttt cttttttttt tccaaatagg aaagtgataa agtaaattga  26760
ctcttggtat tttagacaaa ataccacaat aatctatggg tcataacctc aaataagacc  26820
caccaccacc ccctcttggc actgagtaaa aatttagcca gaattatcca agacactaaa  26880
```

-continued

```
atgtgaaatc tccattgtcg gcatgtagat ttgtatggga ggtgacagca gtgccctgca  26940
gtgtctgcat tgcccaagcg tgctgctgtc cctgcacctc tccatgaggc cattgcttca  27000
taactaattt acacagagaa aatactctgg ctaatctggg acatttactt taattactgt  27060
atttaagtta tgaagttcag tttagtagta attaaaaatt taaggttaga acaatgggat  27120
attgtgggcc agcaaggtaa aggtgcttgc tgccaagcct gattacatat gatctgcatg  27180
ttggaggaag actcctgact tctacaagct gtcttttgac ctccctatgg aagtcatggt  27240
gtggatgccc aaacatacac acacactctg aataaataaa tgttaaaaac aaaaaacata  27300
atctagcctc ttgcctttag gatcacgtcc ttcttacagt gcagacacag ttctcttgag  27360
ctccttctgt cttaccactg cttccgtgcc tcagtccttt tacagttttc cctggaagat  27420
acccttttcct cttacctgag agtttgttca ttctttggga cccacattct agagaactgt  27480
gtctgcactg taagaaggaa gtgatcctaa aggcaagaag ctaaattatt tttttgtttt  27540
taacatttat tatatataca ctatatacat acatatatat attgtgtgtc ttatatttca  27600
aaatagacat caatattttt cttctgtctt tagatgttaa ggaagaagac aaatccaagg  27660
acaatagtgg tgagaaaaca gaccccaaag ggtgagcgat gcttgtgtct gtagacgtca  27720
tgcatgtctt gggggttggg cgggggcatg catacttgag aaatactggc acagcctgag  27780
aacatacaat gagtgcaggt ctgcgtgtgg gtaacgtgct taggctattt gaccggtaac  27840
ttttatgtat gcaatcgtgt ttttcatgat gctcatatta ctgtgcttag aatactttga  27900
tgttaggaga caggctagtt taaggaaaaa acattgggct aagtgaaagc ctattggaga  27960
attttgttat cagaatgcat gtatggctag gtaggtgaag tgttgcggta aatctccaac  28020
ccaaatatgc cctggcaatg aaacacaact caattaatat gaatacatgc tgtgtgccta  28080
gaatgggcag atctaccgct acactaccat cgtcaacaac tgtgagagcc cttagaactt  28140
gcagtttctc caggccacgt gcttctgctc cacttttctt cttccccctc ctctgcatcc  28200
tcaccctccc ctattttctc ctctctctcc ccaccttctt ctccaccttc cctttatctg  28260
cccaatcatc agctctcctt tattttacaa attaggtggg aagcaggttt atgggaagta  28320
aacctgagtg ctgactcatt gcttgtttgt aggccctcac tggagaagga agtagcatca  28380
aatataataa gtaagcccca gggctatcca cacctgtgaa gaggcttgag tctataaatct  28440
cagtccactg gagaggctga gcccagagga ttgccatgaa tttaaatcca cactaagcta  28500
catagtgatt tttaaatcgt cactctgggc tgaagaatga gagtctgtgt tagaagcaag  28560
cacgtgtgct tggtcaccca gttgtttgct aattttgaag gataacttag aatgctcagt  28620
tgtaaaacaa ctggaaagat taaggctttt attgctcaga aaaaaaagaa aaaacaacaa  28680
caacaacaac agtgaatagc ttggtgtgaa tctataagac tgtgcaagta gccaggtcag  28740
tgctcctaaa ccaagactat tacttttaat atttcatgat cctctttcaa cagagccaag  28800
tcagaacaac tcagcaaccc ttgaatttga ctctccaact ttaggaacct cgaaaagtga  28860
gacgattctg ggataagaaa ccttccctgt ttgaggacat tggcttcatt tttatactgtt  28920
ttggcatgga ctgtatttat tttcaaaatg gcttgttttt gtttttcttg gcaagtttta  28980
ttgtgagttt ttctaattat gaagcaaatt ttttttccca ccatgcttta tgtgattgta  29040
tttaaattga tgtgttatta tgtcaaaagc cggatctatt aaagaaacaa ttggcctttc  29100
tgagctgatt tttccatctt ttgtaattat ctttattaaa aaattgtact tggatcgttt  29160
tctgtctgtt tattatgaaa gcttgtttcc aagtcaatga cttgatggtc ttaagactgg  29220
```

aacataccaa aaggaatgtc agtgtcagag accatcacta gatctacaca gtgcttactg 29280
gctctaacag ctatttctta cttcaggaaa aataacagtg tcactttgtg tcaggaagac 29340
tggtatttca taaattattt ccaaattcat aatctgtgca cttgggatga agcaattatt 29400
tttgaactga atcaaatact cagaaattgg aaattgtgaa ttgaaaaaag aaacctgtcc 29460
aaccaataac tggcccaact taagacccat cccatgagcc agcaccagtc cctgacactt 29520
aatgatactc tgttatactt gcagaccgga gcctagtgtg gctgtcctct gagaggctcc 29580
acccagcagc tgactaggac agatgcagat acccacagcc aaacagtgga tggagcttgg 29640
ggacttttat ggaataggag gaaggatttc aggcctccaa ggagatagga actctacagg 29700
aagaccaact gagtcaacta gcctggacct ttgtggctct cagagactga accactaacc 29760
aaagagcata cacgggctgg acctaggtct acccacatag atgtagcaga tgtgcagctt 29820
ggtatttgtg tgagtcccag acaactggag aggaggctat gccaaaagca gttgcctgtc 29880
tggatcttcc agcttggcta ccttgtctgg cctcaatggg aaaggatgtg cctagcctca 29940
gacttgatgt gtcagggcat gtatacaaaa gattgtaggc ggtagaaaca taccctttg 30000
tgatgtcagt gtaaaatgaa ccagctagca aaacctggtt cttgccctgt agtttgatca 30060
caaccagggt ttctactcaa gaagtaaaac ttaatatgct ttggcattcc gcattcattg 30120
agtgtctact cacctttgg taataactgc agctgaatag aattttaagt gctttcacct 30180
aaacttagat tgttattgta gaaagcccac aaatggagtt tcctctccca gtgtgtacaa 30240
cagaaaaatg ttttaggaat ttgccaaagt tggtgaaacc atcctacttg ctagaatcag 30300
gttgctgatt ttgagattag gagaacagag tggtagaaag gaggcagtcg tggagaatgt 30360
tcttacattg tcctgaggtt cgaaggtttc atgttcatgg gttttcccct tttgctatgt 30420
atttgccagg agtccatatc ctttatgact aaggaagcag gatcccttcg ctgcagagac 30480
ttatttagtg tgtaattttc atgaaacaaa gtgtatcctt tggatacttc atctggtatt 30540
gtgatctgcc ttctggcaca tgtcgcataa taattacagt gtgttaagtt ctggtctatg 30600
aatctactag aatgatgtcc cagatgccac agtgattctc cttggttgga tctgggaggt 30660
tctggtttca tagtttaagg ctgtgaaact aagcagtttc agaacaggtg atttgggacg 30720
gtaaaaatac acagatacca gtaatttgta aagtcaaact acagcccaca ttgtttggaa 30780
gaacaaaggc tcctttgca tagcagtaat cacaatttct acaaatgtgt aaaactgatt 30840
ctatgcataa tgaataagat gagtgttaat aatagcctgt cgggacaagg gttgaaaatc 30900
aaaacaatga ggaaataaca agaaccaggt ggagggaggc gaagttcatt tttctgtcac 30960
aagagtgaga tttataaata gaaaagacaa caaaacagaa cctggtaaaa gccatgggaa 31020
tttttcaaaa gtgaaggcca aagcttgaca ccgaacccca cataagttac atacttaaca 31080
gaagttctct agaccagcaa aaacaagtaa aataagatag ggaaccccgg cagtggtggc 31140
gcactccttt aatcccagca cttgggaggc agaggcaggt ggattcctga gtctacagag 31200
tgagttccag gacagcctgg actgcacaga gaaaccctgt ctcggaaaac ccaaaaaaaa 31260
aaaaaaaaaa aaaagatatg ggaaccataa tggacttgtt ccacctcaaa gaactttatt 31320
tctttatttt aaaaataaag ggtctttgtt tttggccagg ggtagagaga aaattcagtg 31380
gttaggagta tttgctgctc ttacacaggg tccaggtttg attccaacca catgctcaca 31440
gccatctgag gatctgacac ccctttcttt gagtaccagg tatacatgta taaaacaccc 31500
atacatgtta actaaaaata gcttaaaaat ttgacaagag ttcaatgaaa cccatgaatg 31560
tagtatcttg ttaggaagac acaatgtcca aggtaattct tataaaggaa aacatttaat 31620

-continued

```
tgaggctggc tttccatcgc ataggttcag tccattatcg tgatgggaag catggcttgc  31680
agatagacat ggtcttgatc agcagggaac aggaggagac tgttccacac tcggccgaac  31740
ttgagcatag gagacctcaa agcctgcccc cacagtgaca cacttcctct aacaaagcca  31800
tacctacaac aagaccacta atagtgccac tacctatggg ccaaacattt aaacacatgt  31860
ctaggggtgg gggttagtac ctattcaaac cactacattc caccttctgg gccccatagt  31920
cttgtacctt taccataatg caaaatgaat ttaatttcaa aagtccacat agtttagcac  31980
agtttcagca gtgtttaagt ccaaagtctc ttctgagatt catgcactct tttttattag  32040
atattttctt catttacatt tcaaatgcta ttctgaaagt acccaatacc ctcccccccc  32100
aactcccccc cccccccgcc ctgctcccca acccactcac ttctgcttcc tggccctggc  32160
attaccctgt actggggcat ataatctttg taagaccaag ggcctctcct cccaattatg  32220
gccgactagg ccatcctctg ctacacattc atgtactctc ttaactttaa ttccttataa  32280
aatcaaaacc aaatcacatg cttccaacat acagtggcac aggagataca ttaccactac  32340
aaaacaggga ggggaacatg atgcggaaat aattaaccaa agcaagactg aaaaccagct  32400
gagtaaactc caaactctgt atctcgatgt ctgacgtcaa aatgctctac agatctccaa  32460
ctcctttcag ctttattaac tgcaaggcgt ttcttttcct ggtctagttc cgttccctgt  32520
tagcagcttt ccttgacagg tatcctatgg ctcagatatc tctagatttt tggggtctac  32580
agggcaatcc aggcttcacc ttcacagctt cacagagtgg cctctctggg cctccatgaa  32640
gagacacccc tgacacattc ccagtctcaa cagctttcct taattgtaga gggaaattcc  32700
aatatccttt tcttctatcc ttgattctaa tgccagaacc caatggtcaa atctgtcaag  32760
ttctgctgct gctggtttga gctggaatat gccccccccc ccccctgttc aattacaagt  32820
tcaacagctt tctgttttcc atggtttctt tcactgccta agcttagctg acatggaact  32880
tggtctatag accagctggc cttgaactca gagatcacat gcctctgtct cctaaatgct  32940
gggattaaag ggtgtgtaca tgcctggacc taagcttttc tttaattcca ttttacaagg  33000
tggaagatta gctgggtggg atcttgccgc aagatcacca ctcacttaat tccactaaat  33060
atctttaatc tgtttatctc cttgaacaaa gagttgggct ttgttccact tcctggttcc  33120
cctttaaccc ttgaaccata cgatttctat ttttcctttc taagcttgat gaaaacactc  33180
cttacaagag tggatcacaa cacaaagtct aaattaggct tttctgagat ttcttttgcc  33240
agtgcaagga aagtaatcta aatctcttga acttagcctc aggcagactc tttggacaga  33300
gggcaaaaaa cacccacatt tgtcaccaaa atatcacaag tacaatctct aggcaacata  33360
ctaaaattct cctctgaaac ctcaatcttg agccaggcct tcacagttca aagaatgctc  33420
agagccatgt tcttactact gtggcccatt aagcagcttt taaagcattc tactgctttc  33480
ctaatacaga gtccccaaat ccacgtccct gcaaagggtc agtcttatca cagcagtacc  33540
ctagtccctg gtaccaactt cttagttagg gtatcattgc tatgaagaga caccatgacc  33600
aaagcaactc ttataaagga aaacatttaa ttggggctgg cttacagtgt cagaggttca  33660
gtccattatc atcattatgt gtaggcagac atggtactgg aggacctgag agttctacat  33720
cttgatctat aggcagcaga atgagacttt cacactagca tatcttgagt ttaggagacc  33780
tcaaaacctg cccccacagt gacacacttc ctccaacaag gctatactta ctccatcaag  33840
gccagacctc ttaatagtgc agctcttcat gggctaagca ttcaaacaca aatgtcttac  33900
acagagtcat tacctacaca aaccaccaca gatagattaa aataatctct tgtacttaat  33960
```

tttacattgt taagattact aaaaggattc agcacttcat t 34001

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: bases at these positions are RNA

<400> SEQUENCE: 45
acccucaagt ctcctg 16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
accctcaagt ctcctg 16

<210> SEQ ID NO 47
<211> LENGTH: 89000
<212> TYPE: DNA
<213> ORGANISM: Mus musculus

<400> SEQUENCE: 47
attccttttc ttcctttgtt ttttttgttt tgttttgttt ttgtttttaa agatcagggt 60
ctccctctgt catcttcttg ctcacagctt cggtgcgacc cctgtaccac ctcctgtcag 120
ctgctttcca gagtgtacat tcctgctgcc tccttactgg gcttattcaa gcacatgtgt 180
gcccagaagc attaaattat tactgattta ataattatta ttattaattg ttccacccgg 240
gcaattggcg gcatggccaa aatcctatgt tcaagagact gggggaagag gactgggagt 300
tgcaggcccg cctgggatac acagtaaggg tcgtcctatg ctagacagac tgtgtctcag 360
gtaaacacag ccctcctaaa aggaaacaaa tacagaacaa atgctgggac ctggccatga 420
aaagaagctc tgagttcttg atacactggg tgtggtggct cctgcctgta agagttagag 480
gcagaaggat tgaagtttaa gaccatcctt ggctacacag ccttgagtca aggctctgtg 540
aaatgaggct ctgtcaaagg taaacaccac catcttcccc cttcccccaa atgtgcttcc 600
agaacctcca gttttgcctg caaagtagtg tattctccca tcttgcgtta gggagtgaat 660
ctccacattg cacttggcag ttaaaaggat gtaggatgtg gtaaagctga agtaacatgg 720
aaacagctgc aatactggct tctgccttac aatggcttgg gtggtgggtg gatggggcac 780
ctggagagat ggtggcctag atccccagga ccctcataaa aagtcaagca tggtggtgag 840
cgtgtgcagt tccggctgct ggctaacctt ctcagctgaa ctgaccagct cttggctgag 900
aaatcctgtt tcaaaaacta agagaagtga caaggcctaa tgtcaagctg tgacctccgt 960
atgcacatgc acagggcagc ataccacagc cacacaaatg agaaaaaatg gaggctggag 1020
gagtggttta gagtgctgct gttggagggg actatagttt ggttctcagc acccataatc 1080
agatgactga caactgctct taacttccac ttcaaggaat tccatgtcct cttctcatct 1140
catgtgccta tatcacaccc aacataaaca cataattaaa ataaaggggc tggagtcgtg 1200
gtggtttagc agtttagagc acttgttgct cctgtagagg aggtgggttc agttctgagc 1260

```
acccatatag cagcttgtaa ctgtacctcc agttctgaga ggatctgatg ccctcttttg   1320
gttttcttgg tcctgcatga ctctggtgaa caaaatattc ctgcaagacc aaacaccatg   1380
catgcaaaag aaaagtttgg ggttagagag acagctcagt ggttaagaac agttgttgtt   1440
cccagcaccc acacatttaa aatctcatat aaaaccatcc agaactccag ttctagggaa   1500
tctgatcctt cctgacttct gtgggcaccg ggcacagatc tggtgcgcat aaaaataaaa   1560
taaatcttta aaacttttta actgttattt tatgtaaatt aaaaaaattg tacatggatt   1620
tttttttttt ttgcctgcat gtcggtatgt gcattatgtc tgtgtctgtt tctagtggag   1680
gccagacgag ggtgtcagat tcctggaact ggaatcactg atggttgtgt gagttgtcat   1740
gcaggtgctg ggaaccaaat ttgagtcggc tcccaaggca gcaagtactg agccattggt   1800
ctaggagaaa aaaaaaatta aagtaaaaat aaacctacag ttgtagccat ccgcaaaaca   1860
cttgcttggc ttaatggaac tgtagacttg accctctgta acgtacagaa ataagcacga   1920
gagggtgaga acgcctttat gaggcagaag tgtcgactca tctttcactg gcactgggat   1980
tcttccagag ttgggatctg cgatgctttc tgctttgttt tgttttttg tttttttgtt   2040
ttagtttttt tgttttgttt tgttttgttt tgtttttcga gacagtgttt ctctgtatag   2100
ccctggctgt catggaactc actctgtaga ccaggctggc cttgaactca gaaatctgcc   2160
tgcctctgcc tcccgagtac tgggattaaa ggcacgcgac accacgcccg actgcgatgc   2220
tttctaaaat atgggtttc actacagcct aagaattcag gtgtaacagc cactgaacct   2280
taccacggtg tgcttccctg agcactgtgg ccttttgctt aaaaagaata tcacaaagtg   2340
atagcaaatg ccaggaagtt ggaagaactt ttatgacaca gttgtcagtg aggattggga   2400
aggtagtagc gtgtatccta gcaggaggga ggctgagaca ggaggaacat caagagtctg   2460
tagccagcat acaaaactat agaaactata gaaaaagatt gcggctctct ttcctcttac   2520
tggttggagt agagaagtga tatttatatc agccaatgag aaatttttac ggaattaact   2580
agtgtcaagt gacaatccag tgttgaagaa tggatccctt acacccttgg caggttgacg   2640
tttctgcgac caataagcca acccgaatca acctagtgag ctgaggcctc agtgtctttt   2700
ccagagaccc cgccttcccg gtctgacaac ccggtttgac ttctattggc tttcacttaa   2760
gagtgacagt tttattaccc agtgaatttg tgagattagc ccttcctcgt gccttttta   2820
ttggctcacg ttcttgagtg gcagtgcttt gaaccaattg gatatagcag tagggttgcg   2880
gactccgccc cggaggccgg gagggttgtt cgctcgggtc gggtgtcgcc tgagaaccgg   2940
atgaggcggc gactctgagg ccgagccggg agcgggcgtc gcggcgaagg ggagaccggg   3000
cgggccggca gagcagagca ggaggaagca acggccacag acacatcgga accgagagtc   3060
ttagtcgggg gatccgcgcg gcggaggcgg acaccatggg caaccgcggg atggaagagc   3120
tcatcccgct ggttaacaag ctgcaggacg ccttcagctc catcggtcag agctgccacc   3180
tggacctgcc gcagatcgcc gtggtgggcg gccagagcgc cggcaaaagt tcggtgctcg   3240
agaacttcgt gggccggtga gcgagcgcgc cggcggcggt tctggggctc cggccgggag   3300
ggcgggcggc ggcctagggc gcggagggcg ggcggggaat ggcggaactg cggctcgcgg   3360
acgccgcagc accggtggca gtggataagg tctggggcaa gagtctccat ggctttccgc   3420
agggactgga gatgcagatc caagtctggg actagtcgat gatagtgggc ggtgtttggg   3480
gcaagacggt cagtgccgac ccctcttggt gcttctagtt ccggctatgg ctgggcaact   3540
ctgacatcgc tttacctgta gtccgggata gatccactcc tctttccttc tgctacctgg   3600
```

-continued

```
aaatcttagt gtgtgtgcta agatgttgaa gataacactt gccacttagc catccatggg   3660
gaatgacccc tggggtctgt ctggccagtt attttctgga gcctgctctc ttgcctggtt   3720
agctggttat ctgttctaga caggcttcct accggcacca tttggttgtc ccatctgtcc   3780
aaactcactc tgaagtccac cgttgtctgg ctagccatct aaggtgacct ctcgtgtgca   3840
aatgcccatc tgtgcccctt atttacgtga gttggcctct gccatctgac tggctgaact   3900
ttgggagcct cctgttatct ggttctcttg ggccgactgg ctctttgaat ccatccatta   3960
gtctgttctc cattcccacc caggcatccc tgcctgtcca tcctctctga gtgacagagg   4020
ttggagaact tgggaagaaa cattctttag gattcttttct tgggctagga tcccctaacc  4080
tagagcttcc cagttggaat gctctctaga tagctctggg agcctcagct tgttccatct   4140
gtccagtggg caaattccac ttgcagctgt ttgtaggatc caggaagtga gtgaaggagg   4200
gatgttgatt tactcctgtc ccctccccct ctgcctctcc ccgcagcagc acttctccat   4260
tccaggaagt gttccatgta tgatgctgca gtgtgtgcct acccagtgtt aacatttgct   4320
ttgctgtgga cattatcatt gtgtgtgtgt gtgtgtgtgt gtgtgtgtgt ccaagtgtgt   4380
gccagagtgc atttgtggaa gtcagagggc ataatctttg tgaagtcctt caaaatttat   4440
gtggggatta aacaccgggc cgcagactta tatagcaagt cctagtatcc attgagctat   4500
gtcattgtcc ttccatctta aattgtagag acatggtctc tcactgacca tgcagctcac   4560
cgatctcatt gggtctctct ctctctctct ctctctctct ctctctctct cacacacaca   4620
cacacacaca cacacacaca caccatgcag ctaactgatc tcactcagct attctcgctg   4680
gccagtgagc tccagggatc cacctctctc tgtctcaccc tatcattggg tcacacacac   4740
acactcacac acacaccctc tgttattgtt gttaccagtc ttttgtggag gcagaacatc   4800
tctaaatttg aggctagctc actctacata gagtagagtt ctagggcagc tagggctaca   4860
tattgagacc cagtctcaaa aaaacctcaa aagttgattc aagactgcag ggactgggta   4920
cttggaagtg tacatttagg ttgaattagc tgcacctgtg atcttaggat tttgggagtc   4980
tgaggcagga gatttcttga gtttgagttc aacatgggct ccattgttag tcctgtctcc   5040
aaaaaaaaaa aaaaaagcca tgagagggct gtgtggtgac gctcgggcat ggagtacttg   5100
cctagcatga ataagaccca ggggtcagtt cccagcacca aactaataag aaatattgtt   5160
gatatttatg ttctctttga ttgcattcat actcaaaaac acctatggct tttaggtaat   5220
gaaataaaaa ttttatgtat atgtatatac acatatccct gtttgtttgt ttgtttgttc   5280
gtttatttat ctatttgttt tttggttttt ttgagacagt gtttctctga gtaacagagc   5340
ctggctgtcc tggagccacc tttataggcc aggctggcct ctaactgaga gacttgcctc   5400
tacctctcaa gtgatgagat taaaggcaag tccaccaagc ctagctattg atcaatgttt   5460
taaaaagcat ctcagaatgt agacaggctg gccttgaaca tacagggatg cacctagttc   5520
tacctcctga gtgctgggat caaaggcata cagcaccgtt cctgggtggg ggttattttg   5580
gtttttttgtt ttttaatttt aaaaaaattt ttgtttgttt attttgaaac agtctcatac  5640
tgtagtccag gctgacctgg aacttactat agcataggtt ggcctccaga attgtagcag   5700
cagttgtccg atttcatttt ctaagtgctg gggtcacaag cacacaccac tatggcatta   5760
agttcatttt actctagaat gcataacgta cctgtgttgc aggactttgc caagaggccc   5820
actcaatccc attctttatt tcctgctatg gactttatta aacagagtca gaactatgag   5880
tctgtctgac ccttgtgctg tttctttcct ctgctgttct tgaatatcca tccaggggca   5940
tctggttgtc agccaggagc aaaggagagt gtgccaaggg cttgggccag cccagcacct   6000
```

```
agggacagct caaaatgctt cctgtcaggg ctgccttaga tttttctaag aacattagtg   6060
tacactagga cagctcagtg ggcccagccc cttgccgaga cttgcatgca gattgctagc   6120
cctggaggcc aagggcttga aatgtaacag gtttcacatg aggtccagat ttctacagag   6180
cctgaaacta ccctgaaggt tttagtaata atgaggtaga ggcctgaggc cccaagcatg   6240
ggtctaccaa agctgtgact ttagtcaagg gcattgattg ggcattctag gccccaggtt   6300
cctgagtgtg tgtctgtgca caagtgtctg aatatgagtg tgtggggtca gagggcagcc   6360
ttaatcatgg ttcctcagga gccgtcgtct ttgtgggttt gagtcacttg tagtctaggc   6420
tgactggcca gcgagcccca gggatctctc tgcctggacc attacagtgc tgtgatgaca   6480
ggcgtgcata gtgatgcctg gcgttttacc tgagcgccaa tgattgaatc ttggctgaca   6540
ttgaaatggc tatagagctg aggctaacct agaactctgg atctcctacc tttaccttct   6600
gagttctggc attgcaggag tgcaccacca tgtttgggtt tatgtagtac tggggatgga   6660
actgagaact ttgtgcatgg taggtgaggc agccagaccc caggtttctc tgctctaaga   6720
cagagctgta tgtaatctgg gcagagtggc agtggtataa tgtctgctcc cccagaagtg   6780
aaaaagtaag actgagaccc tcaccctggg gtgagctgac ttcacgggta actcactgga   6840
tcttctaacc aggactgctt ttaccatttt agaagcgtta gcatttgaaa ccagcatctg   6900
agccagccag ctttgtgagc tagctatggc tctcaggagg gcttggtttc tacctaatcg   6960
ttgctattta attgagggac tggcaaagag gctagctggg ctttttcccc ctaccccacc   7020
cccatttgga caggaaccca ggaagttggg gttccagcct ggaaagcgga ggctagactc   7080
cttcctgtga atgtattgcc tttctgaatc ggaatctcag aaggaagtgg ggttacagtt   7140
tgttccttga gtgtttgact gccttacagc gttacctggt gcatgtcact gaggccgagt   7200
cccacttgtc tatgactttc acgaaggctg gcaagatggc tcagtaggga aaggggtttg   7260
ccaccaagcc tgatgacctg ggttgatttc tgaactccaa tggtagaagc agagaagcaa   7320
tttctgtgtg atgtatgcac acggagacac aagcccaaag aggatacata aatgaaatgt   7380
tcgggaaaaa aatttttttta aagaaaaaca aaaagggagc ccaatactgc agctcagttg   7440
gcaagtgctt agcatgagtg ggggttccac acccagcagc acagaaaccg ggtgcttgga   7500
aagtggaggc agaagatcag gaattcaagg tgtgcttcgc agcagagctg gttctgctag   7560
cctgggctac atgagatcct gcttccctga aaaaataaaa tagagttcca gcctcaggcc   7620
tagaacccag gactcagcta acctgggtgg gctctgttgg gaattaaata aataggtgtg   7680
tgtgtgtgta tgtgtgtgtg tgtgagtgtg tgtgagagag tgtgtgtgtg tgagtgtgtg   7740
tgtgtgagtg tgtgtgtgta aggggggggg gagaaaacgt gtaatagcaa taactcttcc   7800
ataggccaag tgagtgttca ctggacagtg ttttccagtg cttagcacaa ctttgcctca   7860
tgcctagggt tatggccttg agccaaataa ccttccagca gagactagat gaagacactg   7920
gtgccgtcca atagcgctgg gaaacggaga ggggaagagg cagggagaag ttgggaaaga   7980
taccctgaag attggagaag catcccagga tgtggaaata gccagtacag gttctgagct   8040
gacagcgcac ctgagagtgt caggaagctg aactgtggag tgaggtttaa aagggatggc   8100
tgtggggctt ggcacaggcc acttctctcc tggggaggca cattccctgc ctctggctgg   8160
acgcttgggt gggctgttcc acatggtcag ttttctcttt acgcatttcg cctgttcaga   8220
ccttctccca ttttccttgg atcaggaggc acgggtggca gtgtgcacag gtacatttgg   8280
acatgtgttc atatgtgtgt gggtatcaga ggttgtgtgt ggtaggtaca gtgcatgtgg   8340
```

tggtcagagg acagcttgta ggagttgttc ctctcctttg tgggtcccat agagccaact 8400
caagtcatca ggcttggcag caggtgtctt tatccagtga gcatctcacc aggatagtgg 8460
tggtggtggt ggttgttgtt ttgtgttttg aaacagggtt tctctatgta accctggctg 8520
ttctggaact ctgtagatca gggtggcctt gaactcatag agaccagtct gcctctgcct 8580
cctgagtgct aggattaaag gtttaatctg ccatcactac ctggcttttc ttctgttttt 8640
aatacacaat gtttttata cgtaccccag gctggtccca agcttgtgat cctcccccac 8700
tttcccagtg ctgcaatggc agccggttct accaccctgg actcgattga gcatttccag 8760
tgctgggtaa gagctggcca ccgaagggac gcccgttgct ctcactcttg cagttgcttg 8820
gagctgcagc tggtctaggc tgtgccaggt ttgaatacaa atgctgaaat gacaggctcc 8880
ttggttgctg ggagaaactt gggcatctgc tgaaccctaa tttacagggg aggggccaag 8940
tgctagctgt aattaggccc ttattaaagt gtcaatgttt ttggagaaaa tacagtcagt 9000
aatgagctgc tcacatggcc tctctgcaag ctgagcgaat ggaggacgtt gtcatgcctc 9060
ctgagccaga tgctacacta aggaagtctg cttccatgtg tggtagaggt ttctgggagg 9120
ccagccttaa ctttagccag aggctaggag ggcactttgc ttccgtgtag tttctcttta 9180
aggtctactt cctctctctc tctctctctc tgtgcatgct tccatgagtt tatgtgcacc 9240
acacatgtgc agtgcccttg aaggctggaa ctggagctgc agacagttgt gagctgccat 9300
gtggtcctct gcaagagcag taagtgctca tgactgccaa gtgtcttcct cacacctcct 9360
gtttcttttg agatggggcc tcatgaagcc caggctagcc tagaatttcc taagtagctg 9420
agggtgacct taaactccca gtctttcctg tgtctgtgtg ctggaattcc agatgtgtac 9480
catcattctg gtttattcct tgctgggatg gaacccaggg cttgttgcct gctaggcaac 9540
tgaaccagtc taccagctgc atcccaccca agtttttggg agatagttgc tgcttttata 9600
cttttctcag ttacagttac aggttgggaa acagactgga gagggaggtg acatttgtca 9660
tgaaagccag atttctttaa ggttgtcagg tgtgcgtctt cactgtcaag ccttagttgg 9720
gcctaatgga ccaggtgctg gagacttgac agggacccag aactaactag acagaaaaat 9780
gggtgggcag gtaactaaac aacattctgg aagaatgaga aatctggtga tagatagcat 9840
ggagtcagaa gtgagactgg ttttagcatc cactgtcaca tggctgcccc tcagttgaac 9900
tggagactgg tgggacagaa cagtatccac acagaaggac caacaggtag agtgccctgc 9960
acatacctgg ttagctgatg gcccgatgca gatttggcat agcctgggat acatggggct 10020
caggacagta cctgtcagtt tttaattaca agagcagagt gggcacagta gcagacccag 10080
gccgtccagc ttcccggccc ctctggagtc ccgctctcag cggagggtgc ctgctgttct 10140
taggccaccc cttgtcttcc ccacagagca ccctgatcac tctgcttaga ttgctggaca 10200
gctgctttcc ctagctgagt gtgggagctc acgcctgtaa gcacagcgtt tgagaggctg 10260
aagcattagc catagttcaa ggtcagtttg gggcacagag tcagaccttg cctcaggaaa 10320
caaacaagca aacaaacaag caccagaaca ataacacgaa gaaaagctgg ctgtaatccc 10380
agcacctgag aggtgcagga ggagagagaa gtttaaggtg tgcctcttct actcagacaa 10440
gtggaggcta gcctgagcta cagaagacct gtctcaaaaa tcccaaacaa actgaaggga 10500
aaaatggtat aacaacaaag tccacaaaaa caatcttcct ttttcctttt cttttttttt 10560
ttcagatgta tatggtatgc atgtatgtat atgtgtgttt tcatgtgtga gcatgagtgc 10620
ccaaggaggc ctggtatctc ccactgcatc cattgagtca gggcctctca atcaaactct 10680
gagctcactg atccagctag tctggctagc tcattgatcc attgcctttc taggttggac 10740

-continued

```
tcagaagcgg gctacaaaat ccgcctagca tatatgtggg ttctaggaat ccagactctg  10800
gatttcttgt gtagcactta accgctgagc ccacagctgg tttgtggttt gtttgtttgt  10860
ttgttggtgg tgtttttttt ttttttttc ctttttgga tttttgagac agggtttctc  10920
tgtatagccc tggctgtcct ggaactcact ttgtagacca ggctggcctt gaactcagaa  10980
atccgcctgc ctctgcctcc caagtgctgg gactaaaggc gtgtgccacc accgccaggc  11040
ttgttttttt tgttttctgt ttttttttta atgtattttt aatgtacact ggtgatttga  11100
ctgcttgcag gtctgtgtga gacagtgttg gattccctgg agcaggagtt tttggaaagt  11160
tgtcagctgc catatgggta ctaggaattg aacctggatc ctctggaaga gtagtagcca  11220
gtgctcttaa cctctgagcc atttcaccag ccctctacaa ctagctttct ggcctgggca  11280
cttctagaaa tctttccacg tcagtttcca gttgtagctt ggagcatcct gaccgctgag  11340
tgaggcgggc aggagcagca gttggggctg aggtagtcgt gctgttgaga gcagcagctc  11400
tctcggtggg ctgttagcta cagccttgat gatgtgctta ccacaccagg aggcctgtgt  11460
gctccctctc actagcaaaa atcccttgga gtgggtatta tgaagccaac ctcttggctt  11520
ctctcctggg ccttacccag aggcttgtcc ctgtagattc ccctaactga gatttcccag  11580
tcttcctcct gagcctggaa taaagtcttt ggcaaacttc ccaggtgcca aggtccggag  11640
ttctgtgtgt ggaggctttg ggtgggcttc acttaaggct ctccaggtgc ctgtgtgtag  11700
gaggctggag cggcaggcat gcagaacatc ttggaggagg cagctgtctt cttgctgagg  11760
tgaagcagtg gaatgacttg ctgacctgtg ctttgtgcct gtgtggctgt gaagtgcgct  11820
gtggcttatg tgtggacctt ttggtgacag acatcaaagc tcttttgccc tcattgttcc  11880
aggactctaa atgcacttca tggaaggagc cttgtagagt gtagtgtgaa tggggaaggc  11940
tacgtgccct ccccctggcg gtggcagcca cttcacagtt ggagttggat acatgccttc  12000
ggactctctt agaggcctcc ctcctgtccc tatgtcccat gtgccaccta tctgctcaga  12060
gccactcagc ttccacttgt agaacaaaac cagcgactcc caagaacctg ccgatcctgg  12120
caccacactg cttgcgcctc ctcctcttcc tccccgtggg ttcttagcca cctcgctctc  12180
accatatccc ctctctcaag actgtgcctt atgtaatgta tggcactgtg gtcttgagtt  12240
ccacatgtaa ctgggagtga ccttgaactc tgcatctggg gctggagaga tggctcagca  12300
gttaagagct ctgactgctc ttccgaaggt cctgagttca aatcccagca accacatggt  12360
ggctcacaac cattcgtaat gagatctgac tccttctgga gtgtctaaag acaactacag  12420
tgtacttaca tataataaat aaataaatct taaaaaaaaa gaactctgca tcttcatatg  12480
tctatctgag tgctgggatt acaagcactc aatacctgct ttgtgtgcag ctaggcatgg  12540
aactcaggct tgatgcacac taggcaaacc ctcaactggc atatggccag cctgtttcca  12600
gtcctgttat tatcattgct atattggtat tcgtgggtgt atctatatgt gcgcctgtgt  12660
ggaggggagt gatggaggcc aaggactatt ttcacttaaa aactttttttt tttaaatgtg  12720
tatgagtatt tctttctgtt tcatgtacat gtcacccaag gaagaggaca ttggatcccc  12780
tggagatgga gttacacatg gttgtgatcc atcttgtggt tactgggaat tgaaccctgt  12840
ttctctgcaa gagcagcctg tgctcttagc tactgagcca tctctccaga cccttaatta  12900
taattttttg agctagcgtc tcactcagag cctggtctca ttgtctgtcc ttccccttct  12960
ctggagttag gatcacaggc acatatgccg tgctcaggct tttcttttttt tttttttttt  13020
ttttttttta agatttattt atttattata tgtaagtaca ctgtagctgt cttcagacac  13080
```

```
tccagaagag ggcgtcagat cttgttacag atggttgtga gccaccatgt ggttgctggg  13140
atttgaactc cggaccttcg gaagagcagt cgggtgctct tacccactga gccatctcac  13200
caggcttttc tgttttagga agtgaactca tgtttggcca gcaagtgctt tatccatggt  13260
gatgatctcc ctagcctatg atttgtttgt ttattttatt tttgatacag agttttgcta  13320
tacagctcag ctggattcaa acctgaaaag tccttgcctt agcctcccta atgctggggt  13380
tataggcagt gtcactgtac cttggtcctc tgctgccttt ctctagaaaa gctgaggtga  13440
ggtctgactg tgatccacgg gtatgtaagc aaggccagca aggctacctg ggaatatccc  13500
tactccctgg tgaagaagga ggcacccgag agcctgctcc taacgcatgt tcccagactc  13560
tgatggcttg gagagcaggc aggcattgtc ctactgtgat gctgcttacc gaggatacac  13620
cccagcacac agaggccatt cccatcgaaa gccccagagg tggcctcagt acacaactct  13680
gtcctggctc agggcctctg tcttttgtac tgatagatga ggtttttcta gagttgttgt  13740
tctcaatctt ctttagatga cccaaccata aaatgacttt tgttgttact tcaaaactgt  13800
aatttttgtt actgttaaga attgtagtat aaatatctga tatgcaggct atctggtatg  13860
tgacccctgt gaaagggttg tttgacctcc aaagtgttgt gactcacaga ttgagaactg  13920
ctgttctaga ggatggtagc tttctggtct ggaatgcctg ccccagcatc cttagctgca  13980
gggaaccagc cagtggtgag agtgaccttg aattcctgag ccttctgcat ccactattag  14040
tgctggcatt cagagtgtgc cactgtactg agaggacatc atggttgcta gaatcctcat  14100
ggctacccag tgaaggctgg tagagatcaa gtccaggagc ctgtggccgg tatctggagc  14160
cctgctcagc tcagtcttcc tgtgctttag gtccccttgg ccatcatttt gcaatgttga  14220
cttcccactc agccaagcgg aaggaagcct ggcttctgta gcctttgcct aggtggcact  14280
gccaggggac actgtcttgc ataggctgtc aaggatttgg gtataagttg ttttctaggg  14340
aagggcctac atggggtttg ccctggcatg tggtgaaaac tgagtcttaa acttttcttt  14400
tctttgaagt tttcttgagg tctcatgtca cattgctaac ctcaaactaa gttaaatgca  14460
cagccagggc ggggcttgtg cttctgtact tcctgctgtc gcctccctgt gccgacgtta  14520
ctacaccagg cctagatgct gttttttttcc ctccgacaac ctgcttcaac ctcaagtact  14580
gggattgtag gcctttccac cacagtcatg cctggatttt taaaaagttg gtagttttat  14640
gtaatctagg ctgggcctca aacttctgtc acttctgggc tcctgatctt cctgctctgc  14700
tgcctgagtg ctgggattgt cagcagatgc catcacatca ggctttaagg tttctcatgg  14760
cactggggat cgctcccagg gctctaccac tgagttacct cttcttcttt aagaccacat  14820
tagagttatt aatgtaatta ttttgggtat tagagatggt gttctcctgt gtagccctgg  14880
ctgtctatag accaggctgg ctccggattc agagatctgc ctgcctctgt ctcctgagtg  14940
ctgggagtaa ggtaaaggtg tgcactggct acagcagagt tataaagaga ggggctgggc  15000
tcaatgggag aaaggtgctt ggtgccaagc ctaatgacct gaggtgcatc cctgagacct  15060
gtatagtgga agagagcaga ctcctgaaag ttgtcctccc atcaggacca tagcaattcc  15120
acctccaagc agagaaacat caataagatg caatttaaaa acatttaggg catgttgccc  15180
atgtctgcct tccttggcct ctccctactg caggctctgt taagactgtc actgttgatg  15240
gaaggcccct gtcacatggc tgccgttgcc ctcctaacac aggatcgcat gtcccctgct  15300
tccctcctct gctctaggct ctcaggctgt ccgtcctagg ctctcatgac cttggacttt  15360
gatagaacac aaacaacagt aacttctccc agcttatctg gcttgttctc acagctgact  15420
gtgagttttt tcattttggg taaggaacta ctttaggtcc gctttgtgca tcttgtagga  15480
```

ctccataatg tgggccagca ggacattccc agggagaggg catctgccat gtttccttac 15540
ttgaaagtta ctgggtttgg ttttgcatat cttatccttt gtaagtatcc aggccctaaa 15600
ggttttatgc atgaggacgc aagtgtatgt gtgagtttgt gtgcatgtgt gggttcttgc 15660
gtgaaggaca aagattggtg tccaatgtct cccttaagta ctgtggaaga atctctcact 15720
tacacaaagc ttgtctaaat ctgctaatct ggctagccag catgttctgg ggatctcctg 15780
tctctgccca caaacactgg cattacaggc agataccaca agagcttggc gctacgttag 15840
tcctcaagtt tgcatgtaag tgctttgcct gctgagccgc taagccgact ttccaacctt 15900
cattttgatt tttctaggtc tggggatgca actcatggcc tcatgtatac taggaaaggc 15960
ctctacccct gaaccagacc cctattctct ctccatggga ttctagtcag ggttctacc 16020
actgagccac gccctcagtg cctcactgag ggattctagg caggagttcc acctttaaat 16080
aataccccta gtttctcact gatggatttc aggcaagtgc cctcctgctg agtcggcttt 16140
ccagccccta attagggggt agaggggcag agccacacct ccaacccctc attggggcat 16200
tctagataag cactctactg ttgaagcccg tttcctagct gtctcttgca ttttatatag 16260
attataaagt gtaagttgaa aagttgaaga gttgttttat atttttcttt tgcaaagcat 16320
tgtacaatct tgtatttcat tggatggctt ttgtcagatg ggcacagtct cttttggatg 16380
ctgctggagc actgcccagc agttcccaca tctgcacaag ccacatctgt ttatgagtgc 16440
agctctctgc ttagtgttga aatcaggcgc cttgaggacg ctttgttctt tttctcaatt 16500
gttttgaatg ttctaagtcc tttaaacatt aattttgttt ctatttgttt gtctttttga 16560
gaattctatt tttgtttgtt tggtttggtt ttggttttgg ggggttttgt ttgtttgttt 16620
gtttttgttt tttgagacag ggtttctctg tgtagctctg gctgtcctgg agttcgctct 16680
gtagaacagg ctggtctcga actcagaaat ccgcctgtct ctgcctcctg agtgctggga 16740
ttaaaggtgt gcgccaccac gcccggcaag aattcttact ttgtttctca cactgacctg 16800
gagcttgagc cccttctgcc ttggcttgtg cgtgctggta ttagaggtgc agcaccatgc 16860
ccagctctga atgcccattt tacagttagc ttgtggatcg cttgctctgt ctgtctgtca 16920
ggctatccat ctatcaccca tcttagagtt tcactaagca attctgcttg tcttggaact 16980
cactgtgtac acaaggctgg ctttgaacat cagcctccaa gtactgggct taaagatgtg 17040
ggtccccaac cccagttacg ttgtggattt ctactaaaca aaataaaaag ctaagacacg 17100
atagctcagg gatggagacc tagtcaactg tagaccatgt ttctatctat agcaccaaaa 17160
aaggaaataa aaaaggctgt ttataaagac ccgtcgaagc ctatcctgtc ctaggctggc 17220
ttcagaatca tcatgtatct gagggtgacc ttggactccc ggtgctcttg actttacctc 17280
ccaggtgtta gcatgacaag catgcaacca gcacttaagt ctgtgtgatg ctgaggacag 17340
agctcaggac tgtgtatgcc aggcaagcac ttgaccaagt gagccttagg cccagggagg 17400
gtagggtttt acggtattca tttttctgct tcatgtgcac tgtttgtaga tgtaggtatc 17460
agaggatata gttgcaggtg tgggtaaggt gtaggttctg gccgtcacct tgttggagat 17520
gttcagtgct gtgaatgaca gacatatcag gtggccccag tggggaattc tgtctgtgca 17580
caccaaactc ctattagttt tgattgctgt gctatttcat cagctgtcca cgcccctgca 17640
ttgcctgctg cctcactctt gttcatttga ctccccctcc ctgctcccca tagtaggagc 17700
ctgtccaaaa cccaggagca catggtggtg caggcctgtg ctccagccct gatgctggaa 17760
atgttggaaa cgtgttaagt atattggtta gaaaatagcc actcagaaaa catcagtaat 17820

```
tgtgtaccac aaatgcaatt gtatattttt tctttttttat ttttctatgt agacggggct  17880
gttctcagac tcattacaga ggtccacatg cctctgcctt ccaacatgtg agactaaaag  17940
gtgtgtggca tcacatccag ccttaacaac gtgaaatgcg catgaggggg agtgtgtgtg  18000
tgagtgtgtg taagtgtgtg agagtgtgtg tgtgtgtaag agtgtgtgaa agagtgtgtg  18060
tgtgtgtgtg agtgggtatg tatgagagtg tgagtgtgtg tttgtgtgag tgtgtatatg  18120
agtgtgtgtg ttggtgatga gaggacaact tctaagactt gcttctctcc ttcctctctc  18180
tgtcttcaag atttgacaga cagcacctgc tgctgagcca tcatagcccc cttctttatt  18240
ctattccagc cccaccaagc cttgataatc atccccctga tcagcctgaa cctgtctgca  18300
cttcctgacc accgttgtcc ctcaggccgc tctgtcactt cctgcctcct tcaggcttcc  18360
agggaaatgt ctcttcccca gggcaatccc aagaccctat gctactgtac cattggcccc  18420
cttgtaattt cttttagaaa catttatact ccctctttgt ttgacctaag gtttcttcct  18480
cttcctgggt gtgttcctgc tttgcaggta cctgggccat ctccctgtgt caccttacac  18540
ccacctttgc tttagtcacc aagagtcact cagcaaagga gaaaggtgtg ccctttgcca  18600
cactgtgacc tgggccccac ccagctggac caaaacaatt tgtttagtgc tctgtggagc  18660
tggatctcat tgagacactg cacctacata cagcaaaagg aggggacaag gcctgcctgg  18720
gctttgtgtg gacagcaatt ggttttttttg agacagggtc ccatgttgcc cagacaggcc  18780
tcaaacctag aagaggctgg ccttaaactt ctgatctttc tgcctttact ttcccagtgc  18840
tgggatgacc tagcaccaac cacatctgct ttatgggggc tgaagatgga acctggggct  18900
cctatgtact aggcaagccc agtgccaacc atagtcgtag agtttatgcc gagacagcaa  18960
gtcatgagtg tgtgtgaggc acgagaaaca agccaataca agtgtagagg catgaagact  19020
agtgtgggga atggaatcaa tgtctaatac tcatatatga aaacacaatg tcatgtacgt  19080
gaaggccttt ttaaaattgt aaaagcaagt aagcaacaac aacaagccac caaaaaccaa  19140
tagaaagaca gacaggagaa gccagccaca gaagccacac gaatctactt ggaagccaca  19200
cgaatccaca ggctagctcc ccgagacaga gtggagttgt gcttccagga ggtggcaagg  19260
gagggagtga gtgagcgcgt gggggacgta gagcttgggg agattcaaat gtcctgaaat  19320
cattgagaat ggtttcacaa tctgaatcca caaaacccct agcagccact taaaactggt  19380
ggatctaaaa gcctgtgacg cactttcctg aaagacagtg aagccagagg cagaaagcaa  19440
ctctcccatc cccctgcctt acgcctacaa aagaatgaat gccttgaaga caaaactcag  19500
tgctgaggca gggtcactgg agacaggagc attgccaaga gttcaacctg ggctaaggtg  19560
tgagagaccc tctctcaaaa acagtaggag ccatagataa gagaagcata gattgttctt  19620
ctgagatgga cttagccact tcatggggag ctccagccgg ctccagcctt gcgagtgcct  19680
taggtcctgt gcgcgcacgc acgcacgcac gcacgccagc cactccttcc cctgagtttg  19740
ggcacctcgg ctcatcccac aaccaagctc ttgtggtact gtgtctgtgt gtgtggtttg  19800
gactcccagg agctgcctgt ttggcttcct ctcctaatgg tttcaggagt ccactgtctc  19860
ctgtgctgtg ccaagctccg ggcatttacc aattttactt acttattttt ggggattgga  19920
gattgacctg ctcgcatgtt cgacaagcca ctctggcact gactccatcc taagccctcc  19980
tgtgttttgg gatggaatct catcatgtag tctaatccag cctggcctgg gtcagcgagt  20040
gtactgagaa tagtaaaaga tgccttttag acaggtagaa atagctcagt caggatccca  20100
ctacacccaa ggctgcacct gatagccaga acccagtgac atcactcact ccgaataacc  20160
acagtgctag aaccccatga tacccactgt acagtatata agcgaccaag agcagtgctc  20220
```

tgctctgcac atctggagag atgacacctt gatccgtcat gtggctggag agtctcccca 20280
aggatcctga cccttgaatc agatttccat tagacattag acctgaccct cagctaaata 20340
tgatatgtcg cacaggtgag ttaccttagg gagataggct tagaaagaac ataggaattt 20400
agaaccttgt gtgatgacca tcagcaaaat aaaatataac ttttgttata ttaactacac 20460
atactccacc ctcttgctca aaacactttg gggtgggctt taaggtttca aaagctcaca 20520
ccattcccag ttagttctca ttctctgcct cttgcttgca gatcagatgt aagttctcag 20580
cctacaccag atgtactact ccagtgctat ggctgcctgt ctgctgcagt gttccccacc 20640
atgctggtca tagcctaact accttacctc tctggtactg tgagtccagc tcaaatgctt 20700
ccttttacaa gttgcctttc tttttggttt ttcgagacag ggtttctctg tgtagccctg 20760
gctgtcctgg aactcactct gtagaccagg ctggcctcga actcagaaat ctgcctgcct 20820
ctgcctcctg agtgctggga ctaaaggcat gcgccaccac tgcccggctt ataaattgct 20880
tttctcatgg tgttctgtca tggcaataga caagtaggga agagttgggt gtgtggtaca 20940
tgactttaat acgaccactc cagaggtaga ggctggcaga tctttatgag ttcaaggcca 21000
gcctgatcta cataatgagt tacaggatag ccaaagtatg aagaaagacc tgtttcagaa 21060
aaaaaaaaaa aaagaagaag acattagctg aggcatcttt ttcccctccc ctctgcccct 21120
cctctcctcc cactgattta gttatggttg cttgcaaaag gtgtgtatgt gtgcctgtat 21180
gtgtgtacct gtacgtgtgt gtgtgtgtgt gtgtgtgtgt gtgtgtgtct tactgctcat 21240
gacactgcct ctcagagccc tttcactgcc tgtagcccct gggtgagggg atgaggctca 21300
tggccccttc ctctgagcat aatgaaatgc tggcaggctg gatcctgcac agggcgcagg 21360
gctgcatgta gctgcaggtg tgccctgtcc agaagacagt ttctcagcat tcctccttgt 21420
cattatttta tttgctattt atttatttgt ttgtttgttt aagtttttca aggcagggat 21480
tcttttgtac ccttacctgt cctggaactt gctctgtaga tcagattaaa ggcatgcacc 21540
acaacacatg gcgttgttgt tgttgttttt tgttttgttt tgttttttta tatacagtct 21600
ctctatatag atttggctgt tctagaactc cctgtatagg cctcacagag atctacctgc 21660
ctcttgagtg ctgggattag aggcgtatgc ctggcttctt agtatctttc tttttgtgt 21720
tttggttttt ggtttttggt tttttttttt tttttttttt ttttggtttt tcaagacagg 21780
gtttctctgt atagccctgg ctgtcctgga actcactctg tagaccaggc tggccgtgaa 21840
ctcagaaatc tgcctgcctc tgcctcccga gtgctgggat taaagacgtg caccactacg 21900
cctggccctc ttaacagctt tctgttcctg attccaaatg tttcttgaaa cattggaagc 21960
attgatacag ctgtcctgtt cagatctgtc ccgagcaccc tgcggtcact cttccatatt 22020
gatcatgtcc acatgaagtg ttgctcactg cagaggcttt tctgagagag attgagagca 22080
gcctgaatca atagttataa actttagcac ttagaacagt ttgtcagtta acaggggtag 22140
gttcagctgg gcatggcgga gcatgccttt aatccccaca ctcaggagac agacacgaga 22200
tctctgagtt catggccacc ctgattacaa ttaccgttcc agtactacat agagagaccc 22260
tatttaaaca aagaaacatg ctgggctatg gtggtgcaca tctttaatcc cagcacttgg 22320
gaggcagagg caggcggatt tctgagttcg aggccagcct ggtctacaaa gtgagttcag 22380
cacagccatg gcaacacaga gaaaccctgt cttgaaaaaa caaaaacaaa ccaaaaacaa 22440
tcaaacaaac aaacaaacag aaaccaaaga aacaaacaac caacccctcc ccccaaaaca 22500
aacaaacaga caaaaaacct gtagtcaatt ctcccgcaaa tcctggagct ctctaaccac 22560
cagcttttgg ccagctttac agaaccagca ttgagtttct tcctgtagag tggatgtcct 22620
gtggttagtt taccccagta ataatcctga tatcattgct gtgccagtgg acatctcttt 22680
ccagacaggt tgttctggtg gcctgtgggc cacagccaga aggaccactg atggctttct 22740
tttctcagag gcaacagctg tccattagag tgtggtgtct tcagaggtgg ggctaaccct 22800
ttagctctgc tgggtgacca agtgcagcag ccatagcctg tgatatgccc cgggcctccc 22860
tgtctcctct ggcacaaaac tccctttac gctcacagct tccaggagga agggaactgt 22920
ttgatgcttc cgtctgactt cctgagtcgg gtgaagaatg ctggccttgc agggtgagct 22980
cagaagtgtg ccctccagtc cattctgtgg gagagtctct gaagagctga tgctccttct 23040
cttcagggtc tcttacaatc taccatgaag ttgctgcctc tgggcttttt ggagggaagc 23100
ttttttagta atttttttg tttgtttgtt ttttcgagac agggtttctc tctgtagcct 23160
tggctgtcct ggaactcact ttgtagacca gactggcctt gaactcagaa atctgcctgc 23220
ctctgcctcc ggagtgctaa gattaaagac agcgccacca ccgccctctg cagggaagct 23280
tttgaacact taattcaggc cctttattcc ctttacgcct ccagagactt caccatgttc 23340
agccttttgg tttctttgta attttttcc tccagggttt tcaatttcgc ccatgctgtc 23400
cttttagtct ttttcagata atattttatg agactgaaga gatggttaat ggcacttgtt 23460
ctttaagagg acctggttct cttcccacca cccagttggc agctcacagt cctctgtaac 23520
tctagttcct ggagatctga caccctcatg tggtctctga gggcactgca tacatatggt 23580
gcacattcat acatgcaggc aaactctctt gcacataaaa taaaaataca acagatctta 23640
gctgggtgtg atggagtcag agacaggtag atctctgtga gttcaagatg aacctggtct 23700
acatagtggc tccagactag gtaggctaca gagtgaggcc ttgtctcaaa aatatacaaa 23760
tgtttacaaa tattagttca ttcattcatg atttgtgtgt gtgctagtgt gtgagtgcgt 23820
gtgtgcgtat gtgtgtgtga gtgtgctatg tgtaggagtg tatgtacatg gaggacagag 23880
ggcagcttta gagttagctc tccatcttta tattgcttct ggatcacact caggtttctg 23940
acttgcacag caagcttgct tacctactga gctgtcttga cagcccctct tcctttttt 24000
ttttccattt ggttgtgata ttactacatt tattccaaat cttagcaatc tgagtctttt 24060
ttctttggga aattttggat ctttcctctc ctctcagcgc cccaagcccc cccgccccca 24120
ctttttaaaa aacagaacca agttgacctc caattcaatg tctatgcaaa gatgaccttg 24180
aactcctgcc tcccctacct ctactcccct gtgcagtgct gggattgcag gtgtgcactg 24240
ccctgcctgg cttaggtggg gcgagggata ggacccaggg cttcctgtat cctagggggg 24300
cattttacct ttggaacccc aggccttgag gctttggtct gtttgctttt aattcttctg 24360
tagccatcag gcatagcact gctgacgctg gccacattta ttggcatttc ctcaattccc 24420
tctgtcttag ttcttcctta gctttctgct gaggctaggg aacacatttc cctcccctcg 24480
agcccgccgc tctctgccac agctgagcac gcagtctctt ttggagaatg ttctctgtgc 24540
ctttgagggt tgggaagatg tccgagtggg caaggactag tttggtgtgt gaaaggccct 24600
gaattctagc ccatcttgaa gggaaaggag gaaaagtaga caaagcccag agagtgggct 24660
gctgcttctg gatttgggca caaggctttc tttctgcctt gttgctttgg gtggtattca 24720
ctctgaatac tcttgatgtc tactcatccg tcattccagt ttctttcctc tttattgcca 24780
gggagtgggg gatagacagg gtctcactgc ttccctctgg ctggcctgga actcacagag 24840
atctacctgt ctatgttttt tgagtgctat gataaaggtg tgtgccaacc tcatttgttt 24900
ctttaaagga aaaaaaaatt tgttaagctg ggcagtggtg gcacttgcct ttaatcacag 24960
cactcgggag gcagaggcag gcggatctat gagtttgagg acaacctcgt ctatgaagag 25020
agttccagga cagccagggc tacacagaga atccctgtct tgaaccccac tccctccaaa 25080
acaggatttt aaaattttgt gtatatgagt tttgcctgc atatgtgtat gtatagcaca 25140
tgcatgtccg tgtctgagga gaccaataga gtgtgctggg tgtccttgga actagagtta 25200
caggtggtat gggtgctgtg aatcaaaccc ggctcctctt aactgctgag ctagctctcc 25260
agcctaatcc cacccacctt ttgtgtgtgt gtgtgtgggg gggggtagta gtcaggctgt 25320
ctctctatat aacctaggct aatctggact taaactattt ttgccatatt cctctggaat 25380
acaggcatcc taggtgtgtg ttactcttcc tggccatttg tcaattactg aaaagattgt 25440
cattgtccat gcaagccaga ggagcagact ttgggccttc agagcttgca tgaatatctg 25500
cgtaggtgta gttgcctgct ttcattagga gggacacgca ggtaggaagt ccctgaagac 25560
gctgactggc tagatgagca gacctacaat ctctgtattc aggagagaca gacacctcct 25620
cagtaaatac ggtggagggc agtggaggaa gacaccgacc tcagcctgag tccgtgtgct 25680
caggtacaca cgtgcactct cacatcaccc acacacaagc aaaagacatc cacaccgatt 25740
gcattaccta attccctggc cagttctttg acatatcaca tggcattcct tgactttgcc 25800
tcacccacta tctctcatca ctgtcttacc tggacttctg gttgttcttg gttgtcattc 25860
tcctgacagt gcctgagggt caccagactt gtgtgagctg aaggacctga aggaagcagg 25920
tgacagttga ggaggaagca ggtttaaggt ggtgttgagt cacctgacag gaaaggctgt 25980
gctgatgtcc tcacaggggt gccaaggaga agggcatgtg cttcttgtgg ttcttggagt 26040
tgacatcccc ccccagcccc cacaccattc attgcctttg tgacagcacc ctgcacatgg 26100
ccgacaccac acctcgattc ctgtgccacc tctgcctgct tctactggtg tcctaaggac 26160
atggtcacat gttaggaccc catctgcagg tggagacact gtgacagtga tgtccttgtg 26220
caggtcacac atggagagcc tgtgactgaa acatcaggct ttagactcta cccgtggcca 26280
cccatattct taattggtgt caggaggaag cggcaatggc ctcctgtgtt cagagttcac 26340
tggcgtcttc ttaccctggc tcccagatgt gctggggatc agcagacagt gctcaaaagc 26400
tgagggcagg gttgcagcag tttagctggg ggtctcagtg ctcggggttt ttacctgtgg 26460
ctttggtctg agttacttta acctgaagct tcagattcct tatctaccag atgtgagtag 26520
agaaagccgt tatgtgccgt tctagtacag aataccaagt caggggggatt cagggttcag 26580
atcagctgga gctacatttt gagactttag acaaccaaaa gacaaaatgg ggacaggata 26640
agcctcttgg gagtacagca agagtccctt gttcatagtc aggccagctc ctgtggggtg 26700
tgtgtaccct atacaggcca tttattagca ggtgtttgtt tgttttttgt tttggaatgg 26760
gttcatgtag cctaggttgg tctcaaactc agtttgtagc taaggatgac gactactgat 26820
cttcttgtct ccatctgagt gctgggatga aatgcgtgtg ctgccatact tattttatga 26880
agttctggtg atggaactca ggcaaacaca ttgcccgctg agtgccagac agtactggga 26940
catggttccc tgtccttgtg gaactgacag gtaggttact tcagaactgg gaggcaagaa 27000
ggacgtgtga ttgctactgg aggacaaaaa tccagagaca aggggggggg ggagcagggc 27060
agctgtcaga ggagcgtctg caaaggggtc agcctgtgag gtgaatggct atggaatgtt 27120
ctggtggtcc tccctaggga acagttgaac ccatagagtt gggaatccac atccaccagc 27180
catctaacac agaagctgcc acagaaatgg cgatcgctct cagttcctcc cttacgctgc 27240
cttttacaca gcacagcacc tggcccacga tacaaaagtc ttctgccaag gacacagggc 27300

-continued agggctagac atggacacag ctcttccacg agcaggtctg agacatcaag ggccctgaaa 27360
gggcggagtt gagagccatg gcgccacagg tcagacagct tccctgtcat tctgtaaaat 27420
gtttttagct attcgataca actggatgat gacaggtcag atatttgcct gttataaagt 27480
tataaattga tctgcaatca cctggaattc gcatcacctt ggagactgca acataacttt 27540
tgttttgttt gagatagagt ctcatacagc ccaggctggt ctttaactaa cagtaatcct 27600
gcctcctgag tgcaagaaat ttcagatata tacaaccact ctgttttctc atattttttt 27660
aaggcagggt tttgtggagc ccagctggcc tcaggcttac tgtgtaactg aggataacct 27720
tgaactccag atctaccggc caccagtgag tggtggcatc acatgagggc caccacaccc 27780
agggaagcag gtgctgtgtt atcctgagtc catgtgccag ctgtctccct gaagaaagga 27840
tgcaagcaga tgacctcccc cgaggctggc ttagtggcta tcatgcttac ctggcatgca 27900
caaatctctg ggctccatct gccagccaga cacagtgctg cacacctgtg atcttagcac 27960
ttgcagaggc aggagatcag gagtgcaggc tcttactcag cttcagagag gcttcaaagc 28020
ctaggctgca tgagatccta cctcaagata aagaaagcaa accatcaaac acaaaaacat 28080
cccaagtatg gagaagactt cctccataca gagcgtactc tatgctccac atactggagg 28140
gtgccaggcc ctggactatt tctcagaccg gttgccttag cctctcctgc tgggtggaca 28200
tataggtcat tagtggcttt ctcttggaca tcttgctatc tgtcatggtt acctcatgtt 28260
agcagtgact ggtctttgac tgtggtgtct atgtcctgga tcagtgtgct ggggagcaga 28320
tctctgagga gaggggcctc atctcctgtc tattctggag gtgttcatgt tctgctgcag 28380
ctgatcatct gacaaagtga ggaaaaagaa atctggcagg gcccggtggg tgttggctca 28440
ccaggaagca gctagacctc tctgaggaag ggacaaccta gctgagccct tagtgtacac 28500
aggaaactag agctgtcata agaaaggtca ctgtgtgagg ataaacagag gccctgaggc 28560
aggaagatgc tgtgctcttc ctcctctcaa cccagctcca gggaatcgat gggggagtag 28620
tggctgatcg ttgagtaata ccaaggcctc caaggccctt ggggggcagg tggaaccccc 28680
tgaaagttac aagcagagga gtggttacag gttgctccaa gtttactttg gttgtatagg 28740
atggatgctg tcatgggtgt gggtgtgcct gccagaaatg gatgatgggt ttcttttgct 28800
gtattgtcta ccataggttt ttagactggg gactttactg agtctggatg gagttcatca 28860
ctttgggctc ggctaatgag tcccataaac cccaggggtc tttctccatg ccccaagtgc 28920
tgggaggtgg gcatgactgc ttgactttgt gtgggtactg gggatcctca cctgctcctt 28980
cctcacgatt gtttggtgga cacttagtga ccaagccatc tccctagccc caagaatgat 29040
gtatttttag atagtatggc aaaaacttgg taatcctaac ttccctttgg ggcaggtgtc 29100
attgtgcctg cttaaccaac aagaaagctg cgggagggct ggtgagatgg ctcagtgggt 29160
aagagcaccc gactgctctt ccgaaggtct ggagttcaaa tcccagcaac cacatggtgg 29220
ctcacaacca tccataatga gatctgactc cctcttctgg agtgtctgaa gacagcgaca 29280
gtgtacttac atataatcaa taaataaatc tttaaaaaag aaagaaagaa agaaagaaag 29340
aaagaaagaa agaaagaaag aaagaaagaa agaaagaaag aaagaaagca agcaagctgc 29400
gggagctaga ggtggcccaa ctgaccagat tgtccaggaa cgttctagaa gtaatccagt 29460
tctggattac atctgggcct tgaggagttc tggagtcaca gccaccaaga cactctagct 29520
atttcctgtc cttgttcccc gcccaggctg gctctcggat gtgactgtga gcaggtggca 29580
ctaggcctga gtgccaaggg tgggactgat ttgggtcctg ccggattcct ggctagggag 29640
ggactgctgg gcagaagctg ggtggtacgt ggtaagcagc gccagaactg aactcacatg 29700
gccaggcagg tgccgggttg ccactaccac cacctgagct tcagtgtcct tgtctgtgaa 29760
atggcagagt cagtccttca tcccacctgt tttgttccca attctgggtc agtagaaggg 29820
gagattgggg agagcaggct tggtcctgcc atgatgtggc cgctgctggg atagaagcat 29880
ggtgtaggga cagacaggta gggaggaaga ggcttaaggg gcttacagtc agatttggcc 29940
tgtaatgggg gaagactgag cctgtgtggg caggcaggga tggcgttgat aggagcaggc 30000
tgtgcgtgca gagtttagca ggcaacagga aggcttcacc ctgtcacttg agaagagaca 30060
cacccacctt caccagaggc cctggtcagt ttgccagaga tagcaggtgg agcttatgcg 30120
gcatgacctc taatctcatg gcttcaggct ccgaggtctc cggaattacg gagacgggga 30180
agggtctcca cgcaggacct ttacctacat cctgccaggt ttctcaagca atggctgact 30240
catccttcct tgcttctgtt tggcttccct ccctggaggc ctggagaccc acctccagct 30300
gttggttcac atagctgtct ctaccttctc cactctctct gtacagaaaa aaataaacag 30360
acctgggttt tggatcagcc gttgtgctac ctctttttttg tcccctccca ggagcccttt 30420
tcatcctcca aggggcctaa ggcttagagc cctagaggct ctgaggagga aaagctgttt 30480
acaatggtcc ctgtcactag tcctgtgaac ggggatgtcc tcctatgcca taactgagcc 30540
actgcccaga gagggcctga taaagagccc tctctgggca gtggctcaga tgccttctgt 30600
ctcttcaata acattgaatc ctagcagccg acactgattt ataaggcact gttcaagctg 30660
ctggtgactt gaccaaatgc aggagctctg atctgttaca gaaccaacta ccatctgtct 30720
gaggctgaac tagcaggagt gggaaggaag gaaggatagg ctctcaatac agcctctgac 30780
tattactagg tgggcagtcc cctagggaag ggtggcttgg cagaaacccc tgcaaaggtc 30840
aatggtttgt ggcgagagcc actagtgaac ctagatagtc tggagacccg gactgtattg 30900
gtccagctct gagtggacac aagacctttg tagaaaagct ttctgaatat ctgtgttggg 30960
gaaggggtat ttgtgtgtgt gacttattaa catactggcc tagcattcgt gtaaagcctc 31020
aagtccatca gcactacata aacatggtga tgcacatgtg taatcctggc acttgggaag 31080
tagagaccgg gaaggttagg agttacaaac catcctctgc tccatagggt ttgaggccag 31140
cctgggctgc atgagtcact ctgccaaaga aaaaagggaa ggaaacagaa ggaggcagct 31200
ccttttcgga atgagaaatg atgcaacact ttacacttaa ctgaccacct accatgtgct 31260
gtccctgtac caggcctaga gaaatgatct tacgtttacg tatcgaggtg tggatgtctt 31320
tgagccagag ttctcgacat cccccacaaa tttgttgcca tccctcacag ttggcagagt 31380
tttactaacc aggaaaccca gacctgagag agaaggaagc agacccacgt cgcatagcac 31440
agaactggct aagtgggact agaacgttag ggcagccagg acacacagga aaggtcatag 31500
caacagctaa gaaaagtact caggcctgtg gaggcaggtg gcctggggaa ggaagaacta 31560
gatagctgga ggctattgct gctgccagct aaggacagtt ggcatttgta ggagagctgt 31620
ctgggaagcc atagtgtgtg ctctgctgca ctgcccagga aatactcttt aaaaaaaaag 31680
aagaagaaga agggctggag agatggctca gcagttaaga gcactgactg ctcttccaga 31740
ggtcctgagt tcaattccca acaaccacat ggtgacatgc aaccatctgc actgggattc 31800
gatgcactct tctagtgtgt gtctgaagac agctgcattg tactcatata aataaaaaaa 31860
taaacacatc cttaaaaaaa gaatttttta ttttatgtat gaaagtgttt tgcctgtgtg 31920
tgtgtgtgtg tgtgtgtgtt tatgtatcat gcctggtgct tgagatcaga aggtgatgga 31980
ttccctaagt tagagatggc tgttagtcac catgttgggt gctgggaatt gaacctgggt 32040

```
cctctggaag agcaactagt gctcttaact gctgagccat tgctccaact acacacacac 32100
acacacacac acacacacac acacaccca ccctttaaa aatagatttc tttttattta 32160
tgtgtatgag tgctatatct gtaggatgcc agaagagaga atcagacccc attatatatg 32220
gttgtgagcc accatgtggt tgctgggaat tgaactcaga ctcaggacct ctggaagagc 32280
agccagtgtt cttaacggct gagccatctc tctagcctct tctcttctct tttctctctc 32340
atttcctttc cttttctttt cctttctttt ctatgaaaaa cacgcacaca cacttttttt 32400
ttagactaag ctggccttga atttaaagag atctgcctgc ctctgcctcc cagttgctgg 32460
gattaaaggt gtgcactgcc accccccacc tgtatcagac acccattttt ttaaaacagg 32520
agaaagaaaa tgttagattt ttattttacc tatcttatct agatgtctag tgtgtgtgtg 32580
tgtgtgtgtg tgtgtgtgtg tgtgtgtgtg tgtagaggga tagtcttggc atggaagcag 32640
tggagtctaa aggacaactt tccagagctc tgtccttctt ctttgtgaaa cttaagtctt 32700
caaacttggc agcagatgcc tttacccccct tagccatttc actttgctta gtcccagggt 32760
tcagggaaac tgcatgacgt cagctctggc tgccggctcc cagtctgccc agtgacatga 32820
ctgctgtctc ttacttggct tctgccttct ctgttgtctt cccgattgac caccaaggcc 32880
ccagtctttc cttgtgagaa ctggagcttg ttctgggcat cacagccgtc accattgaaa 32940
ctctctatat cccttgtctg ggacagaggc tggtgatgtc tgaggcgtca ccattgtcct 33000
caggctgcct gacatctcag attgaccaaa tgtaaagtca ctgcactgct gtgttatgtg 33060
ttactggtcc tggagagggg gggggggtgt tcagggacag attcaccctc tgagaggctg 33120
cattgtagac tagaagctga gattctggga cctgctgatc agggtcttca gatggacctc 33180
ttgtgattca gtctgagttg ctgccattgc tggtgcaccg cagccttggg cagggcccag 33240
tctctgcacc tcactcagtt ctctgagaag aggcagctga gctacctggg atctccctgc 33300
tgtgctgtta aatccacaca gtgctctact tcctgcttgt cacacctgtg ctactgctcc 33360
acagtgccta cagagtattt gactaaatta gtgaattgat ttagtttagg acttttgaga 33420
cagggtctca actcaggctg gtctataact ctctgtagcc aggtatgacc ttgaactcac 33480
tgaccataac tgtttacaga tttacaacag ccatcattgt tgaggaagag ggtgtctcct 33540
ccctctcatg cctcgctcct tgggctctat tgtagttcag tggtgttttc tttaagatca 33600
aaacaaatcc tccttacttg gtccacccag gaggaagttc cttcgagaag ataaaagact 33660
ctttttcttt tatgtggctg actgcctaag cttttggatg ggtgttagta ttgacctaca 33720
ccccccaccc cccactaatg tcggatgggc cttcaatatt gacctacacc actcccccta 33780
cacctttcct cctgtcggat ggcccatcag cacacacaca cacacacaca cccgctgagc 33840
tgtgaagctt ttaacaggtc atgcctcttt tatttagtgt gtgtgcacac atatgtatca 33900
gtgctcctgt gtatatcgtg gtgcatgtgt ggaggtcaga ggaccacttg tgggttggct 33960
ctctctttcc accatctcag tcctgggcat taagctcagg catcagcctt gctggcagtg 34020
gactttcttc ctcccctctc ctgtctttca ttcctttgca gtgttgggga tggtgccatt 34080
agctgcccat gctagcctgg tgctgtgctg ctgagctgta gccctagttg atgaggctga 34140
cctggcacct gtgttgtagc caaagtcaac cttgacattc tgagtctcct acttccgagt 34200
tccctcctgc ccctcagatt gtcacttgtg tctctggaag ccactcagcc agagttcttc 34260
ctgagcctgg gattcacaga cactctgtat ctatttgcaa attcttcccc cccccccca 34320
cagggtttct ctgtgtagcc ctttgtagac caggctggcc tagaactcag aaatccgcct 34380
gcctctgcct cccgagtact gggattaaag gcatgcacca ccacgccccg gcagtaatga 34440
```

-continued

```
acttttgac cctcctatct cctatgccct gctagtgacc tttcttgaga gacacaatta  34500
agtatgcatc gtaaatacac accctgattg ttctgataac tttaaatcaa aacaaaacaa  34560
aaactgctga tcaccgtaca gatcagcatt gaggctaatt tttgcctccc aagaaagttc  34620
agttgtgtgt cttcctgcct gttcctccaa ggaaaagcct ttgccctgat tcctatcaca  34680
aaagatcagc tttgcctgtt caggttcaag tctatctctg tggtagcttg taacctgggc  34740
cacatgtctg agaagatgtg catggctcca agacagccat actcttctct ccctcttctc  34800
ccctcccccc tctgcctttg tagaccaggc tggcctggaa ctcacacctg cctctgcctc  34860
tgagtgctgg gaataaaggc ctgcgccacc aatgcctggc agctatacta atttttacac  34920
ctagttaggg agaccacaca gggataactg tgggccagcc atgcagcagt gctgatggtg  34980
acctaacttg ggatttttgg cctctacatt agctggtata ggcattagcc accatggcca  35040
ttttcttccg tgctgggaat cctgctgggg aagctctcta ccaactgagc cacaccccag  35100
cccttgtttt attttgagac agcttcttgc tgtgtagtcc tgtctggcct gcctcagctt  35160
ccagggtact ggggtgactg gcggttgttt gttcggttgg ctttgaactt gatccttccc  35220
cagtctttct tgtggctctt ttgccatggg caagattgtc tgaaatacaa tgcaaggagg  35280
gcttagtgga agtgctagag cagattgtgt gtacacagct ctgtgtcttc ctacttagtt  35340
caggtcccct gcagaccttg ggctgcagag cctcggtagc cgagggcttt ccaggaacgc  35400
agctggggtt ggtgcgtttg ttaaaacttg caggaaacag ttgcctagtg cctgtggtca  35460
ccagcagcac tgagtcattt ctgctgcttt ctcttctccc agggacttcc ttccacgagg  35520
atcaggaatt gtcacccgga ggcctctcat tctgcagctc atcttttcca aaacaggtat  35580
gagaaataga aattcaggga ctggagagat ggctcggtgg ttaagagcac tgactgctct  35640
tccagaggtc ctgagttcaa ttcccagcaa ccacatggtg gctcacaacc atctgtaatg  35700
ggatccgttg ccctcttctg gtgtgtctga agacagcaac agtgtactca catacataaa  35760
ataagtaaat ctgtaaaaaa aaaatttaaa aaaagaaaag agaaatagaa attcaaaacc  35820
aagacaaagt agaaataata agtaaagcga gggacgcaga ggtagcagct cgtggacagc  35880
tccctggcat gtcggaagcc ctgctttcac caccaccacc accaccacca ccaccaccac  35940
cccccaccac cacccccacc cccccacccc ccccaccccc cccgcccagc agaatgaacc  36000
tggcctgaag gtgcatagct gtaagcccag caccgggaat gtgagaaggg ctagacgctc  36060
caggtcatcc tgtgatgcat agagagctca gggccacctt gggctacgga agagcatgtc  36120
ttcaaacagc agcaataaat tgaagaacac ccttctacaa ccctgagtcc ccaggcagga  36180
ccaggctacc tggtgcccac agttactttc tgatttattt attttagttt attttatttt  36240
tttgagaagt cttgcctggc aaccagaatt gctgccttgt actttctgta tggtcataga  36300
ccagccccaa ctggaaggac cactgtgcct ggtatttgag gcttgatcca tagtctcatg  36360
ctgccagttg ctcccagtat ggcatgttaa tgaatttaca gatgggaact gaggcccagc  36420
caggttacct gcgtttttag gggccactg gcctgggatc ctcagccaat ccagtgcggc  36480
ctgacattcc agggccctgc agttgttctc ctgattctac cagttaggcg tggaggggag  36540
gctccagcgt aagctgctgg tttggtgtgc caaccacagg atgggctgct gcctcttcca  36600
tcaggcttgt gctcagctct gctgccatag gccctgacct ctatccctgt gcttgctttc  36660
atcgccttca ggggttccac ctcaccttag aaatccctat tttgcacttt ttccttttgg  36720
ctttttgagg caaggtttct ctgtggctgg cctggaactc actctgtaga ccaggctagc  36780
```

-continued

```
ctcgaactca cagtgatcca cctgcctctg cctccaagtg ctggcattaa agctgtgcac  36840
caccactgca tggcttactt ttgtactttt tcatggaaca tcagctgcca ctgttgctgc  36900
tcctggtccc tggccaccct gggaaagcct gcatggctgc agagaaggga gccaggcttt  36960
cccgggctcc tgtcttccct ttgtaggtgc ctgcaaagtg cagacaattg gaagacttgg  37020
ttgtgtgcca ggcttgttat acctgcaggt tggctgctcg tcagggcagc tggtgcccgg  37080
gttagcctct ggttctcttg gacctgagtg ctaggataac agtgctaatg agccactgta  37140
tgtgacttta ttgtagtttt atttattttg aaaattttta tatattttta attgtatgag  37200
tgttttccct acatttctct ctgttcccat gtgtgtgcct ggtccctgta gaggtcagaa  37260
gagggtatca gatcctcagg ccttgcacat ggtaggcaag tgctctgaca tacatcccta  37320
gcctgttgct tgcttgcttg cttgtttgta cttgttagct caggctgacc tccacttgta  37380
tctgggggtg accttgagct cctgatcttc ctgccttcca ggtgctgggt gctgggatta  37440
taagtatgta ctgctctgcc tggttcatgg ggtgctgggg atggaacccc agaattcatg  37500
cagactagat gagcactctg agccatagcc tgtcccacca actgtgtatt ttcacttctt  37560
ttgagacaga gtctcacttt gcagctaggc aggatttgaa ctcattgtat tccagatggg  37620
ccttgaactt ttgattctct atatgaacct cctgagtagc ggggacagca tacccagggc  37680
ctgactggca tgtacaggga acactggggt gctggtggct agcagacctg ttgtgttttg  37740
agattccttc attgccagag tctactggaa tcctgaggtc tagggtaggg ctggggagaa  37800
gaccatgaaa ggaacacctg cccagagctg gcctgcataa aggatcaagt cagtccctga  37860
ctttctccat cttcaaggga acacaaacgt cccacctctg cctgagttta ctacttagat  37920
ctttgttgga acttaccttg gggataagac cagacctgta tagctatggt aagaagggac  37980
cttagactag tgccaaagtg ggtcacatgg gaggaggcat ggctgcttag ggcaaggtga  38040
cagttatagg ggcatagttg gatctttttg ggctgagagg acaggtgtgt ctctcaggtg  38100
tgttctgtcc tgtgtcccct aagcttgaat gcctctgacc ctttgcctaa tggtggcatt  38160
gcccatatta tgcacagcct tggtgggaca ttggaaagca gccctgtgtt tctgtcacat  38220
gtgttatgtt gtcaccaggc tgccccactt ccccacctct ggcctaatag atgctgcaga  38280
catgcattca ccacactcct ctggctgaaa agagtgtatc tgggctgttt agagagcagt  38340
agtgtgtgca gaggtagaga ggccagagag ggaggtatag ctgagcccca gagatcatga  38400
gttcctcaca ctgaagcttg ggacctaagc tacagagcca gggatttggg cagacagctg  38460
ttcactcctg aaaggttcag gagtctaaag atgaggcttg tgaggccaag cgtggtcttc  38520
cccttcagta ctttagacac ccaagtgctt gggagcttct tgttcagact ggtctgttga  38580
gccttgagta gtagctggta ctgtttaaaa attacctaag agcacaggca ccaggaagct  38640
tagtggccca tggatgaacc ctgcccttac ccagaatcat cctgctaaac tctgggtaca  38700
gggcttttct ctcccatcct cagccttcgc cttgacctgg cttggtctat gatcgatggg  38760
ccataaaaga gatgtcagta catagcctgt gcttgccaga gcccagcctg tcttgctctc  38820
caaacacagc catggctcct caccatgttc cacagggtca cttgttagat aaaactgtgc  38880
tttcttgagt tgaattttgt ttaagactga atctcatgta gctcaggctg gacttgaatt  38940
tgcttatacc tgaagctagg gtctaagaaa aaactgagct tggagcaggt gtgactcaag  39000
ttgggggcta gttgtaataa ctgcttcttg taatcatagt agcagtacat cttagacaag  39060
gtgacagtcc ctactggtct caaatctgaa gaagctatag gctaaacagg agtagtgaat  39120
gtgtgctaac gctcctgtgt aaggctctga aaaatccttc atgcacaaat cctttagact  39180
```

```
gttctgtttg tttgtttgat ttttgagtca gagtgttggg taggccagcc tcaaactcaa  39240
tgtgtagctg atggtgagct tgagcctctg ccccatcctg ctgcagtcac atgagcatgc  39300
cgccacatgg ggttcatgtg ctgctggcat caaaaggttc tctaccaaac tgagtcctat  39360
cccgtcgtgt ttttcagatc tattgttgta aggtgcatgc gtgtggatgc gtgtagagtc  39420
cgtggtgttg gatcctcctg agctggagct gctggtgtca tgagcctcct gacaagggtg  39480
ctgagcacca ggcagtttcc ctcaggagca gtagtcagtc atgactgtcg ggccaactct  39540
ccagcctcct tgtggtttgt ttgagactgg aacttatggc cttcattcga accctcaagg  39600
ttcacagaag gttcacagat cctatttggt tgttggttgt gtccgagggt ctttaacatg  39660
tgtctgagca cccaggcatt cttgtccaga catgcatgcc aataccaaat ctgaagaagg  39720
cagaccttgt gggcgtgggc atcaggagcc tgtcaccatg gtttcctctt tggtgggctg  39780
tgattaagtc ctgatccttg tgcttccatc ttccaacacc tacatacatg cttaagaagc  39840
agaagcaggt gctggccagt gtagtgagtc aagcccagcc cgttatagtc acacccatgc  39900
aggcaggtag aagctcctta gaaacccccct tcccagttca tttcctgggc acacagtgat  39960
gctgcccttg gggaactctg gcaagaaggc tggctggccc accaggctta gcagaatgtc  40020
tgctgacccc ggctcacctt tggtttcttc ctttatccct gctgtgtacc aggccctggg  40080
ctgaggcctg tgtagcctgc taagaggccc caggggagaa cctaactggt tcactgtgca  40140
gggaagggca gggagaatcc actctgctgc cagtggggat gtggctatca gaatgctgca  40200
gtgctggccc aggggccagt ggaacatggg gacctggatg agcagagctg tcaatgacat  40260
agaggtatgg cctgggctac tgatgaccaa ctggcaggca gctgaatcca gcacactttt  40320
ttttttcttt gagatagggt ttctctgtat agccctggct gaccgggaac tcactttgta  40380
gaccaggctg gcctcgaact cagaaatcca cctgcctctg cctcccgagt gctgggatta  40440
aaggcatgtg ccaccactgc ccggatcaca ctttttttata taacatttga gcacatgtat  40500
taacaggggt atttttggaa gcagggtctc tttctgcctt ggaattatgt ttaaagtggg  40560
ctgactggtc tgtgagtccc atgtgtcttc ccagcactag gtgacaaaca ttcactccca  40620
catctgtctt atttttgtga gttctgtaaa ccaaatgcag gttctcagga ttgcatagca  40680
agcactttac cgactgagcc gtcagccttg agagcttctt ttcaaggcaa ggctttgctc  40740
tatagcccag gctggcctct aactcataat gctgcctttg gcttccgact gctcctgcag  40800
gtatgagctg ctccagcgag cttaaagcgg gcatttatgt taggacctgc caaaggtatt  40860
gtgtggcttg tatcagtggc atgccctctc tggattctct cttgtgttaa gagagggaga  40920
tgacacagcc ttttacccca gcatttccac attgcacctt ggggctctct gctcattaat  40980
ggcagagatg ttggctgcct ctcttctctg tcttcacaca catttgtttg tctgttctgc  41040
tgatcaaggc agttgaggtg aaggtagggc cctccagagc taattacgct aacaattgta  41100
gcaaacactg ggtgcctgcg agctgctgct gctgctgctc tgctgccagg ttccagcccc  41160
acaaacagaa tgcagatgat aaaggaggcc aaggcagaat gagtggcaag cagggagagg  41220
gagaagggaa ggagccagcc cagccctggc cttggtcctg gctctgctac cttaccctgc  41280
caccatctca catttgctga ctgccttgat ccggaagaga actgaagttc tgtgggggct  41340
gggtgactga tccattttta gtggcagctg caggaagagt atttccgctt gtctcctgga  41400
aggccagagc acggctgccc ttgggaagtg ggtcagctga ttgtgtgtgg gctgaggggg  41460
agtcccagag cctcctgtcc acaccctcac tggccctgct tctagcaccc atgctagaca  41520
```

gagccggtcc tgctgaggtc atcgggtttg agagtcactt cctctacaag gtgtctgacc 41580
tacccagtcc cagcaccacc ccatgtcctc ctgagcctca gatgccatgt ctgtgtgtct 41640
ctgtgagtgt atgctatttg tgctgatgtg cacctgcctg ctgcagagcc tggagaaggg 41700
aggatgtcag gtgccctctt catccctctc cacttgttcc tgttttgttt aaatcagtat 41760
aaccttggcc tgccttgaat tcatagcaat tctccttgcc tctgcctcct gagtagtagg 41820
attaaaggtg tgcaccacca tgctgggact tggaaaccag caagccccag tgagccgcct 41880
cttccccatg cccttttggg ctgagggtta tgtacgtttg tgggatgcct ggttgtgggt 41940
gctgggatcc acatttctac ccttgagttt gcacaacaaa cttctgagtc atctctagcc 42000
acatgctttg tagttcttaa gtcagggtct cacagtagcc caaactggtg cctgccagtc 42060
tcacattcct aaaccctctg cctccacatc cctagatctg gaattacagg cctggattac 42120
aggcccttgt taccatactg ctgtatgcca tgctgggtgc cccaggctcc ttgcatgact 42180
gccaaggccc tgcttgtgga gagtctttcc tgccaggcat tctggccctg agctctttgc 42240
attctctctc tttccagcag ctggccctgt ggtcctgtac tccggatggc caggtgactg 42300
tttcttagat gccccacaca gcactcatcc tggctccttc tccctgcagg agaccttgct 42360
gcctcagagt gtcaaccaga gtgtgttctt gcaacctttg agacaagact tggcacctcc 42420
ccagccttta actgagcaaa tttaagcatc tagatcccag cctggcagct gatgccttca 42480
gttcaaacac aaactcctgc tcatcttttt gtcttttgtc agacagattt cctgtgtggc 42540
ccagttttgt ttgttttttt ttttttctg agacagggtt tctctgtgta gccctggctg 42600
tcctggaact cactctgtag accaggctgg ccttgaactc agaaatccgc ctgcctctgc 42660
ctcccgggtg ctgggactaa aggcgtgcgc caccatgccc agctctgtgt gacccagttt 42720
atctcacgct ccttcctcgg cctcttaagt atgaggtttg caggtgcatg ctgcagtacc 42780
cagctcttct cactgaggtg atggggtctc aagtgtcact ccatcccgga ccacacactg 42840
agctccactc tagcctggga ccaaatccct ttatcaaaaa gaaaagaagc tgtcagtaaa 42900
gagttagtca caaagtatga ctcagtactc ttataacagg ttggttgttg ggtgcacac 42960
ttgtaacccc agcgctgggg tggttgagat ggaccggctg ccagccagcc tgggcaagct 43020
aacgagctta ggctctgttc agaggcactg tcacaaaagc aatagaggaa ggctgtgagg 43080
ctgactctgg ccaccacagg cctgtgtgct tgtgtgcatg aacacgtcat gcacagaagc 43140
agagcagaac cggtagtaca cactttttt ttctcgattt ttttcgaggc agggtttctc 43200
tgtgtagccc tggctgtcct ggaactcact ctgtagacca ggctggcctc gaactcagaa 43260
atctgcctgc ctctgcctcc caagtgctgg gactaaaggc gtgcgccatc atgcccagct 43320
aatgcacact tttaatccta gcaaagatga acaaaggagt gcaaggccgg agctgcttac 43380
acagtgagac tatctcaaaa tataaaccaa cccaataaaa taagagaaag aatgaacgcc 43440
gtgttcctca agttctgcag gactgaagtg gttgcatttc ttcctctgcc tggcacatgc 43500
ctggcacatg catgacactg catgtccttg tgtattctcc tttccctcct tctcaccttg 43560
aacatctttt tcccataaca gaatatgcgg aatttttgca ctgcaagtcc aaaaaattta 43620
cagactttga tgaagtccgg caggagatcg aagcagagac tgaccgggtc acaggcacca 43680
acaaaggcat ctcccctgtg cccatcaacc ttcgggtcta ctcaccacac ggtaaaggcg 43740
gggttgggat agagggaagc tggtactctg ttcctgtcca gtagggtctt cctgagcatt 43800
tgagaagagc atcctggact aggaaggctt ggacatggtg ggcaagagtg ggcataggca 43860
catgcctata accccagctc tggggaggtg aaggacagag gacagaggaa gaccccatct 43920

-continued

```
ccaacaaaag caaaaaacat tagacccagg ctcagtggtc aggcacttgt gtagcatgca  43980
tggaatcaac ccccaggacc acatttaaca taaaaatgaa ccatgagtgg tgttgtgtat  44040
accactaatc ccagcattca gtagacataa agactgtatt tgaaactaat ctcctctaaa  44100
cttttgtaaa aagttttgtt ttaatttttt ttaaatttta ctttatgtga gtgtactttg  44160
cctggatgtc tgtatacata ccagtcacat gcctggggtg cctgaggaag tcagagaggg  44220
agtcagaccc ttggagctgg acttatcagt ggttagaagc caccatgtgg gtgctgggag  44280
ttgaagccag gtcctctggt aaccactcag ctgcattctc tttactgtag ttctttacat  44340
tttcttttct ttgtgtgcat atgtggtgtc acattatgtg gtgcacatgt ggaggtcaga  44400
ggacaacttg aagaagtcaa ttctctcctc cttccatgta ggtcccagta atggaactca  44460
ggtcgtcagg cttagtggaa ggaatcttta cccactgaac tctatcactg accctattta  44520
ttttctgtct ctccctttct ttcaaaacac agctatgtag cccagactag cctcgaactg  44580
cttctatggt ccagttgacc ttgaattcct cgtcgccccc cccccccccc gttcctacct  44640
ccccagtgct gcacttatag acctgtgcac ccagacatgg tctctgctgt gctaggaatg  44700
caaagcagag ctttgtggat gatgggtggg tcctggacca cctgggctta tagcctgagc  44760
tacatggtga gttccaggcc agtctgggct acataccgaa cccctgcctc agaaatgaag  44820
aaggtatgat gggaagacac gtggcttggg aagtagagtg cttgctacac aagggaaagg  44880
cttgcattct cctatagcag ccatgcagaa cgcagcactg cactgcactg cacgtcttta  44940
attacggaac tctgcaggtc tgggcagatg gtccatccct ggtgctcagt agctacccag  45000
tgtagctctg ggctcagtga ggaaaccctt tctcaaaaga agccagcaag atagctcaat  45060
ggtaaagaca ccttctggca agcctggtga ccaagtttag ttcccagaac ccacatggta  45120
aggagacagc tgactaccat ggatcctctg acttctactt cttgatacac aaacacactc  45180
acacatactg acacaaatgc acacttacac acatgcgcac gcacacacac actctccttc  45240
tctctctttc tctaaaaata tattaaattt ttaaaaagta taaatatggt agagaacaat  45300
tgtggaagat atttgtgtga cctctgacct ccacacacgt gtacgcatga gggtactcac  45360
ccaacacaga aagtacacag tgaaatgtgt tctagtagga gtgttaggag tgaccccagg  45420
tgtgactccc cttgggaact tgctggtgtc cactgggttt ctacaggctg tgtgtaggct  45480
ctgaactcta aatggggctc tcaccacctt gcctgttgat ttccccctca gtgttgaact  45540
tgaccctcat cgacctccca ggcatcacta aggtgccggt gggggaccag ccgccagaca  45600
tcgagtacca gatcaaggac atgatcctgc agttcatcag ccgcgagagc agcctcattc  45660
ttgccgtcac acctgccaac atggacttgg ccaactcaga cgccctcaag ctggccaagg  45720
aggtggaccc ccaaggtaac cgcccgcact gggcagcagc cagtagtgct gggtcccctc  45780
cctgaggtgc tttctgtcac agttgtgtta gaagcctcct gagattcagc attccctgta  45840
accacatcac tataaccaac actgtgacag agccaccgtc tttttttttt tctttttttt  45900
cctttttttt ttaattaggt attttcctca tttacatttc caatgctatc ccaaaagtcc  45960
cccataccct cccccccact accctcccca cccactccca cgttttggcc ctggcgttcc  46020
cctgcactga ggcatataaa gtttgcgtgt ccaatgggcc tctctttcca atgatggccg  46080
actaggccat cttctgatac atatgcagct agagtcaaga gctccggggt actggttagt  46140
tcatattgtt gttccacctg tagggttgca gttcccttta gctccttggg tactttctct  46200
agctcctccc ttgggagccc tgtgatccat ccattagctg actgtgagca tccacttctg  46260
```

tgtttgctag gccctggaga gtcactgtct tttaaagagc atacagggtt agttaggctc 46320
ctggtttcag agtgtcctct tgtgattggt ggtttgttgc tgctgggcct gtgagcagat 46380
aacactttcc tgtgcacgtg gggagcaaca tggaataaga aaaggtcaag ggaggcagag 46440
gcaggtggat ttctgaattt gaggccagcc tggtctacaa agtgagttcc aggacagcca 46500
gggctacaca gagaaaccct gtctcgaaaa aacaaaacaa aacaaaacaa aaaaaagaag 46560
aaaaagacaa gggatccctt taagtgtgat gcttcaagtg accccagcga cctacaagct 46620
tcaaggagac ctcacttcac cacctctcag tggctctcct ctacagacag cttagcacac 46680
gggcctttga gagacattta agacccacat tttagtctgc agatttaacc ccagtgaggg 46740
gttgtccgtt cagaggtgcc cagcttgaat gattatctgg gtttgatcag aggtgcccag 46800
aatgaatgat tatctgggtt tgatctgaga atctgttaag agtactttct gctggacatg 46860
gtagcacacg cctttaatcc cagaacttga taggcagtgg caggtggatc cccttgagtt 46920
caagtctagc cagggcttca cagtgaaacc ctgtctagaa agggcttggt ggatggcact 46980
taactgttct ttttattttt ttggtttttc gagacagggt ttctctgtat agccctggct 47040
gtcctggagc tcactttgta gaccaggctg gcctcgaact cagaaatccg cctgcctctg 47100
cctcccgagt gctgggatta aaggcatgtg ccaccacgcc cggctggcac ttaactgttc 47160
ttgcagagaa catgggttcg gtccccgcac ccatacgatg cccacaacaa tctgtggttt 47220
caattcctgg gatctgatgc cctcttctgg cctctgcagg tacaacatgg tacacaaata 47280
tacatgcaca ccaaacactc atacacacac acataactta gttgacctaa tggcatatat 47340
aaatcaataa gacccagtct ttagcagagc cctcccagga cacagttata attccaggca 47400
catctgtctg cattgtgcag ttgtatctgg tgagatgaga acgtctgggc ctggagtagc 47460
tctgttggtg tgtgcctgtc aagcaggcag gatcccagca ctctgtgacg ctggtgtggt 47520
gccgcacact agaggtgaag gcagggggat caagatttca tcatctgcta cactgagagg 47580
ccagcctggg ctacaggaga acctctctca aaaaacaaga agaaataaaa cctggaaaag 47640
tagagaaggg cgcacacacc ctgggagagt ccgggtgggg ttttgagcag aggaggcctg 47700
tgaggccgca gaatgagctg caggtagggc tgtgtgccct cgtcaggagc ttcttagccc 47760
atccagccgt gctgtccgct gtccacacac agtgggcgtg gccatggcaa acattagcag 47820
ggcagtgcag gcggtcacca tttgtgagca catttttctt ttcttttttt ctttttttctt 47880
ttcttttttt ttttttttt ttttttttt ttttttttt tttttttgcc tttgaaaata 47940
ctcatggttt ttacagaaaa gttaccatgg aaaaatcagg agcctgcaaa gctccctttt 48000
tccatgtaga tagcgctggc cacagttcct ttcaaagttt ttcttacacg taaacttatt 48060
ttttaagagg acagtctctc cttatttctg tctgtgcctc tgtggtcatt gcttttgttg 48120
attgcaactt ttctttgttt atttttcaat catggtttca gaatgtagcc ctggcttacc 48180
tgtacttcac tgtgtagacc aaggcagtct cagtatcaga ttctacctgc ctccccctcc 48240
caaatattaa gattacagca agccaccatg ccttgcccta ctttatatta tagtgatagt 48300
gtgttactct gtgggcaggc cccattgtac agttaccctc tcctcaccct cactgtctct 48360
cttctcagca gctggcttcc tgggcaacca tggctcaggc ccctctccac tcatttctct 48420
ccatagtgtg gcctcttccc tatcaactat gaattcttat aggtgtaccc acttcacaat 48480
agtgccagct aaggtagtca cctgtgatgg ccaagttgat cccagtcttc tgtgggcctc 48540
cattagcctc tgtgtgtctt gcacacatgg aacatacagg caacacattc acaggtgtgt 48600
ccaagccggt gcctgggttc cttatgtatc aggtggttct tgttagttag gcaggatctt 48660
ctgtggtcca gattggcttc aaactctgtt tagtgggaga tgaccttaaa cttgtgatcc 48720
tcctgagtct acctcccgag ggctgaggtc acgggtgcac accttgcagg ctcagtgtaa 48780
ccagatgttt aggaaagagc ccaggctcct tggcaagtgc tccgcacctc acctggcaca 48840
gggtcgacct agggtttctg aatgctaagg caagtccatg gagtacatgg gcttctaccc 48900
tggcttggaa gctcagctta taaactgctc gggtgaaccg tggtcaggac cccaaactag 48960
ggatccggga gcaagggagg ctgagaagca cagtggattt atttggtggt gtggctttgc 49020
tgtgggatgt gctaactctg gttgacttgg ggagaacttt gatgggctgg tccttggagt 49080
agtaattggg ccaggttgct caggttcaaa tgtgatgttg agaatgggca ggggggattc 49140
tagtttccgt gatgttcatt ggttctgctg gggtcttgtt atgcgcttac cagtgttctg 49200
tcactagagc agtaactgtc attttatact ctgccaacag ttgtccaggc aaaagatacc 49260
atggcttgtc cctgtctctt ggactgtaga gggccccaag ggcccttgat catgatccct 49320
tctgacctct ggactctttc aggcctacgg accatcggtg tcatcaccaa gctagacttg 49380
atggatgaag gcacagacgc cagggatgtc ctggaaaaca agctactgcc cttgagaaga 49440
ggtatgtaca cagggctggg gtgggccaca gatcaggggt gtatcttttg tggttctcct 49500
ctggacacag tgtttctaca ttacagctgt tttctggaac actaagaagc aggtatgcag 49560
ccacactcgt gctcggtact tgctgtaatc ccagcactct ggaggtgggg ttggggtcag 49620
gaattccagg tcatcttggg ctacatagaa agttctctgt cagcctgggc tacatgagac 49680
cttgtttcaa acaaacaaat acagaatgtt tcatcagaaa tagattgagt tactggaaat 49740
gagtctcagt ggttgtatta ctcagggttc tctagagtca cagaacttat agatagtctc 49800
tatagagtaa aggaatttat tgatgactta cagtctgcag tccaattccc aacaatcgtt 49860
cagtagtagc tgtgaatgga agtccaagga cctagcagtt gttcagcccc acatggcaag 49920
caggcgaaag agcaagagtg agactccctt cttccaatat ccttatatgg tctccagcag 49980
aaggtgtagc caagtttaaa ggtgtgttcc accacacctt taatcccaga tgaccttgaa 50040
ctcccagtct tctggaatcc atagccacta tgcctcaaga tctccatacc aagattcaga 50100
tcagaaactt ctatctccca gcctccaaat tagggtcact ggtgagcctt ccaattctgg 50160
attgtagttc attccagata tagtcaagtt gacaaccagg aatagccact acagtggtat 50220
agcccttgct cagcacatgc aaggaaccag gctcattccc cagcttccca aacaaagcat 50280
aacaaagaga cactgctgct gcttgagtct tccctagcta gtggaggctg gggatgaaa 50340
tgcaggacca gaaagggagt caactacatg gggcagtccc tgttgaactg cacctccagc 50400
ccactcatac ctgcccttga agttcacgat gctttcctca gctaccttcc atgccattca 50460
caccccttggt ggggctcagt gctgccctgt gcccgctctc gtgagtgatt tttggaccag 50520
tctgtttcta gtctccacct ggccagctca gcacaaagcc atagcaccat gtccttcctg 50580
gcgtaacgca taccttgacc ttctttcttc aggctatatc ggcgtggtta accgaagcca 50640
gaaagacatc gagggcaaaa aggacatccg ggctgctctg gcagccgaga ggaaattctt 50700
cctctcccac ccagcctacc ggcacatggc tgaccgcatg ggcaccccac acttgcagaa 50760
aaccctgaac caggtatagc ggaggtttga ggccaccaag ggctggtaac tacagctaaa 50820
tgggaggttg ctgtagtctg gactcctgca atctaaccct gtgcagcctt tgagcacaaa 50880
tcctggcctg gctttcccat gccttctttc tcttgtccat cttgccctta tatttcctag 50940
ggtaggggtc tgtgaggcca tgtgtgtcca ggacaaggta catgccttgt gtgacaggat 51000

-continued

```
acagtaaaca gtatccaccc actgctctgt gcctcacgcc tccttactca cagtgacgac  51060
acagtgagaa aactggagcg cctgcctaga accccctagt gagggtgtgg gggtgtggct  51120
tggtggcaga gcacctgttt agaaccccac agtgggagtg ttacttagca atagagtgca  51180
ggcctaggat gtggaagccc tgggcttcat ctccagtacc gaataaatcc agtgtggtgg  51240
tgctactgta atcccagcac tcaggagctc agaaagccaa agtcattctc agctatgtga  51300
tgtgggataa gtgagagtct acctgagtca aaaaacaaca gcaaagacct ctttgctcat  51360
agattgggac ctgaagagag agccattgtc cttagggaat gtccactgga aagccagctg  51420
gtaaacgagc caccagatga attcctcaag tgttagctgt ggctggaggt tagtgcagaa  51480
tgaagctgag agcagcatcc ctagagcagg tgcagcaggc attgggcagt gtgtcttgta  51540
ggaagggata aagggggctg gagagatggc tcagtggtta agactgctct tccagaggtc  51600
ctgagttcaa ttcccagcaa ccacgtgtaa tgggatctga caccctcttc tggtgggtct  51660
gaagacagtg acagtgtact catgtacaaa aaaataaata aatctttaaa aaaaaaaaaa  51720
aggaagggct aaaagcagag accactggac ctggccaaag tgtggagggg caggaaggaa  51780
aaccctccac agagcctggg gctattgaga accagaggtg tatagcttgg ctggcccccc  51840
tgaattaaga ggtgctctgt ggagcattga ttgtttgtga gctcagcgat gtggtccata  51900
gcagccacct gctgctcagg cctgaggact tcatttcagt ccccaaacta aaggaacggt  51960
agaaggagac agtagactcc atgttctctg acctccaccc aggcacccta acatgtacac  52020
ttacccccca acacacgtac tcacagaagt aaataagaat tctaaaaggc ccacagaaca  52080
acctggctcc cacagacttg gggctcgtca caggccggag cctctgcact gctctcctct  52140
agcattggtg tgttcagaat ctttcttttc cctgctggga atccacctgc tatgcagtgg  52200
ggctcttgct ctgtccctcc cctccctcag tctcccgcag atgtggcccc acgtcctgct  52260
caaagcatat acctttgagt cttagttaga gggccatccc aggcctgcac actggtccca  52320
ccatccccat ccttgggtgt caactgacat ctgctacagg ctctctgctc cacttgttcc  52380
agcttctgtc cccgtctcaa tgatttgtct gtaggtttgt ggctctcttt ggattgcacc  52440
caagactgag tattctggcc tgagggtgga ttgtgttctt tcctggcctc tgggcctgtg  52500
gtaccctgtc tgacccttac cttttctata gcaactgacc aaccacatcc gagagtcact  52560
gccgaccctt cgcagcaagc tgcagagcca actgctgtcc ctggagaagg aagtggaaga  52620
gtacaagaat ttccggcctg atgaccccac gcgcaagacc aaagccctgc tgcagtgcgt  52680
actcactccc cttccccttg cctggcccag tcatcctgct ctccattcag gcccttgtcc  52740
taccctgccc ctgcgagtgt ggggtccagt ctctggacat ttaacatgac actgtcattt  52800
gtagggttca tgtcctgaaa ctgtgtacct gcattacaaa aaaacaggga aaagtcacat  52860
tgtttcaaca agttaccatt gtgtgctaat cccagcattt tagtaagttg ccattgtgtg  52920
ttaatcacag tgttttagta agttgacatt gtgtgttaat cacagtgttt tagtaagttg  52980
tcattgtgtg ttgtgcctca ttcgttgctg tagtcctgtg gcctgtggca ctcaagttgg  53040
acacagctga acaaggtatg ttatctaagc ctgtcatcct gggccttagg aggtggtggc  53100
aggaagataa atcaaaactt gctgagctga gaacgtggat gagcaagtta aagtcgaggg  53160
cctgagctcc atctcctgac ctagtgcaag gagagaaacc cttcctccaa gcctgagggc  53220
gtgcacccgt gatcccgtgg gtcatgggga gatccagtct ggggagacag actgagctcc  53280
gccttcaggg agaaattcag taaagtagag agagatttaa agacagtgga cagtcacttc  53340
tttcctgcgc acgtgcacac acacacacac acacacacac acacacgaaa gagagagaga  53400
```

aaacaagaca ctgtttaaat gaaaaaaaaa gaaaaaggag agagcaagca aatataccat 53460
gatcaactgg gtgtggtggc ctggtgcaaa cttcagccac ttggtaggca tttgggagtc 53520
ccttccttcc ttgcatcatt tagttccaag aggtcaaaca ctgtggccct cagactcagt 53580
gagaagtacc tttacacact gagccatccc aggaccacac ctacccccaa aatatgttct 53640
ttttcgtttt ccttttttt tttatgctta catgaactgt tgatgccttg tgtggttgcc 53700
aagttctccg gtgctcaccc tgtcacctgc tctgcacaga tacaagctga gcctcacagt 53760
gcagagccac ttagtcaaga tttcccagcc taccatgttg tcgctcctgt gggaccgagg 53820
tagagaggta gcggaaagta aagatgctcc tcagccggtc tggagcagct gccttgacag 53880
acagccatgc agtcaatcat gggacctggg gaaggactgc atagctgtgc cctcagaatt 53940
ccatctagaa ttttagtatt aacagatcta ttgaggtctt gagaacaacc aggatagtgc 54000
ccagcactta ccaaagtagc gttgatactt tacacattgg ctgttaaaca gtgatattga 54060
aaaagaaaga aaaatggcca aacatggtgg catacatgcc tgtaatgcta gcatggaagg 54120
cccagacaga agggtctgta gttgaaagcc agttggggtt acacagcaat acctgtattc 54180
acatacaaca atcccatgaa aatgagccac aggactgaca aggtggctca gcgggtaaac 54240
aggcttgctg ccaagatagc ctgagtttta tccccaagac gtacctggta gcaggagaga 54300
actgagtccc ataagtctcc tctgacccca ctcatagact gtggcatgcc tccttccaat 54360
acacaaatgt aacttaaagc ctttgtaaga gcagagctta tctcttgatt catgtaatta 54420
cagggccgtg cagaaaactc tgtcttaacc ttttgccttt tctttcgtga aggatggttc 54480
agcagtttgg agtggacttt gagaagcgaa ttgaaggctc gggagatcaa gtagacacac 54540
tagagttgtc tggtggagcc cgcatcaatc gtatctttca tgagcgcttt ccctttgaac 54600
tggtaaaggt aggtgttcag cctggagtta agtcagacac tctcatgctt ggtctttgtc 54660
ttggccttaa aaattcttac aaaccatgat gttacaagct cctgcatcat gtcagaggct 54720
gctgtcagca aacttggtct gaaggacatg tccccatctt cccagatctc ataatttaga 54780
agctctgagc tgaacaggag gaaagtccat gtttcttcca ctggtggagg gaagaaagat 54840
acatgggggc caacgagata gcccagcagg taccctctgc tctgcccgac tgcctgagtg 54900
tgatctgcag gcagaagcac agaaccaact gcaggttgtc ctctgacctc cacacacaca 54960
ggcactgaca acacacacaa atgtgcacag agggctgaag agatggctca gtggttaaga 55020
gcaactgctg ctcttccgaa agtcctgagt tcgaatccca gcaaccacat ggtggctcac 55080
gaccatctgt aatgagatct gacgccctct tctgatgcat ctgaagaccg ctacagtgta 55140
cttaaataaa tctttaaaaa aaaaaaaaaa aaaagtgcac aatgctaggc ttacaccagt 55200
aactgcagag ttgtgtgagt tgaggcagga ggagactgag tttgaagata acatggcctg 55260
caaaagaccc tgtctcaaaa actgaaacaa aaacaaaaca gaaaagtaaa gcaaactgtc 55320
tttgtgtcct tttcctttga ggccgtagct ctcacctcat aggtgtgtgt atgctagtgt 55380
ggagatcaga gaacagcctg cagtgtcccc taattggttt ctctgtgtta gccctggttg 55440
tcctggaact cactctgtag accaggctgg cctcaaacct agagactgct tgcctgtgcc 55500
tcctgagtgc tgagagtaaa ggtgtgcact gcctctgcca cctagccact acgcacttat 55560
ttttaaatca aggtctcatt gtaactcata tttggctgtg tagtcatgct tgatcttgac 55620
cctctacccc ttatggtagg attacaggct agtgaatgtc agcacatcca gtttgcctgt 55680
gttgtagata gggcccagag ctccacacat atgtggcaag catccggcga gcatgagaac 55740

-continued cgcagcctgg cttagcctta ttttcttaga caggatgtct cacctacctg gaacggtacc 55800
agtaggttag gtctgctggc tggaaagttt agtgttttac ttatgtttat gaacattttg 55860
cctagtgtat gctgtgtgta ccatgtacat gcccaattgc ctacaatgac cacaagaagg 55920
cgccagatcc cagggaatgg agttattgat ttagtgagcc attatgtgag tgctgggaac 55980
tgaacctggg tcctttgcaa aagcagccgg tgctcttaac tgctaagcca tctctgcagt 56040
ccagtatgcc cagatacagc catctctgca gaccagtaca cccagatgca ctcaggtctg 56100
caggcttagt ggcaggtacg ctaacctact gagccatctc tgtgaccttc agttgtttgt 56160
aagtttgagc ttgctacatc atctttgtga gatacactgg tgaatagaaa cagagctagc 56220
cactgttcct gctgtgaggt gccctggacg tggctccatg tgtggttggt ttcttctcag 56280
atggagtttg atgagaaaga tctacgaaga gagatcagct atgctattaa gaacatccac 56340
ggagtcaggc aagttccatg gggaattccc atgttctctt cctgtccatt catgtgggcc 56400
ccccaacctt ctgagtccct ggctagtgag gcctttagaa ggttcatgga tagtttccag 56460
aactgtataa acatcttagt cttcaaggac agagaaagtg cgtgtgtttt ggctgtgact 56520
gtcctaggtc tcttgattac ttgtgtcccc taggatacat gaccttgttc tgtgagatct 56580
atagtgacca gaggttgggt ggaaccagac ttgaatcatg cccacaggcc ccatgtcatc 56640
atgggtcact tgtgggcctc ctggtgtccc ctccttaatt gcaatcaatg aagtataccc 56700
tgttctctag cgtcccaaga tccttgggtt accctgaggg ctccccagtt ggggactctc 56760
tggtatccta cccccagctt taatgggata gttttccttg tcagggacct agccatgctt 56820
agaaagttgc tgaccacacc ctttgtttct ctctgactta tctctccctg cttccccact 56880
gggtctggac gtttttagaa ctgggctctt cacgccggat ttggcgttcg aggccattgt 56940
gaaaaagcag gtggtcaagc tgaaagagcc ctgtctgaaa tgcgtggacc tggttatcca 57000
ggagctaatc agtacagtta ggcagtgcac cagcaaggta ccacacctgc ggacgcgggg 57060
ccgcaggctt ggtatcaggc cccaggttac ctcacttcca agaatcctac agggatggga 57120
ctgtgtcagt ctggacccac tcaggagggg gtgggggaat gctgggcttc ttagaaccag 57180
ctagactggt gacaggtctc ctgggatcct gataccaagc ccagcatgcg tatggtggaa 57240
tggggatgtc atctggctgt gttgctttgc tgcttgcgag ggaagcagat cgggtattcc 57300
tcttcagctg ttggaggcca aggctcccga agcttcactg ttatcccccct tgaaaaatga 57360
caaatgcctg cttctttgga gtgggtcact tctctgttcc catggcactg ggaagaacat 57420
aaacactggt ggcatactga gagctcagtg cccagcttca cagagctact tgggttccac 57480
agtggctctg ccagccttca ctgtgccctg tgctgccctt gttccatccc cacccctccc 57540
aggtaactcc acactcagtc ctcatggtct tcaatgagga ctcatgccca ctcttcatgg 57600
gcaactgcct ccatttggcc caaaccacca ggctcctctg ggaggactgt atcctgggac 57660
agcacgctcc tgccaagcag cgggagtgct tgaggggaag gagagggcgt ctgctagtgc 57720
aacctcgaca ttgtcagctc tgaaagggca gagagcacct gcttcagctg cctgtcctac 57780
tggagcaaag tccccatttg cttcctcagc ttctccagtg ggaaacagag caaaataagc 57840
cagccaagca agggctgggg ttagcgttag ggtgagtttg tagagtgctt ggctggctgc 57900
acaaagcttg gggttccatc cttagcatcc catagaccag atgtggtggc tcatacctgt 57960
gatcccagaa ctggatccag gagttggaag taggaagtta gaagttcaag gtcatcctca 58020
gtatatatac taagttggag gctagcctgt gctacaaggc catttcaaaa actgaagccc 58080
agaggggctg ctgattgaca ccctctggtc ccttatcaca gacgtgatga tttaagattc 58140

-continued

```
ctcacatgcc tttggcccta tgctgagtgt cctgtagcac ttagccttga gctgtaggcc  58200
agcctatgct cccccaggcc ttgcttatcc caagctgctt ccaggacaga tgtgggtgca  58260
ggcttttctg cgtatgcact aaccagctca ttctcctttc ttctctttct ctctttatct  58320
cccgtcctat gtgtgcattt gtgcgtgtgg cctgcactac ccctgggtgt ctctcaacct  58380
cgtcccgccc tcctccgcat gaccaggacg gggctcttca cccccgacat ggcctttgaa  58440
gccatcgtga aaaaacagct tgtaaaactc aaagagccga gtttgaagtg tgttgacctg  58500
gtggtgtcgg agctagccac ggtcattaaa aagtgtgctg agaaggtaac aggtcttgct  58560
cctcctgtcc ctcatcaatt cccacctatc atctcttcat tggtgtcagc cctgagcatc  58620
gggacaacct tgcctacagg ggacccctgc tgggcacagt gccatctgga actttgcgtg  58680
gcaggctgag tgggggaggt acagcgcaca cgtcccaccc tctcagtttt ggggtccagt  58740
tgggaaacct ttgccatgtc caagcacagt cacatctgtg aaaccattct cacttctaga  58800
tgtcacccct tgccaccact gtgtcctcct gtgtgttcct gcattggggt gcgtttagca  58860
gcatctttcc tctcctgggg aaagtgtggc tcgggtcact cactacccca gataaaaaga  58920
agggagtctg aggattggcc acatggctgc caaattcaca gagatcaggg aatattttcc  58980
agcaaagggt tccctgagct cagcgacccc gacgctgtgc cttttatcct ggagcagggc  59040
actatgctca ttcgaatgcc cagtgagggc catcagtttg tcctgcctgc acctagtgct  59100
gggcgggagg gggctgcctg gcacctctgg gtagtaagtg tcattcaccc tctctgccac  59160
tttccacctc caatcgctgg ctttgcaagc ggctctcagc atgcacggca ccctcttgcc  59220
tttcccactc cacatgcccc tgactggcct gcccttgtct cccggctccc ctcccctccc  59280
ctggcctggc catgaagacc ttgtcagctc agcccttgtg cttgctcccc agctgagttc  59340
ctacccccgg ctgcgagagg agaccgagcg aattgtcacc acctacatca gggagcgaga  59400
agggagaacc aaggaccagg tattgtacca gttctctgtt tcctctttgt tcatgtctag  59460
caaattttga gaatttagtt ttgtgaagtg ataatatttt tctttaactc aacctggctt  59520
ccaaataaat tagtcagaga ctctaagatg tacttaatca agctatatga cacaatagct  59580
aagtagttat taatctgttc taatccttga agctaatctg gcgacctccc agccatagtc  59640
tccaaggtac ttgtatcttg tgtctggctc tctgctccaa tatgttccta tatgttccaa  59700
tatgttccta tggtgagcat cacagagatt cctctctttc tttaccctcc cctggctgag  59760
gtcagaagtc cagccataca ctctccagtg ctcagccatt ggcagatcag cttttattga  59820
gaaaacagag aataaaccaa caactgtata cacaacattg agacaagaga tacttagaat  59880
agacaacagt accatgtcca gattgccacc agatatgggg acagaaatca gcatttgaat  59940
aagataagga tatttattta tttatttatt tatttattta tttttgtttg gttgtttggt  60000
ttttcgagac agggtttctc tgtatagccc tggtgatcct ggaactcagt gtatagacca  60060
ggcttgcctt gaactcagaa atctacctgc ctctgccttc caagtgctgg gattaaaggc  60120
gtgcaccaaa catgcttaca ctgtgaggtt ttggttttgg ttttggtttt ggtttttttt  60180
ttttttttaga tattttcttt atttacattt caaatttctt agtttcttct gaaaatcccc  60240
tatcccctcc tcctccccct gatccccaac ccatccattc ctgcttcctg gccctggcat  60300
tcccctatac ttttgcatag aaccttcaca agaccaaggg cctcttctcc cattgatggc  60360
ccactaggcc atcctatgct atatatgcag ctagagccac aagttccacc atgtgttttc  60420
tttgattggt ggtttacagc tgtttatctc gcctgtgttt tccatagcat gcacgtggag  60480
```

```
gctggaggac atctctgagg agggttcttg ccttctcttt atgcagaggt tctgggggtg  60540
atgtgggggg gtcgaactta gttcaccagg cttccaaggc aagtgtcttt atctgcggag  60600
ccatcctaac agctccagat ccattctgag gcctaggacc atgatgcggc taatatagca  60660
cttgcctagc atgcgaagcc ctagtttcca cctccagcac cctgtcagga tgtggtgagg  60720
cacaattgtc atcctaactt gggagcagag ttaggaagat ccgaaactcg gtgtcatccc  60780
ttgactacat aactgagttc aaggccagcc tgggctacag gagactgtgt cgcctaccac  60840
accttcccaa aaaaaagaga gaaaggaaaa aacgaattat tactatctgt ggccaccaac  60900
ctgtatcctg gcctccccat aatgcattga gaagtcttcc accatgattg ttcaggtggc  60960
attaatgtct ttgtgcaact acagattaga ttgttctata catgcaacta aatctttgtt  61020
cattttctca agaccaaggt gttctgttct ttgccgggcc tttccatagt gcttcgggga  61080
gactgtgatt tccaactctg acccagtgtt gagggccatg tgtcacctat ggtggcagtg  61140
gttgactttc tccattgttg ggacattttc tactgtgaat ctactgtatc gttttagagc  61200
tgcccctacc tgctggagaa atgctagggc atctggagcc ttgcacttcc ataccctgag  61260
ctgtcattaa cccttcagga ggggagctgg agccatgcct cctcagtgga cctcgattgt  61320
gttcccagca ctcccatgtt tactcacaat catctatgac tccagttcca ggagctccca  61380
tactcctagt gttgcaagcg ctaggcacgc acagtgtgat cagtcatata tgtaggcctt  61440
gtacatatag aataaaaata atctaattat ggggtctcat tacaggtgct taaatctaaa  61500
ttactgcaag tgttcatatt gggcctgtca tggtgaaaaa actggctcct ttgactttaa  61560
gccagcattt agtactggac ctcttagaca ctctgtaacc ccatggctta ggagatatgg  61620
ctttgatgaa ggggcctgtc atcacagtat ggagtcatca cagtatggag agactgaaat  61680
aggatgagca agaattcaag gctggacaga ctgggttata ttatgagact gtctcaaaat  61740
aaaacaagga cagaatgctt ctgtcataca catagccctg ggttctattc ccagcacctc  61800
aggaacctta cactgatggt gcacttgaga ttgctcagga ggtggaggca ggaggatcgg  61860
gagttgaagg tctttctcag ctgtgtgtta aattagaggt catcctgggc tctgggaaac  61920
cctgtcccca gaaaacaaac agaaagtcaa aacaatacac caccgaaata caccatgaac  61980
acttctgctt gtttccatca ctgctcctga ggctgctgct gctcttcctg tgcacacagc  62040
ctctgggatc cactgtggac actaccaggc ttcacagcag agctgtggga agacagtgtt  62100
caggccttac agagccagct tcagggactc tgcacaacac cccgccctcc ccaacaacct  62160
cctaggtctg tgtatattgt cttggttatc actgaggagc taaagacaca gtgaccaggg  62220
agtgtctggc cttgagccag cagaaacctt tgccagcgga accagagccc ctctgccagg  62280
cagcctggcc tgttgttaat aggaactagg gtagaaagct gcctgagtca gtacagtcca  62340
tggagcgact tcagcctttg caaactagga ccattagcat cctagcagac agggctgtaa  62400
tgaggttggc agtggactat agcggcatct ctgtctgcca gatttgagaa tgcagctgtc  62460
tcaggtatgg gcatgtacac acatgctggg cacctgcaga ggtgattggg cttttagtgc  62520
gtgtggtact gagttccatc tttttttttt tttttttttt tttaagattt attagccaag  62580
catacaagca tagtggtgca cacctttgat cccagcactc aggagggcag aagcaggtgg  62640
accatatgta ggtatatggt ctacagagca agttccagta tagccagagc tacacagaga  62700
agacccatat gggaatgaat attttgtctg catgtaatgt gtgtgtgcta catgcatatc  62760
aggtgcttgt agaggccaga agagagcatc tatcccttgg aaccagagtt cgagacaggt  62820
gggagccacc atgtgagaac tgagaattga actcaggccc tctctccagc cctcagccat  62880
```

-continued

```
actcttaatt ttacattagt atgtttgaaa acagagccac acataagcca agcatgttgg  62940
tgcacatcat taatcccagc acttgggagg cagaggcagg cggatctctg agttcaagga  63000
tagccagggc tacacagaga aatcctgtct caaaaaaaaa ggaggaaaga aaagaaagcc  63060
acacatgggc tgatgctggc ttgaactcgg agtgcagctg tgagagtatc tgtataacat  63120
acacacatgt tgtcacgtgg gtgtgcgtgc atgtgaactg atgagatccc agaggcgagt  63180
ctgacgtcag atgcgctgtg atttgaagct ggctcaggag cagcgtggtg gtaaaacact  63240
ctcctaacat ttataaatcc tgactcccaa caatggcagt atcaataaaa gagaaaaaga  63300
aagagaagag aatgaattcc aatccacttc cataacttaa taacattagg ccccaggtca  63360
caggtcaggc cgtggcccaa ggaagacagc ccacaaggca gtacccatgc ccaccacatt  63420
gagctaccag gcactgtccc cttatcccag ccttcctgtg tggctctttt ccacctgcag  63480
atctcccctt gtcctggtga tttagcctgc ccgctacacc ctgtcgggga gagcaggggg  63540
gggggggatg caccagttat gtctgctgcc ctctgctgtg tgtgtgtgtg tgtactgtgc  63600
cttccttgct gttctgtaca ctgtagtcac acacccctac tttcctctag attcttcttc  63660
tgattgacat tgagcagtcg tacatcaaca caaaccatga agacttcatt ggatttgcca  63720
agtacgtata cagccattgt cagaggggca gcaccaagac cagagtggtc atccatctgc  63780
tggggatgct gggcaaaggg tagagccatt tgagagtgcc ttggagcttt ctgtgctgtg  63840
acttctgtca cagtgtcctc acctagcatg ttgtctatgg acatctcagg gacaaggtgt  63900
gtactctgtg gccattctca gggaagagga ggccagccag gttcatactc tgcatgactt  63960
cttagagctt ttcacagctg gagcaccatg tgggctctgc ctttcacaca ctgtacacag  64020
atacatacgc actgtagact taaaaccaga accttggggt gggatgtttc cattgttagc  64080
acttggctag catgcacaag acctggatta gaccacaggg ccaaaacaac agataccaca  64140
cctgattgta ttggtcctgg gtcagccata agctctggac cagctgggca aacttgggtg  64200
ccacgggggg gggggggggg ggtgtgttct ggtggctcat gcagattttc ttagctttag  64260
acaataggat accaccaggc accaaaagac agacccttgt gtccatctat actactgatg  64320
tactttcgtg ccagatccct tgctggagca gtacacaatc taggccaggt ccacctgtcc  64380
acaggaagtc catgtgttaa gacacagtcc acttgccggg cggtggtggc gcacgccttt  64440
aatcccagca cttgggaggc agagacaggc agatttctga gttcaaggcc atcctggtct  64500
acaaagtgag ttccaggaca gccaagacta tacagagaaa ccctgtctcg aaaaaccaaa  64560
aaaaaaaaaa aaaaaagaca cagtccgctc aaggctcttg gagtccagag ggtggctatg  64620
gggcttttag agctcgggtt ttagagacgt gctaagtggg agggcacaag gctgaactgt  64680
ctattgtctc tgggcagaac tggtggacca tgagctctga gcgggcacat ggtggatgaa  64740
tgaagcgaat gactgactgg tcgatcagaa gccctccctg agcacgtgta gcctagggcc  64800
cttagctggg tgatttcttc cctggggtgg gctgcattgg gggctgggca aggcagcctg  64860
tttaagccct gctcttccag ccgtgcatgg gcagcagagt agcccccatt ggttgctttc  64920
agtttcctca cctcaatgtg tctgcttctc acacttcatc cacagttcct tctcacaatc  64980
tctcctgttt ttcctttgac cactccactt ctttctctgg attccggggc cttcccactt  65040
acccagctgt ttctatactg aggagctggt cacagggtgg gtattgcctg ctgtgtgcct  65100
ttttccctgg tgtgtgaccc ggggcgtcct ccctggggag cctcaaacct gtgggggatg  65160
ttccagaagc ccttgaatta caacagccat tctctcaacc agggccccag ccaggccttg  65220
```

-continued tgaagaggac tctgggtaag acaccataga gcctgccgta tagggcgcac agactgggga 65280
gtcgtggaca gtggcacagc agcctgaggg atgagcactg gggagaccgt cgcagagaaa 65340
tcatgcagtg gctgacaggg gactgcaggg agctggtact ggacagggag atcaataggc 65400
aggacaccag ccagtgaggc aggatggaga caacagctgg tgaccacgcc cctcatcagg 65460
gagaccctgc catggcaccc agtgtctcta gttagggcca tcaccatctt ggctcctgtt 65520
tgagggagct atgtagcaca taatacataa gtagcacatc tggccccttg tcactatact 65580
gttgagtgat ggcttagctt agtctcacct tcttcaggat ggctcattat agacagggcc 65640
taaaggaaac accctgtgat ggctgctgcc gtggcacagt tggtagagca cttgcttagc 65700
atgcatgaag tctagcacca aatcaaaggg gtgtgatagc ccactggaag agagagagag 65760
aaacagcaca attggtccaa agttatcttt ggttatatat ctgaagtaga agccagtcag 65820
gaacacagga gaccctccct ccctcaaaaa aaaaaaaagg ccagtaagat gatttagcag 65880
gtaaaggtgc ttgctgtcta agctgcatga ctagttagat ccctgtgtgc acaatgctgt 65940
gccctccaaa aaaaataaag ataaaaagcc gagccctggg agagtggtgt cagaagagca 66000
ctaaatgggc atctgtgtgg gtccttacca gtctagaata aagagcccat ctcctccaaa 66060
cactcactgc ctttctagca actgactgaa gctttgttgc tgctccctag tctctgttta 66120
ggctacttga actcctgagg tagcccagcc taggcacaga ctcctcctac cttagcctcc 66180
actggggccc ctggcttgta cgctcactta acaactttaa attgagtttc ccaattgaaa 66240
ctcagctggt ttgagctgta ggcagaatct cagagcagcc agccggtggt gaaaccaagt 66300
gtgttgctat ttgtgtcctt ctgcagagga cctgggttct gttcccagaa cccacatcag 66360
gtagctcaca accacctgct actccaggct tccagtgccc tctggcctcc atgcacacct 66420
cacatgtgtg gtgcacataa gctcatgcag gcaggcacac acagtgacat acatacacat 66480
gtacatcttt tttttttttt tttttttttt aaagatttat ttatttatta tatgtaagta 66540
cactgtagct gtcttcagac actccagaag agggcgccag atcttgttag ggatggttgt 66600
gagccaccat gtggttgctg ggaattgaac tcaggacctt cagaagaaca gtcgggtgct 66660
cttatctgtt gagccatctc accagcccac acatgtacat ctttataaaa aaaaaaaaag 66720
aaaagaaaac tataacagat gagtgacagg acacggtttc tttcagatgg ttatattact 66780
gttagaatat gcatcagaat cagtaaggag agtggtgggt agctacagga agtgtagtgt 66840
ggtctgtcta cagcgccact gcatgcagag cacctggcat acacaaagct ctgttttcgt 66900
ccccagcact tcacatactg catatggagg cagcctggag aacttgaagc ccaacaatcc 66960
cagcacttgg gggggctgag gaaggcagat ctctttcagt aactgtccag cctggtctac 67020
atgagatcta agatagccag ggctacatag tgagaacctg gagagacaga gagagagaga 67080
gagagagaga gagagagaga gagagagaga gagagaggaa gagagagagg aagagagaga 67140
ggaagagaga gaggaagaga gagaggaaga gggagctaga gttgctgcgg gtctgtgaag 67200
gggagcacac acgaggcctt gtatttggtc tgctgcattc ccttctcaaa gctgaaggtg 67260
caagaacctc ccatagtggg tttgggcaag tccttctagc agccatttgg ccagtgtaag 67320
ccctagaact atcagggctg gtgatgggag ccacttgtag actgatgaag ggtcagtggt 67380
gggaagagaa tgtaaagaag ccccaggtac gttgtgctca gggtcccctg gaaccagctt 67440
cctgtcccag tcccctgcat cttacacctc ttctttgaag ctctaacttc tagtgacttg 67500
tgggaaatag ctggtgcttc tggagtggcc atgagaaggt tctagaagcc agggttagcc 67560
agatacactt ttctcatttc atgtgctcta gttgttctct atgttcagga gccatggcct 67620

```
tgcctctgcc cttagtgggt cagtgggccc ctagggaagg cacctcagcc cgggccgcca  67680
gggcatctct ttacctccct cccatgtctc atctgaatat gccttctctg cttctgttac  67740
agtgcccagc agaggagcac gcagctgaac aagaagaggg ccatacccaa tcaggtagct  67800
ccccagtctc tgctgtcact cccttctgaa gacaggagca tacttagctc atcatagcat  67860
ttgatatggg aaccgactcc ttagtactag gctgctctgt cagcttctgg gtcatgtagc  67920
tgttagaact aaggcttcca caggaccttg gggcaaattg caaacaccca aaggcctcat  67980
ctgacatcta atgtgaaagt tacaacttga ccctcaaagc aggagatgtg ttacagtgac  68040
cccgaggtgt atgttttcta actcttggcc ccaggaatga aggcaggtag gtagaaacca  68100
tggaaagtgc cacaggcaac tcagggaaga tggggatggt ttgaatgcca cggctggaga  68160
accccaggcc tcctttataa tcccacccca gcttcagagg cttcgcatac ttacagatgg  68220
cttcagagat gccagtatta cgtgtctggt tgggcttgtt tttctgtcca gtttctgcac  68280
tgtcccccaa ttcccttccc atgtcagact ggggtgggga tggggcgctg tgctgtttta  68340
tcttgcacga tttagagcca gatggggaga aatgtaacaa atgcatgatt ttgagttttc  68400
tttttgtatg tgtgcttgcc ataggtagta catatgttgt tgcttttttt tgttttgatg  68460
aagataatga attaaatatt aacaccatga atataattaa tagcatgtaa tttttttctt  68520
ttgctgtttt tttgttcctc tgatcttcct tctcctaccc ttgtgctttc cctgcgttct  68580
ctctgtccct acacgcccct tccatctctc ctgctctccc ttgattgacc cacaacccta  68640
actttacatt ctcaaagggg gagatcttgg taagtacctg cttagtgtgg tagctaactt  68700
agagacctag cagtaaagga ggcctgcctt caccctctgc tcaaaaaact aaaacgtgca  68760
ctaacccggg agctacacgt caccgctgtc actggacctc gcgctgtcct ggggatctgt  68820
tgctctcaca aaaatactaa cccaattgca gctctctggg agacacgccc ctctgctcag  68880
tcctagcagg ttctcttggt gtcctgtagt tcaaagatgg caaatatgca ttcacacatt  68940
gcctccggcc ccacctcagc ttcctagaca tgcagatttt gctcaggacc tgctggaatt  69000
catttctttt tttttttttt tttgtttttt tggttttgtt ttttttttg gttttgtttt  69060
tttgtttttt ttcgagacag ggtttctctg tatagccctg gctgtcctgg acctcacttt  69120
gtagaccatc ctggcctcga actcagaaat ctgcctgcct ctgctgggat taaaggcctg  69180
cgccaccacg cccagcttgg aattcattct tgctgccagg ccttatcctc tttctcttcc  69240
tgcagacatc actgactgac cagaccatgg cttaccacat gaggagattt gcctttctgt  69300
gcctgtggca ggcatgacta aatgatccaa cactctttcc tgtgattttc ctccacagtg  69360
aacccagggc agacactgct aatcaaccct ggcattcttt cttaatatgc acaccattga  69420
ctccccattc tgtagctatt gtgactgatt attttttttt ccattttttta ttaggtattt  69480
aactcattta catttccaat gctataccaa aagtccccca tatccaccca ccgattattt  69540
tttttttaat tttccatatg atatcctact cctttactca cataggcata aataatcagg  69600
ttccctctag cctgctgcct tcatagcagc tggatggtca gttccacttt cccacttttc  69660
ttatccattg cctgggacag atatcacaga gtgatcccag caccttttct gctgtgctca  69720
gaattgttgc catagactac tcctaccagt cagttggtgt gcattgtatt tgccatccta  69780
actgtgggca actcatcttc cttttgctca agggctggga gctggggttg tcagaagggt  69840
gtgaggccca gccctgctga aagctgagtc tgtgtggagg tgctccccgc aagcagcttg  69900
gcctcaagcc ctgacagacc cctttctcca ggatattctc ctgctgccac caccattctc  69960
```

-continued

```
tgcagggata ttcttggagt tttgactttt gcaaaggttg agccacttct gtgtgtaagt  70020
ggtgggtcct tgttgcacct gggtcctggc aaaagcaggc tgggtcaaag tcgaaacctg  70080
ggccagtgtt agagaagagg ggtctaggac cagattagcc tcaggcctgg agcaaagcag  70140
tcaagtagca cttctaggtg gtcattgttc ctaccttgtt ccattctcct ggccacaaaa  70200
gcacacacag cctggagatc ctgagcgtgg ccggccgtag cctcgggtgc cttggccatg  70260
cttggtcttc caagtgatct tcacccagag aggaaaccat catggctcct gccgagctcg  70320
ccttgctact acttgctgct caagcccctg ggatgggtcc tttctgtcct gcatgcctgc  70380
atgccgttac tgtgccccag gaatggccat cctagctgcc tctgctcttg ccacacctcc  70440
cctagctcct tctcacccag ttccttacag ccgtgaccct aggttccaaa tctaccttgg  70500
agataaggag gcacagcctt cgctgttccc tggaatcagt ctgtctgtac ttgtgggatc  70560
ggtgttatct ggggctacat tggggtaccc acatgggcgg ggggctggaa ggaaagggtg  70620
ctcacacagg caggggggcag agaaggaagg gtgcccacac aggtgggggg agtggggagc  70680
ggggagggaa gggcgtctac agaggcaggg ggtgggaggg gcggggggcg ctttggggat  70740
tttgccagct catgtatcct tagtggaggc agctaggcta gacctccaag ggacagagtg  70800
acacagctgt tacacagtag tacagagacc ccactatgtt ggattaatct tcttggggta  70860
cagtggtagc ttgggcctaa gtttctctcc cttggttgac atgtggtgac taagttcaat  70920
aagctcttac gctgggctaa gactgactga aaggaccctg ccacccatcc ctggcaggac  70980
agaacttggc tacaggaccc caggctgggt gagttccagg attaagcagt cagcctacaa  71040
gcctcaccag ccagcctagg tggtctagaa ttgaggttcc tggaatgctg aaaagcctcg  71100
tagctaagcc caggctgttt tggaatgaat ctgtataagt cagtaactct gtttctagca  71160
cgaacactat gccctcctgg ggctccaggc atctctagga gtctgagatc tcttgacttc  71220
ccagggaggg agagattctt gccctcagct ttgatgaggg atgtcaagtg gaagcttatg  71280
ttgttcttgg cccaagaagg gacttaagta ggctggaggg attcctgaac ctttcatagc  71340
tgctttggcc ttcatggcct gctgcttgga acccaaacac acccactgta gcagggtagg  71400
tgggcacagg ccctgtttag gtttggcaac tctagagcca aacaggacag gatagggaaa  71460
ggggaacctc aactctaggg ccccagacac cctattttgg attcttctgc cccatcctac  71520
ctgagaaacc caaacgcagc ctccccacct gtccatagct atacatgtca catgctctgc  71580
agcctggccc atctgttgct gccttggtcc caggcatccc tgttgtcacc tctgcatgct  71640
tcctgctgtc cccagagtac ccaggtcagg gggtgggagg ctcaggtcta catgtgcctc  71700
cgtgtcccag ggatcatggg aatctgaaaa cgtggccccc tcaggctgcc tgtacctagc  71760
agtcaggtga gtccccaggc tgacctggcc tctgttcccc atcagataac agctatggcc  71820
caacgagccc tttccatggt gtgtctctca accgagaccc ctgagttgtt actcatagaa  71880
aagtgtgccc actgggcttc cagctagctg aaacacagtc ccactctggt ggacccttca  71940
gggtctctag tggtcctctg gccagccctc tgggtgggac tgtctcccta gctctggtca  72000
cctacacaca gaagagcttg tgtgagtgag acacctttgt gggtcagtcc atgaaagagg  72060
tcacagctgt cccctgctgt gggttctcca gtgagtcatc tctgcctacc ttgtgcagat  72120
ccccagtgtc acattctgca cagtctggcc ccagccctag ccctggcctc ctggcctaag  72180
ccctttgtta ctcctaggac gtgcattttt gtttcctgtg tcatttacat cactgtaacc  72240
cccaaggggc ttctggggcc ctggcttgcc attctgtccc tgagctagag atgtgccctc  72300
cgactgtctg catccgtccc cacagcggtc ccggctccct gtctgattcc tagctgggaa  72360
```

-continued

```
tgcttggctt gacatggaac taggatcctg gctggggtgg aggtattgct gccacagagc  72420
caggcttcta tccttactgg ggaggagggg gtgggtggag cagcagggct gtcctccctg  72480
ctaagctgag gcctctccac caggtgatcc gcaggggctg gttgaccatc aacaatatca  72540
gcttgatgaa gggtggctcc aaggagtact ggttcgtgct gacagctgag tcattgtctt  72600
ggtacaagga tgaggaggta agcagctggg gacaagggtg gcctgataag gtaggcaagg  72660
gaggtggtcc ccagactgat taccccattc cccagtcac ttgagaaagg gagtttacag  72720
tcaggcatgc tgacgtgctg agacccagca ccagtggtaa ggtccaggcc tgtccaagtt  72780
atgtaggaag tgcccctgtc agacagtcca gctggtaaca tgcttatcct gccacgggag  72840
ctctgactca tcccagaacc taagagaaaa gggaggcgtg aagggcgctc gtattcccag  72900
caggctccgc aggcagtgcc tgctggccag ccaggcttgc ctccttgaca ggctccaggc  72960
aaataagaga cctgactcaa aaagccagag cgcagcgcct gagagatgac acctcaagtg  73020
gttctctgtc ttccagatcc acttgcatga gtatgtgcct acacacaaac ttgagtatac  73080
acccacacaa aagaagaaac aggaaagcaa gccaggggcc gtggtggtgt agcttagcat  73140
gcacggaacc tttggtccca tccccactta gcatcgcatg cgtgcctgcg atgcccacac  73200
tcagcaggct ccttcactaa catagctcgt tcaagggcag cctgcattac agtgaggttt  73260
tatcaggagg acttccgtct gaaggagaga ccctggcctc agttctctgc tgctggatgg  73320
gaactgaggg ggcatcctag tcagggccag gctcccaaca tgtgctctgg tggcctgtac  73380
cagcagtcac ctctgtaggg tgttccagcc accatgtagg agagacccac acacacacca  73440
gtgcaccaaa gggacacaag gactcagtgt ggtaccatat gtgacctgtc catgcacatt  73500
ccattcccat cttaggagct ggccagcacc ctggccctga agtggtgtaa gtgtcacccc  73560
aaggccagac ttccctggtc tagtttctgc tgttgttggt tttttggttt gttggtttgt  73620
tttggttttg gttttggttt tttgagacag ggtttctctg agtagccctg gctgtcctgg  73680
aacttacttt gtagaccagg ctggcctcaa actcagaaat cagcctgcct ctgcctccca  73740
agtgctggga ttaaaggtat gcgccaccat gcctggctct gacctggcca tattttttag  73800
cataacaaag actctgggat tatcccccag aatgaggcac ccagtgttga gtttccagct  73860
ccagctgtaa gaaaagtaac ctgaaagctg ggcagactct gtgtgtgtgt gtgtgtgtgt  73920
gtgtgtgtgt gtgtgttttc aaggttcatt gcagaggagc gtagccctgg gcctagctga  73980
caagcttctt cctttggact gggaatgacc attccaattc ccctcatctg gagacagaaa  74040
gcaggcactt gggcctcact gtagacaagg cctgtagcag ggccacacca ccaccaagag  74100
gtatgaaagg agccctctgt atgtatgcca aagatgaagc tcactgagat ctaggggctg  74160
tggagaccct gacaccttta atggtcctgg taagggacct aagtatccca ggtagcagcc  74220
atccctgaga cccagaccac tcttgtagac aagcccaaga taaagaccag caggggactt  74280
ttctttattt taggagtaaa ccagaagata acagtgtcgt tggaaataag gagaaaggcc  74340
cagttcacct gaggacatcc ctccccaccc cagcgctcgc tcagtcctgg gcctactttt  74400
tccaccctcc tcccagaatc ttccccagtg gagagaggta gcactcacct taggtggtct  74460
ggaagttccc actgttgctg ctggcccaag cccagcctaa ccaatgtgca gactactgta  74520
catgtcccag cctcctgaac aggtagtctg aacactggga tggcggggat ggctgttcag  74580
ttcctcagcg tggccatggt acaggccagg gagtctgctc ctcccaagat cctccattca  74640
gttcatccac gcaccctgaa ctcttctgac gtggcaaggc caaggccact tgctcacatc  74700
```

-continued

```
tggagaaagt tgagattttc aggaaatccg aaagcaggct ggaggagggc ttgggtcgat  74760
ggcccgtgcc gcagaaggag gtccttgtgc agttgcatac tttgcgagca agcgcatgcg  74820
tatgctcgtg tgtgtgtgtg tgtgtgtgtg tgtgtgtgtg tgtgtgtgtg tgtgtgcgtg  74880
cgtgtgagag aaagagagag agagagagat ggcagccacc cgatcctggg cagaatcaca  74940
cataaacagt tccagatgtg gcaagcctag atgtctgtga ctcatttact tggccctggc  75000
ctgctggcag gaagctttct gtctcgtgac accatagggt aggggccaca gagttgcttc  75060
tgggaactta ccctcctctg gaaacagagg ctcctttggg gatccccaaa atcccaggtt  75120
tgtttcttat aacaagacag acttcaggcc gccttccctg tctggagctc tcggtatgca  75180
gtgtgtgtgt gtgtgtgtgt gtgtgcgcgc gcgcacgcgc gtgcgcgtgt gtgcgagtgt  75240
tccacactcc ctgctcacag cctctccgcc tgtgcttcat tcaggcagtc agacctggtg  75300
aggttgactg ggagccagtc catgaattgg ctggaaactg gggccacaac tgtgccaccc  75360
tccccaagag taacactcat cattcctcag acagatgggg atcgggaacg cagaggagaa  75420
gcagtgtgtt caaaggcaga gcaaagcttg aacacagcag ttcctcatac agtgttcaga  75480
ctggccccat tctgcactag agctacgggg gaattcagaa ttgtattcca caaagctgct  75540
ttctgggact ttctgttcgt gcagtggaca gaaacatgag aaagagtcat gaaggatctc  75600
cagtgagcct ggagagagtg ctctgtgggg aagagtactt acgcacctgc gcacccatgg  75660
gtgctgtgag tgcctgggac ttcagcacta ggtgtgcaaa gaggaggagg ctggggcttg  75720
ctggctccag gtttagtaaa agcacttgtc tcacagaagt aaacatcatc ttccccatga  75780
aggcctcttg gttctcctca gtgtgttgca catgacacac acaggaggac atgtccaggt  75840
gatgggctga ggcccagctc agttgttgga gcttttccta gtgcttcatg aactgggtgt  75900
gactcatggc tcaagcggta actccttaca gcattggtga gcaagatgcg agaggatcag  75960
gaattcagct catcttcagc tgaataggga attgaatgct accctgggct ataggagact  76020
ttattctgga aaaaaaaaaa aaagtctgtg tggtgcagaa aatccccagt gagctgttgt  76080
catctacaac cattcttagg ttagttacac agtgtccctg ctctgtgctg gacagacagc  76140
ttcctaatct gagcagacag aaggaaaagt gccccccccc caaaaaaagc tgggcagtgg  76200
tggcacatgc ctttaatccc agcacttggg aggcagaggc aggcagattt ctgagttcga  76260
ggccagcctg gtctacagag tgagttccag gacagtcgga gtatacagag aaaccctgtc  76320
tcagaaaacc aaaaatagaa gaggaaggaa aagtgtcaca ggcctattgt tatggctcct  76380
tgggaggcag gaggaacaca acttcatgga aggcctgtct caaaagcagg aggaggagga  76440
gtgttgcctg cacggccagc atcgtgcttg cctgagagag accctgggtt ccgtccccgg  76500
cttgggtcgc tagagcgctt gtcaggcatg catggagtag caaagccact gacgctcctg  76560
tgacagtggt gcccaggcat cagtttccca ggcctggcgt ctgaaatagc ctcctgcgcg  76620
ccagtctccc tccctgtgag tgattgccgc cataactcag ataatgggga gagccacctg  76680
ggaaggcatg aagttagggc tgtgaggtct gagtgaccac tgcatgtgtg ttctctggat  76740
caaaaacaaa gctgacagcc ttcctttctg gcaactgctg gaccagccag gtggtaggca  76800
gtcatcatag catctgtagt agggtggcat gaggtcagcc ctgagggacc ttctgcatat  76860
agacctagga aggccaggag gggggcagta cagggtgtag ggacaagaac agtctggacg  76920
gggtcggtcc gtacacaggt cctgggatga gagagaatgt taagggaacg tttgaccaaa  76980
aaatcaaaaa cagcacctgg gaggcagagg cagacgaatt tctgagttcg aggacagcct  77040
ggtctacaga gttgagttcc agaatagcca gggctatata gagaaaccct gtctcgaaaa  77100
```

aaacaaaaaa caaacaaaaa acaacaaggg gacgtttgag taaatgtggg gtgacagagc 77160
tctcagcaca ccaagtgccg ggtgttggca gtggctgtca gattgttgct ggctctgccc 77220
cggcagctca ggtgagaccc ctgccctctc tcctcaggag aaagaaaaga agtacatgct 77280
gccactggac aacctcaaga tccgggacgt ggaaaagggc ttcatgtcca acaagcacgt 77340
gtttgccatc ttcaacacag agcagaggtg aggaagagcc agcccagcag gccctttgcc 77400
agggtcttgc ctagcacaga gctatcccag ggacattcct gtgtggtgtg ggcggagcaa 77460
catggacaga caactgacat ggatgcagta agcatgaggg cctcagtgca accctcacac 77520
acatacaact ctcatacaca caacaaccct cacacacaat cctcacacac acatagccct 77580
cacacaaaca cacaaccctc acacacataa tcctcacaaa aacatagcct tcacacacac 77640
agtcttcaca cacacacaca caaaaccctc acacgataca atcctcacac acatacaacc 77700
ttcacacaca caaccctcac atacacacaa cactcacaca cagtacaagg aaacgtctgg 77760
cagggtgctg gggaggcaga aagcaggatc ctcggtgccc gctaaacctg ctgaccggtc 77820
taggcaagtc tgtgagcttc gggccagtga gacagaccct gtctaaaaga gtgaggtgct 77880
cagataaagt gaggaagggc gtctggtgct gacctctgac ctctgcatgc acatacaccc 77940
atgcacttac tcagggctcg acagtgcaga cagtgtaggc tgagtctatt cctgctgcta 78000
taggatattc tggtagacat tgttgctgtg gtcttcctta caaacacctc agtgtctcca 78060
cacctcagtg ggcgatccaa agccagagct ggactgtgtg cggtacttgg tgctatagta 78120
tacctggcag acacacccag aaacctctta acaaactagg gaaggtacta gaaccacctt 78180
cgtacccaga tcaggcagag agcccccaga gcccatggtc ttagtggcca gtcaagtccc 78240
tctaccactc actccaggaa tgtctacaag gaccttcgac agattgaact ggcttgtgac 78300
tcccaggaag atgtggacag ctggaaggct tcgttcctgc gcgctggggt ctacccagag 78360
aaggaccagg tgaggggggtt cctgcgcgct ggggtctacc cagagaagga ccaggtgagg 78420
ggttcctgcg cgctggggtc tacccagaga aggaccaggt gaggggttcc tgtgtgctgg 78480
ggtctaccca gagaaggacc aggtgagggg ttcctgtgtg ctggggtcta cccagagaag 78540
gaaaaggtga gggggttcct gtgtgctggg gtctacccag agaaggaaaa ggtgaggggt 78600
tcctgtgtgc tggggtctac ccagagaagg accaggtgag gggggttcctg cgcgctgggg 78660
tctacccaga gaaggaccag gtgaggggtt cctgtgtgct ggggtctacc cagagaagga 78720
ccaggtgagg ggttcctgtg tgctggggtc tacccagaga aggaaaaggt gagggggttc 78780
ctgtgtgctg gggtctaccc agagaaggaa aaggtgaggg gttcctgtgt gctggggtct 78840
acccagagaa ggaccaggtg agggggttcc tgcacgctgg ggtctaccca gagaaggacc 78900
aggtgagggg ttcctgcgcg ctggggtcta cccagagaag gaccaggtga gggggttcct 78960
gtgtgctggg gtctacccag agaaggaaaa ggtgaggggt tcctgcgcgc tggggtctac 79020
ccagagaagg accaggtgag gggttcctgt gtgctggggt ctacccagag aaggaaaagg 79080
tgaggggttc ctgtgtgctg gggtctaccc agagaaggaa aaggtgaggg gttcctgcgc 79140
gctggggtct acccagagaa ggaccaggtg agggggttcc tgtgtgctgg ggtctaccca 79200
gagaaggaaa aggtgagggg ttcctgcgcg ctggggtcta cccagagaag gaccaggtga 79260
ggggttcctg tgtgctgggg tctacccaga gaaggaaaag gtgaggggtt cctgtgtgct 79320
ggggtctacc cagagaagga aaaggtgagg ggttcctatg tgctggggtc tacccagaga 79380
aggaccaggt gagggggttc ctgcgtgctg ggtctaccc agagaaggaa aaggtgaggg 79440

-continued

```
ggttcctgcg cgctggggtc tacccagaga aggaccaggt gaggggttcc tgtgtgctgg  79500
ggtctaccca gagaaggaaa aggtgagggg ttcctgtgtg ctggggtcta cccagagaag  79560
gaccaggtga gggggttcct gtgtgctggg gtctacccag agaaggaaaa ggtgaggggt  79620
tcctgtgtgc tggggtctac ccagagaagg aaaaggtgag gggttcctgc gtgctggggt  79680
ctacccagag aaggaccagg tgagggggtt cctgtgtgct ggggtctacc cagagaagga  79740
ccaggtgagg ggttcctgtg tgctggggtc tacccagaga aggaccaggt gaagtgttcc  79800
tgtatgctgg ggtctaccca gagaaggacc aggtgagggg gttcctgcgc gctggggtct  79860
acccagagaa ggaaaaggtg aagggacacc ttccctgctg accctgcatg gaggaaggga  79920
cccgtgattt ctaggccaag cgtgtcaagt cagcttttct ttgctatgga gatggcttag  79980
gtgatagcat gaggcctgaa tgttagccct agaactcagt caggagctat gtgtggtggt  80040
gcacactggg gctcaggagc cagccagcca tagcacagca gagatctcca ggtcctagtg  80100
agaggccccg actcaaaagt caatctaaaa gaacactaat aacaagccag acacagcaga  80160
tagcgtatgt gcctatagtt gttgcagagt ctggcaaagt ggacacactt ggggtgaaaa  80220
ggggagtatg gatccctaac gcccacttac cagacagcct agaaaaacct acaaactcca  80280
gattcagtga gagtccctgt ctcaaaatgt attgtgtttt gtttttaggg tgtgtctctg  80340
actagcctat agtttagtct gtagaccagg ctggccttaa actcagatct atctgctcct  80400
gcctcctgaa tgctacaagg cctgggatac aatgtaataa caggtcctgg tatgttgatg  80460
cacaccttta atcccatttc aagaccagct ttgactctat agtgagctct aggatagcca  80520
ggactatgta gaacctgtca ttcattcata gacagacaga cagacagaca gacagacaga  80580
cagacagaca gagtaaacat aaaagttctg aggcactgag ttgggataga ctacatgcac  80640
acaatgtgta agggtgatat gcacataagg tacatacatg aaacacaagt gaataaatac  80700
ctgctacaca ccaagggaaa gaaatgttca gtttggctcc caatgttaga gggctcagtc  80760
catggctgca tggtcccatg tgtataggct gtctcatggc agtggtattg aggtgcggaa  80820
gcgagaagca gaggggaagg catgaaaggg ctggggccaa ggtatccctg gggatacaca  80880
cctagtggcc tacttccccc agcctgaagt tttcagagct tcacaagtaa cagtagtatg  80940
gttctaaaag gacggctttg cagacagaag ccatggctac tcctcaaagg atccaagttc  81000
agtccccacc acccacatga cagttgacag ctgtctgtgg cctctggaca cctgcacaca  81060
cacactgcat atacacatac cataccaatg tacacataaa aatcagaagt acagtactgt  81120
cagctgagac tcaagggacc aacacctgag ccctagggac atcccatatt caaaccatag  81180
cagcatactt cagacctcag agggcaccaa gctggtaccc actgagtcaa gcgaagcgga  81240
ggaggcatgg gttgtcatca gggtccagaa gttctccaga aggggttctc catggtgagg  81300
acggcaagag cacttagggt tcatccacct tgttgtcttt tccctcttgt ccttggggtg  81360
aagtcactac agaccctggc catccaaagg gaggctgtgt tctcatcccc cggctctaac  81420
cagtgttacc ccagtgcaga ctacaaggtc taccagggcc atctggaaca cactcaggtg  81480
gggcatttgt cagcagggta ggcccagcac agtgaaccat ccccctctgt gtcctctgca  81540
ggcagagaat gaggatggag cacaagagaa caccttctcc atggacccgc agctggagcg  81600
acaggtggag accatccgta acctggtgga ctcctacgtg gccatcatca acaagtccat  81660
ccgtgacctt atgccaaaga ccatcatgca cctcatgatc aacaacgtga gtgacagctt  81720
ccaagtcacc aaagatccta gccgcatgcc agtcagccca gcaccagcag gtggaagcag  81780
gagagtcaca agtccaccat cctctcagat actcagccgg tgtagggggc tttcactgtg  81840
```

-continued agaccttgtc tcagcaatga caactgggga agacgggggg aggggtgggg ggtcagaagg 81900
taaaggcgcg cgtgcacgtg cacacacaca cacagtcaat acatactgtt aacttaaaag 81960
caaacctaat tttaaaaagc tgtgcaaagt tagaacaagt tggtttgttt agtagctttt 82020
tggggttttg gtgtgttggt tggttgggtg ggtgggtggg tgggtggttg gtgtgtaggt 82080
tggttggttg gtgtgttggt gggctgcttg gtgtgttggt gggctgcttg gtgtgttggt 82140
gggttgcttg gtgtgttggt gggttgcttg gtgtgttggt gggttgcttg gttggtttgg 82200
ttggttggtt tttgtggtat tggagattga acccaaggca tggtgattct taggcaagca 82260
ctgaatgact gagcacctca gctccttccc tgggagattc taggcagaag ctttacagct 82320
aaacttgact ctcactcagt ctgtgatgga tgctttccca atctcaacag gcttctgagt 82380
tattggctaa tataggggtc tgacctttcc ttcccaccac tgtcctcaga caaaggcctt 82440
catccaccat gagctgctgg cttacctgta ttcatcagca gaccagagca gcctcatgga 82500
agagtcagcc gagcaggctc agcggcggga cgacatgctg cgcatgtacc acgcactgaa 82560
ggaggccctc aacattattg gggacatcag caccagcacc gtgtccacac ccgtgccccc 82620
accggtcgat gacacgtggc tccaaaacac cagcggccac aggtctggac agcagtttgt 82680
cccccaatgt gcatatacaa gttcaagccc caccccttcct attccttctg tcccattagg 82740
aaatagttca cagctgaagt ttggaaaggg acaagagtct taagtgaatg gcacaacacc 82800
tgttctgctt aaagccacag gggagccatg gcttccaggt gccaacctga gctagatctc 82860
tggaggagaa aaccgcacac cccaattctc caccaactct tgcatcttct agtgctttct 82920
ccgtgggtcc aagtagaaag caaaagcaag aagcccagga gacagttacc cgaggttggc 82980
ctcttagaac atagagacgg tacagaacac gttttagaag gcctgtagaa cctagaactc 83040
cattggcctc gagatgggaa agatgggcca gagacactac ggtagtcaca gtccaagtgc 83100
taaagtggca gtcaagggaa tgtcagtaca ggggacccac tacggaccct gtggagccct 83160
caggaaaagg aagagcccaa acctggcaag attcagtccc taggtccagt ggggagcagg 83220
gcaggcagat atgtagaggc agaggtgata catcaggact ggggctgggc tctaagtgga 83280
tcagaaggtc aagtgcagtc tgcacacctg tcccttggag gtttactgtc aggtacacag 83340
gagcctcagc aacatggaat ggtgtggctc aggctggtgg gtgcctctac ccccacctca 83400
gtcacttgtg gtagatgttc acaatatcct tcctccagat tacagccttt ccttcctcca 83460
tagccccact ccacagcgcc gacctgtgtc cagtgtgcac ccaccaggcc ggccacctgc 83520
agtgcggggt cctacaccgg ggcctcccct gattcctatg cctgtggggg ccacatcctc 83580
cttctcagca cctcccatcc catcccggcc tggaccacag agtgtgtttg ccaacaacga 83640
ccccttctct gcgccacctc agataccatc tcggccagca cggattcccc ctggtatccc 83700
tccaggagtg cccaggtaag gcccacgacc tgcatcctag gctccctttg tggtatcttt 83760
cacctttccc cccttctgat ggcttccagt gtagccccaa caggacatag aacagcacag 83820
gcatccctgc ttgtgtcctg agacattgag ccctaaaggg gccaacccct gctcagccag 83880
tgccacagag cagtggacca gctgatgcca gggttcctgc ctgtcctcta agcagcaggt 83940
gacatgtctc actagccctg ggcaccatac cactgttgac cctgctgaag tcagcaatgc 84000
ctggtgagcc aggttctggt ctccacttct gagatcagtg aggcaggcaa gatggcacaa 84060
gtgcttgcta ccaagcctga tgacttgagt tcagtctcta ggaccctctg atggagggag 84120
aggactagct cttcccaagg ctgagaactt gcctataaaa cccaggcaaa ctagtgacat 84180
ggggatacta ggaaagtatc tggacttgac atagtccctt gtacccccaa tctgggagcc 84240
cctcgggtgg gctggaaggg ctgggtcccc atcctcaccc tgcttctgcc ctcactaccc 84300
tccacctccc cgtatcttta ctttctttgc agcagaagag cgcccgctgc gcccagccgg 84360
cccaccatta tccgcccagc cgagccgtcc ctgctcgact aggctgcagg gggcaatgtt 84420
ctgggggggt cctcgtgcac ccacagtgta ggacagtttt ggtggtctgg gccctgctac 84480
ttgccctcca tgctgggacc aggctccccg tgggcaagcc ctgccctttc cctcctcgcc 84540
ctagtggaca tgacaatgaa gggtgaggag gcccacagca cagcacatgg gggctttgca 84600
ctttgggatg aggaggagct ctggctagca gaacaggaac tgcatccttg ggaccatcag 84660
gaaaaaaagg tccaggctag tgtgggggga ctcttctgga gctcctccag agcctttgtt 84720
ctttctgggg tccaggaact gcccaccttt cctaaggact cctcaggagt gagccaggcc 84780
cagcaggtcc agtgctgacc cacctggctc aagttgtata tatagagctc ctttggccat 84840
attaaccaca caagctgagc ccagcccagg ctccgcaccc agaggtgcct ttgtgccttc 84900
ctcaggcctg gagggcctca gctctggcca ccctcactct cctcagcccc ggttgtggtt 84960
tgggctgtat gaactgggga gacatcagag gcctcttggc tcccaaccag atgtccccac 85020
agggtgggcc ctgggtgcct ctgcagcctc ggctcccacc gcctggattg accactgtta 85080
agtgcctgcc tctgtatatc ctattaataa actaaaataa agggaagccc tactggtggc 85140
tacgtgtgtg ggccttttgt gtgtgtccca gctcaggaga ttgagcaccc cctcatgagg 85200
ctgcccacac tcatttacac gcgtgagtct tgtgtcatct gttctgagcc cctcttgtcc 85260
ccatccgtac caggcctcac acacagtgct catgggaaac aggaattcta tccacctctg 85320
tgcgatgctg tggccaagcc ctcctcccag ccccgccagc caccgggacc aggggactca 85380
gttcattcag ccatggttta tggtcttttt ctttcgtgcc aggcgaccac ctccattggc 85440
tcctgcccga cctttcttct gagcttcgtg ggagtgtccc cccttcctgg ctgccctggc 85500
ttgaggctag gtctgtccca agctgacatc cctaagccca gtcaccaggc actattaact 85560
ttctgaccat aatttattga ctccagtgcc caggacaaat gccctctgtt ccttgaggct 85620
catgggccag ccttctctga ggccctgcac ccagagagaa ggaaggggcc tctcccaaac 85680
cacctactag ctggctcccc tctgggccaa ggggccaggg ctccttcctt tcaaataaaa 85740
gtgactgtcc tggcaagaac tctgcagatg tgtctccttc ccagacccta gtgaagtagg 85800
cttaccccag gaggagagca gagacattgc agttggggtg tctagttgga gggtgggggg 85860
cagcaccaca gcttcacccc atcctgatag ctgcaagact gaagctaagg cacgatttca 85920
ggagaaagcc agggcatcca agagcagtgt ccccacactg ctgcgcccag cacttccacc 85980
ctccaaggaa caggcacagt cgctgagccc tccccccttcc gaggggtctg tgagccattg 86040
gcactccctg gtcactgagg aagggagaca catggggcca ctgctaagga cccaactatg 86100
tagtgtctca tctgagtctg ggaggtgtcc agcaagtcac acacccgctg ccctcatcct 86160
ctgtggcagg ggctacgtgg gtacagggcg cttgtcatgg aagaagcgct tgagtgtgca 86220
gacttgcagg acagccacca gcagcaacac agccacattg gcagctgacc agaagttgac 86280
ccgctccagg ttgtcttctt gaagatttcg atcacgagcc tcaaaggctc ggagcagagt 86340
gagcatctgg atgctccgtt ccagccgggt cctcatggtc tctatggatt cctgccaggg 86400
cacaaaggaa cgggtcaggc tgcttaagtc agaatgccta cctaccccac cacgcacggc 86460
tctggctatc cgttcacctg cctcacgtct tctctagaaa ctgaggggtt ttccccttgg 86520
tgtttttttt tttgtttttt gggtgggtgt gagacttttc tttttaagag ggattggggc 86580
acacgtgcat ggcagacgac cccaggtagc caggcttggt gcagttgcct ttgcctatca 86640
agccacttca ccaaactctg ctagtctgtg caagccaagg atgaccttga acttgtgatc 86700
ctcaggacca agagaaccat acccagtgtg tgcagtgctg ggtgtggggg ctcagctgtg 86760
ggagcgtcct aggtaagtgc tctgccaact caattattcc cggccctttc tgttggtttt 86820
gtgagacggg agcttgctat gtaaataagg ttggtcttga actcactggc atcctgcctc 86880
agcctcctca gaactgggat tctaagcatg caccatcata cccagctcac cttgatgtct 86940
tccattttga catcaagcat ctcttctggc tccacagcct ccgcccaacc ttctacctcc 87000
tcctcatctt ggaagctgtc aaagatgagc tcaaagaaca caagcttttc tgagatggtg 87060
ctgaaggagt tgtcaaagca cagcctgtag tctccggcct cagtaggctc caccctgggc 87120
agacagatga gacatagacg tgaccctgga gtgaccagcc agctggtctg tggaaccagt 87180
aggatggtaa cctgaggcca ctggggagct gcagggctgt aactgaacca aggcagggca 87240
ggacttcact cacgtgtgta ccccatcagc ctttcgagac tcactgacca acagcacacc 87300
ctgagggctc tccaaggtga agtccacgtc cagcccagca cctccgatca cctgaagagc 87360
aggtaagaat tggggaactg gcagctttgt gcaagcctat ctgccacaga aagcctgggt 87420
taaaccgaac cgggaaagac ccatgtaaga tcaccaagaa cctatcttta agaagaaaaa 87480
agaacaacca caaatcccag gtatttgctt gagatagagg agtagcgcct gtggagggag 87540
attagtcaga gctgcacttc taccatagag ttaggaaact cgggtcgtcg tagtttagca 87600
gcaagcggtt tttgttttgt tttgttttgt tttaacccag caagctattt ggattccccc 87660
aagggcctat ctgaagacca acatccatcc acacctacaa ggtttcttcc cagtccctaa 87720
gatggataca tccacgtgag gtcttttatc aaccaccctg ccaacgccct tgagtagtct 87780
aaggtggctg tctacctgac cgctaactta atcgtaacct acccaacagc cgccaggaac 87840
ttccctagaa cccaacccaa agagctctga gcagagcatg ccccttctct gcaagactat 87900
tagcgttctg gccacacctc tgccccgccc ctcccgcctg ttggccacgc ccccagccct 87960
gctctattcc gagcccggga ccccctctct cacctggtac tcggtctcaa gactagcatt 88020
ggccggtgcg gactgataga aacactgctt tctcccggcg ggaagcagaa atgtgaactc 88080
gccgtcctgg ataggcggcg gccctgcctc tcccactcct actgctggca ggagtagcca 88140
cagggccagt gctacggccg cgccggccgc catcatccgg gtcaccctct actcacgggg 88200
cgtggaccct ttaaggattt gtcctgccca cctcttattt cggcaaagct cattggcttc 88260
ggcttctgtt cgaccccaaa gccgcggaat gctgactgaa gggccccagg atggggagct 88320
gccctggtaa ttgcctaatc tgctagaaag catactaacg ctactgcgaa cttcgtgaaa 88380
cctacccaag tctgatatca accactgcat ttggtggggg cactgacaaa tctaaaaatg 88440
gtgaagcact tctttacagg caacaattaa gatgactaaa cggggaggtt tgcaggtcct 88500
cccttggcac cgcccgctct ctgccttccc caattcaagg tgcttttgcc cattggtcaa 88560
tcaagtgtag gcgtagccct ccgaggacgg cggctttgtt ggattctgat ctcaacttgt 88620
gtgacgggtg cgacaggcag atatgccagg tgctagtatt ccaatattgg agttctggcg 88680
atgttagttc agtgagcatg gcctcccccg actgcttttc ctttacacct tataccatcc 88740
ctaagggggt ggtggaatgt ttgttggtga gtagaatact gcctcagcct gcgtacaata 88800
catctcaaac ctttgggtca gcaggtccac gtgcatctgt gctgacacat gcagtattcc 88860
agtacttgaa aggctgagtc gggaggtgga aggagttcga ggccatcctc tcgaactggt 88920
atggaactac atagttccag accagcaaaa aaatcaagga atctattttg ggctttgaat 88980
ggctcagaga acacaggcgc 89000

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: bases at these positions are RNA

<400> SEQUENCE: 48
agacuctcgg ttccga 16

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
agactctcgg ttccga 16

<210> SEQ ID NO 50
<211> LENGTH: 18
<212> TYPE: DNA
<213> ORGANISM: Artificial sequence
<220> FEATURE:
<223> OTHER INFORMATION: Primer

<400> SEQUENCE: 50
agaggagacc gagcgaat 18

<210> SEQ ID NO 51
<211> LENGTH: 23
<212> TYPE: DNA
<213> ORGANISM: Artificial sequence
<220> FEATURE:
<223> OTHER INFORMATION: Primer

<400> SEQUENCE: 51
catggtttgt gttgatgtac gac 23

<210> SEQ ID NO 52
<211> LENGTH: 24
<212> TYPE: DNA
<213> ORGANISM: Artificial sequence
<220> FEATURE:
<223> OTHER INFORMATION: Probe

<400> SEQUENCE: 52
cctacatcag ggagcgagaa ggga 24

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
agcactttat tgagtt 16

<210> SEQ ID NO 54
<211> LENGTH: 15000
<212> TYPE: DNA
<213> ORGANISM: Mus musculus

<400> SEQUENCE: 54 tctcaggga aaggtatcct ggattcagta accaaggaac atcacaatgt cacattgcac 60
aacaaacctc acacaagaga tttattggga gagatacaag aaggtggctg cctttccttg 120
gtggagaaac agcaggaaac ggagtgggag gcaagctttc ttggtggtgg agttttccag 180
ggtggaaatt tctagggagg ggattggtaa ggtttggtga gttttcaaac cctgaggtgt 240
gtgcttggac cttacaccct acacatgcac ctcatgatac aacgcccact tcccatacgg 300
agccctgtgc tcaccacagt ccttcttgga ctggctgaat ttaggctcct gcataacctt 360
gtagcccttc cctcctttcc tactgcaaaa ccctcttagc ttgctgtggt aaatacactt 420
ctgtaattcc cgtaattagg aggtggaggc agggaaatag caaagttagg tcactctaga 480
tcaagtccct cttgcaaaaa caaagaaaaa aaccacgccc tctatggtac aaaccagttc 540
ctcttcccta gagttctggc cctccccgg gaggatgtgg tcatagggtc aggtcctggg 600
gccaaggtct gtcctggtac aaccccggac tgaccggttt ctttcacttt ggtcggctct 660
gctatgtggc tcggccttgc ttttgtgatg gctaacgtta tgatggcagt taattttatg 720
tttaaaagtt taaaatgtct gtgcttaaga aaactataaa gcgttaagag tggttaaggc 780
ttagaatttg tttttacaac tattttggtt tctataaatg agcttgtttt gctccagagg 840
accctctgct tggcccagaa caaattgtaa ctttgtattc cttgccttta taaacccttg 900
actgaggtag ctgggtgctg cattagggaa tcccaacttg caaatacgga cctggatgga 960
gccagtatct gaataaaagc ctcttctttg ttagaatgta ttaatggtca gactggcgag 1020
tctctgaatg accccagacc cataacactg tcttcacgtc ctagtggcaa tcaccaaaag 1080
tccctttga aaccaaaagt tgaataagtg tcccgttgtt cctccggtct tgcaaggcct 1140
tgcaaagctg atcacagcct tcctctcttc ctggagcacc aggaacctgt tatagtctgc 1200
ctttattgtc tataaaatga aatcacctat gaagattccc caccctctct tccctggttg 1260
cttggctttt tcttctcaga ctgtcccaga ccagtgatag atgcccacca acccggatca 1320
gtggtagatg cccactaaca atcccagacc ctagtaaggg agggtaaggg ggtgggggtg 1380
ggggttgggg ctggtggcac ttgcctttaa tccctgcatt caggaggcag acgaaagctt 1440
atttctcagt tgtagtctag agatgccatg ctctggctct tgaactaaga aggtaccact 1500
ggcaactctg gaagcccagg agggagggag ggagggaggg aggaagggag ggagggaggg 1560
aggaagggag ggagggaggg agggagggag ggagggaggg agggagggag ggttggttcc 1620
tactgagcaa aataaatgct gggtagaaaa agccacagtg tcctgctccc caccttctgc 1680
ccagcacttc agctgtaaga caaggcaatg ccctttgatt tagcacttca ctctggaaag 1740
agtacaattc tgagatgaca gcgagatcat catccctgtg tatttctgcc tgctcccagt 1800
gacccaagtt gaccgtgatt gaggttattt tgtaaaatat ttccttgagg caccgggaat 1860
caaggccatg catcctaggc gagcattctg ccactgagtc tcatgcttcc accgaggagc 1920
cacatcccca gtccttttgt aagagaattt gccgatgtag gtggccatgg tggcacagga 1980
aattagggag gctgaagcag gcaggagaat cacaattaag tcaacctgag aaacatagtg 2040
tctccagagg aaaagaattt gcaactgtga ttaagggccc atattgagtc tggctacaca 2100

-continued

```
gccctgacta accagaactc actgtgtaga cagctggctg gcctcgaact catacagacc   2160
tacctgcctt tgcatcatgg cagtaaaatc atgtaccgcc atggactctc actctgtggg   2220
agtatccttg atgggcctga cccaatcgga tgagccctga aaagggacca gaagtttcct   2280
ggcaaagcag acacagtgtg aagcaattca atgcagggac attctctgct ccaccctctg   2340
ttttattgct tttaattctt aaaattaatt tatttattct atgtacaatg ttttccctca   2400
tgcatgccca tgcaccatgt gcatgcctga tacctgcaga gtccagaaga ggcaatcaga   2460
acccctggaa ttggagttat agacagctct gagccctcct gtaggtagat gggaatagag   2520
cctggatcct ttggatctaa agtccatacc tgctgagcga cacctccagc cctgacactg   2580
gctttaaagt tagaggaagt aggtggccag aaatgtagaa atcacacgta gccgtggtcg   2640
acagctgaga agaagctggg acatctgtcc tgcagccaca tggaagtgag ttctgaccag   2700
gacctggggg gggatctcac tttagaggct ccagagactt cagcttgaac ctcagcgttc   2760
tgatgatctg ggcagaaact ctaactatgc agcaccaagt gtttacccat gggtctgtgc   2820
atccgtaaaa gtagttttgg ggggcattgt tttagggtgc tcagagtgtg gtaattggtc   2880
acacagcaga aggaagctgc atgaaggaag gtcacataag cattctgtaa gattctgaaa   2940
gcaggttttg tcccatcatt cttaccttac cctcaacagg acctggaaca ccatcctagt   3000
aaagtcagga aaatggaggg caggaaccta actcttcagt ccgctactcc caccagtgac   3060
tccctgctca aaacacttct acagcgctgt tctgctgggt ctcccatgaa gcccttgctc   3120
ctcagaccca ggagcaagct tgaccaatct ctacctctga agcttctgag acctttgccc   3180
gcatctattg atcctcactc ctgggcaggc agcggggcca tcggcagacg ccatgacggc   3240
tctgttgttc ctggggtctc tgctgatgag tctggatctg acactttcgg tgaggacggt   3300
ggacactggg attgagccag agtggcagtg aggggtccct gttccggatt tagcctctgc   3360
ctgtcacctg ctagttcagg tgactgagag acttgtggtg ggggtggggg ttgggggaag   3420
gcacagctag cccagaagat ccaaacaaag gaggtagcag cccatgctgg tggatgtgag   3480
gacacaggct acttttgtgg gggagtcaat gagaagagaa aggaaggcta cactttgtga   3540
ggaaatcctg tactttggcg aggtggcagg aggttgaggc ctataggatc aagggaagtc   3600
taacattgtg ggcaatgttc ctgccttctc tctcctatag gctccaccat ggaaagactc   3660
caagaaattt aaggacgcac ctgatgggcc cacagtgggt aagtgatctg gcctcttttc   3720
ctaatctact ctgtggggat ggctgtgctt tagcctgcgt ggtctcaggc ctctggagca   3780
aggagggatc ctgagccaag ctgttccgtt gacatttaaa cctgggtgcc tacagattca   3840
gatgtgtgcc cggagtgcca ggcttgggct gtcctggatg cctgtgttag agcctggcag   3900
gtactctgta gtgttggaga tgatgtcatc tgatgatgtc atcacacctg cacaccaaca   3960
agtgctcgcc agtttcccca tcttcctccc tttcctttca acactcctgg agaatgtcag   4020
acataaccgg tagagttcag agcttcagtg ggcgatggga gccagaacag agctttagac   4080
tcacccaaga tcacagacac cccaagttgt ctccaaaccc taactttctc acttgtgagt   4140
ttactctctg cttcattttt ccctgtctga aaagttagac gggttgctga ggagaaaggg   4200
ttcctcattg ttgtagatgc tgctgccagg aaaatgccct aacatgttag ctcttaggct   4260
agggcatagc tcactggcag agcacttgcc caacatgcac gcacacacac ctgggtttgg   4320
tctgcagcac tgtgagggga aaaaattcct ttttttttta attttaaaga aaaaattctt   4380
tcttaagctg gagagataac tcagaggtta agagcactgg ctgctcttcc agaggtcctg   4440
agttcaattc ccaacaacca catggtggct cacaaccatc tatctgtact gggatctgat   4500
```

gccttttttct ggtctgtctg aagacagcaa cacatatagt aaataattaa ttaattaaag 4560
aaagaacaat tctttttttaa agatttattt atttatttta tgtatgagtg ttctatctgc 4620
atgtacacct gtatgccaga agagggtatc agatctcatt acagatagct gtgagccacc 4680
atgtggttgc tgggagttga actcaggacc tctacaagaa cagacagtag atctcaaatg 4740
ctgagccatt tttccagccc aagaaaaaaa atcttaactt ttagtaaatt tgacttaggt 4800
gaagggttcc acccccatcc tgccccaaac cctgctatag gacttgtgag tacagaactc 4860
taccacagtg agccttgtct gtggggtcaa gctgaggctt gtagtgtgat gtctctcact 4920
gaagcccaac tcagtgtgac cctccaggct tctgtcctaa ccactctaag ccaatcagct 4980
gctgtccctt tcaacctgac ccaccatggc cccctgtctc caagttctag gacccttccc 5040
tctctctatc accctgttgc taaattgcca ctaaaaggag aaaagaagaa gaagaagaag 5100
aagaagaaga agaagaagaa gaagaagaag aagaagaaga ggaagaaaca aaacacattt 5160
gttgagcacc tactgagtcc tggactcaat gtcccaagca ttgccactaa gcctcacggt 5220
gttcccctga agtagacagt gatttctttt tcattttctc tttgagatta taatataatt 5280
acatcactgg gcagtggtgg cacatgcctt taatcctagc acttgggagg cagaggcagg 5340
cagatttctg agttcgaggc cagcctgctc tacacagtga gttccaggac agccagggct 5400
acacagagaa accctgtctc gaaaacaaaa acaatatata tatatatata tatatatata 5460
tatatataca catatatatg tgtgtgtgtg tgtgtatacg tatatatata tatacacata 5520
tatatataca catatatata tacatatata taatcatatc atccccctcc ctttcttccc 5580
tccaaaccct cccatagccc caataattat ttcttttttt ttttaagatt tatttattta 5640
ttatatgtaa gtacactgta gctgtcctca gatactccag aagagggcat cagattttgt 5700
tacggatggt tgtgagccac catgtggttg ctgggatttg aactcgggac cttcggaaga 5760
gcagtcggcg ctcttaacca ctgagccatc tcgccagccc caataattat ttcttatgat 5820
taactatact tttctcagct accatgaaca tcaagttcac aaattcagtg attccgttca 5880
caaattaggt tccgtgagcc tctggctatg acattttcac caatcattag catgtaatct 5940
tgttacatct ggattctgtt taaagacatt attcagtgtg catgttgttg atcccttaaa 6000
cactaatcta atggccgatg ccactattac tgcctgcctg acaaggtgtc cctgacacgt 6060
tttcttcata aggcgcatac aacttcttgt gttcttgcaa gtaggagcct caggtaacac 6120
ttgggcatac acatagaacc actctgtctc cctgaagtac tgaggatcga acctagagcc 6180
ttgtgtatgc caggcaaatg cttggccact gagttaaaac tctggccctc tttaaaaaga 6240
agtgtgtgtg tatgtgtgtg tgcaagtgca tgtgtgtatg tgtatgtaca tatgtgtgtg 6300
tgtttgtgtg tgtgtatgtg tgtatatgtg tgcgtgtgtg tgtgcaagta catgtgtgtg 6360
tatgtgtgtg tgttcgagca tctttcactg acccattcaa ttccataaag atcatgaagg 6420
cactgtgaac gttggcagtt tctttggctt tctttggcct tgtgctgact tgtgagcaag 6480
cactacacga ctgacctata tcctcagcct gagtcacaag tattgggttg gagggggctt 6540
acaaataaat gtttacaaag caggcagggg cagtggtggg ggggtgcctt taatcccagc 6600
acttggcagg cagaggcagg tgaatttctg agtttgaggc cagcctggtc tacacagtga 6660
gttccaggac agccagggct acacaaagaa accctgtctt gggggtgggg gtgggggaac 6720
aaaacaaaaa acaaaacaaa acaaagcagg caggttcaca aatataaagt cagtgaggat 6780
tggcagttgc attactgttg ccagtttact aagccaaaaa tggccaaggg acctaagtgt 6840

-continued

```
ttgtttgttt gtttgtttgt ttgtttgttt gtttgtttgt tttgtagaca ggctatctct   6900

gtgtaataga cctggctgtc ctggaactca ttctgtagac caggctggcc ttgaactcac   6960

agagatccgc ctgcctcagc ctcccaaatt ctgggatgaa aggcgtgtga cctaaatctt   7020

taatgagctc aactttgtga catgcacctg tgtttcagac ttgctcaggg tcagatatct   7080

attccagctg tctgactcta gaagcctact ttctaagcag gatgcagtct tgaatgcata   7140

gctgaccttt ttccaaatca ggccctgtga ggcagagggt gggcagctgg gtctcagggc   7200

agggctctga ggtgtggtgt tcctacagtt ctcactgtgg atgggaggct ctgccatttt   7260

ccctttcagt accaccgtca gctacaccac aaatgcatcc acaaaaggcg gccaggctcc   7320

cgcccctggt aagacatttt ctaatagggg ttgggggagg gggctggatg aaatggactc   7380

tgtctagcta tctaagcatc gtgtttggtc aaaaggtgtg tgtgtgtgtg tgtgtgtgtg   7440

tgtgtgtgtg tttgtgtgtg tgtgtgaagc aaggctagcc tagccagcct caggcactgc   7500

agggaaacct catctatccc ccaggtgtgc taccaccccc aactttgatg aagatcagca   7560

atggggatac tgcttggagc ccaagaaagt gaaaggtatg tatggcatgc aggccccggg   7620

tggctcaagg ctgtgtgtgt cttgctgctc actccgttcc cacacaccta ctcacctact   7680

aagcatcatc agatgccaaa cacttgggat tctgggcccc gccctttttcc ttctcttaca   7740

gcattctttc aaaagtcaga ggaagaattc tggggaaaga ggccaccatt gtccagatga   7800

gcttgagggt ctagaagctt ggggttctat ggtttgatga caagcaggtg caggcagggt   7860

attggtccct acatatgtcc ttccgactcc ggaagtgctt cgctcttgtt atctacctct   7920

cagaccattg cagcaaacac aacccgtgcc acaaaggagg gacatgtatc aacaccccca   7980

atgggccaca ctgtctctgc cctgaacacc tcactgggaa acattgccag aaaggtaaga   8040

ggaactgcct cccagcaaga tgtccctgga gacccggtgc tttgccatgg tcccattgac   8100

ttccttgtgt ccccagagaa atgctttgag cctcagcttc tcaagttctt ccacgagaat   8160

gagctatggt ttagaacggg gccaggaggt gtggccaggt gcgagtgcaa aggttctgag   8220

gctcactgca agccggtggc cagccagggt aagtgggtgt gcagggactg tggggaggag   8280

ggcagagagt caggaacccc tggtagaagg ctgggtgcaa tgatgtacac aggtaaggct   8340

cagtttgcac ctctccccac cccaccccca gcctgcagca tcaatccgtg ccttaatggg   8400

ggcagctgcc tcctcgtgga ggaccaccca ctgtgccgtt gccctacagg ctacactgga   8460

tatttttgcg acttgggtga gtaagacccc gtgtggaaag gcttgcggag gtggatagag   8520

agaatggaag tgaaccagag ggctccaaca gactcatccg ccgactgcag ggagccatct   8580

ctctttctct agacctttgg gcgacctgct atgaaggcag ggggctcagc taccggggcc   8640

aggctggaac tacgcaatcg ggtgcgccat gtcagcggtg gaccgtggag gccacctacc   8700

ggaacatgac tgagaagcaa gcgctaagct ggggcctggg ccaccacgca ttttgccggt   8760

tcgcgagaag ggaccgggca ggggaacttg ctttctctta gggtcctcga gggcctcccc   8820

acgttctaac agtgctccct cttgagattg caggaaccca gataatgaca cacgtccatg   8880

gtgcttcgtc tggagtggcg acaggctgag ctgggactat tgcggcctgg agcagtgcca   8940

gacgccaacg tttgcacctc tagttgtccc tgagagtcag gaggagtccc cgtcccaggc   9000

accatctctg tcccatgcac caaatggtta ggcagaggag ggggtcccgg cgcagaggac   9060

atgggtctct cttattcctg gcagcccgtg ccaggtatcc atggcctcag ccagtctctc   9120

cttccacaga ctcgaccgat catcagactt ctctgtccaa gaccaacacg atgggctgcg   9180

gacagaggtt ccgcaaggga ctgtcctcgt tcatgcgcgt ggtgggcgga ctagtggctc   9240
```

-continued tgcctgggtc gcacccctac atcgctgcac tgtactgggg taacaacttc tgcgcgggca 9300
gtctcatcgc cccctgttgg gtgctgaccg cggctcactg cctgcagaat cggcaagtgc 9360
caccctcggt gacccccctag accgctccta ccgtacccgc accctactct ttccctgccc 9420
gccattcttg agctccctcg aggggttgga aactaaggca cccccagagc atttgtagcc 9480
ggtctgagcc tgctgcctgt cccccacccg actgcaggcc agcgcccgag gaactgacag 9540
tggtacttgg tcaagatcgc cacaaccaga gctgcgagtg gtgccagact ctggctgtgc 9600
gctcctaccg ccttcacgag ggcttctcct ccatcaccta ccagcacgac ttgggtgggg 9660
tggccctaca gggataggga gaaaggatgg cggagggctg gggccctatg tcgccatcta 9720
acctttgcct ctcggggtag ctctgctgcg cctgcaggaa agcaaaacca acagttgcgc 9780
gatcctgtca cctcacgttc agcctgtgtg tctacccagc ggcgcggccc caccctctga 9840
gacagtgctc tgcgaggtgg ccggctgggg tcaccagttc gagggtaggc acaactgttg 9900
ggcgctggtt ggagactttt ggttatctag gagcgcagtt ggtacgcccc gatgaatctg 9960
ggggacaagt ttcactgaca tgacagttgt aaaaaacgca cagagccctt gtctctgtag 10020
cgtgactttc ccagattcta gaattctctg tcgagattcc agagcccctt gaggtttgtt 10080
ctagtttttt gccttctatt gtggcgttaa acaccatgac caaatccagc ttaggcagga 10140
aaggttttat ttggcttccg aggttgcagg gtttcttgct gtccaccatt gaggaagcca 10200
caacagggag tggaggcagg aactgaggca ggaaacggaa agggacactc cttgctgcct 10260
ttctcttcat ggcttgttca gctttctttt taaaaaattc acttattttt attttatgtg 10320
catgtgagtc tgcctacaag catatgtgtg caccatatgt acatctggta caggggaagc 10380
cagatctgta atacaggtta aaaaccacgg tgtgggggct gggaacggaa ccaaggccct 10440
ctgcaagaac agcaagagct cttaacctct gagctagccc ccaacacctt gcggcttgct 10500
tactttgctt tgcttttctc ttttcctctt cctcttcctc ttcctcttcc tcctcctcct 10560
ctttctcccc ctcttcctct tgttttgttt ttgtttttttg ttttgaaggc agggtttctc 10620
tgtgtagtcc cagctgtccg ggagctgtcc aggagctgtc cagctctgta gaccaggctg 10680
ccttcaacct taagcactcc atctgccttt gcctcccaag tgctgggatt aaaggcttgc 10740
acctttctgg ctcagtttct ttcttacaca atccaggccc acctgttcag ggcggcatca 10800
ctcacagtgg gcggggccct ttcacatcaa ccattaatca agaaaatgcc cggggctggt 10860
gagatggctc agtgggtaag agcacccgac tgctcttccg aaggtccaga gttcaaatcc 10920
cagcaaccac atggtggctc acaaccatct gtaacgagat ctggcgcctt cttctggagt 10980
gtctgaagac agctacagtg tacttacata taattaataa ataaatcttt aaaaaaaaaa 11040
aaaaagaaaa tgccctacag atattgccct aggccaatct tctggaggca tctcttcggg 11100
tgaggttcct tcccccccta gatgactctt gagtgcgtca aattgacaga cagtaaccca 11160
gcacaaggat tacagggaga cttgaactgt cttgtgcttc ttttgggctc caaattataa 11220
aggcttaacc aggactttgt ccccatgctg gagcaatgga gacaatggag agaactattc 11280
tgggagccag gttctgagcc actgtgtgga agaggatagg aagtgcttcc tgtgttttaa 11340
gccctgctct tctctgggct tcagtgtcct tgccatgaaa tacttattgg caggtcccta 11400
tcactcaggc ttgctgtgag ggagcaaagc ggagtaggtg gggaattgtc tggtagcctg 11460
gcccacgcag caagctcagg tcctcccctc tgatttgcag ggctgaagaa atactccacc 11520
ttcctgcagg aggcacaggt tccctttatc gccctggatc gctgctccaa ctctaacgtg 11580
cacggagacg ccattctccc tgggatgctt tgcgctggct tcttggaggg aggcaccgat 11640
gcctgccagg tcagccctgg ggtcctggta ggtaccttgg tccctgcctg tcaagcataa 11700
ggcaagaacc acgtgctgcc tgttccccac ccagggtgac tccgggggcc ctctggtgtg 11760
tgaggaagga actgcagaac atcagctcac cctgcgcgga gtcatcagct ggggctccgg 11820
ctgtggtgac cgcaacaagc ccggagtcta cacagacgtg gccaactacc tggcttggat 11880
ccagaagcat attgcttcat aactaaccag gctttatcct tccctccttg tgtgctcctt 11940
gggatgggac gatgaatgtg gcatgctggg tcacagtgaa gctagtgccc cgacactggg 12000
ggcacagaaa ctcaataaag tgctttgaaa acgttcctca gaattctgtc ttgaaacgtc 12060
aagtgggagc acaggtaagc caactccctc gttgcctgga caaggcaact agccagatgt 12120
cagcataaga ggcgtagact cttgtccgga ccaccatatt ttctcatcct tactttgggt 12180
gagcttttgc cgcccatgtt caagtccacc tgaggtcaat taactggact ctagggagaa 12240
ggcagtcttg gcatattttt aaaacgctac gggtgattcc ttatgcaata gaggttggga 12300
actgtagtta agagtgttcc agacgggaat cgtggtgcgg atagtagctg ctgagcatgt 12360
gtgagaggcc ctgggttaga tcccagcacc accattaaaa gaagggggag gggttgtgtt 12420
gggttgtgtg ggttttgttt gtttgttttg aactttaagc ctggcatggt ggtgcaagtt 12480
ggtgtcaagg aaaatctgag gctgcatctg atgcctctaa gtacaagctg ggttaggagc 12540
cagccagcca gagccttcgg ggatgcggtg actccaaagc gaggtttgta gttcccttgc 12600
aggagaggag cctagttgtc cagatgagta catttcttgc ttttaaaaat gtccttctgt 12660
ttattgattt attgagatat ctgtcgtcct aatgccgaaa ttataggcct atacaatcac 12720
ccagtttatg tggtgcaggg ggatcaatcc caaaactttg ttcttggtct agccaggccc 12780
tctgtcaact gcactgtact gactgcgcta cactccccgt ccttacaccc atctttgcac 12840
agcatcttac tgcatagctt ttgtctggcc tgtgacttgc taggtagcct tgaacttgta 12900
cagatcccct tgcttcatga gtgacaggtt taagtacaag ccaccatgtc tggctttttt 12960
tttttttttt aattaagaaa aaaaaatggg gctggtgaga tggctcagtg ggtaagagca 13020
cccaactgct cttctgaagg tctggagttc aaatcccagc aaccacatgg tggctcacaa 13080
ccatccgtaa tgagatctga tgccctcttc tggagcgtct gaagacagct acagtgtact 13140
tacatgtaat aaataaataa ataaataaat aaatcttaaa aaaaaaaaga aaaaaatgtg 13200
gtttgtgtta tgagtgtgtc acagtgtggt gtgaaggtca gagcacaact ctgtggagcc 13260
agttctctcc ttctgccttt gtgggggctc tggtgataaa actcaggcca ccaggcttat 13320
aagacaatgc acccttactg tctgagcctt tttttttttt ttttatggtt tttcgagaca 13380
ggctttctct gtgtagccct ggctgtcctg gaactcactt tgtagaccag gctggcctcg 13440
aactcagaaa tccgcccgcc tctgcctcct gaatgctggg attaaaggcg tgcaccacca 13500
tgcctggcac ttttttaata attaaaaacc tgagaatttg ggctggagag agaatgactc 13560
agtggttaag agcacggact gctcttccag aggtcctgag ttcaattccc agcaatcaca 13620
tgatggctca caaccatctg taatgggatc caatgccctc ttctggtatg tctgaagaca 13680
gcgacattgt actcatatac ataaaataaa tacatttctt ttattatatc taagtacact 13740
gtagctgtct tcagatgcac cggaagagag cgtcagagct cattaaggat ggttgtgagc 13800
caccatgtgg ttgctgggat ttgaactcag gaccttcaga agagcagtca gtgctcttaa 13860
ccactgagcc atctctccag tcctaaatgt gtctttaaaa aaaaaaaagt taaaatttca 13920
agacttttga gctggtgaga tggctcagtg ggtaagagca cccgactgct cttccgaagg 13980

-continued tccgaagttc aaatcccagc aaccacatgg tggctcacaa ccacccgtaa tgagatctga 14040
tgccctcttc tggtgtgtct gaagacagct acagtgtact tacatataat aaataaatct 14100
taaaaaaatt ttttcaagac ttttaaattg ctgggcagtg gtggcgcatg cctttaatcc 14160
cagcactcgg aggaagaggc aggcggattt ctgagttcga ggccagcctg gtctacaaag 14220
tgagttccag gacagccagg gctatacaga gaaaaaacaa aaaacaaaac aaaaacaaaa 14280
aaaatcaaga cttttatgtg tttctgtgga catgagtgca ggtgcccaag caagccagat 14340
gcactgcttt acctgggtgc tgggaattga actctggtcc tctgaaaatg gcactcagtt 14400
gcgggacctt tttttattta ttttttttatt ttattttatt ttaaatcatg tgtgtgtttg 14460
tgtgtgagct tgcctcagga gttgtcagat ctctcgagtg ggagttacag gctttgtagg 14520
ccaaaagagg tgatgctggg aacggaactc aggctctgtg taatgaatgc tctttcttaa 14580
cgctgagcca cctttccagc ctctcatcca tcttcttcca tttcctccta catgctactt 14640
ttagaaccgc ccccgaaccc ccaccaactc taccgccctc tccttctcct cctagttaga 14700
tgttctgtga cgtttgcctt acgtcacagc cccgccctgc gaacttcggg catgctgcca 14760
gtgttcttag ctctgaatgc agccggccac cccccctaat gcaagcacaa gttgctggga 14820
ctgactgagc ggagatgagt gactggaagg gctacatcag tgcagtgctg cgggatcagc 14880
ggatcgatga cgtggctatc gtgggccact cggacaatcg ctgtgtgtgg gcatcacggc 14940
ctgggggtct gctggctgcc atctccccgc aggaggtggg tgtgctcacc gggccagacc 15000

<210> SEQ ID NO 55
<211> LENGTH: 23
<212> TYPE: RNA
<213> ORGANISM: Artificial sequence
<220> FEATURE:
<223> OTHER INFORMATION: Synthetic oligonucleotide

<400> SEQUENCE: 55
uaaagcacuu uauugaguuu cug 23

<210> SEQ ID NO 56
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(23)
<223> OTHER INFORMATION: bases at these positions are RNA

<400> SEQUENCE: 56
taaagcacuu uauugaguuu cug 23

<210> SEQ ID NO 57
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 57
aaagcacuuu auugaguuuc ug 22

<210> SEQ ID NO 58
<211> LENGTH: 21
<212> TYPE: RNA

<213> ORGANISM: Artificial sequence
<220> FEATURE:
<223> OTHER INFORMATION: Synthetic oligonucleotide

<400> SEQUENCE: 58
gaaacucaau aaagugcuuu a 21

<210> SEQ ID NO 59
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 59
aacucaauaa agugcuuuga a 21

<210> SEQ ID NO 60
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 60
tuaaaaucua cagucauagg att 23

<210> SEQ ID NO 61
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: bases at these positions are RNA

<400> SEQUENCE: 61
uuaaaaucua cagucauagg att 23

<210> SEQ ID NO 62
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 62
uaaaaucuac agucauagga 20

<210> SEQ ID NO 63
<211> LENGTH: 22
<212> TYPE: DNA
<213> ORGANISM: Artificial sequence
<220> FEATURE:
<223> OTHER INFORMATION: Primer

<400> SEQUENCE: 63
ttgttgtagg atatgccctt ga 22

<210> SEQ ID NO 64
<211> LENGTH: 21

<212> TYPE: DNA
<213> ORGANISM: Artificial sequence
<220> FEATURE:
<223> OTHER INFORMATION: Primer

<400> SEQUENCE: 64
gcgatgtcaa taggactcca g 21

<210> SEQ ID NO 65
<211> LENGTH: 31
<212> TYPE: DNA
<213> ORGANISM: Artificial sequence
<220> FEATURE:
<223> OTHER INFORMATION: Probe

<400> SEQUENCE: 65
agcctaagat gagagttcaa gttgagtttg g 31

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
gctgattaga gagaggtccc 20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
tcccatttca ggagacctgg 20

<210> SEQ ID NO 68

<400> SEQUENCE: 68

000

<210> SEQ ID NO 69

<400> SEQUENCE: 69

000

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: n is a, c, g, or t

<400> SEQUENCE: 70
nnnnnnnnnn nnnnnnnnnn 20

<210> SEQ ID NO 71
<211> LENGTH: 12
<212> TYPE: DNA

<213> ORGANISM: Artificial sequence
<220> FEATURE:
<223> OTHER INFORMATION: Synthetic oligonucleotide

<400> SEQUENCE: 71
tttttttttt tt 12

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
gccaggctgg ttatgactca 20

<210> SEQ ID NO 73
<211> LENGTH: 13000
<212> TYPE: DNA
<213> ORGANISM: Mus musculus

<400> SEQUENCE: 73
actgcacagt gagacccttc tatacaaagt aaaagacagt taggcatgca gctcagaggt 60
aggttgtcta cctagcaagc ttgaggtctt gagttcaatc tttttttttt tttttttttt 120
ttttggtttt ctgagacagg gtttctctgt gtagccctgg ctgtcctgga actcactctg 180
tagaccaggc tggcctcgaa ctcagaaatc cgcctgcctc tgcctcccga gtgctgggat 240
taaaggcgtg cgccaccacg cctggccgag ttcaatcttt taactttgga aaagacccac 300
gaaacaaaag aggatgagaa tcagagtggt ttggaaatta ccaaagcctg tttgtgaagt 360
aaaataaaag ttaagaaggg ggaagacagt gggcatttgg gccctagcaa taagaaaagg 420
taatccagaa tgttctctag aaatattccc gtggcgttca ctgggaactc ccttgctgcc 480
ttcataaacc atgtcttttg gtagtttctg gagtgaccct gctgcctgtt tctctctcca 540
aaccctggga gttgcccagt gccgcacagc cattccaaaa gcaaggaaaa gtttgtatga 600
tgtgtgaagg aatcaagaag atggacttac agacaagcac tttagggggc gagggaagga 660
agggggaaag gcttgcctag tttcccttat ctgcagggtt tctaaaacaa caacaacaac 720
aacaacaaaa caaatctcca tagtttatgc cagaagtgag ccccgccttt aatcccagca 780
ctcagaaggt agatcctgac agatctgagt ttccaggcca gccagggata cagttttagg 840
acaatatggc agtgagactc tgtctcaaaa catgtcaccc tatacacttt atcatttttt 900
ttaattccag acagggtttc tctgtgtatc tctggctgtc ctggaactca ctctgtagac 960
caggctggcc ttgaactcag aaatctgcct gcccctgcct cccaagtgtg ccaccactgc 1020
ctggtgactt tatttttatt ttattttttta aagaaacaac aacaaagcgt ggggtctcct 1080
atctgtcttg gctcacctgg aaccctctat gtagaacagc cggccccgaa cttgcagaga 1140
tccagcccta ccattttaaa gattggtttc atttccctgg cctccagaac ggtcttagac 1200
cctcccccca gcagaagcaa agcagaaaca gaaggtcggg ggaggagagg gaggtgggta 1260
ggttaagagg aacgatgaag aacaccttct gctagttaac tttgcctaat tatagatgaa 1320
tcacagatgc ccgacactca gatcaccgcc cataatttag gtgactcaag tttttgtcct 1380
ttcagaacta aaattctaaa aaatttccag gcccaaagca tccatcaagt gtgcctctag 1440
agaggaaccg tttgcactca gtaacattcc attctttagg gcttcttaca gacagaaaaa 1500
gagaaaagta gggcagtttt gcaagggtca cctgaaagct gcttaaacaa gccccaggct 1560

```
tggtacacac agctttaatc cagcacttgt gtaaggacct gagtttgagg ccagcctggt   1620
ccagaaaccc tgtctcagga aaaataaata aggaagaaag aaaaagctta aactggccat   1680
tgggatggga agggaggcaa tggtctaaca ctggacctcc agctttgcta gagccccacc   1740
tcagtctaag ggtgcctctc tcctttagtt ttataataga atattcatgt aattttatgt   1800
ccttagtgac tatcagcctg tatggtcatt aagttctgtc taccctggga aagcctctgc   1860
ccaaacctcc ctattcacag gtcctagaac gtagaggtgg ggagcaggac ggtgccgcca   1920
ggccgtgtgc gatcgcgagc tctggatctc aatgcgcccc ggggcgctgt ttcccacgac   1980
tccagcagct tttctaaaaa tccaggcagc ctccagttta cgggatcaac ccgagactcg   2040
cttccctttg aaaattctag agtataaagt aaacgtacga gcaaagtatg tgtcttaaca   2100
cttaatggat gacatagaga ccaaaaaagc catgtccgtg ggcccagtag gccgcaataa   2160
ggggcgacca ggaaactgca gcacagcccc ccgcagccgc cctgctccca caccagtcat   2220
tccagcaccg tggtgaaggc gcttgggggc ggggcggggc gcgcctgcgc agcgaggctc   2280
tgcagcagaa actttgccta gaccggctgg aaccggttag aaccggtcga acccggccgg   2340
ctgccagccc tcgattcagc agctcacaaa gggaggcggc gactcacgac ccgcgtatcc   2400
ttgcgcctct ccccaccccc tttgtcctcg cgacgggttc cgcggtcctc cccgccctcc   2460
ctggcgcggc ccccgctttc tgcgcccagt gacgctttct ccatggtcct gggagaaaga   2520
gaaaaacatc ctttcccctc cgtcgtagtt ttaggaagcg atgagataga cctggggacc   2580
ttgccgccac gggccgggct ctgacggtta ttagcgcagt gcgggtggtg ctcggcatgg   2640
ccgccaaggt cgccgtgccc tcacctgcag cgaccatggc cttgctgggc tgagaccgca   2700
gcctaacatg gcggacgtag gcaagcacca aagcgctcgt gtacccgggc tcggaaaagt   2760
ggccccgaga gcagccggag gctgcaggtc gtccctacag gagcattccc agtataaacc   2820
agtacaaagt gtcaccacct cagaagccac tcgcagggcc ggtcactttc cgagagacct   2880
ccatcttgtt tcgcatgaaa tggcagccgc tcggggagtt acaaaatggg aagtggaagc   2940
tgaagctgtg ggaaagcctg ttttaacact tgcaacatac gctataccct ctgtcctccc   3000
aggaaaacgc aaaaggtgtt gaaacatctg aaaaacttgg ggctcccatt tttaatagct   3060
attagttcat gtttttctc cttgtgacca gaaattttaa acctatttgt acctatttag   3120
ctggtacaag ctaaacattt ctctgtatta gcaaggtcca agaggcccac acgacgtcaa   3180
gaaaaatcta gaaacttgga agtcaggatc tatttttaac tctctgagga actatttttc   3240
ttccttcacc aaggtggtgg agggttacta ggttccggtg gagtgacgtg tccctttgca   3300
ataaataccg gcgctccggg ctctgcgtca ggcattcagg cagcgagagc agagcagcgt   3360
agagcagcac agctgagctc gtgaggcagg agactcagcc cgaggaaatc gcagataagt   3420
ttttaattaa aaagattgag cagtaaaaag aattagaact ctaaacttaa gctaatagag   3480
tagcttatcg aaatattact tagtcttaat aatctaagaa gatcttaaga gataacatga   3540
aggcttattt aaacagtttg aaaaaggaaa tgaggagaaa agtatttgta ctgtataatg   3600
gaggctgacc agagcagttt aggagattgt aaagggaggt tttgtgaagt tctaaaaggt   3660
tctagtttga aggtcggcct tgtagattaa aacgaaggtt acctaaatag aatctaagtg   3720
gcatttaaaa cagtaaagtt gtagagaata gtttgaaaat gaggtgtagt tttaaaagat   3780
tgagaaaagt aggttaagtt gacggccgtt ataaaaatcc ttcgactggc gcatgtacgt   3840
ttgaaggcat gagttggaaa cagggaagat ggaagtgtta ggctagccgg gcgatggtgg   3900
```

```
cgcacgcctt taatcctagc acttgggagg cagaggcagg cggatttctg agttcgaggc   3960
cagcctggtc tacagagtga gttccaggac agccagggct acacagagaa accctgtctt   4020
gaaaaaacaa aaaggttagg ctagtatttg gagaaagaag attagaaaat ggaagtgaaa   4080
gacgaagaag acatacagga aggtgaagaa aaagctgtta gagaagatag gaaaatagaa   4140
gacaaagcat ctttagaaga cagaaaaggt acttaaaggc acaggtagta ggaagccgaa   4200
gaatagaaga tagaaagaag caagatagaa aaacaaaatg gaagttaaga caactttgga   4260
tgccagcatt caagataggc aaagaagata agattgaggc caaaaggttg gataagatat   4320
aaagtcagaa ggaaattatc tttaaagcca taagttcaaa tttctgatgg agcgagcagt   4380
ttagaagagt ctttagacag ccacatacaa gattgaagct agcaatcaaa gctactagga   4440
ctgaagtaaa aagttaaggc agaatgcctt tgaagagtta gaagaatatt aaaagcctta   4500
acttgtagct taattttgct tgatgacaaa aggacttttg ataacagttt caagattgtc   4560
agcattttgc attggacttg agctgaggtg cttttaaaat cctaacgact agcattggca   4620
gctgacccag gtctacacag aagtgcattc agtgaactag gaagacagga gcggcagaca   4680
ggagtcccga agccagtttg gtgaagctag gaaggactga ggagccagca gcagcagtgc   4740
atggtgaaga tagcccagga aagagtgcgg ttcggtggag gaagctagga agaaggagcc   4800
atacggatgt ggtggtgaag ctgggaaagg gttccaggat ggtggagcga gagcgagttg   4860
gtgatgaagc tagctggcgg cttggcttgt caactgcgcg gaggaggcga gcaggcattg   4920
tggagaggat agatagcggc tcctagacca gcatgccagt gtgcaagaaa ggctgcaggg   4980
agagcatgcg gtgcggtaac attccttgag gtcggcaaca tggtggtggt tttctgtaac   5040
ttggatggta acttgtttac tttgtcttaa tagttatggg ggagttgtag gcttctgtgt   5100
aaagagatat atctggggct gtatgtaggc ctttgcgggt gttgtaggtt tttctttttc   5160
agggttatgt cctcttgcat cttgtcagaa gcttttgagg gctgactgcc aaggcccaga   5220
aagaagaatg gtagatggca agttgtcttt aaccgctcag aggggaatga atggtagagc   5280
cagcacaacc tcccagtttt gtaagacgtt gtagtttgaa cagatgacct accacaagcc   5340
tcactcctgt gtaggggagg taattgggca aagtgctttt gggggaatgg gggcaaaata   5400
tattttgagt tcttttcccc ttaggtctgt ctagaatcct aaaggcagat gactcaaggg   5460
aaccagaaaa aaggaaatcc actctcagga taagcagagc tcgccaggtt tacagtttgt   5520
aggaagtaga ggatggatgc tagctttcac actgagtgtg gaggagctgg ccatggcgga   5580
attgctggta gtttactctt tccccctccc ttaatgagat ttgtaaaatc ctaaacactt   5640
ttacttgaaa tatttgggag tggtcttaac agggaggagt gggtggggga aacgtttttt   5700
ttctaagatt ttccacagat gctatagttg tgttgacaca ctgggttaga gaaggcgtgt   5760
actgctatgc tgttggcacg acaccttcag ggactggagc tgccttttgt ccttggaaga   5820
gttttcccag ttgccgctga agtcagcaca gtgcggcttt ggttcacagt cacctcagga   5880
gaacctcagg agcttggcta ggccagaggt tgaagttaag ttttacagca ccgtgattta   5940
aaatatttca ttaaagggga ggggtaaaac ttagttggct gtggccttgt gtttgggtgg   6000
gtgggggtgt taggtaattg tttagtttat gatttcagat aatcatacca gagaacttaa   6060
atatttggaa aaacaggaaa tctcagcttt caagttggca agtaactccc aatccagttt   6120
ttgcttcttt tttcctttt cttttttga ggcgggcagc taaggaaggt tggttcctct   6180
gccggtccct cgaaagcgta gggcttgggg gttggtctgg tccactggga tgatgtgatg   6240
ctacagtggg gactcttctg aagctgttgg atgaatatag attgtagtgt gtggttctct   6300
```

```
tttgaaattt ttttcaggtg acttaatgta tcttaataac tactatagga acaaaggaag   6360
tggctttaat gaccctgaag gaatttcttc tggtgatagc ttttatatta tcaagtaaga   6420
gatactatct cagttttgta taagcaagtc tttttcctag tgtaggagaa atgattttcc   6480
ttgtgactaa acaagatgta aaggtatgct ttttttcttc ttgtgcattg tatacttgtg   6540
tttatttgta acttataatt taagaattat gataattcag cctgaatgtc ttttagaggg   6600
tgggcttttg ttgatgaggg aggggaaacc tttttttttc tgtagacctt tttcagataa   6660
caccatctga gtcataacca gcctggcagt gtgatgacgt agatgcagag ggagcagctc   6720
cttggtgaat gagtgataag taaaggcaga aaaaataatg tcatgtctcc atggggaatg   6780
agcatgagcc agagattgtt cctactgatg aaaagctgca tatgcaaaaa tttaagcaaa   6840
tgaaagcaac cagtataaag ttatggcaat acctttaaaa gttatggctt atctaccaag   6900
ctttatccac aaaagtaaag aattgatgaa aaacagtgaa gatcaaatgt tcatctcaaa   6960
actgctttta caaaagcaga atagaaatga agtgaaaatg ctgcattaag cctggagtaa   7020
aaagaagctg agcttgttga gatgagtggg atcgagcggc tgcgaggcgg tgcagtgtgc   7080
caatgtttcg tttgcctcag acaggtttct cttcataagc agaagagttg cttcattcca   7140
tctcggagca ggaaacagca gactgctgtt gacagataag tgtaacttgg atctgcagta   7200
ttgcatgtta gggatagata agtgcctttt ttctcttttt ccaaaaagac ctgtagagct   7260
gttgaatgtt tgcagctggc ccctcttagg cagttcagaa ttttgagtag ttttcccatc   7320
cagcctctta aaaattccta agccttgcac cgatgggctt tcatgatggg atagctaata   7380
ggcttttgca tcgtaaactt caacacaaaa gcctacatga ttaatgccta ctttaattac   7440
attgcttaca agattaagga atctttatct tgaagacccc atgaaaggga tcattatgtg   7500
ctgaaaatta gatgttcata ttgctaaaat ttaaatgtgc tccaatgtac ttgtgcttaa   7560
aatcattaaa ttatacaaat taataaaata cttcactaga gaatgtatgt atttagaagg   7620
ctgtctcctt atttaaataa agtcttgttt gttgtctgta gttagtgtgg gcaattttgg   7680
ggggatgttc ttctctaatc ttttcagaaa cttgacttcg aacacttaag tggaccagat   7740
caggatttga gccagaagac cgaaattaac tttaaggcag gaaagacaaa ttttattctc   7800
catgcagtga tgagcattta ataattgcag gcctggcata gaggccgtct aactaaggac   7860
taagtacctt aggcaggtgg gagatgatgg tcagagtaaa aggtaactac atattttgtt   7920
tccagaaagt caggggtcta atttgaccat ggctaaacat ctagggtaag acacttttcc   7980
cccacatttc caaatatgca tgttgagttt aaatgcttac gatcatctca tccactttag   8040
ccttttgtca cctcacttga gccacgagtg gggtcaggca tgtgggttta aagagttttc   8100
ctttgcagag cctcatttca tccttcatgg agctgctcag gactttgcat ataagcgctt   8160
gcctctgtct tctgttctgc tagtgagtgt gtgatgtgag accttgcagt gagtttgttt   8220
ttcctggaat gtggagggag ggggggatgg ggcttacttg ttctagcttt ttttttacag   8280
accacacaga atgcaggtgt cttgacttca ggtcatgtct gttctttggc aagtaatatg   8340
tgcagtactg ttccaatctg ctgctattag aatgcattgt gacgcgactg gagtatgatt   8400
aaagaaagtt gtgtttcccc aagtgtttgg agtagtggtt gttggaggaa aagccatgag   8460
taacaggctg agtgttgagg aaatggctct ctgcagcttt aagtaacccg tgtttgtgat   8520
tggagccgag tccctttgct gtgctgcctt aggtaaatgt ttttgttcat ttctggtgag   8580
gggggttggg agcactgaag cctttagtct cttccagatt caacttaaaa tctgacaaga   8640
```

```
aataaatcag acaagcaaca ttcttgaaga aattttaact ggcaagtgga aatgttttga   8700
acagttccgt ggtctttagt gcattatctt tgtgtaggtg ttctctctcc cctcccttgg   8760
tcttaattct tacatgcagg aacattgaca acagcagaca tctatctatt caaggggcca   8820
gagaatccag acccagtaag gaaaaatagc ccatttactt taaatcgata agtgaagcag   8880
acatgccatt ttcagtgtgg ggattgggaa gccctagttc tttcagatgt acttcagact   8940
gtagaaggag cttccagttg aattgaaatt caccagtgga caaaatgagg acaacaggtg   9000
aacgagcctt ttcttgttta agattagcta ctggtaatct agtgttgaat cctctccagc   9060
ttcatgctgg agcagctagc atgtgatgta atgttggcct tggggtggag ggtgaggtg    9120
ggcgctaagc cttttttaa gatttttcag gtacccctca ctaaaggcac tgaaggctta    9180
atgtaggaca gcggagcctt cctgtgtggc aagaatcaag caagcagtat tgtatcgaga   9240
ccaaagtggt atcatggtcg gttttgatta gcagtgggga ctaccctacc gtaacacctt   9300
gttggaattg aagcatccaa agaaaatact tgagaggccc tgggcttgtt ttaacatctg   9360
gaaaaaaggc tgtttttata gcagcggtta ccagcccaaa cctcaagttg tgcttgcagg   9420
ggagggaaaa gggggaaagc gggcaaccag tttccccagc ttttccagaa tcctgttaca   9480
aggtctcccc acaagtgatt tctctgccac atcgccacca tggcctttg gcctaatcac    9540
agacccttca cccctcacct tgatgcagcc agtagctgga tccttgaggt cacgttgcat   9600
atcggtttca aggtaaccat ggtgccaagg tcctgtgggt tgcaccagaa aaggccatca   9660
attttcccct tgcctgtaat ttaacattaa aaccatagct aagatgtttt atacatagca   9720
cctatgcaga gtaaacaaac cagtatgggt atagtatgtt tgataccagt gctgggtggg   9780
aatgtaggaa gtcggatgaa aagcaagcct ttgtaggaag ttgttggggt gggattgcaa   9840
aaattctctg ctaagacttt ttcaggtgga cataacagac ttggccaagc tagcatctta   9900
gtggaagcag attcgtcagt agggttgtaa aggtttttct tttcctgaga aaacaacctt   9960
ttgttttctc aggttttgct ttttggcctt tccctagctt taaaaaaaaa aaagcaaaag  10020
acgctggtgg ctggcactcc tggtttccag gacggggttc aagtccctgc ggtgtctttg  10080
cttgactctt atatcatgag gccattacat ttttcttgga gggttctaaa ggctctgggt  10140
atggtagctg atatcactgg aacactcccc agcctcagtg ttgaactctt gataattaac  10200
tgcattgtct ttcaggttat gcccaattcg tcttattacc tctgagtcga cacacctcct  10260
actatttatt gaatactttg attttatgaa ataaaaacta aatatctctc attgtgtgct  10320
tctttgtgca taaaacacag gcttatttta agcctaaaga gaccaaatgt ctgatctacc  10380
tcagcttctc cgattagtga ggccttccct gtttccttgg gctgcatggc tctttcatgc  10440
agatggctct aaagttgggc ttgggtccta ggtggccact cttgcacctc aggaacacaa  10500
ggcctttccc tgctgttcag gctctcctcc ctgagaaaac attctggatt gtctatgagg  10560
aagttgggaa aagatggtgt cgaaaagagg tggtgtgcat tgctcctctg ttcctaacac  10620
tggatggaag actagttttc atgtagttta gggaaatagt tatacatggt ctaaaggccc  10680
aaaaacattc ccagagtgta tgcaatactg tgtgtaagtg tgcactgcgt gtgtttggag  10740
gtcagaactt ctctgaggtt ctagagatga agcaagtcct cagccatggc ccaagaatgg  10800
gaaggaactg ggtcctgctg taccacttcc cattccttaa ggaacagttt ggcccggtgt  10860
ggtgcaagca tggtcggtca ctgaaaaaag aaaacccact taggtttcac aggcttgaag  10920
agctgcatgt catccagcaa attactggct gctgtaagga caggccccta ggtcccagtc  10980
ccaggtgccc ttcctgccac tcaatcaagc cttacaccct gggcaaaaac atcctgcgtt  11040
```

```
gaaggttcag ctcccagggc tggaaacttg tgctggcatc taccccagtt caaaggggct  11100
cagcacattg acaactaaaa ctaagccctc aggtgagcaa aatggtctcc ttaaggcaat  11160
catggtcatt ggtgttcctg cagtaaagga cagcatcaca gctgatgtct gtgtactggc  11220
tagttttgta tcaacttgac acagctggaa ttatcacaga gaaagcttca gttggggaag  11280
tgcctccaag agatcctcca cgagatcctg ctctaaggca ttttctcaat tagtgatcaa  11340
gggggaaaga ccccttgtgt gtgggaccat ctctgggctg gtagtcttgg ttcagttcta  11400
taagagagca ggctgagcaa gccaggggaa gcaagccagt aaagaacatc cctccatggc  11460
ctctgcatca gctcctgctt cctgacctgc ttgagttcca gtcctgactt ccttggtgat  11520
gaacagcagt atggaagtgt aagccgaata aaccctgtcc tccccaactt gcttcttggt  11580
catgtttgtg caggaataga aaccctgact aagacagtct gagacctgac agatctgtgc  11640
taaagtctgg taccaactga gctagaccct gccacacacc tcagtaatgg cccattctga  11700
attcacccag agctgaggct ttgccgaggt gaggcacaaa gacttcactg gagagcagga  11760
gatatgaaca gaggttgggg ctcacacttc ctgattgggg gccaggactg gggcaagat   11820
gaaggaacgg taggcatgct tgtaaatttc ccaaagggtt agatccagat cttagctttc  11880
agtgtgtagg ccagggtgac tctgaatttg ggtccttgga cctcaacttt ggaagttgca  11940
gggatgagcc actgggctct gtacagtctt gtgctgccca catgctctag ttgtacaaag  12000
gatactccct caaacaagct ctccccaaat aggcctttga cgtctggacc cagccaccgg  12060
cccaaaagcc gattagtaca gggccagcag catagcatcc ttctactacg gcatgaaatt  12120
aggagaggaa gggtttgaag agagagagtg gaagatgtgg tttttatttt ttatttattt  12180
tatgtatgtg agtacactgt agctgtacag atggttgtga accttcatgt ggttgttggg  12240
agttcacttt taggacctct gctcactcca gtcatctccc ctcgctcagt ccctgctcac  12300
tccagcccaa agatttattt attattatac ataagtacac tgtagctgtc ttcagacaca  12360
ccagaagagg gcgtcagatc tcattacaga tggttgtgag ccaccatgtg ggtgctgaga  12420
tttgaactcc ggaccttcag aaaagcagtc agtgctctta actgctgagc catctctcca  12480
gcctgtgatt tttatatttt aggtagggcc atagtatcac cagacaggta ttccttgtat  12540
ggctcaggat ggtaaaatta aagttgtgcc tcaggctcct gagtgggact gcatggctgc  12600
tccagtatac ctggccacct ggattgttga ctctgaagct caggtcttag tttctgcctc  12660
tgatcagttg acaaacttga tacctgccca gctcacaatg caacctttgc atgcatcctg  12720
gacttagcct tgacaagggt agataggcaa ctgagtagga cgtgactgga cttcgctgcc  12780
atctagtgtg caaatgtagt gcatgcaatg tccttgaact ttttcttgcc atgcctattt  12840
tgttgtttta tttgtttgtt tttggtttat taattttttg taggatctct ctaatctgac  12900
ttcttggaat ttgctatata aactgggctg gccttgaact cacagcagtc ctcctgcctt  12960
tgcctcctca gcaaatcctg ccagcctata tacctccatg                        13000
```

<210> SEQ ID NO 74
<211> LENGTH: 21
<212> TYPE: DNA
<213> ORGANISM: Artificial sequence
<220> FEATURE:
<223> OTHER INFORMATION: Primer

<400> SEQUENCE: 74

```
cggatgaaga gaggcatgtt g                                              21
```

<210> SEQ ID NO 75
<211> LENGTH: 18
<212> TYPE: DNA
<213> ORGANISM: Artificial sequence
<220> FEATURE:
<223> OTHER INFORMATION: Primer

<400> SEQUENCE: 75
ttggccacac cgtccttt 18

<210> SEQ ID NO 76
<211> LENGTH: 23
<212> TYPE: DNA
<213> ORGANISM: Artificial sequence
<220> FEATURE:
<223> OTHER INFORMATION: Probe

<400> SEQUENCE: 76
agacctgggc aatgtggctg ctg 23

<210> SEQ ID NO 77
<211> LENGTH: 20
<212> TYPE: DNA
<213> ORGANISM: Artificial sequence
<220> FEATURE:
<223> OTHER INFORMATION: Primer

<400> SEQUENCE: 77
ctcctcagac cgctttttgc 20

<210> SEQ ID NO 78
<211> LENGTH: 24
<212> TYPE: DNA
<213> ORGANISM: Artificial sequence
<220> FEATURE:
<223> OTHER INFORMATION: Primer

<400> SEQUENCE: 78
taacctggtt catcatcgct aatc 24

<210> SEQ ID NO 79
<211> LENGTH: 20
<212> TYPE: DNA
<213> ORGANISM: Artificial sequence
<220> FEATURE:
<223> OTHER INFORMATION: Probe

<400> SEQUENCE: 79
ccgtcatgcc gacccgcagt 20

<210> SEQ ID NO 80
<211> LENGTH: 52000
<212> TYPE: DNA
<213> ORGANISM: Mus musculus

<400> SEQUENCE: 80
ttgcagtgac tcagcctacc tccttcttac gcaacatttt tttttctttg tccaaccttt 60
actccttcct tatttctccc ctgcaataca cagggccagg agtctcctag accccagttc 120
aaatctgagc tctaaatgcc tacacagtga gttccaggcc actcaagggt acatactgag 180
accttgtctc aacatacacc ctcataaaaa gagaagacag ccacaggatt ctatttatat 240
ggaatactat actgagggct gagagagatg gcacacagcc aagcctgatg acttgagttt 300
gattccaaac ccacgtggta gaggggaaga actgactcct acaagtggtc ctctgacccc 360

```
cgcacagatg ctgtgcatgc cccacaaccc taggaacaaa tacaatcata gaaaataaat    420
gtccagagca agcaaagcca caaatgcagg gagctggtgg cagggatatt aacaagatcc    480
cttttccagg ataatggaat gtcttggagc tagagaggtc ataactgaga atatattaag    540
tggcactgaa ttgcaaacat caaaatctca aatatgtaca tttatataat ataaattata    600
cctcaactta aaaataatca agaatcaggt gtggtggtgc acagtgcatg agcataggag    660
acctcaaaaa tggccccaca gtgacacact tcctcaaacc aacaaggcca catctcctaa    720
tggtgccact ccttatgaac caaacactca aatacatgaa taggaagcta ttcctattca    780
agccaccaca ctgcgcttgg cagcacatgc ctacagtctc agtattaggg agttggaggt    840
atattcaaga tctcaaggtc agtccggact acactgtgag ttcaagggga gtccgagctg    900
cattcaaaga ccctgtgtca aaacaagggg agtggctgat ttggtagagt agttggtcaa    960
catgctcaag gccctaggca tcatcacagc actgcaaaat aaataaacag aatattgaga   1020
taagaggaag aaaacgtcac caactcagcc taagccgtga aagtttaata ccaccgatac   1080
taggaaaaga tggcaggtac cctgataata tgccctggga aggatacggg gattctgcca   1140
aagacgcata aagttaatct tgtagaactc gcaggtcatt gcaggtccaa gaggcactct   1200
ttcaaacaac tgacctcaaa ctaaggctga ggtgaagatc tgggatccag tcttcggtcc   1260
acaaagaagc tataagggat gttattcgga ataaccataa aactttgagt agaaacttgg   1320
gtgaggactg gagatgtggt tacatggtag agtgtctccc ttacacactg gaaaccccag   1380
gttctggccc cagcatcaca aaaatcaggc atggaagctc atacccttaa tcctagcact   1440
gggaggcaaa gccaggaaga ctgggacttc taggtcattc tggtttcagt aagttcaagg   1500
ccagtctggg ttgcacgaga ctctgcctga aaaggagaag cccccaaagt aggacaacaa   1560
cgaagtgggc ctgaaagact gttcagttgt taagagagca gcagcagcag caggaggatc   1620
tgatttcaga ttccagttgt ctcatgtaac aagctggcta ttccacaaat gaccataact   1680
ccagctttga ggggtgcagt gccttccctg gtctctgcat atgcaggtac tcacactagt   1740
gcacacacac acacacacac acacacacac acacacacac acacacacag agaaacacac   1800
acacacaaat aaatctttaa aaagtgtatc cgtgactgtc ctggaatttg ctaggtagac   1860
caggctggct ttgaattcac agatctatct gcctttgcct ctggagaccg tgtgaaccat   1920
gacatcttcc ccaattaaca aaaatacact tatttattat gtagccagtt gggggggggg   1980
gcgcggcagg gaggggagat gggccctcta caatgtagag atcagaggac aacttgtgga   2040
agttgttctc tcctcccact acaggagtgt ctgtgtatgc ccttccagga ttatatgggt   2100
cctctgtttc agtcctttgg tctcctagtg atggagatgt tcaagaacgg cacccttcac   2160
ccgactcctg agatttcccc tgaatgcacc tctagagctt ccattctcac ttcacacaga   2220
gggagtgttc agagcctttg caggtctcct ggatgtaaaa ctcagtgaat ggcaacgaaa   2280
tgataggcct catggtaaaa ccatgtagag tgtgggatgt gctaggagct ggtgtggatt   2340
ttttttacaa agtattttat cttatttctt gcgcacataa gcgtgtgtgt gtgtgtgtgt   2400
gtgtgtgtgt gtgcgcgcgc gtgcgtgcaa gcattcgagc acagtgtgtg taggagtgca   2460
tgtgtatcac ggggtacatg tggcagtcag aagacaatgt atgtgttggt ttttttattt   2520
tagcatggga ggcccaggaa ttgaactcgg gtgtctgtga ttggcagcaa gcacctttcc   2580
ctcttcggta gacctttgtg atcttcacat tgtaggagag ctgcacacag gtacatgaga   2640
ctcatatcca cgaaacccct ggccagattg taaatgctgc ccgcccgggt ttgtggcgca   2700
```

-continued gttggagcct gagttttgag gtgattgatg tttagtgtcc ccatgaaact tctatatggt 2760
ttgcatgggt gcggctactt ttgttcattg gcctctctac acccaggttt agagggtttg 2820
gagtcagggg tgtttgcgtt tgtgtcatga ctgtgtgtgt gagccctggc tttggttgtg 2880
tgctggagga taaggatgga tgtgctcacg agctggatac ctgtcacgtc acgcaggtta 2940
agcccgcatc tcttgtggca gacctgagtg taccgaggtc tgcaagtccc aggcttggcg 3000
ggtagaaggg tcggacccca ggaggccggg caggggggcgg gggcgctcag agccggcccc 3060
ggggcggggc gagccgccca ggcctggggg cggggcagcc cgacagcctc acttcggcga 3120
agttggcggc gcggaggctg gcccgggacg tgcccggagc cctgggaaag agggaggagg 3180
gaggagggag ggtcgtggcc ggccgccatg gggctggggg cccggggccg ccgccgccgt 3240
cgtcgcctga tggccttgcc accgccacca ccgcccatgc gggcgctgcc cctgctgctg 3300
ctgctagcgg ggctgggggc tgcaggtgag ggatcaggga ctcggagggt gggactgggg 3360
ttgcaggggc ggggaagcaa aaaaaaaaaa gtatatatat atatatatat attctcctaa 3420
gtttggaatt tagaggacct gcccccccag gattaaagcc ggggcagaga tgcagcagct 3480
gggggtgtgt atcagtcatg gggttcgcac agattcatga tgggaaggca ggatcctaga 3540
ggcccaagga atcgagaccc ttgaatgaat caagagtcca agagtaggag ctggagttgt 3600
gggaatctgg ggctgaaatt cggaagcgag gtgtaccaaa agtttcaggc tcaccccatc 3660
ctacttctgc ctggagtcct gggaaggtta ggatgggggc tcaaggaccc cccaaggcct 3720
aggacccctt gcacaaaagc gcctccccta tcccgggcgg gccgtgaagg gggggggggg 3780
acaaggaggg ggcgcggagt tctcggagct ctgaactcgg agaaaacgtc tcatgttgga 3840
gagctgcaag acccggcgct ggagcgcgag aagcaggagc tggagccctt gcgaagcccg 3900
cgcccctcc cccgcgtgcc gcccgatccc tcttcaggcc gccgggatcc cgtagtctcg 3960
ggaccccgtc tctgtgccgg gaggagaagg ggcgaggtcc acgtgctcat ctccagcttc 4020
tgggccccca tccctgtggc cgcagcccct ccccagcatg cctgggcccc cctcccctct 4080
tcctccactc tgagctcccc tcccccgctc gggacaatgg cttcgccgtc tagacacccc 4140
ctccccccgg ccggcctcac gctttctttg ccagacaaag cgggacccac gaagggccag 4200
agcggggact gagggggcgc ccccacccct gccccgggag gcctgatcag cgggggaggg 4260
gcataggcag ttggctgtgg ccaggggttc tagggctcct atggtgggac tcagtgctgg 4320
gccgggtgag agttgcatag agagtggctt agcctctagg ctctactagg caggactggg 4380
caggagccac cgcccccgcg gggccagtgc agactcatgg cctgtcacac atagaaaggg 4440
aaaaaaatgc atgtgcacag gtttagtaca gccatagatg cacacttggc acacacaaga 4500
cacacctatg tgtttgctgc tcacatgttg atgtgcattc aggcataggt cacccaagac 4560
ctgctaggca ttcatgttca aggtcacatt tatagctgcc aatccatgac ccagacaagc 4620
acaccagtgg ccacacagct gtatgcttga atactgctgt tcatatagat ggatgcacag 4680
tgcatgcagc tcgtgtgcac atggtgtaca aggctatgct gtttgaagat accagcatgg 4740
taccaagcac atgcactatt agtcactatt agtaatatag tggcctaata cacagactgt 4800
cacacaaact cacaggcata tgtacacaca cacacacaca cacacagagc tcacatggtt 4860
gtgttctccc ccccccccat acagcttcta gtgtgatgtc acaaaattga ataggtcctt 4920
cattcttaac tcatcctttt actgtctctg tttttttttt tttttttttt tttttttttt 4980
ttttggttgg tttctccttt cagtttctgt ctgtccctat ttctcaattc tcccccaatc 5040
tcctttcctt ctctctctga ggaacaaaac ttctacaggg gcccacacct gtctgagcac 5100

```
ataattctcc accagctcag acctggccac acctctcacc atctggcaag actgccacac   5160
ccaaagtggg atacaaccct gagggatggg gacactggac agggcagcac atatcttgca   5220
ccagttctct cccttacact ccatagccta tccatctagt acccaaaacc acctctctat   5280
ggctgctgtt ggttcctcct aggtgtacgc tttgcctact ctttcaagag ctagcaggga   5340
ctacagtaga cacaggctca acactgcctg ccttctccat ctacccaaga catgggcttg   5400
aagctgcaga tcccctttaa cactcagcat ctttacttcc tactctgtgc cttttctctg   5460
ttgtgcacat cctagtcaag gcaacttcct gagcccacac atctggcaca agtcaactcc   5520
tccttctcac ccctgccttg tggttcccag ggcttgagct ggcagggaca gctgcagccc   5580
caacagctgg ggctggggtg gggggccgtg ggaactgtag atagggggcc tcttagtacc   5640
cacacagata ccctcctagc ccagtgcagc tgttgcctgg cagacaggag gggagggtct   5700
gatttggggt tctgtgtgcc tgtctgacct ccccaccttc ttttgccccc acacagcacc   5760
cccttgtctg gatggaagcc catgtgcaaa tggaggtcgg tgcacccacc agcagccctc   5820
cctggaggct gcttgcctgt gagtgtctgg cccagcgcca tcagtgggcc ctgtgtgggg   5880
agggaatagg tcctctgcct ctgagtctcc tgggggatgc tggtatcact tcctccatgt   5940
gtgtggcttc ggtaacctct tgtgtttccc catagggaat cagacagctt taagagcaga   6000
agctctggtg tctctctggc ttgggttcaa atcccgcatc atcttgctaa gtgtctgaga   6060
cttaaccagt tcgttaagtc acagtgctct ggaataaaag attgatttcc aaggccaatg   6120
acagtggctt gacagtgaca aggacgtcca tgccctccca tatgtcagaa tacaggaggc   6180
acccaggaga cctattttag agccctgttt tattttgttc tagtttgtat gacctttggt   6240
tagtcatttc tcttttctga acctcacggc atctgtgaag caggagtgct ttccctggcc   6300
tgtgactgtg caggaaggga cccaagaatt atttgggaaa tgcagaaagt tagagaagag   6360
gaggagggtt tgggagctac cagaggcagg cagaactcta gattctggga catctcgagc   6420
aagtgctggg gaccttccca gccacttttg catctacaat ggcttttctt tcatgaggtt   6480
gactgtaaag atttgaaaag gacctttaac tgggcttacg cttgtatttc ccagcagaag   6540
caggaggtca ttccgtacag ttccagggca gtctgggctc tcacagagtg agcttgtctc   6600
aatgttttgt tttctaaagg gggctggggc agctgagagc ttagtaggta aaggcacttg   6660
ctgccaaact ggacaacctg agttaagtcc tggggaccca aaagatggaa agagagaact   6720
aatctcggca agttgttctc tggcctctgc atgaatacat acacacacag ataatgtaat   6780
aaaaatcaaa actatattaa aaataagaga aacttttgaa acctttttgac gactggagat   6840
ttcaatggtg tttgcccagt acatacaaag ccctgggttg gagggaaagg acctcaaggt   6900
ctgtgggctt attggtttg ttttcttttt aatagtaata gcattccatt cagcagctat   6960
taattagttc gttcatcagt gtgttcattt cctcaatact gtgtgggcta gccagtggat   7020
cagcctcaag ctaggtgggg ccaggatgac ttccgatata gaaaaacaaa aacctttaaa   7080
attcaatggc tggaatctca tttagcttta ttgggggtca ctggccgagg ggcatcctga   7140
ggctgagggt tgggagggtc cttacttgga agcagtcgct tggaagggag gctgaggcgt   7200
ggggcggggc gcctgcgcag tagaactaca cgcctggaca gctgccgaca ggtgaatacg   7260
cctgaggctg ccccgcccct cgacaggtga atcaccggct cacgcggcct ccgggagccc   7320
ggatcgcgcg gagtggagct cgcttaaggc tccagaatag agatttgggg gggacctcag   7380
cctatgttct tctcatccca acccactctt tcaggcttct caaatcctgc tgtctcctta   7440
```

ggagtgaccg cccccctcccc aatgacactt tctcccccac ttctccccag tcttccgacc 7500
gggagaaggc ttcggagttc tccgtcgctt ggtccttgtc tgtcttgcta gtccgttccc 7560
tccttggaag ctgctccccc gcccccctcc cgctccgcta cgtctcccct aaagctaagg 7620
cggcgaggcg ggtccggggc tggaaccggc cggaccggtc ggcgggggcg cgaggtgcag 7680
agcgtgggaa cccgcccgcg gcgcagggag ggtgccgcgc ccagcttggc gatgataccc 7740
gtggtcccca gtgctctgca cgcagcgccc cctcctggcg tgtcatcgtc gccgccttgc 7800
aggactgggt agggggttga gagcatcacc tccaaggttc gaatgtccac cacacccttg 7860
cagggttgag cttcgacagg gttgagcttc gacacgttta tctaggaacg gaattcgggg 7920
tgggggtatt gtagggtgac gctaagaaat gagtcacctg ctttgagttc tgcccttggt 7980
gtttgagaca agactgagct aggggatcct cgctgggagc cggaagggta gggtagagga 8040
gaggagggtt gaggtagggg tgatgtacgt tgtgtcattg catagttgca tagccaggat 8100
tgtttgacta ctccagtccc cttccttagc cctcctcacc tctgtccgta gaaaggttac 8160
aaacttaagt cgtcttttag tttttatttt ctagcactca ggacttagat tttttcgaga 8220
cagggtttct ctgtgtagcc ctggctgttc tggaactcac tctatagacc aggctggcct 8280
cgaactcaga aacccgcctg cctctgcctc ccaagtgctg ggattaaagg cgtgtggcac 8340
ccctgtccca ctactcagga ctatcttgat gggtttgggg aaggggccgc aggccttggt 8400
ccagattgag ggctgaggtg cccatgccaa gccccaccga tccatgagag gaggattgca 8460
tgctcttggg agaaaggagt ttatgatttg tggctatctt cctgcctctc catatgagtg 8520
agagtttccc atattcgtgt gggaggctgt ggcttcttgt ctgtgtatgc caggccagta 8580
tgcccagttg tatgtgtctg tgcggtttct gggtctttct gggtgtgtct gcctcctgga 8640
gtctgaggct tttcatttgt tgttcccagt acctggaatg cccttcccca catcacccctt 8700
tggctcaccc attttttttgc cgtttttttgt tgtttgaaaa tataacaccc actcattcta 8760
tcacccttag gctgcttgtg agtttcctgt ggttgctgta ccagattacc acaaacaggg 8820
tggcttaaaa caacagaaat gtactctgga aaatcctgga ggccggaagt ctgaaattaa 8880
ggcgttgcca gaactggctt tctttactga ccatccaggg ggagaagact ttcttatgtc 8940
ttgtccagtt tctgattggc tcaggcttat ggctgcccca ccctactctc tgcctttgtc 9000
tgcacatgac ctttcttctc tctttagttt ctatctgtct ctctcccgtg tcctgggaaa 9060
ggaacctagg cccctgcaca taccatacaa gaactaccac tgtgtcatgt ccctggcttt 9120
tctcttgtaa agatactgtg tgttggggct ggtggcacga ctcagtagtt tagagcagag 9180
tttggtcccc agctctcatt ggttactcac ctgtaactcc agctccaggg gttttggcct 9240
ctgaggaagg acactgtact caggtgcaca catactcaca cacaaccaca catgcataca 9300
ataaataggg gctgaaaatg gctccacagt taagagcgtg tattattttc tcagaggact 9360
tggatttgat ccctggaatc cgcatgataa ctcataacca tccttaatgc caacgccctc 9420
ttcagacctc catgggcatc aggcacgcac agcatgcacg tacatacatg cgtggaaaac 9480
acttatccac atcaaagtaa aataaatctt ttaaaaattg gcttgaaata caaagtgaac 9540
ttgtcttggt attcttcaca attacattgg caaaaattct tcttcccttt ctttttcttg 9600
tgctgagaat tgaatctagg gctttatgca tcctaggcaa gtgcagtacc actgagctat 9660
attccaaatc ctcttgttat ttgtttaaaa tatatgtatt gatcttgaga cagcgtctca 9720
tgcagtcaag gctagcctca aacttgctat gtggccaagg ctgaccttga actcctcatc 9780
ctcctgcttt ttcctcggaa tgccaggttt gtgtgaacca ccttgcctgg cacatctcct 9840
ttaaaaagaa ataaagtgat agtcacagct tctgggacat gggcgtgttc ttcagtgtac 9900
cacgtccttt gtgagcttgt ggcatgtaca agctgttttt ggtatgttcg tattaatgtg 9960
ttacctgtct atgttttctt tgcctgacct ggctatgagg accaaaaggg taagagtcac 10020
ttttattttg cttgctgctg tgttttagta tgtagtaggt gtcaataata tttgttgtca 10080
gaataaatga ggatggctgg gaatggtggc acttgccttt aaacccagtg ctagaggcag 10140
agaggcagag gggcagaggg gcagaggcag aagagaggca gagaggcaga gaggcagaga 10200
ggcagagagg cagaggcaga gaggcagaga ggcagagagg cagagaggca gagaggcaga 10260
ggcagaagag aggcagagag gcagagaggc agaggcagaa gagaggcaga ggcagaggca 10320
gaggggcaga ggcagagagg cagaggggca gagggacaga ggcagaggca gagaggcaga 10380
gaggcagagg cagagaggca gaggcagaga ggcagagagg cagagaggca gaggcagagg 10440
cagaggggca gaggcagaga ggcagagagg cagaggcaga ggcagagggg cagaggcaga 10500
gaggcagagg ggcagagagg cagaggcaga ggcagaggca aaagagaggc agaggcagag 10560
aggcagaggg acagagaggc agaggcagag aggcagagag gcagaggcag aggcagaggg 10620
gcagaggcag aagagaggca gagaggcaga ggcagaggca gaggcagaga ggcagagagg 10680
cagagaggca gagaggcaga gaggcagaga ggcagagagg cagaggggca gaggcagagg 10740
aagagaggca gagaggcaga gaggcagaga agcagagagg cagaggcaga gacagagaga 10800
cagaggcagg taaattactg tgaattccag tctagccagc gatatgtagt gagaccctgc 10860
ctaaaatata ttaaaaaaaa aaaaaaaaag ggaaggaaga gtaaatggat ttgtctgata 10920
gtctgtctgg cacgagtgtt gtttgataaa cgcatcttgt gttatctgtc tggcattgcc 10980
atgcttttat accgtcccga ccacacatct tcccacaggt gcctgccagg ctgggtgggt 11040
gagcggtgcc agctggaaga cccttgccac tcaggccctt gtgctggccg aggcgtttgc 11100
cagagttcag tggtggcggg caccgcccga ttctcctgtc gttgtctccg tggcttccaa 11160
ggtgaagggg tgtgtctgga cgggaaccct tggtaggcga gaatgtagtc agacccaagc 11220
tcaccctctc ctggttcttc caggcccaga ctgctcccag ccagacccct gcgtcagcag 11280
gccctgtgtt catggtgccc cctgctcagt ggggccggat ggccgatttg cctgtgcctg 11340
cccacctggc taccagggtc aaagctgcca aagtgacata gatgagtgcc gatctggtac 11400
aacttgccgt catggtggta cctgtctcaa tacacctgga tccttccgct gccagtgtcc 11460
tcttggttat acagggctgc tgtgtgagaa ccccgtagtg ccctgtgccc cttccccgtg 11520
tcgtaatggt ggcacctgta ggcagagcag tgatgtcaca tatgactgtg cttgccttcc 11580
tggtaagtaa gttgtgccca gggaaggcag ctggggacaa taggctagcc tcttagtgac 11640
cattgtcacc ttgtcctccc ctacgaggct tcgagggcca gaactgtgaa gtcaacgtgg 11700
atgactgtcc tggacatcgg tgtctcaatg gggaacgtg tgtagacggt gtcaatactt 11760
acaactgcca gtgccctccg gagtggacag gtgggcatca gggctgcaga gaaccagggt 11820
ggctgacctc aggtgggcac acgggcaact tagactagca catctttgtg ccctaggcca 11880
gttctgtaca gaagatgtgg atgagtgtca gctgcagccc aatgcctgcc acaatggggg 11940
tacctgcttc aacctactgg gtggccacag ctgtgtatgt gtcaatggct ggacgggtga 12000
gagctgcagt cagaatatcg atgactgtgc tacagccgtg tgtttccatg ggccacctg 12060
ccatgaccgt gtggcctctt tctactgtgc ctgccctatg ggaagacag gtgagtggcc 12120
cttttctttg taggcaacag aatggtttca gcatgaaagg taaaaacaga ctctgagttg 12180
agcgttagaa agattggggg ctggggatgt ttcttcctgg cagagtgtgt gcttagtgtg 12240
cacaggctct gagtttaatc cttagcgtga aggaagacaa gaaggaggag ggaaggtgga 12300
agaaagaaag gaaagaggga ggaagggttt gctggaccct gggtttggaa agaagcctga 12360
gcctctgtcc tatgaggtgc atagtccaag gcagagactg ttggaattgg ggaactattg 12420
agaggtctaa ctgggaaaaa ggcaggaact atggaagtca caaaggtctg tttgtccctt 12480
acatcttatt ttggtggggg gtggtcagac tctggttgtc aggctaggtg gcaagtacct 12540
tgagtttatt gttgttgttg atgcgttgag acatggtgtc actatttgta catcaggcta 12600
gcctcaaact tgcaagaaag gatccttggg cttctgtgtt ctgagtggtg ggattaagga 12660
attttgttgc tatgcctgaa tagggtcttg atttatcatc ttttaaaata ttaaaaaaag 12720
tgtgtgtgtg tgtgttttgg ctgcatttat gtatgttata ttatgtcatg ctacacgcat 12780
gactggtacg ctgagaggcc agaaaaattc atcagctctc ctgagattgg agttactgat 12840
ggtggtgagc tgccgtgtag gtgtgttggg aatgaaacgt aggtcttctg gaagagcagc 12900
caggattctt agccgctgag cacctctttg ggccccggtg ccttgtttgt aaaatgtttc 12960
taagttattt tcaaatggta tcgaagaagc agattaacag ataatactga accaatattc 13020
caatgtgaaa cgtcctgaat gtttcactgt ttcataataa atggcttttc caggacagcc 13080
agggctatac agagaaaccc tgtctcgaaa aaaaaccaat aaataaataa ataaataaat 13140
aaataaataa aataatatta atagatggct taaaaaaata agaacagata ctaatacagt 13200
gctggttaat atacataaga aacaggaggc aagggccacc ccaaagggtg ctcagggcgt 13260
aaaggcactc gctgagttgg cctggcaagc ctacttctat caagggaatc cactggtaga 13320
aggagaaaac caaccaagtt tcctctggct tctacacatg cactatgaca tgcacacact 13380
ccccagataa gtacattagg aatgatgatg gtgatgatgg tgatgataat gcaaggagct 13440
ggaagcgtag ctgagtgatg gtattcattc gttgtatgct catggtcctg ggatccatt 13500
accagtacca gtcttcttcc tcaaacgcta ggtctggggg aactttgggc caccccgagg 13560
atcagcgctt catttctgct taccttttct caggcctctt gtgtcatctg gatgatgcat 13620
gtgtcagcaa cccctgccat gaggatgcta tctgtgacac aaaccctgtg agtggccggg 13680
ccatctgcac ctgcccacct ggcttcactg gaggggcatg tgaccaggat gtggatgagt 13740
gctcgattgg tgagaagagt accttctgga aaggagcctg aaaacggagg ggtggggcca 13800
tggctggcca cgcccacact ggctgtgtct tctcccccat attcccccctt cttgcaggtg 13860
ccaaccccctg tgaacatttg ggtcggtgtg tgaatacaca gggctcattc ttgtgccaat 13920
gtggccgtgg ctatactgga cctcgctgtg agactgatgt caatgagtgt ctctccgggc 13980
cctgccgcaa ccaggccacg tgtcttgacc gaattggcca gtttacttgc atctgcatgg 14040
caggtgggtg gtgggtatgg cttgggtggg tcatgaaggc tggggcctgg ggtaaaactt 14100
ggtttattgt tatttacttg aagaaaaaat gctgggcata gagacacatg actgaaatcc 14160
cagcacttgt gaggcagaga taggctcatc tctgtgagtt cgaggccagt ttggtctaca 14220
gggtgagttc taggatggct aggattataa agtgagactc tgtctcaaaa taaataaaat 14280
aaaataaaat aaaataaaac aaaacaaaat aaaaagggga tagagagata gcttagtggt 14340
taagagtcct ccctgctttc tagagggctg agtttggttc tcagtaccca tatggggcag 14400
tgcacaacta tctagctcca ggagatctac aatgctcttt tggcctctga agatacccat 14460
gtgtttggga cacacacaca cacacacaca cacacatgca tgcaaataaa caaaattaaa 14520
caaacaaata aacaaaagac atttcaaaag agctgaagtg gcacagtaag acggtctgga 14580
actcactgtg tagaccaggc tggccttgag ctcacagaga tccacctgcc tctgcttccc 14640
aaatactgga tcgaatggca tgtgcctctc ggcctagtgc actttaacca tgagggttcc 14700
aaattgtcag gcttggcagc aagcatcctt atttgagcca tcttgcttgc ccatgactga 14760
gtttaaagtg aagcttcctg gctggagaaa gagagagaga gttatgtgtg tttaggatga 14820
aaccttgaaa actcgataag gtaggtgcag ggtcagagcg gattttacca gataacatca 14880
aaggggagct tcataaacct tagtccatga ggggccacag ctgggtgagg gtccagcttg 14940
tttgaaacta aatctaagcc tgaaagtgtc gtgcacgcct gttatcccag cacttgagca 15000
gctgaggcag gagcatcatt agtttgaggc cagcctcaag gccatagtaa gaatttatct 15060
caacaaaccc acaaccaaat caaagtcccc aaaccaagtg aagaggcctt ctgagggaac 15120
tttctgggcc ctcataccat tcccttcagg cttcacaggg acctactgtg aggtggacat 15180
cgacgaatgt cagagcagcc catgtgtcaa tggtggtgtc tgcaaggaca gagtcaatgg 15240
cttcagctgc acctgcccat caggtgagga ccctgggaca aggagcctgg tgtgtcaggt 15300
tatgacaatg tggaacttaa aaaaaaaagt aattagttac ttaactcttt tgtgtgtggg 15360
ggttctctcc ttccactatg ttatgtacat tttgggaatt gaactcaggt ggtcaagctt 15420
ggctggcaag catgtttatc ttctgagcca tctctctggg ctagtctgta ttgaaattaa 15480
tttaaaacaa agccaagggg gtttcccact caaataaggc aggctgcctg ctttaactgt 15540
ttgtgtcacc tttcatccac tactcacttc caggattcag tgggtccatg tgtcagctgg 15600
atgtggatga gtgtgcaagc actccctgcc ggaatggtgc caagtgtgtg gaccagcctg 15660
acggctatga gtgtcgctgt gcagagggtg agggcggacc gtgagactgt ggcaagagcc 15720
agaaggtggg ctggtgggcc aatgggtgtc aaggaccaat aacagacttg gggatggcct 15780
cagctaggcc aggtcagggc cagtgacgct gatgatggag gtaggcagag gtcttggcaa 15840
gattcagggt gcagctagca gtgagattta aagtgggcgt ttctgggtca ggaacagagc 15900
ttggagctgg gcagaatgga agggagaagg ggtgaggtct gagagctgag ctggaattgg 15960
gctgagatta cagccatgga gaagtgggca gaccctcacc tcccgttctt gcaggctttg 16020
agggcacttt gtgtgagcga aacgtggatg actgctctcc ggatccctgc caccacgggc 16080
gctgtgtcga tggcattgct agcttctcgt gtgcttgtgc cccaggctat acgggcatac 16140
gctgtgagag ccaggtggat gagtgccgca gccagccctg tcgatatggg ggcaaatgtc 16200
tagacttggt ggacaagtac ctctgccgtt gtcctcccgg aaccacaggt ggggcctggg 16260
gctgggctat aacagtacgt gggggtgtgt gggggtctgt gatgaatttg taactggtgc 16320
ttgacaatag taggtactct tgccatactt cttccctccc tgtaggtgtg aactgtgaag 16380
tcaacattga tgactgtgcc agtaacccct gtacctttgg agtttgccgt gatggcatca 16440
accgttatga ctgtgtctgt cagcctggat tcacaggtgg gtaggtggct gccatgtagt 16500
gggggggggg gggcttgtaa gatagggatt aagacacaag tctcttgggt gtccccactt 16560
tattttttta aaaaaggaaa tattacattt catttatttt gtgtatgtct ggaggtcaga 16620
gggcatctgg ggggagtcag ttctctccgt aaaggtctca gggaccccac tcatgtcatc 16680
aggcttgggg acacgtgtgc tttcccccca gttaagtccc tttcttccct ttatcaagat 16740
tatctccaat actcagaagg ccaaggttgg aggattagtg catgtttgaa gctagtctga 16800
gcatcatagt gagcactagg ccagccaggg ctgcatagca agatcatgtc tcaaaataaa 16860
acaatatata gagagggctg gagagataga tggctcagca gtttcaagca cttgctcttg 16920

```
cagacgactc gggtttagtt cctagcatta acacgctggc tcacaagtgc atagttttgt  16980
ttttgttttt gtttttaaa taataaagta aaataagata aaacaaagca aaaaaaaaaa  17040
aaaaaaaaac acatcagaaa tggacaaaac aaaacaaaat caggagggaa aagagcccag  17100
gagaagacac aagaatcgga aactcattca ttcacacact caggagtccc acaaaaacac  17160
caaactggaa actataatgt ataggcagag ggtctgggga gggcctggca ggctccgtgc  17220
atactgcccc agtcttggtg agattgtctg agctttgata atgttgattt agagggcctt  17280
attttcttga ttttctccat cccctctggc tcccagtctc cttctgcctc ttcttcatcg  17340
gaaaagggat ttgaaggaga cacccctag gtttcttagt ctctcactct ctgtgtacag  17400
tctaggagtg ggtctttgta tttgttccca tcagctgcag gaggaagcgt ctgtaatgat  17460
ggctgaacaa ggcactggtc tgtgaggtat taggagtcat tttagcctta cctttttcc  17520
ccttaaggct ggttctaccc ttgccctctg ggctatctag ccgcaggttc ttggtcactg  17580
aagcaatatt gggtatgggt tctgtcttgt ggagtgggcc ttaagtcaca cagatattgg  17640
ttggttactc ctgcaagctc tgtgccacca cagcactagc agatctagag gcaggacacc  17700
actgtagatc aaagggtttg tggttgggtt ggtgtttatg tttctctagc atgcagaaaa  17760
cctttctgta ccaaagaccc tagaatatag aaggctctat gtaggcataa gtttgacttc  17820
tccatgttca gtgagtctca caactgctta taactccaga gtaaacttat aattccagga  17880
atctgacatt ctctgctggc tttcatgggc accaggaatg caccatgatg cactaacata  17940
catccaagca ctcatataaa ataaataaat aaataaataa ataaataatc ttttaaaaag  18000
cagagagaga aagaggagag agatggagag agggagggag ggagggagat aggtgcacac  18060
ctgtgcacac acacacacac acacacacac acacacacac acacaaagtt gggggcgggg  18120
gggggaaacc accttggact atcctgagct tgtttcctca gtggcatggg gctgtcgttc  18180
tgtcagcaga gtgaggtcag gatcagctgt gtgatagaga acaggacgtc cctttccttc  18240
agttggcacc actgtcttcg ttctggaatg aagttgcctg tatgctcccc agggcccctc  18300
tgcaacgtgg agatcaatga gtgtgcatcc agcccatgtg gagagggtgg ctcctgtgtg  18360
gatggggaaa atggcttcca ctgcctctgt ccacctggct ccctgcctcc actttgccta  18420
cctgcgaacc atccctgtgc ccacaagccc tgtagtcatg gagtctgcca tgatgcacca  18480
ggcgggtgag gccctttccc aactcccgac ccctcttctg ctgtctccag ccacctgtca  18540
cacctcactg cctcccccac caggttccgc tgtgtttgtg agcccgggtg gagtggccct  18600
cgctgtagcc agagcctggc tccagatgcc tgtgagtccc agccctgcca ggctggtggc  18660
acctgcacca gtgatggaat aggctttcgc tgcacctgtg cccctggatt ccagggtgtg  18720
tgaccccata ttcctccccc agggcacccg acacccttgt ttcttatgtt tctttcctgc  18780
ttttttgtt tttaaagctt tgcttagtac cttttgttct gtgtgtctct gttacatatg  18840
tctgtgtgtg gagaccagaa ccagaagaag gcatgtgtcg tcttttatca ctctctaccc  18900
attcctctga ggtgtgcagg gtctctccct gaccctgggg tttgtgcttt ctcggatagg  18960
ctggaagcta ctgagtccct gggatgcccc tgtttttctt tcaacttgca gctggggtta  19020
cttgttatag aggtgggagg gtctgagttc tggtcctcat gattgggcct gaggtgctct  19080
taactgctga accatccttc cagccccatc tgcatttcct tccttccttc cttccttcct  19140
tgcttgcttg cttccttcct tccttcttca ttcctttaat ttctctcttt tttgtctttt  19200
ctaaatatca gggtggggac tccagggatg ggggaattgg gagcagtgag tttcaaaact  19260
atctaaacta tctgcttcta acaggccatc agtgtgaggt gctgtccccc tgtactccaa  19320
```

gcctctgtga gcacggaggc cactgtgagt ctgaccctga ccggctgact gtctgttcct 19380
gtcccccagg ctggcaaggt acactaatat cctcctcttc ttctcgtctc ccttctctct 19440
tctttctctt cctcttcctc ttcccctctt tctcctcttc tgcactttgc tccatgttgg 19500
gcaatgccag ggagcccaga gaggactcag tcctgccctg cctttgaagt tgtttctttc 19560
tgggaaaaga cagctggatc cagacattca cagcccagga gtcagctcag gagaagaggg 19620
aagccatatg gagctgagga cactgggata cctgagattt gatgacattt ttgatcgggt 19680
gacttcagag tgtgtattca acatctaaag agataggcag aatatatttc aggagtggca 19740
tgtgccaaac gcccagggat agcggctggt ctttgctttc cttgactcca ccagcgggtt 19800
cttgagctgc aggcatcctc agaccccttt ttacccctgt aacctcaatt gcttcccctc 19860
tcacctccag gcccacgatg ccagcaggat gtggatgaat gtgccggtgc ctcaccctgc 19920
ggcccccatg gtacctgcac caacctgcca gggaatttca ggtgcatctg ccacagggga 19980
tacactggcc ccttctgtga tcaagacatt gacgactgtg accccagtaa gtgcagggat 20040
ctttggggcg cttccttccc cagggaaccc acccatcaag tcataccatg tcctggcact 20100
gtgttgctgt ttcctgactc tcctgacaac tattactccc ctcattcatg agggtcttac 20160
ttccatccca gcaccactgt agaaatgggc aatgggctgc tgggatgact ctgcagggag 20220
aggcactgcc tctaaacctg atgaacctag gtcagtccta caagttgtct tctgatctct 20280
acatgcctgc tatgcacaca cacacacaca cacacacaca cacacacaca cacacacaca 20340
cagagagaga aagagggggc gggagagaga gaaaaaaata acaataataa cccaaaatag 20400
aataaaaagt taaaaatatg ttttatttaa gccaatatag aaaatatttt catttcacat 20460
ataagccttc aaaaatttaa attttgctaa atgtatttta catttgcagc ttgtctcatt 20520
tggcctggca gtgagatcac gggcctatta acctcatgtg gctagtagta gctacactgg 20580
tcaccacagg ctgtgctgag cgtatgaatc agagcaggca gtggcactac aagtattcct 20640
tggttctttg aggttgttcc cacagcctcc atggattaca gactctatgg gtgtttaagt 20700
cccttattgt caaatggctt aatgtttgca aatagcctct gcatctcctc ccagattatt 20760
taaatcatct ccaaataact ttttatttta aaatgtttac atttacctgt tattgtgtgc 20820
atgtgtgtga gcgtgtatgt accacgtgtg gaggtcatag gacagtatag tccttctacc 20880
ttgtgggatc tggtgttcca actcagggtg ttgggtttgg tggctttact caggctgagt 20940
cctatcatca acccagactt catttttaat tgaactggaa ggagggaggg gggagggagg 21000
gagggaaggt gagagagaag gggggggtgt ggaatgcaaa catgctacat tagattgtgg 21060
aggccagagg acagcttgca ggagttgatt ttcttcttcc accatgaggg ttgcagggat 21120
tgagctcaga caggcagtcc tgggtgggca agcaccttta cctactaaag tcatcttgcc 21180
ggtccctcta gatggcttga cacaccaagt acgatggaca tagcatgtat atgtttgcta 21240
tactctattg tttagaaaat aacaagaaaa tagtgtgcat gttctgccct tgggtaatct 21300
ctgattttcc ctattgtcca tctactggtt gaacccacag attctgaact tcagaatagg 21360
tagggccagt tctatagctc aaagggtttt gtttttgttt ttgtttttgt ttttgttttt 21420
tgtttttcga gacagggttt ctctgtatag tcctggctgt cctggaactc actttgtaga 21480
ccaggctggc ctcaaactca gaaattcgcc tgcctctgcc tcccgagtgc tgggattaaa 21540
ggcgtgcgcc accatgcccg gcactcaaag gggctttttt taaaaggata tttttaaaat 21600
gtatttattt gtctatgtgt tgcatgacac atttgtctac gtgagccatg acattcacgt 21660

```
ggtggtcaga ggacatctta tagagggggg ttgaccacaa aaggggacta actttgatct  21720
ctgaccaaga gtgtctcttg tagtctggga tacacacacg tttaatttct gcacttagaa  21780
ggcagagtgc aggctcatct ctgaactatt caaggccagc ctcatctaca tattgaactc  21840
caggctagtc ttggctacat agtaaaacta tttcaaaaac aagcaagcaa acaaaaagga  21900
ctgtcccctc tggcttcttc ctgagtcttc ctgtgtgtaa agcatagctg agtcaggcca  21960
ggctgatgtg ggcataggca ctgaccagat tattttcctg ctcactgcag acccgtgcct  22020
ccatggtggc tcctgccagg atggcgtggg ctccttttcc tgttcttgcc tcgacggctt  22080
tgctggtcct cgctgtgccc gagatgtgga cgaatgtctg agcagcccct gtggccctgg  22140
cacctgtact gatcacgtgg cctccttcac ctgtgcctgt ccacctggtt atggaggctt  22200
ccactgtgag attgacttgc cggactgcag ccccaggtgg gtggagcatg ggctggagac  22260
tcaggggcca gagagggcat cctggactcg gcatctgtta gagggctgga atgatgctgg  22320
cacatggctg aggaatgggc aaggctgctt ggaagtcaca gactccagtt ctttggaggc  22380
ctagactgag gcagcgtccg taggcgaagg agccaggtta gatcttcata gtgctatggc  22440
ttgttgagga tagcaagggt ccgaaattgg gaagtactta gttctagaag gattggggtg  22500
gtctttaagg tcttgaactt cttgtcctgt tctccagttc ctgcttcaat ggagggacct  22560
gtgtggatgg cgtgagctcc ttcagctgtc tgtgtcgccc cggctacaca ggcacacact  22620
gccaatacga ggctgacccc tgcttttccc ggccctgtct gcacgggggc atctgcaacc  22680
ccacccaccc aggatttgaa tgcacctgcc gggagggctt cactgggagt cagtgtcagg  22740
tgggtggtgt ctgaggtcct tggtggaaga gtccagaaat gagggggggac ccgtgggggg  22800
catcctgaag ggataaggcc atctggtttc tagggtctct cccagcactg atcttgaaga  22860
tttcttttgc agaacccagt ggactggtgc agccaggcac cctgtcagaa tgggggtcgc  22920
tgtgtccaga ctggggctta ctgcatttgt ccacctggat ggagtggccg cctgtgcgac  22980
atacaaagcc tgccctgcac ggaggccgca gcccagatgg gtgagggaag catgtggtgc  23040
gtgcgtgtgg ggctgaaggg tggtggtgca tccctcttgc tggcatgagc caaatgagag  23100
cgccatacaa catatgggac taatgaggtg tgtggctcag tatgtgtgtg actggaataa  23160
ctggccagag tgtgactata tctgtcacag tgagacagct gggtgtgtgt gtgactaagc  23220
tgatagagtc atcaaagtgg tgctgtggaa agagaccagg ttagctgaca agtggcctga  23280
cagcttttgg atgtgggtga gacactaggg attgatggca gtggggatgt tagatgaatg  23340
tgtgatgtgg ccggaatagg aaaggtggca tggccacctc tgagtctgat gtcaccctct  23400
gcttttcagg ggtgaggttg gagcagctgt gtcaggaagg tggaaagtgc atagacaagg  23460
gccgctccca ctactgtgtg tgtccagagg gccgtacggg tagtcactgt gaacacgagg  23520
tggatccctg cacggcccag ccttgccagc acgggggcac ttgccgtggt tacatggggg  23580
gctatgtgtg tgaggtaagt gcgtctcagg gagagggaag agaagtcagt catgcttgcc  23640
tgtgtttctg tgtcctggtg tgggtccttc ccctccccg tcggtgggag agcagggatg  23700
tttcatgtgt agtaggtaag cactctgtat cactcagctt catccagagt cagcatggct  23760
gctatagaat ttttttattt tattttattt ttttttttt ttggttagat ttttgagaca  23820
tggtctcgtt atgaagctct ggctgtcctg gaatttgcta tgtagtccaa gctggcttcc  23880
aagtcacagc aatccttctg cctctggctc tatatgagtg ctagataaca gtcatgcgcc  23940
ataatacttg tctgcgtgtc ttttctttcc tccttttctt tatcttttcc tttcccttct  24000
ttccttctct ttctttcttt ctttctttct ttctttcttt ctttctttct ttctttcttt  24060
```

```
ctttctttct ttctttctat tttgagacag agtctcacta tgtagctctg gtgggcttaa  24120
actattagag atctacctac ctcagcctcg tgggtgctag gattaaagga atgagcaacc  24180
aggcctggcc tagcagtcct tttatgggta tatgtctgtg tgtgtgtgtg cacaggagtg  24240
taaatgcaga ggtcaggggc agacatcagg tgtcccctct atcactgtac tttgttcgcc  24300
tgcggttctc tcactgaacc tcaagttagg ctgtagatgg tgagccccag tgatcctcct  24360
gcctccccca ccccacacct gggtgacaca catagaagac cacacctagc tttttaagta  24420
ggtactgagg atttgaactc aaatcttcac gtgtgtgcag caagcgctct tacccactga  24480
accatctctg cagctcctta accctcatgc acttgtggat ggacttgggg catgtgagtt  24540
tctgtctcca gttctgtgtc tctctctggg tatgagtgac ttaccattgt gtctggacat  24600
gtggtctggg gtacctgggt atttttcctg cgtgttctca tcagcctatc tccctctgta  24660
ctgagtgtgc tggtggcctt cccagtctca ccctgaccaa tagcaacttg agggaggaga  24720
ggatttactt cagcttacag gttactgtcc atcattgagg gaggctgtga aagaagccca  24780
aggcagggaa ccatcgtcca gaactgaagc agagaccata gaattgtgtt gctttcccgg  24840
agcggtctgg gtcttcccac atcaatcagc actcaagaaa atgcccccac agacatgcta  24900
taggccaatc tgaaggaggc agtttctcaa gcaagattcc ctcttcccag ataggtctag  24960
gtttggttca agttcatgca cacacacaga taacaagtgt gggcacagtg tgtttccttg  25020
tactgggtaa gtctgccccc tacactggct ttgtgttgga tgtctatgtg tgtccttttg  25080
tggtgagatt ctgtgtgctc acaggtatgc cgaggcacgt ctgtgtccct cggggctgag  25140
tgaattcctt tcttgcctca atacagtgtc cagctggcta tgctggtgac agttgtgagg  25200
ataatataga tgagtgtgct tcccagccct gccagaacgg aggctcctgt atcgatcttg  25260
tggcccgcta tctctgttcc tgtcccccctg gcacactggg tatgttaagg ccagggttgg  25320
gggcaggata agaggatgag tttctagcct ccactgacca tgctcctata ccctaggagt  25380
tctctgtgag atcaatgagg acgactgtga cctaggccca tccttggact caggcgttca  25440
gtgcctacac aatggcacct gtgtggacct ggtgggtggc ttccgctgta actgtccccc  25500
aggatacaca ggtctgcact gtgaggcaga catcaatgag tgtcgcccgg gtgcctgcca  25560
tgcagcgcat actcgggact gcctacaaga tccaggtggg catttccgct gcgtctgcca  25620
tcctggcttc acaggtaaga atggcagaga gcctggccag aaacctgatg tggttctgct  25680
tctgtagttg atcctcctgc atctgtttgt tcagggcctc gctgtcagat tgctctgtcc  25740
ccctgtgagt cccagccatg tcagcatgga ggccagtgcc gtcacagcct aggccgtgga  25800
ggtgggctga ccttcacctg tcactgtgtc ccggtaggtg tgattggtag gggttggaac  25860
ccttggggaa agaaaaggcc tgtggcttta gggaagcata ggtctatacg ggaaaagtag  25920
aaggaaagga ggttctgaaa ttatgaaatt atgaaattat ggtttggagt gtaacttagt  25980
gaaattgtga cttggctttg ttgcctcctg gggaggtatg gcttatcttc aaaatgaggt  26040
cagtagagga aaggttgctg gaattggagg ggtgggggtg gggtgtcagc atttctcaag  26100
tcttgacctc cattcttttc tctcttttcc actctcctgt ttcttctcac taccaatttt  26160
ttctctttct gtctcctcac ttcaccatta gccattctgg ggtctgcgtt gtgagcgggt  26220
ggcacgctct tgccgagagc tgcagtgccc agtgggtatc ccatgccagc agacagcccg  26280
tggaccacgc tgcgcttgtc ctccggggct gtccgggccc tcctgccggg tttctagggc  26340
gtcaccctca ggagctacta acgccagctg cgcctctgcc ccttgtctgc atgggggctc  26400
```

atgcctacct gtacagagtg tccctttctt ccgctgtgtg tgcgctccgg gctggggcgg 26460
cccgcgttgt gagacccctt ccgcagcccc tgaggtcccc gaggagccac ggtgcccgcg 26520
agcggcttgc caggccaagc gaggggacca gaactgcgat cgtgagtgca acaccccagg 26580
ctgtggctgg gatggcggtg actgctcact gaacgtggac gacccctgga ggcagtgtga 26640
ggcactgcag tgctggcgtc tcttcaacaa cagccggtgt gacccggcct gcagctctcc 26700
agcctgcctc tatgacaact ttgactgcta ctctggtggc cgcgaccgca cctgcaagtg 26760
agccccctga ctctgtcctt ctgtctatct atatgttgca ctgtcagtga gccacatctg 26820
tcccagtttg tctgtcagtc tgtttttggc tcgtctgatg ggctgtccct tccagctgct 26880
accaccaggg cactggtggt ttcatccgcc tgtttccacc catgtgcctc atctctgcct 26940
atttatattt ttacctatat atcttgccca tttgcttctg tctgcctgca gttacacatc 27000
ccatctgtcc acacttagga cttgttcatt tgtctttctt aaaattttaa aaattaaact 27060
gggtctagtt gctcacacat tttaatgcca gcatttcaga ggcatagaca gcaggtctct 27120
gtagggattc aaggccagca tgatctacat agtgagttct aggccagcca aggccacaca 27180
gtgataccct gtctcaaaac aaaaacaaac aaacaaacaa acaaagcaaa acaggagccc 27240
acagcaggtg ctcattcaag agcatacaat agtgatactg gttgagcatc ccaaatccca 27300
aacctgaatc cctgagccat gtggggcatg ggcatgatgc cacagtggaa aattccatcc 27360
tttgccccaa tgataagtta cagtcaaaat tcagacacag gttggtctgt agtggcagag 27420
caccttccta gatggcatgt ggcccttggt tcaatccccg cccagcatgg aaataaaaca 27480
accaccaaag gcaggcacac taaaaatata tagttacttt tgggtatgtg tatttttgtc 27540
tttagacttg ggcctcatcc cagaggtgcc ttatataaat tatgtataga gggctgggga 27600
tgtagctcac ttgatggaat gcttgcctaa catccacaga gccaggcttg ggtccccagc 27660
accacctaaa ctgtgagagg tgctgtgtgc ttgtaatctt ggctctcagc aggtggatca 27720
ggaggataat aagttcaaga tcaccctcag caacatagtt ttgttttctt tgttaaaaat 27780
aaggcttcag ccaggtgtgg tggcgcatgc ctttaattcc agcacttggg aggcagaagc 27840
aagtggatat ctgagttcaa agccagcctg gtctacaaag tgagttccag gacagccaga 27900
gctacacaga gaaaccctgt ctcgaaaaac caaaataaat aaataaaata aataaataaa 27960
taaataataa aaataaaaat agggcctcac aattcctggc tggaattggc tgtgtaaatc 28020
aggctggccc tgaacacaca gagatatcct tgtctctgcc tctggagtac tggaattaaa 28080
ggtatatgcc agcctgtctg actaacatag ggagtttgag gccagcttga gatacatgag 28140
atcttatctt aaaatattta tagaaagata tctcattgca tttatttgca tatataatat 28200
ttaagcatat gtgtaaatat tctaaaacta taatttgaac tctgaaatag ttttagtccc 28260
aattatttca aattaggaac acagaacttg tgcttatgca gccaacgact gcatttgcag 28320
aaagcatatg caagaacatt tcccaccacc accatcccca accccatacc agcactgtcc 28380
actactgcta ttctctgtgt gtgcatttag gtgacccgaa gaatctctga gtttgtgttc 28440
tctgtcccca gccctgttta tgagaagtac tgcgccgacc actttgcaga tggccgttgt 28500
gaccagggct gcaacactga ggaatgcggc tgggatgggc tggactgtgc cagcgaggtc 28560
ccggcccttt tggcccgagg ggttctggtc ctcacagttc ttctgcctcc tgaagagttg 28620
ctgcgctcca gtgccgactt tctgcagcga ctcagcgcta ttctgcgcac ctcactgcgc 28680
ttccgcttgg acgcacgtgg ccaggccatg gtcttcccct atcaccggcc aagccctggc 28740
tctgaatccc gggtccgtcg tgagctgggt cctgaggtga tcgggtgagt gactgtggct 28800

```
cagggctggg tacagcggtt agggcacccg tggtccagac cgtctgtttc acgcttctta  28860
gttgagagct ctcttggcaa ggcgtcttcc acaggttttt ccgtgtctgt cgggttgaca  28920
tctttgctat gggggggggg ggggttcatc ctctgtacac tacagggagc ctcgctgcag  28980
cgctgagatt ttactcttca aatgcaggtg acagcacctt cttgtgtgca tgatgtgtgt  29040
gtgtaggtcc ccaagtgcca tgacgacgca tgcctgtaga ggttagagga caacagtgtg  29100
aagtcagttc tctcttctca tcaggatgtc aggcttgcat gatgagcatg ttgcctgtga  29160
gccatttcgc tggcttgttt gttgttttct tctcgttgtt tgctttgttt gtgttttata  29220
ggcactaacc tgaaattcaa tctgtagccc aggttggctt tgaactcatg gttctcctac  29280
tcagcccttc caagtactag gattgcaggc atacaatatc gcccccgaca ctcactctct  29340
ttcctcccca ctctcttcat tcccctttcc cctcatctca caaaagttgt agaacttgct  29400
cactggtgac ctggtagggg gaacctgaag tgggagaggc atttttttga gggtggacca  29460
gggcctgaag attgggccct gacaaggaaa ggagagctga actttagaga tgctgtggtt  29520
tgtgggttct gattggatgc aggcagaagt caagtagatg ggtgaggtga cacatggccc  29580
ctttcttggc taaagtggct tagtgatgag gacatagggc taagcagggg ccaccttgga  29640
acttgctatt cttagggggt cttgaggtat ggggaggaac cccaggagat gactgagggc  29700
tgaagatgca tacaagacaa ctgggtattg gaggccattg gagggaaaga agggagaatc  29760
aaggaagcag gagagaagga aatgaagaag gaatctaagg actctcagag acctaagaat  29820
tgggggacag tagaggacgt ggctcagtgg tagagaacct accttgtata ttcaaggccc  29880
caagttcatc tccaatacca caaagaagga taaaggagaa aaagcaagct tttagagaaa  29940
ctgacatggt acactgtccc agcaaagggc gacaccaaca gactctacca gggcgaatga  30000
agacattatt gaattcacag ctttgagaca ctgtgaccaa taagatctgt tgggagagac  30060
agtggagttg gatgccagct gagagctggg tgggtggtag agacatggag agtggagacg  30120
gatgtggctc tctgaggtcg ggtgtctagg atgctgtaga caagtgttga gcctttgggt  30180
ccctctgctc tgttcccaca gctctgtggt gatgctggag attgacaacc ggctctgtct  30240
gcagtcagct gagaatgacc actgcttccc tgatgcccag agtgctgctg actacctggg  30300
agccttgtca gcagtggagc gacttgattt cccataccca cttcgggatg tgcgaggtga  30360
gctgggaaga agagagggta gtacattaga gcgtgtagcc ccagagatgg ttgaatccta  30420
tagtatggtt gaagccctgt gagtaaagcc ccatcttctg gctgaagctg tcccatagct  30480
aagccaaccc catgggtaag agccacttaa aattgaaacc ttacttgtag tcctgctcca  30540
cggctacagc cctgcttata gctgagtatc gcccatggct gaaatctgct cactcgttcc  30600
tgccctgata cttggctgaa ggctcatctg ctgcttccat cctacaggag agccgctgga  30660
ggccccagag cagagcgtgc cactgctgcc actgctggtg gcaggggctg tctttctact  30720
catcatcttc atcctgggtg tcatggttgc caggcgaaag cgagaacaca gcaccctctg  30780
gttccctgag ggttttgcat tacacaagga catagctgct ggccacaagg gccggaggga  30840
gcctgtggga caagatgcac tgggaatgaa gtaagaacct cacatgctct acatccccaa  30900
ctgtgggtcc cttgtaagct ctagaccata ctcacctcgg tcatattcca acctctgacc  30960
ccagcctaac cttaactaca gactccatct gggccttcag tgttaatcct cttgacctat  31020
gaccccatga tccctgagga ttgccccaac ccctatccct tgacgtgatt ttctatttct  31080
atacatttcc tgactcatat ctttccctga cgccatcctg aactaacctc acaaaattca  31140
```

ttcttatgac tgctaacctc aagactttg tcatttcaac ctgtccctga ccacgactgt 31200
atccttgatg actcctgaat catctctggc ttcaacccac ctgtaccttt gacctcacct 31260 cagaccctg tttctaccca atcctgtgtt aattcccttg tgatcctcaa tcccaagcct 31320
tcaacttgac ttattcctca acaccaatag ccatattctg accttaaccc ttccctatga 31380
caccataact cctgactcct catcctgatg tttcaagcct ggctatcccg tttgtcacaa 31440
gagagtaact cctcttccat gagctttgat aactccttta tcaaagttat gagaggaaac 31500
ttcctttgcc cctgcagttt gtctcatcta tcctcatgca tccatgttcc attgtgtgtg 31560
ccactcttga ctctgagttc accttatgag tctggccacc tcagatgtga ggtgtggagc 31620
aggtataaag accgttgttt ggatccctag aacctgtata aatgccataa aatccttaag 31680
tgctcagtgg gcccggcagc ctgacttgga agatggagtc ctggtcccta gagcaagctg 31740
actagtgagt ctagtcatat ccgtgagctc ttggtttgat tgagggaccc ttcctcgatg 31800
accaagactg aggagagatt cctctttatc aacctcagac ctgtgcaccc aaaacacaca 31860
cctgcactca cagatggaaa gagaaaacat tttgattgcc acctgacatg cttcctgcaa 31920
cttcatctct atcctcctat ccatcattgg aatctttgtc aacgacccag gacccctcct 31980
cagttcctga cccccttacct acctctatga cctctgcctg aaccaaaccc taaaccctct 32040
tcccaggcca gagttctcta gtgtactttc tcacgtcttt ttcttcttgt tttccccaag 32100
gaacatggcc aagggtgaga gtctgatggg ggaggtggtc acagacttga atgactcaga 32160
atgtccagag gccaagagac tgaaggtatt aacctgcttc tctgactctt tccttcaggg 32220
ttccaagttg ggatccccta acagctggag agcccaggga agtctctctt ctcccgattg 32280
cctcagcccc agacaatttc cacatctgtg tggacctcac ttttccctta atgtgattct 32340
gttgctgtgt tgggaggaac agagatttac catgggttcc ctgggtgggt ggggcttccc 32400
cttcttcata tggttcctcc tcacacaggt tcctgctccc aggtctgcct agggtcaccc 32460
tagagcagca gctcttaacc tgtgggttgt gaacctattt gggctgcgct cttcagtttc 32520
agatggctca gtcggtaaag aaagaaaaga aagccaggcg tcttgtggta cacaggtagt 32580
cccagtgaac aacctttcca cagaggttac ctaagaccat tgaaaaacac aggtttttac 32640
attatgattc ataatagtag caaaattaca gttatgaagt agcagtgaaa ataattttat 32700
ggctgggggg tcatcacaac atgaggaact atattaaagg gtggcagcat taagaagagt 32760
gagaaccaat gccctagagg gaacacccta gtccacagag tgattgtttt ctgttccttg 32820
tctagcatcc ccagcctgaa agtgtcccca gctgctctag ggttccatct atctttagga 32880
accacaccca tttatttggg ctgtgctctt cagtttcaga tggctcagtc gctaaagaaa 32940
aaaaaaaaaa aagaaagcca ggcgcttgtg gtacacaggt agtcccagtg ctggtgaggt 33000
ggcaagagca aactcctggc tggttaacta gcctagcctt cttggcaagt tcttagaaga 33060
accctgtctc ataaaggaag atggatcgtg ccagagagtg gtggcacaca cctttaaccc 33120
cagcactcgg gaggcagagg caggtgtttc tctgagtttg aggccagcct ggtctacaaa 33180
gtgagttcca gtacaaccag ggctacacag agaaaccctg tctcaaaaaa tgacacaata 33240
acaacagtaa caaaaagagg gacagtgcta cagagcaatg acataggagg cggttctttg 33300
gcttccatac acacagacac actcgtgtgc acacacacac aagcttgcac actcatgcaa 33360
cctgagggct gggtaatgta tgaaggaaag gtctttctgc ctcagcttct ccagtagctg 33420
ggactgcagg tttgagtcac aacatccagc ctccatattt cttttaccag ggatctgaag 33480
tatccagggt tggaggacta catttaattt tttaaaattt caaatatttt gctcttttta 33540
tttatttata tttattttta aaaattggag actagagaga tgactcaaca gttaaatgct 33600
ggctgctctt ccagaggacc tgtgtttgat tcccagtacc cacacagtgg cttacaaatg 33660
tctgtaactt cagttcctat agatgtttga cgtcttctgg tctcccacca ggcatgcatg 33720
acaggagtgt gccaccgtga cagctgtagt ttgttaattt aaaaatttgc attcacttat 33780
tatttattta ttttgtgtgt gggccgtgtg agctacatta tgggggaggg aggtcagaga 33840
acaactgtgg gcgttattct ctttccactg tgtgaattcc agagatcaaa ctcaggtcat 33900
tgggcttggt gacaagttat ctcttgtttt gataatttaa ataaaaatat ccttttttctt 33960
ttaaaaaaat attaatttgt ttttttttt gagacaggat ttctctgtgt agccttggct 34020
gcccaggaac tcactctgta gaccaagctg gcctcgaact cagaaatccg cctgcctctg 34080
cctcccaagt gctgggatta aaggcgtgcg ccaccaccac ccggcttaga tctacctatt 34140
tctgtctctt gagtcctggg attaaagatg tcccccactg ccacccagct aaatatttat 34200
ttttgtgtat atgtgtacac attggtgtgt gtgccatggc aatgtgtgga gaagcacatt 34260
taatctgcaa gtacgtttac ctgctgagca ctctccccaa ctctgtttta tttttttgag 34320
acagcaggtt gcttttggtc tcctacacct gatacagctt tatcagcagc actggtggga 34380
atgcccaccc ttttttgtta ctgcctttcc cacagcaaat gagaggtgag cgcctgtatc 34440
tgtgtccctc caggtagagg agccgggcat gggtgcagag gagcctgagg actgtcgcca 34500
gtggacccaa caccacctgg ttgctgctga tatccgtgtg gcaccagcca cagcgctgac 34560
tcctcctcag ggagatgcag atgcagacgg agtggatgtc aacgtccgag ggcctggtga 34620
gtgccctccc aaagaggccc tcattggtcc tacctgctgg atcccatgca ggggttctgg 34680
gagcgtctgg gcctctgggc ctctgggcct ctgggcctct gggcctgctg cgtgtgttgt 34740
attctaagtg attggaacgc catgcaaggt gaagcagaag gtgggctggc tgcaactgag 34800
aaccctgagg ctgtgtggac cctggactct ttcttttatg agattaaaat ttccttcttt 34860
tcttttcttt tcttttcttt tcttttcttt tctttatttt tcttttcttt ttttctttat 34920
ttttttcttt ttttgttttt ctttttttag atttatttat tattatatct aagtacactg 34980
ttgctctcct cagacacacc agaagagggt gtcagatctc attatgagtg gttgtgagcc 35040
accatgtggt tgctgggatt tgaactcagg accttcagaa gagcagtcag tgcccttacc 35100
agctgagcca tctcaccagc cctctctttt tgtttttcaa gacagggttc tctgtgtagc 35160
cctggctgtc ctggaactca ctctgtaaac caagctggcc tctgaactct gagatccacc 35220
tgcctctgcc tcttgagtgc tggggttgaa ggtgtttgct cccccaaccc cagctctttc 35280
ttcctgtgta gccctggctg tcctggaact tactctgtag accaggctgg ctccaaaccc 35340
atagagctcc acttacctca tcctcccgag tactgggatt aaaggcttgt tccagcacca 35400
ccactgcctg gctcttgctc ttgctctttc tctctttctc tctttctctc tttctctctt 35460
tctctctttc tttctctttc tctttctttc cctttctttc tctctctctc tctctttctc 35520
cttcttcttc ctcctcctct gcctcctctt cctcttccct ctcctcttct tcctcttcct 35580
cttcctcctc ctctttcttg ttatactttt atataagatt tcactatata gctctggcta 35640
tcctggaact cataatgtag atcaagttgt tgtgaagtca cagagatcct cctgcctctg 35700
tcccccaagt gctggaatta aatgtgtatg ccatcatatc cagctgggat ttatttaaaa 35760
atcacactta tttgtgtgta ttcgtgtact cggaagtcag aggacacctt actggagttg 35820
attatctcct atctcggtcc aagagatctc attcacgctg tccagtttct ctgtagcttc 35880
tctatccatc aagctcctgg atgttcaatc cctccttacc cctctagccc ccttagcttc 35940
agccatacag cttgtcagga gagtctcgga ttagttctga cagggtgaac tagaaccacg 36000
tacttattcc tgggccaatg aatgtggcta gggcctataa tatgcagata agccagtccc 36060
catctggtct aagtagggct tgctattagg gaattcgtga ggagaactag ggaaaaggtg 36120
gttcccttcc cctttattcc aagtgctcgg cttcctggaa tcgcttttgc ggtccatcat 36180
gtaatcttcg tggggtggct ttgcagttgg gagaatttac ctctgtctgt ggcgctgtgt 36240
gtcacagtgc ccctgacatt tgccccagga agacccctat gcctgtgaca cactactggt 36300
tcctgcagat ggcttcaccc cacttatgct ggcctccttc tgtgggggag ccctggagcc 36360
gatgccagct gaggaggatg aggcggatga cacatcagcc agcattatct cagatctgat 36420
ctgtcaaggg gcccagctcg gggcacggac tgaccgcact ggcgagaccg ccctgcattt 36480
ggctgcccgc tatgctagag cggatgcagc caagcgtctc ctggatgctg gggcggacac 36540
caacgcccag gatcattcgg gccgcacccc cctgcacacc gcagtgacag ctgatgccca 36600
gggtgtcttc caggtgagac aggcctgtct cttcagactg cagagctgct gggaggggat 36660
cagacacacc tagattggag ccccggtctg tcttgcaagg cttttgtcat ttggaaatag 36720
gaataggtag tatctcacct agatttcccg ccggcccccc cccccccccc ccaggacagg 36780
gtttctgtat agtcctggct gtgctagaac tcactccaat aaaccaggct ggcctcgaac 36840
tcagaaagat ccacttgcct ctgcctctgg agtgctagga ttaaaggcat gcaccactaa 36900
cactggatag aatttttttc ttttttaatt ttattaatat atgtaagtac actgtagctg 36960
tcttcagaca ctccagaaga gggagtcaga acttgttgca gatggttgta agccaccatg 37020
tggttgctgg gatttgaact ctggaccttc ggaagagcag tcgggtgctc ttacccactg 37080
agccatctca ccagccctgg atagaatttt ttaaaaagta tcattaaaat tacatttatt 37140
tggtgtgtgt gtgtatgtta tgctgattgg tttgtgtttg tttgtgtggc atatgtgtac 37200
ctgggtatgt acattgccca gcttgctgaa gctagaggag gctgttgatt gttctgctct 37260
atcgtgctcc acccaatctt ttgagacaga gcccatcagc gagcctggag ttgagctggt 37320
gtccagaaag ctctcttgat cctcttgtct tcttccccac agccctgggg cacacatgac 37380
caagactggc tttttaggtg gactttgggc tctgacgtca ggtgcttgtc ccctgagcca 37440
tctccctgtc cttccatatc atactgttac ttaaatccat tttgaatgag catattttttt 37500
gatttataat gtgcttagca ggaatagcac ctcattttaa gtcaggagat atctgtagct 37560
cctgggttcc aaagctgtgg catttggggt tcagggtgtg gtatactcct cccttggcat 37620
aatgtcctgc catggctttt gtcgtcgtta gattctcatc aggaaccgct ccactgacct 37680
ggatgcccga atggcagatg gctctactgc actgatcctg gcagcccgcc tggcagtgga 37740
gggcatggtg gaagagctca tcgccagcca tgccgatgtc aatgcagtgg atgagcttgg 37800
taagtgctgc ggaggggatg gggaggggct gtggtgccac tgccctctta atgtgaagtc 37860
acacctacgt tgacagcaag gtgtgcacgc cagggctccc aaacggatgg aacaggaccc 37920
acagagtgtt ctggttcaga aaagatgtag actcccttct cctcccctcc cttccctttt 37980
tcttccactc ccttcctttc ccctccccca tctcctagac cccatccccc actttcacat 38040
tatgatactc ctcttcctcc ccttcctccc gggcttcctt ctagagtcca aatcgttgat 38100
caaacccaaa gtgcttgtct ttgagtctga cttatttcac ttactgtgat gatctccagt 38160
tctattcatt tcttgaagat tgtttaattt ggctcccccg acttttgaga cagggtctca 38220
tgcaagctag gctcgcctcc aacttactgt gtagtcaacg accttgaaat ctggaccctc 38280
ctgcctctgt ttcccaagtt aggcattcgt catcacatcc agcccaattt ctttctttgt 38340
tttggttgag tagcattctg ttgtatgcag tgtgggtggg cacctaggct gagcaactcc 38400
attgtatgca gtgtgggtgg gcacttaggc tgactccata gtgtaccggc ttcgaatagc 38460
aatgtggatg ccacagttcg catgggcatg cagacatctc ttattgtatg ctgactcagc 38520
cctcaagtat agacccaggg gcacaggagt gccatacctg aacctagggt agttcttttt 38580
ttttttttt aagaattatt tatttattat atgcaagtac actgtagctg tcttcacaca 38640
ctctagaaga gcgcgtcaga tctcattacg gatggttgtg agccatcatg tggttgctag 38700
gatttgaact caggaccttt ggaagagcag ttactgctct taaccactga gccatctctc 38760
cagcccccta gggtagttct acatttagtt ttttgaggac cctccatagc attctctata 38820
cttactactt agcatactta gttactttat cattaatagg gcatgaagat ccctttctct 38880
agtgtttgta ttctttcttt ctttttccct tttttggctg ttttcatgat tgaagccatt 38940
ctggtagcat ctaagtacag tttttgtctg tttttatttt tttgttttgt tttgttttca 39000
gacagggtta ctctgtgtag ccctggctgg ccatggaact cacactgtag accaggctgg 39060
ccttgaactc agaaatctgc ctgcctctgc ctcctgagtg ctgggatcaa aggccgggat 39120
caccaccacg cccggctgag accctctttt tctgccaggc acagaaaggc cacctttttgc 39180
cttcctgccc agctataggc tattcagctc tttatttaac caatcaggag acgatggaga 39240
acattgtttt acaaaatacc aagttagacc aaagtctgga ctgtaaccag atctctggga 39300
acagaaatca gcatctgaat acacagtgca caaaaccacc ccccaacggg acttcatcgc 39360
caactggggg taaacgctca tgctttgccc acactgacca agcacacgag cttgcttctt 39420
agtgtgctgt ctagatgctt tgttaaggaa acggactctc ctgctacctg ctagacagtg 39480
ggataaactt gcatgtggtg atctgtgggg gcagctgcct ggtagtggcc tgcttggctt 39540
gggtatgtca tgagcaaggg tcacagcaag ggttcttgta ttcacaggcc gcacagctgt 39600
agacactcta agacacttac acacatttgt ttgacgtacc cttggttctc aacttcatca 39660
gcattgacat ctatggttgg gtaattcttg gtctgcgtgt tggatgaagg tctgggctgt 39720
gcactccggc ctgtggggca gcatcccacc aggagcatcc catctctaca atgttactga 39780
gtatagtggg cttcttccct gggtgggcct ttgtttcaac aacaaaagga tttagaaatg 39840
gtctcagaag gaagctcaaa cacagttaga ctagagtttg atagcaaagc aacagatcaa 39900
gcaagctgtc agtctctctg gaatagagag atggagaaga tgcattcatg tcttttgagc 39960
tgtggctgga aagccgcagc ctggtgggag ctgggggaga ggtgagcttc cgaggacaag 40020
tgcgagctca tgtcctggct ttagccagga tctgaaagaa aaggaattga gaagaaagaa 40080
aaggggtgcg gtggccaatg catttgctat gccagggcga agacctgagt ttggatcttc 40140
agaaacctat gtaaatgcta agtgggtgtg atggccacct gtaattccag acacacacac 40200
acacacacac acacacacac acacataccc catgtataca cagaaaaaga aaaaaatatt 40260
cagaaaagct ggcagggtgc ataatggtgg ctccaatgtg ctgcctgcct gatggatgtc 40320
ctgcaagtag ctgctttgag ggagaggctc ctaggaaggg aaaatacaat atgtcattaa 40380
ggggataatt agtccttccc tgtcaatagc atgtctttag gtgactcaga gtttttggcg 40440
ggacaaaggc agactcttgg acagataatt gacagactct attgggatac ctttaaaaat 40500
agtctattta tgtttacttt atgtgtaggg tgtttcgcct gcatgtatgt ctgtgcaccc 40560
cgtgcatgca gtgcccacac aggccagaag aggagagggc atcagatcct ctggaactgg 40620

-continued

```
agttacagac cgttgtgaac tgttatgtgg gtgctgggaa ctgaacctgg gtcttctaga  40680
agatcagcca gtactcttaa ccactgaacc atctcccagc tccccgaatt aactcttaaa  40740
aggagacagt cataagtagc atgttgggtt ccaccaagga ttggaactag aactcagatt  40800
ctatttaaga agcagctttg cattaagtgg gcctcaacaa actcagacac tcccagcttt  40860
ttatggcaag ttgatgtctc tcctaagtag tcttagtcct gtaagactac tgtaacaggc  40920
aaatgacctg ggggtggggg tggggggagg gcagtcattc atggttgata ttagctaact  40980
tttaaaaggc aacaatagag gggccaaagg tagagagaaa aagacttgat tgtggatgcc  41040
aaaatgccta caggggaaga tgggatgtgc ctcttataag ggaggactcc tgtagtccac  41100
aaggaaagct gggaagtgta gtccttcagc aggaaactcg gtcccaattc tgagaggata  41160
ttaaaaagac gcagggcagg atgtcatagc tttttctttt ctttccccgg aggagagtct  41220
ttatcagagg ggttagttct gggtccagta aagggaaact ctctggccat gttgtatgct  41280
agagtcttga ttagctgtga tggatcaggc cattgtcatt ccgcattcct gaggagagct  41340
gggaaaatat ttattagaag gccacaagca gatgatttgg ttatagagta gagctgagag  41400
attttctggg aaggttgagg gagggggagg agcaggagcc taggcagaag agacaagagt  41460
gagacaaagt gggcagaggc tggtcccagg gtgacagtga ctggtcccat tgccaggact  41520
gctagaaaaa tgagctagca gaagcagcag agggctacaa agcagcagag gacgggaaga  41580
ggggtcaata aagggttaat gtgaagaact gtatctggcc tgtggtggaa gagatcacgg  41640
tccctttct attcagcacc taaacaattg ttgtttaggt gctgaataga aattgttgtt  41700
gtttctcaga tgtgtcagga acaaatggag ctgttgtggg atgagagcca ctgagagagc  41760
tcgaatggga aattctgcgt gggttcagta agcaaaacat ttaaagacac ggtaaaaatg  41820
taggtattaa gataaagaag ggagaaagcg tgaggcaggg gaagagacag agtgggggga  41880
agccaggagg aacttttgtc tggtccctgt gcctttaggc cccatttcaa accaggcagc  41940
atttgttggc gtggtagcag ccctgatcaa ggagggcagc agtcagagct agtccttttg  42000
agttgtagag taccgcgtcc gtcaaggagt tgacctgctc ctagagggtg tcacgctgat  42060
ctgagctggt gacacagagt tcactgatgc agcgaaggct tcagcccagc tgtgacacag  42120
agaagttcac tgaaggtgtc agtccagctg tttcagtcca gagtggcaag aagaggggtg  42180
gcttggctca ttcatggtcc atcatcccct cttagatgtc gtccaaactg ctcttagggg  42240
cctggggtgt tggtctccct gtgacttctt taaggctggc agaagtggga cgaggggagc  42300
agccgtcaga gtgcctcaga agagggtcca tccaagggga catgatagaa cttaagagtt  42360
ggcaaagatc cagaacataa gtcccagggt gataacacac agctgaatgg agacaaagtt  42420
acagaaggaa aactttgaca accagttgaa tacaactgga caactgactg caccagaagg  42480
atacggtagc tgtaagtagc tctttgtgtg cattagaatc ctgccagcta agaatgactg  42540
tggctcagtg ctggacacta gagctttctc tgaggattgg aaggaatatt tgttggccca  42600
gtctgttttg gctgctactg gcctcttgtg gctgatggcc acttgaaaac tggcttggac  42660
caatgaagag ctgttttctt tagttcatcc aatgtttaca atattgggcc agggatatag  42720
ctcagttggt gaagtaatcc tgctaggtcc attctctact accacataaa atcaggcgtg  42780
ttaatcttag gcaggcccag gatcccaggg ctcaggaccc atctgcagcc aggaggatca  42840
gaagttcgtc ttcaggtgca cagtgagtta caggccagcc taggatactt gagtccttgt  42900
gtttgttttg tttttaacta tttaaaaaaa tatttatttt atgtgtatga gtataccata  42960
gctgtcctca aacacaccag aagagggcat tacagatgtt tgtgagccac catgtggttc  43020
```

ctgggaattg aactcaggac ctctggcaga ggataacctt ttaaccgctg agccatttct 43080
ccagcccctg agaccttgtc tcaacaacaa caacaacaac aacaacaaca acaacaacaa 43140
cagttaaacg cacatagtgt tcttgcagag gacctgacag gggttcttac cacctaagtt 43200
gggctcccca caaccatctg taactctagt tccagggaat ctgatgccct cttctggacg 43260
ctgcagatac ctgcacccat atgcacctcc cctgtgcaaa cacacatata cacataatta 43320
aaaactataa aaataaatac atcttaaaag gaaaagccca ccctgaacag gcaatctaga 43380
atataaagac tgaaatcata tcgacaactg cctaaagctt gggatgggag gagactgatc 43440
aatgatgagt aattaaagtg atggaaatgt tgtaaaacct gattaattgt aaattatgac 43500
tcaacaaaaa tatagtcttg tatatataca agaaaagata ttaaaaacaa aaattttgag 43560
acatcgtctt agcgttaact gtcaacttga catagcctag agtctctgag aagtgtgtct 43620
cggatcagtg tgattgtctt gattgttaac tgatatagga gggttcagcc cactgtgggc 43680
agcagtgttc tgggccgtgt gatcctgagc tatacaggaa ggttagctaa ggatgaacct 43740
gcaagtgagc tggcggcacc accatcctgc acggtttctg ctgtgctttg gctgggaagt 43800
gagctcctta gttggagcta atgctgtcaa acctgccttc aggttattgc cttacttcac 43860
tcagtgatgg attgtgatct aagagtgcaa gccaaatagg tcccaagtgc tgtgtgtgcc 43920
accacaacgg aggtgctagg gattaaaccc acacctccgt gcatgccagg caagcacgct 43980
actgacttat cgacaagccc agcacatgtt ctaaatattc tatattttaa aaagctttat 44040
tatataaaaa accatgcaag taaatgaaag taccacatat catgctggag acatggctca 44100
gtagttaaga gcactaactg ctcttagaga ggacctgagt tcaggtccca gcatacacag 44160
agtggtttat aacttcctgt agctccagat ccagaaagac atgatgtccc ctctggcctc 44220
cttgggcact acagtcacat gcacataccc ccacacgtac atataaataa taaaagaaaa 44280
aattttaagg gttggagaga tggctcagca gttaagaata ctgtctgctc ttccagaggt 44340
cctgagttca atccctagga accacatggt ggctcacagc catctgtaat gggatctgat 44400
gccctcttct ggcacgcagg tgtacatgca gatagagcac tcatatataa aataaatatt 44460
ttaaaaaatc atatatccaa attaaccaga cccaaagtct atataacgta ataaatttat 44520
atacagttag aattggcctt ctggcagaag ctatgaaact tcacattaaa ttttatattt 44580
ttagtactga acaaatttta gattcttttt tttttttttc tttttctttt ttgtttttttc 44640
gagacagagt ttctctgtgt agccctggct gtcgtggaac acactttgta gaccaggctg 44700
gcctcgaact cagaaatccg cctgcctctg cctcccgagt gctgggatta aaggcgtgtg 44760
ccaccacgcc cggctatttt aggttcttag gttcttatcc accaccaacc ccaaaagacc 44820
atggcaaatc agaactagaa cacctaagtt tttgtcgtca ttcacaaatg cctcgtgcct 44880
gcacttagtc tttcctcctc ccatacattt agcctttctt gttctcttct ctctgtgttg 44940
tgctgtaccc acatgaacat gtgtggcttt agcttgcatt tccctcatgg gaaatgaacc 45000
tggctaactt ttcacctgat cattggtcgt acgtagatct tccttgagga aataattatt 45060
tggaatttat tttggtggtg ctggagatca aacgcaggct cttctagatg ctactcagcg 45120
ttccagggct cagctgcaca cctaagcacc gagattatca tttctcactg ttattagact 45180
tcatatatat gttagaattg tatatgtgag ccggcagtgg tgacgcacgc ctttaatccc 45240
agcacttggg aggcagaggc aggtggattt ctgagttcaa ggccagcttg gtctacagag 45300
tgagttccag gatagccagg actgcacaga gaaaccctgt ctcgaaaaac caattaaaaa 45360

```
aaaaagaatt gtgtgtgtgt gtgtgtgtgt gtgtgtgtgt gtgtgtgtgt gtgtgtacac  45420
atacacagat cccattacag atggttgtga gccaccatgt ggttgctggg atttgaactc  45480
aggacctctg gaagagcagt cagtgctctt aactgctgag ccacctctct agtccttgcc  45540
aggccatttt ctacacattt ctgcctgttc tgtaatggag aacctgacat gagcctgaca  45600
ctgatgttta tctccttaca gggaaatctg ccttacactg ggctgcagct gtgaacaacg  45660
tggaggctac cttggctctg ctgaaaaatg gagccaacaa ggacatgcag gacagcaagg  45720
tgagccactg gggcctaca gtgctacagc ccctgaatgt gacaaagcag agtcagggag  45780
gaataagcct gttaggggca tccatcttgc ttgcagtcag ctctcaggag tgggattctg  45840
gcctgaaggc tgtgagagca aactgttgaa gtcgctgtgt gacatcgaac gcagttgtcc  45900
ccattgtgac aggggaagca gcagcatgag ctgctgagct tgaacaagcc tacttttctt  45960
ccttccttct ttctttcttt ttgagactaa cttcctacct caggttggcc ttgaactcac  46020
aattctcata tttctactaa ctaaatgctg gtatatgctc tcatgcctgg ctttttcttt  46080
tttcaatgat atattttatt tttaaatagt gtgtgcgtgt aagtatgtgg acatgagttg  46140
cagatatcct tgaagcaaga agagggtgtt gaatccccct agagctgaat ctataggcag  46200
ttgtgaactg cccgtgtgga taccagggat ggcactgaag tcaccaggct gagtgacaag  46260
tgtggttacc cactgtgccg tcttgccgtc ttgccagtct ttacattgtt tccttctctt  46320
ttggagatca tgtcttactg gttaatttag caaaagctga cctcaaactc ttggtgagtc  46380
ttctgcctta gcctctcaag tgctggggtc ataggctcag gttctctctc tgtctgtctc  46440
catctctgtc tttccctccc ttccttcctt ccttccttcc ttccttcctt ccttccttcc  46500
ttccttcctt ctttctttct ttctttcttt ctttctttct ttctttcttt ctttctttct  46560
ttctttcttt ctttctttct aagacaagga ctcactttgt agaccaggct agcctagaac  46620
tcagagaccc ttttgccttt gtgtcctgga tggtaggact gaaggtgtac aggaccacca  46680
gaaccccaac aactcacttt ttaatctttt gtttttttgg tttttcaaga tagggtttct  46740
ctgtatagtc ctggctgtcc tggacctcac tttgtagacc aggacaaaga aactggtaga  46800
actcagaaat ctgcctgcct ctgcctcccg agtgctggga ttaaaggcgt gctttttaat  46860
cttttataac tctttttaaa acttttataa catcaccatg cagtttattt tgatgactgg  46920
aagttttgat gccccttttaa attttgtgcc taaggtaagt cctggccaga tgtgcctgct  46980
acagagagag cttgtttctt caacagagct ggaatccaaa ctcaggtcca tctatttcca  47040
gggtatcaac tcttagttct caggctgccc tagagattag aaagctaggt gttggccaga  47100
gtgactgacc tccgtgggtt ctgcccctcc cccgcctcag gaagagacgc cgctgttctt  47160
ggccgctcgg gagggcagct atgaggctgc caagctgctg ctggatcatc tcgccaaccg  47220
ggagatcaca gatcacttgg acaggctgcc ccgggacgtg gcccaggagc ggctgcacca  47280
ggacattgtg cggttgctgg accagcccag tggacctcga agtccctctg gtccccatgg  47340
cttagggcca ttgctctgcc caccaggggc cttccttcct ggcctcaaag cggtgcagtc  47400
tgggaccaag aagagcagga ggccacctgg caagaccggg ctggggccac agggaactcg  47460
tggtcggggc aagaagctga cactagcctg tccaggacct ctggcagaca gctctgtcac  47520
actgtcaccg gtggactctc tggactcacc acggcctttc agtgggcccc ctgcttcccc  47580
tggaggcttc cccttggagg gcccctatgc caccacggcc accgcggtgt ccttggcaca  47640
gctaggcgca agtagggcgg gtcctctggg gcgccagcct cctgggggct gtgtgctcag  47700
ctttggtctg ctcaatcctg tagctgttcc cctcgactgg gccaggctgc ctccacctgc  47760
```

```
ccctccaggg ccctcattcc tgctgcccct ggctccggga ccccagttgc tcaacccagg  47820
agccccagtt tctccccaag agcggccccc accctacctg gctgctccag gacatggaga  47880
ggaatatcct gcagcaggaa cccgcagtag ccccaccaag gcccgcttcc tgcgggttcc  47940
cagcgagcat ccttatttga ccccgtctcc tgagtcccca gagcactggg ccagcccatc  48000
ccccccatcc ctctcagact ggtctgactc aacacctagc ccagcaactg ctaccaatgc  48060
cacagcctct ggagccctgc ctgctcagcc acaccccata tctgttccct ccctccctca  48120
gtcccagact cagctgggac cccaaccaga agttaccccc aagaggcagg tgatggccta  48180
agttcttgga tttgaggggt gctgaagtga cactcctcta tgacttcttt cttcctcctt  48240
tttaatctta ctctcatccc tttctctctg tcccagcctt cctgcacctc tctgtcttgt  48300
agtgtgacca agttggtcac cagcccagac ccccagtctt cctttattta taatgggtag  48360
gggctgacct tccaccacct tggcccccta agggatctgg gacctccttt tgatccctct  48420
ccctgcctca acttcctccc ccccctcttt ctgcttctca ttgtctcaca ctctgacaag  48480
agtgagttat tattttttc ttttttacat tttgtataga gacaaattca tttaaacaaa  48540
cttattatta ttattatttt ttacaaaata tatatatgga gttgctccct tccccccgct  48600
gcaaattcct ccagcgcccc cgtggggctg agtctgtggg cccgtttggc caatccggac  48660
tctgtgtact gagtacacag atatgactag ggctccacgt actgagtatg tggccctcgt  48720
atgtaccaag tagccagcct tgggcacacc ctcccctggg gtcaggggac atttgggagc  48780
ctccttcccc tccccattcc ccttcctcac ttcactgcat tccagataag acgtgtagac  48840
tcactgggaa aggggtcttg tctgctcaaa gcctcaactc caggctcacc tcccagagcc  48900
tggctcacct tttagggcct ggggtggggg ggcacgtcag gggagatgta ttttgtatgc  48960
attccacttc taattgtaaa tacagggcag aaggtgggag tggctctccc tcttcctgtt  49020
gttctcttgg ctcagcctgc ctaatagaaa tgtttttagg ctgtttttgt aatatggcac  49080
ctggtcacag tcctttgtag ctgaattccc aggtcctgca ctgtacaacc ctcaccttct  49140
cagttccctt accacctaat aaaggaatag ttaataccca agtgtctggt ttctgtgcaa  49200
ggtccaaagt gggggtttct gggcctcttc ctccacaggg ctaacttgaa ctcccatctt  49260
ggggcagagc catgtgcttt gtcagtccac ctttgactcc tttttggtca ggtatctagc  49320
ttcatttctg ttgctttaag caaataccta acagaaaaga aacttaaggg acagagggac  49380
tttttcctaa ctaaatattc caggttacag tccaacattg tgaagaagag gcaggaactt  49440
aaaatagttc accacatcac accacagtca agagcagaga gaaagaagtg agtggatgca  49500
tgcttgcttc cttgtgtcgg gctgaatcat tacactctta aacagtttag aaacccttgt  49560
ttggggaatg atgccaccca cagtaggcag tgtcttccca cattaatttg acttaattac  49620
gacaatctcc taaagacatt ctttcaggtc aactcgatgt agacaacttc tgttcccagg  49680
tgatttgtaa gttctgtcat tgtgacaaaa ctgatcatca tatcaggtgg tttcaatttt  49740
tgaatcttgg gttggaacca ataaagggac tcaaaacaaa aacaggcaaa caaaccaaaa  49800
ggaaaaaaaa aaaacctaca aaactcaata gtgttatttt gagaacttac tttttctttt  49860
aaaaatttta ttattattat tatcattgtt gttgtttttt tttgtttgtt tgttttttga  49920
gacagggttt ctctgtgtag ccttagttgt cctggaactc acaaaagaaa acacacaaaa  49980
taacaccaaa cccagtacac aggaagcagg cctggctcac ctgcagaact gcccgaacaa  50040
ggcaagacag cctatgggac agcaaaacag ggcacaaaga atgagagccc aggagagaga  50100
```

gcaacagaca gaagagacaa accoctaggc gccaccagag aatgattgcc ctggagggga 50160
gaaggtggag tactgggtgc tgggaacacg ccacacacac acactctgtg tgctggtgtt 50220
tgctttgtgc taagccactg agctcaagtg cttgcggttt gcatccagaa actcatccag 50280
ttgagccagt attaccccca gagcaatgtg atggaaatca gcagtggttt gaatccagaa 50340
atataaaaac ggcacttttt ttgctcacct atctattcta gacttctgtg cactgatata 50400
ggttccaggg tctcaaatcc cttaaaattc taatcaactg tgatgggcca ggctggaagc 50460
agcgatgaca cgcgtcctgg aaaccctgcc aagctgtcct gtaccgctgc ttctgcgtgt 50520
gttgataatt aatccttcgg agcgggcgca cgaatgtgag aaattggcta ttttccgctt 50580
ctgaatgatg gctctgagcc actacggcag cttttccatt tcaaatctga ctgtcaaaag 50640
tggtgcatta atcagtattt cgttagtttc aacatttcca gaatccgcct ccccaagtgc 50700
acatacaaag tgcagccatc ctcagccgag aaggcaaggg cggggccttg cttcaggtga 50760
cgactctttc tttctctttg caccactcca tcctctgaga ggctatggct gtgactccgg 50820
agctcacttc cctgcaaagt agtggctctt ggctgagtac ttccaacagg gagacagaac 50880
aggaccggag ggtggcagac ggtgcctcta tccaatggcc ccctgggtga cttccccaga 50940
agcactttat tattattatt attattatta ttattattat tattattatt attattggtg 51000
tggttagttg ttttgagaca ggattgctct ttgtagccca ggctggccgt gaactcagaa 51060
gtccacctgc ctctgcatct ggtgtgctga ttctgatgtc accaccagat gtgagcctcc 51120
accatcagac tcacatccac tacagacgac ctgaatgtct cagccaagct gtatactaga 51180
gaaagtggct actgttacaa aactcagtgg agacacagct ctagcagatg taggtctggc 51240
tgaccacata agcactgact agtgctggag acacactggt actgagcgac agctgtgctg 51300
agaaccatat ctggctgagg tgctgcttgg gtcaacctct cagagtgtcc agcaggaggc 51360
agggcttcca gacctactga tggatgagtc tgggggctgg gcaaactgga cagcattatt 51420
ctgtggagaa gccttagact gtcccccaaa gtaaaagcac cccaaccagc ctgttatact 51480
tcctccctcc cactgtcagg gccaccaacg cccaagagtg caaaaggcac ccaggaaaga 51540
gaaagttaaa aaaacaaggg aaggttgatt ttcctacttc ctgctgcccc taactgccag 51600
acgaggcttc tccccctgcc cctcaagcaa ccctcagact ccgcccatgt ccgtgccccg 51660
ccccctcctc tccaacagtg acgcgtgctg tgctggcatg gctgccggtg ggcaggtgat 51720
gcacatccca ggaacatttt gcccgcccca actgcttcat caccaagcct ccagcaaaga 51780
ggctcaggca gcctgaagcc tcgctgcctg gcatagcgca tttagagtaa cagctcagct 51840
aatctcttcc aagggaggca gagctgctca gcacagcagg agtggggcga gctctggaat 51900
attccagtgt ggttctccca caggcatcta gggacagaga ggagtgtggg ggtgggggac 51960
aagctgagcc tcacaggtgt tcctaggctg atgcttaagt 52000

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
ggaatattgg ttcagt 16

<210> SEQ ID NO 82
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 82
tgtcgaagct caaccc 16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
atctatgtca ctttgg 16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
gaatattggt tcagta 16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
tgtatgtcgc acaggc 16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
acaattctat ggtctc 16

<210> SEQ ID NO 87
<211> LENGTH: 20
<212> TYPE: DNA
<213> ORGANISM: Artificial sequence
<220> FEATURE:
<223> OTHER INFORMATION: Primer

<400> SEQUENCE: 87
catggtcttc ccctatcacc 20

<210> SEQ ID NO 88
<211> LENGTH: 20
<212> TYPE: DNA
<213> ORGANISM: Artificial sequence
<220> FEATURE:
<223> OTHER INFORMATION: Primer

<400> SEQUENCE: 88

-continued

```
tgtcaatctc cagcatcacc                                              20


<210> SEQ ID NO 89
<211> LENGTH: 22
<212> TYPE: DNA
<213> ORGANISM: Artificial sequence
<220> FEATURE:
<223> OTHER INFORMATION: Probe

<400> SEQUENCE: 89

atcacctcag gacccagctc ac                                           22


<210> SEQ ID NO 90
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: bases at these positions are RNA

<400> SEQUENCE: 90

auaaaaucua cagucauagg att                                          23


<210> SEQ ID NO 91
<211> LENGTH: 24
<212> TYPE: DNA
<213> ORGANISM: Artificial sequence
<220> FEATURE:
<223> OTHER INFORMATION: Primer

<400> SEQUENCE: 91

caaaggaggg acatgtatca acac                                         24


<210> SEQ ID NO 92
<211> LENGTH: 20
<212> TYPE: DNA
<213> ORGANISM: Artificial sequence
<220> FEATURE:
<223> OTHER INFORMATION: Primer

<400> SEQUENCE: 92

ctggcaatgt ttcccagtga                                              20


<210> SEQ ID NO 93
<211> LENGTH: 24
<212> TYPE: DNA
<213> ORGANISM: Artificial sequence
<220> FEATURE:
<223> OTHER INFORMATION: Probe

<400> SEQUENCE: 93

cccaatgggc cacactgtct ctgc                                         24
```

LINKAGE MODIFIED OLIGOMERIC COMPOUNDS AND USES THEREOF

SEQUENCE LISTING

The present application is being filed along with a Sequence Listing in electronic format. The Sequence Listing is provided as a file entitled CHEM0101USC1SEQ_ST25.txt created Feb. 11, 2022 which is 593 kb in size. The information in the electronic format of the sequence listing is incorporated herein by reference in its entirety.

FIELD

The present disclosure provides oligomeric compounds (including oligomeric compounds that are antisense agents or portions thereof) comprising a modified oligonucleotide having at least one modified internucleoside linking group.

BACKGROUND

The principle behind antisense technology is that an antisense compound hybridizes to a target nucleic acid and modulates the amount, activity, and/or function of the target nucleic acid. For example, in certain instances, antisense compounds result in altered transcription or translation of a target. Such modulation of expression can be achieved by, for example, target RNA degradation or occupancy-based inhibition. An example of modulation of RNA target function by degradation is RNase H-based degradation of the target RNA upon hybridization with a DNA-like antisense compound.

Another example of modulation of gene expression by target degradation is RNA interference (RNAi). RNAi refers to antisense-mediated gene silencing through a mechanism that utilizes the RNA-induced silencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Another example of modulation of gene expression is the use of antisense compounds in a CRISPR system. Regardless of the specific mechanism, sequence-specificity makes antisense compounds attractive as tools for target validation and gene functionalization, as well as therapeutics to selectively modulate the expression of genes involved in the pathogenesis of disease.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, tolerability, pharmacokinetics, or affinity for a target nucleic acid.

SUMMARY

The present disclosure provides oligomeric compounds (including oligomeric compounds that are antisense agents or portions thereof) comprising modified oligonucleotides consisting of linked nucleosides linked through internucleoside linking groups, wherein at least one of the internucleoside linking groups has Formula VIII:

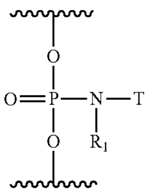

VIII wherein independently for each internucleoside linking group of the modified oligonucleotide having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, and substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl.

The present disclosure provides oligomeric compounds (including oligomeric compounds that are antisense agents or portions thereof) comprising modified oligonucleotides consisting of linked nucleosides linked through internucleoside linking groups, wherein at least one of the internucleoside linking groups has Formula VIII:

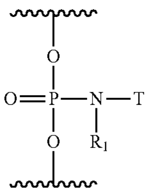

VIII wherein independently for each internucleoside linking group of the modified oligonucleotide having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, a $C_1$-$C_6$ alkyl, and a substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl;

provided that if $R_1$ is H, then T is not:

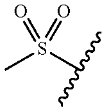

or

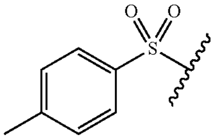

.

The present disclosure provides oligomeric compounds (including oligomeric compounds that are antisense agents or portions thereof) comprising modified oligonucleotides consisting of linked nucleosides linked through internucleoside linking groups, wherein at least one of the internucleoside linking groups has Formula XVII:

XVII

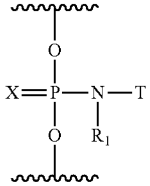

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, C(=O)$R_3$, and P(=O)$R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

In certain embodiments, oligomeric compounds (including oligomeric compounds that are antisense agents or portions thereof) having at least one internucleoside linking group of Formula VIII or Formula XVII have an increased maximum tolerated dose when administered to an animal compared to an otherwise identical oligomeric compound, except that the otherwise identical oligomeric compound lacks the internucleoside linking group of Formula VIII or Formula XVII.

In certain embodiments, the modified oligonucleotides having at least one internucleoside linking group of Formula VIII or Formula XVII have an increased therapeutic index compared to an otherwise identical oligomeric compound, except that the otherwise identical oligomeric compound lacks the at least one internucleoside linking group of Formula VIII or Formula XVII.

DETAILED DESCRIPTION

Figure 1:
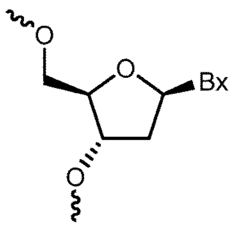
FIG. 1 depicts isomers of 2'-deoxyfuranosyl sugar moieties having formulas I-VII.
Figure 1:
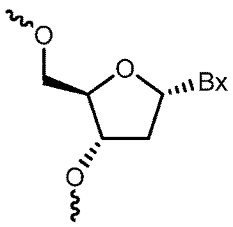
Figure 1:
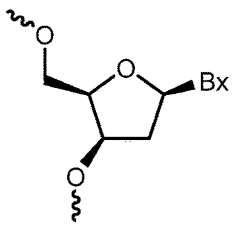
Figure 1:
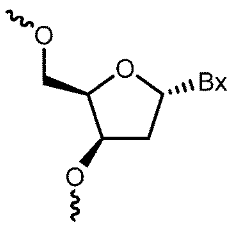
Figure 1:
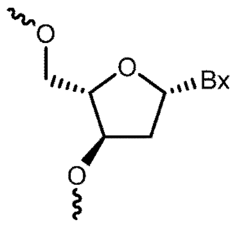
Figure 1:
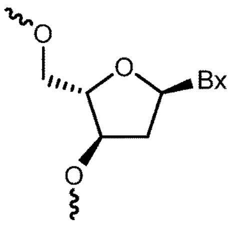
Figure 1:
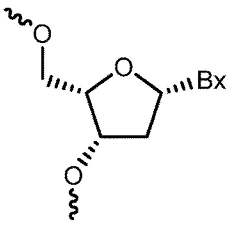
Figure 1:
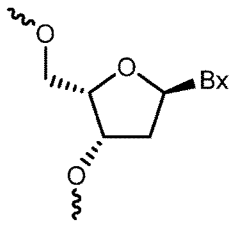

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH(H) sugar moiety and a thymine base could be described as a DNA having a modified sugar (2'-OH in place of one 2'-H of DNA) or as an RNA having a modified base (thymine (methylated uracil) in place of an uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, a modified oligonucleotide having the nucleobase sequence "ATCGATCG" encompasses any modified oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and modified oligonucleotides having other modified nucleobases, such as "ATmCGAUCG," wherein $^{m}$C indicates a cytosine base comprising a methyl group at the 5-position.

As used herein, "2'-substituted" in reference to a furanosyl sugar moiety or nucleoside comprising a furanosyl sugar moiety means the furanosyl sugar moiety or nucleoside comprising the furanosyl sugar moiety comprises a substituent other than H or OH at the 2'-position and is a non-bicyclic furanosyl sugar moiety. 2'-substituted furanosyl sugar moieties do not comprise additional substituents at other positions of the furanosyl sugar moiety other than a nucleobase and/or internucleoside linkage(s) when in the context of an oligonucleotide.

As used herein, "4'-substituted" in reference to a furanosyl sugar moiety or nucleoside comprising a furanosyl sugar moiety means the furanosyl sugar moiety or nucleoside comprising the furanosyl sugar moiety comprises a substituent other than H at the 4'-position and is a non-bicyclic furanosyl sugar moiety. 4'-substituted furanosyl sugar moieties do not comprise additional substituents at other positions of the furanosyl sugar moiety other than a nucleobase and/or internucleoside linkage(s) when in the context of an oligonucleotide.

As used herein, "5'-substituted" in reference to a furanosyl sugar moiety or nucleoside comprising a furanosyl sugar moiety means the furanosyl sugar moiety or nucleoside comprising the furanosyl sugar moiety comprises a substituent other than H at the 5'-position and is a non-bicyclic furanosyl sugar moiety. 5'-substituted furanosyl sugar moieties do not comprise additional substituents at other positions of the furanosyl sugar moiety other than a nucleobase and/or internucleoside linkage(s) when in the context of an oligonucleotide.

As used herein, "administration" or "administering" refers to routes of introducing a compound or composition provided herein to a subject to perform its intended function. Examples of routes of administration that can be used include, but are not limited to, administration by inhalation, subcutaneous injection, intrathecal injection, and oral administration.

As used herein, "antisense activity" means any detectable and/or measurable change attributable to the hybridization of an antisense oligonucleotide to its target nucleic acid. In certain embodiments, antisense activity is a decrease in the amount or expression of a target nucleic acid or protein encoded by such target nucleic acid compared to target nucleic acid levels or target protein levels in the absence of the antisense oligonucleotide.

As used herein, "antisense agent" means an antisense oligonucleotide or an oligonucleotide duplex comprising an antisense oligonucleotide.

As used herein, "antisense compound" means an antisense oligonucleotide or an oligonucleotide duplex comprising an antisense oligonucleotide.

As used herein, "antisense oligonucleotide" means an oligonucleotide that is complementary to a target nucleic acid and is capable of achieving at least one antisense activity. Antisense oligonucleotides include but are not limited to RNAi antisense modified oligonucleotides and RNase H antisense modified oligonucleotides. In certain embodiments, an antisense oligonucleotide is paired with a sense oligonucleotide to form an oligonucleotide duplex. In certain embodiments, an antisense oligonucleotide is unpaired and is a single-stranded antisense oligonucleotide. In certain embodiments, an antisense oligonucleotide comprises a conjugate group.

As used herein, "artificial mRNA compound" is a modified oligonucleotide, or portion thereof, having a nucleobase sequence comprising one or more codons.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety, and the bicyclic sugar moiety is a modified bicyclic furanosyl sugar moiety. In certain embodiments, the bicyclic sugar moiety does not comprise a furanosyl moiety.

As used herein, "cEt" or "constrained ethyl" or "cEt sugar moiety" means a bicyclic sugar moiety, wherein the first ring of the bicyclic sugar moiety is a ribosyl sugar moiety, the second ring of the bicyclic sugar is formed via a bridge connecting the 4'-carbon and the 2'-carbon, the bridge has the formula 4'-$CH(CH_3)$—O-2', and the methyl group of the bridge is in the S configuration. A cEt bicyclic sugar moiety is in the β-D configuration.

As used herein, "complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases are nucleobase pairs that are capable of forming hydrogen bonds with one another. Complementary nucleobase pairs include adenine (A) and thymine (T), adenine (A) and uracil (U), cytosine (C) and guanine (G), 5-methyl cytosine ($^{m}C$) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

As used herein, "conjugate group" means a group of atoms consisting of a conjugate moiety and a conjugate linker.

As used herein, "conjugate moiety" means a group of atoms that modifies one or more properties of a molecule compared to the identical molecule lacking the conjugate moiety, including but not limited to pharmacodynamics, pharmacokinetics, stability, binding, absorption, tissue distribution, cellular distribution, cellular uptake, charge and clearance.

As used herein, "conjugate linker" means a group of atoms comprising at least one bond.

As used herein, "CRISPR compound" means a modified oligonucleotide that comprises a DNA recognition portion and a tracrRNA recognition portion. As used herein, "DNA recognition portion" is nucleobase sequence that is complementary to a DNA target. As used herein, "tracrRNA recognition portion" is a nucleobase sequence that is bound to or is capable of binding to tracrRNA. The tracrRNA recognition portion of crRNA may bind to tracrRNA via hybridization or covalent attachment.

As used herein, "cytotoxic" or "cytotoxicity" in the context of an effect of an oligomeric compound or a parent oligomeric compound on cultured cells means an at least 2-fold increase in caspase activation following administration of 10 μM or less of the oligomeric compound or parent oligomeric compound to the cultured cells relative to cells cultured under the same conditions but that are not administered the oligomeric compound or parent oligomeric compound. In certain embodiments, cytotoxicity is measured using a standard in vitro cytotoxicity assay.

As used herein, "deoxy region" means a region of 5-12 contiguous nucleotides, wherein at least 70% of the nucleosides are stereo-standard DNA nucleosides. In certain embodiments, each nucleoside is selected from a stereo-standard DNA nucleoside (a nucleoside comprising a β-D-2'-deoxyribosyl sugar moiety), a stereo-non-standard nucleoside of Formula I-VII, a bicyclic nucleoside, and a substituted stereo-standard nucleoside. In certain embodiments, a deoxy region supports RNase H activity. In certain embodiments, a deoxy region is the gap of a gapmer.

As used herein, "double-stranded antisense compound" means an antisense compound comprising two oligomeric compounds that are complementary to each other and form a duplex, and wherein one of the two said oligomeric compounds comprises an antisense oligonucleotide.

As used herein, "expression" includes all the functions by which a gene's coded information is converted into structures present and operating in a cell. Such structures include, but are not limited to, the products of transcription and translation. As used herein, "modulation of expression" means any change in amount or activity of a product of transcription or translation of a gene. Such a change may be an increase or a reduction of any amount relative to the expression level prior to the modulation.

As used herein, "gapmer" means an oligonucleotide having a central region comprising a plurality of nucleosides that support RNase H cleavage positioned between a 5'-region and a 3'-region. Herein, the nucleosides of the 5'-region and 3'-region each comprise a 2'-substituted furanosyl sugar moiety or a bicyclic sugar moiety, and the 3'- and 5'-most nucleosides of the central region each comprise a sugar moiety independently selected from a 2'-deoxyfuranosyl sugar moiety or a sugar surrogate. The positions of the central region refer to the order of the nucleosides of the central region and are counted starting from the 5'-end of the central region. Thus, the 5'-most nucleoside of the central region is at position 1 of the central region. The "central region" may be referred to as a "gap", and the "5'-region" and "3'-region" may be referred to as "wings". Gaps of gapmers are deoxy regions.

As used herein, "hepatotoxic" in the context of a mouse means a plasma ALT level that is above 300 units per liter. Hepatotoxicity of an oligomeric compound or parent oligomeric compound that is administered to a mouse is determined by measuring the plasma ALT level of the mouse 24 hours to 2 weeks following at least one dose of 1-150 mg/kg of the compound.

As used herein, "hepatotoxic" in the context of a human means a plasma ALT level that is above 150 units per liter. Hepatotoxicity of an oligomeric compound or parent oligomeric compound that is administered to a human is determined by measuring the plasma ALT level of the human 24 hours to 2 weeks following at least one dose of 10-300 mg of the compound.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "inhibiting the expression or activity" refers to a reduction or blockade of the expression or activity relative to the expression or activity in an untreated or control sample and does not necessarily indicate a total elimination of expression or activity.

As used herein, "internucleoside linkage" or "internucleoside linking group" means a group or bond that forms a covalent linkage between adjacent nucleosides in an oligonucleotide. As used herein "modified internucleoside linkage" means any internucleoside linkage other than a naturally occurring, phosphodiester internucleoside linkage. "Phosphorothioate linkage" means a modified internucleoside linkage in which one of the non-bridging oxygen atoms of a phosphodiester is replaced with a sulfur atom. Modified internucleoside linkages may or may not contain a phosphorus atom. A "neutral internucleoside linkage" is a modified internucleoside linkage that does not have a negatively charged phosphate in a buffered aqueous solution at pH=7.0. A modified internucleoside linkage may optionally comprise a conjugate group.

As used herein, "linked nucleosides" are nucleosides that are connected in a continuous sequence (i.e. no additional nucleosides are present between those that are linked).

As used herein, "maximum tolerated dose" means the highest dose of a compound that does not cause unacceptable side effects. In certain embodiments, the maximum tolerated dose is the highest dose of a modified oligonucleotide that does not cause an ALT elevation of three times the upper limit of normal as measured by a standard assay.

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "modulating" refers to changing or adjusting a feature in a cell, tissue, organ or organism.

As used herein, "MOE" means O-methoxyethyl. "2'-MOE" or "2'-O-methoxyethyl" means a 2'-$OCH_2CH_2OCH_3$ group at the 2'-position of a furanosyl ring. In certain embodiments, the 2'-$OCH_2CH_2OCH_3$ group is in place of the 2'-OH group of a ribosyl ring or in place of a 2'-H in a 2'-deoxyribosyl ring. A "2'-MOE sugar moiety" is a sugar moiety with a 2'-$OCH_2CH_2OCH_3$ group in place of the 2'-OH group of a furanosyl sugar moiety. Unless otherwise indicated, a 2'-MOE sugar moiety is in the β-D ribosyl configuration.

As used herein, a "2'-OMe sugar moiety" is a sugar moiety with a 2'-$CH_3$ group in place of the 2'-OH group of a furanosyl sugar moiety. Unless otherwise indicated, a 2'-OMe sugar moiety is in the β-D ribosyl configuration and is a "stereo-standard 2'OMe sugar moiety".

As used herein, a "2'-F sugar moiety" is a sugar moiety with a 2'-F group in place of the 2'-OH group of a furanosyl sugar moiety. Unless otherwise indicated, a 2'-F sugar moiety is in the β-D ribosyl configuration and is a "stereo-standard 2'-F sugar moiety".

As used herein, "motif" means the pattern of unmodified and/or modified sugar moieties, nucleobases, and/or internucleoside linkages, in an oligonucleotide.

As used herein, "naturally occurring" means found in nature.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a modified nucleobase is a group of atoms capable of pairing with at least one unmodified nucleobase. A universal base is a nucleobase that can pair with any one of the five unmodified nucleobases. 5-methylcytosine ($^{m}$C) is one example of a modified nucleobase.

As used herein, "nucleobase sequence" means the order of contiguous nucleobases in a nucleic acid or oligonucleotide independent of any sugar moiety or internucleoside linkage modification.

As used herein, "nucleoside" means a moiety comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. A modified nucleoside may comprise a conjugate group.

As used herein, "oligomeric compound" means a compound consisting of (1) an oligonucleotide (a single-stranded oligomeric compound) or two oligonucleotides hybridized to one another (a double-stranded oligomeric compound); and (2) optionally one or more additional features, such as a conjugate group or terminal group which may be attached to the oligonucleotide of a single-stranded oligomeric compound or to one or both oligonucleotides of a double-stranded oligomeric compound.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 12-3000 linked nucleosides, and optionally a conjugate group or terminal group. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "parent antisense agent" means an antisense agent other than an RNAi agent that is identical to an antisense agent having at least one internucleoside linkage of Formula XVII, except that the parent antisense agent has a phosphorothioate internucleoside linkage in place of each internucleoside linkage of Formula XVII in the antisense agent having at least one internucleoside linkage of Formula XVII.

As used herein, "parent RNAi agent" means an RNAi agent that is identical to an RNAi agent having at least one internucleoside linkage of Formula XVII, except that the parent RNAi agent has a phosphodiester internucleoside linkage in place of each internucleoside linkage of Formula XVII in the RNAi agent having at least one internucleoside linkage of Formula XVII.

As used herein, "pharmaceutically acceptable carrier or diluent" means any substance suitable for use in administering to an animal. Certain such carriers enable pharmaceutical compositions to be formulated as, for example, liquids, powders, or suspensions that can be aerosolized or otherwise dispersed for inhalation by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds (including oligomeric compounds that are antisense agents or portions thereof), i.e., salts that retain the desired biological activity of the compound and do not impart undesired toxicological effects thereto.

As used herein "pharmaceutical composition" means a mixture of substances suitable for administering to a subject. For example, a pharmaceutical composition may comprise an antisense compound and an aqueous solution.

As used herein, "RNAi agent" means an antisense agent that acts, at least in part, through RISC or Ago2 to modulate a target nucleic acid and/or protein encoded by a target nucleic acid. RNAi agents include, but are not limited to double-stranded siRNA, single-stranded RNA (ssRNA), and microRNA, including microRNA mimics. RNAi agents may comprise conjugate groups and/or terminal groups. In certain embodiments, an RNAi agent modulates the amount, activity, and/or splicing of a target nucleic acid. The term RNAi agent excludes antisense agents that act through RNase H.

As used herein, "RNAi oligonucleotide" means an RNAi antisense modified oligonucleotide or a RNAi sense modified oligonucleotide.

As used herein, "RNAi antisense modified oligonucleotide" means an oligonucleotide comprising a region that is complementary to a target sequence, and which includes at least one chemical modification suitable for RNAi.

As used herein, "RNAi antisense oligomeric compound" means a single-stranded oligomeric compound comprising a region that is complementary to a target sequence, and which includes at least one chemical modification suitable for RNAi.

As used herein, "RNAi sense modified oligonucleotide" means an oligonucleotide comprising a region that is complementary to a region of an RNAi antisense modified oligonucleotide, and which is capable of forming a duplex with such RNAi antisense modified oligonucleotide.

As used herein, "RNAi sense oligomeric compound" means a single-stranded oligomeric compound comprising a region that is complementary to a region of an RNAi antisense modified oligonucleotide and/or an RNAi antisense oligomeric compound, and which is capable of forming a duplex with such RNAi antisense modified oligonucleotide and/or RNAi antisense oligomeric compound.

A duplex formed by an RNAi antisense modified oligonucleotide and/or an RNAi antisense oligomeric compound with a RNAi sense modified oligonucleotide and/or an RNAi sense oligomeric compound is referred to as a double-stranded RNAi compound (dsRNAi) or a short interfering RNA (siRNA).

As used herein, "RNase H agent" means an antisense agent that acts, at least in part, through RNase H to modulate a target nucleic acid and/or protein encoded by a target nucleic acid. In certain embodiments, RNase H agents are single-stranded. In certain embodiments, RNase H agents are double-stranded. RNase H compounds may comprise conjugate groups and/or terminal groups. In certain embodiments, an RNase H agent modulates the amount or activity of a target nucleic acid. The term RNase H agent excludes antisense agents that act principally through RISC/Ago2.

As used herein, "RNase H antisense modified oligonucleotide" means an oligonucleotide comprising a region that is complementary to a target sequence, and which includes at least one chemical modification suitable for RNase H-mediated nucleic acid reduction.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to an antisense compound means such a compound consisting of one oligomeric compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case the compound would no longer be single-stranded.

As used herein, "stabilized phosphate group" refers to a 5'-chemical moiety that results in stabilization of a 5'-phosphate moiety of the 5'-terminal nucleoside of an oligonucleotide, relative to the stability of an unmodified 5'-phosphate of an unmodified nucleoside under biologic conditions. Such stabilization of a 5'-phophate group includes but is not limited to resistance to removal by phosphatases. Stabilized phosphate groups include, but are not limited to, 5'-vinyl phosphonates and 5'-cyclopropyl phosphonate.

As used herein, "stereo-standard nucleoside" means a nucleoside comprising a non-bicyclic furanosyl sugar moiety having the configuration of naturally occurring DNA and RNA as shown below. A "stereo-standard DNA nucleoside" is a nucleoside comprising a β-D-2'-deoxyribosyl sugar moiety. A "stereo-standard RNA nucleoside" is a nucleoside comprising a β-D-ribosyl sugar moiety. A "substituted stereo-standard nucleoside" is a stereo-standard nucleoside other than a stereo-standard DNA or stereo-standard RNA nucleoside. In certain embodiments, $R_1$ is a 2'-substituent and $R_2$-$R_5$ are each H. In certain embodiments, the 2'-substituent is selected from OMe, F, $OCH_2CH_2OCH_3$, O-alkyl, SMe, or NMA. In certain embodiments, $R_1$-$R_4$ are H and $R_5$ is a 5'-substituent selected from methyl, allyl, or ethyl. In certain embodiments, the heterocyclic base moiety Bx is selected from uracil, thymine, cytosine, 5-methyl cytosine, adenine or guanine. In certain embodiments, the heterocyclic base moiety Bx is other than uracil, thymine, cytosine, 5-methyl cytosine, adenine or guanine.

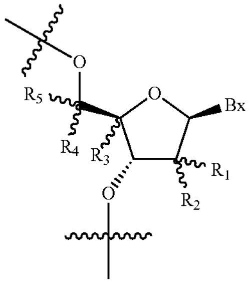

Stereo-standard nucleoside

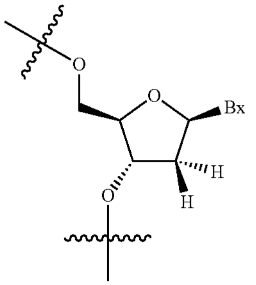

Stereo-standard DNA nucleoside

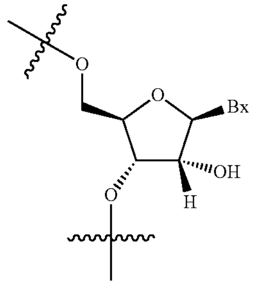

Stereo-standard RNA nucleoside

As used herein, "stereo-non-standard nucleoside" means a nucleoside comprising a non-bicyclic furanosyl sugar moiety having a configuration other than that of a stereo-standard sugar moiety. In certain embodiments, a "stereo-non-standard nucleoside" is represented by formulas I-VII below. In certain embodiments, $J_1$-$J_{14}$ are independently selected from H, OH, F, $OCH_3$, $OCH_2CH_2OCH_3$, O—$C_1$-$C_6$ alkoxy, and $SCH_3$. A "stereo-non-standard RNA nucleoside" has one of formulas I-VII below, wherein each of $J_1$, $J_3$, $J_5$, $J_7$, $J_9$, $J_{11}$, and $J_{13}$ is H, and each of $J_2$, $J_4$, $J_6$, $J_8$, $J_{10}$, $J_{12}$, and $J_{14}$ is OH. A "stereo-non-standard DNA nucleoside" has one of formulas I-VII below, wherein each J is H. A "2'-substituted stereo-non-standard nucleoside" has one of formulas I-VII below, wherein either $J_1$, $J_3$, $J_5$, $J_7$, $J_9$, $J_{11}$, and $J_{13}$ is other than H and/or or $J_2$, $J_4$, $J_6$, $J_8$, $J_{10}$, $J_{12}$, and $J_{14}$ is other than H or OH. In certain embodiments, the heterocyclic base moiety Bx is selected from uracil, thymine, cytosine, 5-methyl cytosine, adenine or guanine. In certain embodiments, the heterocyclic base moiety Bx is other than uracil, thymine, cytosine, 5-methyl cytosine, adenine or guanine.

I

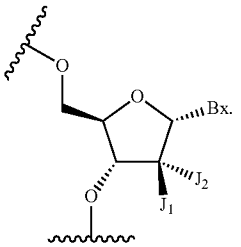

II

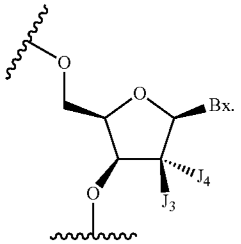

III

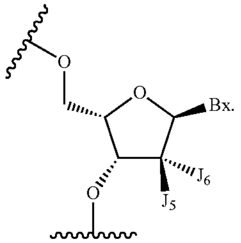

IV

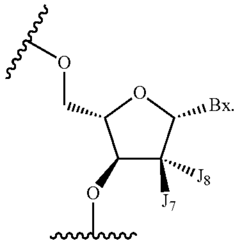

V

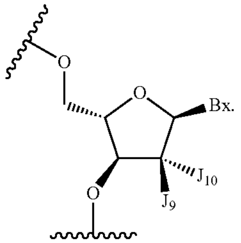

-continued

VI

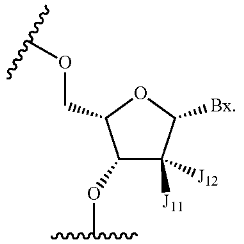

VII

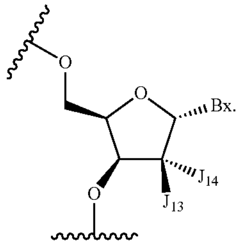

As used herein, "stereo-standard sugar moiety" means the sugar moiety of a stereo-standard nucleoside.

As used herein, "stereo-non-standard sugar moiety" means the sugar moiety of a stereo-non-standard nucleoside.

As used herein, "substituted stereo-non-standard nucleoside" means a stereo-non-standard nucleoside comprising a substituent other than the substituent corresponding to natural RNA or DNA. Substituted stereo-non-standard nucleosides include but are not limited to nucleosides of Formula I-VII wherein the J groups are other than: (1) both H or (2) one H and the other OH.

As used herein, "subject" means a human or non-human animal selected for treatment or therapy.

As used herein, "sugar moiety" means an unmodified sugar moiety or a modified sugar moiety. As used herein, "unmodified sugar moiety" means a β-D-ribosyl moiety, as found in naturally occurring RNA, or a β-D-2'-deoxyribosyl sugar moiety as found in naturally occurring DNA. As used herein, "modified sugar moiety" or "modified sugar" means a sugar surrogate or a furanosyl sugar moiety other than a β-D-ribosyl or a β-D-2'-deoxyribosyl. Modified furanosyl sugar moieties may be modified or substituted at a certain position(s) of the sugar moiety, or unsubstituted, and they may or may not be stereo-non-standard sugar moieties. Modified furanosyl sugar moieties include bicyclic sugars and non-bicyclic sugars. As used herein, "sugar surrogate" means a modified sugar moiety that does not comprise a furanosyl or tetrahydrofuranyl ring (is not a "furanosyl sugar moiety") and that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid," "target RNA," "target RNA transcript" and "nucleic acid target" means a nucleic acid that an oligomeric compound, such as an antisense compound, is designed to affect. In certain embodiments, an oligomeric compound comprises an oligonucleotide having a nucleobase sequence that is complementary to more than one RNA, only one of which is the target RNA of the oligomeric compound. In certain embodiments, the target RNA is an RNA present in the species to which an oligomeric compound is administered.

As used herein, "therapeutic index" means a comparison of the amount of a compound that causes a therapeutic effect to the amount that causes toxicity. Compounds having a high therapeutic index have strong efficacy and low toxicity. In certain embodiments, increasing the therapeutic index of a compound increases the amount of the compound that can be safely administered.

As used herein, "treat" refers to administering a compound or pharmaceutical composition to an animal in order to effect an alteration or improvement of a disease, disorder, or condition in the animal.

As used herein, "translation suppression element," means any sequence and/or secondary structure in the 5'-UTR of a target transcript that reduces, inhibits, and/or suppresses translation of the target transcript. In certain embodiments, a translation suppression element comprises a uORF. In certain embodiments, a translation suppression element does not comprise a uORF. In certain embodiments, a translation suppression element comprises one or more stem-loops. In certain embodiments, a translation suppression element comprises greater than 60%, greater than 70%, or greater than 80% GC content. In certain embodiments, the translation suppression element is a uORF. In certain embodiments, the translation suppression element is a stem-loop.

Certain Embodiments

The present disclosure provides the following non-limiting embodiments:

Embodiment 1. An oligomeric compound comprising a modified oligonucleotide consisting of linked nucleosides linked through internucleoside linking groups, wherein at least one of the internucleoside linking groups has Formula VIII:

VIII

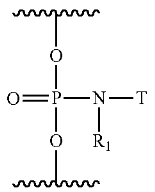

wherein independently for each internucleoside linking group of the modified oligonucleotide having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, an amine, a substituted amine, $C_1$-$C_6$ alkoxy, $C_1$-$C_6$ alkyl, and substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl.

Embodiment 2. An oligomeric compound comprising a modified oligonucleotide consisting of linked nucleosides linked through internucleoside linking groups, wherein at least one of the internucleoside linking groups has Formula VIII:

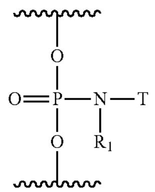

VIII wherein independently for each internucleoside linking group of the modified oligonucleotide having Formula VIII:

$R_1$ is selected from H, $C_1$-$C_6$ alkyl, and substituted $C_1$-$C_6$ alkyl; and T is selected from $SO_2R_2$, C(=O)$R_3$, and P(=O)$R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, a $C_1$-$C_6$ alkyl, and a substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl;

provided that if $R_1$ is H, then T is not:

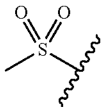

or

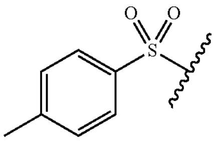

.

Embodiment 3. The oligomeric compound of embodiment 1 or 2, wherein $R_1$ is H.

Embodiment 4. The oligomeric compound of embodiment 1 or 2, wherein $R_1$ is a $C_1$-$C_6$ alkyl.

Embodiment 5. The oligomeric compound of embodiment 4, wherein $R_1$ is methyl.

Embodiment 6. The oligomeric compound of embodiment 1 or 2, wherein $R_1$ is a substituted $C_1$-$C_6$ alkyl;

Embodiment 7. The oligomeric compound of any of embodiments 1-6, wherein T is $SO_2R_2$.

Embodiment 8. The oligomeric compound of embodiment 7, wherein $R_2$ is an aryl.

Embodiment 9. The oligomeric compound of embodiment 7, wherein $R_2$ is a substituted aryl.

Embodiment 10. The oligomeric compound of embodiment 7, wherein $R_2$ is a heterocycle.

Embodiment 11. The oligomeric compound of embodiment 7, wherein $R_2$ is a substituted heterocycle.

Embodiment 12. The oligomeric compound of embodiment 7, wherein $R_2$ is an aromatic heterocycle.

Embodiment 13. The oligomeric compound of embodiment 7, wherein $R_2$ is a substituted aromatic heterocycle.

Embodiment 14. The oligomeric compound of embodiment 7, wherein $R_2$ is a diazole.

Embodiment 15. The oligomeric compound of embodiment 7, wherein $R_2$ is a substituted diazole.

Embodiment 16. The oligomeric compound of embodiment 7, wherein $R_2$ is an amine.

Embodiment 17. The oligomeric compound of embodiment 7, wherein $R_2$ is a substituted amine.

Embodiment 18. The oligomeric compound of embodiment 7, wherein $R_2$ is a $C_1$-$C_6$ alkoxy.

Embodiment 19. The oligomeric compound of embodiment 7, wherein $R_2$ is $C_1$-$C_6$ alkyl.

Embodiment 20. The oligomeric compound of embodiment 7, wherein $R_2$ is substituted $C_1$-$C_6$ alkyl.

Embodiment 21. The oligomeric compound of embodiment 7, wherein T is:

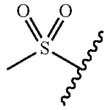

.

Embodiment 22. The oligomeric compound of embodiment 7, wherein T is:

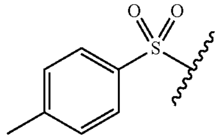

.

Embodiment 23. The oligomeric compound of embodiment 7, wherein T is:

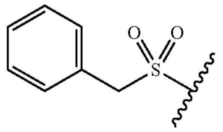

.

Embodiment 24. The oligomeric compound of embodiment 7, wherein T is:

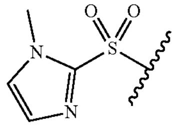

.

Embodiment 25. The oligomeric compound of embodiment 7, wherein T is:

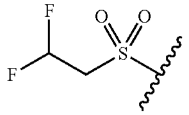

.

Embodiment 26. The oligomeric compound of embodiment 7, wherein T is:

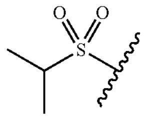

.

Embodiment 27. The oligomeric compound of embodiment 7, wherein T is:

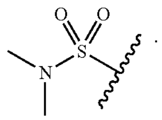 [SMILES: *S(=O)(=O)N(C)C]

Embodiment 28. The oligomeric compound of embodiment 7, wherein T is:

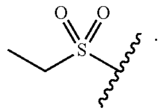 [SMILES: *S(=O)(=O)CC]

Embodiment 29. The oligomeric compound of embodiment 7, wherein T is:

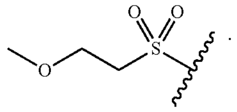 [SMILES: *S(=O)(=O)CCOC]

Embodiment 30. The oligomeric compound of any of embodiments 1-6, wherein T is $C(=O)R_3$.

Embodiment 31. The oligomeric compound of embodiment 30, wherein $R_3$ is an aryl.

Embodiment 32. The oligomeric compound of embodiment 30, wherein $R_3$ is a substituted aryl.

Embodiment 33. The oligomeric compound of embodiment 30, wherein $R_3$ is $CH_3$.

Embodiment 34. The oligomeric compound of embodiment 30, wherein $R_3$ is $N(CH_3)_2$.

Embodiment 35. The oligomeric compound of embodiment 30, wherein $R_3$ is $OCH_3$.

Embodiment 36. The oligomeric compound of embodiment 30, wherein T is:

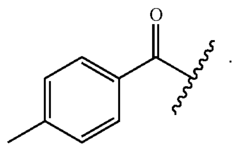 [SMILES: *C(=O)c1ccc(C)cc1]

Embodiment 37. The oligomeric compound of embodiment 30, wherein T is:

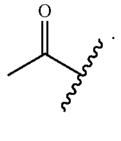 [SMILES: *C(C)=O]

Embodiment 38. The oligomeric compound of embodiment 30, wherein T is:

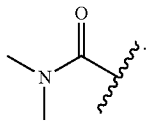 [SMILES: *C(=O)N(C)C]

Embodiment 39. The oligomeric compound of embodiment 30, wherein T is:

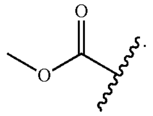 [SMILES: *C(=O)OC]

Embodiment 40. The oligomeric compound of any of embodiments 1-6, wherein T is $P(=O)R_4R_5$ Embodiment 41. The oligomeric compound of embodiment 40, wherein $R_4$ is $OCH_3$.

Embodiment 42. The oligomeric compound of embodiment 40, wherein $R_4$ is OH.

Embodiment 43. The oligomeric compound of embodiment 40, wherein $R_4$ is $C_1$-$C_6$ alkyl.

Embodiment 44. The oligomeric compound of embodiment 40, wherein $R_4$ is substituted $C_1$-$C_6$ alkyl.

Embodiment 45. The oligomeric compound of any of embodiments 40-42, wherein $R_5$ is $OCH_3$.

Embodiment 46. The oligomeric compound of any of embodiments 40-42, wherein $R_5$ is OH.

Embodiment 47. The oligomeric compound of any of embodiments 40-42, wherein $R_5$ is $C_1$-$C_6$ alkyl.

Embodiment 48. The oligomeric compound of any of embodiments 40-42, wherein $R_5$ is substituted $C_1$-$C_6$ alkyl.

Embodiment 49. The oligomeric compound of embodiment 40, wherein T is:

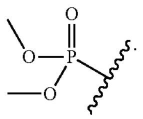

Embodiment 50. The oligomeric compound of embodiment 40, wherein T is:

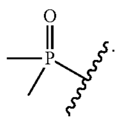

Embodiment 51. The oligomeric compound of any of embodiments 1-50, wherein at least one internucleoside linking group of the modified oligonucleotide is not a linking group of Formula VIII.

Embodiment 52. The oligomeric compound of any of embodiments 1-50, wherein exactly one internucleoside linking group of the modified oligonucleotide is an internucleoside linking group of any of embodiments 1-50.

Embodiment 53. The oligomeric compound of any of embodiments 1-50, wherein exactly two internucleoside linking groups of the modified oligonucleotide are internucleoside linking groups of any of embodiments 1-50.

Embodiment 54. The oligomeric compound of any of embodiments 1-50, wherein exactly three internucleoside linking groups of the modified oligonucleotide are internucleoside linking groups of any of embodiments 1-50.

Embodiment 55. The oligomeric compound of any of embodiments 1-50, wherein exactly four internucleoside linking groups of the modified oligonucleotide are internucleoside linking groups of any of embodiments 1-50.

Embodiment 56. The oligomeric compound of any of embodiments 1-50, wherein exactly five internucleoside linking groups of the modified oligonucleotide are internucleoside linking groups of any of embodiments 1-50.

Embodiment 57. The oligomeric compound of any of embodiments 1-50, wherein at least six internucleoside linking groups of the modified oligonucleotide are internucleoside linking groups of any of embodiments 1-50.

Embodiment 58. The oligomeric compound of any of embodiment 1-51 or 53-57 having at least two linking groups of any of embodiments 1-50, wherein at least two of the linking groups of any of embodiments 1-50 are the same as one another.

Embodiment 59. The oligomeric compound of any of embodiments 1-58, wherein each internucleoside linking group of the modified oligonucleotide that is not an internucleoside linking group of any of embodiments 1-50 is either a phosphodiester internucleoside linking group or a phosphorothioate internucleoside linking group.

Embodiment 60. The oligomeric compound of any of embodiments 1-58, wherein each internucleoside linking group of the modified oligonucleotide is an internucleoside linking group of any of embodiments 1-50.

Embodiment 61. The oligomeric compound of any of embodiments 1-60, wherein at least one nucleoside of the modified oligonucleotide is a modified nucleoside.

Embodiment 62. The oligomeric compound of embodiment 61, wherein at least one nucleoside of the modified oligonucleotide is a modified nucleoside selected from a bicyclic nucleoside and a non-bicyclic substituted nucleoside.

Embodiment 63. The oligomeric compound of any of embodiments 1-62, wherein at least one nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 64. The oligomeric compound of any of embodiments 1-62, wherein each nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 65. The oligomeric compound of any of embodiments 1-62, wherein at least one nucleoside of the modified oligonucleotide is selected from: a 2'-OMe nucleoside, a 2'-F nucleoside, and an RNA nucleoside.

Embodiment 66. The oligomeric compound of any of embodiments 1-62, wherein at least one nucleoside of the modified oligonucleotide is a 2'-OMe nucleoside, and at least one nucleoside of the modified oligonucleotide is an RNA nucleoside.

Embodiment 67. The oligomeric compound of any of embodiments 61-66, wherein the modified oligonucleotide has a region of alternating nucleoside types having the motif ABABA, wherein each A is a stereo-standard nucleoside of a first type and each B is a stereo-standard nucleoside of a second type, wherein the first type and the second type are different from one another.

Embodiment 68. The oligomeric compound of embodiment 67, wherein A and B are selected from 2'-F substituted nucleosides, 2'-OMe substituted nucleosides, and stereo-standard RNA nucleosides.

Embodiment 69. The oligomeric compound of any of embodiments 1-68, wherein the 5'-end of the modified oligonucleotide comprises a stabilized phosphate group.

Embodiment 70. The oligomeric compound of any of embodiments 1-69, wherein the modified oligonucleotide consists of 12-30 linked nucleosides.

Embodiment 71. The oligomeric compound of any of embodiments 1-69, wherein the modified oligonucleotide consists of 16-24 linked nucleosides.

Embodiment 72. The oligomeric compound of any of embodiments 1-69, wherein the modified oligonucleotide consists of 18-22 linked nucleosides.

Embodiment 73. The oligomeric compound of any of embodiments 1-69, wherein the modified oligonucleotide consists of 16 linked nucleosides.

Embodiment 74. The oligomeric compound of any of embodiments 1-69, wherein the modified oligonucleotide consists of 17 linked nucleosides.

Embodiment 75. The oligomeric compound of any of embodiments 1-69, wherein the modified oligonucleotide consists of 18 linked nucleosides.

Embodiment 76. The oligomeric compound of any of embodiments 1-69, wherein the modified oligonucleotide consists of 19 linked nucleosides.

Embodiment 77. The oligomeric compound of any of embodiments 1-69, wherein the modified oligonucleotide consists of 20 linked nucleosides.

Embodiment 78. The oligomeric compound of any of embodiments 1-69, wherein the modified oligonucleotide consists of 21 linked nucleosides.

Embodiment 79. The oligomeric compound of any of embodiments 1-69, wherein the modified oligonucleotide consists of 22 linked nucleosides.

Embodiment 80. The oligomeric compound of any of embodiments 1-69, wherein the modified oligonucleotide consists of 23 linked nucleosides.

Embodiment 81. The oligomeric compound of any of embodiments 1-80, wherein the oligomeric compound is an RNAi compound.

Embodiment 82. The oligomeric compound of embodiment 81, wherein the RNAi compound is a single-stranded RNAi compound comprising an RNAi antisense modified oligonucleotide, wherein the RNAi antisense modified compound is a modified oligonucleotide of any of embodiments 1-78.

Embodiment 83. The oligomeric compound of embodiment 81, wherein the RNAi compound is a double-stranded RNAi compound comprising an RNAi antisense modified oligonucleotide and an RNAi sense modified oligonucleotide, wherein the RNAi antisense modified oligonucleotide and/or the RNAi sense modified oligonucleotide is a modified oligonucleotide of any of embodiments 1-78.

Embodiment 84. The oligomeric compound of embodiment 82 or 83, wherein at least one internucleoside linking group of the RNAi antisense modified oligonucleotide is an internucleoside linking group of any of embodiments 1-50.

Embodiment 85. The oligomeric compound of embodiment 82 or 83, wherein at least two internucleoside linking groups of the RNAi antisense modified oligonucleotide are independently selected internucleoside linking groups of any of embodiments 1-50.

Embodiment 86. The oligomeric compound of any of embodiments 82-85, wherein at least one of the five 3'-most internucleoside linking groups of the RNAi antisense modified oligonucleotide is an internucleoside linking group of any of embodiments 1-50.

Embodiment 87. The oligomeric compound of any of embodiments 82-86, wherein at least two of the five 3'-most internucleoside linking groups of RNAi antisense modified oligonucleotide is an internucleoside linking group of any of embodiments 1-50.

Embodiment 88. The oligomeric compound of any of embodiments 82-87, wherein at least one internucleoside linking group within the seed region of the RNAi antisense modified oligonucleotide is an internucleoside linking group of any of embodiments 1-50.

Embodiment 89. The oligomeric compound of embodiment 83-88, wherein at least one internucleoside linking group of the RNAi sense modified oligonucleotide is an internucleoside linking group of any of embodiments 1-50.

Embodiment 90. The oligomeric compound of embodiment 89, wherein at least one of the first 5 internucleoside linking groups from the 5'-end of the RNAi sense modified oligonucleotide is an internucleoside linking group of any of embodiments 1-50.

Embodiment 91. The oligomeric compound of any of embodiments 89-90, wherein at least one of the five 3'-most 1 internucleoside linking groups of the RNAi sense modified oligonucleotide is an internucleoside linking group of any of embodiments 1-50.

Embodiment 92. The oligomeric compound of any of embodiments 89-91, wherein at least one of the first 5 internucleoside linking groups from the 5'-end of the RNAi sense modified oligonucleotide and at least one of the five 3'-most linking groups of the RNAi sense modified oligonucleotide is an internucleoside linking group of any of embodiments 1-50.

Embodiment 93. The oligomeric compound of any of embodiments 1-92, wherein at least one nucleoside of the modified oligonucleotide is a stereo-non-standard nucleoside.

Embodiment 94. The oligomeric compound of embodiment 93, wherein the internucleoside linking group linking at least one stereo-non-standard nucleoside to an adjacent nucleoside is an internucleoside linking group of any of embodiments 1-50.

Embodiment 95. The oligomeric compound of embodiment 93 or 94, wherein at least two nucleosides of the modified oligonucleotide are stereo-non-standard nucleosides.

Embodiment 96. The oligomeric compound of embodiment 95, wherein at least two stereo-non-standard nucleosides of the modified oligonucleotide are adjacent to one another.

Embodiment 97. The oligomeric compound of embodiment 96, wherein at least two stereo-non-standard nucleosides of the modified oligonucleotide are linked to one another with an internucleoside linking group of any of embodiments 1-50.

Embodiment 98. The oligomeric compound of any of embodiments 95-97, wherein at least one stereo-non-standard nucleoside of the modified oligonucleotide is a stereo-non-standard DNA nucleoside.

Embodiment 99. The oligomeric compound of any of embodiments 95-97, wherein at least one stereo-non-standard nucleoside of the modified oligonucleotide is a substituted stereo-non-standard nucleoside or a stereo-non-standard RNA nucleoside.

Embodiment 100. The oligomeric compound of embodiment 99, wherein the 2'-substituent of the at least one substituted stereo-non-standard nucleoside of the modified oligonucleotide is selected from: 2'-MOE, 2'-OMe, 2'-F, or 2'-OH.

Embodiment 101. The oligomeric compound of any of embodiments 1-100, wherein the modified oligonucleotide comprises a deoxy region consisting of 6-11 linked nucleosides wherein each nucleoside of the deoxy region is either a modified nucleoside or a stereo-standard DNA nucleoside and wherein at least 3 contiguous nucleosides of the deoxy region are stereo-standard DNA nucleosides and not more than three nucleosides of the deoxy region are modified nucleosides.

Embodiment 102. The oligomeric compound of embodiment 101, wherein at least 4 contiguous nucleosides of the deoxy region are stereo-standard DNA nucleosides.

Embodiment 103. The oligomeric compound of embodiment 101, wherein at least 5 contiguous nucleosides of the deoxy region are stereo-standard DNA nucleosides.

Embodiment 104. The oligomeric compound of embodiment 101, wherein at least 6 contiguous nucleosides of the deoxy region are stereo-standard DNA nucleosides.

Embodiment 105. The oligomeric compound of embodiment 101, wherein at least 7 contiguous nucleosides of the deoxy region are stereo-standard DNA nucleosides.

Embodiment 106. The oligomeric compound of embodiment 101, wherein at least 8 contiguous nucleosides of the deoxy region are stereo-standard DNA nucleosides.

Embodiment 107. The oligomeric compound of any of embodiments 101-106, wherein the deoxy region consists of 8-10 linked nucleosides.

Embodiment 108. The oligomeric compound of any of embodiments 101-106, wherein the deoxy region consists of 9 linked nucleosides.

Embodiment 109. The oligomeric compound of any of embodiments 101-106, wherein the deoxy region consists of 10 linked nucleosides.

Embodiment 110. The oligomeric compound of any of embodiments 101-106, wherein the deoxy region consists of 11 linked nucleosides.

Embodiment 111. The oligomeric compound of any of embodiments 101-110 wherein at least 6 nucleosides of the deoxy region are stereo-standard DNA nucleosides.

Embodiment 112. The oligomeric compound of any of embodiments 101-110 wherein at least 7 nucleosides of the deoxy region are stereo-standard DNA nucleosides.

Embodiment 113. The oligomeric compound of any of embodiments 101-110 wherein at least 8 nucleosides of the deoxy region are stereo-standard DNA nucleosides.

Embodiment 114. The oligomeric compound of any of embodiments 101-110 wherein at least 9 nucleosides of the deoxy region are stereo-standard DNA nucleosides.

Embodiment 115. The oligomeric compound of any of embodiments 101-114 wherein two nucleosides of the deoxy region are modified nucleosides.

Embodiment 116. The oligomeric compound of any of embodiments 101-114 wherein one nucleoside of the deoxy region is a modified nucleoside.

Embodiment 117. The oligomeric compound of any of embodiments 101-116 wherein at least one modified nucleoside of the deoxy region is a stereo-standard modified nucleoside or bicyclic nucleoside selected from a β-D-LNA nucleoside, an α-L-LNA nucleoside, an ENA nucleoside, a cEt nucleoside, a 2'-MOE nucleoside, a 2'-OMe nucleoside, a 2'-F nucleoside, and a 5'-alkyl nucleoside.

Embodiment 118. The oligomeric compound of any of embodiments 101-117 wherein at least one modified nucleoside of the deoxy region is stereo-non-standard nucleoside.

Embodiment 119. The oligomeric compound of embodiment 118 wherein the at least one is stereo-non-standard isomeric nucleoside of the deoxy region is a stereo-non-standard DNA nucleoside.

Embodiment 120. The oligomeric compound of embodiment 119 wherein the stereo-non-standard DNA nucleoside is selected from a stereo-non-standard DNA nucleoside having: Formula I, Formula II, Formula III, Formula IV, Formula V, Formula VI, and Formula VII.

Embodiment 121. The oligomeric compound of embodiment 120 wherein the stereo-non-standard DNA nucleoside is selected from a stereo-non-standard DNA nucleoside having: Formula V and Formula II.

Embodiment 122. The oligomeric compound of any of embodiments 118-121 wherein at least one stereo-non-standard nucleoside of the deoxy region is a substituted stereo-non-standard nucleoside.

Embodiment 123. The oligomeric compound of embodiment 122 wherein at least one substituted stereo-non-standard nucleoside has a 2'-substituent selected from: 2'-MOE, 2'-OMe, 2'-F, or 2'-OH.

Embodiment 124. The oligomeric compound of any of embodiments 101-123, wherein the $2^{nd}$ nucleoside from the 5'-end of the deoxy region is a modified nucleoside.

Embodiment 125. The oligomeric compound of any of embodiments 101-124, wherein the $3^{rd}$ nucleoside from the 5'-end of the deoxy region is a modified nucleoside.

Embodiment 126. The oligomeric compound of any of embodiments 101-125, wherein the $4^{th}$ nucleoside from the 5'-end of the deoxy region is a modified nucleoside.

Embodiment 127. The oligomeric compound of any of embodiments 101-126, wherein each nucleoside of the deoxy region is a stereo-standard DNA nucleoside.

Embodiment 128. The oligomeric compound of any of embodiments 101-127 wherein at least one internucleoside linking group within the deoxy region is an internucleoside linking group of any of embodiments 1-50.

Embodiment 129. The oligomeric compound of any of embodiments 101-128, wherein the internucleoside linking group linking the $1^{st}$ and $2^{nd}$ nucleosides of the deoxy region as counted from the 5'-end of the deoxy region is an internucleoside linking group of any of embodiments 1-50.

Embodiment 130. The oligomeric compound of any of embodiments 101-129, wherein the internucleoside linking group linking the $2^{nd}$ and $3^{rd}$ nucleosides of the deoxy region as counted from the 5'-end of the deoxy region is an internucleoside linking group of any of embodiments 1-50.

Embodiment 131. The oligomeric compound of any of embodiments 101-130, wherein the internucleoside linking group linking the $3^{rd}$ and $4^{th}$ nucleosides of the deoxy region as counted from the 5'-end of the deoxy region is an internucleoside linking group of any of embodiments 1-50.

Embodiment 132. The oligomeric compound of any of embodiments 101-131, wherein the internucleoside linking group linking the $4^{th}$ and $5^{th}$ nucleosides of the deoxy region as counted from the 5'-end of the deoxy region is an internucleoside linking group of any of embodiments 1-50.

Embodiment 133. The oligomeric compound of any of embodiments 101-132 wherein one internucleoside linking group in the deoxy region is a linking group of any of embodiments 1-50 and the other internucleoside linking groups of the deoxy region are each phosphodiester or phosphorothioate internucleoside linking groups.

Embodiment 134. The oligomeric compound of any of embodiments 101-133 wherein two internucleoside linking groups in the deoxy region are linking groups of any of embodiments 1-50 and the other internucleoside linking groups of the deoxy region are each phosphodiester or phosphorothioate internucleoside linking groups.

Embodiment 135. The oligomeric compound of any of embodiments 101-134 wherein three internucleoside linking groups in the deoxy region are linking groups of any of embodiments 1-50 and the other internucleoside linking groups of the deoxy region are each phosphodiester or phosphorothioate internucleoside linking groups.

Embodiment 136. The oligomeric compound of any of embodiments 101-135 wherein the deoxy region is flanked on the 5' side by a 5'-region consisting of 1-6 linked 5'-region nucleosides and on the 3' side by a 3'-region consisting of 1-6 linked 3'-region nucleosides; wherein the 3'-most nucleoside of the 5'-region is a modified nucleoside; and the 5'-most nucleoside of the 3'-region is a modified nucleoside.

Embodiment 137. The oligomeric compound of embodiment 136, wherein at least one 5'-region nucleoside is a stereo-standard DNA nucleoside.

Embodiment 138. The oligomeric compound of embodiment 136, wherein each 5'-region nucleoside is a modified nucleoside.

Embodiment 139. The oligomeric compound of any of embodiments 136, wherein at least one 5'-region nucleoside is a 2'-substituted nucleoside.

Embodiment 140. The oligomeric compound of any of embodiments 136, or 138-139 wherein each 5'-region nucleoside is a 2'-substituted nucleoside.

Embodiment 141. The oligomeric compound of any of embodiments 139-140, wherein the 2'-substitutent is selected from among 2'-F, 2'-$OCH_3$, and 2'-MOE.

Embodiment 142. The oligomeric compound of any of embodiments 136-139 or 141, wherein at least one 5'-region nucleoside is a bicyclic nucleoside.

Embodiment 143. The oligomeric compound of embodiment 142, wherein each 5'-region nucleoside is a bicyclic nucleoside.

Embodiment 144. The oligomeric compound of any of embodiments 142-143, wherein the bicyclic 5'-region nucleoside is selected from among a β-D-LNA nucleoside, an α-L-LNA nucleoside, an ENA nucleoside, and a cEt nucleoside.

Embodiment 145. The oligomeric compound of any of embodiments embodiment 136-144, wherein at least one 3'-region nucleoside is a stereo-standard DNA nucleoside.

Embodiment 146. The oligomeric compound of any of embodiments 136-144 wherein each 3'-region nucleoside is a modified nucleoside.

Embodiment 147. The oligomeric compound of any of embodiments 136-146, wherein at least one 3'-region nucleoside is a 2'-substituted nucleoside.

Embodiment 148. The oligomeric compound of any of embodiments 136-144 or 146-147, wherein each 3'-region nucleoside is a 2'-substituted nucleoside.

Embodiment 149. The oligomeric compound of embodiment 147 or 148, wherein the 2'-substituent is selected from among 2'-F, 2'-$OCH_3$, and 2'-MOE.

Embodiment 150. The oligomeric compound of any of embodiments 136-147 or 149, wherein at least one 3'-region nucleoside is a bicyclic nucleoside.

Embodiment 151. The oligomeric compound of embodiment 150, wherein each 3'-region nucleoside is a bicyclic nucleoside.

Embodiment 152. The oligomeric compound of any of embodiments 150-151 wherein the bicyclic 3'-region nucleoside is selected from among a β-D-LNA nucleoside, an α-L-LNA nucleoside, an ENA nucleoside, and a cEt nucleoside.

Embodiment 153. The oligomeric compound of any of embodiments 101-152 wherein the modified oligonucleotide is a gapmer.

Embodiment 154. The oligomeric compound of any of embodiments 1-80 wherein each nucleoside of the modified oligonucleotide is a modified nucleoside and each modified nucleoside of the modified oligonucleotide comprises the same modification.

Embodiment 155. The oligomeric compound of any of embodiments 1-153, wherein the nucleobase sequence of the modified oligonucleotide is complementary to a target nucleic acid.

Embodiment 156. The oligomeric compound of embodiment 155, wherein the nucleobase sequence of the modified oligonucleotide is at least 80% complementary to the target nucleic acid.

Embodiment 157. The oligomeric compound of embodiment 155, wherein the nucleobase sequence of the modified oligonucleotide is at least 85% complementary to the target nucleic acid.

Embodiment 158. The oligomeric compound of embodiment 155, wherein the nucleobase sequence of the modified oligonucleotide is at least 90% complementary to the target nucleic acid.

Embodiment 159. The oligomeric compound of embodiment 155, wherein the nucleobase sequence of the modified oligonucleotide is at least 95% complementary to the target nucleic acid.

Embodiment 160. The oligomeric compound of embodiment 155, wherein the nucleobase sequence of the modified oligonucleotide is 100% complementary to the target nucleic acid.

Embodiment 161. The oligomeric compound of any of embodiments 155-160, wherein the target nucleic acid is a target RNA.

Embodiment 162. The oligomeric compound of embodiment 161, wherein the target RNA is selected from: an mRNA, a pre-mRNA, a microRNA, and a non-coding RNA.

Embodiment 163. The oligomeric compound of embodiment 161, wherein the target RNA is not a microRNA.

Embodiment 164. The oligomeric compound of any of embodiments 1-162, wherein the modified oligonucleotide is not complementary to miR-21.

Embodiment 165. The oligomeric compound of any of embodiments 1-163, comprising a conjugate group.

Embodiment 166. The oligomeric compound of embodiment 164, wherein the conjugate group comprises at least one GalNAc.

Embodiment 167. The oligomeric compound of embodiment 164 or 165, wherein the conjugate group comprises 1-5 linker-nucleosides.

Embodiment 168. The oligomeric compound of any of embodiments 1-80, wherein the oligomeric compound is a CRISPR compound.

Embodiment 169. The oligomeric compound of embodiment 168, wherein the CRISPR compound consists of 20-50 linked nucleosides.

Embodiment 170. The oligomeric compound of embodiment 168, wherein the CRISPR compound consists of 29-32 linked nucleosides.

Embodiment 171. A pharmaceutical composition comprising the CRISPR compound of embodiments 169-170 and a pharmaceutically acceptable carrier or diluent.

Embodiment 172. A method comprising contacting a cell with the CRISPR compound or composition of any of embodiments 169-170.

Embodiment 173. The method of embodiment 172, comprising contacting the cell with a plasmid that encodes Cas9 or Cpf1.

Embodiment 174. The method of embodiment 172-173, wherein the plasmid encodes a tracrRNA.

Embodiment 175. The method of embodiment 174, comprising contacting the cell with an mRNA that encodes Cas9 or Cpf1.

Embodiment 176. The method of any of embodiments 172-175, comprising contacting the cell with a plasmid that encodes a tracrRNA.

Embodiment 177. The method of any of embodiments 172-176 wherein a target gene is edited.

Embodiment 178. The oligomeric compound of any of embodiments 1-80, wherein the oligomeric compound is an artificial mRNA compound.

Embodiment 179. The artificial mRNA compound of embodiment 178, wherein the artificial mRNA oligonucleotide consists of 17-3000 linked nucleosides.

Embodiment 180. The artificial mRNA compound of embodiment 178 or 179, wherein the artificial mRNA oligonucleotide encodes a protein.

Embodiment 181. A pharmaceutical composition comprising the artificial mRNA compound of any of embodiments 178-180 and a pharmaceutically acceptable carrier or diluent.

Embodiment 182. A method comprising contacting a cell with the artificial mRNA compound or composition of any of embodiments 178-181.

Embodiment 183. A pharmaceutical composition comprising the oligomeric compound of any of embodiments 1-182 and a pharmaceutically acceptable carrier or diluent.

Embodiment 184. A method comprising contacting a cell with the oligomeric compound or pharmaceutical composition of any of embodiments 1-167 or 183.

Embodiment 185. A method of modulating the amount or activity of a target nucleic acid in a cell, comprising contacting the cell with the oligomeric compound or pharmaceutical composition of any of embodiments 1-167 or 183, and thereby modulating the amount or activity of the target nucleic acid.

Embodiment 186. A method of modulating the amount or activity of a target nucleic acid in a cell, comprising contacting the cell with the oligomeric compound or pharmaceutical composition of any of embodiments 1-167 or 183.

Embodiment 187. The method of embodiment 186, wherein the amount or activity of a target nucleic acid is reduced.

Embodiment 188. Use of the oligomeric compound or composition of any of embodiments 1-171, 178-181 or 183 for treatment of a disease or condition.

Embodiment 189. Use of the oligomeric compound or composition of any of embodiments 1-171, 178-181 or 183 for a preparation of a medicament for treatment of a disease or condition.

Embodiment 190. An oligomeric compound comprising a modified oligonucleotide consisting of 12-23 linked nucleosides, wherein the modified oligonucleotide comprises a 5'-region, a central region, and a 3'-region wherein:

the 5'-region consists of 1-5 linked nucleosides; wherein at least one 5'-region nucleoside is modified;

the 3'-region consists of 1-5 linked nucleosides; wherein at least one 3'-region nucleoside is modified; and the central region consists of/7-11 linked nucleosides, and has the formula:

$$(N_{d1})_{L1}(N_{d2})_{L2}(N_{d3})_{L3}(N_{d4})_{L4}[(N_d)_{L5}]_q,$$

wherein $N_{d1}$, $N_{d2}$, $N_{d3}$, $N_{d4}$ are independently selected from among a stereo-standard DNA nucleoside, a stereo-non-standard DNA nucleoside, or a 2'-substituted nucleoside; with the proviso that no more than one of $N_{d1}$, $N_{d2}$, $N_{d3}$, or $N_{d4}$ is a 2'-substituted nucleoside;

each $N_d$ is independently selected from among a stereo-standard DNA nucleoside and a stereo-non-standard DNA nucleoside;

q is from 3-8;

wherein each of $L_1$, $L_2$, $L_3$, $L_4$, and each $L_5$ is an internucleoside linkage;

wherein at least two of $L_1$, $L_2$, $L_3$, and $L_4$ are internucleoside linkages having formula VIII:

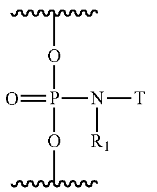

VIII wherein independently for each internucleoside linking group of the modified oligonucleotide having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, an amine, a substituted amine, $C_1$-$C_6$ alkoxy, $C_1$-$C_6$ alkyl, and substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl.

Embodiment 191. The oligomeric compound of embodiment 190, wherein one of $N_{d1}$, $N_{d2}$, $N_{d3}$, or $N_{d4}$ is a 2'-substituted nucleoside.

Embodiment 192. The oligomeric compound of embodiment 191, wherein the 2'-substituted nucleoside is a 2'-OMe nucleoside.

Embodiment 193. The oligomeric compound of embodiment 191, wherein the 2'-OMe nucleoside is a stereo-standard 2'-OMe nucleoside.

Embodiment 194. The oligomeric compound of any of embodiments 191-193, wherein the 2'-substituted nucleoside is $N_{d2}$.

Embodiment 195. The oligomeric compound of embodiment 190, wherein each of $N_{d1}$, $N_{d2}$, $N_{d3}$, $N_{d4}$ and each $N_d$ is a DNA nucleoside.

Embodiment 196. The oligomeric compound of embodiment 195, wherein each DNA nucleoside is a stereo-standard DNA nucleoside.

Embodiment 197. The oligomeric compound of any of embodiments 190-196, wherein $L_1$ and $L_2$ are internucleoside linkages having formula VIII.

Embodiment 198. The oligomeric compound of any of embodiments 190-196, wherein $L_2$ and $L_3$ are internucleoside linkages having formula VIII.

Embodiment 199. The oligomeric compound of any of embodiments 190-196, wherein $L_3$ and $L_4$ are internucleoside linkages having formula VIII.

Embodiment 200. The oligomeric compound of any of embodiments 190-196, wherein $L_1$, $L_2$, and $L_3$ are internucleoside linkages having formula VIII.

Embodiment 201. The oligomeric compound of any of embodiments 190-196, wherein $L_2$, $L_3$, and $L_4$, are internucleoside linkages having formula VIII.

Embodiment 202. The oligomeric compound of any of embodiments 190-196, wherein $L_1$, $L_2$, $L_3$, and $L_4$ are internucleoside linkages having formula VIII.

Embodiment 203. The oligomeric compound of any of embodiments 190-202, wherein $R_1$ is H.

Embodiment 204. The oligomeric compound of any of embodiments 190-202, wherein $R_1$ is a $C_1$-$C_6$ alkyl.

Embodiment 205. The oligomeric compound of embodiment 204, wherein $R_1$ is methyl.

Embodiment 206. The oligomeric compound of any of embodiments 190-202, wherein $R_1$ is a substituted $C_1$-$C_6$ alkyl; Embodiment 207. The oligomeric compound of any of embodiments 190-206, wherein T is $SO_2R_2$.

Embodiment 208. The oligomeric compound of embodiment 207, wherein $R_2$ is an aryl.

Embodiment 209. The oligomeric compound of embodiment 207, wherein $R_2$ is a substituted aryl.

Embodiment 210. The oligomeric compound of embodiment 207, wherein $R_2$ is a heterocycle.

Embodiment 211. The oligomeric compound of embodiment 207, wherein $R_2$ is a substituted heterocycle.

Embodiment 212. The oligomeric compound of embodiment 207, wherein $R_2$ is an aromatic heterocycle.

Embodiment 213. The oligomeric compound of embodiment 207, wherein $R_2$ is a substituted aromatic heterocycle.

Embodiment 214. The oligomeric compound of embodiment 207, wherein $R_2$ is a diazole.

Embodiment 215. The oligomeric compound of embodiment 207, wherein $R_2$ is a substituted diazole.

Embodiment 216. The oligomeric compound of embodiment 207, wherein $R_2$ is an amine.

Embodiment 217. The oligomeric compound of embodiment 207, wherein $R_2$ is a substituted amine.

Embodiment 218. The oligomeric compound of embodiment 207, wherein $R_2$ is a $C_1$-$C_6$ alkoxy.

Embodiment 219. The oligomeric compound of embodiment 207, wherein $R_2$ is $C_1$-$C_6$ alkyl.

Embodiment 220. The oligomeric compound of embodiment 207, wherein $R_2$ is substituted $C_1$-$C_6$ alkyl.

Embodiment 221. The oligomeric compound of embodiment 207, wherein T is:

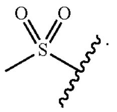

Embodiment 222. The oligomeric compound of embodiment 207, wherein T is:

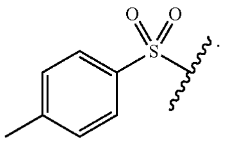 [SMILES: *S(=O)(=O)c1ccc(C)cc1]

Embodiment 223. The oligomeric compound of embodiment 207, wherein T is:

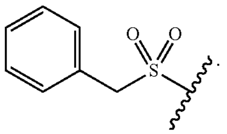 [SMILES: *S(=O)(=O)Cc1ccccc1]

Embodiment 224. The oligomeric compound of embodiment 207, wherein T is:

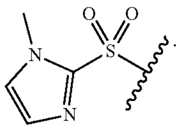 [SMILES: *S(=O)(=O)c1nccn1C]

Embodiment 225. The oligomeric compound of embodiment 207, wherein T is:

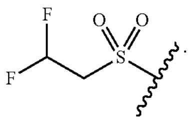

Embodiment 226. The oligomeric compound of embodiment 207, wherein T is:

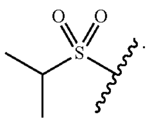 [SMILES: *S(=O)(=O)C(C)C]

Embodiment 227. The oligomeric compound of embodiment 207, wherein T is:

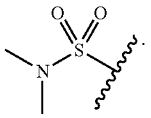 [SMILES: *S(=O)(=O)N(C)C]

Embodiment 228. The oligomeric compound of embodiment 207, wherein T is:

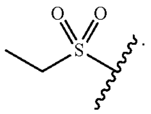 [SMILES: *S(=O)(=O)CC]

Embodiment 229. The oligomeric compound of embodiment 207, wherein T is:

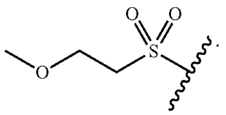 [SMILES: *S(=O)(=O)CCOC]

Embodiment 230. The oligomeric compound of any of embodiments 190-206, wherein T is $C(=O)R_3$.

Embodiment 231. The oligomeric compound of embodiment 230, wherein $R_3$ is an aryl.

Embodiment 232. The oligomeric compound of embodiment 230, wherein $R_3$ is a substituted aryl.

Embodiment 233. The oligomeric compound of embodiment 230, wherein $R_3$ is $CH_3$.

Embodiment 234. The oligomeric compound of embodiment 230, wherein $R_3$ is $N(CH_3)_2$.

Embodiment 235. The oligomeric compound of embodiment 230, wherein $R_3$ is $OCH_3$.

Embodiment 236. The oligomeric compound of embodiment 230, wherein T is:

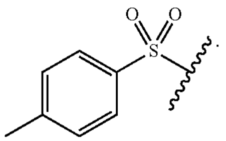 [SMILES: *S(=O)(=O)c1ccc(C)cc1]

Embodiment 237. The oligomeric compound of embodiment 230, wherein T is:

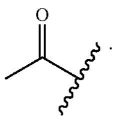

Embodiment 238. The oligomeric compound of embodiment 230, wherein T is:

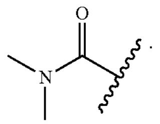 [SMILES: *C(=O)N(C)C]

Embodiment 239. The oligomeric compound of embodiment 230, wherein T is:

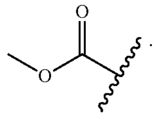 [SMILES: *C(=O)OC]

Embodiment 240. The oligomeric compound of any of embodiments 190-206, wherein T is $P(=O)R_4R_5$.

Embodiment 241. The oligomeric compound of embodiment 240, wherein $R_4$ is $OCH_3$.

Embodiment 242. The oligomeric compound of embodiment 240, wherein $R_4$ is OH.

Embodiment 243. The oligomeric compound of embodiment 240, wherein $R_4$ is $C_1$-$C_6$ alkyl.

Embodiment 244. The oligomeric compound of embodiment 240, wherein $R_4$ is substituted $C_1$-$C_6$ alkyl.

Embodiment 245. The oligomeric compound of any of embodiments 240-242, wherein $R_5$ is $OCH_3$.

Embodiment 246. The oligomeric compound of any of embodiments 240-242, wherein $R_5$ is OH.

Embodiment 247. The oligomeric compound of any of embodiments 240-242, wherein $R_5$ is $C_1$-$C_6$ alkyl.

Embodiment 248. The oligomeric compound of any of embodiments 240-242, wherein $R_5$ is substituted $C_1$-$C_6$ alkyl.

Embodiment 249. The oligomeric compound of embodiment 240, wherein T is:

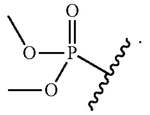 [SMILES: *P(=O)(OC)OC]

Embodiment 250. The oligomeric compound of embodiment 240, wherein T is:

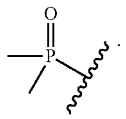 [SMILES: *P(C)(C)=O]

Embodiment 251. The oligomeric compound of any of embodiments 190-250, wherein at least one internucleoside linking group of the modified oligonucleotide is not a linking group of Formula VIII.

Embodiment 252. The oligomeric compound of any of embodiments 190-250, wherein exactly two internucleoside linking groups of the modified oligonucleotide are internucleoside linking groups of any of Formula VIII.

Embodiment 253. The oligomeric compound of any of embodiments 190-250, wherein exactly three internucleoside linking groups of the modified oligonucleotide are internucleoside linking groups of any of Formula VIII.

Embodiment 254. The oligomeric compound of any of embodiments 190-250, wherein exactly four internucleoside linking groups of the modified oligonucleotide are internucleoside linking groups of any of Formula VIII.

Embodiment 255. The oligomeric compound of any of embodiment 190-250 having at least two linking groups of Formula VIII, wherein at least two of the linking groups of Formula VIII are the same as one another.

Embodiment 256. The oligomeric compound of any of embodiments 190-255, wherein each internucleoside linking group of the modified oligonucleotide that is not an internucleoside linking group of Formula VIII is either a phosphodiester internucleoside linking group or a phosphorothioate internucleoside linking group.

Embodiment 257. The oligomeric compound of any of embodiments 190-256, wherein the 5'-region consists of 2-5 linked nucleosides.

Embodiment 258. The oligomeric compound of embodiment 257, wherein the 5'-region consists of 3 linked nucleosides.

Embodiment 259. The oligomeric compound of embodiment 257, wherein the 5'-region consists of 5 linked nucleosides.

Embodiment 260. The oligomeric compound of any of embodiments 190-259 wherein each nucleoside of the 5'-region is a modified nucleoside.

Embodiment 261. The oligomeric compound of any of embodiments 190-259, wherein each nucleoside of the 5'-region is a modified nucleoside comprising a modified sugar.

Embodiment 262. The oligomeric compound of any of embodiments 190-261, wherein each nucleoside of the 5'-region comprises a 2'-substituted furanosyl sugar moiety.

Embodiment 263. The oligomeric compound of any of embodiments 190-261, wherein at least one nucleoside of the 5'-region comprises a bicyclic furanosyl sugar moiety.

Embodiment 264. The oligomeric compound of any of embodiments 190-261, wherein each nucleoside of the 5'-region comprises a bicyclic furanosyl sugar moiety.

Embodiment 265. The oligomeric compound of embodiment 263, wherein each bicyclic sugar moiety of the 5'-region is selected from among cEt, LNA, and ENA.

Embodiment 266. The oligomeric compound of embodiment 263, wherein each bicyclic sugar moiety of the 5'-region is a cEt sugar moiety.

Embodiment 267. The oligomeric compound of embodiment 262, wherein each 2'-substituted furanosyl sugar moiety of the 5'-region is a ribosyl sugar moiety and has a 2'-substituent selected from among 2'-MOE, 2'-OMe, and 2'-NMA.

Embodiment 268. The oligomeric compound of any of embodiments 190-267, wherein each nucleobase of the 5'-region is independently selected from among thymine, uracil, guanine, cytosine, 5-methylcytosine, and adenine.

Embodiment 269. The oligomeric compound of any of embodiments 190-268, wherein the 3'-region consists of 2-5 linked nucleosides.

Embodiment 270. The oligomeric compound of embodiment 269, wherein the 3'-region consists of 3 linked nucleosides.

Embodiment 271. The oligomeric compound of embodiment 269, wherein the 3'-region consists of 5 linked nucleosides.

Embodiment 272. The oligomeric compound of any of embodiments 190-271 wherein each nucleoside of the 3'-region is a modified nucleoside.

Embodiment 273. The oligomeric compound of any of embodiments 190-272, wherein each nucleoside of the 3'-region is a modified nucleoside comprising a modified sugar.

Embodiment 274. The oligomeric compound of any of embodiments 190-273, wherein each nucleoside of the 3'-region comprises a 2'-substituted furanosyl sugar moiety.

Embodiment 275. The oligomeric compound of any of embodiments 190-273, wherein at least one nucleoside of the 3'-region comprises a bicyclic furanosyl sugar moiety.

Embodiment 276. The oligomeric compound of any of embodiments 190-273, wherein each nucleoside of the 3'-region comprises a bicyclic furanosyl sugar moiety.

Embodiment 277. The oligomeric compound of embodiment 276, wherein each bicyclic sugar moiety of the 3'-region is selected from among cEt, LNA, and ENA.

Embodiment 278. The oligomeric compound of embodiment 276, wherein each bicyclic sugar moiety of the 3'-region is a cEt sugar moiety.

Embodiment 279. The oligomeric compound of embodiment 274, wherein each wherein each 2'-substituted furanosyl sugar moiety of the 5'-region is a ribosyl sugar moiety and has a 2'-substituent selected from among 2'-MOE, 2'-OMe, and 2'-NMA.

Embodiment 280. The oligomeric compound of any of embodiments 190-279, wherein each nucleobase of the 5'-region is independently selected from among thymine, uracil, guanine, cytosine, 5-methylcytosine, and adenine.

Embodiment 281. The oligomeric compound of any of embodiments 1-80, wherein each nucleoside of the modified oligonucleotide is a modified nucleoside comprising a modified sugar moiety.

Embodiment 282. The oligomeric compound of embodiment 281, wherein each modified sugar moiety is independently selected from a bicyclic sugar moiety and a 2'-substituted furanosyl sugar moiety.

Embodiment 283. The oligomeric compound of embodiment 282, wherein the three 3'-most nucleosides comprise a bicyclic sugar moiety, and the remaining nucleosides comprise a 2'-substituted furanosyl sugar moiety.

Embodiment 284. The oligomeric compound of embodiment 282, wherein the four 3'-most nucleosides comprise a bicyclic sugar moiety, and the remaining nucleosides comprise a 2'-substituted furanosyl sugar moiety.

Embodiment 285. The oligomeric compound of embodiment 282, wherein the five 3'-most nucleosides comprise a bicyclic sugar moiety, and the remaining nucleosides comprise a 2'-substituted furanosyl sugar moiety.

Embodiment 286. The oligomeric compound of embodiment 282, wherein the six 3'-most nucleosides comprise a bicyclic sugar moiety, and the remaining nucleosides comprise a 2'-substituted furanosyl sugar moiety.

Embodiment 287. The oligomeric compound of any of embodiments 282-286, wherein each bicyclic sugar moiety is selected from among cEt, LNA, and ENA.

Embodiment 288. The oligomeric compound of embodiment 287, wherein the bicyclic sugar moiety is cEt Embodiment 289. The oligomeric compound of any of embodiments 282-289, wherein the 2'-substituted furanosyl sugar moiety is selected from 2'-OMe, 2'-MOE, and 2'-F.

Embodiment 290. The oligomeric compound of any of embodiments 281-289, wherein at least one of the first 10 internucleoside linking groups from the 5'-end of the modified oligonucleotide is an internucleoside linking group of any of embodiments 1-50.

Embodiment 291. The oligomeric compound of embodiment 289, wherein at least 2 of the first 10 internucleoside linking groups from the 5'-end of the modified oligonucleotide are internucleoside linking groups of any of embodiments 1-50.

Embodiment 292. The oligomeric compound of embodiment 289, wherein at least 3 of the first 10 internucleoside linking groups from the 5'-end of the modified oligonucleotide are internucleoside linking groups of any of embodiments 1-50.

Embodiment 293. The oligomeric compound of embodiment 289, wherein at least 4 of the first 10 internucleoside linking groups from the 5'-end of the modified oligonucleotide are internucleoside linking groups of any of embodiments 1-50.

Embodiment 294. The oligomeric compound of embodiment 289, wherein at least 5 of the first 10 internucleoside linking groups from the 5'-end of the modified oligonucleotide are internucleoside linking groups of any of embodiments 1-50.

Embodiment 295. The oligomeric compound of embodiment 289, wherein at least 6 of the first 10 internucleoside linking groups from the 5'-end of the modified oligonucleotide are internucleoside linking groups of any of embodiments 1-50.

Embodiment 296. The oligomeric compound of embodiment 289, wherein the first 2 internucleoside linking groups from the 5'-end of the modified oligonucleotide are internucleoside linking groups of any of embodiments 1-50.

Embodiment 297. The oligomeric compound of embodiment 289, wherein the first 3 internucleoside linking groups from the 5'-end of the modified oligonucleotide are internucleoside linking groups of any of embodiments 1-50. Embodiment 298. The oligomeric compound of embodiment 289, wherein the first 4 internucleoside linking groups from the 5'-end of the modified oligonucleotide are internucleoside linking groups of any of embodiments 1-50.

Embodiment 299. The oligomeric compound of embodiment 289, wherein the first 5 internucleoside linking groups from the 5'-end of the modified oligonucleotide are internucleoside linking groups of any of embodiments 1-50.

Embodiment 300. The oligomeric compound of embodiment 289, wherein the first 6 internucleoside linking groups from the 5'-end of the modified oligonucleotide are internucleoside linking groups of any of embodiments 1-50.

Embodiment 301. A method of increasing translation of a target protein in a cell, comprising contacting the cell with an oligomeric compound of any of embodiments 281-300.

Embodiment 302. The method of embodiment 301, wherein the target protein is encoded by a target nucleic acid comprising at least one translation suppression element and wherein the modified oligonucleotide is complementary to a target site within a translation suppression element region of the target nucleic acid.

Embodiment 303. The method of embodiment 302, wherein the translation suppression element region comprises at least one stem-loop structure.

Embodiment 304. A pharmaceutical composition comprising the oligomeric compound of any of embodiments 190-300 and a pharmaceutically acceptable carrier or diluent.

Embodiment 305. A method comprising contacting a cell with the oligomeric compound or pharmaceutical composition of any of embodiments 190-300.

Embodiment 306. A method of modulating the amount or activity of a target nucleic acid in a cell, comprising contacting the cell with the oligomeric compound or pharmaceutical composition of any of embodiments 190-300, and thereby modulating the amount or activity of the target nucleic acid.

Embodiment 307. The method of embodiment 306, wherein the amount or activity of a target nucleic acid is reduced.

Embodiment 308. The method of embodiment 306, wherein the amount or activity of a target nucleic acid is increased.

Embodiment 309. Use of the oligomeric compound or composition of any of embodiments 190-300 for treatment of a disease or condition.

Embodiment 310. Use of the oligomeric compound or composition of any of embodiments 190-300 for a preparation of a medicament for treatment of a disease or condition.

Embodiment 311. An antisense agent comprising a modified oligonucleotide consisting of linked nucleosides linked through internucleoside linking groups, wherein at least one of the internucleoside linking groups has Formula XVII:

XVII

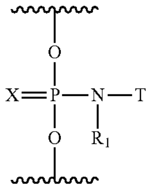

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

Embodiment 312. An antisense agent comprising a modified oligonucleotide consisting of linked nucleosides linked through internucleoside linking groups, wherein at least one of the internucleoside linking groups has Formula XVII:

XVII

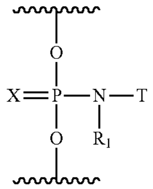

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(O)R_3$, and $P(O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl;

Provided that if X is O and that if $R_1$ is H, then T is not:

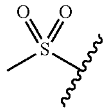

or

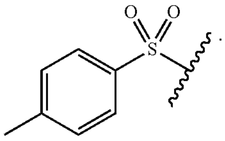

.

Embodiment 313. The modified oligonucleotide of embodiment 311 or 312, wherein for at least one internucleoside linking group of Formula XVII, X is O.

Embodiment 314. The modified oligonucleotide of embodiment 311 or 312, wherein for at least one internucleoside linking group of Formula XVII, X is S.

Embodiment 315. The modified oligonucleotide of embodiment 311 or 312, wherein for at least one internucleoside linking group of Formula XVII, $R_1$ is H.

Embodiment 316. The modified oligonucleotide of embodiment 311 or 312, wherein for at least one internucleoside linking group of Formula XVII, $R_1$ is a $C_1$-$C_6$ alkyl, $C_1$-$C_6$ alkenyl, or $C_1$-$C_6$ alkynyl.

Embodiment 317. The modified oligonucleotide of embodiment 6, wherein $R_1$ is methyl.

Embodiment 318. The modified oligonucleotide of embodiment 311 or 312, wherein for at least one internucleoside linking group of Formula XVII, $R_1$ is a substituted $C_1$-$C_6$ alkyl.

Embodiment 319. The modified oligonucleotide of any of embodiments 311-318, wherein for at least one internucleoside linking group of Formula XVII, T comprises a conjugate group.

Embodiment 320. The modified oligonucleotide of embodiment 319, wherein the conjugate group comprises a carbohydrate or carbohydrate cluster.

Embodiment 321. The modified oligonucleotide of embodiment 319 or 320, wherein the conjugate group comprises at least one GalNAc.

Embodiment 322. The modified oligonucleotide of embodiment 319, wherein the conjugate group comprises a $C_{10}$-$C_{20}$ alkyl chain.

Embodiment 323. The modified oligonucleotide of embodiment 322, wherein the conjugate group comprises $C_{16}$ alkyl.

Embodiment 324. The modified oligonucleotide of any of embodiments 311-318, wherein for at least one internucleoside linking group of formula XVII, T does not comprise a conjugate group.

Embodiment 325. The modified oligonucleotide of any of embodiments 311-324, wherein for at least one internucleoside linking group of Formula XVII, T is $SO_2R_2$.

Embodiment 326. The modified oligonucleotide of embodiment 325, wherein $R_2$ is an aryl.

Embodiment 327. The modified oligonucleotide of embodiment 325, wherein $R_2$ is a substituted aryl.

Embodiment 328. The modified oligonucleotide of embodiment 325, wherein $R_2$ is a heterocycle.

Embodiment 329. The modified oligonucleotide of embodiment 325, wherein $R_2$ is a substituted heterocycle.

Embodiment 330. The modified oligonucleotide of embodiment 325, wherein $R_2$ is an aromatic heterocycle.

Embodiment 331. The modified oligonucleotide of embodiment 325, wherein $R_2$ is a substituted aromatic heterocycle.

Embodiment 332. The modified oligonucleotide of embodiment 325, wherein $R_2$ is a diazole.

Embodiment 333. The modified oligonucleotide of embodiment 325, wherein $R_2$ is a substituted diazole.

Embodiment 334. The modified oligonucleotide of embodiment 325, wherein $R_2$ is an amine.

Embodiment 335. The modified oligonucleotide of embodiment 325, wherein $R_2$ is a substituted amine.

Embodiment 336. The modified oligonucleotide of embodiment 325, wherein $R_2$ is a $C_1$-$C_6$ alkoxy, or $C_1$-$C_6$ alkenyl, $C_1$-$C_6$ alkynyl.

Embodiment 337. The modified oligonucleotide of embodiment 325, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 338. The modified oligonucleotide of embodiment 325, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 339. The modified oligonucleotide of embodiment 325, wherein $R_2$ comprises a carbohydrate or carbohydrate cluster.

Embodiment 340. The modified oligonucleotide of embodiment 325, wherein $R_2$ comprises at least one GalNAc.

Embodiment 341. The modified oligonucleotide of embodiment 325, wherein T is:

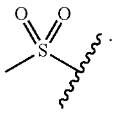 [SMILES: *S(C)(=O)=O]

Embodiment 342. The modified oligonucleotide of embodiment 325, wherein T is:

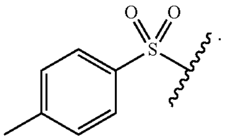 [SMILES: *S(=O)(=O)c1ccc(C)cc1]

Embodiment 343. The modified oligonucleotide of embodiment 325, wherein T is:

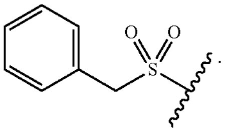

Embodiment 344. The modified oligonucleotide of embodiment 325, wherein T is:

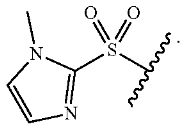 [SMILES: *S(=O)(=O)c1nccn1C]

Embodiment 345. The modified oligonucleotide of embodiment 325, wherein T is:

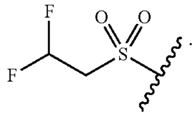

Embodiment 346. The modified oligonucleotide of embodiment 325, wherein T is:

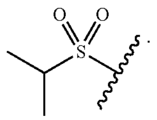 [SMILES: *S(=O)(=O)C(C)C]

Embodiment 347. The modified oligonucleotide of embodiment 325, wherein T is:

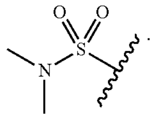 [SMILES: *S(=O)(=O)N(C)C]

Embodiment 348. The modified oligonucleotide of embodiment 325, wherein T is:

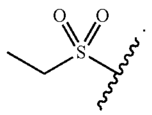 [SMILES: *S(=O)(=O)CC]

Embodiment 349. The modified oligonucleotide of embodiment 325, wherein T is:

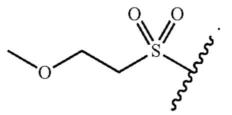

Embodiment 350. The modified oligonucleotide of embodiment 325, wherein T is:

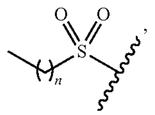

wherein n is from 2 to 20.

Embodiment 351. The modified oligonucleotide of embodiment 350, wherein n is 15.

Embodiment 352. The modified oligonucleotide of any of embodiments 311-324, wherein for at least one internucleoside linking group of Formula XVII, T is C(=O)$R_3$.

Embodiment 353. The modified oligonucleotide of embodiment 352, wherein $R_3$ is an aryl.

Embodiment 354. The modified oligonucleotide of embodiment 352, wherein $R_3$ is a substituted aryl.

Embodiment 355. The modified oligonucleotide of embodiment 352, wherein $R_3$ is $CH_3$.

Embodiment 356. The modified oligonucleotide of embodiment 352, wherein $R_3$ is $N(CH_3)_2$.

Embodiment 357. The modified oligonucleotide of embodiment 352, wherein $R_3$ is $OCH_3$.

Embodiment 358. The modified oligonucleotide of embodiment 352, wherein $R_3$ is a $C_1$-$C_6$ alkoxy.

Embodiment 359. The modified oligonucleotide of embodiment 352, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 360. The modified oligonucleotide of embodiment 352, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 361. The modified oligonucleotide of embodiment 352, wherein $R_3$ comprises a carbohydrate or carbohydrate cluster.

Embodiment 362. The modified oligonucleotide of embodiment 352, wherein $R_{23}$ comprises at least one GalNAc.

Embodiment 363. The modified oligonucleotide of embodiment 352, wherein T is:

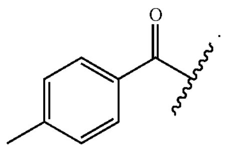 [SMILES: *C(=O)c1ccc(C)cc1]

Embodiment 364. The modified oligonucleotide of embodiment 352, wherein T is:

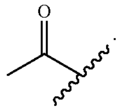 [SMILES: *C(C)=O]

Embodiment 365. The modified oligonucleotide of embodiment 352, wherein T is:

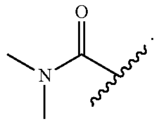

Embodiment 366. The modified oligonucleotide of embodiment 352, wherein T is:

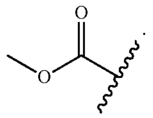 [SMILES: *C(=O)OC]

Embodiment 367. The modified oligonucleotide of embodiment 352, wherein T is:

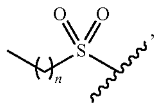

wherein n is from 2 to 20.

Embodiment 368. The modified oligonucleotide of embodiment 367, wherein n is 15.

Embodiment 369. The modified oligonucleotide of any of embodiments 1-14, wherein for at least one internucleoside linking group of Formula XVII, T is P(=O)$R_4R_5$.

Embodiment 370. The modified oligonucleotide of embodiment 369, wherein $R_4$ is $OCH_3$.

Embodiment 371. The modified oligonucleotide of embodiment 369, wherein $R_4$ is OH.

Embodiment 372. The modified oligonucleotide of embodiment 369, wherein $R_4$ is $C_1$-$C_6$ alkyl.

Embodiment 373. The modified oligonucleotide of embodiment 369, wherein $R_4$ is substituted $C_1$-$C_6$ alkyl.

Embodiment 374. The modified oligonucleotide of embodiment 369, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 375. The modified oligonucleotide of embodiment 369, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 376. The modified oligonucleotide of embodiment 369, wherein $R_4$ comprises a carbohydrate or carbohydrate cluster.

Embodiment 377. The modified oligonucleotide of embodiment 369, wherein $R_4$ comprises at least one GalNAc.

Embodiment 378. The modified oligonucleotide of any of embodiments 369-67, wherein $R_5$ is $OCH_3$.

Embodiment 379. The modified oligonucleotide of any of embodiments 369-67, wherein $R_5$ is OH.

Embodiment 380. The modified oligonucleotide of any of embodiments 369-67, wherein $R_5$ is $C_1$-$C_6$ alkyl.

Embodiment 381. The modified oligonucleotide of any of embodiments 369-67, wherein $R_5$ is substituted $C_1$-$C_6$ alkyl.

Embodiment 382. The modified oligonucleotide of embodiment 369, wherein T is:

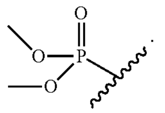

Embodiment 383. The modified oligonucleotide of embodiment 369, wherein T is:

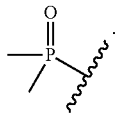

Embodiment 384. The modified oligonucleotide of embodiment 369, wherein T is:

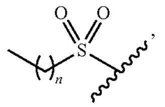

wherein n is from 2 to 20.

Embodiment 385. The modified oligonucleotide of embodiment 384, wherein n is 15.

Embodiment 386. The modified oligonucleotide of any of embodiments 311-385, wherein at least one internucleoside linking group of the modified oligonucleotide is not a linking group of Formula XVII.

Embodiment 387. The modified oligonucleotide of any of embodiments 311-385, wherein exactly one internucleoside linking group of the modified oligonucleotide is an internucleoside linking group of Formula XVII.

Embodiment 388. The modified oligonucleotide of any of embodiments 311-385, wherein exactly two internucleoside linking groups of the modified oligonucleotide are internucleoside linking groups of Formula XVII.

Embodiment 389. The modified oligonucleotide of any of embodiments 311-385, wherein exactly three internucleoside linking groups of the modified oligonucleotide are internucleoside linking groups of Formula XVII.

Embodiment 390. The modified oligonucleotide of any of embodiments 311-385, wherein exactly four internucleoside linking groups of the modified oligonucleotide are internucleoside linking groups of Formula XVII.

Embodiment 391. The modified oligonucleotide of any of embodiments 311-385, wherein exactly five internucleoside linking groups of the modified oligonucleotide are internucleoside linking groups of Formula XVII.

Embodiment 392. The modified oligonucleotide of any of embodiments 311-385, wherein at least six internucleoside linking groups of the modified oligonucleotide are internucleoside linking groups of Formula XVII.

Embodiment 393. The modified oligonucleotide of any of embodiment 311-386 or 388-392 having at least two linking groups of Formula XVII, wherein at least two of the linking groups of Formula XVII are the same as one another.

Embodiment 394. The modified oligonucleotide of any of embodiments 311-393, wherein each internucleoside linking group of the modified oligonucleotide that is not an internucleoside linking group of Formula XVII is either a phosphodiester internucleoside linking group or a phosphorothioate internucleoside linking group.

Embodiment 395. The modified oligonucleotide of any of embodiments 311-386 or 393-394, wherein each internucleoside linking group of the modified oligonucleotide is an internucleoside linking group of Formula XVII.

Embodiment 396. An antisense agent comprising a modified oligonucleotide, wherein at least one region of the modified oligonucleotide has Structure A:

Structure A

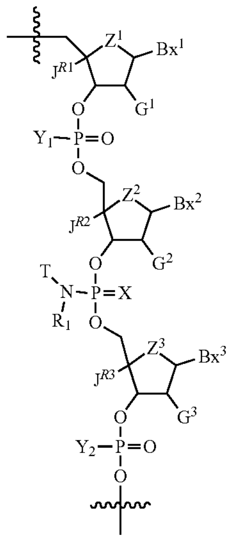

wherein:

each Bx is a heterocyclic base moiety;

X is selected from O or S;

each of $Y_1$, and $Y_2$ is independently selected from OH or SH;

each of $Z^1$, $Z^2$, and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O-[C(R_6)(R_7)]_n-[(C=O)_m-X^G]_j-R_8$;

either $J^{R1}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or O—$[C(R_6)(R_7)]_n$—$[(C{=}O)_m—X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C({=}Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 397. An antisense agent comprising a modified olignucleotide, wherein at least one region of the modified oligonucleotide has Structure B:

Structure B

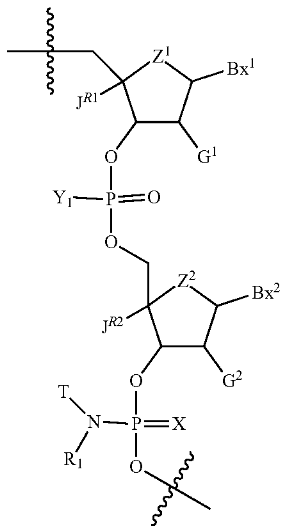

wherein:

each Bx is a heterocyclic base moiety;

X is selected from O or S;

each of $Y_1$ and $Y_2$ is independently selected from OH or SH;

each of $Z^1$ and $Z^2$ are independently selected from —$(CH_2)_p$—$X^Z$—$(CH_2)_q$—, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C({=}O)R_3$, and $P({=}O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or O—$[C(R_6)(R_7)]_n$—$[(C{=}O)_m—X^G]_j$—$R_8$;

either $J^{R2}$ and $G^2$ form a $J^{R2}$ and $G^2$ bridge, or $J^{R2}$ is H and $G^2$ is selected from H, OH, halogen or O—$[C(R_6)(R_7)]_n$—$[(C{=}O)_m—X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_5$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C({=}Q_2)N(J_1)(J_2)$; $Q_2$ is O, S or $NJ_3$;

each $J_1$, $J_2$ and $J_3$ is, independently, H or $C_1$-$C_6$ alkyl.

Embodiment 398. An antisense agent comprising a modified olignucleotide, wherein at least one region of the modified oligonucleotide has Structure C:

Structure C

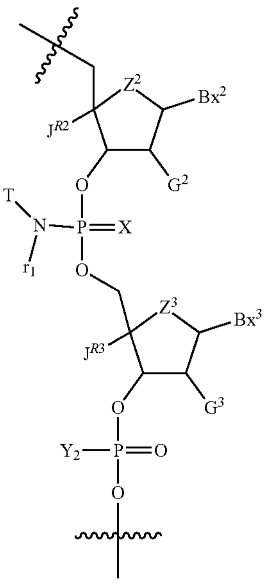

wherein:

each Bx is a heterocyclic base moiety;

X is selected from O or S;

each of $Y_1$ and $Y_2$ is independently selected from OH or SH;

each of $Z^2$ and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R2}$ and $G^2$ form a $J^{R2}$ and Gf bridge, or $J^{R2}$ is H and $G^2$ is selected from H, OH, halogen or $O—[C(R_6)(R_7)]_n—[(C=O)_m—X^G]_j—R_8$;

either $J^{R3}$ and $G^3$ form a $J^{R3}$ and $G^3$ bridge, or $J^{R3}$ is H and $G^3$ is selected from H, OH, halogen or $O—[C(R_6)(R_7)]_n—[(C=O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 399. An antisense agent comprising a modified olignucleotide, wherein at least one region of the modified oligonucleotide has Structure D:

Structure D

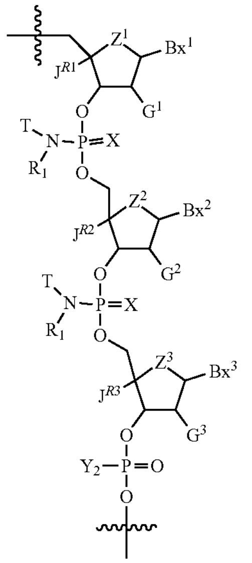

wherein:

each Bx is a heterocyclic base moiety;

X is selected from O or S;

each of $Y_1$ and $Y_2$ is independently selected from OH or SH;

each of $Z^2$ and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O—[C(R_6)(R_7)]_n—[(C=O)_m—X^G]_j—R_8$;

either $J^{R2}$ and $G^2$ form a $J^{R2}$ and $G^2$ bridge, or $J^{R2}$ is H and $G^2$ is selected from H, OH, halogen or $O—[C(R_6)(R_7)]_n—[(C=O)_m—X^G]_j—R_8$;

either $J^{R3}$ and $G^3$ form a $J^{R3}$ and $G^3$ bridge, or $J^{R3}$ is H and $G^3$ is selected from H, OH, halogen or $O—[C(R_6)(R_7)]_n—[(C=O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$; $Q_2$ is O, S or $NJ_3$;

each $J_1$, $J_2$ and $J_3$ is, independently, H or $C_1$-$C_6$ alkyl.

Embodiment 400. An antisense agent comprising a modified olignucleotide, wherein at least one region of the modified oligonucleotide has Structure E:

Structure E

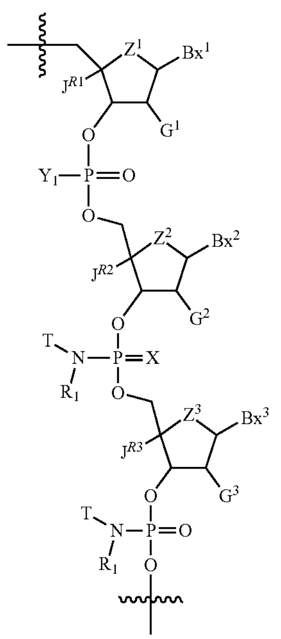

wherein:

each Bx is a heterocyclic base moiety;

X is selected from O or S;

each of $Y_1$ and $Y_2$ is independently selected from OH or SH;

each of $Z^2$ and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O-[C(R_6)(R_7)]_n-[(C=O)_m-X^G]_j-R_8$;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$; $Q_2$ is O, S or $NJ_3$;

each $J_1$, $J_2$ and $J_3$ is, independently, H or $C_1$-$C_6$ alkyl.

Embodiment 401. The modified oligonucleotide of any of embodiments 396-400, wherein each Z is O.

Embodiment 402. The modified oligonucleotide of any of embodiments 396-401, wherein at least one G is selected from H, OH, halogen, $C_1$-$C_6$ alkoxy, $-O(CH_2)_2OCH_3$, or $-OCH_2(C=O)NHCH_3$.

Embodiment 403. The modified oligonucleotide of any of embodiments 396-401, wherein each G is selected from H, OH, halogen, $C_1$-$C_6$ alkoxy, $-O(CH_2)_2OCH_3$, or $-OCH_2(C=O)NHCH_3$.

Embodiment 404. The modified oligonucleotide of any of embodiments 396-402, wherein at least one JR forms a bridge with at least one G, wherein said $J^R$ to G bridge has a formula selected from $4CH(CH_3)-O-$ or $-(CH_2)_k-O'$, wherein k is from 1 to 3.

Embodiment 405. The modified oligonucleotide of any of embodiments 396-402, wherein each $J^R$ and G form a bridge, wherein said $J^R$ to G bridge has a formula selected from $-CH(CH_3)-O-$ or $-(CH_2)_k-O-$, wherein k is from 1 to 3.

Embodiment 406. The modified oligonucleotide of any of embodiments 404 or 405, wherein at least one Z is O and the corresponding $J^R$ to G bridge has a formula $(CH_2)_k-O-$, wherein k is 1.

Embodiment 407. The modified oligonucleotide of any of embodiments 396-406 wherein each nucleoside of structure A, B, C, D, or E is a stereo standard nucleoside.

Embodiment 408. The modified oligonucleotide of any of embodiments 396-406, wherein at least one nucleoside of structure A, B, C, D, or E is a stereo-non-standard nucleoside.

Embodiment 409. The modified oligonucleotide of any of embodiments 404-406 or 408, wherein at least one nucleoside having a $J^R$ to G bridge is in the α-L-ribosyl configuration.

Embodiment 410. The modified oligonucleotide of any of embodiments 396-409, wherein the modified oligonucleotide comprises at least 2, at least 3, at least 4, at least 5, at least 6, at least 7, at least 8, at least 9, or at least 10 regions having structures A, B, C, D, or E.

Embodiment 411. The modified oligonucleotide of any of embodiments 396-410, wherein at least one region having structure A, B, C, D, or E is at the 5' end of the modified oligonucleotide.

Embodiment 412. The modified oligonucleotide of any of embodiments 396-410, wherein at least one region having structure A, B, C, D, or E is at the 3' end of the modified oligonucleotide.

Embodiment 413. The modified oligonucleotide of any of embodiments 396-410, wherein at least one region having structure A, B, C, D, or E is internal to the modified oligonucleotide.

Embodiment 414. An antisense agent, comprising a modified oligonucleotide consisting of 10-30 linked nucleosides, wherein a region of the modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

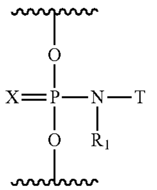

XVII wherein $L_3$ is absent or is a phosphodiester internucleoside linking group, a phosphorothioate internucleoside linking group, or an internucleoside linking group of Formula XVII; wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 415. The modified oligonucleotide of embodiment 414, wherein the modified oligonucleotide comprises at least 2, at least 3, at least 4, at least 5, at least 6, at least 7, at least 8, at least 9, or at least 10 regions having the formula $(N_{g1})_{L1}(N_{g2})_{L2}(N_{g3})_{L3}$.

Embodiment 416. The modified oligonucleotide of embodiment 414, wherein at least one region having the formula $(N_{g1})_{L1}(N_{g2})_{L2}(N_{g3})_{L3}$ is at the 5' end of the oligonucleotide Embodiment 417. The modified oligonucleotide of embodiment 414, wherein at least one region having the formula $(N_{g1})_{L1}(N_{g2})_{L2}(N_{g3})_{L3}$ is internal to the oligonucleotide.

Embodiment 418. The modified oligonucleotide of embodiment 414, wherein at least one region having the formula $(N_{g1})_{L1}(N_{g2})_{L2}(N_{g3})_{L3}$ is at the 3' end of the oligonucleotide.

Embodiment 419. The modified oligonucleotide of any of embodiments 311-418, wherein at least one nucleoside of the modified oligonucleotide is a modified nucleoside.

Embodiment 420. The modified oligonucleotide of embodiment 419, wherein at least one nucleoside of the modified oligonucleotide is a modified nucleoside selected from a bicyclic nucleoside and a non-bicyclic substituted nucleoside.

Embodiment 421. The modified oligonucleotide of any of embodiments 311-420, wherein at least one nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 422. The modified oligonucleotide of any of embodiments 311-421, wherein each nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 423. The modified oligonucleotide of any of embodiments 311-422, wherein at least one nucleoside of the modified oligonucleotide is a stereo-non-standard nucleoside.

Embodiment 424. The modified oligonucleotide of embodiment 423, wherein the internucleoside linking group linking at least one stereo-non-standard nucleoside to an adjacent nucleoside is an internucleoside linking group of Formula XVII.

Embodiment 425. The modified oligonucleotide of embodiment 423 or 424, wherein at least two nucleosides of the modified oligonucleotide are stereo-non-standard nucleosides.

Embodiment 426. The modified oligonucleotide of embodiment 425, wherein at least two stereo-non-standard nucleosides of the modified oligonucleotide are adjacent to one another.

Embodiment 427. The modified oligonucleotide of embodiment 426, wherein at least two stereo-non-standard nucleosides of the modified oligonucleotide are linked to one another with an internucleoside linking group of Formula XVII.

Embodiment 428. The modified oligonucleotide of any of embodiments 423-427, wherein at least one stereo-non-standard nucleoside of the modified oligonucleotide is a stereo-non-standard DNA nucleoside.

Embodiment 429. The modified oligonucleotide of embodiment 428 wherein the stereo-non-standard DNA nucleoside is selected from a stereo-non-standard DNA nucleoside having: Formula I, Formula II, Formula III, Formula IV, Formula V, Formula VI, and Formula VII.

Embodiment 430. The modified oligonucleotide of embodiment 429 wherein the stereo-non-standard DNA nucleoside is selected from a stereo-non-standard DNA nucleoside having: Formula V and Formula II.

Embodiment 431. The modified oligonucleotide of any of embodiments 423-427, wherein at least one stereo-non-standard nucleoside of the modified oligonucleotide is a substituted stereo-non-standard nucleoside or a stereo-non-standard RNA nucleoside.

Embodiment 432. The modified oligonucleotide of embodiment 431, wherein the 2'-substituent of the at least one substituted stereo-non-standard nucleoside of the modified oligonucleotide is selected from: 2'-MOE, 2'-OMe, 2'-F, or 2'-OH.

Embodiment 433. The modified oligonucleotide of any of embodiments 311-432, wherein the modified oligonucleotide consists of 12-30 linked nucleosides.

Embodiment 434. The modified oligonucleotide of any of embodiments 311-433, wherein the modified oligonucleotide consists of 16-24 linked nucleosides.

Embodiment 435. The modified oligonucleotide of any of embodiments 311-434, wherein the modified oligonucleotide consists of 18-22 linked nucleosides.

Embodiment 436. The modified oligonucleotide of any of embodiments 311-434, wherein the modified oligonucleotide consists of 16 linked nucleosides.

Embodiment 437. The modified oligonucleotide of any of embodiments 311-434, wherein the modified oligonucleotide consists of 17 linked nucleosides.

Embodiment 438. The modified oligonucleotide of any of embodiments 311-435, wherein the modified oligonucleotide consists of 18 linked nucleosides.

Embodiment 439. The modified oligonucleotide of any of embodiments 311-435, wherein the modified oligonucleotide consists of 19 linked nucleosides.

Embodiment 440. The modified oligonucleotide of any of embodiments 311-435, wherein the modified oligonucleotide consists of 20 linked nucleosides.

Embodiment 441. The modified oligonucleotide of any of embodiments 311-435, wherein the modified oligonucleotide consists of 21 linked nucleosides.

Embodiment 442. The modified oligonucleotide of any of embodiments 311-435, wherein the modified oligonucleotide consists of 22 linked nucleosides.

Embodiment 443. The modified oligonucleotide of any of embodiments 311-434, wherein the modified oligonucleotide consists of 23 linked nucleosides.

Embodiment 444. The modified oligonucleotide of any of embodiments 311-443, wherein at least one nucleoside of the modified oligonucleotide is selected from: a 2'-OMe nucleoside, a 2'-F nucleoside, and an RNA nucleoside.

Embodiment 445. The modified oligonucleotide of any of embodiments 311-444, wherein at least one nucleoside of the modified oligonucleotide is a 2'-OMe nucleoside, and at least one nucleoside of the modified oligonucleotide is an RNA nucleoside.

Embodiment 446. The modified oligonucleotide of any of embodiments 444-445, wherein the modified oligonucleotide has a region of alternating nucleoside types having the motif ABABA, wherein each A is a stereo-standard nucleoside of a first type and each B is a stereo-standard nucleoside of a second type, wherein the first type and the second type are different from one another.

Embodiment 447. The modified oligonucleotide of embodiment 446, wherein A and B are selected from 2'-F substituted nucleosides, 2'-OMe substituted nucleosides, and stereo-standard RNA nucleosides.

Embodiment 448. The modified oligonucleotide of any of embodiments 311-447, wherein the 5'-end of the modified oligonucleotide comprises a stabilized phosphate group.

Embodiment 449. The modified oligonucleotide of embodiment 448, wherein the stabilized phosphate group is a 5'-vinyl phosphonate or a 5'-cyclopropyl phosphonate.

Embodiment 450. An RNAi agent, comprising a modified oligonucleotide of any of embodiments 311-449.

Embodiment 451. The RNAi agent of embodiment 450, wherein the RNAi agent is a single-stranded RNAi agent comprising an RNAi antisense modified oligonucleotide, wherein the RNAi antisense modified oligonucleotide is a modified oligonucleotide of any of embodiments 311-449.

Embodiment 452. The RNAi agent of embodiment 450, wherein the RNAi agent is an oligomeric duplex comprising an RNAi antisense modified oligonucleotide and an RNAi sense modified oligonucleotide, wherein the RNAi antisense modified oligonucleotide and/or the RNAi sense modified oligonucleotide is a modified oligonucleotide of any of embodiments 311-449.

Embodiment 453. The RNAi agent of embodiment 451 or 452, wherein at least one internucleoside linking group of the RNAi antisense modified oligonucleotide is an internucleoside linking group of Formula XVII.

Embodiment 454. The RNAi agent of embodiment 451 or 452, wherein at least two internucleoside linking groups of the RNAi antisense modified oligonucleotide are independently selected internucleoside linking groups of any of embodiments 311-385.

Embodiment 455. The RNAi agent of any of embodiments 450-454, wherein at least one of the five 3'-most internucleoside linking groups of the RNAi antisense modified oligonucleotide is an internucleoside linking group of Formula XVII.

Embodiment 456. The RNAi agent of any of embodiments 450-454, wherein at least two of the five 3'-most internucleoside linking groups of RNAi antisense modified oligonucleotide is an internucleoside linking group of Formula XVII.

Embodiment 457. The RNAi agent of any of embodiments 450-454, wherein at least one internucleoside linking group within the seed region of the RNAi antisense modified oligonucleotide is an internucleoside linking group of Formula XVII.

Embodiment 458. The RNAi agent of any of embodiments 450-457, wherein at least one region of the RNAi antisense modified oligonucleotide has structure A, B, C, D, or E.

Embodiment 459. The RNAi agent of embodiment 458, wherein at least one region having structure A, B, C, D, or E is within the seed region of the RNAi antisense modified oligonucleotide.

Embodiment 460. The RNAi agent of embodiment 458, wherein at least one region having structure A, B, C, D, or E is at the 3' end of the RNAi antisense modified oligonucleotide.

Embodiment 461. The RNAi agent of any of embodiments 450-457, wherein at least one region of the RNAi antisense modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

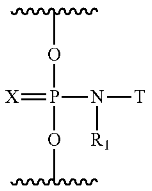

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 462. The RNAi agent of embodiment 461, wherein at least one region having the formula $(N_{g1})_{L1}(N_{g2})_{L2}(N_{g3})_{L3}$ is at the 3' end of the RNAi antisense modified oligonucleotide.

Embodiment 463. The RNAi agent of embodiment 461, wherein at least one region having the formula $(N_{g1})_{L1}(N_{g2})_{L2}(N_{g3})_{L3}$ is within the seed region of the RNAi antisense modified oligonucleotide.

Embodiment 464. The RNAi agent of embodiment 450 or 452-463 wherein at least one internucleoside linking group of the RNAi sense modified oligonucleotide is an internucleoside linking group of Formula XVII.

Embodiment 465. The RNAi agent of embodiment 464, wherein at least one of the first 5 internucleoside linking groups from the 5'-end of the RNAi sense modified oligonucleotide is an internucleoside linking group of Formula XVII.

Embodiment 466. The RNAi agent of any of embodiments 464-465, wherein at least one of the five 3'-most internucleoside linking groups of the RNAi sense modified oligonucleotide is an internucleoside linking group of Formula XVII.

Embodiment 467. The RNAi agent of any of embodiments 464-466, wherein at least one of the first 5 internucleoside linking groups from the 5'-end of the RNAi sense modified oligonucleotide and at least one of the five 3'-most linking groups of the RNAi sense modified oligonucleotide is an internucleoside linking group of Formula XVII.

Embodiment 468. The RNAi agent of any of embodiments 464-467, wherein at least one region of the RNAi sense modified oligonucleotide has structure A, B, C, D, or E.

Embodiment 469. The RNAi agent of embodiment 468, wherein at least one region having structure A, B, C, D, or E is at the 3' end of the RNAi sense modified oligonucleotide.

Embodiment 470. The RNAi agent of embodiment 468, wherein at least one region having structure A, B, C, D, or E is at the 5' end of the RNAi sense modified oligonucleotide.

Embodiment 471. The RNAi agent of any of embodiments 464-467, wherein at least one region of the RNAi sense modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

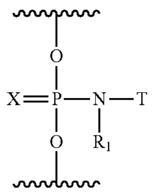

wherein $L_3$ is absent or is phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 472. The RNAi agent of embodiment 471, wherein at least one region having the formula $(N_{g1})_{L1}(N_{g2})_{L2}(N_{g3})_{L3}$ is at the 3' end of the RNAi sense modified oligonucleotide.

Embodiment 473. The RNAi agent of embodiment 471, wherein at least one region having the formula $(N_{g1})_{L1}(N_{g2})_{L2}(N_{g3})_{L3}$ is at the 5' end of the RNAi sense modified oligonucleotide.

Embodiment 474. The modified oligonucleotide of any of embodiments 311-443, wherein each nucleoside of the modified oligonucleotide is a modified nucleoside comprising a modified sugar moiety.

Embodiment 475. The modified oligonucleotide of embodiment 474, wherein each modified sugar moiety is independently selected from a bicyclic sugar moiety and a 2'-substituted furanosyl sugar moiety.

Embodiment 476. The modified oligonucleotide of embodiment 474 or 475, wherein each modified sugar moiety comprises the same modification.

Embodiment 477. The modified oligonucleotide of any of embodiments 474-476, wherein each modified sugar moiety is selected from a 2'-OMe sugar moiety, a 2'-MOE sugar moiety, and a 2'-NMA sugar moiety.

Embodiment 478. The modified oligonucleotide of embodiment 476 or 477, wherein the three 3'-most nucleosides comprise a bicyclic sugar moiety, and the remaining nucleosides comprise a 2'-substituted furanosyl sugar moiety.

Embodiment 479. The modified oligonucleotide of embodiment 476 or 477, wherein the four 3'-most nucleosides comprise a bicyclic sugar moiety, and the remaining nucleosides comprise a 2'-substituted furanosyl sugar moiety.

Embodiment 480. The modified oligonucleotide of embodiment 476 or 477, wherein the five 3'-most nucleosides comprise a bicyclic sugar moiety, and the remaining nucleosides comprise a 2'-substituted furanosyl sugar moiety.

Embodiment 481. The modified oligonucleotide of embodiment 476 or 477, wherein the six 3'-most nucleosides comprise a bicyclic sugar moiety, and the remaining nucleosides comprise a 2'-substituted furanosyl sugar moiety.

Embodiment 482. The modified oligonucleotide of any of embodiments 476 or 478-481, wherein each bicyclic sugar moiety is selected from among cEt, LNA, and ENA.

Embodiment 483. The modified oligonucleotide of embodiment 482, wherein the bicyclic sugar moiety is cEt.

Embodiment 484. The modified oligonucleotide of any of embodiments 476 or 478-481, wherein the 2'-substituted furanosyl sugar moiety is selected from 2'-OMe, 2'-MOE, and 2'-F.

Embodiment 485. The modified oligonucleotide of any of embodiments 474-484, wherein at least one of the ten 5'-most linking groups of the modified oligonucleotide is an internucleoside linking group of Formula XVII.

Embodiment 486. The modified oligonucleotide of embodiment 485, wherein at least 2 of the ten 5'-most linking groups of the modified oligonucleotide are internucleoside linking groups of Formula XVII.

Embodiment 487. The modified oligonucleotide of embodiment 485, wherein at least 3 of the ten 5'-most linking groups of the modified oligonucleotide are internucleoside linking groups of Formula XVII.

Embodiment 488. The modified oligonucleotide of embodiment 485, wherein at least 4 of the ten 5'-most linking groups of the modified oligonucleotide are internucleoside linking groups of Formula XVII.

Embodiment 489. The modified oligonucleotide of embodiment 485, wherein at least 5 of the ten 5'-most linking groups of the modified oligonucleotide are internucleoside linking groups of Formula XVII.

Embodiment 490. The modified oligonucleotide of embodiment 485, wherein at least 6 of the ten 5'-most linking groups of the modified oligonucleotide are internucleoside linking groups of Formula XVII.

Embodiment 491. The modified oligonucleotide of embodiment 485, wherein the two 5'-most internucleoside linking groups are internucleoside linking groups of Formula XVII.

Embodiment 492. The modified oligonucleotide of any of embodiments 478-491, wherein at least one of the ten 3'-most internucleoside linking groups of the modified oligonucleotide is an internucleoside linking group of Formula XVII.

Embodiment 493. The modified oligonucleotide of embodiment 492, wherein at least 2 of the ten 3'-most internucleoside linking groups of the modified oligonucleotide are internucleoside linking groups of Formula XVII.

Embodiment 494. The modified oligonucleotide of embodiment 492, wherein at least 3 of the ten 3'-most internucleoside linking groups are internucleoside linking groups of Formula XVII.

Embodiment 495. The modified oligonucleotide of embodiment 492, wherein at least 4 of the ten 3'-most internucleoside linking groups are internucleoside linking groups of Formula XVII.

Embodiment 496. The modified oligonucleotide of embodiment 492, wherein at least 5 of the ten 3'-most internucleoside linking groups are internucleoside linking groups of Formula XVII.

Embodiment 497. The modified oligonucleotide of embodiment 492, wherein at least 6 of the ten 3'-most internucleoside linking groups are internucleoside linking groups of Formula XVII.

Embodiment 498. The modified oligonucleotide of embodiment 492, wherein the two 3'-most internucleoside linking groups of the modified oligonucleotide are internucleoside linking groups of Formula XVII.

Embodiment 499. The modified oligonucleotide of any of embodiments 474-484, wherein the modified oligonucleotide comprises at least one block of at least 3 consecutive internucleoside linking groups of Formula XVII.

Embodiment 500. The modified oligonucleotide of any of embodiments 474-484, wherein the modified oligonucleotide comprises at least one block of at least 4 consecutive internucleoside linking groups of Formula XVII.

Embodiment 501. The modified oligonucleotide of any of embodiments 474-484, wherein the modified oligonucleotide comprises at least one block of at least 5 consecutive internucleoside linking groups of Formula XVII.

Embodiment 502. The modified oligonucleotide of any of embodiments 474-484, wherein the modified oligonucleotide comprises at least one block of at least 6 consecutive internucleoside linking groups of Formula XVII.

Embodiment 503. The modified oligonucleotide of any of embodiments 499-502, wherein at least one block of consecutive internucleoside linking groups of Formula XVII is at the 5' end of the modified oligonucleotide.

Embodiment 504. The modified oligonucleotide of any of embodiments 499-502, wherein at least one block of consecutive internucleoside linking groups of Formula XVII is at the 3' end of the modified oligonucleotide.

Embodiment 505. The modified oligonucleotide of any of embodiments 311-443, wherein the modified oligonucleotide comprises a deoxy region consisting of 6-11 linked nucleosides wherein each nucleoside of the deoxy region is either a modified nucleoside or a stereo-standard DNA nucleoside and wherein at least 3 contiguous nucleosides of the deoxy region are stereo-standard DNA nucleosides and not more than three nucleosides of the deoxy region are modified nucleosides.

Embodiment 506. The modified oligonucleotide of embodiment 505, wherein at least 4 contiguous nucleosides of the deoxy region are stereo-standard DNA nucleosides.

Embodiment 507. The modified oligonucleotide of embodiment 505, wherein at least 5 contiguous nucleosides of the deoxy region are stereo-standard DNA nucleosides.

Embodiment 508. The modified oligonucleotide of embodiment 505, wherein at least 6 contiguous nucleosides of the deoxy region are stereo-standard DNA nucleosides.

Embodiment 509. The modified oligonucleotide of embodiment 505, wherein at least 7 contiguous nucleosides of the deoxy region are stereo-standard DNA nucleosides.

Embodiment 510. The modified oligonucleotide of embodiment 505, wherein at least 8 contiguous nucleosides of the deoxy region are stereo-standard DNA nucleosides.

Embodiment 511. The modified oligonucleotide of any of embodiments 505-510, wherein the deoxy region consists of 8-10 linked nucleosides.

Embodiment 512. The modified oligonucleotide of any of embodiments 505-510, wherein the deoxy region consists of 9 linked nucleosides.

Embodiment 513. The modified oligonucleotide of any of embodiments 505-510, wherein the deoxy region consists of 10 linked nucleosides.

Embodiment 514. The modified oligonucleotide of any of embodiments 505-510, wherein the deoxy region consists of 11 linked nucleosides.

Embodiment 515. The modified oligonucleotide of any of embodiments 505-510, wherein at least 6 nucleosides of the deoxy region are stereo-standard DNA nucleosides.

Embodiment 516. The modified oligonucleotide of any of embodiments 505-510, wherein at least 7 nucleosides of the deoxy region are stereo-standard DNA nucleosides.

Embodiment 517. The modified oligonucleotide of any of embodiments 505-510, wherein at least 8 nucleosides of the deoxy region are stereo-standard DNA nucleosides.

Embodiment 518. The modified oligonucleotide of any of embodiments 505-510, wherein at least 9 nucleosides of the deoxy region are stereo-standard DNA nucleosides.

Embodiment 519. The modified oligonucleotide of any of embodiments 505-518 wherein two nucleosides of the deoxy region are modified nucleosides.

Embodiment 520. The modified oligonucleotide of any of embodiments 505-518 wherein one nucleoside of the deoxy region is a modified nucleoside.

Embodiment 521. The modified oligonucleotide of any of embodiments 505-520 wherein at least one modified nucleoside of the deoxy region is a stereo-standard modified nucleoside or bicyclic nucleoside selected from a β-D-LNA nucleoside, an α-L-LNA nucleoside, an ENA nucleoside, a cEt nucleoside, a 2'-MOE nucleoside, a 2'-OMe nucleoside, a 2'-F nucleoside, and a 5'-alkyl nucleoside.

Embodiment 522. The modified oligonucleotide of any of embodiments 505-520 wherein at least one modified nucleoside of the deoxy region is stereo-non-standard nucleoside.

Embodiment 523. The modified oligonucleotide of embodiment 522 wherein the at least one is stereo-non-standard nucleoside of the deoxy region is a stereo-non-standard DNA nucleoside.

Embodiment 524. The modified oligonucleotide of embodiment 523 wherein the stereo-non-standard DNA nucleoside is selected from a stereo-non-standard DNA nucleoside having: Formula I, Formula II, Formula III, Formula IV, Formula V, Formula VI, and Formula VII.

Embodiment 525. The modified oligonucleotide of embodiment 524 wherein the stereo-non-standard DNA nucleoside is selected from a stereo-non-standard DNA nucleoside having: Formula V and Formula II.

Embodiment 526. The modified oligonucleotide of embodiment 525 wherein at least one stereo-non-standard nucleoside of the deoxy region is a substituted stereo-non-standard nucleoside.

Embodiment 527. The modified oligonucleotide of embodiment 526 wherein at least one substituted stereo-non-standard nucleoside has a 2'-substituent selected from: 2'-MOE, 2'-OMe, 2'-F, or 2'-OH.

Embodiment 528. The modified oligonucleotide of any of embodiments 505-527, wherein the $2^{nd}$ nucleoside from the 5'-end of the deoxy region is a modified nucleoside.

Embodiment 529. The modified oligonucleotide of any of embodiments 505-527, wherein the $3^{rd}$ nucleoside from the 5'-end of the deoxy region is a modified nucleoside.

Embodiment 530. The modified oligonucleotide of any of embodiments 505-527, wherein the 4' nucleoside from the 5'-end of the deoxy region is a modified nucleoside.

Embodiment 531. The modified oligonucleotide of any of embodiments 528-530, wherein the modified nucleoside in the deoxy region is a 2'-OMe nucleoside.

Embodiment 532. The modified oligonucleotide of any of embodiments 505-518, wherein each nucleoside of the deoxy region is a stereo-standard DNA nucleoside.

Embodiment 533. The modified oligonucleotide of any of embodiments 505-532 wherein at least one internucleoside linking group within the deoxy region is an internucleoside linking group of Formula XVII.

Embodiment 534. The modified oligonucleotide of any of embodiments 505-532, wherein the internucleoside linking group linking the $1^{st}$ and $2^{nd}$ nucleosides of the deoxy region as counted from the 5'-end of the deoxy region is an internucleoside linking group of Formula XVII.

Embodiment 535. The modified oligonucleotide of any of embodiments 505-534, wherein the internucleoside linking group linking the $2^{nd}$ and $3^{rd}$ nucleosides of the deoxy region as counted from the 5'-end of the deoxy region is an internucleoside linking group of Formula XVII.

Embodiment 536. The modified oligonucleotide of any of embodiments 505-535, wherein the internucleoside linking group linking the $3^{rd}$ and $4^{th}$ nucleosides of the deoxy region as counted from the 5'-end of the deoxy region is an internucleoside linking group of Formula XVII.

Embodiment 537. The modified oligonucleotide of any of embodiments 505-536, wherein the internucleoside linking group linking the $4^{th}$ and $5^{th}$ nucleosides of the deoxy region as counted from the 5'-end of the deoxy region is an internucleoside linking group of Formula XVII.

Embodiment 538. The modified oligonucleotide of any of embodiments 505-537, wherein one internucleoside linking group in the deoxy region is a linking group of Formula XVII and the other internucleoside linking groups of the deoxy region are each phosphodiester or phosphorothioate internucleoside linking groups.

Embodiment 539. The modified oligonucleotide of any of embodiments 505-537, wherein two internucleoside linking groups in the deoxy region are linking groups of Formula XVII and the other internucleoside linking groups of the deoxy region are each phosphodiester or phosphorothioate internucleoside linking groups.

Embodiment 540. The modified oligonucleotide of any of embodiments 505-537, wherein three internucleoside linking groups in the deoxy region are linking groups linking groups of Formula XVII and the other internucleoside linking groups of the deoxy region are each phosphodiester or phosphorothioate internucleoside linking groups.

Embodiment 541. The modified oligonucleotide of any of embodiments 505-540, wherein the deoxy region comprises at least one region having structure A, B, C, D, or E.

Embodiment 542. The modified oligonucleotide of embodiment 541, wherein the region having structure A, B, C, D, or E is at the 3' end of the deoxy region.

Embodiment 543. The modified oligonucleotide of embodiment 541, wherein the region having structure A, B, C, D, or E is at the 5' end of the deoxy region.

Embodiment 544. The modified oligonucleotide of any of embodiments 505-540, wherein the deoxy region comprises at least one region having the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

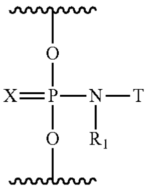

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 545. The modified oligonucleotide of any of embodiments 544, wherein the region having the formula $(N_{g1})_{L1}(N_{g2})_{L2}(N_{g3})_{L3}$ is at the 3' end of the deoxy region.

Embodiment 546. The modified oligonucleotide of any of embodiments 544, wherein the region having the formula $(N_{g1})_{L1}(N_{g2})_{L2}(N_{g3})_{L3}$ is at the 5' end of the deoxy region.

Embodiment 547. The modified oligonucleotide of any of embodiments 505-546 wherein the deoxy region is flanked on the 5' side by a 5'-region consisting of 1-6 linked 5'-region nucleosides and on the 3' side by a 3'-region consisting of 1-6 linked 3'-region nucleosides; wherein the 3'-most nucleoside of the 5'-region is a modified nucleoside; and the 5'-most nucleoside of the 3'-region is a modified nucleoside.

Embodiment 548. The modified oligonucleotide of embodiment 547, wherein the deoxy region consists of 7-11 linked nucleosides, and has the formula:

$$(N_{d1})_{L1}(N_{d2})_{L2}(N_{d3})_{L3}(N_{d4})_{L4}[(N_d)_{L5}]_q;$$

wherein $N_{d1}$, $N_{d2}$, $N_{d3}$, $N_{d4}$ are independently selected from among a stereo-standard DNA nucleoside, a stereo-non-standard DNA nucleoside, or a 2'-substituted nucleoside; with the proviso that no more than one of $N_{d1}$, $N_{d2}$, $N_{d3}$, or $N_{d4}$ is a 2'-substituted nucleoside;

each $N_d$ is independently selected from among a stereo-standard DNA nucleoside and a stereo-non-standard DNA nucleoside;

q is from 3-8;

wherein each of $L_1$, $L_2$, $L_3$, $L_4$, and each $L_5$ is an internucleoside linkage;

wherein at least two of $L_1$, $L_2$, $L_3$, $L_4$ are internucleoside linkages of Formula XVII.

Embodiment 549. The modified oligonucleotide of embodiment 548, wherein one of $N_{d1}$, $N_dZ$, $N_{d3}$, or $N_{d4}$ is a 2'-substituted nucleoside.

Embodiment 550. The modified oligonucleotide of embodiment 549, wherein the 2'-substituted nucleoside is a 2'-OMe nucleoside.

Embodiment 551. The modified oligonucleotide of embodiment 550, wherein the 2'-OMe nucleoside is a stereo-standard 2'-OMe nucleoside.

Embodiment 552. The modified oligonucleotide of any of embodiments 548-551, wherein the 2'-substituted nucleoside is $N_{d2}$ Embodiment 553. The modified oligonucleotide of embodiment 548, wherein each of $N_{d1}$, $N_{d2}$, $N_{d3}$, $N_{d4}$ and each $N_d$ is a DNA nucleoside.

Embodiment 554. The modified oligonucleotide of embodiment 553, wherein each DNA nucleoside is a stereo-standard DNA nucleoside.

Embodiment 555. The modified oligonucleotide of any of embodiments 548-554, wherein $L_1$ and $L_2$ are internucleoside linkages of Formula XVII.

Embodiment 556. The modified oligonucleotide of any of embodiments 548-554, wherein $L_2$ and $L_3$ are internucleoside linkages of Formula XVII.

Embodiment 557. The modified oligonucleotide of any of embodiments 548-554, wherein $L_3$ and $L_4$ are internucleoside linkages of Formula XVII.

Embodiment 558. The modified oligonucleotide of any of embodiments 548-554, wherein $L_1$, $L_2$, and $L_3$ are internucleoside linkages of Formula XVII.

Embodiment 559. The modified oligonucleotide of any of embodiments 548-554, wherein $L_2$, $L_3$, and $L_4$, are internucleoside linkages of Formula XVII.

Embodiment 560. The modified oligonucleotide of any of embodiments 548-554, wherein $L_1$, $L_2$, $L_3$, and $L_4$ are internucleoside linkages of Formula XVII.

Embodiment 561. The modified oligonucleotide of any of embodiments 547-560, wherein the 5'-region consists of 2-5 linked nucleosides.

Embodiment 562. The modified oligonucleotide of embodiment 561, wherein the 5'-region consists of 3 linked nucleosides.

Embodiment 563. The modified oligonucleotide of embodiment 561, wherein the 5'-region consists of 5 linked nucleosides.

Embodiment 564. The modified oligonucleotide of any of embodiments 547-563 wherein each nucleoside of the 5'-region is a modified nucleoside.

Embodiment 565. The modified oligonucleotide of any of embodiments 547-564, wherein each nucleoside of the 5'-region is a modified nucleoside comprising a modified sugar.

Embodiment 566. The modified oligonucleotide of any of embodiments 547-565, wherein at least one nucleoside of the 5'-region comprises a 2'-substituted furanosyl sugar moiety.

Embodiment 567. The modified oligonucleotide of any of embodiments 547-566, wherein each nucleoside of the 5'-region comprises a 2'-substituted furanosyl sugar moiety.

Embodiment 568. The modified oligonucleotide of any or embodiments 547-567, wherein each 2'-substituted furanosyl sugar moiety of the 5'-region has a 2'-substituent selected from among 2'-MOE, 2'-OMe, and 2'-NMA.

Embodiment 569. The modified oligonucleotide of any of embodiments 547-566 or 568, wherein at least one nucleoside of the 5'-region comprises a bicyclic furanosyl sugar moiety.

Embodiment 570. The modified oligonucleotide of any of embodiments 547-566 or 568-569, wherein each nucleoside of the 5'-region comprises a bicyclic furanosyl sugar moiety.

Embodiment 571. The modified oligonucleotide of embodiment 569 or 570, wherein each bicyclic sugar moiety of the 5'-region is selected from among cEt, LNA, and ENA.

Embodiment 572. The modified oligonucleotide of embodiment 571, wherein each bicyclic sugar moiety of the 5'-region is a cEt sugar moiety.

Embodiment 573. The modified oligonucleotide of any of embodiments 547-563, 566 or 569, wherein at least one nucleoside of the 5' region is a stereo-standard DNA nucleoside.

Embodiment 574. The modified oligonucleotide of any of embodiments 547-572, wherein at least one nucleoside of the 5' region is a stereo-non-standard nucleoside.

Embodiment 575. The modified oligonucleotide of any of embodiments 547-574, wherein each nucleobase of the 5'-region is independently selected from among thymine, uracil, guanine, cytosine, 5-methylcytosine, and adenine.

Embodiment 576. The modified oligonucleotide of any of embodiments 547-575, wherein the 3'-region consists of 2-5 linked nucleosides.

Embodiment 577. The modified oligonucleotide of embodiment 576, wherein the 3'-region consists of 3 linked nucleosides.

Embodiment 578. The modified oligonucleotide of embodiment 576, wherein the 3'-region consists of 5 linked nucleosides.

Embodiment 579. The modified oligonucleotide of any of embodiments 547-578, wherein each nucleoside of the 3'-region is a modified nucleoside.

Embodiment 580. The modified oligonucleotide of any of embodiments 547-578, wherein each nucleoside of the 3'-region is a modified nucleoside comprising a modified sugar.

Embodiment 581. The modified oligonucleotide of any of embodiments 547-580, wherein at least one nucleoside of the 3'-region comprises a 2'-substituted furanosyl sugar moiety.

Embodiment 582. The modified oligonucleotide of any of embodiments 547-581, wherein each nucleoside of the 3'-region comprises a 2'-substituted furanosyl sugar moiety.

Embodiment 583. The modified oligonucleotide of any or embodiments 547-582, wherein each 2'-substituted furanosyl sugar moiety of the 3'-region has a 2'-substituent selected from among 2'-MOE, 2'-OMe, and 2'-NMA.

Embodiment 584. The modified oligonucleotide of any of embodiments 547-581 or 583, wherein at least one nucleoside of the 3'-region comprises a bicyclic furanosyl sugar moiety.

Embodiment 585. The modified oligonucleotide of any of embodiments 547-580 or 584, wherein each nucleoside of the 3'-region comprises a bicyclic furanosyl sugar moiety.

Embodiment 586. The modified oligonucleotide of embodiment 584 or 585, wherein each bicyclic sugar moiety of the 3'-region is selected from among cEt, LNA, and ENA.

Embodiment 587. The modified oligonucleotide of embodiment 586, wherein each bicyclic sugar moiety of the 3'-region is a cEt sugar moiety.

Embodiment 588. The modified oligonucleotide of any of embodiments 547-578, 581 or 584, wherein at least one nucleoside of the 3' region is a stereo-standard DNA nucleoside.

Embodiment 589. The modified oligonucleotide of any of embodiments 547-588, wherein at least one nucleoside of the 3' region is a stereo-non-standard nucleoside.

Embodiment 590. The modified oligonucleotide of any of embodiments 547-589, wherein each nucleobase of the 3'-region is independently selected from among thymine, uracil, guanine, cytosine, 5-methylcytosine, and adenine.

Embodiment 591. The modified oligonucleotide of any of embodiments 547-590 wherein the modified oligonucleotide is a gapmer.

Embodiment 592. The modified oligonucleotide of any of embodiments 311-432, wherein the modified oligonucleotide is a CRISPR compound.

Embodiment 593. The modified oligonucleotide of embodiment 592, wherein the CRISPR compound consists of 20-50 linked nucleosides.

Embodiment 594. The modified oligonucleotide of embodiment 592, wherein the CRISPR compound consists of 29-32 linked nucleosides.

Embodiment 595. The modified oligonucleotide of any of embodiments 311-432, wherein the modified oligonucleotide is an artificial mRNA compound.

Embodiment 596. The artificial mRNA compound of embodiment 595, wherein the artificial mRNA oligonucleotide consists of 17-3000 linked nucleosides.

Embodiment 597. The artificial mRNA compound of embodiment 595 or 596, wherein the artificial mRNA oligonucleotide encodes a protein.

Embodiment 598. The modified oligonucleotide of any of embodiments 396-597, wherein each X is P.

Embodiment 599. The modified oligonucleotide of any of embodiments 396-597, wherein each X is S.

Embodiment 600. The modified oligonucleotide of any of embodiments 396-599, wherein at least one $R_1$ is H.

Embodiment 601. The modified oligonucleotide of any of embodiments 396-599, wherein at least one $R_1$ is a $C_1$-$C_6$ alkyl.

Embodiment 602. The modified oligonucleotide of embodiment 601, wherein the at least one $R_1$ is methyl.

Embodiment 603. The modified oligonucleotide of any of embodiments 396-602, at least one $R_1$ is a substituted $C_1$-$C_6$ alkyl.

Embodiment 604. The modified oligonucleotide of any of embodiments 396-603, wherein at least one T comprises a conjugate group.

Embodiment 605. The modified oligonucleotide of embodiment 604, wherein the conjugate group comprises a carbohydrate or carbohydrate cluster.

Embodiment 606. The modified oligonucleotide of embodiment 604 or 605, wherein the conjugate group comprises at least one GalNAc.

Embodiment 607. The modified oligonucleotide of embodiment 604, wherein the conjugate group comprises a $C_{10}$-$C_{20}$ alkyl chain.

Embodiment 608. The modified oligonucleotide of embodiment 607, wherein the conjugate group comprises $C_{16}$ alkyl.

Embodiment 609. The modified oligonucleotide of any of embodiments 396-603, wherein at least one T does not comprise a conjugate group.

Embodiment 610. The modified oligonucleotide of any of embodiments 396-603, wherein each T does not comprise a conjugate group.

Embodiment 611. The modified oligonucleotide of any of embodiments 396-603, wherein at least one T is $SO_2R_2$.

Embodiment 612. The modified oligonucleotide of embodiment 611, wherein $R_2$ is an aryl.

Embodiment 613. The modified oligonucleotide of embodiment 611, wherein $R_2$ is a substituted aryl.

Embodiment 614. The modified oligonucleotide of embodiment 611, wherein $R_2$ is a heterocycle.

Embodiment 615. The modified oligonucleotide of embodiment 611, wherein $R_2$ is a substituted heterocycle.

Embodiment 616. The modified oligonucleotide of embodiment 611, wherein $R_2$ is an aromatic heterocycle.

Embodiment 617. The modified oligonucleotide of embodiment 611, wherein $R_2$ is a substituted aromatic heterocycle.

Embodiment 618. The modified oligonucleotide of embodiment 611, wherein $R_2$ is a diazole.

Embodiment 619. The modified oligonucleotide of embodiment 611, wherein $R_2$ is a substituted diazole.

Embodiment 620. The modified oligonucleotide of embodiment 611, wherein $R_2$ is an amine.

Embodiment 621. The modified oligonucleotide of embodiment 611, wherein $R_2$ is a substituted amine.

Embodiment 622. The modified oligonucleotide of embodiment 611, wherein $R_2$ is a $C_1$-$C_6$ alkoxy, $C_1$-$C_6$ alkenyl, or $C_1$-$C_6$ alkynyl.

Embodiment 623. The modified oligonucleotide of embodiment 611, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 624. The modified oligonucleotide of embodiment 611, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 625. The modified oligonucleotide of embodiment 611, wherein $R_2$ comprises a carbohydrate or carbohydrate cluster.

Embodiment 626. The modified oligonucleotide of embodiment 611, wherein $R_2$ comprises at least one GalNAc.

Embodiment 627. The modified oligonucleotide of embodiment 611, wherein T is:

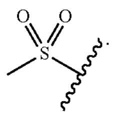 [SMILES: *S(C)(=O)=O]

Embodiment 628. The modified oligonucleotide of embodiment 611, wherein T is:

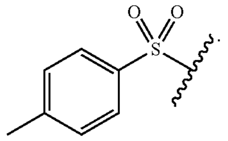 [SMILES: *S(=O)(=O)c1ccc(C)cc1]

Embodiment 629. The modified oligonucleotide of embodiment 611, wherein T is:

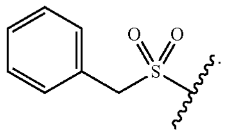 [SMILES: *S(=O)(=O)Cc1ccccc1]

Embodiment 630. The modified oligonucleotide of embodiment 611, wherein T is:

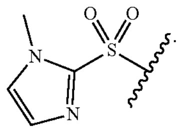 [SMILES: *S(=O)(=O)c1nccn1C]

Embodiment 631. The modified oligonucleotide of embodiment 611, wherein T is:

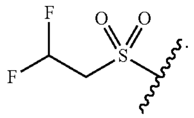

Embodiment 632. The modified oligonucleotide of embodiment 611, wherein T is:

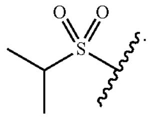 [SMILES: *S(=O)(=O)C(C)C]

Embodiment 633. The modified oligonucleotide of embodiment 611, wherein T is:

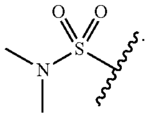 [SMILES: *S(=O)(=O)N(C)C]

Embodiment 634. The modified oligonucleotide of embodiment 611, wherein T is:

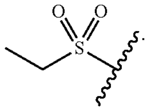 [SMILES: *S(=O)(=O)CC]

Embodiment 635. The modified oligonucleotide of embodiment 611, wherein T is:

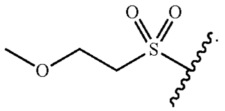 [SMILES: *S(=O)(=O)CCOC]

Embodiment 636. The modified oligonucleotide of embodiment 611, wherein T is:

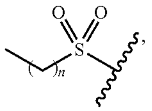

wherein n is from 2 to 20.

Embodiment 637. The modified oligonucleotide of embodiment 636, wherein n is 15.

Embodiment 638. The modified oligonucleotide of any of embodiments 396-603, wherein at least one T is C(=O)$R_3$.

Embodiment 639. The modified oligonucleotide of embodiment 638, wherein $R_3$ is an aryl.

Embodiment 640. The modified oligonucleotide of embodiment 638, wherein $R_3$ is a substituted aryl.

Embodiment 641. The modified oligonucleotide of embodiment 638, wherein $R_3$ is $CH_3$.

Embodiment 642. The modified oligonucleotide of embodiment 638, wherein $R_3$ is $N(CH_3)_2$.

Embodiment 643. The modified oligonucleotide of embodiment 638, wherein $R_3$ is $OCH_3$.

Embodiment 644. The modified oligonucleotide of embodiment 638, wherein $R_3$ is a $C_1$-$C_6$ alkoxy.

Embodiment 645. The modified oligonucleotide of embodiment 638, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 646. The modified oligonucleotide of embodiment 638, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 647. The modified oligonucleotide of embodiment 638, wherein $R_3$ comprises a carbohydrate or carbohydrate cluster.

Embodiment 648. The modified oligonucleotide of embodiment 638, wherein $R_{23}$ comprises at least one GalNAc.

Embodiment 649. The modified oligonucleotide of embodiment 638, wherein T is:

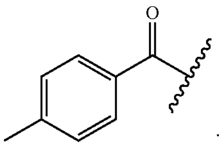 [SMILES: *C(=O)c1ccc(C)cc1]

Embodiment 650. The modified oligonucleotide of embodiment 638, wherein T is:

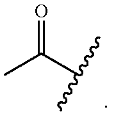

Embodiment 651. The modified oligonucleotide of embodiment 638, wherein T is:

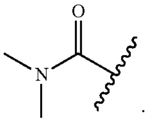 [SMILES: *C(=O)N(C)C]

Embodiment 652. The modified oligonucleotide of embodiment 638, wherein T is:

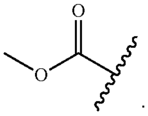 [SMILES: *C(=O)OC]

Embodiment 653. The modified oligonucleotide of embodiment 638, wherein T is:

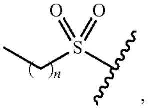

wherein n is from 2 to 20.

Embodiment 654. The modified oligonucleotide of embodiment 653, wherein n is 15.

Embodiment 655. The modified oligonucleotide of any of embodiments 396-603, wherein at least one T is P(=O)$R_4R_5$.

Embodiment 656. The modified oligonucleotide of embodiment 655, wherein $R_4$ is $OCH_3$.

Embodiment 657. The modified oligonucleotide of embodiment 655, wherein $R_4$ is OH.

Embodiment 658. The modified oligonucleotide of embodiment 655, wherein $R_4$ is $C_1$-$C_6$ alkyl.

Embodiment 659. The modified oligonucleotide of embodiment 655, wherein $R_4$ is substituted $C_1$-$C_6$ alkyl.

Embodiment 660. The modified oligonucleotide of embodiment 655, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 661. The modified oligonucleotide of embodiment 655, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 662. The modified oligonucleotide of embodiment 655, wherein $R_4$ comprises a carbohydrate or carbohydrate cluster.

Embodiment 663. The modified oligonucleotide of embodiment 655, wherein $R_4$ comprises at least one GalNAc.

Embodiment 664. The modified oligonucleotide of any of embodiments 655-663, wherein $R_5$ is $OCH_3$.

Embodiment 665. The modified oligonucleotide of any of embodiments 655-663, wherein $R_5$ is OH.

Embodiment 666. The modified oligonucleotide of any of embodiments 655-663, wherein $R_5$ is $C_1$-$C_6$ alkyl.

Embodiment 667. The modified oligonucleotide of any of embodiments 655-663, wherein $R_5$ is substituted $C_1$-$C_6$ alkyl.

Embodiment 668. The modified oligonucleotide of embodiment 655, wherein T is:

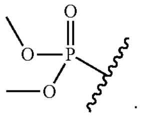

Embodiment 669. The modified oligonucleotide of embodiment 655, wherein T is:

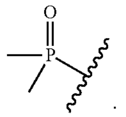 [SMILES: *P(C)(C)=O]

Embodiment 670. The modified oligonucleotide of embodiment 655, wherein T is:

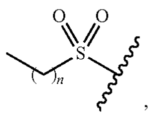

n wherein n is from 2 to 20.

Embodiment 671. The modified oligonucleotide of embodiment 670, wherein n is 15.

Embodiment 672. A chirally enriched population of modified oligonucleotides of any of embodiments 311-671, wherein the population is enriched for modified oligonucleotides comprising at least one particular internucleoside linking group having a particular stereochemical configuration.

Embodiment 673. The chirally enriched population of modified oligonucleotides of embodiment 672, wherein the particular internucleoside linking group having a particular stereochemical configuration is an internucleoside linking group of Formula XVIII, as indicated in Formula XVIIIa and XVIIIb below:

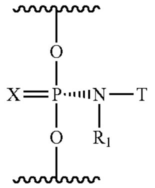

XVIIIa

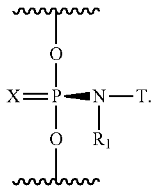

XVIIIb

Embodiment 674. The chirally enriched population of modified oligonucleotides of embodiment 672, wherein the particular internucleoside linking group having a particular stereochemical configuration is a phosphorothioate internucleoside linking group.

Embodiment 675. The chirally enriched population of any of embodiments 672-674, wherein the population is enriched for modified oligonucleotides comprising at least one particular internucleoside linkage having the (Sp) configuration.

Embodiment 676. The chirally enriched population of any of embodiments 672-675, wherein the population is enriched for modified oligonucleotides comprising at least one particular internucleoside linkage having the (Rp) configuration.

Embodiment 677. The chirally enriched population of embodiment 672, wherein the population is enriched for modified oligonucleotides having a particular, independently selected stereochemical configuration at each chiral internucleoside linkage.

Embodiment 678. The chirally enriched population of any of embodiments 672-677, wherein the population is enriched for modified oligonucleotides having the (Sp) configuration at each chiral internucleoside linkage.

Embodiment 679. The chirally enriched population of any of embodiments 672-677, wherein the population is enriched for modified oligonucleotides having the (Rp) configuration at each chiral internucleoside linkage.

Embodiment 680. The chirally enriched population of any of embodiments 672-677, wherein the population is enriched for modified oligonucleotides having the (Rp) configuration at one particular chiral internucleoside linkage and the (Sp) configuration at each of the remaining chiral internucleoside linkages.

Embodiment 681. The chirally enriched population of embodiment 673, wherein each phosphorothioate internucleoside linkage is stereorandom.

Embodiment 682. The modified oligonucleotide of any of embodiments 311-681, wherein the nucleobase sequence of the modified oligonucleotide is complementary to a target nucleic acid.

Embodiment 683. The modified oligonucleotide of embodiment 682, wherein the nucleobase sequence of the modified oligonucleotide is at least 80% complementary to the target nucleic acid.

Embodiment 684. The modified oligonucleotide of embodiment 682, wherein the nucleobase sequence of the modified oligonucleotide is at least 85% complementary to the target nucleic acid.

Embodiment 685. The modified oligonucleotide of embodiment 682, wherein the nucleobase sequence of the modified oligonucleotide is at least 90% complementary to the target nucleic acid.

Embodiment 686. The modified oligonucleotide of embodiment 682, wherein the nucleobase sequence of the modified oligonucleotide is at least 95% complementary to the target nucleic acid.

Embodiment 687. The modified oligonucleotide of embodiment 682, wherein the nucleobase sequence of the modified oligonucleotide is 100% complementary to the target nucleic acid.

Embodiment 688. The modified oligonucleotide of any of embodiments 682-687, wherein the target nucleic acid is a target RNA.

Embodiment 689. The modified oligonucleotide of embodiment 688, wherein the target RNA is selected from: an mRNA, a pre-mRNA, a microRNA, and a non-coding RNA.

Embodiment 690. The modified oligonucleotide of embodiment 688, wherein the target RNA is not a microRNA.

Embodiment 691. The modified oligonucleotide of any of embodiments 311-690, wherein the modified oligonucleotide is not complementary to miR-21.

Embodiment 692. The modified oligonucleotide of any of embodiments 311-691, comprising a conjugate group.

Embodiment 693. The modified oligonucleotide of embodiment 692, wherein the conjugate group comprises at least one GalNAc.

Embodiment 694. The modified oligonucleotide of embodiment 692 or 693, wherein the conjugate group comprises 1-5 linker-nucleosides.

Embodiment 695. A pharmaceutical composition comprising the modified oligonucleotide of any of embodiments 311-694 and a pharmaceutically acceptable carrier or diluent.

Embodiment 696. A method comprising contacting a cell with the modified oligonucleotide or pharmaceutical composition of any of embodiments 311-695.

Embodiment 697. A method of modulating the amount or activity of a target nucleic acid in a cell, comprising contacting the cell with the modified oligonucleotide or pharmaceutical composition of any of embodiments 311-695 and thereby modulating the amount or activity of the target nucleic acid.

Embodiment 698. A method of modulating the amount or activity of a target nucleic acid in a cell, comprising contacting the cell with the modified oligonucleotide or pharmaceutical composition of any of embodiments 311-695.

Embodiment 699. The method of embodiments 696-698, wherein the amount or activity of a target nucleic acid is reduced.

Embodiment 700. The method of embodiments 696-698, wherein the amount or activity of a target nucleic acid is increased.

Embodiment 701. The method of embodiment 700, wherein the target protein is encoded by a target nucleic acid comprising at least one translation suppression element and wherein the modified oligonucleotide is complementary to a target site within a translation suppression element region of the target nucleic acid.

Embodiment 702. The method of embodiment 701, wherein the translation suppression element region comprises at least one stem-loop structure.

Embodiment 703. Use of the modified oligonucleotide or composition of any of embodiments 311-695 for treatment of a disease or condition.

Embodiment 704. Use of the modified oligonucleotide or composition of any of embodiments 311-695 for a preparation of a medicament for treatment of a disease or condition.

Embodiment 705. An antisense agent comprising a modified oligonucleotide consisting of 12-70 linked nucleosides linked through internucleoside linking groups, wherein at least one nucleoside comprises a modified sugar moiety, and wherein at least one of the internucleoside linking groups has Formula XVII:

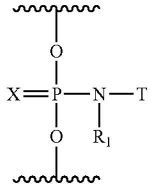

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

Embodiment 706. An antisense agent comprising a modified oligonucleotide consisting of 12-70 linked nucleosides linked through internucleoside linking groups, wherein at least one nucleoside comprises a modified sugar moiety, and wherein at least one of the internucleoside linking groups has Formula XVII:

XVII

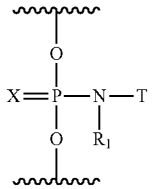

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl, Provided that if X is O and that if $R_1$ is H then T is not:

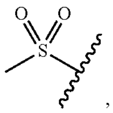,
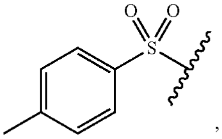,
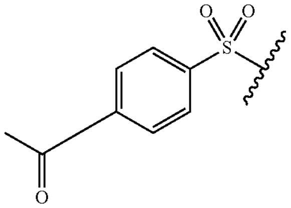,
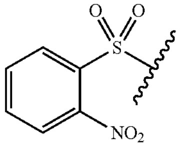,
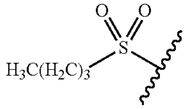, or
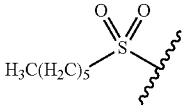.

Embodiment 707. The antisense agent of embodiment 705 or embodiment 706, wherein at least one internucleoside linking group is a phosphodiester or a phosphorothioate internucleoside linking group.

Embodiment 708. The antisense agent of any of embodiments 705-707, wherein at least one nucleoside comprises a 2'-β-D-deoxyribosyl sugar moiety.

Embodiment 709. The modified oligonucleotide of any of embodiments 705-708, wherein for at least one internucleoside linking group of Formula XVII, X is O.

Embodiment 710. The modified oligonucleotide of any of embodiments 705-709, wherein for at least one internucleoside linking group of Formula XVII, X is S.

Embodiment 711. The modified oligonucleotide of embodiment 705 or 706, wherein for at least one internucleoside linking group of Formula XVII, $R_1$ is H.

Embodiment 712. The modified oligonucleotide of embodiment 705 or 706, wherein for at least one internucleoside linking group of Formula XVII, $R_1$ is a $C_1$-$C_6$ alkyl.

Embodiment 713. The modified oligonucleotide of embodiment 710, wherein $R_1$ is methyl.

Embodiment 714. The modified oligonucleotide of embodiment 705 or 706, wherein for at least one internucleoside linking group of Formula XVII, $R_1$ is a substituted $C_1$-$C_6$ alkyl.

Embodiment 715. The modified oligonucleotide of any of embodiments 705-714, wherein for at least one internucleoside linking group of Formula XVII, T comprises a conjugate group.

Embodiment 716. The modified oligonucleotide of embodiment 715, wherein the conjugate group comprises a cell-targeting moiety.

Embodiment 717. The modified oligonucleotide of embodiment 715, wherein the conjugate group comprises a carbohydrate or carbohydrate cluster.

Embodiment 718. The modified oligonucleotide of any of embodiments 715-717, wherein the conjugate group comprises at least one GalNAc.

Embodiment 719. The modified oligonucleotide of embodiment 715, wherein the conjugate group comprises a $C_1$-$C_{20}$ alkyl chain.

Embodiment 720. The modified oligonucleotide of embodiment 719, wherein the conjugate group comprises $C_{16}$ alkyl.

Embodiment 721. The modified oligonucleotide of any of embodiments 705-714, wherein for at least one internucleoside linking group of Formula XVII, T does not comprise a conjugate group.

Embodiment 722. The modified oligonucleotide of any of embodiments 705-714, wherein for at least one internucleoside linking group of Formula XVII, T does not comprise a cell-targeting moiety.

Embodiment 723. The modified oligonucleotide of any of embodiments 705-722, wherein for at least one internucleoside linking group of Formula XVII, T is $SO_2R_2$.

Embodiment 724. The modified oligonucleotide of embodiment 723, wherein $R_2$ is an aryl.

Embodiment 725. The modified oligonucleotide of embodiment 723, wherein $R_2$ is a substituted aryl.

Embodiment 726. The modified oligonucleotide of embodiment 723, wherein $R_2$ is a heterocycle.

Embodiment 727. The modified oligonucleotide of embodiment 723, wherein $R_2$ is a substituted heterocycle.

Embodiment 728. The modified oligonucleotide of embodiment 723, wherein $R_2$ is an aromatic heterocycle.

Embodiment 729. The modified oligonucleotide of embodiment 723, wherein $R_2$ is a substituted aromatic heterocycle.

Embodiment 730. The modified oligonucleotide of embodiment 723, wherein $R_2$ is a diazole.

Embodiment 731. The modified oligonucleotide of embodiment 723, wherein $R_2$ is a substituted diazole.

Embodiment 732. The modified oligonucleotide of embodiment 723, wherein $R_2$ is an amine.

Embodiment 733. The modified oligonucleotide of embodiment 723, wherein $R_2$ is a substituted amine.

Embodiment 734. The modified oligonucleotide of embodiment 723, wherein $R_2$ is a $C_1$-$C_6$ alkoxy, $C_1$-$C_6$ alkenyl, or $C_1$-

$C_6$-alkynl.

Embodiment 735. The modified oligonucleotide of embodiment 723, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 736. The modified oligonucleotide of embodiment 723, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 737. The modified oligonucleotide of embodiment 723, wherein $R_2$ comprises a carbohydrate or carbohydrate cluster.

Embodiment 738. The modified oligonucleotide of embodiment 723, wherein $R_2$ comprises at least one GalNAc.

Embodiment 739. The modified oligonucleotide of embodiment 723, wherein T is:

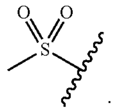 [SMILES: *S(C)(=O)=O]

Embodiment 740. The oligomeric compound of embodiment 739, wherein T is:

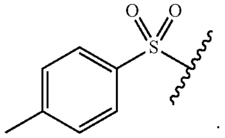 [SMILES: *S(=O)(=O)c1ccc(C)cc1]

Embodiment 741. The modified oligonucleotide of embodiment 723, wherein T is:

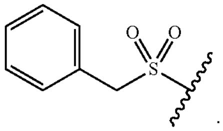 [SMILES: *S(=O)(=O)Cc1ccccc1]

Embodiment 742. The modified oligonucleotide of embodiment 723, wherein T is:

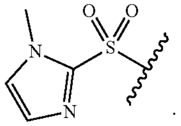

Embodiment 743. The modified oligonucleotide of embodiment 723, wherein T is:

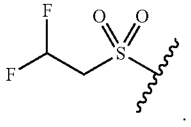

Embodiment 744. The modified oligonucleotide of embodiment 723, wherein T is:

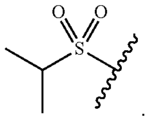 [SMILES: *S(=O)(=O)C(C)C]

Embodiment 745. The modified oligonucleotide of embodiment 723, wherein T is:

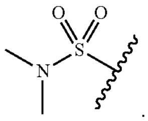 [SMILES: *S(=O)(=O)N(C)C]

Embodiment 746. The modified oligonucleotide of embodiment 723, wherein T is:

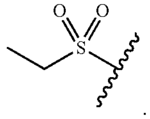 [SMILES: *S(=O)(=O)CC]

Embodiment 747. The modified oligonucleotide of embodiment 723, wherein T is:

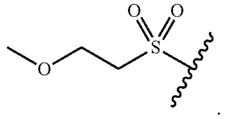 [SMILES: *S(=O)(=O)CCOC]

Embodiment 748. The modified oligonucleotide of embodiment 723, wherein T is:

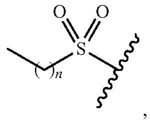

wherein n is from 2 to 20.

Embodiment 749. The modified oligonucleotide of embodiment 748, wherein n is 15.

Embodiment 750. The modified oligonucleotide of any of embodiments 705-722, wherein for at least one internucleoside linking group of Formula XVII, T is C(═O) $R_3$.

Embodiment 751. The modified oligonucleotide of embodiment 750, wherein $R_3$ is an aryl.

Embodiment 752. The modified oligonucleotide of embodiment 750, wherein $R_3$ is a substituted aryl.

Embodiment 753. The modified oligonucleotide of embodiment 750, wherein $R_3$ is $CH_3$.

Embodiment 754. The modified oligonucleotide of embodiment 750, wherein $R_3$ is $N(CH_3)_2$.

Embodiment 755. The modified oligonucleotide of embodiment 750, wherein $R_3$ is $OCH_3$.

Embodiment 756. The modified oligonucleotide of embodiment 750, wherein $R_3$ is a $C_1$-$C_6$ alkoxy.

Embodiment 757. The modified oligonucleotide of embodiment 750, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 758. The modified oligonucleotide of embodiment 750, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 759. The modified oligonucleotide of embodiment 750, wherein $R_3$ comprises a carbohydrate or carbohydrate cluster.

Embodiment 760. The modified oligonucleotide of embodiment 750, wherein $R_{23}$ comprises at least one GalNAc.

Embodiment 761. The modified oligonucleotide of embodiment 750, wherein T is:

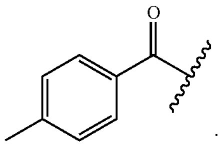 [SMILES: *C(=O)c1ccc(C)cc1]

.

Embodiment 762. The modified oligonucleotide of embodiment 750, wherein T is:

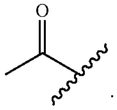 [SMILES: *C(C)=O]

.

Embodiment 763. The modified oligonucleotide of embodiment 750, wherein T is:

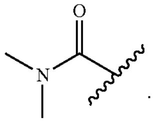 [SMILES: *C(=O)N(C)C]

.

Embodiment 764. The modified oligonucleotide of embodiment 750, wherein T is:

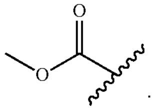

.

Embodiment 765. The modified oligonucleotide of embodiment 750, wherein T is:

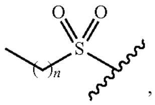

, wherein n is from 2 to 20.

Embodiment 766. The modified oligonucleotide of embodiment 765, wherein n is 15.

Embodiment 767. The modified oligonucleotide of any of embodiments 705-722, wherein for at least one internucleoside linking group of Formula XVII, T is P(=O)$R_4R_5$.

Embodiment 768. The modified oligonucleotide of embodiment 767, wherein $R_4$ is $OCH_3$.

Embodiment 769. The modified oligonucleotide of embodiment 767, wherein $R_4$ is OH.

Embodiment 770. The modified oligonucleotide of embodiment 767, wherein $R_4$ is $C_1$-$C_6$ alkyl.

Embodiment 771. The modified oligonucleotide of embodiment 767, wherein $R_4$ is substituted $C_1$-$C_6$ alkyl.

Embodiment 772. The modified oligonucleotide of embodiment 767, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 773. The modified oligonucleotide of embodiment 767, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 774. The modified oligonucleotide of embodiment 767, wherein $R_4$ comprises a carbohydrate or carbohydrate cluster.

Embodiment 775. The modified oligonucleotide of embodiment 767, wherein $R_4$ comprises at least one GalNAc.

Embodiment 776. The modified oligonucleotide of any of embodiments 767-775, wherein $R_5$ is $OCH_3$.

Embodiment 777. The modified oligonucleotide of any of embodiments 767-775, wherein $R_5$ is OH.

Embodiment 778. The modified oligonucleotide of any of embodiments 767-775, wherein $R_5$ is $C_1$-$C_6$ alkyl.

Embodiment 779. The modified oligonucleotide of any of embodiments 767-775, wherein $R_5$ is substituted $C_1$-$C_6$ alkyl.

Embodiment 780. The modified oligonucleotide of embodiment 767, wherein T is:

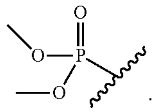 [SMILES: *P(=O)(OC)OC]

.

Embodiment 781. The modified oligonucleotide of embodiment 767, wherein T is:

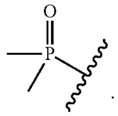 [SMILES: *P(C)(C)=O]

.

Embodiment 782. The modified oligonucleotide of embodiment 767, wherein T is:

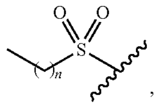

, wherein n is from 2 to 20.

Embodiment 783. The modified oligonucleotide of embodiment 782, wherein n is 15.

Embodiment 784. The modified oligonucleotide of any of embodiments 705-783, wherein at least one internucleoside linking group of the modified oligonucleotide is not a linking group of Formula XVII.

Embodiment 785. The modified oligonucleotide of any of embodiments 705-784, wherein exactly one internucleoside linking group of the modified oligonucleotide is an internucleoside linking group of Formula XVII.

Embodiment 786. The modified oligonucleotide of any of embodiments 705-784, wherein exactly two internucleoside linking groups of the modified oligonucleotide are internucleoside linking groups of Formula XVII.

Embodiment 787. The modified oligonucleotide of any of embodiments 705-784, wherein exactly three internucleoside linking groups of the modified oligonucleotide are internucleoside linking groups of Formula XVII.

Embodiment 788. The modified oligonucleotide of any of embodiments 705-784, wherein exactly four internucleoside linking groups of the modified oligonucleotide are internucleoside linking groups of Formula XVII.

Embodiment 789. The modified oligonucleotide of any of embodiments 705-784, wherein exactly five internucleoside linking groups of the modified oligonucleotide are internucleoside linking groups of Formula XVII.

Embodiment 790. The modified oligonucleotide of any of embodiments 705-784, wherein at least six internucleoside linking groups of the modified oligonucleotide are internucleoside linking groups of Formula XVII.

Embodiment 791. The modified oligonucleotide of any of embodiment 705-783 or 785-787 having at least two linking groups of Formula XVII, wherein at least two of the linking groups of Formula XVII are the same as one another.

Embodiment 792. The modified oligonucleotide of any of embodiments 705-791, wherein each internucleoside linking group of the modified oligonucleotide that is not an internucleoside linking group of Formula XVII is either a phosphodiester internucleoside linking group or a phosphorothioate internucleoside linking group.

Embodiment 793. The modified oligonucleotide of any of embodiments 705-784 or 790, wherein each internucleoside linking group of the modified oligonucleotide is an internucleoside linking group of Formula XVII.

Embodiment 794. An antisense agent comprising a modified oligonucleotide, wherein at least one region of the modified oligonucleotide has Structure A:

Structure A

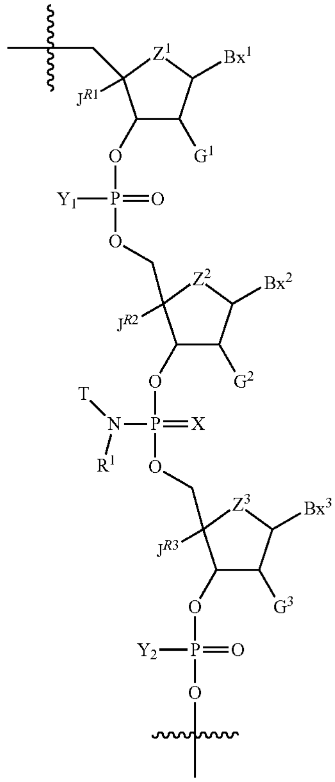

wherein:

each Bx is a heterocyclic base moiety;

X is selected from O or S;

each of $Y_1$ and $Y_2$ is independently selected from OH or SH;

each of $Z^1$, $Z^2$, and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$—C alkyl; and

T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O-[C(R_6)(R_7)]_n-[(C=O)_m-X^G]_j-R_8$;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$; and each $J_1$, $J_2$ and $J_3$ is, independently, H or $C_1$-$C_6$ alkyl.

Embodiment 795. An antisense agent comprising a modified oligonucleotide, wherein at least one region of the modified oligonucleotide has Structure B:

Structure B

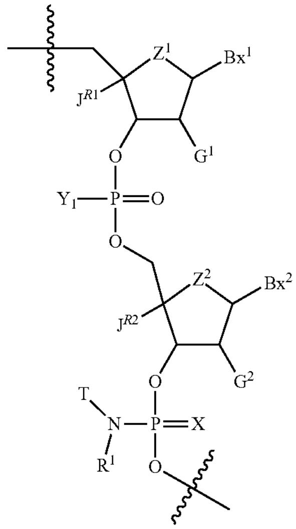

wherein:

each Bx is a heterocyclic base moiety;

X is selected from O or S;

each of $Y_1$ and $Y_2$ is independently selected from OH or SH;

each of $Z_1$ and $Z^2$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O-[C(R_6)(R_7)]_n-[(C=O)_m-X^G]_j-R_8$;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 796. An antisense agent comprising a modified oligonucleotide, wherein at least one region of the modified oligonucleotide has Structure C:

Structure C

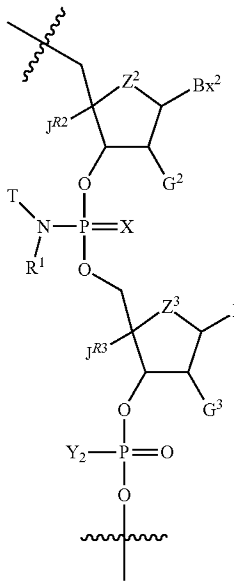

wherein:

each Bx is a heterocyclic base moiety;

X is selected from O or S;

each of $Y_1$ and $Y_2$ is independently selected from OH or SH;

each of $Z^2$ and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or $O-[C(R_6)(R_7)]_n-[(C=O)_m-X^G]_j-R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 797. An antisense agent comprising a modified oligonucleotide, wherein at least one region of the modified oligonucleotide has Structure D:

Structure D

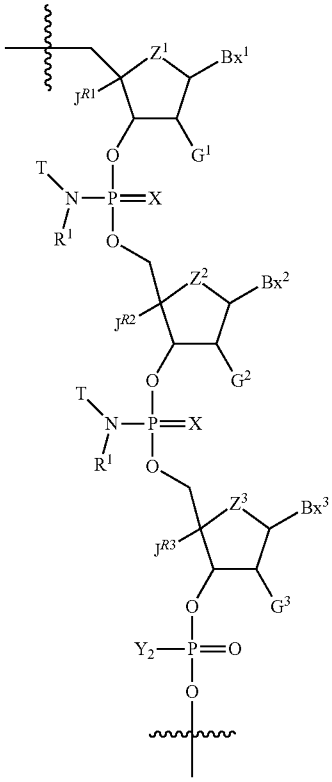

wherein:

each Bx is a heterocyclic base moiety;

X is selected from O or S;

each of $Y_1$ and $Y_2$ is independently selected from OH or SH;

each of $Z^2$ and $Z^3$ are independently selected from —$(CH_2)_p$—$X^Z$—$(CH_2)_q$—, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or O—$[C(R_6)(R_7)]_n$—$[(C{=}O)_m$—$X^G]_j$—$R_8$;

either $J^{R2}$ and $G^2$ form a $J^{R2}$ and $G^2$ bridge, or $J^{R2}$ is H and $G^2$ is selected from H, OH, halogen or O—$[C(R_6)(R_7)]_n$—$[(C{=}O)_m$—$X^G]_j$—$R_8$;

either $J^{R3}$ and $G^3$ form a $J^{R3}$ and $G^3$ bridge, or $J^{R3}$ is H and $G^3$ is selected from H, OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 798. An antisense agent comprising a modified oligonucleotide, wherein at least one region of the modified oligonucleotide has Structure E:

Structure E

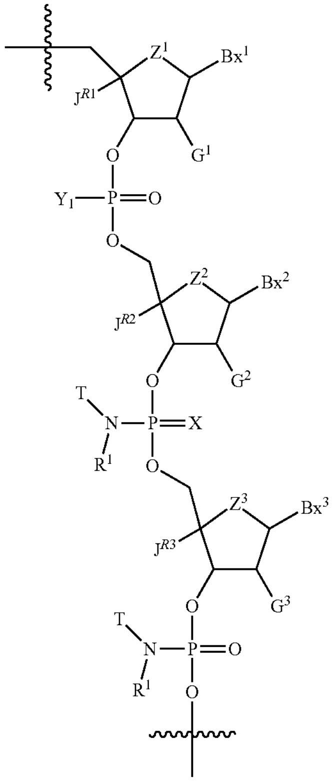

wherein:

each Bx is a heterocyclic base moiety;

X is selected from O or S;

each of $Y_1$ and $Y_2$ is independently selected from OH or SH;

each of $Z^2$ and $Z^3$ are independently selected from $—(CH_2)_p—X^Z—(CH_2)_q—$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O—[C(R_6)(R_7)]_n—[(C=O)_m—X^G]_j—R_8$;

either $J^{R2}$ and $G^2$ form a $J^{R2}$ and $G^2$ bridge, or $J^{R2}$ is H and $G^2$ is selected from H, OH, halogen or $O—[C(R_6)(R_7)]_n—[(C=O)_m—X^G]_j—R_8$;

either $J^{R3}$ and $G^3$ form a $J^{R3}$ and $G^3$ bridge, or $J^{R3}$ is H and $G^3$ is selected from H, OH, halogen or $O—[C(R_6)(R_7)]_n—[(C=O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 799. The modified oligonucleotide of any of embodiments 794-798, wherein each Z is O.

Embodiment 800. The modified oligonucleotide of any of embodiments 794-799, wherein at least one G is selected from H, OH, halogen, $C_1$-$C_6$ alkoxy, $—O(CH_2)_2OCH_3$, or $—OCH_2(C=O)NHCH_3$.

Embodiment 801. The modified oligonucleotide of any of embodiments 794-799, wherein each G is selected from H, OH, halogen, $C_1$-$C_6$ alkoxy, $—O(CH_2)_2OCH_3$, or $—OCH_2(C=O)NHCH_3$.

Embodiment 802. The modified oligonucleotide of any of embodiments 794-801, wherein at least one $J^R$ forms a bridge with at least one G, wherein said $J^R$ to G bridge has a formula selected from $—CH(CH_3)—O—$ or $—(CH_2)_k—O'$, wherein k is from 1 to 3.

Embodiment 803. The modified oligonucleotide of any of embodiments 794-802, wherein each $J^R$ and G form a bridge, wherein said $J^R$ to G bridge has a formula selected from $—CH(CH_3)—O—$ or $—(CH_2)_k—O—$, wherein k is from 1 to 3.

Embodiment 804. The modified oligonucleotide of any of embodiments 802 or 803, wherein at least one Z is O and the corresponding $J^R$ to G bridge has a formula $(CH_2)_k—O—$, wherein k is 1.

Embodiment 805. The modified oligonucleotide of any of embodiments 794-804 wherein each nucleoside of structure A, B, C, D, or E is a stereo standard nucleoside.

Embodiment 806. The modified oligonucleotide of any of embodiments 794-804, wherein at least one nucleoside of structure A, B, C, D, or E is a stereo-non-standard nucleoside.

Embodiment 807. The modified oligonucleotide of any of embodiments 802-804 or 806, wherein at least one nucleoside having a $J^R$ to G bridge is in the α-L-ribosyl configuration.

Embodiment 808. The modified oligonucleotide of any of embodiments 794-807, wherein the modified oligonucleotide comprises at least 2, at least 3, at least 4, at least 5, at least 6, at least 7, at least 8, at least 9, or at least 10 regions having structures A, B, C, D, or E.

Embodiment 809. The modified oligonucleotide of any of embodiments 794-807, wherein at least one region having structure A, B, C, D, or E is at the 5' end of the modified oligonucleotide.

Embodiment 810. The modified oligonucleotide of any of embodiments 794-807, wherein at least one region having structure A, B, C, D, or E is at the 3' end of the modified oligonucleotide.

Embodiment 811. The modified oligonucleotide of any of embodiments 794-807, wherein at least one region having structure A, B, C, D, or E is internal to the modified oligonucleotide.

Embodiment 812. An antisense agent comprising a modified oligonucleotide consisting of 10-30 linked nucleosides, wherein a region of the modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

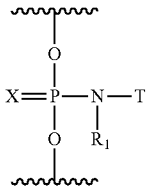

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ is an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 813. The modified oligonucleotide of embodiment 812, wherein the modified oligonucleotide comprises at least 2, at least 3, at least 4, at least 5, at least 6, at least 7, at least 8, at least 9, or at least 10 regions having the formula $(N_{g1})_{L1}(N_{g2})_{L2}(N_{g3})_{L3}$.

Embodiment 814. The modified oligonucleotide of embodiment 812 or 813, wherein at least one region having the formula $(N_{g1})_{L1}(N_{g2})_{L2}(N_{g3})_{L3}$ is at the 5' end of the oligonucleotide Embodiment 815. The modified oligonucleotide of embodiment 812 or 813, wherein at least one region having the formula $(N_{g1})_{L1}(N_{g2})_{L2}(N_{g3})_{L3}$ is internal to the oligonucleotide.

Embodiment 816. The modified oligonucleotide of embodiment 812 or 813, wherein at least one region having the formula $(N_{g1})_{L1}(N_{g2})_{L2}(N_{g3})_{L3}$ is at the 3' end of the oligonucleotide.

Embodiment 817. The modified oligonucleotide of any of embodiments 705-816, wherein at least one nucleoside of the modified oligonucleotide is a modified nucleoside selected from a bicyclic nucleoside and a non-bicyclic substituted nucleoside.

Embodiment 818. The modified oligonucleotide of any of embodiments 705-817, wherein at least one nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 819. The modified oligonucleotide of any of embodiments 705-818, wherein each nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 820. The modified oligonucleotide of any of embodiments 705-819, wherein at least one nucleoside of the modified oligonucleotide is a stereo-non-standard nucleoside.

Embodiment 821. The modified oligonucleotide of embodiment 820, wherein the internucleoside linking group linking at least one stereo-non-standard nucleoside to an adjacent nucleoside is an internucleoside linking group of Formula XVII.

Embodiment 822. The modified oligonucleotide of embodiment 820 or 821, wherein at least two nucleosides of the modified oligonucleotide are stereo-non-standard nucleosides.

Embodiment 823. The modified oligonucleotide of embodiment 822, wherein at least two stereo-non-standard nucleosides of the modified oligonucleotide are adjacent to one another.

Embodiment 824. The modified oligonucleotide of embodiment 823, wherein at least two stereo-non-standard nucleosides of the modified oligonucleotide are linked to one another with an internucleoside linking group of Formula XVII.

Embodiment 825. The modified oligonucleotide of any of embodiments 820-824, wherein at least one stereo-non-standard nucleoside of the modified oligonucleotide is a stereo-non-standard DNA nucleoside.

Embodiment 826. The modified oligonucleotide of embodiment 825 wherein the stereo-non-standard DNA nucleoside is selected from a stereo-non-standard DNA nucleoside having: Formula I, Formula II, Formula III, Formula IV, Formula V, Formula VI, and Formula VII.

Embodiment 827. The modified oligonucleotide of embodiment 826 wherein the stereo-non-standard DNA nucleoside is selected from a stereo-non-standard DNA nucleoside having: Formula V and Formula II.

Embodiment 828. The modified oligonucleotide of any of embodiments 820-827, wherein at least one stereo-non-standard nucleoside of the modified oligonucleotide is a substituted stereo-non-standard nucleoside or a stereo-non-standard RNA nucleoside.

Embodiment 829. The modified oligonucleotide of embodiment 828, wherein the 2'-substituent of the at least one substituted stereo-non-standard nucleoside of the modified oligonucleotide is selected from: 2'-MOE, 2'-OMe, 2'-F, or 2'-OH.

Embodiment 830. The modified oligonucleotide of any of embodiments 705-819, wherein each nucleoside is a stereo-standard nucleoside.

Embodiment 831. The modified oligonucleotide of any of embodiments 705-829, wherein the modified oligonucleotide consists of 12-30 linked nucleosides.

Embodiment 832. The modified oligonucleotide of any of embodiments 705-829, wherein the modified oligonucleotide consists of 16-24 linked nucleosides.

Embodiment 833. The modified oligonucleotide of any of embodiments 705-829, wherein the modified oligonucleotide consists of 18-22 linked nucleosides.

Embodiment 834. The modified oligonucleotide of any of embodiments 705-832, wherein the modified oligonucleotide consists of 16 linked nucleosides.

Embodiment 835. The modified oligonucleotide of any of embodiments 705-832, wherein the modified oligonucleotide consists of 17 linked nucleosides.

Embodiment 836. The modified oligonucleotide of any of embodiments 705-833, wherein the modified oligonucleotide consists of 18 linked nucleosides.

Embodiment 837. The modified oligonucleotide of any of embodiments 705-833, wherein the modified oligonucleotide consists of 19 linked nucleosides.

Embodiment 838. The modified oligonucleotide of any of embodiments 705-833, wherein the modified oligonucleotide consists of 20 linked nucleosides.

Embodiment 839. The modified oligonucleotide of any of embodiments 705-833, wherein the modified oligonucleotide consists of 21 linked nucleosides.

Embodiment 840. The modified oligonucleotide of any of embodiments 705-833, wherein the modified oligonucleotide consists of 22 linked nucleosides.

Embodiment 841. The modified oligonucleotide of any of embodiments 705-832, wherein the modified oligonucleotide consists of 23 linked nucleosides.

Embodiment 842. The modified oligonucleotide of any of embodiments 705-841, wherein at least one nucleoside of the modified oligonucleotide is selected from: a 2'-OMe nucleoside, a 2'-F nucleoside, and an RNA nucleoside.

Embodiment 843. The modified oligonucleotide of any of embodiments 705-842, wherein at least one nucleoside of the modified oligonucleotide is a 2'-OMe nucleoside, and at least one nucleoside of the modified oligonucleotide is a 2'-F nucleoside.

Embodiment 844. The modified oligonucleotide of embodiment 843, wherein each nucleoside of the modified oligonucleotide is selected from a 2'-OMe nucleoside or a 2'-F nucleoside.

Embodiment 845. The modified oligonucleotide of any of embodiments 705-743, wherein at least one nucleoside of the modified oligonucleotide is a 2'-OMe nucleoside, at least one nucleoside of the modified oligonucleotide is a 2'-F nucleoside, and at least one nucleoside of the modified oligonucleotide comprises a sugar surrogate.

Embodiment 846. The modified oligonucleotide of embodiment 845, wherein each nucleoside of the modified oligonucleotide is selected from a 2'-OMe nucleoside, a 2'-F nucleoside, and a nucleoside comprising a sugar surrogate.

Embodiment 847. The modified oligonucleotide of any of embodiments 845-846, wherein the nucleoside comprising a sugar surrogate is selected from:

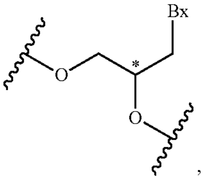
,
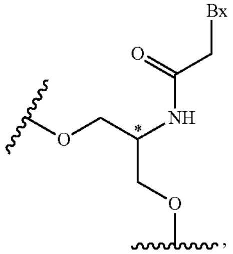
,
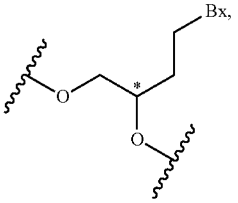

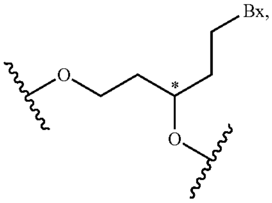

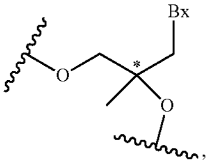
, or
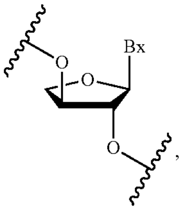
, wherein Bx is a heterocyclic base moiety.

Embodiment 848. The modified oligonucleotide of embodiment 847, wherein the nucleoside comprising a sugar surrogate is GNA.

Embodiment 849. The modified oligonucleotide of any of embodiments 842-848, wherein the modified oligonucleotide has a region of alternating nucleoside types having the motif ABABA, wherein each A is a stereo-standard nucleoside of a first type and each B is a stereo-standard nucleoside of a second type, wherein the first type and the second type are different from one another.

Embodiment 850. The modified oligonucleotide of embodiment 849, wherein A and B are selected from 2'-F substituted nucleosides, 2'-OMe substituted nucleosides, and stereo-standard RNA nucleosides.

Embodiment 851. The modified oligonucleotide of any of embodiments 705-850, wherein the 5'-end of the modified oligonucleotide comprises a terminal group.

Embodiment 852. The modified oligonucleotide of embodiment 851, wherein the terminal group is a stabilized phosphate group.

Embodiment 853. The modified oligonucleotide of embodiment 852, wherein the stabilized phosphate group is a 5'-vinyl phosphonate or a 5'-cyclopropyl phosphonate.

Embodiment 854. The modified oligonucleotide of embodiment 851, wherein the terminal group is selected from

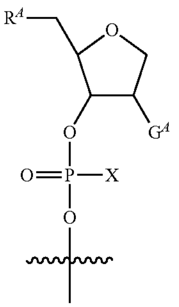

or

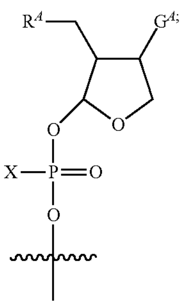

wherein $R^A$ is OH, OP(=O)OH, OP(=O)SH, or a stabilized phosphate group;

$G^A$ is H, OH, OMe, MOE, or a halogen;

X is OH, SH, or $NSO_2R_2$;

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group.

Embodiment 855. The modified oligonucleotide of embodiment 854, wherein $G^A$ is selected from H or OH and X is SH.

Embodiment 856. The antisense agent of any of embodiments 705-855, wherein the antisense agent is an RNAi agent.

Embodiment 857. The RNAi agent of embodiment 856, wherein the RNAi agent is a single-stranded RNAi agent comprising an RNAi antisense modified oligonucleotide, wherein the RNAi antisense modified oligonucleotide is a modified oligonucleotide of any of embodiments 705-855.

Embodiment 858. The RNAi agent of embodiment 856, wherein the RNAi agent is an oligonucleotide duplex comprising an RNAi antisense modified oligonucleotide and an RNAi sense modified oligonucleotide, wherein the RNAi antisense modified oligonucleotide and/or the RNAi sense modified oligonucleotide is a modified oligonucleotide of any of embodiments 705-855.

Embodiment 859. The RNAi agent of embodiment 857 or 858, wherein at least one internucleoside linking group of the RNAi antisense modified oligonucleotide is an internucleoside linking group of Formula XVII.

Embodiment 860. The RNAi agent of embodiment 857 or 858, wherein at least two internucleoside linking groups of the RNAi antisense modified oligonucleotide are independently selected internucleoside linking groups of Formula XVII.

Embodiment 861. The RNAi agent of any of embodiments 857-860, wherein at least one of the five 3'-most internucleoside linking groups of the RNAi antisense modified oligonucleotide is an internucleoside linking group of Formula XVII.

Embodiment 862. The RNAi agent of any of embodiments 857-861, wherein at least two of the five 3'-most internucleoside linking groups of RNAi antisense modified oligonucleotide is an internucleoside linking group of Formula XVII.

Embodiment 863. The RNAi agent of any of embodiments 857-862, wherein 1-3 of the three 3'-most internucleoside linking groups are internucleoside linking groups of Formula XVII, and each of these three internucleoside linking groups that is not an internucleoside linking group of Formula XVII is a phosphodiester or phosphorothioate internucleoside linking group.

Embodiment 864. The RNAi agent of embodiment 863, wherein the two 3'-most internucleoside linking groups are internucleoside linking groups of Formula XVII.

Embodiment 865. The RNAi agent of any of embodiments 857-864, wherein exactly one of the 5'-most and penultimate 5'-most internucleoside linking groups is an internucleoside linking group of Formula XVII.

Embodiment 866. The RNAi agent of any of embodiments 857-865, wherein exactly one of the 5'-most and penultimate 5'-most internucleoside linking groups of the RNAi antisense oligonucleotide is an internucleoside linking groups of Formula XVII, the other of the 5'-most and penultimate 5'-most internucleoside linking groups of the RNAi antisense oligonucleotide is selected from a phosphodiester and a phosphorothioate internucleoside linkage, the two 3'-most internucleoside linking groups of the RNAi antisense oligonucleotide are internucleoside linking groups of Formula XVII, and the remaining internucleoside linking groups of the RNAi antisense oligonucleotide are phosphodiester internucleoside linkages.

Embodiment 867. The RNAi agent of any of embodiments 857-866, wherein the antisense modified oligonucleotide comprises a 3'-overhang.

Embodiment 868. The RNAi agent of embodiment 867, wherein the 3'-overhang consists of two nucleosides.

Embodiment 869. The RNAi agent of any of embodiments 857-865 or 867-868, wherein at least one internucleoside linking group within the seed region of the RNAi antisense modified oligonucleotide is an internucleoside linking group of Formula XVII.

Embodiment 870. The RNAi agent of any of embodiments 857-869, wherein for each internucleoside linking group of Formula XVII, $R_1$ is H and T is $SO_2Me$.

Embodiment 871. The RNAi agent of any of embodiments 857-870, wherein the RNAi antisense modified oligonucleotide consists of 23 linked nucleosides, and the internucleoside linkage motif is selected from: ooooooooooooooooooooaa, aaoooooooooooooooooooo, aaooooooooooooooooooaa, asooooooooooooooooooss, saoooooooooooooooooooo, oooooooooooooooooooaaa, ooooooooooooooooaaaoss, oooooooooooooaaaooooss, ooooooooooaaaoooooooss, oooooooaaaoooooooooooss, ooooaaaoooooooooooooss, saoooaoooooooaoaooooss, ssoooaoooooooaoaooooss, or ssooooooooooooooooooaa, wherein each "a" represents an internucleoside linkage of Formula XVII, each "s" represents a phosphorothioate internucleoside linkage, and each "o" represents a phosphodiester internucleoside linkage.

Embodiment 872. The RNAi agent of embodiment 871, wherein the internucleoside linkage motif of the RNAi antisense modified oligonucleotide is selected from ooooooooooooooooooooaa, asooooooooooooooooooss, or saoooooooooooooooooooo.

Embodiment 873. The RNAi agent of embodiment 871 or 872, wherein the sugar motif of the RNAi antisense modified oligonucleotide from 5' to 3' is yfyfyfyfyfyfyfyfyfyfyfy or yfyyyfyyyyyyyfyfyyyyyyy, wherein "y" represents a 2'-OMe sugar moiety and "f" represents a 2'-F sugar moiety.

Embodiment 874. The RNAi agent of any of embodiments 857-870, wherein the RNAi antisense modified oligonucleotide consists of 21 linked nucleosides, and the internucleoside linkage motif is selected from: aaososososossssssss, ssaaososososososssssss, ssosaaosososossssss, sssososaaosososssssss, sssosososaaosossssss, sssososososaaossssss, sssosososososaasssss, sssososososososaassss, sssososososososssaass, sssosososososossssssaa wherein each "a" represents an internucleoside linkage of Formula XVII, each "s" represents a phosphorothioate internucleoside linkage, and each "o" represents a phosphodiester internucleoside linkage.

Embodiment 875. The RNAi agent of embodiment 874, wherein the internucleoside linkage motif of the RNAi antisense modified oligonucleotide is selected from aaososososososssssss, ssaaososososososssssss, sssososaaosososssssss, sssososososaaosossssss, sssosososososossssaass, or sssososososososssssssaa, wherein each "a" represents an internucleoside linkage of Formula XVII, each "s" represents a phosphorothioate internucleoside linkage, and each "o" represents a phosphodiester internucleoside linkage.

Embodiment 876. The RNAi agent of embodiment 874 or 875, wherein the sugar motif of the RNAi antisense modified oligonucleotide from 5' to 3' is yfyfyfyfyfyfyfyfyfyfyfy, wherein "y" represents a 2'-OMe sugar moiety and "f" represents a 2'-F sugar moiety.

Embodiment 877. The RNAi agent of any of embodiments 873-876 wherein each "a" is a mesyl phosphoramidate linkage.

Embodiment 878. The RNAi agent of any of embodiments 857-878, wherein at least one region of the RNAi antisense modified oligonucleotide has structure A, B, C, D, or E.

Embodiment 879. The RNAi agent of embodiment 878, wherein at least one region having structure A, B, C, D, or E is within the seed region of the RNAi antisense modified oligonucleotide.

Embodiment 880. The RNAi agent of embodiment 878, wherein at least one region having structure A, B, C, D, or E is at the 3' end of the RNAi antisense modified oligonucleotide.

Embodiment 881. The RNAi agent of any of embodiments 857-880, wherein at least one region of the RNAi antisense modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

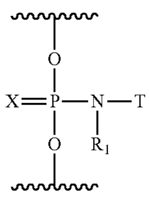

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, substituted $C_1$-$C_6$ alkyl, and a conjugate;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 882. The RNAi agent of embodiment 881, wherein the region having the formula $(N_{g1})_{L1}(N_{g2})_{L2}(N_{g3})_{L3}$ includes one or two 3'-overhang nucleosides.

Embodiment 883. The RNAi agent of embodiment 881, wherein at least one region having the formula $(N_{g1})_{L1}(N_{g2})_{L2}(N_{g3})_{L3}$ is at the 3' end of the RNAi antisense modified oligonucleotide.

Embodiment 884. The RNAi agent of embodiment 883, wherein $L_1$ and $L_2$ are each internucleoside linkages of Formula XVII wherein $R_1$ is H and T is $SO_2Me$, and $L_3$ is a phosphodiester internucleoside linkage.

Embodiment 885. The RNAi agent of embodiment 881, wherein at least one region having the formula $(N_{g1})_{L1}(N_{g2})_{L2}(N_{g3})_{L3}$ is at the 5' end of the RNAi antisense modified oligonucleotide.

Embodiment 886. The RNAi agent of embodiment 885, wherein one of $L_1$ or $L_2$ is an internucleoside linkages of Formula XVII wherein $R_1$ is H and T is $SO_2Me$, the other of $L_1$ or $L_2$ is a phosphorothioate internucleoside linkage, and $L_3$ is a phosphodiester internucleoside linkage.

Embodiment 887. The RNAi agent of embodiment 881, wherein at least one region having the formula $(N_{g1})_{L1}(N_{g2})_{L2}(N_{g3})_{L3}$ is within the seed region of the RNAi antisense modified oligonucleotide.

Embodiment 888. The RNAi agent of any of embodiments 857-887, wherein the region of the RNAi antisense oligonucleotide that is complementary to a target is at least 15 nucleobases.

Embodiment 889. The RNAi agent of any of embodiments 857-888, wherein the region of the RNAi antisense oligonucleotide that is complementary to a target is at least 17 nucleobases.

Embodiment 890. The RNAi agent of any of embodiments 857-889, wherein the region of the RNAi antisense oligonucleotide that is complementary to a target is at least 19 nucleobases.

Embodiment 891. The RNAi agent of any of embodiments 857-890, wherein the region of the RNAi antisense oligonucleotide that is complementary to a target is at least 21 nucleobases.

Embodiment 892. The RNAi agent of any of embodiments 857-890, wherein the region of the RNAi antisense oligonucleotide that is complementary to a target is exactly 19 nucleobases.

Embodiment 893. The RNAi agent of any of embodiments 857-891, wherein the region of the RNAi antisense oligonucleotide that is complementary to a target is exactly 21 nucleobases.

Embodiment 894. The RNAi agent of any of embodiments 857-893, wherein at least one nucleoside of the RNAi antisense modified oligonucleotide is selected from: a 2'-OMe nucleoside, a 2'-F nucleoside, and an RNA nucleoside.

Embodiment 895. The RNAi agent of any of embodiments 857-894, wherein at least one nucleoside of the modified oligonucleotide is a 2'-OMe nucleoside, and at least one nucleoside of the modified oligonucleotide is an RNA nucleoside.

Embodiment 896. The RNAi agent of any of embodiments 857-894, wherein at least one nucleoside of the RNAi antisense modified oligonucleotide is a 2'-OMe nucleoside, and at least one nucleoside of the RNAi antisense modified oligonucleotide is a 2'-F nucleoside.

Embodiment 897. The RNAi agent of embodiment 896, wherein each nucleoside of the RNAi antisense modified oligonucleotide is selected from a 2'-OMe nucleoside or a 2'-F nucleoside.

Embodiment 898. The RNAi agent of any of embodiments 887-894, wherein at least one nucleoside of the RNAi antisense modified oligonucleotide is a 2'-OMe nucleoside, at least one nucleoside of the RNAi antisense modified oligonucleotide is a 2'-F nucleoside, and at least one nucleoside of the modified oligonucleotide comprises a sugar surrogate.

Embodiment 899. The RNAi agent of embodiment 898, wherein each nucleoside of the RNAi antisense modified oligonucleotide is selected from a 2'-OMe nucleoside, a 2'-F nucleoside, and a nucleoside comprising a sugar surrogate.

Embodiment 900. The RNAi agent of any of embodiments 898-899, wherein the nucleoside comprising a sugar surrogate is selected from:

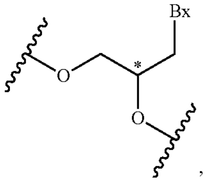

,

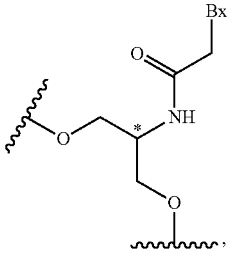

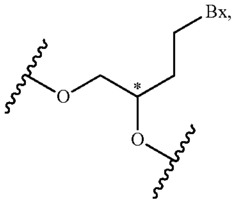

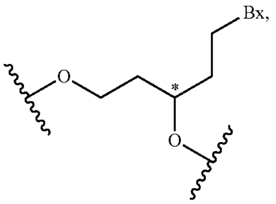

-continued

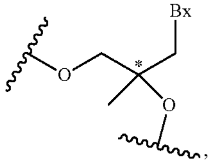

or

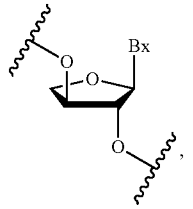

wherein Bx is a heterocyclic base moiety.

Embodiment 901. The RNAi agent of embodiment 900, wherein the nucleoside comprising a sugar surrogate is GNA.

Embodiment 902. The RNAi agent of embodiment 900 or 901, wherein at least one nucleoside comprising a sugar surrogate is one of the nine 5'-most nucleosides of the RNAi antisense modified oligonucleotide.

Embodiment 903. The RNAi agent of any of embodiments 857-902, wherein the modified oligonucleotide has a region of alternating nucleoside types having the motif ABABA, wherein each A is a stereo-standard nucleoside of a first type and each B is a stereo-standard nucleoside of a second type, wherein the first type and the second type are different from one another.

Embodiment 904. The RNAi agent of embodiment 903, wherein A and B are selected from 2'-F substituted nucleosides, 2'-OMe substituted nucleosides, and stereo-standard RNA nucleosides.

Embodiment 905. The RNAi agent of any of embodiments 857-904, wherein the 5'-end of the RNAi antisense modified oligonucleotide comprises a terminal group.

Embodiment 906. The RNAi agent of embodiment 905, wherein the terminal group is a stabilized phosphate group.

Embodiment 907. The RNAi agent of embodiment 906, wherein the stabilized phosphate group is a 5'-vinyl phosphonate or a 5'-cyclopropyl phosphonate.

Embodiment 908. The RNAi agent of embodiment 905, wherein the terminal group is selected from

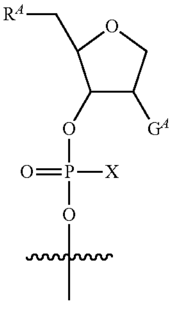

or

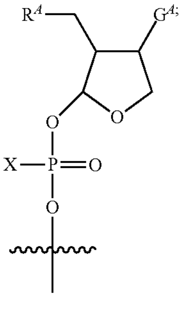

Wherein $R^A$ is OH, OP(=O)OH, OP(=O)SH or a stabilized phosphate group;

$G^A$ is H, OH, OMe, MOE, or a halogen;

X is OH, SH, or $NSO_2R_2$;

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_5$ alkynyl, substituted $C_1$-$C_6$ alkyl, substituted $C_1$-$C_5$ alkenyl substituted $C_1$-$C_6$ alkynyl, and a conjugate group.

Embodiment 909. The RNAi agent of embodiment 908, wherein $G^A$ is selected from H or OH and X is SH.

Embodiment 910. The RNAi agent of any of embodiments 858-909, wherein at least one internucleoside linking group of the RNAi sense modified oligonucleotide is an internucleoside linking group of Formula XVII.

Embodiment 911. The RNAi agent of embodiment 910, wherein at least one of the five 5'-most internucleoside linking groups of the RNAi sense modified oligonucleotide is an internucleoside linking group of Formula XVII.

Embodiment 912. The RNAi agent of embodiment 910, wherein at least two of the five 5'-most internucleoside linking groups of the RNAi sense modified oligonucleotide are internucleoside linking groups of Formula XVII.

Embodiment 913. The RNAi agent of embodiment 910, wherein the two 5'-most internucleoside linking groups of the RNAi sense modified oligonucleotide are internucleoside linking groups of Formula XVII.

Embodiment 914. The RNAi agent of any of embodiments 910-913, wherein at least one of the five 3'-most internucleoside linking groups of the RNAi sense modified oligonucleotide is an internucleoside linking group of Formula XVII.

Embodiment 915. The RNAi agent of any of embodiments 910-913, wherein at least two of the five 3'-most internucleoside linking groups of RNAi sense modified oligonucleotide is an internucleoside linking group of Formula XVII.

Embodiment 916. The RNAi agent of any of embodiments 910-913, wherein the two 3'-most internucleoside linking groups are internucleoside linking groups of Formula XVII.

Embodiment 917. The RNAi agent of embodiment 910, wherein the two 3'-most and the two 5'-most internucleoside linking groups of the RNAi sense oligonucleotide are internucleoside linking groups of Formula XVII, and the remaining internucleoside linking groups of the RNAi sense oligonucleotide are phosphodiester internucleoside linkages.

Embodiment 918. The RNAi agent of any of embodiments 910-917, wherein for each internucleoside linking group of Formula XVII, $R_1$ is H and T is $SO_2Me$.

Embodiment 919. The RNAi agent of any of embodiments 910-918, wherein the RNAi sense modified oligonucleotide consists of 21 linked nucleosides, and the internucleoside linkage motif is selected from: ooooooooooooooooooaa, aaooooooooooooooooaa, ooooooooooooooooooaa, or ssooooaoaaaooooooooo, wherein each "a" represents an internucleoside linkage of Formula XVII, each "s" represents a phosphorothioate internucleoside linkage, and each "o" represents a phosphodiester internucleoside linkage.

Embodiment 920. The RNAi agent of embodiment 919, wherein the internucleoside linkage motif of the RNAi sense modified oligonucleotide is selected from ooooooooooooooooooaa, aaooooooooooooooooaa, or ooooooooooooooooooaa, wherein each "a" represents an internucleoside linkage of Formula XVII, each "s" represents a phosphorothioate internucleoside linkage, and each "o" represents a phosphodiester internucleoside linkage.

Embodiment 921. The RNAi agent of embodiment 919 or 920, wherein the sugar motif of the RNAi sense modified oligonucleotide is selected from: yyyyyyfyfffyyyyyyyyyy or fyfyfyfyfyfyfyfyfyfyf, wherein "y" represents a 2'-OMe sugar moiety and "f" represents a 2'-F sugar moiety.

Embodiment 922. The RNAi agent of embodiment 921, wherein the RNAi sense modified oligonucleotide has an internucleoside linkage motif of aaooooooooooooooooaa wherein each "a" represents an internucleoside linkage of Formula XVII, each "s" represents a phosphorothioate internucleoside linkage, and each "o" represents a phosphodiester internucleoside linkage, and a sugar motif of yyyyyyfyfffyyyyyyyyyy, wherein "y" represents a 2'-OMe sugar moiety and "f" represents a 2'-F sugar moiety.

Embodiment 923. The RNAi agent of any of embodiments 919-922 wherein each "a" is a mesyl phosphoramidate linkage.

Embodiment 924. The RNAi agent of any of embodiments 910-923, wherein at least one region of the RNAi sense modified oligonucleotide has structure A, B, C, D, or E.

Embodiment 925. The RNAi agent of embodiment 924, wherein at least one region having structure A, B, C, D, or E is at the 3' end of the RNAi sense modified oligonucleotide.

Embodiment 926. The RNAi agent of embodiment 924, wherein at least one region having structure A, B, C, D, or E is at the 5' end of the RNAi sense modified oligonucleotide.

Embodiment 927. The RNAi agent of any of embodiments 910-926, wherein at least one region of the RNAi sense modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

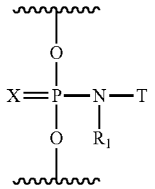

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 928. The RNAi agent of embodiment 927, wherein at least one region having the formula $(N_{g1})_{L1}(N_{g2})_{L2}(N_{g3})_{L3}$ is at the 3' end of the RNAi sense modified oligonucleotide.

Embodiment 929. The RNAi agent of embodiment 928, wherein $L_1$ and $L_2$ are internucleoside linking groups of Formula XVII, wherein $R_1$ is H and T is $SO_2Me$, and $L_3$ is a phosphodiester internucleoside linkage.

Embodiment 930. The RNAi agent of embodiment 927, wherein at least one region having the formula $(N_{g1})_{L1}(N_{g2})_{L2}(N_{g3})_{L3}$ is at the 5' end of the RNAi sense modified oligonucleotide.

Embodiment 931. The RNAi agent of embodiment 930, wherein $L_1$ is a phosphodiester internucleoside linking group and $L_2$ and $L_3$ are each internucleoside linking groups of Formula XVII, wherein $R_1$ is H and T is $SO_2Me$.

Embodiment 932. The RNAi agent of any of embodiments 858-931, wherein the RNAi sense modified oligonucleotide comprises a 3' terminal group and/or a 5' terminal group.

Embodiment 933. The RNAi agent of any of embodiments 858-932, wherein the RNAi sense strand comprises a conjugate group.

Embodiment 934. The RNAi agent of embodiment 933, wherein the conjugate group comprises a cell-targeting moiety.

Embodiment 935. The RNAi agent of embodiment 933, wherein the conjugate group comprises a carbohydrate or carbohydrate cluster.

Embodiment 936. The RNAi agent of embodiment 933, wherein the conjugate group comprises at least one GalNAc.

Embodiment 937. The RNAi agent of embodiment 933, wherein the conjugate group comprises a $C_{10}$-$C_{20}$ alkyl chain.

Embodiment 938. The RNAi agent of embodiment 933, wherein the conjugate group comprises $C_{16}$ alkyl.

Embodiment 939. The RNAi agent of any of embodiments 858-938, wherein the double-stranded region of the oligonucleotide duplex is at least 15 nucleosides.

Embodiment 940. The RNAi agent of any of embodiments 858-938, wherein the double-stranded region of the oligonucleotide duplex is at least 17 nucleosides.

Embodiment 941. The RNAi agent of any of embodiments 858-938, wherein the double-stranded region of the oligonucleotide duplex is at least 19 nucleosides.

Embodiment 942. The RNAi agent of any of embodiments 858-938, wherein the double-stranded region of the oligonucleotide duplex is exactly 19 nucleosides.

Embodiment 943. The modified oligonucleotide of any of embodiments 705-841, wherein each nucleoside of the modified oligonucleotide is a modified nucleoside comprising a modified sugar moiety.

Embodiment 944. The modified oligonucleotide of embodiment 943, wherein each modified sugar moiety is independently selected from a bicyclic sugar moiety and a 2'-substituted furanosyl sugar moiety.

Embodiment 945. The modified oligonucleotide of embodiment 943 or 944, wherein each modified sugar moiety comprises the same modification.

Embodiment 946. The modified oligonucleotide of any of embodiments 943-945, wherein each modified sugar moiety is selected from a 2'-OMe sugar moiety, a 2'-MOE sugar moiety, and a 2'-NMA sugar moiety.

Embodiment 947. The modified oligonucleotide of embodiment 943 or 944, wherein the three 3'-most nucleosides comprise a bicyclic sugar moiety, and the remaining nucleosides comprise a 2'-substituted furanosyl sugar moiety.

Embodiment 948. The modified oligonucleotide of embodiment 943 or 944, wherein the four 3'-most nucleosides comprise a bicyclic sugar moiety, and the remaining nucleosides comprise a 2'-substituted furanosyl sugar moiety.

Embodiment 949. The modified oligonucleotide of embodiment 943 or 944, wherein the five 3'-most nucleosides comprise a bicyclic sugar moiety, and the remaining nucleosides comprise a 2'-substituted furanosyl sugar moiety.

Embodiment 950. The modified oligonucleotide of embodiment 943 or 944, wherein the six 3'-most nucleosides comprise a bicyclic sugar moiety, and the remaining nucleosides comprise a 2'-substituted furanosyl sugar moiety.

Embodiment 951. The modified oligonucleotide of any of embodiments 947-950, wherein each bicyclic sugar moiety is selected from among cEt, LNA, and ENA.

Embodiment 952. The modified oligonucleotide of embodiment 951, wherein the bicyclic sugar moiety is cEt.

Embodiment 953. The modified oligonucleotide of any of embodiments 947-952, wherein the 2'-substituted furanosyl sugar moiety is selected from 2'-OMe, 2'-MOE, and 2'-F.

Embodiment 954. The modified oligonucleotide of any of embodiments 943-953, wherein at least one of the ten 5'-most linking groups of the modified oligonucleotide is an internucleoside linking group of Formula XVII.

Embodiment 955. The modified oligonucleotide of embodiment 954, wherein at least 2 of the ten 5'-most linking groups of the modified oligonucleotide are internucleoside linking groups of Formula XVII.

Embodiment 956. The modified oligonucleotide of embodiment 954, wherein at least 3 of the ten 5'-most linking groups of the modified oligonucleotide are internucleoside linking groups of Formula XVII.

Embodiment 957. The modified oligonucleotide of embodiment 954, wherein at least 4 of the ten 5'-most linking groups of the modified oligonucleotide are internucleoside linking groups of Formula XVII.

Embodiment 958. The modified oligonucleotide of embodiment 954, wherein at least 5 of the ten 5'-most linking groups of the modified oligonucleotide are internucleoside linking groups of Formula XVII.

Embodiment 959. The modified oligonucleotide of embodiment 954, wherein at least 6 of the ten 5'-most linking groups of the modified oligonucleotide are internucleoside linking groups of Formula XVII.

Embodiment 960. The modified oligonucleotide of embodiment 954, wherein the two 5'-most internucleoside linking groups are internucleoside linking groups of Formula XVII.

Embodiment 961. The modified oligonucleotide of any of embodiments 943-960, wherein at least one of the ten 3'-most internucleoside linking groups of the modified oligonucleotide is an internucleoside linking group of Formula XVII.

Embodiment 962. The modified oligonucleotide of embodiment 961, wherein at least 2 of the ten 3'-most internucleoside linking groups of the modified oligonucleotide are internucleoside linking groups of Formula XVII.

Embodiment 963. The modified oligonucleotide of embodiment 961, wherein at least 3 of the ten 3'-most internucleoside linking groups are internucleoside linking groups of Formula XVII.

Embodiment 964. The modified oligonucleotide of embodiment 961, wherein at least 4 of the ten 3'-most internucleoside linking groups are internucleoside linking groups of Formula XVII.

Embodiment 965. The modified oligonucleotide of embodiment 961, wherein at least 5 of the ten 3'-most internucleoside linking groups are internucleoside linking 961 of Formula XVII.

Embodiment 966. The modified oligonucleotide of embodiment 961, wherein at least 6 of the ten 3'-most internucleoside linking groups are internucleoside linking groups of Formula XVII.

Embodiment 967. The modified oligonucleotide of embodiment 961, wherein the two 3'-most internucleoside linking groups of the modified oligonucleotide are internucleoside linking groups of Formula XVII.

Embodiment 968. The modified oligonucleotide of any of embodiments 943-953, wherein the modified oligonucleotide comprises at least one block of at least 3 consecutive internucleoside linking groups of Formula XVII.

Embodiment 969. The modified oligonucleotide of any of embodiments 943-953, wherein the modified oligonucleotide comprises at least one block of at least 4 consecutive internucleoside linking groups of Formula XVII.

Embodiment 970. The modified oligonucleotide of any of embodiments 943-953, wherein the modified oligonucleotide comprises at least one block of at least 5 consecutive internucleoside linking groups of Formula XVII.

Embodiment 971. The modified oligonucleotide of any of embodiments 943-953, wherein the modified oligonucleotide comprises at least one block of at least 6 consecutive internucleoside linking groups of Formula XVII.

Embodiment 972. The modified oligonucleotide of any of embodiments 968-971, wherein at least one block of consecutive internucleoside linking groups of Formula XVII is at the 5' end of the modified oligonucleotide.

Embodiment 973. The modified oligonucleotide of any of embodiments 968-971, wherein at least one block of consecutive internucleoside linking groups of Formula XVII is at the 3' end of the modified oligonucleotide.

Embodiment 974. The modified oligonucleotide of any of embodiments 943-973, wherein for each internucleoside linking group of Formula XVII, $R_1$ is H and T is $SO_2Me$.

Embodiment 975. The modified oligonucleotide of any of embodiments 943-953, wherein the internucleoside linkage motif is selected from: aaaaaasssssssss, sssssaaaaaassss, or sssssssssaaaaaa, wherein each "a" represents an internucleoside linkage of Formula XVII, each "s" represents a phosphorothioate internucleoside linkage, and each "o" represents a phosphodiester internucleoside linkage.

Embodiment 976. The modified oligonucleotide of embodiment 975, wherein each "a" represents a mesyl phosphoramidate internucleoside linkage.

Embodiment 977. The modified oligonucleotide of any of embodiments 705-841, wherein the modified oligonucleotide comprises a deoxy region consisting of 6-11 linked nucleosides wherein each nucleoside of the deoxy region is either a modified nucleoside or a stereo-standard DNA nucleoside and wherein at least 3 contiguous nucleosides of the deoxy region are stereo-standard DNA nucleosides and not more than three nucleosides of the deoxy region are modified nucleosides.

Embodiment 978. The modified oligonucleotide of embodiment 977, wherein at least 5 contiguous nucleosides of the deoxy region are stereo-standard DNA nucleosides.

Embodiment 979. The modified oligonucleotide of embodiment 977, wherein at least 6 contiguous nucleosides of the deoxy region are stereo-standard DNA nucleosides.

Embodiment 980. The modified oligonucleotide of embodiment 977, wherein at least 7 contiguous nucleosides of the deoxy region are stereo-standard DNA nucleosides.

Embodiment 981. The modified oligonucleotide of embodiment 977, wherein at least 8 contiguous nucleosides of the deoxy region are stereo-standard DNA nucleosides.

Embodiment 982. The modified oligonucleotide of any of embodiments 977-981, wherein the deoxy region consists of 8-10 linked nucleosides.

Embodiment 983. The modified oligonucleotide of any of embodiments 977-981, wherein the deoxy region consists of 9 linked nucleosides.

Embodiment 984. The modified oligonucleotide of any of embodiments 977-981, wherein the deoxy region consists of 10 linked nucleosides.

Embodiment 985. The modified oligonucleotide of any of embodiments 977-981, wherein the deoxy region consists of 11 linked nucleosides.

Embodiment 986. The modified oligonucleotide of any of embodiments 977-981, wherein at least 6 nucleosides of the deoxy region are stereo-standard DNA nucleosides.

Embodiment 987. The modified oligonucleotide of any of embodiments 977-981, wherein at least 7 nucleosides of the deoxy region are stereo-standard DNA nucleosides.

Embodiment 988. The modified oligonucleotide of any of embodiments 977-981, wherein at least 8 nucleosides of the deoxy region are stereo-standard DNA nucleosides.

Embodiment 989. The modified oligonucleotide of any of embodiments 977-981, wherein at least 9 nucleosides of the deoxy region are stereo-standard DNA nucleosides.

Embodiment 990. The modified oligonucleotide of any of embodiments 977-989 wherein exactly two nucleosides of the deoxy region are modified nucleosides.

Embodiment 991. The modified oligonucleotide of any of embodiments 977-989 wherein exactly one nucleoside of the deoxy region is a modified nucleoside.

Embodiment 992. The modified oligonucleotide of any of embodiments 977-991 wherein at least one modified nucleoside of the deoxy region is a stereo-standard modified nucleoside or bicyclic nucleoside selected from a β-D-LNA nucleoside, an α-L-LNA nucleoside, an ENA nucleoside, a cEt nucleoside, a 2'-MOE nucleoside, a 2'-OMe nucleoside, a 2'-F nucleoside, and a 5'-alkyl nucleoside.

Embodiment 993. The modified oligonucleotide of any of embodiments 977-991, wherein at least one modified nucleoside of the deoxy region is stereo-non-standard nucleoside.

Embodiment 994. The modified oligonucleotide of embodiment 993, wherein the at least one is stereo-non-standard nucleoside of the deoxy region is a stereo-non-standard DNA nucleoside.

Embodiment 995. The modified oligonucleotide of embodiment 994, wherein the stereo-non-standard DNA nucleoside is selected from a stereo-non-standard DNA nucleoside having: Formula I, Formula II, Formula III, Formula IV, Formula V, Formula VI, and Formula VII.

Embodiment 996. The modified oligonucleotide of embodiment 995, wherein the stereo-non-standard DNA nucleoside is selected from a stereo-non-standard DNA nucleoside having: Formula V and Formula II.

Embodiment 997. The modified oligonucleotide of embodiment 996, wherein at least one stereo-non-standard nucleoside of the deoxy region is a substituted stereo-non-standard nucleoside.

Embodiment 998. The modified oligonucleotide of embodiment 997, wherein at least one substituted stereo-non-standard nucleoside has a 2'-substituent selected from: 2'-MOE, 2'-OMe, 2'-F, or 2'-OH.

Embodiment 999. The modified oligonucleotide of any of embodiments 977-998, wherein the $2^{nd}$ nucleoside from the 5'-end of the deoxy region is a modified nucleoside.

Embodiment 1000. The modified oligonucleotide of any of embodiments 977-998, wherein the $3^{rd}$ nucleoside from the 5'-end of the deoxy region is a modified nucleoside.

Embodiment 1001. The modified oligonucleotide of any of embodiments 977-998 wherein the $4^{th}$ nucleoside from the 5'-end of the deoxy region is a modified nucleoside.

Embodiment 1002. The modified oligonucleotide of any of embodiments 999-1001, wherein the modified nucleoside in the deoxy region is a 2'-OMe nucleoside.

Embodiment 1003. The modified oligonucleotide of any of embodiments 977-989, wherein each nucleoside of the deoxy region is a stereo-standard DNA nucleoside.

Embodiment 1004. The modified oligonucleotide of any of embodiments 977-1003 wherein at least one internucleoside linking group within the deoxy region is an internucleoside linking group of Formula XVII.

Embodiment 1005. The modified oligonucleotide of any of embodiments 977-1004, wherein the internucleoside linking group linking the $1^{st}$ and $2^{nd}$ nucleosides of the deoxy region as counted from the 5'-end of the deoxy region is an internucleoside linking group of Formula XVII.

Embodiment 1006. The modified oligonucleotide of any of embodiments 977-1005, wherein the internucleoside linking group linking the $2^{nd}$ and $3^{rd}$ nucleosides of the deoxy region as counted from the 5'-end of the deoxy region is an internucleoside linking group of Formula XVII.

Embodiment 1007. The modified oligonucleotide of any of embodiments 977-1006, wherein the internucleoside linking group linking the $3^{rd}$ and $4^{th}$ nucleosides of the deoxy region as counted from the 5'-end of the deoxy region is an internucleoside linking group of Formula XVII.

Embodiment 1008. The modified oligonucleotide of any of embodiments 977-1007, wherein the internucleoside linking group linking the $4^{th}$ and $5^{th}$ nucleosides of the deoxy region as counted from the 5'-end of the deoxy region is an internucleoside linking group of Formula XVII.

Embodiment 1009. The modified oligonucleotide of any of embodiments 977-1008, wherein one internucleoside linking group in the deoxy region is a linking group of Formula XVII and the other internucleoside linking groups of the deoxy region are independently selected from phosphodiester and phosphorothioate internucleoside linking groups.

Embodiment 1010. The modified oligonucleotide of any of embodiments 977-1008, wherein two internucleoside linking groups in the deoxy region are linking groups of Formula XVII and the other internucleoside linking groups of the deoxy region are independently selected from phosphodiester and phosphorothioate internucleoside linking groups.

Embodiment 1011. The modified oligonucleotide of any of embodiments 977-1008, wherein three internucleoside linking groups in the deoxy region are linking groups linking groups of Formula XVII and the other internucleoside linking groups of the deoxy region are independently selected from phosphodiester and phosphorothioate internucleoside linking groups.

Embodiment 1012. The modified oligonucleotide of any of embodiments 977-1008, wherein four internucleoside linking groups in the deoxy region are linking groups linking groups of Formula XVII and the other internucleoside linking groups of the deoxy region are each phosphodiester or phosphorothioate internucleoside linking groups.

Embodiment 1013. The modified oligonucleotide of any of embodiments 1009-1012, wherein the internucleoside linking groups of Formula XVII are linking the $1^{st}$ and $2^{nd}$, $2^{nd}$ and $3^{rd}$, $3^{rd}$ and $4^{th}$, and/or the $4^{th}$ and $5^{th}$ nucleosides of the deoxy region, as counted from the 5'-end of the deoxy region.

Embodiment 1014. The modified oligonucleotide of any of embodiments 877-1013, wherein the deoxy region comprises at least one region having structure A, B, C, D, or E.

Embodiment 1015. The modified oligonucleotide of embodiment 1014, wherein the region having structure A, B, C, D, or E is at the 3' end of the deoxy region.

Embodiment 1016. The modified oligonucleotide of embodiment 1014, wherein the region having structure A, B, C, D, or E is at the 5' end of the deoxy region.

Embodiment 1017. The modified oligonucleotide of any of embodiments 877-1016, wherein the deoxy region comprises at least one region having the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

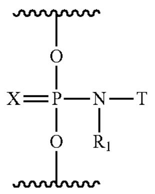

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 1018. The modified oligonucleotide of embodiment 1017, wherein the region having the formula $(N_{g1})_{L1}(N_{g2})_{L2}(N_{g3})_{L3}$ is at the 3' end of the deoxy region.

Embodiment 1019. The modified oligonucleotide of embodiment 1017, wherein the region having the formula $(N_{g1})_{L1}(N_{g2})_{L2}(N_{g3})_{L3}$ is at the 5' end of the deoxy region.

Embodiment 1020. The modified oligonucleotide of any of embodiments 1004-1019, wherein for each internucleoside linkage of Formula XVII, $R_1$ is H and T is $SO_2Me$.

Embodiment 1021. The modified oligonucleotide of any of embodiments 877-1020 wherein the deoxy region is flanked on the 5' side by a 5'-region consisting of 1-6 linked 5'-region nucleosides and on the 3' side by a 3'-region consisting of 1-6 linked 3'-region nucleosides; wherein the 3'-most nucleoside of the 5'-region comprises a modified sugar moiety; and the 5'-most nucleoside of the 3'-region comprises a modified sugar moiety.

Embodiment 1022. The modified oligonucleotide of embodiment 1021, wherein the deoxy region consists of 7-11 linked nucleosides, and has the formula:

$$(N_{d1})_{L1}(N_{d2})_{L2}(N_{d3})_{L3}(N_{d4})_{L4}[N_d)_{L5}]_q;$$

wherein $N_{d1}$, $N_{d2}$, $N_{d3}$, $N_{d4}$ are independently selected from among a stereo-standard DNA nucleoside, a stereo-non-standard DNA nucleoside, or a 2'-substituted nucleoside;

with the proviso that no more than one of $N_{d1}$, $N_{d2}$, $N_3$, or $N_{d4}$ is a 2'-substituted nucleoside;

each $N_d$ is independently selected from among a stereo-standard DNA nucleoside and a stereo-non-standard DNA nucleoside;

q is from 3-8;

wherein each of $L_1$, $L_2$, $L_3$, $L_4$, and each $L_5$ is an internucleoside linkage;

wherein at least two of $L_1$, $L_2$, $L_3$, $L_4$ are internucleoside linkages of Formula XVII.

Embodiment 1023. The modified oligonucleotide of embodiment 1022, wherein one of $N_{d1}$, $N_{d2}$, $N_{d3}$, or $N_{d4}$ is a 2'-substituted nucleoside.

Embodiment 1024. The modified oligonucleotide of embodiment 1023, wherein the 2'-substituted nucleoside is a 2'-OMe nucleoside.

Embodiment 1025. The modified oligonucleotide of embodiment 1024, wherein the 2'-OMe nucleoside is a stereo-standard 2'-OMe nucleoside.

Embodiment 1026. The modified oligonucleotide of any of embodiments 1022-1025, wherein the 2'-substituted nucleoside is $N_{d2}$ Embodiment 1027. The modified oligonucleotide of embodiment 1022, wherein each of $N_{d1}$, $N_{d2}$, $N_{d3}$, $N_{d4}$ and each $N_d$ is a DNA nucleoside.

Embodiment 1028. The modified oligonucleotide of embodiment 1027, wherein each DNA nucleoside is a stereo-standard DNA nucleoside.

Embodiment 1029. The modified oligonucleotide of any of embodiments 1022-1028, wherein $L_1$ and $L_2$ are internucleoside linkages of Formula XVI.

Embodiment 1030. The modified oligonucleotide of any of embodiments 1022-1028, wherein $L_2$ and $L_3$ are internucleoside linkages of Formula XVI.

Embodiment 1031. The modified oligonucleotide of any of embodiments 1022-1028, wherein $L_3$ and $L_4$ are internucleoside linkages of Formula XVI.

Embodiment 1032. The modified oligonucleotide of any of embodiments 1022-1028, wherein $L_1$, $L_2$, and $L_3$ are internucleoside linkages of Formula XVI.

Embodiment 1033. The modified oligonucleotide of any of embodiments 1022-1028, wherein $L_2$, $L_3$, and $L_4$ are internucleoside linkages of Formula XVI.

Embodiment 1034. The modified oligonucleotide of any of embodiments 1022-1028, wherein $L_1$, $L_2$, $L_3$, and $L_4$ are internucleoside linkages of Formula XVI.

Embodiment 1035. The modified oligonucleotide of embodiments 1029-1034, wherein each internucleoside linkage that is not an internucleoside linkage of Formula XVII is a phosphorothioate internucleoside linkage.

Embodiment 1036. The modified oligonucleotide of any of embodiments 1029-1035, wherein for each internucleoside linkage of Formula XVII, $R_1$ is H and T is $SO_2Me$ Embodiment 1037. The modified oligonucleotide of any of embodiments 1021-1036, wherein the 5'-region consists of 2-5 linked nucleosides.

Embodiment 1038. The modified oligonucleotide of embodiment 1037, wherein the 5'-region consists of 3 linked nucleosides.

Embodiment 1039. The modified oligonucleotide of embodiment 1037, wherein the 5'-region consists of 5 linked nucleosides.

Embodiment 1040. The modified oligonucleotide of any of embodiments 1021-1039 wherein each nucleoside of the 5'-region is a modified nucleoside.

Embodiment 1041. The modified oligonucleotide of any of embodiments 1021-1040, wherein each nucleoside of the 5'-region is a modified nucleoside comprising a modified sugar.

Embodiment 1042. The modified oligonucleotide of any of embodiments 1021-1041, wherein at least one nucleoside of the 5'-region comprises a 2'-substituted furanosyl sugar moiety.

Embodiment 1043. The modified oligonucleotide of any of embodiments 1021-1041, wherein each nucleoside of the 5'-region comprises a 2'-substituted furanosyl sugar moiety.

Embodiment 1044. The modified oligonucleotide of any of embodiments 1021-1043, wherein each 2'-substituted furanosyl sugar moiety of the 5'-region has a 2'-substituent selected from among 2'-MOE, 2'-OMe, and 2'-NMA.

Embodiment 1045. The modified oligonucleotide of any of embodiments 1021-1042 or 1044, wherein at least one nucleoside of the 5'-region comprises a bicyclic furanosyl sugar moiety.

Embodiment 1046. The modified oligonucleotide of any of embodiments 1021-1042 or 1044-1045, wherein each nucleoside of the 5'-region comprises a bicyclic furanosyl sugar moiety.

Embodiment 1047. The modified oligonucleotide of embodiment 341 or 342, wherein each bicyclic sugar moiety of the 5'-region is selected from among cEt, LNA, and ENA.

Embodiment 1048. The modified oligonucleotide of embodiment 1047, wherein each bicyclic sugar moiety of the 5'-region is a cEt sugar moiety.

Embodiment 1049. The modified oligonucleotide of any of embodiments 1021-1039, 1042 or 1045, wherein at least one nucleoside of the 5' region is a stereo-standard DNA nucleoside.

Embodiment 1050. The modified oligonucleotide of any of embodiments 1021-1048, wherein at least one nucleoside of the 5' region is a stereo-non-standard nucleoside.

Embodiment 1051. The modified oligonucleotide of any of embodiments 1021-1050, wherein each nucleobase of the 5'-region is independently selected from among thymine, uracil, guanine, cytosine, 5-methylcytosine, and adenine.

Embodiment 1052. The modified oligonucleotide of any of embodiments 1021-1051, wherein the 3'-region consists of 2-5 linked nucleosides.

Embodiment 1053. The modified oligonucleotide of embodiment 1052, wherein the 3'-region consists of 3 linked nucleosides.

Embodiment 1054. The modified oligonucleotide of embodiment 1052, wherein the 3'-region consists of 5 linked nucleosides.

Embodiment 1055. The modified oligonucleotide of any of embodiments 1021-1054, wherein each nucleoside of the 3'-region is a modified nucleoside.

Embodiment 1056. The modified oligonucleotide of any of embodiments 1021-1055, wherein each nucleoside of the 3'-region is a modified nucleoside comprising a modified sugar.

Embodiment 1057. The modified oligonucleotide of any of embodiments 1021-1056, wherein at least one nucleoside of the 3'-region comprises a 2'-substituted furanosyl sugar moiety.

Embodiment 1058. The modified oligonucleotide of any of embodiments 1021-1057, wherein each nucleoside of the 3'-region comprises a 2'-substituted furanosyl sugar moiety.

Embodiment 1059. The modified oligonucleotide of any of embodiments 1021-1058, wherein each 2'-substituted furanosyl sugar moiety of the 3'-region has a 2'-substituent selected from among 2'-MOE, 2'-OMe, and 2'-NMA.

Embodiment 1060. The modified oligonucleotide of any of embodiments 1021-1057 or 1059, wherein at least one nucleoside of the 3'-region comprises a bicyclic furanosyl sugar moiety.

Embodiment 1061. The modified oligonucleotide of any of embodiments 1021-1057 or 1059-1060, wherein each nucleoside of the 3'-region comprises a bicyclic furanosyl sugar moiety.

Embodiment 1062. The modified oligonucleotide of embodiment 1060 or 1061, wherein each bicyclic sugar moiety of the 3'-region is selected from among cEt, LNA, and ENA.

Embodiment 1063. The modified oligonucleotide of embodiment 1062, wherein each bicyclic sugar moiety of the 3'-region is a cEt sugar moiety.

Embodiment 1064. The modified oligonucleotide of any of embodiments 1021-1054, 1057 or 1060, wherein at least one nucleoside of the 3' region is a stereo-standard DNA nucleoside.

Embodiment 1065. The modified oligonucleotide of any of embodiments 1021-1064, wherein at least one nucleoside of the 3' region is a stereo-non-standard nucleoside.

Embodiment 1066. The modified oligonucleotide of any of embodiments 1021-1065, wherein each nucleobase of the 3'-region is independently selected from among thymine, uracil, guanine, cytosine, 5-methylcytosine, and adenine.

Embodiment 1067. The modified oligonucleotide of any of embodiments 1021-1066 wherein the modified oligonucleotide is a gapmer.

Embodiment 1068. The modified oligonucleotide of any of embodiments 1021-1066, wherein the modified oligonucleotide has a sugar motif selected from kkkddddddddddkkk and kkkdyddddddddkkk, wherein each "k" represents a cEt sugar moiety, "y" represents a 2'-OMe sugar moiety, and each "d" represents a β-D-2'-deoxyribosyl sugar moiety.

Embodiment 1069. The modified oligonucleotide of any of embodiments 1021-1066, wherein the modified oligonucleotide has an internucleoside linkage motif selected from: ssssssssssssssa, sssssssssssssas, ssssssssssssass, sssssssssssasss, ssssssssssassss, sssssssssasssss, ssssssssassssss, sssssssasssssss, ssssssassssssss, sssssasssssssss, ssssassssssssss, sssasssssssssss, ssassssssssssss, sasssssssssssss, assssssssssssss, sssssssssssssaa, ssssssssssssaas, sssssssssssaass, ssssssssssaasss, sssssssssaassss, ssssssssaasssss, sssssssaassssss, ssssssaasssssss, sssssaassssssss, ssssaasssssssss, sssaassssssssss, ssaasssssssssss, saassssssssssss, aasssssssssssss, aaaaaaaaaaaaaaa, ssaaaaaaaaaaass, ssaaaaaaaaaasss, sssaaaaaaaaasss, aassssssssssaaa, sssaaasssssssss, ssssaaassssssss, sssaaaassssssss, ssaaassssssssss, ssaaaasssssssss, ssaaaaassssssss, ssaaaaaasssssss, ssaaaaaaassssss, ssaaaaaaaasssss, ssaaaaaaaaassss, sssssssssaaaass, ssssssssaaaaass, sssssssaaaaaass, ssssssaaaaaaass, sssssaaaaaaaass, ssssaaaaaaaaass, sssaaaaaaaaaass, sssaaaaaaaaaaass, ssasasasasasass, sssasasasasasss, ooossssssssssoo, soossssssssssos, aoosssssssssooa, aoasssssssssaoa, aoaaaassssssaoa, aoossssssssssoa, ooasssssssssaoo, aoosaasssssssoa, aossaassssssssoa, aooaaaasssssaoa, aoossssssaaaaoa, sssssaaasssssss, ssssssaaassssss, sssssssaaasssss, ssssssssaaassss, sssssssssaaasss, ssssaaaasssssss, sssssaaaassssss, ssssssaaaasssss, sssssssaaaassss, ssssssssaaaasss, sssaassssssaass, sssaasssssaasss, sssaassssaassss, sssaasssaasssss, sssaassaassssss, sssaasaasssssss, ssaassssssssaass, ssssaasssssaass, sssssaassssaass, ssssssaasssaass, sssssssaassaass, ssssssssaasaass, ssssaasssaassss, sssssaasaasssss, ssssssssssssssS, aaassssssssssss, aaassssssssssaa, aaaaaasssssssss, aooosaassssssooaa, aooosssssssssooaa, soooaassssssssooss, sooosaasssssssooss, soooossaasssssooss, sooosssssaassooss, sssaaaassssssss, ssssaaaaaasssss, or sssssssssaaaaaa wherein each "a" represents an internucleoside linkage of Formula XVII, each "s" represents a phosphorothioate internucleoside linkage, and each "o" represents a phosphodiester internucleoside linkage.

Embodiment 1070. The modified oligonucleotide of embodiment 1069, wherein the modified oligonucleotide has an internucleoside linkage motif selected from: sssaaaassssssss, sssaaasssssssss, ssssaaassssssss, ssssaassssssaass, sssaassssssssss, ssssaasssssssss, sssssaassssssss, or sssssssssaassss, wherein each "a" represents an internucleoside linkage of Formula XVII, each "s" represents a phosphorothioate internucleoside linkage, and each "o" represents a phosphodiester internucleoside linkage.

Embodiment 1071. The modified oligonucleotide of embodiment 1069-1070, wherein each "a" represents a mesyl phosphoramidate internucleoside linkage.

Embodiment 1072. The modified oligonucleotide of any of embodiments 705-841, wherein the modified oligonucleotide is a CRISPR compound.

Embodiment 1073. The modified oligonucleotide of embodiment 1072, wherein the CRISPR compound consists of 20-50 or 29-32 linked nucleosides.

Embodiment 1074. The modified oligonucleotide of any of embodiments 794-1073, wherein each X is O.

Embodiment 1075. The modified oligonucleotide of any of embodiments 794-1073, wherein each X is S.

Embodiment 1076. The modified oligonucleotide of any of embodiments 794-1075, wherein at least one $R_1$ is H.

Embodiment 1077. The modified oligonucleotide of any of embodiments 794-1075, wherein at least one $R_1$ is a $C_1$-$C_6$ alkyl.

Embodiment 1078. The modified oligonucleotide of embodiment 1077, wherein the at least one $R_1$ is methyl.

Embodiment 1079. The modified oligonucleotide of any of embodiments 794-1075, at least one $R_1$ is a substituted $C_1$-$C_6$ alkyl.

Embodiment 1080. The modified oligonucleotide of any of embodiments 794-1079, wherein at least one T comprises a conjugate group.

Embodiment 1081. The modified oligonucleotide of embodiment 1080, wherein the conjugate group comprises a cell-targeting moiety.

Embodiment 1082. The modified oligonucleotide of embodiment 1080, wherein the conjugate group comprises a carbohydrate or carbohydrate cluster.

Embodiment 1083. The modified oligonucleotide of any of embodiments 1080-1082, wherein the conjugate group comprises at least one GalNAc.

Embodiment 1084. The modified oligonucleotide of embodiment 1080, wherein the conjugate group comprises a $C_1$-$C_{20}$ alkyl chain.

Embodiment 1085. The modified oligonucleotide of embodiment 1084, wherein the conjugate group comprises $C_{16}$ alkyl.

Embodiment 1086. The modified oligonucleotide of any of embodiments 794-1085, wherein at least one T does not comprise a conjugate group.

Embodiment 1087. The modified oligonucleotide of any of embodiments 794-1079, wherein each T does not comprise a conjugate group.

Embodiment 1088. The modified oligonucleotide of any of embodiments 794-1087, wherein at least one T is $SO_2R_2$.

Embodiment 1089. The modified oligonucleotide of embodiment 1088, wherein $R_2$ is an aryl.

Embodiment 1090. The modified oligonucleotide of embodiment 1088, wherein $R_2$ is a substituted aryl.

Embodiment 1091. The modified oligonucleotide of embodiment 1088, wherein $R_2$ is a heterocycle.

Embodiment 1092. The modified oligonucleotide of embodiment 1088, wherein $R_2$ is a substituted heterocycle.

Embodiment 1093. The modified oligonucleotide of embodiment 1088, wherein $R_2$ is an aromatic heterocycle.

Embodiment 1094. The modified oligonucleotide of embodiment 1088, wherein $R_2$ is a substituted aromatic heterocycle.

Embodiment 1095. The modified oligonucleotide of embodiment 1088, wherein $R_2$ is a diazole.

Embodiment 1096. The modified oligonucleotide of embodiment 1088, wherein $R_2$ is a substituted diazole.

Embodiment 1097. The modified oligonucleotide of embodiment 1088, wherein $R_2$ is an amine.

Embodiment 1098. The modified oligonucleotide of embodiment 1088, wherein $R_2$ is a substituted amine.

Embodiment 1099. The modified oligonucleotide of embodiment 1088, wherein $R_2$ is a $C_1$-$C_6$ alkoxy, $C_1$-$C_6$ alkenyl, or $C_1$-$C_6$ alkynyl.

Embodiment 1100. The modified oligonucleotide of embodiment 1088, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 1101. The modified oligonucleotide of embodiment 1088, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 1102. The modified oligonucleotide of embodiment 1088, wherein $R_2$ comprises a carbohydrate or carbohydrate cluster.

Embodiment 1103. The modified oligonucleotide of embodiment 1088, wherein $R_2$ comprises at least one GalNAc.

Embodiment 1104. The modified oligonucleotide of embodiment 1088, wherein T is:

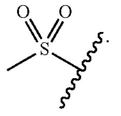 [SMILES: *S(C)(=O)=O]

Embodiment 1105. The modified oligonucleotide of embodiment 1088, wherein T is:

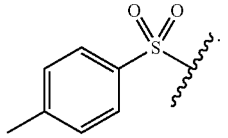 [SMILES: *S(=O)(=O)c1ccc(C)cc1]

Embodiment 1106. The modified oligonucleotide of embodiment 1088, wherein T is:

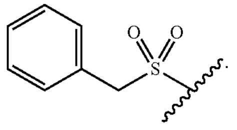 [SMILES: *S(=O)(=O)Cc1ccccc1]

Embodiment 1107. The modified oligonucleotide of embodiment 1088, wherein T is:

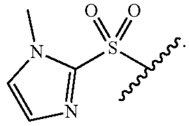 [SMILES: *S(=O)(=O)c1nccn1C]

Embodiment 1108. The modified oligonucleotide of embodiment 1088, wherein T is:

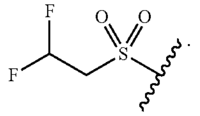

Embodiment 1109. The modified oligonucleotide of embodiment 1088, wherein T is:

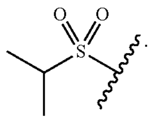 [SMILES: *S(=O)(=O)C(C)C]

Embodiment 1110. The modified oligonucleotide of embodiment 1088, wherein T is:

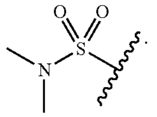 [SMILES: *S(=O)(=O)N(C)C]

Embodiment 1111. The modified oligonucleotide of embodiment 1088, wherein T is:

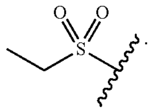 [SMILES: *S(=O)(=O)CC]

Embodiment 1112. The modified oligonucleotide of embodiment 1088, wherein T is:

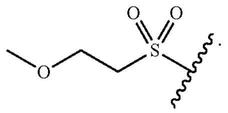 [SMILES: *S(=O)(=O)CCOC]

Embodiment 1113. The modified oligonucleotide of embodiment 1088, wherein T is:

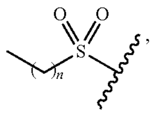

n wherein n is from 2 to 20.

Embodiment 1114. The modified oligonucleotide of embodiment 1113, wherein n is 15.

Embodiment 1115. The modified oligonucleotide of any of embodiments 794-1114, wherein at least one T is C(=O)$R_3$.

Embodiment 1116. The modified oligonucleotide of embodiment 1115, wherein $R_3$ is an aryl.

Embodiment 1117. The modified oligonucleotide of embodiment 1115, wherein $R_3$ is a substituted aryl.

Embodiment 1118. The modified oligonucleotide of embodiment 1115, wherein $R_3$ is $CH_3$.

Embodiment 1119. The modified oligonucleotide of embodiment 1115, wherein $R_3$ is $N(CH_3)_2$.

Embodiment 1120. The modified oligonucleotide of embodiment 1115, wherein $R_3$ is $OCH_3$.

Embodiment 1121. The modified oligonucleotide of embodiment 1115, wherein $R_3$ is a $C_1$-$C_6$ alkoxy.

Embodiment 1122. The modified oligonucleotide of embodiment 1115, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 1123. The modified oligonucleotide of embodiment 1115, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 1124. The modified oligonucleotide of embodiment 1115, wherein $R_3$ comprises a carbohydrate or carbohydrate cluster.

Embodiment 1125. The modified oligonucleotide of embodiment 1115, wherein $R_{23}$ comprises at least one GalNAc.

Embodiment 1126. The modified oligonucleotide of embodiment 1115, wherein T is:

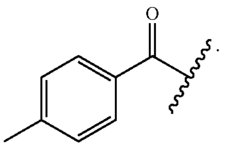 [SMILES: *C(=O)c1ccc(C)cc1]

Embodiment 1127. The modified oligonucleotide of embodiment 1115, wherein T is:

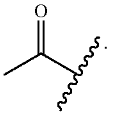 [SMILES: *C(C)=O]

Embodiment 1128. The modified oligonucleotide of embodiment 1115, wherein T is:

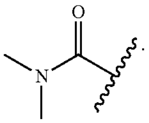 [SMILES: *C(=O)N(C)C]

Embodiment 1129. The modified oligonucleotide of embodiment 1115, wherein T is:

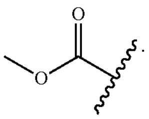 [SMILES: *C(=O)OC]

Embodiment 1130. The modified oligonucleotide of embodiment 1115, wherein T is:

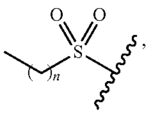

wherein n is from 2 to 20.

Embodiment 1131. The modified oligonucleotide of embodiment 1130, wherein n is 15.

Embodiment 1132. The modified oligonucleotide of any of embodiments 794-1131, wherein at least one T is P(=O)$R_4R_5$.

Embodiment 1133. The modified oligonucleotide of embodiment 1132, wherein $R_4$ is $OCH_3$.

Embodiment 1134. The modified oligonucleotide of embodiment 1132, wherein $R_4$ is OH.

Embodiment 1135. The modified oligonucleotide of embodiment 1132, wherein $R_4$ is $C_1$-$C_6$ alkyl.

Embodiment 1136. The modified oligonucleotide of embodiment 1132, wherein $R_4$ is substituted $C_1$-$C_6$ alkyl.

Embodiment 1137. The modified oligonucleotide of embodiment 1132, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 1138. The modified oligonucleotide of embodiment 1132, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 1139. The modified oligonucleotide of embodiment 1132, wherein $R_4$ comprises a carbohydrate or carbohydrate cluster.

Embodiment 1140. The modified oligonucleotide of embodiment 1132, wherein $R_4$ comprises at least one GalNAc.

Embodiment 1141. The modified oligonucleotide of any of embodiments 1132-1140, wherein $R_5$ is $OCH_3$.

Embodiment 1142. The modified oligonucleotide of any of embodiments 1132-1140, wherein $R_5$ is OH.

Embodiment 1143. The modified oligonucleotide of any of embodiments 1132-1140, wherein $R_5$ is $C_1$-$C_6$ alkyl.

Embodiment 1144. The modified oligonucleotide of any of embodiments 1132-1140, wherein $R_5$ is substituted $C_1$-$C_6$ alkyl.

Embodiment 1145. The modified oligonucleotide of embodiment 1132, wherein T is:

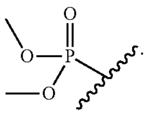

Embodiment 1146. The modified oligonucleotide of embodiment 1132, wherein T is:

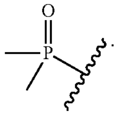

Embodiment 1147. The modified oligonucleotide of embodiment 1132, wherein T is:

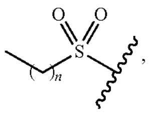

wherein n is from 2 to 20.

Embodiment 1148. The modified oligonucleotide of embodiment 1147, wherein n is 15.

Embodiment 1149. An antisense agent comprising a modified oligonucleotide consisting of 12-50 linked nucleosides linked through internucleoside linking groups, wherein at least one internucleoside linking group is a phosphodiester or a phosphorothioate internucleoside linking group, and wherein at least one of the internucleoside linking groups has Formula XX:

XX

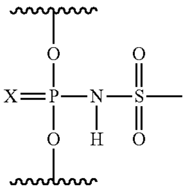

wherein independently for each internucleoside linking group of the modified oligonucleotide having Formula XX, X is selected from O or S.

Embodiment 1150. An antisense agent comprising a modified oligonucleotide, wherein the 5'-terminus of the modified oligonucleotide has Structure F:

Structure F

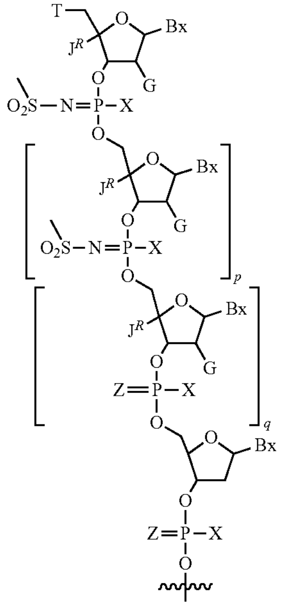

wherein:

p is from 0 to 6;

q is from 0 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1151. An antisense agent comprising a modified oligonucleotide, wherein the 3'-terminus of the modified oligonucleotide has Structure G:

Structure G

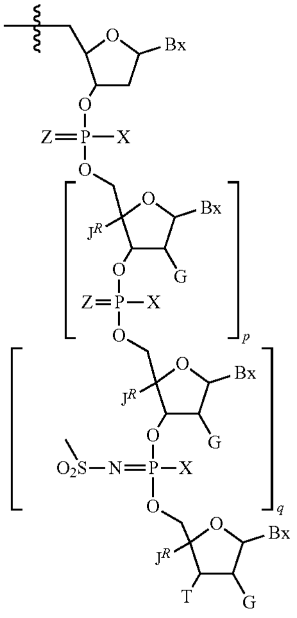

wherein:

p is from 0 to 6;

q is from 1 to 6;

T is OH or a conjugate group;

each Bx is an independently selected heterocyclic base moiety;

each X is independently selected from OH or SH;

each Z is independently selected from O, S, or $NSO_2Me$;

for each $J^R$ and G of the same furanosyl sugar moiety, either $J^R$ and G form a $J^R$ to G bridge, or $J^R$ is H and G is selected from OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1152. The antisense agent of embodiment 1150 or 1151, wherein the sum of p+q is selected from 2, 3, 4, or 5.

Embodiment 1153. An antisense agent comprising a modified oligonucleotide, wherein the 5'-terminus of the modified oligonucleotide has Structure H:

Structure H

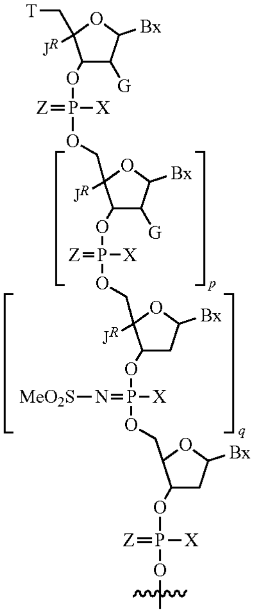

wherein:

p is from 0 to 5;

q is from 1 to 4;

T is OH or a conjugate group;

each Bx is an independently selected heterocyclic base moiety;

each X is independently selected from OH or SH;

each Z is independently selected from O, S, or $NSO_2Me$;

for each $J^R$ and G of the same furanosyl sugar moiety, either $J^R$ and G form a $J^R$ to G bridge, or $J^R$ is H and G is selected from OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1154. An antisense agent comprising a modified oligonucleotide, wherein the 5'-terminus of the modified oligonucleotide has Structure I:

Structure I

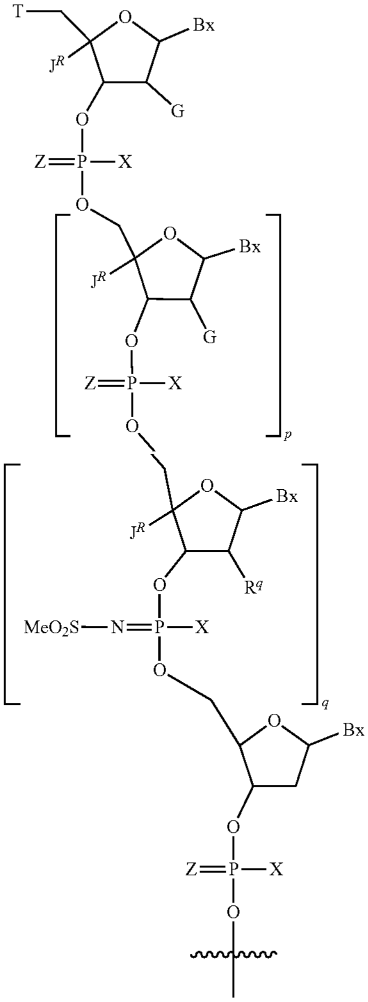

wherein:

p is from 0 to 5;

q is from 1 to 4;

T is OH or a conjugate group;

each Bx is an independently selected heterocyclic base moiety;

each X is independently selected from OH or SH;

each Z is independently selected from O, S, or $NSO_2Me$;

each $R_q$ is H or exactly one $R^q$ is OMe and the other $R_q$ are H;

for each $J^R$ and G of the same furanosyl sugar moiety, either $J^R$ and G form a $J^R$ to G bridge, or $J^R$ is H and G is selected from OH, halogen or $O-[C(R_6)(R_7)]_n-[(C{=}O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$; $Q_2$ is O, S or $NJ_3$;

each $J_1$, $J_2$ and $J_3$ is, independently, H or $C_1$-$C_6$ alkyl.

Embodiment 1155. The antisense agent of embodiment 1154, wherein exactly one $R^9$ is —OMe.

Embodiment 1156. The antisense agent of any of embodiments 1153-1155, wherein the sum of p+q is 2, 3, or 4.

Embodiment 1157. An antisense agent comprising a modified oligonucleotide, wherein the 3'-terminus of the modified oligonucleotide has Structure J:

Structure J

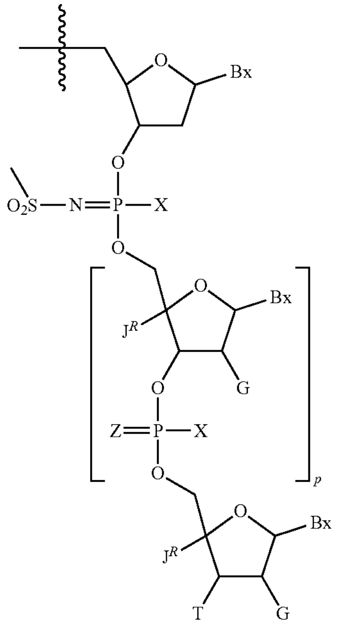

wherein:

p is from 0 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a to G bridge, or $J^R$ is H and G is selected from OH, halogen or $O—[C(R_6)(R_7)]_n—[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1158. The antisense agent of embodiment 1157, wherein p is 2, 3, or 4.

Embodiment 1159. The antisense agent of any of embodiments 1150-1158, wherein each $J^R$ is H and each G is $OCH_2CH_2OCH_3$.

Embodiment 1160. The antisense agent of any of embodiments 1150-1158, wherein each $J^R$ is H and each G is $OCH_3$.

Embodiment 1161. The antisense agent of any of embodiments 1150-1158, wherein each $J^R$ and G form a $J^R$ to G bridge.

Embodiment 1162. The antisense agent of embodiment 1161, wherein the $J^R$ to G bridge has the formula $—CH(CH_3)—O—$.

Embodiment 1163. The antisense agent of embodiment 1149, wherein the antisense agent is an RNAi agent.

Embodiment 1164. The RNAi agent of embodiment 1163, wherein the RNAi agent is a single-stranded RNAi agent comprising an RNAi antisense modified oligonucleotide, wherein the RNAi antisense modified oligonucleotide is a modified oligonucleotide of embodiment 1149.

Embodiment 1165. The RNAi agent of embodiment 1163, wherein the RNAi agent is an oligonucleotide duplex comprising an RNAi antisense modified oligonucleotide and an RNAi sense modified oligonucleotide, wherein the RNAi antisense modified oligonucleotide and/or the RNAi sense modified oligonucleotide is a modified oligonucleotide of embodiment 1149.

Embodiment 1166. The RNAi agent of any of embodiments 1164-1165, wherein the 5'-terminus of the RNAi antisense oligonucleotide has structure K:

Structure K

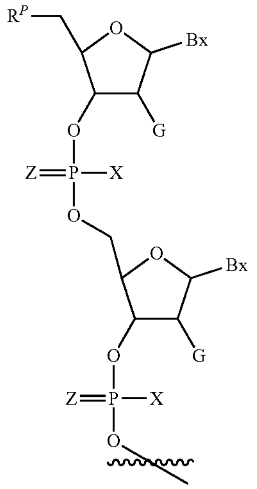

wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1167. The RNAi agent of embodiment 1166, wherein the stabilized phosphate group is 5'-vinyl phosphonate or 5'-cyclopropyl phosphonate.

Embodiment 1168. The RNAi agent of embodiment 1166 or 1167, wherein each G within structure K is independently selected from F or OMe.

Embodiment 1169. The RNAi agent of any of embodiments 1164-1168, wherein the 3'-terminus of the RNAi antisense oligonucleotide has structure L:

Structure L

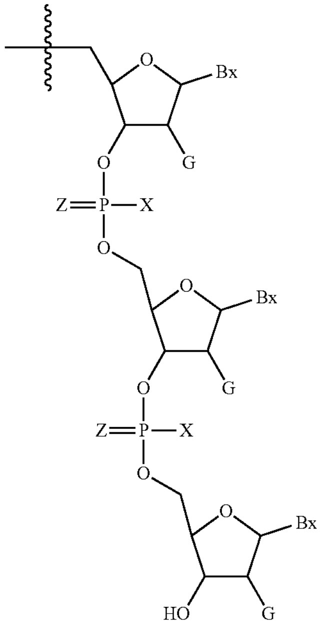

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1170. The RNAi agent of embodiment 1169, wherein each G within Structure L of the RNAi antisense oligonucleotide is independently selected from F or OMe.

Embodiment 1171. The RNAi agent of any of embodiments 1164-1170, wherein at least one region of the RNAi antisense oligonucleotide has structure M:

Structure M

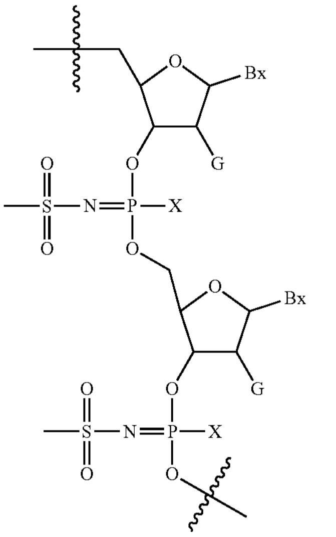

wherein:

each Bx is an independently selected heterocyclic base moiety;

each X is independently selected from OH or SH;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1172. The RNAi agent of embodiment 1171, wherein each G of Structure M within the RNAi antisense oligonucleotide is selected from F or OMe.

Embodiment 1173. The RNAi agent of embodiment 1172, wherein one G is F and the other G is OMe.

Embodiment 1174. The RNAi agent of any of embodiments 1164-1165 or 1169-1173, wherein the 5'-terminus of the RNAi antisense oligonucleotide has structure N:

Structure N

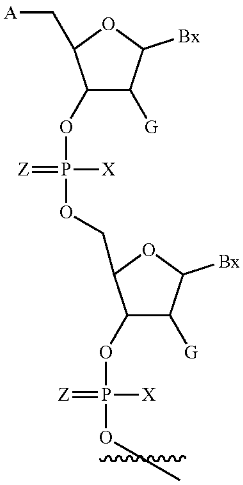

wherein:

A is selected from

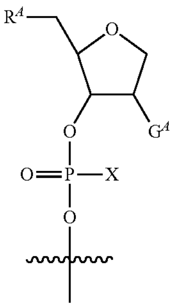

or

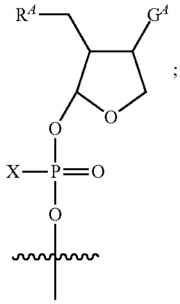

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1175. The RNAi agent of embodiment 1174, wherein each G within structure N of the RNAi antisense oligonucleotide is selected from F or OMe.

Embodiment 1176. The RNAi agent of any of embodiments 1164-1168 or 1171-1175, wherein the 3'-terminus of the RNAi antisense oligonucleotide has structure O:

Structure O

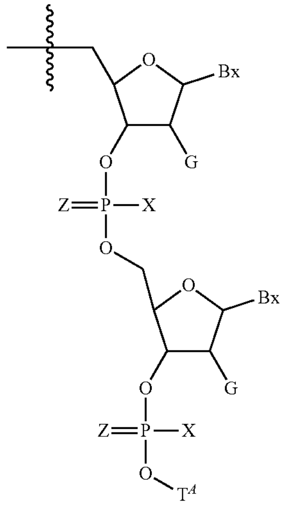

wherein:

$T^A$ is selected from

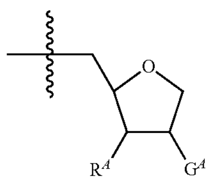

or

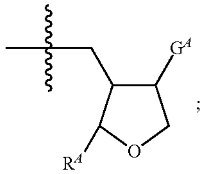

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1177. The RNAi agent of embodiment 1176, wherein each G within structure 0 of the RNAi antisense oligonucleotide is selected from F or OMe.

Embodiment 1178. The RNAi agent of embodiment 1165, wherein the 5'-terminus of the RNAi sense oligonucleotide has structure K:

Structure K

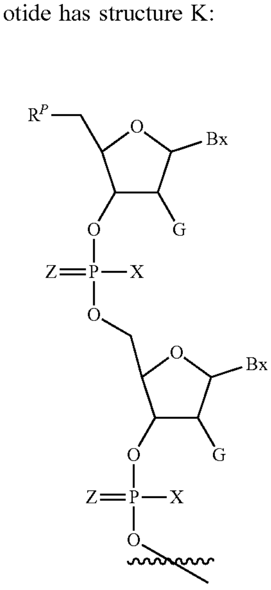

wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1179. The RNAi agent of embodiment 1178, wherein the stabilized phosphate group is 5'-vinyl phosphonate or 5'-cyclopropyl phosphonate.

Embodiment 1180. The RNAi agent of embodiment 1178 or 1179, wherein each G within structure K is independently selected from F or OMe.

Embodiment 1181. The RNAi agent of any of embodiments 1165 or 1178-1180, wherein the 3'-terminus of the RNAi sense oligonucleotide has structure L:

Structure L

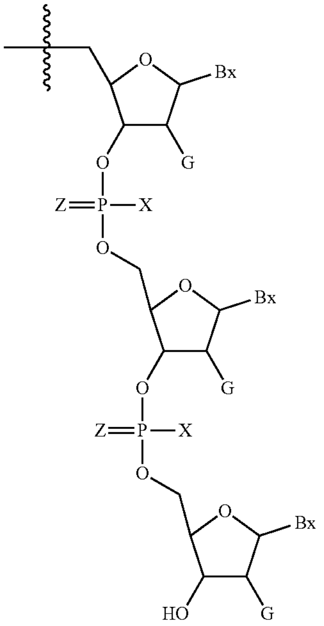

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1182. The RNAi agent of embodiment 1181, wherein each G within Structure L of the RNAi sense oligonucleotide is independently selected from F or OMe.

Embodiment 1183. The RNAi agent of any of embodiments 1165 or 1178-1182 wherein at least one region of the RNAi sense oligonucleotide has structure M:

Structure M

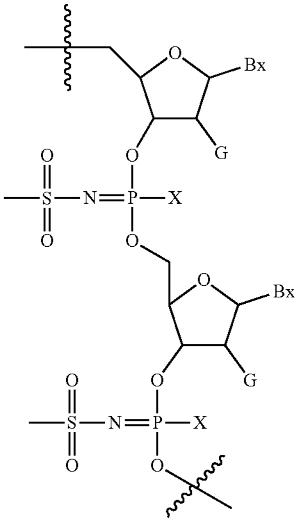

wherein:

each Bx is an independently selected heterocyclic base moiety;

each X is independently selected from OH or SH;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1184. The RNAi agent of embodiment 1183, wherein each G of Structure M within the RNAi sense oligonucleotide is selected from F or OMe.

Embodiment 1185. The RNAi agent of embodiment 1184, wherein one G is F and the other G is OMe.

Embodiment 1186. The RNAi agent of any of embodiments 1165 or 1181-1185, wherein the 5'-terminus of the RNAi sense oligonucleotide has structure N:

Structure N

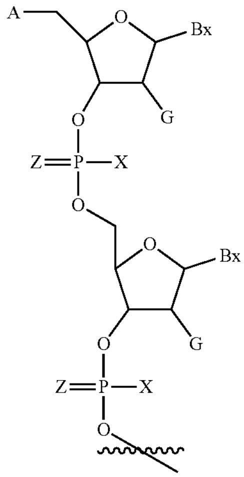

wherein:

A is selected from

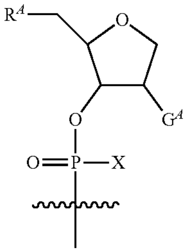

or

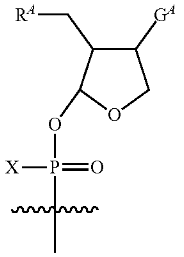

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1187. The RNAi agent of embodiment 1186, wherein each G within structure N of the RNAi sense oligonucleotide is selected from F or OMe.

Embodiment 1188. The RNAi agent of any of embodiments 1165, 1178-1180 or 1183-1187, wherein the 3'-terminus of the RNAi sense oligonucleotide has structure 0:

Structure O

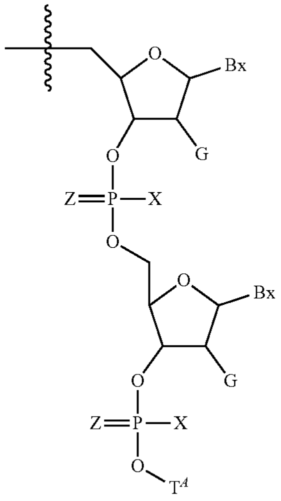

wherein:

$T^A$ is selected from

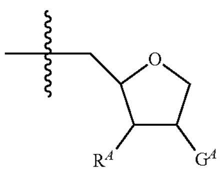

or

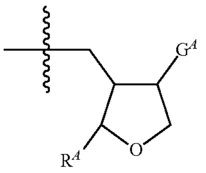

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1189. The RNAi agent of embodiment 1188, wherein each G within structure O of the RNAi sense oligonucleotide is selected from F or OMe.

Embodiment 1190. The antisense agent of any of embodiments 705-909 or 943-1177, comprising a modified oligonucleotide, wherein the nucleobase sequence of the modified oligonucleotide is complementary to a target nucleic acid.

Embodiment 1191. The modified oligonucleotide of embodiment 1190, wherein the nucleobase sequence of the modified oligonucleotide is at least 80% complementary to the target nucleic acid.

Embodiment 1192. The modified oligonucleotide of embodiment 1190, wherein the nucleobase sequence of the modified oligonucleotide is at least 85% complementary to the target nucleic acid.

Embodiment 1193. The modified oligonucleotide of embodiment 1190, wherein the nucleobase sequence of the modified oligonucleotide is at least 90% complementary to the target nucleic acid.

Embodiment 1194. The modified oligonucleotide of embodiment 1190, wherein the nucleobase sequence of the modified oligonucleotide is at least 95% complementary to the target nucleic acid.

Embodiment 1195. The modified oligonucleotide of embodiment 1190, wherein the nucleobase sequence of the modified oligonucleotide is 100% complementary to the target nucleic acid.

Embodiment 1196. The modified oligonucleotide of any of embodiments 1190-1195, wherein the target nucleic acid is a target RNA.

Embodiment 1197. The modified oligonucleotide of embodiment 1196, wherein the target RNA is selected from: an mRNA, a pre-mRNA, a microRNA, and a non-coding RNA.

Embodiment 1198. The modified oligonucleotide of embodiment 1197, wherein the target RNA is not a microRNA.

Embodiment 1199. The antisense agent comprising a modified oligonucleotide of any of embodiments 1-1198, wherein the modified oligonucleotide is not complementary to miR-21.

Embodiment 1200. The antisense agent of any of embodiments 705-1199, comprising a conjugate group.

Embodiment 1201. The antisense agent of embodiment 1200, wherein the conjugate group comprises at least one GalNAc.

Embodiment 1202. The antisense agent of embodiment 1200 or 1201, wherein the conjugate group comprises 1-5 linker-nucleosides.

Embodiment 1203. A pharmaceutical composition comprising the antisense agent of any of embodiments 705-1202 and a pharmaceutically acceptable carrier or diluent.

Embodiment 1204. A method comprising contacting a cell with the antisense agent or pharmaceutical composition of any of embodiments 705-1203.

Embodiment 1205. A method of modulating the amount or activity of a target nucleic acid in a cell, comprising contacting the cell with the antisense agent or pharmaceutical composition of any of embodiments 705-1204 and thereby modulating the amount or activity of the target nucleic acid.

Embodiment 1206. A method of modulating the amount or activity of a target nucleic acid in a cell, comprising contacting the cell with the antisense agent or pharmaceutical composition of any of embodiments 705-1204.

Embodiment 1207. The method of embodiments 1204-1206, wherein the amount or activity of a target nucleic acid is reduced.

Embodiment 1208. The method of embodiments 1204-1206, wherein the amount or activity of a target nucleic acid is increased.

Embodiment 1209. The method of embodiment 1204, wherein the target protein is encoded by a target nucleic acid comprising at least one translation suppression element and wherein the modified oligonucleotide is complementary to a target site within a translation suppression element region of the target nucleic acid.

Embodiment 1210. The method of embodiment 1209, wherein the translation suppression element region comprises at least one stem-loop structure.

Embodiment 1211. Use of the antisense agent or composition of any of embodiments 705-1203 for treatment of a disease or condition.

Embodiment 1212. Use of the antisense agent or composition of any of embodiments 705-1203 for a preparation of a medicament for treatment of a disease or condition.

Embodiment 1213. The antisense agent of any of embodiments 705-856, 943-1162, or 1190-1202, wherein the antisense agent is not an RNAi agent and the parent antisense agent is cytotoxic in vitro.

Embodiment 1214. The antisense agent of embodiment 1213, wherein the parent antisense agent is cytotoxic in a standard in vitro cytotoxicity assay.

Embodiment 1215. The antisense agent of embodiment 1213, wherein the antisense agent of any of embodiments 705-856, 943-1162, or 1190-1202 is not cytotoxic in vitro.

Embodiment 1216. The antisense agent of any of embodiments 1213-1215, wherein the antisense agent of any of embodiments 705-856, 943-1162, or 1190-1202 is not cytotoxic in a standard in vitro cytoxicity assay.

Embodiment 1217. The antisense agent of any of embodiments 705-856, 943-1162, or 1190-1202, wherein the antisense agent is not an siRNA agent and the parent antisense agent is hepatotoxic to the mouse.

Embodiment 1218. The antisense agent of embodiment 1217, wherein the mouse is a BALB/c mouse, wherein 50 mg/kg of the parent antisense agent is administered to the mouse, and wherein the plasma ALT level in the mouse is measured 72 hours following the administration of the parent antisense agent.

Embodiment 1219. The antisense agent of any of embodiments 1217-1218, wherein administration of 50 mg/kg of the antisense agent of any of embodiments 705-856, 943-1162, or 1190-1202 to a mouse is not hepatotoxic to the mouse.

Embodiment 1220. The antisense agent of any of embodiments 705-856, 943-1162, or 1190-1202, wherein the therapeutic index in a mouse of the antisense agent of any of embodiments 705-856, 943-1162, or 1190-1202 is increased relative to the therapeutic index of the parent antisense agent.

Embodiment 1221. The antisense agent of embodiment 1220, wherein the therapeutic index in a mouse of the antisense agent of embodiment 516 is at least two-fold greater than the therapeutic index of the parent antisense agent.

Embodiment 1222. The antisense agent of any of embodiments 1213-1221, wherein the parent antisense agent is identical to the antisense agent of any of embodiments 705-856, 943-1162, or 1190-1202, except that each internucleoside linkage of Formula XVII is replaced with a phosphorothioate internucleoside linkage in the parent antisense agent.

Embodiment 1223. The antisense agent of any of embodiments 1213-1222, wherein the antisense agent is an RNAse H agent.

Embodiment 1224. The antisense agent of any of embodiments 1213-1222, wherein the antisense agent is a gapmer.

Embodiment 1225. The antisense agent of any of embodiments 1213-1222, wherein the antisense agent modulates splicing.

Embodiment 1226. The antisense agent of any of embodiments 1213-1222, wherein the antisense agent increases protein expression.

Embodiment 1227. The antisense agent of any of embodiments 705-942, 1074-1148 or 1163-1202, wherein the antisense agent is an RNAi agent, and the parent RNAi agent is cytoxic in vitro.

Embodiment 1228. The antisense agent of embodiment 1227, wherein the RNAi agent of any of embodiments 705-942, 1074-1148 or 1163-1202, is not cytotoxic in vitro.

Embodiment 1229. The antisense agent of any of embodiments 1227-1228 wherein the RNAi agent of any of embodiments 705-942, 1074-1148 or 1163-1202 is not cytotoxic in a standard in vitro cytoxicity assay.

Embodiment 1230. The antisense agent of any of embodiments 705-942, 1074-1148 or 1163-1202, wherein the antisense agent is an RNAi agent and is hepatotoxic to the mouse.

Embodiment 1231. The RNAi agent of embodiment 1230, wherein the mouse is a BALB/c mouse, wherein 50 mg/kg of the parent RNAi agent is administered to the mouse, and wherein the plasma ALT level in the mouse is measured 72 hours following the administration of the parent RNAi agent.

Embodiment 1232. The RNAi agent of any of embodiments 1230-1231, wherein administration of 50 mg/kg of the RNAi agent of any of embodiments 705-942, 1074-1148 or 1163-1202 to a mouse is not hepatotoxic to the mouse.

Embodiment 1233. The RNAi agent of any of embodiments 705-942, 1074-1148 or 1163-1202, wherein the therapeutic index in a mouse of the RNAi agent of any of embodiments 705-942, 1074-1148 or 1163-1202 is increased relative to the therapeutic index of the parent RNAi agent.

Embodiment 1234. The RNAi agent of embodiment 1233, wherein the therapeutic index in a mouse of the RNAi agent of embodiment 1233 is at least two-fold greater than the therapeutic index of the parent RNAi agent.

Embodiment 1235. The RNAi agent of any of embodiments 1127-1234, wherein the parent RNAi agent is identical to the RNAi agent of any of embodiments 705-942, 1074-1148 or 1163-1202, except that each internucleoside linkage of Formula XVII is replaced with a phosphodiester internucleoside linkage in the parent RNAi agent.

Embodiment 1236. A method of designing an antisense agent comprising starting with a parent antisense agent or a parent RNAi agent and changing the design of that compound in order to arrive at an antisense agent of any one of embodiments 705-1202.

Embodiment 1237. A method of designing an antisense agent comprising identifying an antisense agent or parent RNAi agent and changing the design of that parent antisense agent or parent RNAi agent to arrive at a second antisense agent, wherein the second antisense agent is an antisense agent of any one of embodiments 705-1202.

Embodiment 1238. A method of improving hepatotoxicity of an antisense agent comprising the steps of (i) identifying a parent antisense agent or parent RNAi agent that has plasma ALT levels above 300 units per liter in a mouse, and (ii) providing an antisense agent according to any one of embodiments 705-1202.

Embodiment 1239. The method of embodiment 1236, wherein the method designs antisense agent with improved therapeutic index relative to the parent antisense agent or parent RNAi agent.

Embodiment 1240. The method of embodiment 1236, wherein the method designs an antisense agent with lower hepatotoxicity relative to the parent antisense agent or parent RNAi agent.

Embodiment 1241. The method of embodiment 1237, wherein the second antisense agent has an improved therapeutic index relative to the parent antisense agent or parent RNAi agent.

Embodiment 1242. The method of embodiment 1237, wherein the second antisense agent has reduced hepatotoxicity in a mouse relative to the parent antisense agent or parent RNAi agent.

Embodiment 1243. The method of embodiment 1238, wherein the antisense agent according to any one of embodiments 705-1202 has improved therapeutic index relative to the parent antisense agent or parent RNAi agent.

Embodiment 1244. The method of embodiment 1238, wherein the antisense agent according to any one of embodiments 705-1202 has reduced hepatotoxicity relative to the parent antisense agent or parent RNAi agent.

Embodiment 1245. A method comprising administering an antisense agent of any of embodiments 705-1202 to a mouse and separately administering the parent antisense agent or parent RNAi agent of the antisense agent of any of embodiments 705-1202 to a second mouse, wherein the therapeutic index of the antisense agent of any of embodiments 705-1202 is improved relative to the therapeutic index of the parent antisense agent or parent RNAi agent.

Embodiment 1246. An oligomeric compound comprising a modified oligonucleotide consisting of 12-70 linked nucleosides linked through internucleoside linking groups, wherein at least one nucleoside comprises a modified sugar moiety, and wherein at least one of the internucleoside linking groups has Formula XVII:

XVII

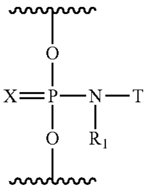

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, C(=O)$R_3$, and P(=O)$R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

Embodiment 1247. An oligomeric compound comprising a modified oligonucleotide consisting of 12-70 linked nucleosides linked through internucleoside linking groups, wherein at least one nucleoside comprises a modified sugar moiety, and wherein at least one of the internucleoside linking groups has Formula XVI:

XVII

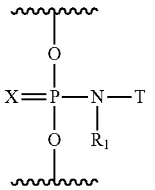

wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, C(=O)$R_3$, and P(=O)$R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl, Provided that if X is O and that if $R_1$ is H, then T is not:

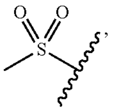, 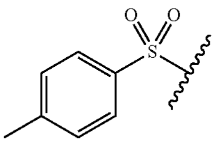,

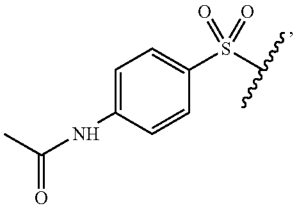,

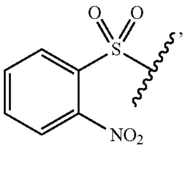, 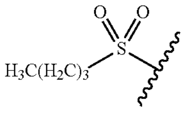, or

-continued

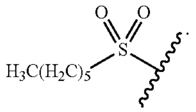

Embodiment 1248. The oligomeric compound of claim 1246 or claim 1247, wherein at least one internucleoside linking group is a phosphodiester or a phosphorothioate internucleoside linking group.

Embodiment 1249. The oligomeric compound of any of claims 1246-1248, wherein at least one nucleoside comprises a 2'-β-D-deoxyribosyl sugar moiety.

Embodiment 1250. The oligomeric compound of any of claims 1246-1249, wherein for at least one internucleoside linking group of Formula XVII, X is O.

Embodiment 1251. The oligomeric compound of any of claims 1246-1250, wherein for at least one internucleoside linking group of Formula XVII, X is S.

Embodiment 1252. The oligomeric compound of claim 1246 or 1247, wherein for at least one internucleoside linking group of Formula XVII, $R_1$ is H.

Embodiment 1253. The oligomeric compound of claim 1246 or 1247, wherein for at least one internucleoside linking group of Formula XVII, $R_1$ is a $C_1$-$C_6$ alkyl.

Embodiment 1254. The oligomeric compound of claim 1253, wherein $R_1$ is methyl.

Embodiment 1255. The oligomeric compound of claim 1246 or 1247, wherein for at least one internucleoside linking group of Formula XVII, $R_1$ is a substituted $C_1$-$C_6$ alkyl.

Embodiment 1256. The oligomeric compound of any of claims 1246-1255, wherein for at least one internucleoside linking group of Formula XVII, T comprises a conjugate group.

Embodiment 1257. The oligomeric compound of claim 1256, wherein the conjugate group comprises a cell-targeting moiety.

Embodiment 1258. The oligomeric compound of claim 1256, wherein the conjugate group comprises a carbohydrate or carbohydrate cluster.

Embodiment 1259. The oligomeric compound of any of claims 1256-1258, wherein the conjugate group comprises at least one GalNAc.

Embodiment 1260. The oligomeric compound of claim 1256, wherein the conjugate group comprises a $C_{10}$-$C_{20}$ alkyl chain.

Embodiment 1261. The oligomeric compound of claim 1257, wherein the conjugate group comprises $C_{16}$ alkyl.

Embodiment 1262. The oligomeric compound of any of claims 1246-1255, wherein for at least one internucleoside linking group of Formula XVII, T does not comprise a conjugate group.

Embodiment 1263. The oligomeric compound of any of claims 1246-1255, wherein for at least one internucleoside linking group of Formula XVII, T does not comprise a cell-targeting moiety.

Embodiment 1264. The oligomeric compound of any of claims 1246-1263, wherein for at least one internucleoside linking group of Formula XVII, T is $SO_2R_2$.

Embodiment 1265. The oligomeric compound of claim 1264, wherein $R_2$ is an aryl.

Embodiment 1266. The oligomeric compound of claim 1264, wherein $R_2$ is a substituted aryl.

Embodiment 1267. The oligomeric compound of claim 1264, wherein $R_2$ is a heterocycle.

Embodiment 1268. The oligomeric compound of claim 1264, wherein $R_2$ is a substituted heterocycle.

Embodiment 1269. The oligomeric compound of claim 1264, wherein $R_2$ is an aromatic heterocycle.

Embodiment 1270. The oligomeric compound of claim 1264, wherein $R_2$ is a substituted aromatic heterocycle.

Embodiment 1271. The oligomeric compound of claim 1264, wherein $R_2$ is a diazole.

Embodiment 1272. The oligomeric compound of claim 1264, wherein $R_2$ is a substituted diazole.

Embodiment 1273. The oligomeric compound of claim 1264, wherein $R_2$ is an amine.

Embodiment 1274. The oligomeric compound of claim 1264, wherein $R_2$ is a substituted amine.

Embodiment 1275. The oligomeric compound of claim 1264, wherein $R_2$ is a $C_1$-$C_6$ alkoxy, $C_1$-$C_6$ alkenyl, or $C_1$-$C_6$-alkynl.

Embodiment 1276. The oligomeric compound of claim 1264, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 1277. The oligomeric compound of claim 1264, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 1278. The oligomeric compound of claim 1264, wherein $R_2$ comprises a carbohydrate or carbohydrate cluster.

Embodiment 1279. The oligomeric compound of claim 1264, wherein $R_2$ comprises at least one GalNAc.

Embodiment 1280. The oligomeric compound of claim 1264, wherein T is:

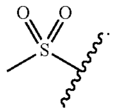 [SMILES: *S(C)(=O)=O]

Embodiment 1281. The oligomeric compound of claim 1264, wherein T is:

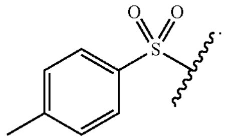 [SMILES: *S(=O)(=O)c1ccc(C)cc1]

Embodiment 1282. The oligomeric compound of claim 1264, wherein T is:

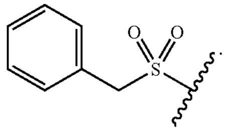 [SMILES: *S(=O)(=O)Cc1ccccc1]

Embodiment 1283. The oligomeric compound of claim 1264, wherein T is:

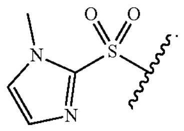 [SMILES: *S(=O)(=O)c1nccn1C]

Embodiment 1284. The oligomeric compound of claim 1264, wherein T is:

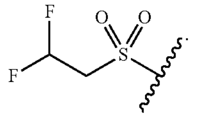

Embodiment 1285. The oligomeric compound of claim 1264, wherein T is:

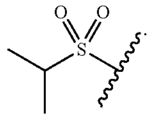 [SMILES: *S(=O)(=O)C(C)C]

Embodiment 1286. The oligomeric compound of claim 1264, wherein T is:

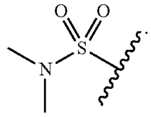 [SMILES: *S(=O)(=O)N(C)C]

Embodiment 1287. The oligomeric compound of claim 1264, wherein T is:

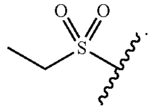

Embodiment 1288. The oligomeric compound of claim 1264, wherein T is:

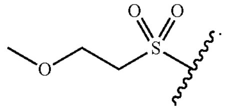 [SMILES: *S(=O)(=O)CCOC]

Embodiment 1289. The oligomeric compound of claim 1264, wherein T is:

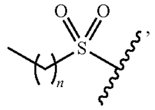

wherein n is from 2 to 20.

Embodiment 1290. The oligomeric compound of claim 1289, wherein n is 15.

Embodiment 1291. The oligomeric compound of any of claims 1246-1290, wherein for at least one internucleoside linking group of Formula XVII, T is $C(=O)R_3$.

Embodiment 1292. The oligomeric compound of claim 1291, wherein $R_3$ is an aryl.

Embodiment 1293. The oligomeric compound of claim 1291, wherein $R_3$ is a substituted aryl.

Embodiment 1294. The oligomeric compound of claim 1291, wherein $R_3$ is $CH_3$.

Embodiment 1295. The oligomeric compound of claim 1291, wherein $R_3$ is $N(CH_3)_2$.

Embodiment 1296. The oligomeric compound of claim 1291, wherein $R_3$ is $OCH_3$.

Embodiment 1297. The oligomeric compound of claim 1291, wherein $R_3$ is a $C_1$-$C_6$ alkoxy.

Embodiment 1298. The oligomeric compound of claim 1291, wherein $R_3$ is $C_1$-$C_{20}$, $C_1$-$C_6$, $C_2$-$C_{20}$, $C_2$-$C_6$, or $C_{10}$-$C_{20}$ alkyl.

Embodiment 1299. The oligomeric compound of claim 1291, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 1300. The oligomeric compound of claim 1291, wherein $R_3$ comprises a carbohydrate or carbohydrate cluster.

Embodiment 1301. The oligomeric compound of claim 1291, wherein $R_{23}$ comprises at least one GalNAc.

Embodiment 1302. The oligomeric compound of claim 1291, wherein T is:

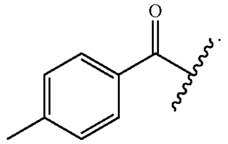 [SMILES: *C(=O)c1ccc(C)cc1]

Embodiment 1303. The oligomeric compound of claim 1291, wherein T is:

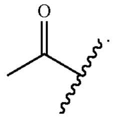 [SMILES: *C(C)=O]

Embodiment 1304. The oligomeric compound of claim 1291, wherein T is:

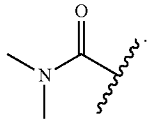

Embodiment 1305. The oligomeric compound of claim 1291, wherein T is:

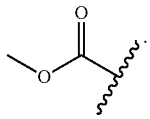

Embodiment 1306. The oligomeric compound of claim 1291, wherein T is:

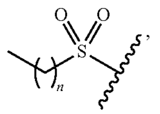

wherein n is from 2 to 20.

Embodiment 1307. The oligomeric compound of claim 1306, wherein n is 15.

Embodiment 1308. The oligomeric compound of any of claims 1246-1263, wherein for at least one internucleoside linking group of Formula XVII, T is $P(=O)R_4R_5$.

Embodiment 1309. The oligomeric compound of claim 1308, wherein $R_4$ is $OCH_3$ Embodiment 1310. The oligomeric compound of claim 1308, wherein $R_4$ is OH.

Embodiment 1311. The oligomeric compound of claim 1308, wherein $R_4$ is $C_1$-$C_6$ alkyl.

Embodiment 1312. The oligomeric compound of claim 1308, wherein $R_4$ is substituted $C_1$-$C_6$ alkyl.

Embodiment 1313. The oligomeric compound of claim 1308, wherein $R_4$ is $C_1$-$C_{20}$, $C_1$-$C_6$, $C_2$-$C_{20}$, $C_2$-$C_6$, or $C_{10}$-$C_{20}$ alkyl.

Embodiment 1314. The oligomeric compound of claim 1308, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 1315. The oligomeric compound of claim 1308, wherein $R_4$ comprises a carbohydrate or carbohydrate cluster.

Embodiment 1316. The oligomeric compound of claim 1308, wherein $R_4$ comprises at least one GalNAc.

Embodiment 1317. The oligomeric compound of any of claims 1308-1316, wherein $R_5$ is $OCH_3$.

Embodiment 1318. The oligomeric compound of any of claims 1308-1316, wherein $R_5$ is OH.

Embodiment 1319. The oligomeric compound of any of claims 1308-1316, wherein $R_5$ is $C_1$-$C_6$ alkyl.

Embodiment 1320. The oligomeric compound of any of claims 1308-1316, wherein $R_5$ is substituted $C_1$-$C_6$ alkyl.

Embodiment 1321. The oligomeric compound of claim 1308, wherein T is:

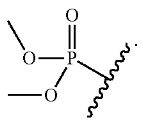

Embodiment 1322. The oligomeric compound of claim 1308, wherein T is:

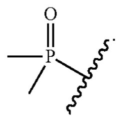 [SMILES: *P(C)(C)=O]

Embodiment 1323. The oligomeric compound of claim 1308, wherein T is:

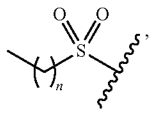

wherein n is from 2 to 20.

Embodiment 1324. The oligomeric compound of claim 1323, wherein n is 15.

Embodiment 1325. The oligomeric compound of any of claims 1246-1324, wherein at least one internucleoside linking group of the modified oligonucleotide is not a linking group of Formula XVII.

Embodiment 1326. The oligomeric compound of any of claims 1246-1325, wherein exactly one internucleoside linking group of the modified oligonucleotide is an internucleoside linking group of Formula XVII.

Embodiment 1327. The oligomeric compound of any of claims 1246-1325, wherein exactly two internucleoside linking groups of the modified oligonucleotide are internucleoside linking groups of Formula XVII.

Embodiment 1328. The oligomeric compound of any of claims 1246-1325, wherein exactly three internucleoside linking groups of the modified oligonucleotide are internucleoside linking groups of Formula XVII.

Embodiment 1329. The oligomeric compound of any of claims 1246-1325, wherein exactly four internucleoside linking groups of the modified oligonucleotide are internucleoside linking groups of Formula XVII.

Embodiment 1330. The oligomeric compound of any of claims 1246-1325, wherein exactly five internucleoside linking groups of the modified oligonucleotide are internucleoside linking groups of Formula XVII.

Embodiment 1331. The oligomeric compound of any of claims 1246-1325, wherein at least six internucleoside linking groups of the modified oligonucleotide are internucleoside linking groups of Formula XVII.

Embodiment 1332. The oligomeric compound of any of claim 1246-1324 or 1326-1331 having at least two linking groups of Formula XVII, wherein at least two of the linking groups of Formula XVII are the same as one another.

Embodiment 1333. The oligomeric compound of any of claims 1246-1332, wherein each internucleoside linking group of the modified oligonucleotide that is not an internucleoside linking group of Formula XVII is either a phosphodiester internucleoside linking group or a phosphorothioate internucleoside linking group.

Embodiment 1334. The oligomeric compound of any of claims 1246-1325 or 1331, wherein each internucleoside linking group of the modified oligonucleotide is an internucleoside linking group of Formula XVII.

Embodiment 1335. An oligomeric compound comprising a modified oligonucleotide, wherein at least one region of the modified oligonucleotide has Structure A:

Structure A

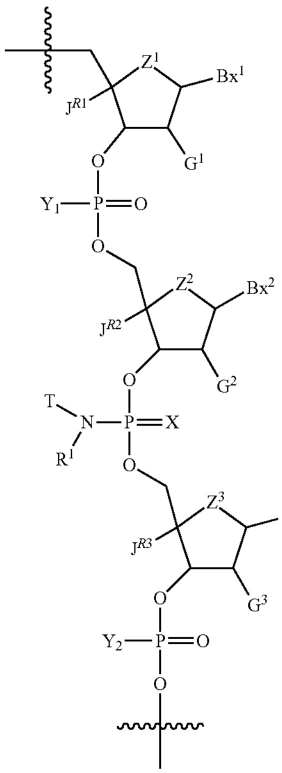

wherein:

each Bx is a heterocyclic base moiety;

X is selected from O or S;

each of $Y_1$ and $Y_2$ is independently selected from OH or SH;

each of $Z^1$, $Z^2$, and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; either $J^{R1}$ and $G^1$ form a $J^{R1}$ to $G^1$ bridge, or $J^{R1}$ is H and $G^1$ is selected from H, OH, halogen or $O-[C(R_6)(R_7)]_n-[(C=O)_m-X^G]_j-R_8$;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1336. An oligomeric compound comprising a modified olignucleotide, wherein at least one region of the modified oligonucleotide has Structure B:

Structure B

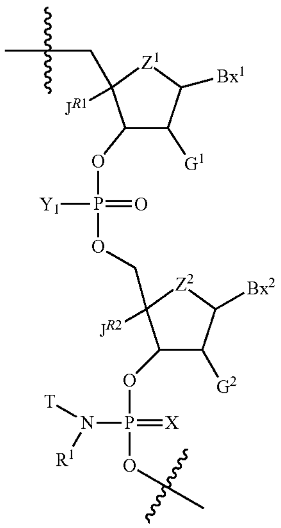

wherein:

each Bx is a heterocyclic base moiety;

X is selected from O or S;

each of $Y_1$ and $Y_2$ is independently selected from OH or SH;

each of $Z^1$ and $Z^2$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or O—$[C(R_6)(R_7)]_n$—$[(C{=}O)_m$—$X^G]_j$—$R_8$;

either $J^{R2}$ and $G^2$ form a $J_{R2}$ and $G^2$ bridge, or $J_{R2}$ is H and $G^2$ is selected from H, OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_5$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1337. An oligomeric compound comprising a modified olignucleotide, wherein at least one region of the modified oligonucleotide has Structure C:

Structure C

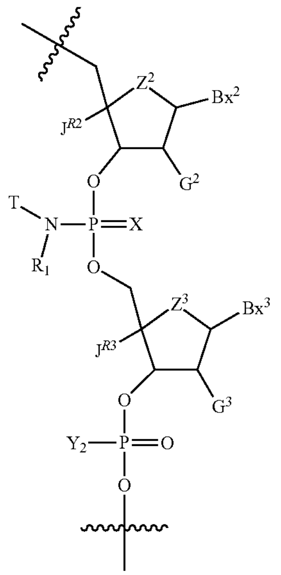

wherein:

each Bx is a heterocyclic base moiety;

X is selected from O or S;

each of $Y_1$ and $Y_2$ is independently selected from OH or SH;

each of $Z^2$ and $Z^3$ are independently selected from —$(CH_2)_p$—$X^Z$—$(CH_2)_q$—, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R2}$ and $G^2$ form a $J_{R2}$ and $G^2$ bridge, or $J_{R2}$ is H and $G^2$ is selected from H, OH, halogen or O—$[C(R_6)(R_7)]_n$—$[(C{=}O)_m X^G]_j$—$R_8$;

either $J^{R3}$ and $G^3$ form a $J^{R3}$ and $G^3$ bridge, or $J^{R3}$ is H and $G^3$ is selected from H, OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$; $Q_2$ is O, S or $NJ_3$;

each $J_1$, $J_2$ and $J_3$ is, independently, H or $C_1$-$C_6$ alkyl.

Embodiment 1338. An oligomeric compound comprising a modified olignucleotide, wherein at least one region of the modified oligonucleotide has Structure D:

Structure D

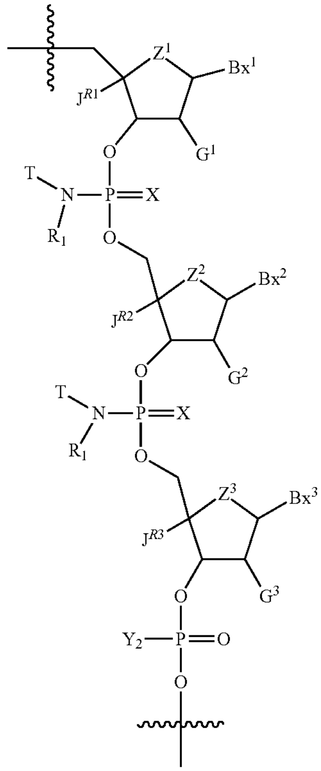

wherein:

each Bx is a heterocyclic base moiety;

X is selected from O or S;

each of $Y_1$ and $Y_2$ is independently selected from OH or SH;

each of $Z^2$ and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O-[C(R_6)(R_7)]_n-[(C=O)_m-X^G]_j-R_8$;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1339. An oligomeric compound comprising a modified olignucleotide, wherein at least one region of the modified oligonucleotide has Structure E:

Structure E

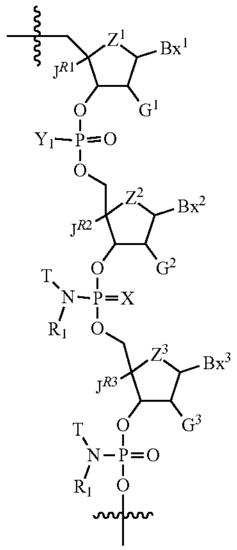

wherein:

each Bx is a heterocyclic base moiety;

X is selected from O or S;

each of $Y_1$ and $Y_2$ is independently selected from OH or SH;

each of $Z^2$ and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or O—$[C(R_6)(R_7)]_n$—$[(C{=}O)_m$—$X^G]_j$—$R_8$;

either $J^{R2}$ and $G^2$ form a $J^{R2}$ and $G^2$ bridge, or $J^{R2}$ is H and $G^2$ is selected from H, OH, halogen or O—$[C(R_6)(R_7)]_n$—$[(C{=}O)_m$—$X^G]_j$—$R_8$;

either $J^{R3}$ and $G^3$ form a $J^{R3}$ and $G^3$ bridge, or $J^{R3}$ is H and $G^3$ is selected from H, OH, halogen or O—$[C(R_6)(R_7)]_n$—$[(C{=}O))_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1340. An oligomeric compound comprising a modified oligonucleotide, wherein the 5'-terminus of the modified oligonucleotide has structure P:

Structure P

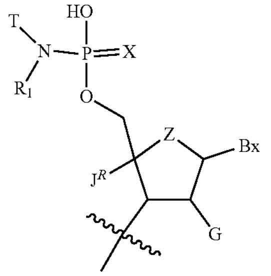

wherein:

each Bx is a heterocyclic base moiety;

X is selected from O or S;

Z is —$(CH_2)_p$—$X^Z$—$(CH_2)_q$—, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C({=}O)R_3$, and $P({=}O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^R$ and G form a $J^R$ to G bridge, or $J^R$ is H and G is selected from H, OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1341. The oligomeric compound of any of claims 1335-1340, wherein each Z is O.

Embodiment 1342. The oligomeric compound of any of claims 1335-1341, wherein at least one G is selected from H, OH, halogen, $C_1$-$C_6$ alkoxy, —$O(CH_2)_2OCH_3$, or —$OCH_2(C{=}O)NHCH_3$.

Embodiment 1343. The oligomeric compound of any of claims 1335-1342, wherein each G is selected from H, OH, halogen, $C_1$-$C_6$ alkoxy, —$O(CH_2)_2OCH_3$, or —$OCH_2(C{=}O)NHCH_3$.

Embodiment 1344. The oligomeric compound of any of claims 1335-1343, wherein at least one $J^R$ forms a bridge with at least one G, wherein said $J^R$ to G bridge has a formula selected from —$CH(CH_3)$—O— or —$(CH_2)_k$—O', wherein k is from 1 to 3.

Embodiment 1345. The oligomeric compound of any of claims 1335-1342 or 1344, wherein each $J^R$ and G form a bridge, wherein said $J^R$ to G bridge has a formula selected from —$CH(CH_3)$—O— or —$(CH_2)_k$—O—, wherein k is from 1 to 3.

Embodiment 1346. The oligomeric compound of any of claims 1344 or 1345, wherein at least one Z is O and the corresponding $J^R$ to G bridge has a formula $(CH_2)_k$—O—, wherein k is 1.

Embodiment 1347. The oligomeric compound of any of claims 1335-1346 wherein each nucleoside of structure A, B, C, D, E, or P is a stereo standard nucleoside.

Embodiment 1348. The oligomeric compound of any of claims 1335-1346, wherein at least one nucleoside of structure A, B, C, D, E or P is a stereo-non-standard nucleoside.

Embodiment 1349. The oligomeric compound of any of claims 1344-1346 or 1348, wherein at least one nucleoside having a $J^R$ to G bridge is in the α-L-ribosyl configuration.

Embodiment 1350. The oligomeric compound of any of claims 1335-1349, wherein the modified oligonucleotide comprises at least 2, at least 3, at least 4, at least 5, at least 6, at least 7, at least 8, at least 9, or at least 10 regions having structures A, B, C, D, or E.

Embodiment 1351. The oligomeric compound of any of claims 1335-1350, wherein at least one region having structure A, B, C, D, or E is at the 5' end of the modified oligonucleotide.

Embodiment 1352. The oligomeric compound of any of claims 1335-1350, wherein at least one region having structure A, B, C, D, or E is at the 3' end of the modified oligonucleotide.

Embodiment 1353. The oligomeric compound of any of claims 1335-1350, wherein at least one region having structure A, B, C, D, or E is internal to the modified oligonucleotide.

Embodiment 1354. An oligomeric compound comprising a modified oligonucleotide consisting of 10-30 linked nucleosides, wherein a region of the modified oligonucleotide has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

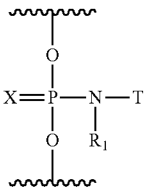

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ is an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 1355. The oligomeric compound of claim 1354, wherein the modified oligonucleotide comprises at least 2, at least 3, at least 4, at least 5, at least 6, at least 7, at least 8, at least 9, or at least 10 regions having the formula $(N_{g1})_{L1}(N_{g2})_{L2}(N_{g3})_{L3}$.

Embodiment 1356. The oligomeric compound of claim 1354 or 1355, wherein at least one region having the formula $(N_{g1})_{L1}(N_{g2})_{L2}(N_{g3})_{L3}$ is at the 5' end of the oligonucleotide Embodiment 1357. The oligomeric compound of claim 1354 or 1355, wherein at least one region having the formula $(N_{g1})_{L1}(N_{g2})_{L2}(N_{g3})_{L3}$ is internal to the oligonucleotide.

Embodiment 1358. The oligomeric compound of claim 1354 or 1355, wherein at least one region having the formula $(N_{g1})_{L1}(N_{g2})_{L2}(N_{g3})_{L3}$ is at the 3' end of the oligonucleotide.

Embodiment 1359. The oligomeric compound of any of claims 1246-1358, wherein at least one nucleoside of the modified oligonucleotide is a modified nucleoside selected from a bicyclic nucleoside and a non-bicyclic substituted nucleoside.

Embodiment 1360. The oligomeric compound of any of claims 1246-1359, wherein at least one nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 1361. The oligomeric compound of any of claims 1246-1360, wherein each nucleoside of the modified oligonucleotide is selected from: a β-D-LNA nucleoside, an α-L-LNA nucleoside, an ENA nucleoside, a cEt nucleoside, a 2'-MOE nucleoside, a 2'-OMe nucleoside, a 2'-F nucleoside, a 2'-NMA nucleoside, a 5'-Me nucleoside, a DNA nucleoside, and an RNA nucleoside.

Embodiment 1362. The oligomeric compound of any of claims 1246-1361, wherein at least one nucleoside of the modified oligonucleotide is a stereo-non-standard nucleoside.

Embodiment 1363. The oligomeric compound of claim 1362, wherein the internucleoside linking group linking at least one stereo-non-standard nucleoside to an adjacent nucleoside is an internucleoside linking group of Formula XVII.

Embodiment 1364. The oligomeric compound of claim 1362 or 1363, wherein at least two nucleosides of the modified oligonucleotide are stereo-non-standard nucleosides.

Embodiment 1365. The oligomeric compound of claim 1364, wherein at least two stereo-non-standard nucleosides of the modified oligonucleotide are adjacent to one another.

Embodiment 1366. The oligomeric compound of claim 1365, wherein at least two stereo-non-standard nucleosides of the modified oligonucleotide are linked to one another with an internucleoside linking group of Formula XVII.

Embodiment 1367. The oligomeric compound of any of claims 1362-1367, wherein at least one stereo-non-standard nucleoside of the modified oligonucleotide is a stereo-non-standard DNA nucleoside.

Embodiment 1368. The oligomeric compound of claim 1367, wherein the stereo-non-standard DNA nucleoside is selected from a stereo-non-standard DNA nucleoside having: Formula I, Formula II, Formula III, Formula IV, Formula V, Formula VI, and Formula VII.

Embodiment 1369. The oligomeric compound of claim 1368 wherein the stereo-non-standard DNA nucleoside is selected from a stereo-non-standard DNA nucleoside having: Formula V and Formula II.

Embodiment 1370. The oligomeric compound of any of claims 1362-1369, wherein at least one stereo-non-standard nucleoside of the oligomeric compound is a substituted stereo-non-standard nucleoside.

Embodiment 1371. The oligomeric compound of claim 1370, wherein the 2'-substituent of the at least one substituted stereo-non-standard nucleoside of the modified oligonucleotide is selected from: 2'-MOE, 2'-OMe, 2'-F, or 2'-OH.

Embodiment 1372. The oligomeric compound of any of claims 1246-1371, wherein each nucleoside of the modified oligonucleotide is a stereo-standard nucleoside.

Embodiment 1373. The oligomeric compound of any of claims 1246-1371, wherein the modified oligonucleotide consists of 12-30 linked nucleosides.

Embodiment 1374. The oligomeric compound of any of claims 1246-1371, wherein the modified oligonucleotide consists of 16-24 linked nucleosides.

Embodiment 1375. The oligomeric compound of any of claims 1246-1371, wherein the modified oligonucleotide consists of 18-22 linked nucleosides.

Embodiment 1376. The oligomeric compound of any of claims 1246-1374, wherein the modified oligonucleotide consists of 16 linked nucleosides.

Embodiment 1377. The oligomeric compound of any of claims 1246-1374, wherein the modified oligonucleotide consists of 17 linked nucleosides.

Embodiment 1378. The oligomeric compound of any of claims 1246-1375, wherein the modified oligonucleotide consists of 18 linked nucleosides.

Embodiment 1379. The oligomeric compound of any of claims 1246-1375, wherein the modified oligonucleotide consists of 19 linked nucleosides.

Embodiment 1380. The oligomeric compound of any of claims 1246-1375, wherein the modified oligonucleotide consists of 20 linked nucleosides.

Embodiment 1381. The oligomeric compound of any of claims 1246-1375, wherein the modified oligonucleotide consists of 21 linked nucleosides.

Embodiment 1382. The oligomeric compound of any of claims 1246-1375, wherein the modified oligonucleotide consists of 22 linked nucleosides.

Embodiment 1383. The oligomeric compound of any of claims 1246-1374, wherein the modified oligonucleotide consists of 23 linked nucleosides.

Embodiment 1384. The oligomeric compound of any of claims 1246-1383, wherein at least one nucleoside of the modified oligonucleotide is selected from: a 2'-OMe nucleoside, a 2'-F nucleoside, and an RNA nucleoside.

Embodiment 1385. The oligomeric compound of any of claims 1246-139, wherein at least one nucleoside of the modified oligonucleotide is a 2'-OMe nucleoside, and at least one nucleoside of the modified oligonucleotide is a 2'-F nucleoside.

Embodiment 1386. The oligomeric compound of claim 1385, wherein each nucleoside of the modified oligonucleotide is selected from a 2'-OMe nucleoside or a 2'-F nucleoside.

Embodiment 1387. The oligomeric compound of any of claims 1246-1385, wherein at least one nucleoside of the modified oligonucleotide is a 2'-OMe nucleoside, at least one nucleoside of the modified oligonucleotide is a 2'-F nucleoside, and at least one nucleoside of the modified oligonucleotide comprises a sugar surrogate.

Embodiment 1388. The oligomeric compound of claim 1387, wherein each nucleoside of the modified oligonucleotide is selected from a 2'-OMe nucleoside, a 2'-F nucleoside, and a nucleoside comprising a sugar surrogate.

Embodiment 1389. The oligomeric compound of any of claims 1387-1388, wherein the nucleoside comprising a sugar surrogate is selected from:

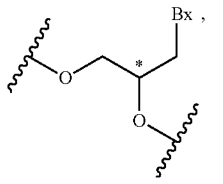

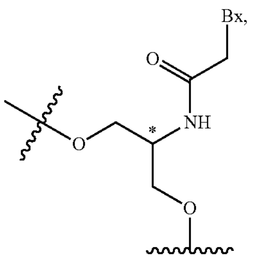

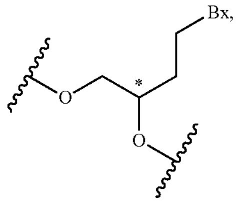

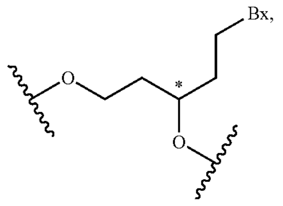

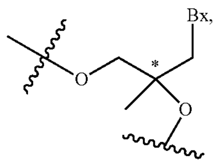

or

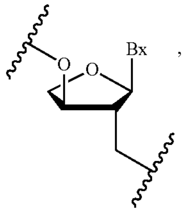

wherein Bx is a heterocyclic base moiety.

Embodiment 1390. The oligomeric compound of claim 1389, wherein the nucleoside comprising a sugar surrogate is GNA.

Embodiment 1391. The oligomeric compound of any of claims 1384-1390, wherein the modified oligonucleotide has a region of alternating nucleoside types having the motif ABABA, wherein each A is a stereo-standard nucleoside of a first type and each B is a stereo-standard nucleoside of a second type, wherein the first type and the second type are different from one another.

Embodiment 1392. The oligomeric compound of claim 1391, wherein A and B are selected from 2'-F substituted nucleosides, 2'-OMe substituted nucleosides, and stereo-standard RNA nucleosides.

Embodiment 1393. The oligomeric compound of any of claims 1246-1392, wherein the 5'-end of the modified oligonucleotide comprises a terminal group.

Embodiment 1394. The oligomeric compound of claim 1393, wherein the terminal group is a stabilized phosphate group.

Embodiment 1395. The oligomeric compound of claim 1394, wherein the stabilized phosphate group is a 5'-vinyl phosphonate or a 5'-cyclopropyl phosphonate.

Embodiment 1396. The compound of claim 1393, wherein the terminal group has Formula XXII:

XXII

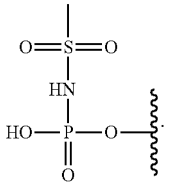

Embodiment 1397. The oligomeric compound of claim 1393, wherein the terminal group is selected from

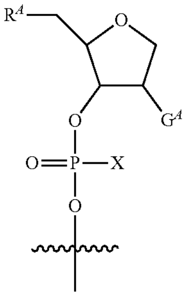
or
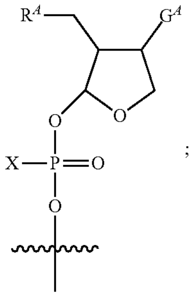
;

wherein $R^A$ is OH, OP(═O)OH, OP(═O)SH, a mesyl phosphoramidate, or a stabilized phosphate group;

$G^A$ is H, OH, OMe, MOE, or a halogen;

X is OH, SH, or $NSO_2R_2$;

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group.

Embodiment 1398. The oligomeric compound of claim 1397, wherein $G^A$ is selected from H or OH and X is SH.

Embodiment 1399. An antisense agent consisting or comprising an oligomeric compound of any of claims 1246-1398.

Embodiment 1400. The antisense agent of claim 1399, wherein the antisense agent is an RNAi agent.

Embodiment 1401. The RNAi agent of claim 1400, wherein the RNAi agent is a single-stranded RNAi agent comprising an RNAi antisense oligomeric compound, wherein the RNAi antisense oligomeric compound is an oligomeric compound of any of claims 1246-1398.

Embodiment 1402. The RNAi agent of claim 1401, wherein the RNAi agent is an oligonucleotide duplex comprising an RNAi antisense oligomeric compound and an RNAi sense oligomeric compound, wherein the RNAi antisense oligomeric compound and/or the RNAi sense oligomeric compound is an oligomeric compound of any of claims 1-153.

Embodiment 1403. The RNAi agent of claim 1401 or 1402, wherein at least one internucleoside linking group of the RNAi antisense oligomeric compound is an internucleoside linking group of Formula XVII.

Embodiment 1404. The RNAi agent of claim 1401 or 1402, wherein at least two internucleoside linking groups of the RNAi antisense oligomeric compound are independently selected internucleoside linking groups of Formula XVII.

Embodiment 1405. The RNAi agent of any of claims 1401-1404, wherein at least one of the five 3'-most internucleoside linking groups of the RNAi antisense oligomeric compound is an internucleoside linking group of Formula XVII.

Embodiment 1406. The RNAi agent of any of claims 1401-1404, wherein at least two of the five 3'-most internucleoside linking groups of RNAi antisense oligomeric compound is an internucleoside linking group of Formula XVII.

Embodiment 1407. The RNAi agent of any of claims 1401-1406, wherein 1-3 of the three 3'-most internucleoside linking groups are internucleoside linking groups of Formula XVII, and each of these three internucleoside linking groups that is not an internucleoside linking group of Formula XVII is a phosphodiester or phosphorothioate internucleoside linking group.

Embodiment 1408. The RNAi agent of claim 1407, wherein the two 3'-most internucleoside linking groups are internucleoside linking groups of Formula XVII.

Embodiment 1409. The RNAi agent of any of claims 1401-1408, wherein exactly one of the 5'-most and penultimate 5'-most internucleoside linking groups is an internucleoside linking group of Formula XVII.

Embodiment 1410. The RNAi agent of any of claims 1401-1409, wherein exactly one of the 5'-most and penultimate 5'-most internucleoside linking groups of the RNAi antisense oligonucleotide is an internucleoside linking groups of Formula XVII, the other of the 5'-most and penultimate 5'-most internucleoside linking groups of the RNAi antisense oligonucleotide is selected from a phosphodiester and a phosphorothioate internucleoside linkage, the two 3'-most internucleoside linking groups of the RNAi antisense oligonucleotide are internucleoside linking groups of Formula XVII, and the remaining internucleoside linking groups of the RNAi antisense oligonucleotide are phosphodiester internucleoside linkages.

Embodiment 1411. The RNAi agent of any of claims 1401-1410, wherein the antisense oligomeric compound comprises a 3'-overhang.

Embodiment 1412. The RNAi agent of claim 1411, wherein the 3'-overhang consists of two nucleosides.

Embodiment 1413. The RNAi agent of any of claims 1401-1409 or 1411-1412, wherein at least one internucleoside linking group within the seed region of the RNAi antisense oligomeric compound is an internucleoside linking group of Formula XVII.

Embodiment 1414. The RNAi agent of any of claims 1401-1413, wherein for each internucleoside linking group of Formula XVII, $R_1$ is H and T is $SO_2Me$.

Embodiment 1415. The RNAi agent of any of claims 1401-1414, wherein the RNAi antisense oligomeric compound comprises an RNAi antisense modified oligonucleotide, wherein the RNAi antisense modified oligonucleotide consists of 23 linked nucleosides, and the internucleoside linkage motif is selected from: ooooooooooooooooooooaa, aaoooooooooooooooooooo, aaooooooooooooooooooaa, asooooooooooooooooooss, saoooooooooooooooooooo, oooooooooooooooooooaaa, ooooooooooooooooaaaoss, oooooooooooooaaaooooss, ooooooooooaaaoooooooss, oooooooaaaooooooooooss, ooooaaaoooooooooooooss, saoooaoooooooaoaooooss, ssoooaoooooooaoaooooss, or ssooooooooooooooooooaa, wherein each "a" represents an internucleoside linkage of Formula XVII, each “s” represents a phosphorothioate internucleoside linkage, and each “o” represents a phosphodiester internucleoside linkage.

Embodiment 1416. The RNAi agent of claim 1415, wherein the internucleoside linkage motif of the RNAi antisense modified oligonucleotide is selected from ooooooooooooooooooaa, asooooooooooooooooss, or saoooooooooooooooooo.

Embodiment 1417. The RNAi agent of claim 1415 or 1416, wherein the sugar motif of the RNAi antisense oligomeric compound from 5' to 3' is yfyfyfyfyfyfyfyfyfyfy or yfyyyfyyyyyyyfyfyyyyyyy, wherein “y” represents a 2'-OMe sugar moiety and “f” represents a 2'-F sugar moiety.

Embodiment 1418. The RNAi agent of any of claims 1401-1414, wherein the RNAi antisense oligomeric compound comprises an RNAi antisense modified oligonucleotide, wherein the RNAi antisense modified oligonucleotide consists of 21 linked nucleosides, and the internucleoside linkage motif is selected from: aaososososososssssss, ssaaososososossssss, ssosaaososososssssss, ssososaaosososssssss, ssosososaaosossssss, ssososososaaossssss, ssosososososaassssss, ssososososososaassss, ssososososososssaass, ssososososososssssaa wherein each “a” represents an internucleoside linkage of Formula XVII, each “s” represents a phosphorothioate internucleoside linkage, and each “o” represents a phosphodiester internucleoside linkage.

Embodiment 1419. The RNAi agent of claim 1418, wherein the internucleoside linkage motif of the RNAi antisense modified oligonucleotide is selected from aaososososososssssss, ssaaososososossssss, or ssososososososssssaa, wherein each “a” represents an internucleoside linkage of Formula XVII, each “s” represents a phosphorothioate internucleoside linkage, and each “o” represents a phosphodiester internucleoside linkage.

Embodiment 1420. The RNAi agent of claim 1418 or 1419, wherein the sugar motif of the RNAi antisense oligomeric compound from 5' to 3' is yfyfyfyfyfyfyfyfyfyfyf, wherein “y” represents a 2'-OMe sugar moiety and “f” represents a 2'-F sugar moiety.

Embodiment 1421. The RNAi agent of any of claims 1415-1420 wherein each “a” is a mesyl phosphoramidate linkage.

Embodiment 1422. The RNAi agent of any of claims 1401-1421, wherein at least one region of the RNAi antisense oligomeric compound has structure A, B, C, D, E, or P.

Embodiment 1423. The RNAi agent of claim 1422, wherein at least one region having structure A, B, C, D, or E is within the seed region of the RNAi antisense oligomeric compound.

Embodiment 1424. The RNAi agent of claim 1422, wherein at least one region having structure A, B, C, D, or E is at the 3' end of the RNAi antisense oligomeric compound.

Embodiment 1425. The RNAi agent of claim 1422, wherein at least one region having structure A, B, C, D, E, or P is at the 5' end of the RNAi antisense oligomeric compound.

Embodiment 1426. The RNAi agent of any of claims 1401-1425, wherein at least one region of the RNAi antisense oligomeric compound has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

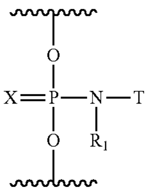

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the RNAi antisense oligomeric compound having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, substituted $C_1$-$C_6$ alkyl, and a conjugate;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 1427. The RNAi agent of claim 1426, wherein the region having the formula $(N_{g1})_{L1}(N_{g2})_{L2}(N_{g3})_{L3}$ includes one or two 3'-overhang nucleosides.

Embodiment 1428. The RNAi agent of claim 1426, wherein at least one region having the formula $(N_{g1})_{L1}(N_{g2})_{L2}(N_{g3})_{L3}$ is at the 3' end of the RNAi antisense oligomeric compound.

Embodiment 1429. The RNAi agent of claim 1428, wherein $L_1$ and $L_2$ are each internucleoside linkages of Formula XVII wherein $R_1$ is H and T is $SO_2Me$, and $L_3$ is a phosphodiester internucleoside linkage.

Embodiment 1430. The RNAi agent of claim 1428, wherein at least one region having the formula $(N_{g1})_{L1}(N_{g2})_{L2}(N_{g3})_{L3}$ is at the 5' end of the RNAi antisense oligomeric compound.

Embodiment 1431. The RNAi agent of claim 1429, wherein one of $L_1$ or $L_2$ is an internucleoside linkages of Formula XVII wherein $R_1$ is H and T is $SO_2Me$, the other of $L_1$ or $L_2$ is a phosphorothioate internucleoside linkage, and $L_3$ is a phosphodiester internucleoside linkage.

Embodiment 1432. The RNAi agent of claim 1426, wherein at least one region having the formula $(N_{g1})_{L1}(N_{g2})_{L2}(N_{g3})_{L3}$ is within the seed region of the RNAi antisense oligomeric compound.

Embodiment 1433. The RNAi agent of any of claims 1401-1432, wherein the region of the RNAi antisense oligonucleotide that is complementary to a target is at least 15 nucleobases.

Embodiment 1434. The RNAi agent of any of claims 1401-1433, wherein the region of the RNAi antisense oligonucleotide that is complementary to a target is at least 17 nucleobases.

Embodiment 1435. The RNAi agent of any of claims 1401-1434, wherein the region of the RNAi antisense oligonucleotide that is complementary to a target is at least 19 nucleobases.

Embodiment 1436. The RNAi agent of any of claims 1401-1435, wherein the region of the RNAi antisense oligonucleotide that is complementary to a target is at least 21 nucleobases.

Embodiment 1437. The RNAi agent of any of claims 1401-1435, wherein the region of the RNAi antisense oligonucleotide that is complementary to a target is exactly 19 nucleobases.

Embodiment 1438. The RNAi agent of any of claims 1401-1436, wherein the region of the RNAi antisense oligonucleotide that is complementary to a target is exactly 21 nucleobases.

Embodiment 1439. The RNAi agent of any of claims 1401-1438, wherein at least one nucleoside of the RNAi antisense oligomeric compound is selected from: a 2'-OMe nucleoside, a 2'-F nucleoside, and an RNA nucleoside.

Embodiment 1440. The RNAi agent of any of claims 1401-1439, wherein at least one nucleoside of the RNAi antisense oligomeric compound is a 2'-OMe nucleoside, and at least one nucleoside of the RNAi antisense oligomeric compound is an RNA nucleoside.

Embodiment 1441. The RNAi agent of any of claims 1401-1440, wherein at least one nucleoside of the RNAi antisense oligomeric compound is a 2'-OMe nucleoside, and at least one nucleoside of the RNAi antisense oligomeric compound is a 2'-F nucleoside.

Embodiment 1442. The RNAi agent of claim 1441, wherein each nucleoside of the RNAi antisense oligomeric compound is selected from a 2'-OMe nucleoside or a 2'-F nucleoside.

Embodiment 1443. The RNAi agent of any of claims 1401-1439, wherein at least one nucleoside of the RNAi antisense oligomeric compound is a 2'-OMe nucleoside, at least one nucleoside of the RNAi antisense oligomeric compound is a 2'-F nucleoside, and at least one nucleoside of the oligomeric compound comprises a sugar surrogate.

Embodiment 1444. The RNAi agent of claim 1443, wherein each nucleoside of the RNAi antisense oligomeric compound is selected from a 2'-OMe nucleoside, a 2'-F nucleoside, and a nucleoside comprising a sugar surrogate.

Embodiment 1445. The RNAi agent of any of claims 1443-1444, wherein the nucleoside comprising a sugar surrogate is selected from:

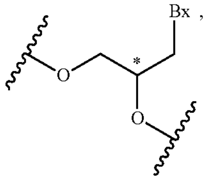

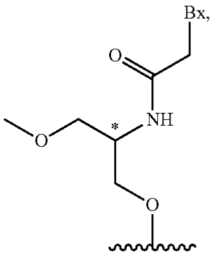

-continued

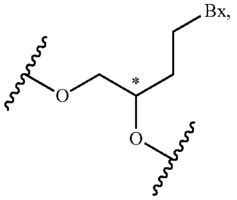

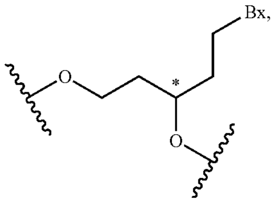

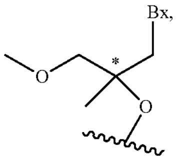

or

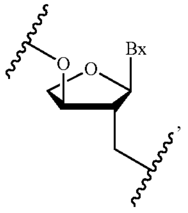

wherein Bx is a heterocyclic base moiety.

Embodiment 1446. The RNAi agent of claim 1445, wherein the nucleoside comprising a sugar surrogate is GNA.

Embodiment 1447. The RNAi agent of claim 1445 or 1446, wherein at least one nucleoside comprising a sugar surrogate is one of the nine 5'-most nucleosides of the RNAi antisense oligomeric compound.

Embodiment 1448. The RNAi agent of any of claims 1401-1447, wherein the oligomeric compound has a region of alternating nucleoside types having the motif ABABA, wherein each A is a stereo-standard nucleoside of a first type and each B is a stereo-standard nucleoside of a second type, wherein the first type and the second type are different from one another.

Embodiment 1449. The RNAi agent of claim 1448, wherein A and B are selected from 2'-F substituted nucleosides, 2'-OMe substituted nucleosides, and stereo-standard RNA nucleosides.

Embodiment 1450. The RNAi agent of any of claims 1401-1449, wherein the 5'-end of the RNAi antisense oligomeric compound comprises a terminal group.

Embodiment 1451. The RNAi agent of claim 1450, wherein the terminal group is a stabilized phosphate group.

Embodiment 1452. The RNAi agent of claim 1451, wherein the stabilized phosphate group is a 5'-vinyl phosphonate or a 5'-cyclopropyl phosphonate.

Embodiment 1453. The RNAi agent of claim 1542, wherein the terminal group has Formula XXII:

XXII

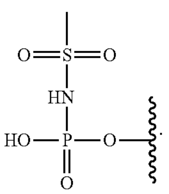

Embodiment 1454. The RNAi agent of claim 1450, wherein the terminal group is selected from:

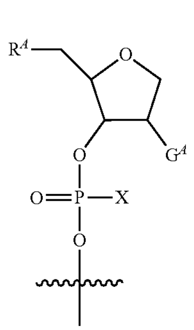
or
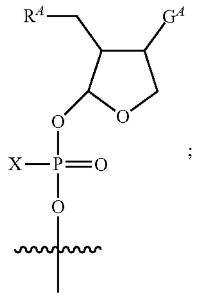
;

wherein $R^A$ is OH, OP(=O)OH, OP(=O)SH, a mesyl phosphoramidate, or a stabilized phosphate group;

$G^A$ is H, OH, OMe, MOE, or a halogen;

X is OH, SH, or $NSO_2R_2$;

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group.

Embodiment 1455. The RNAi agent of claim 1454, wherein $G^A$ is selected from H or OH and X is SH.

Embodiment 1456. The RNAi agent of claim 1402-1455, wherein at least one internucleoside linking group of the RNAi sense oligomeric compound is an internucleoside linking group of Formula XVII.

Embodiment 1457. The RNAi agent of claim 1456, wherein at least one of the five 5'-most internucleoside linking groups of the RNAi sense oligomeric compound is an internucleoside linking group of Formula XVII.

Embodiment 1458. The RNAi agent of claim 1456, wherein at least two of the five 5'-most internucleoside linking groups of the RNAi sense oligomeric compound are internucleoside linking groups of Formula XVII.

Embodiment 1459. The RNAi agent of claim 1456, wherein the two 5'-most internucleoside linking groups of the RNAi sense oligomeric compound are internucleoside linking groups of Formula XVII.

Embodiment 1460. The RNAi agent of any of claims 1456-1459, wherein at least one of the five 3'-most internucleoside linking groups of the RNAi sense oligomeric compound is an internucleoside linking group of Formula XVII.

Embodiment 1461. The RNAi agent of any of claims 1456-1459, wherein at least two of the five 3'-most internucleoside linking groups of RNAi sense oligomeric compound is an internucleoside linking group of Formula XVII.

Embodiment 1462. The RNAi agent of any of claims 1456-1459, wherein the two 3'-most internucleoside linking groups are internucleoside linking groups of Formula XVII.

Embodiment 1463. The RNAi agent of claim 1456, wherein the two 3'-most and the two 5'-most internucleoside linking groups of the RNAi sense oligonucleotide are internucleoside linking groups of Formula XVII, and the remaining internucleoside linking groups of the RNAi sense oligonucleotide are phosphodiester internucleoside linkages.

Embodiment 1464. The RNAi agent of any of claims 1456-1463, wherein for each internucleoside linking group of Formula XVII, $R_1$ is H and T is $SO_2Me$.

Embodiment 1465. The RNAi agent of any of claims 1456-1464, wherein the RNAi sense oligomeric compound consists of 21 linked nucleosides, and the internucleoside linkage motif is selected from: ooooooooooooooooooaa, aaooooooooooooooooaa, ooooooooooooooooooaa, or ssooooaoaaaooooooooo, wherein each "a" represents an internucleoside linkage of Formula XVII, each "s" represents a phosphorothioate internucleoside linkage, and each "o" represents a phosphodiester internucleoside linkage.

Embodiment 1466. The RNAi agent of claim 1465, wherein the internucleoside linkage motif of the RNAi sense oligomeric compound is selected from ooooooooooooooooooaa, aaooooooooooooooooaa, or ooooooooooooooooooaa, wherein each "a" represents an internucleoside linkage of Formula XVII, each "s" represents a phosphorothioate internucleoside linkage, and each "o" represents a phosphodiester internucleoside linkage.

Embodiment 1467. The RNAi agent of claim 1465 or 1466, wherein the sugar motif of the RNAi sense oligomeric compound is selected from: yyyyyyfyfffyyyyyyyyyy or fyfyfyfyfyfyfyfyfyfyf, wherein "y" represents a 2'-OMe sugar moiety and "f" represents a 2'-F sugar moiety.

Embodiment 1468. The RNAi agent of any of claims 1465-1467 wherein each "a" is a mesyl phosphoramidate linkage.

Embodiment 1469. The RNAi agent of any of claims 1456-1468, wherein at least one region of the RNAi sense oligomeric compound has structure A, B, C, D, E or P.

Embodiment 1470. The RNAi agent of claim 1469, wherein at least one region having structure A, B, C, D, or E is at the 3' end of the RNAi sense oligomeric compound.

Embodiment 1471. The RNAi agent of claim 1469, wherein at least one region having structure A, B, C, D, or E is at the 5' end of the RNAi sense oligomeric compound.

Embodiment 1472. The RNAi agent of any of claims 1456-1471, wherein at least one region of the RNAi sense oligomeric compound has the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

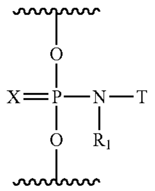

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the RNAi sense oligomeric compound having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 1473. The RNAi agent of claim 1472, wherein at least one region having the formula $(N_{g1})_{L1}(N_{g2})_{L2}(N_{g3})_{L3}$ is at the 3' end of the RNAi sense oligomeric compound.

Embodiment 1474. The RNAi agent of claim 1473, wherein $L_1$ and $L_2$ are internucleoside linking groups of Formula XVII, wherein $R_1$ is H and T is $SO_2Me$, and $L_3$ is a phosphodiester internucleoside linkage.

Embodiment 1475. The RNAi agent of claim 1472, wherein at least one region having the formula $(N_{g1})_{L1}(N_{g2})_{L2}(N_{g3})_{L3}$ is at the 5' end of the RNAi sense oligomeric compound.

Embodiment 1476. The RNAi agent of claim 1475, wherein $L_1$ is a phosphodiester internucleoside linking group and $L_2$ and $L_3$ are each internucleoside linking groups of Formula XVII, wherein $R_1$ is H and T is $SO_2Me$.

Embodiment 1477. The RNAi agent of any of claims 1402-1476, wherein the RNAi sense oligomeric compound comprises a 3' terminal group and/or a 5' terminal group.

Embodiment 1478. The RNAi agent of any of claims 1402-1476, wherein the RNAi sense oligomeric compound comprises a conjugate group.

Embodiment 1479. The RNAi agent of claim 1478, wherein the conjugate group comprises a cell-targeting moiety.

Embodiment 1480. The RNAi agent of claim 1478, wherein the conjugate group comprises a carbohydrate or carbohydrate cluster.

Embodiment 1481. The RNAi agent of claim 1478, wherein the conjugate group comprises at least one GalNAc.

Embodiment 1482. The RNAi agent of claim 1478, wherein the conjugate group comprises a $C_{10}$-$C_{20}$ alkyl chain.

Embodiment 1483. The RNAi agent of claim 1478, wherein the conjugate group comprises $C_{16}$ alkyl.

Embodiment 1484. The RNAi agent of any of claims 1402-1483, wherein the double-stranded region of the oligonucleotide duplex is at least 15 nucleosides.

Embodiment 1485. The RNAi agent of any of claims 1402-1483, wherein the double-stranded region of the oligonucleotide duplex is at least 17 nucleosides.

Embodiment 1486. The RNAi agent of any of claims 1402-1483, wherein the double-stranded region of the oligonucleotide duplex is at least 19 nucleosides.

Embodiment 1487. The RNAi agent of any of claims 1402-1483, wherein the double-stranded region of the oligonucleotide duplex is exactly 19 nucleosides.

Embodiment 1488. The oligomeric compound of any of claims 1246-1383, wherein each nucleoside of the modified oligonucleotide is a modified nucleoside comprising a modified sugar moiety.

Embodiment 1489. The oligomeric compound of claim 1488, wherein each modified sugar moiety of the modified oligonucleotide is independently selected from a bicyclic sugar moiety and a 2'-substituted furanosyl sugar moiety.

Embodiment 1490. The oligomeric compound of claim 1488 or 1489, wherein each modified sugar moiety of the modified oligonucleotide comprises the same modification.

Embodiment 1491. The oligomeric compound of any of claims 1488-1490, wherein each modified sugar moiety of the modified oligonucleotide is selected from a 2'-OMe sugar moiety, a 2'-MOE sugar moiety, and a 2'-NMA sugar moiety.

Embodiment 1492. The oligomeric compound of claim 1488 or 1489, wherein the three 3'-most nucleosides of the modified oligonucleotide comprise a bicyclic sugar moiety, and the remaining nucleosides of the modified oligonucleotide comprise a 2'-substituted furanosyl sugar moiety.

Embodiment 1493. The oligomeric compound of claim 1488 or 1489, wherein the four 3'-most nucleosides of the modified oligonucleotide comprise a bicyclic sugar moiety, and the remaining nucleosides of the modified oligonucleotide comprise a 2'-substituted furanosyl sugar moiety.

Embodiment 1494. The oligomeric compound of claim 1488 or 1489, wherein the five 3'-most nucleosides of the modified oligonucleotide comprise a bicyclic sugar moiety, and the remaining nucleosides of the modified oligonucleotide comprise a 2'-substituted furanosyl sugar moiety.

Embodiment 1495. The oligomeric compound of claim 1488 or 1489, wherein the six 3'-most nucleosides of the modified oligonucleotide comprise a bicyclic sugar moiety, and the remaining nucleosides of the modified oligonucleotide comprise a 2'-substituted furanosyl sugar moiety.

Embodiment 1496. The oligomeric compound of any of claims 1488 or 1489, wherein each bicyclic sugar moiety of the modified oligonucleotide is selected from among cEt, LNA, and ENA.

Embodiment 1497. The oligomeric compound of claim 1496, wherein the bicyclic sugar moiety is cEt.

Embodiment 1498. The oligomeric compound of any of claims 1492-1497, wherein the 2'-substituted furanosyl sugar moiety is selected from 2'-OMe, 2'-MOE, and 2'-F.

Embodiment 1499. The oligomeric compound of any of claims 1488-1498, wherein at least one of the ten 5'-most linking groups of the modified oligonucleotide is an internucleoside linking group of Formula XVII.

Embodiment 1500. The oligomeric compound of claim 1499, wherein at least 2 of the ten 5'-most linking groups of the modified oligonucleotide are internucleoside linking groups of Formula XVII.

Embodiment 1501. The oligomeric compound of claim 1499, wherein at least 3 of the ten 5'-most linking groups of the modified oligonucleotide are internucleoside linking groups of Formula XVII.

Embodiment 1502. The oligomeric compound of claim 1499, wherein at least 4 of the ten 5'-most linking groups of the modified oligonucleotide are internucleoside linking groups of Formula XVII.

Embodiment 1503. The oligomeric compound of claim 1499, wherein at least 5 of the ten 5'-most linking groups of the modified oligonucleotide are internucleoside linking groups of Formula XVII.

Embodiment 1504. The oligomeric compound of claim 1499, wherein at least 6 of the ten 5'-most linking groups of the modified oligonucleotide are internucleoside linking groups of Formula XVII.

Embodiment 1505. The oligomeric compound of claim 1499, wherein the two 5'-most internucleoside linking groups are internucleoside linking groups of Formula XVII.

Embodiment 1506. The oligomeric compound of any of claims 1489-1505, wherein at least one of the ten 3'-most internucleoside linking groups of the modified oligonucleotide is an internucleoside linking group of Formula XVII.

Embodiment 1507. The oligomeric compound of claim 1506, wherein at least 2 of the ten 3'-most internucleoside linking groups of the modified oligonucleotide are internucleoside linking groups of Formula XVII.

Embodiment 1508. The oligomeric compound of claim 1506, wherein at least 3 of the ten 3'-most internucleoside linking groups are internucleoside linking groups of Formula XVII.

Embodiment 1509. The oligomeric compound of claim 1506, wherein at least 4 of the ten 3'-most internucleoside linking groups are internucleoside linking groups of Formula XVII.

Embodiment 1510. The oligomeric compound of claim 1506, wherein at least 5 of the ten 3'-most internucleoside linking groups are internucleoside linking groups of Formula XVII.

Embodiment 1511. The oligomeric compound of claim 1506, wherein at least 6 of the ten 3'-most internucleoside linking groups are internucleoside linking groups of Formula XVII.

Embodiment 1512. The oligomeric compound of claim 1506, wherein the two 3'-most internucleoside linking groups of the oligomeric compound are internucleoside linking groups of Formula XVII.

Embodiment 1513. The oligomeric compound of any of claims 1484-1494, wherein the modified oligonucleotide comprises at least one block of at least 3 consecutive internucleoside linking groups of Formula XVII.

Embodiment 1514. The oligomeric compound of any of claims 1484-1494, wherein the modified oligonucleotide comprises at least one block of at least 4 consecutive internucleoside linking groups of Formula XVII.

Embodiment 1515. The oligomeric compound of any of claims 1484-1494, wherein the modified oligonucleotide comprises at least one block of at least 5 consecutive internucleoside linking groups of Formula XVII.

Embodiment 1516. The oligomeric compound of any of claims 1484-1494, wherein the modified oligonucleotide comprises at least one block of at least 6 consecutive internucleoside linking groups of Formula XVII.

Embodiment 1517. The oligomeric compound of any of claims 1513-1516, wherein at least one block of consecutive internucleoside linking groups of Formula XVII is at the 5' end of the modified oligonucleotide.

Embodiment 1518. The oligomeric compound of any of claims 1513-1516, wherein at least one block of consecutive internucleoside linking groups of Formula XVII is at the 3' end of the modified oligonucleotide.

Embodiment 1519. The oligomeric compound of any of claims 1484-1518, wherein for each internucleoside linking group of Formula XVII of the modified oligonucleotide, $R_1$ is H and T is $SO_2Me$.

Embodiment 1520. The oligomeric compound of any of claims 1484-1494, wherein the internucleoside linkage motif of the modified oligonucleotide is selected from: aaaaaaasssssssss, sssssaaaaaassss, or sssssssssaaaaaa, wherein each "a" represents an internucleoside linkage of Formula XVII, each "s" represents a phosphorothioate internucleoside linkage, and each "o" represents a phosphodiester internucleoside linkage.

Embodiment 1521. The oligomeric compound of claim 1520, wherein each "a" represents a mesyl phosphoramidate internucleoside linkage.

Embodiment 1522. The oligomeric compound of any of claims 1246-1383, wherein the modified oligonucleotide comprises a deoxy region consisting of 6-11 linked nucleosides wherein each nucleoside of the deoxy region is either a modified nucleoside or a stereo-standard DNA nucleoside and wherein at least 3 contiguous nucleosides of the deoxy region are stereo-standard DNA nucleosides and not more than three nucleosides of the deoxy region are modified nucleosides.

Embodiment 1523. The oligomeric compound of claim 1522, wherein at least 5 contiguous nucleosides of the deoxy region are stereo-standard DNA nucleosides.

Embodiment 1524. The oligomeric compound of claim 1522, wherein at least 6 contiguous nucleosides of the deoxy region are stereo-standard DNA nucleosides.

Embodiment 1525. The oligomeric compound of claim 1522, wherein at least 7 contiguous nucleosides of the deoxy region are stereo-standard DNA nucleosides.

Embodiment 1526. The oligomeric compound of claim 1522, wherein at least 8 contiguous nucleosides of the deoxy region are stereo-standard DNA nucleosides.

Embodiment 1527. The oligomeric compound of any of claims 1522-1526, wherein the deoxy region consists of 8-10 linked nucleosides.

Embodiment 1528. The oligomeric compound of any of claims 1522-1526, wherein the deoxy region consists of 9 linked nucleosides.

Embodiment 1529. The oligomeric compound of any of claims 1522-1526, wherein the deoxy region consists of 10 linked nucleosides.

Embodiment 1530. The oligomeric compound of any of claims 1522-1526, wherein the deoxy region consists of 11 linked nucleosides.

Embodiment 1531. The oligomeric compound of any of claims 1522-1526, wherein at least 6 nucleosides of the deoxy region are stereo-standard DNA nucleosides.

Embodiment 1532. The oligomeric compound of any of claims 1522-1526, wherein at least 7 nucleosides of the deoxy region are stereo-standard DNA nucleosides.

Embodiment 1533. The oligomeric compound of any of claims 1522-1526, wherein at least 8 nucleosides of the deoxy region are stereo-standard DNA nucleosides.

Embodiment 1534. The oligomeric compound of any of claims 1522-1526, wherein at least 9 nucleosides of the deoxy region are stereo-standard DNA nucleosides.

Embodiment 1535. The oligomeric compound of any of claims 1522-1534 wherein exactly two nucleosides of the deoxy region are modified nucleosides.

Embodiment 1536. The oligomeric compound of any of claims 1522-1535 wherein exactly one nucleoside of the deoxy region is a modified nucleoside.

Embodiment 1537. The oligomeric compound of any of claims 1522-1536 wherein at least one modified nucleoside of the deoxy region is a stereo-standard modified nucleoside or bicyclic nucleoside selected from a β-D-LNA nucleoside, an α-L-LNA nucleoside, an ENA nucleoside, a cEt nucleoside, a 2'-MOE nucleoside, a 2'-OMe nucleoside, a 2'-F nucleoside, and a 5'-alkyl nucleoside.

Embodiment 1538. The oligomeric compound of any of claims 1522-1537, wherein at least one modified nucleoside of the deoxy region is stereo-non-standard nucleoside.

Embodiment 1539. The oligomeric compound of claim 1538, wherein the at least one is stereo-non-standard nucleoside of the deoxy region is a stereo-non-standard DNA nucleoside.

Embodiment 1540. The oligomeric compound of claim 1539, wherein the stereo-non-standard DNA nucleoside is selected from a stereo-non-standard DNA nucleoside having: Formula I, Formula II, Formula III, Formula IV, Formula V, Formula VI, and Formula VII.

Embodiment 1541. The oligomeric compound of claim 1540, wherein the stereo-non-standard DNA nucleoside is selected from a stereo-non-standard DNA nucleoside having: Formula V and Formula II.

Embodiment 1542. The oligomeric compound of claim 1541, wherein at least one stereo-non-standard nucleoside of the deoxy region is a substituted stereo-non-standard nucleoside.

Embodiment 1543. The oligomeric compound of claim 1542, wherein at least one substituted stereo-non-standard nucleoside has a 2'-substituent selected from: 2'-MOE, 2'-OMe, 2'-F, or 2'-OH.

Embodiment 1544. The oligomeric compound of any of claims 1522-1543, wherein the $2^{nd}$ nucleoside from the 5'-end of the deoxy region is a modified nucleoside.

Embodiment 1545. The oligomeric compound of any of claims 1522-1543, wherein the $3^{rd}$ nucleoside from the 5'-end of the deoxy region is a modified nucleoside.

Embodiment 1546. The oligomeric compound of any of claims 1522-1543, wherein the $4^{th}$ nucleoside from the 5'-end of the deoxy region is a modified nucleoside.

Embodiment 1547. The oligomeric compound of any of claims 299-1546, wherein the modified nucleoside in the deoxy region is a 2'-OMe nucleoside.

Embodiment 1548. The oligomeric compound of any of claims 1522-1537, wherein each nucleoside of the deoxy region is a stereo-standard DNA nucleoside.

Embodiment 1549. The oligomeric compound of any of claims 1522-1548, wherein at least one internucleoside linking group within the deoxy region is an internucleoside linking group of Formula XVII.

Embodiment 1550. The oligomeric compound of any of claims 1522-1549, wherein the internucleoside linking group linking the $4^{th}$ and $2^{nd}$ nucleosides of the deoxy region as counted from the 5'-end of the deoxy region is an internucleoside linking group of Formula XVII.

Embodiment 1551. The oligomeric compound of any of claims 1522-1550, wherein the internucleoside linking group linking the $2^{nd}$ and $3^{rd}$ nucleosides of the deoxy region as counted from the 5'-end of the deoxy region is an internucleoside linking group of Formula XVII.

Embodiment 1552. The oligomeric compound of any of claims 1522-1551, wherein the internucleoside linking group linking the $3^{rd}$ and $4^{th}$ nucleosides of the deoxy region as counted from the 5'-end of the deoxy region is an internucleoside linking group of Formula XVII.

Embodiment 1553. The oligomeric compound of any of claims 1522-1552, wherein the internucleoside linking group linking the $4^{th}$ and $5^{th}$ nucleosides of the deoxy region as counted from the 5'-end of the deoxy region is an internucleoside linking group of Formula XVII.

Embodiment 1554. The oligomeric compound of any of claims 1522-1553, wherein one internucleoside linking group in the deoxy region is a linking group of Formula XVII and the other internucleoside linking groups of the deoxy region are independently selected from phosphodiester and phosphorothioate internucleoside linking groups.

Embodiment 1555. The oligomeric compound of any of claims 1522-1555, wherein two internucleoside linking groups in the deoxy region are linking groups of Formula XVII and the other internucleoside linking groups of the deoxy region are independently selected from phosphodiester and phosphorothioate internucleoside linking groups.

Embodiment 1556. The oligomeric compound of any of claims 1522-1555, wherein three internucleoside linking groups in the deoxy region are linking groups linking groups of Formula XVII and the other internucleoside linking groups of the deoxy region are independently selected from phosphodiester and phosphorothioate internucleoside linking groups.

Embodiment 1557. The oligomeric compound of any of claims 1522-1555, wherein four internucleoside linking groups in the deoxy region are linking groups linking groups of Formula XVII and the other internucleoside linking groups of the deoxy region are each phosphodiester or phosphorothioate internucleoside linking groups.

Embodiment 1558. The oligomeric compound of any of claims 1554-1557, wherein the internucleoside linking groups of Formula XVII are linking the $1^{st}$ and $2^{nd}$, $2^{nd}$ and $3^{rd}$, $3^{rd}$ and $4^{th}$, and/or the $4^{th}$ and $5^{th}$ nucleosides of the deoxy region, as counted from the 5'-end of the deoxy region.

Embodiment 1559. The oligomeric compound of any of claims 1522-1558, wherein the deoxy region comprises at least one region having structure A, B, C, D, E, or P.

Embodiment 1560. The oligomeric compound of claim 1559, wherein the region having structure A, B, C, D, or E is at the 3' end of the deoxy region.

Embodiment 1561. The oligomeric compound of claim 1560, wherein the region having structure A, B, C, D, E, or P is at the 5' end of the deoxy region.

Embodiment 1562. The oligomeric compound of any of claims 1522-1561, wherein the deoxy region comprises at least one region having the formula $(N_{g1})_{L1}(N_{g2})_{L2}(N_{g3})_{L3}$, wherein each $N_g$ is a nucleoside and each L is an internucleoside linking group; wherein each of $L_1$, and $L_2$ is a phosphodiester internucleoside linking group, a phosphorothioate internucleoside linking group, or an internucleoside linking group of Formula XVII:

XVII

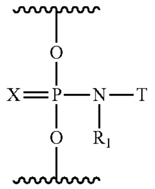

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

Embodiment 1563. The oligomeric compound of claim 1562, wherein the region having the formula $(N_{g1})_{L1}(N_{g2})_{L2}(N_{g3})_{L3}$ is at the 3' end of the deoxy region.

Embodiment 1564. The oligomeric compound of claim 1562, wherein the region having the formula $(N_{g1})_{L1}(N_{g2})_{L2}(N_{g3})_{L3}$ is at the 5' end of the deoxy region.

Embodiment 1565. The oligomeric compound of any of claims 1549-1564, wherein for each internucleoside linkage of Formula XVII, $R_1$ is H and T is $SO_2Me$.

Embodiment 1566. The oligomeric compound of any of claims 1522-1565, wherein the deoxy region is flanked on the 5' side by a 5'-region consisting of 1-6 linked 5'-region nucleosides and on the 3' side by a 3'-region consisting of 1-6 linked 3'-region nucleosides; wherein the 3'-most nucleoside of the 5'-region comprises a modified sugar moiety; and the 5'-most nucleoside of the 3'-region comprises a modified sugar moiety.

Embodiment 1567. The oligomeric compound of claim 1566, wherein the deoxy region consists of 7-11 linked nucleosides, and has the formula:

$$(N_{d1})_{L1}(N_{d2})_{L2}(N_{d3})_{L3}(N_{d4})_{L4}[N_d)_{L5}]_q;$$

wherein $N_{d1}$, $N_{d2}$, $N_{d3}$, $N_{d4}$ are independently selected from among a stereo-standard DNA nucleoside, a stereo-non-standard DNA nucleoside, or a 2'-substituted nucleoside; with the proviso that no more than one of $N_{d1}$, $N_{d2}$, $N_{d3}$, or $N_{d4}$ is a 2'-substituted nucleoside; each $N_d$ is independently selected from among a stereo-standard DNA nucleoside and a stereo-non-standard DNA nucleoside;

q is from 3-8;

wherein each of $L_1$, $L_2$, $L_3$, $L_4$, and each $L_5$ is an internucleoside linkage;

wherein at least two of $L_1$, $L_2$, $L_3$, $L_4$ are internucleoside linkages of Formula XVII.

Embodiment 1568. The oligomeric compound of claim 1567, wherein one of $N_{d1}$, $N_{d2}$, $N_{d3}$, or $N_{d4}$ is a 2'-substituted nucleoside.

Embodiment 1569. The oligomeric compound of claim 1568, wherein the 2'-substituted nucleoside is a 2'-OMe nucleoside.

Embodiment 1570. The oligomeric compound of claim 1569, wherein the 2'-OMe nucleoside is a stereo-standard 2'-OMe nucleoside.

Embodiment 1571. The oligomeric compound of any of claims 1566-1569, wherein the 2'-substituted nucleoside is $N_{d2}$.

Embodiment 1572. The oligomeric compound of claim 1567, wherein each of $N_{d1}$, $N_{d2}$, $N_{d3}$, $N_{d4}$ and each $N_d$ is a DNA nucleoside.

Embodiment 1573. The oligomeric compound of claim 1572, wherein each DNA nucleoside is a stereo-standard DNA nucleoside.

Embodiment 1574. The oligomeric compound of any of claims 1567-1573, wherein $L_1$ and $L_2$ are internucleoside linkages of Formula XVII.

Embodiment 1575. The oligomeric compound of any of claims 1567-1573, wherein $L_2$ and $L_3$ are internucleoside linkages of Formula XVII.

Embodiment 1576. The oligomeric compound of any of claims 1567-1573, wherein $L_3$ and $L_4$ are internucleoside linkages of Formula XVII.

Embodiment 1577. The oligomeric compound of any of claims 1567-1573, wherein $L_1$, $L_2$, and $L_3$ are internucleoside linkages of Formula XVII.

Embodiment 1578. The oligomeric compound of any of claims 1567-1573, wherein $L_2$, $L_3$, and $L_4$ are internucleoside linkages of Formula XVII.

Embodiment 1579. The oligomeric compound of any of claims 1567-1573, wherein $L_1$, $L_2$, $L_3$, and $L_4$ are internucleoside linkages of Formula XVII.

Embodiment 1580. The oligomeric compound of any of claims 1567-1579, wherein each $L_5$ is a phosphorothioate internucleoside linkage.

Embodiment 1581. The oligomeric compound of claims 1567-1580, wherein each internucleoside linkage that is not an internucleoside linkage of Formula XVII is a phosphorothioate internucleoside linkage.

Embodiment 1582. The oligomeric compound of any of claims 1567-1581, wherein for each internucleoside linkage of Formula XVII, $R_1$ is H and T is $SO_2Me$ Embodiment 1583. The oligomeric compound of any of claims 1567-1582, wherein the 5'-region consists of 2-5 linked nucleosides.

Embodiment 1584. The oligomeric compound of claim 1583, wherein the 5'-region consists of 3 linked nucleosides.

Embodiment 1585. The oligomeric compound of claim 1583, wherein the 5'-region consists of 5 linked nucleosides.

Embodiment 1586. The oligomeric compound of any of claims 1566-1585 wherein each nucleoside of the 5'-region is a modified nucleoside.

Embodiment 1587. The oligomeric compound of any of claims 1566-1586, wherein each nucleoside of the 5'-region is a modified nucleoside comprising a modified sugar.

Embodiment 1588. The oligomeric compound of any of claims 1566-1587, wherein at least one nucleoside of the 5'-region comprises a 2'-substituted furanosyl sugar moiety.

Embodiment 1589. The oligomeric compound of any of claims 1566-1588, wherein each nucleoside of the 5'-region comprises a 2'-substituted furanosyl sugar moiety.

Embodiment 1590. The oligomeric compound of any of claims 1566-1589, wherein each 2'-substituted furanosyl sugar moiety of the 5'-region has a 2'-substituent selected from among 2'-MOE, 2'-OMe, and 2'-NMA.

Embodiment 1591. The oligomeric compound of any of claims 1566-1588 or 1590, wherein at least one nucleoside of the 5'-region comprises a bicyclic furanosyl sugar moiety.

Embodiment 1592. The oligomeric compound of any of claims 1566-1588 or 1590-1591, wherein each nucleoside of the 5'-region comprises a bicyclic furanosyl sugar moiety.

Embodiment 1593. The oligomeric compound of claim 1591 or 1592, wherein each bicyclic sugar moiety of the 5'-region is selected from among cEt, LNA, and ENA.

Embodiment 1594. The oligomeric compound of claim 1593, wherein each bicyclic sugar moiety of the 5'-region is a cEt sugar moiety.

Embodiment 1595. The oligomeric compound of any of claims 1566-1594, wherein at least one nucleoside of the 5' region is a stereo-standard DNA nucleoside.

Embodiment 1596. The oligomeric compound of any of claims 1566-1595, wherein at least one nucleoside of the 5' region is a stereo-non-standard nucleoside.

Embodiment 1597. The oligomeric compound of any of claims 1566-1596, wherein each nucleobase of the 5'-region is independently selected from among thymine, uracil, guanine, cytosine, 5-methylcytosine, and adenine.

Embodiment 1598. The oligomeric compound of any of claims 1566-1597, wherein the 3'-region consists of 2-5 linked nucleosides.

Embodiment 1599. The oligomeric compound of claim 1598, wherein the 3'-region consists of 3 linked nucleosides.

Embodiment 1600. The oligomeric compound of claim 1598, wherein the 3'-region consists of 5 linked nucleosides.

Embodiment 1601. The oligomeric compound of any of claims 1566-1600, wherein each nucleoside of the 3'-region is a modified nucleoside.

Embodiment 1602. The oligomeric compound of any of claims 1566-1601, wherein each nucleoside of the 3'-region is a modified nucleoside comprising a modified sugar.

Embodiment 1603. The oligomeric compound of any of claims 1566-1602, wherein at least one nucleoside of the 3'-region comprises a 2'-substituted furanosyl sugar moiety.

Embodiment 1604. The oligomeric compound of any of claims 1566-1603, wherein each nucleoside of the 3'-region comprises a 2'-substituted furanosyl sugar moiety.

Embodiment 1605. The oligomeric compound of any of claims 1566-1604, wherein each 2'-substituted furanosyl sugar moiety of the 3'-region has a 2'-substituent selected from among 2'-MOE, 2'-OMe, and 2'-NMA.

Embodiment 1606. The oligomeric compound of any of claims 1566-1603 or 1605, wherein at least one nucleoside of the 3'-region comprises a bicyclic furanosyl sugar moiety.

Embodiment 1607. The oligomeric compound of any of claims 1566-1603 or 1606, wherein each nucleoside of the 3'-region comprises a bicyclic furanosyl sugar moiety.

Embodiment 1608. The oligomeric compound of claim 1606 or 1607, wherein each bicyclic sugar moiety of the 3'-region is selected from among cEt, LNA, and ENA.

Embodiment 1609. The oligomeric compound of claim 1608, wherein each bicyclic sugar moiety of the 3'-region is a cEt sugar moiety.

Embodiment 1610. The oligomeric compound of any of claims 1566-1609, wherein at least one nucleoside of the 3' region is a stereo-standard DNA nucleoside.

Embodiment 1611. The oligomeric compound of any of claims 1566-1610, wherein at least one nucleoside of the 3' region is a stereo-non-standard nucleoside.

Embodiment 1612. The oligomeric compound of any of claims 1566-1611, wherein each nucleobase of the 3'-region is independently selected from among thymine, uracil, guanine, cytosine, 5-methylcytosine, and adenine.

Embodiment 1613. The oligomeric compound of any of claims 1566-1612 wherein the oligomeric compound is a gapmer.

Embodiment 1614. The oligomeric compound of any of claims 1566-1613, wherein the modified oligonucleotide has a sugar motif selected from kkkddddddddddkkk and kkkdydddddddddkkk, wherein each "k" represents a cEt sugar moiety, "y" represents a 2'-OMe sugar moiety, and each "d" represents a β-D-2'-deoxyribosyl sugar moiety.

Embodiment 1615. The oligomeric compound of any of claims 1566-1614, wherein the modified oligonucleotide has an internucleoside linkage motif selected from: ssssssssssssssa, sssssssssssssas, ssssssssssssass, sssssssssssasss, ssssssssssassss, sssssssssasssss, ssssssssassssss, sssssssasssssss, ssssssassssssss, sssssasssssssss, ssssassssssssss, sssasssssssssss, ssassssssssssss, sasssssssssssss, assssssssssssss, sssssssssssssaa, ssssssssssssaas, sssssssssssaass, ssssssssssaasss, sssssssssaassss, ssssssssaasssss, sssssssaassssss, ssssssaasssssss, sssssaassssssss, ssssaasssssssss, sssaassssssssss, ssaasssssssssss, saassssssssssss, aasssssssssssss, aaaaaaaaaaaaaaa, ssaaaaaaaaaaass, ssaaaaaaaaaasss, sssaaaaaaaaasss, aassssssssssaaa, sssaaasssssssss, ssssaaassssssss, sssaaaassssssss, ssaaassssssssss, ssaaaasssssssss, ssaaaaassssssss, ssaaaaaasssssss, ssaaaaaaassssss, ssaaaaaaaasssss, ssaaaaaaaaassss, ssssssssssaaass, sssssssssaaaass, ssssssssaaaaass, sssssssaaaaaass, ssssssaaaaaaass, sssssaaaaaaaass, ssssaaaaaaaaass, sssaaaaaaaaaass, ssasasasasasass, sssasasasasasss, ooossssssssssoo, soossssssssssos, aoosssssssssooa, aoasssssssssaoa, aoaaaassssssaoa, aoossssssssssoa, ooasssssssssaoo, aoosaasssssssoa, aossaasssssssoa, aooaaaasssssaoa, aoossssssaaaaoa, sssssaaasssssss, ssssssaaassssss, sssssssaaasssss, ssssssssaaassss, sssssssssaaasss, ssssaaaasssssss, sssssaaaassssss, ssssssaaaasssss, sssssssaaaassss, ssssssssaaaasss, sssaassssssaass, sssaasssssaasss, sssaassssaassss, sssaasssaasssss, sssaassaassssss, sssaasaasssssss, ssaasssssssaass, ssssaasssssaass, sssssaassssaass, ssssssaasssaass, sssssssaassaass, ssssssssaasaass, ssssaasssaassss, sssssaasaasssss, ssssssssssssssS, aaassssssssssss, aaassssssssssaa, aaaaassssssssss, aoooosaasssssssooaa, aoooossssssssssooaa, sooooaassssssssooss, soooosaasssssssooss, soooossaassssssooss, soooossssssaassooss, sssaaaassssssss, sssssaaaaaassss, or sssssssssaaaaaa, wherein each "a" represents an internucleoside linkage of Formula XVII, each "s" represents a phosphorothioate internucleoside linkage, and each "o" represents a phosphodiester internucleoside linkage.

Embodiment 1616. The oligomeric compound of claim 1615, wherein the modified oligonucleotide has an internucleoside linkage motif selected from: sssaaaassssssss, sssaaasssssssss, ssssaaassssssss, ssssaasssssaass, sssaassssssssss, ssssaasssssssss, sssssaassssssss, or ssssssssaasssss, wherein each "a" represents an internucleoside linkage of Formula XVII, each "s" represents a phosphorothioate internucleoside linkage, and each "o" represents a phosphodiester internucleoside linkage.

Embodiment 1617. The oligomeric compound of claim 1615 or 1616, wherein each "a" represents a mesyl phosphoramidate internucleoside linkage.

Embodiment 1618. The oligomeric compound of any of claims 1246-1383, wherein the modified oligonucleotide is a CRISPR compound.

Embodiment 1619. The oligomeric compound of claim 1618, wherein the CRISPR compound consists of 20-50 or 29-32 linked nucleosides.

Embodiment 1620. The oligomeric compound of any of claims 1335-1619, wherein each X is O.

Embodiment 1621. The oligomeric compound of any of claims 1335-1619, wherein each X is S.

Embodiment 1622. The oligomeric compound of any of claims 1335-1621, wherein at least one $R_1$ is H.

Embodiment 1623. The oligomeric compound of any of claims 1335-1621, wherein at least one $R_1$ is a $C_1$-$C_6$ alkyl.

Embodiment 1624. The oligomeric compound of claim 1623, wherein the at least one $R_1$ is methyl.

Embodiment 1625. The oligomeric compound of any of claims 1335-1621, at least one $R_1$ is a substituted $C_1$-$C_6$ alkyl.

Embodiment 1626. The oligomeric compound of any of claims 1335-1625, wherein at least one T comprises a conjugate group.

Embodiment 1627. The oligomeric compound of claim 1626, wherein the conjugate group comprises a cell-targeting moiety.

Embodiment 1628. The oligomeric compound of claim 1626, wherein the conjugate group comprises a carbohydrate or carbohydrate cluster.

Embodiment 1629. The oligomeric compound of any of claims 1626-1627, wherein the conjugate group comprises at least one GalNAc.

Embodiment 1630. The oligomeric compound of claim 1626, wherein the conjugate group comprises a $C_{10}$-$C_{20}$ alkyl chain.

Embodiment 1631. The oligomeric compound of claim 1630, wherein the conjugate group comprises $C_{16}$ alkyl.

Embodiment 1632. The oligomeric compound of any of claims 1335-1631, wherein at least one T does not comprise a conjugate group.

Embodiment 1633. The oligomeric compound of any of claims 1335-1625, wherein each T does not comprise a conjugate group.

Embodiment 1634. The oligomeric compound of any of claims 1335-1633, wherein at least one T is $SO_2R_2$.

Embodiment 1635. The oligomeric compound of claim 1634, wherein $R_2$ is an aryl.

Embodiment 1636. The oligomeric compound of claim 1634, wherein $R_2$ is a substituted aryl.

Embodiment 1637. The oligomeric compound of claim 1634, wherein $R_2$ is a heterocycle.

Embodiment 1638. The oligomeric compound of claim 1634, wherein $R_2$ is a substituted heterocycle.

Embodiment 1639. The oligomeric compound of claim 1634, wherein $R_2$ is an aromatic heterocycle.

Embodiment 1640. The oligomeric compound of claim 1634, wherein $R_2$ is a substituted aromatic heterocycle.

Embodiment 1641. The oligomeric compound of claim 1634, wherein $R_2$ is a diazole.

Embodiment 1642. The oligomeric compound of claim 1634, wherein $R_2$ is a substituted diazole.

Embodiment 1643. The oligomeric compound of claim 1634, wherein $R_2$ is an amine.

Embodiment 1644. The oligomeric compound of claim 1634, wherein $R_2$ is a substituted amine.

Embodiment 1645. The oligomeric compound of claim 1634, wherein $R_2$ is a $C_1$-$C_6$ alkoxy, $C_1$-$C_6$ alkenyl, or $C_1$-$C_6$ alkynyl.

Embodiment 1646. The oligomeric compound of claim 1634, wherein $R_2$ is $C_1$-$C_{20}$, $C_1$-$C_6$, $C_2$-$C_{20}$, $C_2$-$C_6$, or $C_{10}$-$C_{20}$ alkyl.

Embodiment 1647. The oligomeric compound of claim 1634, wherein $R_2$ is substituted $C_1$-$C_{20}$, $C_1$-$C_6$, $C_2$-$C_{20}$, $C_2$-$C_6$, or $C_{10}$-$C_{20}$ alkyl.

Embodiment 1648. The oligomeric compound of claim 1634, wherein $R_2$ comprises a carbohydrate or carbohydrate cluster.

Embodiment 1649. The oligomeric compound of claim 1634, wherein $R_2$ comprises at least one GalNAc.

Embodiment 1650. The oligomeric compound of claim 1634, wherein T is:

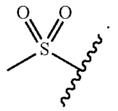

Embodiment 1651. The oligomeric compound of claim 1634, wherein T is:

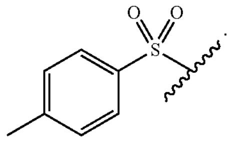 [SMILES: *S(=O)(=O)c1ccc(C)cc1]

Embodiment 1652. The oligomeric compound of claim 1634, wherein T is:

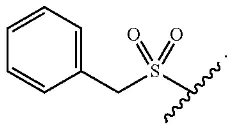 [SMILES: *S(=O)(=O)Cc1ccccc1]

Embodiment 1653. The oligomeric compound of claim 1634, wherein T is:

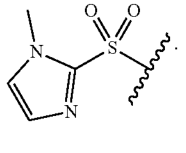 [SMILES: *S(=O)(=O)c1nccn1C]

Embodiment 1654. The oligomeric compound of claim 1634, wherein T is:

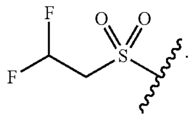 [SMILES: *S(=O)(=O)CC(F)F]

Embodiment 1655. The oligomeric compound of claim 1634, wherein T is:

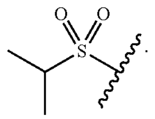 [SMILES: *S(=O)(=O)C(C)C]

Embodiment 1656. The oligomeric compound of claim 1634, wherein T is:

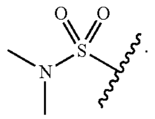 [SMILES: *S(=O)(=O)N(C)C]

Embodiment 1657. The oligomeric compound of claim 1634, wherein T is:

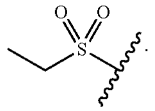 [SMILES: *S(=O)(=O)CC]

Embodiment 1658. The oligomeric compound of claim 1634, wherein T is:

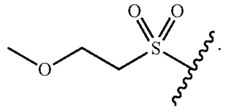 [SMILES: *S(=O)(=O)CCOC]

Embodiment 1659. The oligomeric compound of claim 1634, wherein T is:

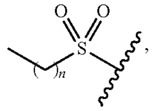

wherein n is from 2 to 20.

Embodiment 1660. The oligomeric compound of claim 1659, wherein n is 15.

Embodiment 1661. The oligomeric compound of any of claims 1335-1660, wherein at least one T is $C(=O)R_3$.

Embodiment 1662. The oligomeric compound of claim 1661, wherein $R_3$ is an aryl.

Embodiment 1663. The oligomeric compound of claim 1661, wherein $R_3$ is a substituted aryl.

Embodiment 1664. The oligomeric compound of claim 1661, wherein $R_3$ is $CH_3$.

Embodiment 1665. The oligomeric compound of claim 1661, wherein $R_3$ is $N(CH_3)_2$.

Embodiment 1666. The oligomeric compound of claim 1661, wherein $R_3$ is $OCH_3$.

Embodiment 1667. The oligomeric compound of claim 1661, wherein $R_3$ is a $C_1$-$C_6$ alkoxy.

Embodiment 1668. The oligomeric compound of claim 1661, wherein $R_3$ is $C_1$-$C_{20}$, $C_1$-$C_6$, $C_2$-$C_{20}$, $C_2$-$C_6$, or $C_1$-$C_{20}$ alkyl.

Embodiment 1669. The oligomeric compound of claim 1661, wherein $R_3$ is substituted $C_1$-$C_{20}$, $C_1$-$C_6$, $C_2$-$C_{20}$, $C_2$-$C_6$, or $C_{10}$-$C_{20}$ alkyl.

Embodiment 1670. The oligomeric compound of claim 1661, wherein $R_3$ comprises a carbohydrate or carbohydrate cluster.

Embodiment 1671. The oligomeric compound of claim 1661, wherein $R_{23}$ comprises at least one GalNAc.

Embodiment 1672. The oligomeric compound of claim 1661, wherein T is:

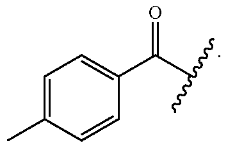 [SMILES: *C(=O)c1ccc(C)cc1]

Embodiment 1673. The oligomeric compound of claim 1661, wherein T is:

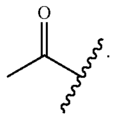

Embodiment 1674. The oligomeric compound of claim 1661, wherein T is:

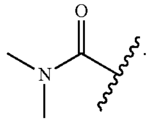 [SMILES: *C(=O)N(C)C]

Embodiment 1675. The oligomeric compound of claim 1661, wherein T is:

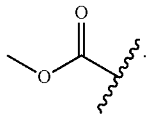 [SMILES: *C(=O)OC]

Embodiment 1676. The oligomeric compound of claim 1661, wherein T is:

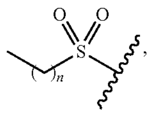

wherein n is from 2 to 20.

Embodiment 1677. The oligomeric compound of claim 1676, wherein n is 15.

Embodiment 1678. The oligomeric compound of any of claims 1335-1677, wherein at least one T is $P(=O)R_4R_5$.

Embodiment 1679. The oligomeric compound of claim 1678, wherein $R_4$ is $OCH_3$.

Embodiment 1680. The oligomeric compound of claim 1678, wherein $R_4$ is OH.

Embodiment 1681. The oligomeric compound of claim 1678, wherein $R_4$ is $C_1$-$C_6$ alkyl.

Embodiment 1682. The oligomeric compound of claim 1678, wherein $R_4$ is substituted $C_1$-$C_6$ alkyl.

Embodiment 1683. The oligomeric compound of claim 1678, wherein $R_4$ is $C_1$-$C_{20}$, $C_1$-$C_6$, $C_2$-$C_{20}$, $C_2$-$C_6$, or $C_1$-$C_{20}$ alkyl.

Embodiment 1684. The oligomeric compound of claim 1678, wherein $R_4$ is substituted $C_1$-$C_{20}$, $C_1$-$C_6$, $C_2$-$C_{20}$, $C_2$-$C_6$, or $C_{10}$-$C_{20}$ alkyl.

Embodiment 1685. The oligomeric compound of claim 1678, wherein $R_4$ comprises a carbohydrate or carbohydrate cluster.

Embodiment 1686. The oligomeric compound of claim 1678, wherein $R_4$ comprises at least one GalNAc.

Embodiment 1687. The oligomeric compound of any of claims 1678-1686, wherein $R_1$ is $OCH_3$.

Embodiment 1688. The oligomeric compound of any of claims 1678-1686, wherein $R_1$ is OH.

Embodiment 1689. The oligomeric compound of any of claims 1678-1686, wherein $R_5$ is $C_1$-$C_6$ alkyl.

Embodiment 1690. The oligomeric compound of any of claims 1678-1686, wherein $R_5$ is substituted $C_1$-$C_6$ alkyl.

Embodiment 1691. The oligomeric compound of claim 1678, wherein T is:

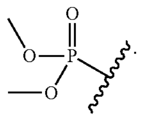 [SMILES: *P(=O)(OC)OC]

Embodiment 1692. The oligomeric compound of claim 1678, wherein T is:

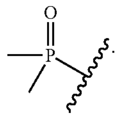

Embodiment 1693. The oligomeric compound of claim 1678, wherein T is:

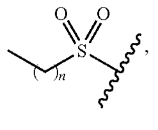

wherein n is from 2 to 20.

Embodiment 1694. The oligomeric compound of claim 1693, wherein n is 15.

Embodiment 1695. An antisense agent comprising a modified oligonucleotide consisting of 12-50 linked nucleosides linked through internucleoside linking groups, wherein at least one internucleoside linking group is a phosphodiester or a phosphorothioate internucleoside linking group, and wherein at least one of the internucleoside linking groups has Formula XX:

XX

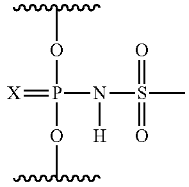

wherein independently for each internucleoside linking group of the modified oligonucleotide having Formula XX, X is selected from O or S.

Embodiment 1696. An antisense agent comprising a modified oligonucleotide, wherein the 5'-terminus of the modified oligonucleotide has Structure F:

Structure F

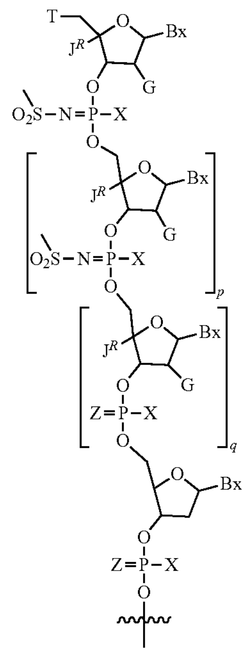

wherein:

p is from 0 to 6;

q is from 0 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1697. An antisense agent comprising a modified oligonucleotide, wherein the 3'-terminus of the modified oligonucleotide has Structure G:

Structure G

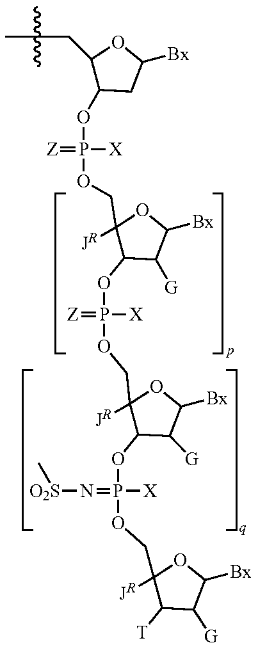

wherein:

p is from 0 to 6;

q is from 1 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or $O—[C(R_6)(R_7)]_n—[(C=O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1698. The antisense agent of claim 1696 or 1697, wherein the sum of p+q is selected from 2, 3, 4, or 5.

Embodiment 1699. An antisense agent comprising a modified oligonucleotide, wherein the 5'-terminus of the modified oligonucleotide has Structure H:

Structure H

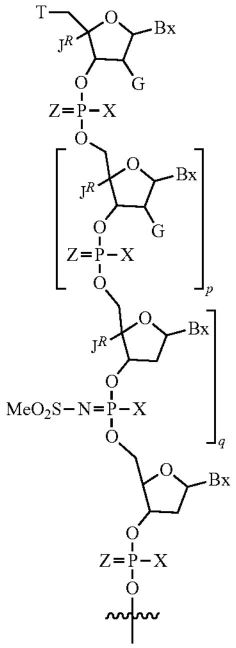

wherein:

p is from 0 to 5;

q is from 1 to 4;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or $O—[C(R_6)(R_7)]_n—[(C=O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$; $Q_2$ is O, S or $NJ_3$;

each $J_1$, $J_2$ and $J_3$ is, independently, H or $C_1$-$C_6$ alkyl.

Embodiment 1700. An antisense agent comprising a modified oligonucleotide, wherein the 5'-terminus of the modified oligonucleotide has Structure I:

Structure I

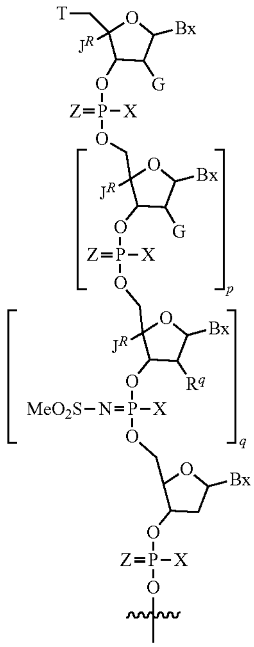

wherein:

p is from 0 to 5;

q is from 1 to 4;

T is OH or a conjugate group;

each Bx is an independently selected heterocyclic base moiety;

each X is independently selected from OH or SH;

each Z is independently selected from O, S, or $NSO_2Me$;

each $R_q$ is H or exactly one $R^q$ is OMe and the other $R_9$ are H;

For each $J^R$ and G of the same furanosyl sugar moiety, either $J^R$ and G form a $J^R$ to G bridge, or $J^R$ is H and G is selected from OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1701. The antisense agent of claim 1700, wherein exactly one $R_q$ is —OMe.

Embodiment 1702. The antisense agent of any of claims 1699-1701, wherein the sum of p+q is 2, 3, or 4.

Embodiment 1703. An antisense agent comprising a modified oligonucleotide, wherein the 3'-terminus of the modified oligonucleotide has Structure J:

Structure J

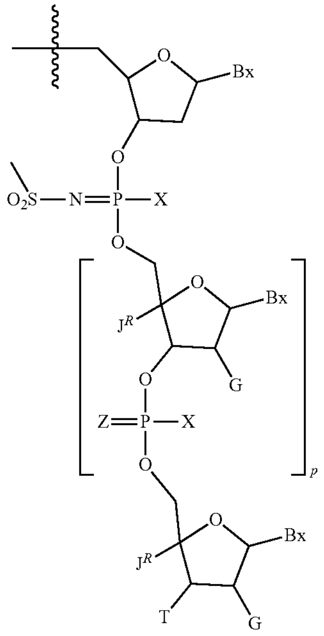

wherein:

p is from 0 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or $O-[C(R_6)(R_7)]_n-[(C=O)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1704. The antisense agent of claim 1703, wherein p is 2, 3, or 4.

Embodiment 1705. The antisense agent of any of claims 1696-1704, wherein each $J^R$ is H and each G is $OCH_2CH_2OCH_3$.

Embodiment 1706. The antisense agent of any of claims 1696-1704, wherein each $J^R$ is H and each G is $OCH_3$.

Embodiment 1707. The antisense agent of any of claims 1696-1704, wherein each $J^R$ and G form a $J^R$ to G bridge.

Embodiment 1708. The antisense agent of claim 1707, wherein the $J^R$ to G bridge has the formula —$CH(CH_3)$—O—.

Embodiment 1709. The antisense agent of claim 1695, wherein the antisense agent is an RNAi agent.

Embodiment 1710. The RNAi agent of claim 1709, wherein the RNAi agent is a single-stranded RNAi agent comprising an RNAi antisense modified oligonucleotide.

Embodiment 1711. The RNAi agent of claim 1709, wherein the RNAi agent is an oligonucleotide duplex comprising an RNAi antisense modified oligonucleotide and an RNAi sense modified oligonucleotide.

Embodiment 1712. The RNAi agent of any of claims 1710-1711, wherein the 5'-terminus of the RNAi antisense oligonucleotide has structure K:

Structure K

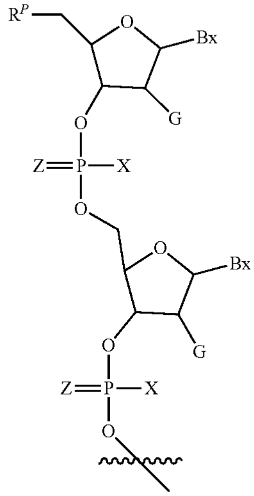

wherein:

$R^P$ is a phosphate, stabilized phosphate group, or a mesyl phosphoramidate;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1713. The RNAi agent of claim 1712, wherein the stabilized phosphate group is 5'-vinyl phosphonate or 5'-cyclopropyl phosphonate.

Embodiment 1714. The RNAi agent of claim 1712, wherein the stabilized phosphate group is a mesyl phosphoramidate.

Embodiment 1715. The RNAi agent of any of claims 1712-1714, wherein each G within structure K is independently selected from F or OMe.

Embodiment 1716. The RNAi agent of any of claims 1712-1715, wherein the 3'-terminus of the RNAi antisense oligonucleotide has structure L:

Structure L

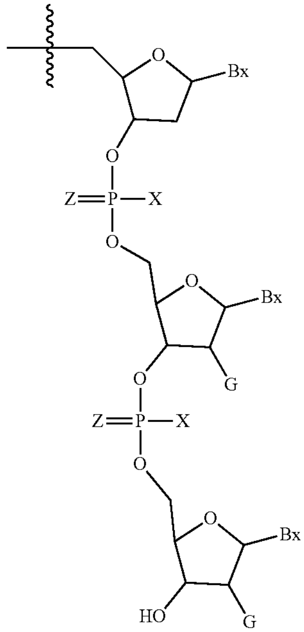

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1717. The RNAi agent of claim 1716, wherein each G within Structure L of the RNAi antisense oligonucleotide is independently selected from F or OMe.

Embodiment 1718. The RNAi agent of any of claims 1710-1717, wherein at least one region of the RNAi antisense oligonucleotide has structure M:

Structure M

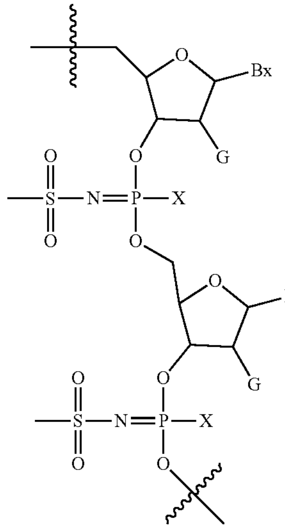

wherein:

each Bx is an independently selected heterocyclic base moiety;

each X is independently selected from OH or SH;

each G is independently selected from OH, halogen or $O—[C(R_6)(R_7)]_n—[(C=O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(-Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1719. The RNAi agent of claim 1718, wherein each G of Structure M within the RNAi antisense oligonucleotide is selected from F or OMe.

Embodiment 1720. The RNAi agent of claim 1719, wherein one G is F and the other G is OMe.

Embodiment 1721. The RNAi agent of any of claims 1710-1711 or 1716-1720, wherein the 5'-terminus of the RNAi antisense oligonucleotide has structure N:

Structure N

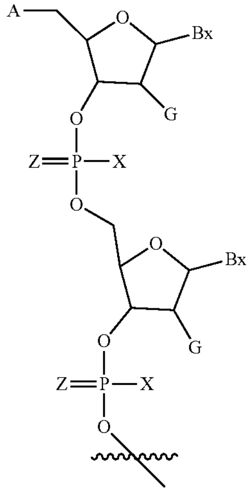

wherein:

A is selected from

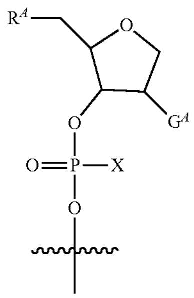

or

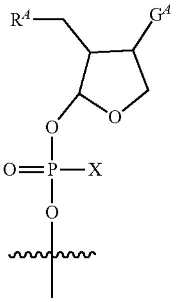

;

$R^A$ is OH, OP(=O)OH, OP(=O)SH, a stabilized phosphate group, or a mesyl phosphoramidate;

$G^A$ is H, OH, OMe, MOE, or a halogen;

each Bx is an independently selected heterocyclic base moiety;

each X is independently selected from OH or SH;

each G is independently selected from OH, halogen or $O—[C(R_6)(R_7)]_n—[(C=O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$; $Q_2$ is O, S or $NJ_3$;

each $J_1$, $J_2$ and $J_3$ is, independently, H or $C_1$-$C_6$ alkyl.

Embodiment 1722. The RNAi agent of claim 1722, wherein each G within structure N of the RNAi antisense oligonucleotide is selected from F or OMe.

Embodiment 1723. The RNAi agent of any of claims 1710-1714 or 1718-1722, wherein the 3'-terminus of the RNAi antisense oligonucleotide has structure 0:

Structure O

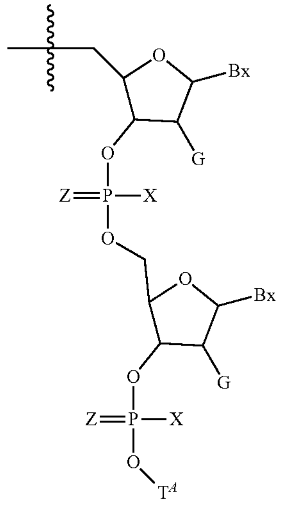

wherein:

$T^A$ is selected from

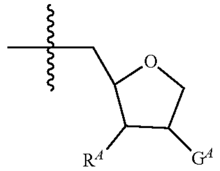 or 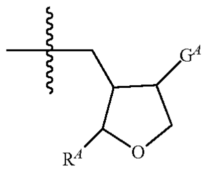 ;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1724. The RNAi agent of claim 1723, wherein each G within structure O of the RNAi antisense oligonucleotide is selected from F or OMe.

Embodiment 1725. The RNAi agent of claim 1711, wherein the 5'-terminus of the RNAi sense oligonucleotide has structure K:

Structure K

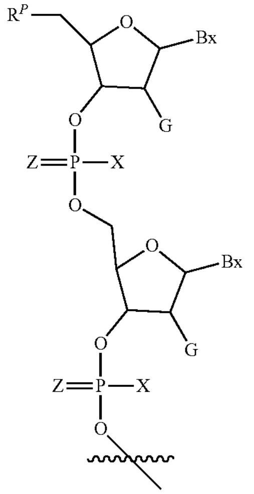

wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1726. The RNAi agent of claim 1725, wherein the stabilized phosphate group is 5'-vinyl phosphonate, 5'-cyclopropyl phosphonate, or 5'-mesyl phosphoramidate.

Embodiment 1727. The RNAi agent of claim 1725 or 1726, wherein each G within structure K is independently selected from F or OMe.

Embodiment 1728. The RNAi agent of any of claims 1711 or 1725-1727, wherein the 3'-terminus of the RNAi sense oligonucleotide has structure L:

Structure L

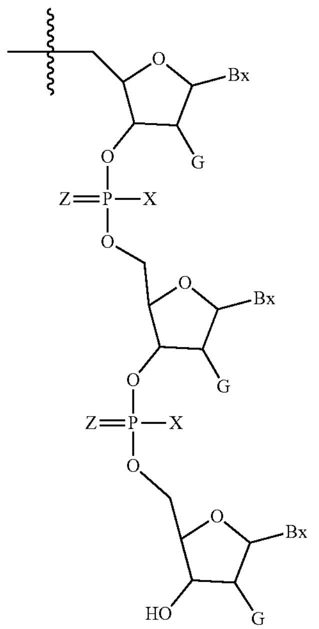

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1729. The RNAi agent of claim 1728, wherein each G within Structure L of the RNAi sense oligonucleotide is independently selected from F or OMe.

Embodiment 1730. The RNAi agent of any of claims 1711 or 1725-1729 wherein at least one region of the RNAi sense oligonucleotide has structure M:

Structure M

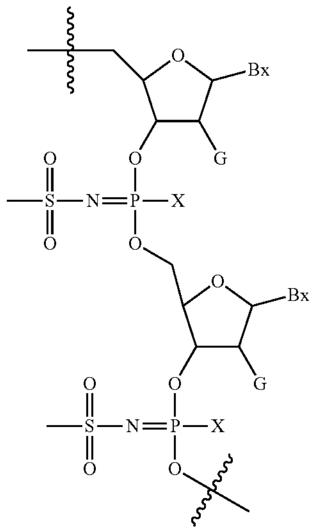

wherein:

each Bx is an independently selected heterocyclic base moiety;

each X is independently selected from OH or SH;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(-Q_2)N(J_1)(J_2)$; $Q_2$ is O, S or $NJ_3$;

each $J_1$, $J_2$ and $J_3$ is, independently, H or $C_1$-$C_6$ alkyl.

Embodiment 1731. The RNAi agent of claim 1730, wherein each G of Structure M within the RNAi sense oligonucleotide is selected from F or OMe.

Embodiment 1732. The RNAi agent of claim 1731, wherein one G is F and the other G is OMe.

Embodiment 1733. The RNAi agent of any of claims 1711 or 1728-1732, wherein the 5'-terminus of the RNAi sense oligonucleotide has structure N:

Structure N

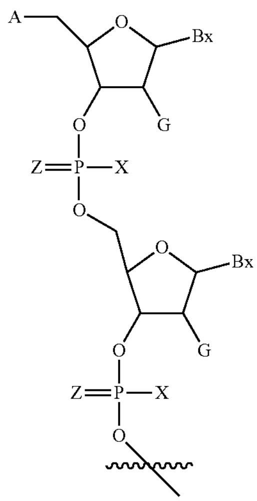

wherein:

A is selected from

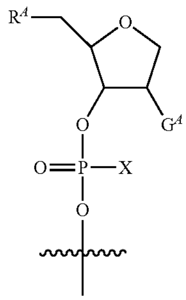

or

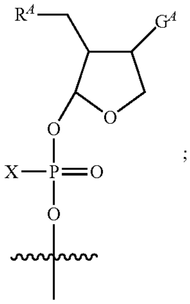

;

$R^A$ is OH, OP(=O)OH, OP(=O)SH, a stabilized phosphate group or a mesyl phosphoramidate;

$G^A$ is H, OH, OMe, MOE, or a halogen;

each Bx is an independently selected heterocyclic base moiety;

each X is independently selected from OH or SH;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1734. The RNAi agent of claim 1733, wherein each G within structure N of the RNAi sense oligonucleotide is selected from F or OMe.

Embodiment 1735. The RNAi agent of any of claims 1711, 1725-1727, or 1730-1734, wherein the 3'-terminus of the RNAi sense oligonucleotide has structure 0:

Structure O

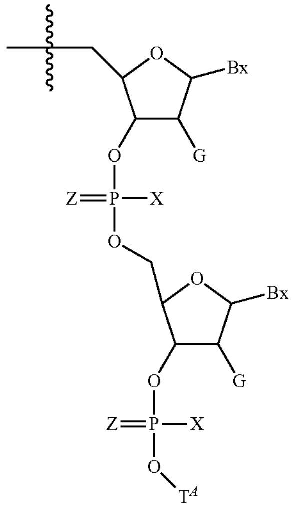

wherein:

$T^A$ is selected from

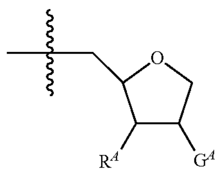

or

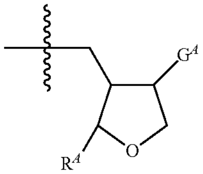

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or O—$[C(R_6)(R_7)]_n$—$[(C{=}O)_m$—$X^G]_j$—$R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

Embodiment 1736. The RNAi agent of claim 1735, wherein each G within structure O of the RNAi sense oligonucleotide is selected from F or OMe.

Embodiment 1737. The oligomeric compound or antisense agent of any of claims 1246-1456 or 1484-1724, comprising at least one modified oligonucleotide, wherein the nucleobase sequence of at least one modified oligonucleotide is complementary to a target nucleic acid.

Embodiment 1738. The modified oligonucleotide of claim 1737, wherein the nucleobase sequence of the modified oligonucleotide is at least 80% complementary to the target nucleic acid.

Embodiment 1739. The modified oligonucleotide of claim 1737, wherein the nucleobase sequence of the modified oligonucleotide is at least 85% complementary to the target nucleic acid.

Embodiment 1740. The modified oligonucleotide of claim 1737, wherein the nucleobase sequence of the modified oligonucleotide is at least 90% complementary to the target nucleic acid.

Embodiment 1741. The modified oligonucleotide of claim 1737, wherein the nucleobase sequence of the modified oligonucleotide is at least 95% complementary to the target nucleic acid.

Embodiment 1742. The modified oligonucleotide of claim 1737, wherein the nucleobase sequence of the modified oligonucleotide is 100% complementary to the target nucleic acid.

Embodiment 1743. The modified oligonucleotide of any of claims 1737-1742, wherein the target nucleic acid is a target RNA.

Embodiment 1744. The modified oligonucleotide of claim 1743, wherein the target RNA is selected from: an mRNA, a pre-mRNA, a microRNA, and a non-coding RNA.

Embodiment 1745. The modified oligonucleotide of claim 1744, wherein the target RNA is not a microRNA.

Embodiment 1746. The antisense agent comprising a modified oligonucleotide of any of claims 1-500, wherein the modified oligonucleotide is not complementary to miR-21.

Embodiment 1747. The antisense agent of any of claims 1246-1746, comprising a conjugate group.

Embodiment 1748. The antisense agent of claim 1747, wherein the conjugate group comprises at least one GalNAc.

Embodiment 1749. The antisense agent of claim 1747 or 1748, wherein the conjugate group comprises 1-5 linker-nucleosides.

Embodiment 1750. A pharmaceutical composition comprising the oligomeric compound of any of claims 1246-1694 or the antisense agent of any of claims 1695-1730 and a pharmaceutically acceptable carrier or diluent.

Embodiment 1751. A method comprising contacting a cell with the oligomeric compound, antisense agent, or pharmaceutical composition of any of claims 1246-1750.

Embodiment 1752. A method of modulating the amount or activity of a target nucleic acid in a cell, comprising contacting the cell with the oligomeric compound, antisense agent, or pharmaceutical composition of any of claims 1246-1750 and thereby modulating the amount or activity of the target nucleic acid.

Embodiment 1753. A method of modulating the amount or activity of a target nucleic acid in a cell, comprising contacting the cell with the oligomeric compound, antisense agent or pharmaceutical composition of any of claims 1246-1750.

Embodiment 1754. The method of claims 1751-1753, wherein the amount or activity of a target nucleic acid is reduced.

Embodiment 1755. The method of claims 1751-1753, wherein the amount or activity of a target nucleic acid is increased.

Embodiment 1756. The method of claim 1753, wherein the target nucleic acid comprises at least one translation suppression element and wherein the modified oligonucleotide is complementary to a target site within a translation suppression element region of the target nucleic acid.

Embodiment 1757. The method of claim 1756, wherein the translation suppression element region comprises at least one stem-loop structure.

Embodiment 1758. Use of the antisense agent or composition of any of claims 1246-1750 for treatment of a disease or condition.

Embodiment 1759. Use of the antisense agent or composition of any of claims 1246-1750 for a preparation of a medicament for treatment of a disease or condition.

Embodiment 1760. The oligomeric compound or antisense agent of any of claims 1246-1749, wherein the oligomeric compound or antisense agent is not an RNAi agent and the parent oligomeric compound or antisense agent is cytotoxic in vitro.

Embodiment 1761. The oligomeric compound or antisense agent of claim 1760, wherein the parent oligomeric compound or antisense agent is cytotoxic in a standard in vitro cytotoxicity assay.

Embodiment 1762. The oligomeric compound or antisense agent of claim 1760, wherein the oligomeric compound or antisense agent of any of claims 1246-1749 is not cytotoxic in vitro.

Embodiment 1763. The oligomeric compound or antisense agent of any of claims 1760-1762, wherein the oligomeric compound or antisense agent of any of claims 1246-1749 is not cytotoxic in a standard in vitro cytotoxicity assay.

Embodiment 1764. The oligomeric compound or antisense agent of any of claims 1246-1749, wherein the antisense agent is not an siRNA agent and the parent antisense agent is hepatotoxic to the mouse.

Embodiment 1765. The oligomeric compound or antisense agent of claim 1764, wherein the mouse is a BALB/c mouse, wherein 50 mg/kg of the parent antisense agent is administered to the mouse, and wherein the plasma ALT level in the mouse is measured 72 hours following the administration of the parent antisense agent.

Embodiment 1766. The oligomeric compound or antisense agent of any of claims 1764-1765, wherein administration of 50 mg/kg of the oligomeric compound or antisense agent of any of claims 1246-1749 to a mouse is not hepatotoxic to the mouse.

Embodiment 1767. The oligomeric compound or antisense agent of any of claims 1246-1749, wherein the therapeutic index in a mouse of the antisense agent of any of claims 1246-1749 is increased relative to the therapeutic index of the parent antisense agent.

Embodiment 1768. The oligomeric compound or antisense agent of claim 1767, wherein the therapeutic index in a mouse of the antisense agent of claim 516 is at least two-fold greater than the therapeutic index of the parent antisense agent.

Embodiment 1769. The oligomeric compound or antisense agent of any of claims 1760-1768, wherein the parent oligomeric compound or antisense agent is identical to the antisense agent of any of claims 1246-1749, except that each internucleoside linkage of Formula XVII is replaced with a phosphorothioate internucleoside linkage in the parent antisense agent.

Embodiment 1770. The oligomeric compound or of any of claims 1760-1769, wherein the oligomeric compound or antisense agent is an RNAse H agent.

Embodiment 1771. The oligomeric compound or antisense agent of any of claims 1760-1769, wherein the oligomeric compound or antisense agent is a gapmer.

Embodiment 1772. The oligomeric compound or antisense agent of any of claims 1760-1769, wherein the oligomeric compound or antisense agent modulates splicing.

Embodiment 1773. The oligomeric compound or antisense agent of any of claims 1760-1769, wherein the oligomeric compound or antisense agent increases protein expression.

Embodiment 1774. The oligomeric compound or antisense agent of any of claims 1246-1749, wherein the oligomeric compound or antisense agent is an RNAi agent, and the parent RNAi agent is cytotoxic in vitro.

Embodiment 1775. The oligomeric compound or antisense agent of claim 1774, wherein the RNAi agent of any of claims 1246-1749 is not cytotoxic in vitro.

Embodiment 1776. The oligomeric compound or antisense agent of any of claims 1774-1775, wherein the oligomeric compound or antisense agent is an RNAi agent and the RNAi agent is not cytotoxic in a standard in vitro cytotoxicity assay.

Embodiment 1777. The oligomeric compound or antisense agent of any of claims 1246-1749, wherein the oligomeric compound or antisense agent is an RNAi agent and is hepatotoxic to the mouse.

Embodiment 1778. The RNAi agent of claim 1777, wherein the mouse is a BALB/c mouse, wherein 50 mg/kg of the parent RNAi agent is administered to the mouse, and wherein the plasma ALT level in the mouse is measured 72 hours following the administration of the parent RNAi agent.

Embodiment 1779. The RNAi agent of any of claims 1777-1778, wherein administration of 50 mg/kg of the RNAi agent to a mouse is not hepatotoxic to the mouse.

Embodiment 1780. The oligomeric compound or antisense agent of any of claims 1246-1749, which is an RNAi agent, wherein the therapeutic index in a mouse of the RNAi agent is increased relative to the therapeutic index of the parent RNAi agent.

Embodiment 1781. The RNAi agent of claim 1780, wherein the therapeutic index in a mouse of the RNAi agent of claim 535 is at least two-fold greater than the therapeutic index of the parent RNAi agent.

Embodiment 1782. The RNAi agent of any of claims 1771-1781, wherein the parent RNAi agent is identical to the oligomeric compound or antisense agent any of claims 1246-1749, except that each internucleoside linkage of Formula XVII is replaced with a phosphodiester internucleoside linkage in the parent RNAi agent.

Embodiment 1783. A method of designing an oligomeric compound or antisense agent comprising starting with a parent oligomeric compound or antisense agent or parent RNAi agent and changing the design of that compound in order to arrive at an oligomeric compound or antisense agent of any one of claims 1246-1749.

Embodiment 1784. A method of designing an oligomeric compound or an antisense agent comprising identifying an oligomeric compound or antisense agent or parent RNAi agent and changing the design of that parent oligomeric compound or antisense agent or parent RNAi agent to arrive at a second antisense agent, wherein the second oligomeric compound antisense agent is an oligomeric compound or antisense agent of any one of claims 1246-1749.

Embodiment 1785. A method of improving hepatotoxicity of an oligomeric compound or antisense agent comprising the steps of (i) identifying a parent oligomeric compound, parent antisense agent or parent RNAi agent that has plasma ALT levels above 300 units per liter in a mouse, and (ii) providing an oligomeric compound or antisense agent according to any one of claims 1246-1749.

Embodiment 1786. The method of claim 1785, wherein the method designs an oligomeric compound or antisense agent with improved therapeutic index relative to the parent oligomeric compound, parent antisense agent, or parent RNAi agent.

Embodiment 1787. The method of claim 1785, wherein the method designs an oligomeric compound or antisense agent with lower hepatotoxicity relative to the parent oligomeric compound, parent antisense agent or parent RNAi agent.

Embodiment 1788. The method of claim 1785, wherein the second oligomeric compound or antisense agent has an improved therapeutic index relative to the parent oligomeric compound, parent antisense agent or parent RNAi agent.

Embodiment 1789. The method of claim 1785, wherein the second oligomeric compound or antisense agent has reduced hepatotoxicity in a mouse relative to the parent oligomeric compound, parent antisense agent or parent RNAi agent.

Embodiment 1790. The method of claim 1785, wherein the oligomeric compound or antisense agent according to any one of claims 1246-1749 has improved therapeutic index relative to the parent oligomeric compound, parent antisense agent or parent RNAi agent.

Embodiment 1791. The method of claim 1785, wherein the oligomeric compound or antisense agent according to any one of claims 1246-1749 has reduced hepatotoxicity relative to the parent oligomeric compound, antisense agent or parent RNAi agent.

Embodiment 1792. A method comprising administering an oligomeric compound or antisense agent of any of claims 1246-1749 to a mouse and separately administering the parent oligomeric compound, parent antisense agent or parent RNAi agent of the antisense agent of any of claims 1246-1749 to a second mouse, wherein the therapeutic index of the antisense agent of any of claims 1246-1749 is improved relative to the therapeutic index of the parent antisense agent or parent RNAi agent.

Certain Compounds

In certain embodiments, compounds described herein are oligomeric compounds (including oligomeric compounds that are antisense agents or portions thereof) comprising or consisting of oligonucleotides consisting of linked nucleosides and having at least one modified internucleoside linking group having Formula VIII or Formula XVII. Oligonucleotides may be unmodified oligonucleotides or may be modified oligonucleotides. Modified oligonucleotides comprise at least one modification relative to an unmodified oligonucleotide (i.e., comprise at least one modified nucleoside (comprising a modified sugar moiety, a stereo-nonstandard nucleoside, and/or a modified nucleobase) and/or at least one modified internucleoside linkage). In certain embodiments, the modified internucleoside linkage is a modified internucleoside linking group having Formula VIII or Formula XVII. In certain embodiments, compounds described herein are oligomeric compounds (including oligomeric compounds that are antisense agents or portions thereof) having at least one modified internucleoside linking group having Formula XVII.

I. Modifications

A. Modified Nucleosides

Modified nucleosides comprise a stereo-non-standard nucleoside, or a modified sugar moiety, or a modified nucleobase, or any combination thereof.

1. Certain Modified Sugar Moieties

In certain embodiments, modified sugar moieties are stereo-non-standard sugar moieties. In certain embodiments, sugar moieties are substituted furanosyl stereo-standard sugar moieties. In certain embodiments, modified sugar moieties are bicyclic or tricyclic furanosyl sugar moieties. In certain embodiments, modified sugar moieties are sugar surrogates. Such sugar surrogates may comprise one or more substitutions corresponding to those of other types of modified sugar moieties.

a. Stereo-Non-Standard Sugar Moieties

In certain embodiments, modified sugar moieties are stereo-non-standard sugar moieties shown in Formula I, Formula II, Formula III, Formula IV, Formula V, Formula VI, and Formula VII:

I

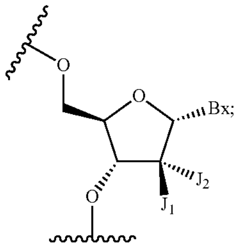

II

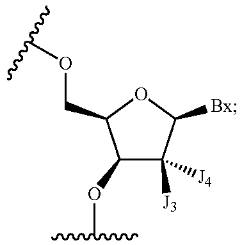

III

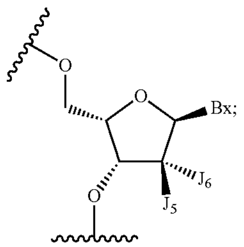

-continued

IV

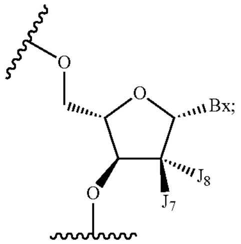

V

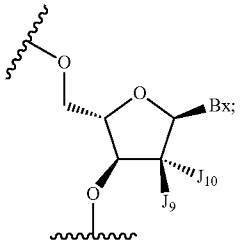

VI

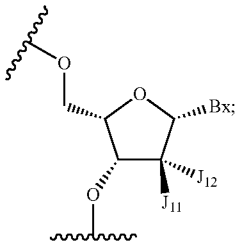

VII

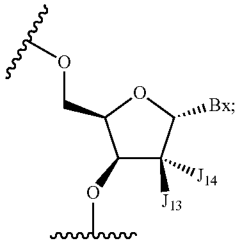

wherein one of $J_1$ and $J_2$ is H and the other of $J_1$ and $J_2$ is selected from H, OH, F, $OCH_3$, $OCH_2CH_2OCH_3$, O—$C_1$-$C_6$ alkoxy, and $SCH_3$;

one of $J_3$ and $J_4$ is H and the other of $J_3$ and $J_4$ is selected from H, OH, F, $OCH_3$, $OCH_2CH_2OCH_3$, O—$C_1$-$C_6$ alkoxy, and $SCH_3$; and wherein one of $J_5$ and $J_6$ is H and the other of $J_5$ and $J_6$ is selected from H, OH, F, $OCH_3$, $OCH_2CH_2OCH_3$, O—$C_1$-$C_6$ alkoxy, and $SCH_3$; and wherein one of $J_7$ and $J_8$ is H and the other of $J_7$ and $J_8$ is selected from H, OH, F, $OCH_3$, $OCH_2CH_2OCH_3$, O—$C_1$-$C_6$ alkoxy, and $SCH_3$; and wherein one of $J_9$ and $J_{10}$ is H and the other of $J_9$ and $J_{10}$ is selected from H, OH, F, $OCH_3$, $OCH_2CH_2OCH_3$, O—$C_1$-$C_6$ alkoxy, and $SCH_3$; and wherein one of $J_{11}$ and $J_{12}$ is H and the other of $J_{11}$ and $J_{12}$ is selected from H, OH, F, $OCH_3$, $OCH_2CH_2OCH_3$, O—$C_1$-$C_6$ alkoxy, and $SCH_3$; and wherein one of $J_{13}$ and $J_{14}$ is H and the other of $J_{13}$ and $J_{14}$ is selected from H, OH, F, $OCH_3$, $OCH_2CH_2OCH_3$, O—$C_1$-$C_6$ alkoxy, and $SCH_3$; and Bx is a is a heterocyclic base moiety.

Certain stereo-non-standard sugar moieties have been previously described in, e.g., Seth et al., WO2020/

072991 and Seth et al., WO2019/157531, both of which are incorporated by reference herein in their entirety.

b. Substituted Stereo-Standard Sugar Moieties

In certain embodiments, modified sugar moieties are substituted stereo-standard furanosyl sugar moieties comprising one or more acyclic substituent, including but not limited to substituents at the 2', 3', 4', and/or 5' positions. In certain embodiments, the furanosyl sugar moiety is a ribosyl sugar moiety. In certain embodiments one or more acyclic substituent of substituted stereo-standard sugar moieties is branched. Examples of 2'-substituent groups suitable for substituted stereo-standard sugar moieties include but are not limited to: 2'-F, 2'-$OCH_3$ ("2'-OMe" or "2'-O-methyl"), and 2'-$O(CH_2)_2OCH_3$ ("2'-MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C({=}O)$—$N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 3'-substituent groups include 3'-methyl (see Frier, et al., The ups and downs of nucleic acid duplex stability: structure-stability studies on chemically-modified DNA: RNA duplexes. Nucleic Acids Res., 25, 4429-4443, 1997.) Examples of 4'-substituent groups suitable for substituted stereo-standard sugar moieties include but are not limited to alkoxy (e.g., methoxy), alkyl, and those described in Manoharan et al., WO 2015/106128. Examples of 5'-substituent groups suitable for substituted stereo-standard sugar moieties include but are not limited to: 5'-methyl (R or S), 5'-allyl, 5'-ethyl, 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836. 2',4'-difluoro modified sugar moieties have been described in Martinez-Montero, et al., Rigid 2',4'-difluororibonucleosides: synthesis, conformational analysis, and incorporation into nascent RNA by HCV polymerase. *J. Org. Chem.,* 2014, 79:5627-5635. Modified sugar moieties comprising a 2'-modification (OMe or F) and a 4'-modification (OMe or F) have also been described in Malek-Adamian, et al., *J. Org. Chem,* 2018, 83: 9839-9849.

In certain embodiments, a 2'-substituted stereo-standard nucleoside comprises a sugar moiety comprising a non-bridging 2'-substituent group selected from: F, $NH_2$, $N_3$, $OCF_3$, $OCH_3$, $SCH_3$, $O(CH_2)_3NH_2$, $CH_2CH{=}CH_2$, $OCH_2CH{=}CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C({=}O)$—$N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted stereo-standard nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C({=}O)$—$N(H)CH_3$ ("NMA").

In certain embodiments, a 2'-substituted stereo-standard nucleoside comprises a sugar moiety comprising a 2'-substituent group selected from: F, $OCH_3$, and $OCH_2CH_2OCH_3$.

In certain embodiments, the 4' O of 2'-deoxyribose can be substituted with a S to generate 4'-thio DNA (see Takahashi, et al., *Nucleic Acids Research* 2009, 37: 1353-1362). This modification can be combined with other modifications detailed herein. In certain such embodiments, the sugar moiety is further modified at the 2' position. In certain embodiments the sugar moiety comprises a 2'-fluoro. A thymidine with this sugar moiety has been described in Watts, et al., J. Org. Chem. 2006, 71(3): 921-925 (4'-S-fluoro5-methylarauridine or FAMU).

c. Bicyclic Nucleosides

Certain nucleosides comprise modified sugar moieties that comprise a bridging sugar substituent that forms a second ring resulting in a bicyclic sugar moiety. In certain such embodiments, the bicyclic sugar moiety comprises a 4' to 2' bridge between the 4' and the 2' furanose ring atoms. In certain such embodiments, the furanose ring is a ribose ring. Examples of sugar moieties comprising such 4' to 2' bridging sugar substituents include but are not limited to bicyclic sugars comprising: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt" when in the S configuration), 4'-$CH_2$—O—$CH_2$-2', 4'-$CH_2$—N(R)-2', 4'-$CH(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—$N(OCH_3)$-2' and analogs thereof (see, e.g., Prakash et al., U.S. Pat. No. 8,278,425), 4'-$CH_2$—O—$N(CH_3)$-2' (see, e.g., Allerson et al., U.S. Pat. No. 7,696,345 and Allerson et al., U.S. Pat. No. 8,124,745), 4'-$CH_2$—C(H)$(CH_3)$-2' (see, e.g., Zhou, et al., *J. Org. Chem.,* 2009, 74, 118-134), 4'-$CH_2$—$C({=}CH_2)$-2' and analogs thereof (see e.g., Seth et al., U.S. Pat. No. 8,278,426), 4'-$C(R_aR_b)$—N(R)—O-2', 4'-$C(R_aR_b)$—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672), 4'-$C({=}O)$—$N(CH_3)_2$-2', 4'-$C({=}O)$—$N(R)_2$-2', 4'-$C({=}S)$—$N(R)_2$-2' and analogs thereof (see, e.g., Obika et al., WO2011052436A1, Yusuke, WO2017018360A1).

Additional bicyclic sugar moieties are known in the art, see, for example: Freier et al., *Nucleic Acids Research,* 1997, 25(22), 4429-4443, Albaek et al., *J. Org. Chem.,* 2006, 71, 7731-7740, Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2017, 129, 8362-8379; Elayadi et al.; Christiansen, et al., *J. Am. Chem. Soc.* 1998, 120, 5458-5463; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat.

No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

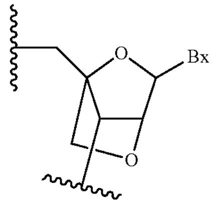

LNA (β-D-configuration) bridge = 4'-$CH_2$—O-2'

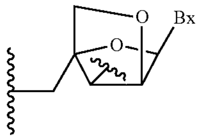

α-L-LNA (α-L-configuration) bridge = 4'-$CH_2$—O-2'

α-L-methyleneoxy (4'-$CH_2$—O-2') or α-L-LNA bicyclic nucleosides have been incorporated into antisense oligonucleotides that showed antisense activity (Frieden et al., *Nucleic Acids Research,* 2003, 21, 6365-6372). Herein, general descriptions of bicyclic nucleosides include both isomeric configurations. When the positions of specific bicyclic nucleosides (e.g., LNA) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

The term "substituted" following a position of the furanosyl ring, such as "2'-substituted" or "2'-4'-substituted", indicates that is the only position(s) having a substituent other than those found in unmodified sugar moieties in oligonucleotides.

d. Sugar Surrogates

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), altritol nucleic acid ("ANA"), mannitol nucleic acid ("MNA") (see, e.g., Leumann, C J. *Bioorg. & Med. Chem.* 2002, 10, 841-854), fluoro HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran).

In certain embodiments, sugar surrogates comprise rings having no heteroatoms. For example, nucleosides comprising bicyclo [3.1.0]-hexane have been described (see, e.g., Marquez, et al., *J. Med. Chem.* 1996, 39:3739-3749).

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate comprising the following structure:

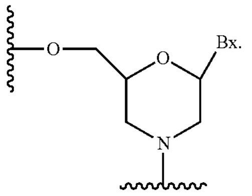

In certain embodiments, morpholinos may be modified, for example by adding or altering various substituent groups from the above morpholino structure. Such sugar surrogates are referred to herein as "modified morpholinos." In certain embodiments, morpholino residues replace a full nucleotide, including the internucleoside linkage, and have the structures shown below, wherein Bx is a heterocyclic base moiety.

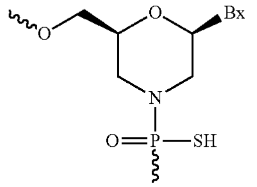

morpholino PS

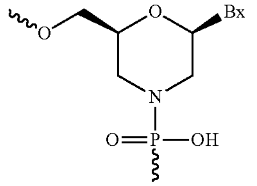

morpholino PO

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.,* 2013, 11, 5853-5865), glycol nucleic acid ("GNA", see Schlegel, et al., *J. Am. Chem. Soc.* 2017, 139:8537-8546) and nucleosides and oligonucleotides described in Manoharan et al., WO2011/133876. In certain embodiments, acyclic sugar surrogates are selected from:

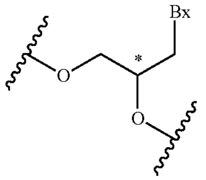

,

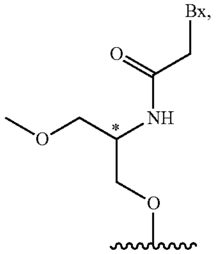

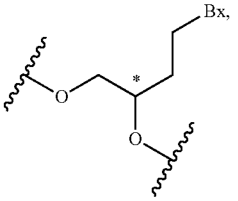

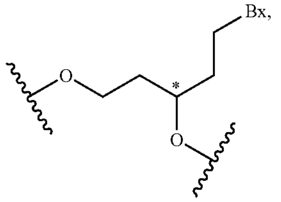

or

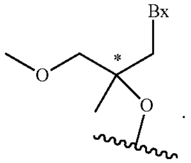

.

Many other bicyclic and tricyclic sugar and sugar surrogate ring systems are known in the art that can be used in modified nucleosides. Certain such ring systems are described in Hanessian, et al., *J. Org. Chem.*, 2013, 78: 9051-9063 and include bcDNA and tcDNA. Modifications to bcDNA and tcDNA, such as 6'-fluoro, have also been described (Dogovic and Leumann, *J. Org. Chem.*, 2014, 79: 1271-1279).

e. Conjugated Nucleosides and Terminal Groups

In certain embodiments, modified sugar moieties comprise a conjugate group and/or a terminal group. Modified sugar moieties are linked to conjugate groups through a conjugate linker. In certain embodiments, modified furanosyl sugar moieties comprise conjugate groups attached at the 2', 3', or 5' positions. In certain embodiments, the 3'-most sugar moiety of the nucleoside is modified with a conjugate group or a terminal group. In certain embodiments, the 5'-most sugar moiety of the nucleoside is modified with a conjugate group or a terminal group. In certain embodiments, a sugar moiety near the 3' end of the nucleoside is modified with a conjugate group. In certain embodiments, a sugar moiety near the 5' end of the nucleoside is modified with a conjugate group.

Examples of terminal groups include but are not limited to conjugate groups, capping groups, phosphate moieties, protecting groups, modified or unmodified nucleosides, and two or more nucleosides that are independently modified or unmodified.

In certain embodiments, terminal groups at the 5'-terminus comprise a stabilized phosphate group. In certain such embodiments, the phosphorus atom of the stabilized phosphate group is attached to the 5'-terminal nucleoside through a phosphorus-carbon bond. In certain embodiments, the carbon of that phosphorus-carbon bond is in turn bound to the 5'-position of the nucleoside.

In certain embodiments, the oligonucleotide comprises a 5'-stabilized phosphate group having the following formula:

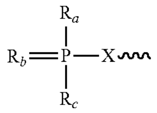

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;

$R_b$ is O or S;

X is substituted or unsubstituted C; and wherein X is attached to the 5'-terminal nucleoside. In certain embodiments, X is bound to an atom at the 5'-position of the 5'-terminal nucleoside. In certain such embodiments, the 5'-atom is a carbon and the bond between X and the 5'-carbon of the 5'-terminal nucleoside is a carbon-carbon single bond. In certain embodiments, it is a carbon-carbon double bond. In certain embodiments, it is a carbon-carbon triple bond. In certain embodiments, the 5'-carbon is substituted. In certain embodiments, X is substituted. In certain embodiments, X is unsubstituted.

In certain embodiments, the oligonucleotide comprises a 5'-stabilized phosphate group having the following formula:

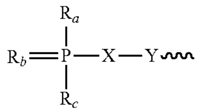

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;

$R_b$ is O or S;

X is substituted or unsubstituted C;

Y is selected from C, S, and N. In certain embodiments, Y is substituted or unsubstituted C. The bond between X and Y may be a single-, double-, or triple-bond.

Certain 5'-stabilized phosphate groups have been previously described; see, e.g., Prakash et al., WO2011/139699 and Prakash et al., WO2011/139702, hereby incorporated by reference herein in their entirety.

In certain embodiments, the stabilized phosphate group is 5'-vinyl phosphonate or 5'-cyclopropyl phosphonate.

In certain embodiments, a terminal group at the 5'-terminus is a 5'-mesyl phosphoramidate, having formula XXI:

XXI

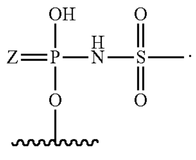

wherein Z is O or S.

In certain embodiments, a terminal group at the 5'-terminus is a 5'-mesyl phosphoramidate, having formula XXI:

XXII

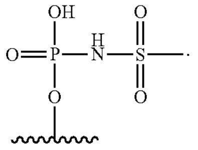

2. Modified Nucleobases

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($-C\equiv C-CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443. In certain embodiments, modified nucleosides comprise double-headed nucleosides having two nucleobases. Such compounds are described in detail in Sorinas et al., *J. Org. Chem,* 2014 79: 8020-8030.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

In certain embodiments, compounds comprise or consist of a modified oligonucleotide complementary to a target nucleic acid comprising one or more modified nucleobases. In certain embodiments, the modified nucleobase is 5-methylcytosine. In certain embodiments, each cytosine is a 5-methylcytosine.

B. Modified Internucleoside Linkages a. Internucleoside Linkages of Formula VIII and XVII In certain embodiments, antisense agents, oligomeric compounds, and modified oligonucleotides described herein having one or more modified internucleoside linkages having Formula VIII or Formula XVII are selected over compounds lacking such internucleoside linkages having Formula VIII or Formula XVII because of one or more desirable properties. In certain embodiments, antisense agents, oligomeric compounds, and modified oligonucleotides described herein having one or more modified internucleoside linkages having Formula VIII or Formula XVII have enhanced cellular uptake. In certain embodiments, antisense agents, oligomeric compounds, and modified oligonucleotides described herein having one or more modified internucleoside linkages having Formula VIII or Formula XVII have enhanced affinity for target nucleic acids. In certain embodiments, antisense agents, oligomeric compounds, and modified oligonucleotides described herein having one or more modified internucleoside linkages having Formula VIII or Formula XVII have increased stability in the presence of nucleases. In certain embodiments, antisense agents, oligomeric compounds, and modified oligonucleotides described herein having one or more modified internucleoside linkages having Formula VIII or Formula XVII have enhanced cellular uptake, enhanced affinity for target nucleic acids, and increased stability in the presence of nucleases. In certain embodiments, antisense agents, oligomeric compounds, and modified oligonucleotides described herein having one or more modified internucleoside linkages having Formula VIII or Formula XVII have enhanced bioavailability. In certain embodiments, antisense agents, oligomeric compounds, and modified oligonucleotides described herein having one or more modified internucleoside linkages having Formula VIII or Formula XVII have enhanced RNase H activity. In certain embodiments, antisense agents, oligomeric compounds, and modified oligonucleotides described herein having one or more modified internucleoside linkages having Formula VIII or Formula XVII have enhanced RNAi activity. In certain embodiments, antisense agents, oligomeric compounds, and modified oligonucleotides described herein having one or more modified internucleoside linkages having Formula VIII or Formula XVII have enhanced CRISPR activity. In certain embodiments, antisense agents, oligomeric compounds, and modified oligonucleotides described herein having one or more modified internucleoside linkages having Formula VIII or Formula XVII have reduced interactions with certain proteins. In certain embodiments, antisense agents, oligomeric compounds, and modified oligonucleotides described herein having one or more modified internucleoside linkages having Formula VIII or Formula XVII have increased interactions with certain proteins.

In certain embodiments, oligomeric compounds (including oligomeric compounds that are antisense agents or portions thereof) comprise or consist of a modified oligonucleotide complementary to a target nucleic acid comprising one or more modified internucleoside linkages having Formula VIII:

VIII

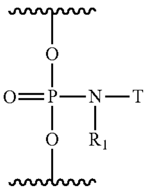

wherein independently for each internucleoside linking group of the oligomeric compound having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, and substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl.

In certain embodiments, oligomeric compounds (including oligomeric compounds that are antisense agents or portions thereof) comprise or consist of a modified oligonucleotide complementary to a target nucleic acid comprising one or more modified internucleoside linkages having Formula VIII:

VIII

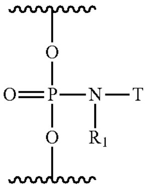

wherein independently for each internucleoside linking group of the oligomeric compound having Formula VIII:

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, a $C_1$-$C_6$ alkyl, and a substituted $C_1$-$C_6$ alkyl;

$R_3$ is selected from an aryl, a substituted aryl, $CH_3$, $N(CH_3)_2$, and $OCH_3$;

$R_4$ is selected from $OCH_3$, OH, $C_1$-$C_6$ alkyl, and substituted $C_1$-$C_6$ alkyl; and $R_5$ is selected from $OCH_3$, OH, $C_1$-$C_6$ alkyl, and substituted $C_1$-$C_6$ alkyl;

provided that if $R_1$ is H, then T is not:

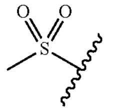

or

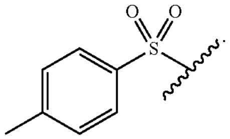

In certain embodiments, oligomeric compounds (including oligomeric compounds that are antisense agents or portions thereof) comprise or consist of a modified oligonucleotide complementary to a target nucleic acid comprising one or more modified internucleoside linkages having Formula XVII:

XVII

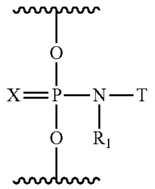

wherein independently for each internucleoside linking group of the oligomeric compound having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

In certain embodiments, compounds comprise or consist of a modified oligonucleotide complementary to a target nucleic acid comprising one or more modified internucleoside linkages having Formula IX:

IX

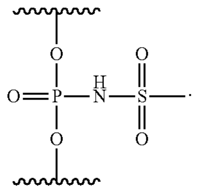

In certain embodiments, compounds comprise or consist of a modified oligonucleotide complementary to a target nucleic acid comprising one or more modified internucleoside linkages having Formula XX:

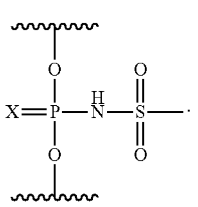

XX wherein independently for each internucleoside linking group of the oligomeric compound having Formula XX, X is selected from O or S.

b. Other Internucleoside Linkages

In certain embodiments, antisense agents, oligomeric compounds, and modified oligonucleotides comprise or consist of a modified oligonucleotide complementary to a target nucleic acid comprising one or more modified internucleoside linkages. In certain embodiments, the modified internucleoside linkages are phosphorothioate linkages. In certain embodiments, each internucleoside linkage of an antisense compound is a phosphorothioate internucleoside linkage.

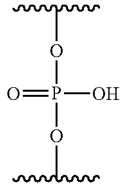

Phosphodiester internucleoside linking group

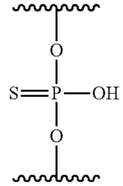

Phosphorothioate internucleoside linking group

In certain embodiments, nucleosides of modified oligonucleotides may be linked together using any internucleoside linkage. The two main classes of internucleoside linkages are defined by the presence or absence of a phosphorus atom. Representative phosphorus-containing internucleoside linkages include unmodified phosphodiester internucleoside linkages, modified phosphotriesters such as THP phosphotriester and isopropyl phosphotriester, phosphonates such as methylphosphonate, isopropyl phosphonate, isobutyl phosphonate, and phosphonoacetate, phosphoramidates, phosphorothioate, and phosphorodithioate ("HS—P═S"). Representative non-phosphorus containing internucleoside linkages include but are not limited to methylenemethylimino ($—CH_2—N(CH_3)—O—CH_2—$), thiodiester, thionocarbamate (—O—C(═O)(NH)—S—); siloxane ($—O—SiH_2—O—$); formacetal, thioacetamido (TANA), alt-thioformacetal, glycine amide, and N,N'-dimethylhydrazine ($—CH_2—N(CH_3)—N(CH_3)—$). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Neutral internucleoside linkages include, without limitation, phosphotriesters, phosphonates, MMI ($3'-CH_2—N(CH_3)—O-5'$), amide-3 ($3'-CH_2—C(═O)—N(H)-5'$), amide-4 ($3'-CH_2—N(H)—C(═O)-5'$), formacetal ($3'-O—CH_2—O-5'$), methoxypropyl, and thioformacetal ($3'-S—CH_2—O-5'$). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

c. Chiral Internucleoside Linkages

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. All phosphorothioate linkages described herein are stereorandom unless otherwise specified. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

($R_p$)

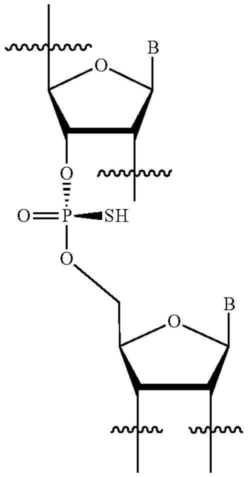

($S_p$)

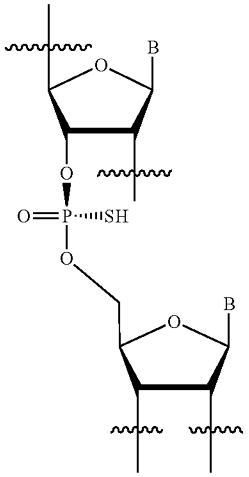

Unless otherwise indicated, chiral internucleoside linkages of modified oligonucleotides described herein can be stereorandom or in a particular stereochemical configuration.

In certain embodiments, an internucleoside linkage of Formula XVII may comprise a chiral center. An internucleoside linkage of Formula XVIII (XVII where X is S) comprises a chiral center. In certain embodiments, modified oligonucleotides comprise chiral linkages of Formula XVIII illustrated below as XVIIIa and XVIIIb.

XVII

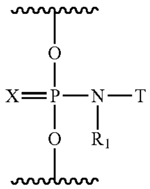

-continued

XVIII

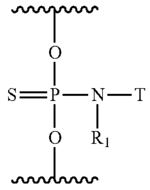

XVIIIa

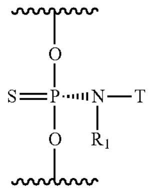

XVIIIb

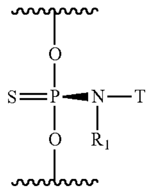

d. Alternatives to 5' to 3' Internucleoside Linkages

In certain embodiments, nucleic acids can be linked 2' to 5' rather than the standard 3' to 5' linkage. Such a linkage is illustrated below.

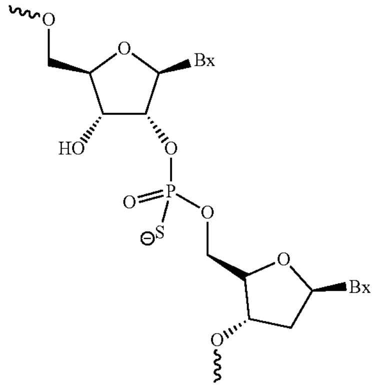

In certain embodiments, nucleosides can be linked by vicinal 2', 3'-phosphodiester bonds. In certain such embodiments, the nucleosides are threofuranosyl nucleosides (TNA; see Bala, et al., *J Org. Chem.* 2017, 82:5910-5916). A TNA linkage is shown below.

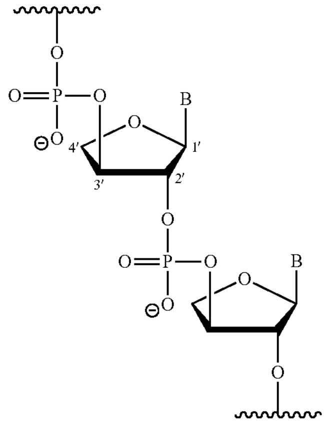

threose nucleic acid
(TNA)

Additional modified linkages include α,β-D-CNA type linkages and related conformationally-constrained linkages, shown below. Synthesis of such molecules has been described previously (see Dupouy, et al., *Angew. Chem. Int. Ed. Engl.,* 2014, 45: 3623-3627; Borsting, et al. *Tetrahedron,* 2004, 60:10955-10966; Ostergaard, et al., *ACS Chem. Biol.* 2014, 9: 1975-1979; Dupouy, et al., *Eur. J. Org. Chem.,* 2008, 1285-1294; Martinez, et al., *PLoS One,* 2011, 6: e25510; Dupouy, et al., *Eur. J. Org. Chem.,* 2007, 5256-5264; Boissonnet, et al., *New J. Chem.,* 2011, 35: 1528-1533.)

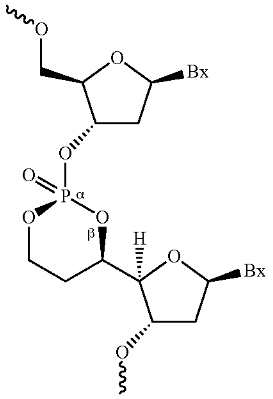

α,β-D-CNA
($R_{C5'}$, $R_P$)

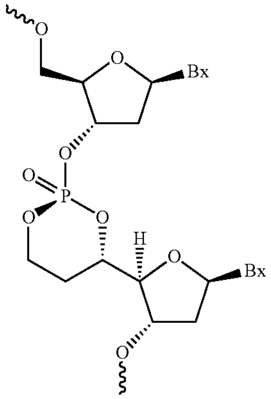

α,β-D-CNA
($S_{C5'}$, $R_P$)

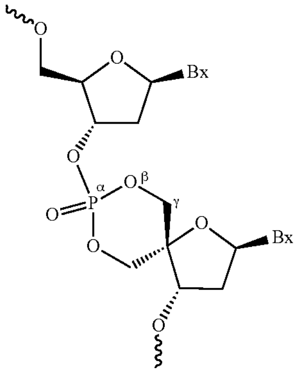

α,β-γ-D-CNA

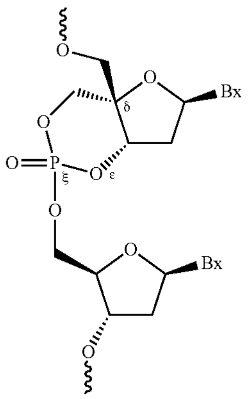

δ,ε,ξ-D-CNA

-continued

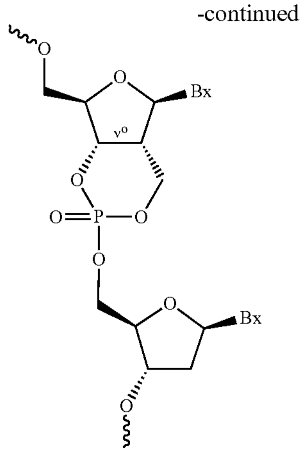

ν°,ε,ξ-D-CNA e. Linkages having conjugate groups

In certain embodiments, an internucleoside linking group may comprise a conjugate group. In certain embodiments, an internucleoside linking group of Formula XVII comprises a conjugate group. In certain embodiments, the conjugate group of a modified oligonucleotide may be attached to the remainder of the modified oligonucleotide through a modified internucleoside having Formula XVII:

XVII

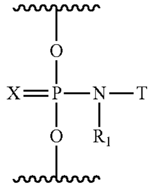

wherein T comprises a conjugate group. In certain embodiments, T is selected from $SO_2R_2$, $C(=O)R_3$, and $P(=O)R_4R_5$, wherein $R_2$, $R_3$, or $R_4$ is a conjugate group. In certain embodiments, the conjugate group comprises a cell-targeting moiety. In certain embodiments, the conjugate group comprises a carbohydrate or carbohydrate cluster. In certain embodiments, the conjugate group comprises GalNAc. In certain embodiments, the conjugate group comprises a lipid. In certain embodiments, the conjugate group comprises $C_{10}$-$C_{20}$ alkyl. In certain embodiments, the conjugate group comprises $C_{16}$ alkyl.

In certain embodiments, the internucleoside linking group comprising a conjugate group has Formula XIX:

XIX

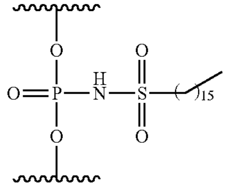

II. Certain Motifs

In certain embodiments, antisense agents, oligomeric compounds, and modified oligonucleotides described herein comprise or consist of oligonucleotides. Modified oligonucleotides can be described by their motif, e.g. a pattern of unmodified and/or modified sugar moieties, nucleobases, and/or internucleoside linkages. In certain embodiments, modified oligonucleotides comprise one or more stereo-non-standard nucleosides. In certain embodiments, modified oligonucleotides comprise one or more stereo-standard nucleosides. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns or motifs of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

A. Certain Sugar Motifs

In certain embodiments, antisense agents, oligomeric compounds, and modified oligonucleotides described herein comprise or consist of oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include without limitation any of the sugar modifications discussed herein.

In certain embodiments, a modified oligonucleotide comprises or consists of a gapmer. The sugar motif of a gapmer defines the regions of the gapmer: 5'-region, central region (gap), and 3'-region. The central region is linked directly to the 5'-region and to the 3'-region with no nucleosides intervening. The central region is a deoxy region. The nucleoside at the first position (position 1) from the 5'-end of the central region and the nucleoside at the last position of the central region are adjacent to the 5'-region and 3'-region, respectively, and each comprise a sugar moiety independently selected from a 2'-deoxyfuranosyl sugar moiety or a sugar surrogate. In certain embodiments, the nucleoside at position 1 of the central region and the nucleoside at the last position of the central region are DNA nucleosides, selected from stereo-standard DNA nucleosides or stereo-non-standard DNA nucleosides having any of formulas I-VII, wherein each J is H. In certain embodiments, the nucleoside at the first and last positions of the central region adjacent to the 5' and 3' regions are stereo-standard DNA nucleosides. Unlike the nucleosides at the first and last positions of the central region, the nucleosides at the other positions within the central region may comprise a 2'-substituted furanosyl sugar moiety or a substituted stereo-non-standard sugar moiety or a bicyclic sugar moiety. In certain embodiments, each nucleoside within the central region supports RNase H cleavage. In certain embodiments, a plurality of nucleosides within the central region support RNase H cleavage.

Herein, the lengths (number of nucleosides) of the three regions of a gapmer may be provided using the notation [# of nucleosides in the 5'-region]-[# of nucleosides in the central region]-[# of nucleosides in the 3'-region]. Thus, a 3-10-3 gapmer consists of 3 linked nucleosides in each of the 3' and 5' regions and 10 linked nucleosides in the central region. Where such nomenclature is followed by a specific modification, that modification is the modification of each sugar moiety of each 5' and 3'-region and the central region nucleosides comprise stereo-standard DNA sugar moieties. Thus, a 5-10-5 MOE gapmer consists of 5 linked nucleosides each comprising 2'-MOE-stereo-standard sugar moieties in the 5'-region, 10 linked nucleosides each comprising a stereo-standard DNA sugar moiety in the central region, and 5 linked nucleosides each comprising 2'-MOE-stereo-standard sugar moieties in the 3'-region. A 5-10-5 MOE gapmer having a substituted stereo-non-standard nucleoside at position 2 of the gap has a gap of 10 nucleosides wherein the $2^{nd}$ nucleoside of the gap is a substituted stereo-non-standard nucleoside rather than the stereo-standard DNA nucleoside. Such oligonucleotide may also be described as a 5-1-1-8-5 MOE/substituted stereo-non-standard/MOE gapmer. A 3-10-3 cEt gapmer consists of 3 linked nucleosides each comprising a cEt in the 5'-region, 10 linked nucleosides each comprising a stereo-standard DNA sugar moiety in the central region, and 3 linked nucleosides each comprising a cEt in the 3'-region. A 3-10-3 cEt gapmer having a substituted stereo-non-standard nucleoside at position 2 of the gap has a gap of 10 nucleoside wherein the $2^{nd}$ nucleoside of the gap is a substituted stereo-non-standard nucleoside rather than the stereo-standard DNA nucleoside. Such oligonucleotide may also be described as a 3-1-1-8-3 cEt/substituted stereo-non-standard/cEt gapmer.

The sugar motif of a 3-10-3 cEt gapmer may also be denoted by the notation kkk-d(10)-kkk, wherein each "k" represents a cEt and each "d" represents a 2'-β-D-deoxyribosyl sugar moiety. This sugar motif is independent of the nucleobase sequence, the internucleoside linkage motif, and any nucleobase modifications. A 5-10-5 MOE gapmer may be denoted by the notation eeeee-d(10)-eeeee or e(5)-d(10)-e(5), wherein each "e" represents a 2'-MOE-β-D-ribofuranosyl sugar moiety, and each "d" represents a 2'-β-D-deoxyribosyl sugar moiety.

In certain embodiments, each nucleoside of a modified oligonucleotide, or portion thereof, comprises a 2'-substituted sugar moiety, a bicyclic sugar moiety, a sugar surrogate, or a 2'-deoxyribosyl sugar moiety. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, PNA, THP, and F-HNA.

In certain embodiments, modified oligonucleotides comprise at least 12, at least 13, at least 14, at least 15, at least 16, at least 17, at least 18, at least 19, or at least 20 nucleosides comprising a modified sugar moiety. In certain embodiments, the modified sugar moiety is selected independently from a 2'-substituted sugar moiety, a bicyclic sugar moiety, or a sugar surrogate. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, THP, and F-HNA.

In certain embodiments, each nucleoside of a modified oligonucleotide comprises a modified sugar moiety ("fully modified oligonucleotide"). In certain embodiments, each nucleoside of a fully modified oligonucleotide comprises a 2'-substituted sugar moiety, a bicyclic sugar moiety, or a sugar surrogate. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, THP, and F-HNA. In certain embodiments, each nucleoside of a fully modified oligonucleotide comprises the same modified sugar moiety ("uniformly modified sugar motif"). In certain embodiments, the uniformly modified sugar motif is 7 to 20 nucleosides in length. In certain embodiments, each nucleoside of the uniformly modified sugar motif comprises a 2'-substituted sugar moiety, a bicyclic sugar moiety, or a sugar surrogate. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, THP, and F-HNA. In certain embodiments, modified oligonucleotides having at least one fully modified sugar motif may also comprise at least 1, at least 2, at least 3, or at least 4 2'-deoxyribonucleosides.

B. Certain Nucleobase Motifs

In certain embodiments antisense agents, oligomeric compounds, and modified oligonucleotides described herein comprise or consist of oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, one nucleoside comprising a modified nucleobase is in the central region of a modified oligonucleotide. In certain such embodiments, the sugar moiety of said nucleoside is a 2'-β-D-deoxyribosyl moiety. In certain such embodiments, the modified nucleobase is selected from: 5-methyl cytosine, 2-thiopyrimidine, 2-thiothymine, 6-methyladenine, inosine, pseudouracil, or 5-propynepyrimidine.

C. Certain Internucleoside Linkage Motifs

In certain embodiments, antisense agents, oligomeric compounds, and modified oligonucleotides described herein comprise or consist of oligonucleotides. In certain embodiments, oligonucleotides comprise modified and/or unmodified internucleoside linkages arranged along the oligonucleotide or region thereof in a defined pattern or motif. In certain embodiments, the modified internucleoside linkages are internucleoside linking groups having Formula VIII. In certain embodiments, some or all of the internucleoside linkages in the 5'-region and 3'-region are modified internucleoside linkages having Formula VIII or Formula XVII. In certain embodiments, the terminal internucleoside linkages are modified internucleoside linkages having Formula VIII or Formula XVII. In certain embodiments, the internucleoside linkage motif comprises at least one phosphodiester internucleoside linkage in at least one of the 5'-region and the 3'-region, and at least one modified internucleoside linkage having Formula VIII or Formula XVII. In certain embodiments, the internucleoside linkage motif comprises at least one phosphorothioate internucleoside linkage in at least one of the 5'-region and the 3'-region, and at least one modified internucleoside linkage having Formula VIII or Formula XVII.

In certain embodiments, modified oligonucleotides comprise at least one region having Structure A:

Structure A

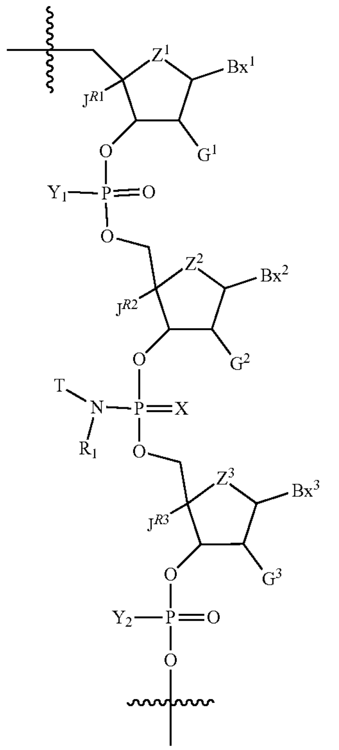

wherein:

each Bx is a heterocyclic base moiety;

X is selected from O or S;

each of $Y_1$ and $Y_2$ is independently selected from OH or SH;

each of $Z^1$, $Z^2$, and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or O—$[C(R_6)(R_7)]_n$—$[(C{=}O)_m$—$X^G]_j$—$R_8$;

either $J^{R2}$ and $G^2$ form a $J^{R2}$ and $G^2$ bridge, or $J^{R2}$ is H and $G^2$ is selected from H, OH, halogen or O—$[C(R_6)(R_7)]_n$—$[(C{=}O)_m$—$X^G]_j$—$R_8$;

either $J^{R3}$ and $G^3$ form a $J^{R3}$ and $G^3$ bridge, or $J^{R3}$ is H and $G^3$ is selected from H, OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C({=}Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having Structure B:

Structure B

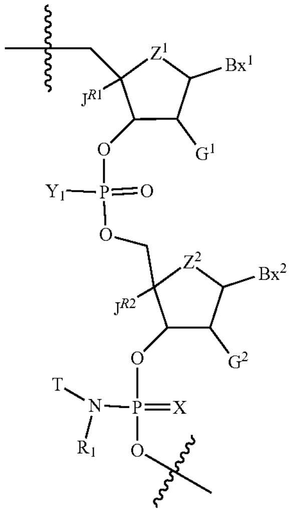

wherein:

each Bx is a heterocyclic base moiety;

X is selected from O or S;

each of $Y_1$ and $Y_2$ is independently selected from OH or SH;

each of $Z^1$ and $Z^2$ are independently selected from —$(CH_2)_p$—$X^Z$—$(CH_2)_q$—, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C({=}O)R_3$, and $P({=}O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or O—$[C(R_6)(R_7)]_n$—$[(C{=}O)_m$—$X^G]_j$—$R_8$;

either $J^{R2}$ and $G^2$ form a $J^{R2}$ and $G^2$ bridge, or $J^{R2}$ is H and $G^2$ is selected from H, OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_5$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C({=}Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having Structure C:

Structure C

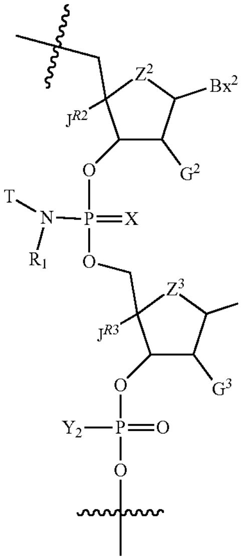

wherein:

each Bx is a heterocyclic base moiety;

X is selected from O or S;

each of $Y_1$ and $Y_2$ is independently selected from OH or SH;

each of $Z^2$ and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R2}$ and $G^2$ form a $J^{R2}$ and $G^2$ bridge, or $J^{R2}$ is H and $G^2$ is selected from H, OH, halogen or $O-[C(R_6)(R_7)]_n-[(C=O)_m-X^G]_j-R_8$;

either $J^{R3}$ and $G^3$ form a $J^{R3}$ and $G^3$ bridge, or $J^{R3}$ is H and $G^3$ is selected from H, OH, halogen or $O-[C(R_6)(R_7)]_n-[(CO)_m-X^G]_j-R_8$;

wherein each $J^R$ to G bridge has a formula independently selected from $-CH(CH_3)-O-$ or $-(CH_2)_k-O-$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having Structure D:

Structure D

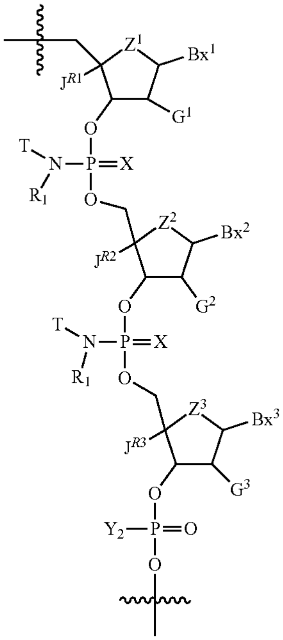

wherein:

each Bx is a heterocyclic base moiety;

X is selected from O or S;

each of $Y_1$ and $Y_2$ is independently selected from OH or SH;

each of $Z^2$ and $Z^3$ are independently selected from $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or $O-[C(R_6)(R_7)]_n-[(C=O)_m-X^G]_j-R_8$;

either $J^{R2}$ and $G^2$ form a $J^{R2}$ and $G^2$ bridge, or $J^R$ is H and $G^2$ is selected from H, OH, halogen or O—$[C(R_6)(R_7)]_n$—$[(C{=}O)_m$—$X^G]_j$—$R_8$;

either $J^{R3}$ and $G^3$ form a $J^{R3}$ and $G^3$ bridge, or $J^{R3}$ is H and $G^3$ is selected from H, OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having Structure E:

Structure E

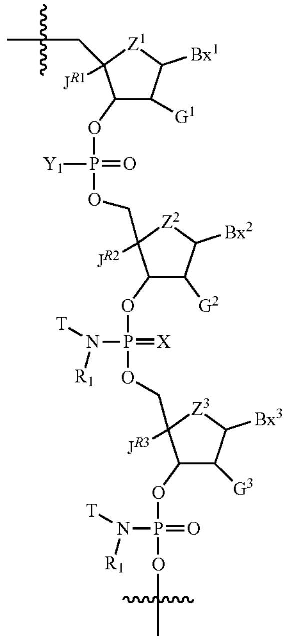

wherein:

each Bx is a heterocyclic base moiety;

X is selected from O or S;

each of $Y_1$ and $Y_2$ is independently selected from OH or SH;

each of $Z^2$ and $Z^3$ are independently selected from —$(CH_2)_p$—$X^Z$—$(CH_2)_q$—, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C({=}O)R_3$, and $P({=}O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^{R1}$ and $G^1$ form a $J^{R1}$ to $G^1$ bridge, or $J^{R1}$ is H and $G^1$ is selected from H, OH, halogen or O—$[C(R_6)(R_7)]_n$—$[(C{=}O)_m$—$X^G]_j$—$R_8$;

either $J^{R2}$ and $G^2$ form a $J^{R2}$ and $G^2$ bridge, or $J^{R2}$ is H and $G^2$ is selected from H, OH, halogen or O—$[C(R_6)(R_7)]_n$—$[(C{=}O)_m$—$X^G]_j$—$R_8$;

either $J^{R3}$ and $G^3$ form a $J^{R3}$ and $G^3$ bridge, or $J^{R3}$ is H and $G^3$ is selected from H, OH, halogen or O—$[C(R_6)(R_7)]$ $[(C{=}O))_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 5'-terminus having structure F:

Structure F

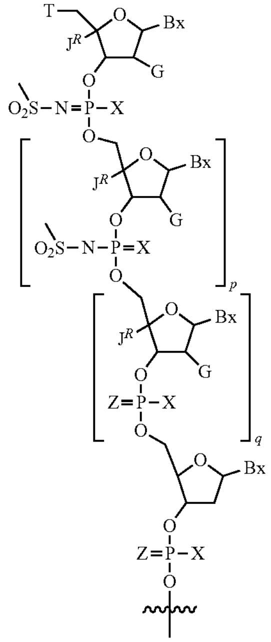

wherein:

p is from 0 to 6;

q is from 0 to 6;

T is OH, a stabilized phosphate group, or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or $O—[C(R_6)(R_7)]_n—[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C({=}Q_2)N(J_1)(J_2)$; $Q_2$ is O, S or $NJ_3$;

each $J_1$, $J_2$ and $J_3$ is, independently, H or $C_1$-$C_6$ alkyl.

In certain embodiments, modified oligonucleotides comprise a 3'-terminus having structure G:

Structure G

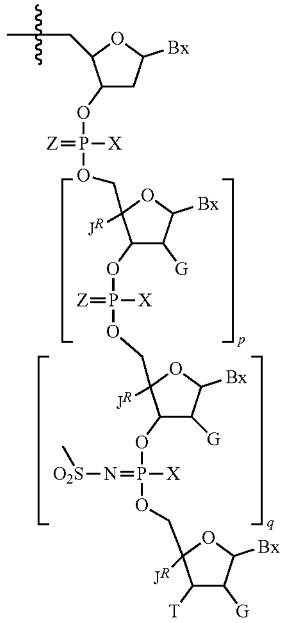

wherein:

p is from 0 to 6;

q is from 1 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or $O—[C(R_6)(R_7)]_n—[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C({=}Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 5'-terminus having structure H:

Structure H

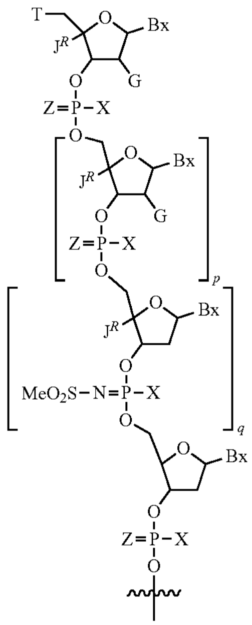

wherein:

p is from 0 to 5;

q is from 1 to 4;

T is OH, a stabilized phosphate group, or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a $J^R$ to G bridge, or $J^R$ is H and G is selected from OH, halogen or $O—[C(R_6)(R_7)]_n—[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 5'-terminus having structure I:

Structure I

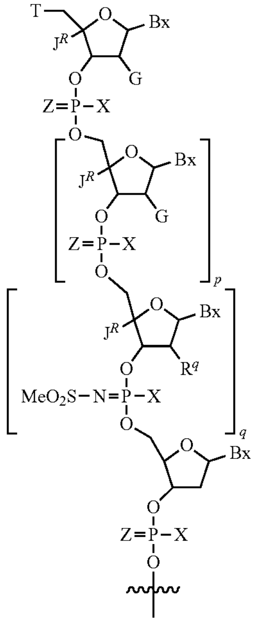

wherein:

p is from 0 to 5;

q is from 1 to 4;

T is OH, a stabilized phosphate group, or a conjugate group;

each Bx is an independently selected heterocyclic base moiety;

each X is independently selected from OH or SH;

each Z is independently selected from O, S, or $NSO_2Me$;

each $R^q$ is H or exactly one $R^q$ is OMe and the other $R^q$ are H;

For each $J^R$ and G of the same furanosyl sugar moiety, either $J^R$ and G form a $J^R$ to G bridge, or $J^R$ is H and G is selected from OH, halogen or $O—[C(R_6)(R_7)]_n—[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 3'-terminus having structure J:

Structure J

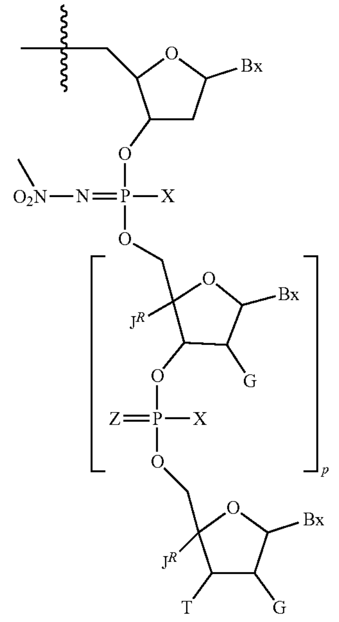

wherein:

p is from 0 to 6;

T is OH or a conjugate group;

each Bx is an independently selected heterocyclic base moiety;

each X is independently selected from OH or SH;

each Z is independently selected from O, S, or $NSO_2Me$;

For each $J^R$ and G of the same furanosyl sugar moiety, either $J^R$ and G form a to G bridge, or $J^R$ is H and G is selected from OH, halogen or $O—[C(R_6)(R_7)]_n—[(C{=}O)_m—X^G]_j—R_8$;

wherein each $J^R$ to G bridge has a formula independently selected from $—CH(CH_3)—O—$ or $—(CH_2)_k—O—$, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 5'-terminus having structure K:

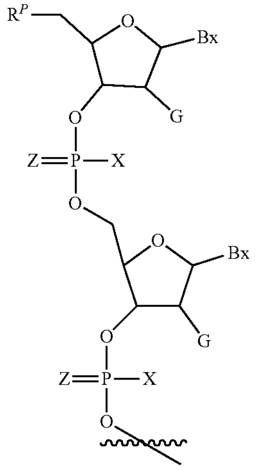

Structure K wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 3'-terminus having structure L:

Structure L

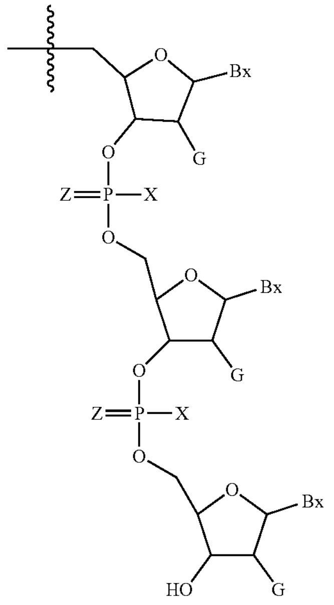

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having structure M:

Structure M

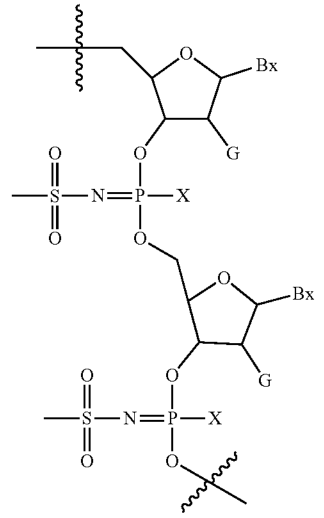

wherein:

each Bx is an independently selected heterocyclic base moiety;

each X is independently selected from OH or SH;

each G is independently selected from OH, halogen or $O—[C(R_6)(R_7)]_n—[(C{=}O)_m—X^G]_j—R_8$; each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(-Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise a 5'-terminus having structure N:

Structure N

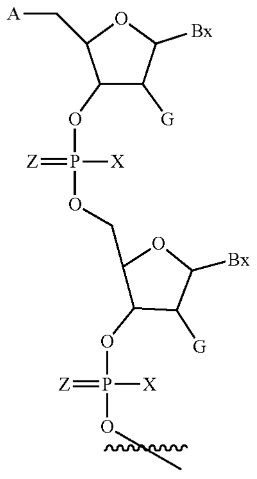

wherein:

A is selected from

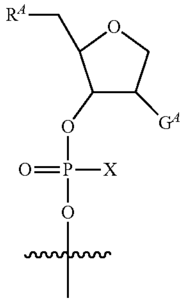

or

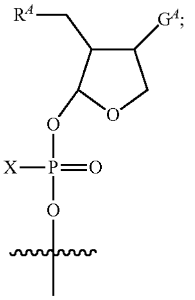

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides have a 3'-terminus having structure O:

Structure O

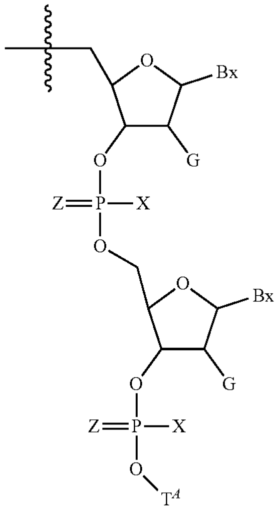

wherein:

$T^A$ is selected from

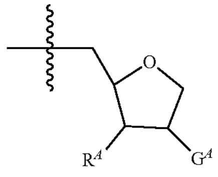

or

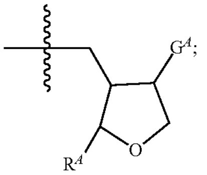

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C{=}O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, modified oligonucleotides comprise at least one region having the formula: $(N_{g1})_{L1}(N_{g2})_{L2}(N_{g3})_{L3}$, wherein each $N_g$ is a nucleoside comprising furanosyl sugar moiety or a sugar surrogate and each L is an internucleoside linking group; wherein each of $L_1$, $L_2$, and $L_3$ is a phosphodiester internucleoside linking group, a phosphorothioate internucleoside linking group, or an internucleoside linking group of Formula XVII:

XVII

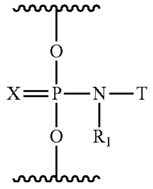

wherein each of $L_1$, and $L_2$ is a phosphodiester internucleoside linking group, a phosphorothioate internucleoside linking group, or an internucleoside linking group of Formula XVII:

wherein $L_3$ is absent or is a phosphodiester internucleoside linking group, a phosphorothioate internucleoside linking group, or an internucleoside linking group of Formula XVII;

wherein at least one of $L_1$, $L_2$, and $L_3$ an internucleoside linking group of Formula XVII; and at least one of $L_1$, $L_2$, and $L_3$ is a phosphorothioate or a phosphodiester internucleoside linking group, wherein independently for each internucleoside linking group of the modified oligonucleotide having Formula XVII:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate;

$R_4$ is selected from $OCH_3$, OH, $C_1$-$C_6$ alkyl, substituted $C_1$-$C_6$ alkyl and a conjugate; and $R_5$ is selected from $OCH_3$, OH, $C_1$-$C_6$ alkyl, and substituted $C_1$-$C_6$ alkyl.

In certain embodiments, the internucleoside linkages within the central region of a modified oligonucleotide are all modified with internucleoside linking groups having Formula VIII or Formula XVII. In certain embodiments, one internucleoside linkage within the central region of a modified oligonucleotide is an internucleoside linking group having Formula VIII or Formula XVII. In certain embodiments, two internucleoside linkages within the central region of a modified oligonucleotide are internucleoside linking groups having Formula VIII or Formula XVII. In certain embodiments, three internucleoside linkages within the central region of a modified oligonucleotide are internucleoside linking groups having Formula VIII or Formula XVII. In certain embodiments, four internucleoside linkages within the central region of a modified oligonucleotide are internucleoside linking groups having Formula VIII or Formula XVII.

In certain embodiments, five internucleoside linkages within the central region of a modified oligonucleotide are internucleoside linking groups having Formula VIII or Formula XVII. In certain embodiments, six internucleoside linkages within the central region of a modified oligonucleotide are internucleoside linking groups having Formula VIII or Formula XVII. In certain embodiments, seven internucleoside linkages within the central region of a modified oligonucleotide are internucleoside linking groups having Formula VIII or Formula XVII. In certain embodiments, eight internucleoside linkages within the central region of a modified oligonucleotide are internucleoside linking groups having Formula VIII or Formula XVII. In certain embodiments, nine internucleoside linkages within the central region of a modified oligonucleotide are internucleoside linking groups having Formula VIII or Formula XVII. In certain embodiments, ten internucleoside linkages within the central region of a modified oligonucleotide are internucleoside linking groups having Formula VIII or Formula XVII. In certain embodiments, each internucleoside linkage within the central region of a modified oligonucleotide is an internucleoside linking groups having Formula VIII or Formula XVII.

In certain embodiments, the internucleoside linking group linking the $2^{nd}$ and $3^{rd}$ nucleosides of the central region as counted from the 5'-end of the central region is an internucleoside linking group of Formula VIII or Formula XVII.

In certain embodiments, the internucleoside linking group linking the $3^{rd}$ and $4^{th}$ nucleosides of the central region as counted from the 5'-end of the central region is an internucleoside linking group of Formula VIII or Formula XVII.

In certain embodiments, the internucleoside linking group linking the $4^{th}$ and $5^{th}$ nucleosides of the central region as counted from the 5'-end of the central region is an internucleoside linking group of Formula VIII or Formula XVII.

In certain embodiments, the central region consists of 7-11 linked nucleosides, and has the formula:

$$(N_{d1})_{L1}(N_{d2})_{L2}(N_{d3})_{L3}(N_{d4})_{L4}[(N_d)_{L5}]_q;$$

wherein $N_{d1}$, $N_{d2}$, $N_{d3}$, $N_{d4}$ are independently selected from among a stereo-standard DNA nucleoside, a stereo-non-standard DNA nucleoside, or a 2'-substituted nucleoside; with the proviso that no more than one of $N_{d1}$, $N_{d2}$, $N_{d3}$, or $N_{d4}$ is a 2'-substituted nucleoside;

each $N_d$ is independently selected from among a stereo-standard DNA nucleoside and a stereo-non-standard DNA nucleoside;

q is from 3-8;

wherein each of $L_1$, $L_2$, $L_3$, $L_4$, and each $L_5$ is an internucleoside linkage;

wherein at least two of $L_1$, $L_2$, $L_3$, $L_4$ is an internucleoside linkage of Formula VIII or Formula XVII.

In certain embodiments, the oligonucleotide comprises at least one block of at least 3 consecutive internucleoside linking groups of Formula VIII or Formula XVII. In certain embodiments, the oligonucleotide comprises at least one block of at least 4 consecutive internucleoside linking groups of Formula VIII or Formula XVII. In certain embodiments, the oligonucleotide comprises at least one block of at least 5 consecutive internucleoside linking groups of Formula VIII or Formula XVII. In certain embodiments, the oligonucleotide comprises at least one block of at least 5 consecutive internucleoside linking groups of Formula VIII or Formula XVII. In certain embodiments, the oligonucleotide comprises at least one block of at least 6 consecutive internucleoside linking groups of Formula VIII or Formula XVII. In certain embodiments, the oligonucleotide comprises at least one block of at least 7 consecutive internucleoside linking groups of Formula VIII or Formula XVII. In certain embodiments, the oligonucleotide comprises at least one block of at least 8 consecutive internucleoside linking groups of Formula VIII or Formula XVII. In certain embodiments, the oligonucleotide comprises at least one block of at least 10 consecutive internucleoside linking groups of Formula VIII or Formula XVII. In certain embodiments, the oligonucleotide comprises at least one block of at least 12 consecutive internucleoside linking groups of Formula VIII or Formula XVII. In certain such embodiments, at least one such block is located at the 3' end of the oligonucleotide. In certain such embodiments, at least one such block is located within 3 nucleosides of the 3' end of the oligonucleotide. In certain such embodiments, at least one such block is located at the 5' end of the oligonucleotide. In certain such embodiments, at least one such block is located within 3 nucleosides of the 5' end of the oligonucleotide.

In certain such embodiments, some or all of the internucleoside linkages in the 5'-region and 3'-region are unmodified phosphate linkages. In certain embodiments, the terminal internucleoside linkages are modified. In certain embodiments, the internucleoside linkage motif comprises at least one phosphodiester internucleoside linkage in at least one of the 5'-region and the 3'-region, wherein the at least one phosphodiester linkage is not a terminal internucleoside linkage, and the remaining internucleoside linkages are internucleoside linking groups of Formula VIII or Formula XVII or phosphorothioate internucleoside linkages.

In certain embodiments, oligonucleotides comprise a region having an alternating internucleoside linkage motif. In certain embodiments, oligonucleotides comprise a region of uniformly modified internucleoside linkages. In certain such embodiments, the internucleoside linkages are internucleoside linking groups of Formula VIII or Formula XVII. In certain embodiments, each internucleoside linkage of the oligonucleotide is selected from phosphodiester, a phosphorothioate, and internucleoside linking group of Formula VIII or Formula XVII. In certain embodiments, each internucleoside linkage of the oligonucleotide is selected from phosphodiester or and an internucleoside linking groups of Formula VIII or Formula XVII. In certain embodiments, each internucleoside linkage of the oligonucleotide is selected from phosphorothioate and an internucleoside linking group of Formula VIII or Formula XVII.

In certain embodiments, each phosphorothioate internucleoside linkage is independently selected from a stereorandom phosphorothioate, a (Sp) phosphorothioate, and a (Rp) phosphorothioate. In certain embodiments, the internucleoside linkages within the central region of a modified oligonucleotide are all modified. In certain such embodiments, all of the phosphorothioate linkages are stereorandom. In certain embodiments, all of the phosphorothioate linkages in the 5'-region and 3'-region are (Sp) phosphorothioates, and the central region comprises at least one Sp, Sp, Rp motif. In certain embodiments, populations of modified oligonucleotides are enriched for modified oligonucleotides comprising such internucleoside linkage motifs.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, modified oligonucleotides comprise a linkage motif comprising all phosphorothioate linkages except for one or two methylphosphonate linkages. In certain embodiments, one methylphosphonate linkage is in the central region of an oligonucleotide.

In certain embodiments, it is desirable to arrange the number of modified internucleoside linking groups having Formula VIII or Formula XVII, phosphorothioate internucleoside linkages, and phosphodiester internucleoside linkages to maintain nuclease resistance. In certain embodiments, it is desirable to arrange the number and position of modified internucleoside linking groups having Formula VIII or Formula XVII, phosphorothioate internucleoside linkages, and the number and position of phosphodiester internucleoside linkages to maintain nuclease resistance. In certain embodiments, the number of phosphorothioate internucleoside linkages may be decreased and the number of modified internucleoside linking groups having Formula VIII or Formula XVII and/or phosphodiester internucleoside linkages may be increased. In certain embodiments, the number of phosphorothioate internucleoside linkages may be decreased and the number of modified internucleoside linking groups having Formula VIII or Formula XVII and/or phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

In certain embodiments, the number of phosphodiester internucleoside linkages may be decreased by replacing phosphodiester internucleoside linkages with modified internucleoside linking groups having Formula VIII or Formula XVII. In certain embodiments, decreasing the number of phosphodiester internucleoside linkages and increasing the number of modified internucleoside linking groups having Formula VIII or Formula XVII increases the therapeutic index of a modified oligonucleotide or oligomeric compound. In certain embodiments, the number of phosphorothioate internucleoside linkages may be decreased by replacing phosphorothioate internucleoside linkages with modified internucleoside linking groups having Formula VIII or Formula XVII. In certain embodiments, decreasing the number of phosphorothioate internucleoside linkages and increasing the number of modified internucleoside linking groups having Formula VIII or Formula XVII increases the therapeutic index of a modified oligonucleotide or oligomeric compound.

In certain embodiments, a double-stranded antisense compound is a double-stranded RNAi compound comprising an RNAi antisense modified oligonucleotide and an RNAi sense modified oligonucleotide, wherein one or both of the RNAi antisense modified oligonucleotide and/or RNAi sense oligomeric compound have one or more modified internucleoside linking groups having Formula VIII or Formula XVII. In certain embodiments, the RNAi antisense modified oligonucleotide comprises at least two, at least three, at least four, at least five, or at least six modified internucleoside linking groups having Formula VIII or Formula XVII. In certain embodiments, the RNAi sense modified oligonucleotide comprises at least two, at least three, at least four, at least five, or at least six modified internucleoside linking groups having Formula VIII or Formula XVII.

In certain embodiments, the RNAi antisense modified oligonucleotide comprises exactly one modified internucleoside linking group having Formula VIII or Formula XVII. In certain embodiments, the RNAi antisense modified oligonucleotide comprises exactly two modified internucleoside linking groups having Formula VIII or Formula XVII. In certain embodiments, the RNAi antisense modified oligonucleotide comprises exactly three modified internucleoside linking groups having Formula VIII or Formula XVII. In certain embodiments, the RNAi antisense modified oligonucleotide comprises exactly four modified internucleoside linking groups having Formula VIII or Formula XVII. In certain embodiments, the RNAi antisense modified oligonucleotide comprises exactly five modified internucleoside linking groups having Formula VIII or Formula XVII. In certain embodiments, the RNAi antisense modified oligonucleotide comprises exactly six modified internucleoside linking groups having Formula VIII or Formula XVII. In certain embodiments, the RNAi antisense modified oligonucleotide comprises at least 6, at least 7, at least 8, or at least 9 modified internucleoside linking groups having Formula VIII or Formula XVII. In certain embodiments, each internucleoside linking group of the RNAi antisense modified oligonucleotide is a modified internucleoside linking groups having Formula VIII or Formula XVII.

In certain embodiments, the RNAi sense modified oligonucleotide comprises exactly one modified internucleoside linking group having Formula VIII or Formula XVII. In certain embodiments, the RNAi sense modified oligonucleotide comprises exactly two modified internucleoside linking groups having Formula VIII or Formula XVII. In certain embodiments, the RNAi sense modified oligonucleotide comprises exactly three modified internucleoside linking groups having Formula VIII or Formula XVII. In certain embodiments, the RNAi sense modified oligonucleotide comprises exactly four modified internucleoside linking groups having Formula VIII or Formula XVII. In certain embodiments, the RNAi sense modified oligonucleotide comprises exactly five modified internucleoside linking groups having Formula VIII or Formula XVII. In certain embodiments, the RNAi sense modified oligonucleotide comprises exactly six modified internucleoside linking groups having Formula VIII or Formula XVII. In certain embodiments, the RNAi sense modified oligonucleotide comprises at least 6, at least 7, at least 8, or at least 9 modified internucleoside linking groups having Formula VIII or Formula XVII. In certain embodiments, each internucleoside linking group of the RNAi sense modified oligonucleotide is a modified internucleoside linking groups having Formula VIII or Formula XVII.

In certain embodiments, at least one of the five 3'-most internucleoside linking groups of the RNAi antisense modified oligonucleotide is a modified internucleoside linking group having Formula VIII or Formula XVII. In certain embodiments, at least two of the five 3'-most internucleoside linking groups of the RNAi antisense modified oligonucleotide are modified internucleoside linking groups having Formula VIII or Formula XVII. In certain embodiments, at least one nucleoside of the seed region of the RNAi antisense modified oligonucleotide is a modified internucleoside linking group having Formula VIII or Formula XVII. In certain embodiments, at least one nucleoside within nucleosides 2 to 8 of the RNAi antisense modified oligonucleotide, counting from the 5' end, is a modified internucleoside linking group having Formula VIII or Formula XVII.

In certain embodiments, the 5'-terminus of the RNAi antisense oligonucleotide has structure K:

Structure K

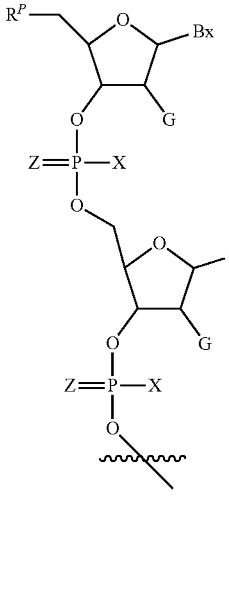

wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O-[C(R_6)(R_7)]_n-[(C{=}O)_m-X^G]_j-R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 3'-terminus of the RNAi antisense oligonucleotide has structure L:

Structure L

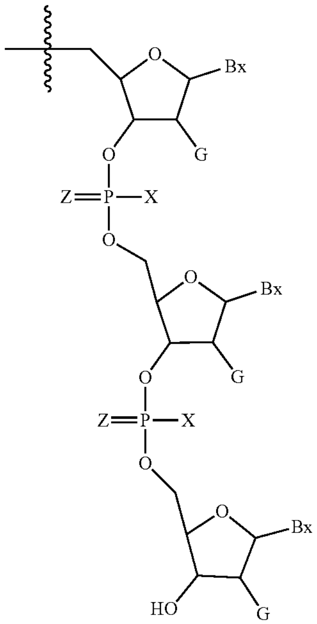

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O-[C(R_6)(R_7)]_n-[(C{=}O)_m-X^G]_j-R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, at least one region of the RNAi antisense oligonucleotide has structure M:

Structure M

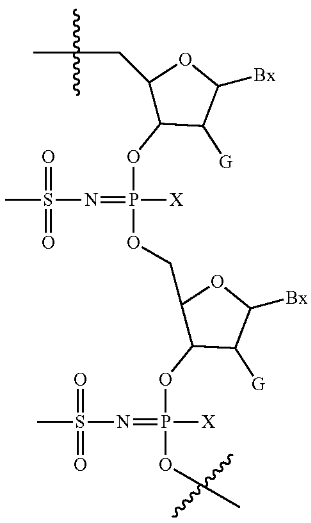

wherein:

each Bx is an independently selected heterocyclic base moiety;

each X is independently selected from OH or SH;

each G is independently selected from OH, halogen or $O—[C(R_6)(R_7)]_n—[(C=O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(-Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 5'-terminus of the RNAi antisense oligonucleotide has structure N:

Structure N

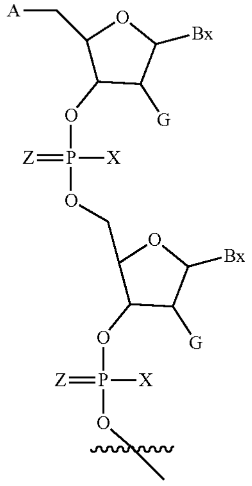

wherein:

A is selected from or

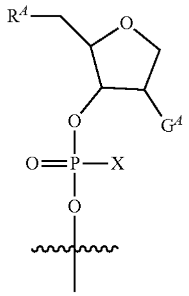

or

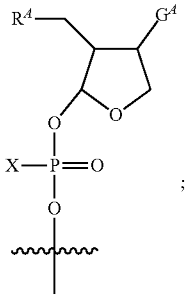

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each G is independently selected from OH, halogen or $O—[C(R_6)(R_7)]_n—[(C=O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 3'-terminus of the RNAi antisense oligonucleotide has structure 0:

Structure O

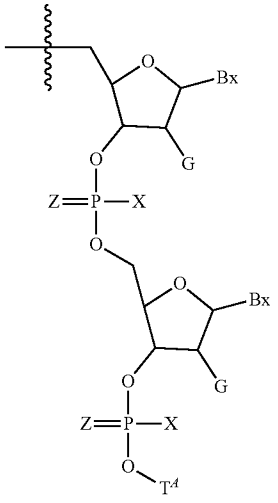

wherein:

$T^A$ is selected from

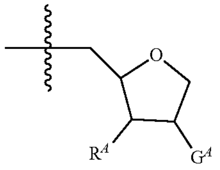

or

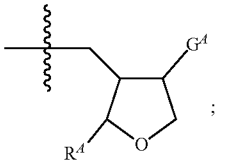

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O-[C(R_6)(R_7)]_n-[(C=O)_m-X^G]_j-R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, at least one of the first 5 internucleoside linkages from the 5' end of the RNAi sense modified oligonucleotide is a modified internucleoside linking group having Formula VIII or Formula XVII. In certain embodiments, at least one of the five 3'-most internucleoside linking groups of the RNAi sense modified oligonucleotide is a modified internucleoside linking group having Formula VIII or Formula XVII. In certain embodiments, at least one of the first 5 internucleoside linkages from the 5' end of the RNAi sense modified oligonucleotide and at least one of the five 3'-most internucleoside linking groups of the RNAi sense modified oligonucleotide is a modified internucleoside linking group having Formula VIII or Formula XVII. In certain embodiments, at least one nucleoside within nucleosides 2 to 8 of the RNAi sense modified oligonucleotide, counting from the 5' end, is a modified internucleoside linking group having Formula VIII or Formula XVII.

In certain embodiments, the 5'-terminus of the RNAi sense oligonucleotide has structure K:

Structure K

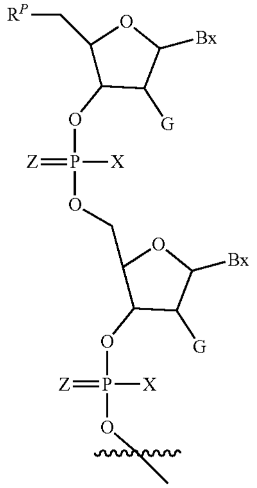

wherein:

$R^P$ is a phosphate or stabilized phosphate group;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O-[C(R_6)(R_7)]_n-[(C=O)_m-X^G]_j-R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 3'-terminus of the RNAi sense oligonucleotide has structure L:

Structure L

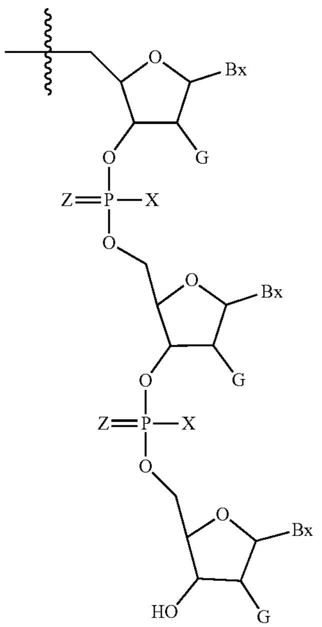

wherein:

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O—[C(R_6)(R_7)]_n—[(C=O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, at least one region of the RNAi sense oligonucleotide has structure M:

Structure M

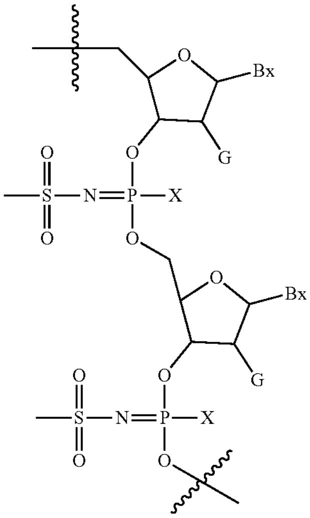

wherein:

each Bx is an independently selected heterocyclic base moiety;

each X is independently selected from OH or SH;

each G is independently selected from OH, halogen or $O—[C(R_6)(R_7)]_n—[(C=O)_m—X^G]_j—R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(-Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments the 5'-terminus of the RNAi sense oligonucleotide has structure N:

Structure N

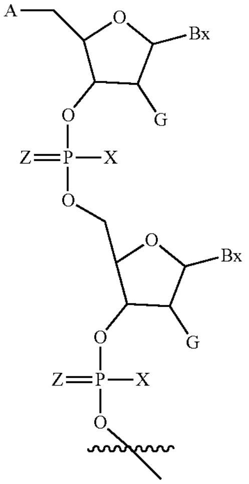

wherein:

A is selected from or

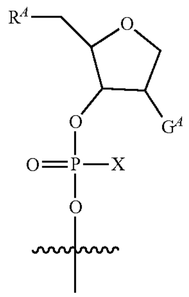

or

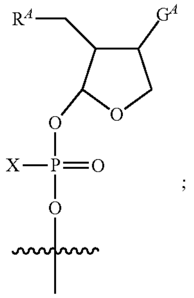

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each G is independently selected from OH, halogen or $O-[C(R_6)(R_7)]_n-[(C{=}O)_m-X^G]_j-R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 3'-terminus of the RNAi sense oligonucleotide has structure 0:

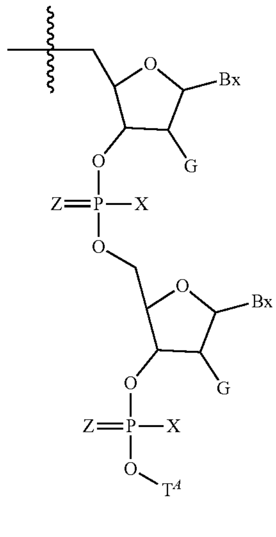

wherein:

$T^A$ is selected from

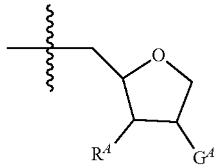

or

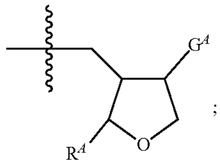

;

$R^A$ is OH, OP(=O)OH, OP(=O)SH, or a stabilized phosphate group;

$G^A$ is H, OH, OMe, MOE, or a halogen;

each Bx is an independently selected heterocyclic base moiety;

each X is independently selected from OH or SH;

each Z is selected from O, S, or $NSO_2Me$;

at least one Z is $NSO_2Me$;

each G is independently selected from OH, halogen or $O-[C(R_6)(R_7)]_n-[(C{=}O)_m-X^G]_j-R_8$;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC(=X_2)J_1$, $OC(=X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, the 5' terminus of the antisense oligonucleotide has structure P:

Structure P

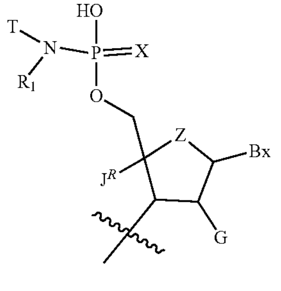

wherein:

each Bx is a heterocyclic base moiety;

X is selected from O or S;

Z is $-(CH_2)_p-X^Z-(CH_2)_q-$, wherein p is 0 or 1, q is 0 or 1, and $X^Z$ is O, S, or $N(E_1)$;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group;

$R_5$ is selected from $OCH_3$, OH, $C_1$-$C_6$ alkyl, and substituted $C_1$-$C_6$ alkyl;

either $J^R$ and G form a $J^R$ to G bridge, or $J^R$ is H and G is selected from H, OH, halogen or O—$[C(R_6)(R_7)]_n$—$[(C{=}O)_m$—$X^G]_j$—$R_8$;

wherein each $J^R$ to G bridge has a formula independently selected from —$CH(CH_3)$—O— or —$(CH_2)_k$—O—, wherein k is from 1 to 3;

each $R_6$ and $R_7$ is, independently, H, halogen, $C_1$-$C_6$ alkyl or substituted $C_1$-$C_6$ alkyl;

each $X^G$ is O, S or $N(E_1)$;

$R_8$ is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to 6;

m is 0 or 1;

j is 0 or 1;

each substituted group comprises one or more optionally protected substituent groups independently selected from halogen, $OJ_1$, $N(J_1)(J_2)$, $NJ_1$, $SJ_1$, $N_3$, CN, $OC({=}X_2)J_1$, $OC({=}X_2)N(J_1)(J_2)$ and $C(=Q_2)N(J_1)(J_2)$;

$Q_2$ is O, S or $NJ_3$;

each $J_1$, $J_2$ and $J_3$ is, independently, H or $C_1$-$C_6$ alkyl.

In certain embodiments, an oligomeric compound (including an oligomeric compound that is an antisense agent or a portion thereof) is a single-stranded RNAi compound or RNAi agent comprising an RNAi antisense modified oligonucleotide. In certain embodiments, the single-stranded RNAi compound or RNAi agent comprising an RNAi antisense modified oligonucleotide comprises at least two, at least three, at least four, at least five, or at least six modified internucleoside linking groups having Formula VIII or Formula XVII. In certain embodiments, the single-stranded RNAi compound or RNAi agent comprising an RNAi antisense modified oligonucleotide comprises exactly one modified internucleoside linking group having Formula VIII or Formula XVII. In certain embodiments, the single-stranded RNAi compound or RNAi agent comprising an RNAi antisense modified oligonucleotide comprises exactly two modified internucleoside linking groups having Formula VIII or Formula XVII. In certain embodiments, the single-stranded RNAi compound or RNAi agent comprising an RNAi antisense modified oligonucleotide comprises exactly three modified internucleoside linking groups having Formula VIII or Formula XVII. In certain embodiments, the single-stranded RNAi compound or RNAi agent comprising an RNAi antisense modified oligonucleotide comprises exactly four modified internucleoside linking groups having Formula VIII or Formula XVII. In certain embodiments, the single-stranded RNAi compound or RNAi agent comprising an RNAi antisense modified oligonucleotide comprises exactly five modified internucleoside linking groups having Formula VIII or Formula XVII. In certain embodiments, the single-stranded RNAi compound or RNAi agent comprising an RNAi antisense modified oligonucleotide comprises exactly six modified internucleoside linking groups having Formula VIII or Formula XVII. In certain embodiments, the single-stranded RNAi compound or RNAi agent comprising an RNAi antisense modified oligonucleotide comprises at least 6, at least 7, at least 8, or at least 9 modified internucleoside linking groups having Formula VIII or Formula XVII. In certain embodiments, each internucleoside linking group of the single-stranded RNAi compound or RNAi agent comprising an RNAi antisense modified oligonucleotide is a modified internucleoside linking groups having Formula VIII or Formula XVII.

In certain embodiments, at least one of the first 5 internucleoside linkages from the 5' end of the single-stranded RNAi compound or RNAi agent comprising an RNAi antisense modified oligonucleotide is a modified internucleoside linking group having Formula VIII or Formula XVII. In certain embodiments, at least one of the five 3'-most internucleoside linking groups from the 3' end of the single-stranded RNAi compound or RNAi agent comprising an RNAi antisense modified oligonucleotide is a modified internucleoside linking group having Formula VIII or Formula XVII. In certain embodiments, at least one nucleoside of the seed region of the single-stranded RNAi compound or RNAi agent comprising an RNAi antisense modified oligonucleotide is a modified internucleoside linking group having Formula VIII or Formula XVII. In certain embodiments, at least one nucleoside within nucleosides 2 to 8 of the single-stranded RNAi compound or RNAi agent comprising an RNAi antisense modified oligonucleotide, counting from the 5' end, is a modified internucleoside linking group having Formula VIII or Formula XVII.

In certain embodiments, the 5'-terminus of the single-stranded RNAi compound or RNAi agent comprising an RNAi antisense modified oligonucleotide has a 5'-terminal group having formula XXI or XXII.

In certain embodiments, an oligomeric compound is a CRISPR compound. In certain embodiments, CRISPR compounds comprise a modified oligonucleotide that comprises a DNA recognition region and a tracrRNA recognition region. In certain embodiments, the DNA recognition region includes a seed region. In certain embodiments, CRISPR compounds have at least one modified internucleoside linking group having Formula VIII or Formula XVII. In certain embodiments, CRISPR compounds have at least two modified internucleoside linking groups having Formula VIII or Formula XVII. In certain embodiments, CRISPR compounds have at least three modified internucleoside linking groups having Formula VIII or Formula XVII. In certain embodiments, CRISPR compounds have at least four modified internucleoside linking groups having Formula VIII or Formula XVII. In certain embodiments, CRISPR compounds have at least five modified internucleoside linking groups having Formula VIII or Formula XVII. In certain embodiments, CRISPR compounds have at least six modified internucleoside linking groups having Formula VIII or Formula XVII. In certain embodiments, CRISPR compounds have at least 10 modified internucleoside linking groups having Formula VIII or Formula XVII. In certain embodiments, CRISPR compounds have at least 15 modified internucleoside linking groups having Formula VIII or Formula XVII. In certain embodiments, CRISPR compounds have at least 20 modified internucleoside linking groups having Formula VIII or Formula XVII. In certain embodiments, CRISPR compounds have at least 25 modified internucleoside linking groups having Formula VIII or Formula XVII. In certain embodiments, each internucleoside linking group of the CRISPR compound is a modified internucleoside linking group having Formula VIII or Formula XVII.

In certain embodiments, CRISPR compounds have exactly one modified internucleoside linking group having Formula VIII or Formula XVII. In certain embodiments, CRISPR compounds have exactly two modified internucleoside linking groups having Formula VIII or Formula XVII. In certain embodiments, CRISPR compounds have exactly three modified internucleoside linking groups having Formula VIII or Formula XVII. In certain embodiments, CRISPR compounds have exactly four modified internucleoside linking groups having Formula VIII or Formula XVII. In certain embodiments, CRISPR compounds have exactly five modified internucleoside linking groups having Formula VIII or Formula XVII. In certain embodiments, CRISPR compounds have exactly six modified internucleoside linking groups having Formula VIII or Formula XVII.

In certain embodiments, the DNA recognition portion of a CRISPR compound has at least one modified internucleoside linking group having Formula VIII or Formula XVII. In certain embodiments, the DNA recognition portion of a CRISPR compound has at least two modified internucleoside linking groups having Formula VIII or Formula XVII. In certain embodiments, the DNA recognition portion of a CRISPR compound has at least three modified internucleoside linking groups having Formula VIII or Formula XVII. In certain embodiments, the DNA recognition portion of a CRISPR compound has at least four modified internucleoside linking groups having Formula VIII or Formula XVII. In certain embodiments, the DNA recognition portion of a CRISPR compound has at least five modified internucleoside linking groups having Formula VIII or Formula XVII. In certain embodiments, the DNA recognition portion of a CRISPR compound has at least six modified internucleoside linking groups having Formula VIII or Formula XVII. In certain embodiments, the DNA recognition portion of a CRISPR compound has at least 10 modified internucleoside linking groups having Formula VIII or Formula XVII. In certain embodiments, each internucleoside linking group of the DNA recognition portion of a CRISPR compound is a modified internucleoside linking group having Formula VIII or Formula XVII.

In certain embodiments, the DNA recognition portion of a CRISPR compound has exactly one modified internucleoside linking group having Formula VIII or Formula XVII. In certain embodiments, the DNA recognition portion of a CRISPR compound has exactly two modified internucleoside linking groups having Formula VIII or Formula XVII. In certain embodiments, the DNA recognition portion of a CRISPR compound has exactly three modified internucleoside linking groups having Formula VIII or Formula XVII. In certain embodiments, the DNA recognition portion of a CRISPR compound has exactly four modified internucleoside linking groups having Formula VIII or Formula XVII. In certain embodiments, the DNA recognition portion of a CRISPR compound has exactly five modified internucleoside linking groups having Formula VIII or Formula XVII. In certain embodiments, the DNA recognition portion of a CRISPR compound has exactly six modified internucleoside linking groups having Formula VIII or Formula XVII. In certain embodiments, at least one internucleoside linking group of the of the seed region of the CRISPR oligonucleotide is a modified internucleoside linking group having Formula VIII or Formula XVII.

In certain embodiments, the tracrRNA recognition portion of a CRISPR compound has at least one modified internucleoside linking group having Formula VIII or Formula XVII. In certain embodiments, the tracrRNA recognition portion of a CRISPR compound has at least two modified internucleoside linking groups having Formula VIII or Formula XVII. In certain embodiments, the tracrRNA recognition portion of a CRISPR compound has at least three modified internucleoside linking groups having Formula VIII or Formula XVII. In certain embodiments, the tracrRNA recognition portion of a CRISPR compound has at least four modified internucleoside linking groups having Formula VIII or Formula XVII. In certain embodiments, the tracrRNA recognition portion of a CRISPR compound has at least five modified internucleoside linking groups having Formula VIII or Formula XVII. In certain embodiments, the tracrRNA recognition portion of a CRISPR compound has at least six modified internucleoside linking groups having Formula VIII or Formula XVII. In certain embodiments, the tracrRNA recognition portion of a CRISPR compound has at least 10 modified internucleoside linking groups having Formula VIII or Formula XVII. In certain embodiments, each internucleoside linking group of the tracrRNA recognition portion of a CRISPR compound is a modified internucleoside linking group having Formula VIII or Formula XVII.

In certain embodiments, the tracrRNA recognition portion of a CRISPR compound has exactly one modified internucleoside linking group having Formula VIII or Formula XVII. In certain embodiments, the tracrRNA recognition portion of a CRISPR compound has exactly two modified internucleoside linking groups having Formula VIII or Formula XVII. In certain embodiments, the tracrRNA recognition portion of a CRISPR compound has exactly three modified internucleoside linking groups having Formula VIII or Formula XVII. In certain embodiments, the tracrRNA recognition portion of a CRISPR compound has exactly four modified internucleoside linking groups having Formula VIII or Formula XVII. In certain embodiments, the tracrRNA recognition portion of a CRISPR compound has exactly five modified internucleoside linking groups having Formula VIII or Formula XVII. In certain embodiments, the tracrRNA recognition portion of a CRISPR compound has exactly six modified internucleoside linking groups having Formula VIII or Formula XVII.

In certain embodiments, an oligomeric compound is an artificial mRNA oligonucleotide. In certain embodiments, an oligomeric compound is an artificial mRNA oligonucleotide having a 5'UTR and a 3'UTR. In certain embodiments, the artificial mRNA oligonucleotide comprises more than 10, more than 20, more than 30, more than 40, more than 50, or more than 100 internucleoside linking groups having Formula VIII or Formula XVII.

In certain embodiments, the artificial mRNA oligonucleotide has exactly one modified internucleoside linking group having Formula VIII or Formula XVII. In certain embodiments, the artificial mRNA oligonucleotide has exactly two modified internucleoside linking groups having Formula VIII or Formula XVII. In certain embodiments, the artificial mRNA oligonucleotide has exactly three modified internucleoside linking groups having Formula VIII or Formula XVII. In certain embodiments, the artificial mRNA oligonucleotide has exactly four modified internucleoside linking groups having Formula VIII or Formula XVII. In certain embodiments, the artificial mRNA oligonucleotide has exactly five modified internucleoside linking groups having Formula VIII or Formula XVII. In certain embodiments, the artificial mRNA oligonucleotide has exactly six modified internucleoside linking groups having Formula VIII or Formula XVII.

In certain embodiments, the artificial mRNA oligonucleotide comprises exactly one modified internucleoside linking group having Formula VIII or Formula XVII. In certain embodiments, the artificial mRNA oligonucleotide comprises exactly two modified internucleoside linking groups having Formula VIII or Formula XVII. In certain embodiments, the artificial mRNA oligonucleotide comprises exactly three modified internucleoside linking groups having Formula VIII or Formula XVII. In certain embodiments, the artificial mRNA oligonucleotide comprises exactly four modified internucleoside linking groups having Formula VIII or Formula XVII. In certain embodiments, the artificial mRNA oligonucleotide comprises exactly five modified internucleoside linking groups having Formula VIII or Formula XVII. In certain embodiments, the artificial mRNA oligonucleotide comprises exactly 6, 7, 8, 9, 10, 11, 12, 13, 14, 15, 16, 17, 18, 19, 20, 21, or 22 modified internucleoside linking groups having Formula VIII or Formula XVII.

In certain embodiments, the artificial mRNA oligonucleotide comprises more than 10, more than 20, more than 30, more than 40, more than 50, or more than 100 modified internucleoside linking groups having Formula VIII or Formula XVII. In certain embodiments, at least one of the first 5 internucleoside linking groups from the 5'-end of the artificial mRNA oligonucleotide is a modified internucleoside linking group having Formula VIII or Formula XVII. In certain embodiments, at least one of the five 3'-most internucleoside linking groups of the artificial mRNA oligonucleotide is a modified internucleoside linking group having Formula VIII or Formula XVII. In certain embodiments, at least one internucleoside linking group of the 5'-UTR of the artificial mRNA oligonucleotide is a modified internucleoside linking group having Formula VIII or Formula XVII. In certain embodiments, at least one internucleoside linking group of the 3'-UTR of the artificial mRNA oligonucleotide is a modified internucleoside linking group having Formula VIII or Formula XVII. In certain embodiments, at least one internucleoside linking group of the coding region of the artificial mRNA oligonucleotide is a modified internucleoside linking group having Formula VIII or Formula XVII.

III. Certain Modified Oligonucleotides

In certain embodiments, antisense agents, oligomeric compounds, and modified oligonucleotides described herein comprise or consist of modified oligonucleotides. In certain embodiments, the above modifications (sugar, nucleobase, internucleoside linkage) are incorporated into a modified oligonucleotide. In certain embodiments, modified oligonucleotides are characterized by their modifications, motifs, and overall lengths. In certain embodiments, such parameters are each independent of one another. Thus, unless otherwise indicated, each internucleoside linkage of a modified oligonucleotide may be modified or unmodified and may or may not follow the modification pattern of the sugar moieties. Likewise, such modified oligonucleotides may comprise one or more modified nucleobase independent of the pattern of the sugar modifications. Furthermore, in certain instances, a modified oligonucleotide is described by an overall length or range and by lengths or length ranges of two or more regions (e.g., a region of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions or segments, A, B, and C, wherein region or segment A consists of 2-6 linked nucleosides having a specified sugar moiety, region or segment B consists of 6-10 linked nucleosides having a specified sugar moiety, and region or segment C consists of 2-6 linked nucleosides having a specified sugar moiety.

Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of 20 for the overall length of the modified oligonucleotide. Unless otherwise indicated, all modifications are independent of nucleobase sequence except that the modified nucleobase 5-methylcytosine is necessarily a “C” in an oligonucleotide sequence. In certain embodiments, when a DNA nucleoside or DNA-like nucleoside that comprises a T in a DNA sequence is replaced with a RNA-like nucleoside, the nucleobase T is replaced with the nucleobase U. Each of these compounds has an identical target RNA.

In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments oligonucleotides have a nucleobase sequence that is complementary to a second oligonucleotide or an identified reference nucleic acid, such as a target nucleic acid. In certain embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 70%, at least 80%, at least 90%, at least 95%, or 100% complementary to the second oligonucleotide or nucleic acid, such as a target nucleic acid.

IV. Certain Conjugated Compounds

In certain embodiments, antisense agents, oligomeric compounds, and modified oligonucleotides described herein comprise or consist of a modified oligonucleotide that optionally comprises a conjugate group. Conjugate groups may be attached to either or both ends of an oligonucleotide and/or at any internal position. In certain embodiments, conjugate groups are attached to the 2-position of a nucleoside of a modified oligonucleotide. In certain embodiments, conjugate groups that are attached to either or both ends of an oligonucleotide are terminal groups. In certain such embodiments, conjugate moieties or terminal groups are attached at the 3' and/or 5'-end of oligonucleotides. In certain such embodiments, conjugate moieties (or terminal groups) are attached at the 3'-end of oligonucleotides. In certain embodiments, conjugate moieties are attached near the 3'-end of oligonucleotides. In certain embodiments, conjugate moieties (or terminal groups) are attached at the 5'-end of oligonucleotides. In certain embodiments, conjugate moieties are attached near the 5'-end of oligonucleotides.

Examples of terminal groups include but are not limited to conjugate moieties, conjugate groups, capping groups, phosphate moieties, protecting groups, modified or unmodified nucleosides, and two or more nucleosides that are independently modified or unmodified.

A. Certain Conjugate Groups and Conjugate Moieties

In certain embodiments, modified oligonucleotides comprise one or more conjugate moieties or conjugate groups. In certain embodiments, conjugate groups modify one or more properties of the molecule, including but not limited to pharmacodynamics, pharmacokinetics, stability, binding, absorption, tissue distribution, cellular distribution, cellular uptake, charge and clearance. In certain embodiments, conjugate moieties impart a new property on the molecule, e.g., fluorophores or reporter groups that enable detection of the molecule.

Certain conjugate groups have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, i, 923-937), a tocopherol group (Nishina et al., *Molecular Therapy Nucleic Acids,* 2015, 4, e220; doi:10.1038/mtna.2014.72 and Nishina et al., *Molecular Therapy,* 2008, 16, 734-740), or a GalNAc cluster (e.g., WO2014/179620).

a. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

b. Conjugate Linkers

In certain embodiments, conjugate groups comprise a conjugate linker that attaches a conjugate moiety to the remainder of the modified oligonucleotide. In certain embodiments, a conjugate linker is a single chemical bond (i.e. conjugate moiety is attached to the remainder of the modified oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to oligomeric compounds, such as the oligonucleotides provided herein. In general, a bifunctional linking moiety comprises at least two functional groups. One of the functional groups is selected to bind to a particular site on an oligomeric compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methyl-cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group or conjugate moiety to be cleaved from the remainder of the oligonucleotide. For example, in certain circumstances oligomeric compounds (including oligomeric compounds that are antisense agents or portions thereof) or modified oligonucleotides comprising a particular conjugate moiety are better taken up by a particular cell type, but once the compound has been taken up, it is desirable that the conjugate group be cleaved to release an unconjugated oligonucleotide. Thus, certain conjugate moieties may comprise one or more cleavable moieties, typically within the conjugate linker. In certain embodiments, a cleavable moiety is a cleavable bond. In certain embodiments, a cleavable moiety is a group of atoms comprising at least one cleavable bond.

In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is a nucleoside comprising a 2'-deoxyfuranosyl that is attached to either the 3' or 5'-terminal nucleoside of an oligonucleotide by a phosphodiester internucleoside linkage and covalently attached to the remainder of the conjugate linker or conjugate moiety by a phosphodiester or phosphorothioate linkage.

In certain such embodiments, the cleavable moiety is a nucleoside comprising a 2'-β-D-deoxyribosyl sugar moiety. In certain such embodiments, the cleavable moiety is 2'-deoxyadenosine.

c. Certain Cell-Targeting Conjugate Moieties

In certain embodiments, a conjugate group comprises a cell-targeting conjugate moiety. In certain embodiments, a conjugate group has the general formula:

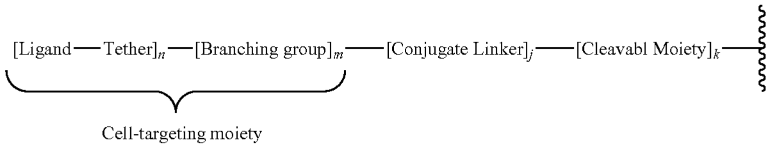

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian lung cell.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry,* 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, oligomeric compounds (including oligomeric compounds that are antisense agents or portions thereof) or modified oligonucleotides described herein comprise a conjugate group found in any of the following references: Lee, Carbohydr Res, 1978, 67, 509-514; Connolly et al., *J Biol Chem,* 1982, 257, 939-945; Pavia et al., *Int J Pep Protein Res,* 1983, 22, 539-548; Lee et al., *Biochem,* 1984, 23, 4255-4261; Lee et al., *Glycoconjugate J,* 1987, 4, 317-328; Toyokuni et al., *Tetrahedron Lett,* 1990, 31, 2673-2676; Biessen et al., *J Med Chem,* 1995, 38, 1538-1546; Valentijn et al., *Tetrahedron,* 1997, 53, 759-770; Kim et al., *Tetrahedron Lett,* 1997, 38, 3487-3490; Lee et al., *Bioconjug Chem,* 1997, 8, 762-765; Kato et al., *Glycobiol,* 2001, 11, 821-829; Rensen et al., *J Biol Chem,* 2001, 276, 37577-37584; Lee et al., *Methods Enzymol,* 2003, 362, 38-43; Westerlind et al., *Glycoconj J,* 2004, 21, 227-241; Lee et al., *Bioorg Med Chem Lett,* 2006, 16(19), 5132-5135; Maierhofer et al., *Bioorg Med Chem,* 2007, 15, 7661-7676; Khorev et al., *Bioorg Med Chem,* 2008, 16, 5216-5231; Lee et al., *Bioorg Med Chem,* 2011, 19, 2494-2500; Kornilova et al., Analyt Biochem, 2012, 425, 43-46; Pujol et al., *Angew Chemie Int Ed Engl,* 2012, 51, 7445-7448; Biessen et al., *J Med Chem,* 1995, 38, 1846-1852; Sliedregt et al., *J Med Chem,* 1999, 42, 609-618; Rensen et al., *J Med Chem,* 2004, 47, 5798-5808; Rensen et al., Arterioscler Thromb Vasc Biol, 2006, 26, 169-175; van Rossenberg et al., *Gene Ther,* 2004, 11, 457-464; Sato et al., *J Am Chem Soc,* 2004, 126, 14013-14022; Lee et al., *J Org Chem,* 2012, 77, 7564-7571; Biessen et al., *FASEB J,* 2000, 14, 1784-1792; Rajur et al., *Bioconjug Chem,* 1997, 8, 935-940; Duff et al., *Methods Enzymol,* 2000, 313, 297-321; Maier et al., *Bioconjug Chem,* 2003, 14, 18-29; Jayaprakash et al., *Org Lett,* 2010, 12, 5410-5413; Manoharan, *Antisense Nucleic Acid Drug Dev,* 2002, 12, 103-128; Merwin et al., *Bioconjug Chem,* 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132.

Compositions and Methods for Formulating Pharmaceutical Compositions

Antisense agents, oligomeric compounds, and modified oligonucleotides described herein may be admixed with pharmaceutically acceptable active or inert substances for the preparation of pharmaceutical compositions. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more oligomeric compounds (including oligomeric compounds that are antisense agents or portions thereof) or a salt thereof. In certain such embodiments, the pharmaceutical composition comprises a suitable pharmaceutically acceptable diluent or carrier. In certain embodiments, a pharmaceutical composition comprises a sterile saline solution and one or more oligomeric compound. In certain embodiments, such pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, a pharmaceutical composition consists of one or more oligomeric compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

An oligomeric compound described herein complementary to a target nucleic acid can be utilized in pharmaceutical compositions by combining the oligomeric compound with a suitable pharmaceutically acceptable diluent or carrier and/or additional components such that the pharmaceutical composition is suitable for injection. In certain embodiments, a pharmaceutically acceptable diluent is phosphate buffered saline. Accordingly, in one embodiment, employed in the methods described herein is a pharmaceutical composition comprising an oligomeric compound complementary to a target nucleic acid and a pharmaceutically acceptable diluent. In certain embodiments, the pharmaceutically acceptable diluent is phosphate buffered saline. In certain embodiments, the oligomeric compound comprises or consists of a modified oligonucleotide provided herein.

Pharmaceutical compositions comprising oligomeric compounds (including oligomeric compounds that are antisense agents or portions thereof) provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the oligomeric compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

Certain Mechanisms

In certain embodiments, oligomeric compounds (including oligomeric compounds that are antisense agents or portions thereof) described herein comprise or consist of modified oligonucleotides. In certain such embodiments, the oligomeric compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA: DNA duplex. The DNA in such an RNA: DNA duplex need not be unmodified DNA. In certain embodiments, compounds described herein are sufficiently "DNA-like" to elicit RNase H activity. Nucleosides that are sufficiently "DNA-like" to elicit RNase H activity are referred to as DNA mimics herein. Further, in certain embodiments, one or more non-DNA-like nucleoside in in the RNA: DNA duplex is tolerated.

In certain antisense activities, hybridization of an antisense agent, oligomeric compound, or modified oligonucleotide described herein to a target nucleic acid results in modulation of the splicing of a target pre-mRNA. For example, in certain embodiments, hybridization of a compound described herein will increase exclusion of an exon. For example, in certain embodiments, hybridization of a compound described herein will increase inclusion of an exon.

In certain antisense activities, antisense agents described herein or a portion of the antisense agent is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain antisense activities, antisense agents, oligomeric compounds, or modified oligonucleotides described herein result in a CRISPR system cleaving a target DNA. In certain antisense activities, compounds described herein result in a CRISPR system editing a target DNA.

In certain antisense activities, hybridization of an antisense agent, oligomeric compound, or modified oligonucleotide described herein to a target nucleic acid results in disruption of secondary structural elements, such as stem-loops and hairpins. For example, in certain embodiments, hybridization of a compound described herein to a stem-loop that is part of a translation suppression element leads to an increase in protein expression.

In certain antisense activities, hybridization of an antisense agent, oligomeric compound, or modified oligonucleotide described herein to a target nucleic acid leads to no-go decay mediated mRNA degradation.

In certain antisense activities, hybridization of an antisense agent, oligomeric compound, or modified oligonucleotide described herein to a target nucleic acid leads to activation of nonsense-mediated decay mRNA degradation.

In certain embodiments, antisense agents, oligomeric compounds, or modified oligonucleotides described herein are artificial mRNA compounds, the nucleobase sequence of which encodes for a protein.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Certain RNAi Agents

In certain embodiments, oligomeric compounds described herein having one or more stinternucleoside linkages Formula VIII or Formula XVII are RNAi agents. In certain embodiments, internucleoside linkages having Formula VIII or Formula XVII can replace one or more phosphorothioate or phosphodiester internucleoside linkages in any RNAi motif. Certain RNAi motifs are described in, e.g., Freier, et al., WO2020/160163, incorporated by reference herein in its entirety; as well as, e.g., Rajeev, et al., WO2013/075035; Maier, et al., WO2016/028649; Theile, et al., WO2018/098328; Nair, et al., WO2019/217459; each of which is incorporated by reference herein.

Target Nucleic Acids, Target Regions and Nucleotide Sequences

In certain embodiments, antisense agents, oligomeric compounds, or modified oligonucleotides described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain embodiments, a pre-mRNA and corresponding mRNA are both target nucleic acids of a single compound. In certain such embodiments, the target region is entirely within an intron of a target pre-mRNA. In certain embodiments, the target region spans an intron/exon junction. In certain embodiments, the target region is at least 50% within an intron. In certain embodiments, the target nucleic acid is a microRNA. In certain embodiments, the target region is in the 5' UTR of a gene. In certain embodiments, the target region is within a translation suppression element region of a target nucleic acid.

Certain Compounds

Certain compounds described herein (e.g., antisense agents, oligomeric compounds, and modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. All tautomeric forms of the compounds provided herein are included unless otherwise indicated.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}H$ hydrogen atoms. Isotopic substitutions encompassed by the compounds herein include but are not limited to: $^{2}H$ or $^{3}H$ in place of $^{1}H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples are intended to illustrate certain aspects of the invention and are not intended to limit the invention in any way.

Example 1: Synthesis of Modified Oligonucleotides with Mesyl Phosphoramidate Internucleoside Linkages Modified oligonucleotides comprising a single mesyl phosphoramidate internucleoside linkage (Formula IX) were synthesized and tested. As shown in Table 1, each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. The modified oligonucleotides are each 3-10-3 cEt gapmers with a sugar motif of: kkkddddddddddkkk (a 3-10-3 cEt motif) where “k” represents a cEt modified sugar moiety, and “d” represents a β-D-2'-deoxyribosyl sugar moiety. Each internucleoside linkage is either a phosphorothioate internucleoside linkage (“s”) or a mesyl phosphoramidate internucleoside linkage (“z”). Each of the compounds in Table 1 has exactly one mesyl phosphoramidate internucleoside linkage of formula IX.

IX

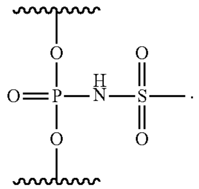

Activity Assay

The modified oligonucleotides were tested for their ability to reduce target RNA in a series of experiments. Cultured mouse 3T3-$L_1$ cells at a density of 20,000 cells per well were transfected using electroporation with modified oligonucleotides diluted to 20 μM, 7 μM, 2 μM, 0.7 μM, 0.3 μM, 0.1 μM, and 0.03 μM. After a treatment period of approximately 16 hours, CXCL12 RNA levels were measured using mouse primer-probe set RTS2605 (forward sequence CCAGAGCCAACGTCAAGCAT, SEQ ID NO: 2; reverse sequence: CAGCCGTGCAACAATCTGAA, SEQ ID NO: 3; probe sequence: TGAAAATCCTCAACACTCCAAACTGTGCC, SEQ ID NO: 4). CXCL12 RNA levels were normalized to total RNA content, as measured by RIBOGREEN®. Activity expressed as half maximal inhibitory concentration (IC50) was calculated using the log (inhibitor) vs response (three parameter) function in GraphPad Prism 7 and is presented in the table below.

TABLE 1

Design and activity of modified oligonucleotides having a single mesyl phosphoramidate internucleoside linkage

| Compound Number | Chemistry Notation (5'-3') | IC50 (nM) | SEQ ID NO. |
|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 84 | 5 |
| 1375403 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}\mathbf{T}_{\underline{\mathbf{kz}}}A_{k}$ | 72 | 5 |
| 1375404 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}\mathbf{T}_{\underline{\mathbf{kz}}}T_{ks}A_{k}$ | 61 | 5 |
| 1375405 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}\mathbf{A}_{\underline{\mathbf{dz}}}T_{ks}T_{ks}A_{k}$ | 97 | 5 |
| 1375406 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}\mathbf{C}_{\underline{\mathbf{dz}}}A_{ds}T_{ks}T_{ks}A_{k}$ | 101 | 5 |
| 1375407 | $G_{ks}{}^{m}C_{ks}A_{ks}T_{ds}G_{ds}T_{ds}T_{ds}{}^{m}C_{ds}T_{ds}{}^{m}C_{ds}\mathbf{A}_{\underline{\mathbf{dz}}}{}^{m}C_{ds}A_{ds}T_{ks}T_{ks}A_{k}$ | 121 | 5 |
| 1375408 | $G_{ks}{}^{m}C_{ks}A_{ks}T_{ds}G_{ds}T_{ds}T_{ds}{}^{m}C_{ds}T_{ds}{}^{m}\mathbf{C}_{\underline{\mathbf{dz}}}A_{ds}{}^{m}C_{ds}A_{ds}T_{ks}T_{ks}A_{k}$ | 103 | 5 |
| 1375409 | $G_{ks}{}^{m}C_{ks}A_{ks}T_{ds}G_{ds}T_{ds}T_{ds}{}^{m}C_{ds}\mathbf{T}_{\underline{\mathbf{dz}}}{}^{m}C_{ds}A_{ds}{}^{m}C_{ds}A_{ds}T_{ks}T_{ks}A_{k}$ | 83 | 5 |
| 1375410 | $G_{ks}{}^{m}C_{ks}A_{ks}T_{ds}G_{ds}T_{ds}T_{ds}{}^{m}\mathbf{C}_{\underline{\mathbf{dz}}}T_{ds}{}^{m}C_{ds}A_{ds}{}^{m}C_{ds}A_{ds}T_{ks}T_{ks}A_{k}$ | 98 | 5 |
| 1375411 | $G_{ks}{}^{m}C_{ks}A_{ks}T_{ds}G_{ds}T_{ds}\mathbf{T}_{\underline{\mathbf{dz}}}{}^{m}C_{ds}T_{ds}{}^{m}C_{ds}A_{ds}{}^{m}C_{ds}A_{ds}T_{ks}T_{ks}A_{k}$ | 90 | 5 |
| 1375412 | $G_{ks}{}^{m}C_{ks}A_{ks}T_{ds}G_{ds}\mathbf{T}_{\underline{\mathbf{dz}}}T_{ds}{}^{m}C_{ds}T_{ds}{}^{m}C_{ds}A_{ds}{}^{m}C_{ds}A_{ds}T_{ks}T_{ks}A_{k}$ | 74 | 5 |
| 1375413 | $G_{ks}{}^{m}C_{ks}A_{ks}T_{ds}\mathbf{G}_{\underline{\mathbf{dz}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 105 | 5 |
| 1375414 | $G_{ks}{}^{m}C_{ks}A_{ks}\mathbf{T}_{\underline{\mathbf{dz}}}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 89 | 5 |
| 1375415 | $G_{ks}{}^{m}C_{ks}\mathbf{A}_{\underline{\mathbf{kz}}}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 43 | 5 |
| 1375416 | $G_{ks}{}^{m}\mathbf{C}_{\underline{\mathbf{kz}}}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 84 | 5 |
| 1375417 | $\mathbf{G}_{\underline{\mathbf{kz}}}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 76 | 5 |

A subscript "k" represents a cEt nucleoside, a subscript "d" represents a stereo-standard DNA nucleoside, a subscript "s" indicates a phosphorothioate internucleoside linkage, a subscript "z" represents an internucleoside linkage of formula IX, which is a mesyl phosphoramidate linkage. A superscript "m" before a C represents a 5-methyl Cytosine The phosphorothioate linkages were incorporated into the modified oligonucleotide using known processes. The phosphoramidate internucleoside linkages were incorporated into the modified oligonucleotides during synthesis using a Staudinger reaction with mesyl azide, a schematic of which is shown below:

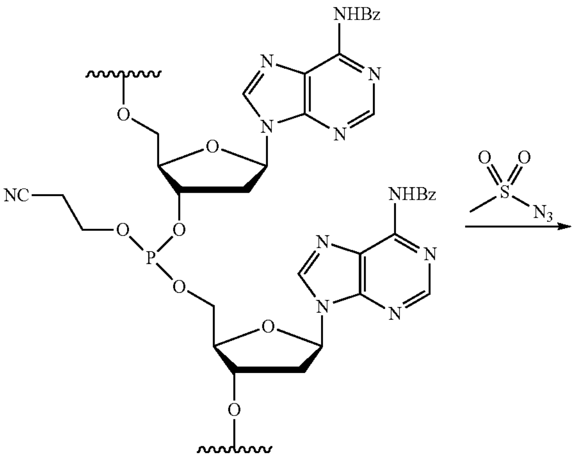

-continued

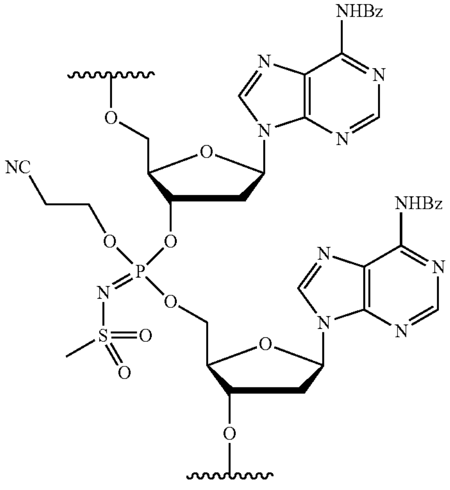

After the final nucleoside was added to the modified oligonucleotide, the modified oligonucleotide was deprotected and the intermediate linkage shown above was converted to the phosphoramidate internucleoside linkage shown below:

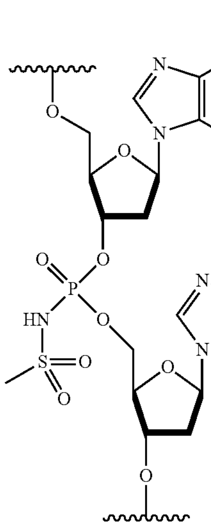

Example 2: Design and Activity of Modified Oligonucleotides with Multiple Mesyl Phosphoramidate Internucleoside Linkages Modified oligonucleotides comprising two consecutive (Table 2) or multiple (Table 3) mesyl phosphoramidate internucleoside linkages (Formula IX) were synthesized and tested. As shown in the tables below, each of the modified oligonucleotides has the same nucleobase sequence, GCATGTTCTCACATTA (SEQ ID NO: 5), which is 100% complementary to mouse CXCL12, GENBANK NT 039353.7 truncated from 69/430,515 to 69/445,350 (SEQ ID NO: 1), at position 6877 to 6892. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each internucleoside linkage is either a phosphorothioate internucleoside linkage ("s") or a mesyl phosphoramidate internucleoside linkage ("z"). Each of the compounds in Table 2 has two mesyl phosphoramidate internucleoside linkages of formula IX, and each compound in Table 3 has multiple mesyl phosphoramidate internucleoside linkages of formula IX.

IX

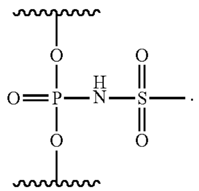

Activity Assay

The modified oligonucleotides were tested for their ability to reduce target RNA in a series of experiments. Cultured mouse 3T3-$L_1$ cells at a density of 20,000 cells per well were transfected using electroporation with modified oligonucleotides diluted to 20 μM, 7 μM, 2 μM, 0.7 μM, 0.3 μM, 0.1 μM, and 0.03 μM. After a treatment period of approximately 16 hours, CXCL12 RNA levels were measured using mouse primer-probe set RTS2605 (forward sequence CCAGAGCCAACGTCAAGCAT, SEQ ID NO: 2; reverse sequence: CAGCCGTGCAACAATCTGAA, SEQ ID NO: 3; probe sequence: TGAAAATCCTCAACACTCCAAACTGTGCC, SEQ ID NO: 4). CXCL12 RNA levels were normalized to total RNA content, as measured by RIBOGREEN®. Activity expressed as half maximal inhibitory concentration (IC50) was calculated using the log (inhibitor) vs response (three parameter) function in GraphPad Prism 7 and is presented in the table below.

TABLE 2

Design and activity of modified oligonucleotides having two consecutive mesyl phosphoramidate internucleoside linkages

| Compound Number | Chemistry Notation (5'-3') | IC50 (nM) Study 1 | IC50 (nM) Study 2 | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 84 | 170 | 5 |
| 1375418 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}\mathbf{T}_{\underline{\mathbf{kz}}}\mathbf{T}_{\underline{\mathbf{kz}}}A_{k}$ | 16 | 117 | 5 |
| 1375419 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}\mathbf{A}_{\underline{\mathbf{dz}}}\mathbf{T}_{\underline{\mathbf{kz}}}T_{ks}A_{k}$ | 23 | 105 | 5 |
| 1375420 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}\mathbf{C}_{\underline{\mathbf{dz}}}\mathbf{A}_{\underline{\mathbf{dz}}}T_{ks}T_{ks}A_{k}$ | 41 | 138 | 5 |
| 1375421 | $G_{ks}{}^{m}C_{ks}A_{ks}T_{ds}G_{ds}T_{ds}T_{ds}{}^{m}C_{ds}T_{ds}{}^{m}C_{ds}\mathbf{A}_{\underline{\mathbf{dz}}}{}^{m}\mathbf{C}_{\underline{\mathbf{dz}}}A_{ds}T_{ks}T_{ks}A_{k}$ | 37 | 83 | 5 |
| 1375422 | $G_{ks}{}^{m}C_{ks}A_{ks}T_{ds}G_{ds}T_{ds}T_{ds}{}^{m}C_{ds}T_{ds}{}^{m}\mathbf{C}_{\underline{\mathbf{dz}}}\mathbf{A}_{\underline{\mathbf{dz}}}{}^{m}C_{ds}A_{ds}T_{ks}T_{ks}A_{k}$ | 61 | 83 | 5 |
| 1375423 | $G_{ks}{}^{m}C_{ks}A_{ks}T_{ds}G_{ds}T_{ds}T_{ds}{}^{m}C_{ds}\mathbf{T}_{\underline{\mathbf{dz}}}{}^{m}\mathbf{C}_{\underline{\mathbf{dz}}}A_{ds}{}^{m}C_{ds}A_{ds}T_{ks}T_{ks}A_{k}$ | 40 | 123 | 5 |
| 1375424 | $G_{ks}{}^{m}C_{ks}A_{ks}T_{ds}G_{ds}T_{ds}T_{ds}{}^{m}\mathbf{C}_{\underline{\mathbf{dz}}}\mathbf{T}_{\underline{\mathbf{dz}}}{}^{m}C_{ds}A_{ds}{}^{m}C_{ds}A_{ds}T_{ks}T_{ks}A_{k}$ | 38 | 146 | 5 |
| 1375425 | $G_{ks}{}^{m}C_{ks}A_{ks}T_{ds}G_{ds}T_{ds}\mathbf{T}_{\underline{\mathbf{dz}}}{}^{m}\mathbf{C}_{\underline{\mathbf{dz}}}T_{ds}{}^{m}C_{ds}A_{ds}{}^{m}C_{ds}A_{ds}T_{ks}T_{ks}A_{k}$ | 33 | 71 | 5 |
| 1375426 | $G_{ks}{}^{m}C_{ks}A_{ks}T_{ds}G_{ds}\mathbf{T}_{\underline{\mathbf{dz}}}\mathbf{T}_{\underline{\mathbf{dz}}}{}^{m}C_{ds}T_{ds}{}^{m}C_{ds}A_{ds}{}^{m}C_{ds}A_{ds}T_{ks}T_{ks}A_{k}$ | 32 | 100 | 5 |
| 1375427 | $G_{ks}{}^{m}C_{ks}A_{ks}T_{ds}\mathbf{G}_{\underline{\mathbf{dz}}}\mathbf{T}_{\underline{\mathbf{dz}}}T_{ds}{}^{m}C_{ds}T_{ds}{}^{m}C_{ds}A_{ds}{}^{m}C_{ds}A_{ds}T_{ks}T_{ks}A_{k}$ | 28 | 87 | 5 |
| 1375428 | $G_{ks}{}^{m}C_{ks}A_{ks}\mathbf{T}_{\underline{\mathbf{dz}}}\mathbf{G}_{\underline{\mathbf{dz}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 33 | 99 | 5 |

TABLE 2-continued

Design and activity of modified oligonucleotides having two consecutive mesyl phosphoramidate internucleoside linkages

| Compound Number | Chemistry Notation (5'-3') | IC50 (nM) Study 1 | IC50 (nM) Study 2 | SEQ ID NO. |
|---|---|---|---|---|
| 1375429 | $G_{ks}{}^{m}C_{ks}A_{\underline{\mathbf{kz}}}T_{\underline{\mathbf{dz}}}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 39 | 83 | 5 |
| 1375430 | $G_{ks}{}^{m}C_{\underline{\mathbf{kz}}}A_{\underline{\mathbf{kz}}}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 21 | 83 | 5 |
| 1375431 | $G_{\underline{\mathbf{kz}}}{}^{m}C_{\underline{\mathbf{kz}}}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 27 | 108 | 5 |

A subscript "k" represents a cEt nucleoside, a subscript "d" represents a stereo-standard DNA nucleoside, subscript "s" indicates phosphorothioate internucleoside linkage, a subscript "z" represents an internucleoside linkage of formula IX, which is a mesyl phosphoramidate linkage. A superscript "m" before a C represents a 5-methyl Cytosine

TABLE 3

Design and activity of modified oligonucleotides containing multiple mesyl phosphoramidate internucleoside linkages

| Compound Number | Chemistry Notation (5'-3') | IC50 (nM) | SEQ ID NO. |
|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 61 | 5 |
| 1375432 | $G_{\underline{\mathbf{kz}}}{}^{m}C_{\underline{\mathbf{kz}}}A_{\underline{\mathbf{kz}}}T_{\underline{\mathbf{dz}}}G_{\underline{\mathbf{dz}}}T_{\underline{\mathbf{dz}}}T_{\underline{\mathbf{dz}}}{}^{m}C_{\underline{\mathbf{dz}}}T_{\underline{\mathbf{dz}}}{}^{m}C_{\underline{\mathbf{dz}}}A_{\underline{\mathbf{dz}}}{}^{m}C_{\underline{\mathbf{dz}}}A_{\underline{\mathbf{dz}}}T_{\underline{\mathbf{kz}}}T_{\underline{\mathbf{kz}}}A_{k}$ | 232 | 5 |
| 1386094 | $G_{ks}{}^{m}C_{ks}A_{\underline{\mathbf{kz}}}T_{\underline{\mathbf{dz}}}G_{\underline{\mathbf{dz}}}T_{\underline{\mathbf{dz}}}T_{\underline{\mathbf{dz}}}{}^{m}C_{\underline{\mathbf{dz}}}T_{\underline{\mathbf{dz}}}{}^{m}C_{\underline{\mathbf{dz}}}A_{\underline{\mathbf{dz}}}{}^{m}C_{\underline{\mathbf{dz}}}A_{\underline{\mathbf{dz}}}T_{ks}T_{ks}A_{k}$ | 810 | 5 |
| 1378793 | $G_{ks}{}^{m}C_{ks}A_{\underline{\mathbf{kz}}}T_{\underline{\mathbf{dz}}}G_{\underline{\mathbf{dz}}}T_{\underline{\mathbf{dz}}}T_{\underline{\mathbf{dz}}}{}^{m}C_{\underline{\mathbf{dz}}}T_{\underline{\mathbf{dz}}}{}^{m}C_{\underline{\mathbf{dz}}}A_{\underline{\mathbf{dz}}}{}^{m}C_{\underline{\mathbf{dz}}}A_{ds}T_{ks}T_{ks}A_{k}$ | 646 | 5 |
| 1386355 | $G_{ks}{}^{m}C_{ks}A_{ks}T_{\underline{\mathbf{dz}}}G_{\underline{\mathbf{dz}}}T_{\underline{\mathbf{dz}}}T_{\underline{\mathbf{dz}}}{}^{m}C_{\underline{\mathbf{dz}}}T_{\underline{\mathbf{dz}}}{}^{m}C_{\underline{\mathbf{dz}}}A_{\underline{\mathbf{dz}}}{}^{m}C_{\underline{\mathbf{dz}}}A_{ds}T_{ks}T_{ks}A_{k}$ | 1158 | 5 |
| 1378794 | $G_{\underline{\mathbf{kz}}}{}^{m}C_{\underline{\mathbf{kz}}}A_{ks}T_{ds}G_{ds}T_{ds}T_{ds}{}^{m}C_{ds}T_{ds}{}^{m}C_{ds}A_{ds}{}^{m}C_{ds}A_{\underline{\mathbf{dz}}}T_{\underline{\mathbf{kz}}}T_{\underline{\mathbf{kz}}}A_{k}$ | 83 | 5 |

A subscript "k" represents a cEt nucleoside, a subscript "d" represents a stereostandard DNA nucleoside, a subscript "s" indicates a phosphorothioate internucleoside linkage, a subscript "z" represents an internucleoside linkage of formula IX, which is a mesyl phosphoramidate linkage. A superscript "m" before a C represents a 5-methyl Cytosine.

Example 3: Caspase Activity of Modified Oligonucleotides in In Vitro Caspase Activation Assays The modified oligonucleotides were tested for their ability to mediate caspase activity in a series of experiments. Cultured mouse HEPA*l*-6 cells at a density of 20,000 cells per well were transfected using electroporation with modified oligonucleotides diluted to 20 μM. After a treatment period of approximately 16 hours, caspase-3 and caspase-7 activation was measured using the Caspase-Glo® 3/7 Assay System ($G^{8090}$, Promega). Results are shown in the tables below. Increased levels of caspase activation correlate with apoptotic cell death and cytotoxicity.

In some cases, the caspase activation mediated by the modified oligonucleotide was confirmed in an additional study. In such cases, the table shows % mock values for both studies 1 and 2 in separate columns.

TABLE 4

In vitro Caspase activation by modified oligonucleotides containing a single mesyl phosphoramidate internucleoside linkage

| Compound No. | Caspase Activation (% Mock) |
|---|---|
| 558807 | 2727 |
| 1375403 | 2508 |

TABLE 4-continued

In vitro Caspase activation by modified oligonucleotides containing a single mesyl phosphoramidate internucleoside linkage

| Compound No. | Caspase Activation (% Mock) |
|---|---|
| 1375404 | 3089 |
| 1375405 | 2660 |
| 1375406 | 2427 |
| 1375407 | 2938 |
| 1375408 | 2546 |
| 1375409 | 2966 |
| 1375410 | 2744 |
| 1375411 | 2571 |
| 1375412 | 1808 |
| 1375413 | 2639 |
| 1375414 | 3028 |
| 1375415 | 2733 |
| 1375416 | 2714 |
| 1375417 | 2627 |

TABLE 5

In vitro Caspase activation by modified oligonucleotides containing two consecutive mesyl phosphoramidate internucleoside linkages

| Compound No. | Caspase Activation (% Mock) Study 1 | Caspase Activation (% Mock) Study 2 |
|---|---|---|
| 558807 | 738 | 848 |
| 1375418 | 821 | 955 |
| 1375419 | 1163 | 1192 |
| 1375420 | 683 | 623 |
| 1375421 | 814 | 749 |
| 1375422 | 662 | 767 |
| 1375423 | 900 | 1165 |
| 1375424 | 1305 | 1212 |
| 1375425 | 606 | 609 |
| 1375426 | 297 | 292 |
| 1375427 | 204 | 193 |
| 1375428 | 398 | 550 |
| 1375429 | 1032 | 728 |
| 1375430 | 1157 | 1271 |
| 1375431 | 869 | 844 |

TABLE 6

In vitro Caspase activation by modified oligonucleotides containing multiple mesyl phosphoramidate internucleoside linkages

| Compound No. | Caspase Activation (% Mock) |
|---|---|
| 558807 | 2290 |
| 1375432 | 161 |
| 1386094 | 142 |
| 1378793 | 165 |
| 1386355 | 141 |
| 1378794 | 2500 |

Example 4: Stability of Modified Oligonucleotides Containing Mesyl Phosphoramidate Internucleoside Linkages The thermal stability (Tm) of duplexes of each of modified oligonucleotides described in the examples above with a complementary RNA 20-mer having the sequence GAUAAUGUGAGAACAUGCCU (SEQ ID NO: 6) was tested. Each modified oligonucleotide was separately hybridized with the complementary RNA strand to form a duplex. Once the duplex was formed, it was slowly heated and the melting temperature was measured using a spectrophotometer and the hyperchromicity method. Results are provided in the table below. This example demonstrates that mesyl phosphoramidate internucleoside linkages can be incorporated into modified oligonucleotides without destabilizing the interaction between the modified oligonucleotide and its complement.

TABLE 7

Tm of modified oligonucleotides complementary to CXCL12

| Compound No. | Tm (° C.) |
|---|---|
| 558807 | 63.5 |
| 1375403 | 63.8 |
| 1375404 | 63.9 |
| 1375405 | 63.5 |
| 1375406 | 63.7 |
| 1375407 | 63.6 |
| 1375408 | 63.9 |
| 1375409 | 64.2 |
| 1375410 | 63.9 |
| 1375411 | 64.0 |
| 1375412 | 63.7 |
| 1375413 | 63.6 |
| 1375414 | 63.3 |
| 1375415 | 63.7 |
| 1375416 | 63.7 |
| 1375417 | 63.3 |
| 1375418 | 63.3 |
| 1375419 | 63.7 |
| 1375420 | 63.4 |
| 1375421 | 63.6 |
| 1375422 | 63.8 |
| 1375423 | 64.2 |
| 1375424 | 64.2 |
| 1375425 | 64.4 |
| 1375426 | 64.4 |
| 1375427 | 63.9 |
| 1375428 | 63.1 |
| 1375429 | 63.4 |
| 1375430 | 63.8 |
| 1375431 | 64.1 |
| 1375432 | 63.7 |
| 1386094 | 64.6 |
| 1378793 | 63.9 |
| 1386355 | 63.3 |
| 1378794 | 63.7 |

Example 5: Design and Synthesis of Modified Internucleoside Linkages

Additional modified internucleoside linkages described herein may be prepared via a Staudinger reaction similar to the reaction in Example 1, but where a substituted azide is used in place of the mesyl azide in Example 1.

For example, during the synthesis of a modified oligonucleotide, reaction of substituted azide (1) below with a 2-cyanoethyl phosphite internucleoside linkage will form the modified oligonucleotide intermediate shown below:

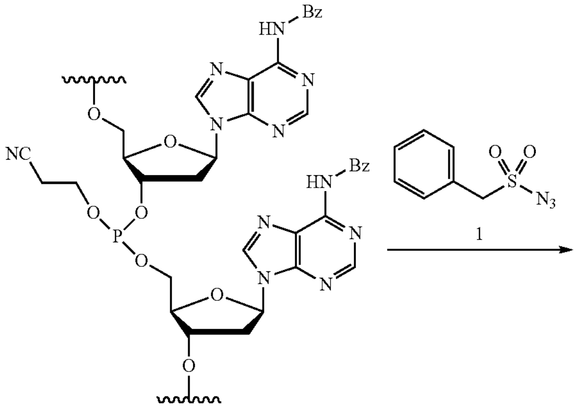

-continued

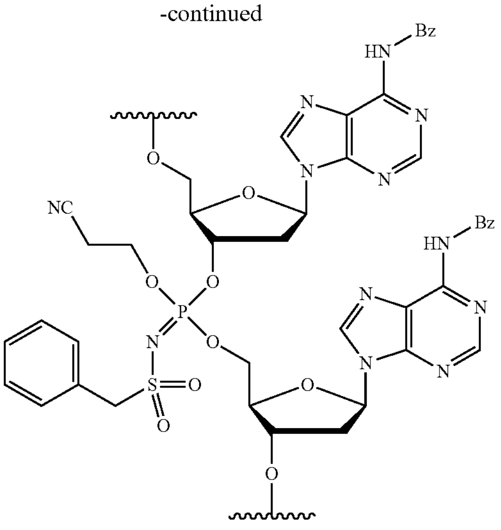

Upon deprotection and purification of the modified oligonucleotide, the modified internucleoside linkage intermediate above becomes the modified internucleoside linkage below:

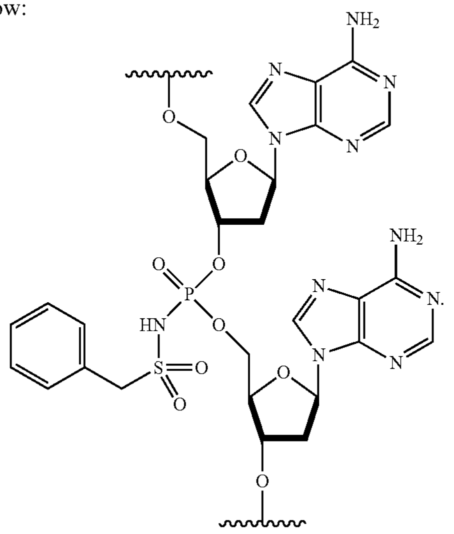

Alternatively, during the synthesis of a modified oligonucleotide, reaction of substituted azide (2) below with a 2-cyanoethyl phosphite internucleoside linkage will form the modified oligonucleotide intermediate shown below:

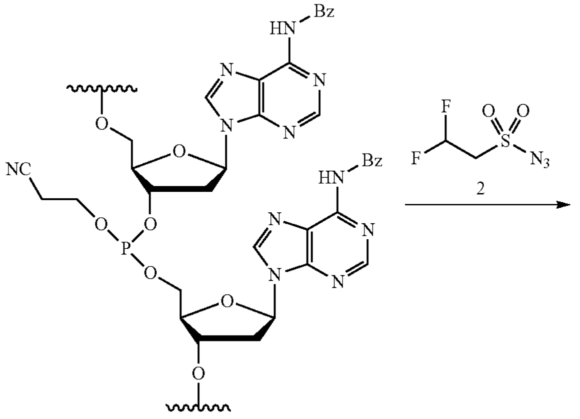

-continued

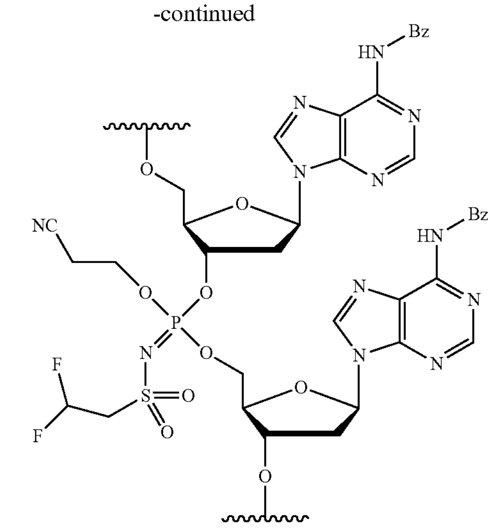

Upon deprotection and purification of the modified oligonucleotide, the modified internucleoside linkage intermediate above becomes the modified internucleoside linkage below:

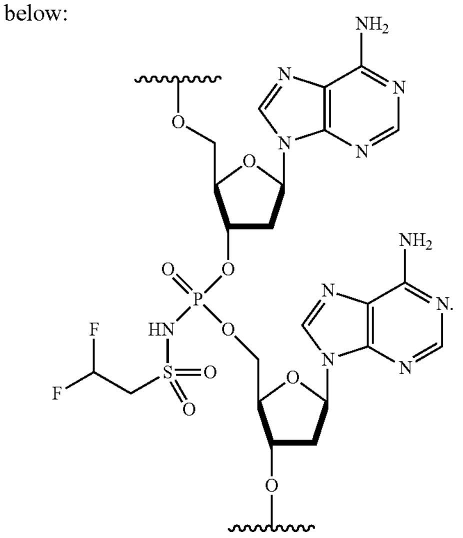

Alternatively, during the synthesis of a modified oligonucleotide, reaction of substituted azide (3) below with a 2-cyanoethyl phosphite internucleoside linkage will form the modified oligonucleotide intermediate shown below:

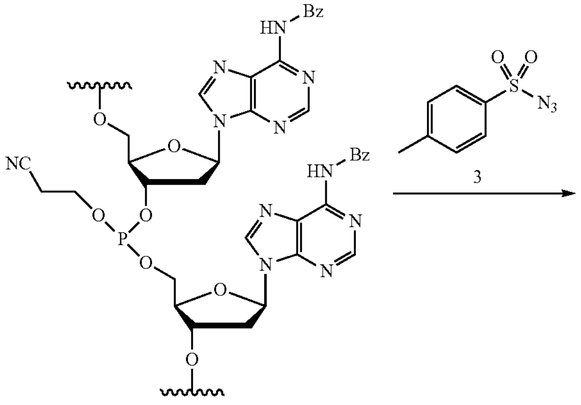

-continued

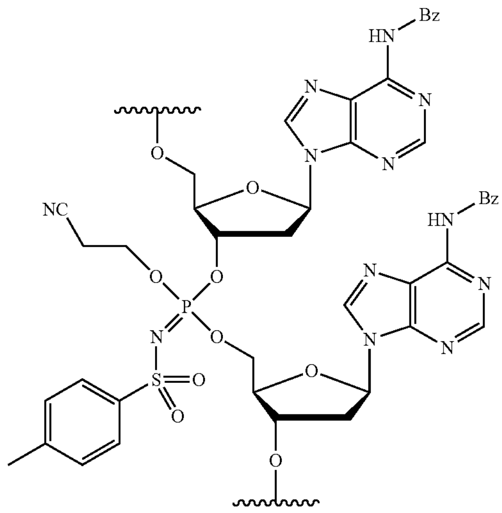

Upon deprotection and purification of the modified oligonucleotide, the modified internucleoside linkage intermediate above becomes the modified internucleoside linkage below:

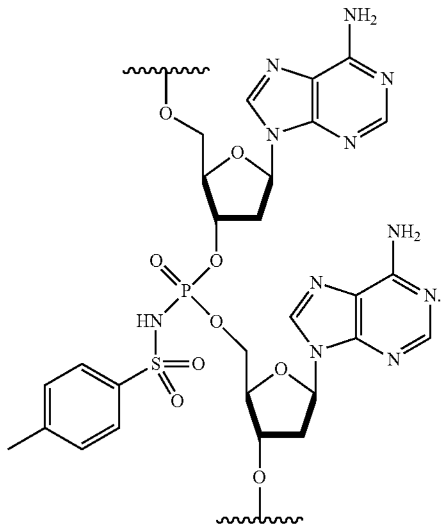

Alternatively, during the synthesis of a modified oligonucleotide, reaction of substituted azide (4) below with a 2-cyanoethyl phosphite internucleoside linkage will form the modified oligonucleotide intermediate shown below:

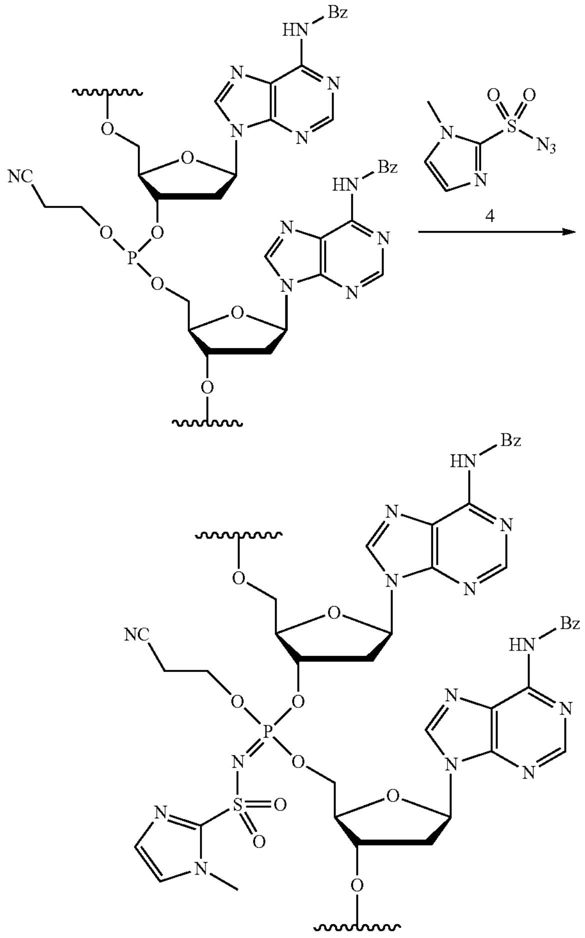

Upon deprotection and purification of the modified oligonucleotide, the modified internucleoside linkage intermediate above becomes the modified internucleoside linkage below:

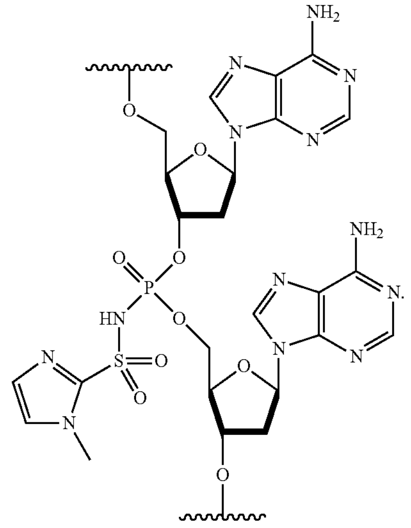

Alternatively, during the synthesis of a modified oligonucleotide, reaction of substituted azide (5) below with a 2-cyanoethyl phosphite internucleoside linkage will form the modified oligonucleotide intermediate shown below:

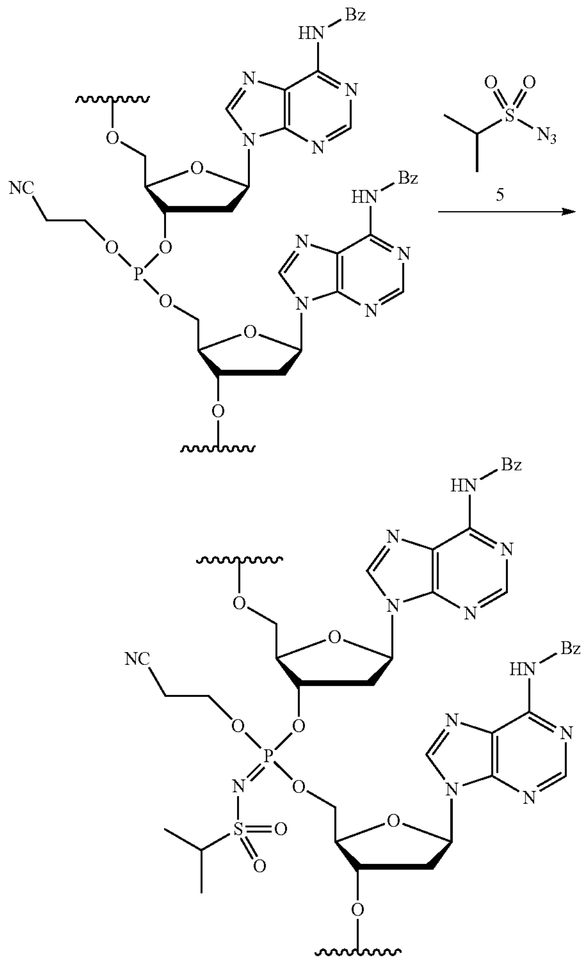

Upon deprotection and purification of the modified oligonucleotide, the modified internucleoside linkage intermediate above becomes the modified internucleoside linkage below:

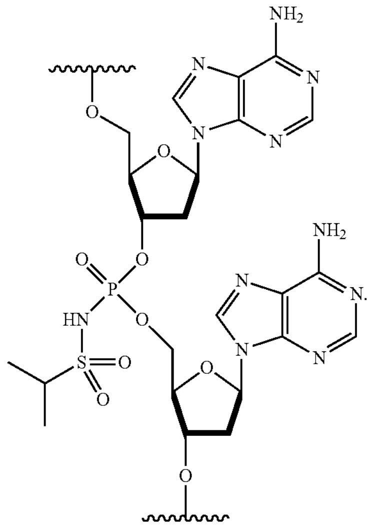

Alternatively, during the synthesis of a modified oligonucleotide, reaction of substituted azide (6) below with a 2-cyanoethyl phosphite internucleoside linkage will form the modified oligonucleotide intermediate shown below:

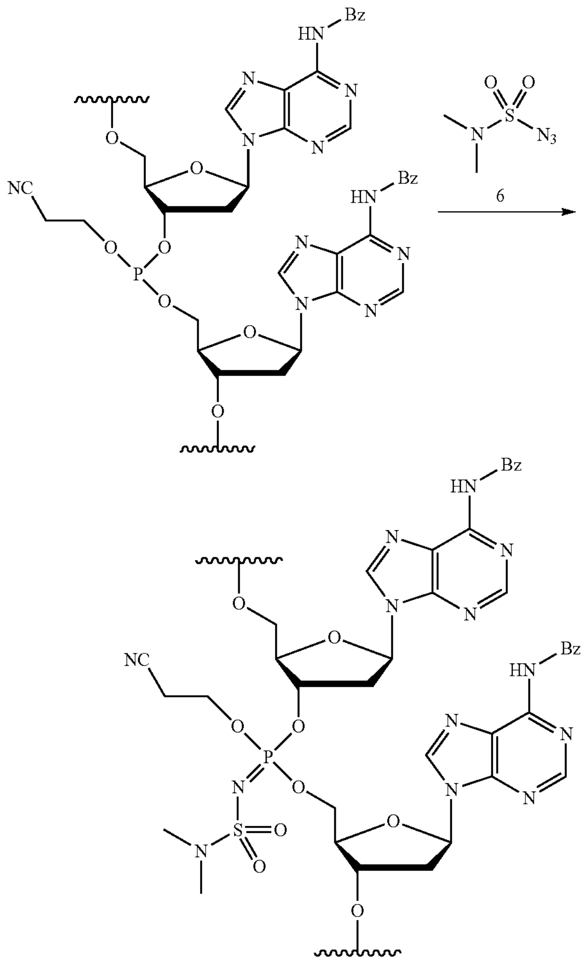

Upon deprotection and purification of the modified oligonucleotide, the modified internucleoside linkage intermediate above becomes the modified internucleoside linkage below:

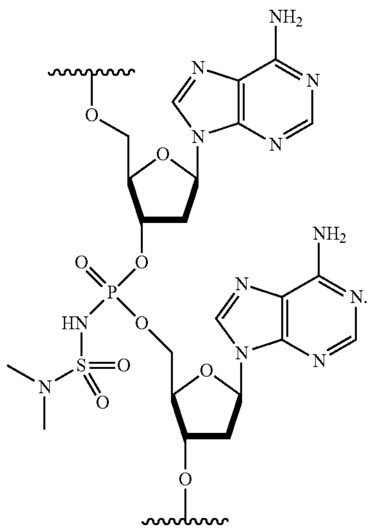

Alternatively, during the synthesis of a modified oligonucleotide, reaction of substituted azide (7) below with a 2-cyanoethyl phosphite internucleoside linkage will form the modified oligonucleotide intermediate shown below:

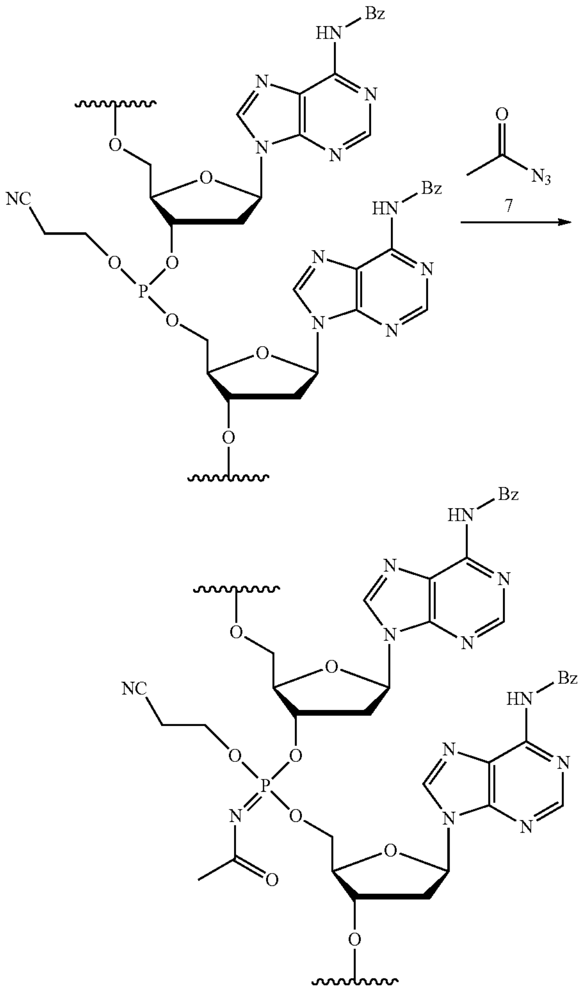

Upon deprotection and purification of the modified oligonucleotide, the modified internucleoside linkage intermediate above becomes the modified internucleoside linkage below:

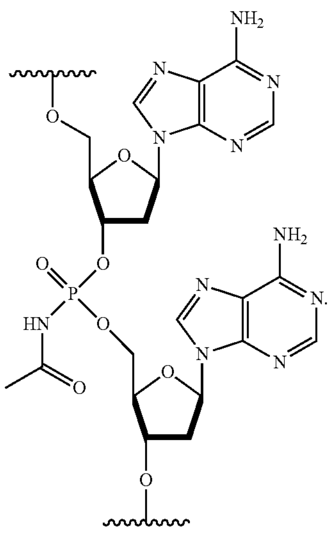

Alternatively, during the synthesis of a modified oligonucleotide, reaction of substituted azide (8) below with a 2-cyanoethyl phosphite internucleoside linkage will form the modified oligonucleotide intermediate shown below:

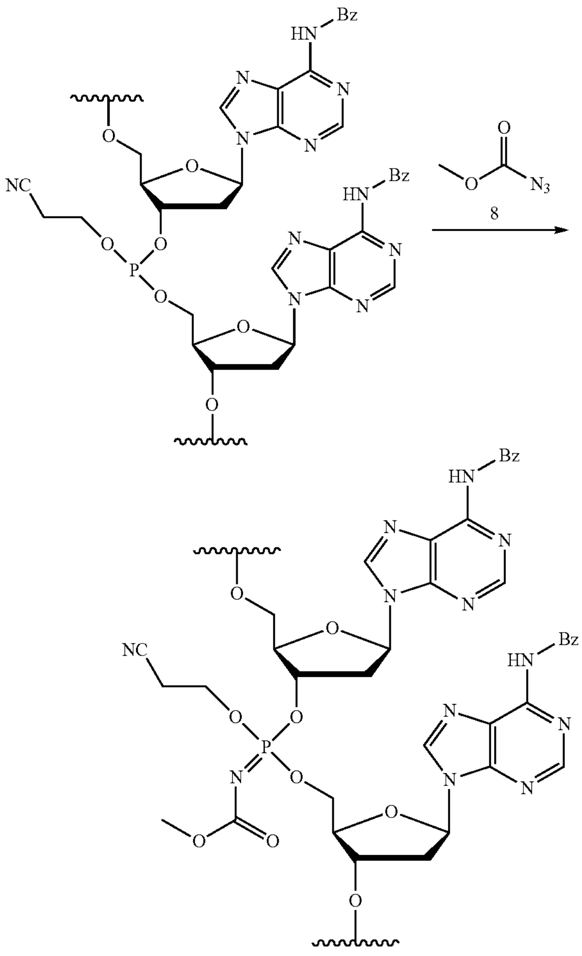

Upon deprotection and purification of the modified oligonucleotide, the modified internucleoside linkage intermediate above becomes the modified internucleoside linkage below:

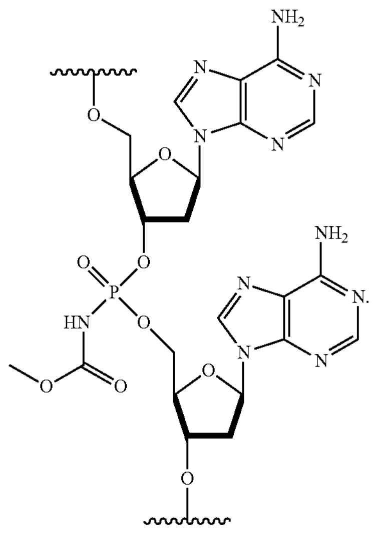

Alternatively, during the synthesis of a modified oligonucleotide, reaction of substituted azide (9) below with a 2-cyanoethyl phosphite internucleoside linkage will form the modified oligonucleotide intermediate shown below:

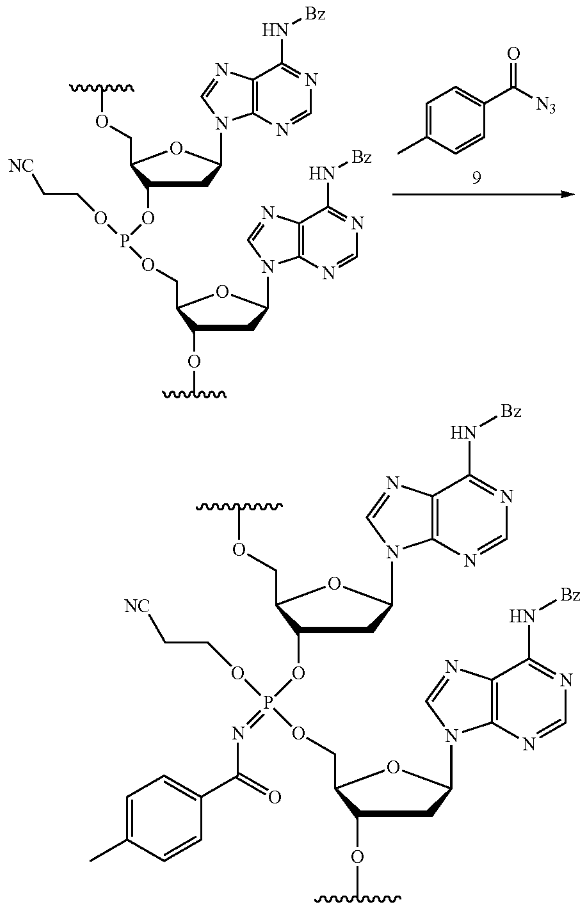

Upon deprotection and purification of the modified oligonucleotide, the modified internucleoside linkage intermediate above becomes the modified internucleoside linkage below:

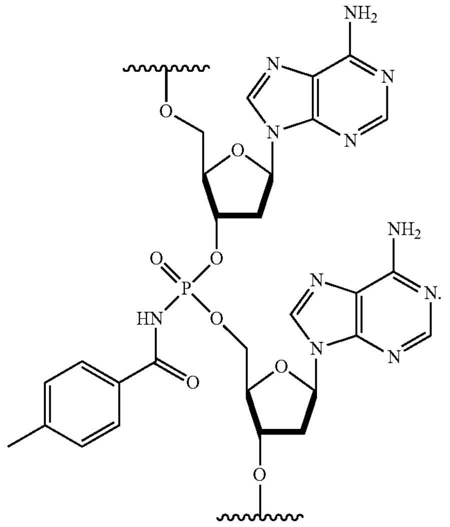

Alternatively, during the synthesis of a modified oligonucleotide, reaction of substituted azide (10) below with a 2-cyanoethyl phosphite internucleoside linkage will form the modified oligonucleotide intermediate shown below:

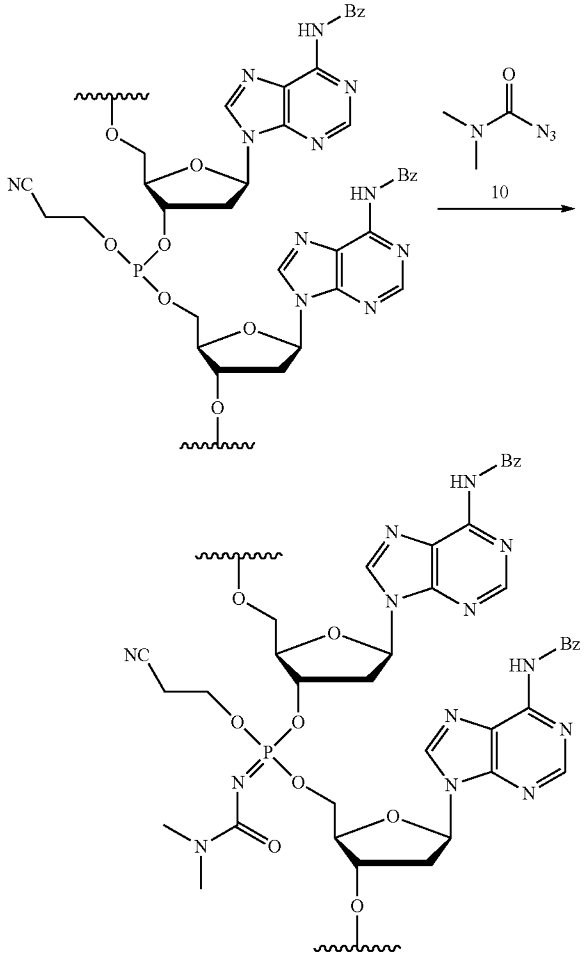

Upon deprotection and purification of the modified oligonucleotide, the modified internucleoside linkage intermediate above becomes the modified internucleoside linkage below:

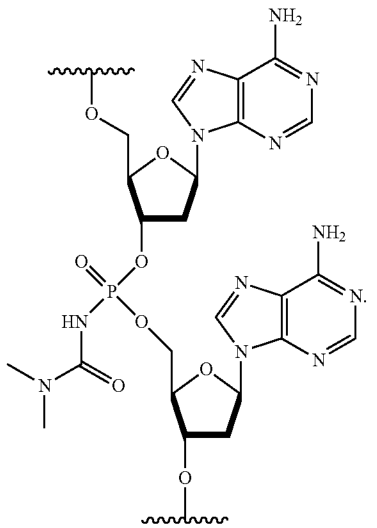

Alternatively, during the synthesis of a modified oligonucleotide, reaction of substituted azide (11) below with a 2-cyanoethyl phosphite internucleoside linkage will form the modified oligonucleotide intermediate shown below:

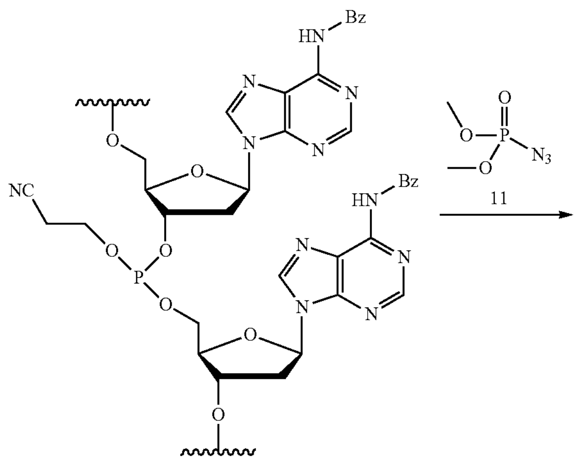

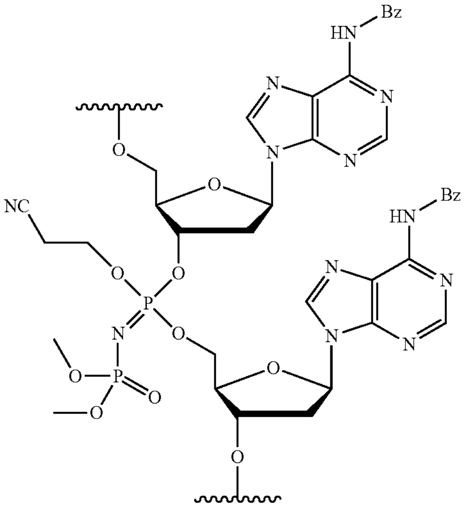

Upon deprotection and purification of the modified oligonucleotide, the modified internucleoside linkage intermediate above becomes the modified internucleoside linkage below:

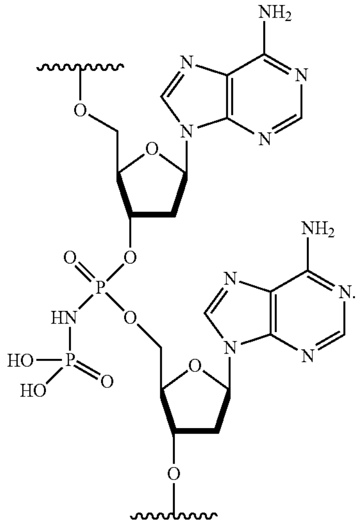

Alternatively, during the synthesis of a modified oligonucleotide, reaction of substituted azide (12) below with a 2-cyanoethyl phosphite internucleoside linkage will form the modified oligonucleotide intermediate shown below:

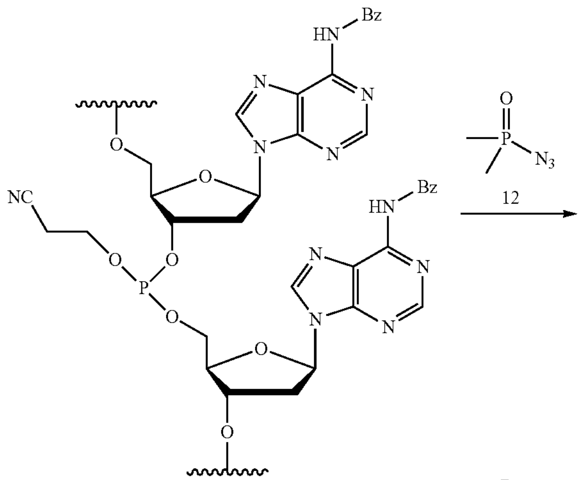

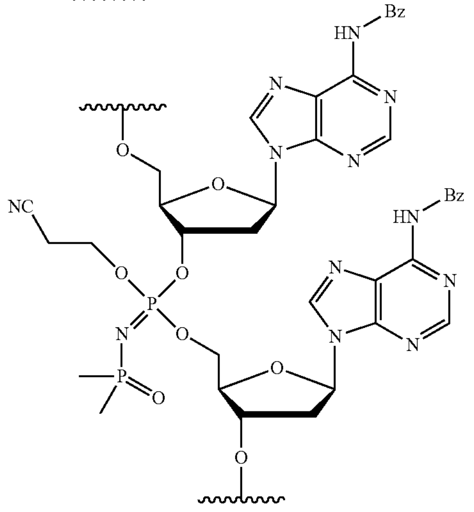

Upon deprotection and purification of the modified oligonucleotide, the modified internucleoside linkage intermediate above becomes the modified internucleoside linkage below:

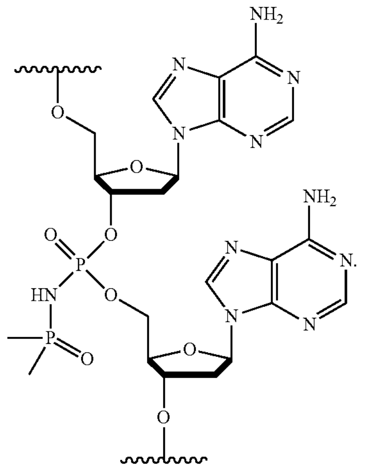

Alternatively, during the synthesis of a modified oligonucleotide, reaction of substituted azide (13) below with a 2-cyanoethyl phosphite internucleoside linkage will form the modified oligonucleotide intermediate shown below:

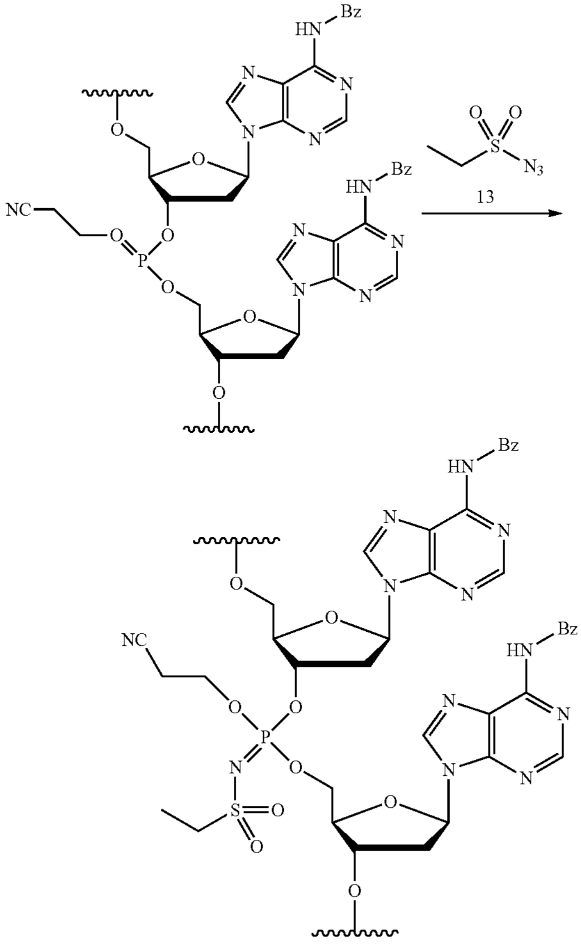

Upon deprotection and purification of the modified oligonucleotide, the modified internucleoside linkage intermediate above becomes the modified internucleoside linkage below:

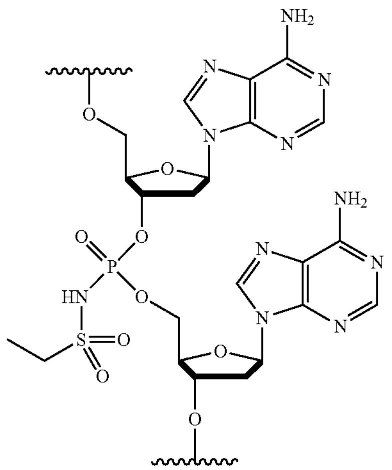

Alternatively, during the synthesis of a modified oligonucleotide, reaction of substituted azide (14) below with a 2-cyanoethyl phosphite internucleoside linkage will form the modified oligonucleotide intermediate shown below:

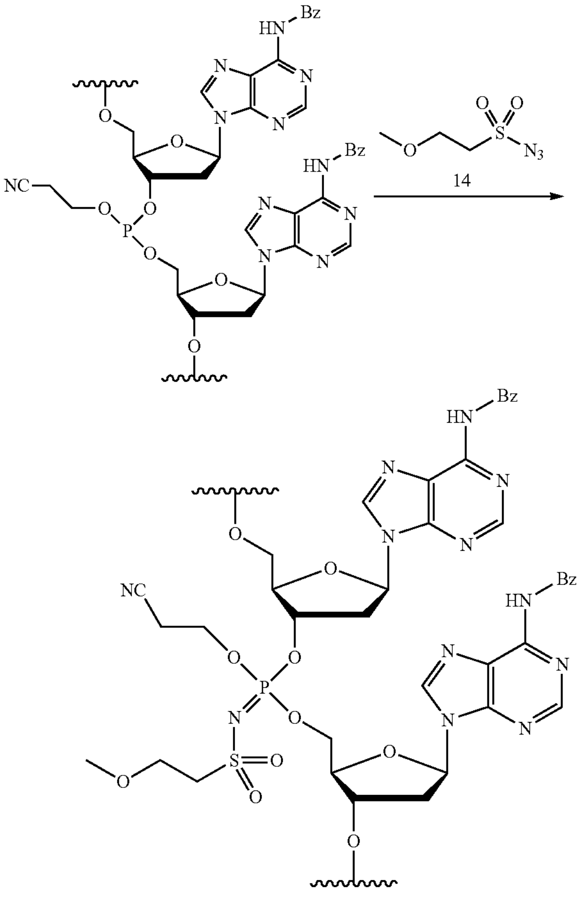

Upon deprotection and purification of the modified oligonucleotide, the modified internucleoside linkage intermediate above becomes the modified internucleoside linkage below:

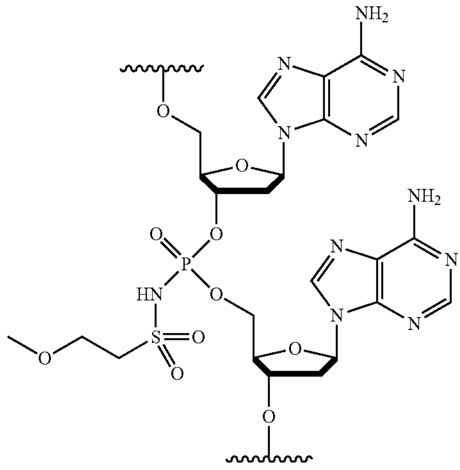

Additional substituted azides are known and readily available or easily synthesized.

Example 6: Activity and Tolerability of Modified Oligonucleotides with Mesyl Phosphoramidate Internucleoside Linkages In Vivo For the in vivo activity and tolerability study in the tables below, 3 BALB/C mice per group were administered modified oligonucleotide by subcutaneous injection and sacrificed after 72 hours. Compound 558807 was dosed at 1.8, 5.5, 16.7, or 50 mg/kg, while other modified oligonucleotides were dosed at 1.8, 5.5, 16.7, 50, or 150 mg/kg.

Tissue were collected and mRNA was isolated and levels of CXCL12 in both liver and kidney samples were measured by RT-qPCR with primer probe set RTS2605 as described above. Levels of P21 were analyzed using primer probe set Mm04207341_m1 (ThermoFisher) in liver and kidney and levels of Tnfrsf10b were analyzed using primer probe set Mm00457866_m1 (ThermoFisher) in liver. Elevated P21 or Tnfrsf10b indicates toxicity. Plasma ALT was measured. Elevations in ALT are associated with liver toxicity.

Expression levels were normalized with Ribogreen® and are presented relative to levels in mice treated with PBS. In addition to compounds containing a mesyl phosphoramidate internucleoside linkage, Compound No. 936053 was tested. This compound has the sequence GCATGTTCTCACATTA (SEQ ID NO: 5) and a sugar motif of kkk-d-m-ddddddddkkk, wherein each "k" represents a cEt nucleoside, each "d" represents a stereo-standard DNA nucleoside, and "m" represents a 2'-OMe nucleoside. Compound No. 936053 was described in WO2019/157531, and is included as a comparator compound as it has reduced toxicity relative to 558807 as well as reduced potency in vivo. Note that at least some of the observed potency of 558807 is "false"; that is, the RNA reduction observed is not specific to RNAse H mediated reduction of CXCL12 RNA, but rather, is related to global reductions in RNA due to cellular toxicity.

Therefore, Compound No. 936503 represents a better comparator compound for determining the relative in vivo potency of compounds comprising mesyl phosphoramidate internucleoside linkages.

TABLE 8

In Vivo Activity and Toxicity of modified oligonucleotides complementary to CXCL12

| Compound ID | position of modifications in the gap (5' to 3') | in vivo CXCL12 ED50 liver (mg/kg) | in vivo CXCL12 ED50 kidney (mg/kg) | ALT @ 50 mg/kg (IU/L) | ALT @ 150 mg/kg (IU/L) |
|---|---|---|---|---|---|
| 558807 | n/a | 1.0 | 31 | 7666 @ 50 mg/kg | |
| 936053 | nucleoside 2 | 5.5 | 38 | 23 | 29 |
| 1375426 | linkages 3-4, 4-5 | 4.1 | 41 | 55 | 4325 |
| 1375427 | linkages 2-3, 3-4 | 4.5 | 52 | 29 | 1519 |
| 1375428 | linkages 1-2, 2-3 | 4.7 | 38 | 473 | 3945 |

TABLE 9

In Vivo Dose-response of liver P21 mRNA upon treatment with modified oligonucleotides complementary CXCL12

| Compound ID | 1.8 mg/kg | 5.5 mg/kg | I 16.7 mg/kg | 50 mg/kg | 150 mg/kg |
|---|---|---|---|---|---|
| | Expression level of P21 mRNA (% Control) | | | | |
| 558807 | 48 | 87 | 1148 | 11488 | n.d. |
| 936053 | 98 | 142 | 137 | 132 | 169 |
| 1375426 | 113 | 114 | 106 | 250 | 6388 |
| 1375427 | 79 | 230 | 179 | 180 | 2171 |
| 1375428 | 142 | 111 | 45 | 788 | 12412 |

TABLE 10

In Vivo Dose-response of kidney P21 mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 108 | 140 | 149 | 649 | n.d. |
| 936053 | 100 | 162 | 151 | 105 | 122 |
| 1375426 | 125 | 151 | 132 | 133 | 156 |
| 1375427 | 156 | 170 | 167 | 122 | 208 |
| 1375428 | 143 | 116 | 104 | 109 | 237 |

Table 9

TABLE 11

In Vivo Dose-response of liver Tnfrsf10b mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 96 | 122 | 870 | 11757 | n.d. |
| 936053 | 151 | 121 | 132 | 148 | 191 |
| 1375426 | 124 | 150 | 115 | 213 | 4869 |
| 1375427 | 116 | 178 | 127 | 280 | 971 |
| 1375428 | 149 | 104 | 118 | 586 | 12528 |

Example 7: Design, Activity and Tolerability of Modified Oligonucleotides Complementary to SOD1 with Mesyl Phosphoramidate Internucleoside Linkages In Vitro Modified Oligonucleotides Modified oligonucleotides comprising two consecutive mesyl phosphoramidate internucleoside linkages (Formula IX) were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each internucleoside linkage is either a phosphorothioate internucleoside linkage ("s") or a mesyl phosphoramidate internucleoside linkage ("z"). Each of the compounds in the tables below has two consecutive internucleoside linkages of formula IX.

IX

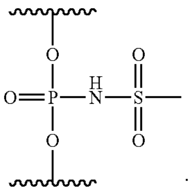

The compounds in the table below have the sequence TGAGGTCCTGCACTGG (SEQ ID NO: 11) and are 100% complementary to mouse SOD1, GENBANK NT_039625.7 truncated from 24924000 to 24933000 (SEQ ID NO: 7), at position 5685 to 5880.

In Vitro Activity Assay

The modified oligonucleotides were tested for their ability to reduce target RNA in a series of experiments. Cultured mouse 3T3-$L_1$ cells at a density of 20,000 cells per well were transfected using electroporation with modified oligonucleotides diluted to 20 μM, 7 μM, 2 μM, 0.7 μM, 0.3 μM, 0.1 μM, and 0.03 μM. After a treatment period of approximately 16 hours, RNA levels were measured using mouse primer-probe set RTS3025 (SOD1; forward sequence: TTTTTTGCGCGGTCCTTTC (SEQ ID NO: 8); reverse sequence: GAGGGACCAGAGAGAGCAAGAC (SEQ ID NO: 9), probe sequence: CGCCTTCCGTCCGTCGGCT (SEQ ID NO: 10)). RNA levels for each target were normalized to total RNA content, as measured by RIBOGREEN®. Activity expressed as half maximal inhibitory concentration (IC50) was calculated using the log (inhibitor) vs response (three parameter) function in GraphPad Prism 7.

In vitro Toxicity Assay

In vitro toxicity of modified oligonucleotides described above was determined as described in Example 3.

TABLE 12

Design, Activity, and Toxicity of modified oligonucleotides having two consecutive mesyl phosphoramidates linkages complementary to SOD1

| Compound Number | Chemistry Notation (5'-3') | SOD1 $IC_{50}$ (μM) | Caspase Activation (% Mock) | SEQ ID NO. |
|---|---|---|---|---|
| 508031 | $T_{ks}G_{ks}A_{ks}G_{ds}G_{ds}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 0.69 | 902 | 11 |
| 1405473 | $T_{ks}G_{ks}A_{ks}G_{ds}\ \mathbf{G}_{\underline{\mathbf{dz}}}\ \mathbf{T}_{\underline{\mathbf{dz}}}{}^{m}C_{ds}{}^{m}C_{ds}T_{ds}G_{ds}{}^{m}C_{ds}A_{ds}{}^{m}C_{ds}T_{ks}G_{ks}G_{k}$ | 0.38 | 273 | 11 |
| 1405474 | $T_{ks}G_{ks}A_{ks}G_{ds}G_{ds}\ \mathbf{T}_{\underline{\mathbf{dz}}}{}^{m}\ \mathbf{C}_{\underline{\mathbf{dz}}}{}^{m}C_{ds}T_{ds}G_{ds}{}^{m}C_{ds}A_{ds}{}^{m}C_{ds}T_{ks}G_{ks}G_{k}$ | 0.33 | 345 | 11 |
| 1405475 | $T_{ks}G_{ks}A_{ks}G_{ds}G_{ds}T_{ds}{}^{m}C_{ds}{}^{m}C_{ds}T_{ds}\ \mathbf{G}_{\underline{\mathbf{dz}}}\ {}^{m}\ \mathbf{C}_{\underline{\mathbf{dz}}}\ A_{ds}{}^{m}C_{ds}T_{ks}G_{ks}G_{k}$ | 0.47 | 844 | 11 |

A subscript "k" represents a cEt nucleoside, a subscript "d" represents a stereostandard DNA nucleoside, a subscript "s" indicates a phosphorothioate internucleoside linkage, a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Example 8: Design, Activity and Tolerability of Modified Oligonucleotides Complementary to HDAC2 with Mesyl Phosphoramidate Internucleoside Linkages In Vitro Modified Oligonucleotides Modified oligonucleotides comprising two consecutive mesyl phosphoramidate internucleoside linkages (Formula IX) were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each internucleoside linkage is either a phosphorothioate internucleoside linkage ("s") or a mesyl phosphoramidate internucleoside linkage ("z"). Each of the compounds in the tables below has two consecutive internucleoside linkages of formula IX.

IX

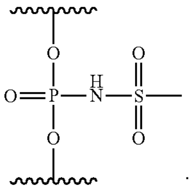

The compounds in the table below are 100% complementary to mouse HDAC2, GENBANK NC_000076.6 truncated from 36972001 to 37005000 (SEQ ID NO: 12), at several positions, as indicated in the table below.

TABLE 13

Positions of modified oligonucleotides complementary to HDAC2

| Compound Number | Sequence (5' to 3') | Start Site | Stop Site | SEQ ID NO: |
|---|---|---|---|---|
| 546108 | TAGTCTCTGTCAGTTA | 8162 | 8177 | 13 |
| | | 8204 | 8219 | |
| | | 8246 | 8261 | |
| | | 8330 | 8345 | |

TABLE 13-continued

| Positions of modified oligonucleotides complementary to HDAC2 | | | | |
|---|---|---|---|---|
| Compound Number | Sequence (5' to 3') | Start Site | Stop Site | SEQ ID NO: |
| 546110 | TCATGTACCTATAGTC | 8173 | 8188 | 14 |
| | | 8215 | 8230 | |
| | | 8257 | 8272 | |
| | | 8299 | 8314 | |
| | | 8341 | 8356 | |

In Vitro Activity Assay

The modified oligonucleotides were tested for their ability to reduce target RNA in a series of experiments. Cultured mouse 3T3-$L_1$ cells at a density of 20,000 cells per well were transfected using electroporation with modified oligonucleotides diluted to 20 μM, 7 μM, 2 μM, 0.7 μM, 0.3 μM, 0.1 μM, and 0.03 μM. After a treatment period of approximately 16 hours, RNA levels were measured using mouse HDAC2 primer-probe set RTS3500 (forward sequence TGATGGTGTTGAGGAAGCTTTTT (SEQ ID NO: 15, reverse sequence: TCCCTCAAGTCTCCTGTTCCA (SEQ ID NO: 16), probe sequence: ACAACAGATCGCGTGATGACCGTCTC, (SEQ ID NO: 17)). RNA levels for each target were normalized to total RNA content, as measured by RIBOGREEN®. Activity expressed as half maximal inhibitory concentration ($IC_{50}$) was calculated using the log (inhibitor) vs response (three parameter) function in GraphPad Prism 7.

In vitro Toxicity Assay

In vitro toxicity of modified oligonucleotides described above was determined as described in Example 3.

Example 9: Design, Activity and Tolerability of Modified Oligonucleotides Having Multiple Mesyl Phosphoramidate Internucleoside Linkages In Vitro Modified Oligonucleotides Modified oligonucleotides comprising multiple mesyl phosphoramidate internucleoside linkages (Formula IX) were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. Each internucleoside linkage is either a phosphorothioate internucleoside linkage ("s") or a mesyl phosphoramidate internucleoside linkage ("z").

IX

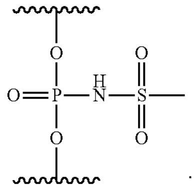

In Vitro Assays

In vitro activity of modified oligonucleotides described above was determined as described in Example 1. In vitro toxicity of modified oligonucleotides described above was determined as described in Example 3.

TABLE 14

| Modified oligonucleotides having two consecutive mesyl phosphoramidate linkages complementary to HDAC2 | | | | |
|---|---|---|---|---|
| Compound Number | Chemistry Notation (5'-3') | HDAC2 $IC_{50}$ (μM) | Caspase Activation (% Mock) | SEQ ID NO. |
| 546108 | $T_{ks}A_{ks}G_{ks}T_{ds}{}^{m}C_{ds}T_{ds}{}^{m}C_{ds}T_{ds}G_{ds}T_{ds}{}^{m}C_{ds}A_{ds}G_{ds}T_{ks}T_{ks}A_{k}$ | 0.57 | 602 | 13 |
| 1405476 | $T_{ks}A_{ks}G_{ks}T_{ds}{}^{m}\mathbf{C}_{\underline{\mathbf{dz}}}\mathbf{T}_{\underline{\mathbf{dz}}}{}^{m}C_{ds}T_{ds}G_{ds}T_{ds}{}^{m}C_{ds}A_{ds}G_{ds}T_{ks}T_{ks}A_{k}$ | 0.24 | 178 | 13 |
| 1405477 | $T_{ks}A_{ks}G_{ks}T_{ds}{}^{m}C_{ds}\mathbf{T}_{\underline{\mathbf{dz}}}{}^{m}\mathbf{C}_{\underline{\mathbf{dz}}}T_{ds}G_{ds}T_{ds}{}^{m}C_{ds}A_{ds}G_{ds}T_{ks}T_{ks}A_{k}$ | 0.31 | 225 | 13 |
| 1405478 | $T_{ks}A_{ks}G_{ks}T_{ds}{}^{m}C_{ds}T_{ds}{}^{m}C_{ds}T_{ds}G_{ds}\mathbf{T}_{\underline{\mathbf{dz}}}{}^{m}\mathbf{C}_{\underline{\mathbf{dz}}}A_{ds}G_{ds}T_{ks}T_{ks}A_{k}$ | 0.28 | 207 | 13 |
| 546110 | $T_{ks}{}^{m}C_{ks}A_{ks}T_{ds}G_{ds}T_{ds}A_{ds}{}^{m}C_{ds}{}^{m}C_{ds}T_{ds}A_{ds}T_{ds}A_{ds}G_{ks}T_{ks}{}^{m}C_{k}$ | 0.20 | 142 | 14 |
| 1405479 | $T_{ks}{}^{m}C_{ks}A_{ks}T_{ds}\mathbf{G}_{\underline{\mathbf{dz}}}\mathbf{T}_{\underline{\mathbf{dz}}}A_{ds}{}^{m}C_{ds}{}^{m}C_{ds}T_{ds}A_{ds}T_{ds}A_{ds}G_{ks}T_{ks}{}^{m}C_{k}$ | 0.61 | 74 | 14 |
| 1405480 | $T_{ks}{}^{m}C_{ks}A_{ks}T_{ds}G_{ds}\mathbf{T}_{\underline{\mathbf{dz}}}\mathbf{A}_{\underline{\mathbf{dz}}}{}^{m}C_{ds}{}^{m}C_{ds}T_{ds}A_{ds}T_{ds}A_{ds}G_{ks}T_{ks}{}^{m}C_{k}$ | 0.43 | 79 | 14 |
| 1405481 | $T_{ks}{}^{m}C_{ks}A_{ks}T_{ds}G_{ds}T_{ds}A_{ds}{}^{m}C_{ds}{}^{m}C_{ds}\mathbf{T}_{\underline{\mathbf{dz}}}\mathbf{A}_{\underline{\mathbf{dz}}}T_{ds}A_{ds}G_{ks}T_{ks}{}^{m}C_{k}$ | 0.63 | 113 | 14 |

A subscript "k" represents a cEt nucleoside, a subscript "d" represents a stereostandard DNA nucleoside, a subscript "s" indicates a phosphorothioate internucleoside linkage, a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Each of the compounds in the table below has three or four consecutive internucleoside linkages of formula IX.

TABLE 15

Design, Activity, and Tolerability of modified oligonucleotides having three or four consecutive mesyl phosphoramidates linkages complementary to CXCL12

| Compound Number | Chemistry Notation (5'-3') | CXCL12 $IC_{50}$ (μM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 0.17 | 1329 | 5 |
| 1405434 | $G_{ks}{}^{m}C_{ks}A_{ks}\mathbf{T}_{\underline{dz}}\mathbf{G}_{\underline{dz}}\mathbf{T}_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | 0.16 | 211 | 5 |
| 1405435 | $G_{ks}{}^{m}C_{ks}A_{ks}T_{ds}\mathbf{G}_{\underline{dz}}\mathbf{T}_{\underline{dz}}\mathbf{T}_{\underline{dz}}{}^{m}C_{ds}T_{ds}{}^{m}C_{ds}A_{ds}{}^{m}C_{ds}A_{ds}T_{ks}T_{ks}A_{k}$ | 0.12 | 240 | 5 |
| 1405436 | $G_{ks}{}^{m}C_{ks}A_{ks}\mathbf{T}_{\underline{dz}}\mathbf{G}_{\underline{dz}}\mathbf{T}_{\underline{dz}}\mathbf{T}_{\underline{dz}}{}^{m}C_{ds}T_{ds}{}^{m}C_{ds}A_{ds}{}^{m}C_{ds}A_{ds}T_{ks}T_{ks}A_{k}$ | 0.12 | 187 | 5 |

A subscript "k" represents a cEt nucleoside, a subscript "d" represents a stereostandard DNA nucleoside, a subscript "s" indicates a phosphorothioate internucleoside linkage, a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Each of the compounds in the table below has multiple internucleoside linkages of formula IX.

TABLE 16

Design, Activity, and Tolerability of modified oligonucleotides having multiple mesyl phosphoramidate linkages complementary to CXCL12

| Compound Number | Chemistry Notation (5'-3') | CXCL12 $IC_{50}$ (μM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 0.20 | 2727 | 5 |
| 1437592 | $G_{ks}{}^{m}C_{ks}\mathbf{A}_{\underline{kz}}\mathbf{T}_{\underline{dz}}\mathbf{G}_{\underline{dz}}T_{ds}T_{ds}{}^{m}C_{ds}T_{ds}{}^{m}C_{ds}A_{ds}{}^{m}C_{ds}A_{ds}T_{ks}T_{ks}A_{k}$ | 0.11 | 1708 | 5 |
| 1437593 | $G_{ks}{}^{m}C_{ks}\mathbf{A}_{\underline{kz}}\mathbf{T}_{\underline{dz}}\mathbf{G}_{\underline{dz}}\mathbf{T}_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | 0.15 | 500 | 5 |
| 1437594 | $G_{ks}{}^{m}C_{ks}\mathbf{A}_{\underline{kz}}\mathbf{T}_{\underline{dz}}\mathbf{G}_{\underline{dz}}\mathbf{T}_{\underline{dz}}\mathbf{T}_{\underline{dz}}{}^{m}C_{ds}T_{ds}{}^{m}C_{ds}A_{ds}{}^{m}C_{ds}A_{ds}T_{ks}T_{ks}A_{k}$ | 0.24 | 308 | 5 |
| 1437595 | $G_{ks}{}^{m}C_{ks}\mathbf{A}_{\underline{kz}}\mathbf{T}_{\underline{dz}}\mathbf{G}_{\underline{dz}}\mathbf{T}_{\underline{dz}}\mathbf{T}_{\underline{dz}}{}^{m}\mathbf{C}_{\underline{dz}}T_{ds}{}^{m}C_{ds}A_{ds}{}^{m}C_{ds}A_{ds}T_{ks}T_{ks}A_{k}$ | 0.26 | 309 | 5 |
| 1437596 | $G_{ks}{}^{m}C_{ks}\mathbf{A}_{\underline{kz}}\mathbf{T}_{\underline{dz}}\mathbf{G}_{\underline{dz}}\mathbf{T}_{\underline{dz}}\mathbf{T}_{\underline{dz}}{}^{m}\mathbf{C}_{\underline{dz}}\mathbf{T}_{\underline{dz}}{}^{m}C_{ds}A_{ds}{}^{m}C_{ds}A_{ds}T_{ks}T_{ks}A_{k}$ | 0.50 | 324 | 5 |
| 1437597 | $G_{ks}{}^{m}C_{ks}\mathbf{A}_{\underline{kz}}\mathbf{T}_{\underline{dz}}\mathbf{G}_{\underline{dz}}\mathbf{T}_{\underline{dz}}\mathbf{T}_{\underline{dz}}{}^{m}\mathbf{C}_{\underline{dz}}\mathbf{T}_{\underline{dz}}{}^{m}\mathbf{C}_{\underline{dz}}A_{ds}{}^{m}C_{ds}A_{ds}T_{ks}T_{ks}A_{k}$ | 0.28 | 193 | 5 |
| 1437598 | $G_{ks}{}^{m}C_{ks}\mathbf{A}_{\underline{kz}}\mathbf{T}_{\underline{dz}}\mathbf{G}_{\underline{dz}}\mathbf{T}_{\underline{dz}}\mathbf{T}_{\underline{dz}}{}^{m}\mathbf{C}_{\underline{dz}}\mathbf{T}_{\underline{dz}}{}^{m}\mathbf{C}_{\underline{dz}}\mathbf{A}_{\underline{dz}}{}^{m}C_{ds}A_{ds}T_{ks}T_{ks}A_{k}$ | 0.44 | 181 | 5 |
| 1437599 | $G_{ks}{}^{m}C_{ks}A_{ks}T_{ds}G_{ds}T_{ds}T_{ds}{}^{m}C_{ds}T_{ds}{}^{m}C_{ds}\mathbf{A}_{\underline{dz}}{}^{m}\mathbf{C}_{\underline{dz}}\mathbf{A}_{\underline{dz}}T_{ks}T_{ks}A_{k}$ | 0.16 | 1290 | 5 |
| 1437600 | $G_{ks}{}^{m}C_{ks}A_{ks}T_{ds}G_{ds}T_{ds}T_{ds}{}^{m}C_{ds}T_{ds}{}^{m}\mathbf{C}_{\underline{dz}}\mathbf{A}_{\underline{dz}}{}^{m}\mathbf{C}_{\underline{dz}}\mathbf{A}_{\underline{dz}}T_{ks}T_{ks}A_{k}$ | 0.14 | 1807 | 5 |
| 1437601 | $G_{ks}{}^{m}C_{ks}A_{ks}T_{ds}G_{ds}T_{ds}T_{ds}{}^{m}C_{ds}\mathbf{T}_{\underline{dz}}{}^{m}\mathbf{C}_{\underline{dz}}\mathbf{A}_{\underline{dz}}{}^{m}\mathbf{C}_{\underline{dz}}\mathbf{A}_{\underline{dz}}T_{ks}T_{ks}A_{k}$ | 0.18 | 1941 | 5 |
| 1437602 | $G_{ks}{}^{m}C_{ks}A_{ks}T_{ds}G_{ds}T_{ds}T_{ds}{}^{m}\mathbf{C}_{\underline{dz}}\mathbf{T}_{\underline{dz}}{}^{m}\mathbf{C}_{\underline{dz}}\mathbf{A}_{\underline{dz}}{}^{m}\mathbf{C}_{\underline{dz}}\mathbf{A}_{\underline{dz}}T_{ks}T_{ks}A_{k}$ | 0.13 | 1927 | 5 |
| 1437603 | $G_{ks}{}^{m}C_{ks}A_{ks}T_{ds}G_{ds}T_{ds}\mathbf{T}_{\underline{dz}}{}^{m}\mathbf{C}_{\underline{dz}}\mathbf{T}_{\underline{dz}}{}^{m}\mathbf{C}_{\underline{dz}}\mathbf{A}_{\underline{dz}}{}^{m}\mathbf{C}_{\underline{dz}}\mathbf{A}_{\underline{dz}}T_{ks}T_{ks}A_{k}$ | 0.32 | 866 | 5 |
| 1437604 | $G_{ks}{}^{m}C_{ks}A_{ks}T_{ds}G_{ds}\mathbf{T}_{\underline{dz}}\mathbf{T}_{\underline{dz}}{}^{m}\mathbf{C}_{\underline{dz}}\mathbf{T}_{\underline{dz}}{}^{m}\mathbf{C}_{\underline{dz}}\mathbf{A}_{\underline{dz}}{}^{m}\mathbf{C}_{\underline{dz}}\mathbf{A}_{\underline{dz}}T_{ks}T_{ks}A_{k}$ | 0.97 | 250 | 5 |
| 1437605 | $G_{ks}{}^{m}C_{ks}A_{ks}T_{ds}\mathbf{G}_{\underline{dz}}\mathbf{T}_{\underline{dz}}\mathbf{T}_{\underline{dz}}{}^{m}\mathbf{C}_{\underline{dz}}\mathbf{T}_{\underline{dz}}{}^{m}\mathbf{C}_{\underline{dz}}\mathbf{A}_{\underline{dz}}{}^{m}\mathbf{C}_{\underline{dz}}\mathbf{A}_{\underline{dz}}T_{ks}T_{ks}A_{k}$ | 1.84 | 152 | 5 |
| 1437606 | $G_{ks}{}^{m}C_{ks}A_{ks}T_{dz}\mathbf{G}_{\underline{dz}}\mathbf{T}_{\underline{dz}}\mathbf{T}_{\underline{dz}}{}^{m}\mathbf{C}_{\underline{dz}}\mathbf{T}_{\underline{dz}}{}^{m}\mathbf{C}_{\underline{dz}}\mathbf{A}_{\underline{dz}}{}^{m}\mathbf{C}_{\underline{dz}}\mathbf{A}_{\underline{dz}}T_{ks}T_{ks}A_{k}$ | 1.69 | 155 | 5 |
| 1441068 | $G_{ks}{}^{m}C_{ks}\mathbf{A}_{\underline{kz}}T_{ds}\mathbf{G}_{\underline{dz}}T_{ds}\mathbf{T}_{\underline{dz}}{}^{m}C_{ds}\mathbf{T}_{\underline{dz}}{}^{m}C_{ds}\mathbf{A}_{\underline{dz}}{}^{m}C_{ds}\mathbf{A}_{\underline{dz}}T_{ks}T_{ks}A_{k}$ | 0.29 | 759 | 5 |
| 1441069 | $G_{ks}{}^{m}C_{ks}A_{ks}\mathbf{T}_{\underline{dz}}G_{ds}\mathbf{T}_{\underline{dz}}T_{ds}{}^{m}\mathbf{C}_{\underline{dz}}T_{ds}{}^{m}\mathbf{C}_{\underline{dz}}A_{ds}{}^{m}\mathbf{C}_{\underline{dz}}A_{ds}T_{ks}T_{ks}A_{k}$ | 0.39 | 1122 | 5 |

A subscript "k" represents a cEt nucleoside, a subscript "d" represents a stereostandard DNA nucleoside, a subscript "s" indicates a phosphorothioate internucleoside linkage, a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Example 10: Design, Synthesis, Activity, and Tolerability of Modified Oligonucleotides Having Various Modified Phosphoramidate Internucleoside Linkages In Vitro Modified oligonucleotides comprising mesyl phosphoramidate internucleoside linkages were synthesized and tested. The modified oligonucleotides are each 3-10-3 cEt gapmers with a sugar motif of (from 5' to 3'): kkkddddddddddkkk (a 3-10-3 cEt motif) wherein "k" represents a cEt modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT_039353.7 truncated from 69/430,515 to 69/445,350 (SEQ ID NO: 1), at position 6877 to 6892. Each internucleoside linkage is either a phosphorothioate internucleoside linkage ("s") or a modified phosphoramidate internucleoside linkage represented by formulas X-XVI, as indicated in the table below.

X

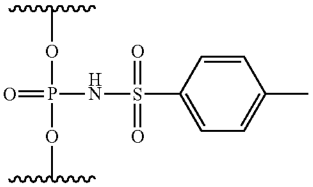

tosyl phosphoramidate

XI

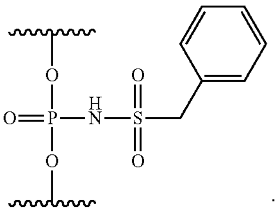

benzylsulfonyl phosphoramidate

XII

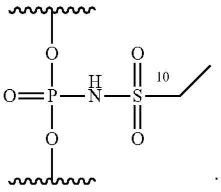

ethylsulfonyl phosphoramidate

XIII

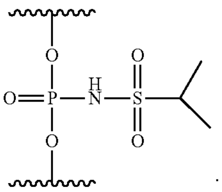

isopropylsulfonyl phosphoramidate

-continued

XIV

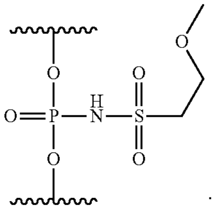

methoxyethylsulfonyl phosphoramidate

XV

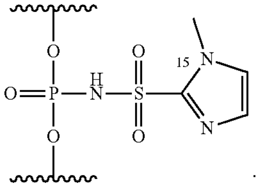

N-methyl imidazole sulfonyl phosphoramidate

XVI

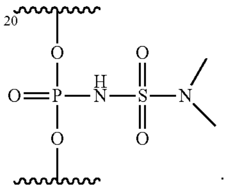

dimethylamino sulfonyl phosphoramidate

Synthesis

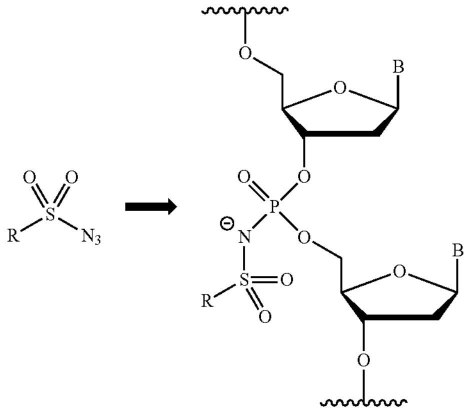

Oligonucleotides were synthesized on a 2 μmol scale using VIMAD UnyLinker support (200 μmol/g) on an ABI 394 DNA/RNA synthesizer. Fully protected nucleoside phosphoramidites were incorporated using standard solid-phase oligonucleotide synthesis, i.e. 3% dichloroacetic acid in dichloromethane for deblocking, 1 M 4,5-dicyanoimidazole 0.1 M N-methylimidazole in acetonitrile as activator for amidite couplings, 20% acetic anhydride in THF and 10% 1-methylimidazole in THF/pyridine for capping and 0.1 M xanthane hydride in pyridine:acetonitrile 3:2 (v:v) for thiolation. Mesyl phosphoramidate couplings were oxidized instead of thiolated using 0.5 M mesyl azide in acetonitrile:

toluene 1:1 (v:v) with oxidation times varying (3×500 s to 6×900 s) depending on the steric hindrance of the substituted azide or the steric hindrance of the phosphoramidite being oxidized (Table 17 and Table 18). Amidites were dissolved to 0.1 M in acetonitrile:toluene 1:1 (v:v) and incorporated using 6 min coupling recycling time for DNA amidites and 10 min for all other amidites. At the end of the solid phase synthesis cyanoethyl protecting groups were removed by a 30 min treatment with 20% diethylamine in toluene. Modified oligonucleotides were deprotected and cleaved using conc. aq. ammonia at room temperature for 48 h or at 55° C. overnight.

TABLE 17

Oxidation times for the various substituted azide analogs using an ABI oligonucleotides synthesizer on 2 μmol scale

| Substituted Azide | R = | Oxidation time |
|---|---|---|
| | methyl | 3 × 500s |
| | ethyl | 3 × 500s |
| | methoxy ethyl | 3 × 650s |
| | isopropyl | 3 × 999s |
| | tosyl | 3 × 500s |
| 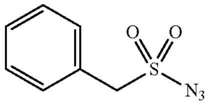 [SMILES: [N-]=[N+]=NS(=O)(=O)Cc1ccccc1] | benzyl | 3 × 500s |
| 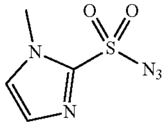 | N-methyl imidazole | 3 × 500s |

TABLE 17-continued

Oxidation times for the various substituted azide analogs using an ABI oligonucleotides synthesizer on 2 μmol scale

| Substituted Azide | R = | Oxidation time |
|---|---|---|
| 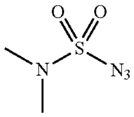 | dimethylamine | 4 × 900s |

TABLE 18

Oxidation times for various sugar phosphoramidites to form mesyl phosphoramidate linkages (R = methyl)

| Sugar modification | Oxidation time |
|---|---|
| DNA | 3 × 500 s |
| cEt | 6 × 900 s |
| OMe | 3 × 650 s |
| MOE | 3 × 650 s |
| 2'-F | 4 × 750 s |
| LNA | 6 × 900 s |

In Vitro Assays

In vitro activity of modified oligonucleotides described above was determined as described in Example 1. In vitro toxicity of modified oligonucleotides described above was determined as described in Example 3. Each experiment is presented in a separate table.

TABLE 19

Design, activity, and tolerability of modified oligonucleotides having modified phosphoramidate linkages of formulas X, XI, or XII complementary to CXCL12

| Compound Number | Chemistry Notation (5'-3') | CXCL12 $IC_{50}$ (nM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 150 | 1336 | 5 |
| 1419483 | $G_{ks}{}^{m}C_{ks}A_{ks}\mathbf{T}_{\underline{dX}}\mathbf{G}_{\underline{dX}}T_{ds}T_{ds}{}^{m}C_{ds}T_{ds}{}^{m}C_{ds}A_{ds}{}^{m}C_{ds}A_{ds}T_{ks}T_{ks}A_{k}$ | 263 | 141 | 5 |
| 1419482 | $G_{ks}{}^{m}C_{ks}A_{ks}T_{ds}\mathbf{G}_{\underline{dX}}\mathbf{T}_{\underline{dX}}T_{ds}{}^{m}C_{ds}T_{ds}{}^{m}C_{ds}A_{ds}{}^{m}C_{ds}A_{ds}T_{ks}T_{ks}A_{k}$ | 299 | 88 | 5 |
| 1419481 | $G_{ks}{}^{m}C_{ks}A_{ks}T_{ds}G_{ds}\mathbf{T}_{\underline{dX}}\mathbf{T}_{\underline{dX}}{}^{m}C_{ds}T_{ds}{}^{m}C_{ds}A_{ds}{}^{m}C_{ds}A_{ds}T_{ks}T_{ks}A_{k}$ | 404 | 79 | 5 |
| 1419480 | $G_{ks}{}^{m}C_{ks}A_{ks}T_{ds}G_{ds}T_{ds}T_{ds}{}^{m}C_{ds}T_{ds}{}^{m}\mathbf{C}_{\underline{dX}}\mathbf{A}_{\underline{dX}}{}^{m}C_{ds}A_{ds}T_{ks}T_{ks}A_{k}$ | 171 | 433 | 5 |
| 1427921 | $G_{ks}{}^{m}C_{ks}A_{ks}\mathbf{T}_{\underline{dXI}}\mathbf{G}_{\underline{dXI}}T_{ds}T_{ds}{}^{m}C_{ds}T_{ds}{}^{m}C_{ds}A_{ds}{}^{m}C_{ds}A_{ds}T_{ks}T_{ks}A_{k}$ | 439 | 134 | 5 |
| 1427922 | $G_{ks}{}^{m}C_{ks}A_{ks}T_{ds}\mathbf{G}_{\underline{dXI}}\mathbf{T}_{\underline{dXI}}T_{ds}{}^{m}C_{ds}T_{ds}{}^{m}C_{ds}A_{ds}{}^{m}C_{ds}A_{ds}T_{ks}T_{ks}A_{k}$ | 431 | 109 | 5 |
| 1427923 | $G_{ks}{}^{m}C_{ks}A_{ks}T_{ds}G_{ds}\mathbf{T}_{\underline{dXI}}\mathbf{T}_{\underline{dXI}}{}^{m}C_{ds}T_{ds}{}^{m}C_{ds}A_{ds}{}^{m}C_{ds}A_{ds}T_{ks}T_{ks}A_{k}$ | 465 | 90 | 5 |
| 1427924 | $G_{ks}{}^{m}C_{ks}A_{ks}T_{ds}G_{ds}T_{ds}T_{ds}{}^{m}C_{ds}T_{ds}{}^{m}A_{a}C_{\underline{\mathbf{dXI}}}\ A_{\underline{\mathbf{dXI}}}{}^{m}C_{ds}A_{ds}T_{ks}T_{ks}A_{k}$ | 181 | 517 | 5 |
| 1417944 | $G_{ks}{}^{m}C_{ks}A_{k}T_{\underline{\mathbf{dXII}}}\ G_{\underline{\mathbf{dXII}}}T_{ds}T_{ds}{}^{m}C_{ds}T_{ds}{}^{m}C_{ds}A_{ds}{}^{m}C_{ds}A_{ds}T_{ks}T_{ks}A_{k}$ | 118 | 982 | 5 |
| 1417943 | $G_{ks}{}^{m}C_{ks}A_{ks}T_{ds}\ G_{\underline{\mathbf{dXII}}}\ T_{\underline{\mathbf{dXII}}}T_{ds}{}^{m}C_{ds}T_{ds}{}^{m}C_{ds}A_{ds}{}^{m}C_{ds}A_{ds}T_{ks}T_{ks}A_{k}$ | 136 | 274 | 5 |

TABLE 19-continued

Design, activity, and tolerability of modified oligonucleotides having modified phosphoramidate linkages of formulas X, XI, or XII complementary to CXCL12

| Compound Number | Chemistry Notation (5'-3') | CXCL12 IC$_{50}$ (nM) | Caspase Activation (% Mock) | SEQ ID NO. |
|---|---|---|---|---|
| 1417942 | G$_{ks}$$^m$C$_{ks}$A$_{ks}$T$_{ds}$G$_{ds}$T**$_{dXII}$**T**$_{dXII}$**$^m$C$_{ds}$T$_{ds}$$^m$C$_{ds}$A$_{ds}$$^m$C$_{ds}$A$_{ds}$T$_{ks}$T$_{ks}$A$_k$ | 167 | 452 | 5 |
| 1417941 | G$_{ks}$$^m$C$_{ks}$A$_{ks}$T$_{ds}$G$_{ds}$T$_{ds}$T$_{ds}$$^m$C$_{ds}$T$_{ds}$$^m$ **C$_{dXI}$**A**$_{dXII}$**$^m$C$_{ds}$A$_{ds}$T$_{ks}$T$_{ks}$A$_k$ | 63 | 2029 | 5 |

A subscript "k" represents a cEt nucleoside, a subscript "d" represents a stereo-standard DNA nucleoside, a subscript "s" indicates a phosphorothioate internucleoside linkage. A subscript "X" represents an internucleoside linkage of formula X; a subscript "XI" represents an internucleoside linkage of formula XI; a subscript "XII" represents an internucleoside linkage of formula XII. Subscripts of nucleotides having a substituted phosphoramidate internucleoside linkage of generic Formula XVII are bold and underlined. A superscript "m" before a C represents a 5-methyl Cytosine.

TABLE 20

Design, activity, and tolerability of modified oligonucleotides having modified phosphoramidate linkages of formulas XIII, XIV, or XV complementary to CXCL12

| Compound Number | Chemistry Notation (5'-3') | CXCL12 IC$_{50}$ (nM) | Caspase Activation (% Mock) | SEQ ID NO. |
|---|---|---|---|---|
| 558807 | G$_{ks}$$^m$C$_{ks}$A$_{ks}$T$_{ds}$G$_{ds}$T$_{ds}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 98 | 986 | 5 |
| 1429189 | G$_{ks}$$^m$C$_{ks}$A$_{ks}$T**$_{dXIII}$** G**$_{dXIII}$**T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 80 | 638 | 5 |
| 1429190 | G$_{ks}$$^m$C$_{ks}$A$_{ks}$T$_{ds}$ G**$_{dXIII}$** T**$_{dXIII}$**$^m$C$_{ds}$T$_{ds}$$^m$C$_{ds}$A$_{ds}$$^m$C$_{ds}$A$_{ds}$T$_{ks}$T$_{ks}$A$_k$ | 113 | 168 | 5 |
| 1429191 | G$_{ks}$$^m$C$_{ks}$A$_{ks}$T$_{ds}$G$_{ds}$T**$_{dXIII}$** T**$_{dXIII}$**$^m$C$_{ds}$T$_{ds}$$^m$C$_{ds}$A$_{ds}$$^m$C$_{ds}$A$_{ds}$T$_{ks}$T$_{ks}$A$_k$ | 111 | 184 | 5 |
| 1429192 | G$_{ks}$$^m$C$_{ks}$A$_{ks}$T$_{ds}$G$_{ds}$T$_{ds}$T$_{ds}$$^m$C$_{ds}$T$_{ds}$$^m$ **C$_{dXIII}$** A**$_{dXIII}$**$^m$C$_{ds}$A$_{ds}$T$_{ks}$T$_{ks}$A$_k$ | 46 | 1004 | 5 |
| 1417948 | G$_{ks}$$^m$C$_{ks}$A$_{ks}$T**$_{dXIV}$**G**$_{dXIV}$**T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 98 | 1270 | 5 |
| 1417947 | G$_{ks}$$^m$C$_{ks}$A$_{ks}$T$_{ds}$ G**$_{dXIV}$** T**$_{dXIV}$**T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 141 | 271 | 5 |
| 1417946 | G$_{ks}$$^m$C$_{ks}$A$_{ks}$T$_{ds}$G$_{ds}$T**$_{dXIV}$** T**$_{dXIV}$**$^m$C$_{ds}$T$_{ds}$$^m$C$_{ds}$A$_{ds}$$^m$C$_{ds}$A$_{ds}$T$_{ks}$T$_{ks}$A$_k$ | 128 | 232 | 5 |
| 1417945 | G$_{ks}$$^m$C$_{ks}$A$_{ks}$T$_{ds}$G$_{ds}$T$_{ds}$T$_{ds}$$^m$C$_{ds}$T$_{ds}$$^m$**C$_{dXIV}$** A**$_{dXIV}$**$^m$C$_{ds}$A$_{ds}$T$_{ks}$T$_{ks}$A$_k$ | 276 | 951 | 5 |
| 1431805 | G$_{ks}$$^m$C$_{ks}$A$_{ks}$T**$_{dXV}$** G**$_{dXV}$**T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 299 | 235 | 5 |
| 1431806 | G$_{ks}$$^m$C$_{ks}$A$_{ks}$T$_{ds}$G**$_{dXV}$** T**$_{dXV}$**$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 152 | 137 | 5 |
| 1431807 | G$_{ks}$$^m$C$_{ks}$A$_{ks}$T$_{ds}$G$_{ds}$T**$_{dXV}$** T**$_{dXV}$**$^m$C$_{ds}$T$_{ds}$$^m$C$_{ds}$A$_{ds}$$^m$C$_{ds}$A$_{ds}$T$_{ks}$T$_{ks}$A$_k$ | 243 | 119 | 5 |
| 1431808 | G$_{ks}$$^m$C$_{ks}$A$_{ks}$T$_{ds}$G$_{ds}$T$_{ds}$T$_{ds}$$^m$C$_{ds}$T$_{ds}$$^m$**C$_{dXV}$** A**$_{dXV}$**$^m$C$_{ds}$A$_{ds}$T$_{ks}$T$_{ks}$A$_k$ | 114 | 556 | 5 |

A subscript "k" represents a cEt nucleoside, a subscript "d" represents a stereo-standard DNA nucleoside, a subscript "s" indicates a phosphorothioate internucleoside linkage. A subscript "XIII" represents an internucleoside linkage of formula XIII; a subscript "XIV" represents an internucleoside linkage of formula XIV; a subscript "XV" represents an internucleoside linkage of formula XV. Subscripts of nucleotides having a modified mesyl phosphoramidate internucleoside linkage of generic Formula XVII are bold and underlined. A superscript "m" before a C represents a 5-methyl Cytosine.

TABLE 21

Design, Activity, and Tolerability of modified oligonucleotides having modified phosphoramidate linkages of formula XVI complementary to CXCL12

| Compound Number | Chemistry Notation (5'-3') | CXCL12 IC$_{50}$ (nM) | Caspase Activation (% Mock) | SEQ ID NO. |
|---|---|---|---|---|
| 558807 | G$_{ks}$$^m$C$_{ks}$A$_{ks}$T$_{ds}$G$_{ds}$T$_{ds}$T$_{ds}$$^m$C$_{ds}$T$_{ds}$$^m$C$_{ds}$A$_{ds}$$^m$CdA$_{ds}$T$_{ks}$T$_{ks}$A$_k$ | 98* | 1026 | 5 |
| 1431745 | G$_{ks}$$^m$C$_{ks}$A$_{ks}$T**$_{dXVI}$**G**$_{dXVI}$**T$_{ds}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 82 | 786 | 5 |
| 1431746 | G$_{ks}$$^m$C$_{ks}$A$_{ks}$T$_{ds}$G**$_{dXVI}$**T**$_{dXVI}$**$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 139 | 344 | 5 |

TABLE 21-continued

| Design, Activity, and Tolerability of modified oligonucleotides having modified phosphoramidate linkages of formula XVI complementary to CXCL12 | | | | |
|---|---|---|---|---|
| Compound Number | Chemistry Notation (5'-3') | CXCL12 $IC_{50}$ (nM) | Caspase Activation (% Mock) | SEQ ID NO. |
| 1431747 | $G_{ks}{}^{m}C_{ks}A_{ks}T_{ds}G_{ds}\mathbf{T}_{\underline{dXVI}}\mathbf{T}_{\underline{dXVI}}{}^{m}C_{ds}T_{ds}{}^{m}C_{ds}A_{ds}{}^{m}C_{ds}A_{ds}T_{ks}T_{ks}A_{k}$ | 137 | 317 | 5 |
| 1431748 | $G_{ks}{}^{m}C_{ks}A_{ks}T_{ds}G_{ds}T_{ds}T_{ds}{}^{m}C_{ds}T_{ds}{}^{m}\mathbf{C}_{\underline{dXVI}}\mathbf{A}_{\underline{dXVI}}{}^{m}C_{ds}A_{ds}T_{ks}T_{ks}A_{k}$ | 82 | 1157 | 5 |

*historical data; not determined in this experiment.

A subscript "k" represents a cEt nucleoside, a subscript "d" represents a stereo-standard DNA nucleoside, a subscript "s" indicates a phosphorothioate internucleoside linkage. A subscript "XVI" represents an internucleoside linkage of formula XVI. Subscripts of nucleotides having a substituted phosphoramidate internucleoside linkage of generic Formula XVII are bold and underlined. A superscript "m" before a C represents a 5-methyl Cytosine.

Example 11: Design and Protein Upregulation Activity of Uniformly 2'-Modified Oligonucleotides Having Mesyl Phosphoramidate Internucleoside Linkages In Vitro

Modified Oligonucleotides

Modified oligonucleotides comprising multiple mesyl phosphoramidate internucleoside linkages (Formula IX) were synthesized and tested. The modified oligonucleotides are uniform 2'-OMe modified oligonucleotides. Each of the modified oligonucleotides has the same nucleobase sequence, TGCAGTGGGGTGATTT (SEQ ID NO: 18), which is 100% complementary to human LDLR mRNA GenBank NM_000527.4. (SEQ ID NO: 19), at position 28 to 43. Each internucleoside linkage is either a phosphorothioate internucleoside linkage ("s") or a mesyl phosphoramidate internucleoside linkage ("z").

IX

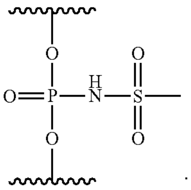

Protein Upregulation

Modified oligonucleotides were tested for their ability to upregulate LDLR protein after transfection in HeLa cells. Compound No. 842196 is a uniform 2'-OMe/phosphorothioate oligonucleotide that upregulates expression of LDLR (Liang, et. al., Nucleic Acids Research 2017). Cells were transfected using 25 nM of modified oligonucleotide and Lipofectamine® 2000 (Invitrogen) for 16 hours. Cells were harvested and LDLR protein was quantified using the Quantikine ELISA Human LDLR Kit (Biotechne, Catalog Number: DLDLR0), normalized to the expression level of untreated control cells. The results show that modified oligonucleotides comprising mesyl phosphoramidate linkages at the 5' end are more effective than a full phosphorothioate counterpart for the upregulation of LDLR.

TABLE 22

| Design and Activity (protein upregulation) of modified oligonucleotides having mesyl phosphoramidate linkages of formula IX complementary to LDLR | | | |
|---|---|---|---|
| Compound Number | Chemistry Notation (5'-3') | Relative LDLR Protein Level | SEQ ID NO. |
| 842196 | $U_{ys}G_{ys}C_{ys}A_{ys}G_{ys}U_{ys}G_{ys}G_{ys}G_{ys}G_{ys}U_{ys}G_{ys}A_{ys}U_{ys}U_{ys}U_{y}$ | 189 | 20 |
| 1405447 | $U_{\underline{\mathbf{yz}}}G_{\underline{\mathbf{yz}}}C_{\underline{\mathbf{yz}}}A_{\underline{\mathbf{yz}}}G_{\underline{\mathbf{yz}}}U_{\underline{\mathbf{yz}}}G_{\underline{\mathbf{yz}}}G_{\underline{\mathbf{yz}}}G_{\underline{\mathbf{yz}}}G_{\underline{\mathbf{yz}}}U_{\underline{\mathbf{yz}}}G_{\underline{\mathbf{yz}}}A_{\underline{\mathbf{yz}}}U_{\underline{\mathbf{yz}}}U_{\underline{\mathbf{yz}}}U_{\underline{y}}$ | 146 | 20 |
| 1405546 | $U_{\underline{\mathbf{yz}}}G_{\underline{\mathbf{yz}}}C_{\underline{\mathbf{yz}}}A_{\underline{\mathbf{yz}}}G_{\underline{\mathbf{yz}}}U_{\underline{\mathbf{yz}}}G_{ys}G_{ys}G_{ys}G_{ys}U_{ys}G_{ys}A_{ys}U_{ys}U_{ys}U_{y}$ | 235 | 20 |
| 1405547 | $U_{ys}G_{ys}C_{ys}A_{ys}G_{ys}U_{\underline{\mathbf{yz}}}G_{\underline{\mathbf{yz}}}G_{\underline{\mathbf{yz}}}G_{\underline{\mathbf{yz}}}G_{\underline{\mathbf{yz}}}U_{\underline{\mathbf{yz}}}G_{ys}A_{ys}U_{ys}U_{ys}U_{y}$ | 181 | 20 |
| 1405548 | $U_{ys}G_{ys}C_{ys}A_{ys}G_{ys}U_{ys}G_{ys}G_{ys}G_{ys}G_{\underline{\mathbf{yz}}}U_{\underline{\mathbf{yz}}}G_{\underline{\mathbf{yz}}}A_{\underline{\mathbf{yz}}}U_{\underline{\mathbf{yz}}}U_{\underline{\mathbf{yz}}}U_{y}$ | 133 | 20 |

A subscript "y" represents a 2'-OMe modified nucleoside, a subscript "s" indicates a phosphorothioate internucleoside linkage, a subscript "z" represents an internucleoside linkage of formula IX, which is a mesyl phosphoramidate linkage. Subscripts of nucleotides having a phosphoramidate internucleoside linkage of generic Formula XVII are bold and underlined. A superscript "m" before a C represents a 5-methyl Cytosine.

Example 12: Design and Activity of siRNA to HRPT1 Having Mesyl Phosphoramidate Internucleoside Linkages in Vitro siRNA

Double-stranded siRNA comprising modified oligonucleotides having mesyl phosphoramidate internucleoside linkages (Formula IX) in the sense and/or antisense strands were synthesized and tested. Each internucleoside linkage is either a phosphorothioate internucleoside linkage ("s"), a phosphodiester internucleoside linkage ("o"), or a mesyl phosphoramidate internucleoside linkage ("z") indicated by formula IX below.

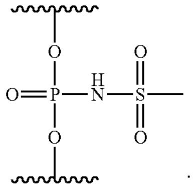

IX

Each antisense strand has the sequence AUAAAAUCUACAGUCAUAGGAAU (SEQ ID NO: 21) and is 100% complementary to GenBank NM_000194.2 (SEQ ID NO: 22) from 444 to 466, and each antisense strand has a 5'-phosphate. Each sense strand has the sequence UCCUAUGACUGUAGAUUUUAU (SEQ ID NO: 23) and is 100% identical to GenBank NM_000194.2 (SEQ ID NO: 22) from 446 to466. Compound No. 1151789 further comprises a 3'-linked $C_7$ amino modifier (Glen Research), shown below:

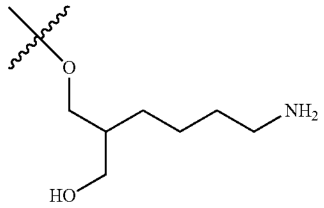 [SMILES: *OCC(CO)CCCCN]

TABLE 23

Design of antisense strand modified oligonucleotides targeted to human/mouse HRPT1 having mesyl phosphoramidate linkages

| Compound ID | Chemical Notation (5' to 3') | SEQ ID NO: |
|---|---|---|
| 1073762 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}Af_{s}U_{y}$ | 21 |
| 1405420 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}\mathbf{A}_{\underline{yz}}\mathbf{U}_{\underline{fz}}U_{y}$ | 21 |
| 1405427 | p.$\mathbf{A}_{\underline{yz}}\mathbf{U}_{\underline{fz}}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{yo}A_{fo}U_{y}$ | 21 |
| 1405428 | p.$\mathbf{A}_{\underline{yz}}\mathbf{U}_{\underline{fz}}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}\mathbf{A}_{\underline{yz}}\mathbf{U}_{\underline{fz}}U_{y}$ | 21 |

A "p." represents a 5'-phosphate. A subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage, a subscript "z" represents an internucleoside linkage of formula IX, which is a mesyl phosphoramidate linkage. Subscripts of nucleotides having a phosphoramidate internucleoside linkage of generic Formula XVII are bold and underlined. A superscript "m" before a C represents a 5-methyl Cytosine.

TABLE 24

Design of sense strand modified oligonucleotides targeted to human/mouse HRPT1 having mesyl phosphoramidate linkages

| Compound ID | Chemical Notation (5' to 3') | SEQ ID NO: |
|---|---|---|
| 1151789 | $U_{fo}C_{yo}C_{fo}U_{yo}A_{fo}U_{yo}G_{fo}A_{yo}C_{fo}U_{yo}G_{fo}U_{yo}A_{fo}G_{yo}A_{fo}U_{yo}U_{fo}U_{yo}U_{fo}A_{yo}U_{fo}$ [3'-amino C7 Tag] | 23 |
| 1405429 | $U_{fo}C_{yo}C_{fo}U_{yo}A_{fo}U_{yo}G_{fo}A_{yo}C_{fo}U_{yo}G_{fo}U_{yo}A_{fo}G_{yo}A_{fo}U_{yo}U_{fo}U_{yo}\mathbf{U}_{\underline{fz}}\mathbf{A}_{\underline{yz}}U_{f}$ | 23 |
| 1405430 | $\mathbf{U}_{\underline{fz}}\mathbf{C}_{\underline{yz}}C_{fo}U_{yo}A_{fo}U_{yo}G_{fo}A_{yo}C_{fo}U_{yo}G_{fo}U_{yo}A_{fo}G_{yo}A_{fo}U_{yo}U_{fo}U_{yo}U_{fo}A_{yo}U_{f}$ | 23 |
| 1405431 | $\mathbf{U}_{\underline{fz}}\mathbf{C}_{\underline{yz}}C_{fo}U_{yo}A_{fo}U_{yo}G_{fo}A_{yo}C_{fo}U_{yo}G_{fo}U_{yo}A_{fo}G_{yo}A_{fo}U_{yo}U_{fo}U_{yo}\mathbf{U}_{\underline{fz}}\mathbf{A}_{\underline{yz}}U_{f}$ | 23 |

A subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage, a subscript "z" represents an internucleoside linkage of formula IX, which is a mesyl phosphoramidate linkage. Subscripts of nucleotides having a phosphoramidate internucleoside linkage of generic Formula XVII are bold and underlined. A superscript "m" before a C represents a 5-methyl Cytosine.

Activity Assay

Activity of various siRNA formed by annealing one antisense strand and one sense strand described above was tested in HeLa cells. HeLa cells were transfected with 6 µL/mL of siRNA using RNAiMAX for 5 hours. RNA was isolated and RNA expression was analyzed via RT-qPCR using primer probe set Hs02800695_m1(ThermoFisher). Incorporation of mesyl phosphoramidate linkages into the 3' end of the antisense strand and into either or both the 3' and 5' ends of the sense strand of siRNA does not lead to a reduction in activity.

TABLE 25

Activity of siRNAs having mesyl phosphoramidate linkages against human HPRT1

| Antisense Strand | Sense Strand | Linkage mod. position in antisense strand | Linkage mod. position in sense strand | IC50 (nM) |
|---|---|---|---|---|
| 1073762 | 1151789 | n/a | n/a | 0.091 |
| 1405420 | 1405429 | 3’ | 3’ | 0.085 |
| 1405420 | 1405430 | 3’ | 5’ | 0.065 |
| 1405420 | 1405431 | 3’ | 3’ and 5’ | 0.066 |
| 1405427 | 1405429 | 5’ | 3’ | 0.457 |
| 1405427 | 1405430 | 5’ | 5’ | 0.831 |
| 1405427 | 1405431 | 5’ | 3’ and 5’ | 1.391 |
| 1405428 | 1405429 | 3’ and 5’ | 3’ | 1.19 |
| 1405428 | 1405430 | 3’ and 5’ | 5’ | 0.816 |
| 1405428 | 1405431 | 3’ and 5’ | 3’ and 5’ | 0.934 |

Example 13: Design and Activity of siRNA to Human/Mouse PTEN Having Mesyl Phosphoramidate Internucleoside Linkages In Vitro siRNA Single-stranded siRNA and double-stranded siRNA comprising modified oligonucleotides having mesyl phosphoramidate internucleoside linkages (Formula IX) in the antisense strands were synthesized and tested. Each internucleoside linkage is either a phosphorothioate internucleoside linkage (“s”), a phosphodiester internucleoside linkage (“o”), or a mesyl phosphoramidate internucleoside linkage (“z”), indicated by formula IX below.

IX

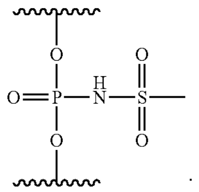

Each antisense strand has the sequence TUAUCUAUAAUGAUCAGGUAA (SEQ ID NO: 24) and has three mismatches to PTEN cDNA, the cDNA of ENSEMBL Accession No. ENST00000371953.8 from ENSEMBL version 99: January 2020, human reference assembly version GRCh38.p13 located on the forward strand of chromosome 10 (CM000682.2) from positions 87,863,625 to 87,971,930 (SEQ ID NO: 26) from 1962 to 1982, and each antisense strand has a 5'-phosphate. For double-stranded siRNA, the sense strand 790973 has the sequence ACCUGAUCAUUAUAGAUAA (SEQ ID NO: 25) and has one mismatch to the cDNA of ENSEMBL Accession No.

ENST00000371953.8 from ENSEMBL version 99: January 2020, human reference assembly version GRCh38.p13 located on the forward strand of chromosome 10 (CM000682.2) from positions 87,863,625 to 87,971,930 (SEQ ID NO: 26) from 1964 to 1982. Each internucleoside linkage of the sense strand is either a phosphodiester internucleoside linkage (“o”) or a phosphorothioate internucleoside linkage (“s”), and the sense strand has the chemical notation (5' to 3'): $A_{fs}C_{ys}C_{fo}U_{yo}G_{fo}A_{yo}U_{fo}C_{yo}A_{fo}U_{yo}U_{fo}A_{yo}U_{fo}A_{yo}G_{fo}A_{yo}U_{fs}A_{ys}A_{f}$ (SEQ ID ON: 25).

TABLE 26

Design of antisense strand modified oligonucleotides targeted to PTEN having mesyl phosphoramidate linkages

| Compound ID | Chemical Notation (5' to 3') | SEQ ID NO: |
|---|---|---|
| 456963 | p.$T_{es}U_{fs}A_{yo}U_{fs}C_{yo}U_{fs}A_{yo}U_{fs}A_{yo}A_{fs}U_{yo}G_{fs}A_{yo}U_{fs}C_{ys}A_{fs}G_{ys}G_{fs}U_{ys}A_{es}A_{e}$ | 24 |
| 1421366 | p.$T_{\underline{ez}}U_{\underline{fz}}A_{yo}U_{fs}C_{yo}U_{fs}A_{yo}U_{fs}A_{yo}A_{fs}U_{yo}G_{fs}A_{yo}U_{fs}C_{ys}A_{fs}G_{ys}G_{fs}U_{ys}A_{es}A_{e}$ | 24 |
| 1439694 | p.$T_{es}U_{f}A_{\underline{yz}}U_{\underline{fz}}C_{yo}U_{fs}A_{yo}U_{fs}A_{yo}A_{fs}U_{yo}G_{fs}A_{yo}U_{fs}C_{ys}A_{fs}G_{ys}G_{fs}U_{ys}A_{es}A_{e}$ | 24 |
| 1440988 | P.$T_{es}U_{fs}A_{yo}U_{fs}C_{\underline{yz}}U_{\underline{fz}}A_{yo}U_{fs}A_{yo}A_{fs}U_{yo}G_{fs}A_{yo}U_{fs}C_{ys}A_{fs}G_{ys}G_{fs}U_{ys}A_{es}A_{e}$ | 24 |
| 1440992 | P.$T_{es}U_{fs}A_{yo}U_{fs}C_{yo}U_{f}A_{\underline{yz}}U_{\underline{fz}}A_{yo}A_{fs}U_{yo}G_{fs}A_{yo}U_{fs}C_{ys}A_{fs}G_{ys}G_{fs}U_{ys}A_{es}A_{e}$ | 24 |
| 1440993 | p.$T_{es}U_{fs}A_{yo}U_{fs}C_{yo}U_{fs}A_{yo}U_{f}A_{\underline{yz}}A_{\underline{fz}}U_{yo}G_{fs}A_{yo}U_{fs}C_{ys}A_{fs}G_{ys}G_{fs}U_{ys}A_{es}A_{e}$ | 24 |
| 1440994 | p.$T_{es}U_{fs}A_{yo}U_{fs}C_{yo}U_{fs}A_{yo}U_{f}U_{\underline{yz}}G_{\underline{fz}}A_{yo}A_{fs}A_{yo}U_{fs}C_{ys}A_{fs}G_{ys}G_{fs}U_{ys}A_{es}A_{e}$ | 24 |
| 1440995 | p.$T_{es}U_{fs}A_{yo}U_{fs}C_{yo}U_{fs}A_{yo}U_{fs}A_{yo}A_{fs}U_{yo}G_{f}A_{\underline{yz}}U_{\underline{fz}}C_{ys}A_{fs}G_{ys}G_{fs}U_{ys}A_{es}A_{e}$ | 24 |
| 1441021 | P.$T_{es}U_{fs}A_{yo}U_{fs}C_{yo}U_{fs}A_{yo}U_{fs}A_{yo}A_{fs}U_{yo}G_{fs}A_{yo}U_{fs}C_{\underline{yz}}A_{\underline{fz}}G_{ys}G_{fs}U_{ys}A_{es}A_{e}$ | 24 |

TABLE 26-continued

| Design of antisense strand modified oligonucleotides targeted to PTEN having mesyl phosphoramidate linkages | | |
|---|---|---|
| Compound ID | Chemical Notation (5' to 3') | SEQ ID NO: |
| 1441022 | P.$T_{es}U_{fs}A_{yo}U_{fs}C_{yo}U_{fs}A_{yo}U_{fs}A_{yo}A_{fs}U_{yo}G_{fs}A_{yo}U_{fs}C_{ys}A_{f}G_{\underline{\mathbf{yz}}}$ $G_{\underline{\mathbf{fz}}}U_{ys}A_{es}A_{e}$ | 24 |
| 1441023 | P.$T_{es}U_{fs}A_{yo}U_{fs}C_{yo}U_{fs}A_{yo}U_{fs}A_{yo}A_{fs}U_{yo}G_{fs}A_{yo}U_{fs}C_{ys}A_{fs}G_{ys}G_{f}U_{\underline{\mathbf{yz}}}$ $A_{\underline{\mathbf{ez}}}A_{e}$ | 24 |

A "p." represents a 5'-phosphate. A subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage, a subscript "z" represents an internucleoside linkage of formula IX, which is a mesyl phosphoramidate linkage. Subscripts of nucleotides having a phosphoramidate internucleoside linkage of generic Formula XVII are bold and underlined. A superscript "m" before a C represents a 5-methyl Cytosine.

Activity Assay

Activity of various siRNA formed by annealing one antisense strand and one sense strand described above was tested in HeLa cells. HeLa cells were transfected with 6 µL/mL of siRNA using RNAiMAX for 6 hours. RNA was isolated and RNA expression was analyzed via RT-qPCR using primer probe set Hs02800695_m1(ThermoFisher).

TABLE 27

| Activity of double-stranded siRNAs having mesyl phosphoramidate linkages against human PTEN | | | |
|---|---|---|---|
| Antisense Strand | Sense Strand | Linkage mod. position in antisense strand | IC50 (nM) |
| 456963 | 790973 | N/A | 0.98 |
| 1421366 | 790973 | Positions 1-2, 2-3 | 2.87 |
| 1439694 | 790973 | Positions 3-4, 4-5 | 2.89 |
| 1440988 | 790973 | Positions 5-6, 6-7 | >10 |
| 1440992 | 790973 | Positions 7-8, 8-9 | 2.17 |
| 1440993 | 790973 | Positions 9-10, 10-11 | 0.84 |
| 1440994 | 790973 | Positions 11-12, 12-13 | >10 |
| 1440995 | 790973 | Positions 13-14, 14-15 | 10.00 |
| 1441021 | 790973 | Positions 15-16, 16-17 | 10.00 |
| 1441022 | 790973 | Positions 17-18, 18-19 | 1.24 |
| 1441023 | 790973 | Positions 19-20, 20-21 | 2.41 |

Example 14: Design of siRNA to SOD-1 Having a $C_{16}$ Modified-Phosphoramidate Internucleoside Linkage Double-stranded siRNA comprising a modified oligonucleotide having a mesyl phosphoramidate internucleoside linkages of Formula XIX in the sense strand was synthesized and tested in vitro.

For the sense strand, each internucleoside linkage is either a phosphorothioate internucleoside linkage ("s"), a phosphodiester internucleoside linkage ("o"), or a modified phosphoramidate internucleoside linkage ("XIX"), as shown below.

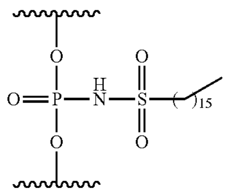

XIX

The sense strand has the chemical notation (5' to 3'): $C_{ys}A_{ys}U_{ys}U_{ys}U_{ys}U_{yXIX}A_{fo}A_{yo}U_{fo}C_{fo}C_{fo}U_{yo}C_{yo}A_{yo}C_{yo}U_{yo}$-$C_{yo}U_{yo}A_{ys}A_{ys}A_{y}$, (SEQ ID NO: 30) wherein a subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage, and a subscript XIX represents an internucleoside linkage of Formula XIX.

The antisense strand has a 5'-vinyl phosphonate (vP). Each internucleoside linkage of the antisense strand is either a phosphodiester internucleoside linkage ("o") or a phosphorothioate internucleoside linkage ("s"). The antisense strand has the chemical notation (5' to 3'): vP-$U_{yo}U_{fo}U_{yo}A_{yo}G_{yo}A_{fo}G_{yo}U_{fo}G_{fo}A_{yo}G_{yo}G_{yo}A_{yo}U_{fo}U_{yo}$ $A_{fo}A_{yo}A_{yo}A_{yo}U_{yo}G_{y}A_{ys}A_{y}$ (SEQ ID NO: 31), wherein a subscript "f" represents a 2'-F modified nucleoside, a subscript "y" represents a 2'-OMe modified nucleoside, a subscript "s" indicates a phosphorothioate internucleoside linkage and a subscript "o" represents a phosphodiester internucleoside linkage.

Example 15: Tolerability of Modified Oligonucleotides Having Mesyl Phosphoramidate Internucleoside Linkages in Vivo in Wild-Type Mice Modified Oligonucleotides Modified oligonucleotides comprising multiple mesyl phosphoramidate internucleoside linkages (Formula IX) were synthesized and tested. The modified oligonucleotides are each 5-10-5 MOE gapmers with a sugar motif of: eeeeeddddddddddeeeee where "e" represents a 2'-MOE modified sugar moiety, and "d" represents a β-D-2'-deoxyribosyl sugar moiety. The modified oligonucleotides are 100% complementary to human MAPT, GENBANK accession number NT_010783.15 truncated from 9240000 to 9381000 (SEQ ID NO: 32).

Each internucleoside linkage is a phosphorothioate interucleoside linkage ("s"), a phosphodiester internucleoside linkage ("o") or a mesyl phosphoramidate internucleoside linkage ("z"), as indicated in the table below.

Oligonucleotides described above were tested in wild-type female $C_{57}$/B16 mice to assess the tolerability of the oligonucleotides. Wild-type female $C_{57}$/B16 mice each received a single IC dose of700 μg of modified oligonucleotide listed in the table below. Each treatment group consisted of 2 mice. A group of 2 mice received PBS as a negative control. At 3 hours post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse. The results are presented in the table below. Oligonucleotides comprising mesyl phosphoramidate internucleoside linkages have similar tolerability in the mouse CNS as the parent oligonucleotide. Oligonucleotides having mesyl terminal phosphoramidate linkages as well as two mesyl phosphoramidate linkages in the deoxy region have improved CNS tolerability.

Example 16: Design, Activity and Tolerability of Modified Oligonucleotides Having Various Mesyl Phosphoramidate Internucleoside Linkages In Vitro

Modified Oligonucleotides

Modified oligonucleotides comprising multiple mesyl phosphoramidate internucleoside linkages (Formula IX), phosphorothioate internucleoside linkages, and phosphodiester internucleoside linkages, were synthesized and tested. The modified oligonucleotides are each 3-10-3 cEt gapmers with a sugar motif of kkkddddddddddkkk (a 3-10-3 cEt motif) where "k" represents a cEt modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT 039353.7 truncated from 69/430,515 to 69/445,350 (SEQ ID NO: 1), at position 6877 to 6892. Each internucleoside linkage is either a phosphorothioate internucleoside linkage (" ", a phosphodiester internucleoside linkage ("o"), or a mesyl phosphoramidate internucleoside linkage ("z").

In Vitro Assays

In vitro activity of modified oligonucleotides described above was determined as described in Example 1. In vitro toxicity of modified oligonucleotides described above was determined as described in Example 3. The internucleoside linkages of the modified nucleosides are indicated in subscripts in the table below.

TABLE 28

CNS Tolerability of modified oligonucleotides containing mesyl phosphoramidate linkages

| Compound ID | Chemical Notation (5' to 3') | SEQ ID NO: | 3 hour FOB |
|---|---|---|---|
| 613039 | $T_{es}G_{eo}{}^{m}C_{eo}A_{eo}T_{eo}G_{ds}G_{ds}T_{ds}G_{ds}T_{ds}A_{ds}G_{ds}{}^{m}C_{ds}{}^{m}C_{ds}{}^{m}C_{ds}{}^{m}C_{eo}{}^{m}C_{eo}{}^{m}C_{es}T_{es}G_{e}$ | 27 | 6, 6 |
| 1405498 | $T_{es}G_{eo}{}^{m}C_{eo}A_{eo}T_{eo}\mathbf{G}_{\underline{\mathbf{dz}}}\mathbf{G}_{\underline{\mathbf{dz}}}T_{ds}G_{ds}T_{ds}A_{ds}G_{ds}{}^{m}C_{ds}{}^{m}C_{ds}{}^{m}C_{ds}{}^{m}C_{eo}{}^{m}C_{eo}{}^{m}C_{es}T_{es}G_{e}$ | 27 | 6, 6 |
| 1405499 | $T_{es}G_{eo}{}^{m}C_{eo}A_{eo}T_{eo}G_{ds}\mathbf{G}_{\underline{\mathbf{dz}}}\mathbf{T}_{\underline{\mathbf{dz}}}G_{ds}T_{ds}A_{ds}G_{ds}{}^{m}C_{ds}{}^{m}C_{ds}{}^{m}C_{ds}{}^{m}C_{eo}{}^{m}C_{eo}{}^{m}C_{es}T_{es}G_{e}$ | 27 | 6, 6 |
| 1405500 | $T_{es}G_{eo}{}^{m}C_{eo}A_{eo}T_{eo}G_{ds}G_{ds}\mathbf{T}_{\underline{\mathbf{dz}}}\mathbf{G}_{\underline{\mathbf{dz}}}T_{ds}A_{ds}G_{ds}{}^{m}C_{ds}{}^{m}C_{ds}{}^{m}C_{ds}{}^{m}C_{eo}{}^{m}C_{eo}{}^{m}C_{es}T_{es}G_{e}$ | 27 | 6, 7 |
| 1405501 | $T_{es}G_{eo}{}^{m}C_{eo}A_{eo}T_{eo}G_{ds}G_{ds}T_{ds}G_{ds}T_{ds}A_{ds}\mathbf{G}_{\underline{\mathbf{dz}}}{}^{m}\mathbf{C}_{\underline{\mathbf{dz}}}{}^{m}C_{ds}{}^{m}C_{ds}{}^{m}C_{eo}{}^{m}C_{eo}{}^{m}C_{es}T_{es}G_{e}$ | 27 | 5, 5 |
| 1421514 | $\mathbf{T}_{\underline{\mathbf{ez}}}G_{eo}{}^{m}C_{eo}A_{eo}T_{eo}G_{ds}G_{ds}T_{ds}G_{ds}T_{ds}A_{ds}G_{ds}{}^{m}C_{ds}{}^{m}C_{ds}{}^{m}C_{ds}{}^{m}C_{eo}{}^{m}C_{eo}{}^{m}\mathbf{C}_{\underline{\mathbf{ez}}}\mathbf{T}_{\underline{\mathbf{ez}}}G_{e}$ | 27 | 6, 5 |
| 1421517 | $\mathbf{T}_{\underline{\mathbf{ez}}}G_{eo}{}^{m}C_{eo}A_{eo}T_{eo}G_{ds}\mathbf{G}_{\underline{\mathbf{dz}}}\mathbf{T}_{\underline{\mathbf{dz}}}G_{ds}T_{ds}A_{ds}G_{ds}{}^{m}C_{ds}{}^{m}C_{ds}{}^{m}C_{ds}{}^{m}C_{eo}{}^{m}C_{eo}{}^{m}\mathbf{C}_{\underline{\mathbf{ez}}}\mathbf{T}_{\underline{\mathbf{ez}}}G_{e}$ | 27 | 4, 4 |
| 613369 | $G_{es}T_{eo}T_{eo}T_{eo}T_{eo}{}^{m}C_{ds}A_{ds}A_{ds}A_{ds}{}^{m}C_{ds}A_{ds}{}^{m}C_{ds}A_{ds}{}^{m}C_{ds}{}^{m}C_{ds}T_{eo}T_{eo}{}^{m}C_{es}A_{es}T_{e}$ | 28 | 0, 0 |
| 1405502 | $G_{es}T_{eo}T_{eo}T_{eo}T_{eo}{}^{m}\mathbf{C}_{\underline{\mathbf{dz}}}\mathbf{A}_{\underline{\mathbf{dz}}}A_{ds}A_{ds}{}^{m}C_{ds}A_{ds}{}^{m}C_{ds}A_{ds}{}^{m}C_{ds}{}^{m}C_{ds}T_{eo}T_{eo}{}^{m}C_{es}A_{es}T_{e}$ | 28 | 0, 0 |
| 1405503 | $G_{es}T_{eo}T_{eo}T_{eo}T_{eo}{}^{m}C_{ds}\mathbf{A}_{\underline{\mathbf{dz}}}\mathbf{A}_{\underline{\mathbf{dz}}}A_{ds}{}^{m}C_{ds}A_{ds}{}^{m}C_{ds}A_{ds}{}^{m}C_{ds}{}^{m}C_{ds}T_{eo}T_{eo}{}^{m}C_{es}A_{es}T_{e}$ | 28 | 1, 1 |
| 1405504 | $G_{es}T_{eo}T_{eo}T_{eo}T_{eo}{}^{m}C_{ds}A_{ds}\mathbf{A}_{\underline{\mathbf{dz}}}\mathbf{A}_{\underline{\mathbf{dz}}}{}^{m}C_{ds}A_{ds}{}^{m}C_{ds}A_{ds}{}^{m}C_{ds}{}^{m}C_{ds}T_{eo}T_{eo}{}^{m}C_{es}A_{es}T_{e}$ | 28 | 1, 1 |
| 1405505 | $G_{es}T_{eo}T_{eo}T_{eo}T_{eo}{}^{m}C_{ds}A_{ds}A_{ds}A_{ds}{}^{m}C_{ds}A_{ds}{}^{m}\mathbf{C}_{\underline{\mathbf{dz}}}\mathbf{A}_{\underline{\mathbf{dz}}}{}^{m}C_{ds}{}^{m}C_{ds}T_{eo}T_{eo}{}^{m}C_{es}A_{es}T_{e}$ | 28 | 2, 2 |
| 1421518 | $\mathbf{G}_{\underline{\mathbf{dz}}}T_{eo}T_{eo}T_{eo}T_{eo}{}^{m}C_{ds}A_{ds}A_{ds}A_{ds}{}^{m}C_{ds}A_{ds}{}^{m}C_{ds}A_{ds}{}^{m}C_{ds}{}^{m}C_{ds}T_{eo}T_{eo}{}^{m}\mathbf{C}_{\underline{\mathbf{ez}}}\mathbf{A}_{\underline{\mathbf{ez}}}T_{e}$ | 28 | 0, 0 |
| 1421519 | $\mathbf{G}_{\underline{\mathbf{dz}}}T_{eo}T_{eo}T_{eo}T_{eo}{}^{m}C_{ds}\mathbf{A}_{\underline{\mathbf{dz}}}\mathbf{A}_{\underline{\mathbf{dz}}}A_{ds}{}^{m}C_{ds}A_{ds}{}^{m}C_{ds}A_{ds}{}^{m}C_{ds}{}^{m}C_{ds}T_{eo}T_{eo}{}^{m}\mathbf{C}_{\underline{\mathbf{ez}}}\mathbf{A}_{\underline{\mathbf{ez}}}T_{e}$ | 28 | 1, 1 |

A subscript "o" indicates a phosphodiester internucleoside linkage, a subscript "s" indicates a phosphorothioate internucleoside linkage, a subscript "z" represents an internucleoside linkage of formula IX, which is a mesyl phosphoramidate linkage. Subscripts of nucletides having a phosphoramidate internucleoside linkage of generic Formula XVII are bold and underlined. A superscript "m" before a C represents a 5-methyl Cytosine.

TABLE 29

Design, Activity, and Tolerability of modified oligonucleotides having multiple mesyl phosphoramidates linkages complementary to CXCL12

| Compound Number | Chemistry Notation (5'-3') | CXCL12 $IC_{50}$ (nM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 101 | 1223 | 5 |
| 1193271 | $G_{ko}{}^{m}C_{ko}A_{ko}T_{ds}G_{ds}T_{ds}T_{ds}{}^{m}C_{ds}T_{ds}{}^{m}C_{ds}A_{ds}{}^{m}C_{ds}A_{ds}T_{ko}T_{ko}A_{k}$ | 87 | 1966 | 5 |
| 1233817 | $G_{ks}{}^{m}C_{ko}A_{ko}T_{ds}G_{ds}T_{ds}T_{ds}{}^{m}C_{ds}T_{ds}{}^{m}C_{ds}A_{ds}{}^{m}C_{ds}A_{ds}T_{ko}T_{ks}A_{k}$ | 58 | 1712 | 5 |
| 1467836 | $\mathbf{G}_{\underline{\mathbf{kz}}}{}^{m}C_{ko}A_{ko}T_{ds}G_{ds}T_{ds}T_{ds}{}^{m}C_{ds}T_{ds}{}^{m}C_{ds}A_{ds}{}^{m}C_{ds}A_{ds}T_{ko}\ T_{\underline{\mathbf{kz}}}A_{k}$ | 100 | 1595 | 5 |
| 1467198 | $\mathbf{G}_{\underline{\mathbf{kz}}}{}^{m}C_{ko}A_{ko}T_{ds}G_{ds}T_{ds}T_{ds}{}^{m}C_{ds}T_{ds}{}^{m}C_{ds}A_{ds}{}^{m}C_{ds}A_{do}T_{ko}\ T_{\underline{\mathbf{kz}}}A_{k}$ | 77 | 1733 | 5 |
| 1467199 | $\mathbf{G}_{\underline{\mathbf{kz}}}{}^{m}C_{kc}\mathbf{A}_{\underline{\mathbf{kz}}}T_{ds}G_{ds}T_{ds}T_{ds}{}^{m}C_{ds}T_{ds}{}^{m}C_{ds}A_{ds}{}^{m}C_{ds}\ \mathbf{A}_{\underline{\mathbf{dz}}}T_{ko}\ T_{\underline{\mathbf{kz}}}A_{k}$ | 63 | 1462 | 5 |
| 1467837 | $G_{ko}{}^{m}C_{ko}\ \mathbf{A}_{\underline{\mathbf{kz}}}T_{ds}G_{ds}T_{ds}T_{ds}{}^{m}C_{ds}T_{ds}{}^{m}C_{ds}A_{ds}{}^{m}C_{ds}\ \mathbf{A}_{\underline{\mathbf{dz}}}T_{ko}\ T_{\underline{\mathbf{kz}}}A_{k}$ | 72 | 1809 | 5 |
| 1467838 | $\mathbf{G}_{\underline{\mathbf{kz}}}{}^{m}C_{ko}A_{ko}T_{ds}\ \mathbf{G}_{\underline{\mathbf{dz}}}\ \mathbf{T}_{\underline{\mathbf{dz}}}T_{ds}{}^{m}C_{ds}T_{ds}{}^{m}C_{ds}A_{ds}{}^{m}C_{ds}A_{ds}T_{ko}\ T_{\underline{\mathbf{kz}}}A_{k}$ | 110 | 693 | 5 |
| 1467839 | $\mathbf{G}_{\underline{\mathbf{kz}}}{}^{m}C_{ko}A_{ks}T_{ds}\ \mathbf{G}_{\underline{\mathbf{dz}}}\ \mathbf{T}_{\underline{\mathbf{dz}}}T_{ds}{}^{m}C_{ds}T_{ds}{}^{m}C_{ds}A_{ds}{}^{m}C_{ds}A_{ds}T_{ko}\ T_{\underline{\mathbf{kz}}}A_{k}$ | 208 | 502 | 5 |
| 1467821 | $\mathbf{G}_{\underline{\mathbf{kz}}}{}^{m}C_{ko}A_{ks}T_{ds}\ \mathbf{G}_{\underline{\mathbf{dz}}}\ \mathbf{T}_{\underline{\mathbf{dz}}}T_{ds}{}^{m}C_{ds}T_{ds}{}^{m}C_{ds}A_{ds}{}^{m}C_{ds}A_{ds}T_{ko}\ T_{\underline{\mathbf{kz}}}A_{k}$ | 172 | 495 | 5 |
| 1467840 | $\mathbf{G}_{\underline{\mathbf{kz}}}{}^{m}C_{ko}A_{ko}\ \mathbf{T}_{\underline{\mathbf{dz}}}\ \mathbf{G}_{\underline{\mathbf{dz}}}\ \mathbf{T}_{\underline{\mathbf{dz}}}\ \mathbf{T}_{\underline{\mathbf{dz}}}{}^{m}C_{ds}T_{ds}{}^{m}C_{ds}A_{ds}{}^{m}C_{ds}\ \mathbf{A}_{\underline{\mathbf{dz}}}T_{ko}\ T_{\underline{\mathbf{kz}}}A_{k}$ | 152 | 654 | 5 |
| 1467841 | $\mathbf{G}_{\underline{\mathbf{kz}}}{}^{m}C_{ko}A_{ko}T_{ds}G_{ds}T_{ds}T_{ds}{}^{m}C_{ds}T_{ds}{}^{m}\mathbf{C}_{\underline{\mathbf{dz}}}\ \mathbf{A}_{\underline{\mathbf{dz}}}{}^{m}\mathbf{C}_{\underline{\mathbf{dz}}}\ \mathbf{A}_{\underline{\mathbf{dz}}}T_{ko}\ T_{\underline{\mathbf{kz}}}A_{k}$ | 132 | 1216 | 5 |

A subscript "k" represents a cEt nucleoside, a subscript "d" represents a stereostandard DNA nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Example 17: Activity and Tolerability of Modified Oligonucleotides with Mesyl Phosphoramidate Internucleoside Linkages In Vivo

Modified Oligonucleotides

GalNAc-conjugated modified oligonucleotides comprising multiple mesyl phosphoramidate internucleoside linkages (Formula IX) and phosphorothioate internucleoside linkages were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT 039353.7 truncated from 69/430,515 to 69/445,350 (SEQ ID NO: 1), at position 6877 to 6892. Each internucleoside linkage is either a phosphorothioate internucleoside linkage ("s"), a phosphodiester internucleoside linkage ("o"), or a mesyl phosphoramidate internucleoside linkage ("z").

The GalNAc moiety is conjugated to the 5' oxygen of the oligonucleotide via a THA linker, as shown below:

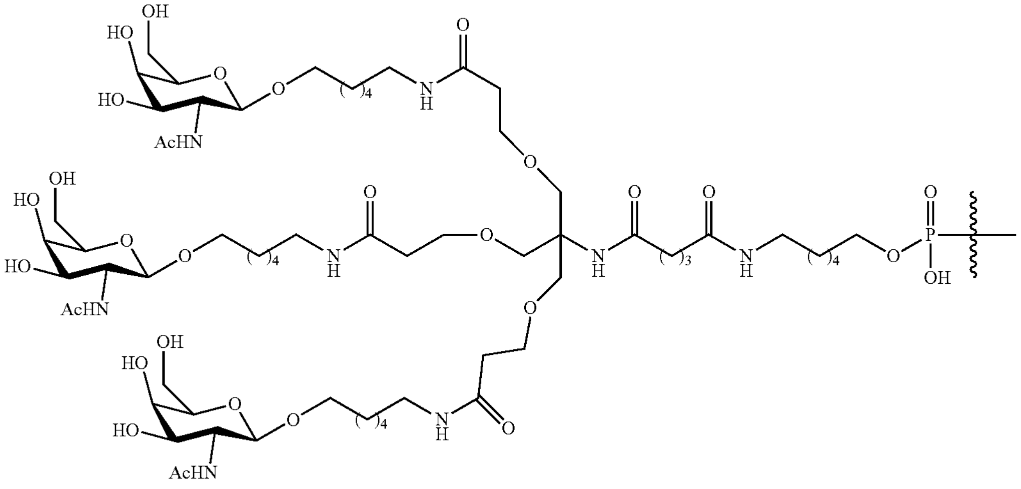

THA-GalNAc

In addition to compounds containing a mesyl phosphoramidate internucleoside linkage, a 3'-GalNAc conjugated version of Compound No. 936053 (1306456) was tested. This compound has the sequence GCATGTTCTCACATTA (SEQ ID NO: 5) and a sugar motif of kkk-d-m-ddddddddd-kkk, wherein each "k" represents a cEt nucleoside, each "d" represents a stereo-standard DNA nucleoside, and "m" represents a 2'-OMe nucleoside. It has a GalNAc conjugated at the 3'-oxygen of the oligonucleotide via a THA linker as shown above.

Compound No. 936053 was described in WO2019/157531. It was chosen as the parent of the comparator compound because it has reduced toxicity relative to 558807 as well as reduced potency in vivo. Note that at least some of the observed potency of 558807 is "false"; that is, the RNA reduction observed is not specific to RNAse H mediated reduction of CXCL12 RNA, but rather, is related to global reductions in RNA due to cellular toxicity. Therefore, Compound No. 936503 represents a better comparator compound for determining the relative in vivo potency of compounds comprising mesyl phosphoramidate internucleoside linkages

TABLE 30

| Compound Number | Chemistry Notation (5'-3') | SEQ ID NO. |
|---|---|---|
| 1306456 | $G_{ks}{}^{m}C_{ks}A_{ks}T_{ds}G_{ys}T_{ds}T_{ds}{}^{m}C_{ds}T_{ds}{}^{m}C_{ds}A_{ds}{}^{m}C_{ds}A_{ds}T_{ks}T_{ks}A_{k}$-THA-GalNAc | 5 |
| 1462752 | THA-GalNAc- $G_{ks}{}^{m}C_{ks}A_{ks}\ \mathbf{T_{\underline{dz}}}\ \mathbf{G_{\underline{dz}}}\ \mathbf{T_{\underline{dz}}}T_{ds}{}^{m}C_{ds}T_{ds}{}^{m}C_{ds}A_{ds}{}^{m}C_{ds}A_{ds}T_{ks}T_{ks}A_{k}$ | 5 |
| 1462753 | THA-GalNAc- $G_{ks}{}^{m}C_{ks}A_{ks}\ \mathbf{T_{\underline{dz}}}\ \mathbf{G_{\underline{dz}}}\ \mathbf{T_{\underline{dz}}}\ \mathbf{T_{\underline{dz}}}{}^{m}C_{ds}T_{ds}{}^{m}C_{ds}A_{ds}{}^{m}C_{ds}A_{ds}T_{ks}T_{ks}A_{k}$ | 5 |
| 1462754 | THA-GalNAc- $G_{ks}{}^{m}C_{ks}A_{ks}\ \mathbf{T_{\underline{dz}}}\ \mathbf{G_{\underline{dz}}}\ \mathbf{T_{\underline{dz}}}\ \mathbf{T_{\underline{dz}}}{}^{m}\ \mathbf{C_{\underline{dz}}}T_{ds}{}^{m}C_{ds}A_{ds}{}^{m}C_{ds}A_{ds}T_{ks}T_{ks}A_{k}$ | 5 |

Study Design

For the in vivo activity and tolerability study in the tables below, 3 BALB/C mice per group were administered modified oligonucleotide by subcutaneous injection and sacrificed after 72 hours. Modified oligonucleotides were dosed at 0.2, 0.6, 1.8, 5.4, or 15 mg/kg.

Tissue were collected and mRNA was isolated and levels of CXCL12 in liver samples were measured by RT-qPCR with primer probe set RTS2605 as described above. Plasma ALT was measured. Elevations in ALT are associated with liver toxicity.

Expression levels were normalized with Ribogreen® and are presented relative to levels in mice treated with PBS.

TABLE 31

In Vivo Activity and Toxicity of modified oligonucleotides complementary to CXCL12

| Compound ID | in vivo CXCL12 ED50 liver (mg/kg) | ALT @ 5.4 mg/kg (IU/L) | ALT @ 15 mg/kg (IU/L) |
|---|---|---|---|
| 1306456 | 0.39 | 29 | 34 |
| 1462752 | 0.17 | 55 | 336 |
| 1462753 | 0.17 | 32 | 107 |
| 1462754 | 0.30 | 34 | 79 |

Example 18: Design, Activity and Tolerability of Modified Oligonucleotides Having Various Mesyl Phosphoramidate, Phosphorothioate, and Phosphodiester Internucleoside Linkages In Vitro Modified Oligonucleotides Modified oligonucleotides comprising multiple mesyl phosphoramidate internucleoside linkages (Formula IX), phosphorothioate internucleoside linkages, and phosphodiester internucleoside linkages, were synthesized and tested. The modified oligonucleotides are each 3-10-3 cEt gapmers with a sugar motif of: kkkddddddddddkkk (a 3-10-3 cEt motif) where "k" represents a cEt modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT 039353.7 truncated from 69/430,515 to 69/445,350 (SEQ ID NO: 1), at position 6877 to 6892. Each internucleoside linkage is either a phosphorothioate internucleoside linkage (" ", a phosphodiester internucleoside linkage ("o"), or a mesyl phosphoramidate internucleoside linkage ("z").

In Vitro Assays

In vitro activity of modified oligonucleotides described above was determined at 100 nM only, and the results are presented as the % expression relative to untreated control cells. For selected compounds, in vitro activity dose response was tested as described in Example 1. In vitro toxicity of modified oligonucleotides described above was determined as described in Example 3. The internucleoside linkages of the modified nucleosides are indicated in subscripts in the table below.

TABLE 32

Design, Activity, and Tolerability of modified oligonucleotides having multiple mesyl phosphoramidates linkages complementary to CXCL12

| Compound Number | Chemistry Notation (5'-3') | CXCL12 at 100 nM (% UTC) | CXCL12 $IC_{50}$ (nM) | Caspase Activation (% Mock) | SEQ ID NO. |
|---|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 34 | 88 | 1287 | 5 |
| 1467797 | $G_{ks}{}^{m}C_{ks}A_{ks}T_{ds}G_{ds}\mathbf{T}_{\underline{\mathbf{dz}}}\mathbf{T}_{\underline{\mathbf{dz}}}{}^{m}\mathbf{C}_{\underline{\mathbf{dz}}}T_{ds}{}^{m}C_{ds}A_{ds}{}^{m}C_{ds}A_{ds}T_{ks}T_{ks}A_{k}$ | 45 | 170 | 393 | 5 |
| 1467798 | $G_{ks}{}^{m}C_{ks}A_{ks}T_{ds}G_{ds}T_{ds}\mathbf{T}_{\underline{\mathbf{dz}}}{}^{m}\mathbf{C}_{\underline{\mathbf{dz}}}\mathbf{T}_{\underline{\mathbf{dz}}}{}^{m}C_{ds}A_{ds}{}^{m}C_{ds}A_{ds}T_{ks}T_{ks}A_{k}$ | 70 | n.d. | 974 | 5 |
| 1467799 | $G_{ks}{}^{m}C_{ks}A_{ks}T_{ds}G_{ds}T_{ds}T_{ds}{}^{m}\mathbf{C}_{\underline{\mathbf{dz}}}\mathbf{T}_{\underline{\mathbf{dz}}}{}^{m}\mathbf{C}_{\underline{\mathbf{dz}}}A_{ds}{}^{m}C_{ds}A_{ds}T_{ks}T_{ks}A_{k}$ | 73 | n.d. | 1023 | 5 |
| 1467800 | $G_{ks}{}^{m}C_{ks}A_{ks}T_{ds}G_{ds}T_{ds}T_{ds}{}^{m}C_{ds}\mathbf{T}_{\underline{\mathbf{dz}}}{}^{m}\mathbf{C}_{\underline{\mathbf{dz}}}\mathbf{A}_{\underline{\mathbf{dz}}}{}^{m}C_{ds}A_{ds}T_{ks}T_{ks}A_{k}$ | 59 | n.d. | 939 | 5 |
| 1467801 | $G_{ks}{}^{m}C_{ks}A_{ks}T_{ds}G_{ds}T_{ds}T_{ds}{}^{m}C_{ds}T_{ds}{}^{m}\mathbf{C}_{\underline{\mathbf{dz}}}\mathbf{A}_{\underline{\mathbf{dz}}}{}^{m}\mathbf{C}_{\underline{\mathbf{dz}}}A_{ds}T_{ks}T_{ks}A_{k}$ | 53 | n.d. | 682 | 5 |
| 1467802 | $G_{ks}{}^{m}C_{ks}A_{ks}T_{ds}\mathbf{G}_{\underline{\mathbf{dz}}}\mathbf{T}_{\underline{\mathbf{dz}}}\mathbf{T}_{\underline{\mathbf{dz}}}{}^{m}\mathbf{C}_{\underline{\mathbf{dz}}}T_{ds}{}^{m}C_{ds}A_{ds}{}^{m}C_{ds}A_{ds}T_{ks}T_{ks}A_{k}$ | 52 | 199 | 269 | 5 |
| 1467803 | $G_{ks}{}^{m}C_{ks}A_{ks}T_{ds}G_{ds}\mathbf{T}_{\underline{\mathbf{dz}}}\mathbf{T}_{\underline{\mathbf{dz}}}{}^{m}\mathbf{C}_{\underline{\mathbf{dz}}}\mathbf{T}_{\underline{\mathbf{dz}}}{}^{m}C_{ds}A_{ds}{}^{m}C_{ds}A_{ds}T_{ks}T_{ks}A_{k}$ | 75 | n.d. | 792 | 5 |
| 1467804 | $G_{ks}{}^{m}C_{ks}A_{ks}T_{ds}G_{ds}T_{ds}\mathbf{T}_{\underline{\mathbf{dz}}}{}^{m}\mathbf{C}_{\underline{\mathbf{dz}}}\mathbf{T}_{\underline{\mathbf{dz}}}{}^{m}\mathbf{C}_{\underline{\mathbf{dz}}}A_{ds}{}^{m}C_{ds}A_{ds}T_{ks}T_{ks}A_{k}$ | 60 | n.d. | 983 | 5 |
| 1467805 | $G_{ks}{}^{m}C_{ks}A_{ks}T_{ds}G_{ds}T_{ds}T_{ds}{}^{m}\mathbf{C}_{\underline{\mathbf{dz}}}\mathbf{T}_{\underline{\mathbf{dz}}}{}^{m}\mathbf{C}_{\underline{\mathbf{dz}}}\mathbf{A}_{\underline{\mathbf{dz}}}{}^{m}C_{ds}A_{ds}T_{ks}T_{ks}A_{k}$ | 50 | n.d. | 1247 | 5 |
| 1467806 | $G_{ks}{}^{m}C_{ks}A_{ks}T_{ds}G_{ds}T_{ds}T_{ds}{}^{m}C_{ds}\mathbf{T}_{\underline{\mathbf{dz}}}{}^{m}\mathbf{C}_{\underline{\mathbf{dz}}}U_{\underline{\mathbf{yz}}}{}^{m}\mathbf{C}_{\underline{\mathbf{dz}}}A_{ds}T_{ks}T_{ks}A_{k}$ | 50 | n.d. | 1062 | 5 |
| 1467807 | $G_{ks}{}^{m}C_{ks}A_{ks}\mathbf{T}_{\underline{\mathbf{dz}}}\mathbf{G}_{\underline{\mathbf{dz}}}T_{ds}T_{ds}{}^{m}C_{ds}T_{ds}{}^{m}C_{ds}A_{ds}{}^{m}\mathbf{C}_{\underline{\mathbf{dz}}}\mathbf{A}_{\underline{\mathbf{dz}}}T_{ks}T_{ks}A_{k}$ | 63 | n.d. | 443 | 5 |
| 1467808 | $G_{ks}{}^{m}C_{ks}A_{ks}\mathbf{T}_{\underline{\mathbf{dz}}}\mathbf{G}_{\underline{\mathbf{dz}}}T_{ds}T_{ds}{}^{m}C_{ds}T_{ds}{}^{m}C_{ds}\mathbf{A}_{\underline{\mathbf{dz}}}{}^{m}\mathbf{C}_{\underline{\mathbf{dz}}}A_{ds}T_{ks}T_{ks}A_{k}$ | 52 | n.d. | 615 | 5 |
| 1467809 | $G_{ks}{}^{m}C_{ks}A_{ks}\mathbf{T}_{\underline{\mathbf{dz}}}\mathbf{G}_{\underline{\mathbf{dz}}}T_{ds}T_{ds}{}^{m}C_{ds}T_{ds}{}^{m}\mathbf{C}_{\underline{\mathbf{dz}}}\mathbf{A}_{\underline{\mathbf{dz}}}{}^{m}C_{ds}A_{ds}T_{ks}T_{ks}A_{k}$ | 51 | n.d. | 408 | 5 |
| 1467810 | $G_{ks}{}^{m}C_{ks}A_{ks}\mathbf{T}_{\underline{\mathbf{dz}}}\mathbf{G}_{\underline{\mathbf{dz}}}T_{ds}T_{ds}{}^{m}C_{ds}\mathbf{T}_{\underline{\mathbf{dz}}}{}^{m}\mathbf{C}_{\underline{\mathbf{dz}}}A_{ds}{}^{m}C_{ds}A_{ds}T_{ks}T_{ks}A_{k}$ | 57 | n.d. | 426 | 5 |
| 1467811 | $G_{ks}{}^{m}C_{ks}A_{ks}\mathbf{T}_{\underline{\mathbf{dz}}}\mathbf{G}_{\underline{\mathbf{dz}}}T_{ds}T_{ds}{}^{m}\mathbf{C}_{\underline{\mathbf{dz}}}\mathbf{T}_{\underline{\mathbf{dz}}}{}^{m}C_{ds}A_{ds}{}^{m}C_{ds}A_{ds}T_{ks}T_{ks}A_{k}$ | 54 | n.d. | 347 | 5 |
| 1467812 | $G_{ks}{}^{m}C_{ks}A_{ks}\mathbf{T}_{\underline{\mathbf{dz}}}\mathbf{G}_{\underline{\mathbf{dz}}}T_{ds}\mathbf{T}_{\underline{\mathbf{dz}}}{}^{m}\mathbf{C}_{\underline{\mathbf{dz}}}T_{ds}{}^{m}C_{ds}A_{ds}{}^{m}C_{ds}A_{ds}T_{ks}T_{ks}A_{k}$ | 36 | 150 | 327 | 5 |
| 1467813 | $G_{ks}{}^{m}C_{ks}\mathbf{A}_{\underline{\mathbf{kz}}}\mathbf{T}_{\underline{\mathbf{dz}}}G_{ds}T_{ds}T_{ds}{}^{m}C_{ds}T_{ds}{}^{m}C_{ds}A_{ds}{}^{m}\mathbf{C}_{\underline{\mathbf{dz}}}\mathbf{A}_{\underline{\mathbf{dz}}}T_{ks}T_{ks}A_{k}$ | 39 | 83 | 1236 | 5 |
| 1467814 | $G_{ks}{}^{m}C_{ks}A_{ks}T_{ds}\mathbf{G}_{\underline{\mathbf{dz}}}\mathbf{T}_{\underline{\mathbf{dz}}}T_{ds}{}^{m}C_{ds}T_{ds}{}^{m}C_{ds}A_{ds}{}^{m}\mathbf{C}_{\underline{\mathbf{dz}}}\mathbf{A}_{\underline{\mathbf{dz}}}T_{ks}T_{ks}A_{k}$ | 78 | 220 | 241 | 5 |
| 1467815 | $G_{ks}{}^{m}C_{ks}A_{ks}T_{ds}G_{ds}\mathbf{T}_{\underline{\mathbf{dz}}}\mathbf{T}_{\underline{\mathbf{dz}}}{}^{m}C_{ds}T_{ds}{}^{m}C_{ds}A_{ds}{}^{m}\mathbf{C}_{\underline{\mathbf{dz}}}\mathbf{A}_{\underline{\mathbf{dz}}}T_{ks}T_{ks}A_{k}$ | 59 | n.d. | 435 | 5 |
| 1467816 | $G_{ks}{}^{m}C_{ks}A_{ks}T_{ds}G_{ds}T_{ds}\mathbf{T}_{\underline{\mathbf{dz}}}{}^{m}\mathbf{C}_{\underline{\mathbf{dz}}}T_{ds}{}^{m}C_{ds}A_{ds}{}^{m}\mathbf{C}_{\underline{\mathbf{dz}}}\mathbf{A}_{\underline{\mathbf{dz}}}T_{ks}T_{ks}A_{k}$ | 67 | n.d. | 714 | 5 |
| 1467817 | $G_{ks}{}^{m}C_{ks}A_{ks}T_{ds}G_{ds}T_{ds}T_{ds}{}^{m}\mathbf{C}_{\underline{\mathbf{dz}}}\mathbf{T}_{\underline{\mathbf{dz}}}{}^{m}C_{ds}A_{ds}{}^{m}\mathbf{C}_{\underline{\mathbf{dz}}}\mathbf{A}_{\underline{\mathbf{dz}}}T_{ks}T_{ks}A_{k}$ | 38 | n.d. | 1146 | 5 |
| 1467818 | $G_{ks}{}^{m}C_{ks}A_{ks}T_{ds}G_{ds}T_{ds}T_{ds}{}^{m}C_{ds}\mathbf{T}_{\underline{\mathbf{dz}}}{}^{m}\mathbf{C}_{\underline{\mathbf{dz}}}A_{ds}{}^{m}\mathbf{C}_{\underline{\mathbf{dz}}}\mathbf{A}_{\underline{\mathbf{dz}}}T_{ks}T_{ks}A_{k}$ | 66 | 129 | 812 | 5 |
| 1467819 | $G_{ks}{}^{m}C_{ks}A_{ks}T_{ds}\mathbf{G}_{\underline{\mathbf{dz}}}\mathbf{T}_{\underline{\mathbf{dz}}}T_{ds}{}^{m}C_{ds}T_{ds}{}^{m}\mathbf{C}_{\underline{\mathbf{dz}}}\mathbf{A}_{\underline{\mathbf{dz}}}{}^{m}C_{ds}A_{ds}T_{ks}T_{ks}A_{k}$ | 84 | n.d. | 181 | 5 |
| 1467820 | $G_{ks}{}^{m}C_{ks}A_{ks}T_{ds}G_{ds}\mathbf{T}_{\underline{\mathbf{dz}}}\mathbf{T}_{\underline{\mathbf{dz}}}{}^{m}C_{ds}\mathbf{T}_{\underline{\mathbf{dz}}}{}^{m}\mathbf{C}_{\underline{\mathbf{dz}}}A_{ds}{}^{m}C_{ds}A_{ds}T_{ks}T_{ks}A_{k}$ | 78 | 231 | 335 | 5 |

A subscript "k" represents a cEt nucleoside, a subscript "d" represents a stereostandard DNA nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methyl Cytosine.

Example 19: In Vitro Activity and Caspase Activation of Modified Oligonucleotides Comprising Modified Oligonucleotides Modified oligonucleotides comprising multiple mesyl phosphoramidate internucleoside linkages (Formula IX), phosphorothioate internucleoside linkages, and phosphodiester internucleoside linkages, were synthesized and tested. The modified oligonucleotides are each 3-10-3 cEt gapmers with a sugar motif of: kkkddddddddddkkk (a 3-10-3 cEt motif) or kkkdyddddddddkkk, where "k" represents a cEt modified sugar moiety, "y" represents a 2'-OMe modified sugar moiety, and "d" represents a β-D-2'-deoxyribosyl sugar moiety. Each of the modified oligonucleotides has the same nucleobase sequence, GCATGTTCTCACATTA (SEQ ID NO: 5), which is 100% complementary to mouse CXCL12, GENBANK NT 039353.7 truncated from 69/430,515 to 69/445,350 (SEQ ID NO: 1), at position 6877 to 6892. Each internucleoside linkage is either a phosphorothioate internucleoside linkage ("s") or a mesyl phosphoramidate internucleoside linkage ("z").

In Vitro Assays

In vitro activity of modified oligonucleotides described above was tested as described in Example 1. In vitro toxicity of modified oligonucleotides described above was determined as described in Example 3. The internucleoside linkages and sugar modifications of the modified nucleosides are indicated in subscripts in the table below.

TABLE 33

Design, Activity, and Tolerability of modified oligonucleotides having multiple mesyl phosphoramidates linkages complementary to CXCL12

| Compound Number | Chemistry Notation (5'-3') | CXCL12 $IC_{50}$ (nM) | Caspase Activation (% Mock) | SEQ ID NO. |
|---|---|---|---|---|
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 54 | 2230 | 5 |
| 936053 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 144 | 102 | 5 |
| 1375418 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{\underline{\mathbf{kz}}}T_{\underline{\mathbf{kz}}}A_{k}$ | 74 | 1983 | 5 |
| 1405468 | $G_{\underline{\mathbf{kz}}}{}^{m}C_{\underline{\mathbf{kz}}}A_{\underline{\mathbf{kz}}}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 88 | 1480 | 5 |
| 1405469 | $C_{\underline{\mathbf{kz}}}{}^{m}C_{\underline{\mathbf{kz}}}A_{\underline{\mathbf{kz}}}T_{ds}G_{ds}T_{ds}T_{ds}{}^{m}C_{ds}T_{ds}{}^{m}C_{ds}A_{ds}{}^{m}C_{ds}A_{ds}T_{\underline{\mathbf{kz}}}T_{\underline{\mathbf{kz}}}A_{k}$ | 58 | 1980 | 5 |
| 1405470 | $G_{\underline{\mathbf{kz}}}{}^{m}C_{\underline{\mathbf{kz}}}A_{\underline{\mathbf{kz}}}T_{ds}G_{ys}T_{ds}T_{ds}{}^{m}C_{ds}T_{ds}{}^{m}C_{ds}A_{ds}{}^{m}C_{ds}A_{ds}T_{ks}T_{ks}A_{k}$ | 86 | 133 | 5 |
| 1405471 | $G_{ks}{}^{m}C_{ks}A_{ks}T_{ds}G_{ys}T_{ds}T_{ds}{}^{m}C_{ds}T_{ds}{}^{m}C_{ds}A_{ds}{}^{m}C_{ds}A_{ds}T_{\underline{\mathbf{kz}}}T_{\underline{\mathbf{kz}}}A_{k}$ | 78 | 131 | 5 |
| 1405472 | $G_{\underline{\mathbf{kz}}}{}^{m}C_{\underline{\mathbf{kz}}}A_{\underline{\mathbf{kz}}}T_{ds}G_{ys}T_{ds}T_{ds}{}^{m}C_{ds}T_{ds}{}^{m}C_{ds}A_{ds}{}^{m}C_{ds}A_{ds}T_{\underline{\mathbf{kz}}}T_{\underline{\mathbf{kz}}}A_{k}$ | 73 | 148 | 5 |
| 1405488 | $G_{ks}{}^{m}C_{ks}A_{ks}T_{ds}G_{ys}T_{\underline{\mathbf{dz}}}T_{\underline{\mathbf{dz}}}{}^{m}C_{ds}T_{ds}{}^{m}C_{ds}A_{ds}{}^{m}C_{ds}A_{ds}T_{ks}T_{ks}A_{k}$ | 110 | 128 | 5 |
| 1405489 | $G_{ks}{}^{m}C_{ks}A_{ks}T_{ds}G_{yz}T_{\underline{\mathbf{dz}}}T_{ds}{}^{m}C_{ds}T_{ds}{}^{m}C_{ds}A_{ds}{}^{m}C_{ds}A_{ds}T_{ks}T_{ks}A_{k}$ | 94 | 182 | 5 |
| 1405490 | $G_{ks}{}^{m}C_{ks}A_{ks}T_{\underline{\mathbf{dz}}}G_{yz}T_{ds}T_{ds}{}^{m}C_{ds}T_{ds}{}^{m}C_{ds}A_{ds}{}^{m}C_{ds}A_{ds}T_{ks}T_{ks}A_{k}$ | 78 | 107 | 5 |
| 1405491 | $G_{ks}{}^{m}C_{ks}A_{ks}T_{ds}G_{ys}T_{ds}T_{ds}{}^{m}C_{ds}T_{ds}{}^{m}C_{\underline{\mathbf{dz}}}A_{\underline{\mathbf{dz}}}{}^{m}C_{ds}A_{ds}T_{ks}T_{ks}A_{k}$ | 130 | 95 | 5 |
| 1405495 | $G_{ks}{}^{m}C_{ks}A_{ks}T_{ds}G_{ys}T_{\underline{\mathbf{dz}}}T_{ds}{}^{m}C_{ds}T_{ds}{}^{m}C_{ds}A_{ds}{}^{m}C_{ds}A_{ds}T_{ks}T_{ks}A_{k}$ | 91 | 74 | 5 |
| 1405496 | $G_{ks}{}^{m}C_{ks}A_{ks}T_{ds}G_{yz}T_{ds}T_{ds}{}^{m}C_{ds}T_{ds}{}^{m}C_{ds}A_{ds}{}^{m}C_{ds}A_{ds}T_{ks}T_{ks}A_{k}$ | 197 | 148 | 5 |
| 1405497 | $G_{ks}{}^{m}C_{ks}A_{ks}T_{ds}G_{ys}T_{ds}T_{ds}{}^{m}C_{ds}T_{ds}{}^{m}C_{ds}A_{\underline{\mathbf{dz}}}{}^{m}C_{ds}A_{ds}T_{ks}T_{ks}A_{k}$ | 126 | 95 | 5 |

A subscript "k" represents a cEt nucleoside, a subscript "d" represents a stereostandard DNA nucleoside, a subscript "s" indicates a phosphorothioate internucleoside linkage, a subscript "z" represents an internucleoside linkage of formula IX, which is a mesyl phosphoramidate linkage, and a subscript "y" represents a 2'-OMe modified nucleoside. Subscripts of nucleotides having an internucleoside linkage of formula IX are bold and underlined. A superscript "m" before a C represents a 5-methyl Cytosine.

Example 20: Design and Activity of siRNA to HRPT1 Having Mesyl Phosphoramidate Internucleoside Linkages in Vitro siRNA Double-stranded siRNA comprising modified oligonucleotides having mesyl phosphoramidate internucleoside linkages (Formula IX) in the sense and/or antisense strands were synthesized and tested. Each internucleoside linkage is either a phosphorothioate internucleoside linkage ("s"), a phosphodiester internucleoside linkage ("o"), or a mesyl phosphoramidate internucleoside linkage ("z").

Each antisense strand has the sequence AUAAAAUCUACAGUCAUAGGAAU (SEQ ID NO: 21) and is 100% complementary to GenBank NM_000194.2 (SEQ ID NO: 22) from 444 to 466, and each antisense strand has a 5'-phosphate. Each sense strand has the sequence UCCUAUGACUGUAGAUUUUAU (SEQ ID NO: 23) and is 100% identical to GenBank NM_000194.2 (SEQ ID NO: 22) from 446 to 466. Compound No. 1151789, 1337113, 1471455, and 1515982 comprise a 3'-linked $C_7$ amino modifier (Glen Research), shown below:

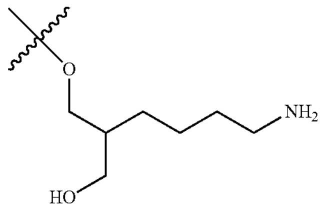 [SMILES: *OCC(CO)CCCCN]

Compound No. 1448688 further comprises a GalNAc conjugated at the 3'-oxygen of the oligonucleotide via a THA linker as shown below:

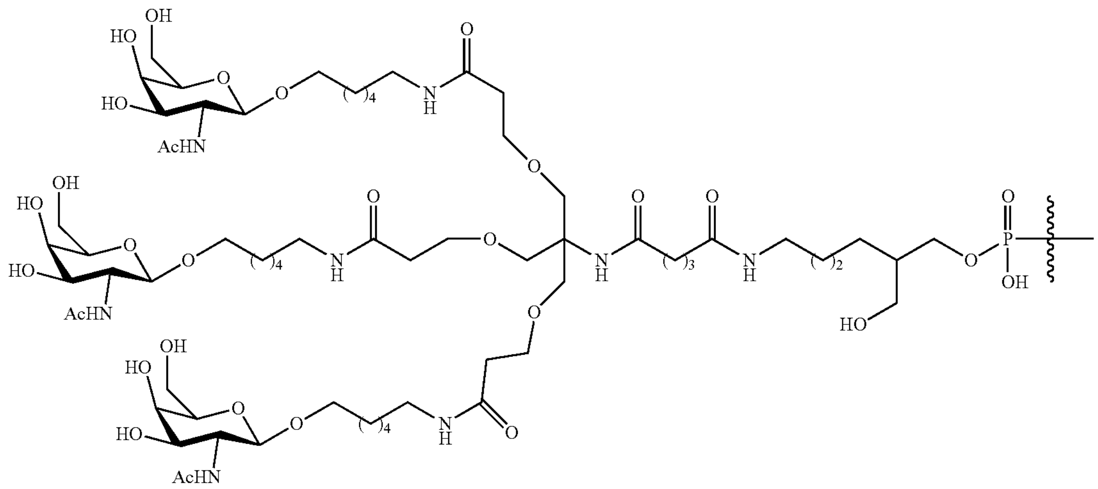

THA-C7-GalNAc

TABLE 34

Design of antisense strand modified oligonucleotides targeted to human/mouse HRPT1 having mesyl phosphoramidate linkages

| Compound ID | Chemical Notation (5' to 3') | SEQ ID NO: |
|---|---|---|
| 1073762 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1337111 | p.$A_{ys}U_{fs}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1465680 | p.$\mathbf{A}_{\underline{\mathbf{yz}}}U_{fs}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1465681 | p.$A_{ys}$ $\mathbf{U}_{\underline{\mathbf{fz}}}$ $A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1465682 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}$ $\mathbf{G}_{\mathbf{fz}}$ $\mathbf{A}_{\underline{\mathbf{yz}}}$ $\mathbf{A}_{\underline{\mathbf{fz}}}U_{y}$ | 21 |
| 1465683 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}$ $\mathbf{U}_{\underline{\mathbf{yz}}}$ $\mathbf{A}_{\underline{\mathbf{fz}}}$ $\mathbf{G}_{\underline{\mathbf{yz}}}G_{fo}A_{ys}A_{fs}U_{y}$ | 21 |
| 1465684 | p.$A_{yo}U_{fo}A_{yo}A_{fo}A_{yo}A_{fo}U_{yo}C_{fo}U_{yo}A_{fo}C_{yo}A_{fo}G_{yo}$ $\mathbf{U}_{\underline{\mathbf{fz}}}$ $\mathbf{C}_{\underline{\mathbf{yz}}}$ $\mathbf{A}_{\underline{\mathbf{fz}}}U_{yo}A_{fo}G_{yo}G_{fo}A_{ys}A_{fs}U_{y}$ | 21 |
| 1465685 | p.$A_{yo}U_{fo}A_{yo}A_{fo}A_{yo}A_{fo}U_{yo}C_{fo}U_{yo}A_{fo}$ $\mathbf{C}_{\underline{\mathbf{yz}}}$ $\mathbf{A}_{\underline{\mathbf{fz}}}$ $\mathbf{G}_{\underline{\mathbf{yz}}}U_{fo}C_{yo}A_{fo}U_{yo}A_{fo}G_{yo}G_{fo}A_{ys}A_{fs}U_{y}$ | 21 |
| 1465686 | p.$A_{yo}U_{fo}A_{yo}A_{fo}A_{yo}A_{fo}U_{yo}$ $\mathbf{C}_{\underline{\mathbf{fz}}}$ $\mathbf{U}_{\underline{\mathbf{yz}}}$ $\mathbf{A}_{\underline{\mathbf{fz}}}C_{yo}A_{fo}G_{yo}U_{fo}C_{yo}A_{fo}U_{yo}A_{fo}G_{yo}G_{fo}A_{ys}A_{fs}U_{y}$ | 21 |
| 1465687 | p.$A_{yo}U_{fo}A_{yo}A_{fo}$ $\mathbf{A}_{\underline{\mathbf{yz}}}$ $\mathbf{A}_{\underline{\mathbf{fz}}}$ $\mathbf{U}_{\underline{\mathbf{yz}}}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1449196 | p.$A_{ys}U_{fs}A_{yo}A_{yo}A_{yo}A_{fo}U_{yo}C_{yo}U_{yo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1466140 | p.$A_{ys}U_{fs}A_{yo}A_{yo}A_{yo}A_{fo}U_{yo}C_{yo}U_{yo}A_{yo}C_{yo}A_{yo}G_{yo}U_{fo}C_{yo}A_{fo}U_{yo}A_{yo}G_{yo}G_{yo}$ $\mathbf{A}_{\underline{\mathbf{yz}}}$ $\mathbf{A}_{\underline{\mathbf{yz}}}U_{y}$ | 21 |
| 1515975 | p.$A_{ys}U_{fs}A_{yo}A_{yo}A_{yo}$ $\mathbf{A}_{\underline{\mathbf{fz}}}U_{yo}C_{yo}U_{yo}A_{yo}C_{yo}A_{yo}G_{yo}$ $\mathbf{U}_{\underline{\mathbf{fz}}}C_{yo}$ $\mathbf{A}_{\underline{\mathbf{fz}}}U_{yo}A_{yo}G_{yo}G_{yo}A_{ys}A_{ys}U_{y}$ | 21 |
| 1515976 | p.$A_{ys}\mathbf{U}_{\underline{\mathbf{fz}}}$ $A_{yo}A_{yo}A_{yo}$ $\mathbf{A}_{\underline{\mathbf{fz}}}U_{yo}C_{yo}U_{yo}A_{yo}C_{yo}A_{yo}G_{yo}$ $\mathbf{U}_{\underline{\mathbf{fz}}}C_{yo}$ $\mathbf{A}_{\underline{\mathbf{fz}}}U_{yo}A_{yo}G_{yo}G_{yo}A_{ys}A_{ys}U_{y}$ | 21 |

A "p." represents a 5'-phosphate. A subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage, a subscript "z" represents an internucleoside linkage of formula IX, which is a mesyl phosphoramidate linkage. Subscripts of nucleotides having a phosphoramidate internucleoside linkage of generic Formula XVII are bold and underlined.

TABLE 35

Design of sense strand modified oligonucleotides targeted to human/mouse HRPT1 having mesyl phosphoramidate linkages

| Compound ID | Chemical Notation (5' to 3') | SEQ ID NO: |
|---|---|---|
| 1151789 | $U_{fo}C_{yo}C_{fo}U_{yo}A_{fo}U_{yo}G_{fo}A_{yo}C_{fo}U_{yo}G_{fo}U_{yo}A_{fo}G_{yo}A_{fo}U_{yo}U_{fo}U_{yo}U_{fo}A_{yo}U_{fo}$ [3'-amino C7 Tag] | 23 |
| 1448688 | $U_{ys}C_{ys}C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}U_{yo}A_{yo}U_{y}$ THA-C7-GalNAc | 23 |
| 1471455 | $\mathbf{U}_{\underline{\mathbf{yz}}}\ \mathbf{C}_{\underline{\mathbf{yz}}}\ C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}\ \mathbf{U}_{\underline{\mathbf{yz}}}\ \mathbf{A}_{\underline{\mathbf{yz}}}U_{yo}$ [3'-amino C7 Tag] | 23 |
| 1515982 | $U_{ys}C_{ys}C_{yo}U_{yo}A_{yo}U_{yo}\ \mathbf{G}_{\underline{\mathbf{fz}}}\ A_{yo}\ \mathbf{C}_{\underline{\mathbf{fz}}}\ \mathbf{U}_{\underline{\mathbf{fz}}}\ \mathbf{G}_{\underline{\mathbf{fz}}}U_{yo}A_{yo}G_{yo}A_{yo}U_{yo}U_{yo}U_{yo}U_{yo}A_{yo}U_{y}$ [3'-amino C7 tag] | 23 |

A subscript "f" represents a 2'-F modified nucleoside, a subscript "y" represents a 2'-OMe modified nucleoside, a subscript "s" indicates a phosphorothioate internucleoside linkage, a subscript "o" represents a phosphodiester internucleoside linkage.

Activity Assay

Activity of various siRNA formed by annealing one antisense strand and the sense strand 1151789 described above was tested in HeLa cells. HeLa cells were transfected with 6 μL/mL of siRNA using RNAiMAX for 5 hours. RNA was isolated and RNA expression was analyzed via RT-qPCR using primer probe set Hs02800695_m1(ThermoFisher).

TABLE 36

Activity of siRNAs having mesyl phosphoramidate linkages against human HPRT1

| Antisense Strand | Sense Strand | IC50 (nM) |
|---|---|---|
| 1073762 | 1151789 | 0.009 |
| 1337111 | 1151789 | 0.037 |
| 1465680 | 1151789 | 0.083 |
| 1465681 | 1151789 | 0.051 |
| 1465682 | 1151789 | 0.016 |
| 1465683 | 1151789 | 0.023 |
| 1465684 | 1151789 | 0.042 |
| 1465685 | 1151789 | 0.045 |
| 1465686 | 1151789 | 0.082 |
| 1465687 | 1151789 | 0.382 |

TABLE 37

Activity of siRNAs having mesyl phosphoramidate linkages against HPRT1

| Antisense Strand | Sense Strand | $IC_{50}$ (nM) |
|---|---|---|
| 1073762 | 1337113 | 0.075 |
| 1449196 | 1471455 | 0.040 |
| 1466140 | 1471455 | 0.049 |

TABLE 37-continued

Activity of siRNAs having mesyl phosphoramidate linkages against HPRT1

| Antisense Strand | Sense Strand | $IC_{50}$ (nM) |
|---|---|---|
| 1515975 | 1448688 | 0.066 |
| 1515976 | 1448688 | 0.137 |
| 1515975 | 1515982 | 2.531 |
| 1515976 | 1515982 | 3.875 |
| 1449196 | 1515982 | 0.190 |

Example 21: Measurement of Viscosity of Modified Oligonucleotides

The viscosity of modified oligonucleotides comprising mesyl phosphoramidate internucleoside linkages was compared to the viscosity of modified oligonucleotides having only phosphorothioate internucleoside linkages. Each nucleobase in the table below is represented by N, representing A, G, T, or $^{m}$C. Each of oligonucleotides A1, A2, and A3 have the same sequence, and each of oligonucleotides B1, B2, and B3 have the same sequence. Oligonucleotides (32-38 mg) were weighed into a glass vial; approximately 100 μL of water was added, and the modified oligonucleotide was dissolved into solution by heating the vial to 55° C. Part (75 μL) of the pre-heated sample was pipetted to a micro-viscometer (PAC Cambridge Viscosity Viscometer). The temperature of the micro-viscometer was set to 25° C. and the viscosity of the sample was measured. The entire 75 μL of sample was them combined with the remaining portion of the sample was diluted appropriately for UV reading at 260 nM (Cary UV instrument). The data below indicates that the incorporation of mesyl phosphoramidate linkages in the gap can reduce viscosity.

TABLE 38

Viscosity

| Compound ID | Chemistry Notation | Viscosity (cP) | SEQ ID NO: |
|---|---|---|---|
| A1 | $N_{ks}N_{ks}N_{ks}N_{ds}N_{ds}N_{ds}N_{ds}N_{ds}N_{ds}N_{ds}N_{ds}N_{ds}N_{ds}N_{ks}N_{ks}N_{k}$ | 90.6 | 29 |
| A2 | $N_{ks}N_{ks}N_{ks}\ \mathbf{N}_{\underline{\mathbf{dz}}}\ \mathbf{N}_{\underline{\mathbf{dz}}}\ \mathbf{N}_{\underline{\mathbf{dz}}}\ \mathbf{N}_{\underline{\mathbf{dz}}}\ N_{ds}N_{ds}N_{ds}N_{ds}N_{ds}N_{ds}N_{ks}N_{ks}N_{k}$ | 46.0 | 29 |
| A3 | $\mathbf{N}_{\underline{\mathbf{kz}}}\ \mathbf{N}_{\underline{\mathbf{kz}}}\ N_{ks}N_{ds}N_{ds}N_{ds}N_{ds}N_{ds}N_{ds}N_{ds}N_{ds}N_{ds}\mathbf{N}_{\underline{\mathbf{dz}}}\ \mathbf{N}_{\underline{\mathbf{kz}}}\ \mathbf{N}_{\underline{\mathbf{kz}}}\ N_{k}$ | 96.2 | 29 |

TABLE 38-continued

| Viscosity | | | |
|---|---|---|---|
| Compound ID | Chemistry Notation | Viscosity (cP) | SEQ ID NO: |
| B1 | $N_{ks}N_{ks}N_{ks}N_{ds}N_{ds}N_{ds}N_{ds}N_{ds}N_{ds}N_{ds}N_{ds}N_{ds}N_{ks}N_{ks}N_{ks}N_{e}$ | 44.5 | 29 |
| B2 | $N_{ks}N_{ks}N_{ks}$ $\mathbf{N}_{\underline{\mathbf{dz}}}$ $\mathbf{N}_{\underline{\mathbf{dz}}}$ $\mathbf{N}_{\underline{\mathbf{dz}}}$ $\mathbf{N}_{\underline{\mathbf{dz}}}$ $N_{ds}N_{ds}N_{ds}N_{ds}N_{ds}N_{ks}N_{ks}N_{ks}N_{e}$ | 17.0 | 29 |
| B3 | $\mathbf{N}_{\underline{\mathbf{kz}}}$ $\mathbf{N}_{\underline{\mathbf{kz}}}$ $N_{ks}N_{ds}N_{ds}N_{ds}N_{ds}N_{ds}N_{ds}N_{ds}N_{ds}N_{ds}$ $\mathbf{N}_{\underline{\mathbf{kz}}}$ $\mathbf{N}_{\underline{\mathbf{kz}}}$ $\mathbf{N}_{\underline{\mathbf{kz}}}$ $N_{e}$ | 9.6 | 29 |

A subscript "k" represents a cEt modified nucleoside, a subscript "d" represents a stereostandard DNA nucleoside, a subscript "e" represents a 2'-MOE modified nucleoside, a subscript "s" indicates a phosphorothioate internucleoside and a subscript "z" represents an internucleoside linkage of formula IX

Example 22: Synthesis and In Vivo Activity of siRNA to SOD-1 Having a $C_{16}$ Modified-Phosphoramidate Internucleoside Linkage Double-stranded siRNA comprising a modified oligonucleotide having a mesyl phosphoramidate internucleoside linkage of Formula XIX in the sense strand was synthesized and tested in vivo.

For the sense strand, each internucleoside linkage is either a phosphorothioate internucleoside linkage ("s"), a phosphodiester internucleoside linkage ("o"), or a modified phosphoramidate internucleoside linkage having a $C_{16}$ moiety, as shown below ("XIX").

XIX

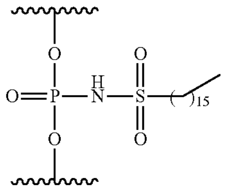

Synthesis

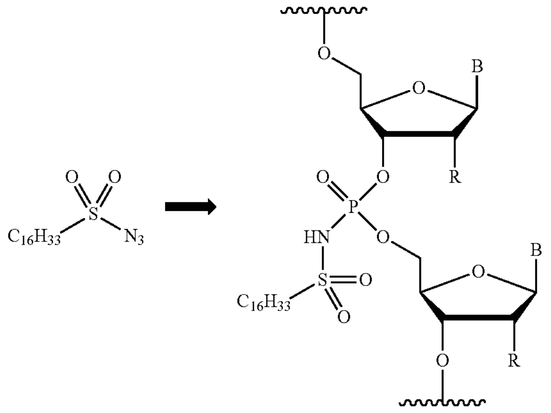

Oligonucleotides were synthesized on a 40 μmol scale using Nittophase UnyLinker support (405 μmol/g) on an AKTA 10 Oligopilot. Fully protected nucleoside phosphoramidites were incorporated using standard solid-phase oligonucleotide synthesis, i.e. 15% dichloroacetic acid in toluene for deblocking, 1 M 4,5-dicyanoimidazole 0.1 M N-methylimidazole in acetonitrile as activator for phosphoramidite couplings, 20% acetic anhydride in THE and 10% 1-methylimidazole in THF/pyridine for capping and 20% tBuOOH in acetonitrile for oxidation or 0.1 M xanthane hydride in pyridine:acetonitrile 3:2 (v:v) for thiolation. Oxidation to form the hexadecyl sulfonyl phosphoramidate linkage (Formula XIX) was performed using 0.5 M $C_{16}H_{33}SO_2N_3$ (hexadecyl sulfonyl azide) in acetonitrile:toluene 1:1 (v/v) with a 90 minute recycle time. Phosphoramidites were dissolved to 0.1 M in acetonitrile:toluene 1:1 (v:v) and incorporated using a 10 min coupling recycling time. At the end of the solid phase synthesis cyanoethyl protecting groups were removed by a 30 min treatment with 20% diethylamine in toluene. Oligonucleotides were deprotected and cleaved using conc. aq. ammonia at room temperature for 48 h.

siRNA Design

Double-stranded siRNA compounds were formed by annealing one antisense strand and one sense strand described below. Compound No. 1521629 is the antisense strand, wherein the sequence (from 5' to 3') UUAGAGUGAGGAUUAAAAUGAG (SEQ ID NO: 33) is 100% complementary to the genomic sequence of rat SOD-1, SEQ ID NO: 34, the complement of GENBANK Accession No. NW 047354.2, truncated from 29807000 to 29819000, at position 6230 to 6251. The non-complementary overhang is highlighted in bold in the table below.

TABLE 39

| Design of antisense strand of modified oligonucleotides | | |
|---|---|---|
| Compound ID | Chemistry Notation (5' to 3') | SEQ ID NO. |
| 1521629 | vP-$\mathbf{T}_{es}U_{fs}U_{yo}A_{yo}G_{yo}A_{fo}G_{yo}U_{fo}G_{fo}A_{yo}G_{yo}G_{yo}A_{yo}U_{fo}U_{yo}A_{fo}A_{yo}A_{yo}A_{yo}U_{yo}G_{ys}A_{ys}G_{y}$ | 33 |

In the table above, a subscript “f” represents a 2'-F modified nucleoside, a subscript “y” represents a 2'-OMe modified nucleoside, a subscript “e” represents a 2'-MOE modified nucleoside, a subscript “s” indicates a phosphorothioate internucleoside linkage, and a subscript “o” represents a phosphodiester internucleoside linkage. Compound No. 1521629 contains a vinyl phosphonate (vP) moiety on the 5'-end.

TABLE 40

| Design of sense strand of modified oligonucleotides | | |
|---|---|---|
| Compound ID | Chemistry Notation (5' to 3') | SEQ ID NO. |
| 1523488 | $C_{ys}A_{ys}U_{yo}U_{yo}U_{yo}U_{yo}A_{fo}A_{yo}U_{fo}C_{fo}C_{fo}U_{yo}C_{yo}A_{yo}C_{yo}U_{yo}C_{yo}U_{yo}A_{ys}A_{ys}A_{y}$ | 30 |
| 1524752 | $C_{ys}A_{ys}U_{yo}U_{yo}U_{yo}$ $\mathbf{U}_{\underline{\mathbf{y[XIX]}}}$ $A_{fo}A_{yo}U_{fo}C_{fo}C_{fo}U_{yo}C_{yo}A_{yo}C_{yo}U_{yo}C_{yo}U_{yo}A_{ys}A_{ys}A_{y}$ | 30 |

In the table above, a subscript “f” represents a 2'-F modified nucleoside, a subscript “y” represents a 2'-OMe modified nucleoside, a subscript “s” indicates a phosphorothioate internucleoside linkage, and a subscript “o” represents a phosphodiester internucleoside linkage. A subscript “[XIX]” represents an internucleoside linkage of Formula XIX. Subscripts of nucleotides having a substituted phosphoramidate internucleoside linkage of generic Formula XVII are bold and underlined.

In Vivo

For the in vivo activity study in the table below, 2-4 Sprague Dawley rats per group were administered siRNA by intrathecal injection at a total dose of 7.5, 30, 75, 90, 300, or 900 μg. One group of four Sprague Dawley rats was injected with PBS as a control.

RNA analysis

Two weeks post treatment, rats were sacrificed and RNA was extracted from cortical brain tissue and spinal cord for real-time qPCR analysis of SOD-1 RNA. Primer probe set RTS592 (forward sequence CGGATGAAGAGAGG-CATGTTG, designated herein as SEQ ID NO: 35; reverse sequence TTGGCCACACCGTCCTTT, designated herein as SEQ ID NO: 36; probe sequence AGACCTGGGCAATGTGGCTGCTG, designated herein as SEQ ID NO: 37) was used to determine the amount of SOD-1 RNA. The median effective dose ($ED_{50}$) of each siRNA was calculated in GraphPad Prism using the equation “log(agonist) vs. response—Find ECanything Least squares fit.”

As shown in the table below, treatment with siRNA with a $C_{16}$ modified-phosphoramidate internucleoside linkage resulted in increased potency in both the cortex and the spinal cord compared to an siRNA lacking a $C_{16}$ modification.

TABLE 41

| In vivo activity of siRNA to SOD-1 | | | |
|---|---|---|---|
| Antisense Strand | Sense Strand | Cortex $ED_{50}$ (μg) | Spinal Cord $ED_{50}$ (μg) |
| 1521629 | 1523488 | 998 | 48 |
| 1521629 | 1524752 | 223 | 15 |

Example 23: Design, Activity, and Tolerability of Modified Oligonucleotides with Mesyl Phosphoramidate Internucleoside Linkages Complementary to Factor XI In Vivo Design of Modified Oligonucleotides GalNAc-conjugated modified oligonucleotides comprising multiple mesyl phosphoramidate internucleoside linkages (Formula IX) and phosphorothioate internucleoside linkages were synthesized and tested. The modified oligonucleotides are 100% complementary to the complement of mouse Factor XI, GENBANK Accession No. NT_039460.6 truncated from 6086000 to 6111000 (SEQ ID NO: 38), at position 22323 to 22338. Each internucleoside linkage is either a phosphorothioate internucleoside linkage (“s”) or a mesyl phosphoramidate internucleoside linkage (“z”).

The modified oligonucleotides in the table below contain the GalNAc moiety conjugated to the 3'-oxygen as shown below:

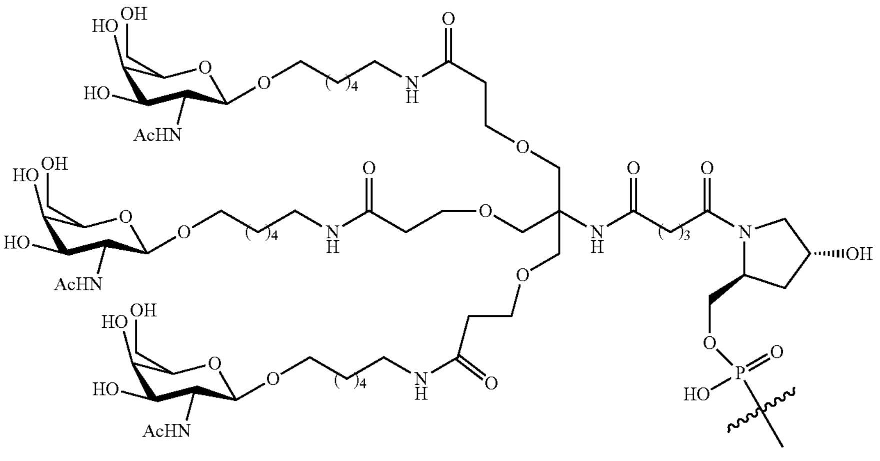

HPPO-GalNAc

TABLE 42

| Design of modified oligonucleotides with mesyl phosphoramidate internucleoside linkages | | |
|---|---|---|
| Compound ID | Chemistry Notation (5' to 3') | SEQ ID NO. |
| 1468445 | $^{m}C_{ks}T_{ks}G_{ks}T_{ds}T_{ds}T_{ds}G_{ds}A_{ds}G_{ds}T_{ds}T_{ds}T_{ds}T_{ds}{}^{m}C_{ks}T_{ks}{}^{m}C_{k}$-HPPO-GalNAc | 39 |
| 1506051 | $^{m}C_{ks}T_{ks}G_{ks}T_{ds}U_{ys}T_{ds}G_{ds}A_{ds}G_{ds}T_{ds}T_{ds}T_{ds}T_{ds}{}^{m}C_{ks}T_{ks}{}^{m}C_{k}$-HPPO-GalNAc | 40 |
| 1505717 | $^{m}C_{ks}T_{ks}G_{ks}\ T_{\underline{\mathbf{dz}}}\ T_{\underline{\mathbf{dz}}}\ T_{\underline{\mathbf{dz}}}\ G_{\underline{\mathbf{dz}}}A_{ds}G_{ds}T_{ds}T_{ds}T_{ds}T_{ds}{}^{m}C_{ks}T_{ks}{}^{m}C_{k}$-HPPO-GalNAc | 39 |

A subscript "k" represents a cEt nucleoside, a subscript "d" represents a stereo-standard DNA nucleoside, a subscript "s" indicates a phosphorothioate internucleoside linkage, and a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methylcytosine. HPPO-GalNAc represents a 3'-GalNAc moiety.

Study Design

For the in vivo activity and tolerability study in the table below, 3 BALB/C mice per group were administered a single dose of modified oligonucleotide by subcutaneous injection and sacrificed after 72 hours. Modified oligonucleotides were administered at 0.31, 0.93, 2.78, 8.33, or 25 mg/kg. One group of four BALB/C mice was injected with PBS.

Liver tissue was collected, mRNA was isolated, and levels of FXI in liver samples were measured by quantitative RTPCR with mouse primer probe set RTS2898 (forward sequence: ACATGACAGGCGCGATCTCT, SEQ ID NO: 41; reverse sequence: TCTAGGTTCACGTACACATCTTTGC, SEQ ID NO: 42; probe sequence: TTCCTTCAAGCAATGCCCTCAGCAAT, SEQ ID NO: 43). Expression levels were normalized to total RNA content as measured with RIBOGREEN®. $ED_{50}$ values were calculated by a least squares fit of data in GraphPad Prism using the equation "[Inhibitor] vs. response—Variable slope (four parameters)" and are presented in the table below. Plasma ALT was also measured and is presented in the table below. Elevations in ALT are associated with liver toxicity. The PBS treated mice have an ALT of 36.75 IU/L.

TABLE 43

| In vivo activity and toxicity of modified oligonucleotides complementary to FXI | | |
|---|---|---|
| Compound ID | in vivo FXI $ED_{50}$ liver (mg/kg) | ALT @ 25 mg/kg (IU/L) |
| 1468445 | 1.1 | 42 |
| 1506051 | 31 | 63 |
| 1505717 | 1.4 | 52 |

Example 24: Design, Activity, and Tolerability of Modified Oligonucleotides with Mesyl Phosphoramidate Internucleoside Linkages Complementary to HDAC2 In Vivo Design of Modified Oligonucleotides GalNAc-conjugated modified oligonucleotides having multiple mesyl phosphoramidate internucleoside linkages (Formula IX) and phosphorothioate internucleoside linkages were synthesized and tested. The modified oligonucleotides are 100% complementary to mouse HDAC2 GENBANK Accession No. NT 039492.7 truncated from 29396000 to 29430000 (SEQ ID NO: 44), at position 19150 to 19165. Each internucleoside linkage is either a phosphorothioate internucleoside linkage ("s") or a mesyl phosphoramidate internucleoside linkage ("z").

The modified oligonucleotides in the table below contain the GalNAc moiety conjugated to the 3'-oxygen as shown below:

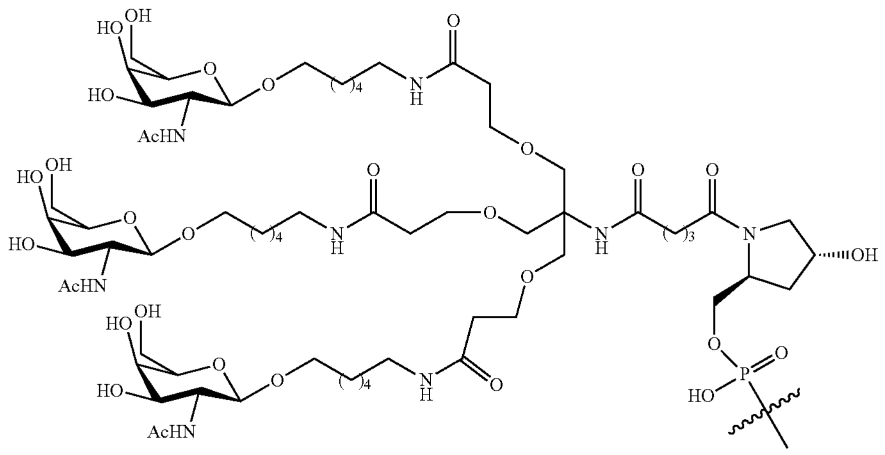

HPPO-GalNAc

TABLE 44

Design of modified oligonucleotides with mesyl phosphoramidate internucleoside linkages

| Compound ID | Chemistry Notation (5' to 3') | SEQ ID NO. |
|---|---|---|
| 1506050 | $A_{ks}{}^{m}C_{ks}{}^{m}C_{ks}{}^{m}C_{ds}U_{ys}{}^{m}C_{ds}A_{ds}A_{ds}G_{ds}T_{ds}{}^{m}C_{ds}T_{ds}{}^{m}C_{ds}{}^{m}C_{ks}T_{ks}G_{k}$ HPPO-GalNAc | 45 |
| 1505715 | $A_{ks}{}^{m}C_{ks}{}^{m}C_{ks}{}^{m}\mathbf{C}_{\underline{\mathbf{dz}}}\mathbf{T}_{\underline{\mathbf{dz}}}{}^{m}\mathbf{C}_{\underline{\mathbf{dz}}}\mathbf{A}_{\underline{\mathbf{dz}}}A_{ds}G_{ds}T_{ds}{}^{m}C_{ds}T_{ds}{}^{m}C_{ds}{}^{m}C_{ks}T_{ks}G_{k}$ HPPO-GalNAc | 46 |

A subscript "k" represents a cEt nucleoside, a subscript "d" represents a stereo-standard DNA nucleoside, a subscript "y" represents a 2'-OMe modified nucleoside, a subscript "s" indicates a phosphorothioate internucleoside linkage, and a subscript "z" represents an internucleoside linkage of formula IX, which is a mesyl phosphoramidate linkage.
Subscripts of nucleotides having an internucleoside linkage of formula IX are bold and underlined.
A superscript "m" before a C represents a 5-methylcytosine.

Study Design

For the in vivo activity and tolerability study in the table below, 3 BALB/C mice per group were administered a single dose of modified oligonucleotide by subcutaneous injection and sacrificed after 72 hours. Modified oligonucleotides were dosed at 0.3, 0.9, 2.8, 8.3, or 25 mg/kg. One group of four BALB/C mice was injected with PBS.

Liver tissue was collected, mRNA was isolated, and levels of HDAC2 in liver samples were measured by quantitative RTPCR with mouse primer probe set Mm00515108_m1 (Applied Biosystems). Expression levels were normalized to total RNA as measured with RIBOGREEN®. $ED_{50}$ values were calculated by a least squares fit of data in GraphPad Prism using the equation "[Inhibitor] vs. response—Variable slope (four parameters)" and are presented in the table below. Plasma ALT was also measured and is presented in the table below. Elevations in ALT are associated with liver toxicity. The PBS treated mice have an ALT of 53 IU/L.

TABLE 45

In vivo activity and toxicity of modified oligonucleotides complementary to HDAC2

| Compound ID | in vivo HDAC2 $ED_{50}$ liver (mg/kg) | ALT @ 25 mg/kg (IU/L) |
|---|---|---|
| 1506050 | 7.5 | 62 |
| 1505715 | 3.9 | 81 |

Example 25: Design, Activity, and Tolerability of Modified Oligonucleotides with Mesyl Phosphoramidate Internucleoside Linkages Complementary to DNM2 In Vivo Design of Modified Oligonucleotides GalNAc-conjugated modified oligonucleotides having multiple mesyl phosphoramidate internucleoside linkages (Formula IX) and phosphorothioate internucleoside linkages were synthesized and tested. Each of the modified oligonucleotides is 100% complementary to mouse DNM2, GENBANK NC_000075.6 truncated from 21422001 to 21511000 (SEQ ID NO: 47), at position 3046 to 3061. Each internucleoside linkage is either a phosphorothioate internucleoside linkage ("s") or a mesyl phosphoramidate internucleoside linkage ("z").

The modified oligonucleotides in the table below contain the GalNAc moiety conjugated to the 3'-oxygen as shown below:

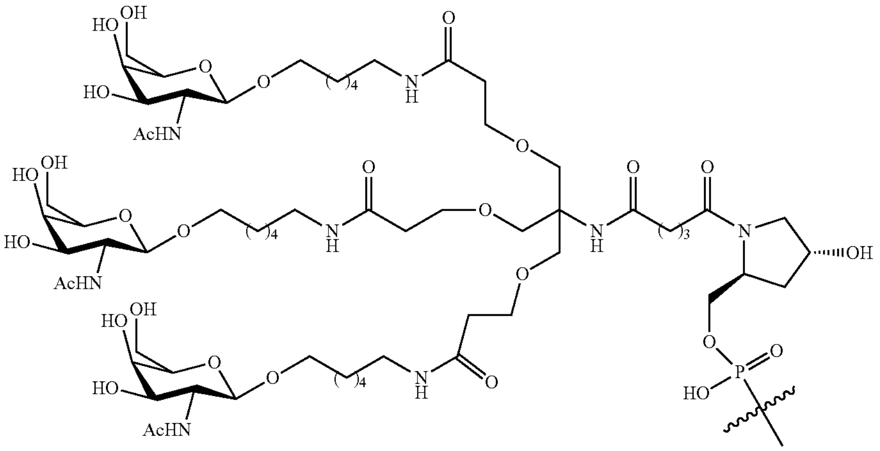

HPPO-GalNAc

TABLE 46

Design of modified oligonucleotides with mesyl phosphoramidate internucleoside linkages

| Compound ID | Chemistry Notation (5' to 3') | SEQ ID NO. |
|---|---|---|
| 1506053 | $A_{ks}G_{ks}A_{ks}{}^{m}C_{ds}U_{ys}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$-HPPO-GalNAc | 48 |
| 1505722 | $A_{ks}G_{ks}A_{ks}{}^{m}\mathbf{C}_{\underline{\mathbf{dz}}}\mathbf{T}_{\underline{\mathbf{dz}}}{}^{m}\mathbf{C}_{\underline{\mathbf{dz}}}\mathbf{T}_{\underline{\mathbf{dz}}}{}^{m}C_{ds}G_{ds}G_{ds}T_{ds}T_{ds}{}^{m}C_{ds}{}^{m}C_{ks}G_{ks}A_{k}$-HPPO-GalNAc | 49 |

A subscript "k" represents a cEt nucleoside, a subscript "d" represents a stereo-standard DNA nucleoside, a subscript "s" indicates a phosphorothioate internucleoside linkage, and a subscript "z" represents an internucleoside linkage of formula IX, which is a mesyl phosphoramidate linkage.
Subscripts of nucleotides having an internucleoside linkage of formula IX are bold and underlined.
A superscript "m" before a C represents a 5-methylcytosine.

Study Design

For the in vivo activity and tolerability study in the table below, 3 BALB/C mice per group were administered a single dose of modified oligonucleotide by subcutaneous injection and sacrificed after 72 hours. Modified oligonucleotides were dosed at 0.1, 0.3, 0.9, 2.8, 8.3, or 25 mg/kg. One group of four BALB/C mice was injected with PBS.

Liver tissue was collected, mRNA was isolated, and levels of DNM2 in liver samples were measured by quantitative RTPCR with primer probe set RTS36436 (forward sequence: AGAGGAGACCGAGCGAAT, SEQ ID NO: 50; reverse sequence: CATGGTTTGTGTTGATGTACGAC, SEQ ID NO: 51; probe sequence: CCTACATCAGGGAGCGAGAAGGGA, SEQ ID NO: 52). Expression levels were normalized to total RNA as measured with RIBOGREEN®. $ED_{50}$ values were calculated by a least squares fit of data in GraphPad Prism using the equation "[Inhibitor] vs. response—Variable slope (four parameters)" and are presented in the table below. Plasma ALT was also measured and is presented in the table below. Elevations in ALT are associated with liver toxicity. The PBS treated mice have an ALT of 38.75 IU/L.

TABLE 47

In vivo activity and toxicity of modified oligonucleotides complementary to DNM2

| Compound ID | in vivo DNM2 $ED_{50}$ liver (mg/kg) | ALT @ 25 mg/kg (IU/L) |
|---|---|---|
| 1506053 | 0.94 | 35 |
| 1505722 | 0.53 | 110 |

Example 26: Design and Activity of Modified Oligonucleotides Complementary to Mouse FXII In Vitro and a Single Dose Duration of Action Study Design of Modified Oligonucleotides GalNAc-conjugated modified oligonucleotides comprising multiple mesyl phosphoramidate internucleoside linkages (Formula IX) and phosphorothioate internucleoside linkages were synthesized and tested. Each of the modified oligonucleotides has the same nucleobase sequence, AGCACTTTATTGAGTT (SEQ ID NO: 53), which is 100% complementary to mouse FXII, the complement of GENBANK NC_000079.6 truncated from 55415001 to 55430000 (SEQ ID NO: 54), at position 12009 to 12024. Each internucleoside linkage is either a phosphorothioate internucleoside linkage ("s"), a phosphodiester internucleoside linkage ("o"), or a mesyl phosphoramidate internucleoside linkage ("z").

The GalNAc moiety is conjugated to the 5' oxygen of compound 1447171 via a THA linker, as shown below:

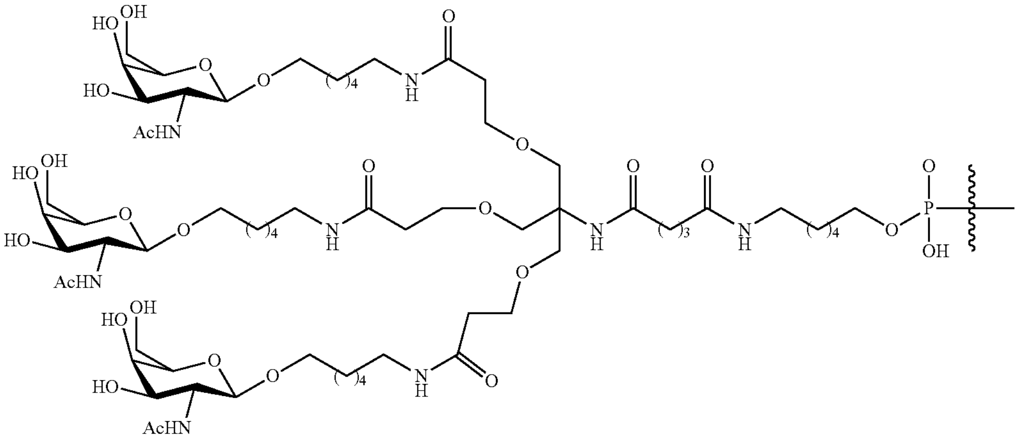

THA-GalNAc

Aside from compound 1447171, the modified oligonucleotides in the table below contain the GalNAc moiety conjugated to the 3'-oxygen as shown below:

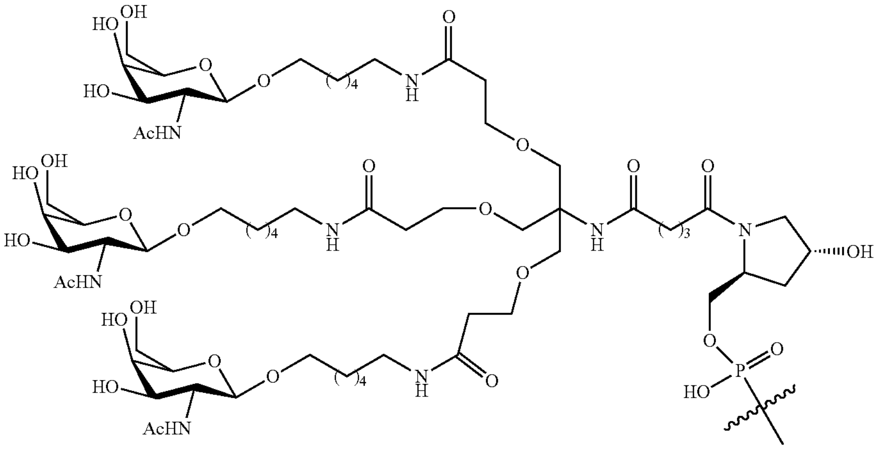

HPPO-GalNAc

Activity Assay

Activity of antisense oligonucleotides was tested in primary mouse hepatocytes. Primary mouse hepatocytes cells were transfected with lipofectamine. Each modified oligonucleotide was transfected at a starting concentration of 200 nM with 5-fold serial dilutions for a total of 8 dilutions. After a treatment period of approximately 24 hours, RNA was isolated and RNA expression was analyzed via quantitative RTPCR using primer probe set RTS2959 (forward sequence CAAAGGAGGGACATGTATCAACAC, SEQ ID NO: 91; reverse sequence: CTGGCAATGTTTCCCAGTGA, SEQ ID NO: 92; probe sequence: CCCAATGGGCCACACTGTCTCTGC, SEQ ID NO: 93). FXII RNA levels were normalized to total GAPDH. Activity expressed as half maximal inhibitory concentration ($IC_{50}$) was calculated using the log (inhibitor) vs normalized response—Variable slope function in GraphPad Prism 7.

TABLE 48

Design and in vitro activity of modified oligonucleotides complementary to mouse FXII

| Compound ID | Chemistry Notation (5' to 3') | $IC_{50}$ (nM) | SEQ ID NO. |
|---|---|---|---|
| 1447171 | THA-GalNAc-$A_{ks}G_{ks}{}^mC_{ks}A_{ds}{}^mC_{ds}T_{ds}T_{ds}T_{ds}A_{ds}T_{ds}T_{ds}G_{ds}A_{ds}G_{ks}T_{ks}T_k$ | n.d. | 53 |
| 1525915 | $A_{ks}G_{ks}{}^mC_{ks}A_{ds}{}^mC_{ds}T_{ds}T_{ds}T_{ds}A_{ds}T_{ds}T_{ds}G_{ds}A_{ds}G_{ks}T_{ks}T_k$-HPPO-GalNAc | 0.0231 | 53 |
| 1525921 | $A_{ks}G_{ko}{}^mC_{ko}A_{ds}{}^mC_{ds}T_{ds}T_{ds}T_{ds}A_{ds}T_{ds}T_{ds}G_{ds}A_{ds}G_{ko}T_{ks}T_k$-HPPO-GalNAc | 0.0175 | 53 |
| 1525920 | $A_{ko}G_{ko}{}^mC_{ko}A_{ds}{}^mC_{ds}T_{ds}T_{ds}T_{ds}A_{ds}T_{ds}T_{ds}G_{ds}A_{ds}G_{ko}T_{ko}T_k$-HPPO-GalNAc | 0.0118 | 53 |
| 1525922 | $A_{ks}G_{ks}{}^mC_{ko}A_{ds}{}^mC_{ds}T_{ds}T_{ds}T_{ds}A_{ds}T_{ds}T_{ds}G_{ds}A_{do}G_{ks}T_{ks}T_k$-HPPO-GalNAc | 0.0135 | 53 |

TABLE 48-continued

| Design and in vitro activity of modified oligonucleotides complementary to mouse FXII | | | |
|---|---|---|---|
| Compound ID | Chemistry Notation (5' to 3') | $IC_{50}$ (nM) | SEQ ID NO. |
| 1525923 | $A_{ks}G_{ks}{}^{m}\mathbf{C}_{\underline{\mathbf{kz}}}A_{ds}{}^{m}C_{ds}T_{ds}T_{ds}T_{ds}A_{ds}T_{ds}T_{ds}G_{ds}\mathbf{A}_{\underline{\mathbf{dz}}}G_{ks}T_{ks}T_{k}$-HPPO-GalNAc | 0.0155 | 53 |
| 1525924 | $A_{ks}G_{ks}{}^{m}C_{ks}\mathbf{A}_{\underline{\mathbf{dz}}}{}^{m}\mathbf{C}_{\underline{\mathbf{dz}}}\mathbf{T}_{\underline{\mathbf{dz}}}\mathbf{T}_{\underline{\mathbf{dz}}}T_{ds}A_{ds}T_{ds}T_{ds}G_{ds}A_{ds}G_{ks}T_{ks}T_{k}$-HPPO-GalNAc | 0.0111 | 53 |
| 1525925 | $A_{ks}G_{ko}{}^{m}C_{ko}\mathbf{A}_{\underline{\mathbf{dz}}}{}^{m}\mathbf{C}_{\underline{\mathbf{dz}}}\mathbf{T}_{\underline{\mathbf{dz}}}\mathbf{T}_{\underline{\mathbf{dz}}}T_{ds}A_{ds}T_{ds}T_{ds}G_{ds}A_{ds}G_{ko}T_{ks}T_{k}$ HPPO-GalNAc | 0.0118 | 53 |
| 1525919 | $\mathbf{A}_{\underline{\mathbf{kz}}}G_{ko}{}^{m}C_{ko}A_{ds}{}^{m}C_{ds}T_{ds}T_{ds}T_{ds}A_{ds}T_{ds}T_{ds}G_{ds}A_{ds}G_{kc}\mathbf{T}_{\underline{\mathbf{kz}}}T_{k}$ HPPO-GalNAc | 0.0292 | 53 |

A subscript "k" represents a cEt nucleoside, a subscript "d" represents a stereo-standard DNA nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined.
A superscript "m" before a C represents a 5-methylcytosine.

Treatment

C57/B6J mice (Jax) were divided into groups of four male mice each for modified oligonucleotide treatment. Each mouse received a single subcutaneous injection of modified oligonucleotide at a dose of 0.9 mg/kg. One group of four mice received subcutaneous injections of PBS. The PBS-injected group served as the control group to which oligonucleotide-treated groups were compared. Prior to the first dose, a tail bleed was performed to determine plasma FXII protein levels at baseline (BL). Tail bleeds were also performed at 48 h, 96 h, 7 days, 14 days, and 21 days following the dose.

Protein Analysis

Mouse FXII protein levels in plasma were determined using a FXII ELISA kit (Molecular Innovations catalog number: MFXIIKT-TOT). The data is presented as percent change from baseline within each treatment group.

TABLE 49

| Reduction of mouse FXII protein in plasma | | | | | | |
|---|---|---|---|---|---|---|
| | FXII protein (% baseline) in plasma at indicated time after injection | | | | | |
| Compound No. | Day 0 (baseline) | 48 hours | 96 hours | 7 day | 14 day | 21 day |
| PBS | 100 | 168 | 257 | 137 | 138 | 118 |
| 1525915 | 100 | 139 | 93 | 23 | 31 | 67 |
| 1525921 | 100 | 90 | 58 | 23 | 38 | 59 |
| 1525920 | 100 | 119 | 101 | 24 | 29 | 65 |
| 1525922 | 100 | 70 | 45 | 18 | 27 | 41 |
| 1525923 | 100 | 89 | 92 | 35 | 48 | 102 |
| 1525924 | 100 | 88 | 54 | 29 | 43 | 58 |
| 1525925 | 100 | 90 | 52 | 20 | 16 | 35 |
| 1525919 | 100 | 95 | 61 | 21 | 29 | 46 |

Example 27: Design and Activity of sARNA Complementary to Mouse FXII in a Single Dose Duration of Action Study Design of siRNA Double-stranded siRNA compounds were formed by annealing one antisense strand and one sense strand described below. siRNA antisense strands containing mesyl phosphoramidate internucleoside linkages were designed as described in the table below and synthesized as described above. Each antisense strand has the sequence (from 5' to 3') UAAAGCACUUJUAUUGAGUUJUCUG (SEQ ID NO: 55) or TAAAGCACUUUAUUGAGUUUCUG (SEQ ID NO: 56), wherein the sequence (from 5' to 3') of AAAGCACUUUAUUGAGUUUCUG (SEQ ID NO: 57) is 100% complementary to mouse FXII, the complement of GENBANK NC_000079.6 truncated from 55415001 to 55430000 (SEQ ID NO: 54), at position 12005 to 12026.

TABLE 50

| Design of antisense strand of modified oligonucleotides complementary to mouse FXII | | |
|---|---|---|
| Compound ID | Chemistry Notation (5' to 3') | SEQ ID NO. |
| 1523579 | $U_{ys}A_{fs}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{ys}U_{ys}G_{y}$ | 55 |
| 1525955 | $U_{ys}A_{fs}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}\mathbf{C}_{\underline{\mathbf{yz}}}\mathbf{U}_{\underline{\mathbf{yz}}}G_{y}$ | 55 |
| 1525956 | $U_{yz}A_{fs}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}\mathbf{C}_{\underline{\mathbf{yz}}}\mathbf{U}_{\underline{\mathbf{yz}}}G_{y}$ | 55 |
| 1525957 | $U_{ys}\mathbf{A}_{\underline{\mathbf{fz}}}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}\mathbf{C}_{\underline{\mathbf{yz}}}\mathbf{U}_{\underline{\mathbf{yz}}}G_{y}$ | 55 |
| 1525958 | $\mathbf{U}_{\underline{\mathbf{yz}}}A_{fo}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}\mathbf{C}_{\underline{\mathbf{yz}}}\mathbf{U}_{\underline{\mathbf{yz}}}G_{y}$ | 55 |
| 1525959 | $T_{es}A_{fo}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}\mathbf{C}_{\underline{\mathbf{yz}}}\mathbf{U}_{\underline{\mathbf{yz}}}G_{y}$ | 55 |
| 1527076 | $U_{ys}A_{fo}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}\mathbf{C}_{\underline{\mathbf{yz}}}\mathbf{U}_{\underline{\mathbf{yz}}}G_{y}$ | 55 |
| 1528437 | $\mathbf{T}_{\underline{\mathbf{ez}}}A_{fo}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}\mathbf{C}_{\underline{\mathbf{yz}}}\mathbf{U}_{\underline{\mathbf{yz}}}G_{y}$ | 56 |

TABLE 50-continued

| Design of antisense strand of modified oligonucleotides complementary to mouse FXII | | |
|---|---|---|
| Compound ID | Chemistry Notation (5' to 3') | SEQ ID NO. |
| 1528438 | $T_{eo}A_{\underline{\mathbf{fz}}}A_{yo}A_{yo}G_{yo}C_{fo}A_{yo}C_{yo}U_{yo}U_{yo}U_{yo}A_{yo}U_{yo}U_{fo}G_{fo}A_{fo}G_{yo}U_{yo}U_{yo}U_{yo}C_{\underline{\mathbf{yz}}}U_{\underline{\mathbf{yz}}}G_{y}$ | 56 |
| 1526197 | vP-$T_{es}A_{fs}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{\mathbf{yz}}}U_{\underline{\mathbf{yz}}}G_{y}$ | 56 |
| 1528440 | z.$T_{es}A_{fs}A_{yo}A_{yo}G_{yo}C_{fo}A_{yo}C_{yo}U_{yo}U_{yo}U_{yo}A_{yo}U_{yo}U_{fo}G_{yo}A_{fo}G_{yo}U_{yo}U_{yo}U_{yo}C_{\underline{\mathbf{yz}}}U_{\underline{\mathbf{yz}}}G_{y}$ | 56 |

In the table, above, a subscript "e" represents a 2'-MOE modified nucleoside, a subscript "y" represents a 2'-OMe modified nucleoside, a subscript "f" represents a 2'-F modified nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined. Compound No. 1526197 contains a vinyl phosphonate (vP) moiety on the 5'-end. Compound No. 1528440 contains a 5'-mesylphosphoramidate having formula XXII:

XXII

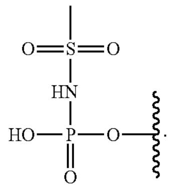

TABLE 51

| Design of sense strand of modified oligonucleotides | | |
|---|---|---|
| Compound ID | Chemistry Notation (5' to 3') | SEQ ID NO. |
| 1523578 | $G_{ys}A_{ys}A_{yo}A_{yo}A_{yo}C_{yo}U_{yo}C_{fo}A_{yo}A_{fo}U_{fo}A_{fo}A_{yo}A_{yo}G_{yo}U_{yo}G_{yo}C_{yo}U_{yo}U_{yo}U_{yo}A_{y}$-HPPO-GalNAc | 58 |
| 1523580 | $A_{ys}A_{ys}C_{yo}U_{yo}C_{yo}A_{yo}A_{fo}U_{yo}A_{fo}A_{fo}A_{fo}G_{yo}U_{yo}G_{yo}C_{yo}U_{yo}U_{yo}U_{yo}G_{yo}A_{yo}A_{y}$-HPPO-GalNAc | 59 |

In the table above, a subscript "f" represents a 2'-F modified nucleoside, a subscript "y" represents a 2'-OMe modified nucleoside, a subscript "s" indicates a phosphorothioate internucleoside linkage, and a subscript "o" represents a phosphodiester internucleoside linkage.

In vitro Activity

Activity of various siRNA formed by annealing one antisense strand and one sense strand described above was tested in primary mouse hepatocytes. Primary mouse hepatocytes cells were transfected with RNAiMAX formulated siRNA. Each modified oligonucleotide was transfected at a starting concentration of 200 nM with 5-fold serial dilutions for a total of 8 dilutions. After a treatment period of approximately 24 hours, RNA was isolated and RNA expression was analyzed via quantitative RTPCR using primer probe set RTS2959 (described herein above). FXII RNA levels were normalized to total GAPDH. Activity expressed as half maximal inhibitory concentration ($IC_{50}$) was calculated using the log (inhibitor) vs normalized response—Variable slope function in GraphPad Prism 7.

TABLE 52a

| Reduction of mouse FXII protein | | | |
|---|---|---|---|
| siRNA Duplex Compound No. | Antisense Compound No. | Sense Compound No. | $IC_{50}$ (nM) |
| 1523582 | 1523579 | 1523578 | 0.0015 |
| 1523583 | 1523581 | 1523580 | 0.0076 |
| 1526140 | 1525955 | 1523578 | 0.0060 |
| 1526171 | 1525956 | 1523578 | 0.1304 |
| 1526182 | 1525957 | 1523578 | 0.0086 |
| 1526193 | 1525958 | 1523578 | 0.1171 |
| 1526194 | 1525959 | 1523578 | 0.0376 |
| 1527077 | 1527076 | 1523578 | 0.0053 |
| 1529977 | 1528437 | 1523578 | 0.1266 |
| 1529978 | 1528438 | 1523578 | 0.0292 |
| 1529980 | 1528440 | 1523578 | 0.00003 |
| 1526198 | 1526197 | 1523578 | 0.0014 |

Treatment

C57/B6J mice (Jax) were divided into groups of four male mice each for treatment with siRNAs. Each mouse received a single subcutaneous injection of oligomeric duplex at a dose of 0.5 mg/kg. One group of four mice received subcutaneous injections of PBS. The PBS-injected group served as the control group to which oligonucleotide-treated groups were compared. Prior to the first dose, a tail bleed was performed to determine plasma FXII protein levels at baseline (BL). Tail bleeds were also performed at 48 h, 96 h, 7 days, 14 days, and 21 days following the dose.

Protein Analysis

Mouse FXII protein levels in plasma were determined using a Molecular Innovations FXII ELISA kit (catalog number: MFXILKT-TOT). The data is presented as percent change in protein, relative to PBS control.

TABLE 52b

| Reduction of mouse FXII protein | | | | | | | | |
|---|---|---|---|---|---|---|---|---|
| siRNA Duplex | Antisense | Sense | FXII protein (% baseline) in plasma at indicated time after injection | | | | | |
| Compound No. | Compound No. | Compound No. | Day 0 (baseline) | 48 hours | 96 hours | 7 day | 14 day | 21 day |
| PBS | N/A | N/A | 100 | 168 | 257 | 137 | 138 | 118 |
| 1523582 | 1523579 | 1523578 | 100 | 75 | 62 | 30 | 40 | 42 |
| 1523583 | 1523581 | 1523580 | 100 | 108 | 155 | 48 | 25 | 33 |
| 1526140 | 1525955 | 1523578 | 100 | 83 | 69 | 32 | 38 | 47 |
| 1526171 | 1525956 | 1523578 | 100 | 143 | 256 | 193 | 112 | 144 |
| 1526182 | 1525957 | 1523578 | 100 | 71 | 60 | 17 | 26 | 39 |
| 1526193 | 1525958 | 1523578 | 100 | 134 | 228 | 144 | 96 | 127 |
| 1526194 | 1525959 | 1523578 | 100 | 131 | 88 | 65 | 64 | 111 |
| 1527077 | 1527076 | 1523578 | 100 | 78 | 60 | 36 | 36 | 96 |
| 1529977 | 1528437 | 1523578 | 100 | 114 | 99 | 80 | 105 | 107 |
| 1529978 | 1528438 | 1523578 | 100 | 111 | 150 | 167 | 109 | 132 |
| 1526198 | 1526197 | 1523578 | 100 | 64 | 25 | 16 | 19 | 30 |

Example 28: Design, Activity, and Tolerability of Modified Oligonucleotides with Mesyl Phosphoramidate Internucleoside Linkages in Combination with Stereo-Non-Standard Nucleosides

Design of Modified Oligonucleotides

Modified oligonucleotides comprising multiple mesyl phosphoramidate internucleoside linkages (Formula IX) and phosphorothioate internucleoside linkages were synthesized and tested. Each of the modified oligonucleotides has the same nucleobase sequence, AGACTCTCGGTTCCGA (SEQ ID NO: 49), which is 100% complementary to mouse DNM2, GENBANK Accession No. NC_000075.6 truncated from 21422001 to 21511000 (SEQ ID NO: 47), at position 3046 to 3061. Each internucleoside linkage is either a phosphorothioate internucleoside linkage ("s") or a mesyl phosphoramidate internucleoside linkage ("z").

TABLE 53

| Design of modified oligonucleotides with mesyl phosphoramidate internucleoside linkages | | |
|---|---|---|
| Compound ID | Chemistry Notation (5' to 3') | SEQ ID NO. |
| 694804 | $A_{ks}G_{ks}A_{ks}{}^{m}C_{ds}T_{ds}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537106 | $A_{ks}G_{ks}A_{ks}{}^{m}C_{\underline{\mathbf{dz}}}T_{\underline{\mathbf{dz}}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537108 | $A_{ks}G_{ks}A_{ks}{}^{m}C_{\underline{\mathbf{dz}}}U_{\underline{\mathbf{yz}}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 48 |
| 1537109 | $A_{ks}G_{ks}A_{ks}{}^{m}C_{\underline{\mathbf{dz}}}T_{\underline{\mathbf{[aDd]z}}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537110 | $A_{ks}G_{ks}A_{ks}{}^{m}C_{\underline{\mathbf{dz}}}T_{\underline{\mathbf{[dx]z}}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537111 | $A_{ks}G_{ks}A_{ks}{}^{m}C_{\underline{\mathbf{dz}}}T_{\underline{\mathbf{[bLd]z}}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537112 | $A_{ks}G_{ks}A_{ks}{}^{m}C_{\underline{\mathbf{dz}}}T_{\underline{\mathbf{[aLd]z}}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537113 | $A_{ks}G_{ks}A_{ks}{}^{m}C_{\underline{\mathbf{dz}}}T_{\underline{\mathbf{[aDdx]z}}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537114 | $A_{ks}G_{ks}A_{ks}{}^{m}C_{\underline{\mathbf{dz}}}T_{\underline{\mathbf{[bLdx]z}}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1537115 | $A_{ks}G_{ks}A_{ks}{}^{m}C_{\underline{\mathbf{dz}}}T_{\underline{\mathbf{[aLdx]z}}}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |

In the table above, a subscript "d" represents a stereo-standard DNA nucleoside, a subscript "y" represents a 2'-OMe modified nucleoside, a subscript "k" represents a cEt nucleoside, a subscript "s" indicates a phosphorothioate internucleoside linkage, and a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methylcytosine. A subscript "[bLd]" represents a 2'-β-L-deoxyribosyl sugar moiety, a subscript "[aDd]" represents a 2'-α-D-deoxyribosyl sugar moiety, a subscript "[aLd]" represents a 2'-α-L-deoxyribosyl sugar moiety, a subscript "[dx]" represents a 2'-β-D-deoxyxylosyl sugar moiety, a subscript "[bLdx]" represents a 2'-β-L-deoxyxylosyl sugar moiety, a subscript "[aDdx]" represents a 2'-α-D-deoxyxylosyl sugar moiety, a subscript "[aLdx]" represents a 2'-α-L-deoxyxylosyl sugar moiety (See FIG. 1)

In Vitro Activity Assay

The modified oligonucleotides were tested for their ability to reduce target RNA in a series of experiments. Cultured mouse 3T3-$L_1$ cells at a density of 20,000 cells per well were transfected using electroporation with modified oligonucleotides diluted to 20 μM, 7 μM, 2 μM, 0.7 μM, 0.3 μM, 0.1 μM, and 0.03 μM. After a treatment period of approximately 16 hours, RNA levels were measured using DNM2 primer probe set RTS36436 (forward sequence: AGAGGAGACCGAGCGAAT, SEQ ID NO: 50; reverse sequence: CATGGTTTGTGTTGATGTACGAC, SEQ ID NO: 51; probe sequence: CCTACATCAGGGAGCGAGAAGGGA, SEQ ID NO: 52). RNA levels for each target were normalized to total RNA content, as measured by RIBOGREEN®.

Activity expressed as half maximal inhibitory concentration ($IC_{50}$) was calculated using the log (inhibitor) vs response (three parameter) function in GraphPad Prism 7.

In Vitro Toxicity Assay

In vitro toxicity of modified oligonucleotides described above was determined as described in Example 3.

TABLE 54

In vitro activity and caspase activation by modified oligonucleotides with mesyl phosphoramidate internucleoside linkages in combination with stereo-non-standard nucleosides

| Compound ID | Caspase Activation (% Mock) | $IC_{50}$ (nM) |
|---|---|---|
| 694804 | 552 | 344 |
| 1537106 | 657 | 295 |
| 1537108 | 178 | 231 |
| 1537109 | 159 | 717 |
| 1537110 | 166 | 421 |
| 1537111 | 144 | 572 |
| 1537112 | 186 | 388 |
| 1537113 | 241 | 860 |
| 1537114 | 278 | 586 |
| 1537115 | 262 | 290 |

Example 29: Design and Activity of siRNA with Mesyl Phosphoramidate Internucleoside Linkages to HPRT1 in Vitro Design of siRNAs Double-stranded siRNAs comprising modified oligonucleotides having mesyl phosphoramidate internucleoside linkages (Formula IX) and having either stereo-standard nucleosides or stereo-non-standard nucleosides were synthesized and tested. Each internucleoside linkage is either a phosphorothioate internucleoside linkage ("s"), a phosphodiester internucleoside linkage ("o"), or a mesyl phosphoramidate internucleoside linkage ("z").

IX

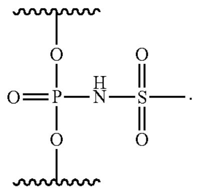

Each antisense strand has either the sequence (from 5' to 3'): TUAAAAUCUACAGUCAUAGGATT (SEQ ID NO: 60) or UUAAAAUCUACAGUCAUAGGATIT (SEQ ID NO: 61), wherein the sequence (from 5' to 3') UAAAAUCUACAGUCAUAGGA (SEQ ID NO: 62) is 100% complementary to GenBank Accession No. NM_000194.2 (SEQ ID NO: 22) from 446 to 465, and each antisense strand has a 5-phosphate.

The sense strand (Compound ID: 1505889) has the chemical notation (5' to 3'): $U_{ys}C_{ys}C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}U_{ys}A_{ys}U_{y}$ (SEQ ID NO: 23), wherein a subscript "f" represents a 2'-E modified nucleoside, a subscript "y" represents a 2'-OMe modified nucleoside, a subscript "s" indicates a phosphorothioate internucleoside linkage, and a subscript "o" represents a phosphodiester internucleoside linkage.

TABLE 55

Design of antisense strand modified oligonucleotides targeted to HPRT1 containing mesyl phosphoramidate internucleoside linkages

| Compound ID | Chemistry Notation (5' to 3') | SEQ ID NO. |
|---|---|---|
| 1512935 | $P.T_{ys}U_{fs}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |
| 1534483 | $p.U_{ys}U_{fs}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534484 | $p.^{T_{yz}}\ U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |
| 1534485 | $p.^{U_{yz}}\ U_{fo}A_{yo}A_{yo}A_{yo}A_{fo}U_{yo}C_{fo}U_{fo}A_{yo}C_{yo}A_{yo}G_{yo}U_{fo}C_{yo}GA_{fo}U_{yo}A_{yo}G_{yo}G_{yo}A_{ys}T_{ds}T_{d}$ | 61 |
| 1534486 | $P.^{U_{fz}}\ U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534487 | $p.^{U_{[f2bDa]z}}\ U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534488 | $P.U_{[f2bDx]o}{}^{U_{fz}}\ A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534489 | $p.U_{[f2aDr]o}{}^{U_{fz}}\ A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534490 | $P.U_{[f2aDa]o}{}^{U_{fz}}\ A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534491 | $P.U_{[f2aDx]o}{}^{U_{fz}}\ A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534493 | $p.U_{[f2aLr]o}{}^{U_{fz}}\ A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534494 | $p.U_{[f2bLx]o}{}^{U_{fz}}\ A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534495 | $p.U_{[f2aLa]o}{}^{U_{fz}}\ A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534496 | $P.U_{[f2aLx]o}{}^{U_{fz}}\ A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |

TABLE 55-continued

| Design of antisense strand modified oligonucleotides targeted to HPRT1 containing mesyl phosphoramidate internucleoside linkages | | |
|---|---|---|
| Compound ID | Chemistry Notation (5' to 3') | SEQ ID NO. |
| 1534497 | P.$U_{[f2bLr]o}U_{\underline{\mathbf{fz}}}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 61 |
| 1534492 | P.$U_{[f2bLa]o}U_{\underline{\mathbf{fz}}}A_{yo}A_{yo}A_{yo}A_{fo}U_{yo}C_{fo}U_{fo}A_{yo}$Cyc$A_{yo}G_{yo}U_{fo}C_{yo}A_{fo}U_{yo}A_{yo}G_{yo}G_{yo}A_{ys}T_{ds}T_{d}$ | 61 |
| 1537089 | p.$T_{\underline{\mathbf{[m2bDx]z}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |
| 1537090 | p.$T_{\underline{\mathbf{[m2bDa]z}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |
| 1537091 | p.$T_{\underline{\mathbf{[m2aDa]z}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |
| 1537092 | p.$T_{\underline{\mathbf{[m2aLa]z}}}U_{fo}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ | 60 |

Figure 2:
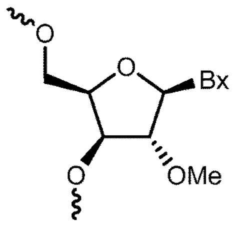
FIG. 2 depicts isomers of 2'-O-methyl furanosyl sugar moieties having formulas I-VII.
Figure 2:
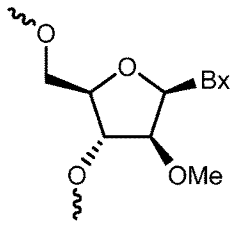
Figure 2:
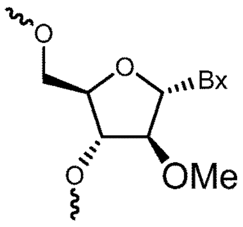
Figure 2:
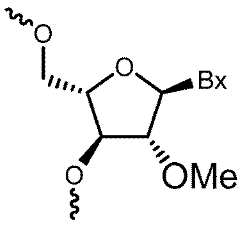
Figure 3:
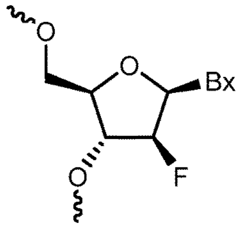
FIG. 3 depicts isomers of 2'-fluoro furanosyl sugar moieties having formulas I-VII.
Figure 3:
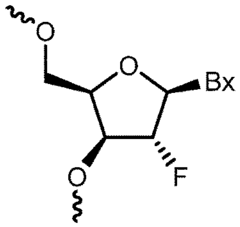
Figure 3:
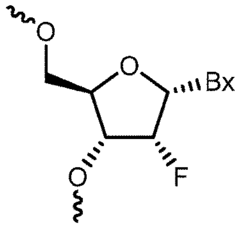
Figure 3:
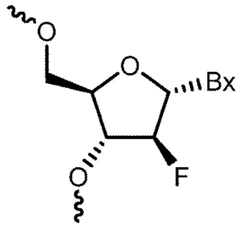
Figure 3:
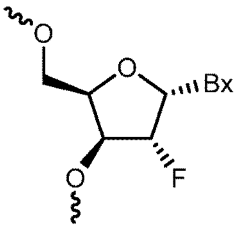
Figure 3:
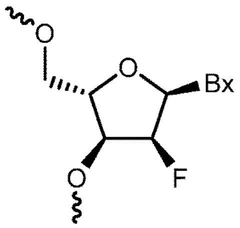
Figure 3:
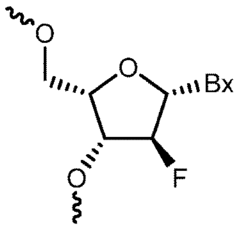
Figure 3:
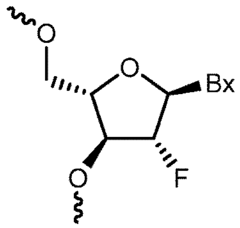
Figure 3:
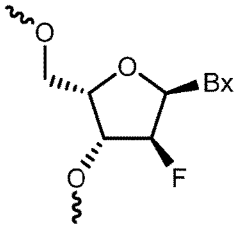
Figure 3:
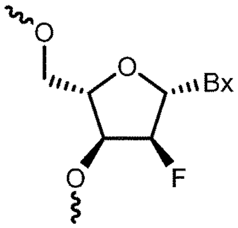
Figure 3:
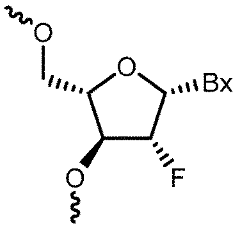

In the table above, a "p." represents a 5'-phosphate, a subscript "d" represents a stereo-standard DNA nucleoside, a subscript "y" represents a 2'-OMe modified nucleoside, a subscript "f" represents a 2'-F modified nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined. A subscript "[f2bDa]" represents a 2'-fluoroβ-D-arabinosyl sugar moiety, a subscript "[f2bDx]" represents a 2'-fluoro-β-D-xylosyl sugar moiety, a subscript "[f2aDr]" represents a 2'-fluoro-α-D-ribosyl sugar moiety, a subscript "[f2aDa]" represents a 2'-fluoro-α-D-arabinosyl sugar moiety, a subscript "[f2aDx]" represents a 2'-fluoro-α-D-xylosyl sugar moiety, a subscript "[f2aLr]" represents a 2'-fluoro-α-L-ribosyl sugar moiety, a subscript "[f2bLx]" represents a 2'-fluoro-β-L-xylosyl sugar moiety, a subscript "[f2aLa]" represents a 2'-fluoro-α-L-arabinosyl sugar moiety, a subscript "[f2aLx]" represents a 2'-fluoro-α-L-xylosyl sugar moiety, a subscript "[f2bLr]" represents a 2'-fluoro-β-L-ribosyl sugar moiety, a subscript "[f2bLa]" represents a 2'-fluoro-β-L-arabinosyl sugar moiety, a subscript "[m2bDx]" represents a 2'-O-methyl-β-D-xylosyl sugar moiety, a subscript "[m2bDa]" represents a 2'-O-methyl-β-D-arabinosyl sugar moiety, a subscript "[m2aDa]" represents a 2'-O-methyl-α-D-arabinosyl sugar moiety, a subscript "[m2aLa]" represents a 2'-O-methyl-α-L-arabinosyl sugar moiety. (See FIG. 2 and FIG. 3)

Activity Assay

Activity of various siRNA formed by annealing one antisense strand and one sense strand described above was tested in HeLa cells. HeLa cells were transfected with RNAiMAX formulated siRNA. Each siRNA compound was transfected at a starting concentration of 10 nM with 5-fold serial dilutions for a total of 8 dilutions. After a treatment period of approximately 6 hours, RNA was isolated and RNA expression was analyzed via quantitative RTPCR using primer probe set RTS35336 (forward sequence TTGTTGTAGGATATGCCCTTGA, SEQ ID NO: 63; reverse sequence: GCGATGTCAATAGGACTCCAG, SEQ ID NO: 64; probe sequence: AGCCTAAGATGAGAGTTCAAGTTGAGTTTGG, SEQ ID NO: 65). HPRT1 RNA levels were normalized to total RNA content, as measured by RIBOGREEN®. $IC_{50}$ values were calculated and are presented in the table below.

TABLE 56

| Activity of siRNAs targeted to HPRT1 containing mesyl phosphoramidate internucleoside linkages and/or stereo-non-standard nucleosides | | |
|---|---|---|
| Antisense Strand | Sense Strand | $IC_{50}$ (nM) |
| 1455005 | 1505889 | 0.01 |
| 1512935 | 1505889 | 0.03 |
| 1534483 | 1505889 | 0.02 |
| 1534484 | 1505889 | 0.06 |
| 1534485 | 1505889 | 0.03 |
| 1534486 | 1505889 | 0.04 |
| 1534487 | 1505889 | 0.04 |
| 1534488 | 1505889 | 0.10 |
| 1534489 | 1505889 | 0.04 |
| 1534491 | 1505889 | 0.04 |
| 1534494 | 1505889 | 0.18 |
| 1534496 | 1505889 | 0.04 |
| 1534497 | 1505889 | 0.08 |
| 1534492 | 1505889 | 0.07 |
| 1537090 | 1505889 | 0.05 |
| 1537091 | 1505889 | 0.06 |
| 1537092 | 1505889 | 0.13 |

Example 30: Evaluation of Proinflammatory Effects in BJAB Assay

Modified oligonucleotides targeting human CRP, human neurology Target X, human CXCL12, human oncology target Y, or human oncology target Z were tested for potential immunostimulatory properties in an in vitro human BJAB activation assay.

Immortalized human Burkitt lymphoma B cells, BJAB cells (DSMZ, Cat #ACC 757), were cultured in RPMI1640 medium containing 20% fetal bovine serum at 37° C. and 5% $CO_2$. Cells were maintained at the optimal recommended density of 0.5-0.7×$10^6$ cells per milliliter. Cells were transferred to 50 mL conical Falcon tubes and centrifuged at 330 RCF for 5 minutes. Cells were resuspended at a concentration of 7.5×$10^5$ cells per milliliter in RPMI culture medium. 50 mL per well of RPMI culture medium containing 200 U/mL penicillin and 200 mg/ml streptomycin was added to v-bottom tissue culture treated 96-well microplate. 50 µL of the cell suspension was added to the v-bottom tissue culture treated 96-well microplate. 11 µl of 10× concentrated modified oligonucleotides was then added to the plate and incubated for 24 hours at 37° C. and 5% $CO_2$.

The modified oligonucleotides were designed as described in the table below, wherein "d" represents a 2'-β-D-deoxyribosyl sugar moiety, "k" represents a cEt sugar moiety, and "e" represents a 2'-MOE sugar moiety. Each internucleoside linkage is either a phosphorothioate internucleoside linkage ("s"), a phosphodiester internucleoside linkage ("o"), a mesyl phosphoramidate internucleoside linkage of Formula IX ("z"), a mesyl phosphoramidate internucleoside linkage of Formula XI ("[XI]"), or a mesyl phosphoramidate internucleoside linkage of Formula XIII ("[XIII]").

Subscripts of nucleotides having a modified mesyl phosphoramidate internucleoside linkage of generic Formula XVII are bold and underlined. All cytosine residues are 5-methylcytosines. A nucleobase represented by N in the table below indicates A, G, T, or ${}^{m}C$. Each oligonucleotide X (X1-X4) has the same sequence; each oligonucleotide Y (Y1-Y3) has the same sequence; and each oligonucleotide Z has the same sequence.

IX

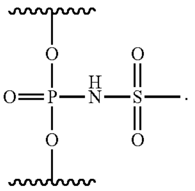

-continued

XI

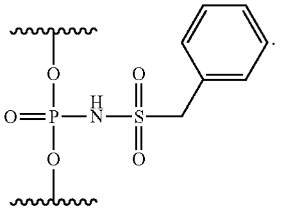

XIII

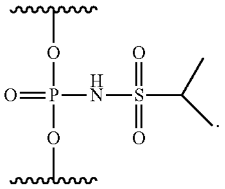

Compound Nos. 353512, 104838, 735746, and 785674 were added to the assay as standards. Compound No. 353512 is an internal standard known to be a high responder for CCL22 release in the assay. Compound No. 104838 is an internal standard known to be a non-responder in the assay (a negative control).

After incubation, total RNA was isolated. The amount of CCL22 mRNA was quantified using quantitative RTPCR. CCL22 PCR results were normalized to total GAPDH. Results are presented in the table below as log fold increase of CCL22, relative to untreated control.

TABLE 57

Design and BJAB inflammatory response of modified oligonucleotides with mesyl phosphoramidate internucleoside linkages for BJAB assay

| Compound ID | Chemistry Notation (5' to 3') | Target | CCL22 log fold increase | SEQ ID NO. |
|---|---|---|---|---|
| 104838 | $G_{es}{}^{m}C_{es}T_{es}G_{es}A_{ds}T_{ds}T_{ds}A_{ds}G_{ds}A_{ds}$ $G_{ds}A_{ds}G_{ds}A_{ds}G_{ds}G_{es}T_{es}{}^{m}C_{es}{}^{m}C_{es}{}^{m}C_{e}$ | Standard-low | 0.32 | 66 |
| 353512 | $T_{es}{}^{m}C_{es}{}^{m}C_{es}{}^{m}C_{ds}A_{ds}T_{ds}T_{ds}T_{ds}{}^{m}C_{ds}A_{ds}$ $G_{ds}G_{ds}A_{ds}G_{ds}A_{ds}{}^{m}C_{ds}{}^{m}C_{ds}T_{es}G_{es}G_{e}$ | Standard-high | 1.48 | 67 |
| X1 | $N_{es}N_{eo}N_{eo}N_{eo}N_{es}N_{ds}N_{ds}N_{ds}N_{ds}N_{ds}$ $N_{ds}N_{ds}N_{ds}N_{ds}N_{ds}N_{eo}N_{eo}N_{es}N_{es}N_{e}$ | Target X | 2.38 | 70 |
| X2 | $N_{\underline{\mathbf{ez}}}N_{\underline{\mathbf{ez}}}N_{eo}N_{eo}N_{es}N_{ds}N_{ds}N_{ds}N_{ds}N_{ds}$ $N_{ds}N_{ds}N_{ds}N_{ds}N_{ds}N_{eo}N_{ec}N_{\underline{\mathbf{ez}}}N_{\underline{\mathbf{ez}}}N_{e}$ | Target X | 1.63 | 70 |
| X3 | $N_{es}N_{eo}N_{eo}N_{eo}N_{es}N_{\underline{\mathbf{dz}}}N_{\underline{\mathbf{dz}}}N_{\underline{\mathbf{dz}}}N_{ds}N_{ds}$ $N_{ds}N_{ds}N_{ds}N_{ds}N_{ds}N_{eo}N_{eo}N_{es}N_{es}N_{e}$ | Target X | 0.70 | 70 |
| X4 | $N_{es}N_{eo}N_{eo}N_{eo}N_{es}N_{ds}N_{ds}N_{ds}N_{ds}N_{ds}$ $N_{ds}N_{ds}N_{\underline{\mathbf{dz}}}N_{\underline{\mathbf{dz}}}N_{\underline{\mathbf{dz}}}N_{eo}N_{eo}N_{es}N_{es}N_{e}$ | Target X | 0.95 | 70 |
| 353512 | $T_{es}{}^{m}C_{es}{}^{m}C_{es}{}^{m}C_{ds}A_{ds}T_{ds}T_{ds}T_{ds}{}^{m}C_{ds}A_{ds}$ $G_{ds}G_{ds}A_{ds}G_{ds}A_{ds}{}^{m}C_{ds}{}^{m}C_{ds}T_{es}G_{es}G_{e}$ | CRP | 1.40 | 69 |
| 1523450 | $T_{es}{}^{m}C_{es}{}^{m}C_{es}{}^{m}C_{\underline{\mathbf{dz}}}A_{\underline{\mathbf{dz}}}T_{\underline{\mathbf{dz}}}T_{ds}T_{ds}{}^{m}C_{ds}A_{ds}$ $G_{ds}G_{ds}A_{ds}G_{ds}A_{ds}{}^{m}C_{ds}{}^{m}C_{ds}T_{es}G_{es}G_{e}$ | CRP | 0.09 | 69 |
| 1523451 | $T_{es}{}^{m}C_{es}{}^{m}C_{es}{}^{m}C_{ds}A_{ds}T_{ds}T_{ds}T_{ds}{}^{m}C_{ds}A_{ds}$ $G_{ds}G_{ds}A_{ds}G_{ds}A_{\underline{\mathbf{dz}}}{}^{m}C_{\underline{\mathbf{dz}}}{}^{m}C_{\underline{\mathbf{dz}}}T_{es}G_{es}G_{e}$ | CRP | 0.57 | 69 |
| Y1 | $N_{ks}N_{ks}N_{ks}N_{ds}N_{ds}N_{ds}N_{ds}N_{ds}N_{ds}N_{ds}N_{ds}N_{ds}N_{ds}N_{ks}N_{ks}N_{k}$ | Target Y | 1.33 | 29 |
| Y2 | $N_{ks}N_{ks}N_{ks}N_{\underline{\mathbf{dz}}}N_{\underline{\mathbf{dz}}}N_{\underline{\mathbf{dz}}}N_{ds}N_{ds}N_{ds}N_{ds}N_{ds}N_{ds}N_{ds}N_{ks}N_{ks}N_{k}$ | Target Y | 0.77 | 29 |
| Y3 | $N_{ks}N_{ks}N_{ks}N_{ds}N_{ds}N_{ds}N_{ds}N_{ds}$NasN$_{ds}N_{\underline{\mathbf{dz}}}N_{\underline{\mathbf{dz}}}N_{\underline{\mathbf{dz}}}N_{ks}N_{ks}N_{k}$ | Target Y | 0.24 | 29 |

TABLE 57-continued

Design and BJAB inflammatory response of modified oligonucleotides with mesyl phosphoramidate internucleoside linkages for BJAB assay

| Compound ID | Chemistry Notation (5' to 3') | Target | CCL22 log fold increase | SEQ ID NO. |
|---|---|---|---|---|
| Z1 | $N_{ks}N_{ks}N_{ks}N_{ds}N_{ds}N_{ds}N_{ds}N_{ds}N_{ds}N_{ds}N_{ds}N_{ds}N_{ds}N_{ks}N_{ks}N_{k}$ | Target Z | 1.15 | 29 |
| Z2 | $N_{kz}N_{kz}N_{ks}N_{ds}N_{ds}N_{ds}N_{ds}N_{ds}N_{ds}N_{ds}N_{ds}N_{ds}N_{ds}N_{kz}N_{kz}N_{k}$ | Target Z | 0.03 | 29 |
| Z3 | $N_{ks}N_{ks}N_{ks}N_{\underline{dz}}N_{\underline{dz}}N_{\underline{dz}}N_{ds}N_{ds}N_{ds}N_{ds}N_{ds}N_{ds}N_{ds}N_{ks}N_{ks}N_{k}$ | Target Z | 0.56 | 29 |
| Z4 | $N_{ks}N_{ks}N_{ks}N_{ds}N_{ds}N_{ds}N_{ds}N_{ds}N_{ds}N_{ds}N_{\underline{dz}}N_{\underline{dz}}N_{\underline{dz}}N_{ks}N_{ks}N_{k}$ | Target Z | 0.05 | 29 |
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.33 | 5 |
| 1375403 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{\underline{kz}}A_{k}$ | CXCL12 | 0.39 | 5 |
| 1375404 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{\underline{kz}}T_{ks}A_{k}$ | CXCL12 | 0.34 | 5 |
| 1375405 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{\underline{dz}}T_{ks}T_{ks}A_{k}$ | CXCL12 | 0.07 | 5 |
| 1375406 | $G_{ks}{}^{m}C_{ks}A_{ks}T_{ds}G_{ds}T_{ds}T_{ds}{}^{m}C_{ds}T_{ds}{}^{m}C_{\underline{dz}}A_{ds}{}^{m}C_{dz}A_{ds}T_{ks}T_{ks}A_{k}$ | CXCL12 | 0.23 | 5 |
| 1375407 | $G_{ks}{}^{m}C_{ks}A_{ks}T_{ds}G_{ds}T_{ds}T_{ds}{}^{m}C_{ds}T_{ds}{}^{m}C_{ds}A_{\underline{dz}}{}^{m}C_{ds}A_{ds}T_{ks}T_{ks}A_{k}$ | CXCL12 | 0.19 | 5 |
| 1375408 | $G_{ks}{}^{m}C_{ks}A_{ks}T_{ds}G_{ds}T_{ds}T_{ds}{}^{m}C_{ds}T_{ds}{}^{m}C_{\underline{dz}}A_{ds}{}^{m}C_{ds}A_{ds}T_{ks}T_{ks}A_{k}$ | CXCL12 | 0.16 | 5 |
| 1375409 | $G_{ks}{}^{m}C_{ks}A_{ks}T_{ds}G_{ds}T_{ds}T_{ds}{}^{m}C_{ds}T_{\underline{dz}}{}^{m}C_{ds}A_{ds}{}^{m}C_{ds}A_{ds}T_{ks}T_{ks}A_{k}$ | CXCL12 | 0.24 | 5 |
| 1375410 | $G_{ks}{}^{m}C_{ks}A_{ks}T_{ds}G_{ds}T_{ds}T_{ds}{}^{m}C_{\underline{dz}}T_{ds}{}^{m}C_{ds}A_{ds}{}^{m}C_{ds}A_{ds}T_{ks}T_{ks}A_{k}$ | CXCL12 | 0.33 | 5 |
| 1375411 | $G_{ks}{}^{m}C_{ks}A_{ks}T_{ds}G_{ds}T_{ds}T_{\underline{dz}}{}^{m}C_{ds}T_{ds}{}^{m}C_{ds}A_{ds}{}^{m}C_{ds}A_{ds}T_{ks}T_{ks}A_{k}$ | CXCL12 | 0.23 | 5 |
| 1375412 | $G_{ks}{}^{m}C_{ks}A_{ks}T_{ds}G_{ds}T_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.37 | 5 |
| 1375413 | $G_{ks}{}^{m}C_{ks}A_{ks}T_{ds}G_{\underline{dz}}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.32 | 5 |
| 1375414 | $G_{ks}{}^{m}C_{ks}A_{ks}T_{\underline{dz}}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.22 | 5 |
| 1375415 | $G_{ks}{}^{m}C_{ks}A_{\underline{kz}}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.55 | 5 |
| 1375416 | $G_{ks}{}^{m}C_{\underline{kz}}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.29 | 5 |
| 1375417 | $G_{\underline{kz}}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.21 | 5 |
| 1375418 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{\underline{kz}}T_{\underline{kz}}A_{k}$ | CXCL12 | 0.25 | 5 |
| 1375419 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{\underline{dz}}T_{\underline{kz}}T_{kz}A_{k}$ | CXCL12 | 0.06 | 5 |
| 1375420 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{\underline{dz}}A_{\underline{dz}}T_{ks}T_{ks}A_{k}$ | CXCL12 | 0.17 | 5 |
| 1375421 | $G_{ks}{}^{m}C_{ks}A_{ks}T_{ds}G_{ds}T_{ds}T_{ds}{}^{m}C_{ds}T_{ds}{}^{m}C_{ds}A_{\underline{dz}}{}^{m}C_{\underline{dz}}A_{ds}T_{ks}T_{ks}A_{k}$ | CXCL12 | 0.05 | 5 |
| 1375422 | $G_{ks}{}^{m}C_{ks}A_{ks}T_{ds}G_{ds}T_{ds}T_{ds}{}^{m}C_{ds}T_{ds}{}^{m}C_{\underline{dz}}A_{\underline{dz}}{}^{m}C_{ds}A_{ds}T_{ks}T_{ks}A_{k}$ | CXCL12 | 0.13 | 5 |
| 1375423 | $G_{ks}{}^{m}C_{ks}A_{ks}T_{ds}G_{ds}T_{ds}T_{ds}{}^{m}C_{ds}T_{\underline{dz}}{}^{m}C_{\underline{dz}}A_{ds}{}^{m}C_{ds}A_{ds}T_{ks}T_{ks}A_{k}$ | CXCL12 | 0.11 | 5 |
| 1375424 | $G_{ks}{}^{m}C_{ks}A_{ks}T_{ds}G_{ds}T_{ds}T_{ds}{}^{m}C_{\underline{dz}}T_{\underline{dz}}{}^{m}C_{ds}A_{ds}{}^{m}C_{ds}A_{ds}T_{ks}T_{ks}A_{k}$ | CXCL12 | 0.18 | 5 |
| 1375425 | $G_{ks}{}^{m}C_{ks}A_{ks}T_{ds}G_{ds}T_{ds}T_{\underline{dz}}{}^{m}C_{\underline{dz}}T_{ds}{}^{m}C_{ds}A_{ds}{}^{m}C_{ds}A_{ds}T_{ks}T_{ks}A_{k}$ | CXCL12 | 0.23 | 5 |
| 1375426 | $G_{ks}{}^{m}C_{ks}A_{ks}T_{ds}G_{ds}T_{\underline{dz}}T_{\underline{dz}}{}^{m}C_{ds}T_{ds}{}^{m}C_{ds}A_{ds}{}^{m}C_{ds}A_{ds}T_{ks}T_{ks}A_{k}$ | CXCL12 | 0.65 | 5 |
| 1375427 | $G_{ks}{}^{m}C_{ks}A_{ks}T_{ds}G_{\underline{dz}}T_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.26 | 5 |
| 1375428 | $G_{ks}{}^{m}C_{ks}A_{ks}T_{\underline{dz}}G_{\underline{dz}}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.15 | 5 |

TABLE 57-continued

Design and BJAB inflammatory response of modified oligonucleotides with mesyl phosphoramidate internucleoside linkages for BJAB assay

| Compound ID | Chemistry Notation (5' to 3') | Target | CCL22 log fold increase | SEQ ID NO. |
|---|---|---|---|---|
| 1375429 | $G_{ks}{}^{m}C_{ks}A_{\underline{kz}}T_{\underline{dz}}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.42 | 5 |
| 1375430 | $G_{ks}{}^{m}C_{\underline{kz}}A_{\underline{kz}}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.27 | 5 |
| 1375431 | $G_{\underline{kz}}{}^{m}C_{\underline{kz}}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.20 | 5 |
| 1375432 | $G_{\underline{kz}}{}^{m}C_{\underline{kz}}A_{\underline{kz}}T_{\underline{dz}}G_{\underline{dz}}T_{\underline{dz}}T_{\underline{dz}}{}^{n}C_{\underline{dz}}T_{\underline{dz}}{}^{n}C_{\underline{dz}}A_{dz}{}^{m}C_{\underline{dz}}A_{\underline{dz}}$<br>$T_{\underline{kz}}A_{k}$ | CXCL12 | 0.00 | 5 |
| 1378793 | $G_{ks}{}^{m}C_{ks}A_{\underline{kz}}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{n}C_{\underline{dz}}A_{ds}T_{ks}T_{ks}A_{k}$ | CXCL12 | -0.04 | 5 |
| 1378794 | $G_{\underline{kz}}{}^{m}C_{\underline{kz}}A_{ks}T_{ds}G_{ds}T_{ds}T_{ds}{}^{m}C_{ds}T_{ds}{}^{m}C_{ds}A_{ds}{}^{m}C_{ds}A_{\underline{dz}}T_{\underline{kz}}T_{\underline{kz}}A_{k}$ | CXCL12 | 0.12 | 5 |
| 1386094 | $G_{ks}{}^{m}C_{ks}A_{\underline{kz}}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{n}C_{\underline{dz}}A_{\underline{dz}}$<br>$T_{ks}T_{ks}A_{k}$ | CXCL12 | -0.12 | 5 |
| 1386355 | $G_{ks}{}^{m}C_{ks}A_{ks}T_{\underline{dz}}G_{\underline{dz}}T_{\underline{dz}}T_{\underline{dz}}{}^{n}C_{\underline{dz}}T_{\underline{dz}}{}^{n}C_{\underline{dz}}A_{\underline{dz}}{}^{n}C_{\underline{dz}}A_{ds}T_{ks}T_{ks}A_{k}$ | CXCL12 | 0.01 | 5 |
| 1405434 | $G_{ks}{}^{m}C_{ks}A_{ks}T_{\underline{dz}}G_{\underline{dz}}T_{\underline{dz}}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.08 | 5 |
| 1405435 | $G_{ks}{}^{m}C_{ks}A_{ks}T_{ds}G_{\underline{dz}}T_{\underline{dz}}T_{\underline{dz}}{}^{m}C_{ds}T_{ds}{}^{m}C_{ds}A_{ds}{}^{m}C_{ds}A_{ds}T_{ks}T_{ks}A_{k}$ | CXCL12 | 0.21 | 5 |
| 1405436 | $G_{ks}{}^{m}C_{ks}A_{ks}T_{\underline{dz}}G_{\underline{dz}}T_{\underline{dz}}T_{\underline{dz}}{}^{m}C_{ds}T_{ds}{}^{m}C_{ds}A_{ds}{}^{m}C_{ds}A_{ds}T_{ks}T_{ks}A_{k}$ | CXCL12 | 0.24 | 5 |
| 1427921 | $G_{ks}{}^{m}C_{ks}A_{ks}T_{\underline{d[XI]}}G_{\underline{d[XI]}}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.19 | 5 |
| 1427922 | $G_{ks}{}^{m}C_{ks}A_{ks}T_{ds}G_{\underline{d[XI]}}T_{\underline{d[XI]}}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.26 | 5 |
| 1427923 | $G_{ks}{}^{m}C_{ks}A_{ks}T_{ds}G_{ds}T_{\underline{d[XI]}}T_{\underline{d[XI]}}{}^{m}C_{ds}T_{ds}{}^{m}C_{ds}A_{ds}{}^{m}C_{ds}A_{ds}T_{ks}T_{ks}A_{k}$ | CXCL12 | 0.44 | 5 |
| 1427924 | $G_{ks}{}^{m}C_{ks}A_{ks}T_{ds}G_{ds}T_{ds}T_{ds}{}^{m}C_{ds}T_{ds}{}^{m}C_{\underline{d[XI]}}A_{\underline{d[XI]}}{}^{m}C_{ds}A_{ds}T_{ks}T_{ks}A_{k}$ | CXCL12 | 0.13 | 5 |
| 1429189 | $G_{ks}{}^{m}C_{ks}A_{ks}T_{\underline{d[XIII]}}G_{\underline{d[XIII]}}T_{ds}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.26 | 5 |
| 1429190 | $G_{ks}{}^{m}C_{ks}A_{ks}T_{ds}G_{\underline{d[XIII]}}T_{\underline{d[XIII]}}T_{ds}{}^{m}C_{ds}T_{ds}{}^{m}C_{ds}A_{ds}{}^{m}C_{ds}A_{ds}T_{ks}T_{ks}A_{k}$ | CXCL12 | 0.39 | 5 |
| 1429191 | $G_{ks}{}^{m}C_{ks}A_{ks}T_{ds}G_{ds}T_{\underline{d[XIII]}}T_{\underline{d[XIII]}}{}^{m}C_{ds}T_{ds}{}^{m}C_{ds}A_{ds}{}^{m}C_{ds}A_{ds}T_{ks}T_{ks}A_{k}$ | CXCL12 | 0.34 | 5 |
| 1429192 | $G_{ks}{}^{m}C_{ks}A_{ks}T_{ds}G_{ds}T_{ds}T_{ds}{}^{m}C_{ds}T_{ds}{}^{m}C_{\underline{d[XIII]}}A_{\underline{d[XIII]}}{}^{m}C_{ds}A_{ds}T_{ks}T_{ks}A_{k}$ | CXCL12 | 0.16 | 5 |
| 1437601 | $G_{ks}{}^{m}C_{ks}A_{ks}T_{ds}G_{ds}T_{ds}T_{ds}{}^{m}C_{ds}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | 0.00 | 5 |
| 1437602 | $G_{ks}{}^{m}C_{ks}A_{ks}T_{ds}G_{ds}T_{ds}T_{ds}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.03 | 5 |
| 1437603 | $G_{ks}{}^{m}C_{ks}A_{ks}T_{ds}G_{ds}T_{ds}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.08 | 5 |
| 1437604 | $G_{ks}{}^{m}C_{ks}A_{ks}T_{ds}G_{ds}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.10 | 5 |
| 1437605 | $G_{ks}{}^{m}C_{ks}A_{ks}T_{ds}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.09 | 5 |
| 1437606 | $G_{ks}{}^{m}C_{ks}A_{ks}T_{\underline{dz}}G_{\underline{dz}}T_{\underline{dz}}T_{\underline{dz}}{}^{m}C_{\underline{dz}}T_{\underline{dz}}{}^{m}C_{\underline{dz}}A_{\underline{dz}}{}^{m}C_{\underline{dz}}A_{\underline{dz}}T_{ks}T_{ks}A_{k}$ | CXCL12 | -0.04 | 5 |
| 1441068 | $G_{ks}{}^{m}C_{ks}A_{\underline{kz}}T_{ds}G_{\underline{dz}}T_{ds}T_{\underline{dz}}{}^{m}C_{ds}T_{\underline{dz}}{}^{m}C_{ds}A_{\underline{dz}}{}^{m}C_{ds}A_{\underline{dz}}T_{ks}T_{ks}A_{k}$ | CXCL12 | -0.04 | 5 |
| 1441069 | $G_{ks}{}^{m}C_{ks}A_{ks}T_{\underline{dz}}G_{ds}T_{\underline{dz}}T_{ds}{}^{m}C_{\underline{dz}}T_{ds}{}^{m}C_{\underline{dz}}A_{ds}{}^{m}C_{\underline{dz}}A_{ds}T_{ks}T_{ks}A_{k}$ | CXCL12 | -0.03 | 5 |

In the table above, a subscript "d" represents a 2'-β-D-deoxyribosyl sugar moiety, "k" represents a cEt sugar moiety, and "e" represents a 2'-MOE sugar moiety. Each internucleoside linkage is either a phosphorothioate internucleoside linkage (" ", a phosphodiester internucleoside linkage ("o"), a mesyl phosphoramidate internucleoside linkage of Formula IX ("z"), a mesyl phosphoramidate internucleoside linkage of Formula XI ("[XI]"), or a mesyl phosphoramidate internucleoside linkage of Formula XIII ("[XIII]"). Subscripts of nucleotides having a modified mesyl phosphoramidate internucleoside linkage of generic Formula XVIII are bold and underlined. All cytosine residues are 5-methylcytosines. A nucleobase represented by N in the table above indicates A, G, T, or $^{m}$C.

Example 31: Exonuclease Stability of Modified Oligonucleotides with Mesyl Phosphoramidate Internucleoside Linkages Oligonucleotides comprising mesyl phosphoramidate internucleoside linkages were synthesized using standard techniques or those described herein. Each oligonucleotide in the table below has the sequence TTTTTTTTTTTT (SEQ ID NO:71).

The oligonucleotides described below were incubated at 5 μM concentration in buffer with snake venom phosphodiesterase (SVPD, Sigma P4506, Lot #SLBV4179), a strong 3'-exonuclease, at the standard concentration of 0.5 mU/mL and at a higher concentration of 2 mU/mL. SVPD is commonly used to measure the stability of modified nucleosides (see, e.g., *Antisense Drug Technology*, Crooke S. T., Ed., CRC Press, 2008). Aliquots were removed at various time points and analyzed by MS-HPLC with an internal standard. Relative peak areas were plotted versus time and half-life was determined using GraphPad Prism. A longer half-life means the 3'-terminal nucleosides have increased resistance to the SVPD exonuclease.

The results in the table below show that modified oligonucleotides comprising mesyl phosphoramidate internucleoside linkages are more stable to exonuclease degradation than unmodified DNA, 2'-MOE, and LNA with phosphodiester linkages. Such compounds are also more stable to exonuclease degradation than PS-linked DNA, and adding a second mesyl phosphoramidate internucleoside linkage on the 3' end increases stability even further.

TABLE 58

Exonuclease resistance of modified oligonucleotides with mesyl phosphoramidate internucleoside linkages

| Compound ID | Chemistry Notation (5' to 3') | SVPD (mU/mL) | $T_{1/2}$ (min) | SEQ ID NO. |
|---|---|---|---|---|
| 7157 | $T_{do}T_{do}T_{do}T_{do}T_{do}T_{do}T_{do}T_{do}T_{do}T_{do}T_{do}T_{d}$ | 0.5 | 0.4 | 71 |
| 395421 | $T_{do}T_{do}T_{do}T_{do}T_{do}T_{do}T_{do}T_{do}T_{do}T_{do}T_{eo}T_{e}$ | 0.5 | 7.1, 4.8 | 71 |
| 395422 | $T_{do}T_{do}T_{do}T_{do}T_{do}T_{do}T_{do}T_{do}T_{do}T_{do}T_{lo}T_{l}$ | 0.5 | 27.8 | 71 |
| 1506055 | $T_{do}T_{do}T_{do}T_{do}T_{do}T_{do}T_{do}T_{do}T_{do}T_{do}T_{ds}T_{d}$ | 0.5 | 46.8 | 71 |
| 1506055 | $T_{do}T_{do}T_{do}T_{do}T_{do}T_{do}T_{do}T_{do}T_{do}T_{do}T_{ds}T_{d}$ | 2 | 8.9 | 71 |
| 1468868 | $T_{do}T_{do}T_{do}T_{do}T_{do}T_{do}T_{do}T_{do}T_{do}T_{do}T_{\underline{\mathbf{dz}}}T_{d}$ | 2 | 29.1 | 71 |
| 1468869 | $T_{do}T_{do}T_{do}T_{do}T_{do}T_{do}T_{do}T_{do}T_{do}T_{\underline{\mathbf{dz}}}T_{\underline{\mathbf{dz}}}T_{d}$ | 2 | 69.6 | 71 |
| 1515981 | $T_{do}T_{do}T_{do}T_{do}T_{do}T_{do}T_{do}T_{do}T_{do}T_{do}T_{\underline{\mathbf{lz}}}T_{l}$ | 2 | 26.7 | 71 |

A subscript "d" indicates a nucleoside comprising an unmodified, 2'-β-D-deoxyribosyl sugar moiety.
A subscript "e" indicates a 2'-MOE sugar moiety.
A subscript "l" indicates an LNA.
A subscript "o" indicates a phosphodiester internucleoside linkage.
A subscript "s" indicates a phosphorothioate internucleoside linkage.
A subscript "z" indicates an internucleoside linkage of formula IX, which is a mesyl phosphoramidate linkage.
Subscripts of nucleotides having an internucleoside linkage of formula IX are bold and underlined.

Example 32: Exonuclease Stability of siRNA Antisense Oligonucleotides with Mesyl Phosphoramidate Internucleoside Linkages Oligonucleotides comprising mesyl phosphoramidate internucleoside linkages were synthesized using standard techniques or those described herein. Each oligonucleotide in the table below has the sequence AUAAAAUCUACAGUCAUAGGAAU (SEQ ID NO: 21).

SVPD Assay

Selected oligonucleotides described below were tested in a 3'-exonuclease assay. Modified oligonucleotides were incubated at 5 μM concentration in buffer with snake venom phosphodiesterase (SVPD, Sigma P4506, Lot #SLBV4179), a strong 3'-exonuclease, at the standard concentration of 2 mU/mL. SVPD is commonly used to measure the stability of modified nucleosides (see, e.g., *Antisense Drug Technology*, Crooke S. T., Ed., CRC Press, 2008). Aliquots were removed at various time points and analyzed by MS-HPLC with an internal standard. Relative peak areas were plotted versus time and half-life was determined using GraphPad Prism. A longer half-life means the 3'-terminal nucleosides have increased resistance to the SVPD exonuclease.

BSPDII Assay

Selected oligonucleotides described below were tested in a 5'-exonuclease assay. Modified oligonucleotides were first incubated with 100 units/mL alkaline phosphatase (AP, Sigma P7923, Lot SLCB86083) in Tris-HCl buffer at pH 8.5 for 30 minutes, until the reaction was complete by MS-HPLC. The pH was adjusted to 6.5 and oligonucleotides were incubated with 5 mU/mL or 10 mU/mL bovine spleen phosphodiesterase II (BSPDII) (see Bernardi, A. and G. Bernardi, "Studies on acid hydrolases: IV. Isolation and characterization of spleen exonuclease." *Biochimica et Biophysica Acta-Nucleic Acids and Protein Synthesis* 155(2): 360-370, 1968).

Aliquots were removed at various time points and analyzed by MS-HPLC with an internal standard. Relative peak areas were plotted versus time and half-life was determined using GraphPad Prism. A longer half-life means the 5'-terminal nucleosides have increased resistance to the PD II exonuclease.

Assay for Tritosome Stability of siRNA Antisense Oligonucleotides

Antisense oligonucleotides having modification patterns suitable for RNAi were investigated for tritosome stability in rat tritosomes. Modified oligonucleotides were incubated at 5 mM for 0 and 48 hours in 20% rat tritosomes in pH 4.5 acetate buffer. Samples were extracted utilizing standard protocols (Chappell, A. E., et al. (2020). "Mechanisms of palmitic acid-conjugated antisense oligonucleotide distribution in mice." *Nucleic Acids Res* 48(8): 4382-4395) and analyzed by MS-HPLC with an internal standard. Relative peak areas for 0 and 48 h time points were determined and percent of full length modified oligonucleotide was calculated. Oligonucleotides lacking the 5'-terminal phosphate are included as "full length" due to rapid removal of this moiety.

Assay for Plasma Stability of siRNA Antisense Oligonucleotides

Antisense oligonucleotides having modification patterns suitable for RNAi were investigated for plasma stability in fresh mouse serum. Modified oligonucleotides were incubated for 0 and 24 hours in 50% fresh mouse serum. Samples were extracted utilizing standard protocols (Chappell, A. E., et al. (2020). "Mechanisms of palmitic acid-conjugated antisense oligonucleotide distribution in mice." *Nucleic Acids Res* 48(8): 4382-4395) and analyzed by MS-HPLC with an internal standard. Relative peak areas for 0 and 24 h time points were determined and % intact modified oligonucleotide calculated.

Assay for Alkaline Phosphatase Enzyme Stability

Antisense oligonucleotides having modification patterns suitable for RNAi were investigated for phosphatase stability utilizing alkaline phosphatase from bovine intestinal mucosa (AP, Sigma P7923, Lot SLCB86083). Modified oligonucleotides were incubated in Tris-HCl buffer at pH 8.5 containing 100 units/ml alkaline phosphatase (AP, Sigma P7923, Lot SLCB86083). Aliquots were removed at 30 minutes and analyzed by HPLC-MS. The 5'-terminal phosphate groups were removed at this time point for oligonucleotides 1337111, 1405420 and 1405428 while the 5'-terminal mesyl phosphoramidate group of 1527118 was still intact. 24- and 48-hour time points were taken for this compound and HPLC-MS analysis revealed that the mesyl phosphoramidate group was still present.

TABLE 59

Design of siRNA antisense oligonucleotides with mesyl phosphoramidate internucleoside linkages

| Compound ID | Chemistry Notation (5' to 3') | SEQ ID NO. |
|---|---|---|
| 1527119 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{yo}A_{fo}U_{y}$ | 22 |
| 1073762 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}$AysAfs$U_{y}$ | 22 |
| 1337111 | p.AysUfs$A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}$AysAfs$U_{y}$ | 22 |
| 1405420 | p.$A_{yo}U_{fo}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}\mathbf{A}_{\underline{\mathbf{yz}}}\mathbf{A}_{\underline{\mathbf{fz}}}U_{y}$ | 22 |
| 1405427 | p.$\mathbf{A}_{\underline{\mathbf{yz}}}\mathbf{U}_{\underline{\mathbf{fz}}}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{yo}A_{fo}U_{y}$ | 22 |
| 1405428 | p.$\mathbf{A}_{\underline{\mathbf{yz}}}\mathbf{U}_{\underline{\mathbf{fz}}}A_{yo}A_{fo}A_{yo}A_{fo}U_{yo}C_{fo}C_{yo}A_{fo}C_{yo}A_{fo}G_{yo}U_{fo}C_{yo}A_{fo}U_{yo}A_{fo}G_{yo}G_{fo}$Ayz$A_{fz}U_{y}$ | 22 |

A subscript "y" represents a 2'-OMe modified nucleoside, a subscript "f" represents a 2'-F modified nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage.

Subscripts of nucleotides haying an internucleoside linkage of formula IX are bold and underlined.

A superscript "m" before a C represents a 5-methylcytosine.

TABLE 60

Nuclease stability of siRNA antisense oligonucleotides with mesyl phosphoramidate internucleoside linkages

| Compound ID | SVPD Assay (3') T½ (min) | BSPII Assay (5') T½ (min) | BSPII Assay (5') Amount (mU/mL) | Tritosome Stability % full length | Plasma Stability % full length | AP Assay Time to remove 5'-moiety |
|---|---|---|---|---|---|---|
| 1527119 | 0.3 | n.d. | N/A | 0 | 0 | >48 hours |
| 1073762 | 4.2 | n.d. | N/A | 0 | 28 | n.d. |
| 1337111 | 5.5 | 29.7 | 10 | 55 | 28 | <30 min |
| 1405420 | 12.8 | 2.7 | 5 | 0 | 58 | <30 min |
| 1405427 | 0.3 | n.d. | N/A | 0 | 0 | n.d. |
| 1405428 | 9.5 | 42.6 | 10 | 100 | 44 | <30 min |

Example 33: Design, Activity, and Tolerability of Modified Oligonucleotides with Mesyl Phosphoramidate Internucleoside Linkages In Vivo

Design of Modified Oligonucleotides

Modified oligonucleotides comprising multiple mesyl phosphoramidate internucleoside linkages (Formula IX) and phosphorothioate internucleoside linkages were designed, synthesized and tested. The modified oligonucleotides are each 5-10-5 MOE gapmers with a sugar motif of: ceeeeeddddddddddeeeee, where "e" represents a 2'-MOE modified sugar moiety, and "d" represents a 2'-p3-D-deoxyribosyl sugar moiety. Each of the modified oligonucleotides has the same nucleobase sequence, GCCAGGCTGGTTATGACTCA (SEQ ID NO: 72), which is 100% complementary to the complement of mouse Malat1, GENBANK Accession No. NC_000085.6 truncated from 5793001 to 5806000 (SEQ ID NO: 73), at position 6668 to 6687. Each internucleoside linkage is either a phosphorothioate internucleoside linkage ("s"), a phosphodiester internucleoside linkage ("o"), or a mesyl phosphoramidate intenucleoside linkage ("z").

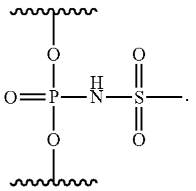

IX

TABLE 61

Design of modified oligonucleotides with mesyl phosphoramidate internucleoside linkages

| Compound ID | Chemistry Notation (5' to 3') | SEQ ID NO. |
|---|---|---|
| 602056 | $G_{es}{}^{m}C_{es}{}^{m}C_{es}A_{es}G_{es}G_{ds}{}^{m}C_{ds}T_{ds}G_{ds}G_{ds}T_{ds}T_{ds}A_{ds}T_{ds}G_{ds}A_{es}{}^{m}C_{es}T_{es}{}^{m}C_{es}A_{e}$ | 72 |
| 626112 | $G_{es}{}^{m}C_{eo}{}^{m}C_{eo}A_{eo}G_{eo}G_{ds}{}^{m}C_{ds}T_{ds}G_{ds}G_{ds}T_{ds}T_{ds}A_{ds}T_{ds}G_{ds}A_{eo}{}^{m}C_{eo}T_{es}{}^{m}C_{es}A_{e}$ | 72 |
| 1454990 | $G_{eo}{}^{m}C_{eo}{}^{m}C_{eo}A_{eo}G_{eo}G_{ds}{}^{m}C_{ds}T_{ds}G_{ds}G_{ds}T_{ds}T_{ds}A_{ds}T_{ds}G_{ds}A_{eo}{}^{m}C_{eo}T_{eo}{}^{m}C_{eo}A_{e}$ | 72 |
| 1469248 | $G_{es}{}^{m}C_{eo}{}^{m}C_{eo}A_{eo}G_{eo}G_{ds}{}^{m}C_{ds}T_{ds}G_{ds}G_{ds}T_{ds}T_{ds}A_{ds}T_{ds}G_{ds}A_{eo}{}^{m}C_{eo}T_{eo}{}^{m}C_{es}A_{e}$ | 72 |
| 1515340 | $G_{es}{}^{m}C_{es}{}^{m}C_{es}A_{es}\mathbf{G}_{\underline{\mathbf{ez}}}\ G_{ds}{}^{m}C_{ds}T_{ds}G_{ds}G_{ds}T_{ds}T_{ds}A_{ds}T_{ds}\mathbf{G}_{\underline{\mathbf{dz}}}\ A_{es}{}^{m}C_{es}T_{es}{}^{m}C_{es}A_{e}$ | 72 |
| 1515341 | $\mathbf{G}_{\underline{\mathbf{ez}}}{}^{m}C_{es}{}^{m}C_{es}A_{es}G_{es}G_{ds}{}^{m}C_{ds}T_{ds}G_{ds}G_{ds}T_{ds}T_{ds}A_{ds}T_{ds}G_{ds}A_{es}{}^{m}C_{es}\mathbf{T}_{\underline{\mathbf{ez}}}\ {}^{m}\ \mathbf{C}_{\underline{\mathbf{ez}}}\ A_{e}$ | 72 |
| 1515342 | $G_{es}{}^{m}C_{es}{}^{m}C_{es}A_{es}G_{eo}G_{ds}{}^{m}C_{ds}T_{ds}G_{ds}G_{ds}T_{ds}T_{ds}A_{ds}T_{ds}G_{do}A_{es}{}^{m}C_{es}T_{es}{}^{m}C_{es}A_{e}$ | 72 |
| 1515344 | $G_{es}{}^{m}C_{es}{}^{m}C_{es}A_{es}G_{es}G_{ds}{}^{m}C_{do}T_{ds}G_{ds}G_{ds}T_{ds}T_{ds}A_{ds}T_{ds}G_{ds}A_{es}{}^{m}C_{es}T_{es}{}^{m}C_{es}A_{e}$ | 72 |
| 1515346 | $G_{es}{}^{m}C_{es}{}^{m}C_{es}A_{es}G_{es}\mathbf{G}_{\underline{\mathbf{dz}}}\ {}^{m}\mathbf{C}_{\underline{\mathbf{dz}}}\ \mathbf{T}_{\underline{\mathbf{dz}}}G_{ds}G_{ds}T_{ds}T_{ds}A_{ds}T_{ds}G_{ds}A_{es}{}^{m}C_{es}T_{es}{}^{m}C_{es}A_{e}$ | 72 |
| 1515347 | $G_{es}{}^{m}C_{es}{}^{m}C_{es}A_{es}G_{es}\ \mathbf{G}_{\underline{\mathbf{dz}}}\ {}^{m}\mathbf{C}_{\underline{\mathbf{dz}}}\ \mathbf{T}_{\underline{\mathbf{dz}}}\ \mathbf{G}_{\underline{\mathbf{dz}}}\ G_{ds}T_{ds}T_{ds}A_{ds}T_{ds}G_{ds}A_{es}{}^{m}C_{es}T_{es}{}^{m}C_{es}A_{e}$ | 72 |
| 1515348 | $G_{es}{}^{m}C_{es}{}^{m}C_{es}A_{es}G_{es}\mathbf{G}_{\underline{\mathbf{dz}}}\ {}^{m}\mathbf{C}_{\underline{\mathbf{dz}}}\ \mathbf{T}_{\underline{\mathbf{dz}}}\ \mathbf{G}_{\underline{\mathbf{dz}}}\ \mathbf{G}_{\underline{\mathbf{dz}}}\ T_{ds}T_{ds}A_{ds}T_{ds}G_{ds}A_{es}{}^{m}C_{es}T_{es}{}^{m}C_{es}A_{e}$ | 72 |
| 1515350 | $G_{ez}{}^{m}C_{eo}{}^{m}C_{eo}A_{eo}G_{eo}G_{ds}{}^{m}C_{ds}T_{ds}G_{ds}G_{ds}T_{ds}T_{ds}A_{ds}T_{ds}G_{ds}A_{eo}{}^{m}C_{eo}\mathbf{T}_{\underline{\mathbf{ez}}}\ {}^{m}\ \mathbf{C}_{\underline{\mathbf{ez}}}\ A_{e}$ | 72 |
| 1515355 | $G_{es}{}^{m}C_{eo}{}^{m}C_{eo}A_{eo}G_{eo}\mathbf{G}_{\underline{\mathbf{dz}}}\ \mathbf{C}_{\underline{\mathbf{dz}}}\ {}^{m}\mathbf{T}_{\underline{\mathbf{dz}}}\ \mathbf{G}_{\underline{\mathbf{dz}}}\ G_{ds}T_{ds}T_{ds}A_{ds}T_{ds}\mathbf{G}_{\underline{\mathbf{dz}}}\ A_{eo}{}^{m}C_{eo}T_{es}{}^{m}C_{es}A_{e}$ | 72 |
| 1524739 | $\mathbf{G}_{\underline{\mathbf{ez}}}\ {}^{m}C_{eo}{}^{m}C_{eo}A_{eo}G_{eo}G_{ds}{}^{m}C_{ds}T_{ds}G_{ds}G_{ds}T_{ds}T_{ds}A_{ds}T_{ds}G_{ds}A_{eo}{}^{m}C_{eo}T_{eo}{}^{m}\ \mathbf{C}_{\underline{\mathbf{ez}}}\ A_{e}$ | 72 |
| 1524740 | $\mathbf{G}_{\underline{\mathbf{ez}}}\ {}^{m}C_{eo}{}^{m}C_{eo}A_{eo}G_{eo}\mathbf{G}_{\underline{\mathbf{dz}}}\ {}^{m}C_{ds}T_{ds}G_{ds}G_{ds}T_{ds}T_{ds}A_{ds}T_{ds}G_{ds}A_{eo}{}^{m}C_{eo}T_{eo}{}^{m}\ \mathbf{C}_{\underline{\mathbf{ez}}}\ A_{e}$ | 72 |
| 1524741 | $\mathbf{G}_{\underline{\mathbf{ez}}}\ {}^{m}C_{eo}{}^{m}C_{eo}A_{eo}G_{eo}\mathbf{G}_{\underline{\mathbf{dz}}}\ {}^{m}\ \mathbf{C}_{\underline{\mathbf{dz}}}\ T_{ds}G_{ds}G_{ds}T_{ds}T_{ds}A_{ds}T_{ds}G_{ds}A_{eo}{}^{m}C_{eo}T_{eo}{}^{m}\ \mathbf{C}_{\underline{\mathbf{ez}}}\ A_{e}$ | 72 |
| 1524742 | $\mathbf{G}_{\underline{\mathbf{ez}}}\ {}^{m}C_{eo}{}^{m}C_{eo}A_{eo}G_{eo}\mathbf{G}_{\underline{\mathbf{dz}}}\ {}^{m}\ \mathbf{C}_{\underline{\mathbf{dz}}}\ \mathbf{T}_{\underline{\mathbf{dz}}}\ G_{ds}G_{ds}T_{ds}T_{ds}A_{ds}T_{ds}G_{ds}A_{eo}{}^{m}C_{eo}T_{eo}{}^{m}\ \mathbf{C}_{\underline{\mathbf{ez}}}\ A_{e}$ | 72 |
| 1524743 | $\mathbf{G}_{\underline{\mathbf{ez}}}\ {}^{m}C_{eo}{}^{m}C_{eo}A_{eo}G_{eo}\ \mathbf{G}_{\underline{\mathbf{dz}}}\ {}^{m}\ \mathbf{C}_{\underline{\mathbf{dz}}}\ \mathbf{T}_{\underline{\mathbf{dz}}}\ \mathbf{G}_{\underline{\mathbf{dz}}}\ G_{ds}T_{ds}T_{ds}A_{ds}T_{ds}G_{ds}A_{eo}{}^{m}C_{eo}T_{eo}{}^{m}\ \mathbf{C}_{\underline{\mathbf{ez}}}\ A_{e}$ | 72 |

TABLE 61-continued

| Design of modified oligonucleotides with mesyl phosphoramidate internucleoside linkages | | |
|---|---|---|
| Compound ID | Chemistry Notation (5' to 3') | SEQ ID NO. |
| 1524744 | $G_{\underline{\mathbf{ez}}}\ {}^{m}C_{eo}{}^{m}C_{eo}A_{eo}G_{ec}G_{\underline{\mathbf{dz}}}\ {}^{m}\ C_{\underline{\mathbf{dz}}}\ T_{\underline{\mathbf{dz}}}\ G_{\underline{\mathbf{dz}}}\ G_{\underline{\mathbf{dz}}}\ T_{ds}T_{ds}A_{ds}T_{ds}G_{ds}A_{eo}{}^{m}C_{eo}T_{eo}{}^{m}\ C_{\underline{\mathbf{ez}}}\ A_{e}$ | 72 |
| 1524745 | $G_{\underline{\mathbf{ez}}}{}^{m}C_{eo}{}^{m}C_{eo}A_{eo}G_{ec}G_{\underline{\mathbf{dz}}}\ {}^{m}\ C_{\underline{\mathbf{dz}}}\ T_{\underline{\mathbf{dz}}}\ G_{\underline{\mathbf{dz}}}\ G_{\underline{\mathbf{dz}}}\ T_{\underline{\mathbf{dz}}}T_{ds}A_{ds}T_{ds}G_{ds}A_{eo}{}^{m}C_{eo}T_{eo}{}^{m}C_{\underline{\mathbf{ez}}}\ A_{e}$ | 72 |

A subscript "e" represents a 2'-MOE modified nucleoside, a subscript "d" represents a stereo-standard DNA nucleoside, a subscript "s" indicates a phosphorothioate intemucleoside linkage, a subscript "o" indicates a phosphodiester internucleoside linkage, and a subscript "z" represents an intemucleoside linkage of formula 1X, which is a mesyl phosphoramidate linkage.
Subscripts of nucleotides having an internucleoside linkage of formula IX are bold and underlined.
A superscript "m" before a C represents a 5-methylcytosine.

Activity in CNS

Oligonucleotides described above were tested in wild-type female C57/B16 mice to assess the activity of the oligonucleotides. Wild-type female C57/B16 mice each received a single ICV bolus of 30 μg of modified oligonucleotide listed in the table below. Each treatment group consisted of 4 mice. A group of 4 mice received PBS as a negative control. Twelve days post treatment, mice were sacrificed and RNA was extracted from cortical brain tissue and spinal cord for quantitative RTPCR analysis to measure the amount of Malat1 RNA using mouse primer probe set RTS592 (forward sequence CGGATGAAGAGAGG-CATGTTG, designated herein as SEQ ID NO: 74; reverse sequence TTGGCCACACCGTCCTTT, designated herein as SEQ ID NO: 75; probe sequence AGACCTGGGCAATGTGGCTGCTG, designated herein as SEQ ID NO: 76). Results are presented as percent mouse Malat1 RNA relative to PBS control, adjusted to mouse Cyclophilin A RNA.

TABLE 62

In vivo CNS activity of modified oligonucleotides complementary to Malat1

| Compound ID | MALAT1 RNA Cortex (% Control) | MALAT1 RNA Spinal Cord (% Control) |
|---|---|---|
| 602056 | 37 | 16 |
| 626112 | 40 | 26 |
| 1454990 | 93 | 68 |
| 1469248 | 53 | 34 |
| 1515340 | 45 | 11 |
| 1515341 | 48 | 17 |
| 1515342 | 56 | 21 |
| 1515344 | 91 | 64 |
| 1515346 | 49 | 19 |
| 1515347 | 51 | 25 |
| 1515348 | 45 | 22 |
| 1515350 | 63 | 38 |
| 1515355 | 78 | 46 |
| 1524739 | 56 | 36 |
| 1524740 | 66 | 29 |
| 1524741 | 69 | 31 |

TABLE 62-continued

In vivo CNS activity of modified oligonucleotides complementary to Malat1

| Compound ID | MALAT1 RNA Cortex (% Control) | MALAT1 RNA Spinal Cord (% Control) |
|---|---|---|
| 1524742 | 76 | 45 |
| 1524743 | 69 | 48 |
| 1524744 | 72 | 58 |
| 1524745 | 74 | 58 |

Example 34: Activity and Tolerability of siRNA with Mesyl Phosphoramidate Internucleoside Linkages to HPRT1 In Vivo siRNA Double-stranded siRNA comprising modified oligonucleotides having mesyl phosphoramidate internucleoside linkages (Formula IX) in the antisense strand were synthesized and tested. Each internucleoside linkage is either a phosphorothioate internucleoside linkage ("s"), a phosphodiester internucleoside linkage ("o"), or a mesyl phosphoramidate internucleoside linkage ("z").

Each antisense strand has the sequence AUAAAAUC-UACAGUCAUAGGAAU (SEQ ID NO: 21) and is 100% complementary to GenBank NM_000194.2 (SEQ ID NO: 22) from 444 to 466, and each antisense strand has a 5'-phosphate. The sense strand, Compound No. 1448688, has the chemical notation $U_{ys}C_{ys}C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}U_{yo}A_{yo}U_{y}$-THA-$C_7$-GalNAc (SEQ ID NO: 23). The THA-$C_7$-GalNAc conjugate is attached to the 3'-oxygen and has the structure below:

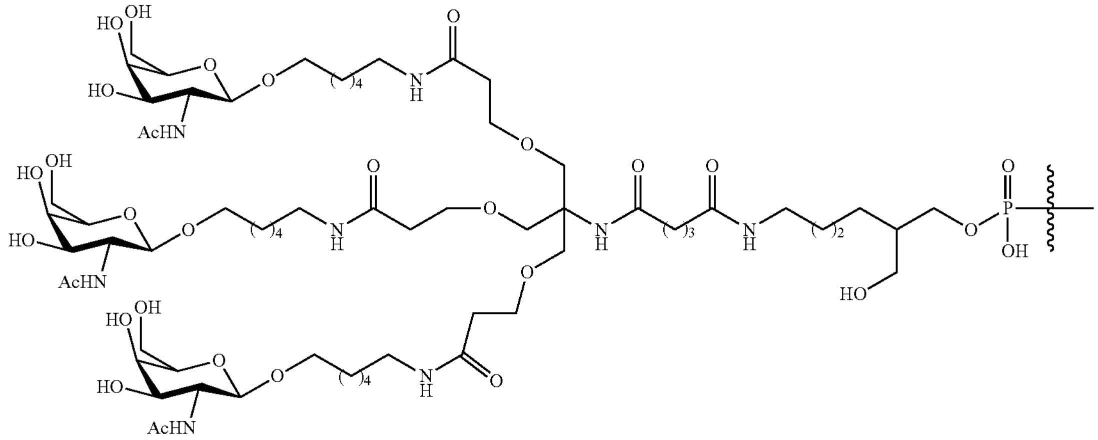

THA-C7-GalNAc

TABLE 63

| Design of antisense strand modified oligonucleotides targeted to HPRT1 containing mesyl phosphoramidate internucleoside linkages | | |
|---|---|---|
| Compound ID | Chemistry Notation (5' to 3') | SEQ ID NO. |
| 1337111 | p.$A_{ys}U_{fs}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1405428 | p.$A_{\underline{\mathbf{yz}}}$ $U_{\underline{\mathbf{fz}}}$ $A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{y}zA_{fz}U_{y}$ | 21 |
| 1465680 | p.$A_{\underline{\mathbf{yz}}}$ $U_{fs}A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |
| 1465681 | p.$A_{ys}$ $U_{\underline{\mathbf{fz}}}$ $A_{yo}A_{fo}A_{yo}A_{fo}U_{yo}C_{fo}U_{yo}A_{fo}C_{yo}A_{fo}G_{yo}U_{fo}C_{yo}A_{fo}U_{yo}A_{fo}G_{yo}G_{fo}A_{ys}A_{fs}U_{y}$ | 21 |

In the table above, a "p." represents a 5'-phosphate, a subscript "y" represents a 2'-OMe modified nucleoside, a subscript "f" represents a 2'-F modified nucleoside, a subscript "s" indicates a phosphorothioate internucleoside linkage, a subscript "o" indicates a phosphodiester internucleoside linkage, and a subscript "z" represents an internucleoside linkage of formula IX, which is a mesyl phosphoramidate linkage. Subscripts of nucleotides having an internucleoside linkage of formula IX are bold and underlined.

In vivo Tolerability and Activity Assay

For the in vivo activity and tolerability study in the table below, 4 C57/B6J male mice per group were administered siRNA by subcutaneous injection and sacrificed after 72 hours. The siRNA compounds were administered at 0.3, 1, or 3 mg/kg. One group of four C57/B6J mice was injected with PBS.

Liver tissue was collected, total RNA was isolated, and levels of HPRT1 in liver samples were measured by quantitative RTPCR with primer probe set RTS43125 (forward sequence: CTCCTCAGACCGCTTTTTGC, SEQ ID NO: 77; reverse sequence: TAACCTGGTTCATCATCGCTAATC, SEQ ID NO: 78; probe sequence: CCGTCATGCCGACCCGCAGT, SEQ ID NO: 79). Expression levels were normalized to total RNA as measured with RIBOGREEN®. $ED_{50}$ values were calculated by a least squares fit of data in GraphPad Prism using the equation "[Inhibitor] vs. response—Variable slope (four parameters)" and are presented in the table below. Plasma ALT was also measured and is presented in the table below. Elevations in ALT are associated with liver toxicity. The PBS treated mice have an ALT of 58.8 IU/L.

TABLE 64

| In vivo activity and toxicity of siRNA to HPRT1 | | | |
|---|---|---|---|
| Antisense Strand | Sense Strand | in vivo HPRT1 $ED_{50}$ liver (mg/kg) | ALT @ 3 mg/kg (IU/L) |
| 1337111 | 1448688 | 0.53 | 58.5 |
| 1405428 | 1448688 | >3 | 22.0 |
| 1465680 | 1448688 | 2.6 | 31.3 |
| 1465681 | 1448688 | 0.69 | 66.0 |

Example 35: Design and Activity of Modified Oligonucleotides with Mesyl Phosphoramidate Internucleoside Linkages In Vivo to Mouse NOTCH3

Design of Modified Oligonucleotides

Modified oligonucleotides comprising multiple mesyl phosphoramidate internucleoside linkages (Formula IX) and phosphorothioate internucleoside linkages were designed, synthesized and tested. The modified oligonucleotides are each 3-10-3 cEt gapmers with a sugar motif of: kkkddddddddddkkk (a 3-10-3 cEt motif), wherein "k" represents a cEt modified sugar moiety and "d" represents a pi-D-2'-deoxyribosyl sugar moiety. Each of the modified oligonucleotides is 100% complementary to the complement of mouse NOTCH3, GENBANK Accession No. NC_000083.6 truncated from 32118001 to 32170000 (SEQ ID NO: 80). Each internucleoside linkage is either a phosphorothioate internucleoside linkage ("s") or a mesyl phosphoramidate internucleoside linkage ("z").

TABLE 65

| Design of modified oligonucleotides with mesyl phosphoramidate internucleoside linkages | | |
|---|---|---|
| Compound ID | Chemistry Notation (5' to 3') | SEQ ID NO. |
| 977131 | $G_{ks}G_{k}sA_{ks}A_{ds}T_{ds}A_{ds}T_{ds}T_{ds}G_{ds}G_{ds}T_{ds}T_{ds}{}^{m}C_{ds}A_{ks}G_{ks}T_{k}$ | 81 |
| 1516016 | $T_{ks}\ \mathbf{G}_{\underline{\mathbf{kz}}}\ \mathbf{T}_{\underline{\mathbf{kz}}}\ {}^{m}C_{ds}G_{ds}A_{ds}A_{ds}G_{ds}{}^{m}C_{ds}T_{ds}{}^{m}C_{ds}A_{ds}A_{ds}{}^{m}\ \mathbf{C}_{\underline{\mathbf{kz}}}\ {}^{m}C_{ks}{}^{m}C_{k}$ | 82 |
| 1516017 | $A_{ks}\ \mathbf{T}_{\underline{\mathbf{kz}}}\ {}^{m}\ \mathbf{C}_{\underline{\mathbf{kz}}}\ T_{ds}A_{ds}T_{ds}T_{ds}G_{ds}T_{ds}{}^{m}C_{ds}A_{ds}{}^{m}C_{ds}T_{ds}T_{ds}\mathbf{T}_{\underline{\mathbf{kz}}}\ G_{ks}G_{k}$ | 83 |
| 1516018 | $G_{ks}\ \mathbf{A}_{\underline{\mathbf{kz}}}\ \mathbf{A}_{\underline{\mathbf{kz}}}\ T_{ds}A_{ds}T_{ds}T_{ds}G_{ds}G_{ds}T_{ds}T_{ds}{}^{m}C_{ds}A_{ds}\mathbf{G}_{\underline{\mathbf{kz}}}\ T_{ks}A_{k}$ | 84 |
| 1516019 | $G_{ks}\mathbf{G}_{\underline{\mathbf{kz}}}\ \mathbf{A}_{\underline{\mathbf{kz}}}\ A_{ds}T_{ds}A_{ds}T_{ds}T_{ds}G_{ds}G_{ds}T_{ds}T_{ds}{}^{m}C_{ds}\mathbf{A}_{\underline{\mathbf{kz}}}\ G_{ks}T_{k}$ | 81 |
| 1516020 | $T_{ks}\ \mathbf{G}_{\underline{\mathbf{kz}}}\ \mathbf{T}_{\underline{\mathbf{kz}}}\ A_{ds}T_{ds}G_{ds}T_{ds}{}^{m}C_{ds}G_{ds}{}^{m}C_{ds}A_{ds}{}^{m}C_{ds}A_{ds}\ \mathbf{G}_{\underline{\mathbf{kz}}}\ G_{ks}{}^{m}C_{k}$ | 85 |
| 1516021 | $A_{ks}{}^{m}\mathbf{C}_{\underline{\mathbf{kz}}}\ \mathbf{A}_{\underline{\mathbf{kz}}}\ A_{ds}T_{ds}T_{ds}{}^{m}C_{ds}T_{ds}A_{ds}T_{ds}G_{ds}G_{ds}T_{ds}{}^{m}\mathbf{C}_{\underline{\mathbf{kz}}}\ T_{ks}{}^{m}C_{k}$ | 86 |

In the table above, a subscript "k" represents a cEt nucleoside, a subscript "d" represents a stereo-standard DNA nucleoside, a subscript "s" indicates a phosphorothioate internucleoside linkage, and a subscript "z" represents an internucleoside linkage of formula IX, which is a mesyl phosphoramidate linkage. Subscripts of nucleotides having an internucleoside linkage of formula IX are bold and underlined. A superscript "m" before a C represents a 5-methylcytosine.

Activity Assay in CNS

Modified oligonucleotides described above were tested in wild-type C57BL6/J mice to assess the CNS activity of the oligonucleotides. Wild-type C57BL6/J mice each received a single ICV bolus of 300 μg of modified oligonucleotide listed in the table below. Each treatment group consisted of 4 mice. A group of 4 mice received PBS as a negative control.

Two weeks post treatment, mice were sacrificed. RNA was extracted from cortical brain tissue and spinal cord for quantitative real-time RTPCR analysis to measure the amount of NOTCH3 RNA using mouse primer probe set RTS36973 (forward sequence CATGGTCTTCCCCTATCACC, designated herein as SEQ ID NO: 87; reverse sequence TGTCAATCTCCAGCATCACC, designated herein as SEQ ID NO: 88; probe sequence ATCACCTCAGGACCCAGCTCAC, designated herein as SEQ ID NO: 89). Results are presented as percent mouse NOTCH3 RNA relative to PBS control, adjusted to mouse GAPDH RNA.

TABLE 66

| In vivo CNS activity of modified oligonucleotides complementary to mouse NOTCH3 | | |
|---|---|---|
| | Mouse NOTCH3 RNA | |
| Compound ID | Cortex (% control) | Spinal Cord (% control) |
| PBS | 100.0 | 100.0 |
| 977131 | 30.5 | 9.5 |
| 1516016 | 14.5 | 8.0 |
| 1516017 | 21.0 | 11.5 |
| 1516018 | 12.0 | 8.0 |
| 1516019 | 10.7 | 6.3 |
| 1516020 | 48.0 | 4.0 |
| 1516021 | 4.0 | 2.7 |

Example 36: Design and Activity of siRNA Having a 5'-Mesyl Phosphoramidate to HPRT1 In Vitro siRNA Design A double-stranded siRNA comprising modified oligonucleotides was synthesized and tested. The antisense strand has the chemical notation z. $A_{ys}Uf_{s}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}T_{ds}T_{d}$ (SEQ ID NO: 90). The first 21 nucleosides of the antisense strand is 100% complementary to GenBank NM_000194.2 (SEQ ID NO: 22) from 446 to 466. The antisense strand has a 5'-mesyl phosphoramidate (z). The sense strand is 1448688, described in Example 20 herein.

TABLE 67

| Activity of siRNAs targeted to HPRT1 containing mesyl phosphoramidate internucleoside linkages and/or stereo-non-standard nucleosides | | | |
|---|---|---|---|
| Compound ID | Antisense Strand | Sense Strand | $IC_{50}$ (nM) |
| 1545957 | 1527118 | 1448688 | 0.02 |

Example 38: Design of siRNA Having 5'-Mesyl Phosphoramidate Moieties

Double-stranded siRNA comprising modified oligonucleotides having 5'-mesyl phosphoramidate terminal groups (Formula XXII) at the 5'-end of the siRNA antisense oligonucleotide were designed.

XXII

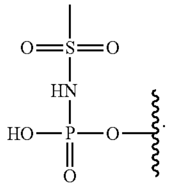

Compound Nos. 1547257, 1547258, 1547259, and 1547296 contain a 2'-O-hexadecyl modified nucleoside ("$16C_2r$"), shown below, wherein Bx is an independently selected heterocyclic base moiety:

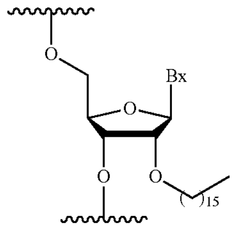

"16C2r"

Compound Nos. 1547286, 1547287, and 1547288 contain the sugar surrogate glycol nucleic acid (GNA) with the chiral center in the S configuration ("Sgna"), shown below, wherein Bx is an independently selected heterocyclic base moiety:

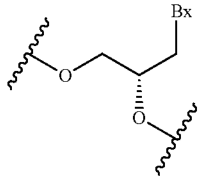

"Sgna"

Compound No. 1448688 has a GalNAc conjugated at the 3'-oxygen of the oligonucleotide via a THA linker as shown below:

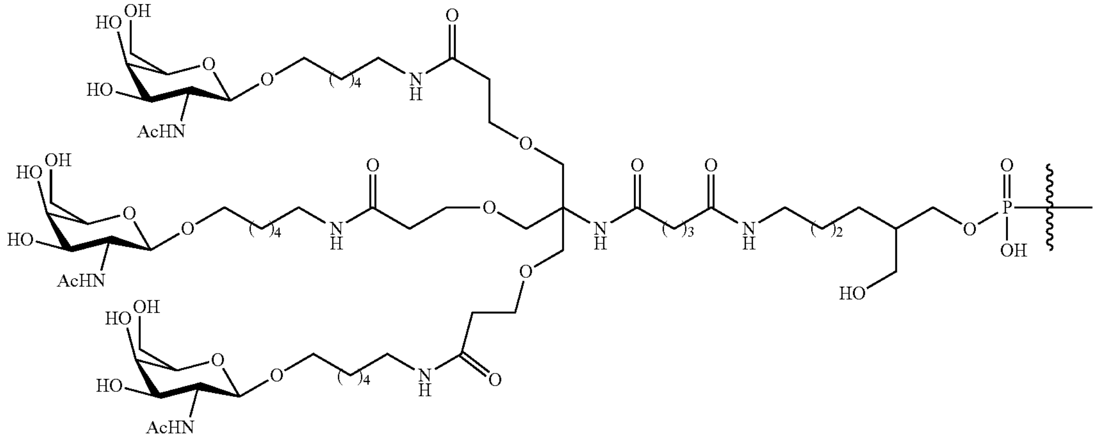

"THA-C7-GalNAc"

TABLE 68

Design of RNAi antisense modified oligonucleotides having 5'-mesyl phosphoramidate modifications

| Compound ID | Chemistry Notation (5' to 3') | SEQ ID NO. |
|---|---|---|
| 1547253 | z.$A_{ys}U_{fs}A_{yo}A_{yo}A_{yo}A_{fo}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1527118 | z.$A_{ys}U_{fs}A_{yo}A_{yo}A_{yo}A_{fo}U_{yo}C_{yo}U_{yo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547254 | z.$A_{ys}U_{fs}A_{yo}A_{yo}A_{yo}A_{fo}U_{yo}C_{yo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547257 | z.$A_{ys}U_{fs}A_{yo}A_{yo}A_{yo}A_{fo}U_{[16C2r]o}C_{fo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547258 | z.$A_{ys}U_{fs}A_{yo}A_{yo}A_{yo}A_{fo}U_{[16C2r]o}C_{yo}U_{yo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547259 | z.$A_{ys}U_{fs}A_{yo}A_{yo}A_{yo}A_{fo}U_{[16C2r]o}C_{yo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547286 | z.$A_{ys}U_{fs}A_{yo}A_{yo}A_{yo}A_{[Sgna]o}U_{yo}C_{fo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547287 | z.$A_{ys}U_{fs}A_{yo}A_{yo}A_{yo}A_{[sgna]o}U_{yo}C_{yo}U_{yo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |
| 1547288 | z.$A_{ys}U_{fs}A_{yo}A_{yo}A_{yo}A_{[sgna]o}U_{yo}r_{yo}U_{fo}A_{yo}C_{yo}A_{yo}G_{yo}U_{fo}C_{yo}A_{fo}U_{yo}A_{yo}G_{yo}G_{yo}A_{ys}A_{ys}U_{y}$ | 21 |

In the table above, a "z." represents a 5'-mesyl phosphoramidate, a subscript "y" represents a 2'-OMe modified nucleoside, a subscript "f" represents a 2'-F modified nucleoside, a subscript "s" indicates a phosphorothioate internucleoside linkage, and a subscript "o" indicates a phosphodiester internucleoside linkage. A subscript "$16C_2r$" represents a 2'-O-hexadecyl modified nucleoside, and a subscript "Sgna" represents a (S)-glycol nucleic acid.

TABLE 69

Design of RNAi sense modified oligonucleotides

| Compound ID | Chemistry Notation (5' to 3') | SEQ ID NO. |
|---|---|---|
| 1448688 | $U_{ys}C_{ys}C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}U_{yo}A_{yo}U_{y}$-THA-C7-GalNAc | 23 |
| 1505889 | $U_{ys}C_{ys}C_{yo}U_{yo}A_{yo}U_{yo}G_{fo}A_{yo}C_{fo}U_{fo}G_{fo}U_{yo}A_{yo}G_{yo}A_{yo}U_{yo}U_{yo}U_{yo}U_{yo}U_{ys}A_{ys}U_{y}$ | 23 |
| 1547296 | $U_{ys}C_{ys}U_{yo}A_{yo}U_{[6C2r]o}G_{fo}A_{yo}C_{fo}U_{fo}G_{fo}U_{yo}A_{yo}G_{yo}A_{yo}U_{yo}U_{yo}U_{yo}U_{yo}U_{ys}A_{ys}U_{y}$ | 23 |
| 1548003 | $U_{ys}C_{ys}C_{yo}U_{yo}A_{yo}U_{y[XIX]}G_{fo}A_{yo}C_{fo}U_{fo}G_{fo}U_{yo}A_{yo}G_{yo}A_{yo}U_{yo}U_{yo}U_{yo}U_{ys}A_{ys}U_{y}$ | 23 |

In the table above, a subscript "y" represents a 2'-OMe modified nucleoside, a subscript "f" represents a 2'-F modified nucleoside, a subscript "s" indicates a phosphorothioate internucleoside linkage, and a subscript "o" indicates a phosphodiester internucleoside linkage. A subscript "$16C_2r$" represents a 2'-O-hexadecyl modified nucleoside. A subscript "[XIX]" represents an internucleoside linkage of Formula XIX.

TABLE 70

Design of siRNA compounds

| siRNA Duplex Compound No. | Antisense Strand Compound No. | Sense Strand Compound No. |
|---|---|---|
| 1547255 | 1547253 | 1448688 |
| 1545957 | 1527118 | 1448688 |
| 1547256 | 1547254 | 1448688 |

TABLE 70-continued

Design of siRNA compounds

| siRNA Duplex Compound No. | Antisense Strand Compound No. | Sense Strand Compound No. |
|---|---|---|
| 1547293 | 1547257 | 1505889 |
| 1547294 | 1547258 | 1505889 |
| 1547295 | 1547259 | 1505889 |
| 1547290 | 1547286 | 1448688 |
| 1547291 | 1547287 | 1448688 |
| 1547292 | 1547288 | 1448688 |
| 1547297 | 1547253 | 1547296 |
| 1547298 | 1527118 | 1547296 |
| 1547299 | 1547254 | 1547296 |
| 1548004 | 1547253 | 1548003 |
| 1548006 | 1527118 | 1548003 |
| 1548007 | 1547254 | 1548003 |

What is claimed:

1. An oligomeric compound comprising a modified oligonucleotide consisting of 12-22 linked nucleosides, wherein the modified oligonucleotide has a 5'-region, a central region, and a 3'-region, wherein:

the 5'-region consists of 1-6 linked nucleosides, each comprising a modified sugar moiety;

the 3'-region consists of 1-6 linked nucleosides, each comprising a modified sugar moiety;

the central region is a deoxy region; and the central region consists of 7-12 linked nucleosides and has the formula (from 5' to 3'): $(N_{d1})_{L1}(N_{d2})_{L2}(N_{d3})_{L3}(N_{d4})_{L4}[(N_d)_{L5}]_q$, wherein:

$N_{d1}$, $N_{d2}$, $N_{d3}$, $N_{d4}$ are independently selected from a stereo-standard DNA nucleoside and a 2'-substituted nucleoside; with the proviso that no more than one of $N_{d1}$, $N_{d2}$, $N_{d3}$, or $N_{d4}$ is a 2'-substituted nucleoside;

q is from 3-8;

each of $L_1$, $L_2$, $L_3$, $L_4$, and each $L_5$ is an internucleoside linkage:

two, three, or four of $L_1$, $L_2$, $L_3$, and $L_4$ are mesyl phosphoramidate internucleoside linkages; and each $L_5$ is a phosphorothioate internucleoside linkage.

2. The oligomeric compound of claim 1, wherein each internucleoside linkage of the 3'-region and each internucleoside linkage of the 5'-region of the modified oligonucleotide is independently selected from a phosphorothioate and a phosphodiester.

3. The oligomeric compound of claim 1, wherein each nucleoside of the deoxy region is a stereo-standard DNA nucleoside.

4. The oligomeric compound of claim 1, wherein exactly one nucleoside of the deoxy region is a 2'-substituted nucleoside, and the remainder of the nucleosides of the deoxy region are stereo-standard DNA nucleosides.

5. The oligomeric compound of claim 4, wherein the 2'-substituted nucleoside comprises a stereo-standard 2'-OMe sugar moiety.

6. The oligomeric compound of claim 1, wherein each modified sugar moiety is independently selected from a bicyclic sugar moiety and a 2'-substituted sugar moiety.

7. The oligomeric compound of claim 6, wherein each bicyclic sugar moiety is independently selected from cEt, LNA, and ENA.

8. The oligomeric compound of claim 6, wherein each 2'-substituted sugar moiety is independently selected from 2'-OMe and 2'-MOE.

9. The oligomeric compound of claim 8, wherein each 2'-substituted sugar moiety is a stereo-standard sugar moiety.

10. The oligomeric compound of claim 1, wherein $L_1$ and $L_2$ are mesyl phosphoramidate internucleoside linkages.

11. The oligomeric compound of claim 1, wherein $L_2$ and $L_3$ are mesyl phosphoramidate internucleoside linkages.

12. The oligomeric compound of claim 1, wherein $L_3$ and $L_4$ are mesyl phosphoramidate internucleoside linkages.

13. The oligomeric compound of claim 1, wherein $L_1$, $L_2$, and $L_3$ are mesyl phosphoramidate internucleoside linkages.

14. The oligomeric compound of claim 1, wherein $L_2$, $L_3$, and $L_4$ are mesyl phosphoramidate internucleoside linkages.

15. The oligomeric compound of claim 1, wherein $L_1$, $L_2$, $L_3$, and $L_4$ are mesyl phosphoramidate internucleoside linkages.

16. The oligomeric compound of claim 1, wherein each of $L_1$, $L_2$, $L_3$, $L_4$ are independently selected from a mesyl phosphoramidate and a phosphorothioate internucleoside linkage, and each $L_5$ is a phosphorothioate internucleoside linkage.

17. The oligomeric compound of claim 4, wherein $N_{d2}$ is a stereo-standard 2'-OMe nucleoside.

18. The oligomeric compound of claim 1, wherein the 5'-region consists of 3 linked nucleosides, each comprising a bicyclic sugar moiety;

the 3' region consists of 3 linked nucleosides, each comprising bicyclic sugar moiety;

and the central region consists of 10 linked nucleosides.

19. The oligomeric compound of claim 18, wherein each bicyclic sugar moiety is a cEt sugar moiety.

20. The oligomeric compound of claim 1, wherein the 5'-region consists of 5 linked nucleosides, each comprising a stereo-standard 2'-MOE sugar moiety;

the 3' region consists of 5 linked nucleosides, each comprising a stereo-standard 2'-MOE sugar moiety; and the central region consists of 10 linked nucleosides.

21. The oligomeric compound of claim 1, wherein the modified oligonucleotide consists of 16-20, 16-18, 18-20, or 18-22 linked nucleosides.

22. The oligomeric compound of claim 1, wherein the modified oligonucleotide consists of 16 linked nucleosides.

23. The oligomeric compound of claim 1, wherein the modified oligonucleotide consists of 20 linked nucleosides.

24. The oligomeric compound of claim 1, wherein the oligomeric compound comprises a conjugate group.

25. The oligomeric compound of claim 24, wherein the conjugate group comprises a conjugate linker and a conjugate moiety.

26. The oligomeric compound of claim 25, wherein the conjugate moiety is selected from a cell-targeting moiety, a lipid, a carbohydrate, a $C_{12}$-$C_{20}$ alkyl, an antibody, an antibody fragment, or a peptide.

27. The oligomeric compound of claim 26, wherein the conjugate moiety comprises a GalNAc.

28. The oligomeric compound of claim 1, wherein each nucleobase of the modified oligonucleotide is independently selected from thymine, uracil, guanine, cytosine, 5-methylcytosine, and adenine.

* * * * *